US009642789B2

(12) United States Patent
Cotsarelis et al.

(10) Patent No.: US 9,642,789 B2
(45) **Date of Patent: *May 9, 2017**

(54) METHODS FOR GENERATING NEW HAIR FOLLICLES, TREATING BALDNESS, AND HAIR REMOVAL

(75) Inventors: George Cotsarelis, Berwyn, PA (US); Mayumi Ito, Philadelphia, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 171 days.

This patent is subject to a terminal disclaimer.

(21) Appl. No.: 12/904,981

(22) Filed: Oct. 14, 2010

(65) Prior Publication Data

US 2011/0092421 A1 Apr. 21, 2011

Related U.S. Application Data

(63) Continuation of application No. 11/887,104, filed as application No. PCT/US2006/011319 on Mar. 28, 2006, now abandoned.

(60) Provisional application No. 60/665,857, filed on Mar. 29, 2005, provisional application No. 60/683,293, filed on May 23, 2005.

(51) Int. Cl.

| | |
|---|---|
| ***A61Q 7/00*** | (2006.01) |
| ***A61K 8/49*** | (2006.01) |
| ***A61K 9/00*** | (2006.01) |
| ***A61B 8/00*** | (2006.01) |
| ***A61K 8/65*** | (2006.01) |
| ***A61Q 5/00*** | (2006.01) |
| ***A61Q 5/10*** | (2006.01) |
| ***A61K 31/506*** | (2006.01) |
| ***A61K 31/517*** | (2006.01) |
| ***A61K 31/65*** | (2006.01) |
| ***A61K 35/36*** | (2015.01) |
| ***A61K 38/18*** | (2006.01) |
| ***A61M 37/00*** | (2006.01) |
| *A61B 17/00* | (2006.01) |
| *A61B 18/00* | (2006.01) |

(52) U.S. Cl.

CPC .............. *A61K 8/4953* (2013.01); *A61K 8/65* (2013.01); *A61K 9/0014* (2013.01); *A61K 31/506* (2013.01); *A61K 31/517* (2013.01); *A61K 31/65* (2013.01); *A61K 35/36* (2013.01); *A61K 38/1825* (2013.01); *A61M 37/00* (2013.01); *A61Q 5/00* (2013.01); *A61Q 5/10* (2013.01); *A61Q 7/00* (2013.01); *A61B 2017/00765* (2013.01); *A61B 2018/00452* (2013.01); *A61K 2800/74* (2013.01); *A61K 2800/805* (2013.01); *A61M 2037/0007* (2013.01)

(58) Field of Classification Search

CPC ...... A61N 5/0617; A61Q 7/00; A61B 18/203; A61B 2018/00452; A61B 2018/00476

See application file for complete search history.

(56) References Cited

U.S. PATENT DOCUMENTS

| | | | | |
|---|---|---|---|---|
| 4,490,365 | A | 12/1984 | Panaretto et al. | |
| 4,919,664 | A | 4/1990 | Oliver et al. | |
| 5,466,695 | A | 11/1995 | Poulos et al. | |
| 6,075,005 | A | 6/2000 | Lurie | |
| 6,159,950 | A | 12/2000 | Crystal et al. | |
| 6,867,179 | B1 | 3/2005 | Gilchrest et al. | |
| 6,936,044 | B2 | 8/2005 | McDaniel | |
| 8,252,749 | B2 | 8/2012 | Steinberg et al. | |
| 8,431,400 | B2 | 4/2013 | Hoffmann et al. | |
| 2002/0065314 | A1 | 5/2002 | Nielsen et al. | |
| 2002/0114772 | A1 | 8/2002 | Morgan et al. | |
| 2002/0132792 | A1 | 9/2002 | Prien et al. | |
| 2003/0007941 | A1 | 1/2003 | Cornelius et al. | |
| 2004/0153131 | A1 | 8/2004 | Yorke | |
| 2005/0049625 | A1 | 3/2005 | Shaya et al. | |
| 2006/0008505 | A1 | 1/2006 | Brandon et al. | |
| 2006/0073117 | A1 | 4/2006 | Li | |
| 2006/0241696 | A1 | 10/2006 | Krco | |
| 2006/0287385 | A1 | 12/2006 | Baxter et al. | |
| 2007/0190075 | A1 * | 8/2007 | Suzuki .................... | A61K 8/97 424/195.17 |
| 2008/0182859 | A1 | 7/2008 | Brunton et al. | |
| 2008/0193423 | A1 | 8/2008 | Brunton et al. | |
| 2011/0086007 | A1 | 4/2011 | Kemp et al. | |

FOREIGN PATENT DOCUMENTS

| | | | |
|---|---|---|---|
| EP | 1634874 | A1 | 3/2006 |
| JP | 2003-081866 | A | 3/2003 |
| WO | WO 99/01034 | | 1/1999 |
| WO | WO 00/31134 | | 6/2000 |
| WO | WO 00/45736 | A1 | 8/2000 |

(Continued)

OTHER PUBLICATIONS

Kawano et al., J. Invest Dermatol 124:877-885, 2005.*
Suzuki et al., J. Invest Dermatol 114;456-463, 2000.*
Blanpain et al., Cell, 118 (2004), pp. 635-648.*
Kimura-Ueki J Invest Dermatol. May 2012;132(5):1338-1345.*
Li Y et al. "Early epidermal destruction with subsequent epidermal hyperplasia is a unique feature of the papilloma-independent squamous cell carcinoma phenotype in PKCepsilon overexpressing transgenic mice" Toxicol Pathol ;33(6):684-94, (2005).
Ley et al. "Hair growth induction by ultraviolet radiation in the marsupial Monodelphis domestica" Arch Dermatol. ;123(8):1032-5, Aug. 1987.
Argyirs T. "Kinetics of epidermal production during epidermal regeneration following abrasion in mice" Am J Pathol. 83(2):329-40, May 1976.
Du Cros. "Fibroblast Growth Factor and Epidermal Growth Factor in Hair Development" Journal Invest Dermatol., vol. 101, pp. 106S-113S, (1993).

(Continued)

*Primary Examiner* — Daniel C Gamett

(74) *Attorney, Agent, or Firm* — Mark S. Cohen; Pearl Cohen; Zedek Latzer Baratz LLP

(57) ABSTRACT

The present invention provides methods of treating baldness in a subject and generating new hair follicles, comprising epidermal disruption and administration of a compound that promotes a differentiation of an uncommitted epidermal cell into a hair follicle cell. The present invention also provides methods for hair removal and inducing hair pigmentation.

16 Claims, 43 Drawing Sheets

(56) References Cited

FOREIGN PATENT DOCUMENTS

| | | |
|---|---|---|
| WO | WO 01/32840 | 5/2001 |
| WO | WO 01/58413 | 8/2001 |
| WO | WO 01/74164 | 10/2001 |
| WO | WO 02/060396 | 8/2002 |
| WO | WO 02/092771 | 11/2002 |
| WO | WO 03/039478 | 5/2003 |
| WO | WO 03/061362 A2 | 7/2003 |
| WO | WO 03/068248 | 8/2003 |
| WO | WO 2004/043415 | 5/2004 |
| WO | WO 2004/060488 A1 | 7/2004 |
| WO | WO 2005/017107 | 2/2005 |
| WO | WO 2010/056759 | 5/2010 |

OTHER PUBLICATIONS

Lo Celso et al. “Transient activation of beta-catenin signalling in adult mouse epidermis is sufficient to induce new hair follicles but continuous activation is required to maintain hair follicle tumours” Development, vol. 131, pp. 1787-1799, (2004).
Mater et al., Transient Activation of β-Catenin Signaling in Cutaneous Keratinocites is Sufficient to Trigger the Active Growth Phase of the Hair Cycle in Mice, Genes and Development, 2003, vol. 17, pp. 1219-1224.
Botchkarev VA et al. “Edar signaling in the control of hair follicle development” J Investig Dermatol Symp Proc. ;10(3):247-51, Dec. 2005.
Fuchs E et al. “Stem cells a new lease on life” Cell. 7;100(1):143-55, Jan. 2000.
Joerg Huelsken et al. “β-Catenin Controls Hair Follicle Morphogenesis and Stem Cell Differentiation in the Skin” Cell, vol. 105, Issue 4, 533-545, May 18, 2001.
Moore et al. “Epidermal Hyperplasia and wool follicle Repression in sheep Infused with Epidermal growth factor” The Journal of Investigation Dermatology, 84:172-175, (1985).
Millar et al. “Molecular Mechanisms Regulating Hair follicle Development” The Journal of Investigation Dermatology 118:216-225, (2002).
International Search Report for International Application No. PCT/US06/11319 Date of Mailing May 28, 2008.
Hallmans et al., Regeneration of Hair Follicles from Experimental Wounds on the Rabbit Ear, Scandinavian Journal of Plastic and Reconstructive Surgery, 1974. vol. 8, No. 3, pp. 207-210.
Jahoda et al., Cellular and Extracelluar Involvement in the Regeneration of the Rat Lower Vibrissa Follicle, Development, 1992, vol. 114, pp. 887-897.
Mattar et al., Inhibition of Epidermal Growth Factor Receptor Tyrosine Kinase Activity by Leflunomide, Federation of European Biochemical Societies, Nov. 1993, vol. 334, No. 2, pp. 161-164.
Mak et al., Epidermal Growth Factor as a Biological Switch in Hair Growth Cycle, The Journal of Biological Chemistry, Jul. 11, 2003, vol. 278, No. 28, pp. 26120-26126.
Danilenko et al., Keratinocyte Growth Factor is an Important Endogenous Mediator of Hair Follicle Growth, Development, and Differentiation, Normalization of the nu/nu Follicular Differentiation Defect and Amelioration of Chemotherapy-Induced Alopecia, American Journal of Pathology, Jul. 1, 1995, vol. 147, No. 147, pp. 145-154.
Srivastava et al., Ectodysplasin-A1 is Sufficient to Rescue Both Hair Growth and Sweat Glands in Tabby Mice, Human Molecular Genetics, 2001, vol. 10, No. 26, pp. 2973-2981.
Han et al., Effect of Minoxidil on Proliferation and Apoptosis in Dermal Papilla Cells of Human Hair Follicle, Journal of Dermatological Science, 2004, vol. 34, pp. 91-98.
Botchkarev et al., Noggin is a Mesenchymally Derived Stimulator of Hair-Follicle Induction, Nature Cell Biology, Jul. 1999, vol. 1, pp. 158-164.
Botchkarev et al., Noggin is Required for Induction of the Hair Follicle Growth Phase in Postnatal Skin, FASEB Journal, 2001, vol. 15., pp. 2205-2214.
Ota et al., Fibroblast Growth Factor 5 Inhibits Hair Growth by Blocking Dermal Papilla Cell Activation, Biochemical and Biophysical Research Communications, 2002, vol. 290, pp. 169-176.
Kashiwagi et al., Specific Inhibition of Hair Follicle Formation by Epidermal Growth Factor in an Organ Culture of Developing Mouse Skin, Developmental Biology, 1997, vol. 189, pp. 22-32.
Mitsuyuki et al., Recent Studies on Mechanism of Hair Loss/Hair Growth and Developing Trend of Hair Growth Drug, 2003, Fragrance Journal, vol. 31, No. 2, pp. 33-40. (English abstract.).
Katsuyuki, Effects of Epidermal Growth Factor and Transforming Growth Factor on Cultured Hair Follicle Cells from Human Scalp, Skin, 1994, vol. 36, No. 2, pp. 125-133. (English abstract.).
Tanabe et al., Basic Technology Meeting of the Japanese Orthopedic Association, Program & Abstract, 2003, vol. 12, p. 118. (English abstract.).
Pestana, A et al. “Effect of ultraviolet light on topical minoxidil-induced hair growth in advanced male pattern baldness”. Journal of the American Academy of Dermatology, 1987.vol. 16(5): pp. 971-976.
Argyris et al., “Factors affecting the stimulation of hair growth during wound healing”, Anatomical Record, vol. 142, No. 2, 1962, pp. 139-145.
Breedis et al., “Regeneration of hair follicles and sebaceous glands from the epithelium of scars in the rabbit”, Cancer Research, vol. 14, No. 8, 1954, p. 17.
Argyris et al., “On the mechanism of hair growth stimulation in wound healing”, Develop. Biol. 9:230-254, 1964.
Johnson et al., “The effect of plucking hairs during different phases of the follicular cycle”, J. Embryol. Exp. Morph. 12: 465-474, 1964.
Kligman et al., “Neogenesis of human hair follicles”, Ann. NY. Acad. Sci. 83: 507-511, 1959.
Mahe et al., “Pro-inflammatory cytokine cascade in human plucked hair”, Skin Pharmacol. 9: 366-375, 1996.
Muller et al., “Hair Neogenesis”, J. Invest. Dermatol. 56:1-9, 1971.
Reynolds et al., “Inductive properties of hair follicle cells”, Ann. NY Acad. Sci. 642: 226-242, 1991.
Buckland et al. “Effect of scalp burns on common male pattern baldness”, British Meidcal Joruna, vol. 293, pp. 20-27, Dec. 1986.
Ito et al. “Hair follicle stem cells in the lower bulge form the secondary germ, a biochmically distinct but functionally equivalent progenitor cell population, at the termination of catagen”, Differentiation (2004) 72:548-557.
McElwee et al. “Cultured Peribulbar Dermal Sheath Cells Can Induce Hair Follicle Development and Contribute to the Dermal Sheath and Dermal Papilla”, The Journal of Investigative Dermatology, vol. 121, No. 6, Dec. 2003.
Argyris “The growth-promoting effects of wounds on hair follicles already stimulated by plucking”, Anat Rec. Jul. 1962;143:183-8.
European Search Report for European Application No. 15165807.7 dated Oct. 21, 2015.
Kligman et al. “The formation of vellus hair follicles from human adult epidermis”, J Invest Dermatol. Jul. 1956;27(1):19-23.
Messenger et al. “Minoxidil: mechanisms of action on hair growth”, Br J Dermatol. Feb. 2004;150(2):186-94.
Kawano et al., J. Invest. Dermatol. 124: 877-885, 2005.
Suzuki et al., J. Invest. Dermatol. 114: 456-463, 2000.
Kimura-Ueki, J. Invest. Dermatol., 2012, 132(5): 1338-1345.
Mimura et al., Functional Cosmetics II, 1996, Chapter 9, Mechanism of hair loss and application of hair growing agent, pp. 124-130.

* cited by examiner

K 17 immuno-stain

Alkaline Phosphatase

Label retaining cells 14 days after wound

AP K17

17 days after wound

| probe set | SEQ ID No | bs-line mean | bs-line SE | expt mean | expt SE | fold change | lower bound:FC | upper bound:FC | diff. of mean |
|---|---|---|---|---|---|---|---|---|---|
| 160841_at | 1 | -4.59 | 7.45 | 117.99 | 26.88 | 117.99 | 8.2 | 100000000 | 122.57 |
| 103589_at | 2 | -1.28 | 6.58 | 112.41 | 43.53 | 112.41 | 7.13 | 100000000 | 113.68 |
| 103562_f_at | 3 | 23.45 | 12.4 | 220.55 | 110.78 | 9.4 | 1.52 | 75.74 | 197.1 |
| 97527_at | 4 | 27.15 | 14.75 | 173.81 | 24.11 | 6.4 | 3.2 | 60.38 | 146.66 |
| 160909_at | 5 | 115.74 | 46.42 | 706.06 | 192.98 | 6.1 | 2.8 | 18.81 | 590.32 |
| 93285_at | 6 | 132.73 | 53.69 | 782.45 | 138.65 | 5.89 | 3.17 | 17.98 | 649.72 |
| 98988_at | 7 | 119.09 | 33.93 | 650.75 | 97.47 | 5.46 | 3.38 | 10.62 | 531.65 |
| 161903_f_at | 8 | 33.82 | 7.85 | 183.08 | 42.87 | 5.41 | 3.03 | 9.65 | 149.26 |
| 97542_at | 9 | 199 | 149.69 | 1009.76 | 317.31 | 5.07 | 1.71 | 100000000 | 810.76 |
| 104701_at | 10 | 181.01 | 54.87 | 893.77 | 110.08 | 4.94 | 3.1 | 10.04 | 712.76 |
| 94057_g_at | 11 | 194.15 | 36.67 | 895.05 | 169.8 | 4.61 | 2.91 | 7.29 | 700.89 |
| 160092_at | 12 | 142.8 | 67.19 | 637.32 | 153.3 | 4.46 | 2.08 | 20.18 | 494.52 |
| 93527_at | 13 | 55.64 | 18 | 246.09 | 25.21 | 4.42 | 2.77 | 9.57 | 190.46 |
| 92978_s_at | 14 | 208.74 | 82.76 | 904.6 | 260.29 | 4.33 | 1.93 | 13.15 | 695.86 |
| 93985_at | 15 | 117.48 | 43.72 | 505.43 | 102.78 | 4.3 | 2.29 | 11.47 | 387.95 |
| 97197_r_at | 16 | 238.01 | 60.95 | 975.35 | 226.41 | 4.1 | 2.27 | 7.7 | 737.34 |
| 160606_r_at | 17 | 105.16 | 32.48 | 420.67 | 154.57 | 4 | 1.47 | 9.32 | 315.51 |
| 92925_at | 18 | 257.38 | 102.47 | 1023.17 | 152.45 | 3.98 | 2.22 | 11.7 | 765.8 |
| 99849_at | 19 | 611.78 | 159.55 | 2401.77 | 484.37 | 3.93 | 2.29 | 7.33 | 1790 |
| 96295_at | 20 | 147.89 | 44.65 | 548.52 | 112.75 | 3.71 | 2.08 | 7.76 | 400.63 |
| 101554_at | 21 | 561.24 | 162.46 | 1994.33 | 289.7 | 3.55 | 2.2 | 6.99 | 1433.09 |
| 101964_at | 22 | 136.06 | 40.77 | 481.38 | 53.63 | 3.54 | 2.25 | 7.09 | 345.33 |
| 93974_at | 23 | 129.04 | 15.59 | 454.75 | 88.15 | 3.52 | 2.31 | 5.03 | 325.71 |
| 93573_at | 24 | 705.68 | 193.8 | 2449.83 | 87.02 | 3.47 | 2.38 | 6.34 | 1744.15 |
| 162206_f_at | 25 | 283.3 | 111.46 | 948.01 | 188.26 | 3.35 | 1.77 | 9.75 | 664.71 |
| 94056_at | 26 | 380.59 | 72.3 | 1264.27 | 225.61 | 3.32 | 2.14 | 5.22 | 883.68 |
| 101019_at | 27 | 50.97 | 13.15 | 169.04 | 59.25 | 3.32 | 1.32 | 6.77 | 118.07 |
| 160894_at | 28 | 234.87 | 60.8 | 773.72 | 130.11 | 3.29 | 2.04 | 6.01 | 538.85 |
| 102363_r_at | 29 | 483.67 | 195.98 | 1579.93 | 198.13 | 3.27 | 1.86 | 9.9 | 1096.27 |
| 104156_r_at | 30 | 461.52 | 147.14 | 1505.8 | 282.6 | 3.26 | 1.86 | 7.14 | 1044.27 |
| 98083_at | 31 | 265.71 | 64.72 | 829.49 | 157.14 | 3.12 | 1.89 | 5.55 | 563.79 |
| 98589_at | 32 | 237.6 | 42.69 | 733.9 | 54.22 | 3.09 | 2.31 | 4.46 | 496.3 |

FIG. 22A (continued)

| | | | | | | | | | |
|---|---|---|---|---|---|---|---|---|---|
| 101410_at | 33 | 77.22 | 17.11 | 236.17 | 12.53 | 3.06 | 2.21 | 4.84 | 158.95 |
| 102362_i_at | 34 | 590.2 | 219.11 | 1763.85 | 203.43 | 2.99 | 1.77 | 7.76 | 1173.65 |
| 102955_at | 35 | 126.89 | 27.41 | 378.95 | 95.38 | 2.99 | 1.62 | 5.21 | 252.05 |
| 96657_at | 36 | 202.33 | 31.51 | 593.78 | 96.07 | 2.93 | 2 | 4.28 | 391.45 |
| 92232_at | 37 | 318.7 | 94.52 | 932.68 | 64.57 | 2.93 | 1.93 | 5.75 | 613.99 |
| 99457_at | 38 | 70.6 | 9.12 | 200.86 | 50.21 | 2.85 | 1.63 | 4.33 | 130.26 |
| 103665_at | 39 | 137.79 | 18.28 | 391.39 | 104.78 | 2.84 | 1.55 | 4.42 | 253.6 |
| 104149_at | 40 | 593.93 | 166.71 | 1682.3 | 182.25 | 2.83 | 1.84 | 5.36 | 1088.37 |
| 92730_at | 41 | 221.49 | 83.2 | 627.03 | 101.25 | 2.83 | 1.59 | 7.57 | 405.54 |
| 93346_at | 42 | 149.96 | 31.14 | 421.18 | 85.61 | 2.81 | 1.7 | 4.66 | 271.23 |
| 95439_at | 43 | 88.13 | 19 | 245.95 | 59.22 | 2.79 | 1.56 | 4.83 | 157.82 |
| 102049_at | 44 | 94.74 | 20.76 | 262.21 | 46.03 | 2.77 | 1.75 | 4.61 | 167.47 |
| 97909_at | 45 | 249.59 | 47.89 | 689.01 | 94.06 | 2.76 | 1.9 | 4.23 | 439.41 |
| 97546_at | 46 | 133.71 | 39.2 | 365.48 | 46.12 | 2.73 | 1.73 | 5.4 | 231.77 |
| 98829_at | 47 | 470.98 | 294.77 | 1272.68 | 140.61 | 2.7 | 1.29 | 100000000 | 801.7 |
| 160834_at | 48 | 141.39 | 33.56 | 380.2 | 57.73 | 2.69 | 1.74 | 4.61 | 238.81 |
| 99076_at | 49 | 76.48 | 15.08 | 204.33 | 17.28 | 2.67 | 1.94 | 4.03 | 127.85 |
| 102791_at | 50 | 103.99 | 28.25 | 276.51 | 56.18 | 2.66 | 1.54 | 5.11 | 172.52 |
| 99548_at | 51 | 304.99 | 77.26 | 808.21 | 116.83 | 2.65 | 1.7 | 4.71 | 503.23 |
| 160273_at | 52 | 666.44 | 103.7 | 1761.34 | 209.34 | 2.64 | 1.93 | 3.73 | 1094.9 |
| 101487_f_at | 53 | 394.46 | 67.78 | 1039.29 | 199.81 | 2.63 | 1.68 | 4.05 | 644.83 |
| 104712_at | 54 | 163.95 | 30.93 | 426.88 | 44.04 | 2.6 | 1.87 | 3.89 | 262.93 |
| 98469_at | 55 | 68.51 | 16.59 | 178.35 | 23.69 | 2.6 | 1.71 | 4.47 | 109.84 |
| 93058_at | 56 | 79.66 | 9.53 | 206.19 | 32.24 | 2.59 | 1.83 | 3.55 | 126.53 |
| 95348_at | 57 | 113.11 | 26.29 | 291.76 | 31.62 | 2.58 | 1.76 | 4.28 | 178.65 |
| 98627_at | 58 | 75.74 | 13.15 | 192.98 | 18.48 | 2.55 | 1.88 | 3.67 | 117.24 |
| 103905_at | 59 | 85.15 | 18.59 | 216.11 | 31.03 | 2.54 | 1.69 | 4.14 | 130.96 |
| 96704_at | 60 | 1004.68 | 292.32 | 2541.06 | 64.9 | 2.53 | 1.71 | 4.86 | 1536.38 |
| 96841_at | 61 | 148.26 | 37.17 | 373.77 | 37.64 | 2.52 | 1.7 | 4.37 | 225.51 |
| 93528_s_at | 62 | 325.47 | 42.91 | 814.6 | 94.75 | 2.5 | 1.87 | 3.38 | 489.14 |
| 103995_at | 63 | 99.71 | 18.04 | 245.79 | 64.04 | 2.47 | 1.34 | 4.07 | 146.08 |
| 93619_at | 64 | 211.26 | 36.62 | 518.24 | 59.87 | 2.45 | 1.77 | 3.57 | 306.98 |
| 99603_g_at | 65 | 189.95 | 54.67 | 464.45 | 56.46 | 2.45 | 1.56 | 4.74 | 274.5 |

FIG. 22A (continued)

| | | | | | | | | | |
|---|---|---|---|---|---|---|---|---|---|
| 97241_at | 66 | 76.34 | 20.54 | 185.14 | 28.15 | 2.43 | 1.52 | 4.51 | 108.8 |
| 93975_at | 67 | 318.9 | 42.47 | 771.29 | 153.37 | 2.42 | 1.56 | 3.52 | 452.39 |
| 92830_s_at | 68 | 951.79 | 313.65 | 2304.83 | 151.2 | 2.42 | 1.54 | 5.31 | 1353.04 |
| 160359_at | 69 | 125.24 | 14.57 | 301.36 | 29.27 | 2.41 | 1.88 | 3.12 | 176.12 |
| 93250_r_at | 70 | 315.77 | 42.86 | 755.99 | 65.92 | 2.39 | 1.86 | 3.18 | 440.23 |
| 101561_at | 71 | 1691.83 | 299.29 | 3988.08 | 129.84 | 2.36 | 1.81 | 3.34 | 2296.25 |
| 160463_at | 72 | 240.25 | 84.32 | 557.92 | 63.82 | 2.32 | 1.4 | 5.56 | 317.68 |
| 94881_at | 73 | 246.87 | 52.18 | 570.73 | 72.1 | 2.31 | 1.58 | 3.68 | 323.86 |
| 162234_f_at | 74 | 104.55 | 14.78 | 240.86 | 33.15 | 2.3 | 1.66 | 3.22 | 136.31 |
| 92777_at | 75 | 354.22 | 125.82 | 815.02 | 57.76 | 2.3 | 1.43 | 5.56 | 460.8 |
| 97413_at | 76 | 186.46 | 42.02 | 426.43 | 57.65 | 2.29 | 1.53 | 3.78 | 239.97 |
| 93290_at | 77 | 220.69 | 54.35 | 506.12 | 81.35 | 2.29 | 1.45 | 4.04 | 285.43 |
| 93193_at | 78 | 106.8 | 15.31 | 243.51 | 20.34 | 2.28 | 1.76 | 3.07 | 136.71 |
| 160369_at | 79 | 171.88 | 14.05 | 391.54 | 74.72 | 2.28 | 1.53 | 3.11 | 219.66 |
| 102788_s_at | 80 | 202.74 | 39.62 | 459.62 | 105.41 | 2.27 | 1.31 | 3.74 | 256.88 |
| 92862_f_at | 81 | 707.54 | 191.58 | 1602.3 | 269.42 | 2.26 | 1.39 | 4.26 | 894.76 |
| 161666_f_at | 82 | 159.92 | 55.82 | 361.44 | 63.64 | 2.26 | 1.28 | 5.47 | 201.53 |
| 100612_at | 83 | 109.28 | 13.06 | 244.41 | 39.49 | 2.24 | 1.57 | 3.09 | 135.13 |
| 100144_at | 84 | 766.09 | 156.62 | 1706.03 | 266.57 | 2.23 | 1.47 | 3.55 | 939.93 |
| 101065_at | 85 | 328.05 | 58.88 | 730.71 | 145.44 | 2.23 | 1.39 | 3.49 | 402.66 |
| 101876_s_at | 86 | 155.5 | 38.86 | 346.44 | 59.57 | 2.23 | 1.38 | 3.98 | 190.94 |
| 92202_g_at | 87 | 330.57 | 53.31 | 733.66 | 40.66 | 2.22 | 1.72 | 3.05 | 403.09 |
| 102371_at | 88 | 1213.29 | 329.9 | 2695.65 | 108.01 | 2.22 | 1.52 | 4.03 | 1482.37 |
| 103846_at | 89 | 1321.78 | 263.93 | 2925.01 | 471.95 | 2.21 | 1.46 | 3.51 | 1603.23 |
| 94375_at | 90 | 146.6 | 20.7 | 321.94 | 52.11 | 2.2 | 1.51 | 3.13 | 175.34 |
| 101995_at | 91 | 98.55 | 18.7 | 215.04 | 21.12 | 2.18 | 1.58 | 3.26 | 116.49 |
| 100156_at | 92 | 99.29 | 9.58 | 216.55 | 45.69 | 2.18 | 1.39 | 3.08 | 117.26 |
| 94452_g_at | 93 | 120.03 | 28.17 | 261.62 | 55.25 | 2.18 | 1.28 | 3.85 | 141.58 |
| 94805_f_at | 94 | 694.87 | 148.44 | 1505.05 | 159.22 | 2.17 | 1.51 | 3.43 | 810.19 |
| 94011_at | 95 | 512.81 | 134.05 | 1106.93 | 232.4 | 2.16 | 1.24 | 4.05 | 594.13 |
| 102381_at | 96 | 135.96 | 23.62 | 291.09 | 59.57 | 2.14 | 1.33 | 3.34 | 155.12 |
| 160617_at | 97 | 202.28 | 37.36 | 430.01 | 58.22 | 2.13 | 1.47 | 3.21 | 227.74 |
| 94246_at | 98 | 466.99 | 78.37 | 985.61 | 170.81 | 2.11 | 1.4 | 3.17 | 518.61 |

FIG. 22A (continued)

| | | | | | | | | | |
|---|---|---|---|---|---|---|---|---|---|
| 101658_f_at | 99 | 285.59 | 88.76 | 603.43 | 91.07 | 2.11 | 1.28 | 4.44 | 317.83 |
| 160651_at | 100 | 451.96 | 149.58 | 951.74 | 153.08 | 2.11 | 1.23 | 4.75 | 499.78 |
| 99835_at | 101 | 126.74 | 16.43 | 265.21 | 28.87 | 2.09 | 1.59 | 2.8 | 138.46 |
| 94384_at | 102 | 744.33 | 121.74 | 1547.75 | 85.27 | 2.08 | 1.61 | 2.88 | 803.42 |
| 99602_at | 103 | 331.17 | 83.9 | 684.41 | 59.53 | 2.07 | 1.41 | 3.59 | 353.24 |
| 93970_at | 104 | 107.79 | 18.66 | 223.33 | 41.74 | 2.07 | 1.33 | 3.18 | 115.53 |
| 94325_at | 105 | 345.93 | 53.16 | 716.7 | 145.74 | 2.07 | 1.3 | 3.12 | 370.77 |
| 102161_f_at | 106 | 714.47 | 196.16 | 1476.07 | 225.27 | 2.07 | 1.29 | 3.9 | 761.6 |
| 99378_f_at | 107 | 649.9 | 166.98 | 1346.61 | 258.64 | 2.07 | 1.23 | 3.81 | 696.72 |
| 100633_at | 108 | 203.48 | 33.65 | 416.96 | 46.25 | 2.05 | 1.5 | 2.93 | 213.48 |
| 92205_at | 109 | 187.34 | 23.61 | 383.05 | 29.19 | 2.04 | 1.62 | 2.65 | 195.7 |
| 98507_at | 110 | 210.52 | 28.44 | 427.41 | 62.39 | 2.03 | 1.45 | 2.82 | 216.88 |
| 94967_at | 111 | 105.62 | 17.9 | 214.5 | 28.22 | 2.03 | 1.44 | 2.97 | 108.88 |
| 160237_at | 112 | 135.67 | 34.39 | 275.02 | 38.2 | 2.03 | 1.31 | 3.6 | 139.35 |
| 98446_s_at | 113 | 141.88 | 41.45 | 287.07 | 41.58 | 2.02 | 1.25 | 4.01 | 145.19 |
| 96926_at | 114 | 144.45 | 27.93 | 290.46 | 15.29 | 2.01 | 1.5 | 2.97 | 146.01 |
| 92845_at | 115 | 170.95 | 17.73 | 342.33 | 49.39 | 2 | 1.47 | 2.66 | 171.38 |
| 100581_at | 116 | 705.51 | 57.45 | 1408.65 | 224.5 | 2 | 1.44 | 2.63 | 703.14 |
| 104480_at | 117 | 184.72 | 13.66 | 369.2 | 61.29 | 2 | 1.43 | 2.63 | 184.47 |
| 96634_at | 118 | 103.53 | 13.51 | 205.16 | 16.27 | 1.98 | 1.56 | 2.6 | 101.63 |
| 94276_at | 119 | 197.58 | 26.99 | 391.41 | 48.86 | 1.98 | 1.46 | 2.71 | 193.84 |
| 95731_at | 120 | 220.03 | 43.23 | 436.14 | 48.05 | 1.98 | 1.4 | 3.02 | 216.12 |
| 98946_at | 121 | 162.82 | 41.36 | 321.71 | 43.79 | 1.98 | 1.28 | 3.51 | 158.89 |
| 92855_at | 122 | 584.64 | 123.66 | 1154.24 | 120.73 | 1.97 | 1.38 | 3.11 | 569.6 |
| 98545_at | 123 | 237.76 | 53.22 | 464.91 | 55.5 | 1.96 | 1.33 | 3.19 | 227.15 |
| 92625_at | 124 | 397.13 | 83.29 | 780.25 | 118.82 | 1.96 | 1.3 | 3.16 | 383.12 |
| 100618_f_at | 125 | 737.43 | 221.94 | 1443.15 | 153.88 | 1.96 | 1.25 | 3.93 | 705.72 |
| 97826_at | 126 | 831.97 | 82.48 | 1620.67 | 288.56 | 1.95 | 1.34 | 2.67 | 788.7 |
| 96592_at | 127 | 190.99 | 39.76 | 373.19 | 46.44 | 1.95 | 1.34 | 3.08 | 182.19 |
| 95446_at | 128 | 345.12 | 51.28 | 672.7 | 111.59 | 1.95 | 1.33 | 2.82 | 327.59 |
| 93728_at | 129 | 165.51 | 34.39 | 321.77 | 28.72 | 1.94 | 1.39 | 3.01 | 156.26 |
| 103035_at | 130 | 212.61 | 41.86 | 413.17 | 40.37 | 1.94 | 1.39 | 2.95 | 200.56 |
| 102821_s_at | 131 | 332.53 | 54.89 | 646.41 | 115.67 | 1.94 | 1.28 | 2.92 | 313.89 |

FIG. 22A (continued)

| | | | | | | | | | |
|---|---|---|---|---|---|---|---|---|---|
| 94485_at | 132 | 174.54 | 18.63 | 337.38 | 17.63 | 1.93 | 1.61 | 2.38 | 162.84 |
| 96041_at | 133 | 581.54 | 85.07 | 1124.91 | 148.43 | 1.93 | 1.4 | 2.71 | 543.37 |
| 94526_at | 134 | 119.03 | 10.37 | 229.15 | 35.02 | 1.93 | 1.4 | 2.53 | 110.12 |
| 102121_f_at | 135 | 203.34 | 36.01 | 393.38 | 52.67 | 1.93 | 1.35 | 2.87 | 190.03 |
| 101502_at | 136 | 227.82 | 30.05 | 439.1 | 70.68 | 1.93 | 1.34 | 2.71 | 211.29 |
| 160253_at | 137 | 559.17 | 112.52 | 1080.53 | 208.1 | 1.93 | 1.2 | 3.14 | 521.36 |
| 93833_s_at | 138 | 118.76 | 25.65 | 228.26 | 30.94 | 1.92 | 1.29 | 3.11 | 109.51 |
| 97890_at | 139 | 886.59 | 114.32 | 1689.19 | 208.5 | 1.91 | 1.42 | 2.57 | 802.6 |
| 92578_at | 140 | 167.52 | 26.78 | 319.95 | 49.6 | 1.91 | 1.31 | 2.79 | 152.43 |
| 96357_at | 141 | 208.53 | 27.17 | 398.66 | 67.01 | 1.91 | 1.31 | 2.69 | 190.13 |
| 95514_at | 142 | 164.5 | 28.56 | 311.09 | 31.76 | 1.89 | 1.38 | 2.73 | 146.59 |
| 93738_at | 143 | 135.63 | 16.76 | 256.05 | 38.57 | 1.89 | 1.35 | 2.59 | 120.42 |
| 92848_at | 144 | 329.18 | 59.95 | 621.01 | 79.59 | 1.89 | 1.32 | 2.82 | 291.83 |
| 97819_at | 145 | 417.76 | 74.71 | 789.92 | 105.09 | 1.89 | 1.32 | 2.82 | 372.16 |
| 103736_at | 146 | 124.32 | 15.56 | 234.82 | 40.52 | 1.89 | 1.29 | 2.65 | 110.49 |
| 103015_at | 147 | 302.46 | 28.21 | 568.15 | 94.81 | 1.88 | 1.32 | 2.52 | 265.69 |
| 101954_at | 148 | 499.7 | 65.21 | 941.2 | 170.98 | 1.88 | 1.26 | 2.69 | 441.5 |
| 97914_at | 149 | 239.83 | 28.01 | 448.44 | 80.3 | 1.87 | 1.27 | 2.62 | 208.61 |
| 103990_at | 150 | 1427.05 | 431.41 | 2668.76 | 224.52 | 1.87 | 1.21 | 3.76 | 1241.72 |
| 94448_at | 151 | 235 | 27.61 | 436.14 | 53.8 | 1.86 | 1.39 | 2.46 | 201.14 |
| 101589_at | 152 | 314.4 | 38.1 | 582.39 | 71.53 | 1.85 | 1.39 | 2.47 | 267.99 |
| 93844_at | 153 | 321.51 | 64.32 | 596.1 | 69.34 | 1.85 | 1.3 | 2.86 | 274.59 |
| 94837_at | 154 | 388.4 | 69.03 | 718.72 | 96.69 | 1.85 | 1.29 | 2.75 | 330.32 |
| 160415_at | 155 | 424.11 | 58.34 | 778.3 | 86.16 | 1.84 | 1.38 | 2.49 | 354.18 |
| 93581_at | 156 | 203.54 | 51.74 | 373.94 | 25.84 | 1.84 | 1.27 | 3.19 | 170.4 |
| 96866_at | 157 | 176.53 | 22.06 | 323.63 | 37.09 | 1.83 | 1.39 | 2.44 | 147.1 |
| 97456_at | 158 | 213.02 | 29.46 | 390.07 | 48.64 | 1.83 | 1.35 | 2.52 | 177.05 |
| 95518_at | 159 | 339.31 | 32.71 | 620.19 | 93.36 | 1.83 | 1.33 | 2.42 | 280.88 |
| 99109_at | 160 | 1264.78 | 364.09 | 2315.1 | 123.26 | 1.83 | 1.23 | 3.49 | 1050.32 |
| 92861_i_at | 161 | 752.97 | 134.96 | 1369.66 | 155.42 | 1.82 | 1.31 | 2.68 | 616.69 |
| 98608_at | 162 | 220.94 | 24.33 | 399.97 | 47.71 | 1.81 | 1.38 | 2.37 | 179.03 |
| 93119_at | 163 | 411.82 | 64.25 | 746.17 | 89.81 | 1.81 | 1.32 | 2.56 | 334.36 |
| 104155_f_at | 164 | 1737.95 | 437.64 | 3138.54 | 128.49 | 1.81 | 1.27 | 3.09 | 1400.59 |

FIG. 22A (continued)

| | | | | | | | | | |
|---|---|---|---|---|---|---|---|---|---|
| 160321_at | 165 | 218.41 | 25.78 | 395.96 | 64.49 | 1.81 | 1.27 | 2.5 | 177.55 |
| 100617_at | 166 | 1161.14 | 143.75 | 2096.53 | 335.8 | 1.81 | 1.26 | 2.5 | 935.39 |
| 103980_at | 167 | 140.65 | 23.54 | 253.19 | 23.59 | 1.8 | 1.34 | 2.56 | 112.54 |
| 94789_r_at | 168 | 601.41 | 109.67 | 1080.26 | 78.55 | 1.8 | 1.34 | 2.61 | 478.85 |
| 99643_f_at | 169 | 319 | 24.89 | 569.9 | 65.84 | 1.79 | 1.4 | 2.23 | 250.9 |
| 99133_at | 170 | 590.99 | 89.73 | 1055.14 | 72.4 | 1.79 | 1.39 | 2.42 | 464.15 |
| 93309_at | 171 | 233.93 | 36.64 | 418.52 | 42.99 | 1.79 | 1.33 | 2.5 | 184.59 |
| 92523_at | 172 | 250.73 | 25.34 | 449.69 | 71.54 | 1.79 | 1.28 | 2.41 | 198.96 |
| 100332_s_at | 173 | 208.03 | 48.17 | 371.64 | 18.02 | 1.79 | 1.28 | 2.9 | 163.61 |
| 160832_at | 174 | 308.34 | 41.38 | 551.8 | 80.83 | 1.79 | 1.27 | 2.49 | 243.46 |
| 103715_at | 175 | 173.45 | 25.07 | 308.76 | 42.06 | 1.78 | 1.28 | 2.49 | 135.31 |
| 93865_s_at | 176 | 169.23 | 21.49 | 299.7 | 39.44 | 1.77 | 1.3 | 2.4 | 130.47 |
| 100557_g_at | 177 | 383.54 | 88.02 | 679.22 | 63.17 | 1.77 | 1.23 | 2.9 | 295.69 |
| 93753_at | 178 | 360.92 | 31.33 | 633.75 | 85.9 | 1.76 | 1.32 | 2.26 | 272.82 |
| 92562_at | 179 | 207.67 | 23.98 | 366.25 | 58.35 | 1.76 | 1.24 | 2.41 | 158.58 |
| 92829_at | 180 | 489.72 | 42 | 854.63 | 124.19 | 1.75 | 1.29 | 2.27 | 364.91 |
| 104410_at | 181 | 246.52 | 31.44 | 430.65 | 61.19 | 1.75 | 1.26 | 2.39 | 184.13 |
| 99106_at | 182 | 144.13 | 12.82 | 252.81 | 42.37 | 1.75 | 1.24 | 2.35 | 108.68 |
| 98059_s_at | 183 | 1207.59 | 325.93 | 2116.17 | 106.63 | 1.75 | 1.2 | 3.16 | 908.58 |
| 160383_at | 184 | 362.28 | 56 | 631.49 | 47.87 | 1.74 | 1.34 | 2.39 | 269.21 |
| 92986_g_at | 185 | 166.57 | 14.19 | 290.15 | 37.21 | 1.74 | 1.33 | 2.22 | 123.57 |
| 93104_at | 186 | 542.76 | 93.36 | 945.49 | 92.87 | 1.74 | 1.28 | 2.5 | 402.74 |
| 95697_at | 187 | 635.08 | 135.07 | 1103.54 | 97.58 | 1.74 | 1.24 | 2.72 | 468.47 |
| 96258_at | 188 | 211.85 | 36.09 | 365.74 | 32.96 | 1.73 | 1.28 | 2.46 | 153.89 |
| 94806_at | 189 | 218.46 | 32.82 | 378.12 | 46.11 | 1.73 | 1.26 | 2.42 | 159.66 |
| 96899_at | 190 | 178.06 | 30.62 | 308.09 | 36.14 | 1.73 | 1.24 | 2.52 | 130.03 |
| 97751_f_at | 191 | 658.6 | 107.19 | 1141.8 | 151.91 | 1.73 | 1.23 | 2.5 | 483.2 |
| 93277_at | 192 | 505.99 | 44.71 | 874.53 | 145.9 | 1.73 | 1.22 | 2.31 | 368.54 |
| 101214_f_at | 193 | 685.55 | 109.92 | 1182.57 | 109.46 | 1.72 | 1.29 | 2.41 | 497.02 |
| 100595_at | 194 | 237.36 | 25.26 | 407.84 | 55.12 | 1.72 | 1.28 | 2.27 | 170.47 |
| 98472_at | 195 | 651.55 | 118.79 | 1119.49 | 134.47 | 1.72 | 1.22 | 2.56 | 467.94 |
| 101989_at | 196 | 570.91 | 114.95 | 974.97 | 77.6 | 1.71 | 1.24 | 2.6 | 404.06 |
| 93029_at | 197 | 187.78 | 36.47 | 321.07 | 37.75 | 1.71 | 1.2 | 2.61 | 133.29 |

FIG. 22A (continued)

| | | | | | | | | | |
|---|---|---|---|---|---|---|---|---|---|
| 96353_at | 198 | 171.48 | 29.57 | 291.99 | 26.09 | 1.7 | 1.27 | 2.44 | 120.52 |
| 99642_i_at | 199 | 290.17 | 36.11 | 492.69 | 65.91 | 1.7 | 1.25 | 2.3 | 202.52 |
| 98505_i_at | 200 | 276.98 | 10.47 | 471.34 | 7(FIG. | 7 | 1.22 | 2.19 | 194.37 |
| 93818_g_at | 201 | 365.43 | 53.8 | 615.41 | 50.44 | 1.68 | 1.3 | 2.28 | 249.98 |
| 94489_at | 202 | 678.41 | 80.48 | 1140.47 | 120.27 | 1.68 | 1.3 | 2.2 | 462.07 |
| 98447_at | 203 | 474.58 | 68.17 | 797.13 | 65.87 | 1.68 | 1.3 | 2.26 | 322.55 |
| 101906_at | 204 | 195.27 | 13.72 | 328.07 | 43.2 | 1.68 | 1.29 | 2.12 | 132.79 |
| 100599_at | 205 | 590.8 | 50.09 | 988.25 | 112.1 | 1.67 | 1.31 | 2.1 | 397.45 |
| 94062_at | 206 | 293.1 | 32.58 | 485.75 | 61.45 | 1.66 | 1.24 | 2.19 | 192.66 |
| 97386_at | 207 | 281.32 | 33.9 | 464.62 | 46.81 | 1.65 | 1.28 | 2.16 | 183.3 |
| 100578_at | 208 | 359.42 | 48.01 | 592.91 | 61.72 | 1.65 | 1.25 | 2.21 | 233.49 |
| 98438_f_at | 209 | 1400 | 229.84 | 2305.65 | 172.46 | 1.65 | 1.25 | 2.3 | 905.65 |
| 103612_at | 210 | 586.37 | 64.7 | 961.03 | 78.44 | 1.64 | 1.31 | 2.08 | 374.66 |
| 160246_at | 211 | 218.98 | 23.47 | 358.79 | 45.78 | 1.64 | 1.23 | 2.15 | 139.81 |
| 92958_at | 212 | 197.31 | 18.13 | 321.1 | 12.53 | 1.63 | 1.39 | 1.94 | 123.79 |
| 93023_f_at | 213 | 1289.41 | 185.86 | 2104.73 | 90.02 | 1.63 | 1.3 | 2.16 | 815.32 |
| 160568_at | 214 | 312.65 | 31.22 | 508.7 | 70.08 | 1.63 | 1.21 | 2.14 | 196.06 |
| 92816_r_at | 215 | 461.32 | 64.04 | 752.55 | 93.39 | 1.63 | 1.2 | 2.24 | 291.23 |
| 98937_at | 216 | 195.45 | 27 | 317.11 | 20.14 | 1.62 | 1.28 | 2.14 | 121.67 |
| 160451_at | 217 | 210.95 | 25.47 | 341.15 | 38.6 | 1.62 | 1.23 | 2.14 | 130.2 |
| 93714_f_at | 218 | 1503.18 | 228.1 | 2418.85 | 193.58 | 1.61 | 1.24 | 2.2 | 915.67 |
| 160090_f_at | 219 | 680.13 | 60.49 | 1097.27 | 134.99 | 1.61 | 1.24 | 2.06 | 417.13 |
| 96755_at | 220 | 262.5 | 36.34 | 420.8 | 38.88 | 1.6 | 1.23 | 2.15 | 158.3 |
| 93354_at | 221 | 674.48 | 86.44 | 1059.32 | 74.23 | 1.57 | 1.25 | 2.04 | 384.83 |
| 93071_at | 222 | 434.6 | 69 | 682.99 | 36.08 | 1.57 | 1.22 | 2.15 | 248.4 |
| 93264_at | 223 | 431.59 | 34.88 | 673.83 | 41.04 | 1.56 | 1.33 | 1.85 | 242.23 |
| 100128_at | 224 | 247.99 | 29.26 | 385.76 | 26.99 | 1.56 | 1.25 | 1.98 | 137.77 |
| 93057_at | 225 | 612.72 | 56.09 | 945.97 | 107.03 | 1.54 | 1.2 | 1.96 | 333.24 |
| 103416_at | 226 | 297.37 | 17.14 | 454.06 | 55.15 | 1.53 | 1.2 | 1.88 | 156.69 |
| 95069_at | 227 | 204.72 | 17.73 | 310.68 | 31.68 | 1.52 | 1.21 | 1.89 | 105.96 |
| 93274_at | 228 | 455.45 | 34.85 | 687.58 | 68.3 | 1.51 | 1.22 | 1.85 | 232.13 |
| 101112_g_at | 229 | 316.94 | 39.38 | 479.63 | 30.55 | 1.51 | 1.22 | 1.94 | 162.69 |
| 96416_f_at | 230 | 1047.69 | 154.71 | 1580.26 | 36.04 | 1.51 | 1.21 | 2 | 532.57 |

FIG. 22A (continued)

| | | | | | | | | | |
|---|---|---|---|---|---|---|---|---|---|
| 96115_at | 231 | 882.18 | 67.27 | 1307.78 | 68.28 | 1.48 | 1.28 | 1.73 | 425.6 |
| 162358_i_at | 232 | 260.46 | 28.47 | 382.39 | 11.42 | 1.47 | 1.23 | 1.8 | 121.92 |

FIG. 22B

| SEQ ID No | A1- High | A2- ctrl | A3- ctrl | A4- ctrl | High-dep A1 | High_dep A2 | High-dep A4 |
|---|---|---|---|---|---|---|---|
| 1 | -5.63 | -17.67 | -5.17 | 6.77 | 83.12 | 169.99 | 100.58 |
| 2 | -2.54 | -14.06 | 0.94 | 10.82 | 87.42 | 54.4 | 195.99 |
| 3 | 23.31 | 8.36 | 7.01 | 53.96 | 38.68 | 206.2 | 417.26 |
| 4 | 19.77 | 2.26 | 24.49 | 58.97 | 205.62 | 127.45 | 188.14 |
| 5 | 139.28 | 52.41 | 114.17 | 154.8 | 635.16 | 417.84 | 1060.26 |
| 6 | 39.56 | 63.62 | 152.7 | 275.17 | 1060.5 | 629.24 | 658.28 |
| 7 | 110.88 | 59.72 | 89.21 | 214.03 | 726.78 | 468.04 | 764.58 |
| 8 | 32.41 | 21.49 | 24.37 | 54.71 | 255 | 107.37 | 188.45 |
| 9 | 331.43 | -167.33 | 163.29 | 469.3 | 481.09 | 1002.95 | 1554.39 |
| 10 | 116.76 | 108.93 | 156.49 | 342 | 1063.9 | 692.84 | 928.59 |
| 11 | 283.17 | 121.9 | 170.16 | 205.78 | 1011.81 | 567.07 | 1110.23 |
| 12 | 74.97 | 22.58 | 143.49 | 331.85 | 942.05 | 448.77 | 522.72 |
| 13 | 42.96 | 17.71 | 59.52 | 96.43 | 288.14 | 207.6 | 245.94 |
| 14 | 444.42 | 87.63 | 119.71 | 180.16 | 943.76 | 445.53 | 1329.18 |
| 15 | 78.04 | 27.45 | 130.69 | 228.96 | 704.54 | 360.25 | 453.08 |
| 16 | 221.31 | 82.68 | 273.71 | 375.27 | 720.98 | 786.45 | 1419.72 |
| 17 | 68.92 | 41.02 | 121.74 | 188.95 | 730.1 | 262.37 | 269.51 |
| 18 | 129.38 | 43.78 | 378.11 | 479.44 | 1325.48 | 831.71 | 919.9 |
| 19 | 418.78 | 404.48 | 559.46 | 1077.69 | 2507.7 | 1533.6 | 3167.77 |
| 20 | 256.89 | 60.48 | 111.55 | 157.48 | 478.62 | 401.72 | 765.65 |
| 21 | 442.7 | 254.33 | 526.58 | 1016.59 | 2409.26 | 1449.07 | 2138.65 |
| 22 | 114.71 | 44.84 | 149.01 | 227.39 | 581.81 | 403.71 | 464.3 |
| 23 | 140.81 | 93.38 | 119.51 | 155.72 | 371.38 | 380.48 | 623.48 |
| 24 | 720.51 | 156.21 | 941.53 | 1000.88 | 2478.16 | 2355.04 | 2547.28 |
| 25 | 192.27 | 92.36 | 240.88 | 605.76 | 1169.42 | 577.85 | 1099.93 |
| 26 | 580.94 | 313.16 | 283.46 | 347.07 | 1341.64 | 851.31 | 1604.33 |
| 27 | 84.02 | 29.36 | 36.55 | 53.49 | 134.3 | 91.56 | 282.49 |
| 28 | 143.01 | 123.84 | 298.75 | 373.89 | 1005.66 | 557.55 | 761.95 |
| 29 | 320.38 | 113.16 | 481.11 | 1025.22 | 1437.46 | 1952.41 | 1354.26 |
| 30 | 296.03 | 137.39 | 718.51 | 695.82 | 2067.83 | 1311.65 | 1152.53 |
| 31 | 214.27 | 126.62 | 314.52 | 408.07 | 1145.61 | 689.57 | 663.78 |
| 32 | 206.21 | 153.91 | 280.51 | 297.21 | 837.74 | 706.2 | 660.62 |
| 33 | 81.04 | 51.06 | 75.14 | 98.1 | 233.5 | 241.15 | 234.39 |
| 34 | 395.98 | 128.67 | 700.46 | 1145.39 | 1809.54 | 2080.32 | 1412.16 |
| 35 | 65.85 | 99.89 | 157.89 | 185.62 | 569.39 | 266.39 | 301.91 |
| 36 | 263.18 | 139.8 | 182.15 | 218.92 | 598.64 | 431.27 | 753.7 |
| 37 | 177.42 | 150.27 | 399.45 | 540.28 | 983.19 | 832.33 | 997.4 |
| 38 | 74.75 | 74.97 | 48.84 | 82.72 | 182.41 | 128.43 | 293.82 |
| 39 | 150.84 | 95.39 | 167.23 | 138.08 | 392.12 | 214.37 | 570.07 |
| 40 | 540.31 | 300.82 | 465.12 | 1073.48 | 1938.91 | 1348.09 | 1771.76 |
| 41 | 132.57 | 108.3 | 176.91 | 468.34 | 826.57 | 495.76 | 559.84 |
| 42 | 202.76 | 65.77 | 160.86 | 161.92 | 501.64 | 253.72 | 509.75 |
| 43 | 70.65 | 48.97 | 117.21 | 117.12 | 212.32 | 168.69 | 357.86 |
| 44 | 59.89 | 73.74 | 89.86 | 151.61 | 354.26 | 227.02 | 207.74 |
| 45 | 262.7 | 140.08 | 223.83 | 362.92 | 768 | 506.51 | 792.68 |
| 46 | 203.13 | 24.19 | 141.14 | 166.52 | 396.35 | 278.68 | 423.13 |
| 47 | 1249.11 | -163.61 | 288.35 | 509.86 | 1213.24 | 1064.64 | 1540.1 |
| 48 | 112.44 | 70.65 | 156.69 | 225.29 | 470.4 | 278.49 | 398.79 |
| 49 | 78.27 | 43.65 | 67.66 | 114.57 | 215.12 | 174.03 | 225.14 |

FIG. 22B(continued)

| | | | | | | | |
|---|---|---|---|---|---|---|---|
| 50 | 132.5 | 26.28 | 122.03 | 135.16 | 277.18 | 181.31 | 371.58 |
| 51 | 262.43 | 112.26 | 371.84 | 470.08 | 711.07 | 681.81 | 1033.8 |
| 52 | 536.76 | 461.17 | 769.77 | 889.81 | 1975.05 | 1352.89 | 1960.32 |
| 53 | 438.88 | 225 | 382.84 | 525.6 | 835.86 | 857.62 | 1428.27 |
| 54 | 141.38 | 90.71 | 202.04 | 223.88 | 495.75 | 346.79 | 438.26 |
| 55 | 74.76 | 50.42 | 52.47 | 86.4 | 192.43 | 139.97 | 206.83 |
| 56 | 79.05 | 66.18 | 67.55 | 103.4 | 264.65 | 154.74 | 201.21 |
| 57 | 80.07 | 90.7 | 102.4 | 176.88 | 281.97 | 349.67 | 243.8 |
| 58 | 68.4 | 106.51 | 76.63 | 59.14 | 167.01 | 225.34 | 186.51 |
| 59 | 83.86 | 39.01 | 93.03 | 123.08 | 222.12 | 160.9 | 264.71 |
| 60 | 1296.17 | 167.7 | 1103.2 | 1462.67 | 2516.18 | 2486.75 | 2606.4 |
| 61 | 149.99 | 61.1 | 151.09 | 218.82 | 346.11 | 438.58 | 339.9 |
| 62 | 215.58 | 309.49 | 355.1 | 416.34 | 941.89 | 641.57 | 866.1 |
| 63 | 137.69 | 69.83 | 69.95 | 117.25 | 233.19 | 145.75 | 360.25 |
| 64 | 176.23 | 129.22 | 287.4 | 244.63 | 611.3 | 538.23 | 410.26 |
| 65 | 135.04 | 70.48 | 243.79 | 312.9 | 563.01 | 370.79 | 457.06 |
| 66 | 65.19 | 25.39 | 94.18 | 120.53 | 218.57 | 131.58 | 207.17 |
| 67 | 356.76 | 227.22 | 367.73 | 327.65 | 715.66 | 626.94 | 1034.2 |
| 68 | 643.68 | 299.61 | 1106.73 | 1751.38 | 2438.92 | 2465.26 | 2012.95 |
| 69 | 119.23 | 94.41 | 135.34 | 146.07 | 349.59 | 254.82 | 301.39 |
| 70 | 360.47 | 304.94 | 200.13 | 397.18 | 812.63 | 626.76 | 826.71 |
| 71 | 1701.31 | 921.16 | 1800.76 | 2328.77 | 4084.28 | 3803.84 | 4121.35 |
| 72 | 101 | 107.87 | 287.29 | 454.65 | 684.09 | 490.91 | 508.17 |
| 73 | 346.1 | 105.04 | 264.96 | 271.03 | 707.56 | 464.44 | 544.27 |
| 74 | 85.55 | 89.81 | 95.56 | 146.28 | 262.05 | 181.42 | 283.51 |
| 75 | 182.89 | 96.32 | 560.09 | 578.66 | 860.12 | 883.46 | 701.98 |
| 76 | 115.65 | 123.07 | 243.02 | 261.83 | 523.34 | 333.37 | 432.41 |
| 77 | 198.8 | 93.34 | 229.65 | 356.53 | 561.03 | 352.4 | 609.09 |
| 78 | 93.9 | 77.62 | 124.29 | 133.58 | 283.15 | 228.24 | 224.33 |
| 79 | 149.09 | 174.43 | 183.43 | 179 | 525.24 | 268.7 | 384.89 |
| 80 | 163.12 | 123.1 | 266.84 | 253.62 | 470.88 | 274.31 | 633.27 |
| 81 | 511.47 | 273.07 | 950.77 | 1091.08 | 1547.45 | 1179.77 | 2083.79 |
| 82 | 131.81 | 52.72 | 137.49 | 317.72 | 382.99 | 247.01 | 456.6 |
| 83 | 119.97 | 78 | 102.46 | 124.31 | 250.65 | 174.67 | 308.27 |
| 84 | 946.19 | 351.71 | 705.88 | 1059.06 | 1534.13 | 1361.23 | 2222.82 |
| 85 | 298.4 | 248.35 | 262.8 | 500.23 | 730.02 | 490.82 | 977.92 |
| 86 | 126.17 | 60.47 | 225.06 | 210.49 | 298.85 | 278.49 | 462.49 |
| 87 | 204.53 | 399.01 | 430.57 | 291 | 748.26 | 669.68 | 788.41 |
| 88 | 897.74 | 464 | 1566.84 | 1913.81 | 2787.91 | 2754.92 | 2592.71 |
| 89 | 1876.3 | 682.31 | 1158.85 | 1527.08 | 3819.6 | 2224.18 | 2746.01 |
| 90 | 109.7 | 130.79 | 142.04 | 203.42 | 416.8 | 240.51 | 313.38 |
| 91 | 70.83 | 65.03 | 116.01 | 137.3 | 243.19 | 178.45 | 227.11 |
| 92 | 104.22 | 80.52 | 100.91 | 111.37 | 166.84 | 178.35 | 305.19 |
| 93 | 160.76 | 41.21 | 121.95 | 155.07 | 261.42 | 168.61 | 355.69 |
| 94 | 1002.21 | 376.59 | 623.8 | 798.55 | 1496.07 | 1240.29 | 1771.65 |
| 95 | 565.29 | 155.67 | 524.23 | 804.82 | 1036.06 | 747.86 | 1536.56 |
| 96 | 83.36 | 127.14 | 137.58 | 196.8 | 262.3 | 209.25 | 402.22 |
| 97 | 170.87 | 118.9 | 283.84 | 230 | 370.12 | 379.44 | 542.27 |
| 98 | 510.11 | 255.73 | 467.06 | 628.25 | 1295.4 | 706.07 | 958.06 |
| 99 | 460.1 | 53.41 | 304.69 | 327.47 | 443.97 | 628.87 | 737.78 |

FIG. 22B(continued)

| | | | | | | | |
|---|---|---|---|---|---|---|---|
| 100 | 863.6 | 207.42 | 306.15 | 435.08 | 951.34 | 699.25 | 1208.97 |
| 101 | 115.92 | 128.12 | 128.12 | 137.12 | 321.41 | 245.54 | 230.42 |
| 102 | 609.66 | 500.34 | 785.38 | 1034.85 | 1585.94 | 1451 | 1624.77 |
| 103 | 264.25 | 164.9 | 333.89 | 561.29 | 779.16 | 607.88 | 694.78 |
| 104 | 123.78 | 64.66 | 93.68 | 149.27 | 251.83 | 142.53 | 276.23 |
| 105 | 448.92 | 217.48 | 316.74 | 404.21 | 792.91 | 438.86 | 920.02 |
| 106 | 872.5 | 136.08 | 872.47 | 976.55 | 1308.91 | 1211.31 | 1907.24 |
| 107 | 782.84 | 160.15 | 782.21 | 875.83 | 1103.1 | 1100.16 | 1844.59 |
| 108 | 183.5 | 120.8 | 230.11 | 274.68 | 502.11 | 346.62 | 406.3 |
| 109 | 145.22 | 154.75 | 215.32 | 223.86 | 402.89 | 331.79 | 416.36 |
| 110 | 242.68 | 131.21 | 227.3 | 239.68 | 545.7 | 407.72 | 334.91 |
| 111 | 152.64 | 73.67 | 94.27 | 97.84 | 216.43 | 168.83 | 260.02 |
| 112 | 137.9 | 40.27 | 191.51 | 171.58 | 349.08 | 223.32 | 253.36 |
| 113 | 231.99 | 37.75 | 125.33 | 172.57 | 318.72 | 207 | 336.68 |
| 114 | 129.7 | 79.03 | 166.88 | 193.5 | 277.7 | 286.34 | 305.25 |
| 115 | 151.91 | 143.6 | 165.79 | 218.92 | 406.76 | 248.28 | 374.11 |
| 116 | 688 | 569.04 | 732.38 | 823.68 | 1470.55 | 998.09 | 1757.45 |
| 117 | 177.77 | 181.58 | 163.05 | 216.72 | 349.95 | 275.4 | 480.9 |
| 118 | 67.73 | 111.6 | 121.41 | 116 | 229.84 | 178.33 | 208.33 |
| 119 | 186.4 | 143.44 | 190.67 | 266.45 | 474.16 | 308.84 | 393.31 |
| 120 | 213.57 | 102.11 | 277.63 | 286.81 | 395.79 | 387.24 | 526.05 |
| 121 | 153.49 | 76.2 | 145.61 | 274.72 | 403.36 | 255.75 | 309.24 |
| 122 | 511.99 | 296.95 | 641.95 | 887.33 | 1370.99 | 960.71 | 1133.77 |
| 123 | 255.48 | 96.57 | 246.27 | 353.38 | 455.98 | 376.23 | 562.17 |
| 124 | 519.52 | 161.83 | 403.43 | 502.64 | 902.52 | 546.05 | 893.71 |
| 125 | 1059.81 | 121.89 | 723.62 | 1035.98 | 1346.69 | 1263.28 | 1730.1 |
| 126 | 794.58 | 646.29 | 894.06 | 979.75 | 1585.26 | 1153.91 | 2124.6 |
| 127 | 182.15 | 100.35 | 187.18 | 293.39 | 300.2 | 373.46 | 449.27 |
| 128 | 310.84 | 246.38 | 333.32 | 488.12 | 876.51 | 493.78 | 651.77 |
| 129 | 152.43 | 89.76 | 166.79 | 251.84 | 357.65 | 267 | 340.43 |
| 130 | 207.57 | 100.38 | 282.81 | 259.08 | 456.54 | 335.38 | 446.38 |
| 131 | 455.54 | 202.21 | 301.47 | 370.84 | 756.41 | 417.26 | 766.51 |
| 132 | 145.05 | 144.44 | 187.68 | 216.41 | 338.95 | 310.57 | 362.17 |
| 133 | 554.11 | 402.15 | 567.63 | 809.76 | 1292.17 | 844.8 | 1249.13 |
| 134 | 130.24 | 103.48 | 113.49 | 126.1 | 297.16 | 184.92 | 204.95 |
| 135 | 186.7 | 119.75 | 289.61 | 216.49 | 446.72 | 288.14 | 445.05 |
| 136 | 189.47 | 168.95 | 262.02 | 293.93 | 548.58 | 309.28 | 462.05 |
| 137 | 638.29 | 239.8 | 626.95 | 717.65 | 999.55 | 774.33 | 1465.56 |
| 138 | 124.73 | 52.62 | 119.62 | 177.26 | 234.37 | 175.19 | 275.85 |
| 139 | 829.09 | 706.34 | 788.34 | 1218.18 | 1732 | 1318.01 | 2016.68 |
| 140 | 196.56 | 96.26 | 168.71 | 211.3 | 409.32 | 239.57 | 313.52 |
| 141 | 194.4 | 142.96 | 233.73 | 262.23 | 436.12 | 272.78 | 488.44 |
| 142 | 144.74 | 96.33 | 183.54 | 226.73 | 338.13 | 260.1 | 343.18 |
| 143 | 132.94 | 103.91 | 170.64 | 131.81 | 328.78 | 200.99 | 237.08 |
| 144 | 385.59 | 190.9 | 277.34 | 461.73 | 691.3 | 466.96 | 705.79 |
| 145 | 479.58 | 201.87 | 479.86 | 510.07 | 855.6 | 589.24 | 927.23 |
| 146 | 82.02 | 125.19 | 133.96 | 156.08 | 293.82 | 157.63 | 253.33 |
| 147 | 242.78 | 269.89 | 348.84 | 344.92 | 707.32 | 393.24 | 610.03 |
| 148 | 565.1 | 394.93 | 387.65 | 642.06 | 946.42 | 655.01 | 1228.65 |
| 149 | 275.94 | 169.57 | 227.25 | 286.38 | 493.91 | 297.39 | 557.13 |

FIG. 22B(continued)

| | | | | | | | |
|---|---|---|---|---|---|---|---|
| 150 | 781.55 | 580.02 | 2127.05 | 2208.06 | 3043.92 | 2702.29 | 2282.46 |
| 151 | 261.4 | 158.9 | 250.2 | 264.02 | 505.64 | 334.83 | 472.08 |
| 152 | 372.91 | 232.5 | 286.71 | 377.42 | 687.16 | 450.09 | 612.82 |
| 153 | 410.42 | 131.97 | 369.05 | 367.78 | 720.73 | 484.99 | 582.85 |
| 154 | 461.07 | 191.03 | 424.7 | 468.61 | 797.92 | 532.2 | 829.45 |
| 155 | 546.5 | 268.31 | 446.34 | 433.67 | 794.32 | 630 | 915.07 |
| 156 | 282.84 | 57.22 | 211.67 | 257.88 | 396.65 | 328.24 | 398.79 |
| 157 | 201.46 | 120.48 | 177.34 | 191.62 | 357.2 | 254.61 | 361.88 |
| 158 | 232.31 | 128.28 | 247.88 | 241.71 | 440.6 | 294.47 | 435.39 |
| 159 | 334.05 | 275.32 | 324.52 | 425.52 | 772.86 | 454.43 | 637.76 |
| 160 | 1051.89 | 397.67 | 1479.38 | 2126.13 | 2268.38 | 2529.2 | 2169.17 |
| 161 | 798.21 | 399.8 | 899.89 | 912.54 | 1287.69 | 1165.36 | 1655.86 |
| 162 | 244.32 | 157.06 | 225.73 | 253.07 | 427.09 | 313.85 | 463.56 |
| 163 | 438.76 | 226.89 | 457.14 | 513.87 | 898.95 | 594.47 | 745.37 |
| 164 | 1352.95 | 718.09 | 2236.02 | 2654.99 | 3278.78 | 3093.26 | 3118.24 |
| 165 | 214.2 | 173.96 | 194.94 | 287.47 | 464.04 | 272.6 | 455.63 |
| 166 | 1255.16 | 786.4 | 1150.85 | 1467.91 | 2159.71 | 1497.04 | 2635.45 |
| 167 | 126.6 | 89.26 | 180.85 | 154.61 | 268.42 | 225.32 | 276.81 |
| 168 | 771.24 | 305.25 | 587.97 | 728 | 1144.4 | 942.94 | 1161.59 |
| 169 | 263.57 | 319.12 | 316.73 | 380.47 | 669.63 | 447.63 | 593.13 |
| 170 | 590.2 | 359.6 | 608.4 | 795.03 | 1151.48 | 940.65 | 1093.9 |
| 171 | 240.81 | 133.89 | 251.93 | 307.57 | 489.86 | 345.71 | 424.47 |
| 172 | 261.55 | 218.92 | 220.14 | 275.29 | 400.11 | 375.64 | 584.55 |
| 173 | 293.62 | 82.87 | 186.43 | 269.33 | 379.84 | 345.41 | 394.6 |
| 174 | 317.27 | 208 | 305.44 | 404.98 | 669.86 | 404.54 | 588.74 |
| 175 | 210.83 | 108.43 | 178.61 | 189.73 | 297.39 | 249.07 | 382.93 |
| 176 | 148.52 | 120.38 | 201.64 | 203.61 | 293.01 | 238.39 | 369.71 |
| 177 | 389.88 | 142.96 | 438.38 | 556.24 | 611.53 | 633.48 | 795.43 |
| 178 | 351.77 | 286.84 | 364.72 | 436.79 | 792.97 | 498.19 | 611.18 |
| 179 | 189.25 | 165.89 | 196.05 | 273.16 | 411.47 | 252.37 | 435.01 |
| 180 | 549.81 | 444.28 | 396.42 | 562.95 | 980.17 | 611.93 | 973.6 |
| 181 | 256.18 | 158.27 | 285.46 | 278.17 | 552.75 | 386.78 | 362.56 |
| 182 | 158.87 | 122.18 | 130.52 | 158.92 | 323.99 | 182.08 | 258.41 |
| 183 | 1266.87 | 291.34 | 1465.85 | 1809.88 | 1981.71 | 2056.61 | 2286.62 |
| 184 | 441.84 | 217.7 | 330.57 | 455.9 | 703.49 | 549.05 | 646.54 |
| 185 | 189.38 | 134.13 | 158.87 | 184.24 | 293.44 | 226.46 | 351.53 |
| 186 | 682.11 | 281.63 | 567.42 | 645.45 | 1043.8 | 769.32 | 1024.99 |
| 187 | 863.99 | 258.52 | 643.98 | 775.24 | 1117.04 | 935.31 | 1259.67 |
| 188 | 250.42 | 107.62 | 249.84 | 237.46 | 404.92 | 391.03 | 300.92 |
| 189 | 268.86 | 131.02 | 211.1 | 263.99 | 412.1 | 289.7 | 433.76 |
| 190 | 202.48 | 88.45 | 208.4 | 211.97 | 366.42 | 245.63 | 315.38 |
| 191 | 763.84 | 372.77 | 638.07 | 864.79 | 1250.89 | 844.06 | 1330.22 |
| 192 | 579.01 | 403.81 | 461.65 | 580.39 | 930.22 | 604.38 | 1090.47 |
| 193 | 759.99 | 385.43 | 693.65 | 904.07 | 1217.27 | 982.86 | 1345.6 |
| 194 | 218.54 | 189.34 | 293.62 | 244.62 | 464.88 | 302.69 | 459.29 |
| 195 | 548.82 | 366.81 | 834.12 | 848.12 | 1219.9 | 862.27 | 1278.38 |
| 196 | 680.15 | 231.09 | 644.14 | 722.42 | 1096.65 | 839.03 | 998.56 |
| 197 | 200.26 | 89.81 | 194.73 | 265.83 | 363.25 | 250.69 | 353.76 |
| 198 | 195.2 | 85.23 | 185.31 | 214.94 | 331.76 | 248.9 | 298.72 |
| 199 | 212 | 250.08 | 339.99 | 361.59 | 598.36 | 376.5 | 508.79 |

FIG. 22B(continued)

| | | | | | | | |
|---|---|---|---|---|---|---|---|
| 200 | 267.45 | 277.85 | 265.49 | 300.01 | 535.99 | 315.33 | 563.39 |
| 201 | 414.1 | 209.26 | 389.63 | 447.03 | 704.17 | 533.38 | 606.64 |
| 202 | 702.54 | 622.66 | 506.76 | 887.7 | 1280.35 | 902.88 | 1236.37 |
| 203 | 562.75 | 314.93 | 512.53 | 482.74 | 699.39 | 791.42 | 899.59 |
| 204 | 176.32 | 180.1 | 192.77 | 232.45 | 379.17 | 247.14 | 362.22 |
| 205 | 629.29 | 458.8 | 613.35 | 651.07 | 1183.61 | 987.06 | 799.55 |
| 206 | 342.38 | 206.66 | 284.15 | 335.68 | 601.51 | 395.73 | 459.67 |
| 207 | 271.67 | 202.61 | 343.8 | 307.21 | 558.1 | 415.73 | 421.02 |
| 208 | 430 | 247.26 | 315.46 | 443.18 | 686.4 | 481.82 | 615.21 |
| 209 | 1559.47 | 729.14 | 1615.57 | 1698.99 | 2185.57 | 2100.15 | 2626.25 |
| 210 | 662.81 | 397.68 | 634.11 | 643.3 | 1107.81 | 940.38 | 839.18 |
| 211 | 222.23 | 162.57 | 220.06 | 269.77 | 416.59 | 274.84 | 388.42 |
| 212 | 198.65 | 151.97 | 226.1 | 213.29 | 320.21 | 308.37 | 336.35 |
| 213 | 1380.47 | 792.07 | 1290.47 | 1682.72 | 2232.77 | 1953.77 | 2136.47 |
| 214 | 372.07 | 247.11 | 335.34 | 290.23 | 459.08 | 423.98 | 642.32 |
| 215 | 566.12 | 321.59 | 390.04 | 561 | 789.62 | 590.84 | 888.3 |
| 216 | 200.62 | 121.34 | 232.22 | 226.78 | 326.33 | 286.45 | 343.48 |
| 217 | 246.19 | 144.99 | 211.15 | 234.88 | 314.82 | 301.03 | 411.93 |
| 218 | 1721.33 | 840.27 | 1669.65 | 1755.13 | 2306.27 | 2166.06 | 2773.47 |
| 219 | 704.75 | 519.05 | 747.7 | 748.74 | 1333.75 | 871.82 | 1091.69 |
| 220 | 259 | 166.63 | 282.19 | 337.55 | 408.79 | 375.26 | 479.62 |
| 221 | 762.24 | 437.4 | 762.93 | 712.17 | 1160.49 | 930.78 | 1073.37 |
| 222 | 421.07 | 252.08 | 477.89 | 578.49 | 728.91 | 622.27 | 701.27 |
| 223 | 436.26 | 347.21 | 430.15 | 487.11 | 692.96 | 626.57 | 710.07 |
| 224 | 255.08 | 191.63 | 252.08 | 299.78 | 352.3 | 389.18 | 420.82 |
| 225 | 643.97 | 457.99 | 643.94 | 704.09 | 1101.19 | 747.64 | 992.5 |
| 226 | 274.58 | 299.77 | 293.16 | 323.11 | 563.29 | 405.68 | 409.07 |
| 227 | 186.13 | 172.79 | 219.76 | 232.07 | 339.35 | 262.31 | 339.85 |
| 228 | 457.34 | 362.32 | 508.79 | 494.57 | 785.83 | 563.9 | 719.97 |
| 229 | 297.86 | 227.4 | 320.96 | 414 | 512.8 | 427.09 | 503.93 |
| 230 | 1134.57 | 717.69 | 898.31 | 1436.2 | 1584.96 | 1523.99 | 1635.62 |
| 231 | 853.21 | 716.93 | 927.26 | 1001.4 | 1324.43 | 1206.98 | 1396.24 |
| 232 | 298.82 | 186.1 | 288.38 | 265.88 | 378.11 | 395.22 | 375.85 |

FIG. 22C

| SEQ ID | common name | description |
|---|---|---|
| 1 | Sphingosine kinase 2 | UI-M-BH1-ame-a-08-0-UI.s1 NIH_BMAP_M_S2 Mus musculus cDNA clone UI-M-BH1-ame-a-08-0-UI 3', mRNA sequence. |
| 2 | Krt1-15 | intermediate filament protein |
| 3 | 1300007C21Rik | truncated; Mouse endogenous retrovirus truncated gag protein, complete cds, clone del env-1 3.1. |
| 4 | RIKEN cDNA 1110038L14 | vr45a06.s1 Knowles Solter mouse 2 cell Mus musculus cDNA clone IMAGE:1123570 5' similar to gb:X54942 CDK |
| 5 | Sprr1a | MSPRR1A; similar to mSPRR1A encoded by GenBank Accession Number M19888; Mus musculus SPRR 1A (Sprr1a) gene |
| 6 | RIKEN cDNA 1300019I03 | UI-M-AQ1-adx-c-06-0-UI.s1 NIH_BMAP_MHI_N Mus musculus cDNA clone UI-M-AQ1-adx-c-06-0-UI 3', mRNA sequence. |
| 7 | Mail-pending | vo32e09.r1 Barstead mouse irradiated colon MPLRB7 Mus musculus cDNA clone IMAGE:1051624 5', mRNA sequence. |
| 8 | MAIL | AV374591 RIKEN full-length enriched, adult male cecum Mus musculus cDNA clone 9130013H11 3', mRNA sequence. |
| 9 | Myln | Mus musculus non-muscle myosin light chain 3 (MLC3nm) mRNA, partial cds. |
| 10 | Stimulated by retinoic acid 14 | M.musculus mRNA for basic-helix-loop-helix protein. |
| 11 | ab, SCD, Scd-1 | stearoyl-CoA desaturase; Mouse stearoyl-CoA desaturase gene, exon 6. |
| 12 | Interferon-related regulator 1 | reading frame interferon beta-2; Messenger RNA fragment for mouse interferon beta (type 2) coding for the C-terminal part. |
| 13 | | Mus musculus mRNA for BTEB-1 transcription factor. |
| 14 | Ser (or cys) proteinase inhib | Mouse RNA for plasminogen activator inhibitor 2. |
| 15 | Expressed sequence AW558171 | UI-M-BH2.3-aoa-g-07-0-UI.s1 NIH_BMAP_M_S3.3 Mus musculus cDNA clone UI-M-BH2.3-aoa-g-07-0-UI 3', mRNA seq |
| 16 | | C78850 Mouse 3.5-dpc blastocyst cDNA Mus musculus cDNA clone J0056C12 3' similar to mouse proviral retroviral insertion |
| 17 | ADAMTS-1 | putative; Mouse mRNA for secretory protein containing thrombospondin motifs, complete cds. |
| 18 | C/EBP, beta | Mouse alpha-1-acid glycoprotein (AGP/EBP) mRNA, complete cds. |
| 19 | | C85523 Mouse fertilized one-cell-embryo cDNA Mus musculus cDNA clone J0209F01 3', mRNA sequence. |
| 20 | DNA segment, Chr 8 ERATO Doi 814, expressed | UI-M-BH2.2-aoo-b-05-0-UI.s1 NIH_BMAP_M_S3.2 Mus musculus cDNA clone UI-M-BH2.2-aoo-b-05-0-UI 3', mRNA seq |
| 21 | Nfkbi | Mus musculus I kappa B alpha gene, exons 2-6, partial cds. |
| 22 | Transketolase | Mus musculus LAF1 transketolase mRNA, complete cds. |
| 23 | RIKEN cDNA 1300002F13 gene | uc89c05.x1 NCI_CGAP_Mam3 Mus musculus cDNA clone IMAGE:2649704 3', mRNA sequence. |
| 24 | MT-I, Mt-1 | Mouse gene for Metallothionein-I (three exons). |
| 25 | Cytokine ind SH2-cont protein 3 | AV374868 RIKEN full-length enriched, adult male cecum Mus musculus cDNA clone 9130017A09 3' similar to U88328 |
| 26 | ab, SCD, Scd-1 | stearoyl-CoA desaturase; Mouse stearoyl-CoA desaturase gene, exon 6. |
| 27 | Ctsc | Cathepsin C |
| 28 | C/EBP, delta | M.musculus mRNA for C/EBP delta. |
| 29 | Jun-B oncogene | Mus musculus transcription factor junB (junB) gene, 5' region and complete cds. |
| 30 | Atf3 | leucine zipper protein; Mus musculus transcription factor LRG-21 mRNA, complete cds. |
| 31 | Immediate early response, erythropoietin 1 | UI-M-BH1-amp-g-08-0-UI.s1 NIH_BMAP_M_S2 Mus musculus cDNA clone UI-M-BH1-amp-g-08-0-UI 3', mRNA sequence. |
| 32 | ADFP | Mouse adipose differentiation related protein (ADFP) mRNA, complete cds. |
| 33 | mCPE-R | Mus musculus mCPE-R mRNA for CPE-receptor, complete cds. |
| 34 | Jun-B oncogene | Mus musculus transcription factor junB (junB) gene, 5' region and complete cds. |
| 35 | Nfil3 | Mus musculus NFIL3/E4BP4 transcription factor mRNA, complete cds. |
| 36 | Sat | putative; Mouse spermidine/spermine N1-acetyltransferase (SSAT) mRNA, complete cds. |
| 37 | Cish3 | Mus musculus suppressor of cytokine signalling-3 (SOCS-3) mRNA, complete cds. |
| 38 | Antigen identified by mAb Ki 67 | M.musculus mRNA for Ki-67. |
| 39 | Expressed sequence C77826 | UI-M-BH2.2-aox-b-05-0-UI.s1 NIH_BMAP_M_S3.2 Mus musculus cDNA clone UI-M-BH2.2-aox-b-05-0-UI 3', mRNA seq |
| 40 | Nuclear factor of kappa light chain gene enhancer in B-cells inhibitor, alpha | ub75b05.x1 Soares_mammary_gland_NMLMG Mus musculus cDNA clone IMAGE:1383537 3' similar to gb:M69043. |

FIG. 22C (continued)

| | | |
|---|---|---|
| 41 | HB-EGF | Mus musculus (clone lambda mouse 1) heparin-binding EGF-like growth factor precursor mRNA, complete cds. |
| 42 | pgk1 | X-linked; Mus musculus X chromosome-linked phosphoglycerate kinase (pgk-1) mRNA, complete cds. |
| 43 | RIKEN cDNA 5033417E09 gene | ud61f11.x1 Sugano mouse liver mlia Mus musculus cDNA clone IMAGE:1450413 3' similar to gb:L32179 |
| 44 | Pyruvate dehydrogenase kinase 4 | Mus musculus mRNA for pyruvate dehydrogenase kinase-like protein. |
| 45 | Leukemia-associated gene | UI-M-AL0-abv-e-12-0-UI.s1 NIH_BMAP_MCO Mus musculus cDNA clone UI-M-AL0-abv-e-12-0-UI 3', mRNA sequence. |
| 46 | Claudin 1 | integral membrane protein localizing at tight junctions; Mus musculus claudin-1 mRNA, complete cds. |
| 47 | Potassium inwardly-rectifying channel, subfamily J, member 12 | M.musculus MB-IRK2 mRNA. |
| 48 | RIKEN cDNA 1110032C13 gene | UI-M-AP1-agn-a-04-0-UI.s1 NIH_BMAP_MST_N Mus musculus cDNA clone UI-M-AP1-agn-a-04-0-UI 3', mRNA sequence. |
| 49 | Thyroid hormone receptor alpha | Mus musculus orphan nuclear receptor Rev-Erb-beta mRNA, partial cds. |
| 50 | Proteosome (prosome, macropain) subunit, beta type 8 (large | Lmp7k, s, f allele; Mus musculus 20S proteasome subunit Lmp7 (Lmp7k, s, f allele) mRNA, complete cds. multifunctional protease 7) |
| 51 | aldh3 | Mus musculus aldehyde dehydrogenase 3 (aldh3) gene, partial cds. |
| 52 | Butyrate response factor 2 | vw64d05.s1 Soares_mammary_gland_NMLMG Mus musculus cDNA clone IMAGE:1248585 3', mRNA sequence. |
| 53 | TSA-1 | Mus musculus thymic shared antigen-1 (TSA-1) gene, complete cds. |
| 54 | c-myc | Mouse c-myc gene exon 3. |
| 55 | MMSTK1 | putative serine/threonine kinase; Mouse mRNA for STK-1 (serine/threonine kinase), complete cds. |
| 56 | EIF 1A | translation initiation factor; Mus musculus eIF-1A (eIF-1A) mRNA, complete cds. |
| 57 | GRO1 oncogene | secretory protein KC precursor; Mouse platelet-derived growth factor-inducible KC protein mRNA, complete cds. |
| 58 | IGF binding protein 2 | M.musculus mRNA for insulin-like growth factor binding protein-2. |
| 59 | Expressed sequence AI314958 | uj34f07.x1 Sugano mouse kidney mkia Mus musculus cDNA clone IMAGE:1921861 3', mRNA sequence. |
| 60 | Mkrn3 | Mus musculus 14-3-3 protein sigma mRNA, complete cds. |
| 61 | | UI-M-BH1-ald-c-09-0-UI.s1 NIH_BMAP_M_S2 Mus musculus cDNA clone UI-M-BH1-ald-c-09-0-UI 3', mRNA sequence. |
| 62 | Kruppel-like factor 9 | UI-M-AH1-agp-g-10-0-UI.s1 NIH_BMAP_MCE_N Mus musculus cDNA clone UI-M-AH1-agp-g-10-0-UI 3', mRNA sequence. |
| 63 | FGF binding protein 1 | heparin and fibroblast growth factor binding; similar to Homo sapiens HBp17 protein encoded by seq in AN M60047; FGFBP-1 |
| 64 | Period homolog (Drosophila) | circadian pacemaker protein; Mus musculus Rigui mRNA, complete cds. |
| 65 | TGFB induc. early growth resp. | zinc finger protein; Mus musculus transcription factor GIF mRNA, complete cds. |
| 66 | RIKEN cDNA 4930455J02 gene | ul21f04.y1 Sugano mouse embryo mewa Mus musculus cDNA clone IMAGE:2088223 5' sim to SW:Y33K_HUMAN Q04323 |
| 67 | RIKEN cDNA 1300002F13 gene | UI-M-BH0-ajd-f-01-0-UI.s1 NIH_BMAP_M_S1 Mus musculus cDNA clone UI-M-BH0-ajd-f-01-0-UI 3', mRNA sequence. |
| 68 | Zinc finger protein 36 | TIS11 (AA 1 - 183); Mouse TPA-induced TIS11 mRNA. |
| 69 | RIKEN cDNA 1190002H23 gene | UI-M-BG1-aic-e-02-0-UI.s1 NIH_BMAP_MSC_N Mus musculus cDNA clone UI-M-BG1-aic-e-02-0-UI 3', mRNA sequence. |
| 70 | High mobility group box 2 | M.musculus mRNA for high mobility group 2 protein. |
| 71 | Metallothionein 2 | metallothionien II; Mouse metallothionein II (MT-II) gene. |
| 72 | Myd116 | MyD116 protein (AA 1-657); Mouse myeloid differentiation primary response mRNA encoding MyD116 protein. |
| 73 | CDK inhibitor 1A (P21) | UI-M-BH1-amo-d-08-0-UI.s1 NIH_BMAP_M_S2 Mus musculus cDNA clone UI-M-BH1-amo-d-08-0-UI 3', mRNA sequence. |
| 74 | Stromal cell derived factor 1 | AV139913 Mus musculus C57BL/6J 10-11 day embryo Mus musculus cDNA clone 2810055D15, mRNA sequence. |
| 75 | Cyr61 | Cyr61 product; Mouse Cyr61 mRNA, complete cds. |
| 76 | RIKEN cDNA 1600029D21 gene | uc30b06.r1 Soares_mammary_gland_NbMMG Mus musculus cDNA clone IMAGE:1399475 5', mRNA sequence. |
| 77 | Purine-nucleoside phosphorylase | Mus musculus purine nucleoside phosphorylase (Np-b) mRNA, complete cds. |
| 78 | BAR, B2AR, ADRBR, ADRB2R | Mouse gene for beta-2-adrenergic receptor. |
| 79 | RIKEN cDNA 2310076D10 gene | UI-M-AH1-agw-h-03-0-UI.s1 NIH_BMAP_MCE_N Mus musculus cDNA clone UI-M-AH1-agw-h-03-0-UI 3', mRNA sequence. |
| 80 | Paired-like homeodomain TF 2 | bicoid-related homeodomain protein; murine homolog of Rieger syndrome; mouse bicoid-rel homeodomain prot solurshin (Rgs) |
| 81 | Keratin complex 1, acidic, gene 17 | epidermal keratin type I; Mouse type I epidermal keratin mRNA, clone pkSCC-50, 3' end. |

FIG. 22C (continued)

| | | |
|---|---|---|
| 82 | Growth arrest and DNA-damage-inducible 45 beta | AV138783 Mus musculus C57BL/6J 10-11 day embryo Mus musculus cDNA clone 2810046L02, mRNA sequence. |
| 83 | Rrm1 | ribonucleotide reductase subunit M1; Mouse ribonucleotide reductase subunit M1 mRNA, complete cds. |
| 84 | Ncl | Mouse nucleolin gene. |
| 85 | PCNA | Murine PCNA gene for proliferating cell nuclear antigen (DNA polymerase delta auxiliary protein). |
| 86 | H-2T17 | MHC H2-TL-T17-c; Mouse MHC class I H2-TL-T17-c mRNA (d haplotype), complete cds. |
| 87 | Expressed sequence AI467657 | vl37g06.y1 Soares mouse NbMH Mus musculus cDNA clone IMAGE:846010 5' similar to SW:PLZF_HUMAN Q05516 |
| 88 | Nr4a1 | Mouse N10 gene for a nuclear hormonal binding receptor. |
| 89 | Lectin, galactose binding, sol 7 | Mus musculus galectin-7 mRNA, complete cds. |
| 90 | HKII | Mus musculus gene for hexokinase II, exon 1 (and joined CDS). |
| 91 | Sequestosome 1 | similar to D. melanogaster Ref(2)Pp protein; Mus musculus oxidative stress-induced protein mRNA, complete cds. |
| 92 | Mcm5, Cdc46, mCD46 | put. mouse homolog of yeast CDC46; Mouse mRNA for mCDC46 protein, complete cds. |
| 93 | DNA segment, Chr 13, WSU 123, e | ul20f06.y1 Sugano mouse embryo mewa Mus musculus cDNA clone IMAGE:2088131 5' similar to SW:YBC4_YEAST P38205 |
| 94 | | Mouse histone H2A.1 gene, complete cds. |
| 95 | RIKEN cDNA 3100004P22 gene | UI-M-BG0-aht-a-11-0-UI.s1 NIH_BMAP_MSC Mus musculus cDNA clone UI-M-BG0-aht-a-11-0-UI 3', mRNA sequence. |
| 96 | Expressed sequence AU018108 | vo73e09.r1 Barstead mouse myotubes MPLRB5 Mus musculus cDNA clone IMAGE:1064776 5', mRNA sequence. |
| 97 | Kruppel-like factor 13 | UI-M-BH2.2-aql-f-08-0-UI.s1 NIH_BMAP_M_S3.2 Mus musculus cDNA clone UI-M-BH2.2-aql-f-08-0-UI 3', mRNA sequence. |
| 98 | E26 avian leuk oncogen 2, 3' dom | ets2 protein; Mouse erythroblastosis virus oncogene homolog 2 (ets-2) mRNA, complete cds. |
| 99 | H2-Q8 | Mouse Q8/9d gene. |
| 100 | TACSTD 2 | vz06h06.x1 Soares_mammary_gland_NbMMG Mus musculus cDNA clone IMAGE:1314971 3' similar to gb:J04152_rna1 |
| 101 | Fosl1 | Fra-1; B-Zip transcription factor; subunit of AP-1 member of the Fos family; Mus musculus fos-related antigen 1 (fra-1) gene |
| 102 | Immediate early response 3 | M.musculus gly96 mRNA. |
| 103 | TGFB inducible early growth resp | zinc finger protein; Mus musculus transcription factor GIF mRNA, complete cds. |
| 104 | RIKEN cDNA 5730403B10 gene | UI-M-AK1-aes-b-10-0-UI.s1 NIH_BMAP_MHY_N Mus musculus cDNA clone UI-M-AK1-aes-b-10-0-UI 3', mRNA sequence. |
| 105 | Pre B-cell leukemia TF 1 | UI-M-BH2.1-apu-g-09-0-UI.s1 NIH_BMAP_M_S3.1 Mus musculus cDNA clone UI-M-BH2.1-apu-g-09-0-UI 3', mRNA seq |
| 106 | MHC Q2-k | Mouse MHC (Qa) Q2-k gene for class I antigen, exons 1-3. |
| 107 | | MHC beta-2-microglobulin; Mouse MHC class I Q4 beta-2-microglobulin (Qb-1) gene, complete cds. |
| 108 | RIKEN cDNA 2810484M10 gene | UI-M-BH2.1-aph-h-08-0-UI.s1 NIH_BMAP_M_S3.1 Mus musculus cDNA clone UI-M-BH2.1-aph-h-08-0-UI 3', mRNA seq |
| 109 | Irs2 | IRS-2; Mus musculus insulin receptor substrate-2 (Irs2) gene, partial cds. |
| 110 | Thra | UI-M-AM1-afw-b-05-0-UI.s1 NIH_BMAP_MAM_N Mus musculus cDNA clone UI-M-AM1-afw-b-05-0-UI 3', mRNA seq |
| 111 | DNA segment, Chr 19, ERATO Doi 410, expressed | UI-M-BH0-akh-e-08-0-UI.s1 NIH_BMAP_M_S1 Mus musculus cDNA clone UI-M-BH0-akh-e-08-0-UI 3', mRNA sequence. |
| 112 | RIKEN cDNA 2700038D15 gene | UI-M-BH1-ame-a-04-0-UI.s1 NIH_BMAP_M_S2 Mus musculus cDNA clone UI-M-BH1-ame-a-04-0-UI 3', mRNA sequence. |
| 113 | Eph receptor B4 | Mus musculus Balb/c eph-related receptor protein tyrosine kinase mRNA, complete cds. |
| 114 | Secreted modular calcium-binding p | ua31a05.r1 Soares_mammary_gland_NbMMG Mus musculus cDNA clone IMAGE:1348304 5', mRNA sequence. |
| 115 | RIKEN cDNA 2610008O03 gene | UI-M-AK1-aet-h-03-0-UI.s1 NIH_BMAP_MHY_N Mus musculus cDNA clone UI-M-AK1-aet-h-03-0-UI 3', mRNA sequence. |
| 116 | Cystatin B | also known as stefin B; Mus musculus cystatin B (Stfb) gene, complete cds. |
| 117 | Expressed sequence AA408168 | ud93d03.r1 Soares_NMPu Mus musculus cDNA clone IMAGE:1478405 5', mRNA sequence. |
| 118 | RIKEN cDNA 5730469M10 gene | UI-M-BG0-aia-g-01-0-UI.s1 NIH_BMAP_MSC Mus musculus cDNA clone UI-M-BG0-aia-g-01-0-UI 3', mRNA sequence. |
| 119 | Hydroxysteroid (17-beta) dehyd 12 | Mus musculus putative steroid dehydrogenase (KiK-I) mRNA, complete cds. |
| 120 | Expressed sequence AU044290 | UI-M-AK1-aes-e-01-0-UI.s1 NIH_BMAP_MHY_N Mus musculus cDNA clone UI-M-AK1-aes-e-01-0-UI 3', mRNA sequence. |
| 121 | WSB-1 | Mus musculus WSB-1 mRNA, complete cds. |

FIG. 22C (continued)

| | | |
|---|---|---|
| 122 | Supp of initiator codon mutations, related sequence 1 (S. cerevisiae) | homolog of human sui1iso1, yeast sui1 and rice gos2; M.musculus mRNA for Sui1. |
| 123 | B-cell receptor-associated prot 37 | M.musculus mRNA for B-cell receptor associated protein (BAP) 37. |
| 124 | NM 2 protein (NM23B) (nucleoside diphosphate kinase) | M.musculus mRNA for nucleoside diphoshate kinase B. |
| 125 | Solute carrier family 25 (mitochondrial carrier; ANT), member 5 | mj83h01.r1 Soares mouse p3NMF19.5 Mus musculus cDNA clone IMAGE:482737 5' similar to gb:J02683 ADP,ATP CARRIER PROTEIN, FIBROBLAST ISOFORM (HUMAN); gb:X70847 M.musculus mRNA for adenine nucleotide translocase |
| 126 | | vw19g10.y1 Soares_mammary_gland_NbMMG Mus musculus cDNA clone IMAGE:1244322 5' sim to SW:ZAN_PIG Q28983 |
| 127 | Pik3r1 | PI3K regulatory subunit; Mus musculus phosphoinositide 3-kinase regulatory subunit p85alpha mRNA, complete cds. |
| 128 | RIKEN cDNA 6330577E15 gene | UI-M-BH1-ami-f-05-0-UI.s2 NIH_BMAP_M_S2 Mus musculus cDNA clone UI-M-BH1-ami-f-05-0-UI 3', mRNA sequence. |
| 129 | TGF beta 1 induced transcript 4 | M.musculus TSC-22 mRNA. |
| 130 | ABS, sub-family B (MDR/TAP), member 2 | Mus musculus antigen processing-associated transporter TAP1-g7 mRNA, complete cds. |
| 131 | Ran | Mouse (clone M2) GTPase (Ran) mRNA, complete cds. |
| 132 | Peroxisomal delta3, delta2-ECI | UI-M-AH0-acu-e-04-0-UI.s1 NIH_BMAP_MCE Mus musculus cDNA clone UI-M-AH0-acu-e-04-0-UI 3', mRNA sequence. |
| 133 | rbm3 | Mus musculus rbm3 mRNA, complete cds. |
| 134 | DNA segment, Chr 10, ERATO Doi 214, expressed | UI-M-AH1-ags-f-11-0-UI.s1 NIH_BMAP_MCE_N Mus musculus cDNA clone UI-M-AH1-ags-f-11-0-UI 3', mRNA sequence. |
| 135 | Keratin complex 1, acidic, gen 19 | AU040563 Mouse four-cell-embryo cDNA Mus musculus cDNA clone J0812H07 3', mRNA sequence. |
| 136 | TG interacting factor | M.musculus mRNA for mTGIF protein. |
| 137 | RIKEN cDNA 1110004C05 gene | UI-M-BH2.3-aqh-c-06-0-UI.s1 NIH_BMAP_M_S3.3 Mus musculus cDNA clone UI-M-BH2.3-aqh-c-06-0-UI 3', mRNA seq |
| 138 | | histone H2B-291A (AA 1 - 126); histone H2A-291A (AA 1 - 135); Mouse H2B and H2A histone genes (291A). |
| 139 | SGK | UI-M-BH1-akw-d-06-0-UI.s1 NIH_BMAP_M_S2 Mus musculus cDNA clone UI-M-BH1-akw-d-06-0-UI 3', mRNA sequence. |
| 140 | EMAP 2 | Mus musculus endothelial-monocyte activating polypeptide II mRNA, complete cds. |
| 141 | Actin related protein 2/3 complex, subunit 1B (41 kDa) | uc66e09.x1 NCI_CGAP_Mam1 Mus musculus cDNA clone IMAGE:2647528 3', mRNA sequence. |
| 142 | Expressed sequence AA536646 | UI-M-AK1-aez-g-04-0-UI.s1 NIH_BMAP_MHY_N Mus musculus cDNA clone UI-M-AK1-aez-g-04-0-UI 3', mRNA sequence. |
| 143 | Solute carrier family 2 (GLUT), mem | facilitated glucose transporter; Mouse facilitated glucose transport protein mRNA, complete cds. |
| 144 | Ornithine aminotransferase | M.musculus Oat mRNA for ornithine aminotransferase. |
| 145 | GST omega 1 | UI-M-AK1-aes-f-05-0-UI.s1 NIH_BMAP_MHY_N Mus musculus cDNA clone UI-M-AK1-aes-f-05-0-UI 3', mRNA sequence. |
| 146 | | UI-M-AK0-adl-e-02-0-UI.s1 NIH_BMAP_MHY Mus musculus cDNA clone UI-M-AK0-adl-e-02-0-UI 3', mRNA sequence. |
| 147 | B-cell leukemia/lymphoma 6 | homolog of human oncogene, BCL-6; Mus musculus BCL-6 mRNA, complete cds. |
| 148 | H2A histone family, member Z | histone H2A.Z; Mus musculus histone H2A.Z (H2A.Z) mRNA, complete cds. |
| 149 | mot2, Hsc74, Hsp74, Hsp74a, mortalin | Mouse gene for mitochondrial stress-70 protein (PBP74/CSA), exon 14,15,16 and 17. |
| 150 | Fosb | fosB protein (AA 1-338); Mouse fosB mRNA. |
| 151 | B-cell leukemia/lymphoma 10 | Mus musculus mRNA for bcl-10 protein. |
| 152 | HMG nucleosomal binding dom 2 | HMG-17 protein (AA 1 - 90); Mouse mRNA for HMG-17 chromosomal protein. |
| 153 | RIKEN cDNA 1500040F11 gene | UI-M-BH1-anw-c-09-0-UI.s1 NIH_BMAP_M_S2 Mus musculus cDNA clone UI-M-BH1-anw-c-09-0-UI 3', mRNA sequence. |
| 154 | EIF 3, subunit 8 (110 kDa) | similar to yeast NIP1 nuclear import protein; transmembrane protein; contains several potential phosphorylation sites for PKC and casein kinase II; Mus musculus NIP1-like protein (NIPIL(A3)) mRNA, complete cds. |
| 155 | Claudin 1 | vv68a06.x1 Stratagene mouse skin (#937313) Mus musculus cDNA clone IMAGE:1227538 3', mRNA sequence. |
| 156 | RIKEN cDNA 2900010I05 gene | UI-M-BG0-ahs-b-12-0-UI.s1 NIH_BMAP_MSC Mus musculus cDNA clone UI-M-BG0-ahs-b-12-0-UI 3', mRNA sequence. |

FIG. 22C (continued)

| | | |
|---|---|---|
| 157 | RIKEN cDNA 2310008N12 gene | UI-M-BH1-alk-c-09-0-UI.s1 NIH_BMAP_M_S2 Mus musculus cDNA clone UI-M-BH1-alk-c-09-0-UI 3', mRNA sequence. |
| 158 | Fatty acid Coenzyme A ligase, long chain 5 | UI-M-AP0-abl-g-11-0-UI.s1 NIH_BMAP_MST Mus musculus cDNA clone UI-M-AP0-abl-g-11-0-UI 3', mRNA sequence. |
| 159 | RIKEN cDNA 1810015C04 gene | UI-M-BH2.1-apa-d-07-0-UI.s1 NIH_BMAP_M_S3.1 Mus musculus cDNA clone UI-M-BH2.1-apa-d-07-0-UI 3', mRNA seq |
| 160 | Ier2 | Mouse growth factor-inducible protein (pip92) mRNA, complete cds. |
| 161 | Keratin complex 1, acidic, gene 17 | epidermal keratin type I; Mouse type I epidermal keratin mRNA, clone pkSCC-50, 3' end. |
| 162 | DNA segment, Chr 6, ERATO Doi 109, expressed | UI-M-AO1-aeg-h-09-0-UI.s1 NIH_BMAP_MPG_N Mus musculus cDNA clone UI-M-AO1-aeg-h-09-0-UI 3', mRNA sequence. |
| 163 | Cytochr c oxidase, subunit Vb | cytochrome c oxidase subunit Vb precursor; Mouse mRNA for mitochondrial cytochrome c oxidase subunit Vb. |
| 164 | Atf3 | leucine zipper protein; Mus musculus transcription factor LRG-21 mRNA, complete cds. |
| 165 | Zinc finger protein 216 | Mus musculus zinc finger protein ZNF216 mRNA, complete cds. |
| 166 | Solute carrier family 25 (mitochondrial carrier; ANT), member 5 | Mus musculus adenine nucleotide translocase mRNA, complete cds. |
| 167 | Epha2 | similar to human eck gene product, Swiss-Prot Accession Number P29317; Mus musculus receptor-protein tyrosine kinase (eck) |
| 168 | Tubb5 | beta-tubulin [AA 1-444] (79 is 1st base in codon); Mouse mRNA for beta-tubulin (isotype Mbeta 5). |
| 169 | Carboxypeptidase E | Mouse mRNA for carboxypeptidase H. |
| 170 | Solute carrier family 3 (activators of dibasic and neutral AA transport), member 2 | 4F2 heavy chain (AA 1-526); Murine mRNA for 4F2 antigen heavy chain. |
| 171 | FGF inducible 14 | Mus musculus fibroblast growth factor inducible gene 14 (FIN14) mRNA, complete cds. |
| 172 | Kcnj6 | Mus musculus G-protein coupled inwardly rectifying K+ channel (Girk2C) mRNA, complete cds. |
| 173 | Peroxiredoxin 5, related seq 3 | CP-2; Mus musculus 1-Cys peroxiredoxin protein 2 gene, complete cds. |
| 174 | Ldlr | Low density lipoprotein receptor |
| 175 | Scin | gelsolin-like protein; Mus musculus ADSEVERIN mRNA, complete cds. |
| 176 | H-2T10 | MHC H2-TL-T10-129; Mouse MHC class I H2-TL-T10-129 mRNA (b haplotype), complete cds. |
| 177 | Expressed sequence C85189 | UI-M-BH2.3-aoj-d-12-0-UI.s1 NIH_BMAP_M_S3.3 Mus musculus cDNA clone UI-M-BH2.3-aoj-d-12-0-UI 3', mRNA sequence. |
| 178 | LPS-induced TNF-alpha factor | UI-M-BH0-aiu-f-10-0-UI.s1 NIH_BMAP_M_S1 Mus musculus cDNA clone UI-M-BH0-aiu-f-10-0-UI 3', mRNA sequence. |
| 179 | NRF2 | CNC basic leucine zipper DNA binding protein; Mus musculus p45 NF-E2 related factor 2 (NRF2) gene |
| 180 | HS 10 kDa protein 1 (chaperonin 10 | heat shock protein 10, HSP10; Mus musculus chaperonin 10 mRNA, complete cds. |
| 181 | Midnolin | UI-M-BH2.1-aqa-h-06-0-UI.s1 NIH_BMAP_M_S3.1 Mus musculus cDNA clone UI-M-BH2.1-aqa-h-06-0-UI 3', mRNA sequence. |
| 182 | Cops6 | similar to human Vpr interacting protein (hVIP) ; 34 kDa human MOV34 isologue; subunit 6 is a 36 kDa component of the COP9 complex which contains a total of 8 distinct subunits, similar to the JAB1-containing signalosome; mouse COPS6 mRNA |
| 183 | | |
| 184 | Silica-induced gene 81 | partial homology to cytochrome C oxidase subunit VII; M.musculus mRNA for cytochrome C oxidase subunit VII homologue. |
| 185 | PTP, receptor type, J | Mus musculus mRNA, one isoform of PTP-RL9. |
| 186 | Btg1 | M.musculus btg1 mRNA. |
| 187 | EIF factor 5a | UI-M-AH0-acw-e-01-0-UI.s1 NIH_BMAP_MCE Mus musculus cDNA clone UI-M-AH0-acw-e-01-0-UI 3', mRNA sequence. |
| 188 | RIKEN cDNA 2010306B17 gene | UI-M-AQ1-aec-e-01-0-UI.s1 NIH_BMAP_MHI_N Mus musculus cDNA clone UI-M-AQ1-aec-e-01-0-UI 3', mRNA sequence. |
| 189 | RIKEN cDNA 2610103L06 gene | UI-M-BH2.1-apy-g-01-0-UI.s1 NIH_BMAP_M_S3.1 Mus musculus cDNA clone UI-M-BH2.1-apy-g-01-0-UI 3', mRNA sequence. |
| 190 | RIKEN cDNA 0610010M09 gene | UI-M-BH2.1-apm-e-09-0-UI.s1 NIH_BMAP_M_S3.1 Mus musculus cDNA clone UI-M-BH2.1-apm-e-09-0-UI 3', mRNA sequence. |
| 191 | | UI-M-AI0-aaq-a-05-0-UI.s1 NIH_BMAP_MBS Mus musculus cDNA clone UI-M-AI0-aaq-a-05-0-UI 3', mRNA sequence. |
| 192 | Heat shock protein, 60 kDa | HSP60 protein (555 AA); Mouse mRNA for HSP60 protein (clones 3T3-7, -9, and -M1). |
| 193 | Gapd | glyceraldehyde-3-phosphate dehydrogenase; Mouse glyceraldehyde-3-phosphate dehydrogenase mRNA, complete cds. |
| 194 | Protein tyrosine phosphatase 4a2 | potentially prenylated protein tyrosine phosphatase; Mus musculus potentially prenylated protein tyrosine phosphatase mPRL-2 |

FIG. 22C (continued)

| | | |
|---|---|---|
| 195 | gene 37 | Murine gene 37 for pot. membrane bound protein. |
| 196 | RIKEN cDNA 1110032G10 gene | UI-M-BH2.3-aqh-b-06-0-UI.s1 NIH_BMAP_M_S3.3 Mus musculus cDNA clone UI-M-BH2.3-aqh-b-06-0-UI 3', mRNA sequence. |
| 197 | Isocitrate dehydrogenase 3 (NAD+), gamma | Mus musculus NAD(H)-specific isocitrate dehydrogenase gamma subunit precursor, mRNA, complete cds. |
| 198 | RIKEN cDNA 1110021D01 gene | UI-M-BH2.1-apy-h-02-0-UI.s1 NIH_BMAP_M_S3.1 Mus musculus cDNA clone UI-M-BH2.1-apy-h-02-0-UI 3', mRNA sequence. |
| 199 | Carboxypeptidase E | Mouse mRNA for carboxypeptidase H. |
| 200 | Cpo | Mouse mRNA for coproporphyrinogen oxidase, complete cds. |
| 201 | Sid394 | Mus musculus mRNA for Sid394p, complete cds. |
| 202 | Protein tyrosine phosphatase 4a1 | Mus musculus protein tyrosine phosphatase (PRL-1) mRNA, complete cds. |
| 203 | mc/EPB | Mouse CCAAT/enhancer binding protein gene, complete cds. |
| 204 | Zinc finger protein 36 | MTA.G11.085.A MTA adult mouse thymus library Mus musculus cDNA clone MTA.G11.085 5' end similar to xenopus XCAP-C |
| 205 | mATF4 | murine homolog of TAXREB67/ATF4; M.musculus mATF4 (mTR67) mRNA, complete cds. |
| 206 | NADH dehydrogenase (ubiquinone) flavoprotein 2 | UI-M-AP1-agg-c-11-0-UI.s1 NIH_BMAP_MST_N Mus musculus cDNA clone UI-M-AP1-agg-c-11-0-UI 3', mRNA sequence. |
| 207 | Expressed sequence AI430822 | UI-M-BH0-ajl-f-03-0-UI.s1 NIH_BMAP_M_S1 Mus musculus cDNA clone UI-M-BH0-ajl-f-03-0-UI 3', mRNA sequence. |
| 208 | Inosine 5'-phosphate dehydrog 2 | IMP dehydrogenase (EC 1.2.1.14); Mouse IMP dehydrogenase mRNA, complete cds. |
| 209 | | MHC Q4 class I antigen (31 AA) (119 is 2nd base in codon); Protein sequence is in conflict with the conceptual translation: Mouse Q4 class I MHC gene (exon 5). |
| 210 | Aquaporin 2 | va26c10.x1 GuayWoodford Beier mouse kidney day 7 Mus musculus cDNA clone IMAGE:732498 3', mRNA sequence. |
| 211 | Expressed sequence AA987150 | UI-M-AO0-ach-a-08-0-UI.s1 NIH_BMAP_MPG Mus musculus cDNA clone UI-M-AO0-ach-a-08-0-UI 3', mRNA sequence. |
| 212 | Expressed sequence C76856 | UI-M-AJ1-agy-b-09-0-UI.s1 NIH_BMAP_MOB_N Mus musculus cDNA clone UI-M-AJ1-agy-b-09-0-UI 3', mRNA sequence. |
| 213 | Hist4 | Mouse histone H3 (H3.2-221) gene, complete cds. |
| 214 | Enolase 1, alpha non-neuron | UI-M-AM0-adv-h-04-0-UI.s1 NIH_BMAP_MAM Mus musculus cDNA clone UI-M-AM0-adv-h-04-0-UI 3', mRNA sequence. |
| 215 | Eif4 | unidentified reading frame; put. eIF-4A (aa 1-390); put. altern. eIF-4A (aa 1-370); Mouse mRNA for initiation factor eIF-4AI. |
| 216 | TGF beta regulated gene 1 | UI-M-BH1-anm-f-07-0-UI.s1 NIH_BMAP_M_S2 Mus musculus cDNA clone UI-M-BH1-anm-f-07-0-UI 3', mRNA sequence. |
| 217 | D6Ertd109e | Mus musculus mRNA for eRF1, partial cds. |
| 218 | Histocompatibility 2, L region | ub83g12.r1 Soares_thymus_2NbMT Mus musculus cDNA clone IMAGE:1395142 5' similar to gb:K01762_rna1 |
| 219 | Aldolase 1, A isoform | aldolase A; Mouse mRNA for aldolase A. |
| 220 | | vr30d10.r1 Barstead mouse myotubes MPLRB5 Mus musculus cDNA clone IMAGE:1122163 5', mRNA sequence. |
| 221 | Apoc1 | Source: M.musculus Apoc1 gene, exons 1 to 3 and complete CDS. |
| 222 | Tripartite motif protein 28 | M.musculus mRNA for TIF1 beta protein. |
| 223 | Ethanol induced 6 | UI-M-AK1-aeu-f-09-0-UI.s1 NIH_BMAP_MHY_N Mus musculus cDNA clone UI-M-AK1-aeu-f-09-0-UI 3', mRNA sequence. |
| 224 | CDC 2 homolog A (S. pombe) | Mouse cell cycle protein (p34 CDC2) mRNA, complete cds. |
| 225 | Basic transcription factor 3 | UI-M-BH2.1-apb-b-08-0-UI.s1 NIH_BMAP_M_S3.1 Mus musculus cDNA clone UI-M-BH2.1-apb-b-08-0-UI 3', mRNA sequence. |
| 226 | MAP kinase 6 | UI-M-AH1-agx-b-06-0-UI.s1 NIH_BMAP_MCE_N Mus musculus cDNA clone UI-M-AH1-agx-b-06-0-UI 3', mRNA sequence. |
| 227 | Expressed sequence C81323 | vz48h05.r1 Soares_thymus_2NbMT Mus musculus cDNA clone IMAGE:1329753 5' similar to SW:SSRP_MOUSE Q08943 |
| 228 | Clk | Mouse serine threonine tyrosine kinase (STY) mRNA, complete cds. |
| 229 | Arha2 | RHOA; Mus musculus Rho family GTPase (ArhA) mRNA, complete cds. |
| 230 | Histone gene complex 1 | M.domesticus (CD-1) mRNA for histone H3 (partial). |
| 231 | Dp1 | Mus musculus GP106 mRNA, complete cds. |
| 232 | RIKEN cDNA 1300019P08 gene | AV218217 RIKEN full-length enriched, adult male hippocampus Mus musculus cDNA clone 2900087J21 3' similar to L12016 |

METHODS FOR GENERATING NEW HAIR FOLLICLES, TREATING BALDNESS, AND HAIR REMOVAL

CROSS-REFERENCE TO RELATED APPLICATIONS

This application is a continuation of U.S. patent application Ser. No. 11/887,104, filed Sep. 25, 2007, now abandoned which is a National Phase Application of PCT International Application No. PCT/US06/11319, International Filing Date Mar. 28, 2006, claiming priority of Provisional Patent Applications, 60/665,857, filed 29 Mar. 2005, and 60/683,293, filed 23 May 2005 all which are incorporated herein by reference in their entirety.

FIELD OF INVENTION

The present invention provides methods of treating baldness in a subject and generating new hair follicles, comprising epidermal disruption and administration of a compound that promotes a differentiation of an uncommitted epidermal cell into a hair follicle cell. The present invention also provides methods for hair removal and inducing hair pigmentation.

BACKGROUND OF THE INVENTION

Follicular neogenesis is defined as the generation of new hair follicles (HF) after birth. Humans are born with a full complement of HF, which can change in size and growth characteristics as in early baldness or can ultimately degenerate and disappear as in late stages of baldness or in permanent scarring (cicatricial) alopecias. Therefore, the generation of new HF is desirable in the treatment of common baldness as well as less common hair loss conditions, such as discoid lupus erythematosis, congenital hypotrichosis, lichen planopilaris and other scarring alopecias.

SUMMARY OF THE INVENTION

The present invention provides methods of treating baldness in a subject and generating new hair follicles (HF), comprising epidermal disruption and administration of a compound that promotes a differentiation of an uncommitted epidermal cell into a hair follicle cell. The present invention also provides methods for hair removal and inducing hair pigmentation.

In one embodiment, the present invention provides a method for generating a hair follicle in a scalp, eyebrow, or scarred region of a subject, comprising the steps of (a) disrupting the epidermis of the scalp, eyebrow, or scarred region; and (b) contacting the scalp, eyebrow, or scarred region with a compound that promotes a differentiation of an uncommitted epidermal cell into a hair follicle cell, thereby generating a hair follicle in a scalp, eyebrow, or scarred region of a subject.

In another embodiment, the present invention provides a method for generating a hair follicle in a scalp, eyebrow, or scarred region of a subject, comprising the steps of: (a) disrupting the epidermis of the scalp, eyebrow, or scarred region; and (b) contacting the scalp, eyebrow, or scarred region with a factor that promotes a differentiation of an uncommitted epidermal cell into a hair follicle cell, thereby generating a hair follicle in a scalp, eyebrow, or scarred region of a subject.

In another embodiment, the present invention provides a method for treating baldness in a scalp, eyebrow, or scarred region, comprising the steps of: (a) disrupting the epidermis of the scalp, eyebrow, or scarred region; and (b) contacting the scalp, eyebrow, or scarred region with a compound that promotes a differentiation of an uncommitted epidermal cell into a hair follicle (HF) cell, thereby treating baldness in a scalp, eyebrow, or scarred region.

In another embodiment, the present invention provides a method for treating baldness in a scalp, eyebrow, or scarred region, comprising the steps of: (a) disrupting the epidermis of the scalp, eyebrow, or scarred region; and (b) contacting the scalp, eyebrow, or scarred region with a factor that promotes a differentiation of an uncommitted epidermal cell into a HF cell, thereby treating baldness in a scalp, eyebrow, or scarred region. In another embodiment, the baldness is an androgenetic alopecia (AGA)-induced baldness. Each possibility represents a separate embodiment of the present invention.

In another embodiment, the present invention provides a method for removal of an HF from a skin or scalp of a subject, comprising the steps of: (a) disrupting an epidermis of the skin or scalp; and (b) contacting the skin or scalp with either: (i) an EGF protein; (ii) an EGF receptor; (iii) a nucleotide encoding an EGF protein or EGF receptor; or (iv) a compound or factor that activates a EGF protein or EGF receptor, thereby removing an HF from a skin or scalp of a subject.

In another embodiment, the present invention provides a method for increasing a size of a hair follicle in a scalp, eyebrow, or scarred region of a subject, the method comprising the steps of: (a) disrupting an epidermis of the scalp, eyebrow, or scarred region; and (b) contacting the scalp, eyebrow, or scarred region with a compound or factor that promotes a differentiation of an uncommitted epidermal cell into a hair follicle cell, thereby increasing a size of a hair follicle in a scalp, eyebrow, or scarred region of a subject.

In another embodiment, the present invention provides a method for generating a hair follicle in a scalp, eyebrow, or scarred region of a subject, comprising the steps of: (a) disrupting an epidermis of said scalp, eyebrow, or scarred region; and (b) contacting said scalp, eyebrow, or scarred region with a cell selected from (a) a precursor cell that is capable of differentiation into a hair follicle cell; (b) an inductive cell that is capable of inducing differentiation of an uncommitted epidermal cell into a hair follicle cell; or (c) a hair follicle or portion thereof, thereby generating a hair follicle in a scalp, eyebrow, or scarred region of a subject. In another embodiment, step (b) is performed 3-12 days after step (a). Each possibility represents a separate embodiment of the present invention.

In another embodiment, the present invention provides a method for treating an AGA in a scalp, comprising the steps of: (a) disrupting an epidermis of said scalp; and (b) contacting said scalp with a cell selected from (a) a precursor cell that is capable of differentiation into a hair follicle cell; (b) an inductive cell that is capable of inducing differentiation of an uncommitted epidermal cell into a hair follicle cell; or (c) a hair follicle or portion thereof, thereby treating an AGA in a scalp. In another embodiment, step (b) is performed 3-12 days after step (a). Each possibility represents a separate embodiment of the present invention.

BRIEF DESCRIPTION OF THE FIGURES

FIG. 22. Transcripts up-regulated at least 2-fold in activated HF cells, as assessed by dChip analysis. (A). Mean values and standard errors of the up-regulated transcripts in non-activated ("bs-line") and activated ("expt") samples and fold-changes and differences between non-activated and activated values are depicted. (B). Raw data for up-regulated transcripts in non-activated and activated cells. "Ctrl" denotes non-activated and "High-dep" denotes activated cells. (C). Additional information about up-regulated transcripts.

DETAILED DESCRIPTION OF THE INVENTION

Figure 1:
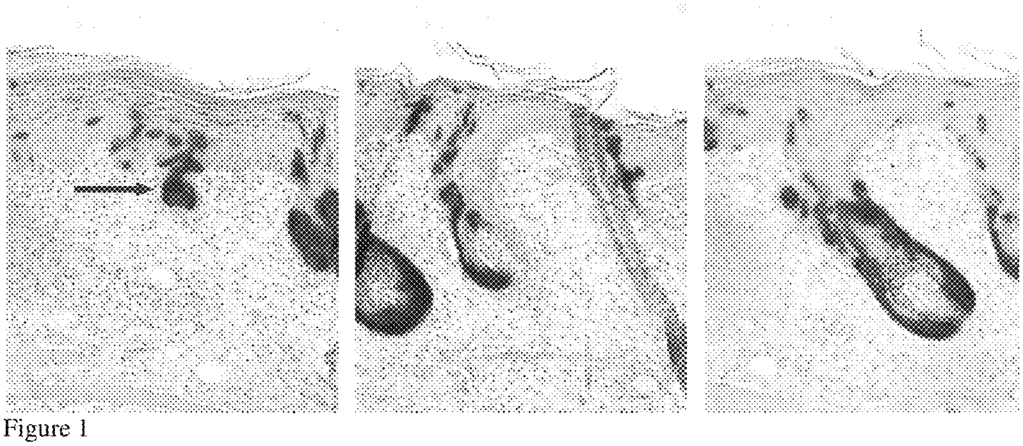
FIG. 1: Epidermal abrasion results in de novo hair follicle (HF) formation. HF at progressive stages of development are depicted in the left, center, and right panels. The arrow in the left panel indicates a hair germ. The dark stained cells are progeny of HF stem cells in the bulge.

The present invention provides methods of treating baldness in a subject and generating new HF, comprising epidermal disruption and administration of a compound that promotes a differentiation of an uncommitted epidermal cell into a hair follicle cell. The present invention also provides methods for hair removal and inducing hair pigmentation.

In one embodiment, the present invention provides a method for generating a hair follicle (HF) in a scalp, eyebrow, or scarred region of a subject, comprising the steps of: (a) disrupting an epidermis of the scalp, eyebrow, or scarred region; and (b) contacting the scalp, eyebrow, or scarred region with a compound that promotes a differentiation of an uncommitted epidermal cell into an HF cell, thereby generating an HF in a scalp, eyebrow, or scarred region of a subject.

In another embodiment, the present invention provides a method for generating an HF in a scalp, eyebrow, or scarred region of a subject, comprising the steps of: (a) disrupting an epidermis of the scalp, eyebrow, or scarred region; and (b) contacting the scalp, eyebrow, or scarred region with a factor that promotes a differentiation of an uncommitted epidermal cell into an HF cell, thereby generating an HF in a scalp, eyebrow, or scarred region of a subject.

In another embodiment, the present invention provides a method for generating a new HF in a scalp, eyebrow, or scarred region of a subject, comprising the steps of: (a) disrupting an epidermis of the scalp, eyebrow, or scarred region; and (b) contacting the scalp, eyebrow, or scarred region with a compound or factor that promotes a differentiation of an uncommitted epidermal cell into a hair follicle cell, thereby generating a new HF in a scalp, eyebrow, or scarred region of a subject.

In another embodiment, the present invention provides a method for increasing the number of HF in a scalp, eyebrow, or scarred region of a subject, comprising the steps of: (a) disrupting an epidermis of the scalp, eyebrow, or scarred region; and (b) contacting the scalp, eyebrow, or scarred region with a compound or factor that promotes a differentiation of an uncommitted epidermal cell into an HF cell, thereby increasing the number of HF in a scalp, eyebrow, or scarred region of a subject.

In another embodiment, the present invention provides a use of a compound or factor that promotes a differentiation of an uncommitted epidermal cell into an HF cell, for the preparation of a pharmaceutical composition for use in a method for generating a hair follicle in a scalp, eyebrow, or scarred region of a subject, the method comprising the steps of: (a) disrupting an epidermis of the scalp, eyebrow, or scarred region; and (b) contacting the scalp, eyebrow, or scarred region with the compound or factor.

In another embodiment, the present invention provides a use of a compound or factor that promotes a differentiation of an uncommitted epidermal cell into an HF cell, for the preparation of a pharmaceutical composition for use in a method for treating baldness in a scalp, eyebrow, or scarred region of a subject, the method comprising the steps of: (a) disrupting an epidermis of the scalp, eyebrow, or scarred region; and (b) contacting the scalp, eyebrow, or scarred region with the compound or factor.

In another embodiment, the present invention provides a use of a compound or factor that promotes a differentiation of an uncommitted epidermal cell into an HF cell, for the preparation of a pharmaceutical composition for use in a method for treating AGA in a scalp of a subject, the method comprising the steps of: (a) disrupting an epidermis of the scalp, eyebrow, or scarred region; and (b) contacting the scalp with the compound or factor.

In another embodiment, the present invention provides a method for increasing a size of a hair follicle in a scalp, eyebrow, or scarred region of a subject, the method comprising the steps of: (a) disrupting an epidermis of the scalp, eyebrow, or scarred region; and (b) contacting the scalp, eyebrow, or scarred region with a compound or factor that promotes a differentiation of an uncommitted epidermal cell into an HF cell, thereby increasing a size of a hair follicle in a scalp, eyebrow, or scarred region of a subject. In another embodiment, the factor is an inhibitor of an EGF protein or an EGFR. In another embodiment, the factor is a Hedgehog protein, a nucleotide encoding same or an activator of same. In another embodiment, the factor is an androgen antagonist. In another embodiment, the factor is any other compound or factor that promotes a differentiation of an uncommitted epidermal cell into an HF cell. Each possibility represents a separate embodiment of the present invention.

In another embodiment, the present invention provides a method for generating a hair follicle in a scalp, eyebrow, or scarred region of a subject, comprising the steps of: (a) disrupting an epidermis of said scalp, eyebrow, or scarred region; and (b) contacting said scalp, eyebrow, or scarred region with a cell selected from (a) a precursor cell that is capable of differentiation into a hair follicle cell; (b) an inductive cell that is capable of inducing differentiation of an uncommitted epidermal cell into a hair follicle cell; or (c) a hair follicle or portion thereof, thereby generating a hair follicle in a scalp, eyebrow, or scarred region of a subject. In another embodiment, step (b) is performed 3-12 days after step (a). Each possibility represents a separate embodiment of the present invention.

The precursor cell of methods and compositions of the present invention, is, in another embodiment, a HF stem cell. In another embodiment, the precursor cell is an epidermal cell. In another embodiment, the precursor cell is a dermal papilla cell. In another embodiment, the precursor cell is a connective tissue sheath cell. In another embodiment, the precursor cell is any other type of cell known in the art that is capable of differentiation into a hair follicle cell. Each possibility represents a separate embodiment of the present invention.

In another embodiment, the present invention provides a method for generating a hair follicle in a scalp, eyebrow, or scarred region of a subject, comprising the steps of: (a) disrupting an epidermis of said scalp, eyebrow, or scarred region; and (b) contacting said scalp, eyebrow, or scarred region with a precursor cell that is capable of differentiation into a hair follicle cell, thereby generating a hair follicle in a scalp, eyebrow, or scarred region of a subject.

In another embodiment, the present invention provides a method for treating an AGA in a scalp, comprising the steps of: (a) disrupting an epidermis of said scalp; and (b) contacting said scalp with a cell selected from (a) a precursor cell that is capable of differentiation into a hair follicle cell; (b) an inductive cell that is capable of inducing differentiation of an uncommitted epidermal cell into a hair follicle cell; or (c) a hair follicle or portion thereof, thereby treating an AGA in a scalp. In another embodiment, step (b) is performed 3-12 days after step (a). Each possibility represents a separate embodiment of the present invention.

In another embodiment, the present invention provides a method for treating an AGA in a scalp, comprising the steps of: (a) disrupting an epidermis of said scalp; and (b) contacting said scalp with a precursor cell that is capable of differentiation into a hair follicle cell, thereby treating an AGA in a scalp.

In another embodiment, the inductive cell is a mesenchymal cell. In another embodiment, the inductive cell is any other type of inductive cell enumerated herein. In another embodiment, the inductive cell is any other type of inductive cell known in the art. Each possibility represents a separate embodiment of the present invention.

"Contacting" as used herein refers, in another embodiment, to bringing the scalp, eyebrow, etc, into to contact with the compound, factor, cell, etc. In another embodiment, the term refers to embedding the compound, factor, cell, etc into the scalp, eyebrow, etc. In another embodiment, the term refers to injecting the compound, factor, cell, etc into the scalp, eyebrow, etc. In another embodiment, term refers to any other type of contacting known in the art. Each possibility represents a separate embodiment of the present invention.

"Promotes a differentiation" refers, in another embodiment, to the act of increasing the percentage of cells that will differentiate as indicated. In another embodiment, the term refers to increasing the number of cells per unit area of skin that will differentiate. In another embodiment, the promoter of differentiation is active in the milieu of the skin. Each possibility represents a separate embodiment of the present invention.

"Uncommitted epidermal cell" refers, in another embodiment, to an epidermal stem cell. In another embodiment, the epidermal cell is a bulge cell. In another embodiment, the epidermal cell is a bulge-derived cell. In another embodiment, the epidermal cell is any other type of cell known in the art that can be induced to differentiate into an HF cell.

The "HF cell" that results from the differentiation is, in another embodiment, an HF stem cell. In another embodiment, the HF cell is a dermal papilla cell. In another embodiment, the HF cell is a bulb cell. In another embodiment, the HF cell is a matrix cell. In another embodiment, the HF cell is a hair shaft cell. In another embodiment, the HF cell is an inner root sheath cell. In another embodiment, the HF cell is an outer root sheath cell. In another embodiment, the HF cell is a melanocyte stem cell. In another embodiment, the HF cell is a melanocyte. Each type of uncommitted epidermal cell and HF cell represents a separate embodiment of the present invention.

In another embodiment, the present invention provides a method for treating baldness in a scalp, eyebrow, or scarred region, comprising the steps of: (a) disrupting an epidermis of the scalp, eyebrow, or scarred region; and (b) contacting the scalp, eyebrow, or scarred region with a compound that promotes a differentiation of an uncommitted epidermal cell into a hair follicle (HF) cell, thereby treating baldness in a scalp, eyebrow, or scarred region. In another embodiment, the baldness is an androgenetic alopecia (AGA)-induced baldness. Each possibility represents a separate embodiment of the present invention.

In another embodiment, the present invention provides a method for treating baldness in a scalp, eyebrow, or scarred region, comprising the steps of: (a) disrupting an epidermis of the scalp, eyebrow, or scarred region; and (b) contacting the scalp, eyebrow, or scarred region with a factor that promotes a differentiation of an uncommitted epidermal cell into a HF cell, thereby treating baldness in a scalp, eyebrow, or scarred region. In another embodiment, the baldness is an androgenetic alopecia (AGA)-induced baldness. Each possibility represents a separate embodiment of the present invention.

In another embodiment, the compound or factor that promotes a differentiation of an uncommitted epidermal cell into a HF cell is administered in a solution. In another embodiment, the compound or factor is administered in a cream. In another embodiment, the compound or factor is administered in an ointment. In another embodiment, the compound or factor is administered in a slow release formulation. In another embodiment, the compound or factor is administered in a liposome encapsulated formulation. In another embodiment, the compound or factor is directly injected. In another embodiment, the compound or factor is administered by any other method known in the art. Each possibility represents a separate embodiment of the present invention.

The compound or factor that promotes a differentiation of an uncommitted epidermal cell into a HF cell is, in another embodiment, an inhibitor of an Epidermal Growth Factor (EGF). In another embodiment, the compound or factor is an inhibitor of an EGF receptor. Each possibility represents a separate embodiment of the present invention.

As provided herein (Example 11), activating one or more pathways in which EGF is involved (by injection of EGF) blocks the formation of HF. Thus, antagonizing the pathway increases HF formation, as demonstrated in Example 12.

In another embodiment, the inhibitor of an EGF or an EGF receptor is panitumumab. In another embodiment, the inhibitor is AG1478. In another embodiment, the inhibitor is nimotuzumab. In another embodiment, the inhibitor is an antibody that binds EGF or EGFR. In another embodiment, the inhibitor is HuMax-EGFR® (Genmab, Copenhagen, Denmark). In another embodiment, the inhibitor is cetuximab. In another embodiment, the inhibitor is IMC 11F8. In another embodiment, the inhibitor is matuzumab. In another embodiment, the inhibitor is SC 100. In another embodiment, the inhibitor is ALT 110. In another embodiment, the inhibitor is PX 1032. In another embodiment, the inhibitor is BMS 599626. In another embodiment, the inhibitor is MDX 214. In another embodiment, the inhibitor is PX 1041. In another embodiment, the inhibitor is any other inhibitor of an EGF or an EGF receptor known in the art. Each possibility represents a separate embodiment of the present invention.

In another embodiment, the compound or factor that promotes a differentiation of an uncommitted epidermal cell into a HF cell is an inhibitor of a tyrosine kinase activity of an EGF receptor. In another embodiment, the inhibitor is gefitinib. In another embodiment, the inhibitor is erlotinib. In another embodiment, the inhibitor is canertinib. In another embodiment, the inhibitor is leflunomide. In another embodiment, the inhibitor is A77 1726. In another embodiment, the inhibitor is pelitinib. In another embodiment, the inhibitor is ZD 1839. In another embodiment, the inhibitor is CL 387785. In another embodiment, the inhibitor is EKI 785. In another embodiment, the inhibitor is vandetanib. In another embodiment, the inhibitor is any other inhibitor of a tyrosine kinase activity of an EGF receptor known in the art. Each possibility represents a separate embodiment of the present invention.

In another embodiment, the EGF or EGFR antagonist is a carboxypeptidase inhibitor from potato (PCI) protein or a homologue, fragment or mimetic thereof. In another embodiment, the EGF or EGFR antagonist is a sprouty protein or a homologue, fragment or mimetic thereof. In another embodiment, the EGF or EGFR antagonist is an Argos protein or a homologue, fragment or mimetic thereof. In another embodiment, the EGF or EGFR antagonist is a lefty protein or a homologue, fragment or mimetic thereof. In another embodiment, the EGF or EGFR antagonist is an antibody that recognizes EGF or EGFR, or a fragment or mimetic thereof. In another embodiment, the EGF or EGFR antagonist is small molecule inhibitor that binds and reduces the activity of EGF or EGFR. In another embodiment, the EGF or EGFR antagonist is CRM197. In another embodiment, the EGF or EGFR antagonist is IMC-C225 (ImClone Systems, New York, N.Y.). In another embodiment, the EGF or EGFR antagonist is any other antagonist of EGF or EGFR known in the art. Each possibility represents a separate embodiment of the present invention.

In another embodiment, the present invention provides a use of an inhibitor of an EGF protein or an EGF receptor for the preparation of a pharmaceutical composition for use in a method for generating a hair follicle in a scalp, eyebrow, or scarred region of a subject, the method comprising the steps of: (a) disrupting an epidermis of the scalp, eyebrow, or scarred region; and (b) contacting the scalp, eyebrow, or scarred region with the inhibitor of an EGF protein or an EGF receptor.

In another embodiment, the present invention provides a use of an inhibitor of an EGF protein or an EGF receptor for the preparation of a pharmaceutical composition for use in a method for treating baldness in a scalp, eyebrow, or scarred region of a subject, the method comprising the steps of: (a) disrupting an epidermis of the scalp, eyebrow, or scarred region; and (b) contacting the scalp, eyebrow, or scarred region with the inhibitor of an EGF protein or an EGF receptor.

In another embodiment, the present invention provides a use of an inhibitor of an EGF protein or an EGF receptor for the preparation of a pharmaceutical composition for use in a method for treating AGA in a scalp of a subject, the method comprising the steps of: (a) disrupting an epidermis of the scalp, eyebrow, or scarred region; and (b) contacting the scalp with the inhibitor of an EGF protein or an EGF receptor.

In another embodiment, the compound or factor that promotes a differentiation of an uncommitted epidermal cell into a HF cell is a β-catenin protein. In another embodiment, the compound or factor is a nucleotide that encodes a β-catenin protein. In another embodiment, the compound or factor is an activator of a β-catenin protein. In another embodiment, the compound or factor is an inhibitor of a protein that suppresses an activity of the β-catenin protein. Each possibility represents a separate embodiment of the present invention.

In another embodiment, the present invention provides a use of (a) a β-catenin protein; (b) a nucleotide encoding a β-catenin protein; or (c) a compound or factor that activates a β-catenin protein, for the preparation of a pharmaceutical composition for use in a method for generating a hair follicle in a scalp, eyebrow, or scarred region of a subject, the method comprising the steps of: (a) disrupting an epidermis of the scalp, eyebrow, or scarred region; and (b) contacting the scalp, eyebrow, or scarred region with the β-catenin protein, nucleotide, compound or factor.

In another embodiment, the present invention provides a use of (a) a β-catenin protein; (b) a nucleotide encoding a β-catenin protein; or (c) a compound or factor that activates a β-catenin protein, for the preparation of a pharmaceutical composition for use in a method for treating baldness in a scalp, eyebrow, or scarred region of a subject, the method comprising the steps of (a) disrupting an epidermis of the scalp, eyebrow, or scarred region; and (b) contacting the scalp, eyebrow, or scarred region with the β-catenin protein, nucleotide, compound or factor.

In another embodiment, the present invention provides a use of (a) a β-catenin protein; (b) a nucleotide encoding a β-catenin protein; or (c) a compound or factor that activates a β-catenin protein, for the preparation of a pharmaceutical composition for use in a method for treating AGA in a scalp of a subject, the method comprising the steps of: (a) disrupting an epidermis of the scalp, eyebrow, or scarred region; and (b) contacting the scalp with the β-catenin protein, nucleotide, compound or factor.

In another embodiment, the compound or factor that promotes a differentiation of an uncommitted epidermal cell into a HF cell is a fibroblast growth factor (FGF) protein. In another embodiment, the compound or factor is a nucleotide that encodes an FGF protein. In another embodiment, the compound or factor is an FGF receptor. In another embodiment, the compound or factor is a nucleotide that encodes an FGF receptor. In another embodiment, the compound or factor is an activator of an FGF protein. In another embodiment, the compound or factor is an activator of FGF receptor. In another embodiment, the compound or factor is an inhibitor of a protein that suppresses an activity of the FGF protein or FGF receptor. In another embodiment, the protein that is inhibited is an FGF binding protein. In another embodiment, the protein that is inhibited is FGF-bp1. Each possibility represents a separate embodiment of the present invention.

Is provided herein, FGF and its receptor are upregulated, under the conditions utilized herein, upon HF stem cell differentiation (Example 9). Moreover, FGF-bp1 is down-regulated, under the conditions utilized herein, upon HF stem cell differentiation. Thus, FGF and its receptor promote differentiation of uncommitted epidermal cells into HF cells.

In another embodiment, the compound or factor that promotes a differentiation of an uncommitted epidermal cell into a HF cell is an ectodysplasin protein (referred to, in another embodiment, as "eda"; in another embodiment, as "ectodermodysplasin protein.") In another embodiment, the ectodysplasin protein is Eda-A1. In another embodiment, the compound or factor is an ectodysplasin receptor (referred to, in another embodiment, as "edar"). In another embodiment, the compound or factor is an activator of an ectodysplasin protein. In another embodiment, the compound or factor is an activator of an ectodysplasin receptor. In another embodiment, the compound or factor is an inhibitor of a protein that suppresses an activity of the ectodysplasin protein or ectodysplasin receptor. Each possibility represents a separate embodiment of the present invention.

In another embodiment, the eda protein of methods and compositions of the present invention has the sequence:
MGYPEVERRELLPAAAPRERGSQGCGCGGAPAR-
AGEGNSCLLFLGFFGLSLALHLLTLCC YLELRSELR-
RERGAESRLGGSGTPGTSGTLSSLGGLDPDSPITSHL-
GQPSPKQQPLEPGEAAL
HSDSQDGHQMALLNFFFPDEKPYSEEESRRVR-
RNKRSKSNEGADGPVKNKKKGKKAGPP GPNGPPG-
PPGPPGPQGPPGIPGIPGIPGTTVMGPPGPPGPPGPQG-
PPGLQGPSGAADKAGTR
ENQPAVVHLQGQGSAIQVKNDLSGGVLNDWSRITM-
NPKVFKLHPRSGELEVLVDGTYFIY SQVEVYYIN-
FTDFASYEVVVDEKPFLQCTRSIETGKTNYNT-
CYTAGVCLLKARQKIAVKM
VHADISINMSKHTTFFGAIRLGEAPAS (GenBank Accession No: NM_001399; SEQ ID No: 274). In another embodiment, the eda protein has a sequence selected from the sequences set forth in GenBank entries NM_001005609, NM_001005610, NM_001005611, NM_001005612, NM_001005613, NM_001005614, NM_001005615, AF040628, AF061194, AF061193, AF061192, AF061191, AF061190, AF061189, and AF060999. In another embodiment, the eda protein is encoded by a nucleic acid molecule having a sequence set forth in the one of the above GenBank entries. In another embodiment, a biologically active fragment of an Eda protein is utilized in a method of the present invention. Each possibility represents a separate embodiment of the present invention.

In another embodiment, the edar protein of methods and compositions of the present invention has the sequence:

MAHVGDCTQTPWLPVLVVSLMCSARAEYSNC-GENEYYNQTTGLCQECPPCGPGEEPYLS CGYGTKD-EDYGCVPCPAEKFSKGGYQICRRHKDCEGFFRATV-LTPGDMENDAECGPCLP GYYMLENRPRNIYGMVCYSCLLAPPNTKECVGATS-GASANFPGTSGSSTLSPFQHAHKELS GQGHLATALI-IAMSTWIMAIAIVLIIMFYILKTKPSAPACCTSHPGKS-VEAQVSKDEEKKEAP DNVVMFSEKDEFEKLTATPAKPTKSENDASS-ENEQLLSRSVDSDEEPAPDKQGSPELCLLS LVHLAREKSATSNKSAGIQSRRKKILDVYANVCGV-VEGLSPTELPFDCLEKTSRMLSSTYN SEKAVVKT-WRHLAESFGLKRDEIGGMTDGMQLFDRISTAGYSIP-ELLTKLVQIERLDAVES LCADILEWAGVVPPASQPHAAS (GenBank Accession No: BC093872; SEQ ID No: 275). In another embodiment, the edar protein has a sequence selected from the sequences set forth in GenBank entries BC093870; BC034919; NM_021783; NM_022336; AY152724; AF298812; AH008077; AF130996; AF130988. In another embodiment, the edar protein is encoded by a nucleic acid molecule having a sequence set forth in the one of the above GenBank entries. In, another embodiment, a biologically active fragment of an Edar protein is utilized in a method of the present invention. Each possibility represents a separate embodiment of the present invention.

In another embodiment, the compound or factor that promotes a differentiation of an uncommitted epidermal cell into a HF cell is a Noggin protein. In another embodiment, the compound or factor is a nucleotide encoding a Noggin protein. In another embodiment, the compound or factor is an activator of a Noggin protein. In another embodiment, the compound or factor is an inhibitor of a protein that suppresses an activity of the Noggin protein. Each possibility represents a separate embodiment of the present invention.

In another embodiment, the Noggin protein of methods and compositions of the present invention has the sequence: MERCPSLGVTLYALVVVLGLRATPAGGQHYLHIRP-APSDNLPLVDLEEHPDPIFDPKEKDLNE TLLRSLLG-GHYDPGFMATSPPEDRPGGGGGAAGGAEDLAEL-DQLLRQRPSGAMPSEIKGLE FSEGLAQGKKQRLSKKLRRKLQMWLWSQTFCPV-LYAWNDLGSRFWPRYVKVGSCFSKRS CSVPEGM-VCKPSKSVHLTVLRWRCQRRGGQRCGWIPIQYPI-ISECKCSC (GenBank Accession No: NM_005450; SEQ ID No: 276). In another embodiment, the Noggin protein has a sequence selected from the sequences set forth in GenBank entries BC034027 and U31202. In another embodiment, the Noggin protein is encoded by a nucleic acid molecule having a sequence set forth in the one of the above GenBank entries. In another embodiment, a biologically active fragment of a Noggin protein is utilized in a method of the present invention. Each possibility represents a separate embodiment of the present invention.

In another embodiment, the compound or factor that promotes a differentiation of an uncommitted epidermal cell into a HF cell is a Hedgehog protein. In another embodiment, the compound or factor is a nucleotide encoding a Hedgehog protein. In another embodiment, the compound or factor is an activator of a Hedgehog protein. In another embodiment, the compound or factor is a sonic Hedgehog protein. In another embodiment, the compound or factor is a nucleotide encoding a sonic Hedgehog protein. In another embodiment, the compound or factor is an activator of a sonic Hedgehog protein. Each possibility represents a separate embodiment of the present invention.

In another embodiment, the Hedgehog protein of methods and compositions of the present invention has the sequence set forth in GenBank Accession No. NM_000193. In another embodiment, the Hedgehog protein has a sequence selected from those set forth in GenBank entries L38518 and NP_000184. In another embodiment, the Hedgehog protein has any other Hedgehog sequence known in the art. In another embodiment, the Hedgehog protein has any other sonic Hedgehog sequence known in the art. Each possibility represents a separate embodiment of the present invention.

In another embodiment, the compound or factor that promotes a differentiation of an uncommitted epidermal cell into a HF cell is a Transforming Growth Factor (TGF)-beta1 protein. In another embodiment, the compound or factor is a nucleotide encoding a TGF-beta1 protein. In another embodiment, the compound or factor is an activator of a TGF-beta1 protein. In another embodiment, the compound or factor is a TGF-beta3 protein. In another embodiment, the compound or factor is a nucleotide encoding a TGF-beta3 protein. In another embodiment, the compound or factor is an activator of a TGF-beta3 protein. In another embodiment, the compound or factor is an antagonist of a TGF-beta1 protein. In another embodiment, the compound or factor is an antagonist of a TGF-beta3 protein. Each possibility represents a separate embodiment of the present invention.

In another embodiment, the TGF-beta1 protein of methods and compositions of the present invention has the sequence set forth in GenBank Accession No. BC000125. In another embodiment, the Hedgehog protein has a sequence selected from those set forth in GenBank entries BC001180, BC022242, and NM_000660. In another embodiment, the TGF-beta1 protein has any other TGF-beta1 sequence known in the art. Each possibility represents a separate embodiment of the present invention.

In another embodiment, the TGF-beta3 protein of methods and compositions of the present invention has the sequence set forth in GenBank Accession No. J03241. In another embodiment, the Hedgehog protein has a sequence selected from those set forth in GenBank entries NM_003239, BC018503, BT007287 and X14149. In another embodiment, the TGF-beta3 protein has any other TGF-beta3 sequence known in the art. Each possibility represents a separate embodiment of the present invention.

In another embodiment, the compound or factor that promotes a differentiation of an uncommitted epidermal cell into a HF cell acts directly on the uncommitted epidermal cell. In another embodiment, the compound or factor acts on the uncommitted epidermal cell via a mesenchymal cell. Each possibility represents a separate embodiment of the present invention.

In another embodiment, the mesenchymal cell is a dermal condensate cell. In another embodiment, the mesenchymal cell is a DP cell. In another embodiment, the mesenchymal cell is another cell type or differentiation stage in the dermal condensate-DP lineage. In another embodiment, the mesenchymal cell is any other type of mesenchymal cell known in the art. Each possibility represents a separate embodiment of the present invention.

The EGFR of methods and compositions of the present invention has, in another embodiment, the sequence: MRPSGTAGAALLALLAALCPASRALEEKKVC-QGTSNKLTQLGTFEDHFLSLQRMFNNCEV VLGNLE-ITYVQRNYDLSFLKTIQEVAGYVLIALNTVERIPLEN-LQIIRGNMYYENSYALAVL SNYDANKTGLKELPMRNLQEILHGAVRFSNNPALCN-VESIQWRDIVSSDFLSNMSMDFQN HLGSCQKCDP-SCPNGSCWGAGEENCQKLTKJICAQQCSGRCRGK- SPSDCCHNQCAAGCTG PRESDCLVCRKFRDEATCKDTCPPLMLYNPTTYQMD-VNPEGKYSFGATCVKKCPRNYVV TDHGSCVRAC-GADSYEMEEDGVRKCKKCEGPCRKVCNGI-GIGEFKDSLSINATNIKHFKN CTSISGDLHILPVAFRGDSFTHTPPLDPQELDILKT-VKEITGFLLIQAWPENRTDLHAFENLEII RGRTKQH-GQFSLAVVSLNITSLGLRSLKEISDGDVIISGNKNLCY-ANTINWKKLFGTSGQKT KIISNRGENSCKATGQVCHALCSPEGCWGPEPRD-CVSCRNVSRGRECVDKCNLLEGEPREF VENSECI-QCHPECLPQAMNITCTGRGPDNCIQCAHYIDGPH-CVKTCPAGVMGENNTLVWK YADAGHVCHLCHPNCTYGCTGPGLEGCPTNGPKIP-SIATGMVGALLLLLVVALGIGLFMR RRHIVRKRTLR-RLLQERELVEPLTPSGEAPNQALLRILKETEFKKIKV-LGSGAFGTVYKGLW IPEGEKVKIPVAIKELREATSPKANKEILDEAYVMAS-VDNPHVCRLLGICLTSTVQLITQLMP FGCLLDYVRE-HKDNIGSQYLLNWCVQIAKGMNYLEDRRLVHRD-LAARNVLVKTPQHVKI TDFGLAKLLGAEEKEYHAEGGKVPIKWMALE-SILHRIYTHQSDVWSYGVTVWELMTFGS KPYDGIPA-SEISSILEKGERLPQPPICTIDVYMIMVKCWMIDAD-SRPKFRELIIEFSKMARDPQ RYLVIQGDERMHLPSPTDSNFYRALMDEEDMDDV-VDADEYLIPQQGFFSSPSTSRTPLLSS LSATSNNST-VACIDRNGLQSCPIKEDSFLQRYSSDPTGALTEDSID-DTFLPVPEYINQSVPKR PAGSVQNPVYHNQPLNPAPSRDPHYQDPHSTAVGN-PEYLNTVQPTCVNSTFDSPAHWAQ KGSHQISLDN-PDYQQDFFPKEAKPNGIFKGSTAENAEYLRVAPQSSE-FIGA (GenBank Accession No: NM_005228; SEQ ID No: 277). In another embodiment, the EGFR has a sequence selected from the sequences set forth in GenBank entries NM_201282, NM_201283, NM_201284, BC094761, AF288738, AY588246, AY573061, X17054, AF125253, U48722, K03193, and AY698024. In another embodiment, the EGFR is encoded by a nucleic acid molecule having a sequence set forth in the one of the above GenBank entries. In another embodiment, a biologically active fragment of an EGFR is utilized in a method of the present invention. Each possibility represents a separate embodiment of the present invention.

The EGF of methods and compositions of the present invention has, in another embodiment, the sequence: MLLTLIILLPVVSKFSFVSLSAPQHWSCPEGTLA-GNGNSTCVGPAPFLIFSHGNSIFRIDTEGTN YEQLV-VDAGVSVIMDFHYNEKRIYWVDLERQLLQRVFLNG-SRQERVCNIEKNVSGMAINW INEEVIWSNQQEGIITVTDMKGNNSHILLSALKYPAN-VAVDPVERFIFWSSEVAGSLYRADL DGVGVKALLET-SEKITAVSLDVLDKRLFWIQYNREGSNSLICSCDY-DGGSVHISKHPTQHNL FAMSLFGDRIFYSTWKMKTIWIANKHTGKDMVRIN-LHSSFVPLGELKVVHPLAQPKAEDDT WEPEQKLCK-LRKGNCSSTVCGQDLQSHLCMCAEG-YALSRDRKYCEDVNECAFWNHGCTL GCKNTPGSYYCTCPVGFVLLPDGKRCHQLVSCPRN-VSECSHDCVLTSEGPLCFCPEGSVLER DGKTCSGC-SSPDNGGCSQLCVPLSPVSWECDCFPGY-DLQLDEKSCAASGPQPFLLFANSQDI RHMHFDGTDYGTLLSQQMGMVYALDHDPVENKIY-FAHTALKWIERANMDGSQRERLIEE GVD-VPEGLAVDWIGRRFYWTDRGKSLIGRSDLNG-KRSKIITKENISQPRGIAVHPMAKRLFW TDTGINPRIESSSLQGLGRLVIASSDLIWPSGITIDFLT-DKLYWCDAKQSVIEMANLDGSKRRR LTQNDVGHP-FAVAVFEDYVWFSDWAMPSVIRVNKRTGKDRVR-LQGSMLKPSSLVVVHPL AKPGADPCLYQNGGCEHICKKRLGTAWCSCREGFM-KASDGKTCLALDGHQLLAGGEVDL KNQVTPLDIL-SKTRVSEDNITESQHMLVAEIMVSDQDDCAPVGCSM-YARCISEGEDATCQC LKGFAGDGKLCSDIDECEMGVPVCPPASSKCINTEG-GYVCRCSEGYQGDGIHCLDIDECQLG VHSCGENA-SCTNTEGGYTCMCAGRLSEPGLICPDSTPPPHLRED-DHHYSVRNSDSECPLSHD GYCLHDGVCMYIEALDKYACNCVVGYIGERC-QYRDLKWWELRHAGHGQQQKVIVVAVC VVV-LVMLLLLSLWGAHYYRTQKLLSKNPKNPYEESSRD-VRSRRPADTEDGMSSCPQPWFV VIKEHQDLKNG-GQPVAGEDGQAADGSMQPTSWRQEPQLCGMGTE-QGCWIPVSSDKGSCP QVMERSFHMPSYGTQTLEG-GVEKPHSLLSANPLWQQRALDPPHQMELTQ (GenBank Accession No: NM_001963; SEQ ID No: 278). In another embodiment, the EGF has a sequence selected from the sequences set forth in GenBank entries BC093731, AY548762, and X04571. In another embodiment, the EGF is encoded by a nucleic acid molecule having a sequence set forth in the one of the above GenBank entries. In another embodiment, a biologically active fragment of an EGF is utilized in a method of the present invention. Each possibility represents a separate embodiment of the present invention.

The beta-catenin protein of methods and compositions of the present invention has, in another embodiment, the sequence: MATQADLMELDMAMEPDRKAAVSHWQQQSYLDS-GIHSGATTTAPSLSGKGNPEEEDVDT SQVLY-EWEQGFSQSFTQEQVADIDGQYAMTRAQRVRAAMF-PETLDEGMQIPSTQFDAAHP TNVQRLAEPSQMLKHAVVNLINYQDDAELATRAI-PELTKLLNDEDQVVVNKAAVMVHQLS KKEAS-RHAIMRSPQMVSAIVRTMQNTND-VETARCTAGTLHNLSHHREGLLAIFKSGGIPAL VKMLGSPVDSVLFYAITTLHNLLLHQEGAKMAVR-LAGGLQKMVALLNKTNVKFLAITTDC LQILAYGN-QESKLIILASGGPQALVNIMRTYTYEKLLWTTSRVLK-VLSVCSSNKPAIVEAGG MQALGLHLTDPSQRLVQNCLWTLRNLSDAATKQEG-MEGLLGTLVQLLGSDDINVVTCAAG ILSNLTCN-NYKNKMMVCQVGGIEALVRTVLRAGDREDITEPA-ICALRHLTSRHQEAEMAQN AVRLHYGLPVVVKLLHPPSHWPLIKATVGLIRNLAL-CPANHAPLREQGAIPRLVQLLVRAHQ DTQRRTSMG-GTQQQFVEGVRMEEIVEGCTGALHILARDVHNRIV-IRGLNTIPLFVQLLYSPIE NIQRVAAGVLCELAQDKEAAEMEAEGATAPLTELLH-SRNEGVATYAAAVLFRMSEDKPQD YKKRLSVELTSS-LFRTEPMAWNETADLGLDIGAQGEPLGYRQD-DPSYRSFHSGGYGQDALG MDPMMEHEMGGHHPGADYPVDGLPDLGHAQDLM-DGLPPGDSNQLAWFDTDL (GenBank Accession No: NM_001904; SEQ ID No: 279). In another embodiment, the beta-catenin protein has a sequence selected from the sequences set forth in GenBank entries BC058926, X87838, AF130085, AB062292, Z19054, and NP_001895. In another embodiment, the beta-catenin protein is encoded by a nucleic acid molecule having a sequence set forth in the one of the above GenBank entries. In another embodiment, a biologically active fragment of a beta-catenin protein is utilized in a method of the present invention. Each possibility represents a separate embodiment of the present invention.

The Wnt protein of methods and compositions of the present invention has, in another embodiment, the sequence: MNRKARRCLGHLFLSLGMVYLRIGGFSSVVALGASI-ICNKIPGLAPRQRAICQSRPDAIIVIGE GSQMGLDEC-QFQFRNGRWNCSALGERTVFGKELKVGSREAAF-TYAIIAAGVAHAITAACT QGNLSDCGCDKEKQGQYHRDEGWKWGGCSADIRY-GIGFAKVFVDAREIKQNARTLMNLH NNEAGRKI-LEENMKLECKCHGVSGSCTTKTCWTTLPQFREL-GYVLKDKYNEAVHVEPVRA SRNKRPTFLKIKKPLSYRKPMDTDLVYIEKSPNY-CEEDPVTGSVGTQGRACNKTAPQASGC DLMC-CGRGYNTHQYARVWQCNCKFHWCCYVKCNTCSER-TEMYTCK (GenBank Accession No: BC008811; SEQ ID No: 280). In another embodiment, the Wnt protein has a sequence selected from the sequences set forth in GenBank entries NM_004625, D83175, U53476, and NP_004616. In another embodiment, the Wnt protein is a Wnt7 protein. In another embodiment, the Wnt protein is a Wnt7a protein. In another embodiment, the Wnt protein is Wnt1 protein. In another embodiment, the Wnt protein is a Wnt3 protein. In another embodiment, the Wnt protein is a Wnt3a protein. In another embodiment, the Wnt protein is a Wnt10 protein. In another embodiment, the Wnt protein is a Wnt10a protein. In another embodiment, the Wnt protein is a Wnt10b protein. In another embodiment, the Wnt protein is encoded by a nucleic acid molecule having a sequence set forth in the one of the above GenBank entries. In another embodiment, a biologically active fragment of a Wnt protein is utilized in a method of the present invention. In another embodiment, a biologically active fragment of a Wnt7 protein is utilized in a method of the present invention. In another embodiment, a biologically active fragment of a Wnt7a protein is utilized in a method of the present invention. Each possibility represents a separate embodiment of the present invention.

In another embodiment, the compound or factor that promotes a differentiation of an uncommitted epidermal cell into a HF cell is a protein encoded by a ribonucleic acid (RNA) molecule having a sequence selected from the sequences set forth in SEQ ID No: 1-232. In another embodiment, the compound or factor is an RNA molecule having a sequence selected from SEQ ID No: 1-232. In another embodiment, the RNA molecule is homologous to a sequence selected from SEQ ID No: 1-232. In another embodiment, the RNA molecule is an isoform of a sequence selected from SEQ ID No: 1-232. In another embodiment, the compound or factor increases an activity of a protein encoded by an RNA molecule having a sequence selected from SEQ ID No: 1-232. In another embodiment, the compound or factor increases an expression or level of a protein encoded by an RNA molecule having a sequence selected from SEQ ID No: 1-232. Each possibility represents a separate embodiment of the present invention.

As provided herein, the transcripts depicted in Table 3 (Example 8; SEQ ID No: 1-232), the proteins they encode, and the pathways in which the proteins participate contribute significantly to HF stem cell activation. Accordingly, under the conditions utilized herein, anagen can be induced by activation of these transcripts, proteins, and pathways. Activation of the transcripts, proteins, and pathways depicted in Table 3 is thus a method for enhancing EDIHN. In another embodiment, activation of these transcripts, proteins, and pathways represents a method for enhancing hair growth in a subject.

In another embodiment, the compound or factor that promotes a differentiation of an uncommitted epidermal cell into a HF cell is a protein encoded by an RNA molecule having a sequence selected from the sequences set forth in SEQ ID No: 233-257. In another embodiment, the compound or factor is an RNA molecule having a sequence selected from SEQ ID No: 233-257. In another embodiment, the RNA molecule is homologous to a sequence selected from SEQ ID No: 233-257. In another embodiment, the RNA molecule is an isoform of a sequence selected from SEQ ID No: 233-257. In another embodiment, the compound or factor increases an activity of a protein encoded by an RNA molecule having a sequence selected from SEQ ID No: 233-257. In another embodiment, the compound or factor increases an expression or level of a protein encoded by an RNA molecule having a sequence selected from SEQ ID No: 233-257. Each possibility represents a separate embodiment of the present invention.

As provided herein, the transcripts depicted in Table 4 (Example 9; SEQ ID No: 233-257), the proteins they encode, and the pathways in which the proteins participate, contribute significantly, under the conditions utilized herein, to induction of epidermal cells to differentiate into HF stem cells. Activation of the transcripts, proteins, and pathways depicted in Table 4 is thus a method for enhancing EDIHN. In another embodiment, activation of these transcripts, proteins, and pathways represents a method for enhancing hair growth in a subject.

In another embodiment, the compound or factor that promotes a differentiation of an uncommitted epidermal cell into a HF cell is a compound or factor that decreases an activity of a protein encoded by an RNA molecule having a sequence selected from the sequences set forth in SEQ ID No: 258-273. In another embodiment, the compound or factor decreases an expression or level of a protein encoded by an RNA molecule having a sequence selected from SEQ ID No: 258-273. Each possibility represents a separate embodiment of the present invention.

As demonstrated by findings of the present invention, the transcripts depicted in Table 5 (Example 9; SEQ ID No: 258-273), the proteins they encode, and the pathways in which the proteins participate, contribute significantly, under the conditions utilized herein, to preventing induction of epidermal cells to differentiate into HF stem cells. Inhibition of the transcripts, proteins, and pathways depicted in Table 5 is thus a method for enhancing EDIHN. In another embodiment, inhibition of these transcripts, proteins, and pathways represents a method for induction of hair growth in a subject.

In one embodiment, the compound that modulates a protein encoded by an RNA molecule having a sequence selected from the sequences set forth in SEQ ID No: 233-273 or the nucleic acid encoding same is administered before the compound that modulates a protein encoded by an RNA molecule having a sequence selected from the sequences set forth in SEQ ID No: 1-232 or the nucleic acid encoding same. In another embodiment, the two compounds are administered simultaneously. Each possibility represents a separate embodiment of the present invention.

In one embodiment, a protein encoded by an RNA sequence selected from SEQ ID No: 1-273, or a compound that modulates the protein, is administered before other proteins encoded by same or compounds that modulate them, in order to further enhance their effect in generating an HF or stimulating hair growth: In another embodiment, the wnt pathway is stimulated before the hedgehog pathway. In another embodiment, the two pathways are stimulated in an overlapping fashion. In another embodiment, the two pathways are stimulated simultaneously. Each possibility represents a separate embodiment of the present invention.

In another embodiment, activating or decreasing expression of an RNA transcript in methods of the present invention occurs via a transcription mechanism (e.g. activation of expression of the RNA). In another embodiment, activating or decreasing expression of the RNA transcript occurs via a translational mechanism. In another embodiment, activating or decreasing expression of the RNA transcript occurs via a post-translational mechanism. Each possibility represents a separate embodiment of the present invention.

In another embodiment, the nucleic acid molecule utilized in methods of the present invention is a deoxyribonucleic acid (DNA) molecule that encodes an RNA molecule having a sequence selected from the sequences set forth in the present invention.

In one embodiment, an RNA molecule of the present invention encodes a protein that plays a role in HF regeneration. In another embodiment, the RNA molecule is itself catalytically active, e.g., a ribozyme, etc. Each possibility represents a separate embodiment of the present invention.

In another embodiment, the compound or factor that promotes a differentiation of an uncommitted epidermal cell into a HF cell is a compound or factor that promotes placodal cell fate. As provided herein, factors that promote placodal cell fate enhance EDIHN, as exemplified in the Examples herein. In another embodiment, the compound or factor acts at the placode stage of HF development.

In another embodiment, the compound or factor inhibits a biological factor that inhibits a differentiation of an uncommitted epithelial cell into an HF cell.

In another embodiment of methods and compositions of the present invention, a composition comprising one of the above compounds or factors is administered. Each of the above types of compounds, factors, and compositions represents a separate embodiment of the present invention.

In one embodiment, the present invention provides a method for generating an HF in a scalp, eyebrow, or scarred region of a subject, comprising the steps of: (a) disrupting an epidermis of the scalp, eyebrow, or scarred region; and (b) contacting the scalp, eyebrow, or scarred region with minoxidil, thereby generating an HF in a scalp, eyebrow, or scarred region of a subject.

In one embodiment, the present invention provides a method for treating baldness in a scalp, eyebrow, or scarred region of a subject, comprising the steps of: (a) disrupting an epidermis of the scalp, eyebrow, or scarred region; and (b) contacting the scalp, eyebrow, or scarred region with minoxidil, thereby treating baldness in a scalp, eyebrow, or scarred region of a subject.

In another embodiment, the present invention provides a use of minoxidil for the preparation of a pharmaceutical composition for use in a method for an HF in a scalp, eyebrow, or scarred region of a subject, the method comprising the steps of: (a) disrupting an epidermis of the scalp, eyebrow, or scarred region; and (b) contacting the scalp, eyebrow, or scarred region with the minoxidil.

In another embodiment, the present invention provides a use of minoxidil for the preparation of a pharmaceutical composition for use in a method for treating baldness in a scalp, eyebrow, or scarred region of a subject, the method comprising the steps of: (a) disrupting an epidermis of the scalp, eyebrow, or scarred region; and (b) contacting the scalp, eyebrow, or scarred region with the minoxidil.

In another embodiment, the present invention provides a method for removal of an HF from a skin or scalp of a subject, comprising the steps of (a) disrupting an epidermis of the skin or scalp; and (b) contacting the skin or scalp with either: (i) an EGF protein; (ii) an EGF receptor; (iii) a nucleotide encoding an EGF protein or EGF receptor; or (iv) a compound or factor that activates a EGF protein or EGF receptor, thereby removing an HF from a skin or scalp of a subject.

In another embodiment, the present invention provides a method for hair removal from a skin or scalp of a subject, comprising the steps of: (a) disrupting an epidermis of the skin or scalp; and (b) contacting the skin or scalp with either: (i) an EGF protein; (ii) an EGF receptor; (iii) a nucleotide encoding an EGF protein or EGF receptor; or (iv) a compound or factor that activates a EGF protein or EGF receptor, thereby removing hair from a skin or scalp of a subject. In another embodiment, the epidermal disruption is light dermabrasion. In another embodiment, the epidermal disruption is a non-scarring method. In another embodiment, administration of the EGF protein, EGF receptor, nucleotide, compound, or factor suppresses HF formation. In another embodiment, the EGF protein, EGF receptor, nucleotide, compound, or factor is administered within several days of healing. In another embodiment, the EGF protein, EGF receptor, nucleotide, compound, or factor is administered within about 1 day of healing. In another embodiment, the EGF protein, EGF receptor, nucleotide, compound, or factor is administered according to any of the timing embodiments enumerated herein for Dkk1 protein. Each possibility represents a separate embodiment of the present invention.

In another embodiment, the present invention provides a use of either: (i) an EGF protein; (ii) an EGF receptor; (iii) a nucleotide encoding an EGF protein or EGF receptor; or (iv) a compound or factor that activates a EGF protein or EGF receptor, for the preparation of a pharmaceutical composition for use in a method for removal of an HF from a skin or scalp of a subject, the method comprising the steps of: (a) disrupting an epidermis of the scalp, eyebrow, or scarred region; and (b) contacting the scalp, eyebrow, or scarred region with the EGF protein, EGF receptor, nucleotide, compound, or factor.

In another embodiment, a composition or method of the present invention is utilized on human skin. In another embodiment, the composition or method is utilized on an area of unwanted hair growth. In another embodiment, the area is the face. In another embodiment, the area is the bikini area. In another embodiment, the area is the legs. In another embodiment, the area is the arms. In another embodiment, the area is the chest.

An "inhibitor" utilized in methods and compositions of the present invention is, in another embodiment, an antibody that binds the protein or biological factor that is the target of the inhibitor. In another embodiment, the inhibitor is a pharmacologic inhibitor. In another embodiment, the inhibitor is any other type of inhibitor known in the art. Each possibility represents a separate embodiment of the present invention.

The step of disrupting the epidermis in methods of the present invention is performed, in another embodiment, by abrading the scalp, eyebrow, or scarred region. In another embodiment, the term "abrading" refers to an act of creating an abrasion. In another embodiment, "abrading" refers to rubbing. In another embodiment, "abrading" refers to wearing away by friction. As provided herein (Example 1), epidermal abrasion causes, under the conditions utilized herein, de novo HF neo-genesis. In another embodiment, the epidermal layer is disrupted.

In one embodiment, “abrasion” has the same meaning as “abrading.” In another embodiment, “abrasion” refers to an area of the scalp or skin from which the epidermis is removed. In another embodiment, “abrasion” refers to an area of the scalp or skin from which the epidermis and dermis are removed. Each definition of “abrading”, and “abrasion” represents a separate embodiment of the present invention.

As provided herein, under the conditions utilized, epidermal disruption by a method of the present invention converts the skin back, in another embodiment, to an embryonic-like state, in which the follicle regenerates. In another embodiment, a subsequent window of opportunity is created, during which the number and size of new HF in the skin can be manipulated. In another embodiment, the administration of a compound or factor that promotes a differentiation of an uncommitted epidermal cell into a HF cell during this window causes regeneration of larger and more numerous HF. The morphology of HF in abraded skin is similar to that of embryonic HF (Example 1-2 and subsequent Examples), and the markers expressed are similar as well.

In another embodiment, the present invention provides a method of stimulating hair growth in a scalp, eyebrow, or scarred region of a subject, comprising performing a method of present invention, thereby stimulating hair growth in a scalp, eyebrow, or scarred region of a subject. As demonstrated in Example 3, EDIHN-induced HF are capable of generating hairs. Thus, methods of the present invention can be used to stimulate hair growth.

“EDIHN,” in another embodiment, refers to HF neogenesis induced by disruption of the epithelial layer. In another embodiment, the term refers to HF neogenesis induced by abrasion. In another embodiment, the term refers to HF neogenesis induced by wounding. In another embodiment, the term refers to HF neogenesis induced by disruption of the epithelial layer, followed by administration of a compound or factor that promotes a differentiation of an uncommitted epidermal cell into a HF cell. Each possibility represents a separate embodiment of the present invention.

In another embodiment, the present invention provides a method of testing an ability of a compound to modulate HF generation in vivo, comprising (a) disrupting an epithelial layer of a first scalp, eyebrow, or scarred region, whereby the first scalp, eyebrow, or scarred region has been contacted with the compound; (b) measuring a first HF generation in the first scalp, eyebrow, or scarred region; (c) disrupting an epithelial layer of a second scalp, eyebrow, or scarred region, wherein the second scalp, eyebrow, or scarred region is a scalp, eyebrow, or scarred region of the first subject or a second subject, whereby the second scalp, eyebrow, or scarred region has not been contacted with the compound; (d) measuring a second. HF generation in the second scalp, eyebrow, or scarred region; and (e) comparing the first HF generation to the second HF generation, whereby a difference between the first HF generation and the second HF generation indicates that the compound modulates an HF generation in vivo (Examples).

In another embodiment, the present invention provides a method of testing an ability of a compound to stimulate hair growth in vivo, comprising disrupting an epithelial layer of a first scalp, eyebrow, or scarred region, whereby the first scalp, eyebrow, or scarred region has been contacted with the compound; measuring a first HF generation in the first scalp, eyebrow, or scarred region; disrupting an epithelial layer of a second scalp, eyebrow, or scarred region, whereby the second scalp, eyebrow, or scarred region has not been contacted with the compound; measuring a second HF generation in the second scalp, eyebrow, or scarred region; and comparing the first HF generation to the second HF generation, whereby a difference between the first HF generation and the second HF generation indicates that the compound stimulates a hair growth in vivo.

In one embodiment, the methods of the present invention of testing a compound are repeated using a plurality of subjects, until a statistically significant sample has been tested.

In another embodiment of methods for testing compounds of the present invention, the first scalp, eyebrow, or scarred region is a scalp, eyebrow, or scarred region of a first subject. In another embodiment, the subject is a subject in need of generation of a new HF. The second scalp, eyebrow, or scarred region, in another embodiment, is a scalp, eyebrow, or scarred region of the first subject. In another embodiment, the second scalp, eyebrow, or scarred region is a scalp, eyebrow, or scarred region of a second subject. Each possibility represents a separate embodiment of the present invention.

In another embodiment, the excisional wounds of methods of the present invention are created using a surgical tool. In one embodiment, the surgical tool is a dermal biopsy punch (Example 2). In another embodiment, the excisional wounds are induced by freezing or cryoinjury. The use of freezing or cryoinjury is well known in the art, and is used, for example by dermatologists to injure skin. In one embodiment, the freezing or cryoinjury results in a blister. In another embodiment, the blister is used as a “chamber” to introduce drugs and or cells into the reepithelialized area. Each possibility represents a separate embodiment of the present invention.

In another embodiment, the excisional wounds of methods of the present invention are not surgically closed. In another embodiment, the excisional wounds are not contacted with a bandage or dressing before they heal or during a period of time after wound induction. In another embodiment, the excisional wounds are not contacted with an ointment before they heal or during a period of time after wound induction. In another embodiment, the excisional wounds are allowed to heal by secondary intention. Each possibility represents a separate embodiment of the present invention.

The subject of methods of the present invention, is, in another embodiment, a human. As provided herein (Example 7) human skin responds to EDIHN in the same manner as mouse skin. In another embodiment, the subject is a male. In another embodiment, the subject is a female. In another embodiment, the subject is any other type of subject known in the art. Each possibility represents a separate embodiment of the present invention.

In another embodiment, the subject is an adult. In one embodiment, “adult” refers to an age greater than about 18 years. In another embodiment, “adult” refers to an age greater than about 20 years. In another embodiment, “adult” refers to an age greater than about 25 years. In another embodiment, “adult” refers to an age greater than about 30 years. In another embodiment, “adult” refers to an age greater than about 35 years. In another embodiment, “adult” refers to an age greater than about 40 years. In another embodiment, “adult” refers to an age greater than about 45 years.

In another embodiment, the subject is elderly. In one embodiment, “elderly” refers to an age greater than about 45 years. In another embodiment, "elderly" refers to an age greater than about 50 years. In another embodiment, "elderly" refers to an age greater than about 55 years. In another embodiment, "elderly" refers to an age greater than about 60 years. In another embodiment, "elderly" refers to an age greater than about 65 years. In another embodiment, "elderly" refers to an age greater than about 70 years.

In another embodiment, the first subject, or, where applicable, both the first subject and the second subject, is a laboratory animal. In another embodiment, the subject(s) is/are mice. In another embodiment, the subject(s) is/are rats. In another embodiment, the subject(s) is/are gerbils. In another embodiment, the subject(s) is/are hamsters. In another embodiment, the subject(s) is/are guinea pigs. In another embodiment, the subject(s) is/are rabbits. In another embodiment, the subject(s) is/are pigs. In another embodiment, the subject(s) is/are dogs. In another embodiment, the subject(s) is/are cats. In another embodiment, the subject(s) is/are primates. In another embodiment, the subject(s) is/are any other laboratory animal known in the art. Each possibility represents a separate embodiment of the present invention.

In another embodiment, the subject(s) has a disease or disorder comprising balding. In another embodiment, the subject(s) does not have a disease or disorder comprising balding. In another embodiment, the disease or disorder is androgenetic alopecia (AGA). In another embodiment, the disease or disorder is male pattern baldness. In another embodiment, the disease or disorder is female pattern baldness. In another embodiment, the disease or disorder is a discoid lupus erythematosis. In another embodiment, the disease or disorder is a congenital hypotrichosis. In another embodiment, the disease or disorder is a lichen planopilaris. In another embodiment, the disease or disorder is a scarring alopecia. In another embodiment, the disease or disorder is any other disease or disorder comprising balding known in the art.

In another embodiment, the scalp, eyebrow, or scarred region(s) has a majority of HF in the telogen stage of the hair cycle. The findings of Examples 5-6 show that (a) EDIHN can restore hair growth to the scalp, eyebrow, or scarred region at the telogen stage; and (b) the efficiency of EDIHN at the telogen stage can be enhanced by depilation prior to abrasion or wound induction. In another embodiment, the scalp, eyebrow, or scarred region(s) has more than about 60% of HF in the telogen stage of the hair cycle. In another embodiment, the scalp, eyebrow, or scarred region(s) has more than about 70% of HF in the telogen stage of the hair cycle. In another embodiment, the scalp, eyebrow, or scarred region(s) has more than about 80% of HF in the telogen stage of the hair cycle. In another embodiment, the scalp, eyebrow, or scarred region(s) has more than about 90% of HF in the telogen stage of the hair cycle. In another embodiment, the scalp, eyebrow, or scarred region(s) does not have a majority of HF in the telogen stage of the hair cycle. Each possibility represents a separate embodiment of the present invention.

In another embodiment of methods and compositions of the present invention, the first step (e.g. epithelial disruption) is performed 3-12 days prior to the second step (e.g. addition of an active compound, factor, cell, etc). In another embodiment, the interval is 4-12 days. In another embodiment, the interval is 5-12 days. In another embodiment, the interval is 4-11 days. In another embodiment, the interval is 6-11 days. In another embodiment, the interval is 6-10 days. In another embodiment, the interval is 6-9 days. In another embodiment, the interval is 6-8 days. In another embodiment, the interval is 7-8 days. In another embodiment, the interval is 5-11 days. In another embodiment, the interval is 5-10 days. In another embodiment, the interval is 7-10 days. In another embodiment, the interval is about 1 week. Each possibility represents a separate embodiment of the present invention.

In another embodiment, a method of the present invention further comprises the step of suppressing an activity or expression of a Wnt protein in the scalp, eyebrow, or scarred region. As provided herein, suppressing Wnt activity induces pigmentation in HF generated by methods of the present invention. In another embodiment, the step of suppressing Wnt activity or expression is performed within about 10 days of epidermal disruption. In another embodiment, the step of suppressing Wnt activity or expression is performed prior to the second step (e.g prior to addition of a compound or factor that promotes HF cell differentiation. Each possibility represents a separate embodiment of the present invention.

In another embodiment, the present invention provides a method for inducing pigmentation of a hair, comprising suppressing expression of a Wnt protein in a follicle of the hair. In another embodiment, the Wnt protein is Wnt1. In another embodiment, the Wnt protein is a Wnt7. In another embodiment, the Wnt protein is a Wnt7a. In another embodiment, the Wnt protein is a Wnt3. In another embodiment, the Wnt protein is a Wnt3a. In another embodiment, the Wnt protein is a Wnt10. In another embodiment, the Wnt protein is a Wnt10a. In another embodiment, the Wnt protein is any other Wnt protein known in the art. Each possibility represents a separate embodiment of the present invention.

In another embodiment, the present invention provides a method for inducing growth of a pigmented scalp hair or eyebrow of a subject, comprising generating a hair follicle in the scalp, eyebrow, or scarred region according to a method of the present invention and suppressing expression of a Wnt protein in the hair follicle, thereby inducing a growth of a pigmented scalp hair or eyebrow of a subject.

In another embodiment, the step of suppressing expression of a Wnt protein comprises inducing an expression of a Dkk1 protein. In another embodiment, the step of suppressing expression of a Wnt protein comprises inducing an expression of any other Wnt inhibitor known in the art. In another embodiment, the step of suppressing expression of a Wnt protein is performed immediately or shortly after epidermal disruption. In another embodiment, the step of inducing expression of a Dkk1 protein is performed immediately or shortly after epidermal disruption. In another embodiment, the step of suppressing expression of a Wnt protein is performed at the time of epidermal disruption. In another embodiment, the step of inducing expression of a Dkk1 protein is performed at the time of epidermal disruption. In another embodiment, the step of suppressing expression of a Wnt protein is performed several days before generation of the follicle. In another embodiment, the step of inducing expression of a Dkk1 protein several days before generation of the follicle. Each possibility represents a separate embodiment of the present invention.

In another embodiment, the step of suppressing expression of a Wnt protein is performed for about 8 days. In another embodiment, the step of inducing expression of a Dkk1 protein is performed for about 8 days. In another embodiment, the step of suppressing expression of a Wnt protein is performed for about 9 days. In another embodiment, the step of inducing expression of a Dkk1 protein is performed for about 9 days. In another embodiment, the step of suppressing expression of a Wnt protein is performed for about 10 days. In another embodiment, the step of inducing expression of a Dkk1 protein is performed for about 10 days. In another embodiment, the step of suppressing expression of a Wnt protein is performed for about 12 days. In another embodiment, the step of inducing expression of a Dkk1 protein is performed for about 12 days. In another embodiment, the step of suppressing expression of a Wnt protein is performed during the period of re-epithelialization. In another embodiment, the step of inducing expression of a Dkk1 protein is performed during the period of re-epithelialization. In another embodiment, expression of a Dkk1 protein is halted after several days. In another embodiment, halting expression of Dkk1 protein after several days induces, or enables induction of Wnt protein expression. In another embodiment, the expression of a Wnt protein is induced about 9 days after the abrating or wounding. In another embodiment, the expression of a Wnt protein is induced following the period of re-epithelialization. In another embodiment, induction of Wnt protein expression is necessary for formation of new HF. Each possibility represents a separate embodiment of the present invention.

In another embodiment, "several" refers to about 1 day. In another embodiment, "several" refers to about 2 days. In another embodiment, "several" refers to about 3 days. In another embodiment, "several" refers to about 5 days. In another embodiment, "several" refers to about 7 days. In another embodiment, "several" refers to about 10 days. In another embodiment, "several" refers to about 12 days. Each possibility represents a separate embodiment of the present invention.

In another embodiment, the step of contacting in methods of the present invention comprises directly contacting the scalp, eyebrow, or scarred region with the compound, RNA, protein, etc. In another embodiment, the step of contacting comprises indirectly contacting the scalp, eyebrow, or scarred region via contacting another site or tissue of the subject, after which the compound, RNA, or protein is transported to the scalp, eyebrow, or scarred region by a biological process; e.g, diffusion, active transport, or circulation in a fluid such as the blood, lymph, interstitial fluid, etc. Each possibility represents a separate embodiment of the present invention.

In another embodiment, the epidermal disruption in methods of the present invention further removes dermal tissue from the scalp, eyebrow, or scarred region. In another embodiment, the epidermal disruption does not remove dermal tissue from the scalp, eyebrow, or scarred region. Each possibility represents a separate embodiment of the present invention.

"Disrupting" an epidermis or epidermal layer refers, in another embodiment, to removing part of the epidermis or epidermal layer. In another embodiment, the term refers to disturbing the intactness of the epidermis or epidermal layer. In another embodiment, the term refers to perforating the epidermis or epidermal layer. In another embodiment, only part of the epidermal layer need be removed. In another embodiment, the entire epidermal layer is removed. In another embodiment, the term refers to abrading the epidermis or epidermal layer (Examples). In another embodiment, the term refers to wounding the epidermis or epidermal layer (Examples). Each possibility represents a separate embodiment of the present invention.

In another embodiment, the epidermal disruption is performed with a tool that comprises sandpaper. In another embodiment, the epidermal disruption is performed with a laser. In another embodiment, the laser is a Fraxel laser. In another embodiment, the laser is a $CO_2$ laser. In another embodiment, the laser is an excimer laser. In another embodiment, the laser is any other type of laser capable of inducing trans-epithelial injury. In another embodiment, the epidermal disruption is performed with a felt wheel. In another embodiment, the epidermal disruption is performed with a surgical tool. In another embodiment, the epidermal disruption is performed with any other tool known in the art that is capable of epidermal disruption. In another embodiment, the epidermal disruption comprises use of a microdermabrasion device. In another embodiment, the epidermal disruption comprises a burn treatment.

In another embodiment, the epidermal disruption comprises a disruption of a follicle of said epidermis and a disruption of an interfollicular region of said epidermis. In another embodiment, the epidermal disruption comprises a disruption of a follicle of said epidermis and does not comprise a disruption of an interfollicular region of said epidermis. Each possibility represents a separate embodiment of the present invention.

In another embodiment, the epidermal disruption comprises a light-based method. In another embodiment, the epidermal disruption comprises irradiation with visible light. In another embodiment, the epidermal disruption comprises irradiation with infrared light. In another embodiment, the epidermal disruption comprises irradiation with ultraviolet radiation. In another embodiment, the epidermal disruption comprises orthovoltage irradiation. In another embodiment, the epidermal disruption comprises X-ray irradiation. In another embodiment, the epidermal disruption comprises any other type of irradiation known in the art.

In another embodiment, the epidermal disruption is performed by mechanical means. In another embodiment, "mechanical means" refers to abrading. In another embodiment, the term refers to wounding. In another embodiment, the term refers to ultrasound. In another embodiment, the term refers to radio-frequency. In another embodiment, the term refers to an electrical process or the use of an electrical current. In another embodiment, the term refers to electroporation. In another embodiment, the term refers to exision. In another embodiment, the term refers to tape-stripping. In another embodiment, the term refers to microdermabrasion. In another embodiment, the term refers to the use of peels. In another embodiment, the term refers to any other type of mechanical means known in the art. Each possibility represents a separate embodiment of the present invention.

In another embodiment, the epidermal disruption comprises chemical treatment. In another embodiment, the chemical is phenol. In another embodiment, the chemical is trichloracetic acid. In another embodiment, the chemical is ascorbic acid. In another embodiment, the chemical is any other chemical capable of epidermal disruption that is known in the art.

Each method or type of method of epidermal disruption represents a separate embodiment of the present invention.

In another embodiment, epidermal trauma is utilized in a method of the present invention.

Each type of epidermal abrasion and epidermal trauma represents a separate embodiment of the present invention.

In another embodiment, the epidermal disruption of methods of the present invention creates an abrasion at least about 1-1.5 centimeters (cm) in width. In another embodiment, the abrasion is at least about 1 cm in width. In another embodiment, the abrasion is at least about 1.5 cm in width. In another embodiment, the abrasion is at least about 2 cm in width. Each type of abrasion represents a separate embodiment of the present invention.

In another embodiment, the scalp, eyebrow, or scarred region is not contacted with a bandage or dressing following the epidermal disruption. In another embodiment, the scalp, eyebrow, or scarred region is not contacted with an ointment following the epidermal disruption. In another embodiment, the scalp, eyebrow, or scarred region is allowed to heal for a period of time without being contacted by any substance, device, ointment, etc., that is ordinarily administered to an abrasion or wound to facilitate healing. In another embodiment, the scalp, eyebrow, or scarred region is allowed to heal for a period of time without being contacted by any substance, device, ointment, etc., that is ordinarily administered to an abrasion or wound to prevent infection. In another embodiment, the period of time is the time it takes the epidermal disruption to heal. In another embodiment, the period of time is any time or range of times between 2 days and 3 weeks. Each possibility represents a separate embodiment of the present invention.

In one embodiment, "following" refers to a period of time of about 2 days. In another embodiment, "following" refers to a period of time of about 3 days. In another embodiment, "following" refers to a period of time of about 4 days. In another embodiment, "following" refers to a period of time of about 5 days. In another embodiment, "following" refers to a period of time of about 7 days. In another embodiment, "following" refers to a period of time of about 10 days. In another embodiment, "following" refers to a period of time of about 2 weeks. In another embodiment, "following" refers to a period of time of about 3 weeks. Each possibility represents a separate embodiment of the present invention.

In another embodiment, a method of the present invention further comprises the step of depilating the scalp, eyebrow, or scarred region. As provided herein, the findings of Example 6 show that the efficiency of EDIHN can be enhanced by depilation prior to abrasion or wound induction.

In another embodiment, the depilation is epilation. In another embodiment, the depilation comprises the step of waxing. In another embodiment, the depilation comprises the step of plucking. In another embodiment, the depilation comprises the use of an abrasive material. In another embodiment, the depilation comprises the use of a laser. In another embodiment, the depilation comprises the use of electrolysis. In another embodiment, the depilation comprises the use of a mechanical device. In another embodiment, the depilation comprises the use of thioglycolic acid. In another embodiment, the depilation comprises the use of any other method of depilation or epilation known in the art. Each possibility represents a separate embodiment of the present invention.

In another embodiment, a method of the present invention further comprises the step of administering a topical retinoid to the scalp, eyebrow, or scarred region. In one embodiment, the topical retinoid induces resting (telogen) BF in the scalp, eyebrow, or scarred region to enter anagen. Each possibility represents a separate embodiment of the present invention.

In another embodiment, the additional step (depilation or administration of a retinoid) is performed prior to the step of disrupting the epidermis. In another embodiment, the additional step is performed following the step of disrupting the epidermis, but prior to the addition of the compound or factor that promotes a differentiation of an uncommitted epidermal cell into a HF cell. In another embodiment, the additional step is performed concurrently with the addition of the differentiation-promoting compound or factor. In another embodiment, the additional step is performed following the addition of the differentiation-promoting compound or factor. Each possibility represents a separate embodiment of the present invention.

In another embodiment, the additional step is performed between about two days and about three weeks before the step of abrading. In another embodiment, the additional step is performed about two days before the step of abrading. In another embodiment, the additional step is performed about three days before the step of abrading. In another embodiment, the additional step is performed about four days before the step of abrading. In another embodiment, the additional step is performed about one week before the step of abrading. In another embodiment, the additional step is performed about ten days before the step of abrading. In another embodiment, the additional step is performed about two weeks before the step of abrading. In another embodiment, the additional step is performed about three weeks before the step of abrading. Each possibility represents a separate embodiment of the present invention.

In another embodiment, the methods of the present invention further comprise the step of contacting the scalp, eyebrow, or scarred region with an inductive cell, capable of inducing an epidermal cell to differentiate into an HF cell. In another embodiment, the HF cell is an HF stem cell. Each possibility represents a separate embodiment of the present invention.

In another embodiment, the inductive cell is a dermal papilla cell. In another embodiment, the inductive cell is a follicular papilla cell. In another embodiment, the inductive cell is a dermal sheath cell. In another embodiment, the inductive cell is a cell that has been genetically modified; for example, with a gene encoding a factor that activates one of the proteins or pathways shown in the present invention to be up-regulated in HF stem cells. In one embodiment, the factor is hedgehog. In another embodiment, the factor is a DP cell protein. In another embodiment, the factor is wingless/int (wnt). In another embodiment, the factor is a Noggin protein. In another embodiment, the factor is a bone morphogenic protein (BMP). In another embodiment, the factor is a fibroblast growth factor (FGF). In another embodiment, the factor is a transforming growth factor beta (TGF-beta) protein. In another embodiment, the factor is sonic hedgehog protein. In another embodiment, the factor is a neurotropin. In another embodiment, the factor is any other factor known in the art that can contribute to induction of an epidermal cell to differentiate into an HF cell. Each possibility represents a separate embodiment of the present invention.

In another embodiment, the inductive cell has been genetically modified with a gene encoding a factor that represses one of the proteins or pathways shown in the present invention to be down-regulated in HF stem cells. In another embodiment, the inductive cell has been genetically modified with a gene encoding a factor that activates one of the proteins or pathways shown in the present invention to be up-regulated in HF stem cells upon their activation.

In another embodiment, the inductive cell is an autologous cell. In another embodiment, the inductive cell is an allogenic cell.

In another embodiment, the inductive cell is derived from a mesenchymal stem cell. In another embodiment, the inductive cell is derived from a mesodermal progenitor cell. In another embodiment, the inductive cell is derived from a hematopoietic stem cell. In another embodiment, the inductive cell is derived from an embryonic stem cell. In another embodiment, the inductive cell is derived from an embryonic carcinoma cell. In another embodiment, the inductive cell is one of the cell types disclosed in United States Patent Application No. 2003/0201815. In another embodiment, the inductive cell is any other type of cell known in the art with inductive properties for an epidermal cell. Each type of inductive cell represents a separate embodiment of the present invention.

In another embodiment, the epidermal cell (e.g. the epidermal cell that is induced to differentiate into an HF cell) is an epidermal stem cell. In another embodiment, the epidermal cell is a bulge cell. In another embodiment, the epidermal cell is any other type of cell known in the art that can be induced to differentiate into an HF stem cell. Each possibility represents a separate embodiment of the present invention.

In another embodiment, a method of the present invention further comprises the step of contacting the scalp, eyebrow, or scarred region with an anti-androgen compound. In one embodiment, the anti-androgen compound is finasteride. In another embodiment, the anti-androgen compound is Fluridil®. In another embodiment, the anti-androgen compound is dutasteride. In another embodiment, the anti-androgen compound is spironolactone. In another embodiment, the anti-androgen compound is cyproterone acetate. In another embodiment, the anti-androgen compound is bicalutamide. In another embodiment, the anti-androgen compound is flutamide. In another embodiment, the anti-androgen compound is nilutamide. In another embodiment, the anti-androgen compound is an inhibitor of an androgen receptor. In another embodiment, the anti-androgen compound is any other anti-androgen compound known in the art. Each possibility represents a separate embodiment of the present invention.

In another embodiment, a method of the present invention further comprises the step of contacting the scalp, eyebrow, or scarred region with an estrogen compound. In another embodiment, a method of the present invention further comprises the step of contacting the scalp, eyebrow, or scarred region, with an estrogen receptor agonist. In another embodiment, a method of the present invention further comprises the step of contacting the scalp, eyebrow, or scarred region with an estrogen analogue. In one embodiment, the estrogen analogue is estradiol. In another embodiment, the estrogen analogue is 17 beta-estradiol. In another embodiment, the estrogen analogue is 17 alpha-estradiol. In another embodiment, the estrogen analogue is ZYC3. In another embodiment, the estrogen compound, estrogen receptor agonist, or estrogen analogue is any other estrogen compound, estrogen receptor agonist, or estrogen analogue known in the art. Each possibility represents a separate embodiment of the present invention.

In another embodiment, a method of the present invention further comprises the step of contacting the scalp, eyebrow, or scarred region with an inhibitor of an EGF protein. In another embodiment, a method of the present invention further comprises the step of contacting the scalp, eyebrow, or scarred region with an inhibitor of an EGFR. In another embodiment, a method of the present invention further comprises the step of contacting the scalp, eyebrow, or scarred region with a compound that reduces an expression of an EGF protein or an EGFR. Each possibility represents a separate embodiment of the present invention.

In another embodiment, a method of the present invention further comprises the step of contacting the scalp, eyebrow, or scarred region with a Hedgehog protein. In another embodiment, a method of the present invention further comprises the step of contacting the scalp, eyebrow, or scarred region with a nucleotide encoding a Hedgehog protein. In another embodiment, a method of the present invention further comprises the step of contacting the scalp, eyebrow, or scarred region with an activator of a Hedgehog protein. Each possibility represents a separate embodiment of the present invention.

In one embodiment, a scalp is treated by a method of the present invention. In another embodiment, an eyebrow is treated. In another embodiment, any other hair-bearing area or region of the skin is treated. Each possibility represents a separate embodiment of the present invention.

In another embodiment, a method of the present invention further comprises the step of contacting the scalp, eyebrow, or scarred region with a lithium compound. In one embodiment, the lithium compound contains a lithium ion. In another embodiment, the lithium compound contains a lithium atom.

In another embodiment, a method of the present invention further comprises the step of contacting the scalp, eyebrow, or scarred region with (2'Z,3'E)-6-bromoindirubin-3'-oxime (BIO). In another embodiment, a method of the present invention further comprises the step of contacting the scalp, eyebrow, or scarred region with any other compound known in the art that is capable of inducing an epidermal cell to differentiate into an HF stem cell. Each compound represents a separate embodiment of the present invention.

In one embodiment, the compound administered as part of methods of the present invention is administered systemically. In another embodiment, the compound is administered topically. In another embodiment, the compound is administered to the site of the abrasion. In another embodiment, the compound is administered to the site of the wound induction. In another embodiment, the compound is administered to the site of the depilation. In another embodiment, the compound is administered during wound healing. In another embodiment, the compound is administered prior to HF neo-genesis. In another embodiment, the compound is administered during HF neo-genesis. Each possibility represents a separate embodiment of the present invention.

In another embodiment, the present invention provides a method of inducing formation of an HF stem cell, comprising performing a method of the present invention. In another embodiment, the present invention provides a method of inducing formation of a DP cell, comprising performing a method of the present invention. Each possibility represents a separate embodiment of the present invention.

In another embodiment, homologues and variants of transcripts and proteins of the present invention are administered in methods of the present invention. In another embodiment, homologues and variants of transcripts and proteins of the present invention are targeted in methods of the present invention. Each possibility represents a separate embodiment of the present invention.

The terms "homology," "homologous," etc, when in reference to any protein or peptide, refer in one embodiment, to a percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. Methods and computer programs for the alignment are well known in the art.

In another embodiment, the term "homology," when in reference to any nucleic acid sequence similarly indicates a percentage of nucleotides in a candidate sequence that are identical with the nucleotides of a corresponding native nucleic acid sequence.

In another embodiment, "homology" refers to identity of greater than 70%. In another embodiment, "homology"

refers to identity of greater than 75%. In another embodiment, "homology" refers to identity of greater than 80%. In another embodiment, "homology" refers to identity of greater than 82%. In another embodiment, "homology" refers to identity of greater than 85%. In another embodiment, "homology" refers to identity of greater than 87%. In another embodiment, "homology" refers to identity of greater than 90%. In another embodiment, "homology" refers to identity of greater than 92%. In another embodiment, "homology" refers to identity of greater than 95%. In another embodiment, "homology" refers to identity of greater than 97%. In another embodiment, "homology" refers to identity of greater than 98%. In another embodiment, "homology" refers to identity of greater than 99%. In another embodiment, "homology" refers to identity of 100%.

Protein and/or peptide homology for any amino acid sequence listed herein is determined, in one embodiment, by methods well described in the art, including immunoblot analysis, or via computer algorithm analysis of amino acid sequences, utilizing any of a number of software packages available, via established methods. Some of these packages may include the FASTA, BLAST, MPsrch or Scanps packages, and may employ the use of the Smith and Waterman algorithms, and/or global/local or BLOCKS alignments for analysis, for example. Each method of determining homology represents a separate embodiment of the present invention.

In another embodiment, the present invention provides a kit, comprising a tools and/or a compound suitable for performing a method of the present invention.

In another embodiment, the present invention provides a device, comprising a tool suitable for epidermal disruption and a means of delivering a compound or factor that promotes a differentiation of an uncommitted epidermal cell into a HF cell.

In other embodiments, the present invention provides a method of treating any disease, disorder, or symptom associated with balding. In other embodiments, the present invention provides a method of treating any disease, disorder, or symptom associated with balding. In other embodiments, the present invention provides a method of treating any disease, disorder, or symptom associated with balding. Each disease, disorder, or symptom represents a separate embodiment of the present invention.

Pharmaceutical Compositions

In another embodiment, methods of the present invention comprise administering a pharmaceutical composition comprising the HF stem cell-inducing or -activating compound and/or its analog, derivative, isomer, metabolite, pharmaceutically acceptable salt, pharmaceutical product, hydrate, N-oxide, or any combination thereof; and a pharmaceutically acceptable carrier. Each possibility represents a separate embodiment of the present invention.

The pharmaceutical compositions containing the HF stem cell-inducing or -activating compound can, in another embodiment, be administered to a subject by any method known to a person skilled in the art, such as topically, parenterally, paracancerally, transmucosally, transdermally, intramuscularly, intravenously, intradermally, subcutaneously, intraperitonealy, intraventricularly, intracranially, intravaginally or intratumorally. Each possibility represents a separate embodiment of the present invention.

In another embodiment, the pharmaceutical compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In one embodiment of the present invention, the HF stem cell-inducing or -activating compounds are formulated in a capsule. In another embodiment, the compositions of the present invention comprise, in addition to the HF stem cell-inducing or -activating compound active compound and the inert carrier or diluent, a hard gelating capsule.

In another embodiment, the pharmaceutical compositions are administered topically to body surfaces and are thus formulated in a form suitable for topical administration. Suitable topical formulations include gels, ointments, creams, lotions, drops and the like. For topical administration, the HF stem cell-inducing or -activating compound or its physiologically tolerated derivatives such as salts, esters, N-oxides, and the like are prepared and applied as solutions, suspensions, or emulsions in a physiologically acceptable diluent with or without a pharmaceutical carrier.

In another embodiment, the pharmaceutical compositions are administered by subcutaneous implantation of a pellet. In another embodiment, the pellet provides for controlled release of HF stem cell-inducing or -activating compound agent over a period of time.

For liquid formulations, pharmaceutically acceptable carriers are, in another embodiment, aqueous or non-aqueous solutions, suspensions, emulsions or oils. Examples of non-aqueous solvents are propylene glycol, polyethylene glycol, and injectable organic esters such as ethyl oleate. Aqueous carriers include, in another embodiment, water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil.

In one embodiment, the pharmaceutical compositions are controlled-release compositions, i.e. compositions in which the HF stem cell-inducing or -activating compound is released over a period of time after administration. Controlled- or sustained-release compositions include, in another embodiment, formulation in lipophilic depots (e.g. fatty acids, waxes, oils). In another embodiment, the composition is an immediate-release composition, i.e. a composition in which all the HF stem cell-inducing or -activating compound is released immediately after administration.

EXPERIMENTAL DETAILS SECTION

Example 1

Depilation and Epidermal Abrasion Causes De Novo Hair Follicle Formation

Materials and Experimental Methods

Depilation and Epidermal Abrasion

Mice were anesthetized with an injection of sodium pentobarbital before the hair on the back was clipped and depilated with Nair (Carter-Wallace, New York, N.Y.), then epidermis was removed using a rotating felt wheel as described by Argyris T, J Invest Dermatol, 75: 360-362, 1980). After scrubbing with 70% ethanol and drying under an incandescent lamp, the basal and supra-basal layers in an area of $(1.5\ cm)^2$ cm of the inter-follicular epidermis were removed by careful abrasion with a felt wheel mounted on a Dremel Moto-tool (Racine, Wis.). After abrasion, the skin was shiny and smooth, and there was no blood. One day later, the abraded area was covered by a fibrin crust, which fell off after 3-7 days, exposing the newly regenerated epidermis. A group of control mice was sacrificed immediately after abrasion to confirm microscopically the complete removal of the interfollicular epidermis.

Immunohistochemistry

Skin samples were fixed in PBS-buffered 10% formalin. Six-micron thick paraffin sections were cut and stained, where applicable, with antibodies.

BrdU Labeling

The protocol described by Bickenbach and colleagues (Bickenbach et al, Cell Tiss Kinet 19: 325-333, 1986; Bickenbach et al, Exp Cell Res 244, 184-195, 1998) was used. Mice were injected with 50 milligrams per kilogram (mg/kg) bodyweight 5-bromo-2'-deoxyuridine (BrdU) every 12 hours for a total of four injections.

Results

Figure 2:
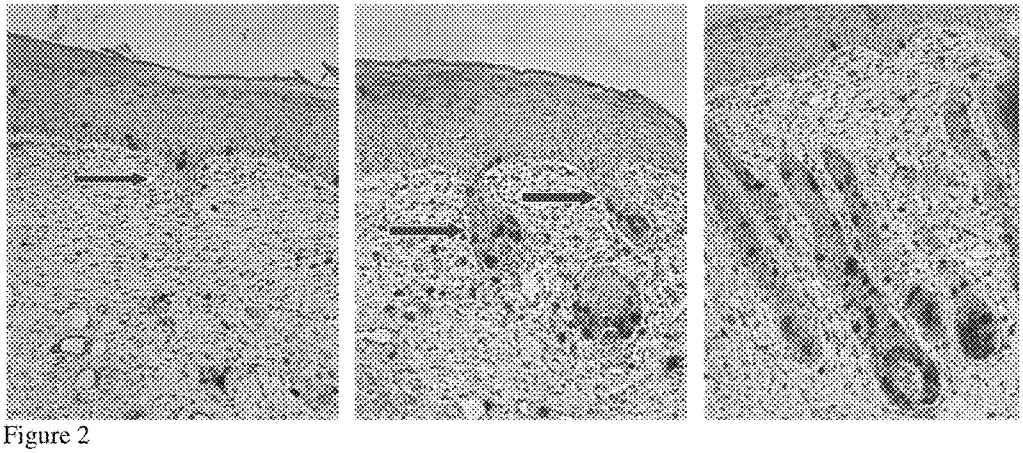
FIG. 2: BrdU labeling of HF following epidermal abrasion. HF at progressive stages of development are depicted in the left, center, and right panels.

An area of the backs of 50-day old mice was subjected to depilation and removal of the epidermis using a rotating felt wheel. Fifteen days later, HF placodes, hair germs and other signs of follicle neogenesis were present (FIG. 1; arrow indicates a hair germ). Morphology of the follicles was similar to embryonic follicle development. To further characterize proliferation in the new follicles, the skin was labeled with BrdU 60 minutes before sacrifice. As depicted in FIG. 2, the proliferation pattern was similar to developing follicles in the embryo.

These findings demonstrate that (a) disruption of the epidermis causes generation of new HF, and that this generation of new HF can occur (b) in adult subjects and (c) during telogen (50-day-old mice are in the second telogen stage of the hair cycle).

Example 2

Induction of a Large Excisional Wound, but not a Small Punch Wound, Causes De Novo Hair Follicle Formation

Materials and Experimental Methods

Punch Wound and Excisional Wound Induction

The backs of 21-day-old mice were depilated as described for Example 1 and sterilized with alcohol, followed by 1% iodine solution. Punch wounds, 4 mm in diameter, were induced using a dermal biopsy punch, down to, but not through, the muscle fascia. Excisional wounds were full thickness and 1 cm in diameter; skin and panniculus carnosus was excised using fine surgical scissors.

Results

Figure 3:
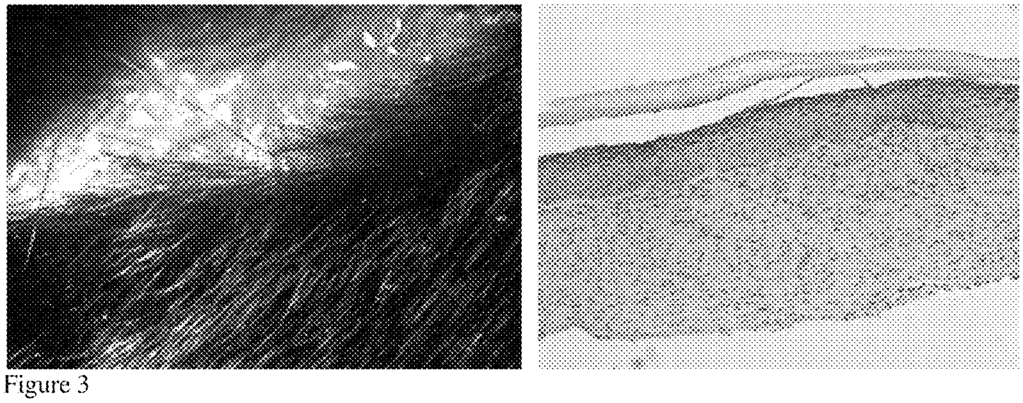
FIG. 3. The wound site did not contain HF immediately after re-epithelialization. Top view (left panel) and tissue section (right panel) of the site 10 days after wound induction.
Figure 4:
FIG. 4. Appearance of hair germs 12 days after wound induction. Arrow indicates hair germ.
Figure 5:
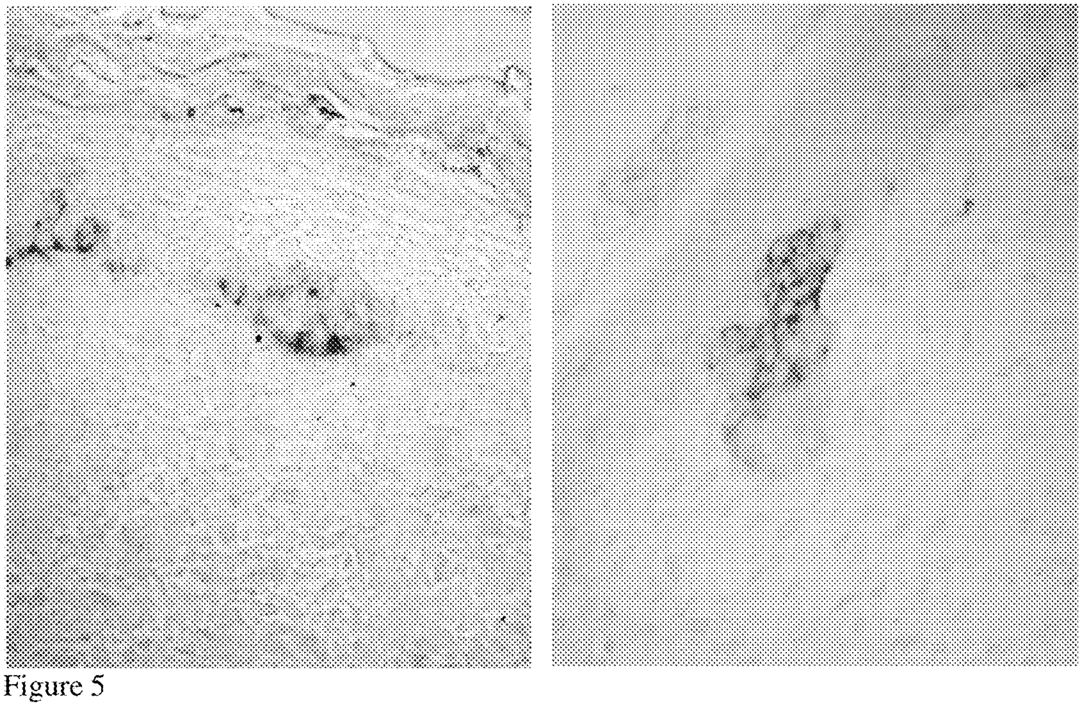
FIG. 5. Epidermal Disruption-Induced HF neogenesis (EDIHN)-induced hair germs express K17. Two different hair germs are depicted in the left and right panels.
Figure 6:
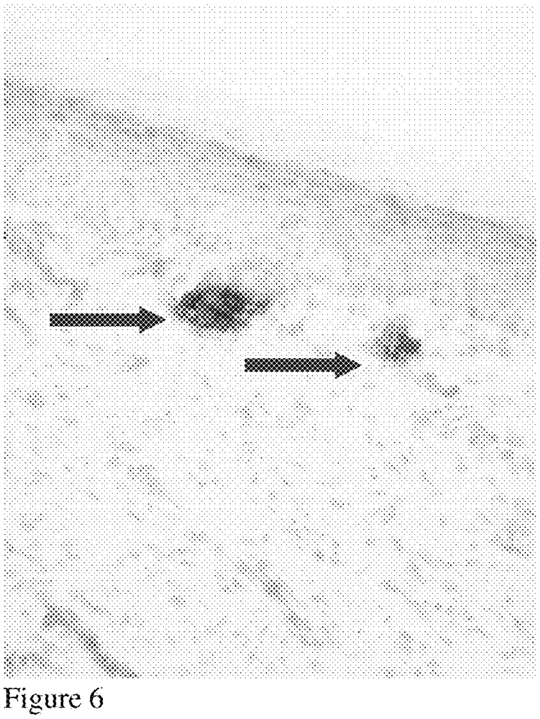
FIG. 6. EDIHN-induced hair germs contain dermal papilla (DP) cells, as evidenced by alkaline phosphatase (AP) staining. Arrows indicate DP cells. Left panel: hair germs. Right panel: HF at a further developmental stage.
Figure 6:
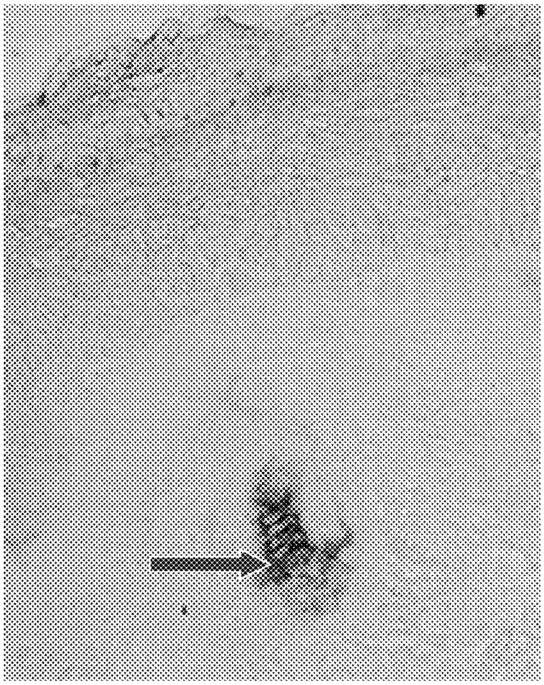

To test whether wounding could induce HF formation, punch wounds or excisional wounds were induced in mice. Both types of wounds exhibited contraction and re-epithelialization following wound induction; however, unlike the mice receiving punch wounds, the mice receiving excisional wounds also exhibited scar formation within 10 days of wound induction (FIG. 3, left panel). No follicles were evident at this time point (FIG. 3, right panel). 12 days after wound induction, hair germs, with similar morphology to fetal hair germs, were observed in the wound site, following BrdU pulse labeling (FIG. 4). Several markers were used to verify that the observed structures were HF. The structures exhibited staining with anti-keratin 17 (K 17), an HF marker (FIG. 5), and staining with anti-alkaline phosphatase at the 12 day time point verified that the structures had dermal papilli containing fibroblasts, as expected for HF (FIG. 6; HF at earlier and later stages are depicted in the left and right panels, respectively).

Figure 7:
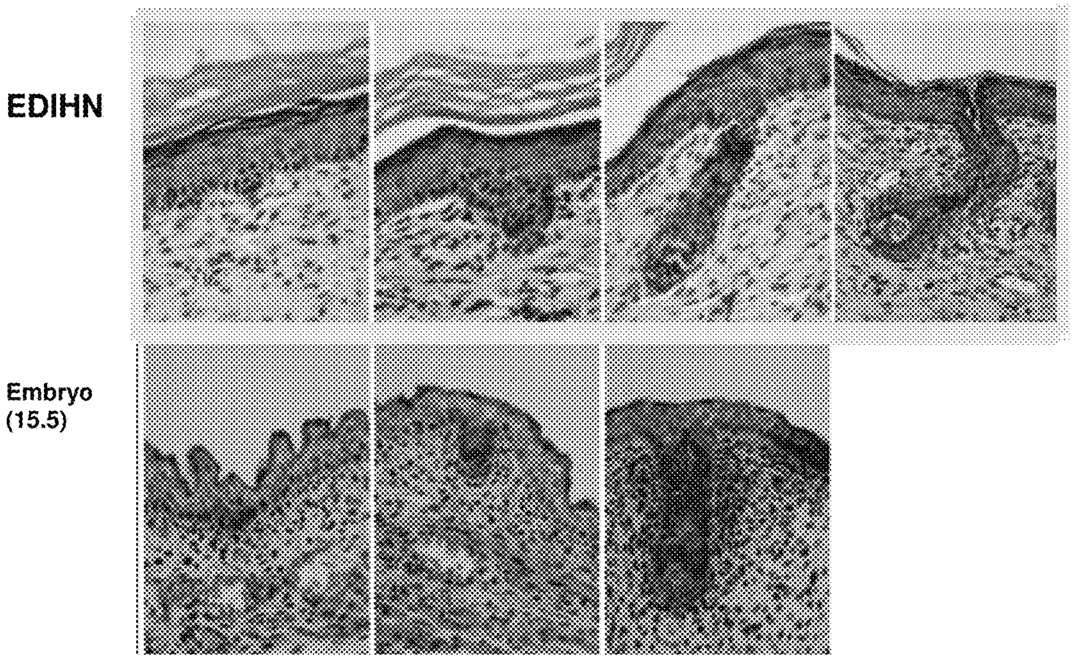
FIG. 7. Histological comparison between EDIHN-induced and embryonic HF. Top left, second from left, third from left, and right panels: Progressive stages of EDIHN-induced HF development. Bottom left, center, and right panels: Progressive stages of and embryonic HF development.
Figure 8:
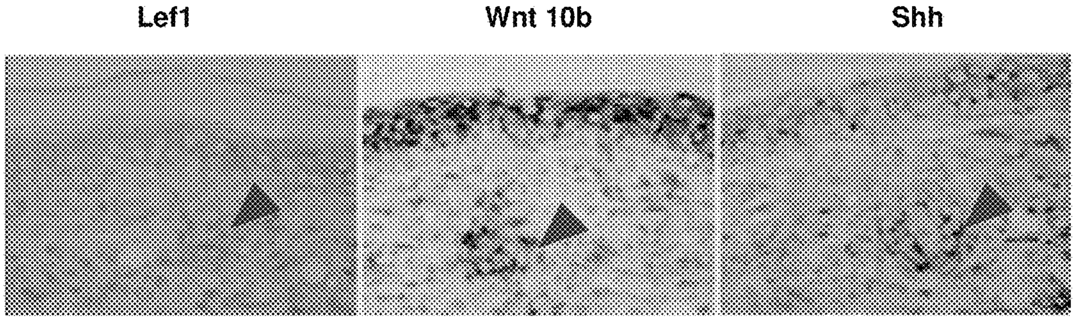
FIG. 8. Induction of several markers of embryonic HF development, Lef1 (left panel), wingless/int (Wnt) 10b (center panel), and sonic hedgehog (Shh; right panel), by EDIHN. HF structures are indicated by arrowheads.
Figure 9:
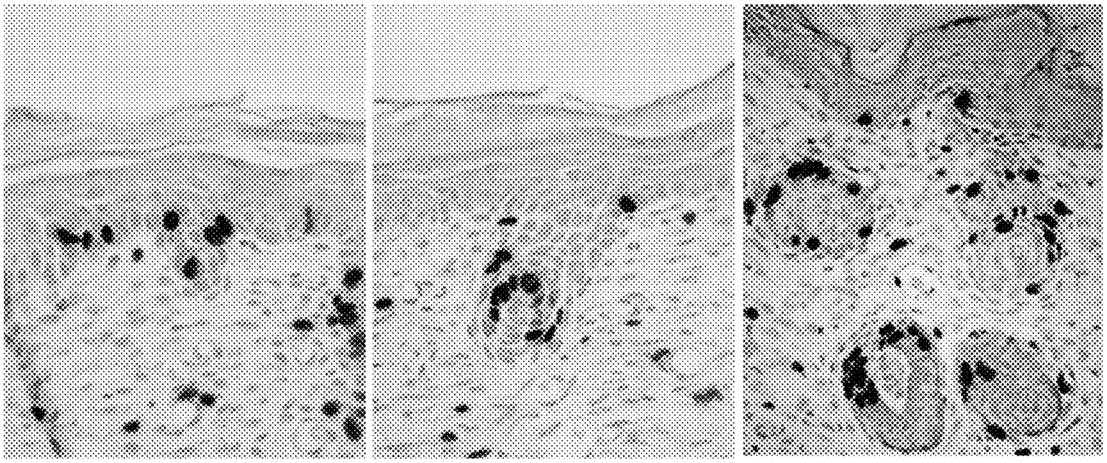
FIG. 9. Proliferative activity during EDIHN, as evidenced by BrdU pulse-labeling. Progressive stages of HF development are depicted in the left, center, and right panels.
Figure 10:
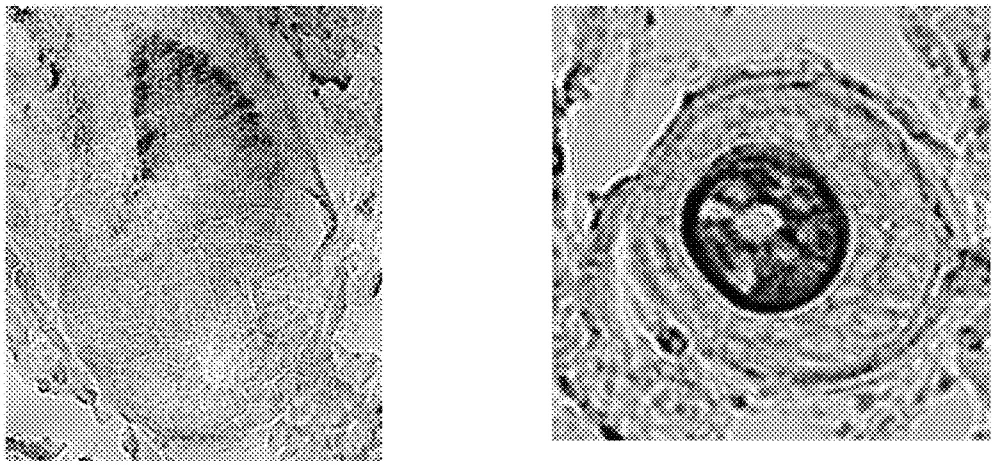
FIG. 10. Induction of HF markers S100A3 (left panel; tissue section parallel to HF axis) and S100A6 (right panel; cross-sectional view of follicle) by EDIHN.

The HF generated by wound induction were further characterized by morphological comparison to embryonic HF, following BrdU staining; a clear correspondence in morphology was observed at various stages (FIG. 7). In addition, several markers of embryonic HF development, namely Lef1, wingless/int (Wnt) 10b, and sonic hedgehog (Shh), were also induced in the epidermal disruption-induced HF neogenesis (EDIHN) (FIG. 8). Additional BrdU staining (FIG. 9) and staining for HF markers S100A3 and S100A6 (FIG. 10; left panel: tissue section parallel to HF axis; right panel: cross-sectional view of follicle) provided further verification that the development of the EDIHN follicles closely paralleled embryonic HF development.

These findings provide further evidence that disruption of the epidermis causes generation of new HF, and that this generation of new HF can occur (b) in adult subjects and (c) during telogen (21-day-old mice are in the first telogen stage of the hair cycle).

Example 3

EDIHN-Induced Hair Follicles Generate Hairs

Figure 11:
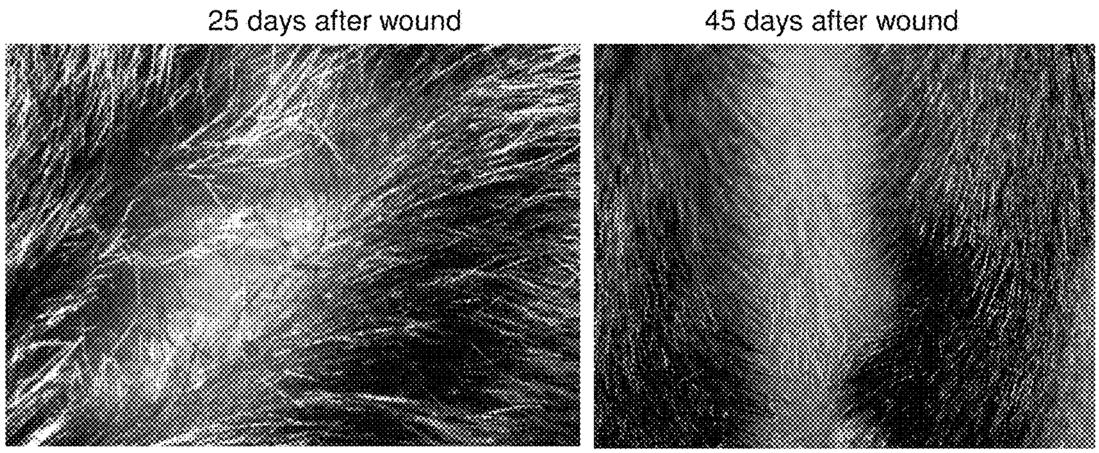
FIG. 11. New hair growth 25 days (left panel) and 45 days (right panel) after wound induction.

At 25 and 45 days after wound induction, wound sites contained new hairs (FIG. 11, left and right panels, respectively). New hairs appeared to lack pigmentation, except when the wnt pathway was inhibited, using Dkk-1 (Dickkopf-1) during the first nine days after wounding (see Example 10).

These findings indicate that EDIHN-induced HF function normally; i.e. are capable of generating hairs.

Example 4

EDIHN Hair Follicles Retain the Ability to Enter into Cyclical Hair Growth

Materials and Experimental Methods

BrdU Labeling 50 mg/kg bodyweight BrdU (Sigma) was injected twice per day for 3 days beginning 20 days after wounding. BrdU was detected 40 days after wounding (17 day chase).

Whole Mounting and Immunofluorescence

Figure 12:
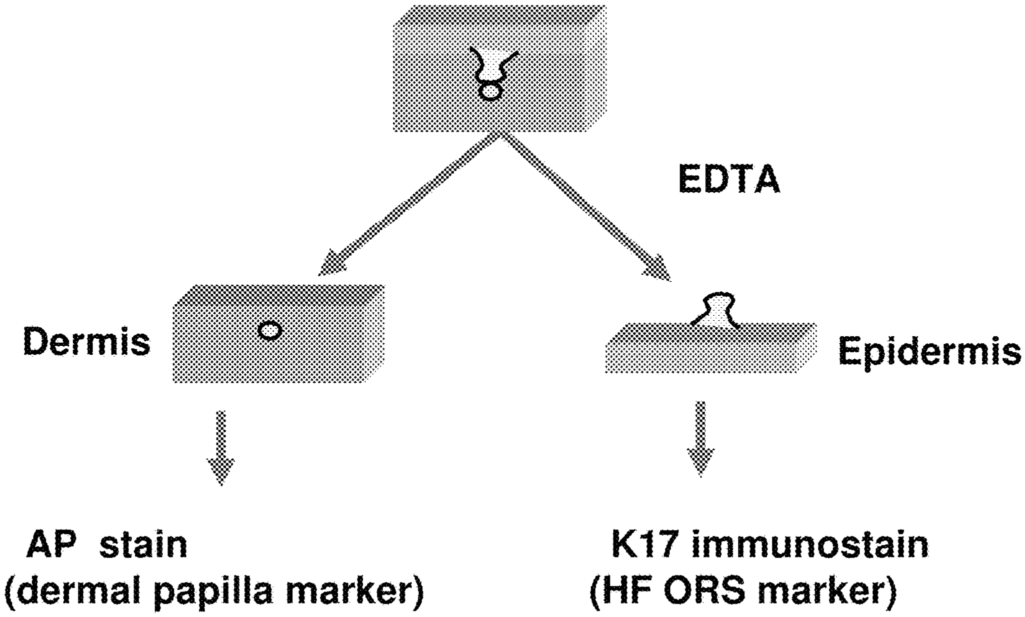
FIG. 12. Schematic of whole-mount EDIHN assay.

HF whole mounts were obtained by incubating fresh skin with EDTA (20 mM in PBS) at 37° C. overnight, then separating the epidermis and dermis. Epidermis was then fixed in 10% formalin for 10 min, room temperature (RT). Dermis was fixed in acetone overnight, RT. After rinsing with PBS, whole mounts were stained with antibodies for immunohistochemistry (schematically depicted in FIG. 12) and were imaged using a Leica confocal microscope.

Results

Figure 13:
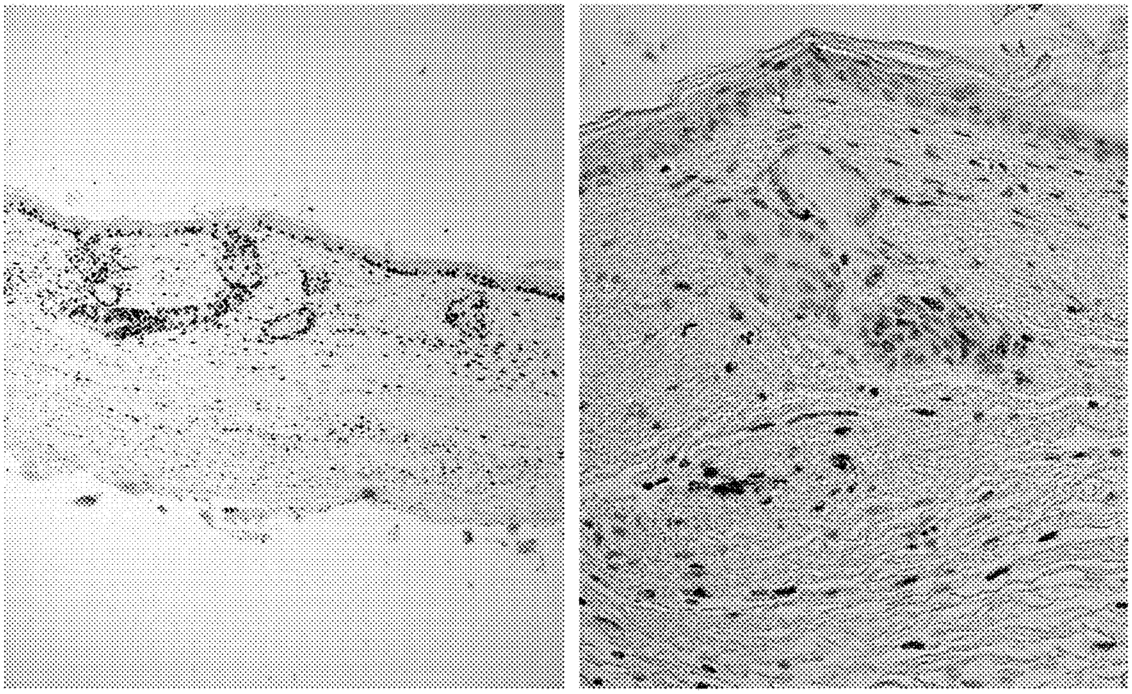
FIG. 13. Repopulation of stem cells in the bulge of EDIHN-induced HF, as evidenced by retention of BrdU label following a chase period. Left panel: lower magnification: 50×. Right panel: higher magnification: 400×.
Figure 14A:
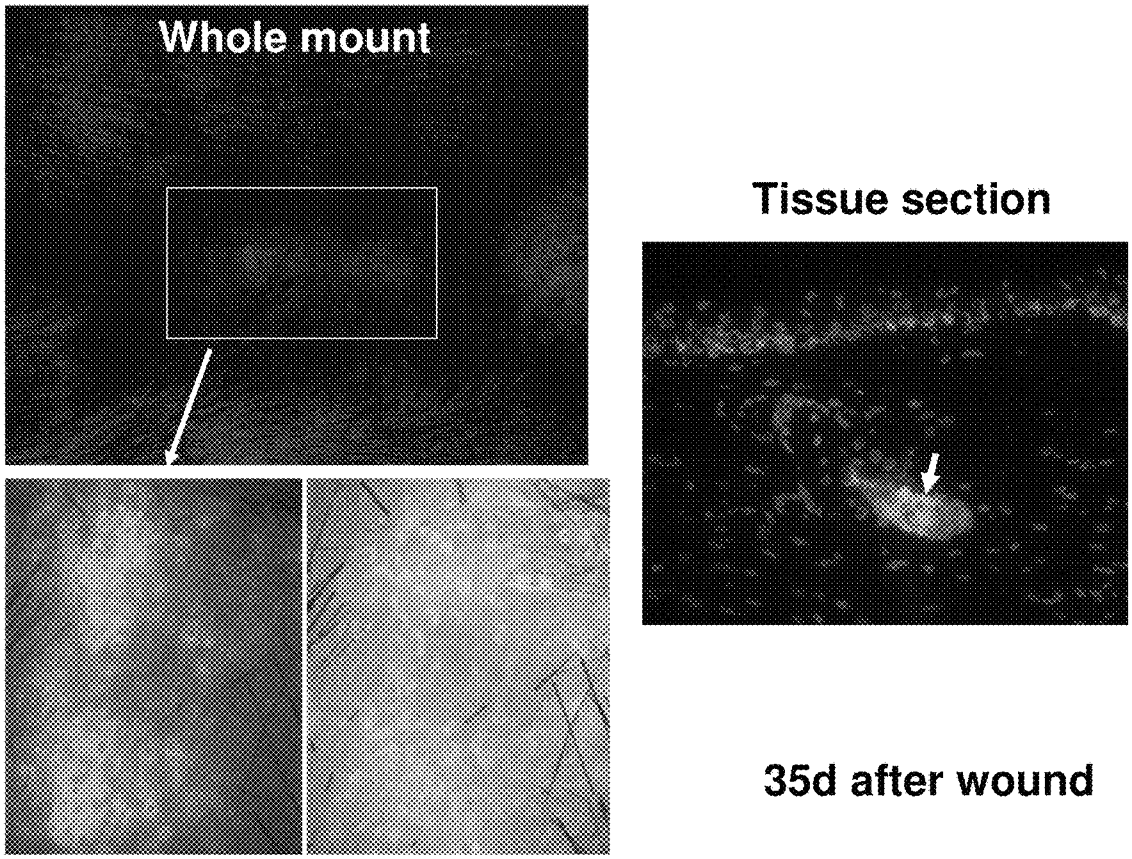
FIG. 14. A. Stem cells in EDIHN-induced HF express K15. Left top panel: Top view of wound site. Bottom, far left panel: epidermis whole mount; bottom, second from left panel: same as [bottom, far left] panel but viewed under white light; right panel: tissue sections. B. Neogenesis HF proceed to next hair cycle.

To determine whether EDIHN-induced HF contain normal levels of HF stem cells, mouse skin was examined for the presence of label-retaining cells at 21 days after wound induction. Retention of BrdU during a long chase period is, under these conditions, one of the hallmarks of HF stem cells. Normal numbers and placement of label-retaining cells (in the bulge of the HF) were observed (FIG. 13). To verify that the label-retaining cells were HF stem cells, K15-eGFP mice were utilized. In these mice, eGFP (enhanced green fluorescent protein) is expressed from the K15 promoter; thus, expression of eGFP identifies HF stem cells. As depicted in FIG. 14A, eGFP-expressing cells were observed in tissue sections (right side) of newly formed hair follicles 35 days following wound induction. eGFP-expressing cells were also seen in the epidermis whole mounts (bottom, far left panel) indicating the conversion of epidermal cells into cells with hair follicle stem cell characteristics. ([bottom, second from left] panel is same as [bottom, far left] panel but viewed under white light) This finding shows that the observed label-retaining cells exhibited HF stem cell properties.

Figure 14B:

To determine whether EDIHN-induced HF cycle normally, mounts were prepared from additional mice at 35, 38 and 45 days after wounding. As depicted in FIG. 14B, the EDIHN-induced HF entered the resting phase, telogen, and then re-entered a new anagen stage.

Figure 15:
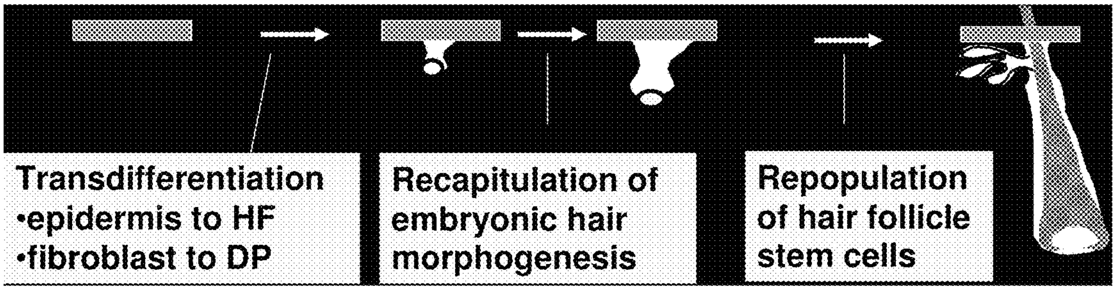
FIG. 15. Schematic of creation of new HF by EDIHN.

In summary, the findings of this Example show that EDIHN-induced HF contain HF stem cells, as do embryonically generated HF. The presence of the HF stem cells shows that EDIHN-induced HF retain the ability to enter into cyclical hair growth in the same manner as embryonically generated HF. The findings also show that wounding induces epidermal cells to assume a hair follicle stem cell state (expressing K15-eGFP). This model is shown schematically in FIG. 15. The findings of Examples 2, 3, and 4 show that EDIHN-induced HF are fully functional and thus able to restore hair growth to a subject in need.

Example 5

Figure 16:
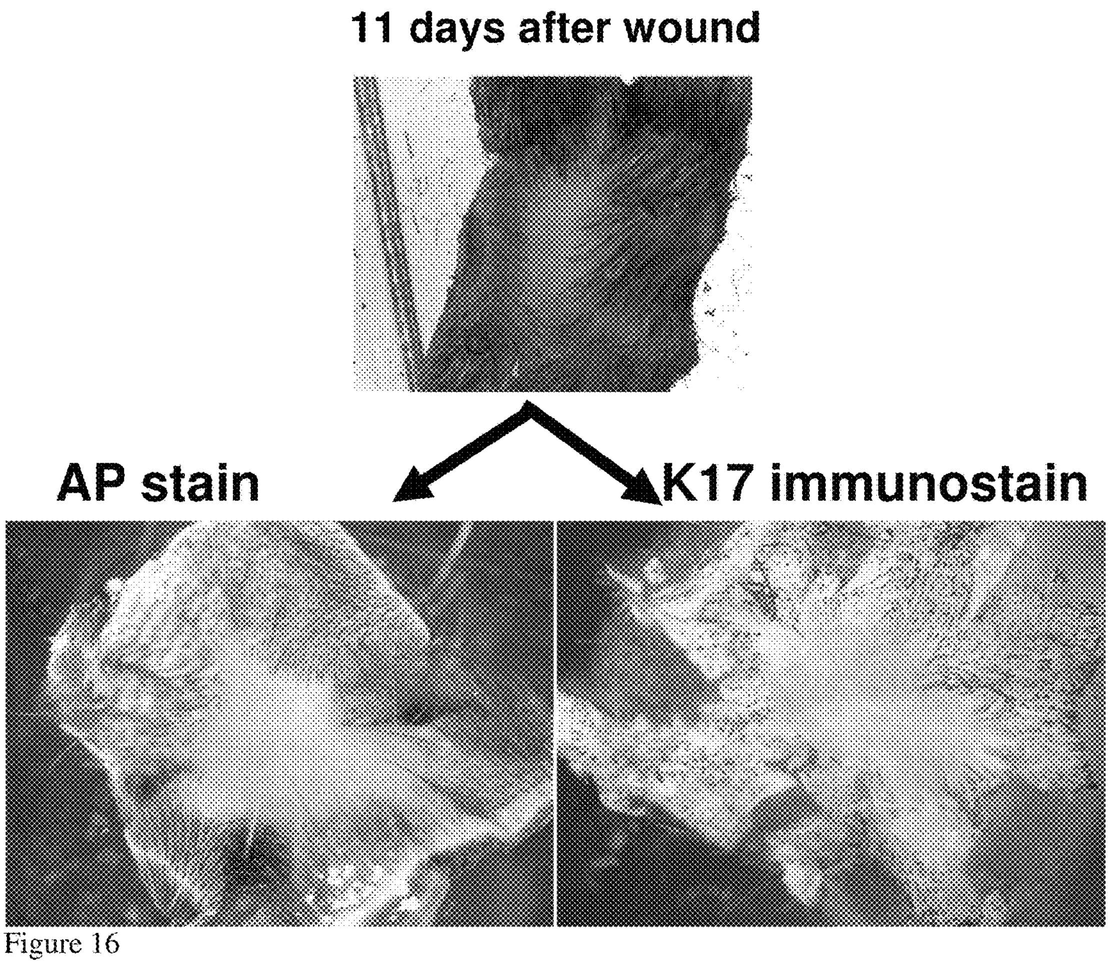
FIG. 16. No new HF are evident 11 days after wound induction in 21-day-old mice. Top panel: macroscopic examination; bottom left panel: AP staining of the dermis; bottom right panel: K17 staining of the epidermis.
Figure 17:
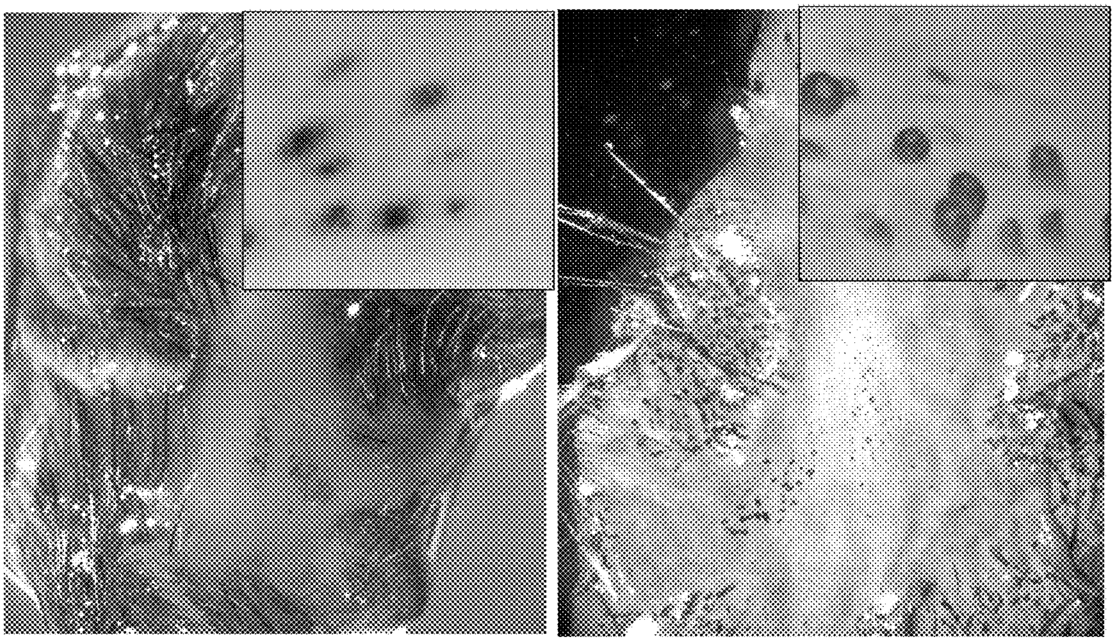
FIG. 17. 14 days after wound induction, new HF have begun to form as evidenced by AP staining of the dermis (left panel) and K17 staining of the epidermis (right panel). Main panels: 10× magnification. Inserts: 80× magnification.
Figure 18:
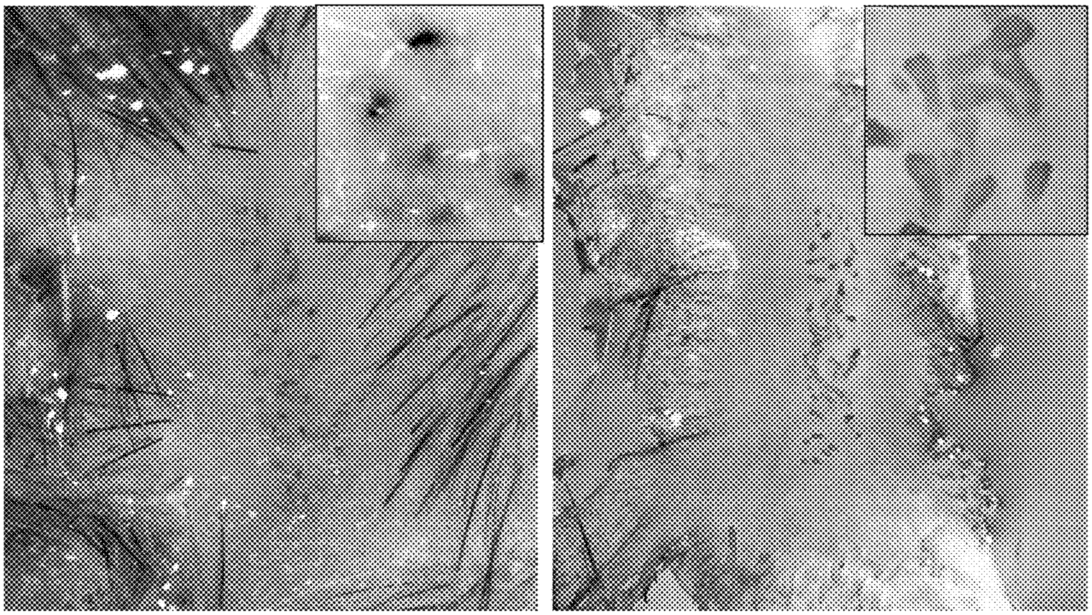
FIG. 18. 17 days after wound induction, new HF are more developed. Left panel: AP staining of the dermis; right panel: K17 staining of the epidermis. Main panels: 10× magnification. Inserts: 80× magnification.

EDIHN-Induces New Hair Follicles in Mice at the Telogen Stage of the Hair Cycle To determine whether EDIHN was induced new hair follicles in mice wounded at the telogen stage of the hair cycle, 21-day-old mice were subjected to EDIHN using a 1-cm excisional wound, as described in Example 2. Skin was then examined by whole-mount assay for indications of new HF. As depicted in FIG. 16, after 11 days, new HF were not evident by macroscopic examination (top panel), AP staining of the dermis (bottom left panel), or K17 staining of the epidermis (bottom right panel). After 14 days, as depicted in FIG. 17, dermal papilla cells were detected in the dermis (left panel) and HF stem cells in the epidermis (right panel), demonstrating that new follicles were being formed. After 17 days, the new follicles were more developed, as shown by examination of the dermis and epidermis (FIG. 18, left and right panels, respectively). This method induced formation of an average of 49 new follicles in the wound, a number that was consistent over three separate experiments, as depicted in Table 1.

TABLE 1

Results of three separate experiments performed on 21-day-old mice.

| Sample | Expt 1 | Expt 2 | Expt 3 | Avg of expts | Std dev of expts |
|---|---|---|---|---|---|
| 1 | 24 | 70 | 55 | | |
| 2 | 29 | 52 | 25 | | |
| 3 | 27 | 85 | 53 | | |
| 4 | 102 | 25 | 80 | | |
| 5 | 53 | 27 | 23 | | |
| Average | 47 | 51.8 | 47.2 | 48.67 | 2.71 |
| Std dev | 32.8 | 26.3 | 23.7 | | |

The findings of this Example demonstrate that EDIHN is capable of inducing formation of new HF in mice at the telogen stage of the hair cycle, despite that fact that these mice do not contain HF at the anagen stage during wounding.

Example 6

In Adult Mice, Induction of Anagen Increases the Efficiency of EDIHN

The experiment described in Example 5 was repeated with mice of different ages, and therefore at different stages of the hair cycle. To ensure that wound scarring occurred, larger wounds were in induced in the older mice. As depicted in Table 2, adult mice at telogen, such as 8-week-old mice, exhibited lower efficiencies of HF formation by EDIHN.

TABLE 2

Efficiency of HF formation by EDIHN in adult mice at various stages of the hair cycle.

| Age | Wound size | Days after wound | Mice exhibiting EDIHN | Hair cycle |
|---|---|---|---|---|
| 3 wk | 1 cm | 20 | 25/25 (100%) | Telogen |
| 4 wk | 1 cm | 20 | 5/5 (100%) | Early anagen |
| 5 wk | 1 cm | 20 | 1/2 (50%) | Anagen |
| 8 wk | 1.5 cm | 30 | 16/35 (46%) | Telogen |
| 14 wk | 1.5 cm | 30 | 1/2 (50%) | N/A* |
| 20 wk | 1.5 cm | 30 | 2/2 (100%) | N/A* |

*The second telogen lasts approximately 40 days in mice. Thus, 14-week-old and 20-week-old mice contained a mixture of telogen and anagen HF.

Figure 19:
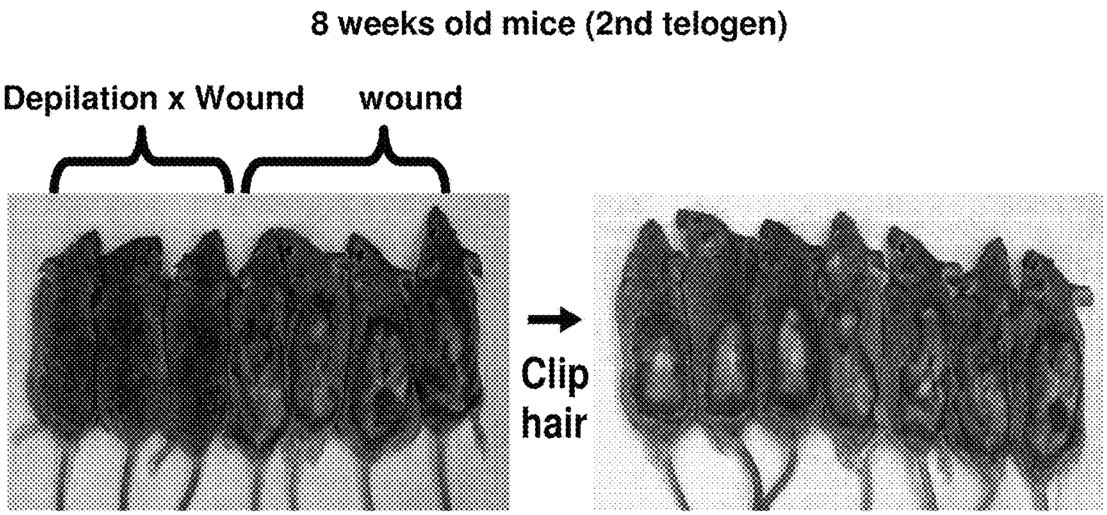
FIG. 19. Wounds closed similar in mice subjected to depilation, then wounding (left 3 mice in each panel) vs. wounding alone (right 4 mice in each panel). Left panel: immediately following wounding. Right panel: 10 days following wounding.
Figure 20:
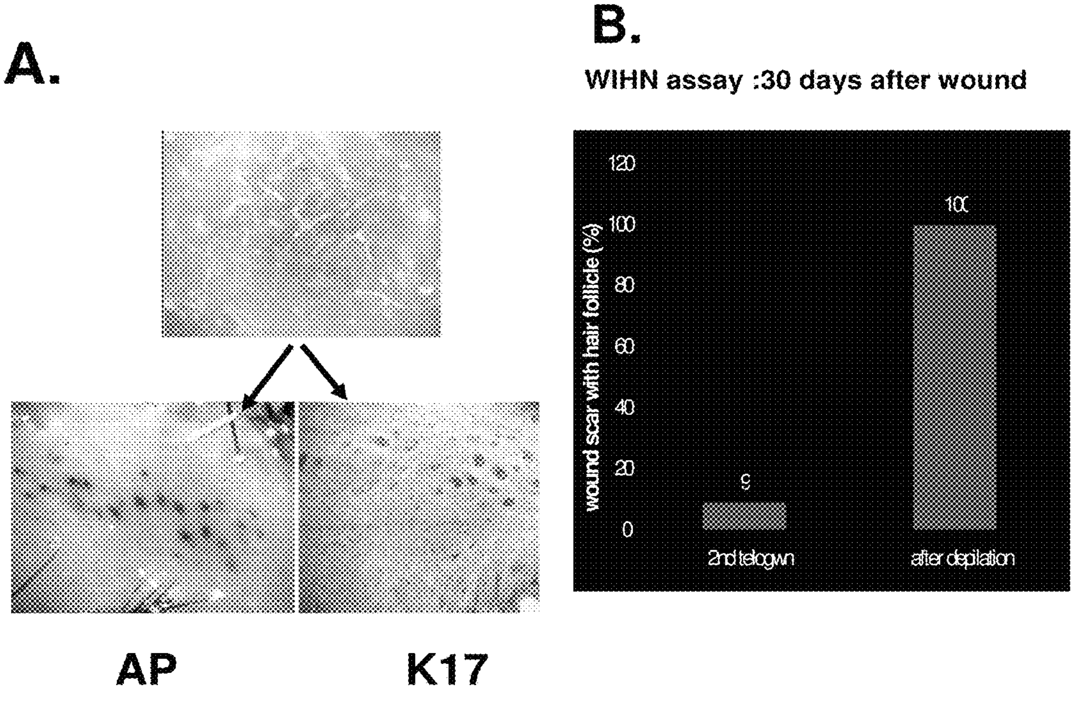
FIG. 20. Anagen induction by depilation prior to wounding enhances the efficiency of EDIHN. A. Top panel: lower left panel AP staining of the dermis; lower right panel: K17 staining of the epidermis. B. Graphical representation of enhancement of EDIHN by depilation.

To determine whether experimental induction of anagen increased the efficiency of EDIHN, 8-week-old mice were depilated several days prior to wound induction. As depicted in FIG. 19, the wounds closed similarly whether or not they were preceded by depilation. As depicted in FIG. 20A-B, the depilated mice exhibited enhanced EDIHN relative to the non-depilated mice depicted in the previous Example by a factor of 11-fold.

The findings of this Example demonstrate that anagen induction enhances EDIHN. In addition, these findings show that EDIHN is capable of not only forming new HF, but also of activating anagen in pre-existing HF in the telogen stage.

Example 7

EDIHN-Induces New Hair Follicles in Human Skin Materials and Experimental Methods Grafting Discarded human adult scalp from the preauricular area obtained from plastic surgery was grafted onto immunodeficient (scid) mice. The graft was bandaged and allowed to heal, then was used in the wound healing study 3 months after grafting.

Results

Figure 21A:
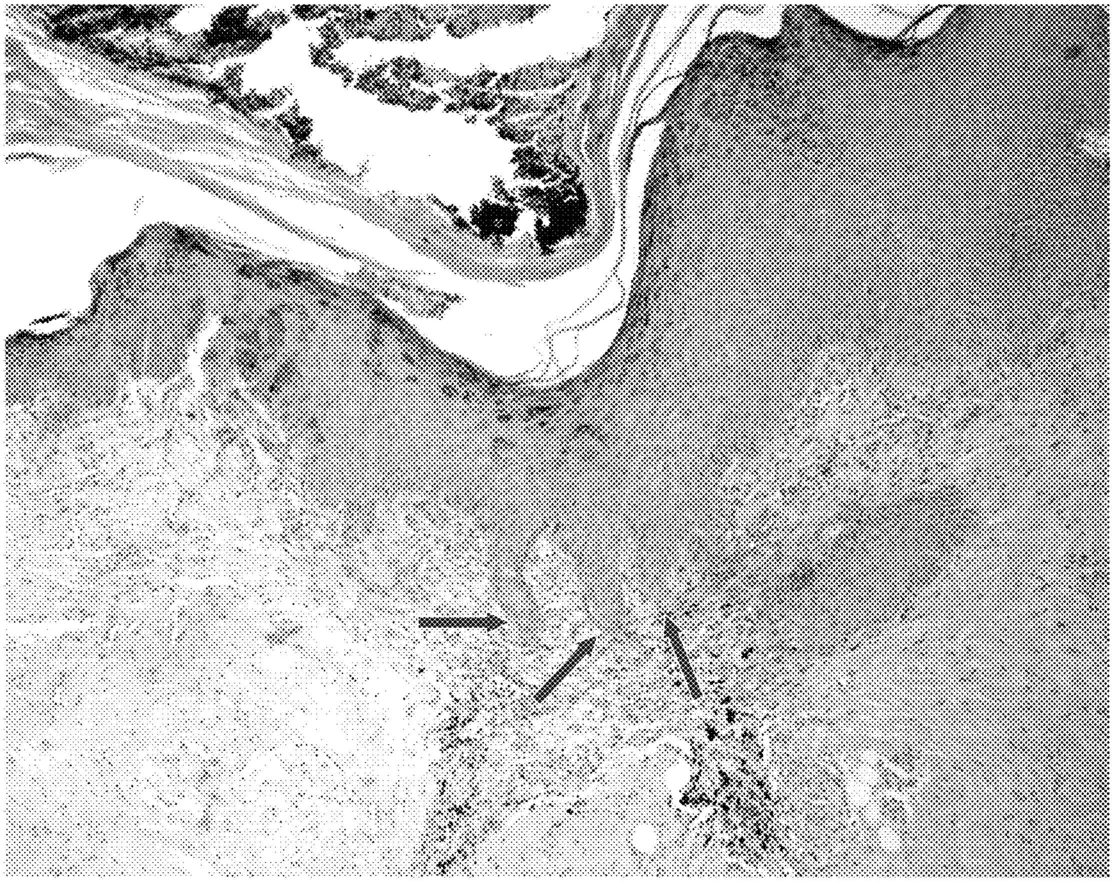
FIG. 21. A. EDIHN in human skin grafted to immunodeficient (scid) mice, seven days after induction of an excisional wound. Arrows indicate new HF. B. Dermal abrasion of human skin grafts results in EDIHN. Human adult skin (W) was grafted onto mice, abraded, and examined seven days later, by staining for S100A6 (first, second, and fourth rows) or S100A4 (third row). Hair germs (HG) and dermal papilla (DP) are indicated. Human fetal skin (F) with normal developing hair follicles is shown for comparison. Mouse skin 17d post wounding was included as a control (top left panel).

To determine whether human skin responded to EDIHN as did mouse skin, human skin was grafted onto SCID (immuno-deficient) mice and subjected to depilation by plucking and wound induction three days later. Seven days following wound induction, formation of new HF was observed in the human skin (FIG. 21A; arrows indicate new HF) by hematoxylin and eosin staining of paraffin embedded tissue sections.

Figure 21B:
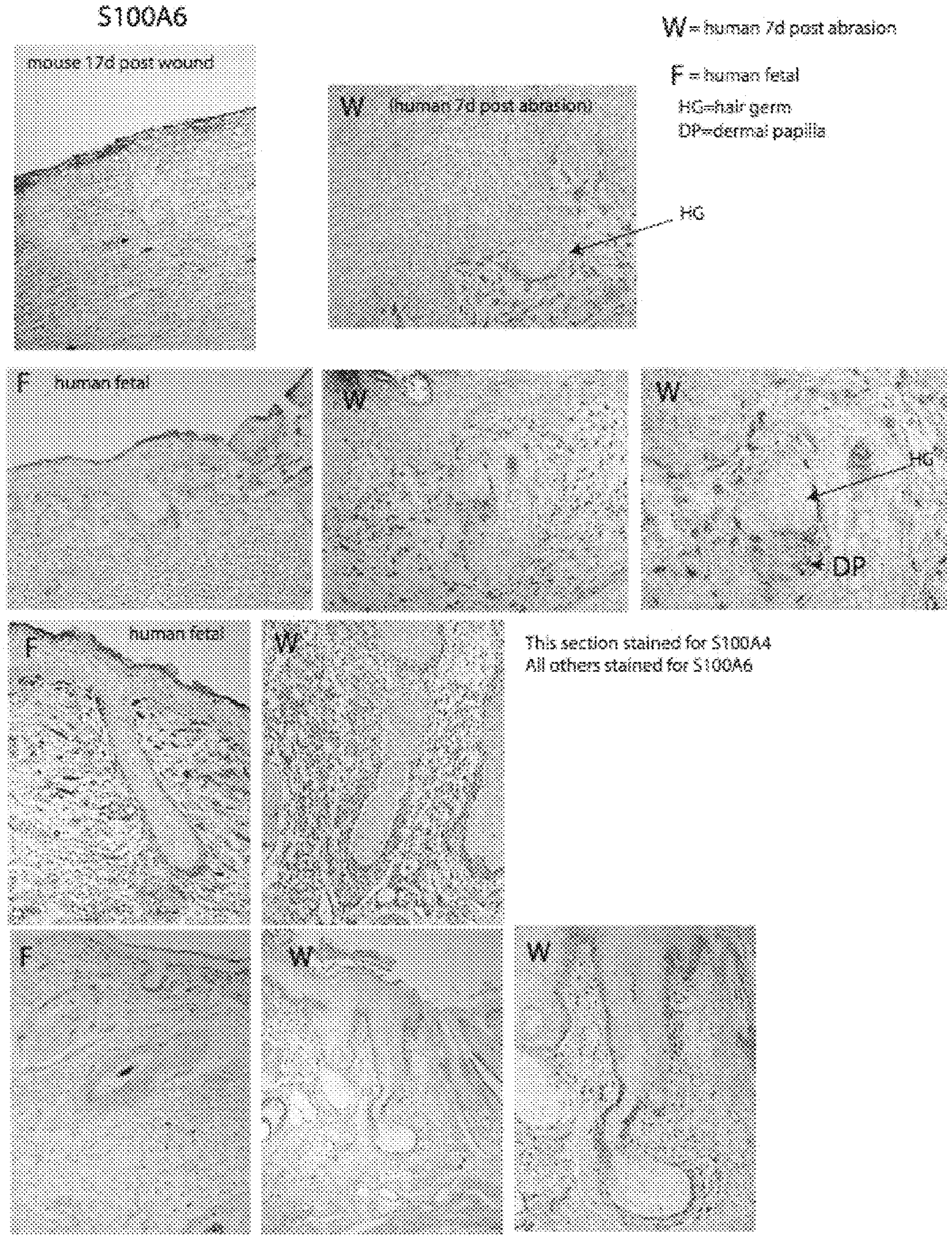

In additional experiments, adult human skin was grafted onto mice, abraded, and examined at 7 days post-abrasion. New HF were generated in the human skin, which mimicked normal hair follicle formation during fetal development, as evidenced by staining for S100A6 or S100A4 (FIG. 21B).

The results of this Example show that EDIHN can be used to generate hair growth in human skin as for mouse skin.

Example 8

Molecular Pathways Activated During HF Stem Cell Activation Materials and Experimental Methods Isolation and Activation of HF Stem Cells K15-eGFP mice were depilated in order to induce formation of new HF. Activated hair follicle stem cells were isolated from K15-eGFP mice using fluorescence-activated cell sorting (FACS) two days after depilation and 5 μg (micrograms) total RNA from the cell population was isolated, reverse-transcribed and hybridized to an Affymetrix (Santa Clara, Calif.) array MG_U74v2 chip. Scanned chip images were analyzed using Affymetrix Microarray Suite 5.0 and GeneSpring software (Silicon Genetics) to detect fold-change differences between activated HF stem cells (HFSCs) and non-activated (telogen) HFSCs. Values were normalized before computing fold-changes and differences between non-activated "bs-line" and activated ("expt") samples.

Results

To identify molecular pathways up-regulated during HF stem cell activation, activated HF stem cells were isolated, and the gene expression patterns of the cells were analyzed to detect up-regulated transcripts. The transcripts depicted in Table 3 were up-regulated at least 2-fold in the activated HF stem cells relative to the cells prior to activation. In some cases, the sequence in Table 3 is a genomic sequence that contains the sequence of the transcript. Data pertaining to the up-regulation of the transcripts and further information about them is provided in FIG. 22.

TABLE 3

RNA transcripts up-regulated during HF stem cell activation.

| SEQ ID No: | Access. # | Sequence |
|---|---|---|
| 1 | AW047343 | uuuuuuuuuuuuuuuuuucuuaaaaauauaaauguauuugucugcaucaugacguucuucggg<br>accuagcuggccagaccacuggccaugggacaaggaggaagucagguguaagucugagcaagga<br>acaggacucugcccuggcaggguggagguggccucacagugucccaugcugggccugguagcg<br>gaaagcacagcacgguagugggacagcuccugccgcacagccaccaccuccugccgcaacagggc<br>guuuuccuucuccaggaaggcagcccgcacagauauccgguucuccuugagucuucuugcaucuc |
| 2 | AF053235 | Sequence below. |

caguuccucagcauggccaccugcagccgccaguucaccuccuccagcuccaugaagggcuccuguggcaucgguggugg cu cuagccgcauguccuccauccuggcuggaggauccugccgggcucccagcaccugcgggggcaugucaguuaccuccucucg cuucuccucugggggagucugugggauuggagguggcuauggugggagcuucagcagcagcaguuugguggaggacuug guaguggauuugguggucgauuugauggauuuggugguguuuuggugcuggucuugguggugcuuggcgguggua uuggugaugggcuccugguggcagugagaaagugaccaugcagaaccucaaugaccgccuggccaccuaccuggacaaggu gcgugcccuggaagaggccaacagagaccuggaggugaagauccgggacugguaccagaggcagcggcccacugagaucaaa gacuacagccccuacuucaagaccauugaggaccugaagagcaagaucauuauugccacccaggagaaugcacaguucacuu ugcagauugacaaugccaggcuggcagcugaugacuucaggaccaaguacgagaaugagcuguucuugcggcaguccgugg agggugacaucaauggccugcgcaaggugcuagaugagcugacccuguccagagcugaccuggaaaugcagauugaaaaccu cagagaagagcuggccuuccugaagaagaaccaugaggaggagaugcuugccuugaggggucagacugguggggacgucaa uguggagauggacgcagcccccggugugga ccucagccgcauucugaaugagaugagggaccaguaugagcagauggcaga gaagaaccgcagagauguggaggccugguuccugagaaagacugaggagcugaacaaagagguggccucuaacagugaucua auccagagcaaccgcagcgagguggcugagcuccgcaggguguuccagggccuggagauugaacugcagucccagcucagca ugaaagcauccuuggagaacagccuagaagagaccaaaggcagauacuguaugcagcugucccagauccagguuugaucag caguguggaggagcagcuggcucagcuucgcugcgagauggagcagcagagccaggaguacaacaucuuguuggaugugaa gacaaggcuggagcaggagaucgccaccuaccgccgucugcuggauggcgagaauauccacuccuccucacagcacuccucu ggacaguccuauucuucucgagaagucuucuccucauccucccgccagccccgguccauccucaaggagcaagguucaacca gcuucagccagagccaaagucagaguuccagggacuaauguuuugccuagagccuccucacccacaacugccucucaagcug agggcuuggggcaggacccuguuuucuuugcgcauuccccaucugucuccccuacccucucaugguggguaggcuaauaaag TABLE 3-continued RNA transcripts up-regulated during HF stem cell activation.

| SEQ ID No: | Access. # | Sequence |
|---|---|---|
| | | cuuuuugguugaugcaaaaaaaaaaaaaaaaa |
| 3 | M26005 | gcgccaguccuccgauagacugagucgcccgguacccguguucucaauaaagccucuug<br>cuguuugcauccgaaucguggucucgcugguccuugagagggucucccucagauugauugac<br>uacccacgucgggggucuuucauuuggaggccccagcgagauuuggagaccccugcccaggg<br>accaccgacccccccgucgggagguaagcuggccagcggucguuucgugucugucucugucuu<br>cgugcguguuugugccggcauuuaauguuugcgccugcgucuguacuaguuagcuaacuag<br>aucuguaucuggcgguuccgcggaagaacugacgaguucguauucccggccgcagccccugg<br>gagacgucccagcggccucgggggcccguuuuguggcccauucuguaucaguaaccacccga<br>gucggacuuuuuggagcuccgccacuguacguggcuuuguuggggacgagagacagagac<br>acuucccgcccccgucugaauuuuugcuuucgguuuuacgccgaaaccgcgccgcgcgucug<br>auuuguuuguuguucuuuuguucuucguuaguuuucuucugucuuuaaguguuuuucgag<br>aucaugggacagaccguaacuaccccucugaguuuaaccuugcagcacuggggagaugucca<br>gcgcauugcauccaaccagucuguggaugucaagaagaggcgcuggauuaccuucuguuccg<br>cugaauggccaacuuucaaugugggauggccucaggaugguacuuucaauuuaaguauuau<br>cucucagguuaagucuagaguguuuuguccugguccccacggacacccggaucaggucccau<br>auaucgucaccugggaggcacuugccuaugacccccuccgugggucaaaccguuugugucu<br>ccuaaacuuccucccucgccgacagcucccguccucccgcccgguccuucugcgcaaccuccg<br>ucccgaucugcccuuuacccugcccuuaccccucuauaaaguccaaaccuccuaagccccag<br>guucucccugauagcggcggaccccucauugaccuucucacagaggaccucccgccguacgg<br>agcacaaccuuccuccucugccagagagaacgauaaagaagaggcggccaccaccuccgaggu<br>uuccccccuucucccaugguguucucgacugcggggaaggagagacccucccgcagcggacu<br>ccaucaucucccaggcauucccacuccgcauggggggagauggccagcuucaguacuggccg<br>uuuuccuccucugauuuaacccuuccuuuucugaagauccagguaaauugacggccuuga |
| 4 | AA681998 | gacguagagccccuugcgcccgguuuccugaucccgcuuacuccucugcgcgccggcaggau<br>ggcccacaagcagaucuacuacucagacaaguacuucgaugagcacuacgaguaccggcaugu<br>cauguuacccagagaacucucuaaacaaguacccaaaacucaucugauguccgaagaggagug<br>gaggagacuugguguccaacagagucuaggaugguucauuacaugauucaugagccagaac<br>cgcauauucuucucuuuagacgaccucuuccaaaagaacaacaaaaaugaagugcagcuggga<br>ucaucuaaucuuuuucaaauuuaauguauauguguauauaagguaguauucagugaauacu<br>ugaaaaguguacaaaccuuucauccauaccugugcaugcgcuguauucuucacagcaacaga<br>gcucagucaaaugcaacugcaaguagg |
| 5 | AF057156 | atuaaaaagccagcugcccaaugccugcacacagaauccacaccaacagagaaccugcucuucu<br>cugaguauuagguaagucucugcuugcaacugauuugaaauucuugcuuauuuuuuuacua<br>ugaaaaacuguucaaagccaacucuauuacagaguugaugugggugcugccuacaguuagu<br>gaacaguagcauuguuugcuuaaauuauagcacauuuuggguccuaggaacuugagagguga<br>uucaguuggucacuguaguagacagccuuggaaucagagauuaaggcaaaaggaaaccucca<br>uucaaauauucauggaaguucacagcuggagacagguuaaggcuucaguccagauagcuuuc<br>agaauuauugcaguucuuacugauaggcauaucaauagcgaaauuuaauuuauuagaggaau<br>cuacuaaaguaaauuuuuaggccaauauagaacauaccauacuuguagucuggcagagaagg<br>ugacauaugaaauugaaaugcgauucauagacagugguagugaaagaaauaaugguggggan<br>gggcugugcangggaggcauggcucaaggacagcacuuaguggguagcacacaccaugaacua<br>ugauggaaaagcauuugauaggcagagacagaaauguaggaaauguguagggauccaugaga<br>gcauaaacuaaaagggcaaaagcauaugagcauggacuaacaugcagccacucugcaaguuau<br>acuaugaucuauuucacaaggagguugguaugcugcugucuuugggugacaccgcuuuccc<br>agauguccuggugugguagguucacaagccucucagaagccauacuuuauugcuuuuuaaga<br>cguauuauuaauauuuuggcuagcauaugguuuagugugagaguuuuauaugcauauguca<br>uuauacuuugcucauuuaugucuuggaacuucuucaacuagguagaaaacaugaccagggag<br>aaugagaguaaggaaagaacccacugagacagacaagagcaaaccauacuucugcuaaucaug<br>uuuaaaaguccagaaaugaucauaccauauuuuauuuucaagugugggaagucagcauggaga<br>ggggcucuuuuucucuaaaggggccugaaauuaaauugacuugauguugagguuaccuucu<br>cuuucaaugaaucacuaaauugucuuuucuguuucccaggacccaagugcuaucuaaccaug<br>aguucccaccagcagaagcagcccugcacuguaccuccucagcugcaccagcagcaggugaag<br>cagccuugccagccaccaccccaggaaccuugugcccccaaaaccaaggaucccugccacccu<br>guuccugagcccugcaaccccaaggggccagagcccugccaccccaaggcacccgagcccugc<br>caccccaaggcaccugagcccugcaaccccaaggugccagagcccugccagccuaaggugcca<br>gagcccugccagccuaaggugccagagcccugcaaccccaaggugccagagcccugccaaccu<br>aaggcaccagagccuugccaccccaaggcgccugagcccugccacccuguuguucccgagccc<br>ugccccucaacugucacuccaucaccauaccagcagaagacaaagcagaaguaauauugucca<br>gagccaugccugaagaccugaucaccagaugcugaggcugcugucuauccugcuuaugaguc<br>ccauugccuugugcuaccaaugcugugaccuucagucuuaaucccucucuccuugcaccacc<br>uaaaaaguugacucucauccucaucuucaagggcuccugagccucuuaacauugcccaaagu<br>cauauugaauggcuacacuuuucauggcucaggauucaucugaagggggugaggagugaga<br>caaguguaugguca auauuuucccccc auuaaaugccauuuaacucc |
| 6 | AI845584 | uuuuuuuuuuuuuuuuuuagccaaaauaguuauuuauuaauaauuuaagguuuuacauucu<br>uauaauaaauuccagcucaaaacuuuacaccacgaacaucauggagcaaguuaauucucccuu<br>ccucucaaccuguugcauccaccaaaugggcgcucauacucgcacacauacacacacuuccag<br>uuucguauuuuuuuuuaaaaggaaagaaaccaacccaaaguauugcauuugaggugacacuc<br>ccugaa |

TABLE 3-continued

RNA transcripts up-regulated during HF stem cell activation.

| SEQ ID No: | Access. # | Sequence |
|---|---|---|
| 7 | AA614971 | aagaugcccuuuggauuggauuggauugaucauguuuaacucagcguauuuuauggaugaa<br>agcuaaauacagauauuuggcaucucuaagguggaaugagcccacuccacacacugauaaaau<br>ucaugcauaguuu |
| 8 | AV374591 | aaccaaaugggaauggggucccccaacnuuncugugguaccagccggguuucucuugcauug<br>gaaacaaacaccuuuguaggcauuugcguauucgugaagagacuguuuuaugaaucaccucu<br>uagauuuaunuaauuaaccuaaguuguugaaguuucuguuucuccuuaagagaaauuacaa<br>aaauucaacauugaagcauaguuucuuguuuucuguugucaaauaguaauaaugugcugug<br>auguuuaugcuuauucauaaagauguuuuacuuuuuaguguaauguuaguucuuuuuaaca<br>uuauuuugcuuaaauuugauaaugcccgacaagaauauauuuugcuuugauuuauacacug<br>auucuuugugacaaauaugacccauuaaaaaugccuuuuaauagacuaacuuaccuuuugua<br>gcuagguacucauguucuuuuuaaaagaugcccuuuggauuggauuggauugaucauguu<br>uaacucagcguauuuuauggaugaaagcuaaauacagauauuuggcaucucuaagguggaau<br>gagcccacuccacacacugauaaaauucaugcauaguuuuaaaugaacauuaauaaacucaug<br>uugucuu |
| 9 | U04443 | gaauucaaggaggcuuuccagcuguuugaccgaacaggugauggcaagauccuguacagcca<br>gugugggaugugaugcgggcccugggccagaacccuaccaacgccgaggugcucaagguuc<br>uaggaacccccaagagugaugagaugaaugugaagguacuggacuuugagcacuuccugccc<br>augcugcagaccguggcgaagaacaaggcccagggaaccuacgaggauuauguugaaggccu<br>ucguguguuugacaaggaaggaaauggcaccgucaugggugcugaaauccgucauguccua<br>gucacacugggcgagaagaugacagaggaagaaguagagaugcuaguggcagggcaugagga<br>cagcaaugguugcaucaacuaugaagcauuugugaggcauauccugucggggugacgggccc<br>gauggggcggagcucguccggauggugcugaauggcugagacauucuguaucccgagucug<br>uucccugcccagugugauuucuguguggcuccagacgcuccccugucacagcaccuuguccc<br>auuugguuucuuuggaugauguuugccuucaccaaauaaaauuugcucucuuugccc |
| 10 | Y07836 | caaccaccuccuaccugccugcccaaagcuccagggcuggagcacggagaccugucaggg<br>auggauuuugcccacauguaccaaguguacaaguccaggcggggaauaaaacggagcgaa<br>gacagcaaggaaacuuacaaacugccgcaccggcugauugagaaaagagacgugaccgg<br>auuaacgagugcauugcccagcugaaggaucuccuacccgaacaucucaaacuuacuacu<br>uugggucacuuggaaaaagcagugguucuggagcuuacguugaagcacgugaaagcauuga<br>caaaucuaauugaucagcagcagcagaaaaucauugcccugcagagcgguuuacaagcuggu<br>gauuugucgggaagaaaucucgaggcagggcaagaaauguucugcucagguuuccagacuu<br>gugcccgugagguacuucaguaccuggcgaagcaugagaacacucgggaccugaaaucuucc<br>cagcucgucacucaucuccaucgugugguccucggagcugcugcaggguggugcuuccagga<br>aaccauuggacucggcucccaaagccgucgacuugaaagagaagcccagcuuccuagccaagg<br>gaucagaaggcccagggaaaaacugugugccagucauccagcggacuuuugcucccucgggu<br>ggggagcagagcggcagugacacggacacagacaguggcuauggaggugaauuggagaaagg<br>ggacuugcgcagugaacagccguacuucaaaagcgaccauggacgcagguucgccgugggag<br>aacgugucagcacaauuaagcaagaauccgaagagcccccccaccacaaagagccgaaugcagc<br>ucucagaagaggaaggccacuucgcgggcagugaucugaugguuccccauuucuugggcca<br>cacccacaucagccuccuuuuugccuucccuucuaucucaucccaccaucggccacugccuac<br>cugccuaugcuggagaaaugcugguaccccaccucugugccaguguuauacccaggccucaa<br>caccucagcugcagcccucuccagcuucaugaacccagacaagauaccgacucccuugcuucu<br>gccccagagacucccuucuccuuuggcacauucgucccuugacucuucggccuugcuccagg<br>cuuugaagcagaucccuccuuuaaacuuagaaaccaaagacuaaacucuggagggaucuccu<br>gcugccuugcuuucuuuccucccuaauuccaaaaaccacgaagguuucccugagugcagaga<br>gaucagcccacccugcagacccacagagaagauucagagugugugugagagugagugagugu<br>gcgugcgugcgugcuuguauguauguuuguauauguaggacaauaaguuccuucugacaca<br>agggagacacgagaaggauagccugacaucagaugacagacuggaggacuguagcacaucuc<br>ugggcguuucccuacccagagaagagcc |
| 11 | M21285 | Sequence below. |

uugcaggcgagggcuuccacaacuaccaccacaccuuccccuucgacuacucugccagugaguaccgcuggcacaucaacuuc accacguucuucaucgacugcauggcugcccugggccuggcuuacgaccggaagaaaguuucuaaggcuacugucuuagcca ggauuaagagaacuggagacgggagucacaagaguagcugagcuuugggcuucugaguuccuguuucaaacguuuucuggc agagauuuaauauucuguugauuaacuaacaacuggauauugcuaucgggguguuaaugaugcauuuaaccuauuccggua caguauucuuauaaaaugagaaagcuuugaucacguuuugagguaauaaauauuuuauuuagcuaggauuaaccaugccac aagacauuauauauuucuaagcacacaugauaaaugcauauacaauuuugcacaacagcuuuaauaauaacaauaaauuug aacauucuauacagagaggaucaaagccaaggaacaugcuguuuugaugcuagggugagcauggugcucagucccuguuug uuugcaugguguccagcuuuguuucuucucugucaucaccaccuucaggcaaauaguugaccaaccacuggccugugucug uccacccuccaaagcccaggccaccuuucuguuuucugaaauacugauccuuccuccugaauacaucccuccuuguuccuag cuucaagacugcugccucaaauagggauagagcaaguccccgcugcagguugugcuagaugggauggagaaauuaucuuca TABLE 3-continued RNA transcripts up-regulated during HF stem cell activation.

| SEQ ID No: | Access. # | Sequence |
|---|---|---|
| | | uuugauacagagcaaguagauugucucgagagaaaaguuagcaugcgugguaugauuuguaaguaaagauggaagagagag |
| | | agagagagagagagagagagagagagagagagagagagagagagagguagccauaucuaacagccuacuuaccaaagaccccaggccucuc |
| | | ugcuuggcaugccuccuuucuguccauccucugaaccccagagauuagugagauuugaauaauuaaaucauuuucagagug |
| | | aaggggguuaaugcagggucugugcuaggggaggguuuuagcuuuugguaacugaagauuuuuucauggaaaaagucuuc |
| | | guguucaaugugccuagaacugauaacuaaacagcugacauuugucggggacagauaugguguguaaacuaugaaaauauaa |
| | | gcaaaaucuucacuuggaacaugaaacuauuucacuuagaaaauaaucgaaggacccgagguguugccuggguugccaguuu |
| | | cuuucguggcugggcaggaacuagugagguugaggggcagugucuguaaguagcugcuaagaggugcauuuccagaugaa |
| | | gcccuuggggaacaucugccagggauccgcaugguguuggcuccauccauugcuuuaguuuccuccuuggauuguguagaa |
| | | acuuggcuucccaugguuuugaaccuuccaugccuucuuugcuuuguggccacccagccugccuagugcugccuaggaagc |
| | | ucuuacccaccugauuucuucugacauuucuuucuuuggccuuuuuuucuuucuccggacaugcagcuaguugccugagu |
| | | guaucaagagcacccaggacuugcugcuguccaggccuguuccucccccaguauccgugggugugggaagagcuguguagcu |
| | | ucaggaagcagagccaggugccaccuuucuguggcuuccagauccucccuaccuccaacucaugugccucugucacagugau |
| | | uucaggaaagcuugguagacccucuagcaacaucucgguucagaaagucucucugguuugugaguuaacagcucagcuaag |
| | | ugcuguuuugucucagugaguuaaccacugaaugcgaggguugguuguugaucugucucgguguguguguagacag |
| | | cauaugcacuucucccugugcgcuuugcaagguaauguggcuuuggcugauccaugcaggcagguagugguacagugcugc |
| | | ugaaaggaagaaguuccccauuuuaucuguuaaaacaccagagacaugggcaagugcuaauggaccucacuucaggaagagg |
| | | gucugcuuccugaagccagugugugaugaaaagugacugagaccugauaucuaaggugagaccugauaccuaacacucugu |
| | | cacacaguccagggccaacagugcuauaggaaagucuagaagaaaacaucacaucaguauuuuagaaccaucaaccaucucuu |
| | | gucccuauagcccaauccagaggccugguuuuuagaacuggcuguguaaggugccaaacacucaguucacuuguagaaucag |
| | | agccuuuuuuccccccuauguuaauugaacacgcgcucugagcuguuuuguugaaguagaaaaucucauagaaaaaucacu |
| | | guagaucuacugaccuauagcccucuggaaaugccuuugagaugguuuuacuuuucuaggucauagaugccugauuauaaa |
| | | gaugaacaauaaaaaucagcuuucuuucuuucucuucugaucuuauuccccagaucugauucaggccauguuccaaagcaagg |
| | | cuacauugagguccuggugucuuuaaguaaaggacaucuuucagauccucucaaagaaggauuuauaacaguuuccagaug |
| | | aauguacuaauagcuuugggugccuuaucucuuuccuaaucuguagugccugugagcucagucucacuccuucccuuagcc |
| | | cggagaccccuuagaucgaguggggaaugaucaagaggcuggcuggagagucaucaguacauugguuugcagaaaucuuuua |
| | | caggcuacauuuuggaauuuuuuuuuuuuuaguaagugaucaaauuuggugggaaguaauucgaguguauucgauuguau |
| | | ugucguccucguuaucauugucaaacauguuauagacggcaguuggcacuggggcugcuaaucucugggguguagucucuga |
| | | aacuguagcuccagugaggugguguggaaagguuagcaaagccaccaucugcuggugcuccagccaaggugcccucuuagccac |
| | | ugaauugcuauguuauccuuucucuuguaacaaacccaccccagagauaaagccuuuaaucaacccaagaaacuccugggcu |
| | | aaguaucugacagucucacaucucaacagugugaauuaaguguccauagcaucagcucaggaggacacucugggagagugcu |
| | | gacaaaaaaggguuauuaaauacugaccuacuacuucaagggcaguucugaggugauuagagcuuuuuuuaaaaaccaaguau |
| | | uuggggauccucagcagagguauucauacagacucccaaagaacuauauauguuccugagaccaucguuuagucuacauugc |
| | | ucuucccagagacugacagauaugaccagucaaagugcaagacuaccuacccacugccaugaaaaccauugcaggaaaccuuu |
| | | cccuuccugaaugagauuuuuuuuuucccuuuuuaugugggguaauuauuugugacccaaguguaauuuggaugauuucc |
| | | auuaauaucaacucuugaagccuacuuguacugauugagauuguauuuguuccuaauaaaaguggaucugguuguacuguc |
| 12 | V00756 | accacuugcagacaaaugaauuccuucgaaauguauuugagguuggacccccugugaugcuu |
| | | gaugcugcaacacuuaaaaccaugaagauuucucguuuugaaaggcauuuauauaacucugc |
| | | agcuuucaaagcucgaacaaaagcucgaagcaaaugccgagauaagagagcagauguuggaga |
| | | auucuuguagaugucugaauuugauggcuguuuucuaaucucuucccuuuauuauuauuuu |
| | | ugcuacuucuaauguauauaagcuuuuagagacaguuuuuuaucuuggucaacuuaaauaa |

TABLE 3-continued

RNA transcripts up-regulated during HF stem cell activation.

| SEQ ID No: | Access. # | Sequence |
|---|---|---|
| | | uuuugauguaggggugguuguauuuuaauuuaauguacaguguuacaaauuaaugagu<br>ucuuuauucucuguaaaaauaacugguaaccacaaauaaaguguuugugauguuuggucgu |
| 13 | Y14296 | auguccgcggccgccuacauggacuucguggcugcccagugucugguuuccaucuccaaccg<br>cgccgccgugccggagcacgggggcgcuccggaagccgagcggcugcgacuaccugagcgcg<br>aggugaccaaggaacacggugacccgggggacaccuggaaggauuauugcacgcuggucacu<br>aucgccaagagcuuguuggaccucaacaaauaccgacccauccagacccccucggugugcagc<br>gacagucuggagagucccgaugaggauauaggauccgacagcgacgugaccaccgaaucugg<br>gucgaguccuucccacagcccggaggagagacaggauucuggcagcgcgcccagcccacucuc<br>ccuccuccacucuggaguggcuucgaaggggaaacacgccuccgaaaagaggcacaagugccc<br>cuacaguggcugugggaaagucuauggaaaauccucccaucuuaaagcccauuacagagugc<br>auacaggugaacggcccuuucccugcacguggccagacugccuuaaaaaguucucgcgcucg<br>gaugagcugacccgccacuaccggacccacacuggggaaaagcaguuccguugcccacugug<br>ugagaagagauucaugaggagugaccaucucaccaagcaugcccggcgucacaccguguucc<br>aucccagcaugaucaagagaucaaaaaaggcucuugccugccccuugugaggugcuccccau<br>ggcagccaggcagagaugggucccccggaaggacagagcucccaggaaacagacugacacaugg<br>aaaucugccacagcagaggcgcgcuggccacaggaggucacugcuucuuuggccaauauucu<br>gauaucucccugcacuguuuccaaaaagcacaugguagcccuaaggucaaagucaacauuug<br>guccccuugcagaggcaacucugaaccgucucugacugaagauucagacugguggguguacau<br>acgucunacugggugaguugaccccuggccucccacagugcagaaccacucucuugaaucac<br>auuaacuuuugagauuuaaaaaaaacccaaacccaacccnncaaaacnccaganacaccgaaac<br>ucuggauccucgaugcuugcugacucucagaauugnuunuucuucucanuuaugcaagcna<br>gagcacaccuacuccagcaugauuugucaucuaaagacuugaaaacaaaacaacaacaacana<br>aaguuacuuauagucaauggauaagcagaguccgaauuuacacuaaucaagacagaccuucg<br>aggggucacgauaaguccggaacuuucaaaccuugcuucguaugaauuguacuaucugaaca<br>uaaacugcacuuuuauuuucuaauaccgagggugaauacgguaaauacaugcuuugagggu<br>agaanccgacggucuguuuggcaccacguuauaaucugcunnuuuuaacgaguaccaccuug<br>gagggcaggcaaauaaaugcuuuuggguauuuucuccuuuguuuuugacaaaugcugcgga<br>ugggggaucgggaucggaggggagugcuuuuaaagauaauaaaaaaugagguaaauaauuu<br>uaacuuaugaauuuguuugaauuc |
| 14 | X16490 | gagauugaaacaauggaagaacuuuccauggcaaacaccauguuugcccucaaucuccuu<br>aagcagauagaaaaaucaaacucuacccagaacaucuuuaucucuccauggagcaucuca<br>ucaacauuggccauaguucuccucggugcugggguaacacugaacagcagauggccaaa<br>gugcugcaguuuaaugaaauuggcaguuaugguaucaccacaagaaacccagagaacuuc<br>aguggcugugauuucgcacaacagauacagaaggaaaauuauccuagugcuauuuuacaggc<br>acaagcaggagauaaaauccauucagccuucucccucucucagcucaacaaucaacaca<br>ccacaggggggauuauuuguuagaaagugcaaacaagcuguuuggagagaagucugcaagauu<br>caaagaagaauacauccaacucucuaagaaauauuacucaacagaaccagaagcagug<br>gacuuccuugaaugugcugaagaagcuagggaaaagauuaauucuugggucaagacucaaac<br>caaaggugaaaucccaaaccugcuacccgaagguucuguagaugaagacaccaagauggugc<br>uggugaaugcugucuacuucaaaggaaaguggaaaacuccauuugagaagaaacuuaauggg<br>cuuuauccuuuccgugugaacucgcaugagagcauaccuguccagaugauguuccuccaugc<br>aaagcugaacauuggauacauaaaggaccugaagacucagauccuagaacuuccgcauacugg<br>aaacaucagcaugcuccuguugcuucccgaugagauugaggacgcauccacuggcuuggaau<br>ugcuggaaagugaaauaaacuuugccaacuucaacaaguggaucagcaaagacacacuggau<br>gaagaugauguuguggucuacauucccaaguucaaacuggcacaaagcuacgaacucaaguc<br>cauucuucaaagcaugggcauggaggaugccuucaacaagggcaaggccaacuucucaggaa<br>ugucugagaggaaugaccuuuuucuuucugagguguuccaucaagccagcguggaugucac<br>cgaggagggcacuguggcagcugguggga cuggggcaguuaugacaggaagaacuggccau<br>gguggcccacaguuuguggccgaucaucccuuucuuuucuuuaucauggacaaaauuaccca<br>cacgauacuauuuguugguagauucuccucacccuaaaaggggaagaccuauuuccacauga<br>gguuuuguagcaugaacuauaagccucagaauugcaucuucaagugccaaaaguuuaaauac<br>uuucuuacacauuuuuauacuucugcuauacacuaaauauaaccuaaaagcaauuguauagc<br>agucuucagugcuuacaguauaacucuauuaaugauuuuguuuccuaaagucagaugaugu<br>cuauuuaguucauccuuauuacugcuuugucuuuauaacuuuaguuuuuacaguguuauu<br>uauuguuuauauaaugguuguuuuacaaauuguuguccucuguuuaaugaaacuguaacac<br>uacagaagcagaaaauuagauaauuuucuauuuaaagaaaaucagccauuuaauuuaauaau<br>gaaggaaaaauaugagucuuccauacuuucccaugauauucacccagaaaaaauguacuuaac<br>aaaagacauguuauaucucuaucauuauauaucauauguacguaucugcaacucaucuauaa<br>uuaggacuacaucauaaguaagcaugcuuacuuacacacugcuaucuguuguauaaaacuua<br>gcaauccuuauuuguuaguuaucuuucuaucacuguaacaaaauaccugagauaauaaaguu<br>caaagauuuauuuugaaaaaaaaaaaa |
| 15 | AW120868 | uuuuuuuuuuuuuuunuaagaauuaacuuuuauuuuugcuuaguuuuauuaaaaaaauaa<br>auaugucauaaagcuuuuguuuccuuuagggagaaaaaaaaggaacaaguuccauaaaauca<br>aacaagcaaugguaacaugucuuaacuugaaaacaacuggggucacugguuuacaaguuaua<br>acugaaugaaugacugccacaguugcccauuuccuccugccaauggcagcaaacaacaggauc<br>aacuagggcaaaauaaauaauuguguggaagcccuga |
| 16 | C78850 | aacuaaacuuccuuguaacuuuugagaacucagcucugguacuuuuucaugccuugcaaaau<br>ggcguuanugcagcuagcuugcuaanccuuaugguggggucuuucauucccccucuuucu<br>ggaaacugnauaaaaaucauuuauucacgugauucuauuucuucuggaucuauugauuugag<br>uuggugauacuguugggucanaaccagggccuguu |

TABLE 3-continued

RNA transcripts up-regulated during HF stem cell activation.

| SEQ ID No: | Access. # | Sequence |
|---|---|---|
| 17 | D67076 | Sequence below. |

gcagcuccgagcuaggugcuaucgcaaggccagagcgcacagcccggcggagagagcagauccuugcucagaucgagucaaa ucgggccaaggcggaggacgaagaguccaggcuccuauucuggacuuguuccccagcuccgggggcgcuucuagguccugc agcagccagcagugcggagccaccaacucggugcuggaaugaaaaaauucccgcgcgccagugcagaaucuuucuaagugac ccggagcuucgggugcuagcucugcacgaacuuucccaucaaagugaucgugaauuuuaagcaucaggagcaggccagcgaa gcucuacgcgucuaaacgucuauccagaccaagaguucucugcggugcagggugcggugccaugcagccaaaagucccuuuu ggggucacgcaagcagaagcccugcuccgacauggggacguccagcgggcagcgagaucucggggcucucuguccgcacac augcuguugcugcuccucgcuuccauaacaaugcugcuaugugcgcggggcgcacacgggcgccccacggaggaagaugagg agcugguccugcccucgcuggagcgcgccccgggccacgauuccaccaccacacgccuucgucuggacgccuuuggccagca gcuacaucugaaguugcagccggacagcgguuucuuggcgccuggcuucacccugcagacuguggggcgcagucccgggguc cgaggcacaacaucuggaccccaccggggaccuggcucacugcuucuacucuggcacggugaacggugaucccggcucugcc gcagcccucagccucugugaaggugugcgguggugccuucuaccuacaaggagaggaguucuucauucagccagcgccugga guggccaccgagcgccuggccccugccgugcccgaggaggagucauccgcacggccgcaguuccacauccugaggcgaaggc ggcggggcaguggcggcgccaagugcggcgucauggacgacgagacccugccaaccagcgacucgcgacccgagagccagaa cacccggaaccaguggccugugcgggaccccacgccucaggacgcgggaaagccaucaggaccaggaagcauaaggaagaagc gauuuguguccagcccccguuauguggaaaccaugcucguagcugaccaguccauggccgacuucccacggcagcggucuaaa gcauuaccuucuaacccuguucucgguggcagccagguuuuacaagcaucccagcauuaggaauucaauuagccugguggu ggugaagaucuuggucauauacgaggagcagaagggaccagaaguuaccuccaaugcagcucucacccuucggaauuucugc agcuggcagaaacaacacaacagccccagugaccgggauccagagcacuaugacacugcaauucuguucaccagacaggauuu auguggcucccacacgugugacacucucggaauggcagauguuggaaccguaugugaccccagcaggagcugcucagucaua gaagaugaugguuugcaagccgccuucaccacagcccaugaauugggccauguguuuaacaugccgcacgaugaugcuaagc acugugccagcuugaauggugugaguggcgauucucaucugauggccucgaugcucuccagcuuagaccauagccagcccu ggucaccuugcagugccuacauggucacguccuuccuagauaauggacacggggaauguuugauggacaagccccagaaucc aaucaagcucccuucugaucuucccgguaccuuguacgaugccaaccgccagugucaguuuacauucggagaggaauccaag cacugcccugaugcagccagcacauguacuacccugugguggcacuggcaccuccgguggcuuacuggugugccaaacaaaac acuucccuugggcagauggcaccagcuguggagaagggaagugguguguggcaguggcaagugcgugaacaagacagacauga agcauuuugcuacuccuguucauggaagcuggggaccaugggaccguggggagacugcucaagaaccugugguggugggag uucaauacacaaugagagaaugugacaacccagucccaaagaacggagggaaguacugugaaggcaaacgaguccgcuacagg uccuguaacaucgaggacuguccagacaauaacggaaaaacguucagagaggagcagugcgaggcgcacaaugaguuuucca aagcuucccuuugggaaugagcccacuguagaguggacacccaaguacgccggcgucucgccaaaggacaggugcaagcucac cugugaagccaaaggcauuggcuacuuuuucgucuuacagcccaagguuguagauggcacucccuguagucagacucuacc ucugucugugugcaagggcagugugugaaagcuggcugugaucgcaucauagacuccaaaaagaaguuugauaaguguggc guuuguggaggaaacgguuccacaugcaagaagaugucaggaauagucacuaguacaagaccuggguaucaugacauuguca caauuccugcuggagccaccaacauugaagugaaacaucggaaucaaagggggguccagaaacaauggcagcuuucuggcuau uagagccgcugaugguaccuauauucugaauggaaacuucacucuguccacacuagagcaagaccucaccuacaaagguacu gucuuaagguacagugguuccucggcugcgcuggaaagaauccgcagcuuuaguccacucaaagaacccuuaaccauccagg uucuuaugguaggccaugcucuccgacccaaaauuaaauucaccuacuuuaugaagaagaagacagagucauucaacgccau ucccacauuuucugagugggugauugaagagugggggagugcuccaagacaugcggcucagguuggcagagaagaguagu TABLE 3-continued RNA transcripts up-regulated during HF stem cell activation.

| SEQ ID No: | Access. # | Sequence |
|---|---|---|
| | | gcagugcagagacauuaacggacacccugcuuccgaaugugcaaaggaagugaagccagccaguaccagaccuugugcagac cuucccuugcccacacuggcaggugggggauuggucaccauguuccaaaacuugcgggaaggguuacaagaagagaaccuuga aaugugugucccacgauggggggcguguuaucaaaugagagcugugauccuuugaagaagccaaagcauuacauugacuuuu gcacacugacacagugcaguuaagaggcguuagaggacaagguagcguggggaggggcugauacacugagugcaagaguac uggagggauccagugagucaaaccaguaagcagugaggugugggcaaggaggugugugugaggggauacauagcaaaggaggu agaucaggacacuacccugccaguuacauucugauaagguaguuaaugaggcacaguagcaucugaaagaccauacagagca cuaaggagccccaaagcacuauuaguaucucuuuucuuauaucuaucgcccaaauaauuuucagagucuggcagaagcccug uugcacuguacuaacuagauacuucuuaucacaaagauugggaaaggcaaagcagaaagaugguaagacugggguuucaaaca aggcuugguuucaaucacuggaggcaaggaggaggggacaaacaagaucauuauucgaagucgcugguugcugugguuuua cggaagguugaugcaucauuccuaucaacagugaaaaguucagcuuguucaacgugacagaaaggcucaucuccgugaaaga gcuccugauuucuucuuacaccaucucaguucuuaacuauaguucauguugagguagaaacaauucaucuauuuauaaaau guacauuggaaaaaaaaagugaaguuuaugagguacacauaaaaaacugaaggaaacaaugagcaacaugccuccugcuuugc uuccuccugagguaaaccugccuggggauugagguuguuuaagauuauccauggcucacaagaggcagaaaauaauacau guugugccagaguuagaauggggguauagagaucagggucccaugagauggggaacauggugaucacucaucucacauggga ggcugcugcag |
| 18 | M61007 | ccgcgggcccgcguucaugcaccgccugcuggccuggacgcagcaugccucccgccgcc gcccgccgccuuuagacccauggaaguggccaacuucuacuacgagcccgacugccuggc cuacggggccaaggcggcccgcgccgcgccgcgcgcccccgccgccgagccggccauugg cgagcacgagcgcgccaucgacuucagccccuaccuggagccgcucgcgcccgccgcgga cuucgccgcgcccgcgcccgcgcaccacgacuuccucuccgaccucuucgccgacgacua cggcgccaagccgagcaagaagccggccgacuacgguuacgugagccucggccgcgcggg cgccaaggccgcgccgcccgccugcuuuccgccgccgccucccgccgcgcucaaggcgga gccgggcuucgaacccgcggacugcaagcgcgcggacgacgcgcccgccauggcggccgg uuucccguucgcccugcgcgccuaccugggcuaccaggcgacgccgagcggcagcagcgg cagccuguccacgucgucgucguccagcccgcccggcacgccgagccccgccgacgccaa ggccgcgcccgccgccugcuucgcggggccgccggccgcgcccgccaaggccaaggccaa gaagacgguggacaagcugagcgacgaguacaagaugcggcgcgagcgcaacaacaucgc ggugcgcaagagccgcgacaaggccaagaugcgcaaccuggagacgcagcacaaggugcu ggagcugacggcggagaacgagcggcugcagaagaagguggagcagcugucgcgagagcu cagcacccugcggaacuuguucaagcagcugcccgagccgcugcuggccucggcgggcca cugcuagcgcggcgcgguggcgugggggggcgccgcggccaccgugcgcccugccccgcgc gcuccggccccgcgcgcgcgcccggaccaccgugcgugcccugcgcgcaccugcaccugc accgaggggacaccgcgggcacaccgcgggcacgcgcggcgcacgcaccugcacagcgca ccggguuucgggacuugaugcaauccggaucaaacguggcugagcgcguguggacacggg acuacgcaacacacguguaacugucuagccgggcccugaguaaucaccuuaaagauguuc cugcgggguuguugauguuuuugguuuuguuuuuguuuuuguuuuguuuuguuuuuuu uuuuggucuuauuauuuuuuuuguauuauauaaaaaaaguucuauuucuaugagaaaagagg cguauguauauuuugagaaccuuuuccguuucgagcauuaaagugaagacauuuuaauaa acuuuuuuggagaauguuuaaaagccaaaaaaaaaa |
| 19 | C85523 | aaaauguagaaggcaagauuuaauaaggcagcaacaugaaagcacacagaccagagcucu gggguucgaaauaaagcagcaacauggaagcacacagagcucuggggucgaaacucauaca ccuuagcacaggguagaggagucucgacggucanccagaauuuuucacaggcuuauauag uaaaacucaaagggggagaacugggcagggaaaguacaaguuuacaucacuagggaguuc ugccaaaggacaangggguucunucagaggaaucuacguaacuaaggngucauguccuauc aaggnaucuacguaacuaaggagucauguccuaucauuuggcaauguacccgnucuuuu gagguuguuccggagggncuuauucucaaaauguuuuucagauuggaaggggugggguunc cgguaaaaaguucuguuuucaaagaggcnguaauuuucuauucuucauuccccauucucc uguaaguauucnnaucuuagaauuucagaaguccauauucncuaugugggggaauaacugg cuuuaacccnaucuuuaaaauggggg |
| 20 | AW122030 | uuuuuuuuuuuuuuuuuaugaaacaguuuuguucagcccaugacuuugugcaugacuguc guccguucuagucaccugugcucuccaucuacugccuuuuaaagcugcgucaugagaagg aucuacacguuccaccaugacucucguuucuugccacaaguagaagaaaugguugauucu uugcuuuucgguuaggccguuaaacaaaacucagucacaccccugccuuccacccucaaa |

TABLE 3-continued

RNA transcripts up-regulated during HF stem cell activation.

| SEQ ID No: | Access. # | Sequence |
|---|---|---|
| | | cugugaucacguggcuguucuuguaguunaaccagggcaacacuauauauuccaggucua<br>uacauugcugaggucuuuuucugguuguucauguaucaguguuucaaccucgugccg |
| 21 | U57524 | Sequence below. |

gcggccgcggcuccagaccccggccuugcgcacccucccccaccuccagcccgcgccucccccccccccacgcauggcucacc accccucggguuucccugucaucccucagguuccugcacuuggcaaucauccacgaagagaagccgcugaccauggaaguca uuggucaggugaagggagaccuggccuuccucaacuuccagaacaaccugcagcaggugcgcugcuugcuugccccgcggu gccccucuuugaccccuugguggagucagauguagcacggucgcccccaaagcguuucuaaauuaauagucacuuaguucu uaucugccuuggcuuuuuugcauucaaaucagccaacgucuuagaaccagaagaaaaaucccuugguuuuagugaggucuu uaugacccaccuagggccuccuguuugccugaucuccuaagagacaaaugggaggaucagauuccauagcgggaggugucu gggguucaggaaacucaagacuaugguuugcuccauggcuuaucccuuucuguuuccucuuccauuuguagacuccacuc cacuuggcugugaucaccaaccagccaggaauugcugaggcacuucugaaagcuggcugugauccugagcuccgagacuuuc gaggaaauaccccucuacaucuugccugugagcagggcugccuggccaguguagcagucuugacgcagaccugcacacccca gcaucuccacuccguccugcaggccaccaacuacaaugguaggucugccaguccauccaaggaugcagaggagggagagaga uggggccacuugagucuuaaacuccgaacguauacaaaguucagacacugugaucuuuuuaaaaaguuuucuccucgaugcc uauaugauauucacucagaacccagauucugaguucuucaaaacugaugauguuugugguuguccucaagacaauagacau gaguugugugaggauugaaacacguaguacaguuuuugucuuccuccuccaggccacacgugucugcaccuagccucuacu cacggcuaccuggccaucguggagcacuuggugacuuugggugcugaugucaacgcucaggugaguacaucucccuuccac cuaaucucuguugggcuggcucugauggugagcagguuuccagaugcagccguaaacuaacgccugauugcuuuugguuuc aggagcccugcaauggccggacagcccuccaccuugcgguggaccugcagaauccugaccugguuucgcucuuguugaaaug uggggcugaugucaacaggguaaccuaccaaggcuacucccccuaccagcuuaccuggggccgcccaaguacccggauacag cagcagcugggccagcugacccuggaaaaucuccagaugcuacccgagagcgaggaugaggagagcuaugacacggagucag aauucacagaggaugaggugaguguuccucccucagcacgcugacggcuguucuagggcugcuuuggaucagagggauuu caguuguuuaacuucucagacucggcuugcaaagcaggaucccaagaauuugucucugguuuguuuuaagagcuuacccuu uugguugaggaaugagggaauucuagaaauugaacccaggccuuagcacauggugauaagcacacguucaaccauuaagcuc cacccccucaauagcuuagacuuuuuuuuuuuuuaaggaaagaauagguaagggaaacuccuacagccuggugcccuuguu cuauuuggguuaaggagaaaaagagcccaagaauaggaguuauuucagcagcagcucuccccuuaucccaaugucuuggua aguucuaggaauuuaauaugucuuuuuccccucucuuguuuuagcugcccuaugaugacuguguguuuggaggccagcgu cugacauuauaaguggaaaguggcaaaaaagaauguggacuuguauauuuguacaaauagaguuuuauuuuucuaaaaaaa aaaaaaaaaaaaaaaaaaaaaaaaaaaguauacuuagcaccacaccacacagcgccuagacccaggcauuuuacuggggugau ucggcuguugucuuugugaaauccgggg

| SEQ ID No: | Access. # | Sequence |
|---|---|---|
| 22 | U05809 | cucucggucacugccggucgcuuccugagccgcugcuggcucugugucucuguccucagc<br>guucucuuccucguccucguccuaccacgccauggaagguuaccauaagccagaucagca<br>gaagcuccaggcccugaaggacacagccaaucgccugcgcaucagcuccauccaggccac<br>caccgcggcaggcucaggccaccccacaucaugcugcagcgcugccgagaucauggcugu<br>ccuguuuuuccauaccaugcgcuacaaggcccuggaucccccgaaacccucacaaugaucg<br>cuuugugcucucuaagggccaugcagcucccauuuuauaugcagucugggcugaagcugg<br>cuuccugcccgaggccgagcugcugaaccugaggaagaucagcucugacuuggacgggca<br>uccugucccgaaacaagccuucaccgauguggccacuggcucccugggccagggccuggg<br>agcugcuugcgggauggcauacacaggcaaauacuuugacaaagccagcuaccgagucua<br>uugcaugcugggagacggggaggucuccgagggcuccgucugggaggccauggccuuugc<br>uggaauuuacaagcuggacaaccucguugccauuuuugacaucaaccgccugggccagag<br>cgacccagccccgcugcagcaccagguggacaucuaccagaagcgcugugaggccuuugg<br>cuggcacaccaucaucguggacggacacagcguggaggagcugugcaaggccuuugguca<br>ggccaagcaccaaccaacagccaucaucgccaagaccuucaagggccgagggaucacagg<br>gauugaagacaaggaggcguggcacgggaagccccuccccaaaaacauggccgagcagau<br>uauccaggagauuuacagccagguucagagcaaaaagaagauccuggccacgccccccuca<br>ggaggaugccccauccguggacauugcuaacauccgaaugccuacgccacccagcuacaa |

TABLE 3-continued

RNA transcripts up-regulated during HF stem cell activation.

| SEQ ID No: | Access. # | Sequence |
|---|---|---|
| | | agugggggacaagauagccacccggaaggccuauggacuggcccucgcuaagcugggcca cgccagugaccguaucauugcccuggauggagacaccaagaauuccaccuucucggagcu cuucaaaaaggagcacccagaccgguucauugagugcuacauugccgagcaaaacauggu gagcauugccgugggcugugccacacgugaccggacagugcccuucugcaguacuuucgc ggccuucuucacacgggccuucgaccagauucgcauggccgccaucucugagagcaacau caaccucuguggcucccacugugguguguccauuggggaagacgggcccucucagauggc ccucgaagaccuggccauguuccggucaguccccauguccaccgucuuuuacccaagcga uggaguugcaacagagaaggcaguggaguuagcagccaacacaaagggcauuugcuucau ccggaccagccgcccagagaaugccauuauuuauagcaacaaugaggauuuccaggucgg ccaagccaagguggucc ugaagagcaaggaugaccaagugacagugaucggggcuggugu aacucugcaugaggccuuggcugcugcagagagucuaaagaaagauaagaucagcauccg ggugcuggaucccuucacuaucaagccccuggacaggaaacucauccuagacucugcccg agcaaccaaaggcaggauccucaccguggaggaccacuacuacgaagguggcauaggaga ggcagugucugcugccguagugggugaaccuggagugacggucacucgccuggcugucag ccaaguaccacgaaguggcaagccagcugagcuacugaagauguucgguauugacaagga cgccauugugcaagcugugaaaggccuugucaccaagggcuagggagggcaugggaugcu gggugggugaacuacacauuccagggagguucuggcagagguggcgaagguguacugagu ggggagguaaauauauguuuug |
| 23 | AW212475 | uuaacggugucauaaauaaguaauauaacuuuauuaaaaugaaaagacaauauucaaaau aaugcaacaaaaugaauaaauccuuuguccaauacuguacacacagugcggagaucagug cauuuuucuaaagcauguuuuaaccuucauuuaguucauacuaaaguaagcuuuaaauag cucaaauaaugucauucagcaguuuaaacugaacagcuuguugggacaug |
| 24 | V00835 | ugaguucucguaaacuccagagcagcgauaggccguaauaucggggaaagcacuauaggg acaugauguuccacacgucacauggg ucguccuauccgagccagucgugccaaaggggcg gucccgcugugcacacuggcgcuccagggagcucugcacuccgcccgaaaagugcgcucg gcucugccaggacgcggggcgcgugacuaugcgugggcuggagcaaccgccugcugggug caaacccuuugcgcccggacucguccaacgacuauaaagagggcaggcuguccucuaagc gucaccacgacuucaacguccugaguaccuucuccucacuuacuccguagcuccagcuuc accagaucucggaauggaccccaacugcuccugcuccaccgguaagacucccgauccuug gucuuuagaauaccaaguugggaccgcagagcggaauccccgaguuguagaggcuuggcg ggaauaggcaccuuuaguuggcgauucauuccgguucuuucuagaauccgcucuugcaaa agccuucauuaguuacgaguauugucgaacggguccuuuggcgggguuggggcuaggauu uagacgcgcaaauguccgguuccugaucacccaguuaguggggacaucuggguugagucc caggcauuacuaaacuuacugugaauugcuugaauuaagaaagaggugaaggaccuuuau gucuugggacucaaagacauaaucccugacuuaaccugugaggagaaaguggggcuagg cucccugcagcuccgaggaggacuuagugaacugagccgggacucgugguguuggccacu gcuguaaugcugccucccucaugcugucuucuuucuccucccaggcggcuccugcacuug caccagcuccugcgccugcaagaacugcaagugcaccuccugcaagaagagugaguuggg acaccuuggguggcggcuaaggcuaggggcggggaacuccuacaaaacuggcucugagaa auguccuuugcuucccggaggccauuguauugucucggggacagaacuauacagagaacu auuuaaaaaaaccgaggucuucucuguuggggacaggaagcagaggucuucagccaggcu gccucuuccuccuucuucuaggcugcugcuccugcugucccgugggcugcuccaaaugug cccagggcugugucugcaaaggcgccgcggacaagugcacgugcugugccugaugugacg aacagcgcugccaccacguguaaauaguaucggaccaacccagcgucuuccuauacaguu ccacccuguuuacuaaaccccc guuuucuaccgaguacguuaauaauaaaagccuguuug agucuaacucugguuucuuggugugguuuggcaauaagaaacuggggugacuugauaguc uggggaucugguuuuggacccccucgugccuuuaccuccgcccucuggcccucacagagg gguaaugucuuuggguaaagccaagcuauaucccauaagcuuccucauggaaaacagcug |
| 25 | AV374868 | gcggcacgaugugucuucggguggcuuuuuuuuuuuguuuugaauaauguuuacaauuu cccucaaucacuuuuauagaaauccaccuccaggcccccccuuuccccacuuaggccuu cgaggcugucugaagaugcuugagaaacucaaccaaaucccaguucaauucagacuuugc acauauauuuauauuuauaaucagaaaagaaacauuucaguaauuuauaauaaaagagca cuauuuuuuaacg |
| 26 | M21285 | See above (same Accession Number). |
| 27 | U74683 | acugccaucgagugguguuccaguugaacuugcucucucugccaucugcuccgcgggcgc cgucagcauggguccc uggacccacuccuugcgcgccguccugcugcuggugcuuuuggg agucugcaccgugcgcuccgacacuccugccaacugcaccuacccugaucugcugggcac cuggguguuccaggugggcccuagaaguucccgaagcgacauuaacugcucggugaugga agcaacagaagaaaagguagugguacaccuuaagaaguuggauacugccuacgacgagcu gggcaauuccgggcauuuuacccucauuuacaaccaaggcuucgagauuguguugaauga cuacaaaugguuugcguuuuucaaguaugaagucagaggccacacagcuaucaguuacug ccaugagaccaugacugggugggucc augaugugcugggccggaacugggcuugcuuugu uggcaagaagguggaaagucacauugagaagguuaauaugaaugcagcacaucuuggagg ucuccaggaaagauauucugaaagacucuacacucacaaccacaacuuugugaaggccau caauaccguucagaagucuuggacugcaacugcauauaaggaauaugagaaaaugagccu gcgagaucugauaaggagaaguggccacagccaaaggaucccaaggcccaaaccugcccc gaugacugaugaaauacagcaacaaauuuuaaauuugccagaaucuugggacuggagaaa cguccaaggcgucaauuauguuagcccuguucgaaaccaagaaucuuguggaagcugcua cucauuugccucuaugguaugcuagaagcaagaauucguauauuaaccaacaauucuca gacaccaauccugaguccucaggagguuguaucuugcagccccuaugcccaagguuguga |

TABLE 3-continued

RNA transcripts up-regulated during HF stem cell activation.

| SEQ ID No: | Access. # | Sequence |
|---|---|---|
| | | uggugggauucccauaccucauugcagggaaguaugcccaagauuuuggggugguggaaga<br>aagcugcuuucccuacacagccaaagauucuccaugcaaaccaagggagaauugccuccg<br>uuacuauucuucugacuacuacuaugugggugguuucuaugguggcugcaaugaagcccu<br>gaugaagcuugagcuggucaaacauggacccauggcaguugccuuugaaguccacgauga<br>cuucccuacacuaccacaguggaaucuaucaccacacugggcugagugacccuuucaaccc<br>cuucgagcugacaaaucaugcuguuuugcuuguggcuauggaagagauccaguuacugg<br>gauagaauacuggauuauaaagaacagcuggggcucuaacuggggggagaguggcuacuu<br>ccguauccgcagaggaacugaugaaugugcaauugagaguauagccguggcggccauacc<br>gauuccuaaauuauaggacauagcucccaguguuacauacgggucuuuaucacucacaga<br>gugauuuagucacaugcugaagacuuuuucagagcaauaucagaagcuuaccacuaagca<br>ucuuuaaaagaauuuugucuuugaacuuaaaaccauccuugauuuuuuucuuuuaauaucu<br>uccccaucaacuacugaacuacuuuucuuuuuaaaguacuugguuaaguaauacuuuuau<br>gagcaguggguucaguuguccaauauuuuuugcaggucaucuacaaugcaaccagauguuu<br>caguucuaaaaaucuauguaaaaguacaagcucguuuuuaaauuauguaagucacaugaa<br>aacauggcaaaaaaauuaguuaaauuuuuuacaaagaguuuuaaauaaaauguuuauguaa<br>ucaguaccauagucuuucuaugugugguuuacaagaauuuuugucaccuacuucuucccuu<br>agaagcauuuaugcuccauggacguacuucuuuauggagaaaaaaaaaa |
| 28 | X61800 | gagcucgaucccuguuccgccuuugcuaugucugaaggcguccugcuuugcgcgugucgg<br>ggccaaauccagauuuucauuucgcuccaggcuuggacggcuaaguagguccaaaccgca<br>caaacaggaaggagggaaggcaaggagugcgggcagagggcggucguucccagcagcac<br>cccagucccuccccgcuccgucuccgacccacuggggccggggcgggcgugcgcgucagc<br>uggggcuagaaaaggcggcgguccggcccggcgaggugacagccaacuuggacgccaggu<br>ccggccgacgccgccaugagcgccgcgcuuuucagccuggacagcccggugcgcggcaca<br>cccuggcccacagaacccgcggccuucuacgagccaggcagggugggacaagcccggccga<br>gggcccgagccaggggaacuggggggagcugggcuccacgacuccugccauguacgacgac<br>gagagcgccaucgacuucagcgccuacauugacuccauggccgccgugcccacccuagag<br>cugugccacgacgaacucuucgccgaccucuucaacagcaaccacaaagcggccggcgcg<br>ggcggccuggagcugcugcagggcggcccuacgcgacccccgggugugggggucugucgcu<br>agggggccgcucaagcgcgaacccgacuggggcgacggcgacgcgccgggcucccugcug<br>ccggcgcaaguggcggugugcgcgcagacaguggugagcuuggcggccgcggcucagccc<br>acuccacccacuucgccggagccuccucgaggcagcccggggccgagccucgcgcccggc<br>acaguccgagaaaagggcgcgggcaagaggggguccggaccgcggcagcccggaguaccgg<br>cagcggcgcgagcgcaacaacaucgcugugcgcaagagccgcgacaaggccaagcgccgc<br>aaccaggagaugcagcagaagcugguggaguugucggccgagaacgagaagcugcaucag<br>cgcguggagcagcucacccgggaccuggcuggccuccggcaguucuucaaaaaacugccc<br>agcccgccuuuccugccgcccaccggcgccgacugccgguaacgcgcggcgugggccuuu<br>gagacucugaacgaccuauaccucagaccccgacagcggggagcagacgccgcccgaauc<br>gcuaguuucuuugggaccugcgagcgacaggaagcugcagcuugggcacuggacugcgag<br>agaagcuauauuaaucuuuccccuuaaauuauuuuuuauaaugguagcauuuucuacguc<br>uuauuaccauugcagcuaagguacauuuguagaaaagacauuuccgacagacuuuuguag<br>auaagaggaagagacugcgcaugcuuuuuauauucauuuuuacaguauuuguaagaauaa<br>gaauaagaauaaagaagcauuuaaaucgcaaaaaaaaa |
| 29 | U20735 | Sequence below. |

uugaggguggccaggccagcguaggaggccagcguaggauccugcugggagcggggaacugagggaagcgacgccgagaaa gcaggcguaccacggagggagagaaaagcuccggaagcccagcagcgccuuuacgcacagcugccaacuggccgcugccgacc gucuccagcucccgaggacgcgcgaccggacaccggguccugccacagccgaggacagcucgccgcucgccgcagcgagcccg gggcggcccuucaggggggaccuuucccagaucgcccaggccgcccggaugugcacgaaaauggaacagccuuucuaucacga cgacucuuacgcagcggcgggauacggucggagcccuggcagccugucucuacacgacuacaaacuccugaaacccaccuug gcgcucaaccuggcggaucccuaucggggucucaaggguccuggggcgcggggucccaggcccggagggcaguggggcaggc agcuacuuuucgggucagggaucagacacaggcgcaucucugaagcuagccuccacggaacuggagcgcuugaucguccccca acagcaacggcgugaucacgacgacgcccacgccuccgggacaguacuuuuaccccgugggggguggcagcgguggagguac agggggcggcgucaccgaggagcaggagggcuuugcggacgguuuugucaagcccuggacgaccugcacaagaugaaccac gugacgcccccccaacgugucccugggcgccagcgggggucccccaggccggcccagggggcgucuaugcugguccggagccgc cucccgucuacaccaaccucagcaguuacucuccagccucugcacccucuggaggcuccgggaccgccgugcggacugggag cucauacccgacggccaccaucagcuaccucccacaugcaccacccuuugcgggcggccacccggcacagcuggguuugaguc guggcgcuuccgccuuuaaagaggaaccgcagaccguaccggaggcacgcagccgcgacgccacgccgccugugucccccauc aacauggaagaccaggagcgcaucaaaguggagcgaaagcggcugcggaacaggcuggcggccaccaagugccggaagcgga agcuggagcgcaucgcgcgccuggaggacaaggugaagacacucaaggcugagaacgcggggcugucgagugcugccgguc TABLE 3-continued RNA transcripts up-regulated during HF stem cell activation.

| SEQ ID No: | Access. # | Sequence |
|---|---|---|
| | | uccuaagggagcaaguggcgcagcucaagcagaaggucaugacccaugucagcaacggcugccaguugcugcuaggggucaa gggacacgccuucugagagccucccuugccccauacggacacccccagccuugaaggcugggcgccugcccccccacuggggu gaggggggcaggcgaugggcacccgccaaaaggccuggggcgcagcucacacacuggacuccggcccgcccgccugcgccca guccuuccaccucgagguuuacauggccccccuuccagcguauuuuguauguuuuuuuuuucugcaaagagacugaauucau auugaauauaaauauuuguguauuuaacaggagggagaagggggcugucgcggcggagcuggccgccgcuugguacucag cugcggggauacuagggagggaccuccgcccccugcccucccccucugcauaguacuguggagaagaaacacgacuucgugu cuaaagucuauuuuaagauguguuugugugugugugguuugacuuuuuauugaaucuauuuaagua |
| 30 | U19118 | Sequence below |
| | | gaauucggcacgagcagcgagacgccgcgcacggugcuuccccaguggagccaaucggcuaacccgcgcuccggcagagucc uuggcgcucgcccgccggcgggacagaccacccgccucuggccgcucucuggacccuggccgccccgagcgaagacuggagc aaaaugaugcuucaacauccaggccaggucucugccucagaagucagugcgaccgccauuguccccugccucucaccuccug ggucacugguauuugaggauuuugcuaaccugacacccuuugucaaggaagagcugagauucgccauccagaauaaacaccu cugccaucggauguccucugcgcuggagucaguuaccgucaacaacagaccccuggagaugucagucaccaagucugaggcg gccccugaagaagaugagaggaaaaggaggcggcgagaaagaaauaaaaauugcugcugccaagugucgaaacaagaaaaagga gaagacagagugccugcagaaagagucagagaaacuggagagugugaaugcugagcugaaggcccagauugaggagcugaag aaugagaaacagcauuugauauacaugcucaaccugcaccggcccaccuguaucguccgggcucagaauggacggacaccgg aagacgagaggaaccucuuuauccaacagauaaaagaaggaacauugcagagcuaagcagagguggcacggaggcaauuggg gaguucuuacugaauccucccuuuuccaccccacacccugaagccauuggaaaacuggcuuccugugcacuucuagaauccca gcagccaagagccguuggggcaggagggccuguggugaccuacugcauugacccacucugcccccgagugaaccguggagca ggcaggagcauccuuugucucaccaauuccaggauuuaggccuuaucaucccggccagucucagaugaccuagcuggcccca ggcuggggguccuaugcaaagcaggaucccacuaaugggauucaggcagaagugucuaccuugauagguggggugggaccac auccucuacuguggcugacaacgcccuuccaagggaauauggaaugagaacauucauuauugagguuguccaauggccaggg uaugcuuucuagaaaauaugcuguucugucccagaaugacugugcauaggguauccguuucagagccugguguugugcuau uuagauguuugucuugcacaacauuggcaugauuuuuccgggaguuucaucagaucugauuucugagagucuggggaucu gccaugguggaaagugccccucaaaagcauuuguguggccacaugaacuggcuggcaccaggggagugaaacuggcugauga ccagcugagccacuuugugccaacagaggauggacgacaccuuucccuguacccacugcagaggaagaacccugggcacagca gcuuuguccuuggcuacaaacuguuacaacgucacacaaugaaggcacaaaguccaacuuucaaaggguguaggacuccaua cucagugacagggcaggaagagccaaagauaaccacagccacagccuguggagaccaggguuggaagccaggugcagggcca ggcaucugcauugugggauguuaauggcacuuuugucuuguagcuauuuugagauguggccagagcauuucagcuggga gaucucccucuggccaccaggacucuggcuacuguuaaaauccugauguuucuguggaauccucaguguuuaaucccacuca auaguaucauuacaguuuucuguaagagaaaauauuacuuauuuaucccaguauuccuagccugucaacauaauaaauaucg gaacaaaaccuggua |
| 31 | AW049031 | uuuuuuuuuuuuuuuuugcugauaagaauucuuuuuauguuauucgaauaaaaaaauaca uucauacagaaauauaacaaucucgcaaaaaacaauuucaaauaaaaucuuguaaaacaaa auuuuacaaaaaucuuacaaagauucuuuagauaacagggugcuucaaaaaaaaagaaau aaagaaauuucacuaauagaaauuuuuuuuuuuaauuucaagcaaaaguuccugcuugau ugaggcucaguugucaccugaccagaauggacugcuuaguauuaaaguuacagcaucgac acggacggcacccagccccagccagaccagcaacgucgcuguguuucauaagugagacgc gccagcacaaguuuccucucucuucuguuuaccuucuuacuuaauggaauugcuauggau aagcacacagcagggccaaaaaaggaguuuuccaaaauccagcaaaucaagug |
| 32 | M93275 | uaguggugaucuggaccgugcggacuugcucgucccucagcucuccuguuaggcgucucu uuucuccaggaggaaaaaauggcagcagcaguaguggauccgcaacagagcgguggugaug agaguggccaaccugcccuuggugagcucuaccuacgaccuuguguccuccgcuuauguc |

TABLE 3-continued

RNA transcripts up-regulated during HF stem cell activation.

| SEQ ID No: | Access. # | Sequence |
|---|---|---|
| | | aguacaaaggaucaguacccguauuugagauccgugugugagauggccgagaagggcgug<br>aagaccgugaccucugcggccaugacaagugcccugcccaucauccagaagcuggagcca<br>caaauugcgguugccaauaccuaugccugcaaggggcuagacaggauggaggaaagacug<br>ccuauucugaaccagccaacguccgagauuguugccagugccagaggugccguaacuggg<br>gcgaaggauguggugacgacuaccauggcuggagccaaggauucuguagccagcacaguc<br>ucagggguggugggauaagaccaaaggagcagugacuggcagcguggaaaggaccaagucu<br>guggucaauggcagcaucaauacaguuuggggauggugcaguucaugaacaguggagua<br>gauaaugccaucaccaagucggagaugcugguagaccaguacuucccucucacucaggag<br>gagcuggagauggaagcaaaaaagguggaaggauuugauagguucagaagccgagcaac<br>uaugaacggcuggagucccugucuaccaagcucugcucucgggcuuaucaccaggcucuc<br>agcaggguuaaagaggccaaacaaaagagccaggagaccauuucucagcucccacuccacu<br>guccaccugauugaauucgccaggaagaauaugcacagugccaaccagaaaauucagggu<br>gcucaggauaagcucuaugucucgugggguggaguggaagagaagcaucggcuacgacgac<br>accgaugagucccacuguguugagcacaucgagucacguacucuggcuaucgcccgcaac<br>cugacccagcagcuccagacuacaugccagacuguccuggucaacgcccaaggguuacca<br>cagaacauucaagaucaggccaaacacuuggggggugauggcaggcgacaucuacuccgua<br>uuccgcaaugcugccucccuuuaaggaaguguccgauggcguccucacaucuagcaagggg<br>cagcugcagaaaaugaaggaauccuuagagaugaaguuauggauuacuuuguuaacaacacg<br>ccucucaacuggcugguagguccccuuuuauccucagucuaccgaggugaacaaggccagc<br>cugaagguccagcagucugaggucaaagcucaguaaaccccuccuugucaccagagcaug<br>auguugcuggccagaugaccccuuuugcuguauugaaauuaacuugguagauggcuuuag<br>cuuagaaaagcagcuucuuagaaccaagggccucauuauggucacucacagcucaguuau<br>ggucuugccccagcuggcccuggcacaggaguucucuuaccuggcuggugaguggccugu<br>guuagucuugugaggaccuggaggaaccuaaaagcucagaugcacuuacagucuugucug<br>uggccuuuguauuguuauuggcuguaaacgucugucuggaccgaauaaagauucacguga |
| 33 | AB000713 | ggcacgagggagcugcaguguucgcgcuugguagcuggugcaucggacucagcuggcuuu<br>gugucccugaggcucaccgaaaaacacuuucucagcccucugacucccagagagagagaga<br>gagagguacuuuuuguggucaccgacuuugaccccugcagaggcugagcgauggcgucua<br>ugggacuacagguccugggaaucuccuuggcaguccugggcuggcuggggaucauccuga<br>guugugcgcuccccaugugggcgggugaccgccuucaucggcagcaacaucgucacggcac<br>agaccagcugggagggccucuggaugaacugcguggugcagagcacaggucagaugcagu<br>gcaagauguacgacucgaugcucgcccugccgcaggaccugcaggccgcccgagcccuua<br>uggucaucagcaucaucgugggugcucuggggaugcuucucucaguggguaggggggcaagu<br>gcaccaacugcauggaggacgagaccgucaaggccaagaucaugaucaccgccggagccg<br>uguucaucguggcaagcaugcugauuauggugcccguguccuggaccgcucacaacguca<br>uccgcgacuucuacaacccuaugguggcuuccgggcagaagagggaaaugggggccucgc<br>uuuacgucggcugggcggccuccgggcugcugcuccugggaggaggccuccucugcugca<br>guugcccaccucguagcaacgacaagcccuacucggccaaguacuccgccgcccgcucug<br>uccccgccagcaacuauguguaagguggggccacucuguccacauugccuuuguuauuuuu<br>uuucggauugagcucauaacagccuguggccccucacauucuccaggaccugcccugcua<br>ugggccacuaacugcuugcuggggacaggcaaacccggacugugcaaaguuacuagcccg<br>uagcucuugggcugcucccacauggcuccuuacggccggcaagaauggauguaaaaauauc<br>uugcugcuuacauccaaauugcgguggauaugggcugaaggcagaagcagcugggaaggg<br>caguagaggcgcaagcugggucccugcuggccgggguagcucagcugugacuuuggacucg<br>gaguggauguccucauguuagcaaacguccacuguccuuucucuaucccccucacucagc<br>cuacacguuacuccagcgcuacucuugccauuacgccccguguuuccgagcacagcuggu<br>ccuaccccaagucauggugugcugagugacugaugaggggccauugagagccggugggcu<br>cugccauggaacccuuccguugauuagcaaugacugugcuugacccacccaccuacccua<br>cuaaugaauuucuguagaguggauggacggguuugagggaagaaggguggagguggauu<br>aaacugguuuggggagggcuggggaccuagaagcagcccagugugucccccaccccuuuucc<br>gcacugucuugcuaauguucugaucacugugcgcccccucccucuucagaaggacccugg<br>gccucuugaguuggccccucugaguucccucccuuugcccauuucaaggacaccggccag<br>ucugcggaaggaagguacggggggggggggggggggugauggcauuguaccagggaguc<br>uccuggacuccccugccuucucugugguuucuuguuuuguaauuaaggucuguucacagc<br>uguaauuauuauuauuuucuacaauaaauggcaccugcauacag |
| 34 | U20735 | See above (same Accession Number). |
| 35 | U83148 | augcagcugagaaaaaugcagaccaucaaaaaggagcccgcaccccuagauccuaccagc<br>agcucagacaagaugcugcugcugaacucugccuuagcugagguggccgaggaccuagcc<br>ucaggugaagauuugcuccugaacgaagggagcauggggaaaaacaaauccucggcgugu<br>cggagaaaacgggaauucauuccggacgagaagaaagacgccauguauugggagaaacgg<br>cggaaaaacaacgaagcugccaaaagaucucgggagaagcgccgccucaaugaccugguu<br>uuggagaacaagcugauugcccugggagaagaaaaugccacuuuaaagcugagcugcuc<br>ucccugaaauuaguuugguuuaauuagcuccacggcguaugcccaagaaauccagaaa<br>cucaguaauuccacagcugucuacuuucaggacuaccagacauccaaggcugccgugagc<br>ucuuuuguggacgagcaugagccugcgaugguagccggaaguugcaucucagucaucaag<br>cacucuccccagagcucgcucuccgaugugucagagguguccucgguggagcacacucag<br>gaaagccccgcacagggaggcugccggagcccugagaacaaguucccugugaucaagcag<br>gagcccguggaguuggagagcuuugccagggaggccagggaggagcggggcacguauucc<br>accuccaucuaccagagcuacaugggaagcucuuucuccacuuacucccacuccccaccc<br>cucuugcagguccaugggucccacuagcaacuccccaagaaccucagaggccgaugagggu<br>guagugggcaagucuucugauggggaagacgaacaacaggucccuaagggccccauccau<br>ucuccaguggagcugcaacggguucacgccacggugguguagaagguuccggaagugaacccu |

TABLE 3-continued

RNA transcripts up-regulated during HF stem cell activation.

| SEQ ID No: | Access. # | Sequence |
|---|---|---|
| | | ucugccuuaccgcacaagcuucggauuaaagccaaggccaugcaggucaaaguggaggcuuuggacagcgaguuugaaggcaugcagaaacucucuucacccgccgaugcgaucgccaaaagacauuuugaccuggagaaacauggaaccucggguauggcccauuccucccucccucccuuucucagugcaggugacgaacauucaagauugguccucaaaucggaacacuggcaucacaaagaacugagcagcaaaacucagaguagcuucaaaacagguguggugggaagucaaagacgguggcuauaagguuuccgaagcugagaauuuguauuugaagcagggaauagcaaacuuaucugcagagguggucucgcucaagagauucauagccacacaaccgaucucggcuucggacuccagguaa |
| 36 | L10244 | gcucccgggaaacgaaugaggaaccaccuccuccugcuguucaaguacaggggccugguccgcaaagggaagaaaagcaaaagacgaaaauggcuaaauuuaagauccguccagccacugccucugacugcagugacauccugcgacugaucaaggaacuggcuaaauaugaauacauggaagaucaagucauuuuaacugagaaagaucuccaagaggauggcuuuggagaacaccccuucuaccacugccugguugcagaagugccuaaagagcacuggaccccugaaggacauagcauuguuggguucgccauguacuauuuuaccuaugacccauggauuggcaaguugcuguaucuugaagacuucuucgugaugagugauuacagaggcuuugguauaggaucagaaauuugaagaaucuaagccagguugccaugaagugucgcugcagcaguaugcacuucuugguagcagaauggaaugaaccaucuaucaacuucuacaaaagaagaggugcuucggaucuguccagugaagagggauggaggcucuucaagauugacaaagaguacuugcuaaaaauggcagcagaggagugaggcgugccgguguagacaaugacaaccuccauugugcuuuagaauaauucucagcuucccuugcuuucuaucuuguguguagugaaauaauagagcgagcacccauuccaaagcuuuauuaccagugacguuguugcauguuugaaauucggucuguuuaaaguggcagucauguauguggguuuggaggcagaauucuugaacaucuuuugaugaagaacaagguggguaugaucuuacuauauaagaaaaacaaaacuucauucuugugagucauuuaaauguguacaauguacacacugguacuuagaguuucuguuuugauucuuuuuuuuuaaauaaacucgcucuuugauuu |
| 37 | U88328 | cgcuggcuccgugcgccauggucacccacagcaaguuucccgccgccgggaugagccgcccccuggacaccagccugcgccucaagaccuucagcuccaaaagcgaguaccagcuggugguggaacgccgugcgcaagcugcaggagagcggauucuacuggagcgccgugaccggcggcgaggcgaaccugcugcucagcgccgagcccgcgggcaccuuucuuauccgcgacagcucggaccagcgccacuucuucacguugagcgucaagacccagucggggaccaagaaccuacgcauccagugugagggggggcagcuuuucgcugcagagugacccccgaagcacgcagccaguucccccgcuucgacuguguacucaagcuggugcaccacuacaugccgccuccagggaccccccuccuuuucuuugccacccacggaacccucguccgaaguuccggagcagccaccugcccaggcacuccccgggaguaccccccaagagagcuuacuacaucuauucuggggggcgagaagauuccgcugguacugagccgaccucucuccucccaacguggccacccuccagcaucuuugucggaagacugucaacggccaccuggacuccuaugagaaagugacccagcugccuggacccauucgggaguuccuggaucaguaugaugcucccacuuuaaggagcaaaagggucagagggggggccugggucggucggucgccucuccuccgaggcacauggcacaagcacaaaaauccagccccaacggucgguagcucccagugagccaggggcagauuggcuucuuccucaggcccuccacucccgcagaguagagcuggcaggaccuggaauucgucugaggggaggggggagcugccaccugcuuucccccucccccagcuccagcuucuuucaaguggagccagccggccuggccugguguggacaauaccuuugacaagcggacucucccccucccccuucccuccacaccccccucugcuucccaagggagguggggacaccuccaaguguugaacuuagaacugcaaggggaaucuucaaacuuucccgcuggaacuuguuugcgcuuugauuugguuugaucaagagcaggcaccuggggggaaggauggaagagaaaagggugugugaagggguuuuuaugcuggccaaagaaauaaccacucccacugcccaaccuaggugaggaguggugggcuccuggcucuggggagaguggcaaggggugaccugaagagagcuauacuggugccaggcucccucuccauggggcagcuaaugaaaccucgcagaucccuugcaccccagaacccucccccguugugaagaggcaguagcauuuagaagggagacagaugaggcuggugagcuggccgccuuuuccaacaccgaagggaggcagaucaacagaugagccaucuuggagcccagguuuccccuggagcagauggaggguucugcuuugucucuccuaugugggggcuaggagacucgccuuaaaaugcccucugucccagggaugggggauuggcacacaaggagccaaacacagccaauaggcagagaguugagggauucacccagguggcuacaggccaggggaaguggcugcaggggagagacccagucacuccaggagacuccugaguuaacacugggaagacauuggccaguccuagucaucucucggucaguagguccgagagcuuccaggcccugcacagcccuccuuucucaccugggggggaggcaggaggugauggagaagccuucccaugccgcucacaggggccucacgggaaugcagcagccaugcaauuaccuggaacugguccugugguuggggagaaacaaguuuucugaagucagguauggggcugggugggggcagcuguguguuggggguggcuuuuuucucucuguuuugaauaauguuuacaauuugccucaaucacuuuuauaaaaauccaccuccagcccgccccucuccccacucaggccuucgaggcugucugaagaugcuugaaaaacucaaccaaaucccaguucaacucagacuuugcacauauauuuauauuuauacucagaaaagaaacauuucaguaauuuauaauaaaagagcacuauuuuuuaaugaaaaaaaaaaaaaaaaaaaaaaaaaaa |
| 38 | X82786 | Sequence below. |

aaggaaucuucaguacagaaacaagacccaaguguaaguuuaacuggcaggaggaaccaaccaaggacaguuaaggag aaaacccaacccuuagaagaacucaccaguuuccaagaggaaacugccaaaagaauaucuuccaaaucuccacaaccgg aagagaaggaaaccuuagcagguuuaaagaggcagcucagaauacaacuaaucaacgaugguguaaaagaagagccca cagcacagagaaagcaaccauccagggaaaccaggaacacacucaaagagccuguaggugacaguauaaauguugaag agguuaagaagucuacaaagcagaaaauugauccaguagcaagugugccugucagcaagaggccacggagguaccc TABLE 3-continued RNA transcripts up-regulated during HF stem cell activation.

| SEQ ID No: | Access. # | Sequence |
|---|---|---|
| | | aaggaaaaggcacaggcccuagaauuggcuggucucaaaggaccaauccaaacccuaggccacacugaugaaucagca<br>agugauaaaggacccacacagaugcccuguaauucucuacaaccagagcaaguugacagcuuccaaagcucaccaagg<br>cgacccaggacaagacgugggaaaguagaggcagaugaagagccuucagcaguaagaaagacaguaucaacaucaagg<br>caaacuaugcgaucccgcaagguccccugaaauugguaacaaugguacccaaguuucaaaggccuccauaaagcagaca<br>uuagauacaguagccaaaguaacuggcagcaggaggcagcuaaggacacauaaaggaugggguucaacccucuugaa<br>guuguuaggugacuccaaagaaauaacccaaauaucagaucacucugagaaacuagcacaugacaccaguauccuuaa<br>gagcacucaacagcaaaagccagacucaguaaaaccucugagaacaugcagaagagugcugagggccucuaaagaggu<br>ccccaaggaaguguugguggacaccagagaccaugcaacauuacaaagcaaaagcaacccuuugcuguccccgaagag<br>gaagucugcaagagauggaagcauugugagaaccagggcuuugcgcucuuuagcaccaaagcaggaagcaacagaug<br>agaagccuguaccugagaaaaaaagggcugcuuccagcaagagguauguaucaccugagccugugaagaugaaacacc<br>ugaaaaucgugucaaacaaacuugaaucuguggaagagcagguuagcacuguuaugaaaacagaagaaauggaagcc<br>aaaagagaaaauccugucacuccagaucagaacucuagguaccgaaagaaaaccaauguaaaacagccaaggcccaagu<br>uugaugcaucugcagagaaugucgggauaaagaaaaacgagaagacuaugaagacugccucccaggagacagagcug<br>cagaauccagaugauggagccaagaaaucuacaucucggggccaagucagugggaaaagaacaugcuugaggucuag<br>aggaacgacugagaugccccagccuugugaagcagaagagaaaacaagcaaaccagcugcagaaaucuugauaaagcc<br>ucaggaagagaaaggagucucuggagagucugauguuagguguuugagguccagaaaaacuagagucgcuuuggac<br>agugaaccuaagccaaggguaacucguggaaccaagaaagaugcaaaaacucugaaggaggaugaagacauuguaugc<br>accaagaaguuaagaacaagaaguuaagaacaagaaguuaccagaaaagugaaacuauguagcaaagacauuuaagaa<br>ggaaaaguaaauuugacuuagugauaaguuccagugugguuuucaccuccaguguaaagaugaacuguaaauacuac<br>ugcuacugccugaguuuaaggaaggaagcuuugagcuuuccuggucauacucucuucagacgccaauggaggucau<br>gaggaagaucaccagggaucucagcgcaauuacaguuuagggugagcaggcagaaauguggcccucuguccuaucc<br>aauaaagcucugaaauucgcugccaaaa |
| 39 | AW122523 | uuuuuuuuuuuuuuuuuaaaucaaaaguuaugaugacuuuauuuuaaaucuuaauacacc<br>aaaaauauuuuucaauguugugagauaagcacuugaaaauaagaauuccaacacugcugu<br>gauuucgcugugaggcuugauagugaauuuucccucugaauaugggguuuagggccuagga<br>agcagaaugccagucauuuuccaaguagcagugagcuaagcccagcccggucaugcucag<br>acccacacuuaacugaaauauucacacuaggaggcggcaccaccaggcaacaccuugauc<br>aaccaggagaacaaaagucugaagugccaccaagcauuggggaaaugauauuguuuagau<br>gcuagugagucagguucuuucaaauguguccuaacuggguugcaaacauaguugcauccu<br>uau |
| 40 | AI642048 | gucuguaaaaaucuguuuaauaaauauacaucuuagaaguaccaaaauaauuaccaacaa<br>aauacaacauauacaacauuuacaagaaggcgacacagaccuuaguuggggcgacuuuu<br>aagcacaugccacugaacaccuggcucuuacaugggaggacacacugggcucacuuacua<br>ggucuaugguggguucaaucaaaagcacaauaaauaaaacgugguccuuucauuagguucu<br>ggaaaaucaccucccccccccccaaaaaaaaucccacaaacaugaaccuuaagagacauu<br>uucuuugaauuucagugaucuguuuccccggauuucacaaagacaacagccgaaucaccc<br>caguaaaaugccugggucuaggcgcugugugguguggugcuaaguauacccuuucucauu<br>uuuuuucuuuuucu |
| 41 | L07264 | cggccgccagaccuucaagggcuggaguggacgcgcggaccgacucugaacagacagacg<br>aaccgcggccgcaagguucccagacaggaucucacccagaggcaggcagcggacagugcc<br>uuaguggaaccucgcuguccuccaccgccuggccccggugcaggcguccaguggccgccg<br>cauccaaagugaucgcugccuccccgucuccgccagcucgggaccaugaagcugcugccg<br>ucggugaugcugaagcucuuucuggccgcaguguuguccgcguuggugaccggugagagu<br>cuggagcggcuucggagaggucuggcggcagcaaccagcaacccugacccucccacugga<br>uccacaaaccagcugcuacccacgggaggugaucgugcucagggggguccaggacuuggaa<br>gggacagaucugaaccuuuucaaaguugcuuucuccuccaagccacaaggccuggccacc<br>ccaagcaaagaaaggaaugggaaaaagaagaagaaaggaaagggguuagggaagaagaga<br>gacccaugccucaggaaauacaaggacuacugcauccacggggagugcagauaccugcag<br>gaguuccguacucccucuugcaaaugccucccugguuaccacggacacaggugucauggg<br>cugacucuaccaguggagaaucccccuauacacauaugaccacacuacagucuuggcugug |

TABLE 3-continued

RNA transcripts up-regulated during HF stem cell activation.

| SEQ ID No: | Access. # | Sequence |
|---|---|---|
| | | guggcuguaguacugucguccgucugucuucuugucaucgugggacuucucauguuuag<br>guaccacaggagaggagguuaugacuuggaaagugaagagaaagugaaguugggcguggc<br>uagcucccacugaggaggaccugagcuauaggaaccuucagaggcuacuucugagacagug<br>guucguuacacguucuacauagaggagaaauauuucaccagcagccaugaaaacgucuuc<br>auucauuuccaguugcuacccugacugggccuccuguaau |
| 42 | M15668 | ucgaccucacggucuugccaaaaugucgcuuuccaacaagcugacuuuggacaagcugga<br>cgugaaggggaagcgggucgugaugaggguggacuucaacguuccuaugaagaacaacca<br>gauaacaaacaaccaaaggaucaaggcugcuguuccaagcaucaaauucugcuuggacaa<br>uggagccaacuccguuguccuuaugagccaccugggccggccugaugguguucccaugcc<br>ugacaaguacuccuuagagccaguugcugcugaacucaaaucucugcugggcaaggaugu<br>ucuguucuugaaggauugugugggcccagaagucgagaaugccugugccaacccagcggc<br>ugggacugucauccugcuggaaaaccuccgcuuucauguagaggaagaagggaagggaaa<br>agaugcuucugggaacaagguuaaagcugagccggccaaaauugaugcuuuccgagccuc<br>acuguccaaacuaggagaugucuaugucaaugaugcuuuugggacugcacaccgagccca<br>uagcuccaugguggugugaaucugccacagaaggcugguggauuuuugaugaagaagga<br>gcugaacuacuuugccaaggcuuuggagaguccugagcgacccuuccuggcuaucuuggg<br>aggcgcuaaaguugcagacaagauccagcugaucaauaauaugcuagacaaagucaauga<br>gaugaucauugguggugaauggccuuuaccuuccuuaagguccucaacaacauggagau<br>uggcacaucucuguaugaugaagaaggagccaagauugucaaagaucucauguccaaagc<br>ugagaaaaaugguguggaagauuaccuugccuguugacuuugucacugcugacaaauuuga<br>ugagaaugccaagacuggccaagcuacuguggccucugguauaccugcuggcuggauggg<br>cuuggacugugguacugagagcagcaagaaauaugccgaggcugugggucgagcuaagca<br>gauuguuuggaauggucccuguuggggguauuugaaugggaagccuuugccaggggaaccaa<br>gucacucauggaugagguggugaaagccacuucuaggggguugcaucacuaucauaggugg<br>uggagacacugccacuugcugugccaaauggaacacagaggauaaagucagccaugugag<br>cacugggggcggugccagucuagagcuccuggaagguaaaguccuuccugggguggaugc<br>ucucagcaauguuuaguauuuucuuuccugccuuugguuccugugcuccuaagcuaaccu<br>gcuguuuuccacaucuccauuugguguuagcgcaagauucagcuaguggcugagaugugg<br>cacagaccuuaacagugcaagcaucucagcucgucuuacugcaucagaugcugguucuuc<br>aagaucccauuuaaauuccuuagugacuaaaaccauugugcauuguagagggcgucuauu<br>uauauucugccugagaaaggaagugagcuguaaaggcugagcucucucucugacguaugu<br>agccucugguuagcuucgucacucacuguucuugacucagcauggcaaucugaugaaauu<br>cccagcuguaagucugcagaaauuuccgaauuc |
| 43 | AI047508 | uuuuuuuuuuuuuuuucauguuuaauaguuuauuucuuauuuuguugcuuauaucuuc<br>aauaaaucauuuugcagguuuuguuacagauuuuugauaagccaacucaaguacugauuu<br>uucauccucucugaaaguuuuaaaccaggaaaggaaaacguuccauggaauccaucuucca<br>cauggugaugagucacaugaacuccaacauucugaagccgcuugacauacaugaguccauc<br>aucucuuaggacaucauacuggcaagugaugauauaggucuuagguaaaugaugcaauau<br>auugucauuggccaacagagggcaugccuucacaucuaugaacccuggauacuuuugagc<br>cagcucagaacuaccaggagugggauuuuuguaaacgggacuuuucuuguaucucucagg<br>gagcaaggaacuccaauucacaaacuguaacaaguggcuagauuccaugguacauguug<br>guuga |
| 44 | AJ001418 | Sequence below. |

gagcacccgggacccugggaccacaacgcacuugcucccucucgaccgcgcuccugacccgcagcccucgccaacccuacgga uccuaaccaccgccagccuaggugggcgucaggaugaaggcagcccgcuucgugaugcgcagcgccagcucgcugagcagcg ccagccuggucccccagggaggucgagcuguucucccgcuacagcccguccccgcuguccaugaagcagcugcuggacuuugg uucagaaaaugccugugaaagaacguccuuugcuuuucugcggcaagagcugcccguccgccuggccaauauccugaaggag auugacauccugccugaccgcuuagugaacacuccuucggugcagcuggugaagagcugguauauccagagccugauggau uugguggaguuccaugagaagagcccagaagaccagaaagcccugucagaguuuguagacacgcuggucaaaguucgaaaca gacaucauaauguggucccuacaauggcucaaggcauccuggaguauaaagacaccugcacaguggaccccguuaccaaucaa aaucuucaguauuuuuuagaccgguuuuacaugaaccgcauuucuacucggaugcucaugaaucagcacauccucauauuca gugacucaaagacgggaaacccaagccacauuggaaguaucgacccaaacugugaugugguagcaguaguccaagaugccuu ugagugugcaaagaugcucugcgaccaguauuaucuaacaucgccagaauuaaaccucacacaagucaauggaaaauuucca ggccaaccaauccacauuguguacguuccuucacaccuucaccacaugcucuucgaacucuucaagaaugccaugagggccac ggucgagcaucaagaaaaccguccuuccuugaccccaguagaggccacugucgucuugggaaaagaagaccuuacaaucaag auuucugaccgaggaggcgguguuccucugaggauuacugaccgccucuuuaguuacacguacuccacugcuccaacaccug ugauggacaauucccggaaugccccuuuggcugguuuugguuauggcuugccaauuucucgucucuacgccaaguauuuuc aaggagaucugaaucucuacucuaugucagguuaugggacagacgcuaucaucuacuuaaaggcuuuaucuucugagucug TABLE 3-continued RNA transcripts up-regulated during HF stem cell activation.

| SEQ ID No: | Access. # | Sequence |
|---|---|---|
| | | uagaaaagcucccagucuuuaacaagucagccuucaaacauuaucagaugagcuccgaagcugaugacugguguaucccaag<br>cagggaaccgaagaaccuggcgaaggagaagcuggcagugugaagcggaugacgccugacauuuuacgggaucaaagugggu<br>cuguggcauugcugcuucgugaaugugugguggacucuaguuuccgcaaaacaacgcaacacaaaaccaagcaagcaaaacaca<br>aacacgaguacaaaccuugaccugaugagggacagagcuugguuggaugacccgggagaagucagggcagggcuccagggga<br>uaacagguguccugcuucuccuuuggcaaugcaaaaugacuccugacuguuccaaauacugaaaagaagucugccucugagu<br>uacagcucuuucucaacaaguacagaguuugaggcuugcaguugcaacagcuggauguuuggugguucuugcugccagcca<br>aauaaauugguguuuagugaacauuuucaguguuuccccgccaugcaaagcuuggcgccuugggagaaauguguguaaaug<br>uacauuguauagguauuagugugcucuagaaaggacaggauggaaggaaucaaagcacuuuaucgagcuuguggcugagca<br>uugcagccuaugugcaaacccagaggaaaaguaucucugucaagacagcuccaguaucaugcagcuuuuuauguuugcacuc<br>aaaaagccagugccuucuggcuggugccgaggcuugggugaaauguuaaauaugcacugaccucagaaagucgaguucaaaa<br>gggagauaaaauugccaaagugauccaaggauugugcauguugggaaacccauaugagagaaaggauucucauacuuagaac<br>uuuccuaugaagaaaugguggguaaacuuucucuaccuagaaguaguggaaauuucaaggucaucuuaaaaaaagaugugcgu<br>uguauauuuuaacuacauucucuacacucuaacauuaacauaucuauucaaauuugucuaguugccaauugucuucagagu<br>gugaaaauuuaaauccuucuugaaguaucuuucgugagaguaguauggaaguaaaacguucucauaucaggaggaugucau<br>uugugaagcauggggacaucaugaacuagugaugugcgugaggcuugggaggcugaaggguaaggaucagcgggaggccau<br>ccauguaggagagagaauuaaaacgaggagcgagggaagcaauggagagagggaagcaagaaaggaaccagaaggcuggcau<br>cauccuauuucccacaggcuaacccaagggaugcucugugccuuuccuggggagggaagggggugaacugguagauuugaa<br>agcaguauggcuucuucugugggucucccucuuacuagacaaggugaaaugauaauucgugucaaauuaaugugaaauuuu<br>uuuccugcauuguaauauuaugaggccugagucgcaguugaguuugaaauuuguauuuaauuucacagugaccuagagcua<br>aggugcucccgguuguggcaauaggagccacaaguauuuucuuucuuucuuucguucuuucuuucuuucuuucuuucuuu<br>cuuucuuucuuucuuucuuuccuuccuuccuuccuuccuuccuuccuuccuuccuuccuuccuucuuccuuuccuuuucu<br>uuucucuucucuucuuuucuuuuuucuguuucuuuuucuuuuuuugcauuguagauguuguccuuaaaagaucagggca<br>gugacuuucacagcaggacuuugacucccacauugguugaucacacaaaacugucagcauuugguaaucugauguauagu<br>uguuuuguugcugauguuuccauugaaauuucagcucugaguuugugcacaugaauacuuacuuguguuuaccaaagguc<br>uaaggcauuugguuacuuaacccaaauauccugaacugugcguaaaguaauagagaaaagcuuuagggucucaauaguguca<br>ccuguguaaaucaaaucaaaauagccuucccuauuauuuaugaacccaugggagacuuuaaacucuuguagauagaugcuaa<br>augcccaggcccacuuaacuuauuaaugugugaauuacauuuauguuuuuaguuuauaugcaaagaauugugauaauuuua<br>uaauaaauauuuuuauuauaauagu |
| 45 | AI838080 | uuuucuuuuuuuuuuucuucucuuuuuucugccaccaacagcacugugcaguuuauua<br>accauucauguacaguagccaucuggggagauugggacagaauugggaucgcaaagugga<br>uagauauucagcaucuaaugguuggcagaagccgccauauacucuucacaaauaucuucc<br>acagucaauacagaacuagccauuaucccagcacaccgauuugugc |
| 46 | AF072127 | agccaggagccucgccccgcagcugcacagagagcaaggguauaggcacuaacuuguuug<br>cagagaccccaucaccuucgggagcucaggugcgcaccuugcaaacuccacuuucugcau<br>cugccacugagcccgcgggagccucggaaagagccauggccaacgcggggcugcagcugc<br>uggguuucauccuggcuucucugggauggaucggcuccaucgucagcacugcccugcccc<br>aguggaagauuuacuccuaugcuggggacaacaucgugaccgcucaggccaucuacgagg<br>gacuguggauguccugcguuucgcaaagcaccgggcagauacagugcaaagucuucgacu<br>ccuugcugaaucugaacaguacuuugcaggcaacccgagccuugaugguaauuggcaucc<br>ugcuggggcugaucgcaaucuuuguguccaccauuggcaugaagugcaugaggugccugg<br>aagaugaugaggugcagaagauguggauggcugucauugggggcauaauauuuuuaauuu<br>caggucuggcgacauuaguggccacagcaugguauggaaacagaauuguucaagaauucu<br>augaccccuugacccccaucaaugccagguaugaauuuggccaggcccucuuuacuggcu<br>gggccgcugccucccucugccuucugggaggugucccuacuuuccugcuccugucccccgga<br>aaacaaccucuuacccaacaccacggccuuaucccaagccaacaccuucuagugggaaag |

TABLE 3-continued

RNA transcripts up-regulated during HF stem cell activation.

| SEQ ID No: | Access. # | Sequence |
|---|---|---|
| | | acuaugugugacagaggcaaaggaagagaucuuccuggagcaaauacaaaauggacauug<br>aaccuaggauugacauuaacgccuuagacuguugaugaugguuaucggaacugugguaga<br>acagaaggaagcauauuuuuauacauccccauggcuaugcaggccuuggcug |
| 47 | X80417 | Sequence below. |
| | | cggcacgagcggccacugaccgagaagugcccccgccuggagucagccugggggcaggccaggguccaccagacccc<br>gggaugaccgcagccagucgggccaaccccuacagcaucguaucaucagaggaggacgggcugcaccugguuaccau<br>gucaggcgccaacgguuuuggcaauggcaaggugcauacacggcgccggugccgcaaccgcuucgucaagaagaacg<br>gucagugcaacauugaauucgccaacauggacgagaagucacaacgcuaccuggcugacauguuuaccacgugugug<br>gacauccgcuggcgcuacaugcugcucaucuucucucuggccuuucuugccuccugguuguuguuuggcaucaucu<br>ucugggucauugcugucgcccacggggaccuggagccagccgagggccguggccguacacccugugugcugcaggu<br>ccacggcuucauggcagccuuucucuucuccauugagacacagaccaccauuggcuacgggcuacgcugugugacug<br>aagagugcccgguggcugucuucaugguggugcgcaguccauugugggcugcaucauugacuccuuaaugaaugg<br>ugccaucauggccaagauggcacggcccaagaagcgcgcacagacucugcuuuucagccauaaugccgugguggcuc<br>ugcgugacggcaagcucugccucauguggcgcgugggcaaccugcguaagagucacaucguggaggcccaugugcg<br>ggcccagcucaucaagcccagggucacagaggagggugaguacaucccacuggaccagauugacaucgaugucggcu<br>uugacaagggccuagaccguaucuuccugguaucacccaucaccaucuugcacgagauugaugaggccagcccacug<br>uuuggcauuagccgucaggaccuugagacagacgacuuugagauuguggucauccuggagggcaugguagaggcca<br>cagccaugaccacacaggcucgcaguuccuaccuggcuaacgagauccuguggggccaccgcuuugagccagugcuc<br>uucgaagagaagaaccaguacaagauugacuauucacacuuccacaagaccuacgaggugccaucuacaccccgcugc<br>agcgccaaggaccugguggagaacaaguuccuccugcccagcgccaacucuuucugcuaugagaacgagcuggccuu<br>ccugaucagagaugaggaggacgaggugucuaccgaccgggauguccgcaccccucagcccgagcaugacuuugaca<br>gacugcaggccagcagcgcugcccuugugcggcccuacagacgggagucggagauuugaaugcccuuggcuuagaug<br>cagcaccacccugaccacaauaggucccaugucccuugggggccugcguuugagcagagcaggccgaaagccucggg<br>ucacagacucaguagcaucuuagucuuuuucauguuuuuucgcaguagcuugggaaaguuggcgggagcguggaug<br>gcccaaaugacuggcucacggccucggaggcugauguauacccaugggcaaggaggugacuucuuggggguaggguu<br>gcucaggaguuagggacucugcuggaggccuuaggugcaggucccaaccccggugggaggaggcuguguauguaca<br>cuucauugguuuuuaacuugggcaagacuguuuacaaaccaaaacaaacaaacaaacaauc<br>caaaaaaaaaaaaaaaaaaaaaaaaaaa |
| 48 | AI847051 | uuuuuuuuuuuuuuguuccuuuuuuggaauucccaaagcugguuuuaauuucaaaaaau<br>uaugaggucucuucccacacuggggauaaugggaugggauagcccaaacuauuaucccagu<br>ucaaccccagccugguccaaacaccauuacugucacugggcccugucauuucacc |
| 49 | U09504 | uccucguccucgucuguuccaucuucuccaaauagcucuaacugugaugccaacggcaau<br>cccaagaacgcugauaucucuagcaucgaugguguucugaagagugaccgcacagauugu<br>ccugugaaaacaggcaaaaccagugcuccuggcaugacuaagagucacaguggaaugaca<br>aaauuuaguggcaugguucuacuguguaaagucuguggggauguggcaucaggauuccac<br>uauggaguucaugcuugugaaggcuguaaggguuucuuucggaggagcauucagcaaaac<br>auccaguauaagaagugccugaagaaugagaacuguuccaucaugaggaugaacaggaac<br>cggugccagcagugccgcuuuaagaagugucugucuguggggaugucacgagaugcuguu<br>cgauuuggccgaauuccuaagcgugaaaaacagagaaugcuaauugaaaugcaaagugca<br>augaagaccaugaugaacacccaguucaguggccaccugcagaaugacaccuuagcagaa<br>cagcaugaucagucagcacuaccagcucaggaacagcugcggcccaagucccagcuggag<br>caagaaaacaucaaaaacacuccuucugauuuugcaaaggaggaagugauugguauggug<br>accagagcccacaaggauaccuuucuguauaaucaggaacaucgagaaaacucaucugag<br>agcaugccaccucagagaggagaacggauucccaggaacauggagcaauauaauuuaaau<br>caagaccaucguggcaguggggauucacaaccacuuccccuguagugagaggcagcaacau<br>cucaguggacaguacaaagggaggaacauaaugcauuacccaaacggccaugccguuugu<br>auugcaaauggacacuguaugaacuucuccagugcuuauacucaaagagucugugauaga<br>auuccaguagguggauguucucagacugagaacagaaauaguuaccugugcaacacugga<br>gggaggaugcaucugguguguccuaugagcaagucuccauauguggacccucagaagucu |

TABLE 3-continued

RNA transcripts up-regulated during HF stem cell activation.

| SEQ ID No: | Access. # | Sequence |
|---|---|---|
| | | ggacaugaaaucugggaagaauuuucaaugaguuuuaccccagcaguaaaagaggugguggaauuugcaaagaggauuccuggcuuccgagaucugucucagcaugaucaggucaaucuguuaaaagcugggacuuuugagguuuuaaugguacgauuugcuucauuauuugaugcaaaggaacggaccgucaccuuucuaagugguaagaaguacaguguggaugaccugcacucaaugggagcaggggaucugcucagcucuauguuugaguucagugagaagcugaaugcccuccagcucagugaugaggaaaugagcuuguucacagcaguuguucugguaucugcagaucgaucuggaauugaaaaugucaacucaguggaggcuuugcaggaaacacucauccgugcacuaaggaccuuaauaaugaaaaaccauccaaaugaggccuccauuuuuacaaaauuacuucuaaaguugccagaucuucgaucuuuaaacaacaugcacucugaggaacucuuggccuuuaaaguucauccuuaa |
| 50 | U22033 | auggcguuacuggaucugugcggugccgcucgggggcagcggcccgagugggcugcccuggaugcgggaagcgggggucgcucggacccgggacacuacaguuucuccgcgcaagcuccggagcucgcacuuccccggggaaugcagcccaccgcauuccugagguccuuugguggugaccaggaaaggaauguucaaauugagauggcccacggcacaaccacacucgccuucaaguuccagcauggcgucaucguggcuguggacuccagggccacugcagggaguuacauuagcucccuuaaggaugaacaaagugaucgagauuaacccuuaccugcuuggcaccaugucugguugugcagccgacugccaguacugggagaggcuguuggccaaggagugcagguuguauuaucuucggaauggggaacgcaucuccgugucugcagcauccaagcugcuuuccaacaugaugcugcaguaccgggggaugggccucuccaugggcagcaugaucuguggcugggacaagaagggaccaggacuuuacuacguagaugacaaugggacucggcucucgggacagauguuuuccacuggcagcgggaacaccuaugccuacggggugauggacagugguuaccggcaggaccucaguccugaagaggccuacgaccuuggccgcagagcuauugcuuaugcuacccacagagacaacuauucuggaggagucgucaacauguaccacaugaaggaagacgguuggggugaaaguggagaguuccgaugucagugaccugcuguacaaguaccgagaggccgcucuguga |
| 51 | AF033034 | Sequence below. |

auuccaggaguuccagcugcuggagaggacuguguagaagguaaccuaccccaucucucuuacuucgucucuagaugggag cagacaaguacauauagccugcuuggagcgaggacuuugaaaggcugagacuugcguccacucugagggcaacuaguccaga cucugacaggucagcauuuccugacugggugcacugaaugccaagcaccagaggucugucaccuuccgacauuggaccaaga gagucccagagacccucaaagacacaggaacagagguguccuuugggugagagaccugugcccugccaagccucucagcccc uagaaaggcggcagggcugaguagcugagugugugcaacuugggagcagccugauuucagugcuugucaccugugagggca aaggcagcaugcuuaaugccaucaguccuacucuucucacccguggaacagacgcauaacugaccuuuuuucgugaccacua uuagggugcauuuaaaaaucaaucucucuuuucugcuccucuuucuccaccuucccucaugugugugucugugugugu guguuucugugugugugugcgugcaccauacagguauaugugccaugacaugugugcaggucaguagacagccuugguug ucagucccugccuucuacuuuguucaaggcagggucuauucuuuauuauugacugcuauccagguacaccaagacaguugg ccugugagguuccagggagucuccugucucuggccccaucuuauagcaggaguugugagauuucagaaaugugcacccac aucuagcuuuauuuggcaucuuggcacccaaacuuggguucucaugcuuuccaagcaaggacuucacccacugaaccaucuc accagcuccacuauggcgguuuucugaaacugaagggaguggggagaaggcgcugagugugaacgggucuggaaggcgggu auaaccuuuaaggcuggcugguucugagagaggaaagccggcuuguguccca uucaggugccaggugcagcaucaaaugug gcuccacccaacggucaguaacuccgcagacagcaccgugguuaacugccucacagagggggcccagggaccuaguuccuua aagcccacuuaguuuugagagacgacauggaggggcaagcccagcccuguccagcugcauucacacgaggcccuucuccucc gaggacccuaccuuuguguuuaguggcugaggcugugugg cucugcuugaagcucuggcuaucaggaaggaccuggcccac cggcuggcaggacaaacuggcccagugaaggcacuguccggucuccugguggaucacaaggaaaggggcguggcauguccag auuugaacccuggaugccucuucccaggguaggaagucuaagggucaacaugaauaggugagggugguggugga aagaauc ugcaugcaaaaucaggcacucaugucugacaucgucaaacacuauauuuauguagauuuauauggggugaggcuuggga gcacuuguauuuuugugugcaauugcaagagcuuccuccacauugcaguguuaaauaucauauggugcuggaccaaccauc ucuggaacgagggugaggguuugguacccgugacuaugguucucuguguaguagaaacggcuucuugggaagagagagga agugcuuugaaaugcauccucucuuguuucauucugcaucauggccagguuucucugcacaaagaugcaauagacauucag gaaaauaagcgcauugcaagaugucaaaagucaugaaaaaugaaaagcaaggucacugcagcugggguguaguguggcugua gaagcacguuuaugauguacagguuccgggagagggaggaagagagagggagggaaggaggaauggaggaagagagggaga TABLE 3-continued RNA transcripts up-regulated during HF stem cell activation.

| SEQ ID No: | Access. # | Sequence |
|---|---|---|

gggagcaagagagggggggagggagggaggggagaagggagagagagagagaagaaagagagggagggaagaaggaauggag gaagagagagaaagaggggaagaaagagagggagggaaggaggggugggaggaagagagaggugugagggauggagggacag agagggagggaaggagaaauggaggaagagagaaacagagagauggaggaagagagaaaagucaccaauuauuuucucccc agucgcccccugcccucacaccaaggguaccccacuuuucuuucacucaugcacacacacuacacccaauguuuagguaaca cauguagggcaggcagagccuuugugaaugugcuugguaguuucugccuuacuucuaaauaaccaaucacacggaugcca caggguuccuuuagacuguccagggcuccggggcucuuagacuguucccaaugugggugucacaugcaaacaguaagcacc uucuuguuuguggugcccaggaugcugcagguacuagaaauuccugcacagaccuuugcuacuucuacacagacuuacccu uuaaaacauuuaauuauauguuuuuuucagcauaaagaucuauuuugauuauuuuuaguugcguguaugggugugugccu gugugugauuguguaauugucuguaugggaguguaagugccuacagaggcaucggauccccuggagcugccguuacaagua agggacugggacucagaccugagugguuuggaugagcagugaaugagcguggugagccaucccaccaugcccuauaaacacu uucaagaggacuuugcuggguauggucaaguuguccccugcgacagccaccccaacuugccauccucauuuacuguacugg aagcagcaaccaccucugcaauuuugcacaagaaccugagagucugaaagacuuuuguuggcacuggccuguguuccacugg gguggacacauuaaucuaaaagcuaagaagcucacuucagcuuugccaggcaaccagcacguuugagcacaacgguguagcc aggaagggugugugggaauuuugaugcuaguuuuucuuuaauuagguugagagugaaaucauggucuguaugcauccaac aacuuaauccaaaaaguugguugcacggcuccuggaagguuuaccggcaaggaaccugucccauuuuguaaguaggugggga cuggagaguugccaagaagcccccucccugccccuuccuccuggcagauucugcuuaaaaugagugugguucacugcaga auagugucaccugucuucagaugucuaaagacauaagaaaggccuagccagcuaagucagaaaaggggacuuuccgguggga augcauuuuccagucucuaggagaagucuuuauccaaauaaaauuagcauaguggugggagucacugccagggcgcuggugc ggaagcacagcccagagccgaggacguggccauccuccuuccucugaugcaaaguguucucuauccccaguuaccaugagca auaucaguagcaucgugaaccgggcccgugaugccuuuaacucaggcaagacucgaccgcugcaguuccggguugagcagcu ggaggcguugcagcgcaugauc

| | | |
|---|---|---|
| 52 | AA960603 | uuuuuuuuccaaaaaauuuuauuggggggaaacuacaaaacauuuacaguacaauguuua cagucacaauuuguagugaacugauuccccaaaauauauuacaacucaaguugacuuaau cuuguuacauucaaaaaccuacuucugucaaaguaguccagagugcacacgcggugcucc aacuguaccuacauacaaacuaaacaacugcucauuuaucugccauccaggaaagccgga gacauuccugccucuuuacauugaaaaauaauaguacaaguuuuuggacugucauugaac aaggcauauucauguaccaccaacauuuc |
| 53 | U47737 | Sequence below. |

ggugauccuccaggaccuaagguuucgguauuaucuucggggccucuucacccggaggugagucugcugagcccgaccuca ggguguucacucgucacgcgagggccuggccacggcggggaagcacugggagagagcgggaggccuugaccgcagcguguag gaucuggggucccggcgcucugcucccgggugcagagugguuggagcaugcgaggcccucugcagcgugcucuguuccuac caucaccccacccccaccccaguccuuccugcacguuucuggagaggcaaaggccccugcugagccuucacugguaccccua ucucgacuccacuugucugcuugggaucuccaaagggggauacacccucguaaacuagagcaggaggcugggggguggggg uaggguagggucugaccaguuagauugaggcuggacccuccccagagugaggagcgggaagcucuuugucuuauccagga uuuugcauaucaaugcugagguucuggugauuaaguagggucccuggcuagcgggggguaaccugaacaaccuuccuccgcu ggccgcuagccaauagacaccuggcuuccgcggaugagcccuuugaguuuguggagguguuccucaggucccccagggcccu gccccguugccugcagauguguggacagacaaaacauuggacucguuuuccaaccacuucaccccuuccuucgcuaguccuc cgguggacgaugggaugccucauugacuuguuuguggcugugcaugccagagcuuccuagcagacagcucagggcuccauc guuccuaaaucccacuguguaacgaaaaaaaaaaaaacaaaaacaacaacaacaacaacaacaaaaacaaaaccagaaaugagga caggcccagcugggcuuggcacugaacuuggccaccuggagcuuuggcuacccacuacaagaugucagcaagucucaggaua gaagaggccuaaggccaguccuggaagauaccaaaacuucaccuccucuauaccccguuccucuaggagaacuguaagccacc TABLE 3-continued RNA transcripts up-regulated during HF stem cell activation.

| SEQ ID No: | Access. # | Sequence |
|---|---|---|
| | | uuugucucugggacgccccucucccacucaacagauggcaccagucaucuuccuccucaagaggccagugguauucaaaaua<br>ggauauugaaaccaagcaagcugguccucuccucuacccuaugccaaagacuucugcccaaagggcccagaaaagucccauag<br>ccaucuggcuggcuagugugcugacugcuacaggugucaguguccccagcgagcagguaguggaguggaggugucuucuu<br>guggaaaugggucccugagccucuaccuuguacagaaaggaauuagugaagcccagaggccuccagcccgugucucugccaca<br>agagagagggggugggggugggggcuguauuugguucccagggcucagggaagguuuucgguucaugcaugcucauuuauc<br>ugaccacugucuuaaccccaggacaaccacuuaacuguccacuuccauaucagaguucuugguuccccuuuacuucgucuau<br>ggagccccugaguuugggaagggguauuaacugaaagguaccauuagaugaacuuggagaaagauuuguaggugccacggg<br>agauuucagguaaaagcucuuuuaauaauuggcuacaauagcagcaggaggaggccaggaauucugagguagagauuugau<br>uagcagcacguggagcaaaggagacuucugacuccuacagguuucagaaaguggggagaggcucucagaugaauggcuugg<br>acugugagguaaguguuaguguagcacgagacuagcuuaaggcuguacaaauuguccgucugauuggugcauugggccagg<br>uagacacuagauaagcaauugggccuuaacucgaguugucuuaauggcuaccccccagggcagcagggagucaauacugcucu<br>ccugucuggggccugaaugcugaaaccaucuacaaaggggacauaaggcauauuggggagguguagagugggccaggccca<br>gggucugcugguaucuaugccaggauccugagugguggugggcguagccugucuuuuaaccaacugccucucucacaguagg<br>cuuacuuuggcuugcgaaccuucagcagaugucugccacuuccaacaugagagucuuccugccugugcuguuggcagcccuu<br>cugggcauggagcaagguauggagcucugagauaacccugcagccugguccucccuccugaucucucauucuuucuccugag<br>uagaugcccagggcuccuccugagccagcccuccuaggaacgucuggccuucccaccuccuacucucuagccaacugaccua<br>guuccccugaugcugugcuggcccagcuacaccuuugucaccucguguugacuuuagccacuccaguaccaaagucugaagu<br>caguugucauuggcuggcuuuuuucccugacccagggcugagcaugcuguugcuucuugucaguggguuggggaucaagg<br>gccccacuggaaagucaccuuacccuggaaggcuuccccaggcaauaggcaggugucaccuacagcauugucccuuuugcag<br>uucauucccugaugugcuucucauguaccgaucagaagaacaauauaaacugccuguggccaguuucaugccaggagaaaga<br>ccauuacuguaucacguuaucugccgcugcgggcuuuggugaguagcugccuguuucccuagccagggccagggaccugcg<br>gggcuuuccccauuuccugcucccugucugucuguccccucauccucacuuuccaugcagggaugucaaccuuggcuaca<br>cccugaacaagggcugcuccccgaucugccccagugaaaaugucaaucucaaucucgguguggcguccgugaacagcuacug<br>cugccaaagcuccuucugcaacuucagcgcagcuggccucggacuucgugccaguaucccacuacugggccuuggacuccug<br>cuuagcuuguuggcucugcugcagcugagccccugaccaucccccauguguucuccauaucccccccagcucaggaaaagccc<br>agcuccuuuuagguccccaggggacccuaggaaccuucagcuccuccugggugugucuaguuccccccuccacacucucucaac<br>gucagggcuaaguaccaaacucacccauaccugcucuguugaagugguacuggcuacccuugcuuccagagccaauccuaua<br>accucccuuggggaaccagcgaagggggugaagaucuccuuggagucucaagaguaccagagucagcgccgaaucuuguggac<br>acacugacaaggaugucuaauccaaauagauguauaucugugugcucaguguaucccugugugaaugaagccacuuggauu<br>cugggguggggcaaagaagaccugaaaagauucuacagcagaaggccugugucgccaccaaaaccccucccccugguaucauu<br>guacccaccuuguacucuguucaggaggcugcccauggaggacugccaccccuccagaugaaggcucccacuacccgaugca<br>guugagucccauccugcccucucugcccacacuggcuuccugcugcuauucuagugccucaaauaaaccguucacacccuu |
| 54 | L00039 | cuuccucccucuacagaagaagagcaagaagaugaggaagaaauugaugugguguucugug<br>gagaagaggcaaaccccugccaagaggucggagucgggcucaucuccauuccgaggccac<br>agcaagccuccgcacagcccacugguccucaagaggugccacgucuccacucaccagcac<br>aacuacgccgcacccccccuccacaaggaaggacuauccagcugccaagagggccaaguug<br>gacaguggcaggguccugaagcagaucagcaacaaccgcaagugcuccagccccaggucc<br>ucagacacggaggaaaacgacaagaggcggacacacaacgucuuggaacgucagaggagg<br>aacgagcugaagcgcagcuuuuuugcccugcgugaccagaucccugaauuggaaaacaac<br>gaaaaggcccccaagguagugauccucaaaaaagccaccgccuacauccuguccauucaa<br>gcagacgagcacaagcucaccucugaaaaggacuuauugaggaaacgacgagaacaguug<br>aaacacaaacucgaacagcuucgaaacucuggugcauaaacugaccuaacucgaggagga |

TABLE 3-continued

RNA transcripts up-regulated during HF stem cell activation.

| SEQ ID No: | Access. # | Sequence |
|---|---|---|
| | | gcuggaaucucucgugagagcuaaggagaacgguuccuucugacagaacugaugcgcugg<br>aauuaaaaugcaugccaaagccuaaccucacaaccuuggcuggggcuuugggacuguaag<br>cuucagccauaauuuuaacugcucaacuaaauaguauaaaagaacuuuuuuuuaugcuuc<br>ccacucuuuuuucuuuuuccuuuuaacagauuuguauuuaauuguuuuuuuaaaaaaucg<br>uuaaaaucuauccaauuuuccauguaaauagggccuugaaauguaaacaacuuuaauaaa<br>acguuuauaacaguuacaaaagauuuuaagacauguaccauaauuuuuuuu |
| 55 | D21099 | gugggacgggcccccucgaggucgacccacgcguccgggaguaccccgaccuuggcug<br>cgugcugacucgcuuccuucugccugcccaggcuugcacuccccggggaucugccucugc<br>aucucuugccuucgcuguuguuucccucucuguccagcucccccucccgcucucgcccugg<br>agaauggcucagaaggagaacgccuacccguggcccuacggcucaaagacgucucagucu<br>ggccugaacacguugucccagagaguccuacggaaggagccugccacgacaucugcgcuu<br>gcucucgugaacugguccaacagccaguccacagcugccccuggccagaaguuggcugag<br>aacaagagucagggcuccacugccucgcaaggaucccagaacaagcagccuuucacuauu<br>gacaacuuugagauugggcguccuuugggcaaaggcaaauuuggaaacguguacuuggcu<br>cgggagaagaagagccguuucaucguggcacucaagauccucuucaagucucagauugag<br>aaggagggguagagcaccagcuucgccgagagaucgaaauccaggcgcaccugaaacau<br>cccaacauccuucaacucuacaacuacuucuacgaccagcagaggaucuacuuaauccug<br>gaauacgccccucgcggggaacucuacaaggaacugcagaagagucggaccuucgaugag<br>cagcggacugccacgaucauggaggaacugucagaugcccugaccuacugccacaagaag<br>aagguaauucacagagacauaaagccggagaaccugcuguuaggucugcagggagaacug<br>aagauugcagacuuuggcuggucggugcaugccccaucccugaggaggaagaccaugugc<br>ggcacgcuggacuaucugcccccagagaugauugaggggcgcaugcauaaugaaauggua<br>gaucuauggugcaucggggugcucugcuaugaacugauggugggggaaccccccccuucgag<br>agcccuagccacagugagacguaucgucggauugucaagguggaccugaaguuccccucu<br>ucugugccuucgggcgcccaggaccucaucuccaagcugcucaaacauaaccccuggcaa<br>cggcugccccuggcggagguugcagcucacccuuggguccgggccaacucaaggaggguu<br>cugccucccucugcccuuuagccugcuccuugguuuuuugucccugucauuuuucagugu<br>ucuuuguaugucuguguauguguucugagaaggggugggaacuggaaacuauuccuagc<br>uccaguucuaggggaucugaucucucuucugaccucuacaggcaaaauuaggcaccccugu<br>ggugcacauauaugcacgccaaacacaugaaguuacaaacaaacaacaaacacacagaua<br>gugcuggagagauggcucggcaguuaaaagcacuggcugcucuucccaggaaccuagaac<br>ucaauucuagcacuacauggugcucacggccacugucuguaacacccaguccuggggaau<br>cuggggccuucgagccucugcaggcacuaggcauggaugugguauacauguaugcaggca<br>aaacacccaugcacugacuuuuaagaaacccucuagucugauuccuuucaauuugucaaa<br>uguugaauguuauuuuuaaaauauuauaagccauuuaauacaauuuuucuuugaaacaug<br>guauagccuagucugucuuaaauucagaaaaauuaugaagaacaacauuuuauaauaaag<br>ucuuaaauguuucauguuuuug |
| 56 | AF026481 | Sequence below. |

uugccuaggaagggcgcgucgucucucugcucguccggcugugacggggaagggucccgcugcguuuuggucacugugag uaccaaguuuggggggauccccgagggacucucgagagcucauuuuagggaugcaggggcuacuccccgguggguagagagcu uucuaguuggcaggagguuucguauguggaggaggccagcuuaggcagaaagcacauguucucagagaugaggacaagacu aagaccgucuaaucccugaucuuuaccuuccggcccgcugaccugggccuggaugcuaaagcccucugcuuucgucuaaaca gcgcuaaauaguaaacaguauugccuaagauaaaugcggauuauuacccgauucagugucgggaaaaggcagcuaggagaga gcggcuggcacgugguaagcacacgguaaguuucgguuaaauuaaaacaaccauccguugagcaucucuuagcaagcuccuu ccacccuucaaacaaucagugauagugcgucuguuucacugauuagggagcuaaggcuccaacagcagcaaaggaacuaauc cgcccucugaucaacauggcguuucuuacagggcauuccuuauacgcuuucccacgugcguaacaggaaucggguguucccg gguuuuguuuuguuguuguuguuuuuguuuuguuuucuuagugaaagaggcagggugggcuccaggccgcugaggauua auaaagagauucuaugaggaggaaauaacaggcagguggguaugaucgaggcaaggcccugaggaaggcuuggguggggguga guagaaccagagccggaaguccacucagcagccuggggcacuuaaagcuucugcuggggcaaaugguaaggcggcguaaggu cacauuccuuucauuucuuccagacucaggaggagaccacaccuuccggagaaccaggccugaaccgagguacuauuuugua gcucucagaagccaggacucugcaacacuguuugcugccuguggaucuucuauauucacagugucccaguugcuucugauc uaccacuguuagauacuucugccacccauccuaagaguauaguuguucuuggaaaggagucucagcugcugucagcaggag ucccucauucgacuccugugguugcccuuuccaccaugccaaagaauaaaggcaaaggaggcaaaaacaggcgcagagguaaa aaugaaaaugaaucugagaaaagagaguugguguuuaaagaggaugggcaggaguaugcucaggugaucaaaaugcuggga aauggacgguuggaagcaaugugcuuugacggugugaggaggcuggccauauaagagggaagcugagaaagaagguuugg auaaauaccucggacauuauauugauuggucuacgagacuaucaagauaacaaagcugauguaaucuuaaaguauaaugcag TABLE 3-continued RNA transcripts up-regulated during HF stem cell activation.

| SEQ ID No: | Access. # | Sequence |
|---|---|---|
| | | augaagcaagaagucugaaggccuauggagaacuuccagaacaugccaaaaucaaugaaacggacacauuugguccuggga<br>ugaugaugaaauccaauuugaugauauuggagaugaugaugaagacauugaugacaucuagccugaccuaagcaugcuacc<br>uuccaaguucucugaagauagcuccacacaguggcaucuugaccuucaucuguuaaguaaaacuucauggcauguguaugac<br>uuguuaaugcaagcuaaugaauuuuauuuuuugaaguacuauauuucuuugaaaaccaaagauguugaguuaucaucuuaa<br>gugacauguuaacacuuugugcuuuugaauauaauugaaccuagcgcacagcagugagcacuguuaagagacugccuuucc<br>auuuguagcuucauuucuggcacgggaguguuuugugucagcaguucugccagguggccaucgaugagcugaaguaaguc<br>cuaguccagcacaucugcuucaggccuuuguacucuagucaucuggcugcguucgagacuucucagcagaacuuauagaug<br>uguacggcugcacuuggagucagacaagauauggcuacuuuuguacuuauggagccaugccauuuuauacuuucacguugu<br>auacauucguuugacccuuuaaguuguugccacccauaaaaaggcaucuuacagugcaguuuuuaaauuacaugguagca<br>auuuugaguuuuaaaaauuagucauugcagaaauuaaauacuuagaggagauaauccauuaucuugauuuuaggaauauaa<br>uaguugacaauguuuauauauaauuuuacuucucuaaggcauacccaaaaauagaaaaugaaaaagagcagugagucuguuc<br>ugaugcuugcauugcauagagaaguuuuccaacaaagcagcuguuaauaacacauaaaauauguuuuacuuugcaaaguagg<br>uuguguuaagucauuuucaaaaaguuaccuacuauaucgaggcucuggauaauuacuauguguugauuaaaguuaguuaca<br>gaauuguacaagcuaagauuuuccuuaaacuaagcuuagguuaaagggagaggagccacagcucaaugaaaacacgguuccug<br>uuuucuaaauggaggcgcccagaaacacaauaaaacauguugguacaaaaaaaaaaaaaaa |
| 57 | J04596 | caugaucccagccacccgcucgcuucucugugcagcgcugcugcugcuggccaccagccg<br>ccuggccacaggggcgccuaucgccaaugagcugcgcugucagugccugcagaccauggc<br>ugggauucaccucaagaacauccagagcuugaagguguugcccucagggccccacugcac<br>ccaaaccgaagucauagccacacucaagaauggucgcgaggcuugccuugacccugaagc<br>ucccuugguucagaaaauuguccaaaagaugcuaaaaggugucccccaaguaacggagaaa<br>gaagacagacugcucugauggcaccgucuggugaacgcuggcuucugacaacacuauaca<br>auuucuuuugaggguccuauuuauuuauguauuuauuuauuccacaaagugugugguuu<br>uuauuuuacauuaauauuuaacagugugguauacauuucaucgaugguaguucaguucugc<br>uuguucaguuuaaagaugguaggcuuaaaauauuucauuaaaacuaauauuuauugggag<br>accacuaagugucaaccacugugcuaguagaagggguguugugcgaaaagaagugcagagag<br>auagaguuuaguauuauguuuuguauguauuagggugaggacaugugugggaggcugug<br>uuuguaugucuugaaaagaaugucaguuauuuauugaaagucgucuuucauauuguaug<br>gucaacacgcacguguugacgcuucccuuggacauuuugugucuaguugguagcccauaa<br>ugggcuuuuacauucuuuaacccuguuucuccuggucucgucucgcucgggacagagacg<br>uucaaaggacuguuacaaaugaaguaaaaauaaaaguuuuauuaag |
| 58 | X81580 | cgucucccgcauucgucugggccgugcaccugcccgcuagcucgcugcacuaccguugcc<br>cacaagccaacaugcugccgagauugggcggccccgcgcugccgcugcuccugccgucgu<br>ugcucuugcugcugcucuugggcgcgggcggcugcggccccggggugcgcgccgaggugc<br>uguuccgcugcccacccugcacgcccgaggcucuggccgcuugcgggcccccacccgacg<br>cgcccugcgccgagcuggugcgagagcccggcugcggcugcugcuccgugugcgcacggc<br>aggagggcgaagcaugcggcgucuacaucccgcgcugcgcccagacgcuacgcugcuauc<br>ccaacccgggcuccgagcugccccugaaggcgcuugucacaggcgcggguaccugugaaa<br>agagacgcgugggcaccaccccacagcagguugcagacagugaugacgaccacucugagg<br>gaggccugguggagaaccacguggaugggaccaugaacauguugggaggugguagcagug<br>cuggccggaagccccucaagucaggcaugaaggagcuggcuguguuccgggagaagguca<br>augaacagcaccggcagaugggcaagggugccaaacaccucagucuggaggagcccaaga<br>aguugcgcccgccucccgccaggaccccuugccagcaggaguuggaccagguccuggagc<br>ggaucuccaccaugcgccuuccggaugaucggggccccuggaacaucucuacucccugc<br>acauccccaacugugacaagcauggccgguacaaccuuaagcagugcaagaugucucuga<br>acggacagcgcggggagugcuggugugugaaccccaauaccgggaagcccauccagggag<br>cucccaccauccggggagaccccgagugccaucucuucuacaacgagcagcaggagacug<br>gugggcccaugcccaaagugugcaguaaaccccagccagucggugccuggcuuccccau<br>cccgaacaccagcagaaauggagggcgucagggugacggguguggaggaguucccaguuu<br>ugacacauguauuuauauuggaaagagaccaacacugagcucagaagcccccucugacc<br>ccccccagcggcuguuaacugaaccucccuugcuucuguuagagaggggaaggugguau<br>ggagggcacugggguacaggccugggaauggggaaagaaauuuuuauuuuugaaucccugu<br>gucucuuuuacuuaagauuaaaggaaggaaaauaaaaaaaaaaaaaaa |
| 59 | AI314958 | gaugugaaaaacguuuuuauuauaaucucuuaaacuuucaguguauauuuucauuacaau<br>cauugguacaauaaauauggaaaugcugagcagacaauuaucacaguggccuaugggcug<br>agggacagggacccaggaauacuguuacccuggauacuucccucagggccaaucaggaggu<br>cuucaaagaguauugagagggagagggauagaaauauuauuaagacugucagugcagcaa<br>cuuuuagaaugucuauuaaagccauggauacaggauuuacgauaacagaagauggauacu |

TABLE 3-continued

RNA transcripts up-regulated during HF stem cell activation.

| SEQ ID No: | Access. # | Sequence |
|---|---|---|
| | | aaaaaagaacagagacucaaguucuccuguaagaggcagaagaaacauugcagaagccag<br>ugccuuccucgggucccccagugugugcccccauccacccacgcauuguguuggucaucuc<br>caccugcccugugcccagcccugugcccacccagguucuccuaggcacccaccuugcacc<br>ucgcacg |
| 60 | AF058798 | gaauucugcgcgguuuugcauuuuuugggucagauuggcuuuuuacaugauuacgaagc<br>uccaacgacuagaccacagggaccgucgccuuggcggccgagcagucguauccaacuugga<br>gacagccaguucgccgugugucugucuguccuucaucgcagucauggagagagccagucu<br>gauccagaaggccaaguuggcugaacaggccgaacgguaugaagacauggcagcuuucau<br>gaagagcgccguggaaaagggcgaggagcucuccugcgaggagcgaaaccugcuuuccgu<br>agccuacaagaacgugguggggcggccagagagcggccuggaggguccuguccagcaucga<br>gcagaagagcaacgaggaggggucagaagagaagggccccgaggugaaagaguaccggga<br>gaagguagagaccgagcucagaggugugugcgacaccguacucggccugcuggacucgca<br>ccucaucaaaggggcuggagaugcagagagccgcgucuucuaccugaagaugaaggguga<br>cuacuaccgcuaccuagccgagguggccacuggcgaugacaagaagcgcaucaucgauuc<br>ugcccggucagccuaccaggaggccauggacaucagcaagaaggagaugccgccuaccaa<br>ccccauccgccugggccuggcccugaacuuuucagucuuccacuacgagauagccaacag<br>ccccgaggaggccaucucgcuggccaagaccaccuucgacgaggccauggccgaccugca<br>cacccucagugaggacuccuacaaggacagcacccucaucaugcagcuccugagagacaa<br>ccugacgcuguggacagccgacagugcuggggaagaggguggugaggcuccggaugaccc<br>ccacaucugaagcagcggaaaaacaacccggguuggcuuggccuuccaguccccagccug<br>gcauagaggauuaaaagggaguggauuuugccuuucccaaacccugaauguucagcaac<br>accuugggaaggucuuucgaagggggcgcagccaagcugaagccaccagggcagggaauu<br>uaauuuuucguguagcuguuuggguggguguuucccaaaaccaucccaccccuguuuuu<br>gaaccccucccccaauucuucccccugagccucccucgggcaccuguugcuuuuggaucc<br>gaauaauccaggagguuccccacccuguggcugagaaauggacuguggcaagggcugugu<br>gugugugagagagagggaaacucugugugugugugugugagagagagagagagagugaa<br>ugagagggaaaaaguuugcuggguguagaccaugguaccaaucaauaaaguugcccuguga<br>gacucaaaaaaaaaaaaaaaaaaaaaaaaaaaaaaaaaaaaaaaaaaa |
| 61 | AW046627 | uuuuuuuuuuuuuuuuuaaauaccaaaacauuuaauugaaauaccuguauaaaaaauaug<br>aucuucagacauuucacacuuuugaacuuauacaaccccaccccugaugcuuagucacac<br>cagggucacagaaacacagcugcuaaaauaaauuaagggcuugagacucuguccccaac<br>cccagcuuucagagccagcaagcagacuguacaaggucaauaauuuaaacccuccccag<br>cgcagagugcucagggugacagggucuc |
| 62 | AI848050 | uuuuuuuuuuuuuuuuuaauguaacgaccggugugcuucaguuuguuuagcagaaccac<br>ucucuugaaucacauuaacuuuugagauuuaaaaaaaacaaaacaaaaaaaaaaaaaaaca<br>acaaaaaaaaaaccaacccuccauagcacagcugucuuuuaugcaagcaagagcacaccu<br>acuccagcaugauuugucaucuaaagacuugaaaacaaaacaacaacaacaaaaaguuac<br>uuauagucaauggauaagcagaguccgaauuuacacuaaucaagacagaccuucgagggg<br>ucacgauaaguccggaacuuucaaaccuugcuucguaugaauuguacuaucugaacauaa<br>acugcacuuuuauuuuc |
| 63 | AF065441 | augagacuccacagccucauccugcucuccuuccuucuccuggcuacucaggcguucuca<br>gaaaaggucagaaagagagccaagaacgcaccacacagcacagcggaggagggguagag<br>gguucagcucccucguuagggaaggcccagaauaagcagagaagcaggacaucuaaaucu<br>cugacgcauggcaaguuugucaccaaagaccaagccacaugcagaugggcugugacugag<br>gaggagcagggcaucagccugaagguccagugcacacaagccgaucaggaguuuucuugu<br>guuuuugcuggugacccaacugacugccuuaaacacgacaaagaccagaucuacuggaaa<br>cagguugcccgcacgcugcgcaaacagaaaaauaucugcaggaacgccaagagugucuug<br>aagaccagagugugcagaaagagauuuccagagucuaaccucaagcuggugaaccccaac<br>gcacguggaaacacgaagcccaggaaggagaaagcagaggucuccgcaagggagcacaac<br>aagguccaagaagcugucuccacggagccaaacagggucaaagaagacaucacacucaau<br>ccagcugcgacccagaccauggccauuagagauccagagugucuagaggauccagaugug<br>cucaaccagaggaagaccgcccuggaguucuguggggaaucuuggagcuccauuugcaca<br>uucuuccucaacauguuacaggcgacaucaugcuaa |
| 64 | AF022992 | Sequence below |

cgggucgacccacgcguccgcccacgcguccggcggagcuucuggguugcgggccgaaacggcaagcggauggagggcgcuc gaacggccaggugucgugauuaaauuagucagcccucagagacaggcguccuaccuccuuuauccagaccucaaaagccccg uugugcacccgugguggcuucuucaccuucccuguuucguccuccacuguauggcccagacaugaguggucccccuagaagg ggccgauggggggaggagaccccaggcccggagaaccuuuuuguccuggaggagucccaucccuggggccccgcagcaccgg ccuuguccaggccccagccuggcugaugacacugaugcaaacagcaauggcucaaguggcaaugaguccaacggacccgagu ccaggggcgcaucucagcggaguucucauaguuccucuucuggcaauggcaaggacucagcucugcuggagaccacugagag cagcaagaguacaaacucacagagcccaucccacccagcagcuccauugccuacagccuccugagugcgagcucagagcagg acaacccaucuaccaguggcugcagcagugaacagucagcucgagccaggacccagaaagaacucaugacugcacuucgggag TABLE 3-continued RNA transcripts up-regulated during HF stem cell activation.

| SEQ ID No: | Access. # | Sequence |
|---|---|---|
| | | cucaaacuucgacugccaccagagcgucggggcaagggccgcucugggaccuuggccacacugcaguacgcucuggccugug |
| | | ucaagcagguucaggcuaaccaggaauauuaccagcaguggagucuggaggagggugagccuugugccauggacaugucua |
| | | cuuacacccuggaggaauuggagcauaucacauccgaauacacacuucgaaaccaggacaccuucucuguggcuguguccuu |
| | | ccugacaggccggauugucuauauuucggagcaggcagguguccugcugcguugcaaacgggauguguuucggggugcccg |
| | | cuucucagagcuccuggcuccccaggaugugggugucuucuauggcucuacuacaccaucucgacugcccaccuggggcacu |
| | | ggcaccucugcagguucaggucucaaggacuucacccaggaaaagucugucuucugccgaaucagaggagguccugaccggg |
| | | auccagggccucgguaccagccauuccgccuaaccccauaugugaccaagauucgggucucagauggagccccugcacagcc |
| | | gugcugccuacucauugccgagcgcauccacucugguuaugaagcuccccggaucccuccugacaagaggaucuucaccacc |
| | | cgacacacaccaagcugccucuuccaggauguagaugaaagggcugccccacugcugguuaccuuccccaggaucuccugg |
| | | gggcuccaguacuucucuuucuacauccugaggaccgaccccucaugcuggccauucauaagaagauacugcagcuggcagg |
| | | ccagcccuuugaccauuccccuauucgcuucugugcucggaacggggaauaugucaccauggacaccagcugggccgguuu |
| | | ugugcaccccuggagccgcaagguggcuuucguguugggucgccauaaagugcgcacggcaccccugaaugaggacgucuu |
| | | cacuccccccagccccagcccagcuccgucccuggacucugauauccaggagcucucagagcagauccaucgauugcugcugc |
| | | agccugugcacagcuccagccccacggggcucuguggaguuggcccucugauguccccugguccucuacacagcccuggcuc |
| | | cuccagugauagcaauggggggacgcugaggggccugggccuccugcuccagugacuuuccagcagaucuguaaggaugu |
| | | gcaucugguaaagcaccagggacaacagcucuucauugaaucucgggccaagccccaccccggccccgccuccuugcuacag |
| | | guacauucaaagccaaaguccuucccugccaguccccaaaccccgaacuggagguggccccaguuccugaccaagccucguua |
| | | gccuuggccccugaggagccagagaggaaagaaaccucuggcuguuccuaccagcagaucaacugccuggacagcauccuca |
| | | gguauuuggagagcugcaacauucccaguacaaccaagcguaaaugugccuccuccuccuccuacacugccucuucagccuc |
| | | ugaugaugacaagcagagggcagguccaguuccuguggggccaagaaagauccgucgucagcaaugcugucuggggaggg |
| | | ggcaacuccucggaaggagccaguggugggaggcacccugagcccgcucgcccuggccaauaaggcagagagcgugguguccc |
| | | gucaccagucaguguagcuucagcuccaccaucguccauguggagacaagaagccccggagucggacaucaucaugaugg |
| | | aagaccugccuggccuggccccuggcccagcccccaguccggcccccagccccacaguagccccugacccaaccccagaugcu |
| | | uaucgcccaguggucugaccaaggccgugcugucccugcacacacagaaggaagagcaagccuuccucaaccgcuucagag |
| | | aucuuggcaggcuucguggacuugacaccucuucuguggcccccucagccccuggcugccaccauggccccauucccccugg |
| | | ucgccgacaccacugccgaucuaaagcaaagcguucccgccaccaccaccaccagacccccggcccgaaacucccugcuaugu |
| | | cucccauccuucaccugugcccucuucuggacccuggccacccccaccagccacgaccccuucccagcaaugguccagcccu |
| | | acccacucccaguauucuccccucgaggaggaccccagccccuucccccugccccuacaucuguguccccugcuaccuucccu |
| | | ucucccuuagugaccccaaugguggccuuggugcucccuaacuaucuauucccuaccccaccuaguuauccauaugggugu |
| | | cccaggccccuguugaggggccacccacgccugcuucccacucgcccucuccaucccugcccccaccaccucucagcccccccc |
| | | accgcccagacuccccacuguucaacucgagaugcagcuccccacuccagcucaaucugcugcagcuugaggaguccccccgc |
| | | acggagggggcgcugcugcaggaggcccaggaagcagugcugggccccugccucccagugaggagacugcugagccagagg |
| | | ccagauugguggagguuacugagucguccaaucaggaugcacuuucaggcuccagcgaccugcuggagcuacugcuccaaga |
| | | agacucucgcucgggcacaggcuccgcagccucaggcucccugggcucuggccugggcucugggucugguucaggauccca |
| | | cgaaggggggaagcaccucagccagcaucacccgcagcagucagagcagccauacaagcaaguacuuuggcagcaucgacucuu |
| | | ccgaggcugaagcuggggcugcucgggccaggacugagccuggggaccaggucauuaagugugugcuccaggaccccaucu |
| | | ggcugcucauggccaaugccgaccagcgugucaugaugacauaccaggugccguccagggaugcagccucugugcugaagca |
| | | agaccgggagaggcuccgggccaugcagaaacagcagccacgguucucagaggaccagaggcgggaacugggugcugugcac |

TABLE 3-continued

RNA transcripts up-regulated during HF stem cell activation.

| SEQ ID No: | Access. # | Sequence |
|---|---|---|

uccugggucc ggaagggccagcugccucgggcccuugaugugauggcgugugugg acuguggcagcagcguucaagauccu
ggccacucugaugacccgcucuucucagaacuggauggauuggggcuggagcccauggaagaggguggaggcgagggguggu
gggugugguguuggcgguggugggggugaugguggugaggaggcccagacccaaauuggggcuaaggguucaagcucuca
ggacucugccauggaggaagaagagcaagguggggg cucauccagcccagcuuuaccugcagaagaaaacagcaccagcuag
auccauuuuggggccgcuuacagcagucuaaugagaggcuuccuuucgaccauguugggguucuuauaacucaagauacag
cuggaccaaccaauaggaaacugccccagcuucucccaacauaggggg cuggacccccauuaccagcccaggcacaggagcug
ccucuagcuucuuagcagaguggaaguucucagccccauuuggaggauuguccacgcccgucccacugaggagacgggcgg
gucuucgguuaagguugcugacaagcugcugaagugg ucuguccaaaucccagcugagccugagucccagucgcaggguug
gggcugcacuuauuuauuugggagagacagcucacucucccaccucaccccaagaugggaggaggggaaccugggaucugu
guaggauccagguccgugaaccccuagcugcucccagggugggggagguuggugg accauggagucccuggugcugccccuc
aggugggacccagguguucucagcucuacccucuaccaaugacauuuguguuuuugauauugugucuguuauuuuuuuu
uaauacaaaaugacaaaaugaaaaaccaaaaa 65 AF064088 Sequence below.

gacagcggagcgcgguggcgucgacgucuagugucucagugcucccgucuguggcuaacuaagcagccagcagccaggcagc
ucgcgaccugcggccaggcagccaaccaugcucaacuucggcgcuucucuccagcaagcuucggaggggaaaauggaacuaa
uuucugaaaagcccagagaggggaugcaucccugggacaaagcugagcagagugacuuugaagcgguggaagcgcucauguc
caugagcugcgacuggaagucucauuucaagaaauaccuugaaaacaggccugucacaccagugucugauaccuccgaggau
gacagcuugcuuccagggacgccugaccuucagacagucccagcauuuuguuuaacgccaccuuacagccccucugacuucg
aacccucc ccaagggucaaaucugacugcaucagcgccaucuacuggccacuucaaaucuuucuccgaugcugccaagccucca
ggcgccacuccuuucaaagaggaggaaaagaauccuuuagcugccccucccucuuccuaaggcucaagccaccagugucaucc
gucacacagcugaugcccaacugugcaaccaccaguccugccccgugaaagcagcuagcauccucaacuaucaggacaauucu
uuccggagaagaacccacggaaauguugaggcuacucgaaagaacauacccugugcugcagugucaccaaacagauccaagcc
ugagcccagcacagugucc gauggugaugagaaggcgggcgcugcacuauaugacuuugcugugccuuccucagagacagu
aauuuguaggucuagccagcuccuucgucccc agugcagaagucaguacuggugucuucaccuacaguauccacugggggg
agugccaccccugccugucaucugccagaugguuccccuuccugccaacaacucucuuguuagcacaguuguccccagcacu
ccuccuagccagccaccagcugucugcucaccuguguuguucaugggcacucaggugccugagggcaccgucguguuugug
guaccccagcccguugugcagagcccaaggccuccaguggugagccccaguggcaccagacugucucccauugccccugcuc
cuggauucucuccuucagcagcaagggucacuccucagauugacucguccagaguaagaagucacaucuguagccacccagg
guguggcaagacuuacuuuaaaaguucccaucugaaggcccacgugaggacacacacaggggaaaaaccuuucagcugcagc
uggaaaggcugugaaaggagguuugcucgcuccgaugaacuguccagacaccggcggacacacacaggugagaagaaguuug
ccugucccauguguga ccgucgguuuaugaggagcgaccauuuaaccaagcaugcccgacgccaccuaucagccaagaagcu
gccaaacuggcaaauggaaguuagcaaguuaaaugacauugcucugccuccgaccccugcuucc gcacagugacggccagaa
gauggagacgcagaauaaacuuuggucagagucaggagccagugaugguggucaagugcuucugcaaggcuguggccccucca
aaagggccuaaaguagaagcccuggccugggggaggccccgccugggugaaaugacaagaagugcuucagccacaggcaggu
cacagaggacagggcucaguucuuaccacagagagagaggagaacccuuuuauuccucccuuauuuuagucuggaaaguuuc
ggcugaggugagcgcagcacagguuuugaaucacauacacauuggggacuuuguuuuugccauuuauacuugagaccagcu
uugcagugugauucuuucaaaggauugguuucaagaauauagaggcuggaaauuacgguacagaaauggagcuagaaaaug
aguuuguguuacacagagaugucaucuucucccagaguuaucuuguuucuuauuccuagucuuuccagucaaauccgugga TABLE 3-continued RNA transcripts up-regulated during HF stem cell activation.

| SEQ ID No: | Access. # | Sequence |
|---|---|---|

uguagcuaaguauaucuaaaacucauuuuuccacuauuguugguauuugaaguugaacagcuguacauugcuguggggggag ccaaaggauuggaacccucauuaauuuaauugcuuggaaaugcagcuaaaauucuucuuuggcauuuuguuuugaaaguuu aggcauuuuacucuacuuuagauuuuaguuugcuugcaguuuuuuguguagauuugaaaauuguauaccaauguguuuuc uguaggcuuaaaauacacugcacuuuguuuagaaaaaaaucuggagaugaaaauauguauuauaaagaagagaugucaagaa uuugagauaacuccuugagaaaguuggcuuuaugucaucagcaaaggacacuuaacgucaagcauacacugugguuuuuuu guuuuuuguuuuuuuuuucaaauuagaaaguuuaaugaccguuacagauggacagugucuuuuuauuuauaggaguuu uucaggaugucagaguagauagguaggaaaauuguuauuagaacauucgcuucuaccuugaaaaggauguuaaugugguca uguucuuagcaccacagugucugggcaucugggaaacuccgagacuuuuuuaaagugucaugaugugaucacaccugcagu uuggggcaucgaauccagggccuugcaugucuucuguaagagcucucaucgcugaccuguaucccccgcaagagcaaugacu uuugcuaacaguauuucuuuucuguuguaaaguggacagaugauacacuuggucgcaaagguaaauuauucaaaauccaca gugaaaaccucaccacacuuucccauuuaaacuauuuccauaucucagagguuucugacaugcaaacuugaacccuugaaag aagaguuuucuuaaaaauuauaaaaaucacgaguuacaauuugcacaauauuuuuuguugaacuuuauaccuuguuuaca auaaagacuuuucuuug

| | | |
|---|---|---|
| 66 | AI787713 | uugucanuugcacgacagaaacugcaggaagaugagaugcgccgggcugcggaggagcgc<br>aggaggguaaaggcugaagaguuagcugccagacaaaggguucuagaaaaaauugaaagg<br>gacaaagcagagagagccaagaaguaugguggguagugugguucucggucauccccacca<br>gcaacagacccagguccuguuccuucuucucccagccaggagccccccuacuaagcgggag<br>uaugaccagugucguauacagguuaggcugccugaugggacuucacugacccagacuuuc<br>cgggcccgggaacagcuggcagcugugaggcucuacguggagcuucaccguggggaggag<br>ccuggacaggaccaggacccugugcaguugcucaguggcuuccccagacgggcuuucuca<br>gaggcugauauggaacggccucugcaggaacugggacucgugccuucugcuguccucauu<br>guggccaagaaguguccccagcugaggguucuccaucccaccaucuc |
| 67 | AI853531 | uuuuuuuuuuuuuuuuucacaaauaaguaauauaacuuuauuaaaaugaaaagacaauau<br>ucaaaauaaugcaacaaaaugaauaaauccuuuguccaauacuguacacacagugcggag<br>aucagugcauuuuucuaaagcauguuuuaaccuucauuuaguucauacuaaaguaagcuu<br>uaaauagcucaaauaaugucauucagcaguuuaaacugaacagcuuguugggacauggca<br>gcagugucccugcuagcaagcaccuucucuuuguguuuaucugcacaagauaaacaauca<br>gaggauguaaaaacugaacacaaacugcgugucucacugaaucucagggcagugaagcag<br>ccagcgugaguuuucaaagcaggaagaugcugaagugaccucuggcauuaagacguucug<br>ugcua |
| 68 | X14678 | Sequence below. |

uucauuggaaagcacauugcucuucucaguaauuucuuuaguaucuucaugaauuuuuuccuuuugcgucguuauuucag caauucuaucugcagaucauaaagguaguauugacagaugugauucuuuuucuuaaacauuucauuuccagguaaggaac ucaauggcuauguuuuucucucccucuagugcauccuucuccuuuucuaccauuuucacucuauuuaacuucaucauguuc agucuggccuuuggguuucaucauagcaaucuguucaacuucacccugcaagauuaaaaaucgauuauggucuaagucaau gccauggcuucuaaggagauuuccaacaucuuuaaacgucuucuucuucccacuuaugugguagacagaagugcuaucucu guaggcgguucuggauacauagaaguugcuguuaggaaggacuucguaaucaucuccuuccuuaucaauuaucuuuugaaa augaacuucuacaguacaacucugaauauccuuguguucaucagaauuauguaucaguaccgauagcuuuuuagaccuuau uuuuugugcucgauagccaaacacaaaaagcauggaaucaauaacauuggauuuuccacugccauuugguccaauaauacag gaaaagcgcuuauggaaagguccccacaaguuucucuccagcauaggacuugaaguuugguuuacaauaugaguuaucaug agacgaggagcuccagcuucacuggccauggcuggagguggggguggagggauacuauucaaaaucuccucuaaacuucug uuauccagcuccucaccuggaggcuuugcgggugcagcgcucccccucaccuacuucgccuacugcaacucccaccaccuccu cucgauacaagaccgagcucugucggaccuacucagaaagcgggcguugucgcuacggggccaagugccaguuugcucacgg ccugggugaacuuucgccaagccaaucgccaccccaaguacaaaacggaacucugccacaaguucuaccuccagggccgcugcc ccuauggcucucgaugccacuucauccacaaccccaccgaggaccuagcucucccuggccagccccaugugcugcgacaaagc TABLE 3-continued RNA transcripts up-regulated during HF stem cell activation.

| SEQ ID No: | Access. # | Sequence |
|---|---|---|

aucagcuucuccggcuugccucaggccgcagaagcucgccgccaccuccaggcuuuucuggcccuucccuguccucuuguuc cuuuucgccuuccagcuccccaccgcccccuggggaucuuccacuuuccccuucugccuucucugcugccccugggaccccu gugacucgaagagacccuaaccaggccuguugccccuccugccgaaggucuacuaccccagcaccaucugggggcccuugg guggccuggcucggagcccaucugcccacucucugggauccgauccugaugacuacgccagcagcggcagcagccugggggg gucagacucaccugucuuugaggcagggguguuugggccuccccagaccccugcacccccaaggcgucuccccaucuucaau cguaucucugucucugagugacaagugccuaccuacccaguauggaucagcuagaucucaaagagagggcagggacugcuca uugcugugggaccuggggcacuccucuaaguuaauaagucccaucuucuggacauuccaagaugcaauaacccauuucccu ggugcugggcuggggcagguccccuaguuugcaaauucaguguuugggguggauccguuccuaggguaccuaagauguuuga gggagacaguugacaguuggucuuccaggccccaagucuucuguuguuuuugagauaggagcuuauuaugguaccccaggc uggcuuugaacucaauauaauccugccuuagccuuuuccaaguucugggguuacagguaugcaccagccccucugcaacucu ggucuccuggaaucuuaagugcugugaagagccggcucccacaauacuauccuaauuuuuacuagacccugaaguucagug uccggugggucgaagccucuccugagaauccuggugcucaaauuucccuccuaaagcaaauagccaaagccauugccaaaucc cuucuccccaaccagugggcccuuuauuuaugacgacuuuauuuauuguauuaagauuuuauaguauuuauauauauugg gucgucuacuccguuuucuuuuuguaauguuaaaacugauacuguauuaaguauaugcuauaauauauuaaauauauugcu

| | | |
|---|---|---|
| 69 | AI854358 | cggacgcugcagaccugaccgacgugcugugcgaguucgacgcggugcuggccgacuucg cgucgcccuuccacgagcgcacuuccacuaugaggagcaccuagagcgcaugaagcggcg cagcagcgccagcgucagcgacagcagcggcuucagcgacucggagagugcagacucagu guacagggacagcuucaccuucagugaugagaagcugaauucuccaaccaacuccucucc agcucuccugcccuccgcugucacuccucggaaagccaaauuaggugacacuaaagagcu cgaagacuucauugccgaucuggacaggaccuuagcauguaugugaagcaaggaguuugg gguc |
| 70 | X67668 | ccgggccgaggagaagucugcaaaacaagaggcuggggauugccuuagcgagaaaucagu ucucuuaggagguuagggaaggaagucuuucucuggaggucugagggaagcgcucguguc agaugccggguugucauggguaagggugaccccaucaagccgcugggcaaaauguccucu uacgccuuuuuugugcagaccugccgggaggagcacaagaagaagcaucccaauucgucg gucaacuucgccgagaucuccaagaaaugcuccaagagauggaagaccaugucugcaaag gaaaacucgaaguuugaagauuggccaagagcgacaaagcuuguuauuacagggagaug aagaacuauguuucucccaaaggugauaagaaaggaaagaaaaaagauccaaaugcuccg aagagaccaccgucugccuucugccuguuuugcucugaaaaucgcccaaagaucaaaauu gaauacccgggccugucuauuggagauacugcgaagaaacugggugagaugugggucugag cagucugccaaagagaaacaaccguaugagcagaaagcagcuaaacuaaaggagaaguau gaaaaggauuuugcugcauaccgugucaagggcaaaagugaagcaggaaagaagggucc ggguaggccagcaggcucaaagaagaaugacucagaagaugaggaagaagaagaggaggaa gaugaagagggggaagaagaggaggaugaagaauaaguggcuauccuaaaguguggaguauau gugcucaggcaguuauuuugcuaagaauguaaauucaagcgcagcucaacauuagcucca guaggaa |
| 71 | K02236 | aucacgcuccuagaacucuucaaaccgaucucucgucgaucuucaa ccgccgccuccacucgccauggaccccaacugcuccugugccuccgguaagggggacugc ugacgggauuucugggagagcuagacaggcuuuuggccccuccuuuaguaauuacuuua aggguacgaccggcuaccccuuccgaaugaauucugaagcacuccugcuccuuuaaacua guccuugagauaguggcucgccuacccgggugauuugccucaccuuccuaggagaacagc guucagguacucccggguccccacucaaccgcgcucacugacugccuucuacuuuuagaug gauccugcuccugcgcuggcgccugcaaaugcaaacaaugcaaauguacuucccugcaaga aaaguaaguuggaucuucucugccauuuccccgucacucuccugggguccccuagcccgcc gcgccgcgccuucccucccgggagcguucagguggugugccucugacaagguuucucgcu cacguucaacucuucucuccccacaggcugcugcuccugcugccccgugggcugugcgaa gugcucccagggcugcaucugcaaagaggcuuccgacaagugcagcugcugugccugaag gggggcggagggguccccacaucuguguaaauagaccauguagaagccuagccuuuuuug uacaacccugacucguucuccauaacuuuuucuauaaagcauguaacugacaauaaaagc cguugacuugauu |
| 72 | X51829 | Sequence below. |

gcucugaguuuguggaagauuacaugcgauaucccgcgcgaccccgcaucccuuugccggccgggacagccuuugcuacagc cugugaaacauugcguccccgagccccacgccugagggcgacaugaacccgcuggcuucgcgagcaguccggacccacgauc gcuuuuggcaaccagaaccggcgcuucagcccccggggugacgugcagcccgccgcccagacacauggccccgagcccaagac cccagcauguccugcacuggagggacgcccacaacuucuaucuccuguccccacugaugggcuugcucagucgggccuggag TABLE 3-continued RNA transcripts up-regulated during HF stem cell activation.

| SEQ ID No: | Access. # | Sequence |
|---|---|---|

ccgccugaggggcccagaagucccagaggcauggcuggcaaaaacaguaacaggagcagaucagauagaagcugcggcucug cugacaccuaccccugucucugguaaccuccucccucauggggagacugaagaaaguggaucuccugaacagagucaagcag cccagaggcucugccuuguggaagcugaaaguuccccuccugaaacuuggggacuuucaaauguugaugaguacaaugcaaa gccaggacaagaugaccuuagagagaaggaaauggaacgcacagcuggcaaggccacacuacagcccgcuggccugcaagggg cugauaagaggcuuggggagguggugggcuagagaagagggaguggcugagcccgcuuaucccacaucacagcuggagggug guccagcugagaaugaagaggauggagaaacagugaagacuuaccaagcuucugcugcuuccauagcuccgggauacaaacc cagcaccccugugccuuucuugggggaggcagaacaucaagccacggaagaaaaaggaacagaaaacaaggcugaccccucca acucuccuucuucaggcucccacuccagagccugggaguacuacucuagagagaagccuaagcaggagggagaagccaaggu agaggcacacagggcagggcagggucacccuugucggaaugcugaggcugaggaaggaggaccugagacaacuuuugucug uacuggaaaugccuuccugaaggccuggguguaucgcccaggagaggacacagaggaagaagacaacagcgauucggauuca gcugaggaagacacagcucagaccggugccaccccccauacaagugccuuccugaaggccuggguguaucgcccaggagagg acacagaggaagaagacagcgauucggauucagcugaggaagacacagcucagaccggugccaccccccauacaagugccuuc cugaaggccuggguguaucgcccaggagaggacacagaggaagaaaacagcgauuuggauucagcugaggaagacacagcuc agaccggugccaccccccauacaagugccuuccugaaggccuggguguaucgcccaggagaggacacagaggaagaaaacagc gauuuggauucagcugaggaagacacagcucagaccggugccaccccacauacaagucccuuccugaaggccuggguguauc gcccaggagaggacacagaagaugacacagaagaggaagaggacagugagaauguggccccaggugacucagaaacagcugac ucaagccagagucccugccuucagccccagcguugucuaccaggagagaagaccaagggacguggggaagagcccccucucu uccagguggccuucuauuuacccggagagaagccagaaucaccuugggcugcaccuaagcugccccuucgacugcagaggcg gcucagauuguucaaagcccccacccgggaucaggaccccgagauuccucuaaaagcucggaagguacacuucgcugagaaa gucacaguccauuuccuugcugucugggcaggaccagcccaagcugcccgucgaggucccugggagcaguuugcacgagauc gaagccgcuuugcucgacgcauugcccaggcagaggagaagcuggguccccuaccuuaccccugauuccagggccagagcaug ggcacgccuuagaaacccaucucuuccacaguccgagccucgcucuuccucugaggccacucccuugacccaagaugugacca cacccucuccccuucccagugaaaccccuucgcccagccuguacuugggagggaggcggggcuaagccugaguaguuuccua uuauuuauuuauuuauuuauuugaauaagaaauaaagccuuuuaauuuguagugau

| | | |
|---|---|---|
| 73 | AW048937 | uuuuuuuuuuuuuuuuuaaucaucgagaaguauuuauugagcaccagcuuuggggucgg<br>gugugaggacucgggacaaugcagggugcugucccuucucgugagacgcuuacaaucuga<br>guggagacagggagggagccacaauacauguucuuggggugcgggcuaagguagacagu<br>ccagaccaggauguuacagaaacagggauguuggggcuggagucagacccacuaagugcu<br>uugacacccacgguauucaacacugagaaaggaucagccauugcucaguguccugugagc<br>ucccuuagcccccaagacaccaucuuggccuggcuccuuguacaacugcuacuaa |
| 74 | AV139913 | cccaaaacccauucagcaaaguucccaaccucgacgggcuagcaguauuuaaccagugau<br>ggguucacuguuguauuuggugaauacuguauuuuguuucaguucuuucucccagauaa<br>uuugaaaacguuccaggagaaggcagcuuccuauaugcagcgugugcuuucuuauucuuu<br>uuuuuaauauaugacaguuauuugagaacccauuucuacuuugaauucauuuucguugaa<br>agugauguuucuucaccuaccauuuuccuauuaaaguucuguauucaaau |
| 75 | M32490 | Sequence below. |

agaccgugagcgagagcgccccagagaagcgccugcaaucucugcgccuccuccgccagcaccucgagagaaggacacccgcc gccucggcccucgccucaccgcacuccgggcgcauuugaucccgcugcucgccggcuuguugguucugugucgccgcgcuc gccccgguuccuccugcgcgccacaaugagcuccagcaccuucaggacgcucgcugucgccgucacccuucuccacuugacca gacuggcgcucuccaccugccccgccgccugccacugcccucuggaggcacccaagugcgccccgggagucggguugguccg ggacggcugcggcugcuguaaggucugcgcuaaacaacucaacgaggacugcagcaaaacucagcccugcgaccacaccaagg gguuggaaugcaauuucggcgccagcuccaccgcucugaaagggaucugcagagcucagucagaaggcagacccugugaaua TABLE 3-continued RNA transcripts up-regulated during HF stem cell activation.

| SEQ ID No: | Access. # | Sequence |
|---|---|---|
| | | uaacuccagaaucuaccaaaacggggaaagcuuccagcccaacuguaaacaccagugcacauguauugauggcgccgugggc ugcauuccucuguguccccaagaacugucucuccccaaucugggcugucccaaccccggcugguggaaagucagcgggcagu gcugugaagagugguuugugaugaagacagcauuaaggacucccuggacgaccaggaugaccuccucggacucgaugccu cggagguggaguuaacgagaaacaaugaguuaaucgcaauuggaaaaggcagcucacugaagaggcuuccugucuuuggcac cgaaccgcgaguucuuuucaacccucugcacgcccauggccagaaaugcaucguucagaccacgucuuggucccagugcucc aagagcugcggaacuggcaucuccacacgaguuaccaaugacaacccagagugccgccuggugaaagagacccggaucugug aagugcguccuuguggacaaccaguguacagcagccuaaaaaagggcaagaaaugcagcaagaccaagaaauccccagaacca gucagauuuacuuaugcaggaugcuccagugucaagaaauaccggcccaaauacugcggcuccugcguagauggccggugcu gcacaccucugcagaccagaacugugaagaugcgguuccgaugcgaagauggagagauguuuuccaagaaugucaugaugau ccaguccugcaaauguaacuacaacugcccgcaucccaacgaggcaucguuccgacuguacagccuauucaaugacauccaca aguucagggacuaagugccuccaggguuccuaguguggggcuggacagaggagaagcgcaagcaucauggagacgugggugg gcggaggaugaauggugccuugcucauucuugaguagcauuaggguauuucaaaacugccaaggggcugauguggacggac agcagcgcagccgcaguuggagaaugccaaggggcugauguggacggacagcagcgcagccgcaguuggagaagacuucgcu ucauaguacuggagcgggcauuauugcuccauauuggagcauguuuacggaugacguucuguuuucuguuuguaaauuau uugcuaaguguauuuuuuugcuccagaccccccccccccuuucuugguucuacaauuguaauagagacaaaauaagauuagu ugggccaagugaaagcccugcuuguccuuugacagaaguaaaugaaagcgccucucauuccuucccgagcggagggggacac ucugugaguguccuuggggcagcuaccugcacucuaaaacugcaaacagaaaccagguguuuuaagauugaauguuuuuuu auuuaucaaaguguagcuuuuggggagggaggggaaauguaauacuggaauaauuuguaaaugauuuuaauuuuauauca gugaagagaauuuauuuauaaaauuaaucauuuaauaaagaaauauuuaccuaaa |
| 76 | AI121305 | ccaauaccacagccgugaccacagccaagaccacagccaaaagccuggccauccgcacuc ucggcagcccccuggcagugcccuccauauccugcuuguuuuucucauuaguaaacuccu cuucuaaagaaaacuggggaagcagaucuccaaccuccaggucauccucccgagcucauu ucaggccagugcuuaaacauacccgaaugaagguuuuauguccucaguccgcagcuccac caccuuggaccacagaccugcaacacuagugcacuugagggauacaaaugcuugccugga ucuuucagggcacaaauuccgcuucuuguaaauacuuaguccauccauccugcgugua |
| 77 | U35374 | auggagaacgaguucacauacgaagauuaugagaccacugccaaguggcuucugcaacac acugaauaucgaccucaaguggcagugaucugugguuccggcuuaggagggcugacugcu cacuuaaaggaggcucagaucuuugacuacaaugagauacccaacuuuccccaaagcaca gugcaaggucacgcaggccgacugguguuuggauugcugaauggcagaugcugugugaug augcaaggccgguuccauauguaugaaggauacucacugucaaaggugacauucccagug agaguuuuccaucuucuggguguggaaacuuuggugggucaccaaugcugcuggaggacuc aaccccaauuuugaaguuggagauauuaugcugauccgugaucacaucaaccuaccuggu uucuguggccagaacccucuccggggccccaacgaugaaagguuuggaguucguuuuccu gccaugucugaugcuuaugaccgggauaugaggcagaaggcuuucagugccuggaaacaa augggggagcaacgaaagcuacaagaaggcaccuacgugauguuggcaggccccaacuuu gagacuguggcagagagucgucugcuaaagaugcugggggcagaugcuguuggcaugagc acagucccagaaguuaucgucgcaaggcacugugggcuccgugucuuugguuucucacuc auuacgaacaagguugucauggauuaugagaacuuggagaaggccaaucacauggaaguu cuggaugccgggaaagcagcugcacagacauuggaaagguuugucuccauucuuauggag agcauuccacucccggaucguggcagcuga |
| 78 | X15643 | Sequence below. |

uuccaggacagcuggggcuccacgagagaaacccugccucccccccaaaaauggcccaaaguucacugacaaacucacauuug ucugauauuuagcuauguaacagcacuuacgguagcaauagaauuugauucucacucaucacaaugaaaauggcuggcgcuc ucucucucccucucuccccauuucaaaucugcaagcacaccccuuagagauggagagaauuugauccauuggagaaucgagc uaaaaauaccaccauggaauugugggaaggauuaaaugcaauaaugcacaaaaggcacauagcagaaugugcccuaaauguca gccauuguuaugguauuauguaaucuacaaaguauguuugcuuacuccgugugaaagacuuucagucuaucaaacauaaua caugugaaaucaaaccuugaaaauuaauuuuuuucccaacagucaagacauuugccagcugcagagauuagcauuucaugaa ucuuagucuugucugauuuuuuuaaugggaaggaacaacuauccucaacuauccuuuuuuuuuuucuguaguuuuaaaau TABLE 3-continued RNA transcripts up-regulated during HF stem cell activation.

| SEQ ID No: | Access. # | Sequence |
|---|---|---|
| | | gaacuccacaaaacauguuuuuaauauagggaauuauaugaaauuguggggugggcagcgagguuaaaggcagaaauagccc |
| | | aauggugg cacauucacugacacagccuaaaagauuagcaaauuacccagccaacacauacaauuaauacaauuaauauuuuu |
| | | auaguuaaaacagaguuacuaaagaaauuguuugaaaagaaaauuaugaagacuggaaagacggcucagugcuuaagagcuu |
| | | uggcuagucuuccagagaaccagggucauccagcacucacaaggcagcuugugagcugauacuaucuguauauucaguccua |
| | | gggaaucugaugcuuuguccugaccuccaaaacaggcacaaaugguggugcacaggcaaauguagagauaagacucccaugca |
| | | cagaacauaaauaacguaguuuaauuuuuuaaauuguaaaacugaaaaugguugcacuugcauuuuuauuuucagcacauc |
| | | cccagauauccgccauauaacaagaaaaugaugccacacucccaagaauuaagaauuacaccucccaacccuacccaaaugugu |
| | | auacucuaggucuaaagaaaugcaaaggaugaaguuacugccuugugcgguucucaaggagggaggaugccaaaaaaauauu |
| | | uuuucacaaagugugcugagaaacucuguagcuguuggagucaucuccugugcucuugccaaauaacugaaaggggauaca |
| | | cuggaugucugugaauggggugucacuuaugagugcuagaagcggguaccuggauguggacacggugucugagugguccg |
| | | cacuccaugucuccacaggagcgcuuauguguguuucuuuccuccugcuucuggguguuccugguuuguuuacagccacc |
| | | ucucuguuggaccaggagacagcugucgucuccagaaugagcgggcacgggugugucucgguggcuguggcugugguucg |
| | | gcauaagucugagcauguccuggucgucagggugcguuugugcugugugugcguguccgggugagcuugcucuuucuguu |
| | | ccuaaaagaaaaugcacccugcgcuaccggcguccagagacucucagcccgcagaggugaccugaacggacagguagcaccuc |
| | | cagacagcgccugguuggcggguugcacagcagccccagauuucucucucuggugccccagcuaggguagcuggaagggag |
| | | cgguggccuggccuccggggagccgcugggccccgccgggcuaacccaggaggaggccggcuaggcugggaggguuagccc |
| | | uuggugcccuacgccugcccgggccagucgcggccgccggccauuggcccaaagaauuguugcacgucacuggcaauucccc |
| | | uagaagucugugcacauaacgggcagggcgcacugcaaggcugcuucucccgcauuuaggcugcggcugcaggcaccgcgag |
| | | cccggagcacccacgagcuuagugugcaggacgcaccccagcacagccaccuacggccgcugaaugaagcuuccaggaguccg |
| | | cccccggccgucgccccgucggaggugcacccgcugagagcgccuggaccgaaaggccggugcgcucaccugcuaaccugcc |
| | | agccauggggccacacgggaacgacagcgacuucuugcuggcacccaacggaagccgagcgccacaccacgacgucacucagg |
| | | aacgggacgaagcgugguuguggg cauggccauccucaugucgguuaucguccuggccaucguguuuggcaacgugcugg |
| | | ucaucacagccauugccaaguucgagcgacuacaaaccgucaccaacuacuucauaaucuccuuggcgugugcugaucuagu |
| | | caugggccuagcgguggugccguuuggggccgucacaccucuaugaaaauguggaauuuuggcaacuucuggugcgaguu |
| | | cuggacuuccauugauguguugugcgucacagccagcaucgagacccugugcgugauugcaguggaucgcuauguugcuau |
| | | cacaucgcccuucaaguaccagagccugcugaccaagaauaaggcccgaguggucauccugaugguauggauuguaucuggc |
| | | cuuaccuccuuuuugccuauccagaugcacugguaccgugccacccacaagaaagcuaucgauuguuacaccgaggagacuu |
| | | gcugugacuucuucacgaaccaggccuacgccaucgcguccucgauugugucuuucuacgugccccugguggugauggucu |
| | | uugucuauucccgggucuuccagguggccaaaaggcagcugcagaagauagacaaaucugaaggaagauuccacgcccaaaa |
| | | ccucagccagguggagcaggaugggcggacgggccacggacuccgaagguccuccaaguucugcuugaaagagcacaaagcc |
| | | cucaagacuuuaggcaucaucaugggcacauucacccucugcuggcugcccuucuucauugucaauaucgugcacguuauca |
| | | gggacaaccucaucccuaaggaaguuuacauucuccuuaacugguugggcuacgucaacucugccuucaauccucuuaucua |
| | | cugucggaguccagauuucaggauugccuuucaagagcuucugugccuucgcaggucuuccuucgaaaccuaugggaacgg |
| | | cuacucuagcaauagcaacggcagaacggacuacacaggggagccaaacacuugucagcuggggcaggagagagaacaggaac |
| | | ugcugugugaggaucccccaggcauggaaggcuuugugaacugucaagguacugugccuagccuuagcguugacucccaag |
| | | gaaggaacuguaguacaaaugacucgccacuguaauacaggcuuucuacucucuaagaccccuccuugacaggacacuaacca |
| | | gacuauuuaacuugaguguaauaacuuuagaauaaaauuguauagagauuugcagaaggggggcacauccuucucgccuu |

TABLE 3-continued

RNA transcripts up-regulated during HF stem cell activation.

| SEQ ID No: | Access. # | Sequence |
|---|---|---|
| | | uuuuuaauuuuuauuuuauuuuuuagcugcaaacaagagagagaacuguauuugagugcuuauuguucuuguauaguuca<br>guuccucuuguauggaacuuaaagguuucugucugaagaguguugguucugaggacugagucugucugucugucugucug<br>ucugucugucuggaugauguuuucauguaucuaccucacuggucaaguauuaagaaugauauauugcugcuggaaaucc<br>auaucuaaaggagagaguuuucuuccuguacccuuggacuugaaauauccugugucuuggaccuuucugcugugacaaugg<br>gcccuuucucucucacuccacuuauuuacucaaauggauucgaggcagggauuugagggacaacacuaguuguuuuguuuu<br>uguuuuuguuuuuuuguuuguuugguucguuuuugguuuguuguuguuuuuuggggguuuguuuuuguuuuuguuuuu<br>uuggguuuuuuuuuuuugcugagaaaagucuaaaguuuacaguaaauaaauuguuuaaccaugacuucauugcacccguuu<br>cuucaaaaccucuugacucuggaguguccuugucucucccacuggaaaccacagguaaacuaugugucgugaccgaugagug<br>gcuuaauguguaagaguaccagaauggcaugcuugcaugcaccgugccuagcccuuccgugugugucuucagagcuccaga<br>ugcaaaccugugccuucccuaacuucacucgugucccaaagcaguccugccuguucacagcauaacccaguauguccuacag<br>uugcucuucugugcugucacuccagaaacccugacucacggaaacagaguuauggacauauguuuuuguccccauaugcuc<br>ugacaccaccuucagccuuacuugcuuaauaacuguguauauuuacaucacugcgucucuuacaguagugccuuuguacug<br>caucagggcuugguguguucaggaugaggaagauguucuguguaauagcuguucaagcaucuagaaauucugagggaaauc<br>aaaggccucggucagagagagagagagagagcaaagcuuuaaaaaacauagcuggugaaugcuucacgcccuucagccucuc<br>cucgcuccgucugcugucccgugucuucuguucccaauucucugcacuucuguguaaaccaggcuucccaugucuggcauu<br>ccgugcauuauaugauauuuggcggcacgucuguaccaguaaauucugguagcacccccuaguuacaauaauugcagacacu<br>cagcgcguacgacccccuaguuacauaugcagacacu |
| 79 | AI849109 | uuuuuuuuuuuuuuuuuuaagcguccaggcuguacuuuauuuuacacaagugguggcccc<br>agaaccacagggacaugaccuggagaguaggcacagugccugaggcugcaagagccaaaua<br>cagggauucaugccuucuccuugguccccaugaccaaauuaaaaaaaaaaaaaaacaacaa<br>aucacacagcacacaucgccacacccauccccuccuuccuuucagcaacagccaauucag<br>cuuucuagccaaagacaguggcuacaacugaauuuacagagaaccaugcagccaagaaac<br>cagagccacggaggggagaggcuugcguugacuucccacaugugcugucccauagcagcu<br>gagugaccccacca |
| 80 | U70132 | agaaagauaagggccagcaaggaaagaaugaggaugugggcgccgaggacccguccaaga<br>agaagcggcaacgccggcagaggacucauuucacuagccagcagcugcaggagcuggaag<br>ccacuuuccagagaaaccgcuacccagacauguccacucgcgaagaaaucgccgugugga<br>ccaaccuuacggaagcccgaguccggguuugguucaagaaucgccgggccaaauggagaa<br>agcgggaacgcaaccagcaggccgagcugugcaagaauggcuuugggccgcaguucaacg<br>ggcucaugcagcccuacgaugacauguaccccggcuauucguacaacaauugggcugcca<br>agggccucacgucagcgucucuguccaccaagagcuuccccuucuucaacuccaugaacg<br>ucaauccccuguccucucagaguauguuuuccccgcccaacuccaucucaucuaugagua<br>ugucguccagcauggugcccuccgcggugaccggcgucccgggcuccagccucaauagcc<br>ugaauaacuugaacaaccugagcagcccgucgcugaauuccgcggugcccacgcccgccu<br>guccuuacgcgccgccgacuccuccguacguuuauagggacacauguaacucgagccugg<br>ccagccugagacugaaagcaaagcagcacuccagcuucggcuacgccagcgugcagaacc<br>cggccuccaaccugagugcuugccaguaugcagucgaccggccggugugaaccgcgccca<br>gggcgcggggauccgaggacugucggagugggcaacucugccccagaaagacugagaauu<br>gugcuagaaguucgugcgcacuaugggaaggaagagggggggaaaaaagaucagaggaaaa<br>gaaaccacugaauucaaagagagagcgccuuugauuucaaaggaaugucccaagugucu<br>acgucuuucgcuaagaguauucccaacaguuggaggacgcguacgcccacaaauguuuga<br>cuggauaugacauuuuaacauuacuauaagcuuguuauuuuuuaaguuuagcauuguuaa<br>cauuaaaaugacugaaaggauguauauauaucgaaaugucaaauuaauuuuauaaaagca<br>guuguuaguacuaucacuacaguguuuuuaaaggcuaggcuuuaaaauaaagcauguuau<br>acagaaucaguuaggauuuuucgcuugcgagcaaaggaauguauauacuaaaugccacac<br>uguauguuucuaacauauuauuauu |
| 81 | M13805 | cugagaggccaggugggcggcgaaaucaacguggagauggaugccgcucccggugugac<br>cugagccgcauccugucagagaugcgugaucaguacgagaagauggcggagaagaaccgc<br>aaggaugccgaagacugguucuucagcaagaccgaggagcugaaccgcgagguggccacc<br>aacagcgagcuggugcagagcggcaagagcgagaucuccgagcucaggcgcaccaugcag<br>gcccuggagauugagcugcagucccagcucagcaugaaagcaucucuggagggcagccug<br>gcagagacagagaaccgcuacugcgugcagcugucucagauccaggggcugaucggcagu<br>guggaggagcagcuggcucagcugcgcugcgagauggagcagcagaaccaggaguacaag<br>auccugcuggaugugaagacaaggcuggagcaggagaucgccaccuaccgccgucugcug<br>gagggagaggaugcccaccugacucaguacaagccaaaagaaccugugaccacccgccag<br>gugcgcaccauuguggaagaaguucaggauggcaaggucaucucaucccgggaacaggug |

TABLE 3-continued

RNA transcripts up-regulated during HF stem cell activation.

| SEQ ID No: | Access. # | Sequence |
|---|---|---|
| | | caccagaccacccguuaaggacucagcuccuuccgcccaguuccccgaggcugcagagag gcagcuucccucuccgcuccggcauuacccuccugcuacagccucuccccagcauuccua ugcuugagaccauuaaagcuugcugaccugaagugaacuguggccuuuguucugaacacu gaaauaaaugaccauggugac |
| 82 | AV138783 | ccccaggggugaaaugaggauuccccacccugcggaacagugaaauguguauaauuaag aggagggcgacgacccuugccgcgggacccgggacucgagcccgggacuucgcagcuaca gcaaaucuauuuuuaauauugugcugagcaagacagaucgcuugcauauuuuuaaaaauu uuuacuacagagacauuccaauaaauucguuaagcc |
| 83 | K02927 | Sequence below. |

cugacagucgucucugucccuucuucgccucggagcugcuaacuggucucgaaccucucagcacuucagcuucuagcggcga ugcaugugaucaagcgagauggccgccaagagcgaguuauguuugacaaauuacaucacgaauccagaaacucuguuaugg acucaacauggacuuuguugauccugcugcagaucaccaugaaaguaauccaaggccuauaguggggucaccacaguggaa cuggacacccuggcugcugagacagccgcgaccuugaccacgaagcacccugacuaugccauccuggcagcaaggauagccg ucucuaacuugcacaaagaaacaaagaaaguguucagugaugugauggaggaucucuacaacuacauaaauccgcacaacgg cagacacucucccaugguggccagcucaacacucgacauuguuauggccaauaaggaucgccugaauucugccauuaucuau gaccgagauuucucuuauaacuacuuuggcuuuaagacacuggaacggucauauuuguugaagaucaaugguaaaguggcu gaaagaccacagcauauguugaugaggguuucuguggggauucacaaagaagauauugaugcugcaauugaaaccuacaacc uacuuucugagaaguguuucacucaugccccuccuacucucuucaaugcugggaccaaccgcccacagcugucuagcuguuu ccucuugaguaugaaagaugacagcauugaaggaauuuaugauacucugaagcagugugccuugauuucuaaguccgcugg gggaauugguguugcugugaguuguauucgggccacugguagcuacaucgcugggacuaauggcaauucuaauggccuug ugccaaugcugagaguauauaacaacacagcucgcuauguggaucaagguggaaacaagcgcccaggcgcguuugcuauuua ccuggagccuuggcacuuagacaucuuugaguuccuugacuugaagaagaacacaggcaaggaagaacagcgagcacgcgau cucuucuuugcacuuuggaucccagaucucuucaugaagcgaguggggagacuaaccaggacuggucauugaugugucccaau gaguguccuggucuggacgaggucuggggagaggaguuugagaaguuauaugaaaguuacgagaagcagggucguguccga aaaguuguaaaagcucagcagcuuugguaugccaucauugagucccagacggagaccgguaccccauacaugcucuacaaag auuccuguaaccggaagagcaaccagcagaaccugggaaccaucaaaugcagcaaccuguguacagaaauaguagaguacacc aguaaagaugagguugcaguuuguaacuuggcuucucuggcucugaauauguaugucacaccggaacauacguaugacuuu gagaaacuggcagaagucacuaaagucauuguccgaaaucugaauaaaaauaauugauauaaacuacuacccuauuccagagg cacacuuaucaaacaaacgccaucggcccauuggaauugggguacaagguuuagcagaugcuuucauccugaugagauaccc cuuugagagcccagaagcccaguuauuaaauaagcagaucuuugaaaccauuuacuauggagcccuggaagccagcugugaa cuagccaaggaguauggccccuaugaaacguaugagggaucuccagucagcaaggguauucuucaguaugacauguggaau guugcuccuacagaccugugggacuggaagccucucaaggagaagauugcaaaguaugguauaaggaacaguuuacuuauu gccccaaugccuacugcuucaacugcccagauucuggggaauaaugaguccauugagccuuauaccaguaacaucuacacuc gaagagucuugucaggggaauuucagauugugaauccucacuuacugaaagaucuuacugagcggggcuuguggaaugaga gaugaaaaucagauuauugcaugcaauggcuccauucagagcauaccagaaauuccugaugaccugaagcaacucuauaag accgugugggaaaucucucagaagacuguucucaagauggcagccgagagaggugcuuucaucgaucagagccagucuuuaa acauccauauugcugagcccaacuauggcaaacucacuaguaugcacuucuacgguuggaagcaggguuuaaagacuggaau guauuacuuaaggacgaggccugccgcuaauccaauccaguucacucugaacaaggaaaaacugaaagauaaggaaaaggcac ugaaggaggaggaggagaaggagagaggaacacagcagccauggugugcucuuuggagaacagagaggagugccugaugugug gauccugagaaaagcggggccugggagacgcagcgggcucucccugcccgagaggcagacgauuugagcauagauaggauagu ggguuugcuugguuaucagcagcucugcuuggacgugccugccaggacagggagccacgacuuacaguacuguuucuacac TABLE 3-continued RNA transcripts up-regulated during HF stem cell activation.

| SEQ ID No: | Access. # | Sequence |
|---|---|---|
| | | aguguaaauaucauuuuuaacaaacagaaaaccaaagccagcuuugauauuaggaaucaagguagaggcuuugggaauacua |
| | | aagagccuuccugcaaauagugaggagacuuaggaagucucgucucuccagcuuucccugccuggccauucucaguuuggg |
| | | caaagagauuuaguuugauuugacugauugccuagaaguaaaaucaagcaauuacucaucagcuaaagaccuuugucuagac |
| | | aaacuucuauaagucauuuugaaauaaacauuucuaagugau |
| 84 | X07699 | Sequence below. |
| | | uugccucagacgcuagcuguagcuggcaggcgguuguacgugcucccagagucgucgguacccgcuacugcagucgcuuucg |
| | | uguggcuuccgcugagcucuuccgagcugcucgcucucccacacgcgccgccgccguaaauccgccaccauggugaagcucgca |
| | | aagguaagaggccuuggcgcgccgacgcggacgacuaggccccugcuuucggagggacgcgcgcgcgcccgcccguccgucg |
| | | cggaggggaggagggcuugcgcgcaaucccgggcgcguucgagggcgccaugcugggggggaaagucucgcgcgacuagcg |
| | | ggaggucucgcggugcuugcccucugacuuagggggaugagaagagcggaggcagguuucccgggagggcgauaucgaggg |
| | | uucggauguagcgggcgggaggggacggugugaggagagaucggaggagcugagagcggauaggggcacggcguggggaaga |
| | | gagggccaaccuuaggcggcgagcggucccggggccccgccuccccgcgcacgugcucuggugcgcgcccgccacgugcucu |
| | | gcggagccccgcacgugucgcgcgacccggggcaguggggggagugucuguaguaccccggaaagggggacggcagcguggg |
| | | gauggaugggguggcccggcgaucugcugucucugccggugaccgggauggacacgugguggaccccugagguggcggcgu |
| | | ggugacucccacgugguggggcuggaagcgagagaaagugggaagcaguuggguuacguggugcugcuuuaagaggugauu |
| | | ucgagauaccccccuuccccagcaaauaacuuaaagggaucccuuuaacuggguuuuuuuuuuuuuuuuuuuuuuuuuuuu |
| | | uguggaagaugccagaaaauagauggccaggauuaggagacuuuauaaccuguggcuguuucuuggugguagaguucuguc |
| | | ugcucaguuaucugugagaaggaaaaaaaaauuaugcgcgguucgcagaaaaaacugccaggagaaugccaugccuggccaa |
| | | gaagaagucuuuaugcuuguguccuuuaguaagaaaaagguggugggccaaaggcaaagugacugaaaaugcgugcaauuuu |
| | | ugugugcguuuguaggcuggcaaaacccacggugaggccaagaaaauggcuccucccuccaaaggagguggaagaggauagu |
| | | gaagaugaagaaaugucagaagaugaagaugacagcaguggagaagaggagguaagaagcuauuugcagcgaagaauuaaaccgg |
| | | uggaauugaaugcuggaagucuuagaaauacaggauauguaguaaaugguugaauggcaagccccuuccucccucccuccc |
| | | ucccucccucccucccucccucccucccuuccuuccuuccuuccuuccuuccuuccuuccuuccuuccuucugcaagacagucggcaaaac |
| | | aggggacagaaacaggcagaauuuugaguuccaggcaagcagggaguagacauaugaaaccuugucucaagaccguuguu |
| | | auggucaugcucaaucagauuucuuagaaaagcucaggugcugaguccaguuuuuuuuuuuuuaaaguauugaaagccaug |
| | | ucuccuuauuucaggguuuaaauguuuaucuuugugugugcgcgcacccauuaagcaugcuugguacccucauacuagaaug |
| | | uacuuggaucccccuggaacuggaguuaaagccacaugugaauguuacauguuacaagaguaacacaugugcuuaacuuuug |
| | | agucaucucuccaguucuugguuguuuguuuuuuuuuuuuuuaagccuaucuaauguccauuuucuugugcucaaaguuag |
| | | ucucuuaauguagcauuggguauaaaggaaugcuuaugauuuguuugcuuucaagguugucaucccucagaaaaaaggcaa |
| | | aaaggcuaccacaaccccagcaagaaggugguuguuucacaaacaaaaaaaggcugcaguucccacaccagcuaagaaagcag |
| | | cugugaccccaggcaaaaaggcaguagccacaccagcuaagaaaaacauuacaccagccaaagucauuccaacaccggguaaga |
| | | agggagcugcacaagcaaaagcguugguaccaacuccugguaaaaagggagcugccacucccagcuaagggggcuaagaacgg |
| | | uaagaaugccaagaaggaagacagugaugaggaugaagaugaagaggaugaagaugauagcgaugaggaugaagaugaugag |
| | | gaagaggaugaguuugagccaccaauaguaaaaggagugaagccagcaaaagcagcuccugcugcuccugccucagaggaug |
| | | aggaagaugaugaggaugaagaugaugaggaagaugaugaugaagaggaggaagaugguggaguuagaucuuaggauauuua |
| | | ggguacugcauguacauucccucacuguuucauuagauuaaaaacucauuuugugcucuuaguucuuuccauaacuuaaua |
| | | gguuuucauuugcuaaguaguuuuuguuuuuuuuaaguauuuguagcauuuaucuugucuggauugguagguagcaaau |
| | | acauuugccugauuugccaucuuucuuccagacucugaggaagaaguuauggagaucacaacagccaaaggaaagaaaacuc |

TABLE 3-continued

| RNA transcripts up-regulated during HF stem cell activation. | | |
|---|---|---|
| SEQ ID No: | Access. # | Sequence |

cugcaaaaguuguuccuaugaaagccaagagugugg cugaggaggaggaugaugaggaagaggaugaagaugacgaggaug aggaugaugaggaagaggaugacgaagaugaugaugaggaagaagaggaggaagguaaccauauuaacuuuuaaaguaugc ugaccuaaguaaggcuuacuggcuaugcuaaagugucugcuuacucaugaauggcauuuuaaaacaucuagaaccuguuaaa gcagcaccuggaaaacggaagaaggagaugaccaagcagaaagaagccccugaagccaagaaacagaaaguagaagguaagcc ugcaaaacuggggaaacagaucagaguagcacuagcacaagugaugagugacaaagggacuuaauacugaaccaugggguug aaaugaaauaugcugaugugcuuuauaguuuaugaugaaauuuguugugugcuuaagugggcugaaaguucauuuuuugu gugugcaggcucagaaccaacuacaccuuucaaucuguucauuggaaaccuuaauccaaacaagucuguuaaugaauuaaaa uuugccaucagugaacuuuuugcuaaaaaugaucuugcuguuguggaugucagaacugguacaaauagguaaguuuuaauu gaauguuacauguguaucagcuagaauuuuuaguuuccaguuguauucuucccugccuuuaaacauggggcuauaucuaac uauguuaguaaaagucaguugucuccucucguggccuuaaguacaguuaaggagcugcaguaagaaagacuauaguauuga acuaaaugaucgagucauagggccugcaauuugaaguuccuguguuugacuugauaaagauaaaaauaaaauuuaaagaagaa aagauauuaaacacauaaaauuuugugcaguaucuacaacuauggaucugcauagucauaugcuuuuagcuaaaaguauucu cuguacuuuuagcggggucaugcuagcuacugcuguuaguuacaauauacugaaugaagaaaucgaggugaauuuguugu aaugucuugguacauggacuuguuuuguuuuuuguuuuuuuuucuuuaagauuuguuuauguauaugagcacacuguag cuguccagaugguuuugagccuucaugugguuguugggaauugaauuuuuaggaucucagcucgcucugcucucagucccu ugcuugcucuggcccaaagauuuauuuguuguuauacauaaguacacuguagcugacuuaagaugcaucagaagagggcau uaggucucauuaugggugguggugagccaccaugugguugcugggauuugaacucaggaccuucagaagagcagucaaugu gcuuacccgcugagccaucucuccagccuuuggacuugguuuuauggaagauaagggugaucuaguuuuauuuuuguuag ugcuguagaugcucugugugugugccacaugguauaagugcagaucaccuucucauaccuguaaucuuguuuuuuccaucu ucaaggaaauuugguuaugugg acuuugagucugcugaagaccuagaaaaggccuuggagcucacugguuuaaaaguguuu ggcaaugaaauuaaacuagaaaaaccaaaaggaagagauaguaagaaagguauguaaggggggucugggugacuggauacuaa cagacuuaggcagucuggugccucuuccuuaguuucauccucauugugaaccaaugagaugucauaggucaugugcuuguu gacagguuugauuccugggauauauaaaugucagggcugacaggaggaauagcuuagugaguaaagaugcuugcugcaaaau guuugaucucuagaagccacaugaagagagaagaaccuuuaaucccagcauuugggagacagaggcaggcagauuucagagu ucgaggccagccuggucuacagagugaguuccaggacauccagggcuacacagagaaacccugucucggaaaaaaaguuuua gcuuauccucugaccacauguguaucgugacaugcuugaagcuuaccuaucucuuaaaugaauucuugaucccuauauuuu gaguuucagaauuuggauuuuaaguguuuguuucuuaguugugcugaaaauugaacgugggcuuuucacaugcuaggcaa auuuguuggguuuuuuuguuuguuuuuuucucaagacaggguuuuucuguguagcccuggcuguccuggagaccaagcua gccuugaacucagaaaucugccugccucccaagugcugggauuaaaggcgugagucaccacugcccugcuaggcaaucacuc uuaaaacugcuacauauccucugucccuuuugcucauuuuacaagguugcugugugcucaaucugcagucuauguuauau gcuuacuggaucuaggcuuuugauguagaaugaaccauaugagugaugagguaucuuagagauggaaacuaagucuaaaua gacuuguuccauauacaacuuaauacauauggucuaaggaacaugauauacauguaaacaaguaggaaggagauaagucugg uguccagggaagccaggagagccucaucugaaacuggacagggguuugugagucaucaggugacaauugaacauagguacu cuucaugcaaaugguuaguaaccauugagccaccucuccaucccuuuauaccauuuuuuuuuuuagcauauauccuuguac uuuauaggaauuauuugcuuuauucucuugugacuuguaaauugauguacuuaauuaaaucuuuuuccaacauaguucga gcugcaagaacacuucuagccaaaaaccucucuuucaacaucacugaggaugaauuaaaggaaguguuugaagacgccaugg agaucagauuagucagccaggaugggaaaaguaaaggguaguuuuguguucuuugaguguuaaaguuuuauuaaguuuagu gucuucuuccccucuccuuguccuugcagucucuagucugcugcuucaaacuuaacuucauaaccagaaaaauugaauaucu TABLE 3-continued RNA transcripts up-regulated during HF stem cell activation.

| SEQ ID No: | Access. # | Sequence |
|---|---|---|

gguccucuggccucuaccucccaaguucugacauuaaaaaugcucaacugaugguuuugaagguguga ucaauuuucag gcucaauccaaauuggcaucuuuugccacaaguacuauccuucccuauuuuaugagagaaaugugauucuaggcaguucag ucuauuguguuggcucuuuuuccuccucaccaguuuaaaggaugaagaugagcuaauacauaguaaaagaacaguaaaagca caugugacuaaguccuucaugucugaugcuugaguaauauuuucucuaacguaguaacugaauugucuuguacucuuucag gauugcuuauauugaauuuaagucugaagcugaugcagagaaaaauuuggaagaaaagcagggggcagaaauugauggacg aucuguuucacucuacuauacuggagagaaaggucaaaggcaagagagaacuggaaagaccagcacuuggagugguaaguua aaggguuuauuguguagugggaacaggaaucauuuguaucuuuguauuuuaaguaauugguuaccuacaauuaguucacc uuuguucauauagcugauguuuagucuucaugagugaaagcuauuugaaaucauuuccuuuggaguauaguaggcaaauaa agcuuuuuguugggu auguuuuguacuuuaaauggcuuaaacuauuuuagaaaauaguguaagacaacaaagaacaguuau cuaauuagaaugaaaaugaaaggagcaaagaaggcauuacuguauauaauggauauacacugguggu ucuagaauuauggu auaugguacaugguugaagugccauuguuucaguuaacauuccaguaaccuuguggauuagguuggagacaugcuuuauag gugacccacuuacugaguguuuaaauauacacagacauacucuaacauaccuugcuaauguguuaucuuuguauuugcagg ugaaucaaagacuuugguuuuaaguaaccuuuccuacagugcaacaaaagaaacucuugaggaaguauuugagaaagcaacu uuuaucaaagugccccagaacccacauggcaaaccuaaaggguaaaauaauuuuuacguuagauguggg cuggacauacaua cucuuacguauaagaguaagacuguccuguuagcuuaaaaaaaaaacuaaaguuuuagcuauacaaagggcaguaaauauuga uaguaaauuacaugcugaugccaaguguuucuaagcuuuauucugagaacugacuuucaaccuucagguaugcauuuauag aauuugcuucauuugaagaugcuaaagaagcuuuaaauuccuguaauaaaauggaaauugagggcagaacaaucaggcugga guugcaaggauccaauucgagaagucguaaguccuuugacaugauaugacuugguugggugauuuuuuuuuuauuuuua ugugccuauaugcucauuuggggcugucuuuauguuguugcugagaaaaugacaacuggauaugaugacugauuaccuga gaaauaauugaugaaaucucaagaaaauuccucuagauagucaaguucugauccagcuaugucaacucaaagcagcaaccuu gauugcccucugaguacgcuuuuuuuuugauccaguguagucuuuuuuuuuuaaccuuaauuucuuguguuaauugcuu uuucugguaaaaggggaaaaaaagacauaacaaaaucaguguaagggaaggcucagugguugagcacugagaggaccuggg uucaaaucccagcacucacauggcaccuaucgagacaggauuucucuguguaguccugccugucguggaacucacucuguag accaggcuggccucaaacucagaaaucugccugccucugccuccuaggugcugggauuaaaggugugcgccaccacugccca acccugucuguaacucuuaagaucugacauagauugcagacaaaacacuaaugcacauaaaaaaauuuuuuuuuuaaaaa ggaaucuacuucagcugaauguggcaguauggcaguauucaccaaggguucauagugaaacaggaauuuucucuuccaga accauccaaaacucuguuugucaaaggucugucugaggauaccacugaagagaccuuaaaagaaucauuugagggcucuguu cgugcaagaauagucacugaucgggaaacugguucuuccaaaggguaagaaggcguaguaguguugcugcuuuuuagugaa uucugcauggagaacuugggucugcaguaucuucucauugagcuccuuucuguccaucagugauagauuauggauucgcac gagaagaagagagaauucacagaacuggcacuuaucuucuguuuuugcagaaguauauuuggcuguugugugagacauuau gagauacuggcgauuuucucgaccugaagaguacuuuggucacucuacuugggugacuugguacuuauuguguuacuuua aaauguguuuacuuaaugggugagguuuuuuuguuuuucuuuucuguuuuagguuugguuuuguagacuuuaauaguga ggaagaugccaaagcugccaaggaggccauggaagauggagaaauugacggaaacaaaguuaccuuggacugggccaaaccu aagggugaagguggcuuugguggucgagguggaggcagaggagguuucggaggcagagguggaggcagagguggaagagg uggauuuggaggaagaggccggggaggcuuuggagguaaggaagggaaaggaacuggaaacggauuccuaaaccugugucc uaaccaaccaccuuaaugggaaggucaguccuaauuguaucacccuuugauguuuuuccuuccuauagguagaggaggcu uccgaggcggcagaggaggagggggagacuucaagccacaaggaaagaagacgaaguuugaauag TABLE 3-continued RNA transcripts up-regulated during HF stem cell activation.

| SEQ ID No: | Access. # | Sequence |
|---|---|---|
| 85 | X57800 | Sequence below. |

uuagacgguugcgcgcgcagaggguugguaguugucgcuguaggccuucgcugccgcuucugcaucgugaaucgggggac cuuggcagccagaccucguuccucuuagaguagcucucaucuagucgccacaacuccgccaccauguuugaggcacgccuga uccagggcuccauccugaagaaggugcuggaggcucucaaagaccucaucaaugaggccugcugggacgucagcucgggcgg cgugaaccugcagagcauggacucgucucacgucuccuugguacagcuuacucugcgcucccgaaggcuucgacacauaccgc ugcgaccgcaaccuagccaugggcgugaaccucaccaggugagcggguggcgggagcggggccccacucuucccgcuuccgc ucuuggcggggcugugacucugcacgcucauuggcuggcuuggccauccgcgcuuucugauuggucuaugguguucggggg cagcccucaccaaagcgcgcgguuccgaaaagcccgcgcuggcaguggcgcccacucuguuuccgcgccaaagccacaaagcg ggaguccgcgggaaaaugagugcuccggagcugugcucauuaaaugccugcagcuuugaguggcuggucuuagcgccuaau aaacgagucuuagugcaaauguaaugucgacuuagagugacaauagaccuuuucuugacuuccagagucucacugcgcauca uggauuugaggggaaucugucaguuuuagcuuuuaacuuugcuacagcuaccuagguuagugccuccuguauacguguu caaggacagugugugacuuauuuuaguacagauacauggauuagugccacuuguauacauuuugaaagauuuacgaaaagg ccagacgugauggggcacauucuccaguacacuagaaaccaaggacaccccgcucaaaaagaugcuuucucgaauguuggcu uuuagugcauuuuacuaagucgguuuuaagaaucacauauacccgguaauuugcuucaccccugagagaguuuggguacc cuuagccccuuuaacaguucuccaaccgugagugugaaagguacaacuuguaauugcuuuuuaaaauauagaugugg auu acauguugauaaagccugucuuuuuuuuuuugggggguagcauguccaaaauucuaaaaugugcugguaaugaagacauca uuacauuaagggcugaagauaaugcagacaccuuagcacuaguauucgaagcaccaaguaaguuaaacaccuuuaaaacucg gaguuacguguuguuucuguuucucaaaaccaaaaaaaauauuaacaauauuguaaauuccaucauagauaggaccgugug gugugcuugguaacauuuuccuucuuuugguagaucaagagaaaguuucagacuaugaaaugaaguuaauggacuuagaug uggagcaacuuggaaucccagugaguuaccuuguuucugauuguguguuacccugcugugauaccagcugaugcguguuc ugaguggagugguguauuggggaugaauggcacacugccauuucacuaaaccacagcagucuaaaguugauugaguuuua aagaaaccagaagucuugcauucugaguucugguuaagaugcuaaaucuugagaacaugaagcugagccuuccccuuuucu agacugaccuuuaacuugugggguuuacaggaacaggaguacagcuguguaauaaagaugccgucgggugaauuugcacgua uaugccgagaccuuagccacauuggagaugcuguugugauauccugugcaaagaaugggggugaaguuuucugcaaguggag agcuuggcaaugggaacauuaaguugucacaaacaaguaauguggauaaagaagaggaggcggugaguaguaagggggcgu ccaguuaggugucugaagcagggauggagccucggcuuuuguuuuuauuuauucauucauuuugagauggagucuugagu agaccaagcuaucuuagagcucagagacgacuccauaagcuuuuacagguagcauuuggaaagcuaaguguacagccuuuug cuuccuggaaauacucuuggcaaauaagugaggguuggcaagugagcaaaagaaaaugguuggggguguauguagcuuuau guguugcagguucaagaguauuugcagucccaagggaaauaagaaagacuucacaaaauguggaaagaguuguauuaaaugc ucuugacaguuacauccauagagaaagcugggcaugaugucucaaacccacaacugauguacucaaagcuacagcaggaaga uucucagcuuaaagucaaccuggcagaaaaucuagcucaaaagaaugaggaagaaauugggaaggcaaaggaagauguucu ccgaguccuccucauucaaguagaacauacuaggccucuuuaauuucuaaguaucccugaaucgaggcuuuuucucaggaau ccaauguauauuucauggcuacacuuuuuuuuuucuuuuuuaaguuuugcuagcuagccugagcaucagaauuacacacag aagucugaacuaaauaggauuuuuagggguuuaguauagugaaauucagagugcuucugcaaguauuuaagguaaaauauaag guguuacuuggccucugcaugaauuuaaaguaaaugaaaguguaagaauucgaacauagauaaacacacaacccaagaacua guucuuaaccuuaaucugcugaauuauuucuacuuccauaucaacuucagcuccucaguucucaaauacugacauguaauuc aucaguauuugucugaugugcaagcauuuccacaacaaaagaaauuaaggaauuuuucaguauccacauguucaaggauugg gaauugaauaaaaauugauaaucauacaaugaagacugguuuacugucccuuagcuugcauucagcugu ugguucuuguuuu TABLE 3-continued RNA transcripts up-regulated during HF stem cell activation.

| SEQ ID No: | Access. # | Sequence |
|---|---|---|
| | | uggaagugguuauguguuaucuucccucucuucaugcauucuuugcaagagaaguauguacaaucugaauaggaacaacuuu cuccuuuguuuugauugcuuggggugugcucuacaggaugggcaagcuagacuuuuuucuucuuuagucaagguuuuca ucaacccuuccaaaaugauaacuauuuguuuugcuuugugguauaauaccgugaucuaauagugugaguuucugaugucua cagugagccuguuuucuccucuagguaaccauagagaugaaugagccuguucaccuaacguuugcucugagguaccugaac uuuuucacaaaagccacuccacugucuccuacaguaacacucaguaugucugcagaugugccccuugguaagaugauaaguu ugaacauuguuuuguaaugugguauuuauaguauucgguggguuuaauuuuuccugucuuucaguuguagaguauaaaaauu gcugacaugggacacuuaaaguauuauuuggcucccaagauugaagaugaggaagcaucuuaggcauugcuagaaauugag aaaacuaaaccuuugaagauugcucccugagaugccagcguguccugaggucuuuucugucaccaaguuuguaccugaguau ucuuaaauauuaauaaaauauguagauaucuucuguaaauaaccuacuuucuuuucucuccauucuccauaauuugcuu aaagaauaagcuccaaaguaaaaacuaguuuuguuaacaugaauguuucugcuuuacaaauacuggugauuuuccaucaaug aucuugacgcuaaaugcaguuuuaagaaauauuguucaauuuaaauaaaguuaacaauuugaaaaguca |
| 86 | M35247 | Sequence below. |
| | | ggugcaggauguaggccugcagaauugucagacccaguggcggcuuuugccacuggaagaauuuccaacauaaaacaga ugaucaguuugggacaaucgauucugcgaccagagguagugucauuugguuacuuuuaaaauucagauugucuggugu uuuccaaucacucgcgacuguaauuugaaguuggguucugagauaauacaaucgcugucgcucuaguuuauaaagcugu ccaagaucugcccagucccagauguccuggguccucagggccgcugugguc ugccaacuucugcagcuggaugccagacc auccuggacucggaucccuuuggguauuucuacaccgcugugucccggccuggccuuggggagcccugguucauaaucg ucggcuauguggacgacaugcagguccugcgcuucagcagcaaggaggagacucccgaggauggcacccuggcuggagca ggaggaagcaggugacugggagcagcagacucguauagucacaauucaaggacagcugucugaaaggaaucugaugaccc ugguucauuuuuacaacaagagcauggacgacucucacacacuacaguggcugcaaggcugcgauguggagccagaucg gcaccugugucucugguacaaccagcucgccuaugauagcgaggaucuccccacccugaacgaaaacccaaguuccugua caguggga aacagcacuguaccucacaucucucaggaccugaagagccacugcucagaucugcugcagaaauaccuggaa aaagggaaggagaggcugcugcguucagacccuccaaaggcacaugugacccgucaccccagaccugaaggugaugucac ccugagguguugggcccugggcuucuacccugcugacaucacccugaccuggcaguugaaugggg aggagcugacccag gacauggagcuuguggagaccaggccugcaggggauggaaccuuccagaagugggcagcugugguggugccucuuggga aagagcagaguuacacaugccauguguaccaugaggggcugccugagccccucauccugagaugggagccugcauggua ccaaaagccuuggauuuggauuguugccaugguuuucauuuuguucaucauuugucucuguguggu uugcauaugcau gaagaagaaugcaggugggagaggaaggcgugacacccaagaagcaggcagagacaguccccaagacucuagcaagacug uuguggaugaugaggagaugggggu uugcuuuuggaagauuaaguccuguaaaacuugucuaggccacuccccaggaac uucaguuggcgagucuuuacugucaccuugacuggauuuaggaucaucugggagaugccccuuugaguggcugggcug ugaggacagcaggccaguucuugccacccuggacagaaacacaucucaccuuucuggcucaaggaucugaacaccugucu cuugccuacucggcuucuagucaggcauuuugucaccuugucaagggucccagggacacaaagcuccccuccucucaccca cagcacucuggguccuacccucagugcuucagggacauuuaaucaggucaaauugggaucaauggcuuugaugcagaaa agaacuguggacuaauagagauagggu uuaauuaaaaaaauauaucuuuuuaauuuu |
| 87 | AI553024 | cuggcacggacauggcugucuucugucugcugugugggaaacgcuuucaggcacaaagcg cacuccagcagcacauggagguccacgcaggcgugcgcagcuauauuugcagugagugca accgcaccuuccccagccacacggcucucaagcgccaccuucgcucacauacagguuuuu uucuccauguguc accaagugaaguuugugccuucuauagcaaagagaauauuuuuaca uccuacuaacaguagauuuuuuuguagugaacauuuuuuguauuuuuauuuauaagucuc auaagaaaaauagcgauguucaguuguauaccuugaaucugcaguuagaagagaauaaag uuaacuc |

TABLE 3-continued

RNA transcripts up-regulated during HF stem cell activation.

| SEQ ID No: | Access. # | Sequence |
|---|---|---|
| 88 | X16995 | Sequence below. |

ggagccccagugcaggaggcugcgaaaguuggggagugugcuagaaggacugcggagcggagcgcacgcgggaccaggcu gcgacugggucgcuggucccggccacagggagugggagccggcugguagguaccccgcagggagcguguuucuguuucua gggacagugcaugaaagagauggggguguacgcgcgggcgaaaaggaagggguguuuucgggucggcuuacgaggaggggug uguagggugcauuuuugguauuaaaggauagcucuuggaguagggugagccagggcuugaaguuuaggaagcgggcgaag ggucugcaaggugcuugguuuugguagguagugggcgcuuguuuaggagguuuccccgcuaggaucuccagugugaggca cucuguacucuggguuuggguguugauugccggguagggggguugucugagcauggacugggaaaagguacucagagcuuc ggcguugcuggggauccauccaaguacaaguaagauuggauuuccacgggucuccuucccggcucucagccccuuucccag uguuuacuuaauacuucauaggcuguacuuagauuuucugauucccuuaccgaacuuucuuucugaaccgugcuggaagac cugggguugcugaaggaaauggccagcuagguuggcuggguaaugguuguguuagacuaaguugucagaguaucuagaa accuaggagcuguagccuggugcagcuacugaaagccgcacguggagccuggguggaaguugcucacgauagagucucgau guaguacugacuagggggagaccccuucugucaucagacagacuuguauaccccaguggucuuuugaaucuguuagguag ggugcagccugcgggcuuggucaccuaacagguguugccaggaccugccccaagccggauucucccacucccucuuucaacc ccgccucuuccuccuccuugagacacccccacccccucaggaggcuagaugcagaucuguaucuuguguugcugacuaucgg ccugaagcuggguagauugguggggguugauccggauguaggauguccaaguggagaaacaggauuugaauggagcuggaa caaacgcccaguccugacugcugccacccuucuuccuccacccccaacccaucccuucccaggcuucuugcaaacagaggcag aaguggccauauuucuuucuuucucccaggugcuguaugcccuagggacuugacacggggcaggcgggguggggaacugguu ggggggggacgugcuguuuuaugggaagucguaugccuagccagcgguggagcuguccuggcuaggcacccaggggguggu guggggaaugggagaaauacugggacuagagggucucaagggccagcagguggugauagucuuuuucuccaccccacccuc ugcuccaccaccccucugccucagcaccccucugcccucagcaccccucugccucagcacccucugccuccagccacccucug ccucagcacccucugccucagcacccucugccucagcacccucugccucagcacccucugccucaguguuccugugugaccu gucuuuucaacuagaaagucuagaacuguacagaccccagaguuggagguggaaagggacacuagguccuggagccuccucu gugggcuuuuuugaccagaugagaacguaagggccuccuccagcuaucccuggucauucaggugcuucagguuugugaccu uugcugagacccuggaugcugcagcaaacagacaucugcuuuagcagagggacagcuugucucugugcauccgcugguagg auccuccacucuguccaauuagcuugcgcugcugcuggguucugaguguucucuuacaaaaugacaagguuagggggcugg agagauggcucaggggcuaagagcacccauguggcaguuugcaacugucuguaacuccuguuccagggggggaucugacacc cucacacggacaaacaugcaggcaaaacaccuauuggcauggaaaaugaaaauaaaugaccggguuagcugagaaauuccuuu ugagaguugucuuuucuccaguccaggacugcucucuggaucuuccugcucaguuccucgccucccuuccauauaugguau uuaagguuuuacuuuuuuuugcguuuucaauuguuuuuaauuguauuuauaugugucucugugugugcacaugagcaug gguguccuacaaggcuagagacaucagauguccuggagcuagaguuacagaugguugugagccaccugauguaguugcugg gaacuggauuuaguuccuguggaagagcagugcaugcucuuaaccacugagcaacuucuccacgcggcccccccccaguaua cgguauuuaaaacucuauagcaaugcuacccaacccauuguggagcuggggauggugagguggccuaguucccccaacucc uggaaacaugucagaaaguacagaguggguggccugugggaucagcaugcggggggugguggugguggugaggugugggggcugc uuucucccgaggcuaccgugauagacaguuguaccuugcuggcagccucuaccccauuuccaggaugucagucucugcagac guaugggggacggugggggaagggguauacagagccauggguguguccugggaauguacucccaggaagugacugguugaaaa gucagcagaucuccugggggauagagggguggggcugaagcucuguggguugccucucucagcccugaccugugaacaggga ggcugggggguuggaggaacacagcuuccccccuguuccugggggggacaugcuggacagccuuuccuagcuccccccggcccac uggggugugggcuggucgucggacugagcucuuuuggaccuggucucugccugugagcuuugugacucguugagauagcau TABLE 3-continued RNA transcripts up-regulated during HF stem cell activation.

| SEQ ID No: | Access. # | Sequence |
|---|---|---|

uugggcugagggauugggagucuucuguucuuugguccugacacccgcuuccuugucuaggccugccaccuggcuccccccc acccccccuccccggccuaccaaguuucuugcuucccuuacugaccccuccuccuccccuccuuugugucuccucccucuccag agaugcccuguauucaagcucaauauggaacaccagcaacgagcccaggaccgcgugaccaccugaccggugauccccuggcc cuugaguucggcaagccuaccauggaccuggccagccccgagacagcaccugccgcaccugcuacacugcccagcuucagcac cuucauggacggguacaccggagaguuugacaccuuccucuaccagcugccggggacgacccagccgugcuccucagcuugu uccucugccuccuccacgucuucuuccucauccucggccaccucccccgcuucggcguccuucaaguuugaggacuuccagg uguacggcugcuacccgggcacccugagcggcccauuagaugagacccuauccuccagcggcucugaguacuauggcagucc cugcucagcccccucgccaucuacacccaacuuccagccgucccagcuuucucccugggacggcucauuuggccacuucuccc cgagccagacuuaugaaggccucugggcauggacagagcaguugccuaaggcuucuucagggccuccgccaccuccaaccuu cuucuccuucaguccucccacuggccccagccccagccuggcccagaguucucugaaauuguucccaccaccagccacccacc agcuuggggagggggagagcuauuccaugccagcagcuuuccccggcuuggcacccaccucuccgaaccgugacacuuccgg cauucuggacgcacccgugaccuccaccaagucccggagcggggcuucagguggcagcgagggccgcugugcagucugugg ugacaaugcuucgugucagcacuauggggucccgcaccugugagggcugcaagggcuucuucaagguauuuuguugguucu gggggacgaugauaucauguuggagguggggguggagugggucauccguugggaucuguagugaccucuccugagguuuc uucccagcugguucuguccugcaggacgagggacaggugugugccaucuuagaggcugggacuuuuuauucagcagggcac acaucucucuagggcugcagaaagcuggggaagggggcagaaggugugugugugugugggccugcaguggugcucagaaaca gaaaaccuagugggcagccucugguucuccacagaacuuguguuucuggcacuggaugaaaggacacaggcagagguuug guucuugcugggggguggacuugggaacaggcuguguguuugucccagugcugggugccugcuuggcnnnncccaccucca nccccuuaguccucuccucugcgccaggaaaagggcagguggacacaugcagacaccuguuagaacaggugucuggacggcc gugggaguuccuagacccuggucuuggguucugggaucuucccugugagguugaaaccuucuccaguaucucccagacucc ucucugcgcucuggcccuccguuucucccucccccuacauccaaauguuaggaaaauagcuaugaacagagggcgcuuuugu cugcgucggccacaggaucuggacgguccccuccccugggcucuccaccccccccccaaaccccaugcucugacagccuguuc cguguccccccuuccuccagcgcacaguacagaaaagcgccaaguacaucugccuggcaaacaaggauugcccuguggacaag aggcggcggaaccgcugccaguucugccgcuuccagaagugccuggcuguggcauggugaaggaagguggguggcaagau ggugcccucggcauaggcgaccugaugggguggacagccgggcucaccaggaucugcaccuaauucccacucccacuucua gauuccagccccuaaaugcagguguagcuuccaccugcuuucuggaaagguggggugaggagggccuugugggguccccca ucauggucugaguucucugucucugacuucucagaaguggggguauagugugcccugaagacccuccuucuccaggucuc cuuucucaauacugcccgucucucugcaguuguacggacagacagccuaaaagggcggcggggccggcuaccuucaaaaccc aagcagccuccagaugccuccccuaccaaucuucucacuucccucauccgggcacacuuggacuccgggccuagcacugccaa auuggacuauuccaaggugaggucuugcccgcccaucugcccugcccugagaacauaugcaaugccuuugugccuguuagg aaaggcucucccuccagggcaacaucaggaaacaagcauccucuauguacuggcuaguuggagaaaugcauugggaugggug uggggucggggagccaguuacaaacagcugccguagcccuguuuuccugugggaauugacaagcacaugggcccagaauag ggcucuuuugcacgccuggaucuggugucccagugcaugagagcucuguaaugcagcuuguguaggcuuugcuguggaccc aaugcaggacacagcugugugaugcaggccuugcuguggagccagugcgugacacagcugugugguggcaggcccucaugug gaacuuaccugcguuccuuucaguuccaggaacuggugcugccccgcuucgggaaggaagaugccggugacgugcaacaau uuuaugacuugcucucugguucccuggacguuauccgaaagugggcagaaaaaaucccuggcuucauugagcuuugcccag gagaccaagaccuguugcuagagucugccuuccuggaacucuucauccuccgccuggcauaccgguaagcugcccaccaucc uccuagcccuggccccagcccugcggccccggccugccuggacccugaguccugacuguucucugccuucugccagaucuaa TABLE 3-continued RNA transcripts up-regulated during HF stem cell activation.

| SEQ ID No: | Access. # | Sequence |
|---|---|---|

acccggugaggggaagcucaucuucugcucaggccugguacuacaccagcugcagugugcccguggcuuuggugauuggau ugacaacauccuggccuucucacggucccugcacagcuuggguguugauguucccgccuuugccugccuguccgcucuggu ccucaucacuggugaguggcagaaacuagacugggcccaaggguugcaggaccauuggguagguagcaucuaacacuuugg ggaccccuagagugccugcaacauugggauguuaggaccugcaaagggacuuagcucuauucgccccuaaagcuuaaaucag ccuccgaaugaccccggacuccucagguacgacuguaggcgcugggcaucuagcuuagggauucuguuuguuuaaaaaccu agcugucaaccucacaagacacaggaacgugcacacaugaauuuuucacauucugcgcuuggauagcuaucgccaugucca gaaacaggaccuacuucagcucuguugggcucccuccuuauugucucuguaagagguaaccacucugccagccucaguggca uuccugucauggauuuuacugugcguaucacaggguauggacucuaguguuaaauguagagguuucugggucccuucucg uuccgcucccauuuccacuuaaauuucuuaggggauccuccugaguagaucaagaccaggagcuggaucuugaaaggguag ggagugauaucuacacccagcucaguccuuagucuguccugcgagacuccaggauuuuagaacaguguggagccuggaccuc cagaaaaccuggauuaggcuuuugccuuggccagccauucagugguuucaaauauugaccagucuggacagugggcuccug ugggacgugcuagagggcuggggaagcuugucagggagaaggcgucaacugagcggggcugacucuaccuucccugcugca gaucgacacgggcuccaggacccucgucggguggaagagcugcagaaucgcauugcuagcugucugaaggagcacauggcua ccguggcaggagacccacagccggccagcugccugucacgucugcugggcaaacugccugagcuucggacccugugcacuca aggccugcagcgcaucuuuugccucaaguuggaggacuugguaccccuccaccuauuguggacaagaucuuuauggacaca uugucuuucugaccccugcccugaacaugugugcgcacacgugcgugcucuucugucacccaugugccuuuaagccuauag cccacggacccccagaccacccuaccccagccugguuuugagcuaagacugacguaccuccucacuccagaagauggacaga gaacucaagaccuggggggaggguguguauucacgggggugaccccacuauuugucuuaucccuccagcucaguccuggccu ucguguguuuuuguaagauaaaccauuuuuaacacauaccacucuguuguaaauaagcugacgcuacuguaaauacagaaag gaagagguugagauggggguugggaggaagggguggggcucccaccagcugggcgagccuccaacucgagaucucuuccgc ucuccuuccauguguacauaacugucacucaagaaggugauugacagauucugauuuauauuuguguauuuuccuggauuu auaggaugugacuuuucugauuaauauauuuaauauauugaauaaaaaauagacauguaguugaaa

| | | |
|---|---|---|
| 89 | AF038562 | ggcacgaggcugugcccgccaugucugcuacccaucacaagaccucccugccucagggcg<br>uccgcgugggcacugucaugagaauucgaggcuuggucccugaccaggcuggcagguucc<br>auguaaaccugcuaugcggugaggagcaaggagcagaugccgccuugcacuuuaacccga<br>ggcuggacacuuccgagguugucuucaacaccaaacaacaaggcaaauggggccgugagg<br>agcgaggcaccggcauccccuuccagcgugggcagcccuuugaagugcuccucaucgcca<br>cagaggaggcuucaaggcuguggucggggaugacgaauaucuccacuuccaccaccggc<br>ugccgcccgcccgcguucgcuugguggaagugggcggagacgugcagcugcauucauuga<br>auaucuucuaagcaaaggacccaagggccuuugcccgguuacggguuggggguuuuuuga<br>ucccacaagaaagguuuuggaucggccaauaacauuuuucuguuguucugaaaaauuaaa<br>aaaaaaaaaaaaaaaaaaaaaaaaaaaaaaaaaaaaaaaaaaaaa |
| 90 | Y11666 | gccacauuguugcaccaacuccagugcuggagucucaggacaccaca<br>ggcuacccggaguuguucugcuuuggagauccgagggcaggagcaucacgccagugacuc<br>ugauaggugcgaucgccggauuggaacagaacugucauuuuuuuccgaaguugagccuua<br>gugacccagugagugaaguuagcgacgggacgcuaagcagcuagaccggucggcaggagu<br>gagacuuaggguaccuucuaguaguugugauuaaaaaaauugaaaaaaagaaaaaaaaaa<br>acccuguuucuggaaacuugaggcccucagcuggugagccaucgugguuaagcuucuuug<br>uguggcuccuggagucuucgaucccagccggacacccgggccugguuucaaagcggucgg<br>acagcgcugccugcuccaucgguagcgcucgagccucgguuucucuauuggccccgacu<br>cgccgcaacaagaugaucgccucgcauaugaucgccugcuuauucacggagcucaaccaa<br>aaccaagugcaga |
| 91 | U40930 | Sequence below. |

cccagcuguuucguccguaccuagaccgcgguuauggcgucguucacggugaaggccuaucuucugggcggaggagg cgacccgcgagauccgccgcuucagcuucugcuucagcccggagccggaggcggaagcccaagccgcggccggcccgggg cccugcgagaggcugcugagccgaguggcugugcuguuccccacgcugaggccuggcggcuuccaggcgcacuaccgcg augaggauggggacuugguugccuuuuccagugaugaggagcugacaauggcuauguccuaugugaaagaugacaucu TABLE 3-continued RNA transcripts up-regulated during HF stem cell activation.

| SEQ ID No: | Access. # | Sequence |
|---|---|---|

uccgcaucuacauuaaagagaagaaggagugccggcgggaacaucgcccaccaugugcucaggaggcaccccgaaacaug gugcacccaaugugaucugugaugguugcaacgggccuguggugggaacucgcuauaagugcagugugugcccagacu acgaccugugcagcgugugcgaggggaagggccugcacagggaacacagcaagcucaucuuucccaaccccuuuggccac cucucugauagcuucucucauagccgcuggcuucggaagcugaaacauggacacuuuggcuggccuggcugggagaugg gcccaccggggaacuggagcccacguccucccucgugcaggggauggccgcccuugcccuacagcugagucagcuucugcu ccaccagaagaucccaaugucaauuuccugaagaaugugggggagagugugggcagcugcccucagcccucuaggcauuga gguugacauugauguggaacauggagggaagagaagccgccugacacccacuaccccagaaaguuccagcacaggcacag aagacaagaguaacacucagccaagcagcugcucuucggaagucagcaaaccugacggggcuggggagggcccugucag ucucugacagagcaaaugaaaaagauagccuuggagucggugggacagccagaggaacagauggagucgggaaacugcuc aggaggagacgaugacuggacacauuugucuucaaaagaaguggacccaucuacaggugaacuccagucucuacagaugc cagaaucggaagggccaagcucucuagaccccucacaggaaggacccacagggcugaaggaagcugcccuauacccacauc ucccaccagaggcugauccccggcugauugagcccucucccagaugcuguccauggguuucucggaugaaggcggcug gcucaccaggcuccuacagaccagaauuacgacaucggggcugcucuggacacgauccaguauucgaagcacccuccacc auugugauagugcuguggccaagccccacccccuuugucuuguaguugcaucacguagagcagcagggcuucuauagau aggcccagugucuuggcauucuuguagaaucuucaggugggaaugugugaugccuuuucaggcaauaggaaagugcau gaggagaguuuugaaugugcauaugcugacgccugagaacagacccagguacccguggcugagcugagcuucccucugcu uccccuaggccuggccucugcagggaacugcagcacacacugcacucccaccugcucuugccgccagcauugcaccagca guccagaauuccugccgacaacccguguuuccuuuauuaaaagugauuaguacaacugcuaguuauuuucaacaaaua aagccauuauguuaagaggggacuguccauagugagugaaagguggcaggcaggggccuacagcuccuagggaauggag aauucaugugaagccgaaugaaggaucuuaucuuauacuguccccccuuucuaauggccacucuuuaguguuugugucua auguuaaugcuuaaagcacaggaccccauguagcuuccucugacuugguuuguaaguaaccuguaauaaaaaugccaua ugcacuuuaacca 92 D26090 Sequence below.

gagggaauugcgggaccccgucuggggaagcucccgccgccccggggugcucagcucucugucucccuugacccaggua cagucaugucgggcuucgacgacccgggcauuuucuacagcgacagcuucgguggcgaccccggugcggaagagggcca ggcccgcaagucgcaacugcagaggcgauucaaggaguuccugagacaguaccgaguggggcaccgaucgcacgggcuuca ccuucaaguacagagaugaacucaagcggcauuacaaccuggguggaauacuggaucgagguggagauggaggaccuggcc aguuuugacgaggaacuggcugaccacuugcauaaacagccggccgagcacuuacagcugcuugaggaagcugccaagga gguggcagaugaggugacccggccccggccagcuggagaugagcugcuccaagacauccaggucaugcucaagucagaug ccagcccgucgagcauucggauucugaagucagacaugaugucacaccuggugaagaucccuggcaucaucauuucagcc ucugcaguccgugccaaggcuacucguaucuccauucagugccgcagcugccacaacacccucaccaauaucgccaugcc caggccuagagggcuaugccuucccaggaagugcaauauggaucaggcugggcgcccaaagugcccacuggauccauacu ucaucaugccugacaagugcaagugugugggacuuccagacucugaaacugcaggagcugccugaugcagucccucaugg ugagaugcccaggcacaugcagcuuuauugugacagguaccugugugacaagguuguuccugggaacagggucaccauc augggcauuuauuccaucaagaaguuuggcuugaaccccagcaagggccgggacaggguaggugugggcauccggagcu cguacauccgagugcugggcauccagguggacacagauggcucuggccgaagcuuugcuggggucugucagcccacagga agaggaggaauuucgucgccuggcugcccuccccaacauauaugagcucaucuccaagagcauuuccccccuccaucuuug ggggcauggauaugaagaaggccauugccugccugcuuuuugggggguucccggaagaggcucccagauggacucacucg TABLE 3-continued RNA transcripts up-regulated during HF stem cell activation.

| SEQ ID No: | Access. # | Sequence |
|---|---|---|
| | | ccgaggugauaucaacuugcugauguugggagacccugguacagccaagucucagcuucugaaguuuguggagaagugc<br>ucucccauuggggguguacacaucugggaaagguagcagugcugcaggcuugacugccucagugauacgggaccccucau<br>cucgaaacuucaucauggaagguggagccaugguucuggccgauggugggguugucuguauugaugaguuugacaaga<br>ugcgggaagaugaccguguugcaauccaugaggcuauggagcagcagaccaucuccauugcuaaagcugggaucacuacc<br>accuugaacucucgcugcucuguucuggcugcagccaacucaguguuuggccgaugggaugagacaaaaggggaggaca<br>auauugacuucaugccuaccaucuugucccgauuugauaugaucuucaucgucaaagaugagcacaaugaggagaggga<br>caugaugcuagccaaacaugugaugacucugcaugugagugcacugacacagacacaggcuguggagggugagaucgac<br>cuggccaagaugaagaaguucauugccuacugccgagcgagguguggaccucggcuaucagcagaggcagcagagaagcu<br>gaagaaccgcuacaucaucaugcggaguggggcucgucagcaugagagggacagugaccggcguuccagcaucccauca<br>cugugcggcagcuggaggcuauugugcgcauugcugaggcccucaguaagaugaaacugcagcccuuugccacugaggc<br>ugauguagaggaggcauugagacuguuccagguguccacacuggaugcugcuuugucuggcaaucugucgggggugga<br>gggcuucacuacccaggaggaccaggagaugcugagccgcauugagaagcaacucaagcgccguuuugccauuggcucuc<br>aggugucugaacacagcauuguccaggacuucaccaaacagaaauauccagagcacgcuauccgaaaggugcugcagcuc<br>augcuacgcagggggugagauccaacaccguaugcagcgcaaggugcucuaucgccucaagugagcccauugcccaucaac<br>ccucaagccugaaaugcugccaccacccuaucucccagucagugcuccaaaccuccuuuugcccugccucuccaccucaga<br>cugcugucugcagcacaucugcagccccuggaaauguacuuuggucuguuggcucauacuguguuugagugucugagg<br>acucucugcucugggugucuaucccugucaugccuucucaacaagaugagucuggagcaggaacaggcccuggaaugu<br>agaugggucuguauauuggcucccgggccacucacugccaagcuucuuuguauguacagagguaauaaagcaauugagu<br>cccuggcugcuaaggucaguggacccagu |
| 93 | AI787627 | ggaugcagccggaagugcagcgugcgugcgguuuggugggucgcugugugcgcuccgcgu<br>gugcagccgcgugggccaugggcggcgggcgcggggccggcgguuccagcagccgccgc<br>agccugagggcgaggaagacgccagcgacggcggcagaaagcgaggccaggcgggcuggg<br>aagguggcuaucccgagaucguaaaggagaacaagcucuucgagcacuacuaucaggaac<br>ucaagaucgugccagagggagaaugggaccaauucauggagucacuccgagaaccucucc<br>cagccacacugagaaucacugggguacaaaagccaugccaaagagauucuccauugcuuga<br>agaacaaguacuuuaaggaguuggagganccugaaguagauggacagaaaguugaguucc<br>acaaccacuaagcugguacccugaagaacu |
| 94 | M33988 | gagcucaaauucuggcuuucuauugguacgauauauuaaccaaugggagaaacacaaac<br>agaauaccuccaguuaguauaaaugcuugcuguucaguugcagaauuuacuauauauucu<br>uuuccuuucucugcuuugccuuuacugauacuuaaacgcauacaugucuggacgcggaaa<br>gcaagggugcaaggcccgcgcuaaggccaagacccgcuccucccgggccggccugcaguu<br>ccccgugggccgcgugcaccggcugcuccgcaagggcaacuacucggagcgcgugggcgc<br>cggcgccccgguguaccuggcggcugugcuggaguaccugacggccgagauccuggagcu<br>ggcgggcaaugcggcccgcgacaacaagaagacgcgcaucaucccgcgccaccugcagcu<br>ggccauccgcaacgacgaggagcucaacaagcugcugggccgcgugaccaucgcgcaggg<br>cggcguccugcccaacauccaggccgugcugcugcccaagaagaccgagagccaccacaa<br>ggccaaggggaaguaaucuggcgauugucuguacugcccaguugaaaguuaaccaaaaca<br>aaggcucuuuucagagccacccacaucuuuccauaaaaugagcugccaccucgugaaacg<br>uucuuccacuacaguuuuuauacuacauaugaaaaaguuacgaaguagcuuucaaucuua<br>guaaauugauuuuaauacuguuagucccugcgauaaaucuuacgaccuuccuuaguuuga<br>gucaaaaguguguaagagaugaaaccuuuagaacauacuauaaauuuuuaguagaaauuu<br>ggcacccagguuugucauucacgucacgauugucuagagcauaaugguaguaagggcuaa<br>gggccauuaaaucccacuuccauaguuuc |
| 95 | AI845182 | uuuuuuuuuuuuuuuuuuggaaaugaagguaauuuauugaaacugguuuugggacaggcga<br>guggacaacuguugaaaggagcuagcgcacagccgggugggagcgggugcuuagccacag<br>auccuaucugaggcccaacuuuuucuuuuccuucugcuucuuacggaccacauccagguu<br>ccgguccuuccacaugcuuuugcgaagcuugaugggggcgugagcccacauacuucccauu<br>caucucucgcauggcgcgcacauagucacugggggucuuugaagcugacaaagccauagcc<br>cuugguuuugccugugcgcuuguca |
| 96 | AA619207 | uucggauccuugccaauauauguaucccauuuggaauggugaucuuaaaaugugagugca<br>ugcauacuaucuuauuuaagauacuugcaccccacccacucccaucucccgaagcuggaa<br>cacugccaacuagguccuuaagaaucacgcaauuaacacaagguuggugcugcuaauuc |

TABLE 3-continued

RNA transcripts up-regulated during HF stem cell activation.

| SEQ ID No: | Access. # | Sequence |
|---|---|---|
| | | uucaugaaaauccaaacacguuaagggaccagggagaugccacugccccccugaauuuuc aucaaaaauagacacguuuauguaaacagaacuauuuuccauauucauagugacuuuuua aguauuugagccuaaagauuuugaucuccauuuuuauaacuauuuaaauuguucacaauu auuacau |
| 97 | AW125783 | cggccgccgccgcccccacacugccccgcguugacgagcgccgcgacggcaaggacagcg ccucgcuuuucgugguggcucggauccuagcggaccucaaccagcaggcgccggcgcccg cccccgcggaacgcagagaaggggccgcugcgcgcaaggcgaggaccccugccgccugc cgccugcgcccccugcgccgccacccggcccagagcccgccuccccgggacaagcaggcg cgccggccgcgccccccagccccgcguggagcgagccggaggcggcauuggagcaggagc ccggccccgcggggagcggcgagccuggccucagacaaaggggucggggaggccggagcc gcgcggaccucgaguccccgcagaggaagcacaagugccacuacgcgggcugcgagaa |
| 98 | J04103 | Sequence below. |

cgucaguccccgccaccuccccggccccgcgcgcccggaucggcccuacggccucgucucgcccggccuugcgcgccgggacc gccgcgaucuccucuccccgccgcccuccggcuggcccugccugcugcggcgcgaugaaugacuuuggaaucaagaacaugg accaaguggccccugucgccaacaguuuucgugggacacucaagcgccagccagccuuugacaccuucgauggcucucuguu ugcugugcucccuucucucagugaagaucagacacuccaagaagugcccacgggccuggauucugucucccaugacucggcc agcugcgagcugccuuugcucacucccugcagcaaggcagugaugagccaagccuuaaaagccaccuucaguggcuuccaaa aggagcaacgacgucuuggcauccccaaaaaccccuggcuguggagcgagcagcaggugugccaguggcuucucugggccac caacgaguucagccuggugaaugugaaccugcaccaguuuggcaugaacggccagaugcuguguaaccucggcaaggagcgc uuccuggagcuggcgccugacuuugugggugacauccucugggaacaucuagagcagaugaucaaagagaaccaagaaaaga cagaagaccaauaugaggaaaacucucaccucaacgcgguuccucauuggaucaacagcaauacauuaggcuucagcauggaa caggcuccauauggaaugcaggcaccaaacuaccccaaagacaaucuccuggacagcaugugcccgccaucggccacgccugc agcucugggcucugagcuccagauguugcccaagucucggcucaacaccgucaaugucaauuacuguuccaucagccaggac uuccccagcagcaacgugaauuugcucaacaacaauucuggaaaacccaaggaccacgacucuccagagaacggugggacag cuucgagagcuccgacucgcugcugagguccuggaacagccagucgucccuacuggauguacagcggguaccuuccuucgag agcuuugaggaggacuguagccagucucugugccucaguaagcugaccauguccuucaaggacuacauccaagagaggagcg acccagucgagcaaggcaaaccaguuauuccugcagcaguacuggcuggcuucacuggaagcggaccaauccaguuguggca guuucuucuggagcuacucucugacaaguccugucaaucuuucaucagcuggacgggggauggaugggaguucaagcuugc ugaccccgaugagguugcccgccgguggggaagaggaaaaauaaaccaaagaugaacuacgagaagcugagccggggcuua cguuacuacuacgacaagaacaucauccacaagacuucgggcaagcgcuacguguaccguuucguaugugaccugcagaacu ugcugggcuucacuccggaggaacugcaugccauccugggcguccagccugauacagaagacugagggccuca

| SEQ ID No: | Access. # | Sequence |
|---|---|---|
| 99 | D90146 | Sequence below. |

auggcucuaacaacgcugcucuugguggugggcggccgcccugacccugaucgagacccgcgcgggugagugcggggucggg agggaaacagccccugugccgcguccccgcuucgcccaccggaccuccgccccuucuccacccgagccccgagcccugcucca cucccggcccgcguacccgaccgggguccccgggaggaggucgggggucucaccgcgcgccgcccccaggcccacacucgcugc gguauuuccacaccgcugugucccggcccggacucggggagccccgguucaucaucgucggcuacguggacgacacgcaguu cgugcgcuucgacagagacgcggaaaauccgaggauggagccgcgggcgcgguggauggagcaggaggggccggaguauug ggagcgggagacacagaucgccaagggccaugagcagaguuuccaagggagccugaggacugcacagagcuacuacaaccag agcaagggcggugagugaccccgggucggaggucacuaccucuccacgucccgaaacagaggccggugagguccccgggugca aaguccgagguucaggagcagaacugacccaggacuggauucccuuucaguuuggaggaguccgcgguggggggguggggg gggggcggaggagggacugaccacuggguccccgcaggcucucacacacuccaguggauguauggcugugacaugggguccg acgggcgccuccuccgcggguaccugcaguucgccuaugaaggccgcgauuacaucgcccugaacgaagaccugaaaacgug gacggcggcggacauggaggcacagaucacccgacgcaaguggggagcaggcugguauugcagagagagaccgggccuaccug TABLE 3-continued RNA transcripts up-regulated during HF stem cell activation.

| SEQ ID No: | Access. # | Sequence |
|---|---|---|

gaggucgcgugaggcucccgcagauaccugcagcucgggaaggagacgcugcugcgcacaggugcaggggccgcgggcagcuc cuccccucugcccucaggcuggggcucaguccuggggaagaagaaacccucagcugggguggugccccuggcucagaggga gagagugacccugggucuccugaucccucaucacagugacugcacugacucucccagggcucagccuucucccuggacagug cccaggcugucucaggagggaaggagagaauuucccugagguaacaacagcugcuccccuucaguuccccuguagccucuguc agccauggccucucccaggccaggguucucagccuacacccacugucuguagacacugacuccuguccugcugaguguguca gcccuuacaccucaugaccugaagucuccuuuacccgaugggagacauggacaucuacacuaggcugguuccccccaguuucu agaacuuuccaaagaauacagucuaccagauccuucccugucuguggguuugcauccuuugacacccaauucuaucuauuc cugcaauggugaauagucacaugagccauuauggguuacccuaaacaaauacuuuucuuguguuuuuccccucucguuuuc uuuuuaucuuuacuuuuuuuuuaaggguauuauguugcuuauaaaucgguuuuucuucggcacuggaaugauauugcucuc ucuccccaccauaccccccacccccgccuauaucauuuguaucaguagcccuggcugucguggaacucacucuguagaccagg cuggccuugaacucagaaaucagccugccucugucucugccucugccucccaagugcugggauuaaaggcuugggccaccac cacugggcagaagaaagguuccugugagcuuaaaauguuuucuggcagaauuaaccauccagaucacuccugauaucccugu gccccaccaaguuacagugcucccccugguggaaucagaacuuggacucugagagacagggucuucugcaauccaggccugag ugagagggaagaccacacacccugugagcccacuguguuccagugagugcugcacugggguccacagcacauuccagggauc cugugugacacaucuguaccuuguccccccagagucaggggcugggagucauuuucucuggcugagugucagagguucacca cauuucugcuacacacucccugauggcuguuuacuuggacugacaguuaauguuggucagcaagaugaccacagugguuua gucucaaugguguacacucuuccaguagcauaugguccugauuucuaauuuagauacgaacucaaacacauaugaaauuucu uauuuuccauuccaucuuccauuauauagcuaccuaucucgugcuauugaacaucacauaaggaugaccauguugacccacu ggcucaugugggauucccucuuagcuucugaguccccucaggaaaaugugcaguccugugcugagggggccagcucugccug caggucacuagugccaugacaguuaaaguguucauacagacacauaguucauuguaauuacugauuuagcguugucuuggc aguuucaguuugcaugcauuuauuuauuuauuuauuuauuuauuuauuuauuuaaaugcauggaaguacacuguugcugu acugaugguuguuugccuuuguguggguuguugggaauugaauuuuuuuuuuuaggaccucucuuugcucuggucgaccc ugcucacuccggucaacucccuaugggucaacucugcucauucagucccugcuuguucuggcccaaagauuuauuuauuauu uauuauacauaaauacacuguagcugacuucagaugcaccagaagagggcgucagaucucauuacagaugguugugagccac cauguggguugcuggaguuugaacucaggaccuucaaaagagcagucagugcucuuacccucugagccaucuccccaguccuc aguuugucuucuuaauugugcgauuucuugaaucuuccaaacagaucccccaaagacacaugugacccaucaccccauaucu uaugaugcugucacccugaggugcugggcccugggcuucuacccuguugacaucacccugacuuggcaguugaaugggggag gagcugacccaggacacggagcuuguggagaccaggccugcaggggauggaaccuuccagaaguggggcagcugugauggug ccuuuuggggaggagcagaauuacacaugccaugugcaccaugaggggcugccugagccccucacccugagaugggguaagg agggugugggugcagagcuguggucagggaaagcuggagcauucugcagacucugagcuggucagggcugagagcuggga ucaugacccucaccuucauuuccuguaccuguccuucccagagccuccuccauacacugucuccaacauggcgaccauugcu auugugguugaccuuggagcuguggccaucauuggagcugugguggcuuuugugaugaauaggaggugaaacacagguag gaaagggcagggucugaguucucucucagucuccuuuagaagugugcucuaaucauuaaugggaaacccaucuacaccccac auugcuaccuucucccaacugggucccucugucaguucugggaacuuccaagaucuuccuugaacucucacagcuuuccuucu cacagguggacaaggaggggacugugcucccagcucccagguuagugugggggacaggauuguccuguggacauugcagugaag cuggagauguuggggagcucugggaacccauaguaacucuuccagagaaaucuuccagggccgcaguuguccaauaugaaua cauauauguacauaugcauauacauuuuuuacccuuggcagggacagcuccuagagcucugauagaucucucccagguggu TABLE 3-continued RNA transcripts up-regulated during HF stem cell activation.

| SEQ ID No: | Access. # | Sequence |
|---|---|---|

aaaggugacacucugggaccugauuggggaggggcaauguggauaugauuggguuucagggacuccacgaauccccucuga gugaguggugggguuguuggaauguugucuucacagugaugggucgugucccuc

| SEQ ID No: | Access. # | Sequence |
|---|---|---|
| 100 | AI563854 | uuaaaucuggagggauuuuucacacagccuaucuuuuuaggugugccuuucccauauuuu auuaaacucgaguuguuguuuuaaaaaaacagcagcauuaucaaagacacaucuguacaa acauuuuacaaaagagaacucucuaggaucagcuacaucaaggacaagcagaaaaauaga ugcaguccaacaaagacauugaaaaugacuu |
| 101 | AF017128 | Sequence below. |

ggucgcuuucugucuguagaggcggcuugccacccgagcagagggucgugaaguuccgaccggaccgguccacagaggu ucaucuggagaggugggucccccuccgaggugaaaggcgccgcugagaaacgcccccaccccccgugguucaagugguuca gcccaagaacuuuucauucauaaaaaagaccagacucccgagaggcgcgagugagucagaaccgcagccgccaacgcggacc cuaccgaacauccagcccagggcauguaccgagacuacggggaaccgggaccgagcuccggggcuggcagcccguacggu cgccccgcgcagccccccgcaagcucaggcacagaccgcccagcagcaggugagacuggccgaaucgucgggggggggggg accugaguuuggacagcaucagggaugcugggauuagucuaguuugcuccgggauuuggacuggggccccgagcagcau cugacucugguggucgcgaccgaggauccugcacguucuguguggucggggaaccuauguacccgguggccaaggggac gagcgcagcgggaagcgcgaauaucugcgaauuccccuucucgcucgcccguaucucccuagcugacugucuuucugccc cuccgucuccguuacggucuuacauuuccuccuaucugccccuaauacgcugucccucuaaauaccugccccaucccugc cuggacaggaucagagguguucucccaucuccaguuaauaacugggaccugggggucugggcacauagagacgggguccau cagaacucagccgggacagagaauucuuagcagccugucccgaggcuguccguguguugcucugguuguccgugucccuu uauccggucaaguccucaucucuuugugcgcaguauagagcccaugggccccaggcagugguuccgagggguuccugga gaccacgaaguguugggaugugcgcggggucaccugcccggccacacucgcgcuccacauucucggcacccgacgucucu cacugcuggauaggggcacuugagagguugcaggugucccauuuccugucgaggggccgcgagcacgugucgccagggga gggaaggagcugcguccguuucgccgagucacagcgggccgagucacugaggcugagucacccugggugccccucccuu ccuggccccaaacggccccuaaggaccgacgaccugggagcgagagagaugccccuggcagugcuucuagcccagaacgggg gucacugagaugcuggguccccccaguauugggcuggggacauagcuguccagacuugccuaagcaugugaggugcuucc uggacuggagggcccccacauccuuagcucacagagcuugaacccaguuucucucccagaacgcugagcccccacccccca ccgacacucaaucccaacacaugccucagauuucugcaagaaaaggaaggaaaggaugccagaccccuuauaggaggcuuu uacucucuucacuuuauuucauggacuuaaaaaaccccaucaauuuugaacuuucaaguuuuuaagucgacagcuaggca ugcauuuaaucccagcauucaggaggcagaggcaggcagaucucugggaguuugaagccaauuuggucuacaaagugac uuccaggucagcuagagcuacauaauagagauccugucucaaaacuuaaaaaauaaaaaacaaaaacaaaagccgauuaaa acucugauuucugagcuaugagagcuggcuucucaacagcaauggaacguugaaugauguuaaauaacagggaaacugag acuaaauaacaugccccagucucaaagcccaucaauggccaagcuccaagcugaugcuggacucccaagcucuggugcuac augucuauagucuuggugccugggagguagaggcagaggaaucgugaguuuaggucuagccugagcuaugugagaucc ugcccaccccacccccggccccccaaacaacaaauucucauccugauucucagaauugccuugggagcuagaagcugaaagu augcccaucugugaggacugggucucaaaucuuaguuucuacuuacuagcugugggucuaugggcaacugcucuccugu cugaaaacaggauuauggcagcugugugagucacuauuuguuaaaauaguuggaacaguguuacgcaguccauacuugau uuaaaacaaaaaaccaaacuaucucuggugggggaaacagacagacgaagagagacauuuugugaccugcccaaaaucacac agcuccugaacaaguaaguuucugguugccaaauguugcuccuuguggucucccaaaacugguaucuacacugagguga agggagacagaaguccagccucuguccccgggaagccccucaguccacacagaccuuaucauuucccuucuuaucucuca gaaguuccaccuugugccaagcaucgacagcagcagccaggaacugcacuggauggugcagccucauuuccugggaccca TABLE 3-continued RNA transcripts up-regulated during HF stem cell activation.

| SEQ ID No: | Access. # | Sequence |
|---|---|---|

cuggcuauccccgaccucuggccuauccccaguacaguccccccucagccccggccaggagucauacgagcccuagggccac cuccgggggugcgucgcaggcccugcgagcagguaagaaacagcgauguuucacuuuccauagcccguaggggguccuac uagacagggacaggaucuugcuacgagggaauuucuuauucagcauugaaguuccugagaggccaagaaggagguaaaa ggucaccuuugagucaaggaaggcuuccuggagaaggcuacacguuaaccuaaaccacggauaggauuugcguauggaa gcugaaaagaaucuucugggaggaggguuggaggcacagaauugaggugaaggggacagaguguuaagugagcaugucu ccacugucugacgugcacaggguggaaggaagccugaugcuggcuuuguaccucggggugacucuucuuuucaacaguc acggaaucucagccuauuucuuuuaauuaucacaaaaagugagugggcagugguggcucacaccuuaaauuucagcacug gggaggcagaggcagguggaucucuggguucaaggccagccugguuuacagagugaguuccaggacagccaaggcuaca gagaaacccugucucaagaaagggaaaaaaaaagugaaugggaaauguauuucaauuuuuccaucuuccaucagaggaag ugaagcauagagggguacucacuuguccagauucauacaaaugugaguaaugagacaggacugguccuggccugagguc uacucaacucccaaagucagagcuuaaugagccacugucucaaugggagcucacagaagccugcagagggagugagcuga gaacuuuugccucccugaaugccuuucuaaaauaaagaagggugugguuuugguugguuuguagaggugggggucuugag agccuccugccuucccaagugcuaggaguauagguguaugcuagauacccgacagggaugacggaucuuuuaggccaua gcacuuucuuuccucucccugaaguacugagacugagucuagugcagggaggccuccauacuaaaaagcuggguguaccc guaaucccagaacucggaaaaucaagacaggaggagccauucaagucacgcucagaaacauggagaguuuaaggucagcc ugggauauauaaacccuaucuccgauaaccaaacaacaaucaaagcaaaccugacuuaaguguuaaguaggaaagaauaug cuguaagucaucagccuggcugggggacugaccgccucugagggacugaagaaccugcuucaagcccggagcccugcacu caaccccuaguggaugcacacacagauccuugccaugauggcucgaagagggauggcaagacccugggagauaugugaga uuggccagagaagagccagcaacaggcuucccagcaagggaacagcuuaccucugugaucagcuggggcgugagcaagag gcaagcccagggugaauccuuccuuuagcccuguccugaggagacaccuuuugaccacggguacuagugggguuggagcu gugagcugugggguagguggcuuccccucggugugcucuggaacuugaacaaaucacucauccuuccugagcuuccucac augugagugugcagagaucuggaugggugacucagcagcggcucuggcugcucccuuagaggauccggguuccaaucuca gcacccacguggcaacucacuguccacaacguccccccaaagguucugaugcccucuucuggccuccaccagcacugaaugc acaaggugcucauacaaacacacaggcaaaauacucagagguaaauuuguucuuuuuuuucuuuugagacaggguuucu cuguauagcccuggcuguccuagaacucacucuacagaccaggcuggccucaaacucacagaggcaucugccugccuccc aaguguugggaccaaagauguaugccaucacuauaagccuuuuuuuuuuuuguaaauuuuauuuaugaaugagugcuuc cauguauaccuucaugccaggagagggcaucagauccuauuauagguggguugugagccaccgugugugggcugggauuug aacucaggaccucugaaagaggagcucuuaacugcuaaaacaucucucuagccccagucuacauauuuuaaaucuuuuuu uaagauugauuuauuuauuauacauaaguacauuguagcugucuucagacacuccagaagagggcgucagaucuuguua uggaugauugugagccaccauggugguugcugggauuugaacucaggaccuuuggaagaguagucaaugcucuuacccgc ugagccaucucaccagccccuuuuuuaaucuuuaaaaaaaaaaggggggggggccuggagagauggcucagccguuaagag cacugaaugcuuuuccagagguccugaguucaauucccaacaaccacaugguagcucacaaccaucuguaaugggaucca augcccucuucugguguaucugaagacagcaagggucuacucacauauguuaaauaaauaaauaaaaaauuuaaaagccag gugguguugguucagacagcagaucucuguuuaaggccagccuggucugaucuacaaaccaaguuccaggacagccagg gcuacacagagaaacccucuaaaaaaccaaucuauguagggggugcuggugaaauggcuccgugggguaaagguacuugcu gcgaaauuaaugaccugaguucaauccuugaaauccacacaguagaaggagagaaccaaccuccaagggugcuaugacaca cacacacacacacacacacacacacacacacacacacacacacgacuauauauaugaauauaugacucuagccaggca TABLE 3-continued

| RNA transcripts up-regulated during HF stem cell activation. | | |
|---|---|---|
| SEQ ID No: | Access. # | Sequence |
| | | uaguguggcacaugccuuuaaucacaguacuugggaggcagaggcaggugaaguuugaggccagccuacagagugaauu |
| | | ccaugacagcuagaacuaugaagaugaacccugucuuuaaaaacaacagcaacauaaagaaucuauguagggaagcuggaa |
| | | gggaugcugauacagucugcaauccuauuacucuagagguggaagccaaagaaucagggguuucaggccggucuugccu |
| | | auacacugagcuaaaggccagccugggacacaugagacuuugucucuuuuaaaaagacaaaacaagggguugguuagau |
| | | ggcucagugggguaagagcacccaacugcucuucugcagguccgaaguucaaaucccagcaaccacaugguggcucacaac |
| | | caucuguaacgaaaucugagucccucuucuggagugucugaaaacaacuacaguguacuuacauauaauaaaaauaaaua |
| | | aaucuuaaaaaaaaaaaaaaaagacaaaacaagccagaugaggucugugaguuccaggccagccuggucuauaaaucaagu |
| | | ucaaggccaggcagggcuacucagagauucugucuaaaauacaaagaaacaaaacuacaaaaagcagaaaaaggaaucuac |
| | | gaaagggcuggugaagggguguaacucagugguagagcauuugccgagcuagcauguaccaagccaugguuugauccc |
| | | uagcacuaagcaaaagaaaaguccuacaaagggcuuuguuggcauaguagauugauucccaguagcuuuuggcacucaag |
| | | agcaccuucuacaauucacagcuccuggggaagaaaucccaucuuccacagaugaggaggcugagaguccugugaaaag |
| | | agauaaucaugucucauacacucaggagagaaggcuacuucugccugagaaaugaaaaggcuuccuggggucccaacauc |
| | | uuaguccaguccuaagaugcggaagggaggaagaucaaaguuuacagagagggaaagcauuucaggaaagaaaccagcag |
| | | uaaagcuaggugugugugagcuggaaaugucaccaaugagaugacaagcguccgguacagagaagcaacuguggagugu |
| | | ugggugguggcaccuagacuacagacugaaggaaagcuggaugaccagcucagggcagcugguggcucagagucagccu |
| | | cauugucucccuucuucuaucccaaccuagaucagcccagaggaggaagagcgccgcagggugagacgcgagcggaacaa |
| | | gcuagcagcugcuaagugcagaaaccgaagaaaggagcugacagacuuccugcaggcggugagcaucauccccaggcccg |
| | | gacccacagagccccaagaggggucucggcucccaagaacacaaaagacccaaaauuacuccucaggacucugucauccuc |
| | | ccugccuguggggaaguccuggaaaaaggauaagggaaaguggcuuaaauauuguuugucgggcuucgaggcagagucg |
| | | aagaugguaggcagcaauucuccuaagaugcccccgucugaugggagucauggccauuuucucccagaggcucacggga |
| | | gggaguugcaguccagacuuguuggggaugacaggcacagucccuacuccagccugaggcuuggggaucuuuagccuuc |
| | | auuuuccuaucuuucugcuaauccuguaaaggagaccgacaaauuggaggaugagaaaucggggcugcagcgagagauu |
| | | gaagagcugcagaagcagaaggaacgccuugagcuggugcuggaagcccaucgccccaucugcaaaaucccagaaggaga |
| | | caagaaggacccagguggguucuggcagcaccagcggugcuagcagcccaccagcccccggccgcccagugccuugcaucu |
| | | cccuuucuccaggacccguacuugaaccggaagcacugcauacccccacgcucaugaccacacccucucugacuccuuuua |
| | | cuccgagucugguuuucaccuauccuagcacaccagaaccuugcuccuccgcucaccgaaagaguagcagcagcaguggc |
| | | gaccccuccuccgacccccugggcucuccuacacuccuggcuuugugaggcacccagccacaucccuugcuggugcuacu |
| | | ccaagccaucccccuuucucccauugauccagcaggccuggaccauacccuugccccaaaccagcagaucuuuuaucucuuc |
| | | cgacuagaacaaacacauuaugcuuugauguagagccagcuuggaggggauccccaaagcugcucacuguuuuucuagag |
| | | cuggccuaucauaauuugcacaaaauuagaggaaaauauguucccucugccagagaacgccuggcagcccagacuuugua |
| | | gauccccagggguccuuugacacccuuacccccuugcagaccacuuucccacaccacgucacuuucuucauguuauccagc |
| | | cuacucuacaccuagacagaaggugcccuuugacuagccuagaacacuaacucacacagcaucaacagccagcagcaccgg |
| | | acauccugcaggcuccuccugaauggcacaacgcaggaggcgccaggggcuucugugaggagcggagcugcacucccuag |
| | | cucugagaagcgcuuagcuucaggguauccgagccuccaccgcaagggcagcugcuauuuauuuuccuaaagagacuauuuuuaua |
| | | caaaccuuccaaaauggaauaaaaggcuug |
| 102 | X67644 | Sequence below. |
| | | ccgugguuuccuaaugguggcuauugacgacgggcacaaagucucauaauuuuagaaacuucacuuauuuugugacccaccu |
| | | aguaugggcaaaggcaggagcuucggacuuccugucuucccucuaucccuuugaauagcgucucgggaguguccccuaagu |

TABLE 3-continued

RNA transcripts up-regulated during HF stem cell activation.

| SEQ ID No: | Access. # | Sequence |
|---|---|---|
| | | aaccauugcaguuuuguguccgugugcucuguugaaaucucugugaugugugugguuuucacgugaacggaggcaggc<br>agagcccggucugugggguucuagugugguucuuuaucuucuuggaaguuugugcaaugacuucccuccuguuuccugcgca<br>uaccuccaaguaaguacgugaauguguuuucugugguccccuugaucuugcuggacuucacuaaggagggugggcuggaccau<br>cugcuacgugucugagagccccucucuagcuaccucauguccggacgugagcuuacucccaauguuuuuacccacaagcauu<br>cacuacucccaggaaagaacgugcacuggggcaccuagagaauaaccaaucaacgcuccgccuacauuuugcuuccuccuug<br>gaauuuccagccccuugcagccaacugcuccccagcugcgaagggcggaguucccccggcccggccccuucuuuggcucua<br>uaaguagcucugcuuugcgggggauuugcacuccucuacacucucugcacaacgucuaaauuaugugccacucgcgcaacca<br>ucuccacaccaugacuggccugagggccccuucuccagcucccuccaccggcccggaacuccggcggggcucuggucccgaa<br>auuuucaccuucgacccucucccggagcgggccgugguguccaccgcgcguuugaacacuucucgcgggcaccgaaaacgca<br>gccgaagggugcucuacccucgagugggugaguaucgcccgagugggcaucaggaggucgcgucgcccuggaacuuguaggu<br>aacaacuaggagcagggaccuucgaucugacguuucccucuuuuaucugcucagguccggcgccagcuaccaaccgaggaac<br>ccaacauugccaagaggguccucuuucuccuguucgccagcaucuucugccagauuuugauggcugaagagggugugucgc<br>agccccuggcuccggaggaugcuaccagcgccgugacaccugagcccauuucugcgcccauuacugcgcccccgguccucga<br>gccuuugaaccugaccucggaguccucggacuaugcgcuggaucuuaaagcuuuucucuagcaacauccggcggccuucuaa<br>acgcgaugggucacaguccgaagaaacaaaggcaccauggaugggguaccuggugcgagagaacguaucccaaacugggauuu<br>cuaaggcaacgcuaacucagaacacuaccgccaagagacaccgcggguccuggcuaggcccacuggggacggacagagacuuu<br>cuccgugucuaauuaauauuuauguauuuauguauauccuccuaggugaaggagggguguauguaauauuuauucuaacu<br>uaugcaggggugcgagauaugccucccugcuguaacacagauauuuauuacgauuuauagggucgguaagacagaguugug<br>ggagggaggacccggguggguaggacucccagcuuggggauuagucuggggggguguaauaagauuaggggguaacacuccg<br>ucuuccagcacuucaacucuguagucuguuguaaggcuuuggaagacccuugggaauccggccuuugaugucuucugguug<br>cuucucaggggcagcugcaggagucuugggguccauggauugucagagggcggcugucuggggucgccuaguauguauguu<br>cugugaacacgaauaaacuugauuugccugucauuauuaucugcaguucucgaaguguaucauucag |
| 103 | AF064088 | See above (same Accession Number). |
| 104 | AI843085 | uuuuuuuuuuuuuuuuuaaauugccgaauuaaguucuuuuaauagauugcauauauagau<br>guuuagccauacucuagaucaacucuuuaagaguagaauuuuauauccaauuuacaugcu<br>ucagauaucaccucuguuuguuacauaaggucuuguauccaaauguccacuuguacacug<br>agagcuuuaggaacaaaaaaggacacagagagaguugccauuuuuagcagcaaugaaaca<br>ucacuaaccccuuuuuacauaccgaauucaagucacuac |
| 105 | AW124932 | cggccgccgguauuuuuuugcaaguauugagaguucuguauguuuugaaaagaguaauuu<br>uaacguuuggugccaagaaguggguuuucucagaguccauugccggcaaugggcaagcc<br>uggcgguacuccucgugccgaau |
| 106 | X58609 | augg<br>cgcugggaacgcugcuccugcugcuggcggccgcccuggcccggacccagaaccgagccg<br>gugagugcagggucgggagggaaacagaacuuuccaaacagucugcggggaggggcgggu<br>gcggcaccggggaagccgcgugcccgcgucgcccaccagacccuccgucucuuuacccgc<br>gucccuagccccgcgcccugcucccccuccugucccgcgcauccgcccgggguccccgggag<br>aaggucggggucucaccgcgcgccgcccccaggcucacacucgaugcgguauuucgagac<br>cgucguguccccggccgggccucggggagccccgguacgucucugucggcuacguggacga<br>cacggaguucgugcgcuucgacagcgacgcggagaaaccgagguaugagccgcgggcgcg<br>guggauggagcaggaggggccggaguauugggagcggaucacgcagaucgccaagggcca<br>ugagcagugguuccgagugagccugaggaaacugcuaggcuacuacaaccagagcgcggg<br>cggugagugaccccgggucggaggucaggccccuccacuucccgacacagggacgcugac<br>guccugguucccaagucugagguucgggaacagaacggacccgggaccgguuucccuuuc<br>aguuuggaggaguccgcgggugggcggggcugaccgcgggguccccgcagguucucacaca<br>cuccaggagauguauggcugugaugugggaucggacgggcgccuccuccgcggguaccgg<br>caguccgccuaugauggcugcgauuacauugcccugaacgaagaccugaaaccuggacu<br>gcgaaggauguggcagcgcugaucaccagacgcaaguggggagcaggauggugcugcagag |

TABLE 3-continued

| RNA transcripts up-regulated during HF stem cell activation. | | |
|---|---|---|
| SEQ ID No: | Access. # | Sequence |
| | | uauuacaaggcuuacauggagggcgagugcgugcagucgcuccgcagauaccuggagcuc gggaaggagacgcugcugcgcacag |
| 107 | M18837 | Sequence below. |

auggcgucaacaaugcugcuucugcugguggcagucgcccagacccugaucgagauccgcgcgggugaguaccggguccgg agggaaauggccucugaggaaaggggagggggcggcacgggggaagccgcgucccggcgucgcccaccugacccuccgcccc uucuccacccuagccccgcgcccugcucccccucccggcccgcucacccgcgggggucccggaaggaguucggggucucaccg cgcccugccuccaggcccacacuugcugaguuauuucuacaccuccgugucccggccgggccuuggggagccccgguucauc ucugucgguuacguggacaacacggaguucgugcgcuucgacagcgacgcggagaauccgagauaugagccgcgggcaccgu ggauggagcaggaggggccggaguauugggagcgggaaacacagaaagccaagggcaaugagcagauuuuccgagugaaccu gaggacccugcucagcuacuacaaccagagcgcgggcggugagugaccccggaucggaggucacgaccccuccacgucccaaa acaggggcccgagacgucccgggccccaaguucgagguucugagcagaacggacgcgggacugguuucccuuucaguuugg aggagccgcgggugggcggggccggggcgugugggcggggcugaccgcgggguccccgcaggcucucacacuauucagguga ucucuggcugugaagugggguccgacgggcgccuccuccgcggguaccagcaguucgccuacgacggccgcgauuacaucgc ccugaacgaagaccugaaaacguggacggcggcggacauggcggcacagaucacccgacgcaagugggagcaggcuggugcu acagagaaaagcaaggccuaccuggagggcgcgugcgugcagucccuccgcagauaccuggagcucgggaaggagacgcugc ugcgcacaggugcaggggccgcgggcagcuccucccucugcccucgggcuggggcucaguccuggggaagaagaaacccuca gcuggggugaugccccugucucagagggagagagugacccuggucuccugaucccucaucacagugacugcacugacucucc cagggcucagccuucucccuggacagugcccaggcugucucaggagggaaggagagaauuucccugagguaacaacagcugc ucccuucaguuccccuguagccucugucagccauggccucucccaggccggguucucagcccacugucuguagacacugacu ccuguccugcugagugugucagcccuuacaccucaggaccagaagucgccuuuaacugaucggagacauggacuacccuaca cuaggcugauugccucaguuuccugaauuuucaaaagaauacauucucccagaucccucccugucuguggguuuccacccc uucgacaaccuaauucucucuauuccuauagugguggucacaucagcccuuaugggguacccuggaggaauaucaauagug gaauuucuucuucuucuucuucuucuucuucuucuucuucuucuucuucuucuucuucuucuucuucuucuucuucuucu ucuucuucuucuucuuccuucucucucucucucucucucucucucucucucucucucucucucucucucucucucucucuc ucuucuucaguuuuugagauaggguuucucuguaugcccuggcuguccuggaacucacuuguagaccaggauggccucgac cucagaaauccgccugccucugccucccagugcugggauuaaaggcguguggccaccuugcccagccuuucuuauuuucuu uacuuuuuuuuuuuuuuuuggagggggguaauuuuguuucuagucaucuuuugucuuuugucugcacuggagugauccug uuucucccugcccuuauauuaucauguguaucagucuccacaggugccagggaaguuaagacaaguuaaaucaggguucuc uuuaaaggagagauuccugugaacuuagacuguuuccugucagaacuaaacauccagaagccuccugcucuuccucuguccc acaaguuacagugcucccccccccccccccagugaaucuggacuuggacucugagagacagggucuucugcaauccagggcug gagugagagggaagaccacacacccugugagcccacuguguugcagugagugcugcacugggguccacagcauacuccaggg auccugugugacacaccuguaccuuguccccccagagucaggggcuggaagucauuuucucuggcugagugucagagguuga caccauuucugcuacacacucugugauggcugcucacuuggacuggcgguuaugcuaguuagcaagaugaacacagugguu uacgucucaguugucacacccuuccaguggcauauggcucuaauuucuacuuuugauacgaacucaaacacuuauuaaauua guuaguuuccauuccaucuuccauucuaguccauucaugcuaaagaacaucacauaaggacugccaggaugacccacuggcu cauguggauucccucuuagcuucugaguccccccagaaaaugugcagcugaggaaaccagcucugccugcaggucaccagug ccaugacaguugaagugucaaacagacacauuguucagugucaucagugauuuaacugugccuuguguagauuucagaggg ucuuguuaauugugguacuuuuuuuuguuuuuuguuuuuuuuuuuuuuuguuuuguuuucaagacaggauuuuucugu auagcccuggcuguccuggaacucacauuguggaccaggcugaccacgaacucagaaaucugccugccucugccucccgagu TABLE 3-continued RNA transcripts up-regulated during HF stem cell activation.

| SEQ ID No: | Access. # | Sequence |
|---|---|---|

gcugggauuaaaggcgugugccaccaccaaccagcuaaucgugagauuucuuucuuuuuucuuuucuuuucuucuuuuuu uuuuuuuuuuuguuguuguuguuuuguuuuuugagacaggguucucuguguaucccuggcuguccuugaacucacuuug uagaccaggcuggccuugaacuuagaaauuugccugccucugcuccggagugcugggauuaaaggcaugugccacuaccaac cagcuaauugugggauuucuuaaaucuuccacacagauccuccaaaggcacaugugacaugucaccacagaucugacggugaa ugucacccugaggugcugggcccugggcuucuacccugcuaacaucauccugaccuggcaguugaauggggaggagcugac ccaggacauggagcuuguggagaccaggccuucaggggauggaaccuuccagaagugggcaucugugguggugccucuugg gaaggagcagaauuacacaugccaugugcaccaugaggggcugccugagccccucacccugagauggggguaaggagggugug ggugcagagcugggggucagggaaagcuggagccuuuugcagacccugagcugcucagggcugagagcugggggucaugaccu caccuucauuuccuguaccuguccuucccagagccuccuccauccacugucuccaacauggcgaacguagcuguucugguug uccuuggagcuuggccaucauugcagcuguggugcuuuugugaugaagagaaggagacacacagguaggaaagggcagag ucugaguuuucucucagccuccuuuagagugugcucugcucaucaauggggaacacaggcacaccccacauugcuacugucu guaacugugucugcucucaguucugggaacuuccuagugucaagcucuucccuugaacucucacagcuuucccuucucacagg uggacaaggaggggacuaugcucuggcucccagguuagugugggggacagaguuguccugaggucauuggagugaagcugg aguuguugggugcucugggaacccauaauagcuucucuguuguaauccucugguggccugugucagaucuugcuauagau auaucuuuguauauauuuuucccuaggcagggacagcucccagagcucugauauguuucucucaagauuguaaaggugaca uucuauggccugauugcagaggggcacuguggacaugguuguuuucagggacucccacaauccccugugagugguggggu uguugggauauugucuucauugugugguuccugacccucauucucuaucaugaagacagcugccuggaguggacuuagu gacagccagugugaccuugggucuucauuuuucuuuagagaacagcgccugauguucccugugagccuaugggcucaaugu gaagaauuguggagcccagccuucgccuacacaccaggaccugucucuugcauugcccuguguucccuuccaccgccaaccu uccgggucugcag

| | | |
|---|---|---|
| 108 | AW124268 | uuuuuuuuuuuuuuuuucagaauaauugcagacaaauuccauuuauuuuucuaaaaaccu cauuaucuaaaauuuauacagccucacauuccuaaaccaccucuggcacuuuucuugaau uaagucaaggcguacacagcuccgaaagaaaaauagagauccgguuccaggaagauggcc augaggacucgcagauaugucuccucggaccuggaagcgugucagccaugggauccacua auccaccauccgguacacagggucacccacucucaggcucccaagcuucuccaccgagaa auacaucccaaaaaguggagaugacugguauauacucuucacagaaggaucacacaggcg auagcucuucagggucuccaguggc |
| 109 | AF090738 | Sequence below. |

cucuagaugaauacacucucaugagggccaccuucucugguaguucaggucgccucugcccauccuucccugcguccucucc caaaguggccuacaacccuuacccagaggacuauggagacauugagauugguucucacaagaguuccgcaguaaccugggg gcagaugauggcuacaugcccaugaccccuggggcagcccuuaggagugguggucccaauagcugcaagagcgaugacuaca ugcccaugagccccacaagcgugucugcucccaagcagauccugcagccacgcuuggcagcggccuugccccccuuccggagc agccgugccagcacccccuucagggguggcaggaccuucccaguaaacggagguggcuacaaagccagcuccccagcggag agcuccccagaagacaguggguacaugcgaauguggugugcucccaagcugucuauggagaacccagacccuaagcuacucc ccaacggggacuaccucaacaugucccccagcgaggcaggcacugcagggaccccaccugacuucucagcagcuuugcgugg aggcagugaaggccucaaaggcaucccgggccacugcuacagcucuuugccccgcucuuauaaggcucccuguuccugcagc ggagacaaugaccaguaugugcucaugagcuccccuguggccggaucuuggaagaggagagacuggagccccaggccaccc caggggcuggcaccuuuggggcagcugguguaguaucauacccagccucaucacucagcagugccuuccuccaugaggccgag ugccaucgguggccgcccugagggcuuccugggccagcgaugucgggcagugcggccuacacgccuaucgcuagagggacu gcagacccuucccagcaugcaagaguacccucuacccacagagcccaagagcccuggcgaguacaucaacauugacuuuggug aggcagguacccgucugucuccgccugcccccccacuacuggcauccgcggccucaucuucuucacugcucucagcuaguag TABLE 3-continued RNA transcripts up-regulated during HF stem cell activation.

| SEQ ID No: | Access. # | Sequence |
|---|---|---|

uccugcuucaucccugggguucaggaaccccaggcaccagcagcgacagccggcagcgcucuccacucucugacuauaugaacc uggacuucaguucucccaaguccccccaagccuagcacccgcaguggggacacaguaggcuccauggauggccuucucucucc agaggcuucaucccccauacccaccacugcccccacguccuucccacuucccccuuccuccuuacagcagccucugccaccugccc cgggagaccuauaccgccugccuccagcaucagcugccacuucccagggucccacugcuggcucccucaauguccuccgagcc ugggggauaaugggugacuauaccgagauggccuuugguguggcugcaaccccgccacaaccuaucguggcaccuccaaagcca gaaggugcccgaguggccagucccacaucgggcuugaagcggcuaagucucauggaucagguaucugggguggaggcuuuc cuucaagucagccagcccccugacccccaccggggugcuaaggucauccgugcagacccacaggggggacgucgucgccacag uucagagaccuuuuccucuaccaccaccgucaccccaguguccccauccuuugcccacaauuccaagcgccacaauucggccu cuguggaaaaugucucacucaggaaaagcagugaaggcagcaguacccugggaggaggugaugagccgcccacauccccagg acaggcacagcccuugguggcugugcccccagugccacaggcuaggccguggaaccccggucagcccggagcuuugauuggc uguccuggaggcagcaguucucccaugcgcagagagaccuccgugggguuuccagaacggccucaacuauaucgccaucgaug ugagaggcgagcaggggucccuuggcgcagucucagccgcagccaggagacaagaacuccuggagccggacccguagccuugg ggggcuccucggcaccgucggaggcucuggcgccagcggagugugugggggguccaggcacuggagcuuugcccucugccag caccuaugcaagcaucgacuuccugucccaucacuugaaggaagccacagucgugaaaggugaggcccuuugaccuugagga ugggggagggagagugggaguauuggguggcu

| | | |
|---|---|---|
| 110 | AI834950 | uuuuuuuuuuuuuuuuucagcugugaacuauuggauuugagacaggaacagaacaaaucg acgggccagaggaggguggagagagcacgagugguuuaaaauaggggaggaugggagcaug gcgguggggguggggggaagaguuauuuacaagaaggcucagggggccagaggcucaucuu ggaauauuuuauaacaauauauauaagauucugguuugcuuuuccuuuucgucucguaaa ggagagagagaauugcauaguucgauucuguccaagggggcagcugcauauggucggccggg cgggucacuggucgu |
| 111 | AI851365 | uuuuuuuuuuuuuuuuuaagugucaccacuugugacagucagcauguuacuaucagcucc agccgcagcguuuuuaaggcguuauagauuaggcaggcaauacaaggaacacgauuaaga aacugacacguaccacacgagcaauuuccagaggcuccucuucugcggugcacacguaac agugcucuuguugacauucagacaguucugagggccacucugagaggcgccuuccuguuc ucaccugacaaggauauuguuugguuugguuugguuugguuuugccuuacuauggcuuuu cuuucaacuacauuuuguguucaugcuuguuagcuaacucaaauuuugucuuuguauauuu acuacuguaaaauuagaauaauuuacuguucaucucaucccucugucacugauggaaccua gagacgccacaagagccacugccgugacauaccucacaagcuacaucccuguccucaaaau |
| 112 | AW047339 | cggccgcggccaccggccugcgccaagcugcugcugcggcagccaguaccucggugaagc ccauuuucagucgcgaccugaacgaggccaagcggagggugcgcgagcucuaccgcgcuu gguaucgggagcgugccgaacaccgugcacuuaaugcagcuggauaucacggugaaacaa ggacgggauaaaguccgagaaauguucaugaagaaugcccaugucacagaccccagagug guugaucugcuggucauuaagggaaagauggagcuccaggaaaccaucaaaguauggaag cagcggacacacguuaugcgguuuuuccaugaaacagaaacaccaaggccaaaggauuuc uuauccaaguucuauaugg |
| 113 | U06834 | Sequence below. |

gcaccugagcgcgggugccuggcgcgcccgaugggaucguugagaggcccucgacggaaaguccccaaacucggaucgcauuc agccaaagugaggcggcgccauggagcucccgagcgcugcugugcugggcuucccucgccacugcuuuagaagagacccugu ugaacacaaaacuggaaacggcggaucugaaaugggugacuuacccucaggcagagggccagugggaggagcuaagcggccu ggaugaggaacagcacagcguccgcaccuaugaggugugcgacaugaagcgucca gggggccaggcucacuggcugcgcacuggcugggucccaaggcgaggugcuguccacguguaugccacgauacgcuucacca ugauggaaugccugucccugccgagggccagucgcuccugcaaggagacauucacugucuucuauuacgagacgaacguga uacggccacggcccauacgcccgccuggauggagaaccccuacaucaagguggacacaguggccgcagaacaucugacucgga agcgcccuggagcugaagccacagggaaaguuaauaucaagacgcugcgccug gguccucucagcaaagcuggcuucuaccuggcuuuccaggaccaaggagccugcauggcucugcucucccugcaucucuuu uacaagaagugcuccuggcugaucacgaacuugaccuacuuccccgagacggugccucgggagcucgugguggccgguggca TABLE 3-continued RNA transcripts up-regulated during HF stem cell activation.

| SEQ ID No: | Access. # | Sequence |
|---|---|---|
| | | gguagcugcguggccaacgcggucccuaccgccaaccccagccccagccucuacugccgggaagauggucaaugggcugagc |
| | | agcaggucacgggcugcagcugcgcgccagguacgaggcugcggaaagcaacaaa |
| | | guaugcagagccuguggccagggaaccuucaagccccaaauaggagacgaguccugccgccgugcccagccaacagccacuc |
| | | gaauaacauugggucuccugucugccugugucgaauuggguauuaccgggcccgcucagaccccggaguucaccuugcac |
| | | uaccccacccucugcuccaagaagcgugguucaccauuugaaugguuccacccugcgccuggaguggagugcuccccuugag |
| | | uccggaaggccgagagaccucacuuaugcuguucgcugccgagagugccguccugggguuccugcuugcccugugggggc |
| | | gacaugaccuucgaccccgguccucgagaccugguugagcgcuggguggcaauccgagggcugcguccugaugucaccuau |
| | | accuuugagguugcugcuuugaauggugugucuaccuuagccacuggaccaccuccuuuugagccugucaaugucaccacu |
| | | gaccgugaggugccuccugcagugucugacauccgagugacucggucgucacccagcagcuugauccugucaugggcuauc |
| | | cccagagcacccaguggggccgugcuggacuacgaggucaaguaucaugagaagggcgcagagggccccagcaguguucguu |
| | | uccugaagacaucagaaaccgagcugagcuccgggggcugaagcggggagccagcuaucugguccagguacgcgcacgguc |
| | | cgaggcuggcuacggucccuucggccaggagcaucacagucagacucaacuggaugagagcgagagcuggcgggagcagcug |
| | | gcccugauugcaggcacugcgguugugggugugguccugguccugguggucgucaucauugcaguucucugccucaggaa |
| | | gcagagcaaugggagggaaguugaguacucggauaagcaugggcaguaucucaucgggcacgguaccaaggucuacauuga |
| | | uccuuuuacuuacgaagacccuaaugaggcagugagggaauuugccaaagagaucgaugucuccuaugucaagauugaaga |
| | | gguaauuggugcaggugaguucggcgaggugugccggggucggcugaaggcaccagggaaaaaggagagcuguguggccau |
| | | caagacucugaaggguggcuacaccgagcgccagagggcugaguuccugagcgaggccuccaucaugggccaguucgagcau |
| | | cccaacaucauccgccucgagggcguggcaccaacagugugccgguuaugauccucacggaauucauggagaacggagccc |
| | | uggacuccuuccugcggcugaacgacgggcaguucacagucauccagcugguggcaugcugaggggcaucgccucgggca |
| | | ugcgguaccuggcugaaaugagcuauguccaccgagaccuggcugcucggaacaucuuggucaacaguaaccuggucugcaa |
| | | ggugucegacuuuggccucuccagauucuuggaggagaacuccucugaucccaccuacacaaguucccugggaggcaagauu |
| | | cccauccgauggaccgccccugaagccauugccuucaggaaguucaccucugccagugaugccuggcgcuaugggaucguca |
| | | ugugggaggucaugucuuuuggggaacggccauacugggacaugagcaaccaggaugugaucaaugccauugaacaggacu |
| | | accggcugccuccuccuccagacugccccaccucccuccaccagcucaugcuggacuguuggcagaaggaccggaaugcccgg |
| | | ccccgcuuuccccagguggucagcgcucuggacaagaugauccggaaucccgcuagccucaaaaucguggccagggagaaug |
| | | gcggggccucacauccacucuuggaccaacggcagccucacuacucugcuuucgguucuguggucgaguggcuucgagcca |
| | | ucaagaugggaagauacgaggaaaguuuugcagcggcuggauucggcuccuuugagauggucagucagaucucugccgagg |
| | | accuucuccgaauuggagucacucuggcaggacaccagaagaaaaucuuggccagugugcagcauaugaagugggaagcuaa |
| | | gccaggagccccugguggggacagggggaccagcccagcaguucugaccuccaaggacucaccaccguggcagauucuucuuu |
| | | ccgggaggcagaguugggugggggacucacaagaugagccccucccccucgucacagccuucccauuggauugcacuuugaac |
| | | agagggggucggagacacagauuuggggaaccgugccauaugggaucauacaugcccuccaggcggggaaccccaacuc |
| | | agagugagucuuucccucaagacugggcaaagaaacaucccuacgucucuaaccucccaucuucccagaggcucucuccccaa |
| | | gcgccuuccaccucaacgggcaugucccugcagaccaaagagaaaggguggaccagccugccaacuugggaguggaaaaugcc |
| | | gucccaggaggcaggaaggggcugucaggacccggugauguaaucauuggguuuugauguccugacuugcugucaccacca |
| | | aaggcaaucauuuuucccuuguaaaugccccucccccucaucugccuucauauugaagguucugaaguuuuacuguuuuuua |
| | | uuuuguuaauuuuuuccuccuuccccccucccucccccuucuuguccagauuuuguguguuaaagggcaccugguuccacua |
| | | ucuccuguugggaacaaggacccaucgauauguucuagaacagugccuuggaaaugcca |

TABLE 3-continued

RNA transcripts up-regulated during HF stem cell activation.

| SEQ ID No: | Access. # | Sequence |
|---|---|---|
| 114 | AA980204 | ggcagcgagacgagcucacggucgaggauacgggugaagcgggacaggagcaggagccgg agccgggccaaagcagaaggugcaggucggcgccggcgguugggcangacccagucaagc cggacagugaggagcggaugcagacggcacgaccauggccacgauggugcuuccucgaga ggagaagcugagucaggacgagauagugcugggcaccaaggcggugauccaggguuuaga gacccugagaggggagcaucgugcccugcuagcuccccuagcuucucaugaagcaggcga ggcugagcgggcucacaggagcgcugccuccuccugcgccgcucccuggaggccaucgag cuggggcuuggggaggcucaggugauccuggcauuaucaagccaucugggggcuguggag ucagagaagcagaagcugcgggcucaggugcggcccugguacaagagaacagugguugcg ugaggagcuggcagggacacagcagaagcucagcgcagugaacaggcgguggcucagcug gagaagagagcagcacaucu |
| 115 | AI843232 | ggcagcgagacgagcucacggucgaggauacgggugaagcgggacaggagcaggagccgg agccgggccaaagcagaaggugcaggucggcgccggcgguugggcangacccagucaagc cggacagugaggagcggaugcagacggcacgaccauggccacgauggugcuuccucgaga ggagaagcugagucaggacgagauagugcugggcaccaaggcggugauccaggguuuaga gacccugagaggggagcaucgugcccugcuagcuccccuagcuucucaugaagcaggcga ggcugagcgggcucacaggagcgcugccuccuccugcgccgcucccuggaggccaucgag cuggggcuuggggaggcucaggugauccuggcauuaucaagccaucugggggcuguggag ucagagaagcagaagcugcgggcucaggugcggcccugguacaagagaacagugguugcg ugaggagcuggcagggacacagcagaagcucagcgcagugaacaggcgguggcucagcug gagaagagagcagcacaucu |
| 116 | U59807 | Sequence below. |

augauguguggcgcgccaucugccacaaugccagccacggccgagacgcaggaggucgccgaccaggugaggcugggcccag gucaggccagucugagccaggccugcggagacccggcggccucagggaccggccugcccagacuggucagguccugcagcgg guuuccggggcggccacaagugugacugggagcugggggcucuggaucugguuggaagauucagggccgggaacuggggc gagucuucugccgcuugcauacaagagggccacucaccuauuagggaacuagccccgggaucgguggagggauccggguggu cccagagaauucaggaaggcaguguuagaaccuagacggcaccuuuuugacuuacacccaggccuaaacaagagaaagccaga cugggcuacugugcuugucuccucaaaagaaagagcuaggacuguuuagcucaguggcaggaauucaacugauaccaccacc accaucaccaacaccgccccucagggaaaaaaaaaaggaucaaaaccagaaguuguagaacuugcuugugccuagucugaaac gagggggguggaccuugggccugggcugcccuuccugugacuguuagcagagcagagauucaguacaagguagggggagguu caggguauuagcaagagaagaaaaguuaaacaaauccucucuucagcucuccugccacgccccaagcccaggacccuguccac uaagccuagcugaucuugggaggguguuugcucugaacugaaguggccaagaaggaagugagucagcuccaugagacccuag aaaugaggaaauguuacagacacacuggccaggcaagggaaccuuggccacgugccacaucagcacucaggaggcagagacag gcgagucucucugaauuugaagccagcccaguuugcuuaguuccaugccagccauagcuacauagugagacccugucccccc ccccccccaaaaaaaaggagcuguguuguucuuuaucaguggggccaacaguuuaccauguccccggaaugaggaguauuga aggcuggcagugugugugugugggggcaccugugcaugaaucuaaguccuuccuucucacccaccauccaggugaagucccc agcuugaaucgaaagaaaaucagaaguuugaugucuuuaaagccauauccuucaagagacagauaguggcuggcaccaaccu cuucaucaagguggguacugauaguagcuugccaugaacuggggacauagucucagaguagagcagagaguguccugcaacuu ccugcagagaaccccuuaaggggacauguacauguucugagaggaugaauuuggggguguuaggguucccggccuuaaagga ggagacaaggguuaucacuggcuaaguuaguggcugguggccuguucuggcucaguuucuaaggcuggguuaagccugga acuggaaccuuaccuuucacucacaugucugucugucugucuuccuccagguugauguugguggagauaaaugcgugcacu ugaggguguuucaacccccucccccaugaaaacaagccuuugacccugucuuccuaucagaccaacaaagaaaggcacgaugag cucuccuacuucuga

| SEQ ID No: | Access. # | Sequence |
|---|---|---|
| 117 | AI152659 | gaaaauguuaagagccaucaaauuucuggauauuuugcuaggaaaaugaaauucuacacu uauuuuuuguagacuuuuuuuaaaugcuguuuacaugaauuguauuuuggaaaaaauauu auacugugcacccugugaugcaugaagugauuuuauguauggucugcuaugugggcagag gucaccuuauuccuaugaucuggaauuguuuacuuucuacaaaguaagcuuuguggggau uuugcuuucauuuucuuuguagcugauguuauuuuaccaggugugcagcaggaauuacac cacuguguggaauuauaaaauacaucccaugugca |
| 118 | AI850090 | uuuuuuuuuuuuuuuuuccuggugaauauuuuuauuagaggugacaguuucccaggugac aguuuuucccaaggaagcaaaucucugcgucuauaagggaagaccacagaaccuucacuu uguaauuuaccuguguaauuuauccaagaacacagcacagcaauugcuuuaugugguacu |

TABLE 3-continued

RNA transcripts up-regulated during HF stem cell activation.

| SEQ ID No: | Access. # | Sequence |
|---|---|---|
| | | cugaccuuaaguaacaaguuguuaacagaaaacacaucaaacaaaaggauaaauucucuaa uuaucaagucagccaucagcuuuucuuaggagagagagagagagagugugugugugugugug ugugugugugugugugugucugucugucugucugucugggguaucccacuuagggccaugu gcauguuagguaaaugcuccaccacugagcuguuucuuagccgcacuuuucucagauuuc agguuuguuuguuuguuuguuuguuuuuuaacuaggcaugaaaauaaacuucacuucaaau |
| 119 | AF064635 | See above sequence (AI850090). |
| 120 | AI843106 | uuuuuuuuuuuuuuuuuguggaaauuacucuuuauugaaaaauaccaguaauacugacag acuucaaaaucaauuuacgguuccagaauacaaaguacuuaaauacauuuuuuuccaaacc uguuuguaucucaaaguuagcauuuuuguaaaucaagauacaaauaugauaacuucacua aaauauuuuccagcuuuauucuuuaaggagcuguauaaccuucaaagucagggucccgag gucagcagggcauggggcagaaugcaccuggcacucccugugcagcagacugcaaccaca uu |
| 121 | AF033186 | auggccagcuuuccccccgaggguuaacgagaaagagaucgugagaucacguacuauaggg gaacucuuggcuccagcagcucccuuuugacaagaaauguggugguggagaacuggacgguu gcuuuugcuccugaugguuccuacuuugcguggucacaaggauaucgcauagugaagcuu gucccgugguccccagugccguaagaacuuucuuuugcaugguuccaaaaauguuaccaau ucaagcugucuaaaauuggcaagacaaaacaguaaugguggucagaaaaacaagccuccu gagcacguuauagacuguggagacauagucuggagucuugcuuuugggucuucaguucca gaaaaacagagucguugcguuaaauauagaauggcaucgguuccgauuuggacaggaucag cuacucccuugccacaggauuaaacaauggucgcaucaaaaucugggauguauauacagga aaacucccuccuuaaauugguagaccacauugaaaugguuagagauuuaacuuuugcucca gaugggagcuuacucccuuguaucagcuucaagagacaaaacucuaagagugugggaccug aaagaugauggaaacauggugaaaguauugcgggcacaucagaauuggguguacaguugu gcauucucucccgacuguucuaugcuguguucaguuggcgccaguaaagcaguuuuccuu uggaauauggauaaaauacaccaugauuaggaagcuggaaggucaucaccaugauguugua gcuugugacuuuucucccugauggagcauugcuagcuacugcauccuaugacacucgugug uaugucugggauccacacaauggagaccuucugauggaguuugggcaccuguuucccucg cccacuccaauauuugcuggaggagcaaaugaccgaugggugagagcugugucuuucagu caugauggacugcauguugccagccuugcugaugauaaaaugguggagguucuggagaauc gaugaggauuguccgguacaaguugcaccuuugagcaauggucuuugcugugccuuuucu acugauggcaguguuuuagcugcugggacacaugauggaagugugauauuuuugggccacu ccaaggcaagucccuagccuucaacauauaugucgcaugucaauccgaagagugaugucc acccaagaaguccaaaaacugccuguuccuuccaaaauauuggcguuucucuccuaccgc gguuag |
| 122 | Z50159 | auggccagcuuuccccccgaggguuaacgagaaagagaucgugagaucacguacuauaggg gaacucuuggcuccagcagcucccuuuugacaagaaauguggugguggagaacuggacgguu gcuuuugcuccugaugguuccuacuuugcguggucacaaggauaucgcauagugaagcuu gucccgugguccccagugccguaagaacuuucuuuugcaugguuccaaaaauguuaccaau ucaagcugucuaaaauuggcaagacaaaacaguaaugguggucagaaaaacaagccuccu gagcacguuauagacuguggagacauagucuggagucuugcuuuugggucuucaguucca gaaaaacagagucguugcguuaaauauagaauggcaucgguuccgauuuggacaggaucag cuacucccuugccacaggauuaaacaauggucgcaucaaaaucugggauguauauacagga aaacucccuccuuaaauugguagaccacauugaaaugguuagagauuuaacuuuugcucca gaugggagcuuacucccuuguaucagcuucaagagacaaaacucuaagagugugggaccug aaagaugauggaaacauggugaaaguauugcgggcacaucagaauuggguguacaguugu gcauucucucccgacuguucuaugcuguguucaguuggcgccaguaaagcaguuuuccuu uggaauauggauaaaauacaccaugauuaggaagcuggaaggucaucaccaugauguugua gcuugugacuuuucucccugauggagcauugcuagcuacugcauccuaugacacucgugug uaugucugggauccacacaauggagaccuucugauggaguuugggcaccuguuucccucg cccacuccaauauuugcuggaggagcaaaugaccgaugggugagagcugugucuuucagu caugauggacugcauguugccagccuugcugaugauaaaaugguggagguucuggagaauc gaugaggauuguccgguacaaguugcaccuuugagcaauggucuuugcugugccuuuucu acugauggcaguguuuuagcugcugggacacaugauggaagugugauauuuuugggccacu ccaaggcaagucccuagccuucaacauauaugucgcaugucaauccgaagagugaugucc acccaagaaguccaaaaacugccuguuccuuccaaaauauuggcguuucucuccuaccgc gguuag |
| 123 | X78683 | Sequence below. |

gaauuccgugugcaaggcgaggucuguaagcuggagcggggcagaggcuggcgggcaccccuuccugaccgcuggugccgc cgccgccgccuucgggaggaucagacauggcccagaacuugaaggacuuagcuggacgccugcccgccgggccucggggcau gggcacggcgcugaagcugcugcuggggggccggggcgguggccuacggcguccgcgaauccguguucaccguggaaggcgg ucauagagccaucuuuuuuaaucguauugguggcgugcagcaggacacgauccuggccgaauuucacuucaggauccccug guuccaguaccccaucaucuaugacauucgggccagaccucggaaaaucucccucccccacaggcuccaaagaccugcagaugg ugaacaucucccugcgugugcugucccgacccaaugcccaggagcucccccagcauguaccagcgucuagggcuggacuauga ggagcgagugcugccguccauuguuaaugaggugcucaagagugugguggccaaguucaaugccucgcagcugaucaccca TABLE 3-continued RNA transcripts up-regulated during HF stem cell activation.

| SEQ ID No: | Access. # | Sequence |
|---|---|---|

gcgggcucaggugucccuguugauccgaagagagcugacagagcgcgccaaggacuucagccucauccuggaugauguagc uaucacagagcugagcuucagccgagaguacacagcugcuguagaagccaagcaaguggcccagcaggaagcccagcgggccc aguuuuugguggagaaagcgaagcaggaacagcgacagaagauugugcaggcugagggggaggcggaggcugccaagaugc uuggagaagcacugagcaagaauccuggcuauaucaagcuccgaaagauccgggccgcccagaacaucucuaaaacgaucgcc acaucacagaaccgaaucuaucucacagcugacaaccuugugcugaaucuacaggaugaaaguuuuacucggggaagugaca gccucauuaaggguaagaaaugaguguggacaucaagaaccccaccaccagagaaguuggcacacuuguccagcuuggagga gccagcucgggggucaagcacagcccacccugccccaggcaucaugugauggacuuuucuguaucugcccucuuggauuaagg aagacugagaccagcccuuucagaggcuuuccuccuuccuguguuggcugggaagcggggguggacaaugugauuucuccgu gauuuccuacagccuugagccucucccagaguggggggagauaaccaccaugccaggaauuc

| | | |
|---|---|---|
| 124 | X68193 | acccaccggcuuucggaccauggccaaccucgagcguaccuucauugccaucaagccaga uggcgugcagcgcggccugguggggcgagaucaucaaacgguucgagcagaagggguuccg ccugguggccaugaaguuccuucgggccucugaagaacaccugaagcagcauuacaucga ccugaaagaccguccuuucuucccggggcuggugaaguacaugaacucggggcccguggu ggccauggucugggaggggcucaauguggugaaaacgggccgagugaugcugggggagac caauccagcugauucaaaaccaggcaccauccguggggauuucugcauucaaguuggcag gaacaucauucauggcagugauucaguggagagugcugagaaagagauccaucugugguu uaagcccgaagaacugaucgacuacaagucuugugcccaugacuggguguacgaguagac augaagaaaccagaauccuuuucagcacuacugaugguuucuggacagagcucuucauc ccacugacaggauggaucaucuuuucuaaaacaauaaagacuuuggaacugaaaaaaaaa aaaaaaaaaaaa |
| 125 | AA062013 | uuuugcuuucaacaugacagaugccgcuguguccuucgccaaggacuucuuggccggugg aguggccgcagcaucuccaagacagcggucacaccaucgagagggucaagcugcugcugc aggugcacaugccagcaagcaaaucacggcagauaagcaauacaagggcaucauagacug cgugguucguaucccccaaggaacagggagugcucugguccuuugggcgugggaaccgggc caaugucaucagauacuuccccaccaaggcucucaacuuggccuucaaaguuaauuccaa gcagaucuuucugggugguguugacaagaggacccaguucuggcgcuacuuuugcaggga accuggcaucagguggguugccgcugggggcuacauccuugggcuuuguguacccucuugau uuuugccgguaccgucuagcagcugaugugggcaagcuggagcuaaagggaauucaaggg ccuugggacugccugguaagacuucaaucugaugggauaagggcuguac |
| 126 | AI465965 | auccgggacccccacggcccccuuugcagcuugccacaagguucugagcccccuuggaauac uuccgccaaugugguaugacaugugugcccauaagggugacaaagccuaucucugccgu agccuggcugcuuauacugcagccugucaggcagcuggggcagcagugaagcccuggagg acagacagcgucugcccucuccaguguccugcccacagccacuacuccaucugcacccgc uccugccagggcuuccugugcugcucucucuggccucacuggcugcaccac |
| 127 | U50413 | Sequence below. |

ggcacgagccgaguuggaggaagcagcggcagcggcagcggcagcgguagcggugaggacggcugugcagccaaggaaccgg gacagcgaagcgacggcaggucgcagcuggaucgcaggagccugggagcugggagcuucagaggccgcugaagcccaggcug ggcagaggaaggaagcgagccgacccggaggugaagcugagaguggagcguggcaguaaaaucagacgacagauggacagug ugacaggaacgucagagaggauugggccucgcugcgagagucagccuggagucaagguguugacaaguugcugagaaggac acgugggaggacgguggcgcgcggagggagagcccugucuucagucaccccguugauggaggacagauggacagcagccgg acggccagucaccucucuuaaaccuuuggauaguggucccuuugugcucugcuggacaccuguuggggauuuuagcccauuc ucugaacucacuuucucuuaaaacguaaacucggacggcagugugcgagccagcuccucuguggcagggcacuagagcugca gacaugagugcagagggcuaccaguacagagcacuguacgacuacaagaaggagcgagaggaagacauugaccuacaccugg gggacauacugacugugaauaaaggcuccuuaguggcacuuggauucagugauggccaggaagcccggccugaagauauug gcugguuaaauggcuacaaugaaaccacuggggagaggggagacuuuccaggaacuuacguugaauacauuggaaggaaaag aauuucacccccuacucccaagccucggcccccucgaccgcuuccuguugcuccggguucuucaaaaacugaagcugacacg gagcagcaagcguugccccuuccugaccuggccgagcaguuugccccuccugauguugccccgccucuccuuauaaagcucc uggaagccauugagaagaaaggacuggaauguucgacucuauacagaacacaaagcuccagcaacccugcagaauuacgacag cuucuugauugugaugccgcgucaguggacuuggagaugaucgacguacacgucuuagcagaugcuuucaaacgcuaucuc TABLE 3-continued RNA transcripts up-regulated during HF stem cell activation.

| SEQ ID No: | Access. # | Sequence |
|---|---|---|

gccgacuuaccaaauccugucauuccuguagcuguuuacaaugagaugaugucuuuagcccaagaacuacagagcccugaag acugcauccagcuguugaagaagcucauuagauugccuaauauaccucaucaguguuggcuuacgcuucaguauuugcuca agcauuuuuucaagcucucucaagccuccagcaaaaaccuuuugaaugcaagaguccucucugagauuuucagccccgugcu uuucagauuuccagccgccagcucugauaauacugaacaccucauaaaagcgauagagauuuuaaucucaacggaauggaau gagagacagccagcaccagcacugccccccaaaccacccaagcccacuacuguagccaacaacagcaugaacaacaauauguccc uugcaggaugcugaaugguacuggggagacaucucaagggaagaagugaaugaaaaacuccgagacacugcugaugggaccu uuuugguacgagacgcaucuacuaaaaugcacggcgauuacacucuuacaccuaggaaaggaggaaauaacaaauuaaucaa aaucuuucaccgugauggaaaauauggcuucucugauccauuaaccuucaacucugugguugaguuaaauaaaccacuaccgg aaugagucuuuagcucaguacaaccccaagcuggaugugaaguugcucuacccaguguccaaauaccagcaggaucaaguug ucaaagaagauaauauugaagcuguagggaaaaaauuacaugaauauaauacucaauuucaagaaaaaaagucgggaauauga uagauuauaugaggaguacacccguacuucccaggaaauccaaaugaaaagaacggcuaucgaagcauuuaaugaaaccauaa aaauauuugaagaacaaugccaaacccaggagcgguacagcaaagaauacauagagaaguuuaaacgcgaaggcaacgagaaa gaaauucaaaggauuaugcauaaccaugauaagcugaagucgcguaucagugagaucauugacaguaggaggagguuggaa gaagacuugaagaagcaggcagcugaguaccgagagaucgacaaacgcaugaacaguauuaagccggaccucauccaguuga gaaagacaagagaccaauacuugauguggcugacgcagaaaggugugcggcagaagaagcugaacgaguggcuggggaauga aaauaccgaagaucaauacucccugguagaagaugaugagGauuugccccaccaugacgagaagacguggaaugucgggagc agcaaccgaaacaaagcggagaaccuauugcgagggaagcgagacggcacuuuccuuguccgggagagcaguaagcagggcu gcuaugccugcuccguagugguagacggcgaagucaagcauugcgucauuaacaagacugccaccggcuauggcuuugccga gcccuacaaccuguacagcucccugaaggagcuggugcuacauuaucaacacaccucccucgugcagcacaaugacuccccuca augucacacuagcauacccaguauaugcacaacagaggcgaugaagcgcugcccucggauccaguuccucaccuucaagccac ccaaggccucugagaagcaaagggcuccucuccagcccgaccugugaacugagcugcagaaaugaagccggcugucugcaca ugggacuagagcuuucuuggacaaaaagaagucggggaagacacgcagccucggacuguuggaugaccagacguuucuaacc uuauccucuuucuuucuuucuuucuuucuuucuuucuuucuuucuuucuuucuuucuuucuuucuuucuuucuuucuaauuua aagccacaacacacaaccaacacacagagagaaagaaaugcaaaaaucucuccgugcagggacaaagaggccuuuaaccauggu gcuuguuaacgcuuucugaagcuuuaccagcuacaaguugggacuuuggagaccagaagguagacagggccgaagagccug cgccuggggccgcuugguccagccugguguagccuggggugucgcuggggugugggugaacccagacacaucacacuguggauu auuuccuuuuuaaaagagcgaaugauauguaucagagagccgcgucugcucacgcaggacacuuugagagaacauugaugca gucuguucggaggaaaaaugaaacaccagaaaacguuuuuguuuaaacuuaucaagucagcaaccaacaacccaccaacagaa aaaaaaaaaaaa

| SEQ ID No: | Access. # | Sequence |
|---|---|---|
| 128 | AW120502 | uuuuuuuuuuuuguuuuaauuuggcuccaaugaucgcauucucaaacuccuuugggaggg cauuagaugacccaguauccgacgacuuagauucacacguguuuuucucccucugagcucu uuucuccaggcucacngucuuuguuuuucaagcuuucuugggccuuugaacaauuuucuu ccuuugaagauucuccugg |
| 129 | X62940 | Sequence below. |

agccgaguaggaccgagcugcugcagacgcgccgggucacucgagccagcaccaccguucucacgcccugagcugcagacagc uaggcgguuuuaucuaguuugaaccaggcugcuggagcuugcucccucccgcccucucucuuuuuuuuccacggggcuguu uuuuuaauuuggcugcaauugcaugaaaucccaaugguguagaccaguggcgauggaucuaggaguuuaccaacugagaca uuuuuccauuucuuucuugucgucuuugcugggaaccgaaaacgcuuccgugagacuugacaauagcucuggugcaagugu gguagcuaucgacaacaaaauagagcaagcuauggaucuggugaaaagccauuugauguaugcggugagggaggaagugga TABLE 3-continued RNA transcripts up-regulated during HF stem cell activation.

| SEQ ID No: | Access. # | Sequence |
|---|---|---|

aguucugaaggagcagaucaaagaacuaauagagaaaaacucccagcuggagcaggagaacaaucugcugaagacgcuggcca guccggagcagcucgcccaguuucaggcccagcugcagacuggcucccccuccggccaccacgcagccacaggggaccacacag cccccugcacagccagcaucccagggcucaggaucaaccgcauagccuccuaggccccaacagaacuggcugcugcugcugcu gucugaacugaacagaccgaagagaugugcuagagagaagccgccuccacagucacccauuucauugcugucuacgaaagag acgugagacucacacgcuguucucgcuuucuccccaguauuaagcacucauaagcuuuuggcuugaagaaauguacuaguu gagugaauuaaagguuaaucagagagugagcagggaugugcccugugcaacguggcagaugucugaggaaugguuuaauug accccgaggagcucugugccuuuucaacccuccccagccgcccacccugcuucugagagcucgggcggcucgccuucguggg gcucgccugcgugggguucgaaagugggcugcuccuggauucugcgcucucuucuccuucccuucaaagaacucggagagg ccagaaacaagacugcaauggggggcgggggggagggaugaugcaguccuuauacaaaaccgacaacugucaccaaagcuuau aaaacacgauaguacugucccucuuuucugaaccaucagaagacacaaaacuguuagugacacaacggugacagguagcugg gaccuaggcuaucuuauuaugaagguuguuuugcuuguuguauauuuguguauguaguguaacgaauuuguaccauagag gacuguccguaacuacuguuuagcuucuacacauugaaauguagauguuucauuggcugucugaaaaggugugggcuugucc uuccuagagagaucuacuuaaaaaacugcuuuguggcaaaaaccacaccugaagaaauuuuaagaauuuggcccaguuaguca cucuguguaaucccggaaucuagcugcugaagucuugcgaaguaaacuccccgugaccgaugucaguuaagcugguggauac cuggagaagugggucaguugcuaaggaaguggauuucccaguagggguuucugcaccucaccuguauagucguucugcgcau gucccccacacaguccccaccuguauuuaccuguucuacuugucaccuuucaauaaagcauaucaaauguugau 130 U60020 Sequence below.

auggcugcgcacgucuggcuggcggccgcccugcuccuucugguggacuggcugcugcugcggcccaugcucccgggaauc uucucccuguugguucccgaggugccgcugcuccgggucugggugguggggccugagucgcugggccauccuaggacuagg gguccgcggggucccucggggucaccgcaggagcccauggcuggcuggcugcuuugcagccgcugguggccgcacugaguuu ggcccugccuggacuugccuuguuccgagagcuggccgccuggggaacacuccgggagggugacagcgcuggauuacugua cuggaacagucguccagaugccuucgcuaucaguuauguggcagcauugcccgcagccgcccuguggcacaaguuggggag ccucugggcgcccagcggcaacagggacgcuggagacaugcugugucggaugcugggcuuccugggcccuaagaagagacg ucucuaccugguucugguucucuugauucucucuuggcuuggggaaauggccauucccuucuucacgggccgcaucacuga cuggauucuucaggauaagacaguuccuagcuucacccgcaacauauggcucauguccauuuucucaccauagccagcacagcg cuggaguuugcaagugauggaaucuacaacaucaccaugggacacaugcacggccgugugcacagagagguguuucgggcc guccuucgccaggagacaggguuuuuccugaagaacccagcagguuccaucacaucucgggugacugaggacacagccaacg ugugcgaguccauuagugacacgcugagccugcugcugugguaccuggggcgagcccugugucucuuggugcuucauguuu ugggggucaccguaccucacucuggucacccugaucaaucugccccugcuuuuucuuuugccuaagaagcugggaaaagug caccagucacuggcagugaaggugcaggagucucuagcaaaguccacgcagguggcccuugaggccuuaucggcgaugccua ccgugcggagcuuugccaacgaggagggugaggcccagaaguucaggcagaaguuggaagaaaugaagacgcuaaacaagaa ggaggccuuggcuuacgucgcugaagucuggaccacgagugucucgggaaugcugcugaagguggaauucuguaccuggg cgggcagcugguggaucagagggacugucagcagcggcaaccuugucucauucguucucuaccagcuucaguucacccaggcu guucagguccugcucucccucuaccccuccaugcagaaggcuguggggcuccucagagaaaauauucgaauacuuggaccgga cuccuugcucuccacucaguggcucguuggcacccucaaacaugaaaggccuuguggaguuccaagaugucucuuuugccu acccaaaccagcccaaaguccaggugcuucaggggcugacguucacccugcauccuggaacggugacagcguugguggacc caauggaucagggaagagcaccguggcugcccugcugcagaaccuguaccagcccaccgggggccagcugcugcuggauggc cagcgccugguccaguaugaucaccauuaccugcacacucagguggccgcagugggacaagagccgcugcuauuuggaagaa TABLE 3-continued RNA transcripts up-regulated during HF stem cell activation.

| SEQ ID No: | Access. # | Sequence |
|---|---|---|
| | | guuuucgagaaaauauugcguauggccugaaccggacuccaaccauggaggaaaucacagcuguggccguggagucuggag<br>cccacgauuucaucucuggguucccucagggcuaugacacagagguaggugagacugggaaccagcugucaggaggucagc<br>gacaggcaguggccuuggcccgagccuugauccggaagccacuccugcuuaucuuggaugaugccaccagugcccuggaugc<br>uggcaaccagcuacggguccagcggcuccuguaugagagccccaagcgggcuucucggacgguucuucuuaucacccagcag<br>cucagccuggcagagcaggcccaccacauccucuuucucagagaaggcucugucggcgagcagggcacccaccugcagcuca<br>ugaagagaggagggugcuaccgggccaugguagaggcucuugcggcuccugcagacuga |
| 131 | L32752 | gaauuccggggccgcucucuccggcaggaucgccgcgauggccgcccagggagagccgca<br>gguccaguucaaggucguccuggugggcgacggcggcaccggaaagacgacauugaugaa<br>gcgccacuugaccggagaguuugagaaggaguauguagccacccugggcguggaggugca<br>cacauuagucuuccauaccaacagaggaccuaucaaguucaaugugugggacacagccgg<br>ucaggagaaguucgggggcugcgcgauggcuacuacauccaagcccagugugccauuau<br>aauguuugacguaacaucaagaguuacuuacaagaaugugccuagcuggcauaaagaucu<br>agugcgugugugugaaaacauccccauuguauuguguggcaacaaaguggauguuaaaga<br>caugaaagugaaggcaaaaccuauucucuuccaccgaaagaagaaucuucaguacuauga<br>cauuucugccagaaguaacuacaacuuugaaaagccuuucuucuggcuugccagaaagcu<br>cauuggagauccuaacuuggaguucguugccaugccugcucuugccccaccugagguagu<br>cauggacccagcuuuggcagcacaguacgagcaugauuuagagguugcucagacgacugc<br>ucucccagaugaggaagaugaccugugagaaagugaagcuggagcccugcgucagaaguc<br>uauuuuaggcaacuguccugugaugccagccagcggugcagugugugugccaccuuauuu<br>agcuaaaggagaucgugcaauucauugggaugcugaaggagaugaaugggcuucggagug<br>aauguggcaguuaaaauacaccuucauuuuuuuggacuugcguauuuagccccuggaac<br>agaguuguucuggauuucaaagauaagacugcuaccguagcaucacaauagucaguggug<br>accggaauuc |
| 132 | AI840013 | uuuuuuuuuuuuuuuuugauuuaugaaaaguuuuauuuaucaguacugugaagaauucuc<br>aucauaauugcuacguuaaucaaggaaaaggcacagagaagcaugugucguuugaguccu<br>cgauacuggaccucccagcccaugcucccuaugaggagucuagcugcuguggugguucuuc<br>acagcuuugguuuucuggagacgaagcucaugauugcguucaugcacuccucugacagcc<br>accuugcuugcagaguagugcacucuucagcguugacugggcguagagcuuuucuuucucau<br>uuuuucugauuaacucuuuggaaauucucauuggguuuggcgggagcuucgcauau |
| 133 | AB020424 | ucgggaaucgauugagagaccgcgaaccuguaaacggaugauaccgagucgggcaggcgu<br>uaugccagcccaacucgggaccucgcaucauguccgcggcuaccuuagaguguuucggga<br>augauuugcgguggaugaacgaaaccccgguacguccugugccaaggagcauaugucagg<br>acggacgcucguuaaugccucagugguggggcaacguucgcucucuaucuauacgacucu<br>cgacaauggauaucucggcucucgcaucgaugaagaacguagcgaaaugcgauacuuggu<br>gugaauugcagaauccugugaaccaucgagucuuugaacgcaaguugcgcccgaggccuu<br>ucgguugagggcacgccugccugggcgucacgccuuguuuugcucugugcccgugcucuu<br>ucgggggcggucauggaugcggagauuggcccuccgugccucgugugcggcgggcuuaag<br>cgcgggggugucggcgucgggaagggcacgacgagugguggacggagcaccagcaggaugu<br>ugugguccccccgucaccuuaaggggcucaagagacccggacuaggcgagccgcgcuucgu<br>aagaggagggcgagcugucucgcaau |
| 134 | AI848453 | uuuuuuuuuuuuuuuuugaaguugcugccccuuuauuggugacccgggcaaguuuaagga<br>gaacaacauuaaagcacacaaaguguauccaugucaccagcucaaccaggaggagugagg<br>gucacggcaggguucucccaugguguaagaaaucaacgcaauuucaucacaccccguuac<br>uuuccaaguuaacgaaccgauaagaaaagauucucccuuaaacugacaaguacaauguac<br>auguacaugauuuuggaauaauuuaauacuuuaaccucaagauacaacuauauucuaaga<br>ccauuauuuuaaaggaacggauccuuacaaaaccaaaauaacccauauagcacgagguug<br>guuuagccuuucuucuucuuucaacaaacgugcaccacauguuucaguagcaaggccgau<br>gccauggauaugagagcugugauuugcagggaccaaccacaucuagaaccggggaggcca<br>aucanacggugggguu |
| 135 | AU040563 | cccuuggaggauaguuuuauugacaagucgaguuagguuuuagaguaaacuuuuaucacc<br>ccagucaggccccuucccaggggaggcucgcugguagcucagauggccuuggugguggggc<br>agauuguuguaguugucuuccuggcccuccagcaggcuucgggagguggcuaucuccugc<br>uccagccuggacuugauguccaguagcugcuuauacuccggguucuggcgcucuaugugc<br>ggcacgcaggugcngcg |
| 136 | X89749 | Sequence below. |
| | | ggacugacuccuugggcagauugccucuccuccuucucaugccagaggcugcugaugaggaaagguccaggggacugucca<br>ugcugucuucauccucagagucacugccugaugcugcaacaagacccuucuuguuuagcaauagugguuggaacacucucu<br>uguaaguuaccggagcacuaguauaggaggaggaucaucgacuacccucccgccacuccacggcugcuggcuccuagaaacc<br>ccagcuucaccucucacugggacucgaguuccagaaugaaaagcaagaagggucuuguugcagcaucaggcagugacucuga<br>ggaugaagacagcauggacaguccccuggaccuuuccucaucagcagccucuggcaugagaaggaggagaggcaaucugccc |

TABLE 3-continued

RNA transcripts up-regulated during HF stem cell activation.

| SEQ ID No: | Access. # | Sequence |
|---|---|---|

aaggagucaguccagauucugcgagacuggcuguaugaacacagauacaacgccuaucccucagagcaagagaaagcacugc ugucccagcagacacaccuguccacacuacaggucuguaacugguucaucaacgcccgccgcaggcuccuuccugacaugcu gagaaaaggauggcaaagauccaaaucaguucacgauuucccgccguggggccaagauuucagaagcuagcucuauugaagcu gcaaugguaucaaaaacuucaugccaacucuagaagagagcccauuucauuccugcguaguuggacccaacccaacccuag ggagaccagugucucccaaaccucccuccccaggauccauuuuggcucgcccgucagugaucugccauaccacugugacugc auugaaggaugggccuuucucucucugucagccgauuggugugggacagaguacagauguaccgcaaauagcacccagcaac uuuacagacaccucucucguguacccagaggacacuugcaaaucuggacccaguccaaacccucagagugguucuuuucaaca cuccuccccuacuccaccagaccucaaccaggauuuuaguggauuccagcuucuaguggauguugcacucaaacgagcggc agagauggagcuucaggccaaacucacagcuuaaccguuuuuucaaacaaaacaguucuccaaaauacgguccugauugccg ggggugauggcaagagaugcauuauuuuauauauuuuuuc 137 AW125390 uuuuuuuuuuuuuuuuuggugguuaucaagugcacuuuauugaauccacuguggauagau
aaaugaguguuacaccugcguguagggaggggcaaggagggacgcagcugcggaggguga
agcacuucaggaccggaagucggaaucccucuauuaagugugaagguuuugagcguuaaga
acaaugaugaugacacuaacaaugguggauaacaaccaucaggaugcugaggaccaaggug
cugauguucaggcacuuagcaguggaggcguaggccugggcuccagucacaucacccacc
aucuuccgaucccuagacuucacggaguaggcauaggcuaugaagcccaggcagcagaag
uucaugaagaguguauugaacagggaccagaccacauggucaggcaccgacaccucucug
ggcauguugaucacaguaguucugacagaagccga 138 X05862 Sequence below.

aagcuucaggauacagugcacacucguaaauaaaaacuacaggcugcugcgaauuauauuucaacugaccggagaggcaaag ccugacuguccauuaacccuuaacuuccaaacgcaaacugcuuacugcaucuuuuggcauuuuaccuuaugccuuguuagg uccaaggcaagagaagcgucaucaauaaccacgcaugugcaacagcuuuuccagaggaaaggugugggguggcucuuaaaaga gccuuugaguuaggagugugaguuaaacgagcucacuuggagcugguguacuuggugacugccuuggugcccuccgacacc gcgugcuuggccagcuccccgggcagcagcaggcgcacggccgucuggaucucccgggacgugauggucgagcgcuuguug uaaugcgccaggcgggaagccucgcucgcgaugcgcucgaagaugucguucacgaacgaguucaugaugcccauggccuug gaggagaugccggugucggggugcacuugcuucagcaccuuguacacguacaccgaguagcucuccuugcggcugcgcuug cgcuucuugccguccuucuucugggccuuggugacggccuucuuggagcccuucuucggggcgggagcggacuuggcggg cucaggcauacugagaggaugaagugaacuaaguugaaaaaggauaacuaaaaguuaaugacuguucuggcugcaauuuuaa acaaacuuacggcuauggcaaccugaaucaccauacgucauguacuaacaguccaaucaaaacaagggauuuucaaaccaggg cgccauugguaaccaauguguaaccaaugaaaucucuccguuuucgcguccagccuugacuauauauacuaugcguauacgu uuuugcuucuuacugcgguggguuaucuacagcugaguuaugucuggacguggcaagcaaggacguggcaagcaaggaggca aggcccgcgccaaggccaagacgcgcuccucccgggccggccugcaguuccccgugggccgcgugcaccggcugcuccgcaa gggcaacuacucggagcgcgugggcgccggcgccccgguguaccuggcggccgugcuggaguaccugacggccgagauccu ggagcuggcgggcaacgcggcccgcgacaacaagaagacgcgcaucaucccgcgccaccugcagcuggccauccgcaacgacg aggagcucaacaagcugcugggccgcgugaccaucgcgcagggcggcguccugcccaacauccaggccgugcugcugcccaa gaagaccgagagccaccacaaggccaaggggaagugaaaccaaacauuacgaaucaccaaggcucuuuucagagccacucacu uucucaaagagaccuaacacuacugggauagugcauuguggggaaauacgugguauuaaccuuccuccuauuuucccugcuug ugguuaguucaaccccuaagccuuaggcuaagaguauauugguuuuuggaaggcaggcacccaaccucggaccuaguacaua aaacagacacaucuugaacuccaggccagccuacucugcaggacgaguuccaggacagaccggacugcacaaagaauugucuu gaaauguuccuuuaucagcacauaugcugauaaacaacuaaucacuguacaaucaauccucacuugaauccuguuuaugugg caugauugacaaguccugccauuuggcaaagucaaaaucagcaaaggauguuaaagcauuuggugguaucacagcuaaaac TABLE 3-continued RNA transcripts up-regulated during HF stem cell activation.

| SEQ ID No: | Access. # | Sequence |
|---|---|---|
| 139 | AW046181 | uuuuuuuuuuuuuuuuaugcaaauaguuuucaagauuuuauugcaaaccaaaauugguuua ucgcacacaaaaaaaguuguguggguaaggaggaggaauuguacaggauuauaacccaugu uaauuacaguacauuaaaaugaugguuuacaaauaagccuguaaguuuaaaauaucuagug uuauaacccaauguacagacuuccuuuacacgauacauacaauaaucaggaaugcaaaag aauaugaacaaagggaaaaaaaacauaaauaaugcccguuuuauaggugacauuuuaaac aauugaaaacaccaaccggcuuugacugacaacuggggcauugguccauaaaaacccuuu cuaaaaauagaaauau |
| 140 | U10118 | Sequence below. |

gaggcugcucaagagcugcgguugggucaccgcuucauguuucucugccgauucuggggaaagauggcaacgaaugaugcu guucugaagaggcuggagcagaagggugcagaggcggaucagaucaucgaauaucucaagcagcagguugcucuucuuaag gagaaagcaauuuugcaggcaacaaugagagaagaaaagaaacuucgaguugaaaaugcuaaacugaaaaaagaaauagaaga gcuaaagcaagagcugauucuggcagaaauucauaacggaguggagcaagugcguguucgauugaguacuccacugcagacg aacuguacugcuucugaaagugugggugcagucuccaucaguagcaaccaccgccucuccugcuacaaaagagcagaucaaag cgggagaagaaaagaaggugaaagagaagacugaaaagaaaggagagaaaaaggagaagcagcagucggcagcagcaaguacu gacuccaagccuaucgacgcaucgcgucuggaucuucgaauugguuguauuguuacugccaagaagcacccugaugcagau ucacuguauguggaggaaguagauguggggagaagcagccccgcgcacggucgucagcgggcuggugaaucauguuccucua gaacagaugcaaaaucguaugguggguuuuacucuguaaucugaagccugcaaagaugcggggaguucugucucaagccaug gugaugugugccaguucaccagagaaaguggagauucuggcccccucccaacggguccguuccuggggacagaauuacuuuu gaugcuuuuccuggagagccugacaaggagcuaaacccuaagaagaagaucugggagcagauccagccugaccugcacacca augcugagugugugggccacauacaaaggagcucccuuugaggugaaggggaaggggaguuugcagagcccaaaccauggccaa uaguggaauuaaauaagugcucuguaacugaaagacauuggcgaaaacuuaauaacaauaaagagaaguguguuuaucacuu acauau

| SEQ ID No: | Access. # | Sequence |
|---|---|---|
| 141 | AW212775 | ggccuuguuuuugguuugcaauaaagaguauuucuuuaaaaggcacauuuuguuaaauag gcaguuccccuccugccucuuccuuuguagcaguguacugcauccuagaaacauuuagca aagcagcccuuagccuccccgaccccccuuucccucccucccagca |
| 142 | AI846302 | uuuuuuuuuuuuuuuuuuaaacaaugacgccguuuauuuaaaauguuuacucccagaaaua uagauauaaaaaaaaaaauaagacaauuaacagcacuaaaccaggcaccuucaaccgaau cccaccauccucguuaacucccuuccuguuacccuuuguagaugaccagaagauuucagg agccccuggacagccagagugguuccugcccagggcuucccgccuuccuccuguccuaga gcuucccgugggaaagcuuggggugagaauuuuagccuaaagggaggggggcuguggccggg cacuuugcgcucauccacugcagg |
| 143 | M22998 | Sequence below. |

acaggguacaguugugcgucagggcguggaggucuggcgggagacgcauaguuacagcgcguccguucuccgucucgcagc cggcacagcuagagcuucgagcgcagcgcggccauggaucccagcagcaagaaggugacgggccgccucauguuggcugugg gaggagcagugcucggaucacugcaguucggcuauaacacuggugucaucaacgcccccccagaagguuauugaggaguucua caaucaaacauggaaccaccgcuacggagagcccaucccauccaccacacucaccacgcuuuggucucucuccguggccaucu ucucugucgggggcaugauugguuccuucucugucggccucuuuguuaaucgcuuuggcaggcggaacuccaugcugaug augaaccuguuggccuuuguggcugcugugcuuaugggcuucuccaaacugggcaaguccuuugagaugcugauccuggg ccgcuucaucaucggugugu acugcggccugacuacuggcuuugugcccauguaugugggagaggugucaccuacagcucu acguggagcccuaggcacacugcaccagcugggaaucgucguuggcauccuuauugcccagguguuuggcuuagacuccau caugggcaaugcagacuuguggccucugcugcucagugucaucuucaucccagcccugcuacaguguauccuguugcccuu cugccccgagagcccccgcuuccugcucaucaaucguaacgaggagaaccgggccaagagugugcugaagaagcuucgaggg acagccgaugugacccgagaccugcaggagaugaaagaagagggucggcagaugaugcgggagaagaagguc accaucuugg agcuguuccgcucacccgccuaccgccagcccauccucaucgcugugggugcugcagcugucccagcagcugucggguaucaa ugcuguguucuacuacucaacgagcaucuucgagaaggcaggugugcagcagccuguguacgccaccaucggcuccgguauc TABLE 3-continued RNA transcripts up-regulated during HF stem cell activation.

| SEQ ID No: | Access. # | Sequence |
|---|---|---|

gucaacacggccuucacuguggugucgcuguuuguuguagagcgagcuggacgacggacccugcaccucauuggccuggcu ggcauggcaggcugugcugugcucaugaccaucgcccuggccuugcuggaacggcugccuuggauguccuaucugagcauc guggccaucuuuggcuuuguggccuucuuugaaguaggcccugguccuauuccaugguucauuguggccgagcuguucag ccaggggccccguccugcugcuauugcuguggcuggcuucuccaacuggaccucaaacuucauugugggcaugugcuucca guauguggagcaacugugcggccccuacgucuucaucaucuucacggugcuccucgugcucuucuucaucuucaccuacuu caaaguccccugagaccaaaggccgaaccuucgaugagaucgcuuccggcuuccggcagggggggugccagccaaagugacaag acacccgaggagcucuuccacccucugggggcggacucccaagugugaggagccccacacccagcccggccugcucccugcag cccaaggaucucucuggagcacaggcagcuagaugagaccucuuccgaaccgacagaucucgggcaagccgggccugggcgc cuuuccucagccagcagugaaguccaggaggauauucaggacuuugauggcuccagaauuuuuaaugaaagcaagacugcu gcucagaucuauucagauaagcagcagguuuuauaauuuuuuuauuacugauuuuguuauuuuuuuuuuuuaucagccac ucuccuaucuccacacuguagucuucaccuugauuggcccagugccugagggugggggaccacgcccuguccagacacuugcc uucuuugccaagcuaaucuguagggcuggaccuauggccaaggacacacuaauaccgaacucugagcuaggaggcuuuacgc uggaggcgguagcugccacccacuuccgcaggccuggaccucggcaccauaggggguccggacuccauuuuaggauucgccca uuccugucucuuccuacccaaccacucaauuaucuuuccuugccugagaccaguuggaagcacuggagugcagggaggaga gggaagggccaggcugggcugccagguucuagucuccugugcacugagggccacacaaacaccaugagaaggaccucggagg cugagaacuuaacugcugaagacacggacacuccugcccugcuguguauagauggaagauauuuauauauuuuuugguugu caauauuaaauacagacacuaaguuauaguauaucuggacaaacccacuuguaaauacaccaacaaacuccuguaacuuuacc uaagcagauauaaau ggcugguuuuuag 144 X64837 Sequence below.

gcuuucuaaacuagcaagcaucgugugggguccuucaggagugggagugcagacagaccugacagcguccgcuaagcgacacu gacuguacuuccacuccugaaggacccacacgaugcuuucuaaacuagcaagucugcagaccauugcugcucugcgccgagg aguccacaccucagucgccucugccacgucuguugccacaaagaagacagagcaaggcccaccauccuccgaguacauuuuug aacgggaaucuaaauaugguguccacacaauuaccauccuuugccuguagcccuggagagaggaaaaggcauuuauauguggga uguggaaggcaggcaguacuucgauuuccugagugcuuauggugcugucagccaaggacacugccacccaaagaucauagau gccaugaagagucagguggacaagcugacauuaacaucucgggcuuucuauaacaauguccuuggugaaauacgaggaguaca ucaccaagcuuuucaacuacaacaaaguucucccuaugaaauacaggaguggaggcuggagagacugcauguaagcucgcucg ucguuggggcuacaccgugaaaggcauccagaaauacaaagcaaagauuguuuuugcugaugggaacuuuuggggucgaac acuaucugcaaucuccaguuccacagauccgaccaguuaugauggcuuuggacccuucaugccaggcuuugaaaccauccca uauaacgaucugcccgcacuggagcgugcucuucaggauccaaauguugcugccuucaugguggagcccauccagggugaa gcaggcguuaucguuccggauccaggauaccugacaggaguucgggaacucugcaccaggcaccagguccuguuuauugcu gaugaaauacagacaggauuggccagaacugguagauggcuggcuguggaucaugagaaugucagaccugauaugguucuu cuugggaaggcccuuucuggcgguuuauacccugugucugcagugcugugugacgaugagauaaugcugaccauuaaacca ggcgagcacggcuccacauacggcggaaacccacuaggcugccgaauugccauugcggcucuugagguuuuagaagaggaga aucuugcugagaaugcagacaagaugggcgcuauccugaggaaggagcucaugaagcugccccucugacguugugaccucag ugagagggaaaggguugcuaaaugccauugucaucagagaaaccaaagacugugaugcuuggaaggugugccugcgacuuc gagauaacgggcuucuggccaagccaacccacggugauaucaucaggcuugccccuccccuugugaucaaggaggaugagau ccgggaguccguggagaucaucaacaagacuaucuuguccuucugagaguaggaacucuggggagccaucuucagacagggc TABLE 3-continued RNA transcripts up-regulated during HF stem cell activation.

| SEQ ID No: | Access. # | Sequence |
|---|---|---|

ucuugugaaacucugcuugcaguggccagagccugucuccugaaaggcauauauuucaguugaugcauaauagagugacac cuaggaaccugcagguggcugcgugacagaaaagugagagcgagaggcgaggcgucucuuuguugagguuugacugugugg gaacuuucuaaggagaaacggacccaucugcguacagccugcagauggaggccugcagucauuuacgugcgucuuuacaguu uccuugcugaugugaaugguuuguauuuagaaguuauuucugagauacuacagaacaguuaaaucauuauaaucaaugaau guuaaguugauugaagguuaagcauauguaaaauacuaguuuaaaguaaacuuuucauuggccaacaccagaauguauuau auagauucugagaauucauuacuaaauuacacuuugcuugauugcaauuuguaaaacauuuauuuucaguauuucuuugaa uaaagcuuaauguuucuuuuuacgccaacagaguauuuuguauuuccauuuugguaauaaucaguguauuauuucauccu gaugacuggcauuucaucaccuauugagaucacuggguguguuucaggccuuuuauucuaaauaaagcuaugaccaguuuc ugucugu

| | | |
|---|---|---|
| 145 | AI843119 | uuuuuuuuuuucuuuuccgacgcccacaagaggaauaagagauuuaaugauggaaagua uggggaaaucacaguuuucagacaugaguaaucaaaaacuugacauuuuucuugauaucc aaaucuagaugucuguaucaaaccagaggugauggccuuggggauggcagugaagacugu uaggaccauuagaucagau |
| 146 | AI837786 | uuuuuuuuuuuuuuuuacaguuuuaaaacaauacacagcuuucucgggcugaagcaauu gcaagaacguauugguauugguauauuacagcuacauacaagguuuaugaauagcaaugg agaaaaaauaaguuauuuaaauauugacuucauaaagagaaagugcaauguuguuaguugu cauaucacuugcuugacaguuuguggggguuucuucccuaucaauuuuaacaaucaagaua acauggacucaagacagaauuuuucgggaaccucacucaguccucacacagcagugacuu gggaaucuacguguguuccaccgcaguugugaaacacacuacuccguguccaggacucau uucucagagaagaaucaauucgaguuccauccacaccuggggucgggacaca |
| 147 | U41465 | Sequence below. |

ccgggcucgaauucucuagacucgaguuuagagaauucgagcucucccaguuuaaagcaaaauuuuggacugugaagcaa ggcacugggcaaacacaacauggccuccccggcugacagcuguauccaguuuacccggcacgcuagugauguucuucucaac cuuaaucgccuccggagucgggacaucuugacggacguugucaucguggugagccgugagcaguuuagagcccauaagaca gugcucauggccugcagcggccuguucuacaguaucuucacugaccaguugaaaugcaaccuuaguguaaucaaucuagauc cugaaaucagcccugagggguuuugcauccuccuggacuucauguacacaucuaggcucaaccugagggaaggcaauaucau ggcggugaugaccacagccauguaccugcagauggagcauguugucgacacaugcaggaaguucaucaaggccagugaagca gaaauggccccugcacuuaaaccuccccgugaagaguuccugaacagccggaugcugaugccccaugacaucauggccuacc gaggucgugaggucguggagaacaauaugccacugagaaauacucccgggugugagagcagagcuuuugcuccuccucugu acaguggccugucaacaccaccagccucuuaucccauguacagccaucucccgcucagcaccuucccucuucucugaugagga gcuccgagaugccccccgaaugccuguggccaacccuuuucccaaggagcgugcccuccccugcgacagugccaggcaaguc ccuaaugaguauagcaggccagccauggaggugucccccaguuugugucacagcaacaucuacucgcccaaggaggcagucc cagaggaggcucggagugacauacacuacagugugccugagggccccaagccugcugucccuucugcucggaaugcuccaua cuuccccugugacaaagccagcaaagaagaagagagaccuucuucggaggaugagauugcccugcauuucgagcccccaau gcacccuugaaccggaagggucugguuaguccccagaguccccagaaauccgacugccagcccaacucacccacagaguccug cagcagcaagaacgccugcauccuucaggccucuggcucuccgccagccaagagccccacugacccgaaagccugcaacugga agaaguauaaguucaucguucucaacagccucaaucagaaugccaaacccgagggcucugagcaggcagagcugggucgccu cuccccucgagccuacccugcaccgcccgcuugccagccgccuauggagcccgcgaaccuugaucuccagucccgaccaagc ucagugccaguggggaggacucuaccaucccccaagccagccggcucaauaaucucgugaacaggucccugggaggcucccc ccgaagcagcagugagagucacucaccacucuacaugcaccccccaaagugcacauccugcggcucucaguccccacagcaua cagagaugugccucccauacugcugggcccacguucccggaggagauggggggaaacccagucagaguauucggauucuagcu gugagaaugggaccuucuucugcaacgaaugugacugccguuucucugaggaggccucgcucaagaggcacacgcugcagac gcacagugacaaaccauacaaaugugaucgcugccaggccuccuuccgcuacaagggcaaccucgccagccacaagacugucc TABLE 3-continued RNA transcripts up-regulated during HF stem cell activation.

| SEQ ID No: | Access. # | Sequence |
|---|---|---|
| | | acacgggugagaaacccuaucgcuguaacauuuguggagcgcaguucaaucggccagccaaccugaagacccacacucgaau<br>ucacucuggagaaaagcccuacaaaugugaaaccuguggggccagguuuguucagguggcccaccuccgugcccacgugcuc<br>auccacacuggagagaagccguaccccugugaaaucuguggcacucgcuuccggcaccuucagacucugaagagccaucugc<br>gcauccacacaggagagaaaccuuaccauugugagaaguguaaccugcacuuucgucacaaaagccaacugcgacuucauuu<br>gcgccagaagcacggcgccaucaccaacaccaaggugcaauaccgcgugucggccgcugaccugccuccggagcuccccaaag<br>ccugcugaaugaagcauggaguguuccucgcccuuuccucuccagccccuucucagaaucuacccaaaggaugcuguaacac<br>uuuauacaaaggucaucccaugauguagugccucucucauccacuagugcaaaucauaguugggguggggguggg |
| 148 | U70494 | ucgcgguccgacggaggagugggcgcugggaucucgcugagcguccgccuggccucgucu<br>cuuccucgcucgucggagcuucagcacgguccgagauggcuggcgguaaggcuggaaagg<br>acuccggaaaggccaagacaaaggcgguuucccgcucgcagcgagccggcuugcaguucc<br>cugugggccguauucaucgacaccugaaaucuaggacaaccagccacggacgugugggcg<br>cgaccgccgcuguguacagcgcagccauccuggaguaccucaccgcagagguacuugagu<br>uggcaggaaaugcgucaaaagacuuaaagguaaagcguaucaccccucgucacuugcagc<br>uugcuauacguggagaugaagaauuggauucucugaucaaagcuaccauugcugguggug<br>gugucaucccacacauccacaaaucgcugaucgggaagaaaggacaacagaagacuguuu<br>aaggaugccuggauuccuuauuaucucaggacucuaaauauuccuaacagcuguccagug<br>uuggugauuccaguggacuguaucucugugaaaaacacaauuuugccuuuuuguaauucu<br>auuugagcaaguuggaggcuuaauuagccuuccaaccaaccaaauuucugcauucgaguc<br>uuaaccauauuuaaguguuacuguggcuucaaagaagcuauugauucugaaguagugggu<br>uuugauugaguugacuguuuuuaaaaaacuguuuggauuuuaauugugaugcagaaguua<br>uaguaacaagcauuugguuuuguacagacauuguuuccacucugguggauaagcucaaua<br>aaggucauaucccaaacuagcuuuaaacuugcuuaauaaucgggucuuaccuuagaucuc<br>acucagcaacaaguacauucucugcuuacuaauuaaacagugcaucuguagucauaaaaa<br>aaaaaaaaaaaaaaaaaaaaaaaaaaaaa |
| 149 | D17666 | Sequence below. |

caccaccgugcacgcagcuccgggcccgugggguguugguucuugcccucguaaccccucuguccagccaccaugauaagc gccagcagagccgcggccgcgcgucucgugggcaccgcugcgucccggagccccgcagccgcccguccccaggugagaagcu gccaugccuuccgguggggcuccaggcccggacucgagugaggcaggccuugccuucgggucagacucuaggaaaaauccg gagcgaagggauguaacggaccuucugugggcauuguuggccuucuugcagggcuuuagcuucgaacugugcugagucaca auccuuggcguuccuaagucuuuaccccgcuaauugagacgucugucccccucuaaccugugcgcuuugaaugugccugg acuuaggcaguggacguaguuuacuggaaannnnnnnnnnnnnnnnnnnnnnnnnnnnnnnnnnnnnnnnnnnnnnnn nnnnnnnnnnnnnnnnnnnnnnnnnnnnnnnnnnnnnnnnnnnnnnnnnnnnuuuuacauacuaaggacuaaagcuug cauguguuccucagaauaugaaaagcccaaguucuuguguaguugauggcugaugcaacuuuuuucccccaggauggcug gaauggccuuagccaugaggcuuuuagauuuguuucaagaagagauuaugcguaaguacaaccucaguuucucugagaaaa aaaaaaaacacuuauugaaccucaaagcuuggauggguugggugcguuauacauuuguacuuguaguuuauucaauaugcc acugguaacaccaacauaaaacacaguucuucguauuggagaccacuguucagaugaccauggaauuucauuucuuacagau cagaagcaaucaagggugcagugguugguauugauuuggguacuacuaacuccuguguggcuguuauggagggcaaacaag caaaggugagcaugauuggaaaccugaggucacuuagauacccagucuggcauuaaguacauaggaaugcugagucggagcc cagguuaguggugggcacuuuaauccuaguaaaggcagagggaucucugaguucaggaccagccuagaguacaaagugagn nnnnnnnnnnnnnnnnnnnnnnnnnnnnnnnnnnnnnnnnnnnnnnnnnnnnnnnnnnnnnnnnnnnnnnnnnnnn nnnnnnnnnnnnnnnnnnnnnnnacuuuaaucagugucuuugggaauuuuagguccuggagaaugcugaaggugccaga acuaccccuucugugguugccuuuacagcagauggagaacgacuuguugguaugccagcaaaacggcaagcugucaccaauc caaacaauaccuucuaugcuacuaagcgucuuauuggacgacgauaugaugacccugaaguacagaaagacacgugaguaau aggaaaaucaguccagaagacuggugcuuugaucaaaguucuguggauaccuugaguucuguggaucaccuuggaucacuu uuucauuauuucugcuugggaagaaaucacaccaccaucagaggcauauagguuuuuuuuuguuauuucuuuguuguug uuguuuuccuauuuauuuguuuguuuguuugggggggggguuucuuuguguauuuuccuggaacucauucuguagaccag TABLE 3-continued RNA transcripts up-regulated during HF stem cell activation.

| SEQ ID No: | Access. # | Sequence |
|---|---|---|

gcuggnnnnnnnnnnnnnnnnnnnnnnnnnnnnnnnnnnnnnnnnnnnnnnnnnnnnnnnnnnnnnnnnnnnnnn nnnnnnnnnnnnnnnnnnnnnnnnnnnnnucaugugauauaugaugaacuuagagugguuaaguuucacagggauaguu uacuuacauaaucuuucugucuuuaaguaagaauguuccuuuuaaaauuguccgugccuccaauggugaugcuugguuga ggcucauggaaaacucuauucuccaagucagauuggagcauuuguguugaugaagaugaaagagacugcagguaaguggau uuauuucacauuuaggaaaauuggaaugugcuguuuauuucucugcauuaauacugauuaacuucauauucuguagauaau ggagucugaagcuunnnnnnnnnnnnnnnnnnnnnnnnnnnnnnnnnnnnnnnnnnnnnnnnnnnnnnnnnnnnnn nnnnnnnnnnnnnnnnnnnnnnnnnnnnnnnnnnnnngaauucaugcuccuccugcugccuccugggugcuaaguugca aggugauagcucagguacucacucuagugucuuucuugggggugcucuuuuccaaggccucucuacauauuaagccacaaag gagucuguugccccucaagaggaugagauguggaauauuaggcuacaguuuuguugccuuuuuuuuauuuuccuaacaug guaccacaauugaauuuuauucuuuguuucccagaaaauuacuugggccacacagcaaaaaaugcugugaucacagucccug cuuauuucaaugauucacagcgacagguaaaauuagaucucuuguuugcugggaguggagguggguaccugaguuaaagg auggaaagauagauuuauuucuacuuucucuaggccacuaaggaugcuggccagauaucugggcuaaaugugcuucgagug aucaaugagccuacagcugcugcucuagcuuacggucuggacaaaucugaagauaaaguguaaguuggucagaugacguagc auuaccugcauuuacagggguuguguguguguguguguguguaauuuuacuacaauuuguguggguccgugugu ugu gguacauuuguacauuuguacauggcauggauauggaugucaaagauunnnnnnnnnnnnnnnnnnnnnnnnnnnnnnn nnnnnnnnnnnnnnnnnnnnnnnnnnnnnnnnnnnnnnnnnnnnnnnnnnnnnnnnnnnnnnnnnnnnnaaaccagu aguuggugugu uacuaauuuuacuuguuucuguaugacaugcuuauaugauacguuaacaggcaugccacuuagguugau aacuacauucaguuauuaaguauuucaggaaauaucauaguuaauaauuaaacuuuuggucuuuuaauucguuccuuuguu uuguuccuuggaacuuaacuuacuuauuuauuuuuuagcauugcuguguaugauuuagguggugga accuuugacauuuc uauccuggaaauucagaaaggaguguuugaggugaaaucuaccaauggggacacuuucuuaggaggggaagacuuugacca agcuuuguugcggcacauugucaaggaguucaagagagagguuaguuaccacugcuuagucaccacugguuaagguguagg cguugg uuguugagaauuuuuguuuguuugcauugcuuuuagcuuuguuaauagcuuuuuuauacuaagguaacuaac uauacuucagauucaugguaaacuaaaccaguuuaguuauauaaucuuagauugggaacaaaagaccaagugacaguguua uaguagggagaagnnnnnnnnnnnnnnnnnnnnnnnnnnnnnnnnnnnnnnnnnnnnnnnnnnnnnnnnnnnnnnn nnnnnnnnnnnnnnnnnnnnnnnnnnnnnnnnnnnnacuacucucucgcagucuauauaugucuccuaauccuauuuau agacagggguugauuugaccaaagacaacauggcgcuucagaggguucgggaagcugcugagaaggcuaaaugugaacuuu ccucaucugugcaggugagggauggaaaaaucccaguacugagcauauuugaauaguguauucuaauuuaccuaaugucag uguagcucuuuacaguuuucuguuggcugaaaacuuggggcaugagcaaaggaacaacuugaugaucaguucuuuucauuu gaaugaaugaaguagauuuauggaugugugu aucuuuugccugcaugugugucuguacuacauuugugcuugguuucugu ggcggccagaagaggguaucagaacugacaugucaguguuggggannnnnnnnnnnnnnnnnnnnnnnnnnnnnnnnnn nnnnnnnnnnnnnnnnnnnnnnnnnnnnnnnnnnnnnnnnnnnnnnnnnnnnnnnnnnnnnnnnnnnncacacugaguc uaaauucugaucaugucuuucagucguguuauguuacuuugagugaguaucaaagaucacgucucccaucugacgugugg u ccugugcagacugacaucaacuugccauaccuuaccauggaugcuucuggaccaaagcauuugaauaugaagcugacucgag cucaguuugaaggcauugucacagaucuaaucaagagaacuauugcuccgugucagaaagcuaugcaggaugcagaagucag caagagugacauaggagaagugauucugguugguggcaugacaaggaugcccaagguauggacucaugguauuucuccuag aggaaaaaaauaacaaugcauucuugaggcaaauggcuuguguugugugugga aacaaaugugauccauucuucuaguguu cuuuaaagagugg ugagaccagacucaccaaaaagugcuuuuagucgccugugauggcucauguaggaggauggccuugag TABLE 3-continued RNA transcripts up-regulated during HF stem cell activation.

| SEQ ID No: | Access. # | Sequence |
|---|---|---|

uucugggutaagaugcagcuacagaauucuaccuugcacacacacuuaaacccagucugguaaagagaaguuguuaagcuunn nnnnnnnnnnnnnnnnnnnnnnnnnnnnnnnnnnnnnnnnnnnnnnnnnnnnnnnnnnnnnnnnnnnnnnnn nnnnnnnnnnnnnnnnnnnnnncagauguaaaauugauaaauacuucuuccuaagauugggcgauuguguagaauaugaga acuguauuuuauaaccccuugucaugugccuucuauuucaaaugauauccucugggaagcuagauaauuaaauucuucucu cauuuaaguggacaguggaugagaugcucugaaguugucaaauacaaacaagucugcagucuuggauaugaaucucucuga cuugcugucuggcaggcguauucuguuuggcuccaucagucgcccugggguguuggcuaacagguucuuucucccugaugc uuagguucagcagacuguacaagaucuuuuggcagagccccgaguaaagcuguuaauccugaugaggcuguagccaucgg agcugccauccagggaggugugugguuggcuggugacguuacagacgugcugcuccuggaugucacucccccucucucuggguau ugagacucugggaggcgucuuuaccaaacuuauuaauaggaacaccacuauuccaaccaaaaagagccagguaagagccauu cuuuuuuccugccuauuaacagucccaaguuguacaagugcuguuuacaaucacuuuaugaacucuuuaaaacuuuguuuc uaagacuauacuaacuggacugggugnnnnnnnnnnnnnnnnnnnnnnnnnnnnnnnnnnnnnnnnnnnnnnnnnnn nnnnnnnnnnnnnnnnnnnnnnnnnnnnnnnnnnnnnnnnnnnnnnnnnnnncuagguguuuucuacugcugcugauggac aaacucaaguagagauuaaagugugucaggggggaacgagagauggcuggagacaacaaacuucuaggacaguucacuuuggu aaguguuuugagucugaguaucaugcuuuuggggucuauagcuugcaaagcuccaaacugcugacauuacaggcauauug uguuauuuuuaaaaagaacguuauguacaugaguuaugaaacccaugauuuuaguuuuuuaccuaaagugcuuuguguu uucagaauuugaaauuuucaaagccugggaaauguucagacucagaagcaaugcuaacucagaaguuaguuuuauccugau uacucauuuuaaaaaacuuaauagcuacugguucuggucagcauugcuacaguagagaaguuuauuugcuguaaauucugg gcacauauaaccaucaugguuauuaacuucuugaagcccagugauuucagaaagcacuaaaacuaccaccaucacuuaaaauc ucaagguuuugaacauucagugaagauacuuguuuuaggaaacaagugguuaguuggccugauuuggaaaugagaauacau gggccuuucaaaggagcucacucuggauauuuauuuuagauuggaauucccccagccccucguggagugccccagauugaa guuacauuugacauugaugccaaugggauugugcacguuucugccaaagauaaaggcacuggucgugagcaacaga 150 X14897 Sequence below.

auaaaauucuuauuuugacacucaccaaaauagucaccuggaaaacccgcuuuuugugacaaaguacagaaggcuuggucaca uuuaaaucacugagaacuagagagaaauacuaucgcaaacuguaaauagacauuacauccauaaaaguuccccaguccuuau uguaauauugcacagugcaauugcuacauggcaaacuaguguagcauagaagucaaagcaaaaacaaaccaaagaaaggagcc acaagaguaaaacuguucaacaguuaaauaguucaaacuaagccauugaaucuaucauugggaucguuaaaaugaaucuuccu acaccuugcaguguaugauuuaacuuuuacagaacacaagccaaguuuaaaaucagcaguagagauauuaaaaugaaaaggu uugcuaauagaguaacauuaaauacccugaaggaaaaaaaaccuaaauaucaaaauaacugauuaaaauucacuugcaaauua gcacacgaauaugcaacuuggaaaucaugcaguguuuuauuuaagaaaacauaaaacaaaacuauuaaaauaguuuuagagg ggguaaaauccagguccucugccaggaugcuaaaauuagacuucaggggaauuuugaagucuucaauuuugaaaccuauua aaaagcccaugauuacaguuaauuaagagcagugcacgcaacagugacacgccuuuagagagcauuacuguguaugaacaug uuggcugcuaccagccacagucaauuuaacaaggcugcucagucaugaacuuaauacagagagagcacgccuaggcagcaag cacagcuugcugggccacuuuccucccugucgugacacaaucaauccguguacuugguguaucugaagcgcacgcugcaccg cggcacugcccggcggguuucugggcggggagcgauccccgcgucgcccccgugaaaccgacagagccuggacuuucagga gguacagcggcggucugaaggggaucugggaucuugcagagggaacuugcaucgaaacuugggcaguucuccgaaccggag acuaagcuuccccgagcagcgcacuuuggagacguguccggucuacucccggacucgcaucucauuccacucggccauagccu uggcuucccggcgaccucagcgugguucacaggggcccccccugugcccagggaaauguuucaagcuuuucccggagacuacga cuccggcucccgguguagcucaucacccuccgccgagucucaguaccugucuucgguggacuccuucggcaguccacccacc TABLE 3-continued RNA transcripts up-regulated during HF stem cell activation.

| SEQ ID No: | Access. # | Sequence |
|---|---|---|

gccgccgccucccaggagugcgccggucucggggaaaugcccggcuccuucgugccaacggucaccgcaaucacaaccagcca
ggaucuucaguggcucgugcaacccacccucaucucuuccauggcccagucccaggggcagccacuggccucccagccucca
gcuguugacccuuaugacaugccaggaaccagcuacucaaccccaggccugagugccuacagcacuggcggggcaagcggaa
gugguggg ccuucaaccagcacaaccaccaguggaccugugucugcccguccagccagagccaggccuagaagaccccgagaa
gagacacuuaccccagaagaagaagaaaagcgaaggguucgcagagagcggaacaagcuggcugcagcuaagugcaggaaccg
ucggagggagcugacagaucgacuucaggcggaaacugaucagcuugaagaggaaaaggcagagcuggagucggagaucgcc
gagcugcaaaaagagaaggaacgccuggaguuuguccugguggcccacaaaccgggcugcaagauccccuacgaagaggggc
cggggccaggcccgcuggccgaggugagagauuugccagggucaacauccgcuaaggaagacggcuucggcuggcugcugc
cgcccccuccaccacccccccugcccuuccagagcagccgagacgcacccccaaccugacggcuucucucuuuacacacagug
aaguucaaguccucggcgaccccuuccccguuguuagcccuucguacacuuccucguuuguccucaccugcccggaggucuc
cgcguucgccggcgcccaacgcaccagcggcagcgagcagccguccgacccgcugaacucgcccucccuucuugcucuguaaa
cucuuuagacaacaaaacaaacaaacccgcaaggaacaaggaggaggaagaugaggaggagaggggaggaagcaguccgggg
gugugugugggacccuuugacucuucugucugaccaccugccgccucugccaucggacaugacggaaggaccucccuuugu
guuuugugcuccgucucugguuuucugugccccggcgagaccggagagcugguugacuuggggacagggggugggggcggg
gauggacaccccuccugcauaucuuuguccuguuacuucaacccaacuucuggggauagauggcuggcugggugggguaggg
uggggugcaacgcccaccuuuggcgucuugcgugaggcuggaggggaaagggugcugagugugggggugcagggugggguug
aggucgagcuggcaugcaccuccagagagacccaacgaggaaaugacagcaccguccuguccuucuuuccccccacccaccca
uccacccucaaggg ugcaggg ugaccaagauagcucuguuuugcuccccucgggccuuagcugauuaacuuaacauuuccaag
agguuacaaccuccuccuggacgaauugagcccccgacugagggaagucgaugcccccuuugggagucugcuaaccccacuu
cccgcugauuccaaaaugugaaccccuaucugacugcucagucuuucccuccugggaaaacuggcucagguuggauuuuuu
uccucgucugcuacagagccccucccaacucaggcccgcucccaccccugugcaguauuaugcuaugucccucucacccuca
cccccaccccaggcgcccuuggccguccucguugggccuuacugguuuugggcagcagggggcgcugcgacgcccaucuug
cuggagcgcuuuauacugugaaugagugg ucggauugcugggugcgccggaugggauugacccccagcccuccaaaacuuu
cccugggccuccccuucuuccacuugcuuccucccucccccuugacagggaguuagacucgaaaggaugaccacgacgcaucc
cgguggccuucuugcucaggccccagacuuuuucucuuuaaguccuucgccuuccccagccuaggacgccaacuucucccca
cccugggagccccgcauccucucacagaggucgaggcaauuuucagagaaguuuucagggcugaggcuuuggcuccccuauc
cucgauauuugaauccccaaauauuuuuggacuagcauacuuaagagggggcugaguucccacuaucccacuccauccaauu
ccuucagucccaaagacgaguucugucccuucccuccagcuuucaccucgugaaucccacgagucagauuucuauuuuuu
aauauuggggagaugggcccuaccgcccguccccgugcugcauggaacauuccauacccuguccugggcccuagguuccaa
accuaaucccaaaccccacccccagcuauuuaucccuuuccugguucccaaaaagcacuuauaucuauuauguauaaauaaau
auauuauauaugagugugcgugugugugcgugugcgugcgugcgugcgugcgugcgagcuuccuuguuuucaagugugc
uguggaguucaaaaucgcuucuggggauuugagucagacuuucuggcugucccuuuuugucaccuuuuuguuguugucuc
ggcuccucuggcuguuggagacagucccggccucucccuuuauccuuucucaagucugucucgcucagaccacuuccaacau
gucuccacucucaaugacucugaucuccggunugucuguuaauucuggauuugucggggacaugcaauuuuacuucuguaa
guaagugugacuggg ugguagauuuuuuacaaucuauaucguugagaauuc 151 AJ006289 Sequence below.

caccugauucccggaggcccgagcccuuagucugggcggggguggcgcgggccggaaggacgccaucccggccugggccaugg
aggcucccgcaccgucccucacggaggaggauuugacugaagugaagaaggacgcuuuagagaauuuacguguuuaccugu TABLE 3-continued RNA transcripts up-regulated during HF stem cell activation.

| SEQ ID No: | Access. # | Sequence |
|---|---|---|
| | | gugagaaaaucauagcugagagacauuuugaucaucuacgugcaaaaaaaauacuaaguagagaagacacugaagaaauuuc<br>uugccgaacuucaaguagaaaacgggcugggaaguuguuagacuacuuacaggagaaccccaggggccuggacacccuggug<br>gaauccauccgcagggagaaaacacagagcuuccugauucagaagauaacggaugaggugcuaaagcuucggaauauaaaac<br>uggagcaccucaaaggccugaagugcagcagcugugagcccuuugcagccggagccaccaacaaccucucuaggugcaauuc<br>cgaugagagcaaucucucugagaaacagagagcauccacugucauguaccacccggagggagaguccagcacggcucccuuc<br>uucucuauggcgucgucccugaacuugccaguccuggaaguuggcaggacugaaaacagcagcuucucuucagccacucuuc<br>cucgaccuggggacccuggggcucccccuuugcccccagaccuucgguuggaagagggggggaaguuguggaaacucaagug<br>agauguuucuccccuuacggucacgggcucuuucacgccaaugauacaucaccgccuaguuguuuuacuagugaugcaaaau<br>gcugugaaggaggccaucuuucuauacaaaccacggugacaggucacucacauucgaugcgugccuuuaaaaucaguguaca<br>cauucucuguaaauaggauuuguuaggguaaagaagcgcucuggggcggcgugguguaaucaugguggucgugacuuuuc<br>cauaauguccuuucuuuuuuauuauuuuuagguguuugcguauuuugaacuuuucauaagauuaauuuuaucggaauauu<br>ucucaauuugagaaaacaacuuguggauugggaauaauguuuuuagcacauuuaugcuacaaauuuucagucugauuguuu<br>uucccacugaucuggcaguauauuuuagcaguaagcuguugugugucaggaaagcuggacacgggaaagcugccgacacac<br>ucagcagugucccacuccuuaguucugagaagccgucggguucugaggagacaccugguggcacugagccuggugaccuca<br>gugggccaaaauuuguuuuauacucacccugccagcgugagugucuuacuuucacaggccuuguguccucagucuuaucuu<br>aaaggauguuaucuuggcagggcaucacuuguaauuaauggaugauacuuguaauugacuaaaguccucgcucugagccgu<br>uuguucuggcuccgagagcgcugacaugugaagcauggugagcagcgagggaacugacaggauguggccguggccagugug<br>gcuuuaguguuugcaucaggcagccaccagcuccauccguguucuuacugcuuuacaaaguuugacuaacuuuacacauuu<br>uaaaaaugcugauugucuucguuuaaauuauaauuuuaccuauuucuugacaucuaacuccuauuuauuucuauuauuuaa<br>aaauuaagaaaugaaaauuugcuauuaacaauaaaguuuuuuuaaugu |
| 152 | X12944 | Sequence below.<br>ggggggggggggucagcgccgacguccccugccgccaccaugcccaaaagaaaggcugaaggggaugcuaaaggagacaaaa<br>ccaaggugaaggacgagccacagagaagaucugcaagguugucugcuaaaccugcuccuccaaagccagagcccaaaccuaaa<br>aaggccccugcgaagaagggagagaagguacccaaggggaagaaggggaaagcugacgccgggaaggaugcgaauaauccug<br>cagaaaauggagaugccaaaacagaccaggcacagaaagcugaaggugcuggagaugccaagugaugugugugcauuuuuga<br>uaacuguguacuucuggugacuguacaguuugaaauacuauuuuuuaucaaguuuuauaaaaaugcagaauuucguuuuac<br>uuuuuuuuuuuuuuuaagcuauauuguuagcacacagaacacuucauuacuggguggggaaggaucaugugucaguaac<br>aaaaucucucccaagcuggauugaggacagaaaaccucuuucccugauaauuuuggaaggcuccuguuggcucccaggagag<br>agauccuggucuugaccuagguggccaccaaggcacaacaaugccuuguggucugggaaaacuauaaauucacuuuuauauc<br>cucuuccccuguacuaucaacauagacuuaauucccuuaaaaaccagagaccuguuggaaccuggcccccaaaauugguuu<br>cccaguccauugagugauggggacuuugcagugacuucauugaguguucucaaaagagcacugguuccuuuuauaaaagau<br>uguggaucuucagauugauaauucugccuaaaagucagggucggcuugugaaaaguuguuaaaacaacauccuuaauguga<br>aaugucaacccucacucuaagcuacuucccccuuuucaaagcauugaaugaagacuucauuggguuuuauaguggcuuucu<br>gauuuugguagucauaucagaagggaauuuggaaguucuuguauauuguugcauugucugcccauguccugccugaauacc<br>augauuguuuaugaaagaaucuuaauaaagcugguuacaguuaggcuggaaaa |
| 153 | AW061302 | uuuuuuuuuuuuuuuuuuggaaguccauaaguaguuuauugucuucaagacuacagugugg<br>auuccucucccagagaagggucuuucagaggcaggggacugucacccaggugcaggccgu<br>cuacuugucauuuucauacauggcuggauucuuccuuuucgacugcucaaacuccugguu<br>gccccauguguagaucagguagaccacuacaaacggcggcgccacgcgcaggaugcgcuc |

TABLE 3-continued

RNA transcripts up-regulated during HF stem cell activation.

| SEQ ID No: | Access. # | Sequence |
|---|---|---|
| | | gcgagugcggcgcaacacguuggggaugccuuugcugaaauagcuugggaaggcgcgcug cucaaagggcgacaagcugua |
| 154 | U67328 | Sequence below. |

caugaagccagagauguggaagaugugucuagacugcaucaaugaacugauggauacguuggaugcacauuccaacaucucu gucggagagaacauuuuggcagagagugagaacuuacacaacuuugaucaguucacucccguguacgacgcugcauccuaacu uugguggagcgaauggaugaagaauuuaccaaaauaaugcaaaauacugauccucacucccaagaguauguggagcaccuga aggaugaggcacaagugugugcaucauugagcgagugcagcgcuaccuggaggagaaagguaccacugaggagaucugccag aucuacuuaaggcgcauccugcacacguacuacaaguuugacuacaaggcccaucagcggcacguuacucccuccugaaggau ccucaaagucugagcaagaccaggcagaaaaugagggugaggacucagcugugcuaauggaaagacugugcaaguacaucua ugccaaggaccguacagaccggauccguaccugugccauccucugccauaucuaccaucaugcgcucccacucccgcugguau caggcccgugaccucaugcucaugagccaccuacaggacaacauucagcacgcagacccgccggugcagauccuguauaaccg uacuauggugcaacugggcaucugugcuuuccgccaaggccugacaaaggaugcacacaauggcacuucuggauauucaguc aaguggugggugccaaggagcuucuaggucaggguugcugcugcgcgcuugcaggagcgaaaucaggaacaggaaaaggua gagcgacgccggcaggugcccuuucaccugcacaucaaccuggagcugcuggagugugucuaucuggugucagcuaugcuc cuggagauccccuacauggcugcccaugagagcgaugcccgccgacgcaunaucagcaagcaguuccaccaccaacugcggg ugggcgagcggcacgcccugcuagguccucccgagucaaugagggagcauguggucgcugccuccaaggccaugaagaugg gcgacuggaagaccugccacaguuucaucauuaaugaaaagaugaaugggaaagugugggaccuuuucccugaggcugacaa aguucgcaccaugcuaguucggaagauccaggaagagucucugaggaccuaccuuuuuaccuacagcagugucuaugacuca aucaguauggagacacuaucagauauguuugagcuggaucuacccacuguucacuccaucaucagcaagaugaucauuaacg aagaauugauggcuucccuggaccagccgacacagacugguggugaugcaccguacugagccccucugcccagcaagaaacuug gcucugcaagcuggcugagaaaacuuggcacccuaguggagaauaauggacggguguuugaccaaaaacagggaaccuaugg uggcuauuuccgagaccccaaggguggcuaccggaaaaauggaggcuaaaugccccgugguggcuacccccagcaacagucu cagacaaccuccugaguuccccacuucagucacccuguggacagaccaucuaaccuuuuucuccuaacucaccccaaucauua aagaucuuuugaggaauuaaaaaaaaagaaagaaaaaaaaaaaaaaaaaaaaaaaaaaaaaaaaaaaaaaaaaaaaaaaa

| SEQ ID No: | Access. # | Sequence |
|---|---|---|
| 155 | AI604314 | uuauuaauuaaaaaacaauuuauugaaaaagaguagugcuuuguacaaauucccauugca gcccccagauaucaacugaucucuuuccagcuuugguaguaggguauaaaaaauaucaaaa cuagguaaguucugauguaagauuucuaugggauuauuuuagaauauauagauuugugua guuuggcaaguaucauuucuaugcauuuacauuacauauuaagcacagauucuguggcaa aacaucuuugcaugauuacuuuacacacacaaauauaguaaaacuuacauaguacaaauu cacauaaagacuccauucugucuauaacuucauccaugugguuuuaccaugaauuauaauu cuuaaccucuccuauaacugucagcuuccauuuaauuuugaaaguaucacuucacaaaga gcacuucauuugcuuuuagaguauacauagacu |
| 156 | AI845121 | cggccgccaagaaguauaacaugcgaguggaagacuacgagccauaccccgaugauggca uggggguauggcgacuacccgaugcuccccaaccgaucacagcaugagagggauccguggu aucaguggggaccacucagaacucaggaugaacuggggugaaccgauacacugggaccuag acauguacaucaggaaucguguggacacgucaccuaccccuguguccugngaugucaugu guaaacaucucuucggcuuuguggcuuucaugguuuucauguucuggguagggcacgugu ucccuuccuaccagccuguggguccgaagcaguacccuuacaaaaaucuguaccuggagcg |
| 157 | AW047756 | uuuuuuuuuuuuuuuuugaugcaaaugucuuuauuuuccacuuaaacaaguuucccuuuu gcacuggccuguggcacaaaacagauggcuggguggugacauuaacugucaaguuaguga gaugcagagauggugagacacugcauuugagugcauaauacuuuuauuccagaggaacgc caugcagcccaguuacaccuuuaggucagaaaggcugaugcgugaccagccucuauugcc ucccuugguaagaaggacccacaagugcagaguccaacagaugcuggcucugagcugaac ucagggcauuccaauuaccacuuucuucuucaccuacacagggccugcucagaguguccuu uuuacaacuccauaagcccuuuggccaaagucccugcagugguuuggggaggaccuucccca cccuucaccagucagugucugaucuggguggag |
| 158 | AI838021 | uuuuuuuuuuuuuuuuuaauaucuguaauaguuuauuucaaagauuugacauuuacaagu agaggcaccacaugcuaucugacaguaaaauacugcagggacugaaggccaaggagagag auccacagaagacaggccuguagugcaggcauugcaucgaccuugcccacagugcuuugu ucccaacucaggacaguacuuuagugcuugcuucauuuacuggaaaaguucacuggacau |

TABLE 3-continued

RNA transcripts up-regulated during HF stem cell activation.

| SEQ ID No: | Access. # | Sequence |
|---|---|---|
| | | aguuuccacuucuuccccccacagcuuccagcucagcaaacuuaagcuacuacuccucgau gcucucauagaggcucuugauuugugucuggaagaacuuggcaagcucuacucguuuggc uuucagugucggugucagaaguccguuuucaa |
| 159 | AW122893 | uuuuuuuuuuuuuuuuucugagguauuaaaauaucuagacugaauuuugccaaauguaag agggagaaaguuccugaagacucugacuacuugcuuauuuuugauugaccuucuaugcuu augucauuacugccucacaacguguuugauguccuuuaaugauacaaagugagccugugc cuucauuuucuugcccauuuugguaccccucgugccg |
| 160 | M59821 | Sequence below. |

gcgcccgaacgucuagcagaguaccugcugcuguaagcuugucgucugggcugcaccgcccgucuuaacccauucucgacuu aacuacucucgucgaacaagcauggaaguacagaaagaagcgcagcgcaucaugacucugucgguauggaagauguaccacu cucgcaugcagcgagguggcuugcgacuccaccggagucugcagcuaucccucguuaugcgcagcgcucgagagcucuaccu cucagccaagguagaagcccaccagcccgaguucccgccaucccgcagggcucuugacccucgccugcacccgccgcgggaag ccgaaguugcaguggaaguagcguccccccgaagccgugcagccuccggagcccauggauacgcaagaggaagugcugcgagu ccaggagaccccugcgcucugugacccgcccccccgcuagagucagccgcaagcgccggagcagcagcgauuugagcgacagua gugaugccggacugguaccaagcaagaaggcccgucuagaagagguggagggggaggcgacgucggagguucccgaucgcc ugcagcuuccuccggcacaaagcgaaggugccuucccuaaccucgcccgcguccuccaaaggcgcuucuccagucuccugaac uguggacccgccgugcccccgccgacgcccccccacgugcgaggccaagccagccugccgcccggccgacaauaugcucaacgu gcuggugcgagcugugguggccuucugagagcucugguggcuucuuucgagcggcgccaccggagcggagaacgcacaccc gaggcgaaggccggcgggggccgugaagaagagccgcggcccgagcugccgagaggccagggcaaggacugaggagcgaggg gcgcgggcgccuucucccagacgugcguccauaggugcuauuaaaggacugucccuuccuuggcuuggagaagggacaccu agaucuugaaucucagggucgaacucucuaggggccaggcugcccuuucaaggccguuucacuaccauucgcguuucggcc ccuacaagugggcacgcuugugcaagcggucagaguugcgucaugggacagacgcgggugcuuccuguugccuugcguggg ugugggggccugggaggaggccaggguguggacccgcccuagggacugggaagugacuugagucaccucgccccccacaggcu gcugugggugagccugaacugaaccaaucaaaucugcgcagaguugaaguggcuggagaccccgggacuggucaaccuagau gaucgccuggcguggaccaccgcgggacgggugggccgcuggucguaguugcugccguagacacagcuucuucgggcagga aagaaaauuuuuuuuuuaccagcguguuuaagaaagucuguuuacuuuucccacgguggguuguuuaauuagcaacuaccu ggaguuuuacaaugucagcuaggaaaauaaagaccaucggugu

| | | |
|---|---|---|
| 161 | M13805 | See above (same Accession Number). |
| 162 | AI845886 | uuuuuuuuuuuuuuuuuugguuccacuuaaguugcauguuuuauuucucccaaucccagca auagcacagaagcccaucauguccaucccagacugguuucuaguaggcugagaugacagg gagccucaguaacgcuaauggcacagagggcucccaaaugccaggcacaacugugccucc acacuggugacugcccagagugcccuggccccaguguguuggcacucagucugacuuuac aacgcaaccugcaccuuugaaagggacagucugggaguggggagugugagggagugaagc ucaaacugccuccugucagcucacccuuucaacauuaaacagagaccaagagagaaacag uuccaauauuucacauauauuucuucuugugcagucuaagccgagaaugccauguaaaug ggucacugcgaaaugcagcaauuuagu |
| 163 | X53157 | gucucgggcgagauggcuucaagguuacuucgcggagugggcgcuuuggcggcgcaggcc cugaggcgcacggcccguggcgcggccgugacccgcuccauggcuucuggagguggugu c cccacugaugaggagcaggcuacugggcuggagagggagaucaugauagcagcacagaag ggacuggacccauacaauaugcuaccuccaaaggcagcuucaggcaccaaggaagacccu aaucuagucccguccaucagcaacaagagaauagugggcugcaucugugaagaggacaac uguacugucaucugguuuuggcugcacaaaggcgagagucagcgaugccccaacugugga acccauuacaagcuggugccccaccaaauggcccacugagccccuguguuaucuuuucag aauguaaagaaaaacuucucucuaauaaagacuagccauugcaccugcuccuccc |
| 164 | U19118 | See above (same Accession Number). |
| 165 | AF062071 | Sequence below. |

gcgcaccgccygyguygcgcgscagcgucgucuaggugcaucgcgggcccccgcagrwagaaaaauauggcucaggagacua accagaccccagggcccaugcuguguaguacaggauguggcuuuuaugggaauccuaggacaaauggaauguguucuguuu TABLE 3-continued RNA transcripts up-regulated during HF stem cell activation.

| SEQ ID No: | Access. # | Sequence |
|---|---|---|

gcuacaaagaacaucuucagagacagcagaauaguggcagaaugagcccaaugggacagcuaguggguuccaacaguccuac cucagauucugcaucuguacagagagcagaugcugguuuaaacaacugugaaggugcugcuggcagcacaucugaaaaauca agaaaugugccuguggcugccuugccuguaacucaacaaaugacagaaaugagcauuucaagagaggacaaaauaacuacccc gaaaacagaggugucagagccaguugucacucagcccaguccaucaguuucucagcccaguucuucucaaagugaagaaaaa gcuccugaguugcccaaaccaaagaagaacagauguuuuauguguagaaagaaaguuggccuuacaggguuugacugccgau guggaaauuuguuuuguggacuucaccguuacucugacaagcacaacuguccauaugauuacaaagcagaagcugcagcaaa aaucagaaaagaaaauccaguuguuguggcugaaaaaauccagagaauauaaaauuacuacaugugaagagacugaaacuuu guuuuuauuuuaauauaucguaggaaaacauuaaagagcagaugcauggccauuuuccuuugauguucucccagaguuuugc uuuauacuugucugucauauaauugaucuuuuaggauguuugggguguuuguuacaggcagaauuggauagauacagcccu acaaauguauaugcccucccucaguaaaauuggacaaaaauaugcacaacaaauugaaauacacauauacuaggaacaaaau uuaguuccacgugccaaacuaaaggaaugaaaucucugcauguuugcagcauaucugccuuuugggaauguaaucaaggua uaaucuuuggcuaguguuaugugccuguacuuaaaaaaaaaaaaaaugguacaccagaaaaggacuggcagucuacuaccaua gucaaacuucaccuuaauuucgacaugacuuuuggaagcaggaagaaagcuacaaaacugguauuugguaccaugugugagc cugguuaaaauuggucuucuaaaagcugucaauuaggacauucugcgaaagguaacaucacaacugguucuaagucaaaccau caagucaacagcagggugccugagauaaucuuggaagcuuauugugcuggccugcaccagaagauaucugcauucucauuac uaaaauuguagcacagaacugcacuaggauuuguuuacaaggagaaauuaaacucuguuugguuuucacauauagcagcuc uguuaaauaacaugcaucugaauuuuaaguugcaaagguaucugaacaguuaauuuuucaugugcaucuuuuguugaaugu uuugguucaagaaagaauguuuaaagcuuuuuaaagacuucaguucuuaauguaacuguacccuucugcauggaaaaucau aaccaacauggcugcaguagacuucuuuagugguauccagcaccacuugcagagggcugcuuuaucauauuguacuugggu guaggacucuaguguucuuggguguauugcaugggcugcauuaucuacagcauuguacaauaacaacuagaaaaggcggua uacuucacugaugcuugucugguaauaucacuucuguguuaaaauggaagguuuuuugugauguaugaaacuuguguuuu uuauauauaaaugaguauaguuagauuaguguugugguaaugccuguuuucaucuguaaaauaguuaaguauguacacaaca aggcacuacuucugauuuuugcaguguucaguccuaguuuuucuuuauuaaaacauugaguuuugcuucaauuuuaugua ccuuaguucuaaguuagauuugcagauguguacagauaguucauauuuauguauugcacauaaucaugcuauucagcauug augcuauauuguauuauguaaaauaauaaaagcaguguacagagggaaaa

| SEQ ID No: | Access. # | Sequence |
|---|---|---|
| 166 | U10404 | augacagaugccgcugugucccuucgccaaggacuucuuggccgguggaguggccgcagcc aucuccaagacagcgguagcacccaucgagagggucaagcugcugcugcaggugcagcau gccagcaagcaaaucacggcagauaagcaauacaagggcaucauagacugcgugguucgu auccccaaggaacagggaguccuguccuucuggcgugggaaccuggccaaugucaucaga uacuuccccacccaggcucucaacuuugccuucaaagauaaaauacaagcagaucuuucug gguggugguggacaagaggacccaguucuggcgcuacuuugcagggaaccuggcaucaggu ggugccgcuggggcuacauccuugugcuuuguguacccucuugauuuugcccguacccgu cuagcagcugauguggggcaaagcuggagcugaaagggaauucaaaggccuuggugacugc cugguuaagaucuacaaaucugaugggauuaagggccuguaccaaggcuuuaauguguca guacagggcauuaucaucuaccgagcugccuacuuugguaucuaugacacugcaaaggga augcucccagaucccaagaauacucacaucuucaucagcuggaugauugcacagucuguc acugcugucgcuggccugacuuccuauccuuuugacacgguucgccgucguaugaugaug cagucuggacgcaaaggaacugauaucauguacacaggcacgcuugacugcuggcggaag aucgcgcgcgaugaagggagcaaggcuuuuuucaagggcgcaugguccaacguucucaga ggcaugggugggcgccuuugugcuugucuuguaugaugagaucaagaaauacacauaa |
| 167 | U07634 | Sequence below. |

cguagaaguugucucugucggcgggcgggcgggcaggauuggggcaccgagaccggcgugcggacagcagggaucgcgggg agcgagggggugcggcauggagcuccgggcagucgguuucugccuggcgcugcugugggguugcgcgcuggcggccgcggc ggcacagggaaaggaaguuguuuuguuggacuucgcagcaaugaagggagagcucggcuggcucacgcaccccuauggcaaa gggugggaccugaugcagaacaucauggacgacaugccuaucuacauguacucggugugcaacgugguauccggcgaccag TABLE 3-continued RNA transcripts up-regulated during HF stem cell activation.

| SEQ ID No: | Access. # | Sequence |
|---|---|---|
| | | gacaacuggcuccgcaccaacuggguguaccgggaggaggccgagcgcaucuuuauugagcucaaguucacggugcgagacu |
| | | guaacagcuucccggguggcgcccaugccugcaaagagaccuucaaccucuacuaugcagagucagauguggacuauggcac |
| | | caacuuccagaagcgccaguucaccaagauugacaccaucgccccugacgagaucacggucagcagugacuucgaggcucgca |
| | | acgucaagcugaacguagaggagcgcaugguggggccccuuacccggaagggcuucuaccuggccuuccaggacaucggcgc |
| | | cugcgugcggcugcucuccguucgcgucuacuacaagaagugucccgagaugcugcagagcuuggccugcuuccccgagacc |
| | | auugcugucgcuguuuccgauacacaaccccuggccacgguggccgguaccugcguggaccaugccguggugccuuauggg |
| | | ggcgagggggcucucaugcacugcacgguggauggcgaguggcuggugccauccgagugccugugccaggaaggcuacgag |
| | | aaggucgaggaugccugccgagccuguucuccaggauucuucaagucugaggcaucugagagcccuucccuggagugucca |
| | | gagcauacccugccauccacagagggugccaccuccugccagugugaagaaggcuauuucagggcaccugaggacccacugu |
| | | ccaugucuugcacacguccacccucugccccuaacuaccucacggcaugcaugggugccaaaguagaacugcguuggacagc |
| | | ucccaaggacacugguggccgccaggacauugucuacagugucacuugugaacagugcugcgcagagucuggcgagugugg |
| | | gcccugugaggccacggugcgcuauucagaaccuccucacgcccugacccgcacgagugugacagucagugaccuggagccc |
| | | cacaugaacuauaccuucgcugucgaagcacgcaauggcgucucaggccuggugacuagccgaagcuuccggacugccagcg |
| | | ucaguauuaaccaaacagagcccccccaaagugaggcuggaggaccgaagcaccaccucccugagugucaccaggagcaucccg |
| | | gugucacagcagagccgugugugggaaguacgaagucaccuaccgcaagaagggggaugccaacagcuauaauggccgccgca |
| | | cggaaggcuucuccgugacccuggaugaccuugcuccggauaccacguaccuggugcaggugcaggcauggacgcaggagg |
| | | gccaaggagccggcagcaaagugcacgaguuccagacgcuguccacggaaggaucucgcaacauggcggugaucggcggugu |
| | | ggcuguagguguuguuuugcuucugguacuggcaggaguuggccucuucauccaucgaaggaggaggaaccugcgggcuc |
| | | gccaguccucugaggauguccguuuuuccaagucagaacaacuaaagccccugaagaccuauguggauccucacacuuacga |
| | | agaccccaaccaggcuguacucaaguuuaccaccgagauccacccauccuguguggcaaggcagaaggucauuggagcagga |
| | | gaguuuggagaggucuauaaagggacgcugaaggcauccucggggaagaaggagauaccgguggccaucaagacacugaaag |
| | | cgggcuacacugagaagcagcggguggacuuccugagcgaggccagcaucaugggccaguuuagccaccacaauaucauccg |
| | | ccuggaggcgguggucucuaaauacaaacccaugaugauuaucacagaguacauggagaauggagcgcuagacaaguuccuu |
| | | agggagaaggauggugaguucagcguacuucaguuggugggcaugcugaggguaucgcauccggcaugaaguaccuggcc |
| | | aacaugaacuacgugcacagagaccuggcugcccgcaacauccucgucaacagcaaccuggugugcaagguguccgauuuug |
| | | gccugucgcgugugcuggaggaugaccccgaggccaccuacaccacaaguggcggcaagaucccuauucgauggacagcccc |
| | | agaggccauuuccuaccgcaaguucaccucagccagcgauguguggagcuacggcauugucaugugggaagugaugacuua |
| | | uggcgaacggcccuuacuggaacugucaaaccacgaggucaugaaagccaucaacgacggcuuccggcuccccacgcccaugg |
| | | acugcccuucagccauuuaccagcucaugaugcagugcuggcagcaagagcgcucccgccggcccaaguuugccgacaucgu |
| | | uagcauccuggacaagcucauccgacgccccgacucccucaagacgcuggcugacuucgauccccgaguguccauccggcug |
| | | cccagcaccagcggcucggagggaguccccuuccguacgguguccgaguggcuggagagcaucaagaucgaacaguacacgg |
| | | aacacuucaugguggcuggcuacacggccaucgagaagguguacagauguccaacgaagacaucaaaaggaucggagugcg |
| | | ucuuccuggccaccagaagcgcauugccuacagccugcugggacucaaggaccaggucaacacaguggggauuccuaucuga |
| | | guccauuggggcugucacacaauacuugaagagccacagugguucucccugccgaucuggugcuggcccacuggaacuuuau |
| | | uuauuucuguuuccucgucuaugccucccuaggacucugcaggggcuuuuugaaugacaccugccugagccugggaaacuu |
| | | ggauugcuggucagggcucucuuuccccugaaaaggacccagcuaagaacuuagcaguuugccauggccuucccagcauccc |
| | | cugaggcuaaaguuccaccaagagucgauaucgacgagggacauuuccaaacggaccuccccaucuucauuuggccuccuga |
| | | gaagccacucuggagcugaggcuaagcacuaagcccaggaccauaugacuagcacuguaccgcccgccccuaguuagagggu |

TABLE 3-continued

RNA transcripts up-regulated during HF stem cell activation.

| SEQ ID No: | Access. # | Sequence |
|---|---|---|

agguuuggacuuggcugguuguggucacaagcaaucucccagugccuuuuacagaccccagucugcccucccgucgagg gccagcuucuugcuuuccuagggcccucucaggaugcuuggcugugcugagguuuuuauuaaauauauauuuuauacuug cggaaagaaugagugugguggcagggacuugccagggcuggagacagaggauccccugcaacaagacauucccgggcugggg gcuggcggaccugcaggagacuuuccgccaccaccccgucuccagccccuuuggacaaaugucgcugucaguguuacagauu ucuuuuauuggguuguuuuuuuguuguauuuuuuugaaccuuaacuuauuauuuuuuuuauauuuauuguuagaaaaug acuuauuucugcucuggaauaaaguugcagaugguuca 168 X04663 Sequence below.
ccaaaaaccuuaauuuucuuucuuguucgguaccuacauuggaaccaccaaaaacaauuauuucaguaaaccguagccauga gggaaaucgugcacauccaggccggacaguguggcaaccagaucggugcuaaguucugggaggucauaagcgaugaacaugg caucgaccccaccgguaccuaccacggugacagcgaccugcagcuggaccgaaucucuguguacuauaaugaagccacaggu ggcaaguaugucccucgagcuaucuugguggaucuagaaccugggacuauggacuccguucgcucagguccuuuuggccag aucuucagaccagacaacuucguuuucggucagucuggggcaggcaacaacugggcuaaaggccacuacacagagggagcug aguugguugacucugucuuggaugguggugcggaaggaggcggagagcugugauugccugcaaggcuuucagcugacccac ucacuggguggaggcacuggcucuggcaugggcacccugcucaucagcaagauccgggaagaauauccugaccguaucauga auaccuucagugugguggcccucgcccaaagucucugauaccguggucgagcccuacaaugccacccugucuguccaucaguu gguugagaacacggaugagaccuacugcaucgacaacgaggcccucuacgacaucugcuuccguacccucaagcucaccacgc caaccuacggagaccugaaccaucucgucucggccaccaugagcggcgucaccaccugccuccguuucccgggccagcuuaau gcugaccuucgaaagcuggcugucaacauggugccauucccacgucuccacuucuucaugccuggcuuugccccucucacca gccguggaagccagcaguaccgggcccucacugugccugaacuuacccagcaggucuucgaugccaagaacaugauggccgc cugcgacccgcgccacggccgguaccucacaguugccgccgucuuccguggacggauguccaugaaggagguggaugagcag augcucaacgugcagaacaagaauagcagcuacuucguggaauggaucccaacaaugucaagacagcugucugugacaucc caccgcguggccucaagauggcagucaccuucauuggaaacagcacagccauccaggagcuguucaagcgcaucucugagca guuuacggcuauguuccgccggaaggcuuuccuccacugguacacgggugagggcauggacgagauggaguucaccgaggc ugagagcaacaugaacgaccuggugucugaguaccagcaguaccaggaugccaccgcggaagaggaagaggauuucggagag gaggcagaagaggaggccuaacggcagagagcccugcaucagcucaggcugcuuagaucccucagccuuucuccaacugccc uuuguccuccaguuucuuucugcugccucugucuuguauuuguuuugcuucuguuuucucauugggguaaauggugcc uggcacauggcaggcacucaauaaauauuuguuugugg 169 X61232 Sequence below.
ggcagacaaaagaggccggcagugcagcucgcgggacgcauggccgggcgcggaggacgggugcugcuggcgcugugugcc gcgcugguggccggcggguggcugcugacgcgugaagcccaggagcccggggcgccagcggcuggcaugaggcgccgccgg cggcuccagcaagaggacggcaucuccuucgaguaccaccgcuauccagagcugcgcgaggcgcuggugucgguauggcugc agugcaccgccaucagcagaaucuacacagugggcgccagcuucgagggccgggagcuccuggucaucgagcugucugacaa ccccgggguccaugagccgggugaaccugaauuuaaauacaucgggaacaugcauggcaaugaggcgguuggacgggaauu gcucauuuucuuggcccaguaccuguguaacgaguaccagaaaggcaaugagacaauugucaaccugauccacagcacccga auucauaucaugcccuccuugaaccccgacggcuuugagaaagccgcauggcagcccgggcagcugaaggacugguuugugg gccgcagcaacgcccagggaauagaucugaaccguaacuucccagaccuggacaggaucguauauguuaaugagaaagaagg cggucccaacaaccaccugcugaagaaucugaagaaaauuguggaccaaaauucaaagcuugcccccgagaccaaggcuguca uucacuggaucauggacauucccauuugugcuuucugccaaucugcacggaggagaccuuguggcuaauuacccauaugaug TABLE 3-continued RNA transcripts up-regulated during HF stem cell activation.

| SEQ ID No: | Access. # | Sequence |
|---|---|---|

agacacggagcgguacugcucacgaauacaguuccugcccugaugacgcaauuuuccaaagcuuggcucgcgcguacucuuc uuucaacccagucaugucugaccccaaucgaccucccugcugcaagaaugacgaugacagcagcuuugaugauggaacgacc aaugguggugcaugguacagcguccccgguggaaugcaagacuucaauuaccugagcagcagcaacugcuuugagaucacug uggagcuuacgugugagaaguucccaccugaagagacucucaaaagcuacugggaagauaacaaaaacucccucaucaacuac cuggagcagauacaccgagguguuaaaggguuuguccgugaccuucaggguaacccgaaugccaacgcaaccaucucugugg augggauagaccaugaugucaccucggcuaaggauggggauuacuggcgauugcuugcuccuggaaacuauaaacuuacag ccuccgauccuggcuaccuggcaaucacaaagaaaguggcaguuccuuuuagcccugcuguuggggguggacuuugagcuug agucuuucucugaaaggaaggaggaggagaaggaagaauugauggaguggugggaaaaugaugucagaaacuuugaauuuuu aagaaaggcuucuaacuaauugcuuucaucuaucuauagacuguaguaagaugcaauguggcucuuuucuuuuagguugug ugcaguugauauuuaacauugauuuauuuuugaucauuaaguaauaguuacuaaucacguaaauacacccggacagaaaua uaaugcuggacaucuucauucuacaucaacauucgcuuaaaucauucgaagccucuuuuaacguaaugggugacaaugucac uugacagaugcaugagagucacgauauagcugacugugacccugcacugcaaucacauaguuccauauaaguuguccuuagu cucuugugcugauucacuguauaaagcaugauccugguaaugcacuuuggaugggaagaaaauguacgugcuuuucagaggg gcucugaacagaaugaaaaccuaguucuugcguguacuuugaagaauggaauuguauuagucagcuguuaaugccacuuca gaaguuuggggguuuugucuugauuguagauugg

| 170 | X14309 | Sequence below. |
|---|---|---|

gccacggacgccucucugaacggggauccaggcaggauuagagcugccucacugacuacaggccgugucgugucaccguuuc ugcaggcaccaugagccaggacaccgaaguggacaugaaagauguggagcugaacgagcuagaaccggagaagcagcccaug aaugcagcggacggggcggcggccggggagaagaacggucuggugaagaucaagguggcggaggacgagacggaggccggg gucaaguucaccggcuuauccaaggaggagcuacugaagguagcgggcagcccuggcugggugcgcacccgcugggcgcug cugcugcucuucuggcucgguuggcugggcaugcuggcgggcgccgugguuaucaucguucgggcgccgcgcugccguga gcugccuguacagaggugguggcacaagggcgcccucuaccgcaucggcgaccuucaggccuuuguaggccgggaugcggg aggcauagcuggucugaagagccaucuggaguacuugagcacccugaaggugaagggccugguguuaggcccaauucacaa gaaccagaaggaugaaaucaaugaaaccgaccugaaacagauuaaucccacuuugggcucccaggaagauuuuaagaccuuc uacaaagugccaagaaaaagagcauucacaucauuuuggaccucacucccaacuaccagggccagaaugcgugguucccucccu gcucaggcugacauuguagccaccaaaaugaaggaagcucugaguucuuggcugcaggacgguguggaugguuuccaauuc cgggaugugggaaagcugaugaaugcacccuuguacuuggcugaguggcagaauaucaccaagaacuuaagugaggacagg cuuuugauugcagggacugaguccucugaccugcagcaaauugucaacauacuugaauccaccagcgaccugcuguugacca gcuccuaccugucaaauuccacuuucacuggggagcguacugaaucccuagucacuagguuuuugaaugccacuggcagcca auggugcagcuggagugugucgcaagcaggacucccucgcagacuuuauaccggaccaucuucuccgacucuaccagcugcug cucuucacucugccagggacuccuguuuuuagcuacggggaugagcuuggccuucagggugcccuuccuggacagccugcg aaggccccacucaugccguggaaugaguccagcaucuuucacaucccaagaccuguaagccucaacaugacagugaagggcca gaaugaagacccuggcucccuccuuacccaguuccggcggcugagugaccuucgggguaaggagcgcucucuguugcacgg ugacuuccaugcacugucuucccucaccugaccucuucuccuacauacgacacugggaccagaaugagcguuaccugguggug cucaacuuccgagauucgggccggucagccaggcuaggggccuccaaccucccugcuggcauaagccugccagccagcgcua aacuuuugcuuaguaccgacagugcccggcaaagccgugaggaggacaccucccugaagcuggaaaaccugagccugaaucc uuaugagggcuugcuguuacaguuccccuuuguggccugauccuuccuaugcagaaccuaccacccuccuuuguucucccc TABLE 3-continued RNA transcripts up-regulated during HF stem cell activation.

| SEQ ID No: | Access. # | Sequence |
|---|---|---|
| | | aggccuuuuggauucuagucuuccucuccuuguuuuuaaacuuuugcagauuacauacgaauucuuauacugggguguuuu ugucuucaaauaaaaacaucaccccugccucaug |
| 171 | U42386 | Sequence below. |

gncuuaagccncguuuauuuugaugnccuguuggcucagunaugnccaagaugccnauuguuuuugcccnuaaauaaaauuu acugaacuugggcuaaaaccaaaccuuggcacacaggugugauacaacuuaacaggaaucaucgauucauccauaaauaaauau aaggaaaaacucaagugguagccugucuuaaggcuuuugauacuugcagauuggggaaaaacaaacaacaaacgucuugaag cauauuaauggaauuaguuucuaauguggcaaacuguauuaaguuaaaaguucugauuugcucacucuauccuggauaggu auuuagaaccugauaauagucuuuaaacaagccauuccagucaugaugaggugauguauggauacaugcauacauucaaagc acuguucucaaaguuaaugcaaguaaauacagcaauuccucuuucaauguuuaggcagaucguuaacuaugagcuagccaaa ugugggcauguuauuacagggaaaguuuaaaggucugauaacuugaaauagguuuaggagaauucaucuacuuagacuuuu uaaaugccugccauaaaaaaauugaaaugguagaauggcugaccacagcaaugaccagcccucaccuagggcucuggaugauu uuuggucuaauaacgcaugcuaguguugauguuuuuuggucaagaugggaaugaacaggaagaauuaugcagcaggcuuua uuuuaaaugccgauucacauuacucuguucaagcugcguugagauguuaaacuggcuuacuauagacuuuguaaaaaaaaa aaaaaccaaacaaauggcuccagaagaguaacaaacugaaaucugagaucacacagguuggaaauauguacauaacugaacaa ggugucaauucugcucuacagugcaguuuagucaguuuuaguugcauagguuuccauuguuuuuauagucuguuuaugcu aaaucuggccaaagaugagcauuguccaccacuaaaaugccuaugccacugggaauucuggguuaauuuugugaccagaaug cagugaucaaaauguucaaucuuuuuacaguggcauaggaagauggcaaaaauuuccuaaagugcaauagauuuucaagug uauugugccuuguucuaaaacuuuuauuaaguaggugcacuugacaguauugaggucauuuguuauggugcuauuucaau uagucuagguuuaggcccuuguacauuuggcccauaacuuuuuacaaaguacuucuuuuauugcacauucagagaauuuua uauauaugucuugugugcguguccuuaaacuuccaaucuuauuuugucucuuggagauuguugaacgcagcuugucuagg aaagggaugggacuagauucuaaaauuuauuugggaccaugggaaugauaguugggaagaaacuuugcacacgacagauuu cuagauacuuuuugcugcuaguuuuauguaauauuuauugaacauuuugacaaauauuuauuuuuguaagccuaaaagug auucuuugaaaguuuaaagaaacuugaccaaaagacaguacaaaaacacuggcacuugaauguugaaugucaccguaugcgu gaaauuauauauuucgggguagugugagcuuuuaauguuaagucauaauaaacucuuaagucaaauuaagcagacccggca uuggcguguagccauaacuuucugauguuaguaaaaacaaaauuggcgacuugaaacuaaaucaugccaagguuugauacac uugucuugagauauuaacgaaacacuuccaaacacugauacaaaguguccagauucucagauguuuguugugugaguuuug uuuaguuguauuuuuuuuucagugaaugucuggcacauugcaauccucaaacaugugguuaucuuuguuguauuggcaua uucagugacuuguacauucagcaauagcauuugagcaaguuuuaucagcaagcaauauuuucaguuauguuuccaaauuaa gaaugggguuuaaacuugcugaauguaaagauugacccucaagucacuguagcuuuaguaguugcuuauuguauuaguuua gaugcuagcacugcaugugcugugcauauucugguuuuauuaaaauaaaaaguugaacugcacagucuccuuuguuguugu caauugugguuuacuuuuagaggugaaaauaaaguugugcucuugccucgugccaauauguacauaacugnacaaggugguc aauncugcucuacagngnaguuuagncaguuuuagungnauagguucccaunguuuuuaungncuguuuaugcuaaaucu ggccaaagaugagcauugcccaccacuaaaaugccuaugccacugggaauccuggguuanuuuggngaccagaaugaaguga ncaaaauguccanucuuuuuacaguggnauaggaagauggnaaaaauunccuaaagugnaauagauuuccaaguguuungu gccugguncuaaaacuuuunuuaaguagggugcacunganaguauugaggncauugguuauggugcuauuuccanuuagu cuagguuuaggcccu TABLE 3-continued RNA transcripts up-regulated during HF stem cell activation.

| SEQ ID No: | Access. # | Sequence |
|---|---|---|
| 172 | U51126 | Sequence below. |

cucggucuccaagaugguggcuaacaaaacgugaggccuagagguugauccuaggucacuggaagcauguccuugaagagg acuaugggcaucugguucuucccucuucuacuuggccacgagguaaccggcuucuuguaccacgugugcucaccucuacaa ucugugcggauucagacuccaagcaacuaggcuacccagugacaggcuaaaaacuacagcucuaacgucuuggaaggcgauu ccauggaccaggauguggaaagcccaguggccauucaccagccaaaguugccuaagcaggccagggacgaccugccgagacac aucagccgagacaggaccaaaaggaaaauccagagguacgugaggaaggaugggaagugcaacguucaccacggcaaugugc gggagacguaccgauaccugacggacaucuucaccacccugguggaccugaaguggagauucaaccuguugaucuuugucau ggucuacacagugacguggcuuuucuuugggaugaucugguggcugauugcguacauccggggagauauggaccacauaga ggaccccucguggacuccuugugucaccaaccucaacggguuugucucugcuuuuuuauucuccauagagacagaaaccacc aucgguuauggcuaccgggucaucacggacaagugcccugaggggauuauucuccucuuaauccaguccguguuggggucc auugucaacgccuucaugguaggauguauguuugugaaaauaucccaacccaagaagagggcagagacccuggucuuuucca cccacgcggugaucuccaugcgggaugggaaacugugcuugauguuccgggugggggacuugaggaauucucacauugugg aggcauccaucagagccaaguugaucaaguccaaacagacuucagagggggaguuuauuccccucaaccagacugauaucaac gugggguacuacacaggggacgaccggcucuuucuggugucaccauugauuauuagccaugaaauuaaccaacagaguccu ucugggagaucuccaaagcgcagcugccuaaagaggaacuggagauuguggucauccuggagggaaugguggaagccacag ggcaguucugaaaucgaaaucaagcagaggucuauaagaacacccuggagaccccaugcugcuggaucuugggguccaugaa cugcuuuuauuugcugcaaucaaaaaugcuagucgcugaucugauaggagaggaaacgagacucagagccugaaggauaaca cgcugagggcugauuucauacacucuucccggcuggaucaucccagcccccacagcguccaggcuuaguuucuuccuuugu uuuaacaaucuauacuuccuccagccugggcgagcuaguauacccagaguugguuuuguuucuuuucagagcuguaagcc cagugcccagugaccucaucugggaggagaguuaagcaauaagaccugaaugcuaacucugggguagaaaccucugcag agacagcgucucugggaagucucuacagagacagaguagggaagucucacgaaggucagagucuuacuuccauaccuggaga aauccgcccguccguucagugccgguuucaacuccucugccaaagacuucuuuccaagacacugguaucagcuaucccagca guaacuuuggcaguauauaaaucaauggcacugccccauaaaaccccguugaguaaaaccuauggucuucaacagcuggga gccuguagcccagcuccugugugaggcuaaggcuguggagaccaugccugcucaccuccucguugaaaagcaaaacacugua agaaaccuaacaugacuuuuuccaacauuucucaggcuggggagaagacuugguccacaaagagcuugaggucuugaucug gaucccuagcauccauggaagaaggugggcaugaucacccacacuccucaucccauagcucugaaugagguaggcagauucc uggggcucaccagcucauccuaacagccaggucccaaugagggacugucuacaaaagaacaagagguggauccugagaagcg acacccaagcuugaccucuagccccuguacacaccuguuaagcaccugggcaucgggacacacacucgcaauuugcaaacaag gcaaauucucacacuucagaaggcacugagagaaucccauaagcucaaaaaguuaggagccaagauugaccauuaaugacuu ggguugaaaagacuaaaccacuggauagaauguuucauuacuaaaacaccuuaccugaaaaguauuacugcucuucuuucug caacuggaccaugcagagauccacaaagagaugcccagagauuauuagugauggucauaugauauacacaaugugga cucua agccaaggccccaucaacucagauccagaggcugacagugugcuuaucuuagagauaccacaguggcugccuaaucaccacg uccuuaagucaggggaguuugauuauuuccuaugaacaccgaguggggacagcggauuaccaaugaagcaauccaaccugac aauccuaaccacccagaagaggaucgcugggggaaagcaugaauuauuuacgugucaacaugugcacacuccggccacgcag cucaacagccaggagugcuucuccacuuagcccugcccuggcauccauuuaugaucucgucuguuguguuaauuacccagcu agcuuuuuucucaaaaauaauaucucccagccauagaccuacucaucugugucccucuuuaauuucaacccacaguuacauca uucacuggcuugcucaguuucuucaacucugaaaugggaaugaugaugaugaugccucuucccccccaagccaccauccucccc cgugaccuuccuagguacagacucaaaccagggaagauuauuuccuucucauaggccacagggugaaaugcaauaaagaaca TABLE 3-continued RNA transcripts up-regulated during HF stem cell activation.

| SEQ ID No: | Access. # | Sequence |
|---|---|---|

aagccuuguagggaggcagagggaaagaccaguccucacaagaggcucccauuguuuccagggacuuugaagcuuggacagaa ugucagaugauccccuuugaaggugcuccaaagagucaaugugaaaaauauugacugaugugugcccuccacaagccaagg ugccucugcccuggucaccuaccaugaauuauaaacugaugauauuugaaauaauaaggaacacuggagccggccagaaagg auucugcagucccauaaauagcaacauucaucacuacaaugccugccaacgguggccgugaauguagauuacccccggcucu ucugaggccacugaggacagggcaaacuaccucugagaauggaggcucacuguucugcaucccacuucuaaauguuccauga auuuuuugagacaucucccauaucccuguuagaaagauucaaccuugugcuauuaaccaaaucauuuugaauuccauaaacc ucuacucuaaaguauacacuuaauucuacaauacagacaacaaauaugacuuuuuccuaugaaagagugauaaagauacugu aucagucugcuuugacucaaaaaaaaaaaaaaaaaaaaaaaaaaaaaaaaaaaaaa 173 AF093853 Sequence below.

uggaaugggugcuaggugaaggcuuuguugaaucaggaugcugagcugguguuuuuacagguccagauaugaugagcugg aguuuugguaggcccagguaccuccuccaaaauugaccacauaauuggucacaaaucaggccuccacagauacaaaaauauu gaaauuaucccaugcauccugucugaucaccacagacuaaggcugaucuucaauaacaacauaaaaaauagaaagccagguuca cugcugcggcugcgccuccuuguucucagcgucaccacugccgccaugcccggaggguugcuucucggggacgaagcccccca acuuugaggccaauaccaccaucggccgcauccgcuucccacgauuuccugggagauucauggggcauucucuuuucccaccc acgggacuuuaccccagugugcaccacagaacuuggcagagcugcaaagcuggcgccagaguucgccaagaggaauguuaag uugauugcucuuucaauagacaguguugaggaucaucuugccuggagcaaggacaucaaugcuuacaauggugaaacaccca cggaaaaguugccauuucccaucauugaugauaagggcagggaccuugccauccuuuugggcauguuggauccagucgaga aggacgauaacaacaugccugugacggcccgugugguguucauuuuuggcccugacaagaaacugaagcugucuauccucu acccugccaccacgagcaggaacuuugaugagauucucagagugguugacucucuccagcugacaggcacaaagccgguugc caccccaguugacuggaagaagggagagagcgugaugguaguccccacccucuccgaagaggaagccaaacaauguuucccu aaaggagucuucaccaaagagcuccccgucuggcaaaaaauaccuccguuauacaccccagccuuaagucuuugcggaaauug gggcugcaucugcacguccagcacuggggccugaggacgucagccggcagccguggguccuugcagcagguccguagaaaga ucguggcaugaucacagccggccuguagaucgcucgcuauacuacugggucauuaaaauggaaauggcaccaaaaccuucuc gggauucuuuacucugugccuucgccagcauucugccccucugccugucacagugcccuacugacuggcucucuuugaaac gaauuauguauugaagauuccuuaggucucugcagggucuuugaucagcaagcaagguagcaguguggggcucugugc uagaaugaugaaacaccuuuuguagcuuuccgaacggaaucuucuguuacccauuuuggagagcacugacauggggagaag cuuucaauucuguauuuuuaguaaauaaaguggggacagccgggagaauucuuacagggaaucuauuguaaguuucuaucg aagugggcucagaaagccuuucgccucccaagagugcgcauguaccucccuagaguuuccacaucugcucucugggugauguc ugccugugaacgcaccuuauaagacgggcggugacaguguuuuaccacucagugccuaguagugggguggccauuucug aauucugcuuuuugagguucaacaaauaaaauccugaucagaaaaaaaaaaaaaauagaaagccaacauucauguggaaacuga acaacacuacucaaugauuccuuggucagagaugaaauaaagaaagaaauuaaagacuuuuuagaguuuaaugaaaaugaag ccacaacauacccaaacuuaugggacacaaugaaggcauuucuaagaggaaaacucauagcccugagugcauccaaaggaaaa aaaaaaaaaccuagagagaguguacacuagcagccugacugcacacuuagaagcucugcaaaaaaaggaaucaaauucaccca agaggaauagacagcaggaaauaaucaaacuuagggcugaaaucaaccaaauggaaacaaaaagaacuauucaaagagugggc caaaccaggagcuaguucuuugagaaaaucaacaagauagauaaacccuuagccagacucacuagagggcacagggacagcau TABLE 3-continued RNA transcripts up-regulated during HF stem cell activation.

| SEQ ID No: | Access. # | Sequence |
|---|---|---|

ccuaauuaacaaaaucagaacugaaaagggagacauaacaacagauccugaagaaauccaaaacaccaccagauccucuacaaa aggcuauacucaacaaaacuggaaccuggaugaaaggaaaagcuucuagacaga 174 Z19521 Sequence below.

augagcaccgcggaucugaugcgucgcugggucaucgcccugcuccuugcugcugccggaguugcaguagaagacucaggc agcaggaacgaguuccaguguagagacggaaaaugcaucgcuagcaagugggugugcgauggcagccccgagugcccggaug gcuccgaugaguccccaaagacaugcaugucugucaccugucaguccaaucaauucagcuguggaggccgugucagccgaug cauuccugacuccuggagaugugauggacagguagacugugaaaaugacucagacgaacaaggcugucccccccaagacgugc ucccaggaugacuuccgaugccaggauggcaagugcaucuccccgcaguuugugugugauggagaccgagauugccuagau ggcucugaugaggcccacugcccagccaccacuuguggccccgcccacuuccgcugcaaaucauccauaugcauccccagucu uugggccugcgacggggaugucgacuguguugacggcucccaugaguggccacagaacugccaggccgaagacacggccucc aaaggcguuagcagccccugcuccucccuggaguuccacugugguagcagugaguguauccaucgcagcuggucugugac ggcgaggcgacugcaaggacaagucagaugaggagcacugcgcgguggccaccugccgaccugaugaauuccagugugcag auggcuccugcauucacgguagccgccagugugaccgugaacaugacugcaaggacaugagcgacgagcucggcugcgucaa ugugacacagugugauggccccaacaaguucaagugucacaguggggagugcaucagcuuggacaaggugugcgacuccgc ccgcgacugccaggacuggucggaugagcccaucaaggagugcaagaccaacgaguguuuggacaacaaugguggcuguucc cacaucugcaaggaccucaagauuggcucugagugccuguguccagcggcuuccgguugguggaccuccacaggugugaa gauauugacgagugucaggagccagacaccugcagccagcucugugugaaccuggaaggcagcuacaagugugagugccagg ccggcuuccacauggacccacacaccagggucugcaaggcuguggggcuccauaggcuaucugcucuucaccaaccgccacga gguccggaagaugacccuggaccgcagcgaguacaccagucugcuccccaaccugaagaauguggguggcucucgacacggag gugaccaacaauagaaucuacugguccgaccugucccaaaaaaagaucuacagcgcccugauggaccaggccccuaacuuguc cuacgacaccaucaucagugaggaccugcaugccccugacgggcuggcgguagacuggauccaccgcaacaucuacuggaca gauucagucccaggcagcguaucugugcugacaccaagggcguaaagaggaggacacuguuccaagaggcagggguccagac ccagagccaucguaguggacccugugcauggcuucauguacuggacagauuggggaacacccgccaagaucaagaaaggggg uugaaugguguggacauccacucacuggugaccgaaaacauccaguggccaaauggcaucacacuagaucuuuccaguggc cgucucuauuggguugauuccaaacuccacucuaucuccagcaucgaugucaaugggggcaaucggaaaaccauuuuggag gaugagaaccggcuggcccacccccuucuccuuggccaucuaugaggacaaaguguauuggacagaugucauaaacgaagcca uuuucagugccaaucgacucacggguucagaugugaauuugguggcugaaaaccucuuguccccggaggacauuguccugu uccacaaggucacacagccuagaggggugaacugguguggagacaacagcccuccuccccaaugguggguugccaguaccugug ccugcccgccccacagaucggucccccacucgcccaaauucaccugcgccugcccugauggcaugcugcuggccaaggacaugc ggagcugccucacagaagucgacacuguacugaccacccaggggacauccgccguccggccuguggucaccgcaucagcuac caggccaccgaagcacagugaggaucucucagcucccaguacuccuaggcagccuguggacaccccagggcucagcacagugg cgucagugacaguguccccaccaaguccagggugacauggcuggcagagggaaugaggagcagccacaugguaugagguuccu guccaucuucuucccuauugcacugguugcccuccuuguccuuggggccguccugcuguggaggaacuggcggcugaagaa caucacaaucaacagcauaaacuuugacaacccagucuaccagaagaccacagaggacgagcuccacauuugccgaagccagg auggcuauaccuaccccucaagacagaugggucagccuggaggacgaugugggcaugagcagccgggagagccgucucuuuccg ggauccauugccaagcuuaggcagaaaagacacucucuccagaccuccccauccagcacugguccugccaccucccuggggucu guguugcucaaagcaagauagagcaaagcugggcugggggggccaagcucagcuuccugucugccccagguucuguuuuaua uauuuauugucugggacagaaaaggcuacuggcugugcuugaaauucga TABLE 3-continued RNA transcripts up-regulated during HF stem cell activation.

| SEQ ID No: | Access. # | Sequence |
|---|---|---|
| 175 | U04354 | Sequence below. |

accggucaucgggcucuucccuugggcucagggcacggaucaaguccucggcucgcucggccagcaccgcggcaccauggcgc aggagcugcagcaccccgaguucgcgcgcgcaggccagcaggcugggcugcaggugugggagggucgagaagcuggaacugg uaccggugccccagggugccuauggugacuuuuacgucggagagcccuaccuggugcugcacaccaccaaguccagcagggg cuucuccuaccgccugcauuucuggcugggaaaggaguguucccaggaugagagcacagcggcugccaucuuuacggucca gauggacgacuauuuggguggcaagccaguccagagcagagagcuucaaggcuaugagucgacugauuuugugggcuauuu caaaggcggucugaaguacaaggcuggaggugggcuucuggacuaaaccauguccucaccaaugaucugacugcgaaaaga cuucugcacgugaagggucggagagugggucagagccacugaaguuccccucagcugggagagcuucaacaagggcgacugcu ucaucauugaccuuggcaccgaaauuuaccagugguguggguuccuccugcaacaaauaugagcgucugaaagcaagccaggu ggccauuggcauccgggacaaugagaggaaaggaagaucucaacucauuguggguggaagaaggaagugaaccaucagagcuc augaagguuuuagggagaaagccugagcuuccagauggggacaaugaugacgaugucguagcagacauaaguaacaggaaga uggcgaagcucuacaugguuucagaugcaaguggguccaugaaaguaacacuggugggcugaagaaaacccguucuccaugg gaauguugcuuucugaagaaugcuucauuuuggaccauggugcugcaaaacaaauuuuuguauggaaagguaaaaaaugcua acccacaggagaggaagacugccaugaagacagcugaggaguuuuuacagaaaaugaaguauucuacuaaauacucaaauuca gguucuuccggaaggcggugaaacaccaauuuucaaacaguucuuuaaggacuggaaggauaaagaccagagugauggcuu ugggaagguguacaucacggagaaaguggcucagauaaagcagauuccguuugaugccucaaaacugcacaguucuccgcag auggcagcccagcacaacaugguggacgauggcucuggcggggguggagaucuggcgugguagagaacagugguagaguccag auugacccaagcuccuauggcgaguucuauggcggugacugcuacauuaucccucuacacuuaucccagaggacagaucaucu acacauggcaaggagcaaaugcuaccagagaugaacugaccauguccgcguuucugacuguccaguuggaccggucccuugg agggcaggcugugcagguccgugucucucaaggcaaagagccugcucaccugcugaguuuguucaaagacaaaccacucauu auuuauaagaaugggacauccaagaaagaagggcaggcaccggcucccccuacacgccuuuuucaaguccggaggaaccugg caucuaucaccagaauuguggagguugacguugaugcaaauucauuaaauucuaaugacacuuuuguccuaaaacugccacg aaacaauggcuucaucuggauaggaaaaggugcuagccaggaggaggagaaaggagcagaguauguggcugauguccucaag ugcaaagcuucaagaauucaagaaggcaaggaaccagaggaauucuggaacucucuuggagggaggggagacuaccagacuu caccauugcuagaaacucgggcugaagaccauccaccucggcuuuaugguugcuccaacaaaacuggaagauucauuauuga agaaguuccgggagaguucacccaggaugaccuggcagaagaugaugucaugcuacuugaugcgugggaacagaucuuuau uuggauuggcaaagaugccaaugaaguugagaaaaaggaaucagugaagucugccaaaauguaccuggagacagacccuucu ggaagagacaagaggacaccgauugucaucaucaagcaagggcacgagccccccacauucacaggcugguuucugggcuggg acuccagcagguggaaaaccagcaacuauccuggcugcauuggggcagcugccacuuuguuguuggggaauuguuuacuu uuuguuauuggcuuuugaagauaaacuccugccaaauggauauauaucuauaucuauaucuauaucuauaucuauaucuau aucuauaucuauaucuauaucuaucuauaucuaaucuauaucuaucuaucuaucuaucuaucuaucuaucuaucuaucuau cuaucuauaugcuccucuuuuccuucucuuucaaagggaauugcuguauguuacuauacugaaauaaccuaaagcaaccauu uguuuucgagcaauuuugcaaucuggggaccucugaggaaguaauuuugucauucagccacugcuagccaaacuugucuuu ucccauagagaggaaggagagccacagugcuucuaagcauuuccccgucugcauacucuguuugcagugagcuuuacuuuau guauggcuuuaacaaugccuugcuguuucccaucucaagucaaugccacuucggaugccauucacucccaagugucccuuacau aggaugaacuucuuuagcuuuuuuagaaaacuaaaaucaugucuuuuaugauaaaacacauuuuauuucuauaaguuuaac uuuauauauuugauagcacaugcucaauagcauaaagaauaugcauugaaugauguuuuucauaauuaaaauauauccuuu ugg TABLE 3-continued RNA transcripts up-regulated during HF stem cell activation.

| SEQ ID No: | Access. # | Sequence |
|---|---|---|
| 176 | M35244 | Sequence below. |

cagggguugagagcaagaaggugcaggauguaggccagcagaauuaucagacccaguggcggcuucugccacuggaagaauuu ccaacauaaaacagaugaucaguuugggacaaucgauucugcgaccagagguagugucaucugguuacuuuuaaaauucaga uugucugguguuuuccaaucacucgcgacuguaaauuugaaguuggauucugagauaaauacaaucgcugucgcucuaguuua uaaagcuguccaagaucugcccagucccagauguccugggucccucagggcggcugguggucugcgcccuucucccugcagcug gaugccagaccauccuggacucggaucccuuuggguucacacucgcuuagguauuucuacaccgcugugucccggccuggc cuuggggagcccugguucauaaucgucggcuauguggacgacaugcagguccugcgcuucagcagcaaggaggagacuccg aggauggcacccuggcuggagcaggaggaagcagaugacugggaacagcagacucauauagucacaauucaaggacagcugu cugaaaggaaucugaugacccugguucauuuuuacaacaagagcauggacgacucucacacacuacaguggcugcaggacug cgauguggagccagaucggcaccugugucucugguacaaccagcucgccuaugauagcgaggaucuccccacccugagcgaa aacccaaguuccuguacaguggggaaacagcacuguaccucagaucucucagcaccuggagggccacugcucagaugugcugc agaaauaccuggaaaaagggaaggagaggcugcugcguucagaccccccaaaggcacaugugacccgucaccccagaccugaa ggugaugucacccugaggugcugggcccuggguuucuacccugcugacaucacccugaccuggcagaaggaugggggaggag cugacccaagauguggaguuuguggagaccaggccugcaggggauggaaccuuccagaagugggcagcugugguggugccu cuuggaaaggugcagaguuacacgugccauguggaccaugaggggcugccugagccccucacccugagaugggagccugcau gguaccaaaagccuuggauuuggauuguugccacgguuuuuuccauuuugcucauuugucucuguguggcucgcagaccca ugaagaagaaugcaggugggagaggaaggcgugacacccaagaagcaggcagagacaguccccaagacucuagcaagacugu uguggaugaugaggagauggggguuugcuuuuggaagauuaaguccuguaaaacuugucuaggccacuccccaggaacuuc aggaucaucugggagaugccccuuugaguggcugggcugugaggacagcaggccaguucuugccacccuggacagaaacaca ucucaccuuucuggcucgaggaucugaacaccugucucuugccuacucggcuucuagucaggcauuuugucaccuugucaa gggucccagggacacaaagcucccuccucucacccacagcacucugggguccuaccccccaaugcuucagggacauuuaaucagg ucaaauugggaucaauggcuuugaugcagaaaagaacuguggacuaauagagauaggguuuaauaaaaaaaaauaucuuuuu

| SEQ ID No: | Access. # | Sequence |
|---|---|---|
| 177 | AW121930 | uuuuuuuuuuuuuuuuucaacuuuaaagacuggauuugagguucagucugggucucuggg ggggaccucugucaucacgccuauaaucaucccgagaguagucaucccuggagcuccacg accgaucaucccgucugucauagcggucuucauagcgguccccaccuccucuguagucau caucucuccgguacccacuuccaaaugcccuucugccacugccuauccuggagucauagc cucggucauagucucugcugccucggucaucauagcgaucccggcccccauagcggucca ugucucugcgugggccguccccgauauccgucccuauacccaucccgauaccggucugaau cguaacgaucucgauacuugucucccaaagcuaucaucgccucuucuaggugggguagucau cacaacugucuguggugggacgggcccuccagucugugucuguuuug |
| 178 | AI852632 | uuuuuuuuuuuuuuuuuggcccccaggcucugucucaaggaugggaauagaucaagccaa acagugaaaaauaaggcaaaucguggcuucggggguuugagacuggcaccaauggcaaauc agcagaggagaugcaaauggggguaacaaucacaguuaguggggguaacaugagcaggcagg aaacccuugagacaacacccaagguccacgucuucgcaugugcagggcacaacuccagca gcaguuucugggcuuggaggcuuguuacucuuccuaccuuucccacccccuaaaagacac caagauggagcccacgaagagauuacaucaagcucuucuggcuggg |
| 179 | U70475 | Sequence below. |

ucuaggacagccagggcuacacagagaaacccugucucaacuaaaacaaagcaaaccccccgaauauuguuuuuuauuugcg gaugucuguuuauugagacgggguucauggcagacaugagugucucagugcauuugcuaucccucucuucuaaaggggcgg ggggggggggugcgcuggagagguggcucagcaguuaagagcacugacuucucuuccagagguccugaguucaauucccagc aaccacaugguggcuuauaaccaucuauagugagaucugaugccuucuucuugccuguaggcagaccacuguauacauaaua aauaaaucuuaaaaggggggggaagguguggagcuaaaaguauggcaauaugcauaaguuuagcuauuucuguuguuuugc agucaucagugagccaaacuaauucgaaugguagcuagaucuuguugcuuuuagcgaauauauauugagugaauggaauu gacagucuucuguauucucauucaguuuguuuguguucuuccccaucagugauaacauguagugaacuaacccgugugac TABLE 3-continued RNA transcripts up-regulated during HF stem cell activation.

| SEQ ID No: | Access. # | Sequence |
|---|---|---|
| | | caucuuaaccauggcuucuccuucccuuuucuguuuuaaacauaggacauggauuugauugacauccuuuggaggcaagaca |
| | | uagaucuuggaguaagucgagaaguguuugacuuuagucagcgacagaaggacuaugagcuggaaaaacagaaaaaacucga |
| | | aaaggaaagacaagagcaacuccagaaggaacaggagaaggccuuuuucgcucaguuucaacuggaugaagaaacaggagaa |
| | | uuccucccaauucagccggcccagcauauccagacagacaccaguggauccgccagcuacucccagguacacucgucguggug |
| | | ggagcuaaggaaaacucuagugagaaagcagacucucuggaguugaguucuuggucugccauuuacugugucuuuugugag |
| | | gaggagaaguucucaaacuucgcuucuugauaaucaggacacagaucacagggaggacuuugugaguucagaaacauccucu |
| | | guggugaugaaacagcggcagaaauacuguugggaguaaaagaaguaggcauugcucauugugguaggcagggcccugauu |
| | | guaugguaacugacuuaacuguguuaaguaugauucccauuuuauauucccaugucuaaacaacuaaagcauuugcccag |
| | | aacacucagaaagaaaugaagggagguuauugccuagcacagagcccugguucaguccccccacgcuguucguuaaaggggag |
| | | ggacuaauaauuugaacacaaucugguuugaaucuaugcaaaucgauuucugaaaugagaccauagguuauuuuaugaaca |
| | | agucuuauugcucguugugacccugugcuuagaacauuucauaaaugaugcucucugugccuuuccccuuccuccagguug |
| | | cccacauucccaaacaagaugccuuguacuuugaagacuguaugcagcuuuuggcagagacauucccauuuguagaugacca |
| | | ugagguauaaaaauguuuguuuaacagcaaaacucccuuaucugauauuaguuccuuucaugugucuccaauuaagagaag |
| | | aaaagaaaauuuuagaaggaaaaaauugaucaaagaaauugucaaguaaacuguaugagagcuauauaaugcuuaaaaauaa |
| | | gaccuguaugggcuggugagauggcucaguugguaagaguacccgacugcucuuccgaagguccagaguucaaaucccagc |
| | | aaccacaagguggcucacaacauccauaacaagaucugacucccucuucuggagugucugaagacagcuacaguguacuuac |
| | | auauaauaaauaaauaaaucuuuaaaaaaaaaaaaauaaggccuguaaacuacaaguccauuuuacuguauagcuggaaacagg |
| | | aaucagaauaauuuucccuggaaacuggauauagauauauaaaauauuuugacuaguaaagaacaacuauuaaucagcauuu |
| | | ggauuaaaaaaaucuuaaucuguuguuugaagcauucugcuagauauuauggguacagauuaaguccuaaugaauguuuuua |
| | | uccauuuugaagucugccuuuaaauacauggagugaaauaaccuaggaguguauuaaauauggagucacugggaggaggaaa |
| | | uguuucauuuuauaaaagcagccugagagcuguaggcccugcugcugucuguucuucaugccuuggcucucacucacauga |
| | | aucaaugucacgucaaucuuggcuuucuucacuugcauuucagucgcuugcccuggauauccccagccacgcugaaaguuca |
| | | gucuucacugccccucaucaggcccagucccucaauagcucucuggaggcagccaugacugauuuaagcagcauagagcagg |
| | | acauggagcaaguuuggcaggagcuauuuuccauucccgaauuacagguaagagagcucuaggagugugcuguuuucugcg |
| | | ggcccuuuuaaauuagucauccuaguuauuuauuauuuacaugcuaccucccucaaaggaagaaauugaugguguauuuaaa |
| | | uuacucaugagagcuucccagacucacuuaacacacauaguuuuuagguaaucagacugaauauuucuggauaaaauucauuc |
| | | aaagacugaaagcuaauuuagaguucugacaaagauaaaauacuuaucuauugaaaaaugggaguugaaggaauuauugaaa |
| | | agaacaccuuggauuuggggguagggaauugaucuaaaaugcacuuagccucugcucauacaaugugaccuucuuuccuag |
| | | ugucuuaaauaccgaaaacaagcagcuggcugauacuaccgcuguucccagcccagaagccacacugacagaaauggacagcaa |
| | | uuaccauuuuuacucaucgaucuccucgcuggaaaaagaagugggcaacugugguccacauuuccuucaugguuuugagga |
| | | uucuuucagcagcauccucuccacugaugaugccagccagcugaccuccuuagacucaaaucccaccuuaaacacagauuuu |
| | | ggcgaugaauuuuauucugcuuucauagcagagcccagugacgguggcagcaugccuuccuccgcugccaucagucaguca |
| | | cucucugaacuccuggacgggacuauugaaggcugugaccugucacuguguaaagcuuucaacccgaagcacgcugaaggca |
| | | caauggaauucaaugacucugacucuggcauuucacugaacacaagucccagccgagcguccccagagcacuccguggaguc |
| | | uuccauuuacggagacccaccgccuggguucagugacucggaaauggaggagcuagauagugccccuggaagugucaaacag |
| | | aacggcccuaaagcacagccagcacauucuccuggagacacaguacagccucugucaccagcucaagggcacagugcuccuau |
| | | gcgugaaucccaaugugaaaauacaacaaaaaaagaaguucccgugaguccuggucaucaaaagccccauucacaaaagaca |
| | | aacauucaagccgcuuagaggcucaucucacacgagaugagcuuagggcaaaagcucuccauauuccauucccugucgaaaa |

TABLE 3-continued

RNA transcripts up-regulated during HF stem cell activation.

| SEQ ID No: | Access. # | Sequence |
| --- | --- | --- |

aaucauuaaccucccuguugaugacuucaaugaaaugauguccaaggagcaauucaaugaagcucagcucgcauugauccga gauauacgcaggagagguaagaauaaagucgccgcccagaacuguaggaaaaggaagcuggagaacauugucgagcuggagc aagacuugggccacuuaaaagacgagagagaaaaacuacucagagaaaagggagaaaacgacagaaaccuccaucuacugaaa aggcggcucagcaccuuguaucuugaagucuucagcauguuacgugaugaggauggaaagccuuacucucccagugaauac ucucugcagcaaaccagagauggcaauguguucccuuguucccaaaagcaagaagccagauacaaagaaaaacuagguucggg aggauggagccuuuucugagcuaguguuuguuuuguacugcuaaaacuuccuacugugaugugaaaugcagaaacacuuua uaaguaacuaugcagaauuauagccaaagcuaguauagcaauaauaugaaacuuuacaaagcauuaaagucucaauguugaa ucaguuucauuuuaacucucaaguuaauuucuuaggcaccauuugggagaguuucuguuuaaguguaaaauacuacagaacu uauuuauacuauucucacuuguuacagucauagacuuauaugacaucuggcuaaaagcaaacuauugaaaacuaaccagacc acuauacuuuuuuauauacuguaugaacaggaaaugacauuuuuauauuaaauuguuuagcucauaaaaaauuaaaaggagc uagcacuaauaaagaauaucaugacuuaaacuacuuuggacuuuuugaauuuauucacacuauuuuccauaggacaaucac ucauuuaccacauuugguuauuuuacauuuucaaaauggguuugaaaauacagaggcauuuuauagccauguguggcaguc caugauuuuuuauucccgacauucaggaggcagaagcaggcagaucccugggcuccaggacggccaaggcuacaugagagcc ugucucaagaaagacaaacccuuucuauacuaaacguuagcuaggauugucaaggagaugguauauauccacaaugguaugc cugcuguacaguacuguggcacagagaacaaaaccuguaaccucccuguguucuuagaaguggcauucuaagaagggcuagga aga

| SEQ ID No: | Access. # | Sequence |
| --- | --- | --- |
| 180 | U09659 | ggccagcaggacucuccuugcagcagcggcccgaguucagaguccggagcugcgguggug gcggcgaaggcgagagucauggcuggacaagcuuuuaggaaguuucuuccgcucuuugac agaguauugguugaaaggagugccgccgaaacuguaaccaaagguggcauuaugcuucca gaaaagucucaaggaaaagugugcaagcaacggucguggcugugggucaggagggaaa ggaaagaguggagagauugaaccugucagugugaaaguuggagauaaaguucuucucca gaauauggaggcaccaaaguaguucuagaugacaaggauuauuucuuauuuagagauagu gacauucuuggaaaguaugucgacugaaaucacuguugaaauggugucacgugaagcugc cauuccacugaugucugaacuauuucaucauguaaauaauuu |
| 181 | AW124785 | uuuuuuuuuuuuuuuuucaggucucauuuucguuuauuugaaauucggugcucguguaag uuuuuucucuucccccucaaauuuuauuucaguaaaaggagacuugggcgagguggauacc ccacagccggauucuucccccccugcccccccaggguggcuaaugcuaucuggggaagucg ucauagggaagagaacuauggguggcuccugccugaggccuccaaucucagcccagugg acauaucacaggcagcuuaaaaaaaaaacccuaaaaaaaaacaccccaaaacacacauuua aauagguauucaagacagcuuuaaaaaaugcacccacucacacccccccucccuuuucuuu uuggaaaaaaaaaauaggaaaaaaaaaaaaaaccaaaccgaauucucgcuuggccucua |
| 182 | AF071315 | Sequence below. |

auuuggcuccgaggccaagaauucggauccaaggcgggcgcggggaaaauggcggcggcagcugcggcgggggcgaauggg agcggaggcagcagcggcauggaaguggaugcagcaguccccagcgugauggccuccggagugacugggaguguuuccguc gcucuucauccccuugucauccuuaacaucucagaccauuggauccgcaugcgcucccaggaggggcggccuaugcaggug a uuggggcucugaucgggaagcaggaggggcgaaauaucgaagugaugaacuccuuugagcugcugucccacaccguggaag agaagauuaucauugacaaagaauauuauuacaccaaggaggagcaguuuaaacagguuuucaaggagcuggaguuucugg guugguauaccacaggggggccaccugaccccucagacauccacguccauaagcaggugugugagauaauugagaguccgcu cuuucugaaguugaacccuaugaccaagcacacagaucuuccugucagcguuuuugagucugucaucgauauaaucaaugga gaggccacaaugcuguuugcugagcucacuuacacucuggccacugaggaagcugaacggaucgguguagaccacguggccc ggaugacagcaacaggcaguggggagaacuccacuguggcugaacaccugauagcucagcauagugccaucaagaugcugca cagccgugugaagcucauuuuagaauaugucaaggccucugaagcaggagagguucccuucaaccaugagauccugcgggag gccuaugcccuaugucacugucucccaguucucagcacugacaaguucaagacagacuuuuaugaucaaugcaaugacgugg ggcucauggccuaccucggcaccaucaccaaaacgugcaacacaaugaaccaguuugugaacaaguucaacguccucuacgac TABLE 3-continued RNA transcripts up-regulated during HF stem cell activation.

| SEQ ID No: | Access. # | Sequence |
|---|---|---|
| | | cgacaaggcauuggccggcgaaugcggggacuguuuuucugaugaugguucuggaagggauggugugugggggcucagaca |
| | | gcuguuccauggaccugaguaccacauucccuuuagagaaacucauuaauaaaagagcagccccuuaaaaaaaaaaaaaaaaa |
| | | aaaaaaaaaaaaaaaa |
| 183 | D49733 | Sequence below. |

aaaacccaauguuugguuuuaaagccaaaaauauaagggaagugcauagguuuggguuuuguuuuuuguuuuuucccgag guccuugaucuuugccccccaaauuugagggcauaaaguaaucccucaguuaccuaaaaacacagccauuccuuugccauucc acucuccuggauuggccgcuucugugcgcgggggagaggugacucacuauuacuacugaggaaaggggagccaguggugga agugggggugagucacugaugggcagcagcuucagcccuccccccaacuuccuuggcucucuggggaugccugauccucuccc ucacuuugcaccuacuuccccuggucccucaccacuacccuuugcccacccacucaaauucuuuggcucugcucuuuacucc agaaggccaaaggcaagcuuagaguugaguaggcaggaaccaacauugugaagccccaggccagaaaggggguguucugcaga gugaggguuggcaugcuggcuccucccucaccauaccugcccccgccccuuuggguacaggauggcuccuuuaagagcagug gauccaccccccuguagaggagggccuauuagagccucugccuggcugucagugacucaguguucgcgggaacgcugccuca gccucaacaccagccaacccagaucccgaggugcgccagcgcccagcccagaucuccacgccugccaggagcgagcuucgccg gcucgcuguccccccugagcagccucuguccuucuguccaagucccgcgcccuucucgggaccccugcccagcgggcagcacu gucacccugccggccauggagaccccgucacagcggcgcgcccacccgcaguggggcgcaggccagcucuaccccacugucgcc cacucggaucacccggcugcaggagaaggaggaccugcaggagcucaaugaccgccuggccguguacaucgaucgcgugcgu ucccuggagaccgagaacgcggggcugcgccuucgcaucacugagucugaagagguggucagccgagagguguccggcauca aggcggccuacgaggccgagcugggggaugcccgcaagacccuugauucuguggccaaggagcgcgcccgccuccagguaga gcugagcaaagugcgugaggaguucaaggagcugaaggcucggugagugaggcccggccggccggcaccagggaggcagca gucgccuguaacuggccaucuagucccccucccuccccggaacugccucccgcgggugacuggcagugccaannnnnnnnnn nnnnnnnnnnnnnnnnnnnnnnnnnnnnnnnnnnnnnnnnnnnnnnnnnnnnnnnnnnnnnnnnnnnnnnnnnnnnnnn nnnnnnnnnnnnnngcuaggccagauauagaaagcuuucuguauuuaauacacaguacaugcaucauucaugucuacauaa uuaagauaaaggaagcugcauuguuaaugggaaaaaaaaauagggucugggaauguagugugccuagcauuuacgaacuucg ggguuuggguuugaucccagcaucucacaaaccacguguaaucccagcacuuggaagguagaggccggaggauccgaaguu uaaggucauucuugacuacuuagcaaauucggggcacccuaggauaccugagacccugucaugaauaaaaaauaaauaauaaa uaaaccaauaugggucuagguugagcagcagcuugggcaggguagggccggaaguuagccagguagaggguugcagucccca ggaggacccuggcugggagcagcaccucaguccccugcccaaccacagggggccaccgggucuuuccggaacuccugagggc gcaaggccuugcucucucuggcccagccauggggaacgcggagggccggugaggcaggcggcaggcgggcgggcggggcgc gggccgucauccccuccugcuccuuauuuuuagcccaguguagagucugggccgccugucccucccccaggacagggggag gaaauunnnnnnnnnnnnnnnnnnnnnnnnnnnnnnnnnnnnnnnnnnnnnnnnnnnnnnnnnnnnnnnnnnnnnnnnn nnnnnnnnnnnnnnnnnnnnnnnnnnnnnngaugccaacaauccuaauguaaugaugcccucuucugacagcugcggggac cgcagagaggucccaucccagaugcacuccugaaaccugcuuuucuuuuucuagcaacaccaagaaggagggggacuuguug gcugcgcaggcccggcucaaggaccucgaggcucuucucaacuccaaggaagcugcccugagcacugcucucagugagaagc gcacauuggagggcgagcuccaugaccugcgggggcagguagccaagguaggccgcuguccugugaccccagugaccccacc ugguccgacauaucauucggucccauuugccugcucaccuucacuucuccagucuagannnnnnnnnnnnnnnnnnnnnnnnn nnnnnnnnnnnnnnnnnnnnnnnnnnnnnnnnnnnnnnnnnnnnnnnnnnnnnnnnnnnnnnnnnnnnnnnnnnnnnnnnnnn nnucuagauggggacagccaucaccucuccuuuggcauuuccugaaccccccucccaccucuccaugaacuuggcuuucuccc ucucagcuugaggcggcccugggagaggcuaagaagcagcuucaggaugagaugcugaggcgaguggaugcugagaacagg TABLE 3-continued RNA transcripts up-regulated during HF stem cell activation.

| SEQ ID No: | Access. # | Sequence |
|---|---|---|

cuacagacgcugaaggaggagcuugacuuccagaagaacauuuacagcgagguaagcgucccgcuguacaggucuuucuuac
uguggacagcugggaggggucaccuaauaaugccaggcuaagcgagggcugcccgugccuggccgguggaguuacgacuuc
uggucucagcuucuaaggaaccauugcgauguucuaaucuaagugucuccccuuaaccuuucaggaacugcgugagaccaag
cgccggcaugagacgcggcuuguggagaucgauaacgggaagcagcgagaguuugagagccggcuggcagaugcccugcag
gagcugcgggcucagcaugaggaccagguggaacaguauaagaaggagcuagaaaagacauacuccgccaaggugcuggccu
cauccuguccucucccuggugcugcccuggggacggguggguggugcagggggccagggaugccuuccucaggcccccag
cuccagguuccugcucucauaacugugugcucccugcagcuggauaaugccaggcagucugcugagaggaacagcaaccucg
ugggggcugcccaugaggaacugcagcagucucgaauccgcauugacagccucucggcccagcucagccagcuccaaaagca
ggugacccucaguuuaccccucccaccuuggcucuggucuaagcagauacugcagaagcccacugagaagggggugggggag
ggacuccaggaccacaugcuaugguucugaaucugaugccugucuggcuuuccagggcucuccuuuagcuagcccugaucc
ucagagccucuauuuuacugugcaugaaggguuuuucauguuucuucugugccugccggagacugaaccagaggccucuug
cuugguagauaggugcuuucucacugaguuacaaacccagccgcauucccuacuuggagauagagcuucccuuggacugga
cauguagcucaguugguacagugcuugcuuauuauacacgauggccuggcuucuauccccaggaccnnnnnnnnnnnnnn
nnnnnnnnnnnnnnnnnnnnnnnnnnnnnnnnnnnnnnnnnnnnnnnnnnnnnnnnnnnnnnnnnnnnnnnnnnnnnnnnn
nnnnnnnnnnucuagagagagccuacagauccugagugucccucugccugccccugugccccucccucuucaucgacauca
gcccuugggagcucaucagacccuuugucuuccccgccccaguuggcagccaaggaggcaaagcugcgugaccuggaggacu
cgcuggcccgugagcgcgauaccagccggcgccugcuggcugagaaagagcgagagauggcggagaugcgggcgaggaugca
gcagcagcuggacgaguaccaggagcugcuggacaucaagcuggcccuggacauggagauccaugccuaucgaaagcugcug
gagggcgaggaggagaggugaacuaggaggggucuacagaacuugucaggggccucuggccgcaacuaccaugacuaacccc
gcaccgugucuccaccuuccccaggcugcgccuguccccagcccuaccucgcagcgcagccguggccgcgccuccucccacu
caucccagucucaggguggaggcagcgucaccaaaaagcgcaagcuggagucuuccgagagccggagcagcuucucgcagca
ugcucgcacuagcgggcguguggcgguagaggaagucgaugaagagggaaaguucgugcggcugcgcaacaaguccaacga
gguggccugugaaccagggugguc uuuucaguggcugggaguucuugguucucguggagcaucugucucccuaucugag
aauuuggagugugugguaguccugucaucuuuaaaauuguugggaagaugcaugauauagggaugggugacccuugagcca
auagucuagguuugaugccagagguaguggugggaagccugucuuucuuuucuuuuucuuuuucuuuuucuuuuucuuuu
ucucuuucuucucucuuuuuuuuuuuccgaugggg ucuugcccagguuggcuuugaucucccuaguuaagcuguucccc
ugccucagccuccauaguagcuggaacugcaggngcacacuggcgnccagccuaccuaagcucccugagugagauaauccaag
agucgguugaacucccuguccuccuuccuccuuccuccuuccuccacccuacuucaggaccaguccaugggcaacuggcaga
ucaggcgucagaauggugacgaucccuuugaugaccuaucgcuucccaccgaaguucacccuaaaggcugggcagguggugac
ggugaguggaagggcacuugggacucuggcuggaguggagaaguuggccucaggacaggagcauuaaaaauaagcacaucu
cuuaaaccaucuuuucccagaucugggcuucaggagcuggggccacccauagccccccuacugacuuggugugg aaggcgca
gaacaccuggggcugugggagcagccuucgcaccgcucucaucaacuccacuggagaagugaguauguugcagccgguagcu
ugcuggacaaggcucccccgggugaccauaaugggaacuagcuaccuccaacccaagggaaccugccuugg guuuaggaucg
cuuuccugagcccaagucccacccaguaagcaagccagaagucuccccaguagaauaaugggugg aagucagccagugagug
uuaauagcagacuccagcuuacagagcaccgagcucucaguugugucccuuuuugcgcgugcgugcgcgcgugugcacaugu
gcauguguuuauccuuaguccccagcaucagagguuggacaagguuguauaaaggcccgggacaguucuaagugguuacua
uggguagacaggcugcacagcccucaccccc ugacucuugggccugggcuuaugucccc acaggaaguggccaugcgcaagc
uggugcgcucacugaccaugguugaggacaaugaggaugacgacgaggauggagaagagcuccuccaucaccaccgugugag TABLE 3-continued RNA transcripts up-regulated during HF stem cell activation.

| SEQ ID No: | Access. # | Sequence |
|---|---|---|

uggcagccgccgcugaggcccagcccacaaggguagcccugccagccuagggcagcucucccaccuccaugccaaagucuuu ucauuaaagaauguuuuggaaugccacuugcugcccuggccuuucuucucucucccucccucuaccuugaacagggaacccag gugucugguaaggaagggaguggggacuugcugaugccauggauacucccacgguggcaguggacaggguucuggauuugu guccugggaaggggcugggaggacagagguggccccagcccugccucucuuccucacucccauugcaugcacacuucucucc ucucuccuuccacccuauugcaugcuucucccucagauuucccugcaacaauguucucuuuccuuccugucccccucacaaauu aagucucuccaucuuugcucuucccucuugauugccccauaagugucuaagauucaggagagaguuaaagccacagcucuuu auuucgaaggcuuccuggcuauuucccccaucaugcccuucccucccagccacaggucucccaaguccccaucacuugguugu cuggguacagacagaggucaccuuccugcccaauggccaggaagcuccaagagcccacagccuaggugccgguccuaagaag ucagucccaaacucgcugucccuccugagccuugucucccuucccaggguucccacugcagcggcucgggggaccccgcuga guacaaccugcgcucacgcaccgugcugugcgggacgugugggcagccugcugacaaggcugccgguggagcgggagccca gguggggcggauccaucucccucuggcucuucugccuccagugucacagucacucgaagcuucccgcaguguggggggcagugg ggguggcagcuucggggacaaccuagucacccgcuccuaccuccugggcaacuccaguccccggagccaggugagucaucuc ugcccuacagcaggacacugcucacugagcagcagggcagggcagcccaagggagugggguccccccucccuugcagucccucu ugcauccugccccuccugucugaaccccagacucgaggucagggcaaggcccagagugugaggguugggggagacaaccccuu uggggucagggagggagaggaagggccagccacugcugcucacaccucugccuucucuucucucuuagagcucccagaacug cagcaucauguaaucugggaccugccaggcagggcugggggcagaggccaccugcucccccccucaccacaugccaccuccug ucugcucccuuaggagagcaggccugaagccaaagaaaaauuuauccccugccuuugguuuuuuuuuuucuucuauuuuuuu uucuuuuucuaagagaaguuauuuucuacagugguuuuauacugaaggaaaaacucaagcaaaaaaaaaaaucuuuaucuca auccuaaguccuucccccuuucuuucuuguaucugccuuaaaaccaaagggcuucucuaggagcccagggaaaggacugcuu uuuauagagucuagauuuuuguccugcugccuuggcuuuacccucaucccaggacccugugacaaugguggccugagaggca ggcauggaguucucuucaccagccuccuccaacagcuggcccacugccacgccagcugcagagaaauggggcgcagagagga ugacugagaaggucaagccccucccccggcacuacacgaggccgaggcucccucugccugccuuaccuucuuccugcccuuccc uagccuggggcgaguggauucccagaggcaaaucugccgugcuugcuuuuucuauauuuuauuuagacaagagaugggaau gacggggaaggagaagggaagaucaguuugagccuaccuuuucccagcuucugagccugguggggcucugucucaaugaugg agggcaaugucaagugggauacagggaagaguggggggacgaaggcucccagagaugggggagaaccugcuggggcugguggag aagucuagaggugcggcgauugguggcuacagcaaacacuaaggaacccuucaccccauuucccaucugcaccucugcucuc cccuccaaaucaauacacuaguuguuuccaucccagaugcuguggugucucuuuguugggugugaugugugguuuucaggg gcagacacaugcacacagaggugccacacauucacuauauauucacuacccagcuauaaaggugugugauaugagggagacuucu agaaaggucagcauauguggggugagcgaggggguguccuuccuaucccucauccauccagcaccuuuuaaaaggggccagca auccacaugugcaucagacacaggagcacagagagacggaggguagaguagggcagaguagcagagcuuccuugcugcccug uagucgcaggcucuugaucgugugaucgcu

| 184 | X80899 | Sequence below. |
|---|---|---|

gcggugcgaagcgggccuccgccaacauguacuacaaguuuagcaguuucacgcagaaguuggcuggagcuugggcuucgg aagccuacaccccgcagggguuaaagccaguuuccacagaagcaccaccuaucauauuugccacaccaaccaaacugaccucc agugugacagcauaugauuauucugggaagaacaaaguuccagagcugcagaaguuuuuccagaaggcugaugguuuccac cugaaacgaggccuuccagaccaaaugcuuuaccggaccaccauggcucugacacugggagggaccaucuacugccugaucg cccucuacauggccucgcagcccagaaacaaaugagcuugccuguggaggacugguucacuuuguggcacaaacccuuugaa uccucacguuucauguuuuccacuuggauagucuacuuaacauuuugcaaacaaaggaaaagauaagaauacauuguuuug TABLE 3-continued RNA transcripts up-regulated during HF stem cell activation.

| SEQ ID No: | Access. # | Sequence |
|---|---|---|

auuuguuuauggugugcagauggccugucagaugucagagcugguuugacaguuaaaacuauuguuuaaggaaaugucac ugagccaucacugagcugugcuucugcuccugauuucccuggaguucugcaggaaaguugcucuccagcucauucguggcc agccgugcucagggccucgggacucaggcggugucugagcgggaagcgaacgcggaagccuuuuggaguguaggugugauu gaggaaggaaaacaaaagccagcggacagguggugaagugagggcugaguuagccacccuagggauucguccgccuugcaga aaacauugagaggaaugauagcaaccugccucuauuugugggcaguugguuucaaaggguugugugucucgcccagaaccu agggaaaugggguguuuguuccaucguggggaggagcaccugucagugcugcacauuagacagcugugucaggacuucuccuu uaauaaugcuguggcuuuacguuaugauugaccggacugcggaauaaacacuggaaucaaaaaaaaaaaaaaaaaaaa 185 D83203 Sequence below.

cugagacagaacgaaacguccgcagauaacuacccguucuggcucuuguuaguucuauguguauggauaaaugucuugggag guuuugaaaugccacaagccuugcuggcccagggugcagcugccucugccguucagaccucagauuauaaggacagaacaca gcacggaaguggggggaucagaaccaugggagauccaggacgaaggguccugugcgcaggugcggcaccgaauccuauauu ugacauugaagcugucgucagcccaacuaguguguuauuaacauggaagcacaaugacucaggcgcuucagaauguagaaua gagaauaagauggagagcaaucugacguuuccuguuaaaaaccagacaucauguaacauuacaggcuuaagcccagguacuu cguauacauucuccaucaucucuguaacaaccaaugagaccuugaacaaaacuaucacaacagagcccuggccagugucugau cuccaugucaccucugugggugugacacaggcucgucucaccuggagcaaugcaaauggcacugccuccuaccggaugcuga uugaagaguugaccacacauucccucagucaauauuucaggucugaagccggggaccaauaauacguucgcuuucccagaauc aaaugagacacaggcugacuuugcaguugcagaggaggucccggaugccaaugguaccaagagaaucccagugaccaaccua ucccaaccacacaagaauucucuugccucuguggacccacccucuggccaggaucccucccucacagagaucuugcuuacuga ccuaaagccugauacucaguacaaugccaccaucuauuucucaagcagcaaauggcacugaaggacagcccaggaacaaagugu uuaaaacaaauuccacccagguuucugacguccgagcuaugaacaucagugccucaagcaugacccugaccuggaaaagcaau uacgauggguccccguacuucaauugucuacaaaauacacguggcugggggggaccacuccgucaaccaaacugucaauaaga cugaggccaucaucccucggacucagcuccagcaccuuguacaacaucacaguucauccuuuccugggucagacggagggcac accaggcuuccuccaaguguacacuucccccgaucaggucucugacuuccgagugacaaaugucagcacaagggcaauuggu uuggcuuggaggagcaaugacuccaaguccuucgagauuuucaucaagcaggacggaggugagaagcaucgaaaugcuucg acgggaaaccagagcuauaugguugaagauuuaaagccuggaaccaguuaccauuuugagauaaauuccacgaggaccagacg ggacagaagggcuguccaguacagugaaugggagcacugaccccagugccgugacugacauccggguggucaacauuagcac cacugaaaugcaguuggaguggcagaauacggacgaugccucuggauacacuuaccauuuaguucuagagucuaaaaguggc uccaucaucaggaccaacaguucucagaaguggaucacaguagggagccucaccccaggcaccuuauacaaugucacaaucuu uccagaaguggaccagauccagggaaucuccaacuccauuacccaguacacacggcccagcagugugucccacauugaaguaa acaccaccaccaccacggcagccauccgauggaagaacgaggacacagccucugcuuccuaugccuacuccguccuuaucuug aagacuggagauggcagcaauguaaccagcaacuucacaaaagacccuucuauucuaaucccugaguuaaucccuggcgucu cuuacacagugaagauccuuacacaaguuggggaugguacaacaucacugguaccugguuggaagcuguucuguacggaacc ugaaucagugaccuccuuccacugugaaguggucccuaaggagccagcauugguucucaagugggccugccccuuuggcau guacacaggcuucgagcugggggucaggagugauuccugggacaauaugacacgccuagagaacugcacaucggaugaugac acagagugcaggacggaagucgccuauuugaauuuuucuaccucguacaacaucagcaucgccaccuugucaugugggaaga uggcgcuucccgcccagaacaucugcaccacuggcaucacagacccaccuacuccggauggauccccuaauauuacaucgguc agucacaauucaguaaagguuaaguucagcggguuugaagccagccacggaccuaucaaagccuaugcugucauccucacca ccggggaagcugcccaaccuucugcagauguuuugaaguacacguaugaggauuucaaaaggggagccucggauacuuaug TABLE 3-continued RNA transcripts up-regulated during HF stem cell activation.

| SEQ ID No: | Access. # | Sequence |
|---|---|---|
| | | ucacauaccucauaagaauagaagagaagggacagucucagggcuugucugaagucuugaacuaugaaauugaugugggaa<br>ccaauccacuacccucggcuacuacaacgggaggcuggagccucugggcuccuaccgggauuguguugcuggcuuuaccaau<br>auuaccuacaaccuucagaaugacggccucaucaauggggaugagagcuaugugucuuucaguccauauucagaggccgug<br>uucuugccccaggauccaggugucaucugcggagcaguguuuggauguaucuuuggugcccuggccaucacagcugugga<br>ggcuucaucuucuggagaaagaaaaggacagaugccaagaauaaugaaguguccuuuucucaaauuaaaccuaaaaaaucca<br>aguuaauccgaguggagaauuuugaggccuacuuuaagaaacagcaagcugacucuaacugugguuugcagaggaauaug<br>aggaccugaagcugauugggauaaguuuaccuaaauacacagcugagauagccgagaacagagggaagaaccgcuacaacaa<br>uguucugcccuaugauauuucucgagucaaacuuucaguccagacccauucgacagaugacuacaucaaugccaacuauaug<br>ccuggcuaccauuccaagaaagauuucauugccacacaaggaccuuuacccaacacuuugaaagauuucuggcgu augguuu<br>gggagaaaaacguauaugccauuguuauguugaccaaaugcguggagcagggaaggaccaaaugugaggaguacuggccuu<br>ccaagcaggcucaggacuacggggacauaacuguggcgaugacaucagaagucguucuuccagaauggaccaucagagauuu<br>ugguggugaaaaauaugcagaauagcgagagccauccucugcggcaguuccauuucaccuccuggccugaccacgguguuccu<br>gacaccacugaccugcucaucaacuuucgguaccugguccgggauuacaugaagcagauacccccgagucaccaauucugg<br>ugcauugcagugcugggguuggaaggacgggcacuuucaucgccaucgaucgccugaucuaucagauagagaaugagaaca<br>ccguggacguguaugggauugucuaugaccuucggaugcacaggccucugauggugcagacagaggaccaguauguuuucc<br>ucaaucaguguguuuuggauauuaucagagcccagaaagacucaaaaguugaucucaucuaucagaacacaacggcaaugac<br>aaucuaugaaaaccucgagccaaguuccuugaaugugacuauguugcuucauccacagcugaacgauuuuggauguugggu<br>ucuagguccuggcuguugcuggucugcuaggauccagggccuuguugacaucugggaagauguaaauugucccgcugaagg<br>ccgcaguuuuagauguggccacuagauggagccagagcacugguaugaaggagcaccagggccguguaaggcaaaagaggac<br>ccagaaaaagaaacuuaacuuguucacuccugagaaaccugcaagucaacaagccaaggaagugccuuugcaugcauuuggu<br>agccuuuccaaucccgcuuauuacauaauauguucauguucauggcaaaaaaaaaaaaaauaaaauaaaauaaauaaaaaagg<br>aaaacaaaauaaaaaaaaucuuagaacauu |
| 186 | Z20410 | gccccucaagggcauccugggcuacacugagcaccagguggucuccucugacuucaaca<br>gcgacacccacuccuccaccugacgcuggggcuggcauugcccucaacgaccacuuuguc<br>aagcucauuuccugguaugacaacgaauuugcuacagcaacagggugugga ccucaugg<br>cccacauggccuccaagguaagccccuggaccaccagccccagcaaggcacaagaggaagg<br>agagacccu |
| 187 | AI839906 | uuuuuuuuuuuuuuuuucauauuaaacuuguaguuuuauucagguuugauuuuuaaca<br>aaugugucagggagagagcccacaggaaaggguaaagcccgugggggcaaggccuuccca<br>gaugccugaggagggaucgugucccucccccccuccucuucucaccaccccuacagggg<br>uuugggaagagacacaggcagggaaggggcugguccccagucuguacaguggugcuugg<br>gggugaaggacuauggagaacaggggaccagaucggggaugaguaggauaaagggcaca<br>agaccauuuaccagaauccagcuuucugauuccaaauugaauuaaaaagaaaaaaaggag<br>aggggaaccuaaaccacaagcaguacccaacucccuuucccccaucagggcugc |
| 188 | AI843448 | uuuuuuuuuuuuuuuuuagggaagaggcugaugccagauaaguuuuuauuauauuaaa<br>aaaaaaaaaaaaaccagugcaacuggaaaucagggugagucgcuggaggugagugagagu<br>cggaaggcccuccacaccucaguggugg caggaucuggacccguagccuaagccuggucu<br>gauccagccgagaugcuggaaagcagagcacacggugg ugcccaucagggcaaagagggc<br>aagagagcccacggcuccuccauaccgcuugcuagggucuccuguguaguagccauaugc<br>guaaaggacucgcccaauaauccaggccaggcccaggccagaagcuaugcgcggguggua<br>aacaccucccaccguuaggaaaaa |
| 189 | AW125336 | cggccgcgugaguuuugacugagcuucugcangaaguucanaugcaacuccauacauca<br>guucauuuucuagcauuaccacuggguuauuaucacgaauggccgauuuaauaagucc u<br>uuugcauccucggaauuccaggggcugaccacuuuuaaaccugggcagugcccauacca<br>ugcagcaaagcauugcgagugcugagcagcuacaccugcugaggcgccauugggcccccu<br>gaauacuaugggcaca |
| 190 | AW123802 | uuuuuuuuuuuuuuuuugaagggccauuggaguuuauuuacagacaaccuuaggugag<br>gccuuuuccucuaggaucuacaugcuuuugaaguuacuugguuucaggcuucuugucu |

TABLE 3-continued

RNA transcripts up-regulated during HF stem cell activation.

| SEQ ID No: | Access. # | Sequence |
|---|---|---|
| | | ccagcuucgagcuugagacucucaggaggcuggcgauaggcagggaaagccucccaggg gcuguucaggucaaacuugcggaauucuugugccagcucccacugguucagccacuaccc gcuuuaccucaucgucguaacgaagcucaacauagccagugaggggaaagucuuuccgga aaggaugucccucgaagccauaaucugucaggauccuucuuaaaucaggguggguuaaaa aaaaaaaaaaaaaaaaaa |
| 191 | AI835771 | uuuuuuuuuuuuuuuuuugggggggcagcgaacuuuauugaugguauucaaaaaaauagg gagggcucccuaggcccccccuguuauuauggggggucugggauggaaauuuugagggaa augcucaauuuggggggcccauuugggaaaaggcccccuugcccaaguccuugcugg gguggggugguccaagguuucuuacucccuuggaggccauuuuggccaagagguccaccac ccuguugcuguagccguauucauugucaaaccaagaaaugagcuugacaaauuugucau ugaaaaaaaugccaaccccggaaucaaagg |
| 192 | X53584 | Sequence below. |

gcuccucaucucacucgggccuaugccaaagauguaaaauuuggugcggaugcucgagccuuaaugcuucaagguguagac cuuuuagccgaugcuguagcuguuacaaugggccaaagggaagaacagugauuauugaacagaguuggggaagucccaaa guaacaaaagauggggucacuguugcaaagucaauugauuuaaaggauaaauacaaaaauaucggagcuaagcuuguucagg auguugccaauaacacaaaugaagaggcuggggauggcaccaccacugccacuguucuggcacggucuauugccaaggaggg cuuugagaagaucagcaaaggggcuaauccaguggaaauccggagaggugugauguuggcuguggaugcuguaauugcuga acuuaagaaacagucuaaaccugugacaaccccugaagaaauugcucagguugcuacaauuucugcaaacggagacaaagaca uugggaacaucauuucugaugcaaugaagaagguuggaagaaagggugucaucacagugaaggauggaaaaacccugaauga ugagcuagaaauuauugaaggcaugaaguuugauagaggauauauuuccccauauuuuauuaacacaucaaaaggucaaaaa ugugaauuccaagaugccuauguuuuguugagugaaaagaaauuuuccaguguucaguccauugucccugcucuugaaauu gcuaaugcucaucggaagccauuggucauaaucgccgaagauguugacggagaagcucuaagcacgcugguuuugaacaggc uaaaaguuggucuucagguuguagcagucaaagcuccaggguuuggggacaacaggaagaaccagcuuaaagauauggcua ucgcuacugguggugcgguguuuggagaagaggguuugaaucuaaaucuugaagauguucaagcucaugauuuagggaaa guuggagaggucaucgucaccaaagaugaugccaugcuuuugaaaggaaaaggugacaaagcucacauugaaaaacguauuc aagaaaucacugagcagcuagacaucacaacuagugaauaugaaaaagaaaagcugaacgagcgacuugcuaaacuuucagau ggaguagcuguguugaagguuggaggaacaagugauguugaagugaaugagaagaaagacagaguuacugaugcucucaau gcuacaagagcagcuguugaagaaggcauuguucuaggaggggggcugcgcucugcuucggugcaucccagccuuggauuca uuaaagccugcuaaugaagaccagaaaauagguauagaaauuauuaaaagagcacuuaaaauuccugcaaugacgauugcua agaaugcagguguugaaggaucuuugauaguugagaaaauucugcagaguucccucagaaguugguuaugacgccaugcuug gagauuuugugaacauggugggaaaaagggaucauugauccaacaaagguugugagaacugccuuacuggaugcugcugggg uggccucccuugcuaacuacagccgaagcuguagugacagaaauuccuaaagaagagaaggacccuggaaugggugcaauggg uggcaugggagggggguaugggaggcggcauguucuaacuccuagaguagugcuuugcccuuaucaaugaacugugacagga agcucaaggcagguuccucaccaauaacuucagagaagucaccuggagaaaaugacugaagagaaggcuggcugaccacugu aaucaucaguuacugguuucccuuugacgauauauaaagguuuacugcugucauuguccaugccuacagauaaauuuauuuug uauuuuugaauaaagaacauuuguacauuccugaugcugguugcaagagccauauaccaguguccugcuuucaacuuaaau cacugaggcaucucuacucuucugugagucaucaggacuguagcgcugugucaacaaaacauagagaguucagaagacagcc uuucuguggaagggugggaaugauuguguacaaaguagagaaguauccaauuaugugacaaccuuuguguaa

193 M32599 acagccgcaucuucuugugcagugccagccucgucccguagacaaaauggugaaggucggugugaacggauuuggccguau ugggcgccuggucaccagggcugccauuugcaguggcaaaguggagauuguugccaucaacgaccccuucauugaccucaac uacauggucuacauguuccaguaugacuccacucacggcaaauucaacggcacagucaaggccgagaaugggaagcuuguca ucaacgggaagcccaucaccaucuuccaggagcgagaccccacuaacaucaaauggggugaggccggugcugaguaugucgu TABLE 3-continued RNA transcripts up-regulated during HF stem cell activation.

| SEQ ID No: | Access. # | Sequence |
|---|---|---|
| | | ggagucuacuggugucuucaccaccauggagaaggccggggcccacuugaaggguggagccaaacgggucaucaucuccgcc<br>ccuucugccgaugccccauguuugugauggguguggaaccacgagaaauaugacaacucacucaagauugucagcaaugcau<br>ccugcaccaccaacugcuuagccccccuggccaaggucauccaugacaacuuuggcauuguggaagggcucaugaccacagu<br>ccaugccaucacugccacccagaagacuguggauggccccucuggaaagcuguggcgugauggccguggggcugcccagaac<br>aucaucccugcauccacuggugcugccaaggcugugggcaaggucaucccagagcugaacgggaagcucacuggcauggccu<br>uccguguuccuaccccaaugugucgucguggaucugacgugccgccuggagaaaccugccaaguaugaugacaucaagaa<br>gguggugaagcaggcaucugagggcccacugaagggcaucuugggcuacacugaggaccagguugucuccugcgacuucaa<br>cagcaacucccacucuuccaccuucgaugccggggcuggcauugcucucaaugacaacuuugucaagcucauuuccugguau<br>gacaaugaauacggcuacagcaacaggguggguggaccucauggccuacauggccuccaaggaguaagaaacccuggaccaccc<br>accccagcaaggacacugagcaagagaggcccuaucccaacucggcccccaacacugagcaucucccucacaauuuccauccca<br>gacccccauaauaacaggaggggccuagggagcccucccuacucucuugaauaccaucaauaaaguucgcugcacccac |
| 194 | AF035644 | agaagcuuccuaaggaacaagcaaguugaauagagaaaauagugaucaauaauaggcauu<br>uuaguggucuuuuuaauguuuucugcugcggaacauuucaagauuuauugauuuccucc<br>uccccccauuuuuuucccaccacacucacacacgcacgcucacacuuuuuauuugccauaa<br>ugaaccguccagccccuguggagaucucuuaugagaacaugcguuuucugauaacucaca<br>accccaccaaugcgacucucaacaaguucacagaggaacuuaagaaguacggagugacaa<br>cuuugguucgaguuugugaugcuacauaugauaaagcuccaguugaaaaagaaggaaucc<br>acguucuagauuggccguuugaugauggagcuccaccccuaaucagauaguagaugauu<br>ggcuaaaccuguuaaaaaccaaauuucgugaagagccaggcuguuguguugcagugcauu<br>guguugcaggauugggaagggcuccugugcuaguugcgcuugcauugauugaaugcggaa<br>ugaaguaugaagaugcuguucaauuuauaagacaaaaaagaagaggagcauucaauucca<br>aacagcugcuuuacuuggagaaguaccgaccuaagaugcgguuacgcuucagagauacca<br>augggcacugcuguguucaguagaaguagaagcaggcuggcuggaucguggcauuagagg<br>gaa |
| 195 | Y00629 | Sequence below. |
| | | auucagguuccucacagacccagggggugaggauguugcuuuuugcccacuugcuucagcugcuggucagcgccacagucc<br>cgacccagaguaguaagugaggggaggggugaggggagggguugggagcgaaaaagacucugugaggaaaagcgggagggu<br>ggugguggcggaggugcagcaccccaaguuccgccgcccuguccuagucccucccccgccuuuaccugggaccuugagccug<br>ggggaggucggggucucaccgcgcgccgcccccaggcccacacucgcugcgguauuucaccaccgccgugucccggcccggc<br>cucggggagccccgguucaucauugucggcuacguggacgacacgcaguucgugcgcuucgacagcgacgcggaaaauccga<br>ggauggagccucgggcgcgguggauugagcaggaggggccggaguauugggagcgggagacuuggaaagccagggacaugg<br>ggaggaacuucagaguaaaccugaggacccugcucggcuacuacaaucagaguaacgacggugagugcggcugggaucacag<br>cuaugaucacuccaugucccugagacgggccugggucaucuugacccgcugagacaaaguuucauccaaacgccuacccag<br>aaccucagacaaaaaagcccccgcagaguucugcuuagguuugggguuguacuuuuguuucucuuuuguuuugagauaucu<br>acuaacauugggcaaaguggccacagguggcgcucaucagcguaucccuuccagaaucucacacgcugcaguggauguacgg<br>cugcgacguggggcccgaugggcgccugcuccgcggguauugucaggaggccuacgauggccaggauuacaucucccugaa<br>cgaggaccugcguuccuggaccgcgaaugacauagccucacagaucucuaagcacaagucagaggcagucgaugaggcccac<br>caacagagggcauaccugcaagguccuugcguggaguggcuccauagauaccuacggcugggaaaugagacacugcagcgcu<br>caggugcccuggagagcucuccucacuuuuccucugcgguuuggggaaauccuugagguauaaccucaggggcagaacgc<br>uguucagcgggcacagcgcggaggaggagggagagggacucccaaaacugcuuuuccccuguagggauucuaauccuuaaca<br>aaagcagaucaggcucgacaauggcccuggacccaugggggagggggcucuuucucaggccucccuccuugcccuacucag<br>ugucucuauagucagacuccagcuuuucucaaucucuuggcccucauccagcucaggaccagaagcccuucccaugagucug<br>cagagaccuggagccuccuguccauguuguccugcucacauccuaaggcaucccuaagagcagauccucccaggugcaggug<br>cucuagcuggugucuagaugauggacaccauaaucccaccgcaguccuccuguccaccccaggacggucacaugaacacugc |

TABLE 3-continued

RNA transcripts up-regulated during HF stem cell activation.

| SEQ ID No: | Access. # | Sequence |
|---|---|---|

ugaguccccagaagaaagcaagaugccucaucccuuucaacucucucccucagacccuccaaaggcacaugugacccaucaccc uagaucugaagaugaagucacccugaggugcugggcccugggcuucuacccugcugacaucacccugaccuggcaguugaau ggggaggagcugacccaggacauggagcuuguggagaccaggccugcaggggauggaaccuuccagaagugggcagcuguc guggugccucuugggaaggagcaguauuacacaugccauguguaccaugaggggcugccugagccccucacccugagaugg gguaaggaggguguggguggcugaacuggggucagggaaagcuggagccuucugcagacccugaguuggucauggcucagag cugggaucauaacccucaccuucauuuccuguaccuguccuucccagagccucccuccauccacugucuccaacaugguaauc auagcuguucugguuguccuuggagcugugaucauccuuggagcugugguggcuuuugugaugaagaggaggagacacau agguaggaaagggcagggucugaguuuucucucagccuccuuuugcagugugcucugcuccuuaaugggaaacauagccac acccacauugcugcagucuccaacugggucagcugucaguuccgggaacucccuagggcugguguuucucuggucucucau ggcuuuucuucucacagguguaaaaggaugcuaugcucauguucuagguaagugcgagagaggggcaggggacacccuugu cccugaggcucucaggauggagcugggauuuguuccagcccauaaucuccucuugccacauccucucugucuccucugugu gccuuguuaucucuucuacugcaggcagcaagagcuuccagaccucugacuggccucagaaggcaugaaaaucccuggggggg gcuggugagauggcucagugguaagagcacugacugcucuucugaagguccagaguucaaaucccagcaaccacauggug gcucacaaccauccguaacgagaucugacucccucuucuggagugucugaagacagcuacaaaguacuuacauauaauaaa

| | | |
|---|---|---|
| 196 | AW125380 | uuuuuuuuuuuguucccuugaaagccagauguuccaaaaaguagccugcuccauuguucu<br>ucucagucucauagcgacugccagcgucaauccacacucccaccgugcagguagcaugcg<br>aggacugcuccgaggccacacgcagcccguuguccaagaugcugaccugggucuccggca<br>cgcucuggagggccugggcgaagguugcgguaccccgcaaggcagguaaccucagcaggg<br>ccggcgagcggcgggugcgccucgugccg |
| 197 | U68564 | Sequence below. |

ggugcuuaauguuuugaccuguagagguccucacuuuucgucauggcgcugaagguggcgauagcugcuggcggugcugc aaaggcaaugcucaagccaacucuccucugccguccuugggagguucuggcugcccauguggccccccgaaggagcauuucc ucacaacaaacaauuccuccaucugcuaaguaugguggggcggcauacagugacuaugaucccaggggauggcaucggcccag agcucauguugcauguuaagucuguauucaggcaugcaugugugccgguggacuuugaagaggugcauguaagcuccaacg cugaugaggaggacauccgcaaugccaucauggccauccgccggaaccguguggcccugaagggcaacauugaaacaaauca uaaccugccaccaucccacaaaucucgaaacaacauccuucgcaccagccuagaccucuaugccaacgucauccacuguaaga gccugccaggaguggugacccggcacaaggacauagacauccucauuguacgggaaaacacagaaggcgaguacagcagccu ggagcaugagagcguagcaggaguggugggagagcuugaagauuaucaccaaagccaagucccugcgcauugcugaauaugc uuucaagcuggcccaggagaguggggcguaagaaagugacggcugugcacaaggccaacaucaugaaacuggggugauggacuc uuccuccagugcugcagggaaguagcagcccacuacccucagaucaccuuugacagcaugauuguagacaacacacaacaaugca gcugguaucccggccucagcaguuugaugucauggugaugccuaaucucuaugguaacauugucaacaacgucugugcagg gcuaguuggaggcccaggccuuguggcuggggccaacuauggccauguguaugcaguauucgagacagcuacaaggaacac aggcaaaaguauugccaauaagaacauugcuaacccgacugccacacugcuagcaagcugcaugaugcuagaccaccucaagc uccacuccuaugccacuuccauccgcaaagcugucuuagcauccauggacaaugaaaauaugcauaccccagauauuggagg ccagggcaccacaucccaagccauccaggacaucauucgucauauccgcaucauuaauggacgggcuguggaggcuuagcua ucccuacaguuuugcucagcuugucuguaggacucucuucucacuuuagcacuccagcuagcuugggggacaggacccaga auaaagccacuucuguuccagaaaaaa

| | | |
|---|---|---|
| 198 | AW125346 | uuuuuuuuuuuuuuuuuguucuuaaauagaaaacuuuauuuucacugauaaugucacugua<br>acauaauuucauagcagaccugugcaaaagaucccacaucaccaaugucuccaagagauu<br>ucacacacuucugggcaggacgcacagcucugccccccaccccguguugacagucaacau<br>uuuaccccccgcuaugaguacagaaaggcgaggcaucauaacgaagccgccugaaggcagc<br>gugagcugaagucggacgcuugccaccucugaaugaauggucaccacagcaacagcacau |

TABLE 3-continued

RNA transcripts up-regulated during HF stem cell activation.

| SEQ ID No: | Access. # | Sequence |
| --- | --- | --- |
| | | gguugccucagugugcucagggugggucuuugaaaaaacgucccacuauguaaauaugcu<br>gcacuuaucccuucaacauugu |
| 199 | X61232 | See above (same Accession Number). |
| 200 | D20333 | gauccuguauaugugguuuugggggagcuaugauaaguuuuauggcaaacgguugguau<br>uguuaacuuuuuauugucaucaaaaguucauaaaaguccuauuaauccccauauucunnn<br>ncugcccuuaacucugguauacaccaaaaagaaaucuuuacuuuccuuguuuuaucauua<br>uaaaaauaaaguauuuugcuaguauggaaa |
| 201 | AB025218 | aguccgcgucccggcgucggcccgucccgcaccauggugacgcucgccgagcugcuggcg<br>cugcuggccgcgcugcuggccacggccucgggcuacuuugucagcaucgacgcgcacgcc<br>gaggagugcuucuucgagcgggucaccuccggcaccaagaugggccucaucuucgaggug<br>gcggagggcggcuuccuggacaucgacguggagaucacaggaccagauaauaaaggaauc<br>uauaaaggagaccgggaguccagcgggaaguacacauuugcagcccacauggaugggaca<br>uacaaguucugcuuuagcaauaggauguccacuaugacuccaaagauaguaauguucacc<br>auugacauugggggaggcucccaaaggacaagacauggagacagaagcucaucagaacaag<br>cuagaagaaaugauuaaugagcuggcaguggcaaugacagccguaaagcacgaacaggag<br>uacauggaaguccgggagagaauacacagagccaucaaugacaacacaaacagcagagug<br>guccuuugguccuucuucgaagcucuuguucuaguugccaugacauugggacagaucuac<br>uaccugaagagauuuuuugaaguccggaggguuguuuaaaaggccuuuuccuguugaucc<br>caaauucaugauuuacu |
| 202 | U84411 | Sequence below. |

gcauuggcucugggcugcggccggcucggcgacgcuccucgggcagcucacugcauggucgucuggugcccccgccgccug cauccccgccgccgccccgcgacgcccaccgccgccugcccugccgccgccgccugcgccgccucgggaccggcuguaugauu aggccacaaucuucaaugaguagacauauuccucaguucugugguguucucggucacacauuuauggaguuucugaagggc aguggagauuacugccaggcacagcacgaccucuaugcagacaagugaacuguagaaauucauuacuacuccaccaagaaacc cccauaagaguggauaaccuggacacaggcguguugaauugaaaucugcacagcauuugagaagagcucagaccuggauggg guaaaccucagugccacuuccuuuguauugccucuaguauuacugggauugaagagucacugcuucuuguuuaggagguuc auuucauuggcccguuucucccaauuucauacucaagcacugagaauuucaaguggaguauaucgaauaucgaaguagacu ucagguuguuuuuugguuuuguuuuguuuuuuuuuuguuuugguuuuuuuuuuuuuuuucuguuuugguuuaaaucau uucuguauucaauuuuuuaauucuuucauaacccuauugggguguuuuuuuaaacuaaauuaacauggcucgaaugaaccgc ccugcuccuguggaagucacauacaagaacaugcgauuucuuauuacacacaauccaaccaaugcgaccuuaaacaaauuuau agaggaacuuaagaaguauggaguuaccacaauaguaagaguaugugaagcaacuuacgacacuacucuuguggagaaagaa ggcauucauguucuugacuggccuuuugaugauggugcaccaccauccaaccagauugucgaugacuggcuaagucuugug aagauuaaguuucgugaagaaccugguugcuguauugcuguccauugugucgcaggccuuggcagagcuccggugcuugu ugcccuagcauuaauugaagguggaaugaaauaugaagaugcaguacaauucauaagacaaaagcggcguggagcuuuuaac agcaagcaacuuuuguaucuggagaaguaccguccgaaaaugcggcuccgcuucaaggauuccaauggucauagaaacaacu guuguauucaauaaaacugggggugccugaugccauugccuuggaaguggaacuucagaugggaccugauuugucaugcaua uuacccaaugugucggcuuacugaauaagucuacugcagcuccacaggaauacugaaaaaccagucuuaccaggccacaagu uugacagaauugcaaccucuauauuugggcuaugaucaacauguuuggacacuuagcaaaagauuuuugcuguucagcauu uaaaaugugcuuauuauuuguaccaauugaccuuuccuaaaauaagguauugaguuaugucauuaaauguacuccugugcc agaauauuauuagucuauaaggaauuuagaaggauuaggugccaaaauacccagcacaauacuuguauauuuuuagcaucau acagaaccaaaauugcaggaacugagaacucucagaccauccaugguguauuccuucagucauuucaaacacugcagggcuc cucucguuaucugccugcucacucuguuuacaucucccacacuuaugccagaauacgucagguuugcuuagccauccuuua uuuuuuuuauuuuuuuuuuuuaacuaagucuugcgcugauuauuuaauaugucugucucauuuuguuuuguuuugggaaa ccucugucugaaaaaucaacuuuguuacagaagcacauaucuucaacaaugucuccagacaaaaagccuuauaguuaauuua auguuugcacucagaagugcaaccuaacagggagggccugaaaaagaaacgagaggaggcuauuaaauauuuuuaguaauau guugccuuugucaugugcagaacauguagaguaugcucuuaauuuaguaaauauuuuuaagacauagagauacauguguag TABLE 3-continued RNA transcripts up-regulated during HF stem cell activation.

| SEQ ID No: | Access. # | Sequence |
|---|---|---|

cuaacccauucuuauucaaaauucuggaauuuuguguuuuccnauaccuaucaggaaguuuccagcuuguuugaauuaugg cuuuccucuucccaaucucuugcaaaaaagacaaaguggaugaaucugcuagugaacugagcagaaauguuuuauaacgcc uuuugagcuauguaacuuaauaauuggauacuugaucauuuguuuuauuauguaaucggauaaaaauggugauguguauua aaguuaguucaaccauauauuuauacugucugggaaugugugguuauaguucugugggagaaauaguuugucaguguuca ccagcuuguaaaaacuuaguaugagagcuucaacauuuaaauaaaugaugaaccgcauucgucacugaggacacuuuugccu aaaauuaacuuaauuuguagaaaacaauggauucaguuaauaucauuucaauuuauggaaaaaauuguuaggguugccaag ugcuuuuuauuaaaaguuucucuuuaaaggucuagauaauugugaaucaguugaauguugggcaccgaggggaaacaguuu guaauagaugaucuagauuuuucaguucaguuccaucagucacuuguagcucugcaauuuccagaccaguuuucucauuuu uaaguucauuacaugccuguauauauuuugaaauuaacuugaaccugaguauuuggcacaugauggcuuaauaaauuuuaa cuuuc 203 M62362 Sequence below.

acgcuccccaaccuccaccuccccucgcucggccucuauaugcucccgggcucccuaguguuggcuggaagugggugacuua gaggcuuaaaggaggggcgccuaaccacggaccacgugugugcgggggcgacagcgccgccgggguggggcugagcgcugc aagccggguucgccuugcagcgcaggagucagugggcguugcgccacgaucucucuccacuagcacuaugcucccgccccac ucaccgccuuggaaagucacaggagaaggcgggcucuaagacccagcaggcaccauccuacuggcgccuucgauccgagaccc guuuggacaccaggggggcgaugccgacccucuauaaaagcgguccccgcgcgggccuggccauucgcgacccgaagcugcgc gggcgcgagccaguuggggcacuggguggggcggcggcgacagcggcgccacgcgcaggcuggaggccgccgaggcucgcca ugccgggagaacucuaacucccccauggagucggccgacuucuacgagguggagccgcggcccccgaugagcagucaccucc agagcccccccgcacgcgcccagcaacgcccgccuuuggcuuuccccggggcgcgggccccgcgccgcccccagccccaccugc cgccccggagccgcugggcggaucugcgagcacgagacgucuauagacaucagcgccuacaucgacccggccgccuucaacga cgaguuccuggccgaccucuuccagcacagccgacagcaggagaaggccaaggcggcggcgggccccgcggguggcggcggu gacuuugacuacccgggagccccggcgggcccccggcggcgcggucauguccgcgggggcgcacgggcccccucccggcuacg gcugugcggcggccggcuaccuggacggcaggcuggagccccuguacgagcgcgucggggcgcccgcgcuacggccgcugg ugaucaaacaagagccccgcgaggaggacgaggcgaagcagcuggcgcuggccggccucuuccccuaccagccaccgccgcca ccgccaccgccgcacccgcacgcgucucccgcgcaccuggccgcccccacuugcaguuccagaucgcgcacugcggccagac caccaugcaccuacagccuggccaccccacaccgccgcccacgcccgugcccagcccgcacgcugcgcccgccuugggugcug cgggccugccuggccccgggagcgcgcucaagggcuuggccggugcgcaccccgaccuccgcacgggaggcggcggcggugg cagcggugccggugcgggcaaagccaagaagucgguggacaagaacagcaacgaguaccggguacggcgggaacgcaacaaca ucgcggugcgcaagagccgagauaaagccaaacaacgcaacguggagacgcaacagaaggugcuggaguugaccagugacaa ugaccgccugcgcaagcggguggaacagcugagccgugaacuggacacgcugcggggcaucuuccgccagcugccugagagc uccuuggucaaggccauggcaacugcgcgugaggcgcgcggcugcgggaccgccuugggccggcccccuggcuggagaccca gaggaugguuucgggucgcuggaucucuaggcugcccgggccgcgcaagccaggacuaggagauuccgguguggccugaaa gccuggccugcuccgcgugucccucccuuccucugagccggacucggugcgucuaagaugagggagucaggccguggugg uuucuccuugagaccgagagacuuuuccgcggagcugagcugggggcccggcaguacuaguauuaaggaaguaaccuugug ccuuggauacucaaaacucgcuccuuuuccuaccgaguagggggagcaaaaaugugccuugauauuuuauuuggaggauuc cugcuuccucucgggccucagcuggcccccgugagaaaaaugaagggugcaggcccagggcaggaggaagauacaggaagcu gagaucccggcagugcccugagcugccccucagucccugucuuuagaggggagggacuuagguguuggggauuugagucug uguccucacccccagcuacagggagguggagggcuccuaaucccuugcuuuuugcaccuccaccuacauccccccccccccac TABLE 3-continued RNA transcripts up-regulated during HF stem cell activation.

| SEQ ID No: | Access. # | Sequence |
|---|---|---|
| | | ucagcuuacaacaggccagguuuccugggugaguucauggagaaugggggcaccacccccagucagacagaaagcugaguug ugaguuagccaugugguaggagacagagaccuagguuucugggcuuugugggguggggggauaggaggacacggggaccau uagccuugugguguacuguaugucgccagccgcuguugcugaaggaacuugaagcacaaucgauccaucccagagggacugg aguuaugacaagcuucccaaauauuuugcuuuaucauccgauaucaacacuuguaucuggucucuguguccccagcggugcc uugugcaauggcagugugcacgucuaugcuaaaccaccauuuuauuuggucuuuuguuuuguuuugguuuugcucugauu cuugccaaacugagacucuucacuaacggcugggggaaggagcugagugaggcucucauucuuuuugguuuagggauguu uggguuuuuucgucugccucccagaggaccaaugaaaugaagugggcuuccccccucuccccuaguuguccaagggguguaug uaguagugggucuuagcuuccuccggcuaagacuuaggcuuccccacccacccaacccccaucccccaacggcccuggcucugg gucuggaaagaaggccaccuccagccaguucauacacacaccccuguggcugggagcagggcuggaccgcuuccuucucuuc uuuuuuuggggggggggacacaaaguuucaugcuagaugucguauguauuauaucuauaaauauaaacauaucaaacucaa |
| 204 | AA032310 | gaagcucagugucgugaaauggaaaccaaaccuuggagccaucgcugaguauaaaaaaaa ggaagauuuauauucngcaaagaguagccgaacuggacaaaauuacuucugaaagagaua auuuuagacaagcauaugaagaucuucgaaaacaaaggcugaaugaauuuauggcugguu uuuacguaauaacaaauaaacuaaaagaaaacuaccagaugcucacauugggaggagaug cugaacuggagcuuguggacaguuuagauccuuuuucugaaggaaucauguucaguguuc ggccaccuaagaaaaguuggaagaagaucuuuaaccucucaggaggcgagaaaacccuua guucccuggccuuaguguuug |
| 205 | M94087 | Sequence below. gccgguuugaguugugcgcucgggugucccuuuccucuucccucccgcagggcuugcggccaccauggcguauuagaggc agcagugccugcggcagcguuggccuuugcagcggcggcagcagcaccaggcucugcagcggcaacccccaccggccuaagc cauggcgcucuucacgaaauccagcagcagugugcuguaacggacaaagauaccuucgaguuaagcacauuccuggaaucc agcaaagccccacaacaugaccgagaugagcuuccugaacagcgaaguguuggcgggggacuugaugucccccuucgaccag ucggguuuggggggcugaagaaagccuaggucucuuagaugacuaucuggagguggccaagcacuugaaaccucaugggguuc uccagcgacaaggcgggcucccucggaauggccggcuauggaugauggcuuggccagugccucagacaccggcaaggaggaug ccuuuuccgggacagauuggauguuggagaaaauggaucugaaagaguuugacuucgaugcucuguuucgaauggaugacc uggaaaccaugccagaugagcucuugaccacguuggaugacacaugugaucuuuuugccccucuaguccaagagacuaauaa ggagcccccucagacagugaacccaauuggccaucucccagaaaguuuaauaaaagucgaccagguugccccccuuuacauuc uugcagccuuucccccuguuccccagggguucugucuuccacuccagagcauuccuuuaguuuagagcuaggcagugaaguu gauaucucugaaggagacaggaagccugacucugcugcuuacauuacucuaaucccuccauguguaaaggaggaagacacuc ccucugacaaugacaguggcaucuguaugagcccggaguccuaccugggcucuccccagcauagccccuccaccuccagggc cccaccagacaaucugccuucuccaggugguucccgugggucuccucggcccaaaccuuaugacccaccuggaguuaguuug acagcuaaagugaagacugagaaauuggauaagaagcugaaaaagauggagcaaaacaagacagcagccacuagguaccgcca gaagaagcgggcugagcaggaggcccucacuggcgaguguaaggagcuagaaaaaaagaaugaggcucugaaagagaaggca gauucucuggccaaggagauccaguaucugaaagaccugauagaagagguccguaaggcaagggggaagaagagaguuccgu aauaggguagucaggugcuuugugcuuguacauagucuuguguugcugugguuugcuguaauaaauuauuuuguagugaaa gu |
| 206 | AI847609 | uuuuuuuuuuuuuuuauguagggaaguucauauuuuauuuguccagugacauuuuuuac aguugaauacaaguuaaaggccugcuugcacaccaaagccagguccuuuggguggguucag ucaaagaaguaaggccuccagcuggcucacaacagaagcggccacuccuuggcccugguuu gggaacuuuuccagcuuugaguucaucaauaaucucuucaauauccuugggugucagauc cucauaguaguugucauuuauuugaaccaucggugcauuuacacaggccccuaaacauuc cacuucuauaagagugaaaaguuugucagguguagucucuccaaccuuuauuccaa |
| 207 | AI853294 | uuuuuuuuuuuuuuuugggggugaauauagccaaguauuccauuuauuaacaaaauagu cuuagcaagggagagcucuguucaccccacaagaggccccgcagccgaggccggcccgaag |

TABLE 3-continued

RNA transcripts up-regulated during HF stem cell activation.

| SEQ ID No: | Access. # | Sequence |
|---|---|---|
| | | ccccagcgcugcugcguaagaccgggagggagggaaggguguuggggagaagacuuguauu aagucuuuaauccuagccaccgcaggaacccacggaaaccuaaugccagcuuuggcgauu gcuggcucaggucugggacauggcgaagggagugcucugauccuagggcuccccugagucc ccagccugccccaacagagcuccuaaaguugucuggucugcugacuugaggacugguaa gcuuuggagggauccaucaaggauuccccgaccccaccccuaucgccagggga |
| 208 | M33934 | Sequence below. |

ccucugcggcgcgguccucggagcggcgcgguucucggagccacgcgucugucuuccuccgugguucauggcggacuaccug auuagcggaggcaccucuuacgugccggacgacgggcucacagcgcagcagcucuucaacugcggggacggccucaccuaca augauuuucucauucuuccugggguauaucgacuucacugcagaucagguggacuugacgucugcucuaacuaagaagauua cacuaaagaccccauugguuuccucacccauggacacugucacagaggcuggaauggccaucgcgauggcgcuuacaggagg uauugguuucauccaccacaacugcacaccugaauuccaggccaaugaaguucggaaagugaagaaauacgaacagggauuc aucacugaccccgugguccuuagccccaaggaucguguacgcgauguuuuugaggccaaagccaggcauggcuucuguggu aucccccaucacagauacaggccggaugggggagucgauuggugggcaucaucucccucaagggacauugauuuccucaaggagg aagagcaugaccgguucuuggaagagaucaugacuaagagggaagauuuggguggucgccccugccggcgucacucugaaag aggcaaaugagauucugcagcgaaguaaaaagggaaaguugcccauugugaaugaaaaugaugagcugguagccaucauugc ccggacagaccuaaagaagaaucgugauuaccccccuggccuccaaagaugccaagaagcaacugcugugugggggcagccauu ggcacucaugaggaugacaaguauaggcuggacuuacuggcccuugcugguguggauguaguggguuuuggacucuucccag ggaaacuccaucuuccaaaucaauaugaucaaauacaucaaggagaaguaucccagucuacaggucauuggaggcaauguag ucacugcugcgcaagccaagaaccucauagaugcagguguagaugcuuugcgagucggcaugggaagugguuccaucugca ucacccaggaaguguuggccugugggcggccccaagccacagcaguguacaaggucucugaguaugcccgucgcuuuggug uuccuguuauugcugauggaggaauccaaaaugugggucauauugccaaagcuuuggcucuuggggcuuccacagucauga ugggcucccuccuggcugccaccacugaggccccuggcgaguacuucuucucagaugggauccggcugaagaaauaccgagg uaugguucucuugaugccauggacaaacaucucagcagccagaaccgauacuucagugaagcugacaaaaucaaaguggcc caaggaguuucaggggcagugcaggacaaggggucuauccacaaguucguuccuuaccugauugcuggcauccagcauucc ugucaagacauuggugccaagaguuuaacccaagucagagccaugacguacucgggggagcuuaaauuugagaagaggacau ccucugcucagguggaagguggcguccacagccuccauucguacgagaaacggcuuuucugaaaacagauccaguauaugcc uugaauuuuucaauaaaaguuugggaaaaaaaaagugaaaaaaaaaaaaaaaaaaaaaaaaaaaaaaaaaaaaa

| SEQ ID No: | Access. # | Sequence |
|---|---|---|
| 209 | X16202 | gugugggugcagagcuggggucagggaaagcuggagccuuuugcagacccugagcugcuc acggcugagagcuggggucauuacccucaccuucauuuccuguaccuguccuucccagag ccuccuccauccacugucuccaacauggcgaacguagcuguucugguuguccuuggagcu uggccaucauugcagcugugguggcuuuugugaugaagagaaggagacacacagguagga aagggcagagucugaguuuuu |
| 210 | AI661431 | acaggaggggaaggccaaagcaagaaugaaaguccccccgccccguaucaccacgggcacu cggggucacccucaggaacaugcagucucugcacgugaggaaagaaacacgcagagaugg acgagcacuuuuacacccuaauaaaauuagaugcacuaaccacagaccccccu |
| 211 | AI839109 | uuuuuuuuuuuuuuuuuaaaaaaaaaaaauggcaucuuuuauucaucaaucccuguuacac acugaaauacaugcaucuuucuuauguuacuuagcaacguccuuucuauccuuucaccca uaaaucagucugaugaauucaucuuuaaauucaagaaguuuuucuuuuugaaacgcuacu uacauuuuauugucucaauaucaaagccaaucuagagauuuauucuuccuacaggugaaa uagauguuaauacgggaacagucaguacauguucaagaugacaucaaaguuaugcccuaa gcagauauuucaaggcaauaucaugccacuagcucugagacucuaaguaucacugauagu acuaaaagguagaagucagcuucaaaaacacacucuugcaauggacacugcucaugaugu cuaagauuguucacucccacagucaugauuucagaugcacaguuuuuuuugcuuuccuga gcauucgguuugac |
| 212 | AI849135 | uuuuuuuuuuuuuuuuuaagagugucaccaaagcuuuauuuacaugcgucaucaucucuu uuacaaacuagauuaugguuuuaaauggaauacacaggcaauaucuacaaacgccacggg aaguacgcaccuccauucccaccgggaaggggcagauucccaaaucaaacugguuuugauc cuugagaagaaaggcggcagagcuaacucacggcagcguaugguuagacaagguccucag uacccagaaugcagcaggauugcgucugccucaaaccagacgaccaacugcugcaggugu |

TABLE 3-continued

RNA transcripts up-regulated during HF stem cell activation.

| SEQ ID No: | Access. # | Sequence |
|---|---|---|
| | | uuaaacauggccacgcgccacacgaaauucuaguuugugugggguagaagcaagaaaaaa<br>aaaaaaccauggcgccucgugccg |
| 213 | M32459 | gguccggauaguaaacugcucccuuacaucuccuuaaauauaaaguaaggaaaaagaaaa<br>aacucaguucggguaaccaaguucaacaaguaauccuuggggccgcugugguaucgccaa<br>aaucuacauaguaucucuuauuaaaauguuuugacgaaaauguaacaauuacgguacuua<br>augguaacaauguggcugaggaagcaauaguuaacaaagaggagcuaagcuaugcaacaa<br>accagauuucuauuggucacaaauuugaaguugagaccuguuauccaauuaccaaguacu<br>uccgcauacaucaucauaggcauuugaagauuucaaccaaucaggagcauguuccuucua<br>uaaaggaacccagaaccuaaccucugcauuuccuauuucuuuguagaaauggcucguacg<br>aagcagaccgcucgcaaguccacuggcggcaaggccccgcgcaagcagcuggccaccaag<br>gccgcccgcaagagcgccccggccaccggcggcgugaagaaaccucaccgcuaccguccc<br>ggcaccguggcgcugcgcgagauccggcgcuaccagaagucgaccgagcugcugauccgc<br>aagcugccguuccagcgccuggugcgcgagaucgcgcaggacuucaagaccgaccugcgc<br>uuccagagcucggccgucauggcucugcaggaggcgagcgaggccuaccuugugggucug<br>uuugaggacaccaaccugugcgccauccacgccaagcgugucaccaucaugcccaaggac<br>auccagcuggcccgccguauccgcggcgagcgggcuuaauaggcacgcuuucuacacugg<br>cacguaaaccaaaacggcucuuuuaagagccaccuccauuauccaccaaagaugcuugaa<br>guacaaguugugagaguuuucuaggguuuccuauuauagccuuucuugacaaugugagca<br>ccacccgacgaagcagucugag |
| 214 | AI841389 | uuuuuuuuuuuuuuuuuggacuucugcggcuuuuauuuuugcauguaaaccacuggggg<br>agggggaucuugauggugggcacccuagagauuacacuggaguuccgagggcuccagaca<br>cuagcugggaagucaggugacagaaacaaugauucagaccaaucacaugauugcaaaacu<br>gggucuccagcagggauucugguggucagguguggaugccuaaggaagcagugacauggg<br>aggggcacgcacugggcuggccuugagcugcugggaugacaucagggauagaggaccuag<br>cagcugguggcuccagggaucuccgguccaugcuuuauuuggccagggggguuccugaagg<br>accugccagcaaacuuggcuuugcugcccagcucuuccucaauucugaggaucugauugu<br>acuu |
| 215 | X03039 | Sequence below. |

auucuaaggaucaugucugcgagucaggauucucgauccagagacaauggccccgacgggauggagccggaaggcgucaucg agaguaacuggaacgagauuguggauagcuuugaugacaugaaucucucagagucccuccuccgugguauuuaugccuaug guuuugagaagcccucugccauccagcagcgagcuauucuuccuuguaucaaggguuaugaugugauugcucaagcccagu cugggacugggaaaacagcuacauuugccauaucaauucugcagcagauugaauuagaucuaaaggccacucaggcuuuggu ucuggcacccacacgugaauuggcucagcagauacaaaagguggguuauggcauuaggagacuacaugggugccucuuguca ugccugcauuggggcaccaaugugcgugcugaggugcagaagcugcagauggaagcuccccauaucaucgugggguacccc uggccggguguuugacaugcuuaaccggagauaccuguccccaaauacaucaagauguucguacuggaugaagcagaugaa auguuaagccgaggguucaaggaucagaucuaugacauauuccagaagcucaacagcaacacacagguaguuuuguugucug cuacaaugccuucugauguccuugaggugaccaagaaauuuaugagagacccuauucggauucuugucaagaaggaagaau ugacccuggagggguauccgccaauucuacaucaauguggaacgagaggaguggaagcuugacacauugugugacuuguaug agacgcugaccaucacccaggcagucaucuuuaucaacaccagaaggaagguggacuggcucaccgagaagaugcaugcccga gauuucacuguuucugccaugcacggagauauggaccaaaaggaacgagaugugaucaugagggaguuccggucuggcucu agcagaguauuaauuaccacugaccuguuggccagaggcauugaugugcagcaggucuccuuagucaucaacuaugaccuuc ccaccaacagggaaaacuacauccacagaaucggucgagguggucgguuuggucguaagggguguggcuauuaacauggug a ccgaagaagacaagaggacucuucgagacauugagacuuucuacaacaccuccauugaagagaugccccucaacguugcugac cucauuugaggggcuguccugcgaccuggcccuagcccaggguucaguccugggguggggcuaaggaagagcuggaggggg gaggggagggagccaagggauggacaucuuguuuuuguuuuggcuuuuuuuuuuuuuuuguuucaguuuuuuuucucuau gaauaaaugucacuuuuugaggc

| SEQ ID No: | Access. # | Sequence |
|---|---|---|
| 216 | AW049795 | uuuuuuuuuuuuuuuuuugccaggauauauuuauuacugaaaguacaagcaacugagguuu<br>acccugggaacacccacaaugaaacguguaucuucccuguuucucagaugcugccuccuu<br>ccacagagugaguuuucguuuaaaacucauaaugaggagaaggcagggggcuccaccccu<br>uuccuguucaaucugaagacugaauugggcuacacugggauggagauuucaggugcugca<br>ggucagugucaaccaaggguucgugugucaggaacucuggcugguaagaugacacaaagg<br>cuucaugcugaagcucagggagguccagggagccuggcagaauggaaucaucauggucau<br>caucaaacgucugugucuggaaggcuucaaggcucauaauugcaucauucucuggcaguu<br>ccugagagagcugccccuuccugggguuugcacgcaucaaauuucacccacugguaauuga |

TABLE 3-continued

RNA transcripts up-regulated during HF stem cell activation.

| SEQ ID No: | Access. # | Sequence |
|---|---|---|
| | | cacaguuuugagcuucgggacaacucuuaaucagguuguggaugguuggaugagaaaacc caaagaagucggcaccgcauga |
| 217 | D87691 | Sequence below. |

auuguaacagaagaaggaaaggaaaagaaaguuaacauugacuuugaaccuuucaaaccaauuaauacaucauuguauuugu gcgacaauaaguuucauacagaggcucuuacagcguuacuuucagaugacagcaaguuugguuuuauuguaauagacggaa guggugcucuuuuggcacgcuccaaggaaacaccagagaaguccugcacaaauucacuguggaucucccaaagaaacacgg cagaggaggucaaucagccuugcguuuugcccguuuaagaauggaaaagagacauaacuauguucggaaaguagccgagacu gcugugcagcuguuuauuucuggagaccaagugaauguggcugguuugguuuuagcuggaucagcugacuuuaaaacuga acuaagucaaucugacauguuugaccagagguugcaaucuaaaguuuuaaaauuaguugauauauccuaugguggugaaaa uggauucaaccaagcuauugaauuaucuacugaaguucucuccaacgugaaguucauucaagagaagaaauuaauaggacga uauuuugaugaaauuagccaggacacaggcaaguacuguuuuggaguugaagauacacuaaaggcuuuggaaaugggagcu guacaaauucuaauagucuaugaaaaucuggauauaaugagauacguucuucauugccaaggcacagaagaggagaaaauuc ucuauuuaacuccagaacaagagaaggauaaaucucacuucacagacaaagagacuggacaggaacacgaacugauagaaagc augccucucuuggaauggguuugcuaacaacuauaaaaaaauuuggagcuacacuagaaauugcacagauaagucacaagaag gaucacaguuugugaaaggauuugguggaauuggagguaucuugugguaccgaguagauuuccagggaauggaguaccaag gaggagaugaugaauuuuuugaccuugaugacuacuagguagucgacaugggucggcaaccgugccucacccuccagcau ucaacccaaggagcauacccgugguggaguccaacagaucccugccuuacaauuggagcauuuccagaacuuaauccgugag cauuggauacugaaaagaaaagugaaacaaaaccagacccaacccuacacuuugguuugucgguggucagcgcagcagccg acaacuaagucucu

| SEQ ID No: | Access. # | Sequence |
|---|---|---|
| 218 | AI117211 | cagaggagucauuguugcugugguggcuuuugugaugaagaggaggagaaacacagcgua agccagcugccuggaguggacuaagugacagacaaugucuucacacaucuccugugacau ccagagcccucaguuuucuuuagucaaguaucugauguucccugugagccuaugggucaa agugaagaacugugcagcccagccugcccugcacacagaacccugucccugcacugcccu ggguucccuuccacagccaaccuugcugcuccagccaaacacugggcgacaucugcaucc ugccagcuccaugcugcccugagcugcagcuccucacuuccacacugagaguaagaaucu gaaugggaccuugauucuuaacauccugaccgaggguugauuucuuguuaauuucaugga uugagaauacuuagagauuuugguuugucuugauuuuuuuucaag |
| 219 | Y00520 | ugaauaaaaacgaggagccgaagauucuaggggcuacagcugcgcuuuugcagcacuga acaugguuccggguacucaagauauugcguuuguguuuggagagguguagauuguagauu ccagccgagaagaccaggaaaagauaaggauaaagaaugucauauaucucaggagcuaga ucacuucccgaugaacaaguaagaauugccucaacaaaaauggauggaauuggaccgaaa aaagccauucagcuucguuaucgauuagguaucagugggaacaucaagaugaaugaguua acuaaguaucagaucgaccaaauugaacaaaugauagcucaagaucauguuguucauugg gaauugaagaggggagaacgagcagacaucgaacgauuaauuucuauuucucguuaucgu ggaauucgucaucaagauggaucgcccuuacgcggucaacgaacucauacuaaugcaagg acugcucgcaagcaaauucggaaaugaaagaaggcuaccgaaagaacaagcaacggauuu cgcgcucaucccuugcuaaagcgcauacguuuucuugcuccuugguacuugucugaucaa ucacacuguucauuaguucacuugauuuuucguucgaugucuugaaccgcuuacuaauca cguauacguauaguaggccccuucgccacuccacgucuggcccgucuuggucucgcuca cuucgcccgccuaucguaucggcucggcuucguccgucaagcgacagcuucugccucuga cggcuucacuaucgcucaugacugguaguacucuauguaguagucggccuuuguuaagcuu |
| 220 | AA638002 | uauaaccauguuagaagcggaaguuggccugaaaaccugaggcuuaggcuucauagcugg gcuguagauuggauuuaaacccaguuggagugcaaagucaugguguugcucaaggugauga cagugaacagaguaug |
| 221 | Z22661 | caugggccuccugagaga uccuuagauccagguuagugcauaggaaaguguccccccacuaccuacagcuaagggauu gggguggugggaucaugguggagggccgguggugaauacuagcgaugucccccgcuacccg ugcgucugccuccagggugccccuccaaccaggaugaggcucuucaucgcucuuccuguc cugauuguggucguagccaugaccuuggaagguaagaaagagccuuggaagguaagaaag augcuuggaagugugaaguuggccuugugccugcggcccaggcuuagaagacccucgagg agggcucugagguccccuuucugugucaucauucccacuaccgcccucccaucguccccccau cccaccugccaggugccuuauuuuugugucaaagugggugcugaaggaggcaacucuguc cagaaaagacgcaguaaccaaugaccuaggauaccacccuuuggaauuggcuaaucuucc uagaaggggcggacgguaaaaacaaggaggugagaggugcaguaaaaucaaguguccaau acccucccccaugcuaaugaguuugcucgcaacccucucgcggcaggcccagcccccgcc |

TABLE 3-continued

RNA transcripts up-regulated during HF stem cell activation.

| SEQ ID No: | Access. # | Sequence |
|---|---|---|
| | | caggcggccccggauuuguccggaacauuggagagcauaccggauaaacugaaggaguuu gggaacacuuuggaagacaaggcccgggcagccauugaacauaucaaacagaaggaaauu uugaccaagacccg |
| 222 | X99644 | Sequence below. |

cagcgccuggggcgcggcgggcgucggcccaggagacgcguggcggcgcucggccucgcggcaucggcggcugccuggccg uuggcggcgagcgcacuugcgccugcgcagcggggucgcgugcccucccccugggcggcccccccacccccccggcggcg ugugaauggcggccucggcggcagcgacugcagcggccucggccgcgacggccgccucggcggccucugguagcccagggu c gggcgagggcucggcgggcggugagaagcguccggcugcuuccucagccgcggcggccucugcagccgcgucguccccugc gggggcgguggcgaggcgcaggagcuucuggagcacugcggcgugugucgcgagcgccugcggcccgagcgggauccucg gcugcugcccugucuacauucggccugcagugccugccugggccccgcuacacccgccgcagcgaauaauucgggggauggc ggcucggcgggcgacggcgcuaugguggauuguccagugugcaaacagcagugcuacuccaaagacaucguggagaauuau uuuaugcgugauaguggcaguaaggccucuucugauucccaggaugcuaaccagugcugcacuagcugugaagauaaugcc ccagccacuagcuauuguguggagugcucugaaccacuuugugagaccuguguggaggcucaccagcgggugaaauacacca aggaccacacugugcgcuccacaggaccugcuaagacucgagauggagagcgaacagucuacuguaaugugcacaagcauga gccccucgugcuguucugugagagcugugacacacucaccugccgcgacugccagcucaacgcucacaaggaccaucaguac caguuuuuggaagaugcagugaggaaccaacguaaacucuuggcuucacuggugaaacgucuuggggacaaacaugccacac uucagaaaaacaccaaggagguucgaagcucgauccgccaggugucugaugugcagaagcgagugcagguugaugucaagau ggccauucugcagaucaugaaggagcugaauaagcgggg ucgaguucuggucaaugaugcccagaaggugaccgaggguca gcaggaacgucuggagcgccagcacuggaccaugaccaaaauucagaagcaccaggaacacauuuugcguuuugccucuugg gcucuggagagugauaacaauacagcucucuugcucucuaagaagcugaucuauuuccagcugcaucgggcccucaaaauga uuguggauccuguggagccucauggugagaugaaguuucagugggaucucaaugccuggaccaagagugcugaagccuuug gcaagauuguggcugagcguccugguacgaacuccacagguccugggcccauggcuccuccaagagccccaggcccucuaag caagcaagguucuggcaguagccagcccauggaaguacaagagggauauggcuuugggucagaugaucccuauucaagugca gagccgcauguaucaggcaugaagcggucccgcucuggugagggagagguaaguggccucuuaaggaaggugccacgugug agccuugaacgccuggaucuggaccucaccucugacagccagccaccagucuucaaggucuuuccuggaagcacuacugagg acuacaaucugauuguuauugagcguggugcugcugcagcagcugcuggucaggcugggacugugccaccaggagccccug gugccccaccccuuccuggcauggccauugucaaggaagaagagacagaagcugcuauuggagcucccccggcugcccccga ggguccugaaaccaagccuguguugaugccucugacugaagguccuggugccgagggaccucgucuagcuucaccuagugg caguaccagcucaggcuuggagguggugGcuccugagguuacuucagccccaguaagugggccagguauccuggaugacag ugccacuaucugccgagucugccagaaaccaggugaccuggucauguguaaccagugcgaauuuugcuuccaccuggauug ccaccucccugcccugcaggauguuccaggggaggaauggaguugcucacucugccacgugcucccugaccuaaaggaggaa gauggaagccucagccuggauggagcagauagcacuggugugg ugacuaaacucucaccagccaaccagcggaaaugugagc guguucuccuggcccuguucugccaugaaccaugccgucccuugcaucagcuggcuaccgacucuacauucuccauggagca gccugguggua cccuagaccugaccuugauucgugcucgccuccaagagaagcugucaccuccuuauagcucccccaggag uuugcucaagaugugggccgcauguucaaacaguucaacaagcugacugaggacaaggcagauguucaguccaucaucggcu ugcagcgcuucuuugagacacgcaugaaugaugccuuuggugacaccaaguuucugcugugcugguagaaccaccaccau ugaaccuucccagugcuggccuaaguucucaggagcucucuggcccuggugauggccccugaagcuggggcucuuguggu c agcccaguccagcucuggucucuguauuuucaccccauacccuguccuugguggccugacuccuguucuugcuggcccca TABLE 3-continued ucguccccucagucccucuucacaaaaugguuuuuacuucuguggauuuaauaaaaacuucacugagucaguuaaaaaaaaa aaa RNA transcripts up-regulated during HF stem cell activation.

| SEQ ID No: | Access. # | Sequence |
|---|---|---|
| 223 | AI843895 | uuuuuuuuuuuuuuuuuaaaaauaauuucauuuuuuaauauucuguacaaaauuucucaa<br>ccuaugaaaauaaaguuugcaaaagucaaaguaguacaugggccugcccuggagccaggc<br>ccagccggaucuacacuauguacaggucucccagggugagccucagcuagggaaaagcca<br>cuaaggugccuacagagcaagagggugccaucgggccagugcagccucugcaauuuccag<br>aucugccacuagaggucggcaugguccugauugcuugucaggcucacccucuggaagacc<br>acagccaaugacaaagguccucaagggaaagcuuuggggucuagcuggaagugacggugg<br>guccgccgcccaggcgcaggagcaucugcuggcaguccagcaguaaccggugaucgccaa |
| 224 | M38724 | uccgucguaaccuguugaguaacuauggaagacuauaucaaaauagagaaaauuggagaa<br>gguacuuacgguguggugguauaaggguagacacagagucacuggccagauaguggccaug<br>aagaagaucagacuugaaagcgaggaagaaggagugcccaguacugcaauucgggaaauc<br>ucucuauuaaaagaacuucgacauccaaauauagucagccugcaggaugugcucaugcag<br>gacuccaggcuguaucucaucuuugaguuccuguccauggaccucaagaaguaccuggac<br>uccaucccuccugggcaguucauggauucuucacucguuaagaguuacuuacaccaaauc<br>cuccagggaauuguguuuugccacucccggcgaguucuucacagagacuugaaaccucaa<br>aaucuauugauugaugacaaaggaacaaucaaacuggcugauuucggccuugccagagcg<br>uuuggaauaccgauacgaguguacacacacgagguagugacgcugugguaccgaucucca<br>gaaguguugcugggcucggcucguuacuccacuccgguugacaucuggaguauagggacc<br>auauuugcagaacuggccaccaagaagccgcuuuuccacggcgacucagagauugaccag<br>cucuucaggaucuucagagcucugggcacuccuaacaacgaaguguggccagaagucgag<br>ucccugcaggacuacaagaacaccuuucccaaguggaagccggggagccucgcaucccac<br>gucaagaaccuggacgagaacggcuuggauuugcucucaaaaaugcuagucuaugauccu<br>gccaaacgaaucucuggcaaauggcccugaagcacccguacuuugaugacuuggacaau<br>cagauuaagaagauguagcccucuggauggaugucccugucugcuggucguaggggaaga<br>ucg |
| 225 | AW122989 | uuuuuuuuuuuuuuuuuacuaggcaaagaauuuuauuaacccuuuccaaacuuuauuccc<br>aggcuucuucagcuuuauuugccgcaaagaaugaauuagguauagcgaaacugaaaaga<br>gcugcaguguccgggggcuugggcuuaaaaauauuagagaucuagauuuuaucagaucca<br>uaauaaacaaaaaaauuuuaaaaagcagucaugauauaaaauagcagcuccuguaauuuc<br>ugcaaguaucaccuucuucagaaguugcuucaauucaguuugccucauucuuagaagccu<br>caucaaaauucuccaccagaucuggaacuucaucaucaucauccucuccaguagcaaggg<br>gugcuuuuccauccacagauuguuugggcagagcuucagccagucuccuuaaacuaguca<br>ggcugucugcaccaagcugguugaggaugcugggaagcauuucugucagcugcuuuguc |
| 226 | AI844810 | uuuuuuuuuuuuuuuuuauucaugcuugccuagggauggggaauagaucauucaauaaaa<br>acauacaguaaaaacagggggugggggagggggaaggcuuaucauguacaauguuuaaacu<br>acaauagugauguaccuuaauuacuuccaugcacacaagucuaacauuacaaguuuuuaa<br>aaaauaaacaccauuaagacuucuaggagcauuuuauaauaaauuccuaauuuuuucuuu<br>guagauagaucaagcaccuccaaaauacagauuccuauacacagugagcacuuuacuuaa<br>cguacauggacagccucaggacgagcugacgucucggaucagcucggcaggcaacaaacc<br>auagugccaaauggaaagaagggcaguugcaaauaaacuuaaaacuaaguuaacuuuuau<br>aauuaaauacagaaaauauacugauuugcuaaaaauaaauaagaugugauguauuuaaca<br>cuucacuauaaagaaugaacaccaugacauccucgugccg |
| 227 | AA940430 | agaagaaggaggagugggaccgcaagcaugaggaugcuaguagggaguaugagaaaggca<br>ugaaagaguaugaaggaggaagaggggacucaucuaaaagggacaagucuaagaagaaaa<br>agaaaguaaaagcaaagauggaaaaaaaguccacuccuucccggggcucgucauccaagu<br>cuucauccaggcaguugagugacagcuucaagagcaaagaguuuguguccagugaugaga<br>gcucuucaggcgagaacaagagcaaaaagaagaggaggcggacgaggacucugaagagga<br>gcuagccaguaccccuccaagcucagaggacucugccucgggaucugaugaauaaaggag<br>ggaauucccaccccgucacagcuccagucucucacauaguccuuggauucugugccaucu<br>gaguaacugcucuugguggcuuccacugcccugaggcuuugagggaag |
| 228 | M38381 | Sequence below. |

aucgucguaaucguuugcagacuucucgccgucgccuuguaagcuuugucuucgccuugcaagcuuugucuucaggguug gaaagaugagacauucaaagagaacuuacuguccugacugggaugaaagagacugggauuauggaacauggagaagcagcag cagucacaaaagaaagaagagaucacauagcagcgcccgugagcaaaagcgcugcagguacgaucacuccaaaacgacagaca gcuauuaucuggaaagcagauccauaaaugagaaagcuuaucauagucgacgcuauguugaugaauacaggaaugacuacau gggcuacgagccagggcaucccuauggagaaccuggaagcagauaccagaugcauaguagcaaguccucugguaggagugga agaagcaguuacaaaaguaaacacaggagucgccaccacacaucgcagcaccauucacacgggaagagucaccgaaggaaaaga ucgaggaguguagaggaugaugaggagggucaccugaucugucagaguggagacguacuaagugcaagauaugaaauuguu gauacuuuaggugaaggugcuuucggaaaaguggugaaugcaucgaucauaaagugggagguagacguguagcaguaaaa TABLE 3-continued RNA transcripts up-regulated during HF stem cell activation.

| SEQ ID No: | Access. # | Sequence |
|---|---|---|
| | | auaguuaaaaauguggauagauacugugaagcugcucaaucggaaauacaaguuuuggaacacuugaauacaacagaccccc auaguacuuuccguuguguccagauguuggaguggguuuugagcaucgaggucacauuugcauuguguuugaacuucugggg cuuaguacuuaugauuucauuaaggaaaacaguuuucugccguuucgaauggaucauaucaggaagauggcauaucaaaua ugcaaaucuguaaacuuuuugcauaguaauaaaauugacucauacagacuugaagccugaaaacaucuuauuugugaagucu gacuacacagaggcuuauaaucccaaaaugaaacgugaugaacguacuauaguaaauccagauauuaaaguggugga cuuug gaagugcaacauaugaugaugaacaccacagcacauugguaucuacaagacauuauagagcaccggaaguuauuuuagcccu cggguggucacagccaugugaugucuggagcauaggauguauucuuaucgaguauuaucuuggauuuacaguuuuuucga cucaugauagcagggaacauuuagcaaugauggaaaggauucuuggaccacuaccaaagcacaugauacagaaaaccaggaaa cgcagauauuuccaucaugaucgauuagauugggaugaacacaguucugcuggcagauauguuucucggcgcuguaaaccu cugaaggaguuuaugcuaucucaggaugccgaacaugagcuucucuuugaccucauugggaaaauguuggaguaugauccc gccaaaagaauuacucucaaagaagcccuaaagcauccuuucuuuuacccacuuaaaaaagcauacgugauuuauaaacacagu gcucugaaaggaaucuuacagacuguaucagucuagcuuuuaauuaaguuauuuuguauagcuuaaauuuguaaaacauuuu auguuuuuuagaugcuuuauuaaauacauggccaaaccaaauaacaucuuucaguaauuauagaaugauuuauuuggaaua aaauuugugcuuaugaauguaaaaaaa |
| 229 | AF014371 | ggacucgcgacaagcguccucagcgcgaagaggcggacucggaguccucgccuugagccu ugcaucugagaaguuccagguacuuuguacaacugcaucccagaaccuguguguuuucag caccuuuuauaagugauggcugccaucaggaagaaacuggugauuguuggugauggagcuu gugguaagacaugcuugcucauagucuucagcaaggaccaguucccagaggucuaugugc ccacgguguuugaaaacuauguggcggauaucgagguggaugggaagcagguagaguugg cuuuaugggacacagcuggacaggaagauuaugacugccugaggccucucucuuauccag acaccgauguuauauugaugugguuuuuccauugacagcccugauaguuuagaaaacaucc cagaaaaauggacuccagaagucaagcauuucuguccaaaugugcccaucauccugguug ggaacaagaaggaccuucggaaugacgagcacacgagacgggaguuggccaaaaugaagc aggagccgguaaaaccugaagaaggcagagauauggcaaacaggauuggcgcuuuugggu acauggaguguucagcaaagaccaaagauggagugagagagguuuuugagauggccacga gagcugcucugcaagcuagacgugggaagaaaaagucugggugccucaucuugugaagcc uugugaacgcagccucaugcgguuaauuugaagugcuguuuauuaaucuuaguguaugau uacuggccuuucauuuaucuauaauuuaccuaaga |
| 230 | Z30939 | uucaagaccgaccugcgcuuccagagcucggccgucauggcucugcaggaggcgagcgag gccuaccucgugggucuguuugaggacaccaaccugugcgccauccacgccaagcguguc accaucaugcccaaggacauccagcuggcccgucgcauucgugggg agagggcguaaauu aggguagugagugaauuuggaccccaaaggcucuuuucagagccacccacauuuucuaua aaaggcuguauaucgauaagcuuuuauaaaccccacucagcaacucc |
| 231 | U28208 | uuaugugauaaaaaaauucaacuugguauuaacuuaacuaagggccuuggugcuggugcu uugccugauguugguaaaggugcagcagaagaaucaauugaugaaauuauggagcauaua aaagauagccauaugcucuuuaucacagcagggaugggugguguacuggaacaggugcu gcaccgguaauugcaaaagcagccagagaagcaagagcgguaguuaaagauaaaggagca aaagaaaaaaagauacugacuguuggaguuguaacuaagccguucgguuuugaaggugug cgacguaugcgcauugcagagcuuggacuugaagaguugcaaaaauacguagauacacuu auugucauucccaaucaaaauuuauuuagaauugcuaacgagaaaacuacauuugcugac gcauuucaacucgccgauaaauguucugcauauuggcauaagaggaguaacugauuugaug aucaugccaggacugauuaaucuugauuuugcugauauagaaacaguaaugagugagaug gguaaggcaaugauugguacuggagaagcagaaggagaagauagggcaauuagugcugca gaggcugcgauaucuaauccauugcuugacaauguaucaaugaaaggugcgcaaggaaua uugauuaauauuacugguggugagacaugacucuauuugaaguugauucugcagccaau agagugcgugaagaaguggaugaaaaugcaaauauaauauuuggugccacuuuugaucag gcgauggagggaagaguuagaguuucuguucuugcaacuggcauugauagcuguaacgac aauucaucuguuaaucaaaacaagaucccagcagaggaaaaaaauuuuaaauggccuuau aaucaaauuccaacauuagaaacaaaagaauaugcuucaacugag |
| 232 | AV218217 | ugaucaggucacauuccggugccuuccacccccuauggcacgggcgccccgccuugccau accacagcucccuccaggcuuagaccuggcuucaccgcauuucaggugcuauaccccccc cugcuuuucccccauugcccuuaaaugccccucggccccuccauccccccggaacaggg uggcacuugccacucucaggaccaccuugccaaggagaauaaaccgaauccuguugcu |

Thus, the transcripts identified in this Example, the proteins they encode, and the pathways in which the proteins participate contribute significantly to HF stem cell activation. Accordingly, anagen can be induced by activation of these transcripts, proteins, and pathways.

Example 9

Molecular Pathways Activated During Induction of Epidermal Cells to Differentiate into HF Stem Cells The gene expression pattern of HF stem cells was analyzed as described in Example 8 and compared to non-bulge basal keratinocytes. 157 genes were differentially expressed in the HF stem cells, as assessed by microarray analysis and quantitative polymerase chain reaction (qPCR). A group of selected genes with increased expression in HF stem cells is depicted in Table 4. A group of selected genes with decreased expression in HF stem cells is depicted in Table 5.

TABLE 4

Genes up-regulated in HF stem cells. Numbers in parentheses are the fold increase as determined by quantitative real time PCR.

| Gene Name/<br>Protein name/<br>GenBk Acces #. | Fold<br>Incr. | Sequence | SEQ ID No. |
|---|---|---|---|
| | | Cell surface proteins | |
| Cd34/Cd34<br>antigen<br>AI847784,<br>AI173145 | 43<br>(189) | uuuuuuuuuuuuuuuuuucacucaucacguuuauucagaagagaauacacccaa<br>uccucucaucucuggaaaguuuuguuccuagccaucauuaagaucaggacccc<br>uguucuccccuuaaccccaggagaggaagcuuauagucuuuguagauauucug<br>aaccucugaucacaaaggguuauaaaauagugaagggguuuggacuaggaaag<br>gcacagacugaaaggaaucugccaggggacugaggccacagcucccccaggag<br>ucagaggaagggggaagucacguauuuuauagaaggccaagggccucagagca<br>agaguauuccuuugaagagcuca | 233 |
| | | Calcium-related | |
| S100a4/S100A4<br>(mts)<br>X15986 | 35<br>(144) | ugguggagcaggucucaggaaucucuucgcuucagcuucaaucauggccugug<br>gucuggucgccagcaaccugaaucucaaaccuggggaaugucucaaaguucgg<br>ggagagguggccucggacgccaagagcuuugugcugaaccugggaaaagacag<br>caacaaccugugccuacacuucaauccucgcuucaaugcccauggagacgcca<br>acaccauuguguguaacaccaaggaagaugggaccuggggaaccgaacaccgg<br>gaaccugccuuccccuuccagcccgggagcaucacagaggugucaucaccuuu<br>gaccaggcugaccugaccaucaagcugccagacggacaugaauucaaguuccc<br>caaccgccucaacauggaggccaucaacuacauggcggcggauggagacuuca<br>agauuaagugcguggccuuugagugaagccagccagccuguagcccucaauaa<br>aggcagcugccucugcu | 234 |
| | | Transcription Factors and related genes | |
| Id2 helix-<br>loop-helix<br>protein<br>AF077861 | 11<br>(25) | gugguucuucggcgccagguucgcccgcuucugcccuuagguaacauucucua<br>aacugcguuucucucccaaucuuuugcaggcauuuggggacuuuuucuuuucu<br>uuuuacuuucucuuuuucuuuugcacaagaagaagucuacaagaucuuuuaag<br>acuuuuguuaucagccauuucaccaggagaacacguugaauggaccuuuuuaa<br>aaagaaagcggaaggaaaacuaaggaugaucgucuugcccaggugucuuguuc<br>uccggccuggacugugauaccguuauuuaugagagacuuucagugcccuuucu<br>acaguuggaagguuuucuuuauauacuauucccaccauggggagcgaaaaggu<br>uaaaaaaaagaaaaaaaucacaaggaauugcccaauguaagcagacuuugccu<br>uuucacaaagguggagcgugaauuccaggaggacccaguauucgguuacuuaa<br>augaagucuucggucagaaauggccuuuuugacacgagccuacugaaugcugu<br>guauauauuuauauauaaauauauauauauugagugaaccuuguggacucuuu<br>aauuagaguuuucuuguauaguggcagaaauaaccuauuucugcauuaaaaug<br>uaaugacguacuuaugcuaaacuuuuuauaaaaguuuaguuguaaacuuaacc<br>cuuuuauacaaaauaaaucaaguguguuuauugaauguugauugcuugcuuua<br>uuucagacaaccagugcuuugauuuuuuuuuaugcuauguuauaacugaaccc<br>aaauaaauaccaguucaaauuuauguagacuguauuaagauuauaauaaaaug<br>ugucugacaucaa | 235 |
| Id4<br>AJ001972 | 4<br>(12) | cgaugaaggcggugagcccggugcgccccucgggccgcaaggcgccgucgggc<br>ugcggcggcggggagcuggcgcuacgcugccuggcggagcacggccacagccu<br>ggguggcucggcagccgccgccgccgcugcggcggccgcgcgcugcaaggcgg<br>ccgaggcggcggccgaugagccggcgcugugccugcagugcgauaugaacgac<br>ugcuacagucgccugcggaggcucgugccuaccaucccgcccaacaagaaagu<br>cagcaaaguggagauccugcagcacguuaucgacuacauccuggaccugcagc<br>uggcgcuggagacucacccugcuuugcugagacagccgccaccgcccgcgcca<br>ccucuccacccggccggggcuuguccggucgcgccgccgcggaccccacucac<br>cgcgcucaacacugacccggugagaagccuuggcgggcacccugggcaucgcg<br>ggaaagguggcggggcggcgagauacggguggucuugcuccucucagggaaug<br>acagccgcuucucccgucuccaccgagagccgccugcugggcuuggugaucca<br>cuggucccugagccgagggcgguugggcuuggagcccugcgucuccggagugu<br>cccuugcaucacaggaggcuuccccagcuucgggcucgggugggggacucugcu | 236 |

TABLE 4-continued

Genes up-regulated in HF stem cells. Numbers in parentheses are the fold increase as determined by quantitative real time PCR.

| Gene Name/ Protein name/ GenBk Acces #. | Fold Incr. | Sequence | SEQ ID No. |
|---|---|---|---|
| | | caugcgcacucuaaccgcuuuuccccuugguguuggguugcuguuccaggaug cgcacucuaaccgcuuuuccccuugguguuggguugcuguuccaggccggcgc cgugaacaagcagggugacagcauucucugccgcu | |
| Peg3/ Paternally expressed gene 3 zinc finger protein AF038939 | 12 | Sequence below. | 237 |

acuagucucgaccauguaccaucacggagacgacaccaacagugacaugaacagugacgacgacaugagccgaaguggagagaa
accccacccccucgaccaucucaugcuuuuggcagugagcgagaccuggagcgcaggggcagaagcagagauguggagccucgag
accgcuggccauacaccaggaaucccagaagcaggcugccucaacgggaucuuucucuuccugugaugucaagaccacauuuugg
acuggacagagaugaugacagacguuccauggauuaugagucucgaucccaggaugccgagucauaccagaauguuguggaacuc
aaagaggacaagaagccucagaauccaauucaggacaaccuggagaacuacagaaagcugcucucgcugggaguccagcuugccg
aagaugaccgacacucucacaugacacaaggccacucaucgagguccaagagagcugccuacccaagcaccagccgaggucucaa
acccaugccugaggccaaaaagccaucccacaggcgugggaucugugaggacgagucuuucucauggagugauaauggaaaaauu
caucaaggauguggcucgcaaccccaaauccggaagagcaagggagcugaacgagcguccuccuccaagguuccccaggccuaau
gauaacuggaaggacaguuccuccagcagaagagagucagugauccaggagagggguuaugaagggagcgcauuuaggggcggcu
uccgguucaacgcagaccuggcuuccagaagcagagcucuagaaaggaagaggcguuaccacuuugauucugaugagcggguuc
gggccaugagcauaaaagcugugugaggaagaagccuuuugagugugguggcugagaugagacaggcuaugagcaugggcaaccug
aacagcccuuccuucucugagucgcagucaaucgauuuuggggccaacccauacgugugugaugagugcgggaggcaguucagug
ucaucucugaguuuguugagcaccagaucaugcacacuagggagaaccucuaugaauauggagaguccuuuauucauagcguggc
ugucaaugaggugcaaagaagucagggugggggaaacgcuuugaguguaaggaauguggagaaaccuucaguaggagugcugcc
cuggcagagcaccgccaaauccaugcuagagaauaucuugcagaauguagagaucaggaggaugaggagaccaucaugccuagcc
cgaccuuuagugagcugcagaagauguauggcaaagauaaguucuaugagugcaagguguggcaaggagaccuuucugcacaguuc
cgcccugauugagcaccagaaauccaugguagaggcaacucagaugacagagauaaugagcgugaacgcgaacgugaucgucuac
gugcacgugcacgagagcagcgugagcgcgaacgugaacgggagcgugagcgugagcuuggggaacccuuucugaccuguccaaa
cuucaaugaguuucggaagauguacaggaaagacaaaaucuaugagugcaaaguguguggggagagcuuucuucaucucucaucc
cugagggagcaucagaaaauccauacuagaggaaacccauuugaaaauaagagcaggaugugcgaggagaccuuugucccuaguc
agucucuccgacggcgccagaaaacuuacagagagaagcuguucgacuuuaacaaugccagggaugcacugaugggaaacucaga
cuccagcgagcaucagaaaaaccguucccgaaggaacuucuuugagggcagaggauuugagaaacccuucguugaaucucagaag
agucauacuauaacaagaccaccugaaaacaaagacgaugacaagccguucacaaucagugucaacccuaaugacaagcugaaac
uccccaucauggaaaauggcucccagggcaaauccugugagaggucuguuauucauagcuugggcuccgcagaagcucagaagag
ucaugguggacuggguucaguaaaccaagaccaguggcagagucuagcacccagagcucaagcagcauuuacuaccccagagca
cacucuggaggcaacaccuaugaaggaaaagaauacaaggacucuaucauccauagcuugccagcuccucgaccucugaaacguc
auagagcaaaugaccauauucaaugugaugagggggagaauccuccauuuauaucccagauauuauuaauaagggaaggaagau
uccugccagagaagaugcuuaugaaggaaguagcagcagcaacuaccacacaccaaauguaucccgugcugagccuccaagucuu
ucuggagagucccaugacucuaagcaggaugucacguuuucaguucccagcucaaguguucgugaacaccagaaagcucgugcca
aaaagaaguacauugagcccaggaacaacgagaccucuguuauccacucccuaccuuuuggugaguugcuugcaggucaccguag
ggcaaaguucuuugagugucaggaaugcggggaggccuuugcucguaggucugagcucauugagcaccagaagauucaugauaga
gaaagaccuucuggaagccgacauuaugagcgcucugucauccgcagccuugcgcccagugacccucagaccaguuaugcccaag
aacguuucauccaagaacaagugcguaaauucagagcguuuggacaacgcucaacuaccagcaacaaccucaguguacagaaaau
cuaugcccaagagacauuuaaugccgaggagccccaugauaaagaaacucauggucaaaaaauucaugacaaagagccauauggu
aaggagcccaguggcaaggagccccauggugaugagccccaggacaaagaaccccuuguucaggagaugcgcagugaagagcccc
augaugauaagccccauggccaggagccccaugaugauaagccccauggccaggagccccaugaugauaagccccauggccagga
gccccacggugaugagccccauggccaggagccccacggugaugagccccaugacaaggaacccauugaucaggagaugcgcagu
gaagagccccacagugaagagucucauggugaugagccccauggugaagagucccauggccaggagaaaguugaagaugcuacca
uucaggccucaguuucugaagagcaucagaaagaugacgcuggugaugcaaucuaugaaugccaggacugugggcugggcuuuac
ugaucucaaugaccucacaagccaccaggacacccauagcagaaaggcucugguugacagucgugaauaugcacauucugaaguu
caugcccacuccgucagcgaauuugagaaaaaugcucuggagagaaacuauaugaauguccaaaauguggggagucuuucauuc
acagcucguuacuuuucgagcaccagagaguucacgaacaagaccagcuguauuccguaaaggccuguuaugacgcuuucaucgc
ucuguugcccguuagaccaaggagaaauugcacuguugaaaggaauccugccguuucugggucagccauucgaugccgucagugu
ggacaaggcuucauucacaguucugcccuaaaugagcacaugagacagcacagagauaaugaaauaauggaacagagugagcuuu
cagaugagauuuucauucaaggccuagcccucacugaguaucaggggagugaaacagaagagaagcuuuucgagugcacaaucug
uggggaaugcuucuucacugccaaacagcucggggaccaccacaccaaaguucacaaggaugagcccuaugaguaugggcccucc
uacacccaugccuccuuucucaccgagccccucaggaagcacaucccacuguacgaaugcaaagauugcggccaguccuuccuag
acgacacugucaucgcugagcgcaugguguuucauccugagcgagaaggugggucagaaauaguagcugccacugcccaagaggu
cgaagccaauguccucaucccacaagaaguacugcgaauccaggggucaaaugcagaagcugcugagcccgaaguggaggcugca
gagcccgagguggaggcugcagagccugagguggaggcugcagagccuauuggagaggcugaagggccagauggagaagcugcug
agccugauggcgaggcugagcagcccaauggagaggcugaacagccaaacggugaugcugacgagccagacggagccgggaucga
agacccagaagagagagcugacgagccugaggaagacgucgaagagccagagggagaugcagaugagcccgauggugcagacauu
gaagacccagaagaggaaggagaagaucaagagauugagguugaagaaccauacuacaacugucaugaaugcgcagaaacguucg
cuuccagcucagccuuuggcgagcaucugaaaagucacgccagugugaucaucuucgagccggccaaugcuccuggagagugcuc
uggcuacauugaacgggccagcaccagugcagguggugcggagcaggcagacgacaaguacuucaaaugugaugugugcgggcaa
cucuucaacgaccgccucucccuugccagacaccagaauucucacacugguugaguaaccaggcugaagaaaagaagagcaaagc
caaaccuucuucccagaaccagacccuuaauaaaucacaaagagagccuaaaccaacccauaaugucuauaagaaauucaccuuc
cuguauacauaccggacuucacaucaaagacuuucacucucaucacagacugaaaaaagaaaagacauugaacgcagggacucuu
ucaguuuuagcuguucccuauggaacaucaguguauauuugggaaagcuagagugaacaucuacaucuuccauuucaucuaagua
acuagauugagggaaaccuagugacaauuccagaccacagagguugccccagucgacuguaaaugauaccccuuucauacccuau
acauaaugauuccugccauguauauaaaugagcaaaucagugauacauauauuuggauuuagugugcuauagaauuuacaguuua
cucuacagagcuaccuagccugguacucugauuuuuucccugaggaggaagagagcaacaauuuagcauauauuuguaaguauug
uccaugcagaagcuuuucugugcaucauuugaaccccauuaguauccuuuccaguaauggaguguucuguccccuaccucuuaga TABLE 4-continued Genes up-regulated in HF stem cells. Numbers in parentheses are the fold increase as determined by quantitative real time PCR.

| Gene Name/ Protein name/ GenBk Acces #. | Fold Incr. | Sequence | SEQ ID No. |
|---|---|---|---|

uaguccugugaaggugugggugugaaagaucgugugucuuugaauccuggcugugugaaacaggcauuuuagcuucuacagcca
uuuggugugcacccagaccccuugagacugauuguguaacccuuuacaauauauggauuugucucugugacccaaauacaaccca
ucccuacauuuauauaccuuacagugguuuucuugc Growth Factors, Receptors and Related genes

| Gene Name/ Protein name/ GenBk Acces #. | Fold Incr. | Sequence | SEQ ID No. |
|---|---|---|---|
| Fz2/<br>Frizzled 2<br>AW123618 | 9<br>(17) | uuuuuuuuuuuuuuuuuuaccguucuuuauuuaaaaaaauaaaauaggaguccg<br>uagggugcacccuccccccuccugagugaaggagggcacggugcaguccggac<br>cugggagaggggaaagcccggcaggcaggcgagaccgcuucacacagugcucu<br>cgccaugccggcuguuggugagacgaguguagaacuuccuccacgagugcagu<br>gucuugccggaccagauccagaagcccgacgugaugcccacgaugagcgucau<br>gagguauuugaucauguagacugugaagucgggcgacaugcggggcguguagu<br>gggccgggcaggggauggcuaggcucuugcagugcuggcuuacccaggagcgc<br>ucccagugcucgcggaaggccugcucauagaaguagcaggcgaug | 238 |
| Dkk3/<br>Dickkopf3<br>AJ243964 | 6<br>(22) | Sequence below. | 239 |

ggccgcgucgacgccucuccagcugcucuguggcagcccagcuaccggucgugaccagauccagcuugcagcucagcuuuguuca
uucgaauugggcggcggccagcgcggaacaaacaugcagcggcucggggguauuuugcuguguacacugcuggcggcggcggucc
ccacugcuccugcuccuuccccgacggucacuuggacuccggcggagccgggcccagcucucaacuacccucaggaggaagcuac
gcucaaugagauguuucgagagguggaggagcugauggaagacacucagcacaaacugcgcagugccguggaggagauggaggcg
gaagaagcagcugcuaaaacguccucugaggugaaccuggcaagcuuaccucccaacuaucacaaugagaccagcacggagacca
gggugggaaauaacacaguccaugugcaccaggaaguucacaagauaaccaacaaccagaguggacaggugguggucuuuuucugaga
cagucauuacaucuguaggggaugaagaaggcaagaggagccaugaauguaucauugaugaagacugugggcccaccagguacug
ccaguucuccagcuucaaguacaccugccagccaugccgggaccagcagaugcuaugcacccgagacagugagugcuguggagac
cagcugugugccuggggucacugcacccaaaaggccaccaaaggugggcaaugggaccaucugugacaaccagagggauugccagc
cuggccuguguugugccuuccaaagaggccugcuguuccccgugugcacaccccugcccguggagggagagcucugccaugaccc
caccagccagcugcuggaucucaucaccugggaacuggagccugaaggagcuuuggaccgaugccccugcgccaguggccuccua
ugccagccacacagccacagucugguguacaugugcaagccagccuucgugggcagccaugaccacagugaggagagccagcugc
ccagggaggccccggaugaguacgaagauguuggcuucauaggggaagugcgccaggagcuggaagaccuggagcggagccuagc
ccaggagauggcauuugaggggccugccccuguggagucacuaggcggagaggaggagauuuaggcccagacccagcugagucac
ugguagaugugcaauagaaauggcuaauuuauuuucccaggagugucccccaagugugggaauggccgcagcuccuucccaguagcu
uuuccucuggcuugacaagguacagugcaguacauuucuuccagccgcccugcuucucuggcuugggaaagacaggcauggcggg
uaagggcagcggugagucgucccucgcuguugcuagaaacgcugucuuguucuucauggauggaagauuuguuugaagggagagg
augggaagggggugaagucugcucaugauggauuugggggauacagggaggaggaugccugccuugcagacguggacuuggcaaaa
uguaaccuuugcuuuugucuugcgccgcucccaugggcugaggcaguggcuacacaagagcuaugcugcucuguggccucccaca
uauucaucccuguguuucagcuccuaccucacugucagcacagcccuucauagccacgccccucuugcucaccacagccuagga
ggggaccagaggggacuucucucagagccccaugcucucucucucaaccccauaccagccucugugccagcgacagcccuuccaa
auggagggagugaaauccuuugguuuuauuauuuucuccuucaaggcacgccugccacuaaggucaggcugacuugcaugucccu
caacguucguagcagugugguggacacugucuuccaccgacugcuucaauaccucugaaagccagugcucggagugcaguucgug
uaaauuaauuugcaggaaguauacuuggcuaauuguagggcuaggauugugaaugaaauuugcaaagucgcuuagcaacaaugga
aagccuuucucagucacaccgagaagucacaaccaagccagguuguguagaguacagcugugacauacagacagaagaaggcugg
gcuggaugucaggccucagaugacgguuucaggugccaggaacuauuaccauucuguaucuauccagaguuauuaaaauugaaag
uugcacacauuuguauaagcaugccuuucuccugaguuuuaaauuauauguauacacaaacauguggcccucaaagaucaugcac
aaaccacuacucuuugcuaauucuuggacuuuucucuuugauuuucaauaaauacaaauccccuucaugcaaaaaaaaaaaaaaa

| Gene Name/ Protein name/ GenBk Acces #. | Fold Incr. | Sequence | SEQ ID No. |
|---|---|---|---|
| Sfrp1/<br>Secreted<br>frizzled-related<br>protein 1<br>U88566 | 6 | Sequence below. | 240 |

gcacgagcagcccgcagcccgccgcgccugugcgagccgggacagcacucggccccgcgcgcuccccgccccgcgccagccccgc
cgcggcgaccugcugcagcggaggaccccaucgaucggagacccggggagcagcgcgcagcccgcgagccgacgggccccgacug
cgucuuuguccccggaggcuccgggaaguuugcagcgggacgcgcgcgugaaggcagcgugggcagccccgacgucgccgagcaa
caugggcgucgggcgcagcgcgcggggucgcggcggggccgccucgggagugcugcuggcguuggccgccgcucugcuggccgcg
gguucggccagcgaguacgacuacgugagcuuccaguccgacaucggcucguaucagagcgggcgcuucuacaccaagcccccgc
agugcguggacaucccgguggaccugaggcugugccacaacgugggcuacaagaagauggugcugcccaaccugcuggagcacga
gaccauggcagaggugaagcagcaggccagcagcugggugccgcugcucaacaagaacugccacaugggcacccaggucuuccuc
uguucgcucuucgcgcccgucugucuggaccggcccaucuacccgugucgcuggcucugcgaggccgugcgcgacucgugcgagc
cggucaugcaguucuucggcuucuacuggcccgagaugcucaaaugugacaaguuccccgagggcgacgucugcaucgccaugac
cccgcccaauaccacggaagccucuaagccccaagguacaaccgugugucuccaugcgacaacgaguugaagucagaggccauc
auugaacaucucugugcaagcgaguuugcacugaggaugaaaaucaaagaagugaagaaggaaaacggugacaagaagauuguccc
ccaagaagaagaaacccuugaagcuggggcccaucaagaagaaggagcugaaggcgcuugugcuguuccugaagaacggugccga
cugucccugccaccagcuggacaaccucagccacaacuuucucaucaugggccgcaaggugaagagccaguaccugcugacagcc
auucacaaguggggacaagaaaaacaaggaguucaaaaacuucaugaagagaaugaaaaaccacgagugucccaccuuccagucug
uuuuuaagugauacuggggcggacuggggaaggggaguguggcuuggggugaggugggggcgcguggaugacccuggcucuung
gggcucacauauugcucucacccauacaguuguggcuuuugcauugcaccuggcucuguuccuacagcgaacccucucccuuncc
uccauagccacauccagcuaaggccacggccuuuagauuaggaaggcuuuuuuuuuuuuaagggcugcagcagggccagcagcga
cgugcaaaaggagaggcagaauccuuucacugagccuggggcacaaaaaacagaaaauguunnccgguuuggaaaaacaaaacaa
aacggauuguaaagaacugcagacggacagcugcucagcucaacguuguucgggacaucauuaccaauugcuuguggagucuaag
ccucuacagguagaagagucugaucauugccaagccaggcugcuuucaguuuauuauuaaucccccucuuucugccuuagauaga
ccaucgccaccuucaaaacacacacacacacacacacacacacacacacacacacacacacacacacacacuucugaaaguag TABLE 4-continued Genes up-regulated in HF stem cells. Numbers in parentheses are the fold increase as determined by quantitative real time PCR.

| Gene Name/ Protein name/ GenBk Acces #. | Fold Incr. | Sequence | SEQ ID No. |
|---|---|---|---|
| | | ccaggguaucccaguauagaacgggauagcuaaggguuuggguggggaggccacugcuacucuaccuucagcuuuugaacuggcca<br>ccuuugauaggaaacugaggucucagauggacacuucuaccaguccaucgggauacaaggaugccaggcaagggucugcuuuugu<br>cugaaggagguacgugggcaugaagagacaugaggcauuucaggcugagaagcaacagcuacuaguuuucaacaauagaguggaa<br>gaaaugagcaaagguagaaaugucaagcaggucacaagucagggugauuggggaauccugugccaacagccucacuuuguaauu<br>ccaucugucacuuucaaaagaacagcagcauaagacagggauaaaagcccacauacccuccaaggcuugaguaaaaguccacacu<br>cagcauuucaaagacuaacgucguugacugcccaaggcugcccucuuaauacaccgccuaugcaugugcuguggaaggcaacucu<br>gugcaugugcuguggaggagaugggccucauggcugugcuggcugcccggaaucaguauagcguggaaggagacaguauccauag<br>acucugcuuuucugcaaggaaagcccuuuuccuuauacaugauugccuauaauucagacaaauuuaaaaucgcugccugccugag<br>cccuccaccuuuacuuuugcauucuccggucauauucuuuugaggcuaaagugcccuauccgaggagaugguuucaaaggcuaac<br>uaaucugcagcuuuucccaagugcccagagguauuucucaaaguugguaugcuuaauaagugauguaaauauuccaguucucuua<br>ggcagccuuacuccuguugucccug | |
| Dab2/Disabled homolog 2 U18869 | 15 | Sequence below. | 241 |

aauuccgaguggccgcgcggcuauuuaaguggcguuacuccgcguccucggcgcugcagccuugaggcuucgggcgcgggggaag
ucaugcuggcuccacagaagcacuagcuaguccguguacuuuguggguucuguccuuuugagaccugcccgccggggauuggcug
guaucagugacugucuacugcuggauuuucugcuugccuucccgucaugucuaacgaaguagaaacaagcacaaccaauggccag
ccugaccaacaggcugccccgaaagcgccaucaaagaaggagaagaagaaagguucugaaaagacagacgaguacuuguuggcca
gguucaaaggugaugguguuaaauacaaggccaagcuaaucgguauugaugaugugccugaugcucgaggagacaaaaugaguca
ggauucuaugaugaaacucaagggaauggcagcagcuggucgcucucagggacaacacaagcaaagaaucugggucaacauuucc
uugucuggcauaaaaaucauugaugagaaaacuggggguaauugaacaugaacauccaguaaauaagauuuccuucauugcucgug
augugacagacaacagagacauuugguuaugugugugggaggugaaggccagcaucaauuuuuugcuauaaaaacagggcaacagg
cugagccauuagucgucgaucuuaaagaccuuuuucaaguuaucuauaauguaaagaaaaaggaagaagauaagaaaaagguuga
agaagccaacaaagcagaagagaauggaagugaggcccuaaugacccuugaugaucaagcuaacaaauugaagcuggguguugac
cagauggauuuguuuggggacaugucuacaccuccugaccuaaauaguccaacagaaagcaaagauauccuguuaguggaucuaa
acucugaaaucgacaccaaucagaacucuuuaagagaaaauccauucuuaacaaauggagucaccuccuguucucucccucgacc
aaagccucaggcauccuucuugccugagaacgccuuuucugccaaucucaacuucuuucccaccccuaacccugauccuuuccgu
gaugaucccuuugcacagccagaccaaucggcacccucuucguucgauucucucacaucuccagaucagaagaaagcgagucuga
guagcucgucuacuccacagaguaaagggccccugaacgucgauacugauuacuuuggucagcaauuugaccagcucucuaaccg
gacuggcaaaccggaagcucagggaggcccguggcccuacccaaguucgcagacccagcaagcagugagaacucaaaauggggua
ucugaaagagaacagaacggcuuccauaucaaaucuuccccgaacccuuuugugggaagcccucccaaaggacuaucgguaccga
auggcguaaagcaggacuuggaaaguucuguccaguccucagcacugacuccauagccauuaucccaccuccacaaaguaccaaa
ccaggaagaggcagaaggacugcuaagucuucagcaaacgacuugccugcuucagacaucuuugccucagaaccuccaggccaga
uguccccacaggacaaccugcagucccgcagucgaacuuccuggaucucuucaaaggcaaugcuccucccccaguggggcccu
uguaggucuagguacggucccaguaacacccccccaagcaggacccuggacgccuguugucuacaguccuucgacaacuggguc
ccaggagccauaauaaguggccagccucccaguuuucgccagccacucguuuuugguacaaccccagcaguacaagucuggaauc
agucuccaucauuugcaaccccagcuuccccuccaccccccacaguuuggugucuaccacaucuguggcgcccaacgcuugguc
auccacaagcccucuggggaauccuuuucagaguaauaauaucuuuccaccucccaccauguccacucaguccucuccucagccu
augauguccucuguucuggccacaccgccucaaccaccuccccgaaauggcccacuaaaggacauucccagugacgcuuucacug
gcuuagacccccuuggggauaaagaggucaaggaagugaaagaaauguuuaaggacuuccagcugcggcagccaccucuuguucc
cucaaggaagggggagacgccucccucugggacuucaagcgccuucuccaguuacuucaacaauaaaguuggcauuccucaggag
cauguagaccaugaugauuuugaugccaaucaacuguugaacaagauuaaugaaccaccaaagccagccccgagacaaggugucc
ucuuggguaccaagucugcugacaauucacucgagaacccuuucuccaaaggguucagcucaucaaaccccucugugguuucuca
gccugcaucuucugauccccacaggagcccuuucggaaauccuuuugccuagcuucugaaguuguaaugaugacuauccagauga
gcaaaagacuggcuuuggucaagaaugaagcagacagccagaaacauguugaccucuguccucgcuccagcuuugacguauuauc
uguuacccuauuuguuuuggccucuuguacuuguaaaaugccuuucauuuuccugucuaggcuaaagcuaaacuuaaacuauggc
uuuacguaaauuaagcuccuaaacucucuagcuccaauauaaaugaaguagcuucccuaucaaaucccugucuguugugcccccu
ugaaacuuccagaauauucuccauucuacccuccauuugggaggagcggcuaccuuuacccuuaauaucacacugccuugaguca
auguccaaauacucauagcucucaaagucauuugggguuccuggugugcggccuaaaccuaaagcauccuauuaauagggaagua
agacaccuugcuuccuauguccacucagggagaauuuuauuuaauaaaaugaaagcaagacuaacuucucaaauccacccaagga
ccauuuugagauggucguuucucagcuaacugcaccauuuaccaauccugccccaagugguggcuuacauuugacuugaagaagag
aaagagcuaacucaaaacacaaggcauuauucaaagcuaauaaaacaauuucucccuggggccccacauuguuuucauuccagau
acguugcagcuguuugacccugaugacauuaugcccuacauuuuccuugaagauccugauuuuauuucaugugauuuuuguuucu
caauaaagaugauuauugugugcacggaauuc

| Gene Name/ Protein name/ GenBk Acces #. | Fold Incr. | Sequence | SEQ ID No. |
|---|---|---|---|
| Cktsf1b1/ Gremlin, Cysteine knot superfamily 1, BMP antagonist 1 AF045801 | 12 (12) | Augaaucgcaccgcauacacugugggagcguugcuucuccuccuggggacccu<br>acugccaacagcugaggggaaaaagaaagguucccaaggagccauuccgccuc<br>cugacaaggcucagcacaaugacucugagcagacccaguccccaccacaaccu<br>ggcuccaggacccgggggcggggccagggggcggggcaccgccaugccuggaga<br>ggaggugcuugaguccagccaagaggcccugcacgugacagagcgcaaguauc<br>ugaagcgagauuggugcaaaacucagccccugaagcagaccauccacgaggag<br>ggcugcaacagccgcacuaucaucaaccgcuucuguuauggccagugcaacuc<br>cuucuacaucccccaggcacauccgaaaggaggaagggguccuuucagucuugcu<br>ccuucugcaagcccaagaaguucaccaccaugauggucacacucaacugucccu<br>gagcuacagccacccaccaagaagaaaagggucacacgcgugaagcagugccg<br>uugcauauccaucgacuuggauuaa | 242 |

TABLE 4-continued

Genes up-regulated in HF stem cells. Numbers in parentheses are the fold increase as determined by quantitative real time PCR.

| Gene Name/ Protein name/ GenBk Acces #. | Fold Incr. | Sequence | SEQ ID No. |
|---|---|---|---|
| Fgfr1/Fibroblast growth factor receptor 1 U22324 | 10 | Sequence below. | 243 |
| | | guggaauauccauggagguacggagccuuguuaccaaccuuuaaccgcagaacugggauguggggcuggaagugccuccucuucu<br>gggcugugcuggucacagccacucucugcacugccaggccagccccaaccuugcccgaacaagcucagcccuggggagucccugu<br>ggaaguggagucucuccugguccacccuggcgaccugcuacagcuucgcugucggcuucgcgaugaugugcagagcaucaacugg<br>cugcgggaugggugcagcugguggagagcaaccguacccgcaucacaggggaggagguggaggugcgggacuccauccccgcug<br>acucuggccucuacgcuugcgugaccagcagccccucuggcagcgauaccaccuacuucuccgucaaugucucagaugcacuccc<br>auccucggaagaugaugacgacgacgaugacuccuccucggaggagaaagagacggacaacaccaaaccaaaccguaggccugua<br>gcucccuacuggacauccccagagaaaauggagaagaaacugcaugcggugcccgcugccaagacggugaaguucaagugcccgu<br>cgagugggacacccaaccccacucugcgcugguugaaaaauggcaaagaguuuaagccugaccaccgaauuggaggcuacaaggu<br>ucgcuaugccaccuggagcaucauaauggauucugguggugccuucugacaagggcaacuacaccugcaucguggagaaugaguau<br>gggagcaucaaccacaccuaccagcuugacgucguggaacgaucuccgcaccgacccauccuucaggcagggcugccugccaacg<br>agacaguggcccugggcagcaauguggaguucauguguaagguguacagcgauccgcagccucacauucaguggcugaagcacau<br>cgaggugaacgggaguaagaucgggccagacaacuugccguauguccagauccugaagacugcuggaguuaauaccaccgacaag<br>gaaauggaggugcuucaucuacggaaugucuccuuugaggaugcgggggaguauacgugcuuggcgguaacucuaucggacucu<br>cccaucacucugcaugguugaccguucuggaagcccuggaagagagaccagcugugaugaccucaccgcucuaccuggagaucau<br>uaucuacugcaccggggccuuccugaucuccugcauguugggcucugucaucaucuauaagaugaagagcggcaccaagaagagc<br>gacuuccauagccagauggcugugcacaagcuggccaagagcaucccucugcgcagacagguaacagugucagcugacuccagug<br>cauccaugaacucugggguucuccugguucggcccucacggcucuccuccagcgggacccccaugccggcuggagucuccgaaua<br>ugagcucccugaggauccccgcugggagcugccacgagacagacuggucuuaggcaaaccacuuggcgagggcugcuucgggcag<br>gugguguuggcugaggccaucgggcuggauaaggacaaacccaaccgugugaccaaaguggccgugaagauguugaaguccgacg<br>caacggagaaggaccugucggaucugaucucggagauggagaugaugaaaaugauugggaagcacaagaauaucaucaaccuucu<br>gggagcgugcacacaggaugguccucuuuaugucauuguggaguacgccuccaaaggcaaccuccgggaguaucuacaggcccgg<br>aggccuccugggcuggaguacugcuauaaccccagccacaaccccgaggaacagcugucuuccaaagaucugguauccugugccu<br>aucagguggcucggggcauggaguaucuugccucuaagaaguguauacaccgagaccuggcugcuaggaacguccuggugaccga<br>ggauaacguaaugaagaucgcagacuuuggcuuagcucgagacauucaucauaucgacuacuacaagaaaaccaccaacggccgg<br>cugccugugaaguggauggccccugaggcguuguuugaccggaucuacacacaccagagcgauguguggucuuuuggagugcucu<br>ugugggagaucuucacucuggguggcuccccauaccccggugugccuguggaggaacuuuucaagcugcugaaggagggucaucg<br>aauggacaagcccaguaacuguaccaaugagcuguacaugaugaugcgggacugcuggcaugcagugcccucucagagaccuacg<br>uucaagcaguugguggaagaccuggaccgcauuguggccuugaccuccagccaggaguaucuggaccuguccauaccgcuggacc<br>aguacucacccagcuuucccgacacaggagcuccaccugcuccucaggggaggacucugucuucucucaugagccguuaccugag<br>gagcccugucugccucgacaccccacccagcuugccaacaguggacucaaacggcgcuga | |
| Fgf1/Fibroblast growth factor 1 M30641 | 10 | auggcugaaggggagaucacaaccuucgcagcccugaccgagagguucaaccu<br>gccucuaggaaacuacaaaaagcccaaacugcucuacugcagcaacgggggcc<br>acuucuugaggauccuuccugauggcaccguggaugggacaagggacaggagc<br>gaccagcacauucagcugcagcucagugcggaaagugcgggcgaaguguauau<br>aaaggguacggagaccggccaguacuuggccauggacaccgaagggcuuuuau<br>acggcucgcagacaccaaaugaggaaugucuguuccuggaaaggcuggaagaa<br>aaccauuauaacacuuacaccuccaagaagcaugcggagaagaacugguuugu<br>gggccucaagaagaacgggagcuguaagcgcgguccucggacucacuauggcc<br>agaaagccaucuuguuucugccccucccggugucuucugacuag | 244 |
| Gpr49/G protein-coupled receptor 49 FEX AF110818 | 63 (377) | Sequence below. | 245 |
| | | auggacaccuccugcguccacaugcuccuguccuugcuggcgcugcugcaguugguggccgccggcagcucaccgggaccagaug<br>cgauaccgcggggcugcccaucacacugucacugugagcuggauggcaggaugcugcucaggguggacugcucggaccuggggcu<br>cucggagcugcccuccaaccucagcgucuucaccuccuaccuggaccucaguaugaacaacaucagucagcuacccgccagucuc<br>cuacaucgccucugcuuccuagaagaguuacgucuugcuggaaaugcuuugacacacauucccaagggagcguucacgggccuuc<br>acagccucaaagugcuuaugcugcagaacaaccagcugagaaagguuccggaggaagcgcuacagaauuugagaagccuucaauc<br>ccugcgccuagaugccaaccacaucagcuacgugccacccagcuguuucagcggccugcacucccugaggcaccuguggcuagau<br>gacaaugcucucacagacgucccuguccaggcuuucagaaguuuaucagcccugcaagccaugaccuuggcccugaacaaaauac<br>accacauagcagacuacgccuuuggaaaccucuccagccucgugguucugcaucuccauaauaauagaauccacucccugggaaa<br>gaaaugcuuugauggacuccacagccuggagacuuuagauuuaaauuauaauaaccuugaugaauuccccacugcaaucaagaca<br>cucuccaaccuuaaggaacuaggauuccacagcaacaacaucaggucaauaccggagcgagcguucguaggcaacccuucucuua<br>ucacaauacacuucuaugacaaccccauccaauuuguuggaguaucugcuuuucagcauuugccugaacuaagaacacugacuuu<br>gaauggugccucgcacauuacugaauuuccucacuugacaggaacugccacccuggagagucugacuuuaacuggagcaaagauc<br>ucaucucuuccccaggccgucugugaucaguuaccuaaucuccaagugcuagauuugucuuacaaccuacucgaagacuuaccca<br>guuugucaggcugccaaaaacuucagaaaauugaccugaggcauaacgagaucuaugaaauuaagggcagcacuuuucagcaguu<br>guuuaaccuccgaucucugaacuuagcauggaauaaaauugcuaucauucaccccaaugcguuuucuacguugccgucucuaaua<br>aaguuggaccuaucauccaaucuccugucguccuucccuguacuggguuacaugguuuaacucacuuaaaauuaacagggaaccg<br>agccuuacagagccugauaccaucugcaaacuucccagagcucaagauuauagaaaugccaucugcuuaccaguguugugcauuu<br>gggggugugagaaugucuauaaaauuucuaaccaauggaauaaagacgacggcaacagugugguacgaccuucauaagaaagacg<br>cuggguuauuucaaguucaagaugagcgggaccuugaagauuuccuacuugacuuugaggaagaccugaaugcccuucacucggu<br>gcagugcucgccuuccccaggucccuucaagcccugugagcaccuauuugguagcuggcugauccgaaucgggguguggaccacg<br>gcaguacugacgcuuuccugcaangccuugguggcuuugaccguguucagaacuccccuguacaucucuuccauaaagcugcuaa<br>uuggggguaaucgcgguaguggacauucucaugggggncuccagugcugugcuggcugccguggaugcauucacuuuuggccguuu<br>ugcucagcacggugcgugguggggaagacggaaucggcugccaaaucguuggcuuccuguccauuuuugcuuccgaaucgucgauc | |

TABLE 4-continued

Genes up-regulated in HF stem cells. Numbers in parentheses are the fold increase as determined by quantitative real time PCR.

| Gene Name/ Protein name/ GenBk Acces #. | Fold Incr. | Sequence | SEQ ID No. |
|---|---|---|---|

uuccugcucacucuggcagcgcuggaacgagguuuuucugucaagugcucuucgaaguugaagugaaagcucccccuuuuuagcc
ngagagcgauguuuugcuauguguccuguuggcccugaccaungccacaauccccuugcuaggaggcaguaaguacaaugccucu
ccccucugccugcccuugcccuuuggggagcccagaccacgggcuacaugguggcucucguguugcucaacucucucuguuuccu
cauaaugaccauugccuacacaaagcucuacugcaguuuggagaaaggagagcuggagaaucuuugggauuguucgauggugaag
cacauugcucuguugcucuucgccaacugcauccuuuacugccccguggcuuucuuauccuucuccucuuugcuaaaccucaccu
uuaucaguccugacgucauuaaauuuauacuucucgugaucgucccacuuccuuccugucucaacccacuucucuacauugucuu
caaucccccauuuuaaggaggauaugggcagccugggaaagcauacccguuucuggaugagaucaaaacacgcgagucugcugucc
auuaacucggacgaugnugagaaacgguccugugagucaacccaagccunaguauccuuuacccacgccagcauagccuaugacu
ugccuuccacuuccggggcaucaccagcuuaccccaugacugaaagcugucaucucucuucaguugcauuugucccaugucucua
gugacuaugagagaggaacguuuuuaagaguuggaaaccugaaaagugauuucuaucagagcaguagcuaagaaaagcugagcua
aaaaccuaccuuaaaacccaagcaaacaucucnaaauugguguggaaacaguggugccuuagagcaggagagcaucauuaaacac
cgcuuguaucauuuguucagcuaagaaggaaagccaucaagucacuuaggugaacccagaugagaaaagcagccugaaaugcucu
ucgcauuguagucucuucugacucaccagcauagucucccauagugagaagacncguuggaugacucaauggguguauuuaaauc
cacaaauuccuuguuuaaaagguuagaguuuuaagaaaaaaaaaaaaaaaa

| Igfbp5/ insulin-like growth factor binding protein 5 L12447 | 37 | Sequence below. | 246 |
|---|---|---|---|

uuuuuuuucuucaccuccucccuuuucaaggccuccaagcuaauuauuucuguugcuuuggagugagcaauucugugguucucuc
caccaccaccccaauucugacccgaucccgccugggggguuucuacggucuccgcucacucugcgugcaccuggcgcgccucuuu
uuuucacccccaaccuguugcaagucuuuaauccucgcaauugggacuugcgugcaggcaccugaauccuccuugccucauanuu
ugcaaguguuuggggagagcaccugcucuaccugcaagagauuuaaaaggaaaaaaucuccaggcucccucuuucuccacaca
cucucgcucuccugccccgccccgagguaaagccagacuccgagaaaauggugaucagcgugguccuccugcugcuggccgccua
ugccguaccggcucaaggccuggguucuuucgugcauugugaacccugcgacgagaaagcucuguccauguguccccccagcccu
cugggcugugagcuggucaaagagcccggcuguggcugcugcaugacuugcgcccuggcggagggacagucgugugggugucuaca
cagagcgcugcgcccaggguuugcgcugccuccccggcaggaugaggagaagccgcugcacgcccugcugcacggccgcggggu
uugccucaacgaaaagagcuacggcgagcaaaccaagauagagagagacucucgggaacacgaggaacccaccaccuccgagaug
gcugaagagaccuacucccccaaggucuuccggcccaagcacacucgcauuuccgagcugaaggcugaggcugugaagaaggacc
gcagaaagaagcugacccaguccaaguuugugggggggugcagagaacacugcccaccccagagucaucccugcaccugagaugag
acaggaauccgaacaaggccccugccgcagacacauggaagcuucccuccaggaguucaaagccagcccacgcauggugccccgu
gcuguguaccugcccaacugugaccgcaaaggauucuacaagagaaagcaguguaagcccucccguggccgcaaacguggcaucu
gcuggugugugggacaaguacggaaugaagcugccgggcauggaguacguggaugggggacuuucagugccacgccuucgacagcag
uaacguugagugacgcguccccucccuuccucccccuauccuaccccccccagccccaacuccagccagcgccucccuccaccccca
ggacgucacuacauuucaucucauuuaggggaaauauauauacauauauauuugaggaaacugaggaccucggaaucucuagcaa
gggcuaaggagacacuccccaccaugaccccggaaauguauuccuuuuugaagcaaguugaacggacagagaagggaaggagaga
agaagcaagagggagcgagagauggaaagaaagcaaagcguuggaauagaggaaaagagggaaggacagauaggauuagagagag
aagagagaaacagcaaggcagaaaggacuccacaaccaaggcugaaucugcccuuuugcuuucagcucuagccuggggucagaaa
aaguguggcauucagugacacccaguuuagauuggucaaggggagaaaagaaacaaggugugucagugccucucgggucugucccc
cuccugcagccagcaguguggauggcuagaccccucacccuccucucccucuuacccaagugcagggugauuucauccccaaauuu
acaaagacuaaaaugcauuccaucccucugaaaauaaacaaaagugagugauugaagauagguuuuccccccagcagacaagugaa
cucagaaugugugcaaauuuuacucuuguuaaagauuuuuuuuaagaagucaguacgcacccccaacacuggaaagacuugauucu
ccagggugacaagcaauucagaagcgcguggcuucggcccuugauuucacuagacucaaagcuggcccggcagccucuguggagg
aggaugagagguggagaaaaccaaggggcuuguacucacccacaagacuccauguagacuuuauaggcauauaaaucuauuuucu
uuaccuuuuuuucccuuucccuuucuuucgaaguuuugcauuaccucuuuaaaguaguuuuuuuuaggacacugaagaucuuccu
cauucugggaaaaauccauauuucacaaauacaacccagaacgccagcuuggccugcguccaggcagccuuucucgugagcuaca
aguguggcucuuuugugggggcaccgauuuggaucuucucaugauuccaaacgugugugaagugaauccaccaagccagguaacu
gccagcacccaagggugcaucaagugcauagcccaggucaccccauuucagccuuccaacccgcagaaaguaacugucucacacc
acaccacauaaaccugccagauccaucuguaacccacuggccugcccagaccuuuuuuucccaucugcauuuuuuuuuuugaacu
gcauuuugaaagccucccucagaugccaggcugacagaucagagagaaacuaacaugagagaugacagaggaggaggaaguggag
gguggggcagagacuuccacagagagacauagaagauggagcagaggucugggggugggggaggacaagaaagagacagagagag
gaaaauaccaauagaauuuuccuuggugucucccaucuaaucaacucucugagauuugagaggaaaaagaaggcaggggaagaac
uugagguagaaaugaggucaguucaagucacagggcccagaugguggguaacugaggcaggauccagacuugagacacacgguug
gaaacaaggcugguuagccugacuggguauugaagggugaagaggaugccuuggaaagacagcacaacuucaguucaacuucagg
cccccaaggaggaacugaggccaaagaauccuucaagugcuucaugagucuccucugcccgacucaaacauccuucccugugaug
gaggaugguagaaagcccaggacaacucaggcccggaucuucacgacuguugucauuugccagccugauuuugauccaagagaag
caucucauugcccacuggcuucuucaacaaagaggugcuuaacaaaaggcucaggacuaucuuugaagacugaagauaaccuucc
aggagaggagacucggacauugguacaggaggccccuuuuggcgggggacacagcucuuugcgcucucuugauggcauggcauag
uagaggcccccuccaacccggaacauggagcaacacaaagggagagcaaagaaacugacgugcgucgacucauaggacauggggug
gcugcgggcacagaaagggaugccuccuguugccuggacaggacaguuggcugggaaggaaagagaaaauugaucuucauaagac
aaagggccugaugggauggcaauagaaggacuuaccagaccugcagggucaguauacccaucaccccgcacaacauccccagccc
ccaacucaaacuucaauauaucuuaggccaguauccuagaccuaagucucuccuuucugccauuauuucuccgcaucuugagcag
ucaucugacugagauuugccaaguggauacuggguaccacugccccccaagaaaagacugagccaggaacugccuacucgcucc
cccucccgagccuggagcuaacuccugugaggggugcucucuucaccccacaacuuacuagaccuugagugagccucugucccuu
augugggcucuucgcugugagccacagauggaggucauuguauagacaguuagccuuccccaggucagccuaccucccccaaacu
ugugagucuccccgcugcucauauggagaggcaugucuaagacagcaagucuucuagaggaagcuugccuuuaacagacagaugg
aacuaaaccuuccaaaugggagaucuggcugaacccaggauacagagaccauggacauggaugggguucaucaagagaagagggau
guccuucuccagguuagggagagagaaggcaaguuugcaacgaucccaucaugcccugagcaagaagcuuuuggcccaggcuagc
cuuuaacuccauuagaggccucucuguuggguuuauccacagcaguaggcccaaguauggccugucccccaccucuacuaucccgu
ggaagguuucuucccaccccuuuuugacaaaugccucacucgagcaguggaaagauagcucucuuccccccucuucugccagguaa
caaagagaccuaaccaggaccuauucuccaccccagccagucuugaccagccagaacaaagcagggaaccuggagaauaaaagac
ucuacguuccucugacaaagacucuacguuucucugacggccaggccuaaacagacaaggcuugggaacaucugccccacaggau TABLE 4-continued Genes up-regulated in HF stem cells. Numbers in parentheses are the fold increase as determined by quantitative real time PCR.

| Gene Name/ Protein name/ GenBk Acces #. | Fold Incr. | Sequence | SEQ ID No. |
|---|---|---|---|
| acggaggaggucagcugugcucacuccucuucuccuuccaagacccucuuccgaccaugacuuaucuccaugguaacauccucac caucauucucccacuaccaaggguugccauggcaaccucccaaccaccugcccaucccaggcaggcagcuguccuucugcucaga acccuagaggacucuaggugaaauuuuacagcuuaagagaggagugagccaaggagaagagacccuguaguccucuggcuuucaa gagaaagaaggcuaugauuuaaaacacaguagaagggaaagaggucucgucgaggucgaccucucccggggagcuuaggggguugu acugucuuuauuuuuuaaaccacuaaagugcaaunuuuccugcacucuuguuaccccgccucucuucccuguuagguuuucauuu ccuugagcagacuuucuugguuuuuuaauggaguauagacuuucaccacuucacagacucuggccuccucuccaagucucucugg auggggaaaaggaagguagagggucagaggggaagggguccccucgucaccccgcauccauucacccccacuucucuggucccuag ucaccggcuucaccccnaucuccgacaccaucacugucacacaguagccugucacacggauaguacaguucagacaagacuccuu cagauuccgagacgccuaccgguuguuuuugguuuuuguuuuguuuucuuuuguuuguuuguuuguuuguuuuuuacaacagcaa uaaccacaucacauauuacuguagcucucuauaguguuacguucagacaccguagcucuguccucucuuauuuuguugguuuuga cuuaaaaaaaaaauacuuaugcuuuuuacuggugaaacagauugaaaaaaaaauugaacaacaaaccaguuugugaaaaaaaaaaa aaaugugaaaaaaaaucaccccgauguggaagagcucggcuccucuuuagcauuuuguacuuaaggaaauaaaaaagaaaaaccu ggaagaucucacauuuuauuacaaagugaaaaaaaaa | | | |
| Myoc/trabecular meshwork induced gluco-corticoid protein AF041335 | 111 | Sequence below. | 247 |
| guccagucugcagucuguauucggaagacauagauacuaaauacauggcaacucuuuuuuuuguuuguuuuaauucaucaggaug uggagcgcuagucuggguaggagagccagucacccugaggacagcugaaacaaucgcuggcaaguauggaguguggaugagagac cccaagcccacccaccccuacacccaggaaagcacauggaggauugacacgguuggcacagagauccgccagguguuugaguaca gucagauaagccaguucgagcagggcuauccuuccaagguccaugugcucccucgggcacuggagagcacgggugcugguggugua ugcggggagccucuauuuccagggggcugaguccagaacuguggucagguaugagcuagacacggagaccgugaaggcagagaag gaaauuccuggagcuggcuaccacggacacuucccguacgcgugggguggcuacacagacauugacuuagcuguggaugagagcg gccucugggucaucuacagcacggaggaagccaagggggccauaguccucuccaaauugaacccagcgaaccuggaacuugagcg uaccugggagacuaacauccguaagcagucuguggccaaugccuuuguuaucuguggcaucuuguacacggugagcagcuacucu ucagcccaugcaaccgucaacuucgccuacgacacuaaaacggggaccaguaagacccugaccaucccauucacgaaucgcuaca aguacagcaguaugauugacuacaacccccuggagaggaagcuguuugccugggacaacuucaacauggucaccuaugauaucaa gcucuuggagaugugaggagccucuaugccuaccagcaaaggccagaaaaggugaaguuccgggcucccgggugaagcagcuguc agcagaggcagccagaugcauggaguuucuccuccugcuaaagauuuuguuuauccgggucaauguacagcuagcuccccucuga cugacacguccuccaggcuuguauagucgcauagacucuguucucuucugucagcuuucaaagggcuguuccucuuuuaaaaauc acauagug | | | |
| Itm2a/E25 putative Integral membrane protein 2A L38971 | 30 | Sequence below. | 248 |
| gggagaccugagcucgcugcugccuguggaagacugggagaggagacacuaagugcgcucaagcaagcgcgauccucuccucuuu caaccugcagcccaagauacugauucgagccgcgccuuaccgcgcagcccgaagauucaccauggugaagaucgccuucaacacc ccuacggcggugcaaaaggaggaggcgcggcaagauauagaggcgcucgucagucgcacuguccgagcucaaauccugacuggca aggagcucagaguugucccgcaggagaaagauggcucaucugggagaugcaugcuuacucuccuaggccucucauucaucuuggc aggacugauuguuggguggagccugcauuuacaaguacuucaugcccaagagcaccauuuaccauggugagaugugcuucuuugau ucugaggauccugucaauuccauuccuggaggagagccauacuuucugccugugacugaggaggcugauauccgugaggaugaca acauugccaucauugaugugccugugcccaguuucucugauagcgauccggcggcaauuauucacgacuuugagaagggaaugac ugcuuaacuggacuugcuuuugggaaacuguuaucugaugccccucaauacuuccauuguuaugacuccaaagaaucugguggaa cuuuuuggaaaacuggcaaguggcaaguauuugccucauacuuaugugguucgugaagaccugguugcuguggaagaaauucgug auguuaguaaccuugguauuuuuauuuaccaacuuugcaacaaccgaaaauccuuccgccuuagacgcagagaccuucugcuggg uuucaacaagcgugccauugacaaaugcuggaagauuagacacuuccccaaugaauuuaucguugaaaccaagaucugucaggag ugaaaugugacagauaaagaguauccuugauaauaagaagucaggaacuuaccgucugacuuggaaaauugaaauugaugggaua cucaugcuauuuacucauacauuuacucuauugcuuauacuggaaaaggaaagggaaagggggagaaaacuacuaaccacugca agcgauuguccaauucuacuuuaauugacauugcuugcuguuuucaacaagucaaaugauuaucuuuucucuugaauuuauaggg uuuagauuucugaaagcagcaugaaugugucaucuuaccauccugacaauaaagcccauccucugguuuuauuuaaagcaagcuc uuuccaacaucacuuggcuagagcaugcuuuaaauuuaaaauauuugaaauuguuuuugacauuuuuuugugugaaacauguca aaucucuuaccauucuuugguuuucuucuuuauuauguucaacucuccugauuucagaaguuacauuuuugcauuucuaucaggu gcuguguaacgaaucugacugauaugugaacaaucuucaugaggaagcaauuuuuuacucauguaaugauucuuucucacugaua ucuguauugugaaauccacagaacuguacaggugcugaaugcuguaaggaguucugguuguaugaauucuacaacccuauaauaa aguuuaccguauucaauca | | | |
| Eps8/epidermal growth factor receptor pathway substrate 8 L21671 | 15 | Sequence below. | 249 |
| ggccauuaccaaucgcgacccgcgcacacacggcccgggcggcgggcgaagcgggcucccggggcgcugggcgcagggcgcgggg caagccccagcagcgugucugcaacggggcgcggcgggcgcuccagcuccgggaucuuucucccucggucaccucccucgcgucu agggaggucguggcacucccugaggagcgcggcugcucggagggcggauccuagaacagaggcgugagagccggcaugaagguc auaugucuaaccgcuccagugggguauggagucuacccuucucaacugaaugguuacggaucuucaccacccuauucccagaugga cagagaacacagcucaagaacaagugcaaaggcccuuuaugaacaaaggaagaacuaugcccgagacagugucagcagugugucg gacgugucccaguaccgcguggaacacuugaccaccuucgugcuggaucggaaagaugcaaugaucacugucgaggacggaauaa gaaagcugaaguugcuggaugccaagggcaaaguguggacucaagauaugauucuccaaguggaugaccgagcugugagccugau ugacuuagagucaaagaaugaauuggagaauuuuccucuaaacacaaucucgcauugucaagcaguggugcaugcaugcagcuau | | | |

TABLE 4-continued

Genes up-regulated in HF stem cells. Numbers in parentheses are the fold increase as determined by quantitative real time PCR.

| Gene Name/ Protein name/ GenBk Acces #. | Fold Incr. | Sequence | SEQ ID No. |
|---|---|---|---|

gacuccauucucgccuugguaugcaaagagccaacgcagagcaagccagaccuucaccuuuuuccagugugaugagguuaaggca
aaccuaauuagugaagauaucgaaagugcaaucagugacaguaaaggugggaaacagaagaggcggccggaggcccugaggauga
uugccaaagcagauccuggcaucccuccuccucccagagcuccugccccugugccaccggggacugucacacagguggacguuag
gagucgcguagcagccuggucugccugggcagcugaccagggugacuucgagaagccccggcaguaccacgagcaagaagagacg
cccgagaugauggcagcccggaucgacagggaugugcaaaucuuaaaccauauuuuggaugacauugaauuuuuuaucaccaaac
uccaaaaagccgccgaagcguuuucugagcuuucuaaaaggaagaaaaguaagaaaaguaaaaggaaaggaccuggagagggcgu
uuuaacacugagggcaaaaccgccaccuccugacgaguuuguugacuguuuccagaaguuuaaacauggauucaaccuucuggcc
aaguugaagucccauauccagaacccgagugcuucagaucugguucauuuuuuguuuacuccacuaaauauggugguccaggcaa
cagguggcccugaacuggccaguucgguacucagcccacuguugacaaaagacacaguugauuucuuaaacuacacagccacugc
ggaggaacggaagcuguggaugucacugggagauaguuggugaaagugagagcagaguggccgaaagaacaguucaucccaccu
uacgucccgagguuccgcaacggcugggagcccccgaugcugaacuucaugggcgcgcccacagagcaagacauguaucaacugg
ccgaguccguggccaacgcagaacaccagcgcaaacaggacagcaagaggcuguccacagagcauuccaauguguccgacuaucc
uccagccgacggauaugcguacaguagcagcauguaccacagaggaccacaugcagaccacggggaggcugccaugccuuucaag
ucaacuccuaaucaccaaguagauaggaauuaugacgcagucaaaacacaacccaagaaauacgccaaauccaaguacgacuuug
uggcgaggaacagcagcgagcucucgguuaugaaagaugaugucuuagagauacucgacgaucgaaggcagugguggaaaguccg
gaaugccaguggagacucuggguuugugccaaauaacauucuggauaucaugagaacuccagaaucuggaguggggcgcgcugac
cccccauacacacauaccauacagaaacaaaggacggaauacggccugagaucagcugacacuccuucugccccaucacccccuc
caacgccagcacccguuccgguccccuuccaccuucuguaccagcacccguuucugugcccaagguuccagcagaugucacccg
ccagaacagcagcuccagugacaguggggcagcauugugcgggacagccagagauacaaacaacucccaguggaccgaaggaag
ucccagauggaagagguucaggaugagcucuuccagaggcugaccaucgggcgcagugcugcgcagaggaaguuccacgugccac
ggcagaacguuccagugaucaauaucacuuaugacuccucaccggaagaaguaaagacuuggcugcagucaaagggauucaaucc
cgugacugucaauagccucgggguguugaacggagcacaacucuuuucucucaacaaagacgaacugaggucugucugcccggaa
ggugccagagucuuuaaccaaaucacuguucagaaagcugcuuuggaggacaguaauggaagcuccgaguuacaagagaucaugc
ggagacggcaggagaagaucagcgccgcugcgagcgacucgggaguggagucuuuugaugaagggagcagccacugaguccauga
acuuccuuauucuuggugugguegguugaacagugauggacaugcuuuguuuuaagaagccuugaagggaaugucaaagcugucgu
cuugguauauguaauuuaucgccauauaaggaaacaguauaugccugaguaagcagaggacccgcugcuucugugcacauuaguu
ugauuaaaacugagaagcggguaggugagauggcucagcaaguaaaggugcuugcugccaagcccaaugacccaaguucgagucc
cugggucuacaugguaggagagagcuggcuucugcaaguuguccucugaccaccacacauaaauaaauaacaaauguaauuuaca
aacuuuuaaaagaaaauguaauuuaaaaaaccagacguucuagacuguucugggcuugggaauauuuuuuucacuuuccuaaggu
guacuuuccuuugcuacauuaauuauugcagccuuguucgaugaucuaaguggggauauuugacaauggcagauuuauucauugc
aacaaggaaagacacagccauugaugaaaaaaaaaagaaagucucagcuuucagugacugggauaccugcuguccagggaggagg
cucaguuagacuacccucugcuuacuugaggucugacaugcccaaugagaguguauuuagcuuuauuuaaaguucuuaaugccaa
caguuuuaaaaaucacauuuaaaugaacuguacaagguagccagaccuugaauguaugaauagacuauauaauaugucccgagaa
acuuuguuacucucagcucuguugauugcgaaaucuugcauagauuaugcuuugauuuaguuucu

| Fyn/Fyn proto-oncogene M27266 | 10 | Sequence below. | 250 |
|---|---|---|---|

ccugggccccgccgcggacgcgcggagccgccugggccgcgccggaggagggcggggagaggaccaugugaaugugcuccggagc
ugagcgccaagccaagcaguguuugaaaggaacaggaugcugaucuaaucguggcaaaaagucaguccgaccgcugguuucgaag
acauguggugLauauaaaguuugugauaguugguggaaauuugggagcuuggauaaugggcugugugcaauguaaggauaaagaa
gcagcgaaacugacagaggagagggacggcagccugaaccagagcucugggLaccgcuauggcacagaccccaccccucagcacu
accccagcuucggcgugaccuccaucccgaacuacaacaacuuccacgcagcugggggccagggacucaccgucuuugggggugu
gaacuccuccucucacacugggacccuacgcacgagaggagggacaggagugacacuguuuguggcgcuuuaugacuaugaagca
cggacggaagaugaccugaguuuucacaaaggagaaaaauuucaaauauugaacagcucggaaggagauuggugggaagcccgcu
ccuugacaaccggggaaacugguuacauucccagcaauuacguggcuccaguugacuccauccaggcagaagagugguacuuugg
aaaacuuggccgcaaagaugcugagagacagcuccuguccuuuggaaacccaagagguaccuuucuuauccgcgagagccaaacc
accaaaggugccuacucacuuuccauccgugauugggaugauaugaaaggggaccacgucaaacauuauaaaauccgcaagcuug
acaaugguggauacuauaucacaacgcgggcccaguuugaaacacuucagcaacugguacagcauuacucagagaaagcugaugg
uuuguguuuuaacuuaacugugguuucaucaaguuguaccccacaaacuucuggauuggcuaaagaugcuugggaaguugcacgu
gacucguuguuucuggagaagaagcuggggcagggguguuucgcugaaguguggcuugguaccuggaauggaaauacaaaaguag
ccauaaagacccuuaagccaggcaccaugucuccggaguccuuccuggaggaggcgcagaucaugaagaagcugaagcaugacaa
gcuggugcagcucuacgcggucgugucugaggagcccauuuacaucgucacggaguacaugagcaaaggaaguuugcuugacuuc
uuaaaagauggugaaggaagagcucugaaguugccaaaccuuguggacauggcggcacagguugcugcaggaauggcuuacaucg
agcgcaugaauuauauccacagagaucugcgaucagcaaacauucuaguggggaauggacuaauuugcaagauugcugacuuugg
auuggcucgguugauugaagacaaugaauacacagcaagacaaggugcgaaguuucccauuaaguggacagcccccgaagcggcc
cuguauggaagguucacaaucaagucugacguauggucuuuuggaaucuuacucacagagcugguacaccaaaggaagagugcca
uacccaggcaugaacaaccgggaggugcuggagcagguggagagaggcuauaggaugcccugcccacaggacugcccgaucuccc
ugcacgagcucaugauccacugcuggaaaaaggauccggaagagcgcccgaccuucgaguacuugcagggcuuccuggaggacua
cuuuacggccacagagccccaguaucagcccggugaaaaccugugagagccugcgcuucagacgccucuucccgaggccucccua
ccccucccccauuagcuuccaauucuguagccagcugccccagagcaggagaaccguccaggaucagauugcaugugacucuugaa
gcugaacuuccacggcccucauuaaugacacuuguccccaguccgaaccuccucugugaaccaucugagacagaacguguuauu
ucucagacuuggaaaugcauuguaucgauguuaugucaaaggccaaaccucuguucaguguaaauagcugcuccugugccaacaa
ucccagugcuuuccuuuuuuaaaaaagaaaaagcaaauccuaugugauuuuaacucugauuucaccugauucaacuaaaaaaaaa
aaaguauuauuuuccaaaaguggccucuuugucuaaaacaauaaaauuuuuuuucauguuuuaacaaaaaaaaaaaaaaaaaaa
aaaa

| Col6a1/ Procollagen, type VI, alpha 1 X66405 | 36 | Sequence below. | 251 |
|---|---|---|---|

cccucccuggcucucuccucagcucugggcucugacugcagcaagcagagacaaccucucacucucgccuuucccagcgcccacc
cugacccuggcccacauuugacggugacucgcaggccagccagaaacaugaggcuggcccacgcucugcugccccugcugcuaca TABLE 4-continued Genes up-regulated in HF stem cells. Numbers in parentheses are the fold increase as determined by quantitative real time PCR.

| Gene Name/ Protein name/ GenBk Acces #. | Fold Incr. | Sequence | SEQ ID No. |
|---|---|---|---|

agccugcugggguggccacacaggacauccagggcuccaaagcgauugccuuccaagacugcccuguggaucuauucuucgugcuc
gacaccucggagaguguggccuugaggcugaaaccuuauggggccuugguggacaaggugaaguccuucacuaagcgcuucauug
acaaccugagagacagguacuaccggugugaccgcaaccugguuuggaaugcgggugcgcugcacuacagugacgagguggagau
cauccgagggcucacgcgcaugcccaguggccgcgaugagcucaaggccagcguggaugcggucaaguacuucgggaaaggcacc
uacaccgacugcgccauuaagaaggggcuggaggagcugcucauagggggcucccaccugaaggagaacaaguacuugaucgugg
ugaccgacgggcauccucuagagggcuacaaggaaccaugcggggggucuggaagaugcaguaaaugaggccaaacaccugggcau
caaggucuuuucuguggccaucacaccugaccaccuggagccacgucuaaguaucauugccacagaccacacauaccggcgcaau
uucacggcagcugacugggggcauagccgcgaugcagaagaggucaucagccagaccauugacaccauuguggacaugauuaaaa
auaacguggaacaaguguguuguucuuuugagugccaggcugccagaggaccuccagggccccgaggcgacccugguaugaggg
ggagcgaggaaagccaggucuuccgggagagaagggagaagcuggagacccuggacgaccuggggaucuuggaccagucggguac
caggguaugaagggagaaaaggggagccguggagagaaggguuccagaggaccgaaagguuacaagggcgagaaaggcaagcgcg
gaaucgacggggucgacggcaugaagggagagacgggguacccaggacuaccgggcugcaagggcuccccaggauuugauggcau
ucaaggacccccggguccccaagggugaugcuggugccuuugggaugaagggagaaaaggguggaagcuggagcagacggugaggcu
gggagaccagggaacucagggucaccuggagaugagggugauccuggagagccugguccccccggagaaaaggagaggccggug
augaaggaaaugcuggcccagacggugccccuggagagaggggguggcccuggugaaagaggaccucgggggaccccuggugugag
aggaccaaggggagacccgggugaagcuggaccacagggugaccaaggaagagaggggcccgucggcaucccuggagacucgggu
gaggcuggccccauuggaccuaaaggauaccgaggugaugagggucccucagguccugagggccucagaggagccccaggaccug
uugguccuccuggagaccccggacugaugggugagagaggugaggauggaccaccaggaaacggcacggaagguuuccccggcuu
cccuggguauccaggcaacagaggcccuccugggcuaaauggcacaaaaggcuacccuggccucaagggggaugagggugaagug
ggagacccaggagaggauaacaacgacauuucaccccguggggucaaaggggcaaagggauaccgaggcccagaaggaccccagg
gaccuccaggacauguggggaccaccugggccagaugagugugagauccuggauaucaucaugaaaaugugcuccugcugugagug
cacauguggacccauugacauccucuucgugcuggacagcucggagagcauuggccuacagaacuuugagauugccaaggacuuc
aucaucaaggucauugaccgguugagcaaggaugagcuggucaaauuugagccagggcagucucacgcgggcgugguacaguaca
gccacaaccagaugcaagagcacguggacaugcggagccccaacguccgcaacgcccaggacuucaaagaagcugucaagaagcu
acaauggauggcugguggcacauucaccggagaagcgcugcaguacacccgggaccggcuacucccacccacacagaacaaccga
auugcccuggucauuacggauggacguucugacacucaacgggacacgacaccucucagugugcucuguggugcagacauucagg
ugaguuucugugggaaucaaggauguguuuggcuuuguggcgggcuccgaccagcucaaugucauuuccugccaaggcuuaucgc
aaggucguccagguaucucccuggugaaggagaacuaugcagagcuucucgaugacggcuuucugaagaacauaacagcccagau
cuguauagauaagaaguguccggauuauaccuguccaaucacauucuccuccccggcugacaucaccauccugcuagacagcuca
gccagugucggcagccacaacuucgaaaccaccaaggucuucgccaagcgccuagcugagcgauuccugucagcaggcagggcgg
auccuucccaggaugugcggguggccgugguacaguauaguggccaggggcagcaacagccaggucgggcggcucuucaguucuu
acagaauuacacagugcuggccagcucuguggacagcauggauuucaucaacgacgccacagacgucaacgaugcucugagcuac
gugacucguuucuaccgggaagccucgucaggugccaccaagaagagagugcuguuguuucagacggcaacucucaggggggcca
cagcagaggccauugagaaggcugugcaggaggcccagcgugcaggcauugagaucuuugugguggugggugggaccccaggugaa
cgagccccacauccgugugcuugucacuggcaagacugcagaguacgacguggccuuuggcgagcgccaccuauuccguguacca
aacuaccaggcccugcuacguggcguacucuaccagacagucuccaggaagguggcacugggcuagagggccacacacguggcug
gacacacauggcauggagacacauuucaacaggccuucccgcccuucccacugacaaaacaggaauaggaaaugugacccaacug
gucaacucaacugucuuaaagggaacgcugagaugcacacucuuugcuuuguguaaugucccuguggcucaccugagcuccuau
cuagaucccgcccuugguuuguacaucaugguggccaucuugcugaccccucccccaucugggacuggauccagccaucucgucu
uccuccucacugccccuaaccuauccguggugucuucacaccaucacugcaguuuccgucuguguucugucuuccaugcucaaca
ugaagcagaccuucucaugaguucagcuugcuggauuauggcuuuuaggaaauugaacacaggaggaguuccaaacacaaacuug
gaggagaccccuccucuucaucaggugcuugucagugaccuacaugcaucuuggucugguccuuaguggcuaguccuuccacucu
gaaagcaaaggugcuaucuaucuguaagggcucucucuacacacccagaggcuuagcuuggacaguucacacucaaguguccugu
cagaaucaauccagagcuuucucccucaaaauagugacuugucucccccugguccccaaaggcucccccuuuaguuaguuucuuca
uggcucccccacauuccccguaaucugauccaagccagcuaucucugcuaauaaagguuuccauuuuucaaaaaaaaaaaaaa

| Gene Name/ Protein name/ GenBk Acces #. | Fold Incr. | Sequence | SEQ ID No. |
|---|---|---|---|
| Tnc/Tenascin C<br>AV230686<br>X56304 | 17 | accccaugccccacccccaccuucgauguuuugaacauuucuaacaacugaag<br>ccaguaaagucauauucuuuaaauuuccaggacauucauauuauucacauaau<br>cauggucauggugaugauggaaacugaggacuuuaaaagagauuuucccuucc<br>caaacguuucuggacaguaccugauuguauuuuuuuuguuuuguuuuguuuuu<br>uaauaaaagcacaguacuuuucc | 252 |
| Krt2-6a/Keratin complex 2, basic gene 6a (keratin 6a)<br>K02108 | 10 | Sequence below. | 253 |

gucugcccugccguuucucuacuucccagccuucucaucuccaggaaccaugucuaccaaaaccaccaucaaaagucaaaccagc
caccguggcuacagugccagcucagccagagugcuuggacucaaccgcucgggcuucagcagugugucccgugugccgcucccggg
gcagcgguggcuccagugcaaugugugggaggagcuggcuuuggcagcaggagccucuauggugugggggagcuccaagaggaucuc
caucggagggggcagcuguggcauuggaggaggcuauggcagccgauucggaggaagcuucggcauugguggugggagcugguagu
ggcuuuggcuucgguggugggagcuggcuuugguggugggcuaugggggagcuggcuucccggugugcccacuuggaggcauccaag
aggucaccaucaaccagagccuccucacaccccugaaccugcaaauugaccccaccauccagcgggucaggacugaggagaggga
gcagaucaagacccucaauaacaaguuugccuccuucaucgacaaggugcgguucauggagcagcagaacaaggucauggacacc
aagugggcccugcugcaagagcaggacaccaagaccgugaggcagaacauggagcccauguuugagcaguacaucagcaaccucc
gcagacagcuggacagcaucauuggagagaggggucgcaugaacucagagcugaggaacaugcaggaacucguagaagaacuacg
gaacaaauaugaagaugaaaucaacaagcgcacagacgcagagaaugaauucgugacccugaagaaggauguagaugcugccuac
augaacaaaguugaacugcaagccaaggcagacagucuaacagaugauaucaacuucuugagagcucucuaugaagcagaacugu
cucagaugcaaacucacaucucagacacaucuguggucccucuccauggucaacaaccguagccucguccuagacagcaucaucgc
ugaggucaaggcccaguuugaggucauagcucagagaagucgggcugaagcugagucauuguaccagacuaaauaugaggagcug
caggucacagcuggcagacauggggacgaccugcgcaacaccaagcaggagauugcugagaucaaccgcaugauccagaggcuga
gaucugagaucgaccacguuaagaagcagugugccaaccugcaagcugcuauugcugaugcugagcaacguggggagauggcccu
gaaggaugcaaggggcaagcuggaagggcuggaggaugcccugcagaaggccaaacaggacauggccaugcugcugaaggaguac TABLE 4-continued Genes up-regulated in HF stem cells. Numbers in parentheses are the fold increase as determined by quantitative real time PCR.

| Gene Name/ Protein name/ GenBk Acces #. | Fold Incr. | Sequence | SEQ ID No. |
|---|---|---|---|

caugaacucaugaaugucaagcuggcccuugauguggaaauugccaccuacaggaagcugcuggaaggagaggagugcagguuga
auggugaagguguuggaccagucaacaucucugugguggcaguccaccguguccagcggcuauggcagugccgggggugccagcag
cagcuuaggcauggguggaggcagcagcuacuccuauagcagcagccauggccuuggagguggcuucagugcuggcaguggcaga
gccaucggagguggccucagcucuucugguggccucagcucuucuaccaucaaauacaccaccaccuccuccagcaagaagagcu
acaggcagugaauucugucaccaagagcuugucucuggucccagaugucauggcugcagcugaaccacaugcuugguucccgga
agggaacgaaucccaaccucuggccucccccauggcucaguucuacauuuguguugcacgucagcaccuauacauguucuuuggug
acccagaccccaaaauguugcagaauguagaccuccaagacgaaaccccaaacccuacccagaauacccaccuaaauucugucau
gguucugacuuccuccagagucuguaaaauaaaaugcccccacaacaaac

| | | | |
|---|---|---|---|
| Potassium channel, subfamily K, member 2 AI849601 | 14 | uuuuuuuuuuuuuuuuugauuuuaauuacaaacuuuauuuguccuccaguuca<br>caguuuauacgugguacaucccaccaugucagcuuccagaacggcuauucagg<br>agauggguggagcuuucuuuguaaaggaacccgacauuuuaaaauuuugguua<br>gaaucuucauagguuuauaaaaguacucucugcaagcgaacuggauauauuua<br>cauuuauagcuuaaauucaaauuuuggaaaauaggaaucuuuuuguguuuuua<br>aacauccuggguuuaugucuuaagacuuuacucugaaugccacaugaucacgu<br>aagcccaagccucccccagaagggaaaaaucaguuuugc | 254 |
| Skd3/Supressor of K+ transport defect 3 AI837887 | 4 | uuuuuuuuuuuuuuuuuugggugccaugccacagcaaggggccuuuauuagaug<br>uucagggcacagacagguggaugcuagaugguguagcacaccuucucagggug<br>gagugguggccuggauguccaguuugcgggucuugcuguccuuaucaaugaucu<br>ccagucgcaauguagguggacgcuucucagccuggggugagggcagcucacgg<br>cucuugaggaggugcuuguccgaauccuccacagugauacccagggugcaacc<br>cccugg | 255 |
| Clic4/Chloride intracellular channel 4 (mito-chondrial) AI845237 | 3 | uuuuuuuuuuuuuuuuucugacacaguaguaauccuuccagacuccuuacacaa<br>uauuacaacucccccaguacauaaauguuccuauaccaugcacacagcaacau<br>gggguccacugaugucgcaggcgacuuuucuaaugguggaacauagcaccuca<br>aguucugccaucuacacagugaagggacgugauggucggggcuccagagugac<br>agcaaacugccucuugggugacacgcuuguggcgaagugccucc | 256 |
| Col18a1/ Endostatin (alpha 1 (XVIII) collagen) L22545 | 5 | Sequence below. | 257 |

gagaauguugcugaggaggugggggcugcugcagcuccuuggagacccccuaccugagaagaucucacaaaucgaugacccucacg
ucgggccggccuacaucuuuggaccagacuccaacaguggccagguggcccaguaucauuucccaaaacucuucuuccgggacuu
uucgcugcuguuucauguccggccagccacagaggcagcaggggugcuauuugccaucacagaugcugcccagggugguagucuca
cugggcgugaagcucucagagguccgagauggacagcaaaacaucucauugcucuacacggagccugggggccagccagacccaga
cgggagccagcuuccgccuaccugcauuuguugggcaguggacacacuucgcgcucagcgucgacggaggcucuguggcucucua
cguagacugugaagaauuccagagggugccauuugcucgggccucgcagggacuggagcuagagcguggcgcuggccucuuugug
ggucaggcuggaacagcagacccugacaaguuccaggggaugaucucagagcugaagguacgcaaaacccccgggugagcccug
ugcacugucuggaugaagaagaugaugaugaagaccgggcaucuggagauuuuggaaguggcuuugaagaaagcagcaagucaca
caaggaggauacaucucuacuaccugggcucccucagccaccuccugucacuuccccaccccuggcuggaggcagcaccacagaa
gauccuagaacagaagaaacggaggaagacgccgcgguagauucuauaggagcugagacccuuccuggcacagguucaagcggug
caugggaugaggcuauccagaaccccggaagggggcuugauaaagggagguaugaaaggacaaaagggagaaccaggugcccaggg
cccaccuggcccagcuggcccccaggguccugccgguccagugguccagagccccaacucacaaccugucccuggagcacaagga
cccccgggaccucaggggccaccagggaaggauggcacuccaggaagggauggugaaccgggugacccuggugaagaugggagac
cgggugacacuggaccucaaggcuuuccagggaccccaggagaugugggcccuaagggcgagaagggagauccugguauugggcc
ccgaggaccuccagggccuccagggccaccaggacccuccuucagacaagacaagcugaccuucauugacauggagggauccggu
uucagcggagacauagagagccuuagaggcccacgaggcuucccuggcccccgggggcccccugguguccccaggacuuccuggug
agccaggacgcuuugggaucaaugguuccuaugcaccaggaccugcaggccuuccugguguaccugggaaggaaggacccccccgg
uuuuccagguccccccgggaccuccagguccuccaggcaaagagggcccaccaggaguggccggccagaaaggcaguguuggugau
gugggcaucccaggacccaaggggagcaaaggagaccuugggcccaucgguaugccuggcaagucuggcuuggcuggauccccug
ggccaguuggacccccaggaccuccagggccuccagggccaccaggaccaggauuugcugcuggauucgaugauauggaaggcuc
uggaauaccccucuggacaacagcccgaagcucugaugggcugcagggaccucccgggucgccgggacucaaggggggauccugga
guggcaggccuaccuggagccaagggagaaguuggagcagauggagcccagggcaucccuggucccccaggaagagaaggugcag
cuggaucuccggggccaaaaggagagaaggggaugccgggagaaaagggaaacccaggaaaagauggagugggccggccgggccu
cccugggccuccaggaccuccagggcuggugaucuaugugucaagugaggauaaagcaauagugagcacgccaggaccugagggc
aagccaggguacgcaggcuuuccuggaccugcuggaccgaagggugaccuggguuccaaaggcgagcagggucuuccgggguuua
agggugagaagggagagccaggcacuaucuuuaguccugauggcagacgucugggccauccccagaagggagccaaggagagcc
aggcuuucgaggacccccggguccuuauggacgaccugggcacaaggugaaauuggcuucccuggacggccgggucgaccugga
acgaauggcuuaaagggagagaagggagagccuggagaugccagccuuggguucagcaugaggggauugccuggccccccugggc
cuccaggacccccagguccuccugggaugcccaucuaugacagcaaugcauuuguggagucuggccgaccuggacuaccaggaca
gcagggugugcaggggccuucaggaccaaaggguacaaaggagagguggggccaccugggccaccagggcaauuccccauugac
cucuuccaccuggaagcggaaaugaagggggacaagggagaccgaggggaugcuggacagaaaggagagaggggagaaccugggg
cuccugguguggauucuucagcucaaguguaccuggcccacccggcccaccuggauacccuggaauuccggguccaaagggaga
gagcauccgggggccaccuggcccuccuggcccgcagggaccuccuggcauuggcuaugagggucgccaggucccccaggaccu
ccaggaccuccaggaccucccuccuucccuggcccucacagacagacugucaguguuccugguccuccgggcccaccugguccuc
caggucccccaggagccauggguccucugcugggcaggugaggaucugggccacauaccagaccaugcuggacaagauccggga
ggugccggagggcuggcucaucuuuguggccgagagggaagagcucuauguacgcguuagaaauggcuuccggaaggugcugcug
gaggcccggacagcccuccugagaggcacgggcaaugagguggcugcuuuccagcccccauugguccagcuucaugagggcaguc
cauacacccggagggaguacuccuauuccacggcacgacccuggcgagcagaugacauccuggccaacccaccgcgccugccaga TABLE 4-continued Genes up-regulated in HF stem cells. Numbers in parentheses are the fold increase as determined by quantitative real time PCR.

| Gene Name/<br>Protein name/<br>GenBk Acces #. | Fold<br>Incr. | Sequence | SEQ ID No. |
|---|---|---|---|

ccgccagccuuacccuggaguuccacaucaccacaguuccuaugugcaccugccgccagcccgccccacccucucacuugcucau
acucaucaggacuuucagccagugcuccaccugguggcacugaacaccccccugucuggaggcaugcgugguauccguggagcag
auuuccagugcuuccagcaagcccgagccguggggcugucgggcaccuuccgggcuuuccuguccucuaggcugcaggaucucua
uagcaucgugcgccgugcugaccgggggucugugcccaucgucaaccugaaggacgaggugcuaucucccagcugggacucccug
uuuucuggcucccagggucaagugcaacccggggcccgcaucuuuucuuuugacggcagagauguccugagacacccagccuggc
cgcagaagagcguauggcacggcucggaccccagugggcggaggcugauggagaguuacugugagacauggcgaacugaaacuac
uggggcuacaggucaggccuccucccugcugucaggcaggcuccuggaacagaaagcugcgagcugccacaacagcuacaucguc
cugugcauugagaauagcuucaugaccucuuucuccaaauaggccucugccagcuaggguggcagacagaggccaugcagaacuu
ugacacagcgcagggagcauucagucagcacccagggcucuggcugggauacaacuccuguauaguucccauuuuuauguaaucc
ucaagaaauaaaaggaagccaaagaguaaaaaaaaa

TABLE 5

| Gene Name/Protein | Fold Decr | Sequence | SEQ ID No. |
|---|---|---|---|
| | | Growth Factors, Receptors and Downstream genes | |
| GNA-14<br>Mouse G protein alpha subunit (GNA-14)<br>M80631 | 32 | Sequence below. | 258 |

aacugccuucgagaagcguuagccuagagauccgagccucuucuccauaccauaguugguucaggugguuuccucuucaa
accuugcgucugcggauaauccgcgcggccgggcguuaagcuccaggucccugucgcuccgucgagguggcaagccaugg
ccggcugcugcuguuugucugcggaggagaaagagucucagcgcaucagcgcggagaucgagcggcacguucgccgcgac
aagaaggacgcgcgccgggagcucaagcugcuguugcugggaaccggugagagugggaaaagcaccuuuaucaagcagau
gaggauaauccauggguccuggcuacagugaugaagauagaaagggcuucacgaagcugguuuaccaaaacauauucacgg
ccaugcaagccaugaucagagcaauggauacccugaggauacaauacaugugugagcagaauaaggaaaaugcccagauc
aucagggaaguggaaguagacaaggucacugcacucucuagagaccagguggcagccaucaagcagcuguggcuggaucc
cggaauccaggaguguuacgacaggaggagggaguaccagcugucagacucugccaaauauuaccugacggacauugagc
guaucgccaugcccucuuucgugccaacacaacaggaugugcuucguguuagagugcccaccacuggcaucauagaauau
ccauucgaccuggaaaacaucaucuuccgaaugguggauguugguggccagcgaucugaacgacggaaauggauucacug
cuuugagagugucaccuccaucauuuucuugguugcucugagugaauaugaccagguucuggcugagugugacaaugaga
accgcauggaggagagcaaagcccuguuuagaaccaucaucaccuaccccugguuucugaacuccuccgugauucuguuc
uuaaacaagaaggaucuucuagaggagaaaaucauguacucucaucuaauuagcuacuucccagaguacacaggaccaaa
gcaagaugucaaagcggccagggacuuuauccugaagcuguaucaagaccagaauccugacaaagagaagguuaucuauu
cucacuucacuugugcuacagacaccgagaauauccgcuuuguguuugcugcugucaaagacacaauccuacagcuaaac
cuacgggaguucaacuugguguaaauggagggccuacuccuccgagacagaggguggaucugagcccuuccugccugaucu
acaagugcuucuggaccaggaccuaaggacauuauguagcccacaggacagagaugguagugcaaugugaaaaauacuu
caccaacccuuuuaagugucuuuaauucuucacugucuaacucuuuuucucgccuuuugguugaacgauuagguaucauu
uuugagugguucccccucuccuauuuuuuuaaacuagugucaacaguuauuaaaaaaucaugc

| Gene Name/Protein | Fold Decr | Sequence | SEQ ID No. |
|---|---|---|---|
| Ly6/Lymphocyte antigen 6 complex<br>X04653 | 12 | gaauucccugcaaccuugucugagaggaagcaaggacuggugugagga<br>gggagcugugagguuuuaucugugcagcccuucucugaggauggacac<br>uucucacacuacaaaguccuguuugcugauucuucuuguggcccuacu<br>gugugcagaaagagcucagggacuggaguguuaccagugcuauggagu<br>cccauuugagacuucuugcccaucaauuaccugccccuacccugaugg<br>agucuguguuacucaggaggcagcaguuauugugguucucaaacaag<br>gaaaguaaagaacaaucuuugcuuacccaucugcccuccuaauauuga<br>aaguauggagauccuggguacuaaggucaaugugaagacuuccuguug<br>ccaggaagaccucugcaaugcagcaguucccaauggaggcagcaccug<br>gaccauggcaggggugcuucuguucagccugagcucaguccuccugca<br>gaccuugcucugaugguccucccaaugaccuccacccuuguccuuuua<br>uccucaugugcaacaauucuuccuggagcccucuagugaugaauuaug<br>aguuauagaagcuccaaggugggaguagugugugaaauaccauguuuu<br>gccuuuauagcccugcugguagguaggugcucuaauccucucuaggg<br>cuuucaagucuguacuuccuagaaugucauuuuguuguggauugcugc<br>ucaugacccuggaggcacacagccagcacagugaagaggcagaauucc<br>aagguauuaugcuaucaccauccacacauaaguaucugggguccugca<br>auguucccacauguauccugaauguccccuguugaguccaauaaacc<br>cuuuguucuccc | 259 |
| Bmp4/Bone morphogenetic protein 4<br>L47480 | 11 | Sequence below. | 260 |

ggaagaaagagagggagggaaaagagaaggaagaguagaugugagagggugugcugagggugggaaggcaagagcgcga
ggccuggcccggaagcuaggugaguucggcauccgagcugagagaccccagccuaagacgccugcgcugcaacccagccu
gaguaucuggucuccgucccugaugggauucucgucuaaaccgucuuggagccugcagcgauccagucucuggcccucga TABLE 5-continued

| Gene Name/Protein | Fold Decr | Sequence | SEQ ID No. |
|---|---|---|---|
| | | ccagguucauugcagcuuucuagagguccccagaagcagcugcuggcgagcccgcuucugcaggaaccaauggugagcag | |
| | | ggcaaccuggagaggggcgcuauucugaggauucgaggugcacccguaguagaagcuggggauggggcucaggcuguaac | |
| | | cgaggcaaaaguuggccuauuccuccuuccuucuccaacaguguuggaggugggaugauggaggcuaaaaggcaccucca | |
| | | uauauguuacugcgucuaucaaccuacuuuagggaggugcgggccaggagaggcggaaggagagaaggccuuggaagaga | |
| | | ggucauugggaagaacugugggguuugguggguuugcuuccacuuagacuauaagagugggagaggagggagucaacucu | |
| | | aaguuucaacaccaguggggacugaggacugcuucauuaggagagagaaccuagccagagcuagcuuugcaaaagaggc | |
| | | uguaguccugcuuugcucuaaagcgcgacccgggauagagaggcuuccuugagcgggguguucaccuaaucuuguccccaa | |
| | | cgcacccccucccagccccugagagcuagcgaacuguagguacacaacucgcucccaucuccaggagcuauuuucuuaga | |
| | | caugggcacccaugauucugccuucugguacucucccccucccugggaaagggguguaagguuccgacggaaccguggcca | |
| | | ggaugccgaaaggcuaccugugcgggucuucugccaugcugugucugugcggacaugccagcagggcuaaugaggagcuu | |
| | | gcgauacuccaaaggguucgggaauugcggggucccuuacacgcaguggaguugggccccuuuuacucagaagguuuccgc | |
| | | cacggcuuugguugauaguuuuuuuaguauccugguuuaugaacugaagguuuugugagauguugaaucacuagcagggu | |
| | | cauauuuggcaaaccgaggcuacuauuaaauuuugguuuuagaagaagauucuggggagaaagugaaggguaacugccuc | |
| | | caggagcuguaucaaccccauuaagaaaaaaaaaaaauaccaggagaugaaaauuuacuuugaucuguauuuuuuaauuaa | |
| | | aaaaaaucagggaagaaaggagugauuagaaagggauccugagcgucggcgguuccacggugcccucgcuccgcgugcgc | |
| | | cagucgcuagcauaucgccaucucuuucccccuuaaaagcaaauaaacaaaucaacaauaagcccuuugcccuuuccagc | |
| | | gcuuucccaguuauucccagcggcgacgcgugucggggaauagagaaaucgucucagaaagcugcgcugaugguggugag | |
| | | agcggacugucgcucagggggcgcccgcggucucugcacccagggcagcagugugggauggcgcugggcagccaccgccg | |
| | | ccaggaaggacgugacucuccauccuuuacacuucuuucucaaagguuucccgaaagugcccccgccucgaaaacuggg | |
| | | gccggugcgggggggggagagguuagguugaaaaccagcuggacacgucgaguuccuaagugaggcaaagaggcggggu | |
| | | ggagcgggcucuggagcgggggaguccugggacucgguccucggauggaccccgugcaaagaccuguuggaacaagaguu | |
| | | cgcgcuuccgagguuagaacaggccaggcaucuuaggauagucaggucacccccccccccaaccccacccgaguuguguu | |
| | | ggugaauuucuuggaggaaucuuagccgcgauucuguagcuggugcaaaaggaggaaaggggugggggaaggaaguggcn | |
| | | gngcgggggguggcgguggggguggagguggguuuaaaaaguaagccaagccagagggagaggucgagugcaggccgaaagc | |
| | | uguucucggguuuguagacgcuugggaucgcgcuugggucucccuuucgugccggguaggaguuguaaagccuuugcaac | |
| | | ucugagaucguaaaaaaaaugugaugcgcucuuucuuuggcgacgccuguuuuggaaucuguccggaguuagaagcucag | |
| | | acguccacccccccacccccgcccacccccucugccuugaauggcaccgccgaccgguuucugaaggaucugcuuggcug | |
| | | gagcggacgcugagguuggcagacacggugugggggacucuggcggggcuacuagacaguacuucagaagccgcuccuucu | |
| | | aacuuucccacaccgcucaaaccccgacacccccgcggcggacugaguuggcgacgggggucagagucuucuggcugaaag | |
| | | uuagauccgcuaggggucggcugccugucgcuagaagcauuauuuggccucucggagacccguguggaggaagugcugga | |
| | | gugugcgaguguguuugcgugugugugugugugugugugugugugugugugugugugugugcgcgcgcccuuggaggg | |
| | | ucccuaugcgcuuuccuuuucauggaacgcugucgugaggcucccugauccucaggcuucagauaacccguccccgaacc | |
| | | uggccagaugcauugcacugcgcgccgcagguagagacgugccccacguccccugcgugcagcgacuacgaccgagagcc | |
| | | gcgccagugugguguccccgccgagaguuccucagagcaggcggggacaacucccagacggcuggggcuccagcugcgggc | |
| | | gcggagguuggccucgcucgcaggggcuggacccagccggggugggaggauggaggaggggcgggcgggcucuucgguga | |
| | | guggggcggggccucugggguccacgugacuccuaggggcuggaagaaaaacagagccugucugcuccagagucucauuau | |
| | | aucaaauaucauuuuaggagccauuccguagugccauucggagcgacgcacugccgcagcuucucugagccuuuccagca | |
| | | aguuuguucaagauuggcucccaagaaucauggacuguuauuaugccuuguuuucugucagugaguagacaccucuucuu | |
| | | ucccuucuugggauuucacucuguccucccaucccugaccacugucugucccucccgucggacuuccauuucagugcccc | |
| | | gcgcccuacucucaggcagcgcuaugguucucuuucuggucccugcaaggccagacacucgaaauguacgggcuccuuuu | |
| | | aaagcgcucccacuguuuucucugauccgcugcguugcaagaaagagggagcgcgagggaccaaauagaugaaagguccu | |
| | | cagguuggggcugucccuugaagggcuaaccacucccuuaccagucccgauauauccacuagccugggaaggccaguucc | |
| | | uugccucauaaaaaaaaaaaaaaaaacaaaaaacaaacagucguuugggaacaagacucuuuagugagcauuuucaacgc | |
| | | agcgaccacaaugaaauaaaucacaaagucacuggggcagccccuugacuccuuuucccagucacuggaccuugcugccc | |
| | | gguccaagcccugccggcacagcucuguucucccccuccuccuguucuuaaccagcuggaaguuguggaaauugggcugga | |
| | | gggcggaggaagggcgggggugggggguggagaaggugggggggggggaggcugaagguccgaagugaagagcgauggc | |
| | | auuuuaauucuccccuccnccucccccccuuuaccuccucaauguuaacuguuuauccuugaagaagccacgcugagaucau | |
| | | ggcucagauagccguugggacaggauggaggcuaucunauuuggggguuauuugaguguaaacaaguuagaccaaguaauu | |
| | | acagggcgauucuuacuuucgggccgugcauggcugcagcuggugugugugugugguagggugugagggagaaaacacaaa | |
| | | cuugaucuuucggaccuguuuuacaucuugaccgucgguugcuaccccuauaugcauaugcagagacaucucuauuucuc | |
| | | gcuauugaucgguguuuauuuauucuuuaaccuuccaccccaaccccccuccccagagacaccaugauuccugguaaccga | |
| | | augcugauggucguuuuauuaugccaaguccugcuaggaggcgcgagccaugcuaguuugauaccugagaccgggaagaa | |
| | | aaaagucgccgagauucagggccacgcgggaggacgccgcucagggcagagccaugagcuccugcgggacuucgaggcga | |
| | | cacuucuacagauguuugggcugcgccgccguccgcagccuagcaagagcgccgucauuccggauuacaugagggaucuu | |
| | | uaccggcuccagucuggggaggaggaggaggaagagcagagccagggaaccgggcuugaguacccggagcgucccgccag | |
| | | ccgagccaacacugugaggaguuuccaucacgaaggucaguuucugcucuuaguccuggcgguguaggugggguagagc | |
| | | rccggggcagaggguggggguggggcagcuggcagggcaagcugaaggggguuguggaagccccccggggaagaagaguuca | |
| | | uguuacaucaaagcuccgaguccuggagacuguggaacagggccucuuaccuucaacuuuccagagcugccucugagggu | |
| | | acuuucuggagaccaaguaguggugugauggggagggguuacuuugggagaagcggacugacaccacucagacuncu | |
| | | gcuaccncccagnggguguucuuuagcuauaccaaagncagggauucugcccguuuuguuccaaagcaccuacugaauuu | |
| | | aauauuacancugugguguuugucagguuuaucaauaggggccuuguaauacgaucugaauguuuccuagcggauguuucu | |
| | | uuuuccaaaguaaaucugaguuauuaauccuccagcaucauuacuguguuggaauuuauuuucccuucuguaacaugauc | |
| | | aacaaggcgugcucuguguuucuaggaucgcuggggaauguuugguaacauacucaaaaguggagagggagagagggugg | |
| | | ccccucuuuuucuuuacaaccacuuguaaagaaaacuguacacaaagccaagaggggcuuuaaaaggggaguccaagggu | |
| | | gguggaguaaaagaguugacacauggaaauuauuaggcauauaaaggagguugggagauacuuucugucuuugguguuug | |
| | | acaaaugugagcuaaguuuugcugguuugcuagcugcuccacaacucugcuccuucaaauuaaaaggcacaguaauuucc | |
| | | uccccuuagguuucuacuauauaagcagaauucaaccaauucugcuauuuuuuguuuuuguuucuuguuuuuguuuuguu | |
| | | ugguuuuuuuuuuuuuuuuuuuuuuuuuugucucagaaaagcucaugggccuuuucuuuuccccuuucaacugugccuaga | |
| | | acaucuggagaacaucccagggaccagugagagcucugcuuuucguuuccucuucaaccucagcagcaucccagaaaaug | |
| | | aggugaucuccucggcagagcuccggcucuuucgggagcagguggaccagggcccugacugggaacagggcuuccaccgu | |
| | | auaaacauuuaugagguuaugaagcccccagcagaaaugguuccuggacaccucaucacacgacuacuggacaccagacu | |
| | | aguccaucacaaugugacacggugggaaacuuucgaugugagcccugcaguccuucgcuggacccgggaaaagcaaccca | |
| | | auuaugggcuggccauugaggugacucaccuccaccagacacggacccaccagggccagcaugucagaaucagccgaucg | |
| | | uuaccucaagggaguggagauugggcccaacuccgcccccuccuggucacuuuuggccaugauggccggggccauaccuu | |
| | | gacccgcaggagggccaaacguagucccaagcaucacccacagcgguccaggaagaagaauaagaacugccgucgccauu | |
| | | cacuauacguggacuucagugacgugggcuggaaugauuggauuguggccccacccggcuaccaggccuucuacugccau | |
| | | ggggacugucccuuuccacuggcugaucaccucaacucaaccaaccaugccauugugcagacccuagucaacucuguuaa | |

TABLE 5-continued

| Gene Name/Protein | Fold Decr | Sequence | SEQ ID No. |
|---|---|---|---|

uucuaguaucccuaaggccuguuguguccccacugaacugagugccauuuccauguuguaccuggaugaguaugacaagg
ugguguugaaaaauuaucaggagaugguugguagaggggugguggaugccgcugagaucagacguccggagggcggacacac
acacacacacacacacacacacacacacacacacacacaguucccauucaaccaccuacacauaccacacaaacugcuuc
ccuauagcuggacuuuuaucuuaaaaaaaaaaaaaaagaaagaaagaaagaaagaaagaaagaaaaaaaaugaaagacagaaaag
aaaaaaaaaacccuaaacaacucaccuugaccuuauuuaugacuuuacgugcaaauguuuugaccauauugaucauauuu
ugacaaauauauuuauaacuacauauuaaaagaaaauaaaaugag

| Gene Name/Protein | Fold Decr | Sequence | SEQ ID No. |
|---|---|---|---|
| Il1r2/Interleukin 1 receptor, type II AV223216 X59769 | 11 | gaaucccacuuacaugcgagcaucucuauauacauccucaaucuaucc ccucgaauccacggacuuaucagucaaucaauacuacagucaaagaau uuuuuucuacguuauccuggagcauugcgcuggcaccucuuuuucuaa ucaucuugguugugggccaauauggaugcgcagacggugugaaacgca gggcuggaaagacauauggacugaccaagcuacggacugacaaccagg acuucccuuccagcccaaacuaaauaaaggaaaugaa | 261 |
| Wnt3a/wingless-related MMTV integration site 3A X56842 | 4 | Sequence below. | 262 |

gaauucaugucuuacggucaaggcagagggcccagcgccacugcagccgcgccaccucccagggccgggccagcccaggc
guccgcgcucucggggugacucccccgcugcgcgcucaagccggcgauggcuccucucggauaccucuuagugcucug
cagccugaagcaggcucugggcagcuacccgaucugguggucccuuggcugugggaccccaguacucccucucugagcacuc
agcccauucucugugccagcaucccaggccugguaccgaagcagcugcgcuucugcaggaacuacguggagaucaugccc
agcguggcugagggugucaaagcgggcauccaggagugccagcaccaguuccgaggccggcguuggaacugcaccaccgu
cagcaacagccuggccaucuuuggcccuguucuggacaaagccacccgggagucagccuuuguccaugccaucgccuccg
cuggaguagcuuucgcagugacacgcuccugugcagagggaucagcugcuaucugugggugcagcagccgccuccagggc
uccccaggcgagggcuggaagugggggcggcuguagugaggacauugaauuuggaggaauggucucucgggaguuugccga
ugccagggagaaccggcccggaugcccgcucugccaugaaccgucacaacaaugaggcugggcgccaggccaucgccaguc
acaugcaccucaagugcaaaugccacgggcuaucuggcagcugugaagugaagaccugcugguggucgcagccggacuuc
cgcaccaucggggauuuccucaaggacaaguaugacagugccucggagaugguggguagagaaacaccgagagucucgugg
cuggguggagacccugaggccacguuacacguacuucaaggugccgacagaacgcgaccuggucuacuacgaggccucac
ccaacuucugcgaaccuaaccccgaaaccggcuccuucgggacgcgugaccgcaccugcaaugugagcucgcauggcaua
gaugggugcgaccuguugugcugcgggcgcgggcauaacgcgcgcacugagcgacggagggagaaaugccacuguguuuu
ccauuggugcugcuacgucagcugccaggagugcacacgugucuaugacgugcacaccugcaaguaggagagcuccuaac
acgggagcaggguucauuccgagggggcaagguuccuaccugggggcgggguuccuacuuggaggggucucuuacuugggg
acucgguucuuacuugagggcggagauccuaccugugagggucucauaccuaaggacccgguuucugccuucagccuggg
cuccuauuugggaucugggguuccuuuuuaggggagaagcuccugucugggauacggguuucugcccgaggguggggcucc
acuuggggauggaauuccaauuugggccggaaguccuaccucaauggcuuggacuccucucuugacccgacagggcucaa
auggagacagguaagcuacucccucaacuaggugggguucgugcggaugggugggaggggagagauuagggucccuccuc
ccagaggcacugcucuaucuagauacaugagagggugcuucaggguggcccuauuugggcuugaggaucccgugggggc
ggggcuucaccccgacuggguggaacuuuuggagacccccuuccacuggggcaaggcuucacugaagacucaugggaugg
agcuccacggaaggaggaguuccugagcgagccugggcucugagcaggccauccagcucccaucuggccccuuuccaguc
cugguguaagguucaaccugcaagccucaucugcgcagagcaggaucuccuggcagaaugaggcauggagaagaacucag
gggugauaccaagaccuaacaaaccccgugccugguaccucuuuuaaagcucugcaccccuucuucaagggcuuuccua
gucuccuuggcagagcuuuccugaggaagauuugcagucccccagaguucaagugaacacccauagaacagaacagacuc
uauccugaguagagaggguucucuaggaaucucuaugggggacugcuaggaaggaucccugggcaugacagccucguaugau
agccugcauccgcucugacacuuaauacucagaucuccccgggaaacccagcucauccgguccgugaugucccaugccccaa
augccucagagauguugccucacuuugaguuguaugaacuucggagacauggggacacagucaagccgcagagccagggu
uguuucaggacccaucugauuccccagagccugcuguugaggcaaggucaccagauccguuggccaccacccugucccg
agcuucucuagugucugucuggccuggaagugaggugcuacauacagcccaucugccacaagagcuuccugauugguacc
acugugaaccguccucccccuccagacaggggaggggauguggccauacaggagugugcccggagagcgcggaaagagg
aagagaggcugcacacgcguggugacugacugucuucugccuggaacuuugcguucgcgcuuguaacuuuauuuucaaug
cugcuauauccacccaccacuggauuuagacaaaagugauuuucuuuuuuuuuuuucuuucuuucuaugaaagaaauu
auuuuaguuuauaguauguuuguuucaaauaauggggaaaguaaaaagagagaaaaaaaaaaaaaaaaaaaaaaaaaaa
aaaaaaaaaa

| Gene Name/Protein | Fold Decr | Sequence | SEQ ID No. |
|---|---|---|---|
| Il12rb2/ Interleukin 12 receptor, beta 2 U64199 | 3 | Sequence below. | 263 |

cgcaccggagguccacacugccgcguggacuccagcgauggcgcugcgcuaggcuagcgggugccaggaucccucucugc
guccugugcgcgggaagagcucuggagaaccagaguugcauucuggaguugaagacucauggcacagacuguuagagaau
gcucauuggcacuucuuuuuuuguucauguggcugcugauuaaagcaaauauagaugugugcaagcuuggcacugugacc
guccagccugccccugugauuccucuuggguagcugccaauauuuccugcuccuugaaucccaagcaaggcuguucaca
uuaucccaguucuaacgaauuaaucccucuuaaaguuugucaaugaugucccuuguugaaaaucuccauggcaagaaagucc
augaccacacuggucacuccuccacuuuucaagucaccaaccugucccuugguaugaccuuguuugucugcaagcuaaac
uguagcaacucucaaaagaagccaccagucccaguaugugggguggagaucucaguuggguguugcuccagagccaccuca
aaacauaucauguguccaggaaggagaaaauggaacuguggccuguuccuggaacucuggaaaaguuacuuaucugaaaa
ccaauuacacuuuacaguuaaguggaccaaacaaucugaccugucagaaacaauguuuuucugacaaucgucagaauugc
aaucgccuggaucuugggaucaaucuaagcccugauuuagcugaauccagguucauaguccguguuacugccaucaacga
ucuuggaaauucuucuucacuuccgcauacguucacguucuuggacauagugaucccucuucucccgugggacaucagaa
ucaacuuucuaaaugcuucugggagcagagguacacugcagugggaagaugaggggcaagugguacucaaucaacucaga
uaucagccucuuaacagcacguccuggaacauggucaaugcuacaaaugccaaaggaaaauaugaccugcgagaucugag
accguuuacagaauaugaauuucaaaucucccucuaagcuacaucucucuggaggaaguugggaguaauuggagugagucac
ugagaacacgaacaccagaggaagagccuguugggauauuagacaucugguacaugaaacaagacaugacuaugacagac
agcagaucucucuuuucuggaagagucugaauccaucagaggcaaggggaagauccuccacuaucaggugacguuacaa
gaggugacaaagaaaacaacacugcagaauacuacaagacacaccucccuggaccagggucaucccccgaacuggggcuug TABLE 5-continued

| Gene Name/Protein | Fold Decr | Sequence | SEQ ID No. |
|---|---|---|---|
| | | gacggcaucagugucugcagccaacucaaaaggcgcuucugcacccacucacauuaacauaguggaccuauguggcacug<br>gguugcuggcuccucaccaggucucugcaaagucggagaacauggacaacauucuagugaccuggcagccuccuaagaaa<br>gcugauucugcuguucgggaguacauaguggaauggagagcucuccaaccagggagcaucacgaaguuuccccacacug<br>gcugcggaucccccggacaacaugucugcucugauuucagagaacauaaagcccuauaucuguuaugaaaucagggugc<br>augcacugucagagagccaaggagggugcagcuccauccggggugacuccaagcacaaagcaccagugaguggcccucac<br>auuacugccaucacagagaaaaggaacgccuuuucauuuccuggacccacauuccauucccggagcaaaggggcugcau<br>ccuccauuacagaauauacuggaaagaacgagacucgacagcacaaccugagcucugcgaaauucaguaccgacgcucuc<br>aaaacucacauccaauaagcagccuacagcccagggugacauauguccuauggaugacagcugugacagcugcuggugaa<br>aguccccaaggaaaugaaagggaauuuuguccacagggcaaagccaacuggaaagcauucgugauaucaagcauuugcau<br>cgcuaucaucacggugggcacguucucaauucguuacuuccggcaaaaggcauuuacucuccugucuacucucaaaccuc<br>aaugguauagcagaaccauuccagauccagcaaacagcacuuggguaaagaaguaucccauucuggaggagaagauccag<br>cuaccuacggauaaucuccugauggcauggcccacuccugaagagccugagccccugaucauccaugaaguccucuacca<br>caugaucccaguugucagacaaccauauuacuucaaaagaggccaaggauuccaaggcuacucuaccuccaagcaagaug<br>caauguauauugccaauccacaagcuacaggaacucucacagcugagaccagacaacuagugaaccuauacaaggugcua<br>gaaagcagagacccugacucaaaacuggccaaccugaccagccccuugacagucaccccagugaacuaccuuccuagcca<br>ugaaggcuauuuacccuccaacauagaagaucugucaccacaugaggcugacccaacugauucuuuugaccuggagcauc<br>aacauauuucucuuuccauuuuugcaucaaguucucuccgcccacucaucuucgguggugagcggcugacucuagaucgg<br>uuaaagaugggcuaugacucccucaugaguaaugaggcuugauacuagaaagccaacguaccucauuuuaucugcccagu<br>uccuacuccaaaggucugugacagugaagacaagccagcugucucuggauaaaguuagcuucaccauagguacuuaaguc<br>uuauggauaagguggcaauacaccaacacugauaucauauagaaaggaccccaagauagucaugcuc | |
| Wnt10a/Wingless-related MMTV integration site 10a U61969 | 3 | Sequence below. | 264 |
| | | ggcacgaguucacccucugcaugcguucccccucccccccucuccagcaaacacggcgcgccaguccaaagcggacucagug<br>gccucggggacgggagcaugccaccuccuguggugacgucacuugggguagaacccuuagacacuacaugggggggggg<br>guacagaacucccgagccaggacagucacucacucuucaggcgguggggcugggccagacaguaccgcccccaccgcgcc<br>cgccucgcacacccucggaagcgcaggcucgcagcgcggcgcugggguggggguugcgccccagaacuucggccuccag<br>uccccagcccgcugcaccuccuuacccucuagaggccccccuccccccuuacccucuagaggcaccaggaguugucgcaagg<br>ggcccuugggaaauucccuggaccccugugccaggaggugcccgguucgcccgcuccccauccacccccccgagggcggu<br>gcccgggggcgcugccccauggagcggggaggcgggcgccgucugcugcgggagcugugaccugaguaggagcugugugu<br>cgcagccgccccaccccugccgaucaugcgccggcgacccugguucgccagucccacugggcugugagcccccccacuccu<br>ggccugucacggcccgcgcgccaugggcagcgcccacccucgccccuggcugcggcucccacaagggccccagccgcggc<br>cugaguucugggcgcuccuguucuuccuacugcugcuggcugccgcugugcccaggucagcacccaacgacauccugggc<br>cuccgccuaccccccagagcccgugcucaacgccaacacagugugccugacauugcccggccugagccggcggcagaugga<br>ggugugugugcgucacccugacguggccgccucugcuauccagggcauccagaucgccauccaugagugccagcaucagu<br>uccgggaccagcgcuggaacugcuccagccuggagacucggaacaaagucccccuacgagagccccaucuucagccgaggu<br>uuucgagagagugcuuucgccuacgccauagcagcugccgggguggugcacgcaguguccaacgcgugcgcucuggguaa<br>acugaaggcuugcgguugcgacgccuccagacguggggacgaagaagcuuuccgcuggaagcugcaccgcuugcagcugg<br>acgcgcugcagcgcggaaagggcuugagccacggggucccugaacacccggccauacuuccugccagcccaggucugcag<br>gacuccugggaguggggguggcugcaguccggaugugggcuucggagaacgcuucucuaaggacuuucuggacucccgaga<br>gccucacagagacauccaugcucgaaugagacuccacaacaaccgugugggccggcaggcggugauggagaacaugcggc<br>guaagugcaaaugccacggcaccucaggcagcugccagcucaagaccugcuggcaggugacgccugaguuccgcacagua<br>ggggcgcugcugcgcaaccgcuuccaccgcgccacgcucauccggccgcacaaccgcaacgguggccagcuggagcccgg<br>ccccgcgggagcacccucgccagcaccgggcacuccagggcugcgccgcagggccagccacuccgaccuggucuacuuug<br>agaaaucucccgacuucugugagcgcgagccgcgccuggacucggcaggcacugugggccgccugugcaauaagagcagc<br>acgggucccgauggcugcggcagcaugugcuguggccgcggccacaacauucugcgccagacgcgcagcgagcgcugcca<br>cugccgguuccacuggugcugcuucguggucugcgaagaaugccgcaucaccgagugggucagcgucugcaagugagcag<br>acccaagcuccucugggucucaagaugguuguccucuuggugccuggcuucugccgcuagcggaucugagccaggcagc<br>aagcagcagccuuggcuccugagagagguggguuggcucuuacagccccgagggucuacaauacaccagacaguccagauc<br>ugauugacauuccuccgcucaccucuguagguuccccucuuucuguuccuagcucagacagcugggggugauaguggaga<br>cuguuccacacccuaggacagguacaccaaagcagcccagccuggcaugccuaccuccugucaucucuucuucccuuccc<br>caggagugauaggcaaugcacugaagcugaugggcaccggggaagaaaacuaaaaggcagaaauggccgucaucgggcug<br>aagugacucuaagggcuccagaccucugcuccugucuuucacuuaacagauauuuauuuuugcgcucucuuugagacacu<br>cucugggaaaaagaagcuccggagucuacaggcugauuaagggacauggacaauaaaccaguaaacacacaaaaaaaaaa<br>aaaaaaaa | |
| Ifngr2/Inter-feron-gamma receptor precursor M28233 | 3 | Sequence below. | 265 |
| | | gaauuccgggccgcuugcacuuggcgacuagucugcggcggacgugacgccaaggccacgggcagcgcggguccccuguc<br>agaggugucccucgcgcaggaaugggcccgcaggcggcagcuggcaggaugauucugcugguggucccugaugcugucugc<br>gaaggucgggaguggagcuuugacgagcaccgaggauccugagccucccucggugccuguaccgacgaauguucuaauua<br>agucuuauaacuugaacccugucguaugcugggaauaccagaacaugucacagacuccuauuuuuacuguacagguaaag<br>guguauucggguuccuggacugauuccugcaccaacauuucugaucauuguuguaauaucuaugaacaaauuauguaucc<br>ugauguaucugccugggccagaguuaaagcuaagguuggacaaaaagaaucugacuaugcacggucaaaagaguuccuua<br>ugugccuaaagggaaaggucgggccccccuggccuggagaucaggaggaagaaggaagaacagcucuccguccucguauuu<br>cacccugaagucguugugaauggagagagccagggaaccauguuuggugacgggagcaccuguuacacauucgacuauac<br>uguguauguggagcauaaccggaguggggagauccuacauacgaaacauacggucgaaaaagaagaguguaaugagacuc<br>ugugugaguuaaacaucucaguauccacacuggauuccagauauuguauuucaguagacggaaucucaucuuucuggcaa<br>guuagaacagaaaaaucgaaagacgucuguaucccuccuuuccaugaugacagaaaggauucaauuuggauucuggugguu<br>ugcuccucuuaccgucuuuacaguaguuauccugguauuugcguauugguauacuaagaagaauucauucaagagaaaaa<br>gcauaauguuaccuaaguccuugcucucugugguaaaaagugccacguuagagacaaaaccugaaucgaaguauucacuu<br>gucacaccgcaccagccagcuguccuagagagugagacggugaucugugaagagccccuguccacagugacagcuccaga | |

TABLE 5-continued

| Gene Name/Protein | Fold Decr | Sequence | SEQ ID No. |
|---|---|---|---|
| | | cagccccgaagcagcagaacaggaagaacuuucaaaagaaacaaaggcucuggaggcuggaggaagcacgucugccauga ccccagacagcccuccaacuccgacacaaagacgcagcuuuucccuguuaaguaguaaccagucaggcccuuguagccuc accgccuaucacucccgaaacggcucugacaguggccucgugggaucgggcagcuccauaucggacuuggaaucucuccc aaaacaacaacucagaaacaaagauggcagagcacgacccuccacccgugagaaaggcccccauggccuccgguuaugac aaaccgcacauguugguggacgugcuuguggauguugggggaaggagucucucaugggguauagacucacaggagaggc ccaggagcuguccuaaggucucccgaggccugcugguggaaagaaacugaccuuuuaggcaguuuuucugcauugauuu caugaaagaagcuauacauuagcuaauacuaaccacauagaauaucagacuuagauacgugaauaaggauccugugggca cugcuggguccacucugcaaaugccaagacuaucaaaggaacguauugucgcuucuggcuccuucccagguggcuagca ucugugaguuugccucggcuagccuugcuuccuacagccgccacugcuccucccacccugaucaucucacaggacagggug gaccggguuuuuuuuuuuuucacacaccuuuguauauguaaguucauguauauaauauguuuacauguuucacuuuga acugaaagcuacucaaagccagccguaagucuaugguagaaugugauggaacauguugguggaagcuuguacaauagaac acauuggugggagcuuguacauacuuuuuuauggagcauuacuuacgauuuuuuaaguaaaauguuuugaaaccaaaaaa aaaaaaaggaauuc | |
| Fgfbp1/Fibroblast growth factor binding protein 1 AF065441 | 3 | augagacuccacagccucauccugcucuccuuccuucuccuggcuacu caggcguucucagaaaaggucagaaagagagccaagaacgcaccacac agcacagcggaggagggguagaggguucagcucccucguuagggaag gcccagaauaagcagagaagcaggacaucuaaaucucugacgcauggc aaguuugucaccaaagaccaagccacaugcagaugggcugugacugag gaggagcagggcaucagccugaagguccagugcacacaagccgaucag gaguuuucuuguguuuuugcuggugacccaacugacugccuuaaacac gacaaagaccagaucuacuggaaacagguugcccgcacgcugcgcaaa cagaaaaauaucugcaggaacgccaagagugucuugaagaccagagug ugcagaaagagauuuccagagucuaaccucaagcuggugaaccccaac gcacguggaaacacgaagcccaggaaggagaaagcagaggucuccgca agggagcacaacaagguccaagaagcugucuccacggagccaaacagg gucaaagaagacaucacacucaauccagcugcgacccagaccauggcc auuagagauccagagugucuagaggauccagaugugcucaaccagagg aagaccgcccuggaguucugugggaaucuuggagcuccauuugcacau ucuuccucaacauguuacaggcgacaucaugcuaa | 266 |
| | | Transcription Factors and Releated Genes | |
| Klf5/Kruppel-like factor 5 AA611766 | 5 | | 267 |
| Gata3/GATA binding protein 3 X55123 | 4 | Sequence below. | 268 |
| | | gcuaaacuaucccgcaaagauuuuucuuuccucccuaaacccuccuuuuugcucuccuuuucuauacccuuaacugcaaa caaaccauuaaacgaccccucuccugggccuccgacggcaggaguccgcggaccucccaggccgacagcccucccucuac ccgcgagguuccgggccgggcgagagggcgcgagcacagccgaggacauggaggugacugcggaccagccgcgcugggug agccaccaucaccccgcgguccucaacggucagcacccagacacgcaccacccgggccucggccauucguacauggaagc ucaguauccgcugacggaagagguggacguacuuuuuaacaucgauggucaaggcaaccacgucccguccuacuacggaa acuccgucagggcuacggugcagagguauccuccgacccaccacgggagccagguaugccgcccgccucugcugcacgga ucucugcccuggcuggauggcggcaaagcccugagcagccaccacaccgccucgcccuggaaccucagccccuucuccaa gacguccauccaccacggcucuccggggccucuguccguuuacccuccggcuucauccucuucucuggcggccggccacu ccaguccucaucucuucaccuucccgcccaccccgccgaaagacgucucccccagacccgucgcuguccaccccgggaucc gccgggucggccaggcaagaugagaaagagugccucaaguaucaggugcagcugccagauagcaugaagcuggagacguc ucacucucgaggcagcaugaccacccugggugggccucauccucagcccaccaccccauuaccaccuauccgcccuaug ugcccgaguacagcucuggacucuucccacccagcagccugcugggaggauccccuaccggguucggauguaagucgagg cccaaggcacgauccagcacagaaggcagggagugugugaacugcggggcaaccucuaccccacuguggcggcgagaugg uaccgggcacuaccuuugcaaugccugcggacucuaccauaaaaugaaugggcagaaccggcccccuuaucaagcccaagc gaaggcugucggcagcaaggagagcagggacauccugcgcgaacugucagaccaccaccaccacccucuggaggaggaac gcuaauggggacccggucugcaaugccugugggcuguacuacaagcuucauaauauuaacagaccccugacuaugaagaa agaaggcauccagacccgaaaccggaagaugucuagcaaaucgaaaaagugcaaaaaggugcaugacgcgcuggaggacu uccccaagagcagcuccuucaacccggccgcucucuccagacacaugucaucccugagccacaucucucccuucagccac uccagccacaugcugaccacaccgacgcccaugcauccgcccuccggccucuccuucggaccucaccacccuuccagcau ggucaccgccaugguuagagaggcagagcccugcuccacaugcgugaggagucuccaagugugcgaagaguucccuccga ccccuucuacuugcguuuuucgcaggagcaguaucaugaagcccgaaagcgacagaucuguguuuuugaaggcagaaagc aaaauguuugcuucuuuuuucaaaggagcucgaggugguguucugcauuccaaccacugaauccggaucccauuugugaau aagccauucagacucauauucccuauuuaacagggucucuagugcugugaaaaaaauauugcugaacauugcauauaacu uauauuguaagaaauacuguacauuugaggaagacuuuauuguaccuggauagcuguaagaaaggcaugaaggacgccaa gaguuuuaaggaauauaggggnnuuaaaguauggagauacagaagaaaccacuaagucugauguccaaaugggcacacug ucaguuuuguuucccuucaguuguuugaugcauuuaaaaaaaaaaaaaaagaaagaa | |
| Stimulated by retinoic acid 14, basic-helix-loop-helix protein Y07836 | 3 | Sequence below. | 269 |
| | | caaccaccuccuaccugccugcccaaagcuccagggcuggagcacggagaccugucagggauggauuuugcccacaugua ccaaguguacaaguccaggcggggaauaaaacggagcgaagacagcaaggaaacuuacaaacugccgcaccggcugauug agaaaaagagacgugaccggauuaacgagugcauugcccagcugaaggaucuccuacccgaacaucucaaacuuacuacu uugggucacuuggaaaaagcagugguucuggagcuuacguugaagcacgugaaagcauugacaaaucuaauugaucagca | |

TABLE 5-continued

| Gene Name/Protein | Fold Decr | Sequence | SEQ ID No. |
|---|---|---|---|
| | | gcagcagaaaaucauugcccugcagagcgguuuacaagcuggugauuugucgggaagaaaucucgaggcagggcaagaaa<br>uguucugcucagguuuccagacuugugcccgugagguacuucaguaccuggcgaagcaugagaacacucgggaccugaaa<br>ucuucccagcucgucacucaucuccaucguguggucucggagcugcugcagggugguguucccaggaaaccauuggacuc<br>ggcucccaaagccgucgacuugaaagagaagcccagcuuccuagccaagggaucagaaggcccagggaaaaacugugugc<br>cagucauccagcggacuuuugcucccucggguggggagcagagcggcagugacacggacacagacaguggcuauggaggu<br>gaauuggagaaaggggacuugcgcagugaacagccguacuucaaaagcgaccauggacgcagguucgccgugggagaacg<br>ugucagcacaauuaagcaagaauccgaagagcccccaccacaaagagccgaaugcagcucucagaagaggaaggccacu<br>ucgcgggcagugaucugaugguucccauuucuugggccacacccacaucagccucuuuuugccuucccuucuaucuc<br>aucccaccaucggccacugccuaccugccuaugcuggagaaaugcugguaccccaccucugugccaguguuauacccagg<br>ccucaacaccucagcugcagcccucuccagcuucaugaacccagacaagauaccgacucccuugcuucugccccagagac<br>ucccuucuccuuuggcacauucgucccuugacucuucggccuugcuccaggcuuugaagcagaucccuccuuuaaacuua<br>gaaaccaaagacuaaacucuggagggaucuccugcugccuugcuuucuuucccucccuaauuccaaaaaccacgaagguuu<br>cccugagugcagagagaucagcccacccugcagacccacagagaagauucagagugugugugagagugagugagugugcg<br>ugcgugcgugcuuguauguauguuuguauauguaggacaauaaguuccuucugacacaagggagacacgagaaggauagc<br>cugacaucagaugacagacuggaggacuguagcacaucucugggcguuucccuacccagagaagagcc | |
| Mki67/antigen identified by monoclonal antibody Ki67 X82786 | 4 | Sequence below. | 270 |
| | | agucaccgacguuguauaacgacggccagugaauuguaauacgacucacuauagggcgaauuggguaccggcccccccu<br>cgaggucgacgguaucgauaagcuugauaucgaauucucgnccgcgugcgggucuggucggggcggagcgaaggccgcgg<br>guggccguggucgguccuccgcggcuaaggagccgagggcuccgacgcgggcugcgcccggugagcggcggccagagcua<br>acuugcgcugacuggaccagcugaggagcggcccggcggggcgacugcgagcuucaccgagaggcuucuccgcccugguc<br>cgcagucccgacggccgggcggaccauggcguccucggcucaccuggucaccaucaagcggagcggcgaugacggcgcac<br>acuucccgcugagccucagcuccugccuguuuggaaggaguauugaaugugacauucguauccagcugccuguagugucu<br>caaagacauugcccaauuguaguccaagagcaagaggcgauauuauauaauuucaguucuaccaauccaacucaaguaaa<br>cgggguuacuauagaugagccugugaggcugagacauggagacauaauaaccaucauugaccgcuccuuuagguaugaag<br>auggaaaucaugaggauggaagcaaaccaacagaauuuccaggaaagucccuuggaaaggaaccaucaaggcgagccuca<br>agagauagcuucugugcugacccugauggggaaggucaagauaccaaagcuucaaaaaugacugcuucaagaagaucuuu<br>uguguaugccaagggccuuucugcagauagcccugccucagauggcucaaagaacaguguuagccaagacucaucagggc<br>auguagaacagcacacuggcagaaacauaguagagcccacuucuggggaucucuuuuaagaaguccaggucuacaggga<br>gcaguuacagggaaccgaagucuucuuccuacacagagccuuagcaauagcaacgaaaaggaaucucccuuugagaaacu<br>uuaucaaucaaugaaggaagaguuggauguaaaaucccagaaaucuuguaggaaaucagaaccccaaccugaccgugcag<br>cagaggaaucgcgggagacacagcuauuggugucaggcagggcaagagcaaagucuaguggaagcaccccuguuacugca<br>gccucuucacccaaaguaggaaagaucuggacugagagauggcgcgguggaauggugccuguccagacuuccacagagac<br>agcuaaaaugaagaccccugugcggcauucacagcaacuuaaggaugaagacucucguguuacuggcagacgacauucug<br>ugaaucuggaugaagguggaagugcccaggcaguccauaaaacagucacuccugggaaacuggcgacuagaaaccaaacu<br>ccgguggaggcuggggauguuggcagccccgcugauacaccagaacauuccucuuccccccagagaaguauuccugcaaa<br>gguagaggcuccaucugcagagacacaaaaucggcucucuuuaacucagcgccuuguuccaggugaaaagaaaacuccca<br>aggguuccuucagcaagccugagaaacuggccacagccgccgaacagacuugcucuggccuaccuggucuuaguuccguu<br>gauaucagcaacuuuggugauuccauuaacaagagugagggaaugccuaugaagagaagacguguauccuuugguggaca<br>ucuaagaccugaauuauuugaugaaaacuugccuccuaauacaccacugaaaagaggagaaacgccaaccaagaggaagu<br>cucuuggcacucacagcccagcuguccucaagacaaucaucaaggaacggccccagucuccagggaaacaagagucuccu<br>gggauaacgccaccgaggacaaaugaucaaagacgcagaucaggcaggacuuccaguggaagcaauuucuuaugugagac<br>agacauucccaagaaagcaggcaggaagagcgguaaccugccugcgaagagagcauccaucagccggagucagcauggca<br>uucuacagaugauuugcuccaaaaggcgaaguggagcuucugaagccaacuugauuguugcaaaaucaugggcugauguu<br>guaaaacuuggcgugaaacaaacacaaacgaaaguugcgaaacaugucccuccaaagcagacgagcaagagacaaagaag<br>acccagcacuccaaagaaacccacaagcaaucuucacaaucaauuuacuacaggccaugcaaacucucccuguaccauug<br>uaguagguagagcgcagauugaaaaaguaagugugccugcccgacccuacaaaaugcugaauaacuugaugcuaaaccga<br>aaaguggacuucagugaagaucugucaggacuaacugaaauguucaagacuccagugaaggagaagcagcagcagaugag<br>ugauacaggcuccguacuuuccaauucagcgaauuugucugaaagacaauugcaaguaacuaauucaggagacauaccug<br>agcccaucaccacagagauuuugggagaaaaagugcuauccaguacucggaaugcagcaaagcagcagucugauagauau<br>ucugcaaguccuaccuuaagacggcggagcaucaaacaugaaaacacagugcaaacuccuaagaauguccauaacauuac<br>ugaccuugagaagaagacuccggucucugagacagagccccugaagacugcaucgagugugagcaaguuaagaagaucua<br>gagagcucagacauacccuuguggaaacuaugaaugaaaaaacagaagcaguccuugcugagaacaccacagcaagacau<br>uuaaggggggacauuucgagaacaaaaaguagaucaacaggugcaggacaaugaaaacgcuccucaaagaugcaaggaaag<br>uggugaauuaagugaagguucagaaaagacaucagcuaggagaucaagugccaggaagcagaagccgacaaaagacuuac<br>uaggaagucagauggucacccaaacagcagacuaugcugaggaacuacuuagucaaggacaaggaaccauacaaaaccua<br>gaggaauccaugcacaugcaaaacacaucaauaagugaggaucaaggaauuacagaaaagaaagugaacauaauaguaua<br>ugcaaccaaagagaagcacucgccaaagaccccuggcaaaaaggcacaaccucuagaagggccagcuggucucaaggaac<br>acuuugaaacaccaaaccccaaagauaaaccuauaacggaagacagaacuagaguccuuugcaaaucaccacaagucaca<br>acagagaauaucacaacaaacacaaagccacagacuagcacaucugggaagaaaguagacaugaaggaagaaagcucugc<br>cuugacaaaacguauacauaugccaggggaauccaggcauaaucccaaaauuuuaaaacuugagugugaggauaucaaag<br>cuuugaagcaaucugaaaaugaaaugcugaccucaacaguaaauggaagcaagaggacuuuaggaaaaucuaaaaaaaag<br>gcucagccccuggaagaccugacuuguuuccaggaacucuuuauaucaccaguuccuacuaacauaaucaaaaaaauucc<br>cagcaaaucuccacacacaaccagucagaaccccagcgagcacaaagagacucuccaagacaggucucaguaaaguggau<br>gugagacaagaaccuucaacacuugggaaaagaacgaagucaccaggcagagccccaggcacaccagcaccagugcagga<br>agaaaaugacugcacagccuacauggaaacuccaaagcagaaacuggagucuauagaaaauuuaacagggcuuaggaaac<br>aguccagaacaccuaaagacaucacugguuuccaggauaguuuccaaauaccagaucaugcuaauggcccauuagugguu<br>gucaaaaccaaaaaaauguucuuuaauucuccacaaccagaaagugccauaacccgaaagagcagagagagacagucuag<br>ggcaaguauaaguaaaauagauguuaaagaagaacuuuuagaaucagaggaacaccuacaauuaggagaagguguagaca<br>cauuucagguauccaccaacaaagucauuagaucaucuaggaaaccugcaaagcguaaacuggauucaacagcugguaug<br>ccuaacagcaagaggaugcgcuguucuucaaaggauaacacaccaugccuagaagaccugaauggcuuccaagagcucuu<br>ccaaaugccaggcuaugcuaaugacucuuugaccacuggaaucucaacaaugcuugcuagaucaccacaauuaggaccag<br>uuagaacccaaaucaacaaaaagagucugcccaagaucaucuugagaaaaauggaugugacagaagaaauuucaggucuc | |

TABLE 5-continued

| Gene Name/Protein | Fold Decr | Sequence | SEQ ID No. |
|---|---|---|---|
| | | uggaagcagucacugggcagaguccacaccacacaagagcaggaggauaaugcaaucaaagcaauuauggagauuccaaa<br>ggaaacacugcagacugcagcagauggaacuaggcuuaccagacagccacaaacaccuaaggaaaaaguucaaccgcugg<br>aagaucacagugucuuccaagaacucuuccaaacaucacgcuacuguucugauccauuaauugguaacaaacaaacaaga<br>auguccuugagaucuccacaaccaggauuuguuagaacuccacgaaccucaaagagacuggcuaagacaaguguugggaa<br>uauugcugugagagaaaagaucucuccagugagucugccacagugugcuacaggggagguuguacacauacccauagggc<br>cagaagaugacacagagaacaaaggugugaaggaauccacaccucagacacuggacucaucagcaagucgaacugucagc<br>aagaggcagcaaggggcacaugaggaaaggccucaguucucaggagacuuauuucaucccccaagagcucuuucaaacacc<br>agccaguggcaaagacccaguaacuguugaugaaacuacaaaaauagcucugcagucuccacaaccaggacauaucauaa<br>acccagcaagcaugaagagacaguccaacaugagucucaggaaagacaugagagaauuuuccauacuugaaaaacaaaca<br>cagucacgaggcagagacgcaggcacaccagcaccaaugcaggaagaaaauggcaccacagccauuauggaaacaccaaa<br>gcagaaacuggauuucauaggaaauucaacaggacauaagaggaggccucggacacccaaaaacagggcucagccccuag<br>aagaccuggauggcuuccaagaacucuuucaaacaccagcuggugccagugacccugugaguguugaagaaagugcaaag<br>auaucuuuggcaucuucacaagcagaaccagucagaaccccagcaaguacaaagagacgcuccaagacaggucucaguaa<br>aguggaugugagacaagaaccuucaacacuugggaaaagaaugaagucacuaggcagagccccaggcacaccagcaccag<br>ugcaggaagaaaaugacagcacagccuucauggaaacuccaaagcagaaacuggauuucacaggaaauucaucaggacau<br>aagaggaggccacagacaccuaagaucagggcucagccccuagaagaccuggauggcuuccaagaacucuuccaaacacc<br>agcuggugccaaugacucagugacuguugaggaaaguguaaagaugucuuuggaaucuucacaagcagaaccagucaaaa<br>ccccggcaagcacaaagagacucuccaagacaggucucaguaagguggaugugagagaagacccuucaauacuugagaaa<br>aaaacaaagucaccaggcacaccagcaccagugcaggaagaaaaugacugcacagccuucauggaaacuccaaagcagaa<br>acuggauuucacaggaaauucaucaggacauaagaggaggccacggacaccuaagaucagagcucagccccuagaagacc<br>uggauggcuuccaagaacucuuccaaacaccagcuggugcuagugacucagugacuguugaggaaagugcaaagaugucu<br>uuggaaucuucacaagcaaaaccagucaaaaccccggcaagcacaaagagacucuccaagacaggucucaguaaggugga<br>ugugagagaagacccuucaacacuugggaaaaaaacaaagucaccaggcagagccccaggcacaccagcaccagugcagg<br>aagaaaaugacagcacagccuucauggaaacuccaaagcagaaacuggauuuugcagagaauucaucagggaguaagaga<br>aggucacgaacaucuaagaacaggucucagccccuagaagaccuggauggcuuccaagaacucuuccaaacaccagcugg<br>ugccaguaacccugugaguguugaagaaagugcaaagauaucuuuggaaucuucacaagcagaaccagucagaacccggg<br>caagcacaaagagacuuuccaagacaggucucaauaagauggaugugagagaagggcacucuccgcucaguaagucaagc<br>ugugcaucacagaaagucaugcaaacccucacacuuggagaagaucauggcagagagaccaaagaugggaagguauuguu<br>agcucagaaauuggaaccagcaauauauguuacucguggcaagaggcagcaaaggucauguaagaaaaggucccaguccc<br>cagaagaccucucugguguucaggaggucuuccaaacaucaggccauaacaaggauucagugacaguggacaaucuugca<br>aaacugcccagcucgucuccaccacuagagccaacagacacuucaguaaccucacggagacaggccagaacuggucugag<br>gaaaguucacgugaaaaugaacuuucaggaggcauaaugcauccacaaauaucaggggaaauuguggacuuaccuagaga<br>accagaaggugaaggcaaagucauuaaaacaaggaagcaaucuguaaaacggaaauuggacacagaagucaaugugccuc<br>gcaguaagaggcaaagaauuacaagagcagaaaagacccuagaggaucugccuggcuuccaagagcucugccaagcucca<br>agcuugguaauggacucaguuauuguugagaaaaccccaaagaugcccgacaaaucuccagaaccuguggauacaacuuc<br>agagacacaggcaagaagaagacucaggagacugguuguuacugaagagcccauaccacaaagaaagacuacaagaguug<br>uaaggcaaaccagaaacacacagaaagagcccauaagugacaaucaagguauggaagaguuuaaggaaucuucaguacag<br>aaacaagacccaaguguaaguuuaacuggcaggaggaaccaaccaaggacaguuaaggagaaaacccaacccuuagaaga<br>acucaccaguuuccaagaggaaacugccaaaagaauaucuuccaaaucuccacaaccggaagagaaggaaaccuuagcag<br>guuuaaagaggcagcucagaauacaacuaaucaacgaugguguaaaagaagagcccacagcacagagaaagcaaccaucc<br>agggaaaccaggaacacacucaaagagccuguaggugacaguauaaauguugaagagguuaagaagucuacaaagcagaa<br>aauugauccaguagcaagugugccugucagcaagaggccacggagguacccaaggaaaaggcacaggcccuagaauugg<br>cuggucucaaaggaccaauccaaacccuaggccacacugaugaaucagcaagugauaaaggacccacacagaugcccugu<br>aauucucuacaaccagagcaaguugacagcuuccaaagcucaccaaggcgacccaggacaagacgugggaaaguagaggc<br>agaugaagagccuucagcaguaagaaagacaguaucaacaucaaggcaaacuaugcgaucccgcaaggucccugaaauug<br>guaacaaugguacccaaguuucaaaggccuccauaaagcagacauuagauacaguagccaaaguaacuggcagcaggagg<br>cagcuaaggacacauaaaggaugggguucaacccucuugaaguuguuaggugacuccaaagaaauaacccaaauaucaga<br>ucacucugagaaacuagcacaugacaccaguauccuuaagagcacucaacagcaaaaagccagacucaguaaaaccucug<br>agaacaugcagaagagugcugagggccucuaaagaggucccccaaggaaguguugguggacaccagagaccaugcaacauu<br>acaaagcaaaagcaacccuuugcugucccccgaagaggaagucugcaagagauggaagcauugugagaaccagggcuuugc<br>gcucuuuagcaccaaagcaggaagcaacagaugagaagccuguaccugagaaaaaaagggcugcuuccagcaagagguau<br>guaucaccugagccugugaagaugaaacaccugaaaaucgugucaaacaaacuugaaucuguggaagagcagguuagcac<br>uguuaugaaaacagaagaaauggaagccaaaagagaaaauccugucacuccagaucagaacucuagguaccgaaagaaaa<br>ccaauguaaaacagccaaggcccaaguuugaugcaucugcagagaaugucgggauaaagaaaaacgagaagacuaugaag<br>acugccucccaggagacagagcugcagaauccagaugauggagccaagaaaucuacaucucggggccaagucagugggaa<br>aagaacaugcuugaggucuagaggaacgacugagaugccccagccuugugaagcagaagagaaacaagcaaaccagcug<br>cagaaaucuugauaaagccucaggaagagaaaggagucucuggagagucugauguuagguguuugagguccagaaaaacu<br>agagucgcuuuggacagugaaccuaagccaaggguaacucguggaaccaagaaagaugcaaaaacucugaaggaggauga<br>agacauuguaugcaccaagaaguuaagaacaagaaguuaagaacaagaaguuaccagaaaagugaaacuauguagcaaag<br>acauuuaagaaggaaaaguaaauuugacuuagugauaaguuccagugugguuuucaccuccaguguaaagaugaacugua<br>aauacuacugcuacugccugaguuuaaggaaggaagcuuugagcuuuccuggucauacucucuucagacgccaauggagg<br>ucaugaggaagaucaccagggaucucagcgcaauuacaguuuaggggugagcaggcagaaauguggcccucuguccuauc<br>caauaaagcucugaaauucgcugccaaaa | |
| Cks2/CDC28 protein kinase regulatory subunit 2, sim to cdk regulatory subunit 2 AA681998 | 4 | gacguagagccccuugcgcccgguuuccugaucccgcuuacuccucug<br>cgcgccggcaggauggcccacaagcagaucuacuacucagacaaguac<br>uucgaugagcacuacgaguaccggcaugucauguuacccagagaacuc<br>ucuaaacaaguacccaaaacucaucugauguccgaagaggaguggagg<br>agacuuggugucccaacagagucuaggaugggguucauuacaugauucau<br>gagccagaaccgcauauucuucucuuuagacgaccucuuccaaaagaa<br>caacaaaaaugaagugcagcugggaucaucuaaucuuuuucaaauuua<br>auguauauguguauauaagguaguauucagugaauacuugaaaagugu<br>acaaaccuuucauccauaccugugcaugcgcuguauucuucacagcaa<br>cagagcucagucaaaugcaacugcaaguagg | 271 |
| Ccng2/Cyclin G2 U95826 | 3 | Sequence below. | 272 |

TABLE 5-continued

| Gene Name/Protein | Fold Decr | Sequence | SEQ ID No. |
|---|---|---|---|
| | | cuacccuagacaaucacggcuuagccggcgcgcggagucgaucgucucggucgcuagagcuguccugagcucgaacgguc<br>cgacgcccccgccgcgccgguccgugacgccggggccgacacgaugaaggauuuggggccaagcacuuggcagguggcg<br>aaggggguucagcuuuucggauuguugaacuucuaccuggaacaagaacagagauaccaaccucgggaaaaagggcugauc<br>uugauggaggcuaccccggagaaugauaacacuuuguguucaagacugagaaaugccaaaguggaagauuuaagaaguuu<br>aacuaacuucuuuggaucuggcacugaaacuuucguucuggcugucaauauuuggauagauucuuggcccuuaugaagg<br>ugaaaccgaaacaccuguccugcauuggcgucugcugcuuuuugcuggccgccaggcuggcggaagaagaaggugacguu<br>ccccccacgcacgacgugauccgcaucagucaguguaaaugcacagcgucugacauuaaacgcauggagaaaaucaucuc<br>agagaaacugcacuaugagcuggaagcuaccacugccuuaaacuuuuugcacuuguaccacgcgauuguauuuugucaca<br>cuucagaaaggaaggagauucucagccucgauaaacucgaagcgcagcugaaagcuugcaacugccgaguugucuucucc<br>aaagcaagaccaucuguauuagcucugugccuucucaauuuggaaauagaaacgauaaaauccguggaacugcuggaaau<br>ucucuugcuuguuaaaaaacauuugaagcucagcgacacugaauucuuuuacuggagggaacugguuucuaaaugucuag<br>cagaguauucuucgccucgcugcugcaagccugaucugaagaagcugguauggauuguuucgcgacgcacugcgcagaac<br>cuccacagcagcuacuacaguguuccugagcugcccacuaucccagagggggguugcuuugacggaagugaaagugagga<br>cucuggugaagacaugaguuguggagaggagagucucagcagcuccccacccagcgaucaggagugcaccuucuucuuug<br>acuuccaaguggcucagacacugugcuuuccaccauagaggaaucugacauuguucugugucagggaauuuauaagugug<br>uguaccuagguuucaaagcaauaaacuuggggguugaauaggguaguuuuccuagguuuccagcccccgucuagucagg | |
| Prc1/Protein regulator of cytokinesis 1 DNA segment, Chr 7 AA856349 | 3 | aacuaccuugggcagguucuauuaacugcaccuaacucagacgugagu<br>aggacagaaggaagcugucccgggcgaacugaggucacaaagacuugc<br>uuuugauucaagagagaccuuaaaggcuaguuaugauaguuaaguaca<br>aguuuuaacaucugguagcuaacuuuuuuucucuaccccguaauucua<br>cuaugacugcucuucuagagguccugaguucaaaucccagcaaccaca<br>ugguggcucacaaccaucuauaaugggaucugaugcccucuucuggug<br>ugc | 273 |

Thus, the transcripts identified in this Example, the proteins they encode, and the pathways in which the proteins participate, contribute significantly to induction of epidermal cells to differentiate into HF stem cells. Activation of the transcripts, proteins, and pathways depicted in Table 4 is thus a method for enhancing EDIHN. In addition, inhibition of the transcripts, proteins, and pathways depicted in Table 4 is thus a method for preventing EDIHN and eliminating hair follicles. In addition, inhibition of the transcripts, proteins, and pathways depicted in Table 5 is a method for enhancing EDIHN. In addition, activation of the transcripts, proteins, and pathways depicted in Table 5 is thus a method for enhancing EDIHN.

Example 10

Expression of Wnt-1 Inhibitors During the First Nine Days after Wounding Causes Pigmentation of New HF

Materials and Experimental Methods

In this Example, doubly transgenic mice expressing both tetO-Dkk1 and K5-rtTA were utilized. When these mice are fed chow formulated with 1 g/kg doxycycline (BioServ, Laurel, Md.), they express Dkk1, under the control of the K5 promoter, in the basal epidermis. The control mice also received doxycycline, but they were K5-rtTA negative and thus did not express Dkk1.

Results

Figure 23A:
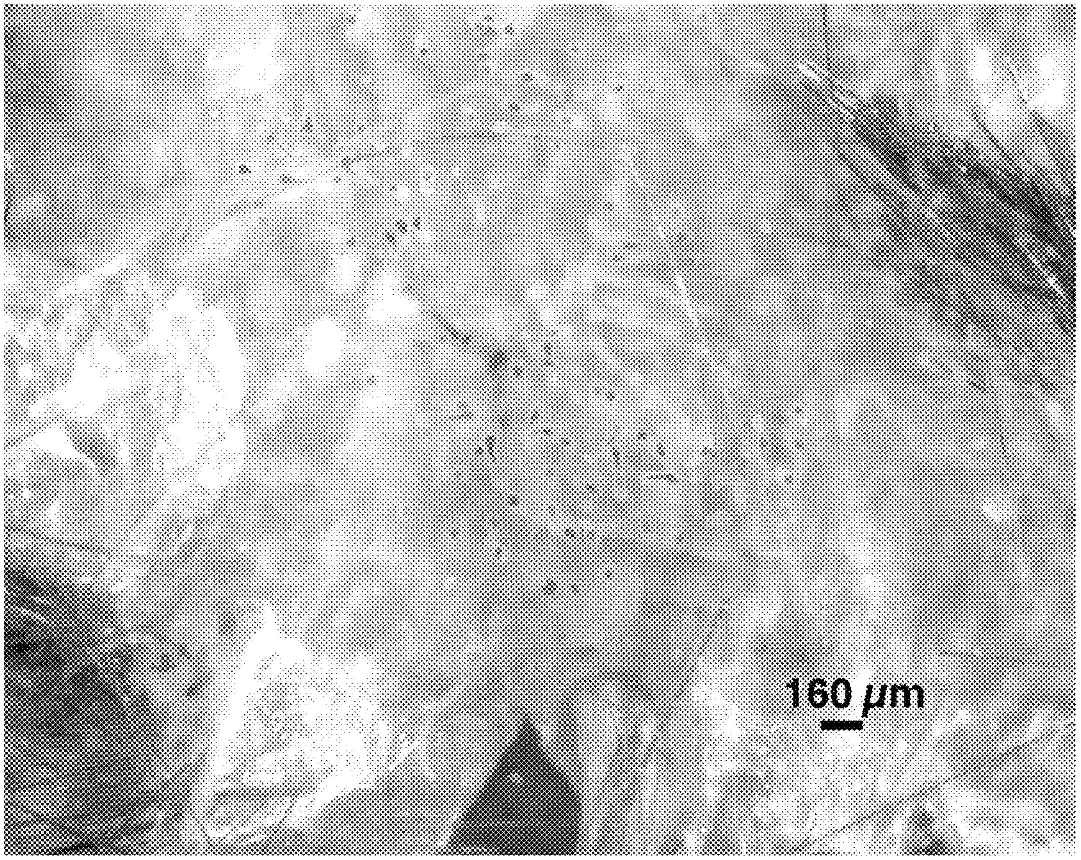
FIG. 23. Pigmented hair follicle neogenesis observed in the skin of Dkk1-expressing mice following EDIHN A. 3.2× magnification. B. 8× magnification.
Figure 23B:
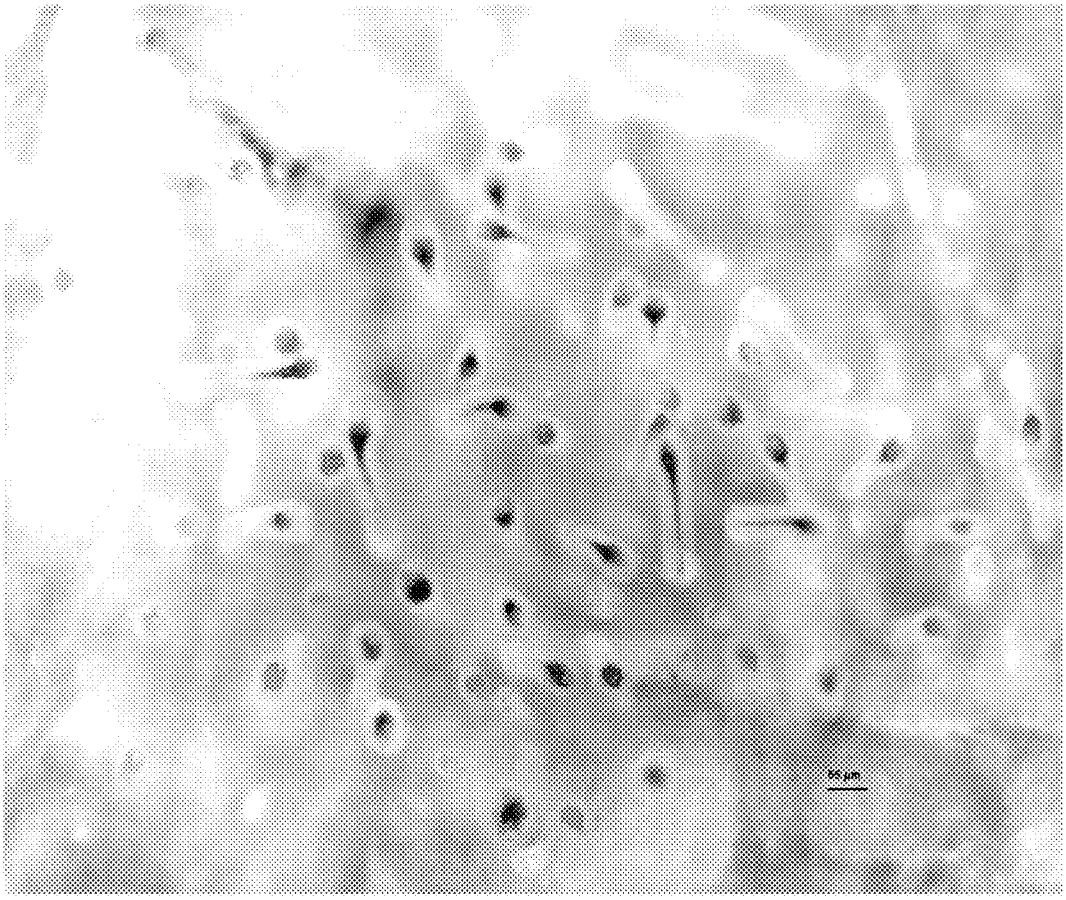
Figure 24:
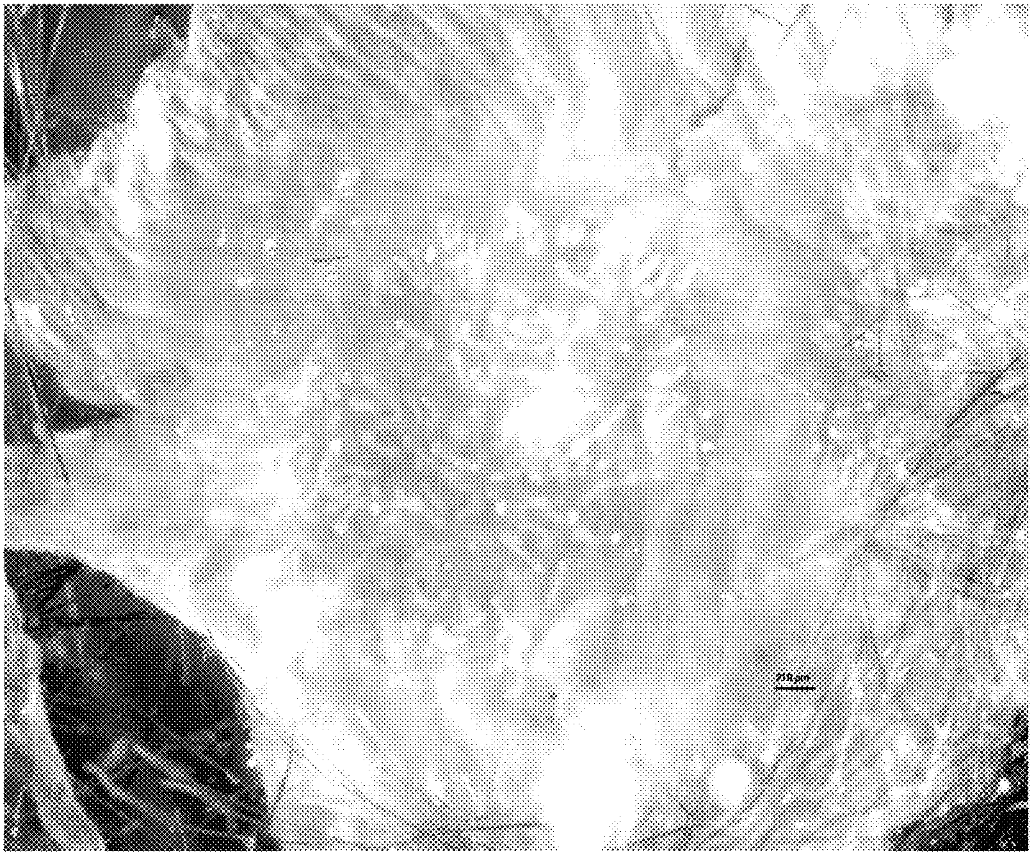
FIG. 24. Control mice lacked pigmented HF.
Figure 25A:
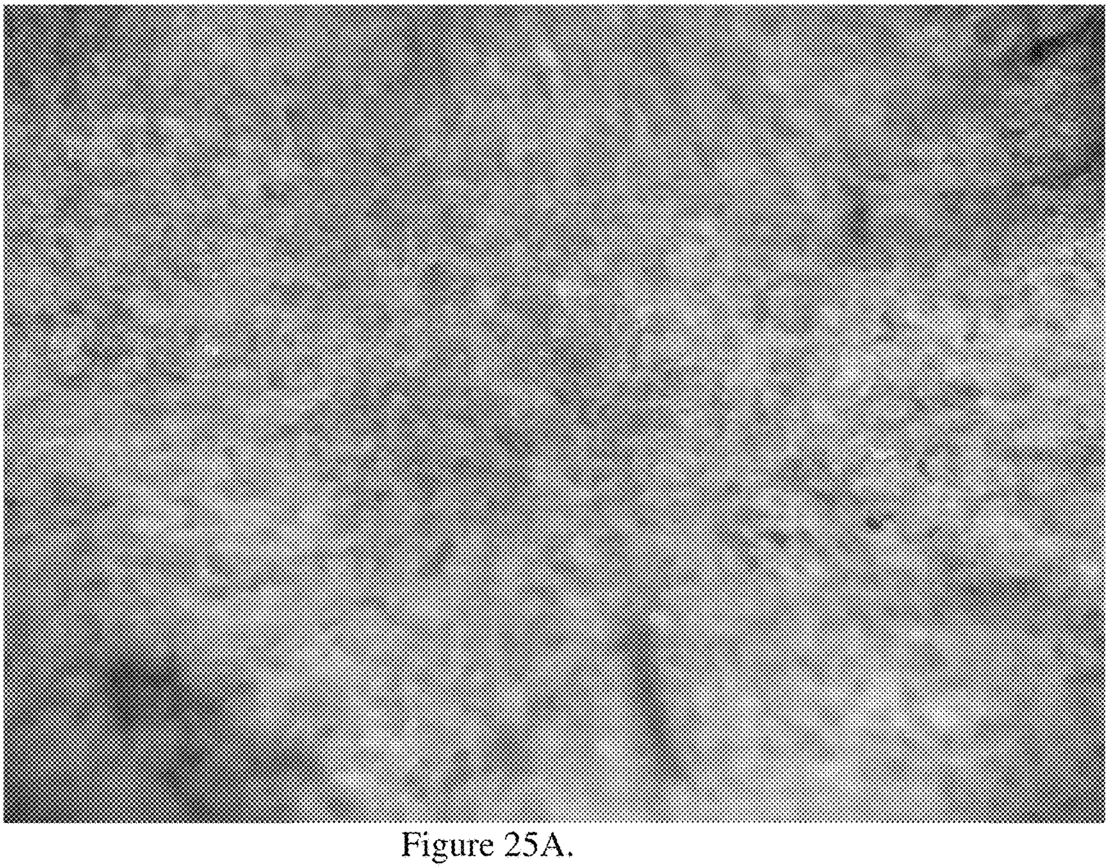
FIG. 25. EGF inhibits HF formation by EDIHN. A. K17 staining of wounded skin of representative mouse treated with EGF. Magnification is 4×. B. High magnification view (10×) of skin depicted in (A). C. K17 staining of wounded skin of representative control mouse that received no EGF after wounding. Magnification is 4×. D. Higher magnification view (10×) of skin depicted in (D).
Figure 25B:
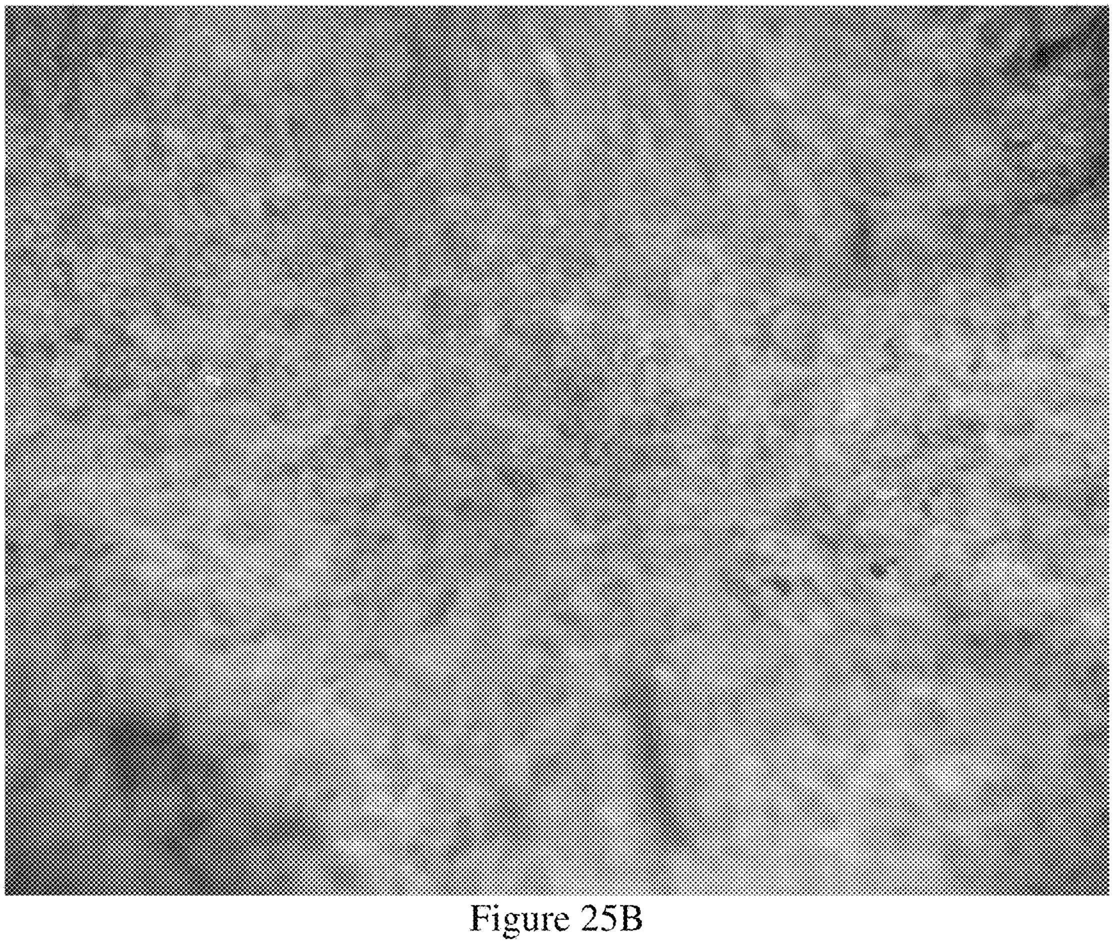
Figure 25C:
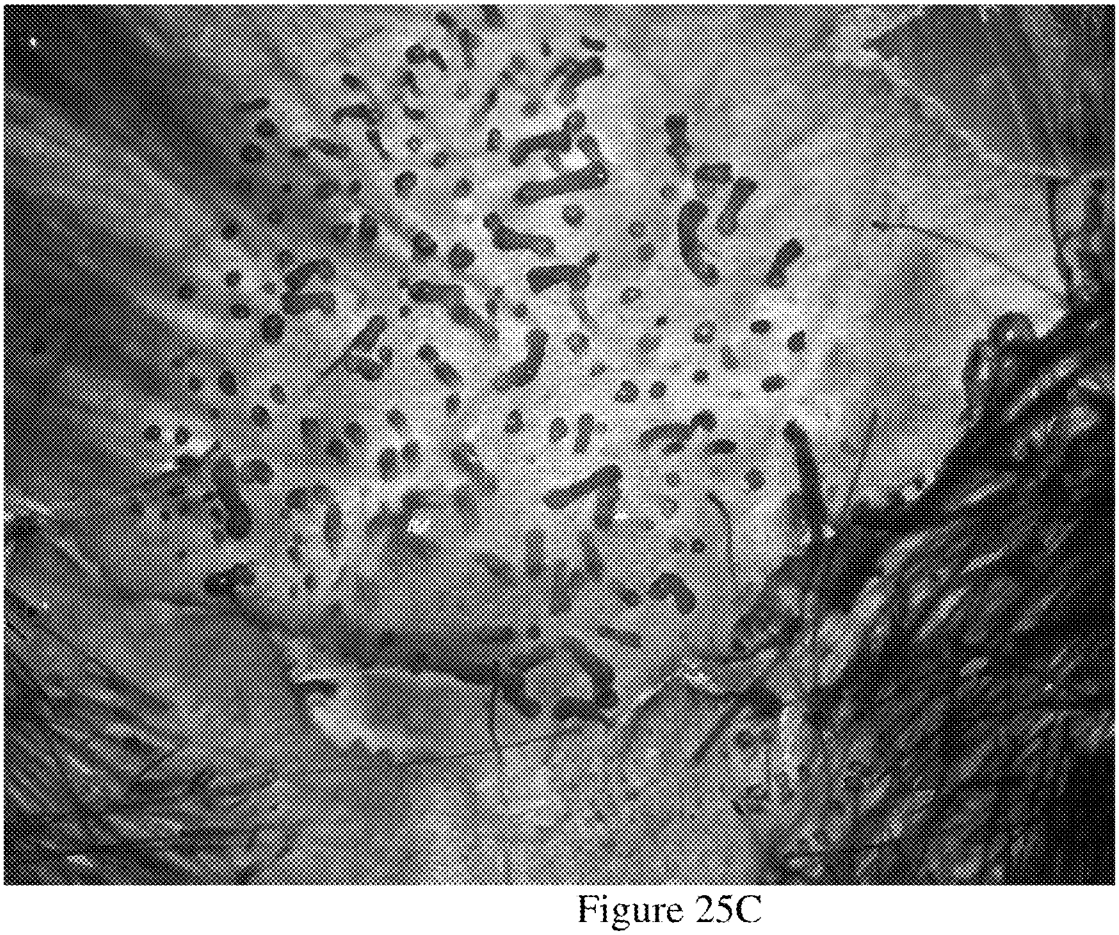
Figure 25D:
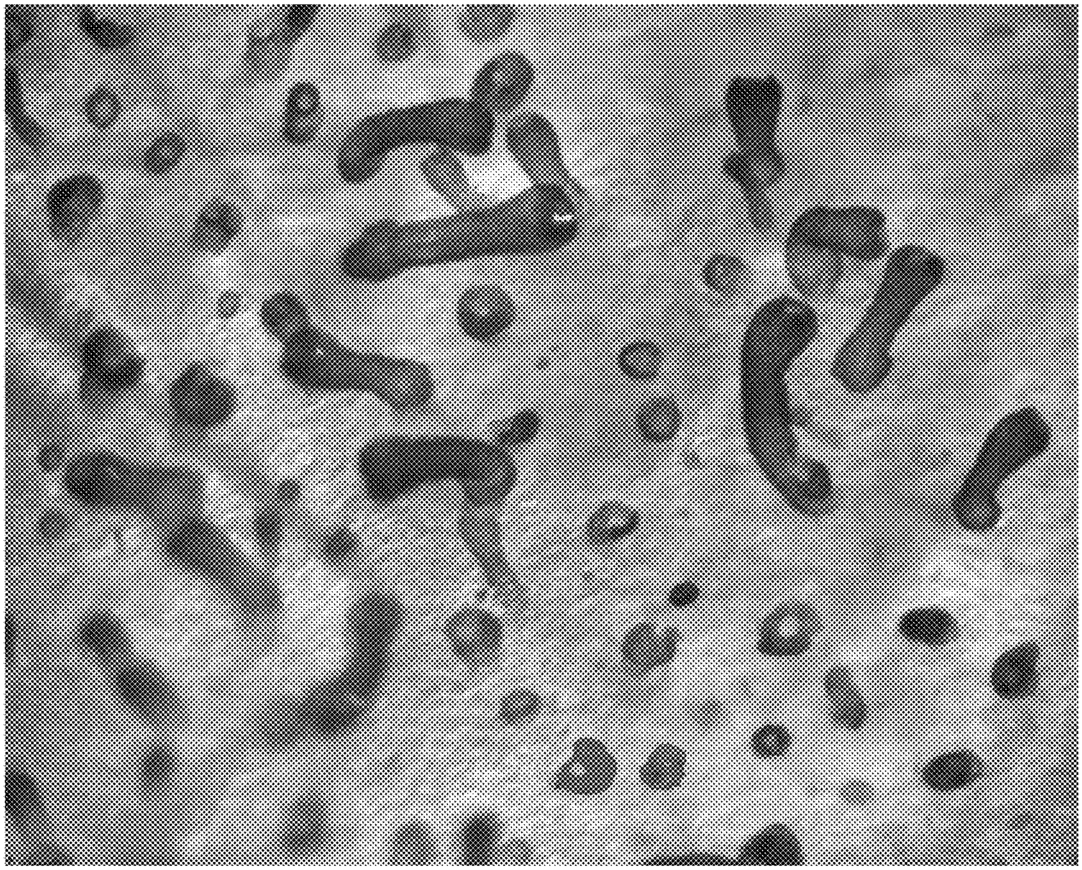

A 1 $cm^2$ wound was induced on the lower back of the doubly transgenic mice at 21 days or 50 days old. Mice were placed on doxycycline-containing chow immediately after wounding to induce Dkk1 expression, and then doxycycline was discontinued after completion of the re-epithelialization at 9 days after wounding. Dkk1 expression inhibits Wnt activity, which in turn induces follicle pigmentation. At 22 days after wounding, pigmented HF were observed in the excised skin after preparing the epidermal sheet (FIG. 23A-B). Control mice lacked pigmented HF (FIG. 24).

In other experiments, continued expression of Dkk1 after the 9-day period inhibited formation of new HF.

The findings of this Example show that pigmented HF can be produced by suppressing expression of Wnt1 or by inducing expression of Dkk1 during the period of re-epithelialization, then inducing expression of Wnt1. In addition, the findings of this Example show that factors that inhibit neonatal hair follicle formation (e.g. Dkk1) also inhibit EDIHN, thus further supporting the notion that hair follicles formed by EDIHN are similar to normal hair follicles.

Example 11

Inhibition of EDIHN by Epidermal Growth Factor Injection 21 day-old mice were wounded as described in previous Examples. Starting from day 11 after wounding, a time point corresponding to the point at which the wound had recently reepithelialized, 10 μL of 1 μg/ml EGF was injected into the wound bed. EGF was injected once per day after this point for a total of 5 days. Three days later, the skin was collected, and whole-mount EDIHN assays were performed. EGF prevented HF formation as assessed by gross morphology. In addition, whole mounts of control and treated skin were analyzed with anti-K17 antibody immunostaining. All mice injected with EGF (n=4) exhibited no new HF formation (FIGS. 25 A-B), while control mice (n=2) had many new HF, as expected. (FIGS. 25 C-D).

In an additional experiment, recombinant EGF (1 microgram (mcg)/microliter (mcl)) was injected at days 11, 13 and 15 after wounding. Skin was collected at 18 days after wounding and stained for K17 and alkaline phosphotase. Once again, administration of EGF inhibited EDIHN.

The findings of this Example show that EGF inhibits HF formation. Thus, inhibiting EGF, EGFR, or one of the pathways in which they participate increases EDIHN-induced HF formation.

Example 12

Enhancement of EDIHN by Inhibition of EGF Receptor

Figure 26A:
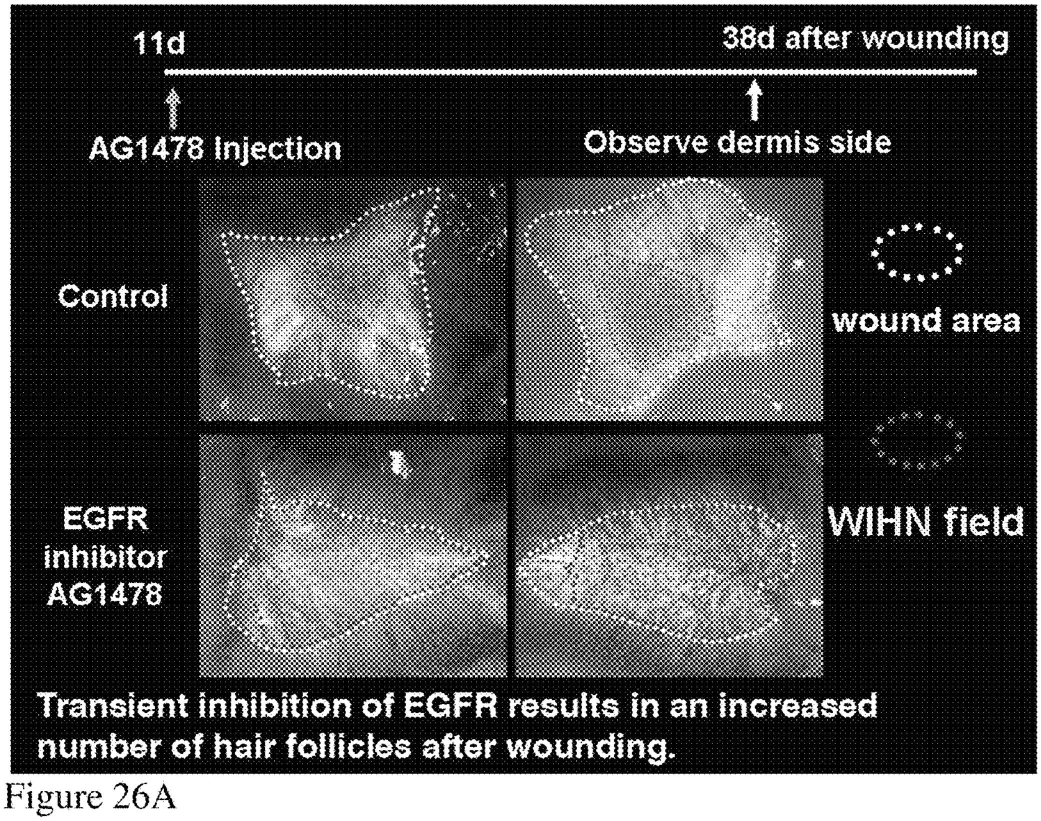
FIG. 26. Administration of an EGF receptor inhibitor (AG1478) leads to generation of more and larger HF compared with controls. A. Top: skin of 2 control mice. Outer dashed line indicates the extent of the wounded area after contraction and healing; inner dashed line indicates the area of neogenesis. Bottom: skin of 2 treated mice, in which the wounded area and area of neogenesis largely coincide, with the exception of a small area on the left side of the encircled area in each panel. B. Large hair follicles developed in the wounded area in the AG1478-injected mice. Left panel: epidermis stained for K17, with three large hair follicles next to each other. Right panel: dermis stained for AP with large coalescing DP areas. Scale Bars: 200 μm.
Figure 26B:
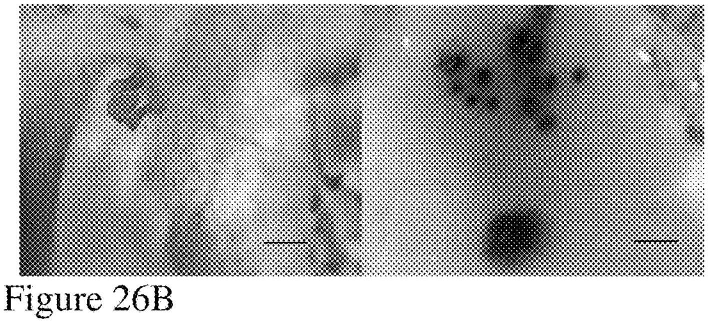

To determine the effect of administration of EGF receptor inhibitors on DIHN, the inhibitor AG1478 (150 μM in 10 μL volume) was administered as a single injection 11 days after incisional wounding (1 $cm^2$) to the middle of the wound near the skin surface. EGF receptor inhibitor administration led to generation of more and larger hair follicles compared with control mice that were wounded only (FIG. 26A). As shown in FIG. 26B, large hair follicles developed in the wounded area in the AG1478-injected mice. Left panel: epidermis stained for K17, with three large hair follicles next to each other. Right panel: dermis stained for AP with large coalescing dermal papilla areas.

The findings of this Example confirm the results of the previous Example, and show that more and larger HF can be generated when EDIHN comprises, or is followed by, administration of EGFR inhibitors, or with compounds with a similar mechanism of action; e.g. Hedgehog protein and androgen antagonists.

Example 13

Enhancement of EDIHN by Expression of a β-Catenin Activator

Figure 27A:
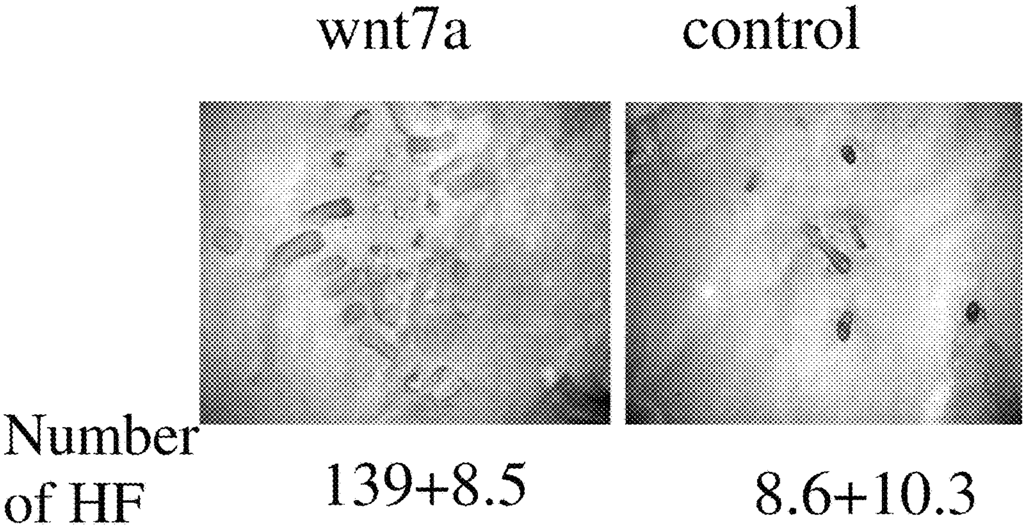
FIG. 27. A. Increased hair follicle formation in K14-Wnt7a mice. Left panel: Wnt7a transgenic mice. Right panel: control (wild-type) mice. B. Quantiation of experiment with 4 week old mice. C. Quantiation of experiment with 3 week old mice
Figure 27B:
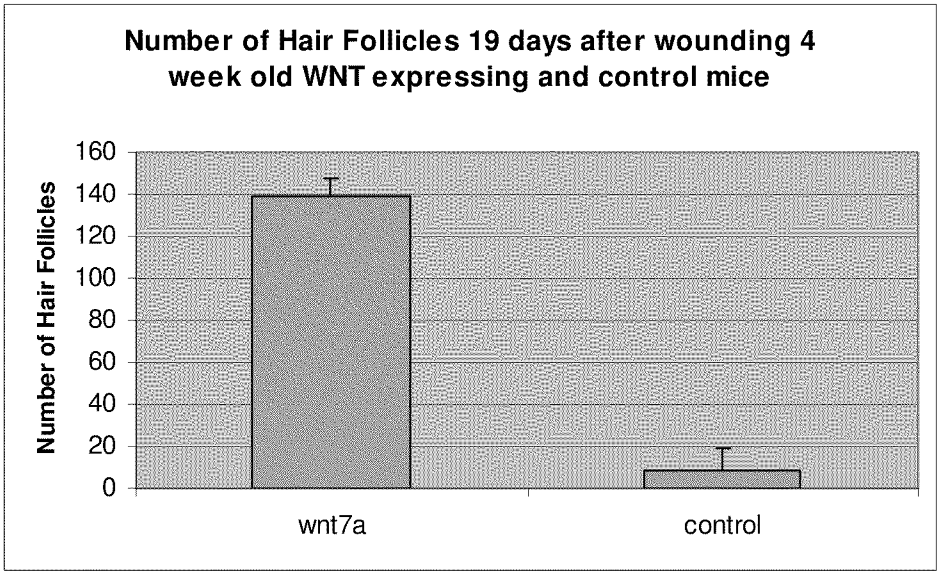
Figure 27C:
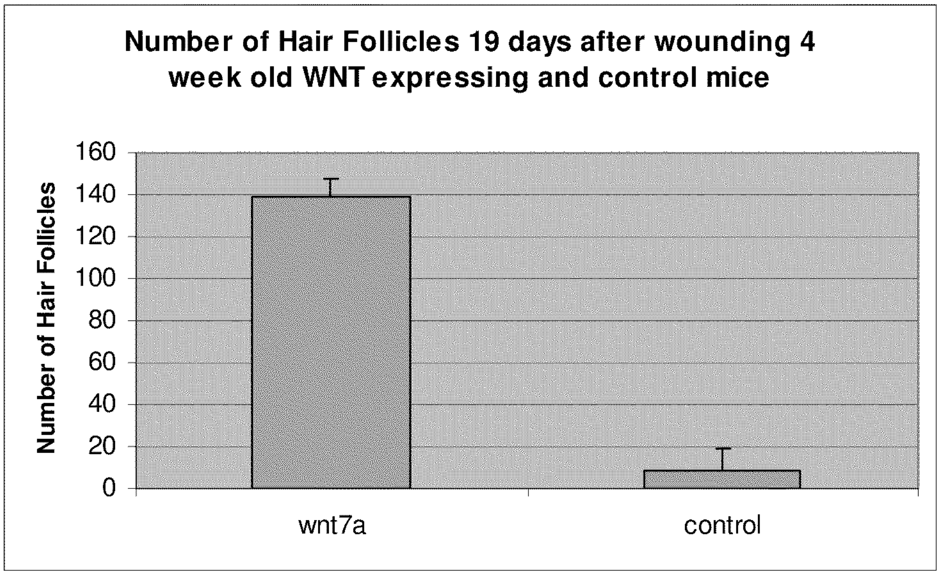

To determine the effect of administration of β-catenin activators on EDIHN, K14-Wnt7 transgenic mice, which overexpress the β-catenin pathway activator, Wnt7, in the epidermis, were subjected to EDIHN, then HF formation was measured 19 days after wounding. In each of 2 separate experiments, with 4 week old and 3 week old mice, the transgenic mice developed significantly larger numbers of HF compared to control, non-transgenic littermate mice (FIG. 27 A-C).

Thus, administration of β-catenin activators leads to an increase in EDIHN. The findings of Examples 11-13 show that new HF can be generated by (a) disrupting the epidermis; and (b) administering a factor that promotes a differentiation of an uncommitted epidermal cell into a HF cell.

Example 14

Enhancement of EDIHN by Administration of FGF

To determine the effect of fibroblast growth factor (FGF) on EDIHN, recombinant FGF is administered 11 days after incisional wounding, as described in Example 11. FGF administration enhances HF formation, showing that new HF can be generated by (a) disrupting the epidermis; and (b) administering FGF, a nucleotide encoding FGF, or a factor that increases signaling by FGF.

Example 15

Enhancement of EDIHN by Administration of EDAR

To determine the effect of fibroblast growth factor (FGF) on EDIHN, K14-Eda-A1 transgenic mice, which overexpress (ectodysplasin-A1) Eda-A1 in the epidermis, are subjected to EDIHN, then HF formation is measured 19 days after wounding as described in Example 13. The transgenic mice developed significantly larger numbers of HF compared to control, non-transgenic littermate mice, showing that new HF can be generated by (a) disrupting the epidermis; and (b) administering a factor that enhances signaling by ectodysplasin.

Example 16

Enhancement of EDIHN by Administration of Minoxidil

To determine the effect of minoxidil on EDIHN, recombinant FGF is administered 11 days after incisional wounding, as described in Example 11. Minoxidil administration enhances HF formation, showing that new HF can be generated by (a) disrupting the epidermis; and (b) administering a minoxidil.

Example 17

Removal of HF by Abrasion and Administration of EGF

Hair-bearing regions of the epidermis of mice is abraded, as described in Example 1, then administering recombinant EGF, as described in Example 1. This method prevents hair re-growth in the abraded areas, showing that hair can be removed by (a) disrupting the epidermal layer; and (b) administering EGF, a nucleotide encoding EGF, or a factor that increases signaling by EGF.

What is claimed is:

1. A method for enhancing hair follicle neogenesis in a scarred region of a subject, said method comprising:

(i) disrupting the basal and suprabasal epidermal layers of said scarred region of said subject; and (ii) contacting the disrupted area of the scarred region of said subject with a compound comprising minoxidil, thereby enhancing hair follicle neogenesis in said scarred region of said subject.

2. The method of claim 1, wherein said disrupting is performed using a light-based method.

3. The method of claim 1, wherein said disrupting is performed using a laser.

4. The method of claim 3, wherein said laser is a CO2 laser, a fractional laser, or an excimer laser.

5. The method of claim 3, wherein said laser induces transepithelial injury.

6. The method of claim 1, wherein said disrupting is performed by abrading.

7. The method of claim 6, wherein said abrading comprises wearing away said epidermis or dermis by friction.

8. The method of claim 1, wherein said disrupting is performed using a mechanical method.

9. The method of claim 8, wherein said mechanical method comprises use of a tool that comprises sandpaper or a rotating felt wheel.

10. The method of claim 1, wherein said disrupting is performed by perforating.

11. The method of claim 10, wherein said perforating comprises use of a surgical tool.

12. The method of claim 11, wherein said surgical tool induces punch wounds.

13. The method of claim 1, wherein said disrupting is performed by freezing or cryoinjury.

14. The method of claim 1, wherein the step of contacting is performed 3-12 days after the step of disrupting.

15. The method of claim 1, wherein said subject is a human.

16. The method of claim 1, further comprising administering a lithium compound in an amount effective to stimulate hair growth in said scarred region.

* * * * *

UNITED STATES PATENT AND TRADEMARK OFFICE

CERTIFICATE OF CORRECTION

PATENT NO. : 9,642,789 B2
APPLICATION NO. : 12/904981
DATED : May 9, 2017
INVENTOR(S) : George Cotsarelis et al.

It is certified that error appears in the above-identified patent and that said Letters Patent is hereby corrected as shown below:

In the Specification

After Line 16, in Column 1, please insert the following:
--GOVERNMENT INTEREST STATEMENT
This invention was made with government support under grant numbers AR046837 and AR055309 awarded by the National Institutes of Health. The government has certain rights in the invention.--

Signed and Sealed this
Second Day of November, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 273

<210> SEQ ID NO 1
<211> LENGTH: 321
<212> TYPE: RNA
<213> ORGANISM: Homo sapiens

<400> SEQUENCE: 1

uuuuuuuuuu uuuuuuucuu aaaaauauaa auguauuugu cugcaucaug acguucuucg     60

ggcaccuagc uggccagacc acuggccaug ggacaaggag gaagucaggu guaagucuga    120

gcaaggaaca ggacucugcc cuggcagggu ggagguggcc ucacagugu c ccaugcuggg    180

ccugguagcg ugaaagcaca gcacgguagu gggacagcuc cugccgcaca gccaccaccu    240
```

```
ccugccgcaa cagggcguuu uccuucucca ggaaggcagc ccgcacagau auccgguucu    300

ccuugagucu ucuugcaucu c                                              321


<210> SEQ ID NO 2
<211> LENGTH: 1580
<212> TYPE: RNA
<213> ORGANISM: Homo sapiens

<400> SEQUENCE: 2

caguuccuca gcauggccac cugcagccgc caguucaccu ccuccagcuc caugaagggc     60

uccuguggca ucgguggugg cucuagccgc auguccucca uccuggcugg aggauccugc    120

cgggcuccca gcaccugcgg gggcauguca guuaccuccu cucgcuucuc cucuggggga    180

gucuguggga uuggaggugg cuauggugg agcuucagca gcagcaguuu ugguggagga     240

cuugguagug gauuuggugg ucgauuugau ggauuuggug gugguuuugg ugcuggucuu    300

gguggugguc uuggcggugg uauuggugau gggcuccugg ugggcaguga gaaagugacc    360

augcagaacc ucaaugaccg ccuggccacc uaccuggaca aggugcgugc ccuggaagag    420

gccaacagag accuggaggu gaagauccgg gacugguacc agaggcagcg gcccacugag    480

aucaaagacu acagccccua cuucaagacc auugaggacc ugaagagcaa gaucauuauu    540

gccacccagg agaaugcaca guucacuuug cagauugaca augccaggcu ggcagcugau    600

gacuucagga ccaaguacga gaaugagcug uucuugcggc aguccgugga gggugacauc    660

aauggccugc gcaaggugcu agaugagcug acccugucca gagcugaccu ggaaaugcag    720

auugaaaacc ucagagaaga gcuggccuuc cugaagaaga accaugagga ggagaugcuu    780

gccuugaggg gucagacugg uggggacguc aauguggaga uggacgcagc ccccggugug    840

gaccucagcc gcauucugaa ugagaugagg gaccaguaug agcagauggc agagaagaac    900

cgcagagaug uggaggccug guuccugaga aagacugagg agcugaacaa agagguggcc    960

ucuaacagug aucuaaucca gagcaaccgc agcgaggugg cugagcuccg cagggguguuc  1020

cagggccugg agauugaacu gcagucccag cucagcauga aagcauccuu ggagaacagc   1080

cuagaagaga ccaaaggcag auacuguaug cagcuguccc agauccaggg uuugaucagc   1140

agugugggagg agcagcuggc ucagcuucgc ugcgagaugg agcagcagag ccaggaguac  1200

aacaucuugu uggaugugaa gacaaggcug gagcaggaga ucgccaccua ccgccgucug   1260

cuggauggcg agaauaucca cuccuccuca cagcacuccu cuggacaguc cuauucuucu   1320

cgagaagucu ucuccucauc cucccgccag ccccggucca uccucaagga gcaagguuca   1380

accagcuuca gccagagcca aagucagagu uccagggacu aauguuuugc cuagagccuc   1440

cucacccaca acugccucuc aagcugaggg cuuggggcag gacccuguuu ucuuugcgca   1500

uuccccaucu gucuccccua cccucucaug gugguaggcu aauaaagcuu uuugguugau   1560

gcaaaaaaaa aaaaaaaaaa                                                1580


<210> SEQ ID NO 3
<211> LENGTH: 1357
<212> TYPE: RNA
<213> ORGANISM: Homo sapiens

<400> SEQUENCE: 3

gcgccagucc uccgauagac ugagucgccc ggguacccgu guucucaaua aagccucuug     60

cuguuugcau ccgaaucgug gucucgcugg uccuugagag ggucuccuca gauugauuga    120

cuacccacgu cgggggucuu ucauuuggag gccccagcga gauuuggaga ccccugccca    180
```

-continued

```
gggaccaccg accccccguc gggagguaag cuggccagcg gucguuucgu gucugucucu    240
gucuucgugc guguuugugc cggcauuuaa uguuugcgcc ugcgucugua cuaguuagcu    300
aacuagaucu guaucuggcg guuccgcgga agaacugacg aguucguauu cccggccgca    360
gccccuggga gacgucccag cggccucggg ggcccguuuu guggcccauu cuguaucagu    420
aaccacccga gucggacuuu uuggagcucc gccacuguac guggcuuugu ugggggacga    480
gagacagaga cacuucccgc ccccgucuga auuuuugcuu ucgguuuuac gccgaaaccg    540
cgccgcgcgu cugauuuguu uguuguucuu uuguucuucg uuaguuuucu ucugucuuua    600
aguguuuuuc gagaucaugg gacagaccgu aacuaccccu cugaguuuaa ccuugcagca    660
cuggggagau guccagcgca uugcauccaa ccagucugug gaugucaaga agaggcgcug    720
gauuaccuuc uguuccgcug aauggccaac uuucaaugug ggauggccuc aggaugguac    780
uuucaauuua aguauuaucu cucagguuaa gucuagagug uuuuguccug gucccacgg    840
acacccggau caggucccau auaucgucac cugggaggca cuugccuaug accccccucc    900
gugggucaaa ccguuugugu cuccuaaacu uccucccucg ccgacagcuc ccguccuccc    960
gcccgguccu ucugcgcaac cuccgucccg aucugcccuu uacccugccc uuaccccuc   1020
uauaaagucc aaaccuccua agccccaggu ucucccugau agcggcggac cccucauuga   1080
ccuucucaca gaggaccucc cgccguacgg agcacaaccu uccuccucug ccagagagaa   1140
cgauaaagaa gaggcggcca ccaccuccga gguuuccccc ccuucuccca uggugucucg   1200
acugcgggga aggagagacc cucccgcagc ggacuccauc aucucccagg cauucccacu   1260
ccgcaugggg ggagauggcc agcuucagua cuggccguuu uccuccucug auuuaacccu   1320
uccuuuucug aagauccagg uaaauugacg gccuuga                            1357
```

<210> SEQ ID NO 4
<211> LENGTH: 463
<212> TYPE: RNA
<213> ORGANISM: Homo sapiens

<400> SEQUENCE: 4

```
gacguagagc cccuugcgcc cgguuuccug aucccgcuua cuccucugcg cgccggcagg     60
auggcccaca agcagaucua cuacucagac aaguacuucg augagcacua cgaguaccgg    120
caugucaugu uacccagaga acucucuaaa caaguaccca aaacucaucu gauguccgaa    180
gaggagugga ggagacuugg uguccaacag agucuaggau ggguucauua caugauucau    240
gagccagaac cgcauauucu ucucuuuaga cgaccucuuc caaaagaaca acaaaaauga    300
agugcagcug ggaucaucua aucuuuuuca aauuuaaugu auauguguau auaagguagu    360
auucagugaa uacuugaaaa guguacaaac cuuucaucca uaccugugca ugcgcuguau    420
ucuucacagc aacagagcuc agucaaaugc aacugcaagu agg                      463
```

<210> SEQ ID NO 5
<211> LENGTH: 1973
<212> TYPE: RNA
<213> ORGANISM: Homo sapiens
<220> FEATURE:
<221> NAME/KEY: misc_feature
<222> LOCATION: (558)..(558)
<223> OTHER INFORMATION: n is a, c, g, or u
<220> FEATURE:
<221> NAME/KEY: misc_feature
<222> LOCATION: (569)..(569)
<223> OTHER INFORMATION: n is a, c, g, or u

<400> SEQUENCE: 5
auuaaaaagc cagcugccca augccugcac acagaaucca caccaacaga gaaccugcuc 60
uucucugagu auuagguaag ucucugcuug caacugauuu gaaauucuug cuuauuuuuu 120
uacuaugaaa aacuguucaa agccaacucu auuacagagu ugaugugggg ugcugccuac 180
aguuagugaa caguagcauu guuugcuuaa auuauagcac auuuugggcuc uaggaacuug 240 agaggugauu caguugguca cuguaguaga cagccuugga aucagagauu aaggcaaaag 300
gaaaccucca uucaaauauu cauggaaguu cacagcugga gacagguuaa ggcuucaguc 360
cagauagcuu ucagaauuau ugcaguucuu acugauaggc auaucaauag cgaaauuuaa 420
uuuauuagag gaaucuacua aaguaaauuu uuaggccaau auagaacaua ccauacuugu 480
agucuggcag agaaggugac auaugaaauu gaaaugcgau ucauagacag ugguagugaa 540
agaaauaaug guggggangg gcugugcang ggaggcaugg cucaaggaca gcacuuagug 600
guagcacaca ccaugaacua ugauggaaaa gcauuugaua ggcagagaca gaaauguagg 660
aaauguguag ggauccauga gagcauaaac uaaaagggca aaagcauaug agcauggacu 720
aacaugcagc cacucugcaa guuauacuau gaucuauuuc acaaggaggu ugguaugcug 780
cugucuuugg gugacaccgc uuucccagau guccuggugu guagguucac aagccucuca 840
gaagccauac uuuauugcuu uuuaagacgu auuauuaaua uuuuggcuag cauaugguuu 900
agugugagag uuuuauaugc auaugucauu auacuuugcu cauuuauguc uuggaacuuc 960
uucaacuagg uagaaaacau gaccagggag aaugagagua aggaaagaac ccacugagac 1020
agacaagagc aaaccauacu ucugcuaauc auguuuaaaa guccagaaau gaucauacca 1080
uauuuuauuu ucaagugugg aagucagcau ggagaggggc ucuuuuucuc uaaaggggcc 1140
ugaaauuaaa uugacuugau guugagguua ccuucucuuu caaugaauca cuaaauuguc 1200
uuuucuguuu cccaggaccc aagugcuauc uaaccaugag uucccaccag cagaagcagc 1260
ccugcacugu accuccucag cugcaccagc agcaggugaa gcagccuugc cagccaccac 1320
cccaggaacc uugugccccc aaaaccaagg aucccugcca cccuguuccu gagcccugca 1380
accccaaggg gccagagccc ugccacccca aggcacccga gcccugccac cccaaggcac 1440
cugagcccug caaccccaag gugccagagc ccugccagcc uaaggugcca gagcccugcc 1500
agccuaaggu gccagagccc ugcaacccca aggugccaga gcccugccaa ccuaaggcac 1560
cagagccuug ccaccccaag gcgccugagc ccugccaccc uguuguuccc gagcccugcc 1620
ccucaacugu cacuccauca ccauaccagc agaagacaaa gcagaaguaa uauuguccag 1680
agccaugccu gaagaccuga ucaccagaug cugaggcugc ugucuauccu gcuuaugagu 1740
cccauugccu ugugcuacca augcugugac cuucagucuu aaucccucuc uccuugcacc 1800
accuaaaaag uugacucuca uccucaucuu caagggcucc ugagccucuu aacauugccc 1860
aaagucauau ugaauggcua cacuuuucau ggcucaggau ucaucugaag ggggugagga 1920
gugagacaag uguaugguca auauuuuccc cccauuaaau gccauuuaac ucc 1973

<210> SEQ ID NO 6
<211> LENGTH: 254
<212> TYPE: RNA
<213> ORGANISM: Homo sapiens

<400> SEQUENCE: 6
uuuuuuuuuu uuuuuuuagc caaaauaguu auuuauuaau aauuuaaggu uuuacauucu 60
uauaauaaau uccagcucaa aacuuuacac cacgaacauc auggagcaag uuaauucucc 120
cuuccucuca accuguugca uccaccaaau gggcgcucau acucgcacac auacacacac 180
uuccaguuuc guauuuuuuu uuaaaaggaa agaaaccaac ccaaaguauu gcauuugagg 240
ugacacuccc ugaa 254

<210> SEQ ID NO 7
<211> LENGTH: 137
<212> TYPE: RNA
<213> ORGANISM: Homo sapiens

<400> SEQUENCE: 7
aagaugcccu uuggauugga uuggauugau cauguuuaac ucagcguauu uuauggauga 60
aagcuaaaua cagauauuug gcaucucuaa gguggaauga gcccacucca cacacugaua 120
aaauucaugc auaguuu 137

<210> SEQ ID NO 8
<211> LENGTH: 622
<212> TYPE: RNA
<213> ORGANISM: Homo sapiens
<220> FEATURE:
<221> NAME/KEY: misc_feature
<222> LOCATION: (27)..(27)
<223> OTHER INFORMATION: n is a, c, g, or u
<220> FEATURE:
<221> NAME/KEY: misc_feature
<222> LOCATION: (30)..(30)
<223> OTHER INFORMATION: n is a, c, g, or u
<220> FEATURE:
<221> NAME/KEY: misc_feature
<222> LOCATION: (133)..(133)
<223> OTHER INFORMATION: n is a, c, g, or u

<400> SEQUENCE: 8
aaccaaaugg gaaugggguc cccaacnuun cuguggguacc agccggguuu cucuugcauu 60
ggaaacaaac accuuuguag gcauuugcgu auucgugaag agacuguuuu augaaucacc 120
ucuuagauuu aunuaauuaa ccuaaguugu ugaaguuucu guuucuccuu aagagaaauu 180
acaaaaauuc aacauugaag cauaguuucu uguuuucugu ugucaaauag uaauaaugug 240
cugugauguu uaugcuuauu cauaaagaug uuuuacuuuu uaguguaaug uuaguucuuu 300
uuaacauuau uuugcuuaaa uuugauaaug cccgacaaga auauauuuug cuuugauuua 360
uacacugauu cuuugugaca aauaugaccc auuaaaaaug ccuuuuaaua gacuaacuua 420
ccuuuuguag cuagguacuc auguucuuuu uuaaaagaug cccuuuggau uggauuggau 480
ugaucauguu uaacucagcg uauuuuaugg augaaagcua aauacagaua uuuggcaucu 540
cuaaggugga augagcccac uccacacacu gauaaaauuc augcauaguu uuaaaugaac 600
auuaauaaac ucauguuguc uu 622

<210> SEQ ID NO 9
<211> LENGTH: 613
<212> TYPE: RNA
<213> ORGANISM: Homo sapiens

<400> SEQUENCE: 9
gaauucaagg aggcuuucca gcuguuugac cgaacaggug auggcaagau ccuguacagc 60
cagugugggg augugaugcg ggcccugggc cagaacccua ccaacgccga ggugcucaag 120
guucuaggaa cccccaagag ugaugagaug aaugugaagg uacuggacuu ugagcacuuc 180
cugcccaugc ugcagaccgu ggcgaagaac aaggcccagg gaaccuacga ggauuauguu 240
gaaggccuuc guguguuuga caaggaagga aauggcaccg ucaugggugc ugaaauccgu 300
cauguccuag ucacacuggg cgagaagaug acagaggaag aaguagagau gcuaguggca 360
gggcaugagg acagcaaugg uugcaucaac uaugaagcau uugugaggca uauccugucg 420
gggugacggg cccgaugggg cggagcucgu ccggauggug cugaauggcu gagacauucu 480
guaucccgag ucuguucccu gcccagugug auuucugugu ggcuccagac gcucccccugu 540 cacagcaccu ugucccauuu gguuucuuug gaugauguuu gccuucacca aauaaaauuu 600
gcucucuuug ccc 613

<210> SEQ ID NO 10
<211> LENGTH: 1508
<212> TYPE: RNA
<213> ORGANISM: Homo sapiens

<400> SEQUENCE: 10
caaccaccuc cuaccugccu gcccaaagcu ccagggcugg agcacggaga ccugucaggg 60
auggauuuug cccacaugua ccaaguguac aaguccaggc ggggaauaaa acggagcgaa 120
gacagcaagg aaacuuacaa acugccgcac cggcugauug agaaaaagag acgugaccgg 180
auuaacgagu gcauugccca gcugaaggau cuccuacccg aacaucucaa acuuacuacu 240
uugggucacu uggaaaaagc agugguucug gagcuuacgu ugaagcacgu gaaagcauug 300
acaaaucuaa uugaucagca gcagcagaaa aucauugccc ugcagagcgg uuuacaagcu 360
ggugauuugu cgggaagaaa ucucgaggca gggcaagaaa uguucugcuc agguuuccag 420
acuugugccc gugagguacu ucaguaccug gcgaagcaug agaacacucg ggaccugaaa 480
ucuucccagc ucgucacuca ucuccaucgu guggucucgg agcugcugca ggguggugcu 540
uccaggaaac cauuggacuc ggcucccaaa gccgucgacu ugaaagagaa gcccagcuuc 600
cuagccaagg gaucagaagg cccagggaaa aacugugugc cagucaucca gcggacuuuu 660
gcucccucgg guggggagca gagcggcagu gacacggaca cagacagugg cuauggaggu 720
gaauuggaga aaggggacuu gcgcagugaa cagccguacu ucaaaagcga ccauggacgc 780
agguucgccg ugggagaacg ugucagcaca auuaagcaag aauccgaaga gcccccccacc 840 acaaagagcc gaaugcagcu cucagaagag gaaggccacu ucgcgggcag ugaucugaug 900
gguuccccau uucuugggcc acacccacau cagccuccuu uuugccuucc cuucuaucuc 960
aucccaccau cggccacugc cuaccugccu augcuggaga aaugcuggua ccccaccucu 1020
gugccagugu uauacccagg ccucaacacc ucagcugcag cccucuccag cuucaugaac 1080
ccagacaaga uaccgacucc cuugcuucug ccccagagac ucccuucucc uuuggcacau 1140
ucgucccuug acucuucggc cuugcuccag gcuuugaagc agaucccucc uuuaaacuua 1200
gaaaccaaag acuaaacucu ggagggaucu ccugcugccu ugcuuucuuu ccucccuaau 1260
uccaaaaacc acgaagguuu cccugagugc agagagauca gcccacccug cagacccaca 1320
gagaagauuc agagugugug ugagagugag ugagugugcg ugcgugcgug cuuguaugua 1380
uguuuguaua uguaggacaa uaaguuccuu cugacacaag ggagacacga gaaggauagc 1440
cugacaucag augacagacu ggaggacugu agcacaucuc ugggcguuuc ccuacccaga 1500
gaagagcc 1508

<210> SEQ ID NO 11
<211> LENGTH: 3660
<212> TYPE: RNA
<213> ORGANISM: Homo sapiens

<400> SEQUENCE: 11
uugcaggcga gggcuuccac aacuaccacc acaccuuccc cuucgacuac ucugccagug 60
aguaccgcug gcacaucaac uucaccacgu ucuucaucga cugcauggcu gcccugggcc 120
uggcuuacga ccggaagaaa guuucuaagg cuacugucuu agccaggauu aagagaacug 180
gagacgggag ucacaagagu agcugagcuu ugggcuucug aguuccuguu ucaaacguuu 240
ucuggcagag auuuaauauu cuguugauua acuaacaacu ggauauugcu aucggggugu 300
uaaugaugca uuuaaccuau uccgguacag uauucuuaua aaaugagaaa gcuuugauca 360
cguuuugagg uaauaaauau uuuauuuagc uaggauuaac caugccacaa gacauuauau 420
auuucuaagc acacaugaua aaugcauaua caauuuugca caacagcuuu aaauaauaac 480
aauaaauuug aacauucuau acagagagga ucaaagccaa ggaacaugcu guuuugaugc 540
uagggugagc auggugcuca gucccuguuu guuugcaugg uguccagcuu uguuucuucu 600
cugucaucac caccuucagg caaauaguug accaaccacu ggccuguguc uguccacccu 660
ccaaagccca ggccaccuuu cuguuuucug aaauacugau ccuuccuccu gaauacaucc 720
cuccuuguuc cuagcuucaa gacugcugcc ucaaauaggg auagagcaag uccccgcugc 780
agguugugcu agaugggaug gagaaauuau cuucauuuga uacagagcaa guagauuguc 840
ucgagagaaa aguuagcaug cgugguauga uuuguaagua aagauggaag agagagagag 900
agagagagag agagagagag agagagagag agagguagcc auaucuaaca gccuacuuac 960
caaagacccc aggccucucu gcuuggcaug ccuccuuucu guccauccuc ugaaccccag 1020
agauuaguga gauuugaaua auuaaaucau uuucagagug aagggggcuua augcaggguc 1080
ugugcuaggg gaggguuuua gcuuuuggua acugaagauu uuuucaugga aaaagucuuc 1140
guguucaaug ugccuagaac ugauaacuaa acagcugaca uuugucgggg acagauaugg 1200
ugugaaacua ugaaaauaua agcaaaaucu ucacuuggaa caugaaacua uuucacuuag 1260
aaaauaaucg aaggacccga gguguugccu ggguugccag uuucuuucgu ggcugggcag 1320
gaacuaguga gguugagggg cagugucugu aaguagcugc uaagaggugc auuuccagau 1380
gaagcccuug gggaacaucu gccagggauc cgcauggugu uggcuccauc cauugcuuua 1440
guuuccuccu uggauugugu agaaacuugg cuucccaugg uuuugaaccu uccaugccuu 1500
cuuugcuuug uggccaccca gccugccuag ugcugccuag gaagcucuua cccaccugau 1560
uucuucugac auuucuuucu uuggccuuuu uuucuuucuc cggacaugca gcuaguugcc 1620
ugaguguauc aagagcaccc aggacuugcu gcuguccagg ccuguuccuc ccccaguauc 1680
cgugggugug gaagagcugu guagcuucag gaagcagagc caggugccac cuuucugugg 1740
cuuccagauc cucccuaccu ccaacucaug ugccucuguc acagugauuu caggaaagcu 1800
ugguagaccc ucuagcaaca ucucgguuca gaaagucucu cugguuugug aguuaacagc 1860
ucagcuaagu gcuguuuugu cucagugagu uaaccacuga augcgagggu ugguuguuga 1920
ucugucucgg ugugugucgg aguagacagc auaugcacuu cucccugugc gcuuugcaag 1980
guaauguggc uuuggcugau ccaugcaggc agguaguggu acagugcugc ugaaaggaag 2040
aaguucccca uuuuaucugu uaaaacacca gagacauggg caagugcuaa uggaccucac 2100
uucaggaaga gggucugcuu ccugaagcca gugugugaug aaaagugacu gagaccugau 2160
aucuaaggug agaccugaua ccuaacacuc ugucacacag uccagggcca acagugcuau 2220
aggaaagucu agaagaaaac aucacaucag uauuuuagaa ccaucaacca ucucuugucc 2280

```
cuauagccca auccagaggc cugguuuuua gaacuggcug uguaaggugc caaacacuca   2340
guucacuugu agaaucagag ccuuuuuucc ccccuauguu aauugaacac gcgcucugag   2400
cuguuuuguu gaaguagaaa aucucauaga aaaaucacug uagaucuacu gaccuauagc   2460
ccucuggaaa ugccuuugag augguuuuac uuuucuaggu cauagaugcc ugauuauaaa   2520
gaugaacaau aaaaucagcu uucuuucuuu cucuucugau cuuauucccc agaucugauu   2580
caggccaugu uccaaagcaa ggcuacauug agguccuggu gucuuuaagu aaaggacauc   2640
uuucagaucc ucucaaagaa ggauuuauaa caguuuccag augaauguac uaauagcuuu   2700
gggugccuua ucucuuuccu aaucuguagu gccugugagc ucagucucac uccuucccuu   2760
agcccggaga ccccuuagau cgagugggaa uagucaagag gcuggcugga gagucaucag   2820
uacauugguu ugcagaaauc uuuuacaggc uacauuuugg aauuuuuuuu uuuuuaguaa   2880
gugaucaaau uuggugggaa guaauucgag uguauucgau uguauugucg uccucguuau   2940
cauugucaaa cauguuauag acggcaguug gcacuggggc ugcuaaucuc ugggguguagu  3000
cucugaaacu guagcuccag ugagguggug ugaaagguua gcaaagccac caucugcugg   3060
ugcuccagcc aaggugccuc uuagccacug aauugcuaug uuauccuuuc ucuuguaaca   3120
aacccacccc agagauaaag ccuuuaauca acccaagaaa cuccugggcu aaguaucuga   3180
cagucucaca ucucaacagu gugaauuaag uguccauagc aucagcucag gaggacacuc   3240
ugggagagug cugacaaaaa aggguuauua auacugaccu acuacuucaa gggcaguucu   3300
gaggugauua gagcuuuuuu uaaaaaccaa guauuugggg auccucagca gagguauuca   3360
uacagacucc caaagaacua uauauguucc ugagaccauc guuuagucua cauugcucuu   3420
cccagagacu gacagauaug accagucaaa gugcaagacu accuacccac ugccaugaaa   3480
accauugcag gaaaccuuuc ccuuccugaa ugagauuuuu uuuuucccuu uuuauguggg   3540
guaauuauuu gugacccaag uguaauuugg augauuucca uuaauaucaa cucuugaagc   3600
cuacuuguac ugauugagau uguauuuguu ccuaauaaaa guggaucugg uuguacuguc   3660
```

<210> SEQ ID NO 12
<211> LENGTH: 429
<212> TYPE: RNA
<213> ORGANISM: Homo sapiens

<400> SEQUENCE: 12

```
accacuugca gacaaaugaa uuccuucgaa auguauuuga gguuggaccc ccugugaugc     60
uugaugcugc aacacuuaaa accaugaaga uuucucguuu ugaaaggcau uuauauaacu    120
cugcagcuuu caaagcucga acaaaagcuc gaagcaaaug ccgagauaag agagcagaug    180
uuggagaauu cuuguagaug ucugaauuug auggcuguuu ucuaaucucu uccuuuauua    240
uuauuuuugc uacuucuaau guauauaagc uuuuagagac aguuuuuuau cuuggucaac    300
uuaaauaauu uuugauguag gggugggguug uauuuuaauu uaauguacag uguuacaaau   360
uaaugaguuc uuuauucucu guaaaaauaa cugguaacca caaauaaagu guuugugaug    420
uuuggucgu                                                             429
```

<210> SEQ ID NO 13
<211> LENGTH: 1639
<212> TYPE: RNA
<213> ORGANISM: Homo sapiens
<220> FEATURE:
<221> NAME/KEY: misc_feature
<222> LOCATION: (1003)..(1003)
<223> OTHER INFORMATION: n is a, c, g, or u
<220> FEATURE:
<221> NAME/KEY: misc_feature
<222> LOCATION: (1098)..(1099)
<223> OTHER INFORMATION: n is a, c, g, or u
<220> FEATURE:
<221> NAME/KEY: misc_feature
<222> LOCATION: (1106)..(1106)
<223> OTHER INFORMATION: n is a, c, g, or u
<220> FEATURE:
<221> NAME/KEY: misc_feature
<222> LOCATION: (1112)..(1112)
<223> OTHER INFORMATION: n is a, c, g, or u
<220> FEATURE:
<221> NAME/KEY: misc_feature
<222> LOCATION: (1158)..(1158)
<223> OTHER INFORMATION: n is a, c, g, or u
<220> FEATURE:
<221> NAME/KEY: misc_feature
<222> LOCATION: (1161)..(1161)
<223> OTHER INFORMATION: n is a, c, g, or u
<220> FEATURE:
<221> NAME/KEY: misc_feature
<222> LOCATION: (1171)..(1171)
<223> OTHER INFORMATION: n is a, c, g, or u
<220> FEATURE:
<221> NAME/KEY: misc_feature
<222> LOCATION: (1182)..(1182)
<223> OTHER INFORMATION: n is a, c, g, or u
<220> FEATURE:
<221> NAME/KEY: misc_feature
<222> LOCATION: (1245)..(1245)
<223> OTHER INFORMATION: n is a, c, g, or u
<220> FEATURE:
<221> NAME/KEY: misc_feature
<222> LOCATION: (1436)..(1436)
<223> OTHER INFORMATION: n is a, c, g, or u
<220> FEATURE:
<221> NAME/KEY: misc_feature
<222> LOCATION: (1472)..(1473)
<223> OTHER INFORMATION: n is a, c, g, or u

<400> SEQUENCE: 13
auguccgcgg ccgccuacau ggacuucgug gcugcccagu gucugguuuc caucuccaac 60
cgcgccgccg ugccggagca cgggggcgcu ccggaagccg agcggcugcg acuaccugag 120
cgcgagguga ccaaggaaca cggugacccg ggggacaccu ggaaggauua uugcacgcug 180
gucacuaucg ccaagagcuu guuggaccuc aacaaauacc gacccaucca gacccccucg 240
gugugcagcg acagucugga gagucccgau gaggauauag gauccgacag cgacgugacc 300
accgaaucug ggucgagucc uucccacagc ccggaggaga gacaggauuc uggcagcgcg 360
cccagcccac ucucccuccu ccacucugga guggcuucga aggggaaaca cgccuccgaa 420
aagaggcaca agugccccua caguggcugu gggaaagucu auggaaaauc cucccaucuu 480
aaagcccauu acagagugca uacaggugaa cggcccuuuc ccugcacgug gccagacugc 540
cuuaaaaagu ucucgcgcuc ggaugagcug acccgccacu accggaccca cacuggggaa 600
aagcaguucc guugcccacu gugugagaag agauucauga ggagugacca ucucaccaag 660
caugcccggc gucacaccgu guuccauccc agcaugauca agagaucaaa aaaggcucuu 720
gccugccccu ugugaggugc uccccauggc agccaggcag agaugggucc ccggaaggac 780
agagcuccca ggaaacagac ugacacaugg aaaucugcca cagcagaggc gcgcuggcca 840
caggagguca cugcuucuuu ggccaauauu cugauaucuc ccugcacugu uuccaaaaag 900
cacaugguag cccuaagguc aaagucaaca uuuggucccc uugcagaggc aacucugaac 960
cgucucugac ugaagauuca gacugguggu guacauacgu cunacugggu gaguugaccc 1020
cuggccuccc acagugcaga accacucucu ugaaucacau uaacuuuuga gauuuaaaaa 1080

```
aaacccaaac ccaacccnnc aaaacnccag anacaccgaa acucuggauc cucgaugcuu   1140

gcugacucuc agaauugnuu nuucuucuca nuuaugcaag cnagagcaca ccuacuccag   1200

caugauuugu caucuaaaga cuugaaaaca aaacaacaac aacanaaagu uacuuauagu   1260

caauggauaa gcagaguccg aauuuacacu aaucaagaca gaccuucgag gggucacgau   1320

aaguccggaa cuuucaaacc uugcuucgua ugaauuguac uaucugaaca uaaacugcac   1380

uuuuauuuuc uaauaccgag ggugaauacg guaaauacau gcuuugaggg uagaanccga   1440

cggucuguuu ggcaccacgu uauaaucugc unnuuuuaac gaguaccacc uuggagggca   1500

ggcaaauaaa ugcuuuuggg uauuuucucc uuuguuuuug acaaaugcug cggaaugggg   1560

aucgggaucg gaggggagug cuuuuaaaga uaauaaaaaa ugagguaaau aauuuuaacu   1620

uaugaauuug uuugaauuc                                                1639
```

<210> SEQ ID NO 14
<211> LENGTH: 1929
<212> TYPE: RNA
<213> ORGANISM: Homo sapiens

<400> SEQUENCE: 14

```
gagauugaaa caauggaaga acuuuccaug gcaaacacca uguuugcccu caaucuccuu     60

aagcagauag aaaaaucaaa cucuacccag aacaucuuua ucucuccaug gagcaucuca    120

ucaacauugg ccauaguucu ccucggugcu gggggguaaca cugaacagca gauggccaaa   180

gugcugcagu uuaaugaaau uggcaguuau gguaucacca caagaaaccc agagaacuuc    240

aguggcugug auuucgcaca acagauacag aaggaaaauu auccuagugc uauuuuacag    300

gcacaagcag gagauaaaau ccauucagcc uucuccucuc ucagcucaac aaucaacaca    360

ccacaggggg auuauuuguu agaaagugca aacaagcugu uuggagagaa gucugcaaga    420

uucaaagaag aauacaucca acucucuaag aaauauuacu caacagaacc agaagcagug    480

gacuuccuug aaugugcuga agaagcuagg gaaaagauua auucuugggu caagacucaa    540

accaaaggug aaaucccaaa ccugcuaccc gaagguucug uagaugaaga caccaagaug    600

gugcugguga augcugucua cuucaaagga aaguggaaaa cuccauuuga gaagaaacuu    660

aaugggcuuu auccuuuccg ugugaacucg caugagagca uaccugucca gaugauguuc    720

cuccaugcaa agcugaacau uggauacaua aaggaccuga agacucagau ccuagaacuu    780

ccgcauacug gaaacaucag caugcuccug uugcuucccg augagauuga ggacgcaucc    840

acuggcuugg aauugcugga aagugaaaua aacuuugcca acuucaacaa guggaucagc    900

aaagacacac uggaugaaga ugauguugug gucuacauuc ccaaguucaa acuggcacaa    960

agcuacgaac ucaaguccau ucuucaaagc augggcaugg aggaugccuu caacaagggc   1020

aaggccaacu ucucaggaau gucugagagg aaugaccuuu uucuuucuga ggguguuccau   1080

caagccagcg uggaugucac cgaggagggc acuguggcag cuggugggac uggggcaguu   1140

augacaggaa gaacuggcca ugguggccca caguuugugg ccgaucaucc cuuucuuuuc   1200

uuuaucaugg acaaaauuac ccacacgaua cuauuuguug guagauucuc cucacccuaa   1260

aaggggaaga ccuauuucca caugagguuu uguagcauga acuauaagcc ucagaauugc   1320

aucuucaagu gccaaaaguu uaaaauacuu cuuacacauu uuuauacuuc ugcuauacac   1380

uaaaauauaac cuaaaagcaa uuguauagca gucuucagug cuuacaguau aacucuauua  1440

augauuuugu uuccuaaagu cagaugaugu cuauuuaguu cauccuuauu acugcuuugu   1500

cuuuauaacu uuaguuuuua caguguuauu uauuguuuau auaaugguug uuuuacaaau   1560
```

uguuguccuc uguuuaauga aacuguaaca cuacagaagc agaaaauuag auaauuuucu 1620
auuuaaagaa aaucagccau uuaauuuaau aaugaaggaa aaauaugagu cuuccauacu 1680
uucccaugau auucacccag aaaaaaugua cuuaacaaaa gacauguuau aucucuauca 1740
uuauauauca uauguacgua ucugcaacuc aucuauaauu aggacuacau cauaaguaag 1800
caugcuuacu uacacacugc uaucuguugu auaaaacuua gcaauccuua uuuguuaguu 1860
aucuuucuau cacuguaaca aaauaccuga gauaauaaag uucaaagauu uauuuugaaa 1920
aaaaaaaaa 1929

<210> SEQ ID NO 15
<211> LENGTH: 284
<212> TYPE: RNA
<213> ORGANISM: Homo sapiens
<220> FEATURE:
<221> NAME/KEY: misc_feature
<222> LOCATION: (16)..(16)
<223> OTHER INFORMATION: n is a, c, g, or u

<400> SEQUENCE: 15
uuuuuuuuuu uuuuunuaag aauuaacuuu uauuuuugcu uaguuuuauu aaaaaaauaa 60
auaugucaua aagcuuuugu uuccuuuagg gagaaaaaaa aggaacaagu uccauaaaau 120
caaacaagca augguaacau gucuuaacuu gaaaacaacu ggggucacug guuuacaagu 180
uauaacugaa ugaaugacug ccacaguugc ccauuuccuc cugccaaugg cagcaaacaa 240
caggaucaac uagggcaaaa uaaauaauug uguggaagcc cuga 284

<210> SEQ ID NO 16
<211> LENGTH: 219
<212> TYPE: RNA
<213> ORGANISM: Homo sapiens
<220> FEATURE:
<221> NAME/KEY: misc_feature
<222> LOCATION: (70)..(70)
<223> OTHER INFORMATION: n is a, c, g, or u
<220> FEATURE:
<221> NAME/KEY: misc_feature
<222> LOCATION: (88)..(88)
<223> OTHER INFORMATION: n is a, c, g, or u
<220> FEATURE:
<221> NAME/KEY: misc_feature
<222> LOCATION: (132)..(132)
<223> OTHER INFORMATION: n is a, c, g, or u
<220> FEATURE:
<221> NAME/KEY: misc_feature
<222> LOCATION: (205)..(205)
<223> OTHER INFORMATION: n is a, c, g, or u

<400> SEQUENCE: 16
aacuaaacuu ccuuguaacu uuugagaacu cagcucuggu acuuuuucau gccuugcaaa 60
auggcguuan ugcagcuagc uugcuaancc uuauggugggg gucuuucauu ccccccucuu 120
ucuggaaacu gnauaaaauc auuuauucac gugauucuau uucuucugga ucuauugauu 180
ugaguuggug auacuguugg gucanaacca gggccuguu 219

<210> SEQ ID NO 17
<211> LENGTH: 4179
<212> TYPE: RNA
<213> ORGANISM: Homo sapiens

<400> SEQUENCE: 17
cagcuccgag cuaggugcua ucgcaaggcc agagcgcaca gcccggcgga gagagcagau 60

```
ccuugcucag aucgagucaa aucgggccaa ggcggaggac gaagagucca ggcuccuauu    120
cuggacuugu uccccagcuc cgggggcgcu ucuagguccu gcagcagcca gcagugcgga    180
gccaccaacu cggugcugga augaaaaaau ucccgcgcgc cagugcagaa ucuuucuaag    240
ugacccggag cuucgggugc uagcucugca cgaacuuucc caucaaagug aucgugaauu    300
uuaagcauca ggagcaggcc agcgaagcuc uacgcgucua aacgucuauc cagaccaaga    360
guucucugcg gugcagggug cggugccaug cagccaaaag ucccuuuugg ggucacgcaa    420
gcagaagccc ugcuccgaca ugggggacgu ccagcgggca gcgagaucuc ggggcucucu    480
guccgcacac augcuguugc ugcuccucgc uuccauaaca augcugcuau gugcgcgggg    540
cgcacacggg cgccccacgg aggaagauga ggagcugguc cugcccucgc uggagcgcgc    600
cccgggccac gauuccacca ccacacgccu ucgucuggac gccuuuggcc agcagcuaca    660
ucugaaguug cagccggaca gcgguuucuu ggcgccuggc uucacccugc agacuguggg    720
gcgcaguccc ggguccgagg cacaacaucu ggaccccacc ggggaccugg cucacugcuu    780
cuacucuggc acggugaacg gugaucccgg cucugccgca gcccucagcc ucugugaagg    840
ugugcguggu gccuucuacc uacaaggaga ggaguucuuc auucagccag cgccuggagu    900
ggccaccgag cgccuggccc cugccgugcc cgaggaggag ucauccgcac ggccgcaguu    960
ccacauccug aggcgaaggc ggcggggcag uggcggcgcc aagugcggcg ucauggacga   1020
cgagacccug ccaaccagcg acucgcgacc cgagagccag aacacccgga accaguggcc   1080
ugugcgggac ccccacgccuc aggacgcggg aaagccauca ggaccaggaa gcauaaggaa  1140
gaagcgauuu guguccagcc cccguuaugu ggaaaccaug cucguagcug accaguccau   1200
ggccgacuuc cacggcagcg gucuaaagca uuaccuucua acccuguucu cgguggcagc   1260
cagguuuuac aagcauccca gcauuaggaa uucaauuagc cugguggugg ugaagaucuu   1320
ggucauauac gaggagcaga agggaccaga aguuaccucc aaugcagcuc ucacccuucg   1380
gaauuucugc agcuggcaga aacaacacaa cagccccagu gaccgggauc cagagcacua   1440
ugacacugca auucuguuca ccagacagga uuuauguggc ucccacacgu gugacacucu   1500
cggaauggca gauguuggaa ccguauguga ccccagcagg agcugcucag ucauagaaga   1560
ugaugguuug caagccgccu ucaccacagc ccaugaauug ggccaugugu uuaacaugcc   1620
gcacgaugau gcuaagcacu gugccagcuu gaauggugug aguggcgauu cucaucugau   1680
ggccucgaug cucuccagcu uagaccauag ccagcccugg ucaccuugca gugccuacau   1740
ggucacgucc uuccuagaua auggacacgg ggaauguuug auggacaagc cccagaaucc   1800
aaucaagcuc ccuucugauc uucccgguac cuuguacgau gccaaccgcc agugucaguu   1860
uacauucgga gaggaaucca agcacugccc ugaugcagcc agcacaugua cuacccugug   1920
gugcacuggc accuccggug gcuuacuggu gugccaaaca aaacacuucc cuugggcaga   1980
uggcaccagc uguggagaag ggaagugguug ugucaguggc aagugcguga acaagacaga  2040
caugaagcau uuugcuacuc cuguucaugg aagcugggga ccauggggac cguggggaga   2100
cugcucaaga accugugguug guggaguuca auacacaaug agagaaugug acaacccagu  2160
cccaaagaac ggagggaagu acugugaagg caaacgaguc cgcuacaggu ccuguaacau   2220
cgaggacugu ccagacaaua acggaaaaac guucagagag gagcagugcg aggcgcacaa   2280
ugaguuuucc aaagcuuccu uugggaauga gcccacugua gaguggacac ccaaguacgc   2340
cggcgucucg ccaaaggaca ggugcaagcu caccugugaa gccaaaggca uuggcuacuu   2400
uuucgucuua cagcccaagg uuguagaugg cacucccugu aguccagacu cuaccucugu   2460
```

```
cugugugcaa gggcagugug ugaaagcugg cugugaucgc aucauagacu ccaaaaagaa   2520
guuugauaag uguggcguuu guggaggaaa cgguuccaca ugcaagaaga ugucaggaau   2580
agucacuagu acaagaccug gguaucauga cauugucaca auuccugcug gagccaccaa   2640
cauugaagug aaacaucgga aucaaagggg guccagaaac aauggcagcu uucuggcuau   2700
uagagccgcu gaugguaccu auauucugaa uggaaacuuc acucugucca cacuagagca   2760
agaccucacc uacaaaggua cugucuuaag guacaguggu uccucggcug cgcuggaaag   2820
aauccgcagc uuuaguccac ucaaagaacc cuuaaccauc cagguucuua ugguaggcca   2880
ugcucuccga cccaaaauua aauucaccua cuuuaugaag aagaagacag agucauucaa   2940
cgccauuccc acauuuucug agugggugau ugaagagugg ggggagugcu ccaagacaug   3000
cggcucaggu uggcagagaa gaguagugca gugcagagac auuaacggac acccugcuuc   3060
cgaaugugca aaggaaguga agccagccag uaccagaccu ugugcagacc uucccugccc   3120
acacuggcag gugggggauu ggucaccaug uuccaaaacu ugcgggaagg guuacaagaa   3180
gagaaccuug aaaugugugu cccacgaugg gggcguguua ucaaaugaga gcugugaucc   3240
uuugaagaag ccaaagcauu acauugacuu uugcacacug acacagugca guuaagaggc   3300
guuagaggac aagguagcgu ggggaggggc ugauacacug agugcaagag uacuggaggg   3360
auccagugag ucaaaccagu aagcagugag guguggcaag gaggugugug uaggggauac   3420
auagcaaagg agguagauca ggacacuacc cugccaguua cauucugaua agguaguuaa   3480
ugaggcacag uagcaucuga aagaccauac agagcacuaa ggagccccaa agcacuauua   3540
guaucucuuu ucuuauaucu aucgcccaaa uaauuuucag agucuggcag aagcccuguu   3600
gcacuguacu aacuagauac uucuuaucac aaagauuggg aaaggcaaag cagaaagaug   3660
guaagacugg guuucaaaca aggcuugguu ucaaucacug gaggcaagga ggaggggaca   3720
aacaagauca uuauucgaag ucgcugguug cugugguuuu acggaagguu gaugcaucau   3780
uccuaucaac agugaaaagu ucagcuuguu caacgugaca gaaaggcuca ucuccgugaa   3840
agagcuccug auuucuucuu acaccaucuc aguucuuaac uauaguucau guugagguag   3900
aaacaauuca ucuauuuaua aaauguacau uggaaaaaaa aagugaaguu uaugagguac   3960
acauaaaaac ugaaggaaac aaugagcaac augccuccug cuuugcuucc uccugaggua   4020
aaccugccug gggauugagg uuguuuaaga uuauccaugg cucacaagag gcaguaaaau   4080
aauacauguu gugccagagu uagaaugggg uauagagauc agggucccau gagaugggga   4140
acauggugau cacucaucuc acaugggagg cugcugcag                          4179
```

<210> SEQ ID NO 18
<211> LENGTH: 1416
<212> TYPE: RNA
<213> ORGANISM: Homo sapiens

<400> SEQUENCE: 18

```
ccgcgggccc gcguucaugc accgccugcu ggccugggac gcagcaugcc ucccgccgcc     60
gcccgccgcc uuuagaccca uggaaguggc caacuucuac uacgagcccg acugccuggc    120
cuacggggcc aaggcggccc gcgccgcgcc gcgcgccccc gccgccgagc cggccauugg    180
cgagcacgag cgcgccaucg acuucagccc cuaccuggag ccgcucgcgc ccgccgcgga    240
cuucgccgcg cccgcgcccg cgcaccacga cuuccucucc gaccucuucg ccgacgacua    300
cggcgccaag ccgagcaaga agccggccga cuacgguuac gugagccucg gccgcgcggg    360
```

```
cgccaaggcc gcgccgcccg ccugcuuucc gccgccgccu cccgccgcgc ucaaggcgga    420

gccgggcuuc gaacccgcgg acugcaagcg cgcggacgac gcgcccgcca uggcggccgg    480

uuucccguuc gcccugcgcg ccuaccuggg cuaccaggcg acgccgagcg gcagcagcgg    540

cagccugucc acgucgucgu cguccagccc gcccggcacg ccgagccccg ccgacgccaa    600

ggccgcgccc gccgccugcu ucgcggggcc gccggccgcg cccgccaagg ccaaggccaa    660

gaagacggug gacaagcuga gcgacgagua caagaugcgg cgcgagcgca acaacaucgc    720

ggugcgcaag agccgcgaca aggccaagau gcgcaaccug gagacgcagc acaaggugcu    780

ggagcugacg gcggagaacg agcggcugca gaagaaggug gagcagcugu cgcgagagcu    840

cagcacccug cggaacuugu ucaagcagcu gcccgagccg cugcuggccu cggcgggcca    900

cugcuagcgc ggcgcggugg cgugggggc gccgcggcca ccgugcgccc ugccccgcgc    960

gcuccggccc cgcgcgcgcg cccggaccac cgugcgugcc cugcgcgcac cugcaccugc   1020

accgagggga caccgcgggc acaccgcggg cacgcgcggc gcacgcaccu gcacagcgca   1080

ccggguuucg ggacuugaug caauccggau caaacguggc ugagcgcgug uggacacggg   1140

acuacgcaac acacguguaa cugucuagcc gggcccugag uaaucaccuu aaagauguuc   1200

cugcgggguu guugauguuu uugguuuugu uuuuguuuuu uguuuuguuu uguuuuuuuu   1260

uuuggucuua uuauuuuuuu uguauuauau aaaaaaguuc uauuucuaug agaaaagagg   1320

cguauguaua uuuugagaac cuuuuccguu ucgagcauua aagugaagac auuuuaauaa   1380

acuuuuuugg agaauguuua aaagccaaaa aaaaaa                             1416


<210> SEQ ID NO 19
<211> LENGTH: 566
<212> TYPE: RNA
<213> ORGANISM: Homo sapiens
<220> FEATURE:
<221> NAME/KEY: misc_feature
<222> LOCATION: (154)..(154)
<223> OTHER INFORMATION: n is a, c, g, or u
<220> FEATURE:
<221> NAME/KEY: misc_feature
<222> LOCATION: (254)..(254)
<223> OTHER INFORMATION: n is a, c, g, or u
<220> FEATURE:
<221> NAME/KEY: misc_feature
<222> LOCATION: (262)..(262)
<223> OTHER INFORMATION: n is a, c, g, or u
<220> FEATURE:
<221> NAME/KEY: misc_feature
<222> LOCATION: (287)..(287)
<223> OTHER INFORMATION: n is a, c, g, or u
<220> FEATURE:
<221> NAME/KEY: misc_feature
<222> LOCATION: (305)..(305)
<223> OTHER INFORMATION: n is a, c, g, or u
<220> FEATURE:
<221> NAME/KEY: misc_feature
<222> LOCATION: (354)..(354)
<223> OTHER INFORMATION: n is a, c, g, or u
<220> FEATURE:
<221> NAME/KEY: misc_feature
<222> LOCATION: (378)..(378)
<223> OTHER INFORMATION: n is a, c, g, or u
<220> FEATURE:
<221> NAME/KEY: misc_feature
<222> LOCATION: (419)..(419)
<223> OTHER INFORMATION: n is a, c, g, or u
<220> FEATURE:
<221> NAME/KEY: misc_feature
<222> LOCATION: (449)..(449)
<223> OTHER INFORMATION: n is a, c, g, or u
<220> FEATURE:
<221> NAME/KEY: misc_feature
```

<222> LOCATION: (492)..(493)
<223> OTHER INFORMATION: n is a, c, g, or u
<220> FEATURE:
<221> NAME/KEY: misc_feature
<222> LOCATION: (521)..(521)
<223> OTHER INFORMATION: n is a, c, g, or u
<220> FEATURE:
<221> NAME/KEY: misc_feature
<222> LOCATION: (550)..(550)
<223> OTHER INFORMATION: n is a, c, g, or u

<400> SEQUENCE: 19
aaaauguaga aggcaagauu uaauaaggca gcaacaugaa agcacacaga ccagagcucu 60
ggggucgaaa uaaagcagca acauggaagc acacagagcu cuggggucga aacucauaca 120
ccuuagcaca ggguagagga gucucgacgg ucanccagaa uuuuucacag gcuuauauag 180
uaaaacucaa agggggagaa cugggcaggg aaaguacaag uuuacaucac uagggaguuc 240
ugccaaagga caangggguuc unucagagga aucuacguaa cuaaggnguc auguccuauc 300
aaggnaucua cguaacuaag gagucauguc cuaucauuug gcaauguacc cggnucuuuu 360
gagguuguuc cggagggncu uauucucaaa auguuuuuca gauuggaagg ggugggguunc 420 cgguaaaaag uucuguuuuc aaagaggcng uaauuuucua uucuucauuc cccauucucc 480
uguaaguauu cnnaucuuag aauuucagaa guccauauuc ncuaugugg gaauaacugg 540 cuuuaacccn aucuuuaaaa uggggg 566

<210> SEQ ID NO 20
<211> LENGTH: 358
<212> TYPE: RNA
<213> ORGANISM: Homo sapiens
<220> FEATURE:
<221> NAME/KEY: misc_feature
<222> LOCATION: (269)..(269)
<223> OTHER INFORMATION: n is a, c, g, or u

<400> SEQUENCE: 20
uuuuuuuuuu uuuuuuuaug aaacaguuuu guucagccca ugacuuugug caugacuguc 60
guccguucua gucaccugug cucuccaucu acugccuuuu aaagcugcgu caugagaagg 120
aucuacacgu uccaccauga cucucguuuc uugccacaag uagaagaaau gguugauucu 180
uugcuuuucg guuaggccgu uaaacaaaac ucagucacac cccugccuuc cacccucaaa 240
cugugaucac guggcuguuc uuguaguuna accagggcaa cacuauauau uccaggucua 300
uacauugcug aggucuuuuu cugguuguuc auguaucagu guuuucaacc ucgugccg 358

<210> SEQ ID NO 21
<211> LENGTH: 2149
<212> TYPE: RNA
<213> ORGANISM: Homo sapiens

<400> SEQUENCE: 21
gcggccgcgg cuccagaccc cggccuugcg cacccucccc ccaccuccag cccgcgccuc 60
cccccccccc acgcauggcu caccaccccu cggguuuccc ugucaucccu cagguuccug 120
cacuuggcaa ucauccacga agagaagccg cugaccaugg aagucauugg ucaggugaag 180
ggagaccugg ccuuccucaa cuuccagaac aaccugcagc aggugcgcug cuugcuugcc 240
ccgcggugcc ccucuuugac cccuuggugg agucagaugu agcacggucg cccccaaagc 300
guuucuaaau uaauagucac uuaguucuua ucugccuugg cuuuuuugca uucaaaucag 360
ccaacgucuu agaaccagaa gaaaaauccc uugguuuuag ugaggucuuu augacccacc 420
uagggccucc uguuugccug aucuccuaag agacaaaugg gaggaucaga uuccauagcg 480
ggaggugucu gggguucagg aaacucaaga cuaugggguuu gcuccauggc uuaucccuuu 540
cuguuuccuc uuccauuugu agacuccacu ccacuuggcu gugaucacca accagccagg 600
aauugcugag gcacuucuga aagcuggcug ugauccugag cuccgagacu uucgaggaaa 660
uaccccucua caucuugccu gugagcaggg cugccuggcc aguguagcag ucuugacgca 720
gaccugcaca ccccagcauc uccacuccgu ccugcaggcc accaacuaca augguagguc 780
ugccagucca uccaaggaug cagaggaggg agagagaugg ggccacuuga gucuuaaacu 840
ccgaacguau acaaaguuca gacacuguga ucuuuuuaaa aaguuuucuc cucgaugccu 900
auaugauauu cacucagaac ccagauucug aguucuucaa aacugaugau guuugugguu 960
guccucaaga caauagacau gaguugugug aggauugaaa cacguaguac aguuuuuguc 1020
uuccuccucc aggccacacg ugucugcacc uagccucuac ucacggcuac cuggccaucg 1080
uggagcacuu ggugacuuug ggugcugaug ucaacgcuca ggugaguaca ucucccuucc 1140
accuaaucuc uguugggcug gcucugaugg ugagcagguu uccagaugca gccguaaacu 1200
aacgccugau ugcuuuuggu uucaggagcc cugcaauggc cggacagccc uccaccuugc 1260
gguggaccug cagaauccug accugguuuc gcucuuguug aaaugugggg cugaugucaa 1320
caggguaacc uaccaaggcu acuccccua ccagcuuacc uggggccgcc caaguacccg 1380
gauacagcag cagcugggcc agcugacccu ggaaaaucuc cagaugcuac ccgagagcga 1440
ggaugaggag agcuaugaca cggagucaga auucacagag gaugagguga guguuccucc 1500
ccucagcacg cugacggcug uucuagggcu gcuuuggauc agagggauuu caguuguuua 1560
acuucucaga cucggcuugc aaagcaggau cccaagaauu ugucucuggu uuguuuuaag 1620
agcuuacccu uuugguugag gaaugaggga auucuagaaa uugaacccag gccuuagcac 1680
auggugauaa gcacacguuc aaccauuaag cuccacccc ucaauagcuu agacuuuuuu 1740
uuuuuuuaag gaaagaauag guaagggaaa cuccuacagc cuggugcccu uguucuauuu 1800
ggguuaagga gaaaaagagc ccaagaauag gaguuauuuc agcagcagcu cuccccuuau 1860
cccaaugucu uggugaaguu cuaggaauuu aauaugucuu uuuccccucu cuuguuuuag 1920
cugcccuaug augacugugu guuuggaggc cagcgucuga cauuauaagu ggaaaguggc 1980
aaaaaagaau guggacuugu auauuuguac aaauagaguu uuauuuuucu aaaaaaaaaa 2040
aaaaaaaaaa aaaaaaaaaa aaaaaguaua cuuagcacca caccacacag cgccuagacc 2100
caggcauuuu acuggggguga uucggcuguu gucuuuguga aauccgggg 2149

<210> SEQ ID NO 22
<211> LENGTH: 2062
<212> TYPE: RNA
<213> ORGANISM: Homo sapiens

<400> SEQUENCE: 22
cucucgguca cugccggucg cuuccugagc cgcugcuggc ucugugucuc uguccucagc 60
guucucuucc ucguccucgu ccuaccacgc cauggaaggu uaccauaagc cagaucagca 120
gaagcuccag gcccugaagg acacagccaa ucgccugcgc aucagcucca uccaggccac 180
caccgcggca ggcucaggcc accccacauc augcugcagc gcugccgaga ucauggcugu 240
ccuguuuuuc cauaccaugc gcuacaaggc ccuggauccc cgaaacccuc acaaugaucg 300
cuuugugcuc ucuaagggcc augcagcucc cauuuuauau gcagucuggg cugaagcugg 360
cuuccugccc gaggccgagc ugcugaaccu gaggaagauc agcucugacu uggacgggca 420

-continued

```
uccugucccg aaacaagccu ucaccgaugu ggccacuggc ucccugggcc agggccuggg    480

agcugcuugc gggauggcau acacaggcaa auacuuugac aaagccagcu accgagucua    540

uugcaugcug ggagacgggg aggucuccga gggcuccguc ugggaggcca uggccuuugc    600

uggaauuuac aagcuggaca accucguugc cauuuuugac aucaaccgcc ugggccagag    660

cgacccagcc ccgcugcagc accaggugga caucuaccag aagcgcugug aggccuuugg    720

cuggcacacc aucaucgugg acggacacag cguggaggag cugugcaagg ccuuugguca    780

ggccaagcac caaccaacag ccaucaucgc caagaccuuc aagggccgag ggaucacagg    840

gauugaagac aaggaggcgu ggcacgggaa gccccucccc aaaaacaugg ccgagcagau    900

uauccaggag auuuacagcc agguucagag caaaaagaag auccuggcca cgcccccuca    960

ggaggaugcc ccauccgugg acauugcuaa cauccgaaug ccuacgccac ccagcuacaa   1020

aguggggggac aagauagcca cccggaaggc cuauggacug gcccucgcua agcugggcca   1080

cgccagugac cguaucauug cccuggaugg agacaccaag aauuccaccu ucucggagcu   1140

cuucaaaaag gagcacccag accgguucau ugagugcuac auugccgagc aaaacauggu   1200

gagcauugcc gugggcugug ccacacguga ccggacagug cccuucugca guacuuucgc   1260

ggccuucuuc acacgggccu ucgaccagau ucgcauggcc gccaucucug agagcaacau   1320

caaccucugu ggcucccacu guggugugu cauuggggaa gacgggcccu cucagauggc   1380

ccucgaagac cuggccaugu uccggucagu ccccaugucc accgucuuuu acccaagcga   1440

uggaguugca acagagaagg caguggaguu agcagccaac acaaagggca uuugcuucau   1500

ccggaccagc cgcccagaga augccauuau uuauagcaac aaugaggauu uccaggucgg   1560

ccaagccaag gugguccuga agagcaagga ugaccaagug acagugaucg ggcuggugu   1620

aacucugcau gaggccuugg cugcugcaga gagucuaaag aaagauaaga ucagcauccg   1680

ggugcuggau cccuucacua ucaagccccu ggacaggaaa cucauccuag acucugcccg   1740

agcaaccaaa ggcaggaucc ucaccgugga ggaccacuac uacgaaggug gcauaggaga   1800

ggcagugucu gcugccguag ugggugaacc uggagugacg gucacucgcc uggcugucag   1860

ccaaguacca cgaaguggca agccagcuga gcuacugaag auguucggua uugacaagga   1920

cgccauugug caagcuguga aaggccuugu caccaagggc uagggagggc augggaugcu   1980

gggugggugga acuacacauu ccagggaggu ucuggcagag guggcgaagg uguacugagu   2040

ggggagguaa auauauguuu ug                                            2062
```

<210> SEQ ID NO 23
<211> LENGTH: 230
<212> TYPE: RNA
<213> ORGANISM: Homo sapiens

<400> SEQUENCE: 23

```
uuaacggugu cauaaauaag uaauauaacu uuauuaaaau gaaaagacaa uauucaaaau     60

aaugcaacaa aaugaauaaa uccuuugucc aauacuguac acacagugcg gagaucagug    120

cauuuuucua aagcauguuu uaaccuucau uuaguucaua cuaaaguaag cuuuaaauag    180

cucaaauaau gucauucagc aguuuaaacu gaacagcuug uugggacaug               230
```

<210> SEQ ID NO 24
<211> LENGTH: 1560
<212> TYPE: RNA
<213> ORGANISM: Homo sapiens

<400> SEQUENCE: 24
ugaguucucg uaaacuccag agcagcgaua ggccguaaua ucggggaaag cacuauaggg 60
acaugauguu ccacacguca caugggucgu ccuauccgag ccagucgugc caaaggggcg 120
gucccgcugu gcacacuggc gcuccaggga gcucugcacu ccgcccgaaa agugcgcucg 180
gcucugccag gacgcggggc gcgugacuau gcgugggcug gagcaaccgc cugcugggug 240
caaacccuuu gcgcccggac ucguccaacg acuauaaaga gggcaggcug uccucuaagc 300
gucaccacga cuucaacguc cugaguaccu ucuccucacu uacuccguag cuccagcuuc 360
accagaucuc ggaauggacc ccaacugcuc cugcuccacc gguaagacuc ccgauccuug 420
gucuuuagaa uaccaaguug ggaccgcaga gcggaauccc cgaguuguag aggcuuggcg 480
ggaauaggca ccuuuaguug gcgauucauu ccgguucuuu cuagaauccg cucuugcaaa 540
agccuucauu aguuacgagu auugucgaac ggguccuuug gcgggguugg ggcuaggauu 600
uagacgcgca aauguccggu uccugaucac ccaguuagug gggacaucug gguugagucc 660
caggcauuac uaaacuuacu gugaauugcu ugaauuaaga aagaggugaa ggaccuuuau 720
gucuugggac ucaaagacau aaucccugac uuaaccugug aggagaaaag uggggcuagg 780
cucccugcag cuccgaggag gacuuaguga acugagccgg gacucguggu guuggccacu 840
gcuguaaugc ugccucccuc augcugucuu cuuucuccuc ccaggcggcu ccugcacuug 900
caccagcucc ugcgccugca agaacugcaa gugcaccucc ugcaagaaga gugaguuggg 960
acaccuuggg uggcggcuaa ggcuaggggc ggggaacucc uacaaaacug gcucugagaa 1020
auguccuuug cuucccggag gccauuguau ugucucgggg acagaacuau acagagaacu 1080
auuuaaaaaa accgaggucu ucucuguugg ggacaggaag cagaggucuu cagccaggcu 1140
gccucuuccu ccuucuucua ggcugcugcu ccugcugucc cgugggcugc uccaaaugug 1200
cccagggcug ugucugcaaa ggcgccgcgg acaagugcac gugcugugcc ugaugugacg 1260
aacagcgcug ccaccacgug uaaauaguau cggaccaacc cagcgucuuc cuauacaguu 1320
ccacccuguu uacuaaaccc ccguuuucua ccgaguacgu uaauaaauaa agccuguuug 1380
agucuaacuc ugguuucuug gugugguuug gcaauaagaa acuggggaga cuugauaguc 1440
uggggaucug guuuuggacc cccucgugcc uuuaccuccg cccucuggcc cucacagagg 1500
gguaaugucu uuggguaaag ccaagcuaua ucccauaagc uuccucaugg aaaacagcug 1560

<210> SEQ ID NO 25
<211> LENGTH: 253
<212> TYPE: RNA
<213> ORGANISM: Homo sapiens

<400> SEQUENCE: 25
gcggcacgau gugucuucgg guggcuuuuu uuuuuuuguu uugaauaaug uuuacaauuu 60
cccucaauca cuuuuauaga aauccaccuc caggcccccc ccuuucccca cuuaggccuu 120
cgaggcuguc ugaagaugcu ugagaaacuc aaccaaaucc caguucaauu cagacuuugc 180
acauauauuu auauuuauaa ucagaaaaga aacauuucag uaauuuauaa uaaaagagca 240
cuauuuuuua acg 253

<210> SEQ ID NO 26
<211> LENGTH: 3660
<212> TYPE: RNA
<213> ORGANISM: Homo sapiens

<400> SEQUENCE: 26

-continued

```
uugcaggcga gggcuuccac aacuaccacc acaccuuccc cuucgacuac ucugccagug     60
aguaccgcug gcacaucaac uucaccacgu ucuucaucga cugcauggcu gcccugggcc    120
uggcuuacga ccggaagaaa guuucuaagg cuacugucuu agccaggauu aagagaacug    180
gagacgggag ucacaagagu agcugagcuu ugggcuucug aguuccuguu ucaaacguuu    240
ucuggcagag auuuaauauu cuguugauua acuaacaacu ggauauugcu aucggggugu    300
uaaugaugca uuuaaccuau uccgguacag uauucuuaua aaaugagaaa gcuuugauca    360
cguuuugagg uaauaaauau uuuauuuagc uaggauuaac caugccacaa gacauuauau    420
auuucuaagc acacaugaua aaugcauaua caauuuugca caacagcuuu aaauaauaac    480
aauaaauuug aacauucuau acagagagga ucaaagccaa ggaacaugcu guuuugaugc    540
uagggugagc augugcuca gucccuguuu guuugcaugg uguccagcuu uguuucuucu    600
cugucaucac caccuucagg caaauaguug accaaccacu ggccuguguc uguccacccu    660
ccaaagccca ggccaccuuu cuguuuucug aaauacugau ccuuccuccu gaauacaucc    720
cuccuuguuc cuagcuucaa gacugcugcc ucaaauaggg auagagcaag uccccgcugc    780
agguugugcu agaugggaug gagaaauuau cuucauuuga uacagagcaa guagauuguc    840
ucgagagaaa aguuagcaug cgugguauga uuuguaagua aagauggaag agagagagag    900
agagagagag agagagagag agagagagag agagguagcc auaucuaaca gccuacuuac    960
caaagacccc aggccucucu gcuuggcaug ccuccuuucu guccauccuc ugaaccccag   1020
agauuaguga gauuugaaua auuaaaucau uuucagagug aagggggcua augcaggguc   1080
ugugcuaggg gaggguuuua gcuuuuggua acugaagauu uuuucaugga aaaagucuuc   1140
guguucaaug ugccuagaac ugauaacuaa acagcugaca uuugucgggg acagauaugg   1200
ugugaaacua ugaaaauaua agcaaaaucu ucacuuggaa caugaaacua uuucacuuag   1260
aaaauaaucg aaggacccga gguguugccu ggguugccag uuucuuucgu ggcugggcag   1320
gaacuaguga gguugagggg cagugucugu aaguagcugc uaagaggugc auuuccagau   1380
gaagcccuug gggaacaucu gccagggauc cgcauggugu uggcuccauc cauugcuuua   1440
guuuccuccu uggauugugu agaaacuugg cuucccaugg uuuugaaccu uccaugccuu   1500
cuuugcuuug uggccaccca gccugccuag ugcugccuag gaagcucuua cccaccugau   1560
uucuucugac auuucuuucu uuggccuuuu uuucuuucuc cggacaugca gcuaguugcc   1620
ugaguguauc aagagcaccc aggacuugcu gcuguccagg ccuguuccuc ccccaguauc   1680
cgugggugug gaagagcugu guagcuucag gaagcagagc caggugccac cuuucugugg   1740
cuuccagauc cucccuaccu ccaacucaug ugccucuguc acagugauuu caggaaagcu   1800
ugguagaccc ucuagcaaca ucucgguuca gaaagucucu cugguuugug aguuaacagc   1860
ucagcuaagu gcuguuuugu cucagugagu uaaccacuga augcgagggu ugguuguuga   1920
ucugucucgg ugugugucgg aguagacagc auaugcacuu cucccugugc gcuuugcaag   1980
guaauguggc uuuggcugau ccaugcaggc agguaguggu acagugcugc ugaaaggaag   2040
aaguucccca uuuuaucugu uaaaacacca gagacauggg caagugcuaa uggaccucac   2100
uucaggaaga gggucugcuu ccugaagcca gugugugaug aaaagugacu gagaccugau   2160
aucuaaggug agaccugaua ccuaacacuc ugucacacag uccagggcca acagugcuau   2220
aggaaagucu agaagaaaac aucacaucag uauuuuagaa ccaucaacca ucucuugucc   2280
cuauagccca auccagaggc cugguuuuua gaacuggcug uguaaggugc caaacacuca   2340
```

guucacuugu agaaucagag ccuuuuuucc ccccuauguu aauugaacac gcgcucugag 2400
cuguuuuguu gaaguagaaa aucucauaga aaaaucacug uagaucuacu gaccuauagc 2460
ccucuggaaa ugccuuugag augguuuuac uuuucuaggu cauagaugcc ugauuauaaa 2520
gaugaacaau aaaaucagcu uucuuucuuu cucuucugau cuuauucccc agaucugauu 2580
caggccaugu uccaaagcaa ggcuacauug agguccuggu gucuuuaagu aaaggacauc 2640
uuucagaucc ucucaaagaa ggauuuauaa caguuuccag augaauguac uaauagcuuu 2700
gggugccuua ucucuuuccu aaucuguagu gccugugagc ucagucucac uccuucccuu 2760
agcccggaga ccccuuagau cgagugggaa uagucaagag gcuggcugga gagucaucag 2820
uacauugguu ugcagaaauc uuuuacaggc uacauuuugg aauuuuuuuu uuuuuaguaa 2880
gugaucaaau uuggugggaa guaauucgag uguauucgau uguauuugucg uccucguuau 2940 cauugucaaa cauguuauag acggcaguug gcacuggggc ugcuaaucuc ugggugguagu 3000 cucugaaacu guagcuccag ugaggugguug ugaaagguua gcaaagccac caucugcugg 3060
ugcuccagcc aaggugccuc uuagccacug aauugcuaug uuauccuuuc ucuuguaaca 3120
aacccacccc agagauaaag ccuuuaauca acccaagaaa cuccugggcu aaguaucuga 3180
cagucucaca ucucaacagu gugaauuaag uguccauagc aucagcucag gaggacacuc 3240
ugggagagug cugacaaaaa aggguuauua auacugaccu acuacuucaa gggcaguucu 3300
gaggugauua gagcuuuuuu uaaaaaccaa guauuugggg auccucagca gagguauuca 3360
uacagacucc caaagaacua uauauguucc ugagaccauc guuuagucua cauugcucuu 3420
cccagagacu gacagauaug accagucaaa gugcaagacu accuacccac ugccaugaaa 3480
accauugcag gaaaccuuuc ccuuccugaa ugagauuuuu uuuuucccuu uuuaugugg 3540 guaauuauuu gugacccaag uguaauuugg augauuucca uuaauaucaa cucuugaagc 3600
cuacuuguac ugauugagau uguauuuguu ccuaauaaaa guggaucugg uuguacuguc 3660

<210> SEQ ID NO 27
<211> LENGTH: 1969
<212> TYPE: RNA
<213> ORGANISM: Homo sapiens

<400> SEQUENCE: 27
acugccaucg aguggguguuc caguugaacu ugcucucucu gccaucugcu ccgcgggcgc 60
cgucagcaug ggucccugga cccacuccuu gcgcgccguc cugcugcugg ugcuuuuggg 120
agucugcacc gugcgcuccg acacuccugc caacugcacc uacccugauc ugcugggcac 180
cuggguguuc caggugggcc cuagaaguuc ccgaagcgac auuaacugcu cggugaugga 240
agcaacagaa gaaaagguag ugguacaccu uaagaaguug gauacugccu acgacgagcu 300
gggcaauucc gggcauuuua ccccucauuua caaccaaggc uucgagauug uguugaauga 360
cuacaaaugg uuugcguuuu ucaaguauga agucagaggc cacacagcua ucaguuacug 420
ccaugagacc augacugggu ggguccauga ugugcugggc cggaacuggg cuugcuuugu 480
uggcaagaag guggaaaguc acauugagaa gguuaauaug aaugcagcac aucuuggagg 540
ucuccaggaa agauauucug aaagacucua cacucacaac cacaacuuug ugaaggccau 600
caauaccguu cagaagucuu ggacugcaac ugcauauaag gaauaugaga aaaugagccu 660
gcgagaucug auaaggagaa guggccacag ccaaaggauc ccaaggccca aaccugcccc 720
gaugacugau gaaauacagc aacaaauuuu aaauuugcca gaaucuuggg acuggagaaa 780
cguccaaggc gucaauuaug uuagcccugu ucgaaaccaa gaaucuugug gaagcugcua 840
cucauuugcc ucuaugggua ugcuagaagc aagaauucgu auauuaacca acaauucuca 900
gacaccaauc cugaguccuc aggagguugu aucuugcagc cccuaugccc aagguuguga 960
ugguggauuc ccauaccuca uugcagggaa guaugcccaa gauuuugggg ugguggaaga 1020
aagcugcuuu cccuacacag ccaaagauuc uccaugcaaa ccaagggaga auugccuccg 1080
uuacuauucu ucugacuacu acuaugūggg ugguuucuau gguggcugca augaagcccu 1140
gaugaagcuu gagcugguca aacauggacc cauggcaguu gccuuugaag uccacgauga 1200
cuuccuacac uaccacagug gaaucuauca ccacacuggg cugagugacc cuuucaaccc 1260
cuucgagcug acaaaucaug cuguuuugcu ugugggcuau ggaagagauc caguuacugg 1320
gauagaauac uggauuauaa agaacagcug ggcucuaac ugggggggaga guggcuacuu 1380 ccguauccgc agaggaacug augaaugugc aauugagagu auagccgugg cggccauacc 1440
gauuccuaaa uuauaggaca uagcucccag uguuacauac gggucuuuau cacucacaga 1500
gugauuuagu cacaugcuga agacuuuuuc agagcaauau cagaagcuua ccacuaagca 1560
ucuuuaaaga auuuugucuu ugaacuuaaa accauccuug auuuuuuucu uuuaauaucu 1620
uccccaucaa cuacugaacu acuuuucuuu uuaaaguacu ugguuaagua auacuuuuau 1680
gagcaguggu ucaguugucc aauauuuuuu gcaggucauc uacaaugcaa ccagauguuu 1740
caguucuaaa aaucuaugua aaaguacaag cucguuuuua aauuauguaa gucacaugaa 1800
aacauggcaa aaaaauuagu uaaauuuuuu acaaagaguu uuaaauaaau guuuauguaa 1860
ucaguaccau agucuuucua ugugguuua caagaauuuu ugucaccuac uucuucccuu 1920
agaagcauuu augcuccaug gacguacuuc uuuauggaga aaaaaaaaa 1969

<210> SEQ ID NO 28
<211> LENGTH: 1478
<212> TYPE: RNA
<213> ORGANISM: Homo sapiens

<400> SEQUENCE: 28
gagcucgauc ccuguuccgc cuuugcuaug ucugaaggcg uccugcuuug cgcgugucgg 60
ggccaaaucc agauuuucau uucgcuccag gcuuggacgg cuaaguaggu ccaaaccgca 120
caaacaggaa ggagggaagg caaggagugc gggcagaggg cgggucguuc ccagcagcac 180
cccagucccu ccccgcuccg ucuccgaccc acuggggccg gggcgggcgu gcgcgucagc 240
uggggcuaga aaaggcggcg guccggcccg gcgaggugac agccaacuug gacgccaggu 300
ccggccgacg ccgccaugag cgccgcgcuu uucagccugg acagcccggu gcgcggcaca 360
cccuggccca cagaacccgc ggccuucuac gagccaggca ggguggacaa gcccggccga 420
gggcccgagc caggggaacu gggggagcug ggcuccacga cuccugccau guacgacgac 480
gagagcgcca ucgacuucag cgccuacauu gacuccaugg ccgccgugcc cacccuagag 540
cugugccacg acgaacucuu cgccgaccuc uucaacagca accacaaagc ggccggcgcg 600
ggcggccugg agcugcugca gggcggcccu acgcgacccc cgggugguggg gucugucgcu 660 agggggccgc ucaagcgcga acccgacugg ggcgacggcg acgcgccggg cucccugcug 720
ccggcgcaag uggcggugug cgcgcagaca guggugagcu uggcggccgc ggcucagccc 780
acuccaccca cuucgccgga gccuccucga ggcagcccgg ggccgagccu cgcgcccggc 840
acaguccgag aaaagggcgc gggcaagagg gguccggacc gcggcagccc ggaguaccgg 900
cagcggcgcg agcgcaacaa caucgcugug cgcaagagcc gcgacaaggc caagcgccgc 960

-continued

```
aaccaggaga ugcagcagaa gcugguggag uugucggccg agaacgagaa gcugcaucag   1020

cgcguggagc agcucacccg ggaccuggcu ggccuccggc aguucuucaa aaaacugccc   1080

agcccgccuu uccugccgcc caccggcgcc gacugccggu aacgcgcggc gugggccuuu   1140

gagacucuga acgaccuaua ccucagaccc cgacagcggg gagcagacgc cgcccgaauc   1200

gcuaguuucu uugggaccug cgagcgacag gaagcugcag cuugggcacu ggacugcgag   1260

agaagcuaua uuaaucuuuc cccuuaaauu auuuuuuaua augguagcau uuucuacguc   1320

uuauuaccau ugcagcuaag guacauuugu agaaaagaca uuuccgacag acuuuuguag   1380

auaagaggaa gagacugcgc augcuuuuua uauucauuuu uacaguauuu guaagaauaa   1440

gaauaagaau aaagaagcau uuaaaucgca aaaaaaaa                             1478
```

<210> SEQ ID NO 29
<211> LENGTH: 1786
<212> TYPE: RNA
<213> ORGANISM: Homo sapiens

<400> SEQUENCE: 29

```
uugagggugg ccaggccagc guaggaggcc agcguaggau ccugcuggga gcggggaacu     60

gagggaagcg acgccgagaa agcaggcgua ccacggaggg agagaaaagc uccggaagcc    120

cagcagcgcc uuuacgcaca gcugccaacu ggccgcugcc gaccgucucc agcucccgag    180

gacgcgcgac cggacaccgg guccugccac agccgaggac agcucgccgc ucgccgcagc    240

gagcccgggg cggcccuuca gggggaccuu ucccagaucg cccaggccgc ccggaugugc    300

acgaaaaugg aacagccuuu cuaucacgac gacucuuacg cagcggcggg auacggucgg    360

agcccuggca gccugucucu acacgacuac aaacuccuga aacccaccuu ggcgcucaac    420

cuggcggauc ccuaucgggg ucucaagggu ccuggggcgc ggggguccagg cccggagggc    480

aguggggcag gcagcuacuu uucgggucag ggaucagaca caggcgcauc ucugaagcua    540

gccuccacgg aacuggagcg cuugaucguc cccaacagca acggcgugau cacgacgacg    600

cccacgccuc cgggacagua cuuuuacccc cgugggggug gcagcggugg agguacaggg    660

ggcggcguca ccgaggagca ggagggcuuu gcggacgguu uugucaaagc ccuggacgac    720

cugcacaaga ugaaccacgu gacgcccccc aacgеguccc ugggcgccag cgggggсuccc    780

caggccggcc cagggggcgu cuaugcuggu ccggagccgc cucccgucua caccaaccuc    840

agcaguuacu cuccagccuc ugcacccucu ggaggcuccg ggaccgccgu gcggacuggg    900

agcucauacc cgacggccac caucagcuac cucccacaug caccacccuu ugcgggcggc    960

cacccggcac agcuggguuu gagucguggc gcuuccgccu uuaaagagga accgcagacc   1020

guaccggagg cacgcagccg cgacgccacg ccgccugugu cccccaucaa cauggaagac   1080

caggagcgca ucaaagugga gcgaaagcgg cugcggaaca ggcuggcggc caccaagugc   1140

cggaagcgga agcuggagcg caucgcgcgc cuggaggaca aggugaagac acucaaggcu   1200

gagaacgcgg ggcugucgag ugcugccggu cuccuaaggg agcaaguggc gcagcucaag   1260

cagaagguca ugacccaugu cagcaacggc ugccaguugc ugcuaggggu caagggacac   1320

gccuucugag agccucccuu gccccauacg gacaccccca gccuugaagg cugggcgccu   1380

gccccccacu ggggugaggg gggcaggcga ugggcacccg ccaaaaggcc uggggcgcag   1440

cucacacacu ggacuccggc ccgcccgccu gcgcccaguc cuuccaccuc gagguuuaca   1500

uggcccccuu ccagcguauu uuguauguuu uuuuuuucug caaagagacu gaauucauau   1560

ugaauauaau auauuugugu auuuaacagg agggagaagg gggcugucgc ggcggagcug   1620
```

gccgccgcuu gguacucagc ugcggggaua cuagggaggg accuccgccc ccugcccucc 1680
cccucugcau aguacugugg agaagaaaca cgacuucgug ucuaaagucu auuuuaagau 1740
guguuugugu gugugaguuu gacuuuuuau ugaaucuauu uaagua 1786

<210> SEQ ID NO 30
<211> LENGTH: 1897
<212> TYPE: RNA
<213> ORGANISM: Homo sapiens

<400> SEQUENCE: 30
gaauucggca cgagcagcga gacgccgcgc acggugcuuc cccaguggag ccaaucggcu 60
aacccgcgcu ccggcagagu ccuuggcgcu cgcccgccgg cgggacagac cacccgccuc 120
uggccgcucu cuggacccug gccgccccga gcgaagacug gagcaaaaug augcuucaac 180
auccaggcca ggucucugcc ucagaaguca gugcgaccgc cauuguccccc ugccucucac 240 cuccuggguc acugguauuu gaggauuuug cuaaccugac acccuuuguc aaggaagagc 300
ugagauucgc cauccagaau aaacaccucu gccaucggau guccucugcg cuggagucag 360
uuaccgucaa caacagaccc cuggagaugu cagucaccaa gucugaggcg gccccugaag 420
aagaugagag gaaaaggagg cggcgagaaa gaaauaaaau ugcugcugcc aagugucgaa 480
acaagaaaaa ggagaagaca gagugccugc agaaagaguc agagaaacug gagaguguga 540
augcugagcu gaaggcccag auugaggagc ugaagaauga gaaacagcau uugauauaca 600
ugcucaaccu gcaccggccc accuguaucg uccgggcuca gaauggacgg acaccggaag 660
acgagaggaa ccucuuuauc caacagauaa aagaaggaac auugcagagc uaagcagagg 720
uggcacggag gcaauugggg aguucuuacu gaauccuccu uuuccacccc acacccugaa 780
gccauuggaa aacuggcuuc cugugcacuu cuagaauccc agcagccaag agccguuggg 840
gcaggagggc cugugguggac cuacugcauu gacccacucu gcccccgagu gaaccgugga 900
gcaggcagga gcauccuuug ucucaccaau uccaggauuu aggccuuauc aucccggcca 960
gucucagaug accuagcugg ccccaggcug ggguccuaug caaagcagga ucccacuaau 1020
gggauucagg cagaaguguc uaccuugaua gguggggugg gaccacaucc uccacugugg 1080
cugacaacgc ccuuccaagg gaauauggaa ugagaacauu cauuauugag guuguccaau 1140
ggccagggua ugcuuucuag aaaauaugcu guucugucc agaaugacug ugcauagggu 1200
auccguuuca gagccuggug uugugcuauu uagauguuug ucuugcacaa cauuggcaug 1260
auuuuuccgg gaguuucauc agaucugauu ucugagaguc uggggaucug ccauggugga 1320
aagugccccu caaaagcauu ugugugggcca caugaacugg cuggcaccag gggagugaaa 1380
cuggcugaug accagcugag ccacuuugug ccaacagagg auggacgaca ccuuucccug 1440
uacccacugc agaggaagaa cccugggcac agcagcuuug uccuuggcua caaacuguua 1500
caacgucaca caaugaaggc acaaagucca acuuucaaag gguguaggac uccauacuca 1560
gugacagggc aggaagagcc aaagauaacc acagccacag ccuguggaga ccaggguugg 1620
aagccaggug cagggccagg caucugcauu gugggauguu aauggcacuu uugucuugua 1680
gcuauuuuga gauguggucc agagcauuuc agcugggaga ucucccucug gccaccagga 1740
cucuggcuac uguuaaaauc cugauguuuc uguggaaucc ucaguguuua aucccacuca 1800
auaguaucau uacaguuuuc uguaagagaa aauauuacuu auuuauccca guauuccuag 1860
ccugucaaca uaauaaauau cggaacaaaa ccuggua 1897

<210> SEQ ID NO 31
<211> LENGTH: 473
<212> TYPE: RNA
<213> ORGANISM: Homo sapiens

<400> SEQUENCE: 31
uuuuuuuuuu uuuuuuugcu gauaagaauu cuuuuuaugu uauucgaaua aaaaauacau 60
ucauacagaa auauaacaau cucgcaaaaa acaauuucaa auaaaaucuu guaaaacaaa 120
auuuuacaaa aaucuuacaa agauucuuua gauaacaggg ugcuucaaaa aaaaagaaau 180
aaagaaauuu cacuaauaga aauuuuuuuu uuuaauuuca agcaaaaguu ccugcuugau 240
ugaggcucag uugucaccug accagaaugg acugcuuagu auuaaaguua cagcaucgac 300
acggacggca cccagcccca gccaguccag caacgucgcu guguuucaua agugagacgc 360
gccagcacaa guuuccucuc ucuucuguuu accuucuuac uuaauggaau ugcuauggau 420
aagcacacag cagggccaaa aaaggaguuu uccaaaaucc agcaaaucaa gug 473

<210> SEQ ID NO 32
<211> LENGTH: 1680
<212> TYPE: RNA
<213> ORGANISM: Homo sapiens

<400> SEQUENCE: 32
uaguggugau cuggaccgug cggacuugcu cgucccucag cucuccuguu aggcgucucu 60
uuucuccagg aggaaaaaau ggcagcagca guaguggauc cgcaacagag cguggugaug 120
agaguggcca accugcccuu ggugagcucu accuacgacc uuguguccuc cgcuuauguc 180
aguacaaagg aucaguaccc guauuugaga uccgugugug agauggccga gaagggcgug 240
aagaccguga ccucugcggc caugacaagu gcccugccca ucauccagaa gcuggagcca 300
caaauugcgg uugccaauac cuaugccugc aaggggcuag acaggaugga ggaaagacug 360
ccuauucuga accagccaac guccgagauu guugccagug ccagaggugc cguaacuggg 420
gcgaaggaug uggugacgac uaccauggcu ggagccaagg auucuguagc cagcacaguc 480
ucaggggugg uggauaagac caaaggagca gugacuggca gcguggaaag gaccaagucu 540
guggucaaug gcagcaucaa uacaguuuug ggauggugc aguucaugaa caguggagua 600
gauaaugcca ucaccaaguc ggagaugcug guagaccagu acuucccucu cacucaggag 660
gagcuggaga uggaagcaaa aaagguggaa ggauuugaua ugguucagaa gccgagcaac 720
uaugaacggc uggagucccu gucuaccaag cucugcucuc gggcuuauca ccaggcucuc 780
agcaggguua aagaggccaa acaaaagagc caggagacca uuucucagcu ccacuccacu 840
guccaccuga uugaauucgc caggaagaau augcacagug ccaaccagaa aauucagggu 900
gcucaggaua agcucuaugu cucgugggug gaguggaaga gaagcaucgg cuacgacgac 960
accgaugagu cccacugugu ugagcacauc gagucacgua cucuggcuau cgcccgcaac 1020
cugacccagc agcuccagac uacaugccag acuguccugg ucaacgccca aggguuacca 1080
cagaacauuc aagaucaggc caaacacuug ggggugaugg caggcgacau cuacuccgua 1140
uuccgcaaug cugccuccuu uaaggaagug uccgauggcg uccucacauc uagcaagggg 1200
cagcugcaga aaaugaagga auccuuagau gaaguuaugg auuacuuugu uaacaacacg 1260
ccucucaacu ggcugguagg ucccuuuuau ccucagucua ccgaggugaa caaggccagc 1320
cugaaggucc agcagucuga ggucaaagcu caguaaaccc cuccuuguca ccagagcaug 1380
auguugcugg ccagaugacc ccuuuugcug uauugaaauu aacuugguag auggcuuuag 1440
cuuagaaaag cagcuucuua gaaccaaggg ccucauuaug gucacucaca gcucaguuau 1500
ggucuugccc cagcuggccc uggcacagga guucucuuac cuggcuggug aguggccugu 1560
guuagucuug ugaggaccug gaggaaccua aaagcucaga ugcacuuaca gucuugucug 1620
uggccuuugu auuguuauug gcuguaaacg ucugucugga ccgaauaaag auucacguga 1680

<210> SEQ ID NO 33
<211> LENGTH: 1783
<212> TYPE: RNA
<213> ORGANISM: Homo sapiens

<400> SEQUENCE: 33
ggcacgaggg agcugcagug uucgcgcuug guagcuggug caucggacuc agcuggcuuu 60 guguccccuga ggcucaccga aaaacacuuu cucagcccuc ugacuccaga gagagagaga 120
gagagguacu uuuuguggguc accgacuuug accccugcag aggcugagcg auggcgucua 180
ugggacuaca gguccuggga aucuccuugg caguccuggg cuggcugggg aucauccuga 240
guugugcgcu ccccaugugg cgggugaccg ccuucaucgg cagcaacauc gucacggcac 300
agaccagcug ggagggccuc uggaugaacu gcguggugca gagcacaggu cagaugcagu 360
gcaagaugua cgacucgaug cucgcccugc cgcaggaccu gcaggccgcc cgagcccuua 420
uggucaucag caucaucgug ggugcucugg ggaugcuucu cucaguggua gggggcaagu 480
gcaccaacug cauggaggac gagaccguca aggccaagau caugaucacc gccggagccg 540
uguucaucgu ggcaagcaug cugauuaugg ugcccguguc cuggaccgcu cacaacguca 600
uccgcgacuu cuacaacccu auggguggcuu ccgggcagaa gagggaaaug ggggccucgc 660
uuuacgucgg cugggcggcc uccgggcugc ugcuccuggg aggaggccuc cucugcugca 720
guugcccacc ucguagcaac gacaagcccu acucggccaa guacuccgcc gcccgcucug 780
uccccgccag caacuaugug uaaggugggc cacucugucc acauugccuu uguuauuuuu 840
uuucggauug agcucauaac agccugugggc cccucacauu cuccaggacc ugcccugcua 900
ugggccacua acugcuugcu ggggacaggc aaacccggac ugugcaaagu uacuagcccg 960
uagcucuugg gcugcuccac auggcucccuu acggccggca agaauggaug uaaaaaauauc 1020 uugcugcuua cauccaaauu gcgguggaua ugggcugaag gcagaagcag cugggaaggg 1080
caguagaggc gcaagcuggg uccugcuggc cggggguagcu cagcugugac uuuggacucg 1140
gaguggaugu ccucauguua gcaaacgucc acuguccuuu cucuaucccc cucacucagc 1200
cuacacguua cuccagcgcu acucuugcca uuacgccccg uguuuccgag cacagcuggu 1260
ccuaccccaa gucauggugu gcugagugac ugaugagggg ccauugagag ccggugggcu 1320
cugccaugga acccuuccgu ugauuagcaa ugacugugcu ugacccaccc accuacccua 1380
cuaaugaauu ucuguagagu ggauggacgg guuugaggga agaagggugg agguggauua 1440
aacugguuug gggagggcug gggaccuaga agcagcccag ugugucccca ccccuuuucc 1500
gcacugucuu gcuaauguuc ugaucacugu gcgcccccuc ccucuucaga aggacccugg 1560
gccucuugag uuggccccuc ugaguucccu cccuuugccc auuucaagga caccggccag 1620
ucugcggaag gaagguacgg gggggggggg ggggggugau ggcauuguac cagggagucu 1680
ccuggacucc ccugccuucu cugugguuuc uuguuuugua auuaaggucu guucacagcu 1740
guaauuauua uuauuuucua caauaaaugg caccugcaua cag 1783

<210> SEQ ID NO 34

<211> LENGTH: 1786
<212> TYPE: RNA
<213> ORGANISM: Homo sapiens

<400> SEQUENCE: 34
uugagggugg ccaggccagc guaggaggcc agcguaggau ccugcuggga gcggggaacu 60
gagggaagcg acgccgagaa agcaggcgua ccacggaggg agagaaaagc uccggaagcc 120
cagcagcgcc uuuacgcaca gcugccaacu ggccgcugcc gaccgucucc agcucccgag 180
gacgcgcgac cggacaccgg guccugccac agccgaggac agcucgccgc ucgccgcagc 240
gagcccgggg cggcccuuca gggggaccuu ucccagaucg cccaggccgc ccggaugugc 300
acgaaaaugg aacagccuuu cuaucacgac gacucuuacg cagcggcggg auacggucgg 360
agcccuggca gccugucucu acacgacuac aaacuccuga aacccaccuu ggcgcucaac 420
cuggcggauc ccuaucgggg ucucaagggu ccuggggcgc gggguccagg cccggagggc 480
aguggggcag gcagcuacuu uucgggucag ggaucagaca caggcgcauc ucugaagcua 540
gccuccacgg aacuggagcg cuugaucguc cccaacagca acggcgugau cacgacgacg 600
cccacgccuc cgggacagua cuuuuacccc cgugggggug gcagcggugg agguacaggg 660
ggcggcguca ccgaggagca ggagggcuuu gcggacgguu uugucaaagc ccuggacgac 720
cugcacaaga ugaaccacgu gacgcccccc aacgugcccc ugggcgccag cgggggcccc 780
caggccggcc cagggggcgu cuaugcuggu ccggagccgc cucccgucua caccaaccuc 840
agcaguuacu cuccagccuc ugcacccucu ggaggcuccg ggaccgccgu gcggacuggg 900
agcucauacc cgacggccac caucagcuac cucccacaug caccacccuu ugcgggcggc 960
cacccggcac agcuggguuu gagucguggc gcuuccgccu uuaaagagga accgcagacc 1020
guaccggagg cacgcagccg cgacgccacg ccgccugugu cccccaucaa cauggaagac 1080
caggagcgca ucaaagugga gcgaaagcgg cugcggaaca ggcuggcggc caccaagugc 1140
cggaagcgga agcuggagcg caucgcgcgc cuggaggaca aggugaagac acucaaggcu 1200
gagaacgcgg ggcugucgag ugcugccggu cuccuaaggg agcaaguggc gcagcucaag 1260
cagaagguca ugacccaugu cagcaacggc ugccaguugc ugcuaggggu caagggacac 1320
gccuucugag agccucccuu gccccauacg gacacccca gccuugaagg cugggcgccu 1380
gccccccacu ggggugaggg gggcaggcga ugggcacccg ccaaaaggcc uggggcgcag 1440
cucacacacu ggacuccggc ccgcccgccu gcgcccaguc cuuccaccuc gagguuuaca 1500
uggcccccuu ccagcguauu uuguauguuu uuuuuuucug caaagagacu gaauucauau 1560
ugaauauaau auauuugugu auuuaacagg agggagaagg gggcugucgc ggcggagcug 1620
gccgccgcuu gguacucagc ugcggggaua cuagggaggg accuccgccc ccugcccucc 1680
cccucugcau aguacugugg agaagaaaca cgacuucgug ucuaaagucu auuuuaagau 1740
guguuugugu gugugugu uu gacuuuuuau ugaaucuauu uaagua 1786

<210> SEQ ID NO 35
<211> LENGTH: 1389
<212> TYPE: RNA
<213> ORGANISM: Homo sapiens

<400> SEQUENCE: 35
augcagcuga gaaaaaugca gaccaucaaa aaggagcccg caccccuaga uccuaccagc 60
agcucagaca agaugcugcu gcugaacucu gccuuagcug agguggccga ggaccuagcc 120
ucaggugaag auuugcuccu gaacgaaggg agcaugggga aaaacaaauc cucggcgugu 180

```
cggagaaaac gggaauucau uccggacgag aagaaagacg ccauguauug ggagaaacgg    240
cggaaaaaca acgaagcugc caaaagaucu cgggagaagc gccgccucaa ugaccugguu    300
uuggagaaca agcugauugc ccugggagaa gaaaaugcca cuuuaaaagc ugagcugcuc    360
ucccugaaau uaaaguuugg uuuaauuagc uccacggcgu augcccaaga aauccagaaa    420
cucaguaauu ccacagcugu cuacuuucag gacuaccaga cauccaaggc ugccgugagc    480
ucuuuugugg acgagcauga gccugcgaug guagccggaa guugcaucuc agucaucaag    540
cacucucccc agagcucgcu cuccgaugug ucagaggugu ccucggugga gcacacucag    600
gaaagccccg cacagggagg cugccggagc ccugagaaca aguucccugu gaucaagcag    660
gagcccgugg aguuggagag cuuugccagg gaggccaggg aggagcgggg cacguauucc    720
accuccaucu accagagcua caugggaagc ucuuucucca cuuacuccca cuccccaccc    780
cucuugcagg uccaugggucc cacuagcaac uccccaagaa ccucagaggc cgaugagggu    840
guagugggca agucuucuga uggggaagac gaacaacagg ucccuaaggg ccccauccau    900
ucuccagugg agcugcaacg gguucacgcc acggugguga agguuccgga agugaacccu    960
ucugccuuac cgcacaagcu ucggauuaaa gccaaggcca ugcaggucaa aguggaggcu   1020
uuggacagcg aguuugaagg caugcagaaa cucucuucac ccgccgaugc gaucgccaaa   1080
agacauuuug accuggagaa acauggaacc ucggguaugg cccauuccuc ccucccuccu   1140
uucucagugc aggugacgaa cauucaagau ugguccuca aaucggaaca cuggcaucac   1200
aaagaacuga gcagcaaaac ucagaguagc uucaaaacag guguggugga agucaaagac   1260
gguggcuaua agguuuccga agcugagaau uuguauuuga agcagggaau agcaaacuua   1320
ucugcagagg uggucucgcu caagagauuc auagccacac aaccgaucuc ggcuucggac   1380
uccagguaa                                                           1389
```

<210> SEQ ID NO 36
<211> LENGTH: 961
<212> TYPE: RNA
<213> ORGANISM: Homo sapiens

<400> SEQUENCE: 36

```
gcucccggga aacgaaugag gaaccaccuc cuccugcugu ucaaguacag gggccuggug     60
cgcaaaggga agaaaagcaa aagacgaaaa uggcuaaauu uaagauccgu ccagccacug    120
ccucugacug cagugacauc cugcgacuga ucaaggaacu ggcuaaauau gaauacaugg    180
aagaucaagu cauuuuaacu gagaaagauc uccaagagga uggcuuugga gaacaccccu    240
ucuaccacug ccugguugca gaagugccua aagagcacug gaccccugaa ggacauagca    300
uuguuggguu cgccauguac uauuuuaccu augacccaug gauuggcaag uugcuguauc    360
uugaagacuu cuucgugaug agugauuaca gaggcuuugg uauaggauca gaaauuuuga    420
agaaucuaag ccagguugcc augaagugucc gcugcagcag uaugcacuuc uugguagcag    480
aauggaauga accaucuauc aacuucuaca aaagaagagg ugcuucggau cuguccagug    540
aagagggaug gaggcucuuc aagauugaca aagaguacuu gcuaaaaaug gcagcagagg    600
agugaggcgu gccgguguag acaaugacaa ccuccauugu gcuuuagaau aauucucagc    660
uucccuugcu uucuaucuug uguguaguga aauaauagag cgagcaccca uuccaaagcu    720
uuauuaccag ugacguuguu gcauguuuga aauucggucu guuuaaagug gcagucaugu    780
augugguuug gaggcagaau ucuugaacau cuuuugauga agaacaaggu gguaugaucu    840
```

-continued

```
uacuauauaa gaaaaacaaa acuucauucu ugugagucau uuaaaaugugu acaauguaca    900

cacugguacu uagaguuucu guuuugauuc uuuuuuuuua aauaaacucg cucuuugauu    960

u                                                                     961
```

<210> SEQ ID NO 37
<211> LENGTH: 2187
<212> TYPE: RNA
<213> ORGANISM: Homo sapiens

<400> SEQUENCE: 37

```
cgcuggcucc gugcgccaug gucacccaca gcaaguuucc cgccgccggg augagccgcc     60

cccuggacac cagccugcgc cucaagaccu ucagcuccaa aagcgaguac cagcuggugg    120

ugaacgccgu gcgcaagcug caggagagcg gauucuacug gagcgccgug accggcggcg    180

aggcgaaccu gcugcucagc gccgagcccg cgggcaccuu ucuuauccgc gacagcucgg    240

accagcgcca cuucuucacg uugagcguca agacccaguc ggggaccaag aaccuacgca    300

uccagugugga gggggcagc uuuucgcugc agagugaccc ccgaagcacg cagccaguuc    360

cccgcuucga cuguguacuc aagcuggugc accacuacau gccgccucca gggaccccu    420

ccuuuucuuu gccacccacg gaacccucgu ccgaaguucc ggagcagcca ccugcccagg    480

cacuccccgg gaguaccccc aagagagcuu acuacaucua uucugggggc gagaagauuc    540

cgcugguacu gagccgaccu cucuccucca acguggccac ccuccagcau cuuugucgga    600

agacugucaa cggccaccug gacuccuaug agaaagugac ccagcugccu ggacccauuc    660

gggaguuccu ggaucaguau gaugcuccac uuuaaggagc aaaaggguca gaggggggcc    720

ugggucgguc ggucgccucu ccuccgaggc acauggcaca agcacaaaaa uccagcccca    780

acggucggua gcucccagug agccaggggc agauuggcuu cuuccucagg cccuccacuc    840

ccgcagagua gagcuggcag gaccuggaau ucgucugagg ggaggggggag cugccaccug    900

cuuucccccc ucccccagcu ccagcuucuu ucaaguggag ccagccggcc uggccuggug    960

ggacaauacc uuugacaagc ggacucuccc cuccccuucc uccacacccc cucugcuucc   1020

caagggaggu ggggacaccu ccaaguguug aacuuagaac ugcaagggga aucuucaaac   1080

uuucccgcug gaacuuguuu gcgcuuugau uugguuugau caagagcagg caccuggggg   1140

aaggauggaa gagaaaaggg ugugugaagg guuuuuaugc uggccaaaga aauaaccacu   1200

cccacugccc aaccuaggug aggaguggug gcuccuggcu cuggggagag uggcaagggg   1260

ugaccugaag agagcuauac uggugccagg cuccucucca uggggcagcu aaugaaaccu   1320

cgcagauccc uugcacccca gaacccuccc cguugugaag aggcaguagc auuuagaagg   1380

gagacagaug aggcugguga gcuggccgcc uuuuccaaca ccgaagggag gcagaucaac   1440

agaugagcca ucuuggagcc cagguuuccc cuggagcaga uggaggguuc ugcuuugucu   1500

cuccuaugug gggcuaggag acucgccuua aaugcccucu gucccaggga uggggauugg   1560

cacacaagga gccaaacaca gccaauaggc agagaguuga gggauucacc caggugggcua   1620

caggccaggg gaaguggcug caggggagag acccagucac uccaggagac uccugaguua   1680

acacugggaa gacauuggcc aguccuaguc aucucucggu caguaggucc gagagcuucc   1740

aggcccugca cagcccuccu uucucaccug gggggaggca ggaggugaug gagaagccuu   1800

cccaugccgc ucacaggggc cucacgggaa ugcagcagcc augcaauuac cuggaacugg   1860

uccuguguug gggagaaaca aguuuucuga agucagguau ggggcugggu ggggcagcug   1920

uguguugggg uggcuuuuuu cucucuguuu ugaauaaugu uuacaauuug ccucaaucac   1980
```

uuuuauaaaa auccaccucc agcccgcccc ucuccccacu caggccuucg aggcugucug 2040
aagaugcuug aaaaacucaa ccaaauccca guucaacuca gacuuugcac auauauuuau 2100
auuuauacuc agaaaagaaa cauuucagua auuuauaaua aaagagcacu auuuuuuaau 2160
gaaaaaaaaa aaaaaaaaaa aaaaaaa 2187

<210> SEQ ID NO 38
<211> LENGTH: 2046
<212> TYPE: RNA
<213> ORGANISM: Homo sapiens

<400> SEQUENCE: 38
aaggaaucuu caguacagaa acaagaccca aguguaaguu uaacuggcag gaggaaccaa 60
ccaaggacag uuaaggagaa aacccaaccc uuagaagaac ucaccaguuu ccaagaggaa 120
acugccaaaa gaauaucuuc caaaucucca caaccggaag agaaggaaac cuuagcaggu 180
uuaaagaggc agcucagaau acaacuaauc aacgauggug uaaaagaaga gcccacagca 240
cagagaaagc aaccauccag ggaaaccagg aacacacuca aagagccugu aggugacagu 300
auaaauguug aagagguuaa gaagucuaca aagcagaaaa uugauccagu agcaagugug 360
ccugucagca agaggccacg gaggguaccc aaggaaaagg cacaggcccu agaauuggcu 420
ggucucaaag gaccaaucca aacccuaggc cacacugaug aaucagcaag ugauaaagga 480
cccacacaga ugcccuguaa uucucuacaa ccagagcaag uugacagcuu ccaaagcuca 540
ccaaggcgac ccaggacaag acgugggaaa guagaggcag augaagagcc uucagcagua 600
agaaagacag uaucaacauc aaggcaaacu augcgauccc gcaaggaccc ugaaauuggu 660
aacaauggua cccaaguuuc aaaggccucc auaaagcaga cauuagauac aguagccaaa 720
guaacuggca gcaggaggca gcuaaggaca cauaaaggau gggguucaac ccucuugaag 780
uuguuaggug acuccaaaga aauaacccaa auaucagauc acucugagaa acuagcacau 840
gacaccagua uccuuaagag cacucaacag caaaagccag acucaguaaa accucugaga 900
acaugcagaa gagugcugag ggccucuaaa gagguccccca aggaagugu ggugggacacc 960 agagaccaug caacauuaca aagcaaaagc aacccuuugc uguccccgaa gaggaagucu 1020
gcaagagaug gaagcauugu gagaaccagg gcuuugcgcu cuuuagcacc aaagcaggaa 1080
gcaacagaug agaagccugu accugagaaa aaaagggcug cuuccagcaa gagguaugua 1140
ucaccugagc cugugaagau gaaacaccug aaaaucgugu caaacaaacu ugaaucugug 1200
gaagagcagg uuagcacugu uaugaaaaca gaagaaaugg aagccaaaag agaaaauccu 1260
gucacuccag aucagaacuc uagguaccga aagaaaacca auguaaaaca gccaaggccc 1320
aaguuugaug caucugcaga gaaugucggg auaaagaaaa acgagaagac uaugaagacu 1380
gccucccagg agacagagcu gcagaaucca gaugauggag ccaagaaauc uacaucucgg 1440
ggccaaguca gugggaaaag aacaugcuug aggucuagag gaacgacuga gaugccccag 1500
ccuugugaag cagaagagaa aacaagcaaa ccagcugcag aaaucuugau aaagccucag 1560
gaagagaaag gagucucugg agagucugau guuagguguu ugagguccag aaaaacuaga 1620
gucgcuuugg acagugaacc uaagccaagg guaacucgug gaaccaagaa agaugcaaaa 1680
acucugaagg aggaugaaga cauuguaugc accaagaagu uaagaacaag aaguuaagaa 1740
caagaaguua ccagaaaagu gaaacuaugu agcaaagaca uuuaagaagg aaaaguaaau 1800
uugacuuagu gauaaguucc aguguggguuu ucaccuccag uguaaagaug aacuguaaau 1860

-continued acuacugcua cugccugagu uuaaggaagg aagcuuugag cuuuccuggu cauacucucu 1920
ucagacgcca auggagguca ugaggaagau caccagggau cucagcgcaa uuacaguuua 1980
ggggugagca ggcagaaaug uggcccucug uccuauccaa uaaagcucug aaauucgcug 2040
ccaaaa 2046

<210> SEQ ID NO 39
<211> LENGTH: 423
<212> TYPE: RNA
<213> ORGANISM: Homo sapiens

<400> SEQUENCE: 39
uuuuuuuuuu uuuuuuuaaa ucaaaaguua ugaugacuuu auuuuaaauc uuaauacacc 60
aaaaauauuu uucaauguug ugagauaagc acuugaaaau aagaauucca acacugcugu 120
gauuucgcug ugaggcuuga uagugaauuu ucccucugaa uauggguuua gggccuagga 180
agcagaaugc cagucauuuu ccaaguagca gugagcuaag cccagcccgg ucaugcucag 240
acccacacuu aacugaaaua uucacacuag gaggcggcac caccaggcaa caccuugauc 300
aaccaggaga acaaaagucu gaagugccac caagcauugg ggaaaugaua uuguuuagau 360
gcuagugagu cagguucuuu caaaugugucu cuaacugggu ugcaaacaua guugcauccu 420
uau 423

<210> SEQ ID NO 40
<211> LENGTH: 434
<212> TYPE: RNA
<213> ORGANISM: Homo sapiens

<400> SEQUENCE: 40
gucuguaaaa aucuguuuaa uaaauauaca ucuuagaagu accaaaauaa uuaccaacaa 60
aauacaacau auacaacauu uacaagaagg cgacacagac cuuaguuggg ggcgacuuuu 120
aagcacaugc cacugaacac cuggcucuua caugggagga cacacugggc ucacuuacua 180
ggucuauggu gguucaauca aaagcacaau aaauaaaacg ugguccuuuc auuagguucu 240
ggaaaaucac cuccccccccc cccaaaaaaa aucccacaaa caugaaccuu aagagacauu 300
uucuuugaau uucagugauc uguuuccccg gauuucacaa agacaacagc cgaaucaccc 360
caguaaaaug ccugggucua ggcgcugugu ggugugguggc uaaguauacc cuuucucauu 420
uuuuuucuuu uucu 434

<210> SEQ ID NO 41
<211> LENGTH: 1000
<212> TYPE: RNA
<213> ORGANISM: Homo sapiens

<400> SEQUENCE: 41
cggccgccag accuucaagg gcuggagugg acgcgcggac cgacucugaa cagacagacg 60
aaccgcggcc gcaagguucc cagacaggau cucacccaga ggcaggcagc ggacagugcc 120
uuaguggaac cucgcugucc uccaccgccu ggccccggug caggcgucca guggccgccg 180
cauccaaagu gaucgcugcc uccccgucuc cgccagcucg ggaccaugaa gcugcugccg 240
ucggugaugc ugaagcucuu ucuggccgca guguuguccg cguuggugac cggugagagu 300
cuggagcggc uucggagagg ucuggcggca gcaaccagca acccugaccc ucccacugga 360
uccacaaacc agcugcuacc cacgggaggu gaucgugcuc agggggucca ggacuuggaa 420
gggacagauc ugaaccuuuu caaaguugcu uucuccucca agccacaagg ccuggccacc 480
ccaagcaaag aaaggaaugg gaaaaagaag aagaaaggaa agggguuagg gaagaagaga 540
gacccaugcc ucaggaaaua caaggacuac ugcauccacg gggagugcag auaccugcag 600
gaguuccgua cucccucuug caaaugccuc ccugguuacc acggacacag gugucauggg 660
cugacucuac caguggagaa uccccuauac acauaugacc acacuacagu cuuggcugug 720
guggcuguag uacugucguc cgucugucuu cuugucaucg ugggacuucu cauguuuagg 780
uaccacagga gaggagguua ugacuuggaa agugaagaga aagugaaguu gggcguggcu 840
agcucccacu gaggaggacc ugagcuauag gaaccuucag aggcuacuuc ugagacagug 900
guucguuaca cguucuacau agaggagaaa uauuucacca gcagccauga aaacgucuuc 960
auucauuucc aguugcuacc cugacugggc cuccuguaau 1000

<210> SEQ ID NO 42
<211> LENGTH: 1653
<212> TYPE: RNA
<213> ORGANISM: Homo sapiens

<400> SEQUENCE: 42
ucgaccucac ggucuugcca aaaugucgcu uuccaacaag cugacuuugg acaagcugga 60
cgugaagggg aagcgggucg ugaugagggu ggacuucaac guuccuauga agaacaacca 120
gauaacaaac aaccaaagga ucaaggcugc uguuccaagc aucaaauucu gcuuggacaa 180
uggagccaac uccguugucc uuaugagcca ccugggccgg ccugauggug uucccaugcc 240
ugacaaguac ucccuuagagc caguugcugc ugaacucaaa ucucugcugg gcaaggaugu 300
ucuguucuug aaggauugug ugggcccaga agucgagaau gccugugcca acccagcggc 360
ugggacuguc auccugcugg aaaaccuccg cuuucaugua gaggaagaag ggaagggaaa 420
agaugcuucu gggaacaagg uuaaagcuga gccggccaaa auugaugcuu uccgagccuc 480
acuguccaaa cuaggagaug ucuaugucaa ugaugcuuuu gggacugcac accgagccca 540
uagcuccaug guggguguga aucugccaca gaaggcuggu ggauuuuuga ugaagaagga 600
gcugaacuac uuugccaagg cuuuggagag uccugagcga cccuuccugg cuaucuuggg 660
aggcgcuaaa guugcagaca agauccagcu gaucaauaau augcuagaca aagucaauga 720
gaugaucauu gguggugggaa uggccuuuac cuuccuuaag guccucaaca acauggagau 780
uggcacaucu cuguaugaug aagaaggagc caagauuguc aaagaucuca uguccaaagc 840
ugagaaaaau ggugugaaga uuaccuugcc uguugacuuu gucacugcug acaaauuuga 900
ugagaaugcc aagacuggcc aagcuacugu ggccucuggu auaccugcug gcuggauggg 960
cuuggacugu gguacugaga gcagcaagaa auaugccgag gcuguggguc gagcuaagca 1020
gauuguuugg aaugguccug uugggguauu ugaaugggaa gccuuugcca ggggaaccaa 1080
gucacucaug gaugaggugg ugaaagccac uucuaggggu ugcaucacua ucauaggugg 1140
uggagacacu gccacuugcu gugccaaaug gaacacagag gauaaaguca gccaugugag 1200
cacugggggc ggugccaguc uagagcuccu ggaagguaaa guccuuccug ggguggaugc 1260
ucucagcaau guuuaguauu uucuuuccug ccuuugguuc cugugcuccu aagcuaaccu 1320
gcuguuuucc acaucuccau uuggguguuag cgcaagauuc agcuaguggc ugagaugugg 1380
cacagaccuu aacagugcaa gcaucucagc ucgucuuacu gcaucagaug cugguucuuc 1440
aagaucccau uuaaauuccu uagugacuaa aaccauugug cauuguagag ggcgucuauu 1500
uauauucugc cugagaaagg aagugagcug uaaaggcuga gcucucucuc ugacguaugu 1560
agccucuggu uagcuucguc acucacuguu cuugacucag cauggcaauc ugaugaaauu 1620
cccagcugua agucugcaga aauuuccgaa uuc 1653

<210> SEQ ID NO 43
<211> LENGTH: 485
<212> TYPE: RNA
<213> ORGANISM: Homo sapiens

<400> SEQUENCE: 43
uuuuuuuuuu uuuuuucaug uuuaauaguu uauuucuuau uuuguugcuu auaucuucaa 60
uaaaucauuu ugcagguuuu guuacagauu uuugauaagc caacucaagu acugauuuuu 120
cauccucucu gaaaguuuua aaccaggaaa ggaaaacguu ccauggaauc caucuuccac 180
auggugauga gucacaugaa cuccaacauu cugaagccgc uugacauaca ugaguccauc 240
aucucuuagg acaucauacu ggcaagugau gauauagguc uuagguaaau gaugcaauau 300
auugucauug gccaacagag ggcaugccuu cacaucuaug aacccuggau acuuuugagc 360
cagcucagaa cuaccaggag ugggauuuuu guaaacggga cuuuucuugu aucucucagg 420
gagcaaggaa cuccaauuca caaacuguaa caaguggcua gauuccaugg guacauguug 480
guuga 485

<210> SEQ ID NO 44
<211> LENGTH: 3449
<212> TYPE: RNA
<213> ORGANISM: Homo sapiens

<400> SEQUENCE: 44
gagcacccgg gacccuggga ccacaacgca cuugcucccu cucgaccgcg cuccugaccc 60
gcagcccucg ccaacccuac ggauccuaac caccgccagc cuaggugggc gucaggauga 120
aggcagcccg cuucgugaug cgcagcgcca gcucgcugag cagcgccagc cuggucccca 180
gggaggucga gcuguucucc cgcuacagcc cguccccgcu guccaugaag cagcugcugg 240
acuuugguuc agaaaaugcc ugugaaagaa cguccuuugc uuuucugcgg caagagcugc 300
ccguccgccu ggccaauauc cugaaggaga uugacauccu gccugaccgc uuagugaaca 360
cuccuucggu gcagcuggug aagagcuggu auauccagag ccugauggau uugguggagu 420
uccaugagaa gagcccagaa gaccagaaag cccugucaga guuuguagac acgcugguca 480
aaguucgaaa cagacaucau aauguggucc cuacaauggc ucaaggcauc cuggaguaua 540
aagacaccug cacaguggac cccguuacca aucaaaaucu ucaguauuuu uuagaccggu 600
uuuacaugaa ccgcauuucu acucggaugc ucaugaauca gcacauccuc auauucagug 660
acucaaagac gggaaaccca agccacauug gaaguaucga cccaaacugu gaugugg.uag 720 caguagucca agaugccuuu gagugugcaa agaugcucug cgaccaguau uaucuaacau 780
cgccagaauu aaaccucaca caagucaaug gaaaauuucc aggccaacca auccacauug 840
uguacguucc uucacaccuu caccacaugc ucuucgaacu cuucaagaau gccaugaggg 900
ccacggucga gcaucaagaa aaccguccuu ccuugacccc aguagaggcc acugucgucu 960
ugggaaaaga agaccuuaca aucaagauuu cugaccgagg aggcggugu ccucugagga 1020 uuacugaccg ccucuuuagu uacacguacu ccacugcucc aacaccugug auggacaauu 1080
cccggaaugc cccuuuggcu gguuuugguu auggcuugcc aauuucucgu cucuacgcca 1140
aguauuuuca aggagaucug aaucucuacu cuaugucagg uuaugggaca gacgcuauca 1200
ucuacuuaaa ggcuuuaucu ucugagucug uagaaaagcu cccagucuuu aacaagucag 1260
ccuucaaaca uuaucagaug agcuccgaag cugaugacug guguauccca agcagggaac 1320
cgaagaaccu ggcgaaggag aagcuggcag ugugaagcgg augacgccug acauuuuacg 1380
ggaucaaagu gggucugugg cauugcugcu ucgugaaugu guguggacuc uaguuuccgc 1440
aaaacaacgc aacacaaaac caagcaagca aaacacaaac acgaguacaa accuugaccu 1500
gaugagggac agagcuuggu uggaugaccc gggagaaguc agggcagggc uccaggggau 1560 aacaggugucc cugcuucucc uuuggcaaug caaaaugacu ccugacuguu ccaaauacug 1620
aaaagaaguc ugccucugag uuacagcucu uucucaacaa guacagaguu ugaggcuugc 1680
aguugcaaca gcuggauguu ugguggguucu ugcugccagc caaauaaauu gguguuuagu 1740
gaacauuuuc aguguuuccc cgccaugcaa agcuuggcgc cuugggagaa augugugua a 1800 auguacauug uauagguauu agugugcucu agaaaggaca ggauggaagg aaucaaagca 1860
cuuuaucgag cuuguggcug agcauugcag ccuaugugca aacccagagg aaaaguaucu 1920
cugucaagac agcuccagua ucaugcagcu uuuuauguuu gcacucaaaa agccagugcc 1980
uucuggcugg ugccgaggcu ugggugaaau guuaaauaug cacugaccuc agaaagucga 2040
guucaaaagg gagauaaaau ugccaaagug auccaaggau ugugcauguu gggaaaccca 2100
uaugagagaa aggauucuca uacuuagaac uuuccuauga agaaauggug guaaacuuuc 2160
ucuaccuaga aguaguggaa auuucaaggu caucuuaaaa aagaugugcg uuguauauuu 2220
uaacuacauu cucuacacuc uaacauuaac auaucuauuc aaauuugucu aguugccaau 2280
ugucuucaga gugugaaaau uuaaauccuu cuugaaguau cuuucgugag aguaguaugg 2340
aaguaaaacg uucucauauc aggaggaugu cauuugugaa gcaugggggac aucaugaacu 2400 agugaugugc gugaggcuug ggaggcugaa ggguaaggau cagcgggagg ccauccaugu 2460
aggagagaga auuaaaacga ggagcgaggg aagcaaugga gagagggaag caagaaagga 2520
accagaaggc uggcaucauc cuauuuccca caggcuaacc caagggaugc ucugugccuu 2580
uccuggggag ggaagggggu gaacugguag auuugaaagc aguauggcuu cuucuguggg 2640
ucucccucuu acuagacaag gugaaaugau aauucguguc aaauuaaugu gaaauuuuuu 2700
uccugcauug uaauauuaug aggccugagu cgcaguugag uuugaaauuu guauuuaauu 2760
ucacagugac cuagagcuaa ggugcucccg guuguggcaa uaggagccac aaguauuuuc 2820
uuucuuucuu ucguucuuuc uuucuuucuu ucuuucuuuc uuucuuucuu ucuuucuuuc 2880
cuuccuuccu uccuuccuuc cuuccuuccu uccuuccuuc cuucuuccuu uccuuuucuu 2940
uucucuucuc uucuuuucuu uuuucuguuu cuuuuucuuu uuuugcauug uagauguugu 3000
ccuuaaaaga ucagggcagu gacuuucaca gcaggacuuu gacucccaca uugguugauc 3060
acacaaaacu gucagcauuu ggguaaucug auguauaguu guuuuguugc ugauguuucc 3120
auugaaauuu cagcucugag uuugugcaca ugaauacuua cuuguguuua ccaaaggucu 3180
aaggcauuug guuacuuaac ccaaauaucc ugaacugugc guaaaguaau agagaaaagc 3240
uuuagggucu caauaguguc accuguguaa aucaaaucaa aauagccuuc ccuauuauuu 3300
augaacccau gggagacuuu aaacucuugu agauagaugc uaaaugccca ggcccacuua 3360
acuuauuaau gugugaauua cauuuauguu uuuaguuuau augcaaagaa uugugauaau 3420
uuuauaauaa auauuuuuau uauaauagu 3449

<210> SEQ ID NO 45
<211> LENGTH: 226
<212> TYPE: RNA

<213> ORGANISM: Homo sapiens

<400> SEQUENCE: 45
uuuucuuuuu uuuuuuucuu cucuuuuuuc ugccaccaac agcacugugc aguuuauuaa 60
ccauucaugu acaguagcca ucuggggaga uugggacaga auugggaucg caaaguggau 120
agauauucag caucuaaugg guuggcagaa gccgccauau acucuucaca aauaucuucc 180
acagucaaua cagaacuagc cauuauccca gcacaccgau uugugc 226

<210> SEQ ID NO 46
<211> LENGTH: 952
<212> TYPE: RNA
<213> ORGANISM: Homo sapiens

<400> SEQUENCE: 46
agccaggagc cucgccccgc agcugcacag agagcaaggg uauaggcacu aacuuguuug 60
cagagacccc aucaccuucg ggagcucagg ugcgcaccuu gcaaacucca cuuucugcau 120
cugccacuga gcccgcggga gccucggaaa gagccauggc caacgcgggg cugcagcugc 180
uggguuucau ccuggcuucu cugggaugga ucggcuccau cgucagcacu gcccugcccc 240
aguggaagau uuacuccuau gcuggggaca acaucgugac cgcucaggcc aucuacgagg 300
gacuguggau guccugcguu ucgcaaagca ccgggcagau acagugcaaa gucuucgacu 360
ccuugcugaa ucugaacagu acuuugcagg caacccgagc cuugauggua auuggcaucc 420
ugcuggggcu gaucgcaauc uuugugucca ccauuggcau gaagugcaug aggugccugg 480
aagaugauga ggugcagaag auguggaugg cugucauugg gggcauaaua uuuuuaauuu 540
caggucuggc gacauuagug gccacagcau gguauggaaa cagaauuguu caagaauucu 600 augacccuu gacccccauc aaugccaggu augaauuugg ccaggcccuc uuuacuggcu 660
gggccgcugc cucccucugc cuucugggag guguccuacu uuccugcucc uguccccgga 720
aaacaaccuc uuacccaaca ccacggccuu aucccaagcc aacaccuucu agugggaaag 780
acuaugugug acagaggcaa aggaagagau cuuccuggag caaauacaaa auggacauug 840
aaccuaggau ugacauuaac gccuuagacu guugaugaug guuaucggaa cugugguaga 900
acagaaggaa gcauauuuuu auacaucccc auggcuaugc aggccuuggc ug 952

<210> SEQ ID NO 47
<211> LENGTH: 1777
<212> TYPE: RNA
<213> ORGANISM: Homo sapiens

<400> SEQUENCE: 47
cggcacgagc ggccacugac cgagaagugc ccccgccugg agucagccug ggggcaggcc 60 agggucacc agaccccggg augaccgcag ccagucgggc caaccccuac agcaucguau 120
caucagagga ggacgggcug caccugguua ccaugucagg cgccaacggu uuuggcaaug 180
gcaaggugca uacacggcgc cggugccgca accgcuucgu caagaagaac ggucagugca 240
acauugaauu cgccaacaug gacgagaagu cacaacgcua ccuggcugac auguuuacca 300
cgugugugga cauccgcugg cgcuacaugc ugcucaucuu cucucuggcc uuucuugccu 360
ccugguuguu guuuggcauc aucuucuggg ucauugcugu cgcccacggg gaccuggagc 420
cagccgaggg ccguggccgu acacccugug ugcugcaggu ccacggcuuc auggcagccu 480
uucucuucuc cauugagaca cagaccacca uuggcuacgg gcuacgcugu gugacugaag 540
agugcccggu ggcugucuuc augguggugg cgcaguccau ugugggcugc aucauugacu 600

-continued

```
ccuucaugaa uggugccauc auggccaaga uggcacggcc caagaagcgc gcacagacuc     660

ugcuuuucag ccauaaugcc gugguggcuc ugcgugacgg caagcucugc cucauguggc     720

gcgugggcaa ccugcguaag agucacaucg uggaggccca ugugcgggcc cagcucauca     780

agcccagggu cacagaggag ggugaguaca ucccacugga ccagauugac aucgaugucg     840

gcuuugacaa gggccuagac cguaucuucc ugguaucacc caucaccauc uugcacgaga     900

uugaugaggc cagcccacug uuuggcauua gccgucagga ccuugagaca gacgacuuug     960

agauuguggu cauccuggag ggcaugguag aggccacagc caugaccaca caggcucgca    1020

guuccuaccu ggcuaacgag auccuguggg gccaccgcuu ugagccagug cucuucgaag    1080

agaagaacca guacaagauu gacuauucac acuuccacaa gaccuacgag gugccaucua    1140

caccccgcug cagcgccaag gaccuggugg agaacaaguu ccuccugccc agcgccaacu    1200

cuuucugcua ugagaacgag cuggccuucc ugaucagaga ugaggaggac gaggugucua    1260

ccgaccggga uguccgcacc ccucagcccg agcaugacuu ugacagacug caggccagca    1320

gcgcugcccu ugugcggccc uacagacggg agucggagau uugaaugccc uuggcuuaga    1380

ugcagcacca cccugaccac aauaggaccc augucccuug ggggccugcg uuugagcaga    1440

gcaggccgaa agccucgggu cacagacuca guagcaucuu agucuuuuuc auguuuuuuc    1500

gcaguagcuu gggaaaguug gcgggagcgu ggauggccca aaugacuggc ucacggccuc    1560

ggaggcugau guauacccau gggcaaggag gugacuucuu gggguagggu ugcucaggag    1620

uuagggacuc ugcuggaggc cuuaggugca ggucccaacc ccggugggag gaggcugugu    1680

auguacacuu cauugguuuu uaacuugggc aagacuguuu acaaaccaaa acaaacaaac    1740

aaacaaucca aaaaaaaaaa aaaaaaaaaa aaaaaaa                             1777
```

<210> SEQ ID NO 48
<211> LENGTH: 175
<212> TYPE: RNA
<213> ORGANISM: Homo sapiens

<400> SEQUENCE: 48

```
uuuuuuuuuu uuuuguuccu uuuuuggaau ucccaaagcu gguuuuaauu ucaaaaaauu      60

augaggucuc uucccacacu ggggauaaug ggaugggaua gcccaaacua uuaucccagu     120

ucaaccccag ccugguccaa acaccauuac ugucacuggg cccugucauu ucacc          175
```

<210> SEQ ID NO 49
<211> LENGTH: 1629
<212> TYPE: RNA
<213> ORGANISM: Homo sapiens

<400> SEQUENCE: 49

```
uccucguccu cgucuguucc aucuucucca aauagcucua acugugaugc caacggcaau      60

cccaagaacg cugauaucuc uagcaucgau gguguucuga agagugaccg cacagauugu     120

ccugugaaaa caggcaaaac cagugcuccu ggcaugacua agagucacag uggaaugaca     180

aaauuuagug gcaugguucu acuguguaaa gucugugggg auguggcauc aggauuccac     240

uauggaguuc augcuuguga aggcuguaag gguuucuuuc ggaggagcau ucagcaaaac     300

auccaguaua agaagugccu gaagaaugag aacuguucca ucaugaggau gaacaggaac     360

cggugccagc agugccgcuu uaagaagugu cugucugugg ggaugucacg agaugcuguu     420

cgauuuggcc gaauuccuaa gcgugaaaaa cagagaaugc uaauugaaau gcaaagugca     480
```

-continued

```
augaagacca ugaugaacac ccaguucagu ggccaccugc agaaugacac cuuagcagaa    540

cagcaugauc agucagcacu accagcucag gaacagcugc ggcccaaguc ccagcuggag    600

caagaaaaca ucaaaaacac uccuucugau uuugcaaagg aggaagugau ugguauggug    660

accagagccc acaaggauac cuuucuguau aaucaggaac aucgagaaaa cucaucugag    720

agcaugccac cucagagagg agaacggauu cccaggaaca uggagcaaua uaauuuaaau    780

caagaccauc guggcagugg gauucacaac cacuuccccu guagugagag gcagcaacau    840

cucaguggac aguacaaagg gaggaacaua augcauuacc caaacggcca ugccguuugu    900

auugcaaaug gacacuguau gaacuucucc agugcuuaua cucaaagagu cugugauaga    960

auuccaguag guggauguuc ucagacugag aacagaaaua guuaccugug caacacugga   1020

gggaggaugc aucuggugug uccuaugagc aagucuccau auguggaccc ucagaagucu   1080

ggacaugaaa ucugggaaga auuuucaaug aguuuuaccc cagcaguaaa agagguggug   1140

gaauuugcaa agaggauucc uggcuuccga gaucugucuc agcaugauca ggucaaucug   1200

uuaaaagcug ggacuuuuga gguuuuaaug guacgauuug cuucauuauu ugaugcaaag   1260

gaacggaccg ucaccuuucu aagugguaag aaguacagug uggaugaccu gcacucaaug   1320

ggagcagggg aucugcucag cucuauguuu gaguucagug agaagcugaa ugcccuccag   1380

cucagugaug aggaaaugag cuuguucaca gcaguuguuc ugguaucugc agaucgaucu   1440

ggaauugaaa augucaacuc aguggaggcu uugcaggaaa cacucauccg ugcacuaagg   1500

accuuaauaa ugaaaaacca uccaaaugag gccuccauuu uuacaaaauu acuucuaaag   1560

uugccagauc uucgaucuuu aaacaacaug cacucugagg aacucuuggc cuuuaaaguu   1620

cauccuuaa                                                           1629
```

<210> SEQ ID NO 50
<211> LENGTH: 831
<212> TYPE: RNA
<213> ORGANISM: Homo sapiens

<400> SEQUENCE: 50

```
auggcguuac uggaucugug cggugccgcu cgggggcagc ggcccgagug ggcugcccug     60

gaugcgggaa gcgggggucg cucggacccg ggacacuaca guuucuccgc gcaagcuccg    120

gagcucgcac uuccccgggg aaugcagccc accgcauucc ugagguccuu ugguggugac    180

caggaaagga auguucaaau ugagauggcc cacggcacaa ccacacucgc cuucaaguuc    240

cagcauggcg ucaucguggc uguggacucc agggccacug cagggaguua cauuagcucc    300

uuaaggauga acaaagugau cgagauuaac ccuuaccugc uuggcaccau gucugguugu    360

gcagccgacu gccaguacug ggagaggcug uuggccaagg agugcagguu guauuaucuu    420

cggaaugggg aacgcaucuc cgugucugca gcauccaagc ugcuuuccaa caugaugcug    480

caguaccggg ggaugggccu cuccaugggc agcaugaucu guggcuggga caagaaggga    540

ccaggacuuu acuacguaga ugacaauggg acucggcucu cgggacagau guuuuccacu    600

ggcagcggga acaccuaugc cuacggggug auggacagug guuaccggca ggaccucagu    660

ccugaagagg ccuacgaccu uggccgcaga gcuauugcuu augcuaccca cagagacaac    720

uauucuggag gagucgucaa cauguaccac augaaggaag acgguugggu gaaaguggag    780

aguuccgaug ucagugaccu gcuguacaag uaccgagagg ccgcucugug a             831
```

<210> SEQ ID NO 51
<211> LENGTH: 3601

<212> TYPE: RNA
<213> ORGANISM: Homo sapiens

<400> SEQUENCE: 51
auuccaggag uuccagcugc uggagaggac uguguagaag guaaccuacc ccaucucucu 60
uacuucgucu cuagauggga gcagacaagu acauauagcc ugcuuggagc gaggacuuug 120
aaaggcugag acuugcgucc acucugaggg caacuagucc agacucugac aggucagcau 180
uuccugacug ggugcacuga augccaagca ccagaggucu gucaccuucc gacauuggac 240
caagagaguc ccagagaccc ucaaagacac aggaacagag guguccuuug ggugagagac 300
cugugcccug ccaagccucu cagccccuag aaaggcggca gggcugagua gcugagugug 360
ugcaacuugg gagcagccug auuucagugc uugucaccug ugagggcaaa ggcagcaugc 420
uuaaugccau caguccuacu cuucucaccc guggaacaga cgcauaacug accuuuuuuc 480
gugaccacua uuagggugca uuuaaaaauc aaucucucuc uuuucugcuc cucuuucucc 540
accuucccuc augugugugu cugugugugu guguuucugu gugugugugc gugcaccaua 600
cagguauaug ugccaugaca ugugugcagg ucaguagaca gccuugguug ucagucccug 660
ccuucuacuu uguucaaggc agggucuauu cuuuauuauu gacugcuauc cagguacacc 720
aagacaguug gccugugagg uuccagggag ucuccugucu cuggccccca ucuuauagca 780
ggaguuguga gauuucagaa augugcaccc acaucuagcu uuauuuggca ucuuggcacc 840
caaacuuggg uucucaugcu uuccaagcaa ggacuucacc cacugaacca ucucaccagc 900
uccacuaugg cgguuuucug aaacugaagg gaguggggag aaggcgcuga gugugaacgg 960
gucuggaagg cggguauaac cuuuaaggcu ggcugguucu gagagaggaa agccggcuug 1020
ugucccauuc aggugccagg ugcagcauca aauguggcuc cacccaacgg ucaguaacuc 1080
cgcagacagc accgugguua acugccucac agagggggcc cagggaccua guuccuuaaa 1140
gcccacuuag uuuugagaga cgacauggag gggcaagccc agcccugucc agcugcauuc 1200
acacgaggcc cuucuccucc gaggacccua ccuuuguguu uaguggcuga ggcugugugg 1260
cucugcuuga agcucuggcu aucaggaagg accuggccca ccggcuggca ggacaaacug 1320
gcccagugaa ggcacugucc ggucuccugg uggaucacaa ggaaaggggc guggcauguc 1380
cagauuugaa cccuggaugc cucuucccag gguaggaagu cuaaggguca acaugaauag 1440
gugagggugg ugguggaaag aaucugcaug caaaaucagg cacucauguc ugacaucguc 1500
aaacacuaua uuuauguaga uuuauauggg ggugaggcuu ggggagcacu uguauuuuug 1560
ugugcaauug caagagcuuc cuccacauug caguguuaaa uaucauaugg ugcuggacca 1620
accaucucug gaacgagggu gaggguuugg uacccgugac uaugguucuc uguguaguag 1680
aaacggcuuc uugggaagag agaggaagug cuuugaaaug cauccucucu uguuucauuc 1740
ugcaucaugg ccagguuucu cugcacaaag augcaauaga cauucaggaa aauaagcgca 1800
uugcaagaug ucaaaaguca ugaaaaauga aaagcaaggu cacugcagcu gggguguagu 1860
guggcuguag aagcacguuu augauguaca gguuccggga gagggaggaa gagagaggga 1920
gggaaggagg aauggaggaa gagagggaga gggagcaaga gaggggggag ggagggaggg 1980
gagaagggag agagagagag aagaaagaga gggagggaag aaggaaugga ggaagagaga 2040
gaaagagggg aagaaagaga gggagggaag gaggggugga ggaagagaga ggugugaggg 2100
auggagggac agagagggag ggaaggagaa auggaggaag agagaaacag agagauggag 2160
gaagagagaa aagucaccaa uuauuuuucu ccccagucgc ccccugcccu cacaccaagg 2220
guacccccac uuuucuuuca cucaugcaca cacacuacac ccaauguuua gguaacacau 2280
guagggcagg cagagccuuu gugaaugugc uugguaguuu ucugccuuac uucuaaauaa 2340
ccaaucacac ggaugccaca ggguuccuuu agacugucca gggcuccggg gcucuuagac 2400
uguucccaau gugggguguca caugcaaaca guaagcaccu ucuuguuugu ggugcccagg 2460
augcugcagg uacuagaaau uccugcacag accuuugcua cuucuacaca gacuuacccu 2520
uuaaaacauu uaauuauaug uuuuuuucag cauaaagauc uauuuugauu auuuuuaguu 2580
gcguguaugg gugugugccu gugugugauu guguaauugu cuguauggga guguaagugc 2640
cuacagaggc aucggauccc cuggagcugc cguuacaagu aagggacugg gacucagacc 2700
ugagugguuu ggaugagcag ugaaugagcg uggugagcca ucccaccaug cccuauaaac 2760
acuuucaaga ggacuuugcu ggguaugguc aaguuguccc ccugcgacag ccaccccaac 2820
uugccauccu cauuuacugu acuggaagca gcaaccaccu cugcaauuuu gcacaagaac 2880
cugagagucu gaaagacuuu uguuggcacu ggccuguguu ccacuggggu ggacacauua 2940
aucuaaaagc uaagaagcuc acuucagcuu ugccaggcaa ccagcacguu ugagcacaac 3000
gguguagcca ggaagggugu gugggaauuu ugaugcuagu uuuucuuuaa uuagguugag 3060
agugaaauca uggucuguau gcauccaaca acuuaaucca aaaaguuggu ugcacggcuc 3120
cuggaagguu uaccggcaag gaaccugucc cauuuuguaa guagguggga cuggagaguu 3180
gccaagaagc cccccucccu gccccccuucc uccuggcaga uucugcuuaa aaugagugug 3240
guucacugca gaauaguguc accugucuuc agaugucuaa agacauaaga aaggccuagc 3300
cagcuaaguc agaaaagggg acuuuccggu gggaaugcau uuuccagucu cuaggagaag 3360
ucuuuaucca aauaaaauua gcauaguggu ggagucacug ccagggcgcu ggugcggaag 3420
cacagcccag agccgaggac guggccaucc uccuuccucu gaugcaaagu guucucuauc 3480
cccaguuacc augagcaaua ucaguagcau cgugaaccgg gcccgugaug ccuuuaacuc 3540
aggcaagacu cgaccgcugc aguuccgggu ugagcagcug gaggcguugc agcgcaugau 3600
c 3601

<210> SEQ ID NO 52
<211> LENGTH: 329
<212> TYPE: RNA
<213> ORGANISM: Homo sapiens

<400> SEQUENCE: 52
uuuuuuuuuc caaaaaauuu uauuggggga aacuacaaaa cauuuacagu acaauguuua 60
cagucacaau uuguagugaa cugauucccc aaaauauauu acaacucaag uugacuuaau 120
cuuguuacau ucaaaaaccu acuucuguca aaguagucca gagugcacac gcggugcucc 180
aacuguaccu acauacaaac uaaacaacug cucauuuauc ugccauccag gaaagccgga 240
gacauuccug ccucuuuaca uugaaaaaua auaguacaag uuuuuggacu gucauugaac 300
aaggcauauu cauguaccac caacauuuc 329

<210> SEQ ID NO 53
<211> LENGTH: 3671
<212> TYPE: RNA
<213> ORGANISM: Homo sapiens

<400> SEQUENCE: 53
ggugauccuc caggaccuaa gguuucggua uuaucuucgg ggccucuuca cccggaggug 60
agucugcuga gcccgaccuc agguguucac ucgucacgcg agggccuggc cacggcgggg 120

-continued

```
aagcacuggg agagagcggg aggccuugac cgcagcgugu aggaucuggg gucccggcgc    180
ucugcucccg ggugcagagu gguuggagca ugcgaggccc ucugcagcgu gcucuguucc    240
uaccaucacc ccaccccac cccaguccuu ccugcacguu ucuggagagg caaaggcccc    300
ugcugagccu ucacugggua ccccuaucuc gacuccacuu gucugcuugg gaucuccaaa    360
gggggauaca cccucguaaa cuagagcagg aggcuggggg gugggggguag ggguagggguc    420
ugaccaguua gauugaggcu ggacccuccc cagagugagg agcgggaagc ucuuugucuu    480
auccaggauu uugcauauca augcugaggu ucuggugauu aaguagggguc ccuggcuagc    540
gggggguaacc ugaacaaccu uccuccgcug gccgcuagcc aauagacacc uggcuuccgc    600
ggaugagccc uuugaguuug uggaggugu ccucaggucc ccagggcccu gccccguugc    660
cugcagaugu guggacagac aaaacauugg acucguuuuc caaccacuuc accccuuccu    720
ucgcuagucc uccggugggac gaugggaugc cucauugacu uguuugugggc ugugcaugcc    780
agagcuuccu agcagacagc ucagggcucc aucguuccua aaucccacug uguaacgaaa    840
aaaaaaaaaa caaaaacaac aacaacaaca acaacaaaaa caaaaccaga aaugaggaca    900
ggcccagcug ggcuuggcac ugaacuuggc caccuggagc uuuggcuacc cacuacaaga    960
ugucagcaag ucucaggaua gaagaggccu aaggccaguc cuggaagaua ccaaaacuuc    1020
accuccucua uaccccguuc cucuaggaga acuguaagcc accuuugucu cugggacgcc    1080
ccucucccac ucaacagaug gcaccaguca ucuuccuccu caagaggcca gugguauuca    1140
aaauaggaua uugaaaccaa gcaagcuggu ccucuccucu acccuaugcc aaagacuucu    1200
gcccaaaggg cccagaaaag ucccauagcc aucuggcugg cuagugugcu gacugcuaca    1260
ggugucagug uccccagcga gcagguagug gaguggaggu gucuucuugu ggaaaugggu    1320
ccugagccuc uaccuuguac agaaaggaau uagugaagcc cagaggccuc cagcccgugu    1380
cucugccaca agagagaggg ggugggggug gggcuguauu ugguucccag ggcucaggga    1440
agguuuucgg uucaugcaug cucauuuauc ugaccacugu cuuaacccca ggacaaccac    1500
uuaacugucc acuuccauau cagaguucuu gguuccccuu uacuucgucu auggagcccc    1560
ugaguuuggg aaggggguauu aacugaaagg uaccauuaga ugaacuugga gaaagauuug    1620
uaggugccac gggagauuuc agguaaaagc ucuuuuaaua auuggcuaca auagcagcag    1680
gaggaggcca ggaauucuga gguagagauu ugauuagcag cacguggagc aaaggagacu    1740
ucugacuccu acagguuuca gaaaguggggg agaggcucuc agaugaaugg cuuggacugu    1800
gagguaagug uuaguguagc acgagacuag cuuaaggcug uacaaauugu ccgucugauu    1860
ggugcauugg gccagguaga cacuagauaa gcaauugggc cuuaacucga guugucuuaa    1920
uggcuacccc cagggcagca gggagucaau acugcucucc ugucuggggc cugaaugcug    1980
aaaccaucua caaaggggac auaaggcaua uuggggaggu guagaguggg ccaggcccag    2040
ggucugcugg uaucuaugcc aggauccuga gugguggugg cguagccugu cuuuuaacca    2100
acugccucuc ucacaguagg cuucuuuggc uugcgaaccu ucagcagaug ucugccacuu    2160
ccaacaugag agucuuccug ccugugcugu uggcagcccu ucugggcaug gagcaaggua    2220
uggagcucug agauaacccu gcagccuggu ccuccuccug aucucucauu cuuucuccug    2280
aguagaugcc cagggcuccu ccugagccag cccuccuagg aacgucuggc cuucccaccu    2340
ccuacucucu agccaacuga ccuaguuccc cugaugcugu gcuggcccag cuacaccuuu    2400
gucaccucgu guugacuuua gccacuccag uaccaaaguc ugaagucagu ugucauuggc    2460
```

uggcuuuuuu cccugaccca gggcugagca ugcuguugcu ucuugucagu ggguugggga 2520
ucaagggccc cacuggaaag ucaccuuacc cuggaaggcu uccccaggca auaggcaggu 2580
gucaccuaca gcauuguccc uuuugcaguu cauucccuga ugugcuucuc auguaccgau 2640
cagaagaaca auauaaacug ccuguggcca guuucaugcc aggagaaaga ccauuacugu 2700
aucacguuau cugccgcugc gggcuuuggu gaguagcugc cuguuucccu agccagggcc 2760
agggaccugc ggggcuuucc ccauuuccug cuacccuguc ugucuguccc cucauccuca 2820
cuuuccaugc agggaauguc aaccuuggcu acacccugaa caagggcugc uccccgaucu 2880
gccccaguga aaaugucaau cucaaucucg guguggcguc cgugaacagc uacugcugcc 2940
aaagcuccuu cugcaacuuc agcgcagcug gccucggacu ucgugccagu aucccacuac 3000
ugggccuugg acuccugcuu agcuuguugg cucugcugca gcugagcccc ugaccauccc 3060
ccauguguuc uccauauccc cccagcucag gaaaagccca gcuccuuuua ggucccaggg 3120
gacccuagga accuucagcu ccuccugggu gugucuaguu cccccuccac acucucucaa 3180
cgucagggcu aaguaccaaa cucacccaua ccugcucugu ugaaguggua cuggcuaccc 3240
uugcuuccag agccaauccu auaaccuccc uuggggaacc agcgaagggg ugaagaucuc 3300
cuuggagucu caagaguacc agagucagcg ccgaaucuug uggacacacu gacaaggaug 3360
ucuaauccaa auagauguau aucugugugc ucaguguauc ccugugugaa ugaagccacu 3420
uggauucugg ggugggcaaa gaagaccuga aaagauucua cagcagaagg ccugugucgc 3480
caccaaaacc ccucccccug guaucauugu acccaccuug uacucuguuc aggaggcugc 3540
ccauggagga cugccacccc uccagaugaa ggcucccacu acccgaugca guugaguccc 3600
auccugcccu cucugcccac acuggcuucc ugcugcuauu cuagugccuc aaauaaaccg 3660
uucacacccu u 3671

<210> SEQ ID NO 54
<211> LENGTH: 951
<212> TYPE: RNA
<213> ORGANISM: Homo sapiens

<400> SEQUENCE: 54
cuuccucccu cuacagaaga agagcaagaa gaugaggaag aaauugaugu ggugucugug 60
gagaagaggc aaaccccugc caagaggucg gagucgggcu caucuccauu ccgaggccac 120
agcaagccuc cgcacagccc acugguccuc aagaggugcc acgucuccac ucaccagcac 180
aacuacgccg caccccccuc cacaaggaag gacuauccag cugccaagag ggccaaguug 240
gacaguggca ggguccugaa gcagaucagc aacaaccgca agugcuccag ccccaggucc 300
ucagacacgg aggaaaacga caagaggcgg acacacaacg ucuuggaacg ucagaggagg 360
aacgagcuga agcgcagcuu uuuugcccug cgugaccaga ucccugaauu ggaaaacaac 420
gaaaaggccc ccaagguagu gauccucaaa aaagccaccg ccuacauccu guccauucaa 480
gcagacgagc acaagcucac cucugaaaag gacuuauuga ggaaacgacg agaacaguug 540
aaacacaaac ucgaacagcu ucgaaacucu ggugcauaaa cugaccuaac ucgaggagga 600
gcuggaaucu cucgugagag cuaaggagaa cgguuccuuc ugacagaacu gaugcgcugg 660
aauuaaaaug caugccaaag ccuaaccuca caaccuuggc uggggcuuug ggacuguaag 720
cuucagccau aauuuuaacu gcucaacuaa auaguauaaa agaacuuuuu uuuaugcuuc 780
ccacucuuuu uucuuuuucc uuuuaacaga uuuguauuua auuguuuuuu uaaaaaaucg 840
uuaaaaucua uccaauuuuc cauguaaaua gggccuugaa auguaaacaa cuuuaauaaa 900
acguuuauaa caguuacaaa agauuuuaag acauguacca uaauuuuuuu u 951

<210> SEQ ID NO 55
<211> LENGTH: 1822
<212> TYPE: RNA
<213> ORGANISM: Homo sapiens

<400> SEQUENCE: 55
gugggacggg ccccccucga ggucgaccca cgcguccggg aguacccccg accuuggcug 60
cgugcugacu cgcuuccuuc ugccugccca ggcuugcacu ccccggggau cugccucugc 120
aucucuugcc uucgcuguug uuucccucuc uguccagcuc cccucccgcu cucgcccugg 180
agaauggcuc agaaggagaa cgccuacccg uggcccuacg gcucaaagac gucucagucu 240
ggccugaaca cguuguccca gagaguccua cggaaggagc cugccacgac aucugcgcuu 300
gcucucguga acugguccaa cagccagucc acagcugccc cuggccagaa guuggcugag 360
aacaagaguc agggcuccac ugccucgcaa ggaucccaga acaagcagcc uuucacuauu 420
gacaacuuug agauugggcg uccuuugggc aaaggcaaau uuggaaacgu guacuuggcu 480
cgggagaaga agagccguuu caucguggca cucaagaucc ucuucaaguc ucagauugag 540
aaggaggggg uagagcacca gcuucgccga gagaucgaaa uccaggcgca ccugaaacau 600
cccaacaucc uucaacucua caacuacuuc uacgaccagc agaggaucua cuuaauccug 660
gaauacgccc cucgcgggga acucuacaag gaacugcaga agagucggac cuucgaugag 720
cagcggacug ccacgaucau ggaggaacug ucagaugccc ugaccuacug ccacaagaag 780
aagguaauuc acagagacau aaagccggag aaccugcugu uaggucugca gggagaacug 840
aagauugcag acuuuggcug gucggugcau gccccauccc ugaggaggaa gaccaugugc 900
ggcacgcugg acuaucugcc cccagagaug auugaggggc gcaugcauaa ugaaauggua 960
gaucuauggu gcaucggggu gcucugcuau gaacugaugg uggggaaccc ccccuucgag 1020
agcccuagcc acagugagac guaucgucgg auugucaagg uggaccugaa guuccccucu 1080
ucugugccuu cgggcgccca ggaccucauc uccaagcugc ucaaacauaa ccccuggcaa 1140
cggcugcccc uggcggaggu ugcagcucac ccuugggucc gggccaacuc aaggaggguu 1200
cugccucccu cugcccuuua gccugcuccu ugguuuuuug ucccugucau uuuucagugu 1260
ucuuuguaug ucuguguaug uguucugaga agggguggga acuggaaacu auuccuagcu 1320
ccaguucuag ggaucugaau cucucuucug accucuacag gcaaaauuag gcaccccugu 1380
ggugcacaua uaugcacgcc aaacacauga aguuacaaac aaacaacaaa cacacagaua 1440
gugcuggaga gauggcucgg caguuaaaag cacuggcugc ucuucccagg aaccuagaac 1500
ucaauucuag cacuacaugg ugcucacggc cacugucugu aacacccagu ccuggggaau 1560
cuggggccuu cgagccucug caggcacuag gcauggaugu gguauacaug uaugcaggca 1620
aaacacccau gcacugacuu uuaagaaacc cucuagucug auuccuuuca auuugucaaa 1680
uguugaaugu uauuuuuaaa auauuauaag ccauuuaaua caauuuuucu uugaaacaug 1740
guauagccua gucugucuua aauucagaaa aauuaugaag aacaacauuu uauaauaaag 1800
ucuuaaaugu uucauguuuu ug 1822

<210> SEQ ID NO 56
<211> LENGTH: 2663
<212> TYPE: RNA
<213> ORGANISM: Homo sapiens

<400> SEQUENCE: 56
uugccuagga agggcgcguc gucucucugc ucguccggcu gugacgggga agggucccgc 60
ugcguuuugg ucacugugag uaccaaguuu gggggauccc cgagggacuc ucgagagcuc 120
auuuuaggga ugcaggggcu acuccccggu gguagagagc uuucuaguug gcaggagguu 180
ucguaugugg aggaggccag cuuaggcaga aagcacaugu ucucagagau gaggacaaga 240
cuaagaccgu cuaaucccug aucuuuaccu uccggcccgc ugaccugggc cuggaugcua 300
aagcccucug cuuucgucua aacagcgcua aauaguaaac aguauugccu aagauaaaug 360
cggauuauua cccgauucag ugucgggaaa aggcagcuag gagagagcgg cuggcacgug 420
guaagcacac gguaaguuuc gguuaaauua aaacaaccau ccguugagca ucucuuagca 480
agcuccuucc acccuucaaa caaucaguga uagugcgucu guuucacuga uuagggagcu 540
aaggcuccaa cagcagcaaa ggaacuaauc cgccucugau caacauggcg uuucuuacag 600
ggcauuccuu auacgcuuuc ccacgugcgu aacaggaauc ggguguuccc ggguuuuguu 660
uuguuguugu uguuuuuguu uuguuuucuu agugaaagag gcagggnggg cuccaggccg 720
cugaggauua auaaagagau ucuaugagga ggaaauaaca ggcaggugu augaucgagg 780
caaggcccug aggaaggcuu gggugggggug aguagaacca gagccggaag uccacucagc 840
agccuggggc acuuaaagcu ucugcugggg caaaugguaa ggcggcguaa ggucacauuc 900
cuuucauuuc uuccagacuc aggaggagac cacaccuucc ggagaaccag gccugaaccg 960
agguacuauu uuguagcucu cagaagccag gacucugcaa cacuguuugc ugccugugga 1020
ucuucuauau ucacaguguc ccaguugcuu cugaucuacc acuguuagau acuucugcca 1080
cccauccuaa gaguauaguu guucuuggaa aggagucuca gcugcuguca gcaggagucc 1140
cucauucgac uccugugguu gcccuuucca ccaugccaaa gaauaaaggc aaaggaggca 1200
aaaacaggcg cagagguaaa aaugaaaaug aaucugagaa aagagaguug guguuuaaag 1260
aggaugggca ggaguaugcu caggugauca aaaugcuggg aaauggacgg uuggaagcaa 1320
ugugcuuuga cggugugagg aggcugugcc auauaaagagg gaagcugaga aagaagguuu 1380
ggauaaauac cucggacauu auauugauug gucuacgaga cuaucaagau aacaaagcug 1440
auguaaucuu aaaguauaau gcagaugaag caagaagucu gaaggccuau ggagaacuuc 1500
cagaacaugc caaaaucaau gaaacggaca cauuugguccc uggggaugau gaugaaaucc 1560
aauuugauga uauuggagau gaugaugaag acauugauga caucuagccu gaccuaagca 1620
ugcuaccuuc caaguucucu gaagauagcu ccacacagug gcaucuugac cuucaucugu 1680
uaaguaaaac uucauggcau guguaugacu uguuaaugca agcuaaugaa uuuuauuuuu 1740
ugaaguacua uauuucuuug aaaaccaaag auguugaguu aucaucuuaa gugacauguu 1800
aacacuuugu gcuuuugaau auaauugaac cuagcgcaca gcagugagca cuguuaagag 1860
acugccuuuc cauuuguagc uucauuucug gcacgggagu guuuuguguc agcaguucug 1920
ccagguggcc aucgaugagc ugaaguaagu ccuaguccag cacaucugcu ucaggccuuu 1980
guacucuagu caucuggcug cguucgagac uucucagcag aacuuauaga uguguacggc 2040
ugcacuugga gucagacaag auauggcuac uuuuguacuu auggagccau gccauuuuau 2100
acuuucacgu uguauacauu cguuugaccc uuuaaguugu ugccacccau aaaaaggcau 2160
cuuacagugc aguuuuuaaa uuacaugggu agcaauuuug aguuuuaaaa auuagucauu 2220
gcagaaauua aauacuuaga ggagauaauc cauuaucuug auuuuaggaa uauaauaguu 2280
gacaauguuu auauauaauu uuacuucucu aaggcauacc caaaaauaga aaaugaaaaa 2340
gagcagugag ucuguucuga ugcuugcauu gcauagagaa guuuuccaac aaagcagcug 2400
uuaauaacac auaaaaauaug uuuuacuuug caaaguaggu uguguuaagu cauuuucaaa 2460
aaguuaccua cuauaucgag gcucuggaua auuacuaugu guugauuaaa guuaguuaca 2520
gaauuguaca agcuaaguuu uccuuaaacu aagcuuaggu uaaagggaga ggagccacag 2580
cucaaugaaa acacgguucc uguuuucuaa auggaggcgc ccagaaacac aauaaaacau 2640
guugguacaa aaaaaaaaaa aaa 2663

<210> SEQ ID NO 57
<211> LENGTH: 884
<212> TYPE: RNA
<213> ORGANISM: Homo sapiens

<400> SEQUENCE: 57
caugauccca gccacccgcu cgcuucucug ugcagcgcug cugcugcugg ccaccagccg 60
ccuggccaca ggggcgccua ucgccaauga gcugcgcugu cagugccugc agaccauggc 120
ugggauucac cucaagaaca uccagagcuu gaaggguguug ccccucagggc cccacugcac 180 ccaaaccgaa gucauagcca cacucaagaa uggucgcgag gcuugccuug acccugaagc 240
ucccuugguu cagaaaauug uccaaaagau gcuaaaaggu guccccaagu aacggagaaa 300
gaagacagac ugcucugaug gcaccgucug gugaacgcug gcuucugaca acacuauaca 360
auuucuuuug agggucuau uuauuuaugu auuuauuuau uccacaaagu guguggguuuu 420 uauuuuacau uaauauuuaa caguguggau acauuucauc gaugguaguu caguucugcu 480
uguucaguuu aaagauggua ggcuuaaaau auuucauuaa aacuaauauu uauugggaga 540
ccacuaagug ucaaccacug ugcuaguaga aggguguugu gcgaaaagaa gugcagagag 600
auagaguuua guauuauguu uuguauguau uagggugagg acaugugugg gaggcugugu 660
uuguaugucu ugaaaagaau gucaguuauu uauugaaagu cgucuuucau auuguauggu 720
caacacgcac guguugacgc uucccuugga cauuuugugu cuaguuggua gcccauaaug 780
ggcuuuuaca uucuuuaacc cuguuucucc uggucucguc ucgcucggga cagagacguu 840
caaaggacug uuacaaauga aguaaaaaua aaaguuuuau uaag 884

<210> SEQ ID NO 58
<211> LENGTH: 1310
<212> TYPE: RNA
<213> ORGANISM: Homo sapiens

<400> SEQUENCE: 58
cgucucccgc auucgucugg gccgugcacc ugcccgcuag cucgcugcac uaccguugcc 60
cacaagccaa caugcugccg agauugggcg gccccgcgcu gccgcugcuc cugccgucgu 120
ugcucuugcu gcugcucuug ggcgcgggcg gcugcggccc cggggugcgc gccgaggugc 180
uguuccgcug cccacccugc acgcccgagg cucuggccgc uugcgggccc ccacccgacg 240
cgcccugcgc cgagcuggug cgagagcccg gcugcggcug cugcuccgug ugcgcacggc 300
aggagggcga agcaugcggc gucuacaucc cgcgcugcgc ccagacgcua cgcugcuauc 360
ccaacccggg cuccgagcug ccccugaagg cgcuugucac aggcgcgggu accugugaaa 420
agagacgcgu gggcaccacc ccacagcagg uugcagacag ugaugacgac cacucugagg 480
gaggccuggu ggagaaccac guggauggga ccaugaacau guugggaggu gguagcagug 540
cuggccggaa gccccucaag ucaggcauga aggagcuggc uguguuccgg gagaagguca 600
augaacagca ccggcagaug ggcaagggug ccaaacaccu cagucuggag gagcccaaga 660
aguugcgccc gccucccgcc aggaccccuu gccagcagga guuggaccag guccuggagc 720
ggaucuccac caugcgccuu ccggaugauc ggggcccccu ggaacaucuc uacucccugc 780 acaucccaa cugugacaag cauggccggu acaaccuuaa gcagugcaag augucucuga 840
acggacagcg cggggagugc uggugugaa accccaauac cgggaagccc auccagggag 900
cucccaccau ccggggagac cccgagugcc aucucuucua caacgagcag caggagacug 960
guggggccca ugcccaaagu gugcaguaaa ccccagccag ucggugccug gcuuccccau 1020
cccgaacacc agcagaaaug gagggcguca gggugacggg uguggaggag uucccaguuu 1080
ugacacaugu auuuauauug gaaagagacc aacacugagc ucagaagccc cccucugacc 1140
ccccccagcg gcuguuaacu gaaccucccu ugcuucuguu agagagggga agggugguau 1200
ggagggcacu ggguacaggc cugggaaugg ggaaagaaau uuuuauuuuu gaaucccugu 1260
gucucuuuua cuuaagauua aaggaaggaa aaauaaaaaa aaaaaaaaaa 1310

<210> SEQ ID NO 59
<211> LENGTH: 487
<212> TYPE: RNA
<213> ORGANISM: Homo sapiens

<400> SEQUENCE: 59
gaugugaaaa acguuuuuau uauaaucucu uaaacuuuca guguauauuu ucauuacaau 60
cauugguaca auaaaauaugg aaaugcugag cagacaauua ucacaguggc cuaugggcug 120
agggacaggg acccaggaau acuguuaccc uggauacuuc cucagggcca aucaggaggu 180
cuucaaagag uauugagagg gagagggaua gaaauauuau uaagacuguc agugcagcaa 240
cuuuuagaau gucuauuaaa gccauggaua caggauuuac gauaacagaa gauggauacu 300
aaaaaagaac agagacucaa guucuccugu aagaggcaga agaaacauug cagaagccag 360
ugccuuccuc ggguccccag ugugugcccc cauccaccca cgcauugugu uggucaucuc 420
caccugcccu gugcccagcc cugugcccac ccagguucuc cuaggcaccc accuugcacc 480
ucgcacg 487

<210> SEQ ID NO 60
<211> LENGTH: 1430
<212> TYPE: RNA
<213> ORGANISM: Homo sapiens

<400> SEQUENCE: 60
gaauucugcg cgguuuugca uuuuuugggu cagauuggcu uuuuacauga uuacgaagcu 60
ccaacgacua gaccacaggg accgucgccu uggcggccga gcagucguau ccaacuugga 120
gacagccagu ucgccgugug ucugucuguc cuucaucgca gucauggaga gagccagucu 180
gauccagaag gccaaguugg cugaacaggc cgaacgguau gaagacaugg cagcuuucau 240
gaagagcgcc guggaaaagg gcgaggagcu cuccugcgag gagcgaaacc ugcuuuccgu 300
agccuacaag aacguggugg gcggccagag agcggccugg agguccugu ccagcaucga 360 gcagaagagc aacgaggagg ggucagaaga gaagggcccc gaggugaaag aguaccggga 420
gaagguagag accgagcuca gaggugugug cgacaccgua cucggccugc uggacucgca 480
ccucaucaaa ggggcuggag augcagagag ccgcgucuuc uaccugaaga ugaaggguga 540
cuacuaccgc uaccuagccg agguggccac uggcgaugac aagaagcgca ucaucgauuc 600
ugcccgguca gccuaccagg aggccaugga caucagcaag aaggagaugc cgccuaccaa 660

```
ccccauccgc cugggccugg cccugaacuu uucagucuuc cacuacgaga uagccaacag    720

ccccgaggag gccaucucgc uggccaagac caccuucgac gaggccaugg ccgaccugca    780

cacccucagu gaggacuccu acaaggacag cacccucauc augcagcucc ugagagacaa    840

ccugacgcug uggacagccg acagugcugg ggaagagggu ggugaggcuc cggaugaccc    900

ccacaucuga agcagcggaa aaacaacccg gguuggcuug gccuuccagu ccccagccug    960

gcauagagga uuaaaaggga gugggauuuu gccuuuccca aacccugaau guucagcaac   1020

accuugggaa ggucuuucga agggggcgca gccaagcuga agccaccagg gcagggaauu   1080

uaauuuuucg uguagcuguu ugggugggug uuucccaaaa ccaucccacc ccuguuuuuu   1140

gaacccccuc cccaauucuu cccccugagc cuccccucggg caccuguugc uuuuggaucc   1200

gaauaaucca ggagguuccc cacccugugg cugagaaaug gacuguggca agggcugugu   1260

gugugugaga gagagggaaa cucugugugu guguguguga gagagagaga gagagugaau   1320

gagagggaaa aaguuugcug ggugugacca ugguaccaau caauaaaguu gcccugugag   1380

acucaaaaaa aaaaaaaaaa aaaaaaaaaa aaaaaaaaaa aaaaaaaaaa              1430
```

<210> SEQ ID NO 61
<211> LENGTH: 268
<212> TYPE: RNA
<213> ORGANISM: Homo sapiens

<400> SEQUENCE: 61

```
uuuuuuuuuu uuuuuuuaaa uaccaaaaca uuuaauugaa auaccuguau aaaaaauaug     60

aucuucagac auuucacacu uuugaacuua uacaacccca ccccugaugc uuagucacac    120

cagggucaca gaaacacagc ugcuaaaaua aauuaagggc uugagacucu gucccccaac    180

cccagcuuuc agagccagca agcagacugu acaaggucaa uaauuuaaac ccucccccag    240

cgcagagugc ucagggugac agggucuc                                       268
```

<210> SEQ ID NO 62
<211> LENGTH: 377
<212> TYPE: RNA
<213> ORGANISM: Homo sapiens

<400> SEQUENCE: 62

```
uuuuuuuuuu uuuuuuuaau guaacgaccg gugugcuuca guuuguuuag cagaaccacu     60

cucuugaauc acauuaacuu uugagauuua aaaaaaacaa aacaaaaaaa aaaaaaaaca    120

acaaaaaaaa aaccaacccu ccauagcaca gcugucuuuu augcaagcaa gagcacaccu    180

acuccagcau gauuugucau cuaaagacuu gaaaacaaaa caacaacaac aaaaaguuac    240

uuauagucaa uggauaagca gaguccgaau uuacacuaau caagacagac cuucgagggg    300

ucacgauaag uccggaacuu ucaaaccuug cuucguauga auuguacuau cugaacauaa    360

acugcacuuu uauuuuc                                                   377
```

<210> SEQ ID NO 63
<211> LENGTH: 756
<212> TYPE: RNA
<213> ORGANISM: Homo sapiens

<400> SEQUENCE: 63

```
augagacucc acagccucau ccugcucucc uuccuucucc uggcuacuca ggcguucuca     60

gaaaagguca gaaagagagc caagaacgca ccacacagca cagcggagga gggggguagag   120
```

```
gguucagcuc ccucguuagg gaaggcccag aauaagcaga gaagcaggac aucuaaaucu    180

cugacgcaug gcaaguuugu caccaaagac caagccacau gcagaugggc ugugacugag    240

gaggagcagg gcaucagccu gaagguccag ugcacacaag ccgaucagga guuuucuugu    300

guuuuugcug gugacccaac ugacugccuu aaacacgaca aagaccagau cuacuggaaa    360

cagguugccc gcacgcugcg caaacagaaa aauaucugca ggaacgccaa gagugucuug    420

aagaccagag ugugcagaaa gagauuucca gagucuaacc ucaagcuggu gaaccccaac    480

gcacguggaa acacgaagcc caggaaggag aaagcagagg ucuccgcaag ggagcacaac    540

aagguccaag aagcugucuc cacggagcca aacaggguca aagaagacau cacacucaau    600

ccagcugcga cccagaccau ggccauuaga gauccagagu gucuagagga uccagaugug    660

cucaaccaga ggaagaccgc ccuggaguuc uguggggaau cuuggagcuc cauuugcaca    720

uucuuccuca acauguuaca ggcgacauca ugcuaa                              756


<210> SEQ ID NO 64
<211> LENGTH: 4701
<212> TYPE: RNA
<213> ORGANISM: Homo sapiens

<400> SEQUENCE: 64

cgggucgacc cacgcguccg cccacgcguc cggcggagcu ucuggguugc gggccgaaac     60

ggcaagcgga uggagggcgc ucgaacggcc aggugucgug auuaaauuag ucagccccuca   120

gagacaggcg uccuaccucc uuuauccaga ccucaaaagc cccguugugc acccguggug    180

gcuucuucac cuucccuguu ucguccucca cuguauggcc cagacaugag ugguccccua    240

gaaggggccg augggggagg agaccccagg cccggagaac cuuuuugucc uggaggaguc    300

ccauccccug gggccccgca gcaccggccu uguccaggcc ccagccuggc ugaugacacu    360

gaugcaaaca gcaauggcuc aaguggcaau gaguccaacg gacccgaguc caggggcgca    420

ucucagcgga guucucauag uuccucuucu ggcaauggca aggacucagc ucugcuggag    480

accacugaga gcagcaagag uacaaacuca cagagcccau ccccacccag cagcuccauu    540

gccuacagcc uccugagugc gagcucagag caggacaacc caucuaccag uggcugcagc    600

agugaacagu cagcucgagc caggacccag aaagaacuca ugacugcacu ucgggagcuc    660

aaacuucgac ugccaccaga gcgucggggc aagggccgcu cugggaccuu ggccacacug    720

caguacgcuc uggccugugu caagcagguu caggcuaacc aggaauauua ccagcagugg    780

agucuggagg agggugagcc uugugccaug gacaugucua cuuacacccu ggaggaauug    840

gagcauauca cauccgaaua cacacuucga aaccaggaca ccuucucugu ggcugugucc    900

uuccugacag gccggauugu cuauauuucg gagcaggcag guguccugcu gcguugcaaa    960

cgggaugugu uucggggugc ccgcuucuca gagcuccugg cuccccagga ugugggugcuc  1020

uucuauggcu cuacuacacc aucucgacug cccaccuggg gcacuggcac cucugcaggu   1080

ucaggucuca aggacuucac ccaggaaaag ucugucuucu gccgaaucag aggagguccu   1140

gaccgggauc cagggccucg guaccagcca uuccgccuaa ccccauaugu gaccaagauu   1200

cggguc ucag auggagcccc ugcacagccg ugcugccuac ucauugccga gcgcauccac  1260

ucugguuaug aagcuccccg gaucccuccu gacaagagga ucuucaccac ccgacacaca   1320

ccaagcugcc ucuuccagga uguagaugaa agggcugccc cacugcuggg uuaccuuccc   1380

caggaucucc ugggggcucc aguacuucuc uuucuacauc cugaggaccg accccucaug   1440

cuggccauuc auaagaagau acugcagcug gcaggccagc ccuuugacca uuccccuauu   1500
```

-continued cgcuucugug cucggaacgg ggaauauguc accauggaca ccagcugggc cgguuuugug 1560
caccccugga gccgcaaggu ggcuuucgug uugggucgcc auaaagugcg cacggcaccc 1620
cugaaugagg acgucuucac ucccccagcc cccagcccag cuccgucccu ggacucugau 1680
auccaggagc ucucagagca gauccaucga uugcugcugc agccugugca cagcuccagc 1740
cccacggggc ucuguggagu uggcccucug auguccccug guccucuaca cagcccuggc 1800
uccuccagug auagcaaugg gggggacgcu gaggggccug ggccuccugc uccagugacu 1860
uuccagcaga ucuguaagga ugugcaucug guaaagcacc agggacaaca gcucuucauu 1920
gaaucucggg ccaagccccc accccggccc cgccuccuug cuacagguac auucaaagcc 1980
aaaguccuuc ccugccaguc cccaaacccc gaacuggagg uggccccagu uccugaccaa 2040
gccucguuag ccuuggcccc ugaggagcca gagaggaaag aaaccucugg cuguuccuac 2100
cagcagauca acugccugga cagcauccuc agguauuugg agagcugcaa cauucccagu 2160
acaaccaagc guaaaugugc cuccuccucc uccuacacug ccucuucagc cucugaugau 2220
gacaagcaga gggcaggucc aguuccugug gggggccaaga aagauccguc gucagcaaug 2280
cugucugggg agggggcaac uccucggaag gagccagugg ugggaggcac ccugagcccg 2340 cucgccccugg ccaauaaggc agagagcgug guguccguca ccagucagug uagcuucagc 2400
uccaccaucg uccauguggg agacaagaag cccccggagu cggacaucau caugauggaa 2460
gaccugccug gccuggcccc uggcccagcc cccaguccgg cccccagccc cacaguagcc 2520
ccugacccaa ccccagaugc uuaucgccca gugggucuga ccaaggccgu gcugucccug 2580
cacacacaga aggaagagca agccuucuc aaccgcuuca gagaucuugg caggcuucgu 2640
ggacuugaca ccucuucugu ggcccccuca gccccuggcu gccaccaugg ccccauuccc 2700
ccuggucgcc gacaccacug ccgaucuaaa gcaaagcguu cccgccacca ccaccaccag 2760 acccccggc ccgaaacucc cugcuauguc ucccauccuu caccugugcc cucuucugga 2820
cccuggccac ccccaccagc cacgaccccc uucccagcaa ugguccagcc cuacccacuc 2880
ccaguauucu ccccucgagg aggaccccag ccccuucccc cugccccuac aucuguguccc 2940 ccugcuaccu ucccuucucc cuuagugacc ccaauggugg ccuuggugcu cccuaacuau 3000
cuauucccua ccccaccuag uuauccauau ggggugucccc aggccccugu ugaggggcca 3060
cccacgccug cuucccacuc gcccucucca ucccugcccc caccaccucu cagccccccc 3120
caccgcccag acuccccacu guucaacucg agaugcagcu ccccacucca gcucaaucug 3180
cugcagcuug aggaguccccc ccgcacggag gggggcgcug cugcaggagg cccaggaagc 3240
agugcugggc cccugccucc cagugaggag acugcugagc cagaggccag auuggugggag 3300 guuacugagu cguccaauca ggaugcacuu ucaggcucca gcgaccugcu ggagcuacug 3360
cuccaagaag acucucgcuc gggcacaggc uccgcagccu caggcucccu gggcucuggc 3420
cugggcucug ggucugguuc aggaucccac gaaggggggaa gcaccucagc cagcaucacc 3480
cgcagcaguc agagcagcca uacaagcaag uacuuuggca gcaucgacuc uuccgaggcu 3540
gaagcugggg cugcucgggc caggacugag ccuggggacc aggucauuaa gugugugcuc 3600
caggacccca ucuggcugcu cauggccaau gccgaccagc gugucaugau gacauaccag 3660
gugccgucca gggaugcagc cucugugcug aagcaagacc gggagaggcu ccgggccaug 3720
cagaaacagc agccacgguu cucagaggac cagaggcggg aacugggugc ugugcacucc 3780
uggguccgga agggccagcu gccucgggcc cuugauguga uggcgugugu ggacuguggc 3840
agcagcguuc aagauccugg ccacucugau gacccgcucu ucucagaacu ggauggauug 3900
gggcuggagc ccauggaaga ggguggaggc gaggguggug gguguggugu uggcggugu 3960 gggggugaug guggugagga ggcccagacc caaauugggg cuaaggguuc aagcucucag 4020
gacucugcca uggaggaaga agagcaaggu gggggcucau ccagcccagc uuuaccugca 4080
gaagaaaaca gcaccagcua gauccauuuu ggggccgcuu acagcagucu aaugagaggc 4140
uuccuuucga ccauguuggg guucuuauaa cucaagauac agcuggacca accaauagga 4200
aacugcccca gcuucuccca acauaggggg cuggaccccc auuaccagcc caggcacagg 4260
agcugccucu agcuucuuag cagaguggaa guucucagcc ccauuuggag gauuguccac 4320
gcccguccca cugaggagac gggcgggucu ucgguuaagg uugcugacaa gcugcugaag 4380
uggucugucc aaaucccagc ugagccugag ucccagucgc aggguugggg cugcacuuau 4440
uuauuuggga gagacagcuc acucucccac cucaccccaa gaugggagga ggggaaccug 4500
ggaucugugu aggauccagg uccgugaacc ccuagcugcu ccaggguggg ggagguuggu 4560
ggaccaugga gucccuggug cugcccccuca ggugggaccc agguguucuc agcucuaccc 4620
ucuaccaaug acauuugugu uuuugauauu gugucuguua uuuuuuuuuu aauacaaaau 4680
gacaaaauga aaaaccaaaa a 4701

<210> SEQ ID NO 65
<211> LENGTH: 3036
<212> TYPE: RNA
<213> ORGANISM: Homo sapiens

<400> SEQUENCE: 65
gacagcggag cgcgguggcg ucgacgucua gugucucagu gcucccgucu guggcuaacu 60
aagcagccag cagccaggca gcucgcgacc ugcggccagg cagccaacca ugcucaacuu 120
cggcgcuucu cuccagcaag cuucggaggg gaaaauggaa cuaauuucug aaaagcccag 180
agaggggaug caucccuggg acaaagcuga gcagagugac uuugaagcgg uggaagcgcu 240
cauguccaug agcugcgacu ggaagucuca uuucaagaaa uaccuugaaa acaggccugu 300
cacaccagug ucugauaccu ccgaggauga cagcuugcuu ccagggacgc cugaccuuca 360
gacaguccca gcauuuuguu uaacgccacc uuacagcccc ucugacuucg aacccuccca 420
agggucaaau cugacugcau cagcgccauc uacuggccac uucaaaucuu ucuccgaugc 480
ugccaagccu ccaggcgcca cuccuuucaa agaggaggaa aagaauccuu uagcugcccc 540
uccucuuccu aaggcucaag ccaccagugu cauccgucac acagcugaug cccaacugug 600
caaccaccag uccugccccg ugaaagcagc uagcauccuc aacuaucagg acaauucuuu 660
ccggagaaga acccacggaa auguugaggc uacucgaaag aacauacccu gugcugcagu 720
gucaccaaac agauccaagc cugagcccag cacaguguccc gaugguugaug agaaggcggg 780 cgcugcacua uaugacuuug cugugccuuc cucagagaca guaauuugua ggucucagcc 840
agcuccuucg uccccagugc agaagucagu acuggugucu ucaccuacag uauccacugg 900
gggagugcca ccccugccug ucaucugcca gaugguuccc cuuccugcca acaacucucu 960
uguuagcaca guugucccca gcacuccucc uagccagcca ccagcugucu gcucaccugu 1020
guuguucaug ggcacucagg ugccugaggg caccgucgug uuuguggguac cccagcccgu 1080 ugugcagagc ccaaggccuc caguggugag ccccaguggc accagacugu cucccauugc 1140
cccugcuccu ggauucucuc cuucagcagc aagggucacu ccucagauug acucguccag 1200
aguaagaagu cacaucugua gccacccagg guguggcaag acuuacuuua aaaguuccca 1260
ucugaaggcc cacgugagga cacacacagg ggaaaaaccu uucagcugca gcuggaaagg 1320
cugugaaagg agguuugcuc gcuccgauga acuguccaga caccggcgga cacacacagg 1380
ugagaagaag uuugccuguc ccauguguga ccgucgguuu augaggagcg accauuuaac 1440
caagcaugcc cgacgccacc uaucagccaa gaagcugcca aacuggcaaa uggaaguuag 1500
caaguuaaau gacauugcuc ugccuccgac cccugcuucc gcacagugac ggccagaaga 1560
uggagacgca gaauaaacuu uggucagagu caggagccag ugauggugc aagugcuucu 1620 gcaaggcugu ggcccuccaa aagggccuaa aguagaagcc cuggccuggg ggaggccccg 1680
ccugggugaa augacaagaa gugcuucagc cacaggcagg ucacagagga cagggcucag 1740
uucuuaccac agagagagag gagaacccuu uuauuccucc cuuauuuuag ucuggaaagu 1800
uucggcugag gugagcgcag cacagguuuu gaaucacaua cacauugggg acuuuguuuu 1860
ugccauuuau acuugagacc agcuuugcag ugugauucuu ucaaaggauu gguuucaaga 1920
auauagaggc uggaaauuac gguacagaaa uggagcuaga aaaugaguuu guguuacaca 1980
gagaugucau cuucuccuag aguuaucuug uuucuuauuc cuagucuuuc cagucaaauc 2040
cguggaugua gcuaaguaua ucuaaaacuc auuuuuccac uauuguuggu auuugaaguu 2100
gaacagcugu acauugcugu gggggagcca aaggauugga acccucauua auuuaauugc 2160
uuggaaaugc agcuaaaauu cuucuuuggc auuuuguuuu gaaaguuuag gcauuuuacu 2220
cuacuuuaga uuuuaguuug cuugcaguuu uuuguguaga uuugaaaauu guauaccaau 2280
guguuuucug uaggcuuaaa auacacugca cuuuguuuag aaaaaaaucu ggagaugaaa 2340
auauguauua uaaagaagag augucaagaa uuugagauaa cuccuugaga aaguuggcuu 2400
uaugucauca gcaaaggaca cuuaacguca agcauacacu gugguuuuuu uguuuuuuug 2460
uuuuuuuuuu ucaaauuaga aaguuuaaug accguuacag auggacagug ucuuuuuauu 2520
uauaggaguu uuucaggaug ucagaguaga uagguaggaa aauuguuauu agaacauucg 2580
cuucuaccuu gaaaaggaug uuaaugugu cauguucuua gcaccacagu gucugggcau 2640
cugggaaacu ccgagacuuu uuuaaagugu caugauguga ucacaccugc aguuuggggc 2700
aucgaaucca gggccuugca ugucuucugu aagagcucuc aucgcugacc uguaucccc 2760 gcaagagcaa ugacuuuugc uaacaguauu ucuuuucugu uguaaagugg acagaugaua 2820
cacuuggucg caaagguaaa uuauucaaaa uccacaguga aaccucacc acacuuuccc 2880 auuuaaacua uuuccauauc ucagagguuu cugacaugca aacuugaacc cuugaaagaa 2940
gaguuuucuu aaaaauuaua aaaaaucacg aguuacaauu ugcacaauau uuuuuguuga 3000
acuuuauacc uuguuuacaa uaaagacuuu ucuuug 3036

<210> SEQ ID NO 66
<211> LENGTH: 526
<212> TYPE: RNA
<213> ORGANISM: Homo sapiens
<220> FEATURE:
<221> NAME/KEY: misc_feature
<222> LOCATION: (7)..(7)
<223> OTHER INFORMATION: n is a, c, g, or u

<400> SEQUENCE: 66
uugucanuug cacgacagaa acugcaggaa gaugagaugc gccgggcugc ggaggagcgc 60
aggaggguaa aggcugaaga guuagcugcc agacaaaggg uucuagaaaa aauugaaagg 120
gacaaagcag agagagccaa gaaguauggu gguagugugg guucucgguc auccccacca 180

-continued

```
gcaacagacc caggucccugu uccuucuucu cccagccagg agccccccuac uaagcgggag    240

uaugaccagu gucguauaca gguuaggcug ccugauggga cuucacugac ccagacuuuc    300

cgggcccggg aacagcuggc agcugugagg cucuacgugg agcuucaccg uggggaggag    360

ccuggacagg accaggaccc ugugcaguug cucaguggcu uccccagacg ggcuuucuca    420

gaggcugaua uggaacggcc ucugcaggaa cugggacucg ugccuucugc uguccucauu    480

guggccaaga agugucccag cugagggguuc uccaucccac caucuc                526
```

```
<210> SEQ ID NO 67
<211> LENGTH: 425
<212> TYPE: RNA
<213> ORGANISM: Homo sapiens

<400> SEQUENCE: 67

uuuuuuuuuu uuuuuuucac aaauaaguaa uauaacuuua uuaaaaugaa aagacaauau     60

ucaaaauaau gcaacaaaau gaauaaaucc uuuguccaau acuguacaca cagugcggag    120

aucagugcau uuuucuaaag cauguuuuaa ccuucauuua guucauacua aaguaagcuu    180

uaaauagcuc aaauaauguc auucagcagu uuaaacugaa cagcuuguug ggacauggca    240

gcaguguccc ugcuagcaag caccuucucu uuguguuuau cugcacaaga uaaacaauca    300

gaggauguaa aaacugaaca caaacugcgu gucucacuga aucucagggc agugaagcag    360

ccagcgugag uuuucaaagc aggaagaugc ugaagugacc ucuggcauua agacguucug    420

ugcua                                                              425
```

```
<210> SEQ ID NO 68
<211> LENGTH: 2282
<212> TYPE: RNA
<213> ORGANISM: Homo sapiens

<400> SEQUENCE: 68

uucauuggaa agcacauugc ucuucucagu aauuucuuua guaucuucau gaauuuuuuc     60

cuuuugcguc guuauuucag caauucuauc ugcagaucau aaagguagua uugacagaug    120

ugauucuuuu ucuuaaacau uucauuucca ggguaaggaa cucaauggcu auguuuuucu    180

cuccccucuag ugcauccuuc uccuuuucua ccauuuucac ucuauuuaac uucaucaugu    240

ucagucuggc cuuugggguuu caucauagca aucuguucaa cuucacccug caagauuaaa    300

aaucgauuau ggucuaaguc aaugccaugg cuucuaagga gauuuccaac aucuuuaaac    360

gucuucuucu ucccacuuau gugguagaca gaagugcuau cucuguaggc gguucuggau    420

acauagaagu ugcuguuagg aaggacuucg uaaucaucuc cuuccuuauc aauuaucuuu    480

ugaaaaugaa cuucuacagu acaacucuga auauccuugu guucaucaga auuauguauc    540

aguaccgaua gcuuuuuaga ccuuauuuuu ugugcucgau agccaaacac aaaaagcaug    600

gaaucaauaa cauuggauuu uccacugcca uuugguccaa uaauacagga aaagcgcuua    660

uggaaagguc ccacaaguuu cucuccagca uaggacuuga aguuuugguu uacaauauga    720

guuaucauga gacgaggagc uccagcuuca cuggccaugg cuggaggugg ggguggaggg    780

auacuauuca aaaucuccuc uaaacuucug uuauccagcu ccucaccugg aggcuuugcg    840

ggugcagcgc ucccccucacc uacuucgccu acugcaacuc ccaccaccuc cucucgauac    900

aagaccgagc ucugucggac cuacucagaa agcgggcguu gucgcuacgg ggccaagugc    960

caguuugcuc acggccuggg ugaacuucgc caagccaauc gccaccccaa guacaaaacg   1020

gaacucugcc acaaguucua ccuccagggc cgcugccccu auggcucucg augccacuuc   1080
```

auccacaacc ccaccgagga ccuagcucuc ccuggccagc cccaugugcu gcgacaaagc 1140
aucagcuucu ccggcuugcc ucaggccgca gaagcucgcc gccaccucca ggcuuuucug 1200
gcccuucccu guccucuugu uccuuuucgc cuuccagcuc cccaccgccc ccuggggauc 1260
uuccacuuuc cccuucugcc uucucugcug ccccugggac cccugugacu cgaagagacc 1320
cuaaccaggc cuguugcccc uccugccgaa ggucuacuac ccccagcacc aucugggggc 1380
ccuugggugg ccuggcucgg agcccaucug cccacucucu gggauccgau ccugaugacu 1440
acgccagcag cggcagcagc cugggggggu cagacucacc ugucuuugag gcaggggugu 1500
uugggccucc ccagacccu gcaccccaa ggcgucuccc caucuucaau cguaucucug 1560
ucucugagug acaagugccu accuacccag uauggaucag cuagaucuca aagagagggc 1620
agggacugcu cauugcugug gggaccuggg gcacuccucu aaguuaauaa gucccaucuu 1680
cuggacauuc caagaugcaa uaacccauuu cccuggugcu gggcuggggc agguccccuag 1740 uuugcaaauu caguguuugg guggauccgu uccuagggua ccuaagaugu uugagggaga 1800
caguugacag uuggucuucc aggccccaag ucuucuguug uuuuugagau aggagcuuau 1860
uaugguaccc caggcuggcu uugaacucaa uauaauccug ccuuagccuu uuccaaguuc 1920
ugggguuaca gguaugcacc agccccucug caacucuggu cuccuggaau cuuaagugcu 1980
gugaagagcc ggcucccaca auacuauccu aauuuuuacu agacccugaa guucaguguc 2040
cgguggucga agccucuccu gagaauccug gugcucaaau uucccuccua aagcaaauag 2100
ccaaagccau ugccaaaucc cuucuccccc aaccaguggg cccuuuauuu augacgacuu 2160
uauuuauugu auuaagauuu uauaguauuu auauauauug ggucgucuac uccguuuuuc 2220
uuuuuguaau guuaaaacug auacuguauu aaguauaugc uauaauauau uaauauauug 2280
cu 2282

<210> SEQ ID NO 69
<211> LENGTH: 364
<212> TYPE: RNA
<213> ORGANISM: Homo sapiens

<400> SEQUENCE: 69
cggacgcugc agaccugacc gacgugcugu gcgaguucga cgcggugcug gccgacuucg 60
cgucgcccuu ccacgagcgc acuuccacua ugaggagcac cuagagcgca ugaagcggcg 120
cagcagcgcc agcgucagcg acagcagcgg cuucagcgac ucggagagug cagacucagu 180
guacagggac agcuucaccu ucagugauga gaagcugaau ucuccaacca acuccucucc 240
agcucuccug cccuccgcug ucacuccucg gaaagccaaa uuaggugaca cuaaagagcu 300
cgaagacuuc auugccgauc uggacaggac cuuagcaugu augugaagca aggaguuugg 360
gguc 364

<210> SEQ ID NO 70
<211> LENGTH: 847
<212> TYPE: RNA
<213> ORGANISM: Homo sapiens

<400> SEQUENCE: 70
ccgggccgag gagaagucug caaaacaaga ggcuggggau ugccuuagcg agaaaucagu 60
ucucuuagga gguuagggaa ggaagucuuu cucuggaggu cugagggaag cgcucguguc 120
agaugccggg uugucauggg uaagggugac cccaucaagc cgcugggcaa aauguccucu 180
uacgccuuuu uugugcagac cugccgggag gagcacaaga agaagcaucc caauucgucg 240
gucaacuucg ccgagaucuc caagaaaugc uccaagagau ggaagaccau gucugcaaag 300
gaaaacucga aguuugaaga uuuggccaag agcgacaaag cuuguuauua cagggagaug 360
aagaacuaug uuucucccaa aggugauaag aaaggaaaga aaaaagaucc aaaugcuccg 420
aagagaccac cgucugccuu cugccuguuu ugcucugaaa aucgcccaaa gaucaaaauu 480
gaauacccgg gccugucuau uggagauacu gcgaagaaac ugggugagau guggucugag 540
cagucugcca aagagaaaca accguaugag cagaaagcag cuaaacuaaa ggagaaguau 600
gaaaaggauu uugcugcaua ccgugucaag ggcaaaagug aagcaggaaa gaagggucccu 660 gguaggccag caggcucaaa gaagaaugac ucagaagaug aggaagaaga agaggaggaa 720
gaugaagagg gggaagaaga ggaugaagaa uaaguggcua uccuaaagug uggaguauau 780
gugcucaggc aguuauuuug cuaagaaugu aaauucaagc gcagcucaac auuagcucca 840
guaggaa 847

<210> SEQ ID NO 71
<211> LENGTH: 779
<212> TYPE: RNA
<213> ORGANISM: Homo sapiens

<400> SEQUENCE: 71
aucacgcucc uagaacucuu caaaccgauc ucucgucgau cuucaaccgc cgccuccacu 60
cgccauggac cccaacugcu ccugugccuc cgguaagggg gacugcugac gggauuucug 120
ggagagcuag acaggcuuuu uggccccucc uuuaguaauu acuuuaaggg uacgaccggc 180
uaccccuucc gaaugaauuc ugaagcacuc cugcuccuuu aaacuagucc uugagauagu 240
ggcucgccua cccgggugau uugccucacc uuccuaggag aacagcguuc agguacuccc 300
gggucccacu caaccgcgcu cacugacugc cuucuacuuu uagauggauc cugcuccugc 360
gcuggcgccu gcaaaugcaa acaaugcaaa uguacuuccu gcaagaaaag uaaguuggau 420
cuucucugcc auuuccccgu cacucuccug ggguccuag cccgccgcgc cgcgccuucc 480 cuccccgggag cguucaggug gugugccucu gacaagguuu cucgcucacg uucaacucuu 540
cucuccccac aggcugcugc uccugcugcc ccgugggcug ugcgaagugc ucccagggcu 600
gcaucugcaa agaggcuucc gacaagugca gcugcugugc cugaaggggg gcggaggggu 660
ccccacaucu guguaaauag accauguaga agccuagccu uuuuuguaca acccugacuc 720
guucuccaua acuuuuucua uaaagcaugu aacugacaau aaaagccguu gacuugauu 779

<210> SEQ ID NO 72
<211> LENGTH: 2275
<212> TYPE: RNA
<213> ORGANISM: Homo sapiens

<400> SEQUENCE: 72
gcucugaguu uguggaagau uacaugcgau aucccgcgcg accccgcauc ccuuugccgg 60
ccgggacagc cuuugcuaca gccugugaaa cauugcgucc ccgagcccca cgccugaggg 120
cgacaugaac ccgcuggcuu cgcgagcagu ccggacccac gaucgcuuuu ggcaaccaga 180
accggcgcuu cagcccccgg ggugacgugc agcccgccgc ccagacacau ggccccgagc 240
ccaagacccc agcauguccu gcacuggagg gacgcccaca acuucuaucu ccugucccca 300
cugaugggcu ugcucagucg ggccuggagc cgccugaggg gcccagaagu cccagaggca 360
uggcuggcaa aaacaguaac aggagcagau cagauagaag cugcggcucu gcugacaccu 420

-continued

```
accccugucu cugguaaccu ccucccucau ggggagacug aagaaagugg aucuccugaa    480
cagagucaag cagcccagag gcucugccuu guggaagcug aaaguucccc uccugaaacu    540
uggggacuuu caaauguuga ugaguacaau gcaaagccag gacaagauga ccuuagagag    600
aaggaaaugg aacgcacagc uggcaaggcc acacuacagc ccgcuggccu gcaaggggcu    660
gauaagaggc uuggggaggu gguggcuaga gaagagggag uggcugagcc cgcuuauccc    720
acaucacagc uggagggugg uccagcugag aaugaagagg auggagaaac agugaagacu    780
uaccaagcuu cugcugcuuc cauagcuccg ggauacaaac ccagcacccc ugugccuuuc    840
uugggggagg cagaacauca agccacggaa gaaaaaggaa cagaaaacaa ggcugacccc    900
uccaacucuc cuucuucagg cucccacucc agagccuggg aguacuacuc uagagagaag    960
ccuaagcagg agggagaagc caagguagag gcacacaggg cagggcaggg ucacccuugu   1020
cggaaugcug aggcugagga aggaggaccu gagacaacuu uugucuguac uggaaaugcc   1080
uuccugaagg ccugggugua ucgcccagga gaggacacag aggaagaaga caacagcgau   1140
ucggauucag cugaggaaga cacagcucag accggugcca ccccccauac aagugccuuc   1200
cugaaggccu ggguguaucg cccaggagag gacacagagg aagaagacag cgauucggau   1260
ucagcugagg aagacacagc ucagaccggu gccacccccc auacaagugc cuuccugaag   1320
gccugggugu aucgcccagg agaggacaca gaggaagaaa acagcgauuu ggauucagcu   1380
gaggaagaca cagcucagac cggugccacc ccccauacaa gugccuuccu gaaggccugg   1440
guguaucgcc caggagagga cacagaggaa gaaaacagcg auuuggauuc agcugaggaa   1500
gacacagcuc agaccggugc cacccccacau acaaguccu uccugaaggc cugggugua u   1560
cgcccaggag aggacacaga agaugacaca gaagaggaag aggacaguga gaauguggcc   1620
ccaggugacu cagaaacagc ugacucaagc cagaguccu gccuucagcc ccagcguugu   1680
cuaccaggag agaagaccaa gggacguggg gaagagcccc cucucuucca gguggccuuc   1740
uauuuacccg gagagaagcc agaaucaccu ugggcugcac cuaagcugcc ccuucgacug   1800
cagaggcggc ucagauuguu caaagccccc acccgggauc aggaccccga gauuccucua   1860
aaagcucgga agguacacuu cgcugagaaa gucacagucc auuuccuugc ugucugggca   1920
ggaccagccc aagcugcccg ucgagguccc ugggagcagu uugcacgaga ucgaagccgc   1980
uuugcucgac gcauugccca ggcagaggag aagcuggguc ccuaccuuac cccugauucc   2040
agggccagag caugggcacg ccuuagaaac ccaucucuuc cacaguccga gccucgcucu   2100
uccucugagg ccacucccuu gacccaagau gugaccacac ccucuccccu ucccagugaa   2160
accccuucgc ccagccugua cuugggaggg aggcggggcu aagccugagu aguuuccuau   2220
uauuuauuua uuuauuuauu ugaauaagaa auaaagccuu uuaauuugua gugau        2275
```

<210> SEQ ID NO 73
<211> LENGTH: 355
<212> TYPE: RNA
<213> ORGANISM: Homo sapiens

<400> SEQUENCE: 73

```
uuuuuuuuuu uuuuuuuaau caucgagaag uauuuauuga gcaccagcuu uggggucggg     60
ugugaggacu cgggacaaug cagggugcug ucccuucucg ugagacgcuu acaaucugag    120
uggagacagg gagggagcca caauacaugu ucuuggggug cgggcuaagg guagacaguc    180
cagaccagga uguuacagaa acagggaugu uuggggcugg agucagaccc acuaagugcu    240
```

uugacaccca cgguauucaa cacugagaaa ggaucagcca uugcucagug uccugugagc 300
ucccuuagcc cccaagacac caucuuggcc uggcuccuug uacaacugcu acuaa 355

<210> SEQ ID NO 74
<211> LENGTH: 289
<212> TYPE: RNA
<213> ORGANISM: Homo sapiens

<400> SEQUENCE: 74
cccaaaaccc auucagcaaa guucccaacc ucgacgggcu agcaguauuu aaccagugau 60
ggguucacug uuguauuugg ugaauacugu auuuuguuuc aguucuuucu cccagauaau 120
uugaaaacgu uccaggagaa ggcagcuucc uauaugcagc gugugcuuuc uuauucuuuu 180
uuuuaauaua ugacaguuau uugagaaccc auuucuacuu ugaauucauu uucguugaaa 240
gugauguuuc uucaccuacc auuuuccuau uaaaguucug uauucaaau 289

<210> SEQ ID NO 75
<211> LENGTH: 2018
<212> TYPE: RNA
<213> ORGANISM: Homo sapiens

<400> SEQUENCE: 75
agaccgugag cgagagcgcc ccagagaagc gccugcaauc ucugcgccuc cuccgccagc 60
accucgagag aaggacaccc gccgccucgg cccucgccuc accgcacucc gggcgcauuu 120
gaucccgcug cucgccggcu uguugguucu gugucgccgc gcucgccccg guuccuccug 180
cgcgccacaa ugagcuccag caccuucagg acgcucgcug ucgccgucac ccuucuccac 240
uugaccagac uggcgcucuc caccugcccc gccgccugcc acugcccucu ggaggcaccc 300
aagugcgccc cgggagucgg guugguccgg gacggcugcg gcugcuguaa ggucugcgcu 360
aaacaacuca acgaggacug cagcaaaacu cagcccugcg accacaccaa gggguuggaa 420
ugcaauuucg gcgccagcuc caccgcucug aaagggaucu gcagagcuca gucagaaggc 480
agacccugug aauauaacuc cagaaucuac caaaacgggg aaagcuucca gcccaacugu 540
aaacaccagu gcacauguau ugauggcgcc gugggcugca uuccucugug uccccaagaa 600
cugucucucc ccaaucuggg cugucccaac ccccggcugg ugaaagucag cgggcagugc 660
ugugaagagu ggguuuguga ugaagacagc auuaaggacu cccuggacga ccaggaugac 720
cuccucggac ucgaugccuc ggagguggag uuaacgagaa acaaugaguu aaucgcaauu 780
ggaaaaggca gcucacugaa gaggcuuccu gucuuuggca ccgaaccgcg aguucuuuuc 840
aacccucugc acgcccaugg ccagaaaugc aucguucaga ccacgucuug gucccagugc 900
uccaagagcu gcggaacugg caucuccaca cgaguuacca augacaaccc agagugccgc 960
cuggugaaag agacccggau cugugaagug cguccuugug gacaaccagu guacagcagc 1020
cuaaaaaagg gcaagaaaug cagcaagacc aagaaauccc cagaaccagu cagauuuacu 1080
uaugcaggau gcuccagugu caagaaauac cggcccaaau acugcggcuc cugcguagau 1140
ggccggugcu gcacaccucu gcagaccaga acugugaaga ugcgguuccg augcgaagau 1200
ggagagaugu uuuccaagaa ugucaugaug auccaguccu gcaaauguaa cuacaacugc 1260
ccgcauccca acgaggcauc guuccgacug uacagccuau ucaaugacau ccacaaguuc 1320
agggacuaag ugccuccagg guuccuagug ugggcuggac agaggagaag cgcaagcauc 1380
auggagacgu gggugggcgg aggaugaaug gugccuugcu cauucuugag uagcauuagg 1440
guauuucaaa acugccaagg ggcugaugug gacggacagc agcgcagccg caguuggaga 1500
augccaaggg gcugaugugg acggacagca gcgcagccgc aguuggagaa gacuucgcuu 1560
cauaguacug gagcgggcau uauugcucca uauuggagca uguuuacgga ugacguucug 1620
uuuucuguuu guaaauuauu ugcuaagugu auuuuuuugc uccagacccc cccccccuuu 1680
cuugguucua caauuguaau agagacaaaa uaagauuagu ugggccaagu gaaagcccug 1740
cuuguccuuu gacagaagua aaugaaagcg ccucucauuc cuuccccgagc ggagggggac 1800 acucugugag uguccuuggg gcagcuaccu gcacucuaaa acugcaaaca gaaaccaggu 1860
guuuuaagau ugaauguuuu uuuauuuauc aaaguguagc uuuuggggag ggaggggaaa 1920
uguaauacug gaauaauuug uaaaugauuu uaauuuuaua ucagugaaga gaauuuauuu 1980
auaaaauuaa ucauuuaaua aagaaauauu uaccuaaa 2018

<210> SEQ ID NO 76
<211> LENGTH: 358
<212> TYPE: RNA
<213> ORGANISM: Homo sapiens

<400> SEQUENCE: 76
ccaauaccac agccgugacc acagccaaga ccacagccaa aagccuggcc auccgcacuc 60
ucggcagccc ccuggcagug cccuccauau ccugcuuguu uuucucauua guaaacuccu 120
cuucuaaaga aaacugggga agcagaucuc caaccuccag gucauccucc cgagcucauu 180
ucaggccagu gcuuaaacau acccgaauga agguuuuaug uccucagucc gcagcuccac 240
caccuuggac cacagaccug caacacuagu gcacuugagg gauacaaaug cuugccugga 300
ucuuucaggg cacaaauucc gcuucuugua aauacuuagu ccauccaucc ugcgugua 358

<210> SEQ ID NO 77
<211> LENGTH: 870
<212> TYPE: RNA
<213> ORGANISM: Homo sapiens

<400> SEQUENCE: 77
auggagaacg aguucacaua cgaagauuau gagaccacug ccaaguggcu ucugcaacac 60
acugaauauc gaccucaagu ggcagugauc uguggguuccg gcuuaggagg gcugacugcu 120
cacuuaaagg aggcucagau cuuugacuac aaugagauac ccaacuuucc ccaaagcaca 180
gugcaagguc acgcaggccg acugguguuu ggauugcuga auggcagaug cugugugaug 240
augcaaggcc gguuccauau guaugaagga uacucacugu caaaggugac auucccagug 300
agaguuuucc aucuucuggg uguggaaacu uuggugguca ccaaugcugc uggaggacuc 360
aaccccaauu uugaaguugg agauauuaug cugauccgug aucacaucaa ccuaccuggu 420 uucugugggcc agaacccucu ccggggcccc aacgaugaaa gguuuggagu ucguuuuccu 480
gccaugucug augcuuauga ccgggauaug aggcagaagg cuuucagugc cuggaaacaa 540
augggggagc aacgaaagcu acaagaaggc accuacguga uguuggcagg ccccaacuuu 600
gagacugugg cagagagucg ucugcuaaag augcuggggg cagaugcugu uggcaugagc 660
acagucccag aaguuaucgu cgcaaggcac ugugggcucc gugucuuugg uuucucacuc 720
auuacgaaca agguugucau ggauuaugag aacuuggaga aggccaauca cauggaaguu 780
cuggaugccg ggaaagcagc ugcacagaca uuggaaaggu uugucuccau ucuuauggag 840
agcauuccac ucccggaucg uggcagcuga 870

<210> SEQ ID NO 78

<211> LENGTH: 4928
<212> TYPE: RNA
<213> ORGANISM: Homo sapiens

<400> SEQUENCE: 78

```
uuccaggaca gcuggggcuc cacgagagaa acccugccuc ccccccaaaa auggcccaaa     60
guucacugac aaacucacau uugucugaua uuuagcuaug uaacagcacu uacgguagca    120
auagaauuug auucucacuc aucacaauga aaauggcugg cgcucucucu cucccucucu    180
ccccauuuca aaucugcaag cacaccccuu agagauggag agaauuugau ccauuggaga    240
aucgagcuaa aaauaccacc auggaauugu gggaaggauu aaaugcaaua augcacaaaa    300
ggcacauagc agaaugugcc cuaaauguca gccauuguua ugguauuaug uaaucuacaa    360
aguauguuug cuuacuccgu gugaaagacu uucagucuau caaacauaau acaugugaaa    420
ucaaaccuug aaaauuaauu uuuuucccaa cagucaagac auuugccagc ugcagagauu    480
agcauuucau gaaucuuagu cuugucugau uuuuuuaaug ggaaggaaca acuauccuca    540
acuauccuuu uuuuuuuucu guaguuuuaa aaugaacucc acaaaacaug uuuuuaauau    600
agggaauuau augaaauugu gggguggca gcgagguuaa aggcagaaau agcccaaugg    660
uggcacauuc acugacacag ccuaaaagau uagcaaauua cccagccaac acauacaauu    720
aauacaauua auauuuuuau aguuaaaaca gaguuacuaa agaaauuguu ugaaaagaaa    780
auuaugaaga cuggaaagac ggcucagugc uuaagagcuu uggcuagucu uccagagaac    840
cagggucauc cagcacucac aaggcagcuu gugagcugau acuaucugua uauucagucc    900
uagggaaucu gaugcuuugu ccugaccucc aaaacaggca caaaugugu gcacaggcaa    960
auguagagau aagacuccca ugcacagaac auaaauaacg uaguuuaauu uuuuaaauug   1020
uaaaacugaa aaugguugca cuugcauuuu uauuuucagc acauccccag auauccgcca   1080
uauaacaaga aaaugaugcc acacucccaa gaauuaagaa uuacaccucc caacccuacc   1140
caaaugugua uacucuaggu cuaaagaaau gcaaaggaug aaguuacugc cuugugcggu   1200
ucucaaggag ggaggaugcc aaaaaaaauau uuuuucacaa agugugcuga gaaacucugu   1260
agcuguugga gucaucuccu gugcucuugc caaauaacug aaaggggaua cacuggaugu   1320
cugugaaugg ggugucacuu augagugcua gaagcgggua ccuggaugug gacacggugu   1380
cugagugguc cgcacuccau gucuccacag gagcgcuuau guguguuucu uuccuccugc   1440
uucugggugu uccuggguuu guuuacagcc accucucugu uggaccagga gacagcuguc   1500
gucuccagaa ugagcgggca cgggugugc ucggugggcug uggcugugu ucggcauaag   1560
ucugagcaug uccuggucgu cagggugcgu uugugcugug ugugcguguc cgggugagcu   1620
ugcucuuucu guuccuaaaa gaaaaugcac ccugcgcuac cggcguccag agacucucag   1680
cccgcagagg ugaccugaac ggacagguag caccuccaga cagcgccugg uuggcggguu   1740
gcacagcagc cccagauuuc ucucucuggu gccccagcua ggguagcugg aagggagcgg   1800
uggccuggcc uccggggagc cgcugggccc cgccgggcua acccaggagg aggccggcua   1860
ggcugggagg guuagcccuu ggugcccuac gccugcccgg gccagucgcg gccgccggcc   1920
auuggcccaa agaauuguug cacgucacug gcaauucccc uagaagucug ugcacauaac   1980
gggcagggcg cacugcaagg cugcuucucc cgcauuuagg cugcggcugc aggcaccgcg   2040
agcccggagc acccacgagc uuagugugca ggacgcaccc cagcacagcc accuacggcc   2100
gcugaaugaa gcuuccagga guccgccccc ggccgucgcc ccgucggagg ugcacccgcu   2160
gagagcgccu ggaccgaaag gccggugcgc ucaccugcua accugccagc caugggggca   2220
```

```
cacgggaacg acagcgacuu cuugcuggca cccaacggaa gccgagcgcc acaccacgac   2280
gucacucagg aacgggacga agcgugggu guggcaugg ccauccucau gucgguuauc   2340
guccuggcca ucguguuugg caacgugcug gucaucacag ccauugccaa guucgagcga   2400
cuacaaaccg ucaccaacua cuucauaauc uccuuggcgu gugcugaucu agucaugggc   2460
cuagcggugg ugccguuugg ggccagucac accucuauga aaauguggaa uuuuggcaac   2520
uucuggugcg aguucuggac uuccauugau guguugugcg ucacagccag caucgagacc   2580
cugugcguga uugcagugga ucgcuauguu gcuaucacau cgcccuucaa guaccagagc   2640
cugcugacca agaauaaggc ccgagugguc auccugaugg uauggauugu aucuggccuu   2700
accuccuuuu ugccuaucca gaugcacugg uaccgugcca cccacaagaa agcuaucgau   2760
uguuacaccg aggagacuug cugugacuuc uucacgaacc aggccuacgc caucgcgucc   2820
ucgauugugu cuuucuacgu gccccuggug gugauggucu uugucuauuc ccgggucuuc   2880
cagguggcca aaaggcagcu gcagaagaua gacaaaucug aaggaagauu ccacgcccaa   2940
aaccucagcc agguggagca ggaugggcgg acgggccacg gacuccgaag guccuccaag   3000
uucugcuuga aagagcacaa agcccucaag acuuuaggca ucaucauggg cacauucacc   3060
cucugcuggc ugcccuucuu cauugucaau aucgugcacg uuaucaggga caaccucauc   3120
ccuaaggaag uuuacauucu ccuuaacugg uugggcuacg ucaacucugc cuucaauccu   3180
cuuaucuacu gucggagucc agauuucagg auugccuuuc aagagcuucu gugccuucgc   3240
aggucuuccu ucgaaaccua ugggaacggc uacucuagca auagcaacgg cagaacggac   3300
uacacagggg agccaaacac uugucagcug gggcaggaga gagaacagga acugcugugu   3360
gaggaucccc caggcaugga aggcuuugug aacugucaag guacugugcc uagccuuagc   3420
guugacuccc aaggaaggaa cuguaguaca aaugacucgc cacuguaaua caggcuuucu   3480
acucucuaag accccuccuu gacaggacac uaaccagacu auuuaacuug aguguaauaa   3540
cuuuagaaua aaauuguaua gagauuugca gaaggggggg cacauccuuc ucgccuuuuu   3600
uuaauuuuua uuuuauuuuu uagcugcaaa caagagagag aacuguauuu gagugcuuau   3660
uguucuugua uaguucaguu ccucuuguau ggaacuuaaa gguuucuguc ugaagagugu   3720
ugguucugag gacugagucu gucugucugu cugucugucu gucugucugg augauguuuu   3780
cauguaucua ccucacuggu caaguauuaa gaaugauaua uauugcugcu ggaaauccau   3840
aucuaaagga gagaguuuuc uuccuguacc cuuggacuug aaauauccug ugucuuggac   3900
cuuucugcug ugacaauggg cccuuucucu cucacuccac uuauuuacuc aaauggauuc   3960
gaggcaggga uuugagggac aacacuaguu guuuuguuuu uguuuuuguu uuuuuguuug   4020
uuugguucgu uuuugguuug uuguuguuuu uuggggguuug uuuuuguuuu uguuuuuuug   4080
gguuuuuuuu uuuugcugag aaaagucuaa aguuuacagu aaauaaauug uuuaaccaug   4140
acuucauugc acccguuucu ucaaaaccuc uugacucugg aguguccuug ucucucccac   4200
uggaaaccac agguaaacua ugugucguga ccgaugagug gcuuaaugug uaagaguacc   4260
agaauggcau gcuugcaugc accgugccua gcccuuccgu gugugucuuc agagcuccag   4320
augcaaaccu gugccuuccc uaacuucacu cgugucccaa agcaguccug ccuguucaca   4380
gcauaaccca guauguccua caguugcucu ucugugcugu cacuccagaa acccugacuc   4440
acggaaacag aguuauggac auauguuuuu guccccauau gcucugacac caccuucagc   4500
cuuacuugcu uaauaacugu guauauuuac aucacugcgu cucuuacagu agugccuuug   4560
```

```
uacugcauca gggcuuggug uguucaggau gaggaagaug uucuguguaa uagcuguuca   4620

agcaucuaga aauucugagg gaaaucaaag gccucgguca gagagagaga gagagagcaa   4680

agcuuuaaaa aacauagcug gugaaugcuu cacgcccuuc agccucuccu cgcuccgucu   4740

gcugucccgu gucuucuguu cccaauucuc ugcacuucug uguaaaccag gcuucccaug   4800

ucuggcauuc cgugcauuau augauauuug gcggcacguc uguaccagua aauucuggua   4860

gcaccccua guuacaauaa uugcagacac ucagcgcgua cgaccccua guuacauaug   4920

cagacacu                                                            4928


<210> SEQ ID NO 79
<211> LENGTH: 374
<212> TYPE: RNA
<213> ORGANISM: Homo sapiens

<400> SEQUENCE: 79

uuuuuuuuuu uuuuuuuaag cguccaggcu guacuuuauu uuacacaagu gguggcccca     60

gaaccacagg gacaugaccu ggagaguagg cacagugccu gaggcugcaa gagccaaaua    120

cagggauuca ugccuucucc uuggucccca ugaccaaauu aaaaaaaaaa aaaacaacaa    180

aucacacagc acacaucgcc acacccaucc ccuccuuccu uucagcaaca gccaauucag    240

cuuucuagcc aaagacagug gcuacaacug aauuuacaga gaaccaugca gccaagaaac    300

cagagccacg gaggggagag gcuugcguug acuucccaca ugugcugucc cauagcagcu    360

gagugacccc acca                                                      374


<210> SEQ ID NO 80
<211> LENGTH: 1285
<212> TYPE: RNA
<213> ORGANISM: Homo sapiens

<400> SEQUENCE: 80

agaaagauaa gggccagcaa ggaaagaaug aggauguggg cgccgaggac ccguccaaga     60

agaagcggca acgccggcag aggacucauu ucacuagcca gcagcugcag gagcuggaag    120

ccacuuucca gagaaaccgc uacccagaca uguccacucg cgaagaaauc gccgugugga    180

ccaaccuuac ggaagcccga guccggguuu gguucaagaa ucgccgggcc aaauggagaa    240

agcgggaacg caaccagcag gccgagcugu gcaagaaugg cuuugggccg caguucaacg    300

ggcucaugca gcccuacgau gacauguacc ccggcuauuc guacaacaau ugggcugcca    360

agggccucac gucagcgucu cuguccacca agagcuuccc cuucuucaac uccaugaacg    420

ucaaucccu guccucucag aguauguuuu ccccgcccaa cuccaucuca ucuaugagua    480

ugucguccag cauggugccc uccgcgguga ccggcguccc gggcuccagc cucaauagcc    540

ugaauaacuu gaacaaccug agcagcccgu cgcugaauuc cgcggugccc acgcccgccu    600

guccuuacgc gccgccgacu ccuccguacg uuuauaggga cacauguaac ucgagccugg    660

ccagccugag acugaaagca aagcagcacu ccagcuucgg cuacgccagc gugcagaacc    720

cggccuccaa ccugagugcu ugccaguaug cagucgaccg gccgguguga accgcgccca    780

gggcgcgggg auccgaggac ugucggagug ggcaacucug ccccagaaag acugagaauu    840

gugcuagaag uucgugcgca cuaugggaag gaagaggggg gaaaaaagau cagaggaaaa    900

gaaaccacug aauucaaaga gagagcgccu uugauuucaa aggaaugucc ccaagugucu    960

acgucuuucg cuaagaguau ucccaacagu uggaggacgc guacgcccac aaauguuuga   1020

cuggauauga cauuuuaaca uuacuauaag cuuguuauuu uuuaaguuua gcauuguuaa   1080
```

```
cauuaaaaug acugaaagga uguauauaua ucgaaauguc aaauuaauuu uauaaaagca   1140

guuguuagua cuaucacuac aguguuuuua aaggcuaggc uuuaaaauaa agcauguuau   1200

acagaaucag uuaggauuuu ucgcuugcga gcaaaggaau guauauacua aaugccacac   1260

uguauguuuc uaacauauua uuauu                                         1285
```

<210> SEQ ID NO 81
<211> LENGTH: 801
<212> TYPE: RNA
<213> ORGANISM: Homo sapiens

<400> SEQUENCE: 81

```
cugagaggcc aggugggcgg cgaaaucaac guggagaugg augccgcucc cgguguggac     60

cugagccgca uccugucaga gaugcgugau caguacgaga agauggcgga gaagaaccgc    120

aaggaugccg aagacugguu cuucagcaag accgaggagc ugaaccgcga gguggccacc    180

aacagcgagc uggugcagag cggcaagagc gagaucuccg agcucaggcg caccaugcag    240

gcccuggaga uugagcugca gucccagcuc agcaugaaag caucucugga gggcagccug    300

gcagagacag agaaccgcua cugcgugcag cugucucaga uccaggggcu gaucggcagu    360

guggaggagc agcuggcuca gcugcgcugc gagauggagc agcagaacca ggaguacaag    420

auccugcugg augugaagac aaggcuggag caggagaucg ccaccuaccg ccgucugcug    480

gagggagagg augcccaccu gacucaguac aagccaaaag aaccugugac cacccgccag    540

gugcgcacca uuguggaaga aguucaggau ggcaagguca ucucaucccg ggaacaggug    600

caccagacca cccguuaagg acucagcucc uuccgcccag uuccccgagg cugcagagag    660

gcagcuuccc ucuccgcucc ggcaucaccc uccugcuaca gccucucccc agcauuccua    720

ugcuugagac cauuaaagcu ugcugaccug aagugaacug uggccuuugu ucugaacacu    780

gaaauaaaug accaugguga c                                              801
```

<210> SEQ ID NO 82
<211> LENGTH: 216
<212> TYPE: RNA
<213> ORGANISM: Homo sapiens

<400> SEQUENCE: 82

```
ccccaggggu gaaaugagga uucccccacc cugcggaaca gugaaaugug uauaaauuaag     60

aggagggcga cgacccuugc cgcgggaccc gggacucgag cccgggacuu cgcagcuaca    120

gcaaaucuau uuuuaauauu gugcugagca agacagaucg cuugcauauu uuuaaaaauu    180

uuuacuacag agacauucca auaaauucgu uaagcc                              216
```

<210> SEQ ID NO 83
<211> LENGTH: 2901
<212> TYPE: RNA
<213> ORGANISM: Homo sapiens

<400> SEQUENCE: 83

```
cugacagucg ucucuguccc uucuucgccu cggagcugcu aacuggucuc gaaccucuca     60

gcacuucagc uucuagcggc gaugcaugug aucaagcgag auggccgcca agagcgaguu    120

auguuugaca aaauuacauc acgaauccag aaacucuguu auggacucaa cauggacuuu    180

guugauccug cucagaucac caugaaagua auccaaggcc uauauagugg ggucaccaca    240

guggaacugg acacccuggc ugcugagaca gccgcgaccu ugaccacgaa gcacccugac    300
```

-continued

```
uaugccaucc uggcagcaag gauagccguc ucuaacuugc acaaagaaac aaagaaagug    360
uucagugaug ugauggagga ucucuacaac uacauaaauc cgcacaacgg cagacacucu    420
cccauggugg ccagcucaac acucgacauu guuauggcca auaaggaucg ccugaauucu    480
gccauuaucu augaccgaga uuucucuuau aacuacuuug gcuuuaagac acuggaacgg    540
ucauauuugu ugaagaucaa ugguaaagug gcugaaagac cacagcauau guugaugagg    600
guuucugugg ggauucacaa agaagauauu gaugcugcaa uugaaaccua caaccuacuu    660
ucugagaagu gguucacuca ugccccuccu acucucuuca augcugggac caaccgccca    720
cagcugucua gcuguuuccu cuugaguaug aaagaugaca gcauugaagg aauuuaugau    780
acucugaagc agugugccuu gauuucuaag uccgcugggg gaauuggugu ugcugugagu    840
uguauucggg ccacugguag cuacaucgcu gggacuaaug gcaauucuaa uggccuugug    900
ccaaugcuga gaguauauaa caacacagcu cgcuaugugg aucaaggugg aaacaagcgc    960
ccaggcgcgu uugcuauuua ccuggagccu uggcacuuag acaucuuuga guuccuugac   1020
uugaagaaga acacaggcaa ggaagaacag cgagcacgcg aucucuucuu ugcacuuugg   1080
aucccagauc ucuucaugaa gcgaguggag acuaaccagg acuggucauu gaugugcccc   1140
aaugaguguc cuggucugga cgaggucugg ggagaggagu uugagaaguu auaugaaagu   1200
uacgagaagc agggucgugu ccgaaaaguu guaaaagcuc agcagcuuug guaugccauc   1260
auugaguccc agacggagac cgguacccca uacaugcucu acaaagauuc cuguaaccgg   1320
aagagcaacc agcagaaccu gggaaccauc aaaugcagca accuguguac agaaauagua   1380
gaguacacca guaaagauga gguugcaguu uguaacuugg cuucucuggc ucugaauaug   1440
uaugucacac cggaacauac guaugacuuu gagaaacugg cagaagucac uaaagucauu   1500
guccgaaauc ugaauaaaau aauugauaua aacuacuacc cuauuccaga ggcacacuua   1560
ucaaacaaac gccaucggcc cauuggaauu gggguacaag guuuagcaga ugcuuucauc   1620
cugaugagau accccuuuga gagcccagaa gcccaguuau uaaauaagca gaucuuugaa   1680
accauuuacu auggagcccu ggaagccagc ugugaacuag ccaaggagua uggccccuau   1740
gaaacguaug agggaucucc agucagcaag gguauucuuc aguaugacau guggaauguu   1800
gcuccuacag accuguggga cuggaagccu cucaaggaga agauugcaaa guaugguaua   1860
aggaacaguu uacuuauugc cccaaugccu acugcuucaa cugcccagau ucuggggaau   1920
aaugagucca uugagccuua uaccaguaac aucuacacuc gaagagucuu gucaggggaa   1980
uuucagauug ugaauccuca cuuacugaaa gaucuuacug agcggggcuu guggaaugag   2040
agaugaaaaa ucagauuauu gcaugcaaug gcuccauuca gagcauacca gaaauuccug   2100
augaccugaa gcaacucuau aagaccgugu gggaaaucuc ucagaagacu guucucaaga   2160
uggcagccga gagaggugcu uucaucgauc agagccaguc uuuaaacauc cauauugcug   2220
agcccaacua uggcaaacuc acuaguaugc acuucuacgg uuggaagcag gguuuaaaga   2280
cuggaaugua uuacuuaagg acgaggccug ccgcuaaucc aauccaguuc acucugaaca   2340
aggaaaaacu gaaagauaag gaaaaggcac ugaaggagga ggaggagaag gagaggaaca   2400
cagcagccau ggugugcucu uuggagaaca gagaggagug ccugaugugu ggauccugag   2460
aaaagcgggg ccugggagac gcagcgggcu cuccugcccg agaggcagac gauuugagca   2520
uagauaggau aguggguuug cuugguuauc agcagcucug cuuggacgug ccugccagga   2580
cagggagcca cgacuuacag uacuguuucu acacagugua aauaucauuu uuaacaaaca   2640
gaaaaccaaa gccagcuuug auauuaggaa ucaagguaga ggcuuuggga auacuaaaga   2700
```

gccuuccugc aaauagugag gagacuuagg aagucucguc ucuccagcuu ucccugccug 2760
gccauucuca guuugggcaa agagauuuag uuugauuuga cugauugccu agaaguaaaa 2820
ucaagcaauu acucaucagc uaaagaccuu ugucuagaca aacuucuaua agucauuuug 2880
aaauaaacau uucuaaguga u 2901

<210> SEQ ID NO 84
<211> LENGTH: 8752
<212> TYPE: RNA
<213> ORGANISM: Homo sapiens

<400> SEQUENCE: 84
uugccucaga cgcuagcugu agcuggcagg cgguuguacg ugcuccagag ucgucgguac 60
ccgcuacugc agucgcuuuc guguggcuuc cgcugagcuc uuccgagcug cucgcucucc 120
acacgcgccg ccgccguaau ccgccaccau ggugaagcuc gcaaagguaa gaggccuugg 180
cgcgccgacg cggacgacua ggccccugcu uucggaggga cgcgcgcgcg cccgcccguc 240
cgucgcggag gggaggaggg cuugcgcgca aucccgggcg cguucgaggg cgccaugcug 300
ggggggaaag ucucgcgcga cuagcgggag gucucgcggu gcuugcccuc ugacuuaggg 360
ggaugagaag agcggaggca gguuuccggg agggcgauau cgaggguucg gauguagcgg 420
gcgggagggg acggugugag gagagaucgg aggagcugag agcggauagg ggcacggcgu 480
gggaagagag ggccaaccuu aggcggcgag cggucccggg gccccgccuc cccgcgcacg 540
ugcucuggug cgcgcccgcc acgugcucug cggagccccg cacgugucgc gcgacccggg 600
gcaguggggg agugucugua guaccccgga aaggggggacg gcagcguggg gauggauggg 660
uggcccggcg aucugcuguc ucugccggug accgggaugg acacguggug gaccccugag 720
guggcggcgu ggugacucca cgugguggggg cuggaagcga gagaaagugg gaagcaguug 780
gguuacgugg ugcugcuuua agaggugauu ucgagauacc cccuucccca gcaaauaacu 840
uaaagggauc ccuuuaacug gguuuuuuuu uuuuuuuuuu uuuuuuuuuu uguggaagau 900
gccagaaaau agauggccag gauuaggaga cuuuauaacc uguggcuguu ucuuggugua 960
gaguucuguc ugcucaguua ucugugagaa ggaaaaaaaa auuaugcgcg guucgcagaa 1020
aaaacugcca ggagaaugcc augccuggcc aagaagaagu cuuuaugcuu guguccuuua 1080
guaagaaaaa gguggugggcc aaaggcaaag ugacugaaaa ugcgugcaau uuuugugugc 1140
guuuguaggc uggcaaaacc cacggugagg ccaagaaaau ggcuccuccu ccaaaggagg 1200
uggaagagga uagugaagau gaagaaaugu cagaagauga agaugacagc aguggagaag 1260
aggagguaag aagcuauuug cagcgaauua aaccggugga auugaauguc uggaagucuu 1320
agaaauacag gauauguagu aaaugguuga auggcaagcc ccuuccuccc ucccucccuc 1380
ccucccuccc ucccucccuc ccucccuucc uuccuuccuu ccuuccuucc uuccuuccuu 1440
cugcaagaca gucggcaaaa caggggacag aaacaggcag aauuuugagu uccaggcaag 1500
cagggaguag uacauaguga aaccuugucu caagaccguu guuaugguca ugcucaauca 1560
gauuucuuag aaaagcucag gugcugaguc caguuuuuuu uuuuuuaaag uauugaaagc 1620
caugucuccu uauuucaggg uuuaauguuu aucuuugugu gugcgcgcac ccauuaagca 1680
ugcuugguac ccucauacua gaauguacuu ggaucccccug gaacuggagu uaaagccaca 1740
ugugaauguu acauguuaca agaguaacac augugcuuaa cuuuugaguc aucucuccag 1800
uucuugguug uuuguuuuuu uuuuuuuaag ccuaucuaau guccauuuuc uugugcucaa 1860

-continued

```
aguuagucuc uuaauguagc auuggguaua aaggaaugcu uaugauuugu uugcuuucaa   1920
gguugucauc ccucagaaaa aaggcaaaaa ggcuaccaca accccagcaa agaagguggu   1980
uguuucacaa acaaaaaagg cugcaguucc cacaccagcu aagaaagcag cugugacccc   2040
aggcaaaaag gcaguagcca caccagcuaa gaaaaacauu acaccagcca aagucauucc   2100
aacaccgggu aagaagggag cugcacaagc aaaagcguug guaccaacuc cugguaaaaa   2160
gggagcugcc acuccagcua agggggcuaa gaacgguaag aaugccaaga aggaagacag   2220
ugaugaggau gaagaugaag aggaugaaga ugauagcgau gaggaugaag augaugagga   2280
agaggaugag uuugagccac caauaguaaa aggagugaag ccagcaaaag cagcuccugc   2340
ugcuccugcc ucagaggaug aggaagauga ugaggaugaa gaugaugagg aagaugauga   2400
ugaagaggag gaagauggug aguuagaucu uaggauauuu aggguacugc auguacauuc   2460
ccucacuguu ucauuagauu aaaaacucau uuugugcucu uaguucuuuc cauaacuuaa   2520
uagguuuuca uuugcuaagu aguuuuuguu uuuuuuaagu auuuguagca uuuaucuugu   2580
cuggauuggu agguagcaaa uacauuugcc ugauuugcca ucuuucuucc agacucugag   2640
gaagaaguua uggagaucac aacagccaaa ggaaagaaaa cuccugcaaa aguuguuccu   2700
augaaagcca agagugugge ugaggaggag gaugaugagg aagaggauga agaugacgag   2760
gaugaggaug augaggaaga ggaugacgaa gaugaugaug aggaagaaga ggaggaaggu   2820
aaccauauua acuuuuaaag uaugcugacc uaaguaaggc uuacuggcua ugcuaaagug   2880
ucugcuuacu caugaauggc auuuuaaaac aucuagaacc uguuaaagca gcaccuggaa   2940
aacggaagaa ggagaugacc aagcagaaag aagccccuga agccaagaaa cagaaaguag   3000
aagguaagcc ugcaaaacug ggaaacaga ucagaguagc acuagcacaa gugaugagug   3060
acaaagggac uuaauacuga accauggggu ugaaaugaaa uaugcugaug ugcuuuauag   3120
uuuaugauga aauuuguugu gugcuuaagu gggcugaaag uucauuuuuu gugugugcag   3180
gcucagaacc aacuacaccu uucaaucugu ucauuggaaa ccuuaaucca aacaagucug   3240
uuaaugaauu aaaauuugcc aucagugaac uuuuugcuaa aaaugaucuu gcuguugugg   3300
augucagaac ugguacaaau agguaaguuu uaauugaaug uuacauguga aucagcuaga   3360
auuuuuaguu uccaguugua uucuucccug ccuuuaaaca uggggcuaua ucuaacuaug   3420
uuaguaaaag ucaguugucu ccucucgugg ccuuaaguac aguuaaggag cugcaguaag   3480
aaagacuaua guauugaacu aaaugaucga gucauagggc cugcaauuug aaguuccugu   3540
guuugacuug auaaagauaa aauaaaauuu aaagaagaaa agauauuaaa cacauaaaau   3600
uuugugcagu aucuacaacu auggaucugc auagucauau gcuuuuagcu aaaaguauuc   3660
ucuguacuuu uagcggggguc caugcuagcu acugcuguua guuacaauau acugaaugaa   3720
gaaaucgagg ugaauuuguu guaaugucuu gguacaugga cuuguuuugu uuuuuguuuu   3780
uuuuucuuua agauuuguuu auguauauga gcacacugua gcuguccaga ugguuuugag   3840
ccuucaugug guuguuggga auugaauuuu uaggaucuca gcucgcucug cucucagucc   3900
uugcuugcuc uggcccaaag auuuauuugu uguuauacau aaguacacug uagcugacuu   3960
aagaugcauc agaagagggc auuaggucuc auuaugggug guggugagcc accauguggu   4020
ugcugggauu ugaacucagg accuucagaa gagcagucaa ugugcuuacc cgcugagcca   4080
ucucuccagc cuuuggacuu gguuuuaugg aagauaaggg ugaucuaguu uuauuuuugu   4140
uagugcugua gaugcucugu gugugugcca caugguauaa gugcagauca ccuucucaua   4200
ccuguaaucu uguuuuuucc aucuucaagg aaauuugguu auguggacuu ugagucugcu   4260
```

-continued gaagaccuag aaaaggccuu ggagcucacu gguuuaaaag uguuuggcaa ugaaauuaaa 4320
cuagaaaaac caaaaggaag agauaguaag aaagguaugu aagggggucu gggugacugg 4380
auacuaacag acuuaggcag ucuggugccu cuuccuuagu uucauccuca uugugaacca 4440
augagauguc auaggucaug ugcuuguuga cagguuugau uccugggaua uauaauguca 4500
gggcugacag gaggaauagc uuagugagua aagaugcuug cugcaaaaug uuugaucucu 4560
agaagccaca ugaagagaga agaaccuuua aucccagcau uugggagaca gaggcaggca 4620
gauuucagag uucgaggcca gccuggucua cagagugagu uccaggacau ccagggcuac 4680
acagagaaac ccugucucgg aaaaaaaguu uuagcuuauc cucugaccac auguguaucg 4740
ugacaugcuu gaagcuuacc uaucucuuaa augaauucuu gaucccuaua uuuugaguuu 4800
cagaauuugg auuuuaagug uuuguuucuu aguugugcug aaaauugaac gugggcuuuu 4860
cacaugcuag gcaaauuugu uggguuuuuu uguuuguuuu uuucucaaga cagggguuuuu 4920 cuguguagcc cuggcugucc uggagaccaa gcuagccuug aacucagaaa ucugccugcc 4980
ucccaagugc ugggauuaaa ggcgugaguc accacugccc ugcuaggcaa ucacucuuaa 5040
aacugcuaca uauccucugu ccccuuuugc ucauuuuaca agguugcugu gugcucaauc 5100
ugcagucuau guuauaugcu uacuggaucu aggcuuuuga uguagaauga accauaugag 5160
ugaugaggua ucuuagagau ggaaacuaag ucuaaauaga cuuguuccau auacaacuua 5220
auacauaugg ucuaaggaac augauauaca uguaaacaag uaggaaggag auaagucugg 5280
uguccaggga agccaggaga gccucaucug aaacuggaca gggguuugug agucaucagg 5340
ugacaauuga acaugguac ucuucaugca aaugguuagu aaccauugag ccaccucucc 5400
aucccuuuau accauuuuuu uuuuuagcau auauccuugu acuuuauagg aauuauuugc 5460
uuuauucucu ugugacuugu aaauugaugu acuuaauuaa aucuuuuucc aacauaguuc 5520
gagcugcaag aacacuucua gccaaaaacc ucucuuucaa caucacugag gaugaauuaa 5580
aggaaguguu ugaagacgcc auggagauca gauuagucag ccaggauggg aaaaguaaag 5640
gguaguuuug ugucuuugag uguuaaaguu uuauuaaguu uagugucuuc uuccccucuc 5700
cuuguccuug acagucucua gucugcugcu ucaaacuuaa cuucauaacc agaaaauuga 5760
auaucugguc cucuggccuc uaccucccaa guucugacau uaaaaaugcu caacugaugg 5820
guuuugaagg ugugaucaau uuuacaggcu caauccaaau uggcaucuuu ugccacaagu 5880
acuauccuuc ccuauuuuau gagagaaaug ugauucuagg caguucaguc uauuguguug 5940
gcucuuuuuc cuccucacca guuuaaagga ugaagaugag cuaauacaua guaaaagaac 6000
aguaaaagca caugugacua aguccuucau gucugaugcu ugaguaauau uuucucuaac 6060
guaguaacug aauugucuug uacucuuuca ggauugcuua uauugaauuu aagucugaag 6120
cugaugcaga gaaaaauuug gaagaaaagc agggggcaga aauugaugga cgaucuguuu 6180
cacucuacua uacuggagag aaaggucaaa ggcaagagag aacuggaaag accagcacuu 6240
ggagugguaa guuaaagggu uuauugugua gugggaacag gaaucauuug uaucuuugua 6300
uuuuaaguaa uugguuaccu acaauuaguu caccuuuguu cauauagcug auguuuaguc 6360
uucaugagug aaagcuauuu gaaaucauuu ccuuuggagu auaguaggca aauaaagcuu 6420
uuuguugggu auguuuugua cuuuaaaugg cuuaaacuau uuuagaaaau aguguaagac 6480
aacaaagaac aguuaucuaa uuagaaugaa aaugaaagga gcaaagaagg cauuacugua 6540
uauaauggau auacacuggu gguucuagaa uuaugguaua ugguacaugg uugaagugcc 6600
auuguuucag uuaacauucc aguaaccuug uggauuaggu uggagacaug cuuuauaggu 6660
gacccacuua cugaguguuu aaauauacac agacauacuc uaacauaccu ugcuaaugug 6720
uuaucuuugu auuugcaggu gaaucaaaga cuuugguuuu aaguaaccuu uccuacagug 6780
caacaaaaga aacucuugag gaaguauuug agaaagcaac uuuuaucaaa gugccccaga 6840
acccacaugg caaaccuaaa ggguaaaaua auuuuuacgu uagauguggg cuggacauac 6900
auacucuuac guauaagagu aagacugucc uguuagcuua aaaaaaaacu aaaguuuuag 6960
cuauacaaag ggcaguaaau auugauagua aauuacaugc ugaugccaag uguuucuaag 7020
cuuuauucug agaacugacu uucaaccuuc agguaugcau uuauagaauu ugcuucauuu 7080
gaagaugcua aagaagcuuu aaauuccugu aauaaaaugg aaauugaggg cagaacaauc 7140
aggcuggagu ugcaaggauc caauucgaga agucguaagu ccuuugacau gauaugacuu 7200
gguuggguga uuuuuuuuuu uauuuuuaug ugccuauaug cucauuuggg gcugucuuua 7260
uguuguugcu gagaaaauga caacuggaua ugaugacuga uuaccugaga aauaauugau 7320
gaaaucucaa gaaaauuccu cuagauaguc aaguucugau ccagcuaugu caacucaaag 7380
cagcaaccuu gauugcccuc ugaguacgcu uuuuuuuuga uccaguguag ucuuuuuuuu 7440
uuuaaccuua auuucuugug uuaauugcuu uuucugguaa aaggggggaaa aaaagacaua 7500 acaaaaucag uguaagggaa ggcucagugg uugagcacug agaggaccug gguucaaauc 7560
ccagcacuca cauggcaccu aucgagacag gauuucucug uguaguccug ccugucgugg 7620
aacucacucu guagaccagg cuggccucaa acucagaaau cugccugccu cugccuccua 7680
ggugcuggga uuaaaggugu gcgccaccac ugcccaaccc ugucuguaac ucuuaagauc 7740
ugacauagau ugcagacaaa acacuaaugc acauaaaaaa auuuuuuuuu uuaaaaaagg 7800
aaucuacuuc agcugaaugu ggcaguaugg caguauucac caaggguuca uagugaaaca 7860
ggaauuuuuc ucuuccagaa ccauccaaaa cucuguuugu caaaggucug ucugaggaua 7920
ccacugaaga gaccuuaaaa gaaucauuug agggcucugu ucgugcaaga auagucacug 7980
aucgggaaac ugguucuucc aaaggguaag aaggcguagu aguguugcug cuuuuuagug 8040
aauucugcau ggagaacuug ggucugcagu aucuucucau ugagcuccuu ucuguccauc 8100
agugauagau uauggauucg cacgagaaga agagagaauu cacagaacug gcacuuaucu 8160
ucuguuuuug cagaaguaua uuuggcuguu gugugagaca uuaugagaua cuggcgauuu 8220
ucucgaccug aagaguacuu uggucacucu acuuggguga cuugguacuu auuguguuac 8280
uuuaaaaugu guuuacuuaa uggugaggu uuuuuuguuu uucuuuucug uuuuagguuu 8340
gguuuuguag acuuuaauag ugaggaagau gccaaagcug ccaaggaggc cauggaagau 8400
ggagaaauug acggaaacaa aguuaccuug gacugggcca aaccuaaggg ugaaggugge 8460 uuuggugguc gagguggagg cagaggaggu uucggaggca gagguggagg cagaggugga 8520
agagguggau uuggaggaag aggccgggga ggcuuuggag guaaggaagg gaaaggaacu 8580
ggaaacggau uccuaaaccu guguccuaac caaccaccuu aaaugggaag gucaguccua 8640
auuguaucac ccuuugaugu uuuuccuucc uauagguaga ggaggcuucc gaggcggcag 8700
aggaggaggg ggagacuuca agccacaagg aaagaagacg aaguuugaau ag 8752

<210> SEQ ID NO 85
<211> LENGTH: 3889
<212> TYPE: RNA
<213> ORGANISM: Homo sapiens

<400> SEQUENCE: 85

-continued

```
uuagacgguu gcgcgcgcag aggguuggua guugucgcug uaggccuucg cugccgcuuc     60
ugcaucguga aucgggggac cuuggcagcc agaccucguu ccucuuagag uagcucucau    120
cuagucgcca caacuccgcc accauguuug aggcacgccu gauccagggc uccauccuga    180
agaaggugcu ggaggcucuc aaagaccuca ucaaugaggc cugcugggac gucagcucgg    240
gcggcgugaa ccugcagagc auggacucgu cucacgucuc cuugguacag cuuacucugc    300
gcuccgaagg cuucgacaca uaccgcugcg accgcaaccu agccaugggc gugaaccuca    360
ccaggugagc ggguggcggg agcggggccc cacucuuccc gcuuccgcuc uuggcggggc    420
ugugacucug cacgcucauu ggcuggcuug gccauccgcg cuuucugauu ggucuauggu    480
gucgggggca gcccucacca aagcgcgcgg uuccgaaaag cccgcgcugg caguggcgcc    540
cacucuguuu ccgcgccaaa gccacaaagc gggaguccgc gggaaaauga gugcuccgga    600
gcugugcuca uuaaaugccu gcagcuuuga guggcugguc uuagcgccua auaaacgagu    660
cuuagugcaa auguaauguc gacuuagagu gacaauagac cuuuucuuga cuuccagagu    720
cucacugcgc aucauggauu ugaggggaaa ucugucaguu uuagcuuuua acuuugcuac    780
agcuaccuag guuagugccu ccuguauacg uguucaagga caguguguga cuuauuuuag    840
uacagauaca uggauuagug ccacuuguau acauuuugaa agauuuacga aaaggccaga    900
cgugaugggg cacauucucc aguacacuag aaaccaagga caccccgcuc aaaaagaugc    960
uuucucgaau guuggcuuuu agugcauuuu acuaagucgg uuuuaagaau cacauauacc   1020
cgguaauuug cuucaccccu gagagaguuu gggguacccu uagccccuuu aacaguucuc   1080
caaccgugag ugugaaaugg uacaacuugu aauugcuuuu uaaaauauag auguggauua   1140
cauguugaua aagccugucu uuuuuuuuuu ggggggguagc auguccaaaa uucuaaaaug   1200
ugcugguaau gaagacauca uuacauuaag ggcugaagau aaugcagaca ccuuagcacu   1260
aguauucgaa gcaccaagua aguuaaacac cuuuaaaacu cggaguuacg uguuguuucu   1320
guuucucaaa accaaaaaaa auauuaacaa uauuguaaau uccaucauag auaggaccgu   1380
guggugugcu ugguaacauu uuccuucuuu ugguagauca agagaaaguu ucagacuaug   1440
aaaugaaguu aauggacuua gauguggagc aacuuggaau cccagugagu uaccuuguuu   1500
cugauugugu guuacccugc ugugauacca gcugaugcgu guucugagug gagugguggu   1560
auuggggaug aauggcacac ugccauuuca cuaaaccaca gcagucuaaa guugauugag   1620
uuuuaaagaa accagaaguc uugcauucug aguucugguu aagaugcuaa aucuugagaa   1680
caugaagcug agccuucccc cuuuucuaga cugaccuuua acuuguggguu uuacaggaac   1740
aggaguacag cuguguaaua aagaugccgu cgggugaauu ugcacguaua ugccgagacc   1800
uuagccacau uggagaugcu guugugauau ccugugcaaa gaauggggug aaguuuucug   1860
caaguggaga gcuuggcaau gggaacauua aguugucaca aacaaguaau guggauaaag   1920
aagaggaggc ggugaguagu aagggggcgu ccaguuaggu gucugaagca gggauggagc   1980
cucggcuuuu guuuuuauuu auucauucau uuugagaugg agucuugagu agaccaagcu   2040
aucuuagagc ucagagacga cuccauaagc uuuuacaggu agcauuugga aagcuaagug   2100
uacagccuuu ugcuuccugg aaauacucuu ggcaaauaag ugaggguugg caagugagca   2160
aaagaaaaug guugggggug uauguagcuu uauguguugc agguucaaga guauuugcag   2220
ucccaaggga aauaagaaag acuucacaaa auguggaaag aguuguauua aaugcucuug   2280
acaguuacau ccauagagaa agcugggcau gaugucucaa acccacaacu gauguacuca   2340
```

aagcuacagc aggaagauuc ucagcuuaaa gucaaccugg cagaaaaucu agcucaaaaa 2400
gaaugaggaa gaaauuggga aggcaaagga agauguucuc cgaguccucc ucauucaagu 2460
agaacauacu aggccucuuu aauuucuaag uaucccugaa ucgaggcuuu uucucaggaa 2520
uccaauguau auuucauggc uacacuuuuu uuuuucuuuu uuaaguuuug cuagcuagcc 2580
ugagcaucag aauuacacac agaagucuga acuaaauagg auuuuuaggg uuuaguauag 2640
ugaaauucag agugcuucug caaguauuua agguaaauau aagguguuac uuggccucug 2700
caugaauuua aaguaaauga aaguguaaga auucgaacau agauaaacac acaacccaag 2760
aacuaguucu uaaccuuaau cugcugaauu auuucuacuu ccauaucaac uucagcuccu 2820
caguucucaa auacugacau guaauucauc aguauuuguc ugaugugcaa gcauuuccac 2880
aacaaaagaa auuaaggaau uuuucaguau ccacauguuc aaggauuggg aauugaauaa 2940
aauugauaau cauacaauga agacugguuu acugucccuu agcuugcauu cagcuguugg 3000
uucuuguuuu uggaaguggu uauguguuau cuuccucucu ucaugcauuc uuugcaagag 3060
aaguauguac aaucugaaua ggaacaacuu ucuccuuugu uuugauugcu uggggugugg 3120
cucuacagga ugggcaagcu agacuuuuuu cuucuuuagu caagguuuuc aucaacccuu 3180
ccaaaaugau aacuauuugu uuugcuuugu gguauaauac cgugaucuaa uagugugagu 3240
uucugauguc uacagugagc cuguuuucuc cucuagguaa ccauagagau gaaugagccu 3300
guucaccuaa cguuugcucu gagguaccug aacuuuuuca caaaagccac uccacugucu 3360
ccuacaguaa cacucaguau gucugcagau gugccccuug guaagaugau aaguuugaac 3420
auuguuuugu aaugugguau uuauaguauu cggugguuua auuuuuccug ucuuucaguu 3480
guagaguaua aaauugcuga caugggacac uuaaaguauu auuuggcucc caagauugaa 3540
gaugaggaag caucuuaggc auugcuagaa auugagaaaa cuaaaccuuu gaagauugcu 3600
ccugagaugc cagcgugucc ugaggucuuu ucugucacca aguuuguacc ugaguauucu 3660
uaaauauuaa aauaaaauau guagauaucu ucuguaaaua accuacuuuc uuuucucucc 3720
auucuccaua auuugcuuaa agaauaagcu ccaaaguaaa aacuaguuuu guuaacauga 3780
auguuucugc uuuacaaaua cuggugauuu uccaucaaug aucuugacgc uaaaugcagu 3840
uuuaagaaau auuguucaau uuaaauaaag uuaacaauuu gaaaaguca 3889

<210> SEQ ID NO 86
<211> LENGTH: 1720
<212> TYPE: RNA
<213> ORGANISM: Homo sapiens

<400> SEQUENCE: 86
ggugcaggau guaggccugc agaauuguca gacccagugg cggcuuuugc cacuggaaga 60
auuuccaaca uaaaacagau gaucaguuug ggacaaucga uucugcgacc agagguagug 120
ucauuugguu acuuuuaaaa uucagauugu cuggugguuu ccaaucacuc gcgacuguaa 180
uuugaaguug gguucugaga uaauacaauc gcugucgcuc uaguuuauaa agcuguccaa 240
gaucugccca gucccagaug uccugggucc ucagggccgc ugugg ucugc caacuucugc 300 agcuggaugc cagaccaucc uggacucgga ucccuuuggg uauuucuaca ccgcuguguc 360
ccggccuggc cuuggggagc ccugguucau aaucgucggc uauguggacg acaugcaggu 420
ccugcgcuuc agcagcaagg aggagacucc gaggauggca cccuggcugg agcaggagga 480
agcaggugac ugggagcagc agacucguau agucacaauu caaggacagc ugucugaaag 540
gaaucugaug acccugguuc auuuuuacaa caagagcaug gacgacucuc acacacuaca 600
guggcugcaa ggcugcgaug uggagccaga ucggcaccug ugucucuggu acaaccagcu 660
cgccuaugau agcgaggauc uccccacccu gaacgaaaac ccaaguuccu guacaguggg 720
aaacagcacu guaccucaca ucucucagga ccugaagagc cacugcucag aucugcugca 780
gaaauaccug gaaaaaggga aggagaggcu gcugcguuca gacccuccaa aggcacaugu 840
gacccgucac cccagaccug aaggugaugu cacccugagg uguugggccc ugggcuucua 900
cccugcugac aucacccuga ccuggcaguu gaaugggggag gagcugaccc aggacaugga 960
gcuuguggag accaggccug caggggaugg aaccuuccag aagugggcag cugugguggu 1020
gccucuuggg aaagagcaga guuacacaug ccauguguac caugaggggc ugccugagcc 1080
ccucauccug agaugggagc cugcauggua ccaaaagccu uggauuugga uuguugccau 1140
gguuuucauu uuguucauca uuugucucug ugugguuugc auaugcauga agaagaaugc 1200
aggugggaga ggaaggcgug acacccaaga agcaggcaga gacagucccc aagacucuag 1260
caagacuguu guggaugaug aggagauggg gguuugcuuu uggaagauua aguccuguaa 1320
aacuugucua ggccacuccc caggaacuuc aguuggcgag ucuuuacugu caccuugacu 1380
ggauuuagga ucaucuggga gaugccccuu ugaguggcug ggcugugagg acagcaggcc 1440
aguucuugcc acccuggaca gaaacacauc ucaccuuucu ggcucaagga ucugaacacc 1500
ugucucuugc cuacucggcu ucuagucagg cauuuuguca ccuugucaag ggucccaggg 1560
acacaaagcu cccuccucuc acccacagca cucugggucc uacccucagu gcuucaggga 1620
cauuuaauca ggucaaauug ggaucaaugg cuuugaugca gaaaagaacu guggacuaau 1680
agagauaggg uuuaauuaaa aaauauaucu uuuuaauuuu 1720

<210> SEQ ID NO 87
<211> LENGTH: 367
<212> TYPE: RNA
<213> ORGANISM: Homo sapiens

<400> SEQUENCE: 87
cuggcacgga cauggcuguc uucugucugc ugugugggaa acgcuuucag gcacaaagcg 60
cacuccagca gcacauggag guccacgcag gcgugcgcag cuauauuugc agugagugca 120
accgcaccuu ccccagccac acggcucuca agcgccaccu ucgcucacau acagguuuuu 180
uucuccaugu gucaccaagu gaaguuugug ccuucuauag caaagagaau auuuuuuaca 240
uccuacuaac aguagauuuu uuuguaguga acauuuuuug uauuuuuauu uauaagucuc 300
auaagaaaaa uagcgauguu caguuguaua ccuugaaucu gcaguuagaa gagaauaaag 360
uuaacuc 367

<210> SEQ ID NO 88
<211> LENGTH: 7879
<212> TYPE: RNA
<213> ORGANISM: Homo sapiens
<220> FEATURE:
<221> NAME/KEY: misc_feature
<222> LOCATION: (4457)..(4460)
<223> OTHER INFORMATION: n is a, c, g, or u
<220> FEATURE:
<221> NAME/KEY: misc_feature
<222> LOCATION: (4471)..(4471)
<223> OTHER INFORMATION: n is a, c, g, or u

<400> SEQUENCE: 88
ggagccccag ugcaggaggc ugcgaaaguu gggggagugu gcuagaagga cugcggagcg 60

-continued

```
gagcgcacgc gggaccaggc ugcgacuggg ucgcuggucc cggccacagg gaguggggagc    120
cggcugggua gguaccccgc agggagcgug uuucuguuuc uagggacagu gcaugaaaga    180
gauggggugu acgcgcgggc gaaaaggaag gguguuuucg ggucggcuua cgaggagggg    240
uguguagggu gcauuuuugg uauuaaagga uagcucuugg aguagggguga gccagggcuu    300
gaaguuuagg aagcgggcga agggucugca aggugcuugg uuuugguagg uagugggcgc    360
uuguuuagga gguuuccccg cuaggaucuc cagugugagg cacucuguac ucuggguuug    420
gguguugauu gccggguagg ggguugucug agcauggacu gggaaaaggu acucagagcu    480
ucggcguugc uggggaucca uccaaguaca aguaagauug gauuuccacg ggucuccuuc    540
ccggcucuca gcccccuuuc ccaguguuua cuuaauacuu cauaggcugu acuuagauuu    600
ucugauuccc uuaccgaacu uucuuucuga accgugcugg aagaccuggg gguugcugaa    660
ggaaauggcc agcuagguug gcuggguaau gguuguguua gacuaaguug ucagaguauc    720
uagaaaccua ggagcuguag ccuggugcag cuacugaaag ccgcacgugg agccugggug    780
gaaguugcuc acgauagagu cucgauguag uacugacuag gggggagacc ccuucuguca    840
ucagacagac uuguauaccc caguggucuu uugaaucugu uagguagggu gcagccugcg    900
ggcuugguca ccuaacaggu guugccagga ccugccccaa gccggauucu cccacucccu    960
cuuucaaccc cgccucuucc uccuccuuga gacaccccca cccccucagg aggcuagaug   1020
cagaucugua ucuuguguug cugacuaucg gccugaagcu ggguagauug guggggguug   1080
auccggaugu aggaugucca aguggagaaa caggauuuga auggagcugg aacaaacgcc   1140
caguccugac ugcugccacc cuucuuccuc cacccccaac ccaucccuuc ccaggcuucu   1200
ugcaaacaga ggcagaagug gccauauuuc uuucuuucuc ccaggugcug uaugcccuag   1260
ggacuugaca cggggcaggc ggggugggaa cugguugggg ggggacgugc uguuuuaugg   1320
gaagucguau gccuagccag cgguggagcu guccuggcua ggcacccagg ggugguguggg   1380
ggaaugggag aaauacuggg acuagagggu cucaagggcc agcaggugu gauagucuuu   1440
uucuccaccc cacccucugc uccaccaccc cucugccuca gcaccccucu gcccucagca   1500
ccccucugcc ucagcacccu cugccuccag ccacccucug ccucagcacc cucugccuca   1560
gcacccucug ccucagcacc cucugccuca gcacccucug ccucaguguu ccugugugac   1620
cugucuuuuc aacuagaaag ucuagaacug uacagacccc agaguuggag guggaaaggg   1680
acacuagguc cuggagccuc cucugugggc uuuuuugacc agaugagaac guaagggccu   1740
ccuccagcua ucccugguca uucaggugcu ucagguuugu gaccuuugcu gagacccugg   1800
augcugcagc aaacagacau cugcuuuagc agagggacag cuugucucug ugcauccgcu   1860
gguaggaucc uccacucugu ccaauuagcu ugcgcugcug cuggguucug aguguucucu   1920
uacaaaauga caagguuagg gggcuggaga gauggcucag ggcuaagag cacccaugug   1980
gcaguuugca acugucugua acuccuguuc cagggggga cugacacccu cacacggaca   2040
aacaugcagg caaaacaccu auuggcaugg aaaaugaaaa uaaaugaccg gguuagcuga   2100
gaaauuccuu uugagaguug ucuuuucucc aguccaggac ugcucucugg aucuuccugc   2160
ucaguuccuc gccucccuuc cauauauggu auuuaagguu uuacuuuuuu uugcguuuuc   2220
aauuguuuuu aauuguauuu auaugugucu cugugugugc acaugagcau ggguguccua   2280
caaggcuaga gacaucagau guccuggagc uagaguuaca gaugguugug agccaccuga   2340
uguaguugcu gggaacugga uuuaguuccu guggaagagc agugcaugcu cuuaaccacu   2400
gagcaacuuc uccacgcggc cccccccag uauacgguau uuaaaacucu auagcaaugc   2460
```

```
uacccaaccc auuguggagc uggggauggu gagguggccu aguuccccccc aacuccugga   2520
aacaugucag aaaguacaga gugggugccu gugggaucag caugcggggg gugguggugg   2580
ugaggugugg ggcugcuuuc ucccgaggcu accgugauag acaguuguac cuugcuggca   2640
gccucuaccc cauuuccagg augucagucu cugcagacgu augggggacg gugggggaagg   2700
gguauacaga gccaugggug ugccugggaa uguacuccca ggaagugacu gguugaaaag   2760
ucagcagauc ucccuggggga uagaggggug ggcugaagcu cugugggguug ccucucucag   2820
cccugaccug ugaacaggga ggcugggggu uggaggaaca cagcuucccc cuguuccugg   2880
ggggacaugc uggacagccu uuccuagcuc ccccggccca cuggggugug gcuggucguc   2940
ggacugagcu cuuuuggacc uggucucugc cugugagcuu ugugacucgu ugagauagca   3000
uuugggcuga gggauuggga gucuucuguu cuuugguccu gacacccgcu uccuugucua   3060
ggccugccac cuggcucccc ccacccccccu ccccggccua ccaaguuucu ugcuucccuu   3120
acugaccccu ccuccucccu ccuuugugucc uccucccucu ccagagaugc ccuguauuca   3180
agcucaauau ggaacaccag caacgagccc aggaccgcgu gaccaccuga ccggugaucc   3240
ccuggcccuu gaguucggca agccuaccau ggaccuggcc agccccgaga cagcaccugc   3300
cgcaccugcu acacugccca gcuucagcac cuucauggac ggguacaccg gagaguuuga   3360
caccuuccuc uaccagcugc cggggacgac ccagccgugc uccucagcuu guuccucugc   3420
cuccuccacg ucuucuuccu cauccucggc caccuccccc gcuucggcgu ccuucaaguu   3480
ugaggacuuc caggguguacg gcugcuaccc gggcacccug agcggcccau uagaugagac   3540
ccuauccucc agcggcucug aguacuaugg caguccccugc ucagccccccu cgccaucuac   3600
acccaacuuc cagccguccc agcuuucucc cugggacggc ucauuuggcc acuucucccc   3660
gagccagacu uaugaaggcc ucugggcaug gacagagcag uugccuaagg cuucuucagg   3720
gccuccgcca ccuccaaccu ucuucuccuu caguccuccc acuggcccca gccccagccu   3780
ggcccagagu ucucugaaau uguucccacc accagccacc caccagcuug gggagggggga   3840
gagcuauucc augccagcag cuuucccccgg cuuggcaccc accucuccga accgugacac   3900
uuccggcauu cuggacgcac ccgugaccuc caccaagucc cggagcgggg cuucaggugg   3960
cagcgagggc cgcugugcag ucugugguga caaugcuucg ugucagcacu auggggguccg   4020
caccugugag ggcugcaagg gcuucuucaa gguauuuugu ugguucuggg ggacgaugau   4080
aucauguugg aggugggggu ggagugggguc auccguuggg aucuguagug accucuccug   4140
agguuucuuc ccagcugguu cuguccugca ggacgaggga caggugugug ccaucuuaga   4200
ggcugggacu uuuuauucag cagggcacac aucucucuag ggcugcagaa agcuggggaa   4260
gggggcagaa ggugugugug uguguggccu gcaguggugc ucagaaacag aaaaccuagu   4320
gggcagccuc ugguucucca cagaacuugu guuucuggca cuggaugaaa ggacacaggc   4380
agaggguuug guucuugcug ggggugggacu ugggaacagg cugugugguuu gucccagugc   4440
ugggugccug cuuggcnnnn cccaccucca nccccuuagu ccucuccucu gcgccaggaa   4500
aagggcaggu ggacacaugc agacaccugu uagaacaggu gucuggacgg ccgugggagu   4560
uccuagaccc uggucuuggg uucugggauc uucccugugga gguugaaacc uucuccagua   4620
ucucccagac ucccucucugc gcucuggccc uccguuucuc ccucccccua cauccaaaug   4680
uuaggaaaau agcuaugaac agagggcgcu uuugucugcg ucggccacag gaucuggacg   4740
guccccuccc cugggcucuc cacccccccc ccaaacccca ugcucugaca gccuguuccg   4800
```

-continued

```
ugucccccu uccuccagcg cacaguacag aaaagcgcca aguacaucug ccuggcaaac   4860

aaggauugcc cuguggacaa gaggcggcgg aaccgcugcc aguucugccg cuuccagaag   4920

ugccuggcug ugggcauggu gaaggaaggu ggguggcaag auggugcccu cggcauaggc   4980

gaccugaugg ggugggacag ccgggcucac caggaucugc accuaauucc cacucccacu   5040

ucuagauucc agccccuaaa ugcaggugua gcuuccaccu gcuuucugga aaggguggggg   5100

ugaggagggc cuuguggggu ccccaucaug gucugaguuc ucugucucug acuucucaga   5160

aguggggugu auagugugcc cugaagaccc uccuucucca ggucuccuuu cucaauacug   5220

cccgucucuc ugcaguugua cggacagaca gccuaaaagg gcggcggggc cggcuaccuu   5280

caaaacccaa gcagccucca gaugccuccc cuaccaaucu ucucacuucc cucauccggg   5340

cacacuugga cuccgggccu agcacugcca aauuggacua uuccaaggug aggucuugcc   5400

cgcccaucug cccugcccug agaacauaug caaugccuuu gugccuguua ggaaaggcuc   5460

ucccuccagg gcaacaucag gaaacaagca uccucuaugu acuggcuagu uggagaaaug   5520

cauugggaug gguguggggu cggggagcca guuacaaaca gcugccguag cccuguuuuc   5580

cugugggaau ugacaagcac augggcccag aauagggcuc uuuugcacgc cuggaucugg   5640

ugucccagug caugagagcu cuguaaugca gcuuguguag gcuuugcugu ggacccaaug   5700

caggacacag cugugugaug caggccuugc uguggagcca gugcgugaca cagcugugug   5760

gugcaggccc ucauguggaa cuuaccugcg uuccuuucag uuccaggaac uggugcugcc   5820

ccgcuucggg aaggaagaug ccggugacgu gcaacaauuu uaugacuugc ucucugguuc   5880

ccuggacguu auccgaaagu gggcagaaaa aaucccuggc uucauugagc uuugcccagg   5940

agaccaagac cuguugcuag agucugccuu ccuggaacuc uucauccucc gccuggcaua   6000

ccgguaagcu gcccaccauc cuccuagccc uggccccagc ccugcggccc cggccugccu   6060

ggacccugag uccugacugu ucucugccuu cugccagauc uaaacccggu gaggggaagc   6120

ucaucuucug cucaggccug guacuacacc agcugcagug ugcccguggc uuuggugauu   6180

ggauugacaa cauccuggcc uucucacggu cccugcacag cuugggugu u gauguucccg   6240

ccuuugccug ccuguccgcu cugguccuca ucacugguga guggcagaaa cuagacuggg   6300

cccaaggguu gcaggaccau uggguaggua gcaucuaaca cuuuggggac cccuagagug   6360

ccugcaacau ugggauguua ggaccugcaa agggacuuag cucuauucgc cccuaaagcu   6420

uaaaucagcc uccgaaugac cccggacucc ucagguacga cuguaggcgc ugggcaucua   6480

gcuuaggau ucuguuuguu uaaaaaccua gcugucaacc ucacaagaca caggaacgug   6540

cacacaugaa uuuuucacau ucugcgcuug gauagcuauc gccauggucc agaaacagga   6600

ccuacuucag cucuguuggg cucccuccuu auugucucug uaagagguaa ccacucugcc   6660

agccucagug gcauuccugu cauggauuuu acugugcgua ucacagggua uggacucuag   6720

uguuaaaugu agagguuucu gggucccuuc ucguuccgcu cccauuucca cuuaaauuuc   6780

uuaggggauc cuccugagua gaucaagacc aggagcugga ucuugaaagg guagggagug   6840

auaucuacac ccagcucagu ccuuagucug uccugcgaga cuccaggauu uuagaacagu   6900

guggagccug gaccuccaga aaaccuggau uaggcuuuug ccuuggccag ccauucagug   6960

guuucaaaua uugaccaguc uggacagugg gcuccugugg gacgugcuag agggcugggg   7020

aagcuuguca gggagaaggc gucaacugag cggggcugac ucuaccuucc cugcugcaga   7080

ucgacacggg cuccaggacc cucgucgggu ggaagagcug cagaaucgca uugcuagcug   7140

ucugaaggag cacauggcua ccguggcagg agacccacag ccggccagcu gccugucacg   7200
```

ucugcugggc aaacugccug agcuucggac ccugugcacu caaggccugc agcgcaucuu 7260
uugccucaag uuggaggacu ugguaccccc uccaccuauu guggacaaga ucuuuaugga 7320
cacauugucu uucugacccc ugcccugaac augugugcgc acacgugcgu gcucuucugu 7380
cacccaugug ccuuuaagcc uauagcccac ggaccccccag accacccuac ccccagccug 7440
guuuugagcu aagacugacg uaccuccuca cuccagaaga uggacagaga acucaagacc 7500
ugggggaggg uguguauuca cgggggugac cccacuauuu gucuuauccc uccagcucag 7560
uccuggccuu cgugguguuuu uguaagauaa accauuuuua acacauacca cucuguugua 7620
aauaagcuga cgcuacugua aauacagaaa ggaagagguu gagauggggg uugggaggaa 7680 ggggugggggc ucccaccagc ugggcgagcc uccaacucga gaucucuucc gcucuccuuc 7740
cauguguaca uaacugucac ucaagaaggu gauugacaga uucugauuua uauuugugua 7800
uuuuccugga uuuauaggau gugacuuuuc ugauuaauau auuuaauaua uugaauaaaa 7860
aauagacaug uaguugaaa 7879

<210> SEQ ID NO 89
<211> LENGTH: 586
<212> TYPE: RNA
<213> ORGANISM: Homo sapiens

<400> SEQUENCE: 89
ggcacgaggc ugugcccgcc augucugcua cccaucacaa gaccucccug ccucagggcg 60
uccgcguggg cacugucaug agaauucgag gcuuggucccc ugaccaggcu ggcagguucc 120
auguaaaccu gcuaugcggu gaggagcaag gagcagaugc cgccuugcac uuuaacccga 180
ggcuggacac uuccgagguu gucuucaaca ccaaacaaca aggcaaaugg ggccgugagg 240
agcgaggcac cggcaucccc uuccagcgug ggcagcccuu ugaagugcuc cucaucgcca 300
cagaggaagg cuucaaggcu guggucgggg augacgaaua ucuccacuuc caccaccggc 360
ugccgcccgc ccgcguucgc uugguggaag ugggcggaga cgugcagcug cauucauuga 420
auaucuucua agcaaaggac ccaagggccu uugcccgguu acggguuggg gguuuuuuga 480
ucccacaaga aagguuuggg aucggccaau aacauuuuuc uguuguucug aaaaauuaaa 540
aaaaaaaaaa aaaaaaaaaa aaaaaaaaaa aaaaaaaaaa aaaaaa 586

<210> SEQ ID NO 90
<211> LENGTH: 540
<212> TYPE: RNA
<213> ORGANISM: Homo sapiens

<400> SEQUENCE: 90
gccacauugu ugcaccaacu ccagugcugg agucucagga caccacaggc uacccggagu 60
uguucugcuu uggagauccg agggcaggag caucacgcca gugacucuga uaggugcgau 120
cgccggauug gaacagaacu gucauuuuuu uccgaaguug agccuuagug acccagugag 180
ugaaguuagc gacgggacgc uaagcagcua gaccggucgg caggagugag acuuagggua 240
ccuucuagua guugugauua aaaaaauuga aaaaaagaaa aaaaaaaacc cuguuucugg 300
aaacuugagg cccucagcug gugagccauc gugguuaagc uucuuugugu ggcuccugga 360
gucuucgauc ccagccggac acccgggccu gguuucaaag cggucggaca gcgcugccug 420
cuccaucggu agcgcucgag ccucgguuuc ucuauuuggc cccgacucgc cgcaacaaga 480
ugaucgccuc gcauaugauc gccugcuuau ucacggagcu caaccaaaac caagugcaga 540

<210> SEQ ID NO 91
<211> LENGTH: 2000
<212> TYPE: RNA
<213> ORGANISM: Homo sapiens

<400> SEQUENCE: 91
cccagcuguu ucguccguac cuagaccgcg guuauggcgu cguucacggu gaaggccuau 60
cuucugggca aggaggaggc gacccgcgag auccgccgcu ucagcuucug cuucagcccg 120
gagccggagg cggaagccca agccgcggcc ggcccggggc ccugcgagag gcugcugagc 180
cgaguggcug ugcuguuccc cacgcugagg ccuggcggcu uccaggcgca cuaccgcgau 240
gaggaugggg acuugguugc cuuuuccagu gaugaggagc ugacaauggc uauguccuau 300
gugaaagaug acaucuuccg caucuacauu aaagagaaga aggagugccg gcgggaacau 360
cgcccaccau gugcucagga ggcaccccga aacauggugc accccaaugu gaucugugau 420
gguugcaacg ggccuguggu gggaacucgc uauaagugca gugugugccc agacuacgac 480
cugugcagcg ugugcgaggg gaagggccug cacagggaac acagcaagcu caucuuuccc 540
aaccccuuug gccaccucuc ugauagcuuc ucucauagcc gcuggcuucg gaagcugaaa 600
cauggacacu uuggcuggcc uggcugggag augggcccac cggggaacug gagcccacgu 660
ccuccucgug caggggaugg ccgcccuugc ccuacagcug agucagcuuc ugcuccacca 720
gaagauccca augucaauuu ccugaagaau gugggggaga guguggcagc ugcccucagc 780
ccucuaggca uugagguuga cauugaugug gaacauggag ggaagagaag ccgccugaca 840
cccacuaccc cagaaaguuc cagcacaggc acagaagaca agaguaacac ucagccaagc 900
agcugcucuu cggaagucag caaaccugac ggggcugggg agggcccugc ucagucucug 960
acagagcaaa ugaaaaagau agccuuggag ucggugggac agccagagga acagauggag 1020
ucgggaaacu gcucaggagg agacgaugac uggacacauu ugucuucaaa agaaguggac 1080
ccaucuacag gugaacucca gucucuacag augccagaau cggaagggcc aagcucucua 1140
gaccccucac aggaaggacc cacagggcug aaggaagcug cccuauaccc acaucuccca 1200
ccagaggcug auccccggcu gauugagucc cucucccaga ugcuguccau ggguuucucg 1260
gaugaaggcg gcuggcucac caggcuccua cagaccaaga auuacgacau cggggcugcu 1320
cuggacacga uccaguauuc gaagcacccu ccaccauugu gauagugcug uggccaagcc 1380 ccaccccuu ugucuuguag uugcaucacg uagagcagca gggcuucuau agauaggccc 1440
agugucuugg cauucuugua gaaucuucag gugggaaugu gugaugccuu uucaggcaau 1500
aggaaagugc augaggagag uuuugaaugu gcauaugcug acgccugaga acagacccag 1560
guacccgugg cugagcugag cuuccucugc uuccccuagg ccuggccucu gcagggaacu 1620
gcagcacaca cugcacuccc accugcucuu gccgccagca uugcaccagc aguccagaau 1680
uccugccuga caacccgugu uuccuuuauu aaaagugauu aguacaacug cuaguuauuu 1740
ucaacaaaua aagccauuau guuaagaggg gacuguccau agugagugaa agguggcagg 1800
caggggccua cagcuccuag ggaauggaga auucauguga agccgaauga aggaucuuau 1860
cuuauacugu cccccuuucu aauggccacu cuuuaguguu ugugucuaau guuaaugcuu 1920
aaagcacagg acccccaugu agcuuccucu gacuugguuu guaaguaacc uguaauaaaa 1980
ugccauaugc acuuuaacca 2000

<210> SEQ ID NO 92
<211> LENGTH: 2649

-continued

<212> TYPE: RNA
<213> ORGANISM: Homo sapiens

<400> SEQUENCE: 92
gagggaauug cgggaccccg ucuggggaag cucccgccgc cccggggugc ucagcucucu 60
gucucccuug acccagguac agucaugucg ggcuucgacg acccgggcau uuucuacagc 120
gacagcuucg guggcgaccc cggugcggaa gagggccagg cccgcaaguc gcaacugcag 180
aggcgauuca aggaguuccu gagacaguac cgagugggca ccgaucgcac gggcuucacc 240
uucaaguaca gagaugaacu caagcggcau uacaaccugg gugaauacug gaucgaggug 300
gagauggagg accuggccag uuuugacgag gaacuggcug accacuugca uaaacagccg 360
gccgagcacu uacagcugcu ugaggaagcu gccaaggagg uggcagauga ggugacccgg 420
ccccggccag cuggagauga gcugcuccaa gacauccagg ucaugcucaa gucagaugcc 480
agcccgucga gcauucggau ucugaaguca gacaugaugu cacaccuggu gaagaucccu 540
ggcaucauca uuucagccuc ugcaguccgu gccaaggcua cucguaucuc cauucagugc 600
cgcagcugcc acaacacccu caccaauauc gccaugccca ggccuagagg gcuaugccuu 660
cccaggaagu gcaauaugga ucaggcuggg cgcccaaagu gcccacugga uccauacuuc 720
aucaugccug acaagugcaa guguguggac uuccagacuc ugaaacugca ggagcugccu 780
gaugcagucc cucauggugga gaugcccagg cacaugcagc uuuauuguga cagguaccug 840
ugugacaagg uuguuccugg gaacaggguc accaucaugg gcauuuauuc caucaagaag 900
uuuggcuuga accccagcaa gggccgggac aggguaggug ugggcauccg gagcucguac 960
auccgagugc ugggcaucca gguggacaca gauggcucug gccgaagcuu ugcugggucu 1020
gucagcccac aggaagagga ggaauuucgu cgccuggcug cccuccccaa cauauaugag 1080
cucaucucca agagcauuuc cccuccauc uuuggggggca uggauaugaa gaaggccauu 1140
gccugccugc uuuuuggggg uucccggaag aggcucccag auggacucac ucgccgaggu 1200
gauaucaacu ugcugauguu gggagacccu gguacagcca agucucagcu ucugaaguuu 1260
guggagaagu gcucucccau ugggguguac acaucuggga aagguagcag ugcugcaggc 1320
uugacugccu cagugauacg ggaccccuca ucucgaaacu ucaucaugga agguggagcc 1380
augguucugg ccgauggugg gguugucugu auugaugagu uugacaagau gcgggaagau 1440
gaccguguug caauccauga ggcuauggag cagcagacca ucuccauugc uaaagcuggg 1500
aucacuacca ccuugaacuc ucgcugcucu guucuggcug cagccaacuc aguguuuggc 1560
cgaugggaug agacaaaagg ggaggacaau auugacuuca ugccuaccau cuugucccga 1620
uuugauauga ucuucaucgu caaagaugag cacaaugagg agagggacau gaugcuagcc 1680
aaacauguga ugacucugca ugugagugca cugacacaga cacaggcugu ggagggugag 1740
aucgaccugg ccaagaugaa gaaguucauu gccuacugcc gagcgaggug uggaccucgg 1800
cuaucagcag aggcagcaga gaagcugaag aaccgcuaca ucaucaugcg gagugggggcu 1860 cgucagcaug agagggacag ugaccggcgu uccagcaucc ccaucacugu gcggcagcug 1920
gaggcuauug ugcgcauugc ugaggcccuc aguaagauga aacugcagcc cuuugccacu 1980
gaggcugaug uagaggaggc auugagacug uuccaggugu ccacacugga ugcugcuuug 2040
ucuggcaauc ugucgggggu ggagggcuuc acuacccagg aggaccagga gaugcugagc 2100
cgcauugaga agcaacucaa gcgccguuuu gccauuggcu cucaggugu c ugaacacagc 2160 auuguccagg acuucaccaa acagaaauau ccagagcacg cuauccgaaa ggugcugcag 2220
cucaugcuac gcagggguga gauccaacac cguaugcagc gcaaggugcu cuaucgccuc 2280
aagugagccc auugcccauc aacccucaag ccugaaaugc ugccaccacc cuaucuccca 2340
gucagugcuc caaaccuccu uuugcccugc cucuccaccu cagacugcug ucugcagcac 2400
aucugcagcc ccuggaaaug uacuuugguc uguuggcuca uacuguguuu gagugucuga 2460
ggacucucug cucugggugu cuaucccccug ucaugccuuc ucaacaagau gagucuggag 2520
caggaacagg cccuggaaug uagaugggguc uguauauugg cucccgggcc acucacugcc 2580
aagcuucuuu guauguacag agguaauaaa gcaauugagu cccuggcugc uaaggucagu 2640
ggacccagu 2649

<210> SEQ ID NO 93
<211> LENGTH: 450
<212> TYPE: RNA
<213> ORGANISM: Homo sapiens
<220> FEATURE:
<221> NAME/KEY: misc_feature
<222> LOCATION: (389)..(389)
<223> OTHER INFORMATION: n is a, c, g, or u

<400> SEQUENCE: 93
ggaugcagcc ggaagugcag cgugcgugcg guuugguggg ucgcugugug cgcuccgcgu 60
gugcagccgc gugggccaug gggcggcggg cgcggggccg gcgguuccag cagccgccgc 120
agccugaggg cgaggaagac gccagcgacg gcggcagaaa gcgaggccag gcgggcuggg 180
aagguggcua ucccgagauc guaaaggaga acaagcucuu cgagcacuac uaucaggaac 240
ucaagaucgu gccagaggga gaaugggacc aauucaugga gucacuccga gaaccucucc 300
cagccacacu gagaaucacu ggguacaaaa gccaugccaa agagauucuc cauugcuuga 360
agaacaagua cuuuaaggag uuggagganc cugaaguaga uggacagaaa guugaguucc 420
acaaccacua agcugguacc cugaagaacu 450

<210> SEQ ID NO 94
<211> LENGTH: 929
<212> TYPE: RNA
<213> ORGANISM: Homo sapiens

<400> SEQUENCE: 94
gagcucaaau ucuggcuuuc uauuggguac gauauauuaa ccaaugggag aaacacaaac 60
agaauaccuc caguuaguau aaaugcuugc uguucaguug cagaauuuac uauauauucu 120
uuuccuuucu cugcuuugcc uuuacugaua cuuaaacgca uacaugucug gacgcggaaa 180
gcaagggugc aaggcccgcg cuaaggccaa gacccgcucc ucccgggccg gccugcaguu 240
ccccgugggc cgcgugcacc ggcugcuccg caagggcaac uacucggagc gcgugggcgc 300
cggcgccccg guguaccugg cggcugugcu ggaguaccug acggccgaga uccuggagcu 360
ggcgggcaau gcggcccgcg acaacaagaa gacgcgcauc aucccgcgcc accugcagcu 420
ggccauccgc aacgacgagg agcucaacaa gcugcugggc cgcgugacca ucgcgcaggg 480
cggcguccug cccaacaucc aggccgugcu gcugcccaag aagaccgaga gccaccacaa 540
ggccaagggg aaguaaucug gcgauugucu guacugccca guugaaaguu aaccaaaaca 600
aaggcucuuu ucagagccac ccacaucuuu ccauaaaaug agcugccacc ucgugaaacg 660
uucuuccacu acaguuuuua uacuacauau gaaaaaguua cgaaguagcu uucaaucuua 720
guaaauugau uuuaauacug uuagucccug cgauaaaucu uacgaccuuc cuuaguuuga 780
gucaaaagug uguaagagau gaaaccuuua gaacauacua uaaauuuuua guagaaauuu 840
ggcacccagg uuugucauuc acgucacgau ugucuagagc auaaugguag uaagggcuaa 900
gggccauuaa aucccacuuc cauaguuuc 929

<210> SEQ ID NO 95
<211> LENGTH: 325
<212> TYPE: RNA
<213> ORGANISM: Homo sapiens

<400> SEQUENCE: 95
uuuuuuuuuu uuuuuuugga aaugaaggua auuuauugaa acugguuuug ggacaggcga 60
guggacaacu guugaaagga gcuagcgcac agccgggugg gagcgggugc uuagccacag 120
auccuaucug aggcccaacu uuuucuuuuc cuucugcuuc uuacggacca cauccagguu 180
ccgguccuuc cacaugcuuu ugcgaagcuu gauggggcgu gagcccacau acuucccauu 240
caucucucgc auggcgcgca cauagucacu ggggucuuug aagcugacaa agccauagcc 300
cuugguuuug ccugugcgcu uguca 325

<210> SEQ ID NO 96
<211> LENGTH: 367
<212> TYPE: RNA
<213> ORGANISM: Homo sapiens

<400> SEQUENCE: 96
uucggauccu ugccaauaua uguaucccau uuggaauggu gaucuuaaaa ugugagugca 60
ugcauacuau cuuauuuaag auacuugcac cccacccacu cccaucuccc gaagcuggaa 120
cacugccaac uagguccuua agaaucacgc aauuaacaca agguugggug cugcuaauuc 180
uucaugaaaa uccaaacacg uuaagggacc agggagaugc cacugccccc cugaauuuuc 240
aucaaaaaua gacacguuua uguaaacaga acuauuuucc auauucauag ugacuuuuua 300
aguauuugag ccuaaagauu uugaucucca uuuuuauaac uauuuaaauu guucacaauu 360
auuacau 367

<210> SEQ ID NO 97
<211> LENGTH: 418
<212> TYPE: RNA
<213> ORGANISM: Homo sapiens

<400> SEQUENCE: 97
cggccgccgc cgcccccaca cugccccgcg uugacgagcg ccgcgacggc aaggacagcg 60
ccucgcuuuu cgugguggcu cggauccuag cggaccucaa ccagcaggcg ccggcgcccg 120
cccccgcgga acgcagagaa ggggccgcug cgcgcaaggc gaggaccccc ugccgccugc 180
cgccugcgcc cccugcgccg ccacccggcc cagagcccgc cuccccggga caagcaggcg 240
cgccggccgc gccccccagc cccgcgugga gcgagccgga ggcggcauug gagcaggagc 300
ccggccccgc ggggagcggc gagccuggcc ucagacaaag gggucgggga ggccggagcc 360
gcgcggaccu cgaguccccg cagaggaagc acaagugcca cuacgcgggc ugcgagaa 418

<210> SEQ ID NO 98
<211> LENGTH: 1552
<212> TYPE: RNA
<213> ORGANISM: Homo sapiens

<400> SEQUENCE: 98
cgucaguccc cgccaccucc ccggccccgc gcgcccggau cggcccuacg gccucgucuc 60
gcccggccuu gcgcgccggg accgccgcga ucuccucucc ccgccgcccu ccggcuggcc 120
cugccugcug cggcgcgaug aaugacuuug gaaucaagaa cauggaccaa guggccccug 180
ucgccaacag uuuucguggg acacucaagc gccagccagc cuuugacacc uucgauggcu 240
cucuguuugc ugugcucccu ucucucagug aagaucagac acuccaagaa gugcccacgg 300
gccuggauuc ugucucccau gacucggcca gcugcgagcu gccuuugcuc acucccugca 360
gcaaggcagu gaugagccaa gccuuaaaag ccaccuucag uggcuuccaa aaggagcaac 420
gacgucuugg cauccccaaa aaccccuggc uguggagcga gcagcaggug ugccaguggc 480
uucucugggc caccaacgag uucagccugg ugaaugugaa ccugcaccag uuuggcauga 540
acggccagau gcuguguaac cucggcaagg agcgcuuccu ggagcuggcg ccugacuuug 600
ugggugacau ccucugggaa caucuagagc agaugaucaa agagaaccaa gaaaagacag 660
aagaccaaua ugaggaaaac ucucaccuca acgcgguucc ucauuggauc aacagcaaua 720
cauuaggcuu cagcauggaa caggcuccau auggaaugca ggcaccaaac uaccccaaag 780
acaaucuccu ggacagcaug ugcccgccau cggccacgcc ugcagcucug ggcucugagc 840
uccagauguu gcccaagucu cggcucaaca ccgucaaugu caauuacugu uccaucagcc 900
aggacuuccc cagcagcaac gugaauuugc ucaacaacaa uucuggaaaa cccaaggacc 960
acgacucucc agagaacggu ggggacagcu ucgagagcuc cgacucgcug cugagguccu 1020
ggaacagcca gucgucccua cuggauguac agcggguacc uuccuucgag agcuuugagg 1080
aggacuguag ccagucucug ugccucagua agcugaccau guccuucaag gacuacaucc 1140
aagagaggag cgacccaguc gagcaaggca aaccaguuau uccugcagca guacuggcug 1200
gcuucacugg aagcggacca auccaguugu ggcaguuucu ucuggagcua cucucugaca 1260
aguccuguca aucuuucauc agcuggacgg gggauggaug ggaguucaag cuugcugacc 1320
ccgaugaggu ugcccgccgg ugggggaaga ggaaaaauaa accaaagaug aacuacgaga 1380
agcugagccg ggcuuacgu uacuacuacg acaagaacau cauccacaag acuucgggca 1440
agcgcuacgu guaccguuuc guaugugacc ugcagaacuu gcugggcuuc acuccggagg 1500
aacugcaugc cauccugggc guccagccug auacagaaga cugagggccu ca 1552

<210> SEQ ID NO 99
<211> LENGTH: 4043
<212> TYPE: RNA
<213> ORGANISM: Homo sapiens

<400> SEQUENCE: 99
auggcucuaa caacgcugcu cuugguggug gcggccgccc ugacccugau cgagacccgc 60
gcgggugagu gcggggucgg gagggaaaca gccccugugc cgcguccccg cuucgcccac 120
cggaccuccg ccccuucucc acccgagccc cgagcccugc uccacucccg gcccgcguac 180
ccgaccgggg ucccgggagg aggucggggu cucaccgcgc gccgccccca ggcccacacu 240
cgcugcggua uuuccacacc gcuguguccc ggcccggacu cggggagccc cgguucauca 300
ucgucggcua cguggacgac acgcaguucg ugcgcuucga cagagacgcg gaaaauccga 360
ggauggagcc gcgggcgcgg uggauggagc aggaggggcc ggaguauugg gagcgggaga 420
cacagaucgc caagggccau gagcagaguu uccaagggag ccugaggacu gcacagagcu 480
acuacaacca gagcaagggc ggugagugac cccgggucgg aggucacuac cucuccacgu 540
cccgaaacag aggccgguga ggucccgggu gcaaaguccg agguucagga gcagaacuga 600
cccaggacug gauucccuuu caguuuggag gaguccgcgg uggggggggug gggggggggc 660

-continued

```
ggaggaggga cugaccacug ggucccgcag gcucucacac acuccagugg auguauggcu    720
gugacauggg guccgacggg cgccuccucc gcggguaccu gcaguucgcc uaugaaggcc    780
gcgauuacau cgcccugaac gaagaccuga aaacguggac ggcggcggac auggaggcac    840
agaucacccg acgcaagugg gagcaggcug guauugcaga gagagaccgg gccuaccugg    900
aggucgcgug aggcuccgca gauaccugca gcucgggaag gagacgcugc ugcgcacagg    960
ugcagggggcc gcgggcagcu ccucccucug cccucaggcu ggggcucagu ccuggggaag   1020
aagaaacccu cagcuggggu ggugccccug gcucagaggg gagagaguga cccugggucu   1080
ccugaucccu caucacagug acugcacuga cucucccagg gcucagccuu cucccuggac   1140
agugcccagg cugucucagg agggaaggag agaauuuccc ugagguaaca acagcugcuc   1200
ccuucaguuc cccuguagcc ucugucagcc auggccucuc ccaggccagg guucucagcc   1260
uacacccacu gucuguagac acugacuccu guccugcuga gugugucagc ccuuacaccu   1320
caugaccuga agucuccuuu acccgauggg agacauggac aucuacacua ggcugguucc   1380
cccaguuucu agaacuuucc aaagaauaca gucuaccaga uccuucccug ucuguggggu   1440
uugcauccuu ugacacccaa uucuaucuau uccugcaaug gugaauaguc acaugagcca   1500
uuaugggUua cccuaaacaa auacuuuucu uguguuuuuc cccucucguu uucuuuuuau   1560
cuuuacuuuu uuuuuaaggg uauuauguug cuuauaaucg guuuuucuuc ggcacuggaa   1620
ugauauugcu cucucucccc accauacccc cacccccgcc uauaucauuu guaucaguag   1680
cccuggcugu cguggaacuc acucuguaga ccaggcuggc cuugaacuca gaaaucagcc   1740
ugccucuguc ucugccucug ccucccaagu gcugggauua aaggcuuggg ccaccaccac   1800
ugggcagaag aaagguuccu gugagcuuaa aauguuuucu ggcagaauua accauccaga   1860
ucacuccuga uaucccugug ccccaccaag uuacagugcu cccccuggug aaucagaacu   1920
uggacucuga gagacagggu cuucugcaau ccaggccuga gugagaggga agaccacaca   1980
cccugugagc ccacuguguu ccagugagug cugcacuggg guccacagca cauuccaggg   2040
auccugugug acacaucugu accuugucccc ccagagucag gggcugggag ucauuuucuc   2100
uggcugagug ucagagguuc accacauuuc ugcuacacac ucccugaugg cuguuuacuu   2160
ggacugacag uuaauguugg ucagcaagau gaccacagug guuuagucuc aaugguguca   2220
cucuuccagu agcauauggu ccugauuucu aauuuagaua cgaacucaaa cacauaugaa   2280
auuucuuauu uuccauucca ucuuccauua uauagcuacc uaucucgugc uauugaacau   2340
cacauaagga ugaccauguu gacccacugg cucaugugga uucccucuua gcuucugagu   2400
ccccucagga aaaugugcag uccugugcug agggggccag cucugccugc aggucacuag   2460
ugccaugaca guuaaagugu ucauacagac acauaguuca uuguaauuac ugauuuagcg   2520
uugucuuggc aguuuucagu uugcaugcau uuauuuauuu auuuauuuau uuauuuauuu   2580
auuuaaugca uggaaguaca cuguugcugu acugaugguu guuugccuuu guguguugu    2640
ugggaauuga auuuuuuuuu uuaggaccuc ucuuugcucu ggucgacccu gcucacuccg   2700
gucaacuccu augggucaac ucugcucauu cagucccugc uuguucuggc ccaaagauuu   2760
auuuauuauu uauuauacau aaauacacug uagcugacuu cagaugcacc agaagagggc   2820
gucagaucuc auuacagaug guugugagcc accauguggu ugcuggaguu ugaacucagg   2880
accuucaaaa gagcagucag ugcucuuacc cucugagcca ucuccccagu ccucaguuug   2940
ucuucuuaau ugugcgauuu cuugaaucuu ccaaacagau cccccaaaga cacaugugac   3000
```

ccaucacccc auaucuuaug augcugucac ccugaggugc ugggcccugg gcuucuaccc 3060
uguugacauc acccugacuu ggcaguugaa uggggaggag cugacccagg acacggagcu 3120
uguggagacc aggccugcag gggauggaac cuuccagaag ugggcagcug ugauggugcc 3180
uuuuggggag gagcagaauu acacaugcca ugugcaccau gaggggcugc cugagccccu 3240
cacccugaga ugggguaagg agggugugg ugcagagcug uggucaggga aagcuggagc 3300
auucugcaga cucugagcug gucagggcug agagcuggga ucaugacccu caccuucauu 3360
uccuguaccu guccuuccca gagccuccuc cauacacugu cuccaacaug gcgaccauug 3420
cuauuguggu ugaccuugga gcuguggcca ucauuggagc uguggugggcu uuugugauga 3480 auaggaggug aaacacaggu aggaaagggc agggucugag uucucucuca gucuccuuua 3540
gaagugugcu cuaaucauua augggaaacc caucuacacc ccacauugcu accuucucca 3600
acugggucuu cugucaguuc ugggaacuuc caagaucuuc cuugaacucu cacagcuuuc 3660
cuucucacag guggacaagg aggggacugu gcuccagcuc cagguuagug uggggacagg 3720
auuguccugu ggacauugca gugaagcugg agauguuggg gagcucuggg aacccauagu 3780
aacucuucca gagaaaucuu ccagggccgc aguuguccaa uaugaauaca uauauguaca 3840
uaugcauaua cauuuuuuac ccuuggcagg gacagcuccu agagcucuga uagaucucuc 3900
ccagguggua aaggugacac ucugggaccu gauuggggag gggcaaugug gauaugauug 3960
gguuucaggg acuccacgaa uccccucuga gugaguggug gguuguugga auguugucuu 4020
cacagugaug ggucgugucc cuc 4043

<210> SEQ ID NO 100
<211> LENGTH: 211
<212> TYPE: RNA
<213> ORGANISM: Homo sapiens

<400> SEQUENCE: 100
uuaaaucugg agggauuuuu cacacagccu aucuuuuuag gugugccuuu cccauauuuu 60
auuaaacucg aguuguuguu uuaaaaaaac agcagcauua ucaaagacac aucuguacaa 120
acauuuuaca aaagagaacu cucuaggauc agcuacauca aggacaagca gaaaaauaga 180
ugcaguccaa caaagacauu gaaaaugacu u 211

<210> SEQ ID NO 101
<211> LENGTH: 8252
<212> TYPE: RNA
<213> ORGANISM: Homo sapiens

<400> SEQUENCE: 101
ggucgcuuuc ugucuguaga ggcggcuugc cacccgagca gagggucgug aaguuccgac 60
cggaccgguc cacagagguu caucuggaga ggugggaccc cuccgaggug aaaggcgccg 120
cugagaaacg cccccacccc ccgugguuca agugguucag cccaagaacu uuucauucau 180
aaaaaagacc agacuccgag aggcgcgagu gagucagaac cgcagccgcc aacgcggacc 240
cuaccgaaca uccagcccag ggcauguacc gagacuacgg ggaaccggga ccgagcuccg 300
gggcuggcag cccguacggu cgccccgcgc agcccccgca agcucaggca cagaccgccc 360
agcagcaggu gagacuggcc gaaucgucgg gggggggggg accugaguuu ggacagcauc 420
agggaugcug ggauuagucu aguuugcucc gggauuugga cuggggcccc gagcagcauc 480
ugacucuggu ggucgcgacc gaggauccug cacguucugu guggucgggg aaccuaugua 540
cccgguggcc aaggggacga gcgcagcggg aagcgcgaau aucugcgaau uccccuucuc 600

-continued

```
gcucgcccgu aucucccuag cugacugucu uucugccccu ccgucuccgu uacggucuua    660
cauuuccucc uaucugcccc uaauacgcug ucccucuaaa uaccugcccc aucccugccu    720
ggacaggauc agagguguuc uccaucucca guuaauaacu gggaccuggg gucugggcac    780
auagagacgg gguccaucag aacucagccg ggacagagaa uucuuagcag ccuguccgag    840
gcuguccgug uguugcucug guuguccgug ucccuuuauc cggucaaguc cucaucucuu    900
ugugcgcagu auagagccca ugggccccag gcagugguuc cgagggguuc cuggagacca    960
cgaaguguug ggaugugcgc ggggucaccu gcccggccac acucgcgcuc cacauucucg   1020
gcacccgacg ucucucacug cuggauaggg gcacuugaga gguugcaggu guccauuucc   1080
ugucgagggg ccgcgagcac gugucgccag gggagggaag gagcugcguc cguuucgccg   1140
agucacagcg ggccgaguca cugaggcuga gucacccugg gugccccucc cuuccuggcc   1200
ccaaacggcc ccuaaggacc gacgaccugg gagcgagaga ugccccuggc agugcuucua   1260
gcccagaacg gggucacug agaugcuggg ucccccagua uugggcuggg gacauagcug   1320
uccagacuug ccuaagcaug ugaggugcuu ccuggacugg agggccccca cauccuuagc   1380
ucacagagcu ugaacccagu uuucucuccc agaacgcuga gcccccaccc ccaccgacac   1440
ucaaucccaa cacaugccuc agauuucugc aagaaaagga aggaaaggau gccagacccc   1500
uuauaggagg cuuuuacucu cuucacuuua uuucauggac uuaaaaaacc ccaucaauuu   1560
ugaacuuuca aguuuuuaag ucgacagcua ggcaugcauu uaaucccagc auucaggagg   1620
cagaggcagg cagaucucug ggaguuugaa gccaauuugg ucuacaaagu gacuuccagg   1680
ucagcuagag cuacauaaua gagauccugu cucaaaacuu aaaaaauaaa aaacaaaaac   1740
aaaagccgau uaaaacucug auuucugagc uaugagagcu ggcuucucaa cagcaaugga   1800
acguugaaug auguuaauaa cagggaaacu gagacuaaau aacaugcccc agucucaaag   1860
cccaucaaug gccaagcucc aagcugaugc uggacuccca agcucuggug cuacaugucu   1920
auagucuugg ugccugggag guagaggcag aggaaucgug aguuuagguc uagccugagc   1980
uaugugagau ccugcccacc ccacccccgg cccccaaaca acaaauucuc auccugauuc   2040
ucagaauugc cuugggagcu agaagcugaa aguaugccca ucugugagga cugggucuca   2100
aaucuuaguu ucuacuuacu agcugugggu cuaugggcaa cugcucuccu gucugaaaac   2160
aggauuaugg cagcugugug agucacuauu uguuaaauag uuggaacagu guuacgcagu   2220
ccauacuuga uuuaaaacaa aaaaccaaac uaucucuggu ggggaaacag acagacgaag   2280
agagacauuu ugugaccugc ccaaaaucac acagcuccug aacaaguaag uuucugguug   2340
ccaaauguug cuccuugugg ucucccaaaa cugguaucua cacugaggug aagggagaca   2400
gaaguccagc cucugucccc gggaagcccc ucaguccaca cagaccuuau cauuucccuu   2460
cuuaucucuc agaaguucca ccuugugcca agcaucgaca gcagcagcca ggaacugcac   2520
uggauggugc agccucauuu ccugggaccc acuggcuauc cccgaccucu ggccuauccc   2580
caguacaguc cccucagcc ccggccagga gucauacgag cccuagggcc accuccgggg   2640
gugcgucgca ggcccugcga gcagguaaga aacagcgaug uuucacuuuc cauagcccgu   2700
aggggucua cuagacaggg acaggaucuu gcuacgaggg aauuucuuau ucagcauuga   2760
aguuccugag aggccaagaa ggagguaaaa ggucaccuuu gagucaagga aggcuuccug   2820
gagaaggcua cacguuaacc uaaaccacgg auaggauuug cguauggaag cugaaaagaa   2880
ucuucuggga ggaggguugg aggcacagaa uugaggugaa ggggacagag uguuaaguga   2940
```

-continued

```
gcaugucucc acugucugac gugcacaggg uggaaggaag ccugaugcug gcuuuguacc   3000

ucggggugac ucuucuuuuc aacagucacg gaaucucagc cuauuucuuu uaauuaucac   3060

aaaaagugag ugggcagugg uggcucacac cuuaaauuuc agcacugggg aggcagaggc   3120

agguggaucu cuggguucaa ggccagccug guuuacagag ugaguuccag gacagccaag   3180

gcuacagaga aacccugucu caagaaaggg aaaaaaaaag ugaaugggaa auguauuuca   3240

auuuuuccau cuuccaucag aggaagugaa gcauagaggg guacucacuu guccagauuc   3300

auacaaaugu gaguaaugag acaggacugg uccuggccug aggucuacuc aacucccaaa   3360

gucagagcuu aaugagccac ugucucaaug ggagcucaca gaagccugca gagggaguga   3420

gcugagaacu uuugccuccc ugaaugccuu ucuaaaauaa agaagggugu guuuugguug   3480

guuuguagag gugggggucuu gagagccucc ugccuuccca agugcuagga guauaggugu   3540

augcuagaua cccgacaggg augacggauc uuuuaggcca uagcacuuuc uuuccucucc   3600

cugaaguacu gagacugagu cuagugcagg gaggccucca uacuaaaaag cuggguguac   3660

ccguaauccc agaacucgga aaaucaagac aggaggagcc auucaaguca cgcucagaaa   3720

cauggagagu uuaaggucag ccugggauau auaaacccua ucuccgauaa ccaaacaaca   3780

aucaaagcaa accugacuua aguguuaagu aggaaagaau augcuguaag ucaucagccu   3840

ggcuggggga cugaccgccu cugagggacu gaagaaccug cuucaagccc ggagcccugc   3900

acucaacccc uaguggaugc acacacagau ccuugccaug auggcucgaa gagggauggc   3960

aagacccugg gagauaugug agauuggcca gagaagagcc agcaacaggc uucccagcaa   4020

gggaacagcu uaccucugug aucagcuggg gcgugagcaa gaggcaagcc cagggugaau   4080

ccuuccuuua gcccuguccu gaggagacac cuuuugacca cggguacuag uggguuggag   4140

cugugagcug uggguaggug gcuuccccuc ggugugcucu ggaacuugaa caaaucacuc   4200

auccuuccug agcuuccuca caugugagug ugcagagauc uggaugggug acucagcagc   4260

ggcucuggcu gcuccuuaga ggauccgggu uccaaucuca gcacccacgu ggcaacucac   4320

uguccacaac guccccccaaa gguucugaug cccucuucug gccuccacca gcacugaaug   4380

cacaaggugc ucauacaaac acacaggcaa aauacucaga gguaaauuug uucuuuuuuu   4440

ucuuuugaga cagggguucu cuguauagcc cuggcugucc uagaacucac ucuacagacc   4500

aggcuggccu caaacucaca gaggcaucug ccugccuccc aaguguuggg accaaagaug   4560

uaugccauca cuauaagccu uuuuuuuuuu uguaaauuuu auuuaugaau gagugcuucc   4620

auguauaccu ucaugccagg agagggcauc agauccuauu auaggugguu gugagccacc   4680

gugugugggcu gggauuugaa cucaggaccu cugaaagagg agcucuuaac ugcuaaaaca   4740

ucucucuagc cccagucuac auauuuuaaa ucuuuuuuua agauugauuu auuuauuaua   4800

cauaaguaca uuguagcugu cuucagacac uccagaagag ggcgucagau cuuguuaugg   4860

augauuguga gccaccaugu gguugcuggg auuugaacuc aggaccuuug gaagaguagu   4920

caaugcucuu acccgcugag ccaucucacc agccccuuuu uuaaucuuua aaaaaaaaag   4980

ggggggggcc uggagagaug gcucagccgu uaagagcacu gaaugcuuuu ccagaggucc   5040

ugaguucaau ucccaacaac cacaugguag cucacaacca ucuguaaugg gauccaaugc   5100

ccucuucugg uguaucugaa gacagcaagg gucuacucac auauguuaaa uaaauaaaua   5160

aaaauuuaaa agccaggugg uguugguuca gacagcagau cucuguuuaa ggccagccug   5220

gucugaucua caaaccaagu uccaggacag ccagggcuac acagagaaac ccucuaaaaa   5280

accaaucuau guagggggug cugguggaaau ggcuccgugg guaaagguac uugcugcgaa   5340
```

auuaaugacc ugaguucaau ccuugaaauc cacacaguag aaggagagaa ccaaccucca 5400
agggugcuau gacacacaca cacacacaca cacacacaca cacacacaca cacacacaca 5460
cacgacuaua uauaugaaua uaugacucua gccaggcaua guguggcaca ugccuuuaau 5520
cacaguacuu gggaggcaga ggcaggugaa guuugaggcc agccuacaga gugaauucca 5580
ugacagcuag aacuaugaag augaacccug ucuuuaaaaa caacagcaac auaaagaauc 5640
uauguaggga agcuggaagg gaugcugaua cagucugcaa uccuauuacu cuagaggugg 5700
aagccaaaga aucagggguu ucaggccggu cuugccuaua cacugagcua aaggccagcc 5760
ugggacacau gagacuuugu cucuuuuaaa aagacaaaac aagggggguug guuagauggc 5820
ucaguggcua agagcaccca acugcucuuc ugcagguccg aaguucaaau cccagcaacc 5880
acauggugggc ucacaaccau cuguaacgaa aucugagucc cucuucugga gugucugaaa 5940
acaacuacag uguacuuaca uauaauaaaa auaaauaaau cuuaaaaaaa aaaaaaaaag 6000
acaaaacaag ccagaugagg ucugugaguu ccaggccagc cuggucuaua aaucaaguuc 6060
aaggccaggc agggcuacuc agagauucug ucuaaaauac aaagaaacaa aacuacaaaa 6120
agcagaaaaa ggaaucuacg aaagggcugg ugaaggggug uaacucagug guagagcauu 6180
ugccgagcua gcauguacca agccaugggu uugaucccua gcacuaagca aaagaaaagu 6240
ccuacaaagg gcuuuguugg cauaguagau ugauucccag uagcuuuugg cacucaagag 6300
caccuucuac aauucacagc uccuggggga agaaauccca ucuuccacag augaggaggc 6360
ugagaguccu gugaaaagag auaaucaugu cucauacacu caggagagaa ggcuacuucu 6420
gccugagaaa ugaaaaggcu uccuggggguc ccaacaucuu aguccagucc uaagaugcgg 6480
aagggaggaa gaucaaaguu uacagagagg gaaagcauuu caggaaagaa accagcagua 6540
aagcuaggug ugugugagcu ggaaauguca ccaaugagau gacaagcguc cgguacagag 6600
aagcaacugu ggaguguugg gugguggcac cuagacuaca gacugaagga aagcuggaug 6660
accagcucag ggcagcuggu ggcucagagu cagccucauu gucucccuuc uucuauccca 6720
accuagauca gcccagagga ggaagagcgc cgcagggguga gacgcgagcg gaacaagcua 6780
gcagcugcua agugcagaaa ccgaagaaag gagcugacag acuuccugca ggcggugagc 6840
aucaucccca ggcccggacc cacagagccc caagaggggu cucggcuccc aagaacacaa 6900
aagacccaaa auuacuccuc aggacucugu cauccucccu gccugugggg aaguccugga 6960
aaaaggauaa gggaaagugg cuuaaaauau guuugucggg cuucgaggca gagucgaaga 7020
ugguaggcag caauucuccu aagaugcccc cgucugaugg gagucauggc cauuuucucc 7080
cagaggcuca cgggagggag uugcagucca gacuuguugg ggaugacagg cacaguccu 7140
acuccagccu gaggcuuggg gaucuuuagc cuucauuuuc cuaucuuucu gcuaauccug 7200
uaaaggagac cgacaaauug gaggaugaga aaucggggcu gcagcgagag auugaagagc 7260
ugcagaagca gaaggaacgc cuugagcugg ugcuggaagc ccaucgcccc aucugcaaaa 7320
ucccagaagg agacaagaag gacccaggug guucuggcag caccagcggu gcuagcagcc 7380
caccagcccc cggccgccca gugccuugca ucucccuuuc uccaggaccc guacuugaac 7440
cggaagcacu gcauaccccc acgcucauga ccacacccuc ucugacuccu uuuacuccga 7500
gucugguuuu caccuauccu agcacaccag aaccuugcuc cuccgcucac cgaaagagua 7560
gcagcagcag uggcgacccc uccuccgacc cccugggcuc uccuacacuc cuggcuuugu 7620
gaggcaccca gccacauccc uugcuggugc uacuccaagc cauccccuuu cucccauuga 7680
uccagcaggc cuggaccaua cccuugcccc aaaccagcag aucuuuuauc ucuucccgacu 7740 agaacaaaca cauuaugcuu ugauguagag ccagcuugga ggggaucccc aaagcugcuc 7800
acuguuuuuc uagagcuggc cuaucauaau uugcacaaaa uuagaggaaa auauguuccc 7860
ucugccagag aacgccuggc agcccagacu uuguagaucc ccaggggucc uuugacaccc 7920
uuaccccuug cagaccacuu ucccacacca cgucacuuuc uucauguuau ccagccuacu 7980
cuacaccuag acagaaggug cccuuugacu agccuagaac acuaacucac acagcaucaa 8040
cagccagcag caccggacau ccugcaggcu ccuccugaau ggcacaacgc aggaggcgcc 8100
aggggcuucu gugaggagcg gagcugcacu cccuagcucu gagaagcgcu uagcuucagg 8160
guauccgagc cuccaccgca agggcagcug cuauuuauuu uccuaaagag acuauuuuua 8220
uacaaaccuu ccaaaaugga auaaaaggcu ug 8252

<210> SEQ ID NO 102
<211> LENGTH: 1938
<212> TYPE: RNA
<213> ORGANISM: Homo sapiens

<400> SEQUENCE: 102
ccguggguuc cuaauggugc uauugacgac gggcacaaag ucucauaauu uuagaaacuu 60
cacuuauuuu gugacccacc uaguaugggg caaaggcagg agcuucggac uuccugucuu 120
cccucuaucc cuuugaauag cgucucggga gugucccuaa guaaccauug caguuuugug 180
uccgugugcu cuguugaaau cucugugaug uguguauggu uuucacguga acggaggcag 240
gcagagcccg gucugugggu ucuagugugu ucuuuaucuu cuuggaaguu ugugcaauga 300
cuucccuccu guuuccugcg cauaccucca aguaaguacg ugaauguguu uucugugguc 360
ccuugaucuu gcuggacuuc acuaaggagg guggcuggac caucugcuac gugucugaga 420
gccccucucu agcuaccuca uguccggacg ugagcuuacu cccaauguuu uuacccacaa 480
gcauucacua cucccaggaa agaacgugca cuggggcacc uagagaauaa ccaaucaacg 540
cuccgccuac auuuugcuuc cuccuuggaa uuuccagccc cuugcagcca acugcucccc 600
agcugcgaag ggcggaguuc cccccggccc ggccccuucu uuggcucuau aaguagcucu 660
gcuuugcggg ggauuugcac ucccucuacac ucucugcaca acgucuaaau uaugugccac 720
ucgcgcaacc aucuccacac caugacuggc cugagggccc cuucuccagc ucccuccacc 780
ggcccggaac uccggcgggg cucugguccc gaaauuuuca ccuucgaccc ucucccggag 840
cgggccgugg uguccaccgc gcguuugaac acuucucgcg ggcaccgaaa acgcagccga 900
agggugcucu acccucgagu ggugaguauc gcccgagugg gcaucaggag gucgcgucgc 960
ccuggaacuu guagguaaca acuaggagca gggaccuucg aucugacguu ucccucuuuu 1020
aucugcucag guccggcgcc agcuaccaac cgaggaaccc aacauugcca agagggu ccu 1080 cuuucuccug uucgccauca ucuucugcca gauuuugaug gcugaagagg gugugucgca 1140
gccccuggcu ccggaggaug cuaccagcgc cgugacaccu gagcccauuu cugcgcccau 1200
uacugcgccc ccgguccucg agccuuugaa ccugaccucg gaguccucgg acuaugcgcu 1260
ggaucuuaaa gcuuuucucu agcaacaucc ggcggccuuc uaaacgcgau gggucacagu 1320
ccgaagaaac aaaggcacca uggaugggua ccugguguga gagaacguau cccaaacugg 1380
gauuucuaag gcaacgcuaa cucagaacac uaccgccaag agacaccgcg gguccuggcu 1440
aggcccacug gggacggaca gagacuuucu ccgugucuaa uuaauauuua uguauuuaug 1500
uauauccucc uaggugaagg aggggugua u guaauauuua uucuaacuua ugcaggggug 1560
cgagauaugc cucccugcug uaacacagau auuuauuacg auuuauaggg ucgguaagac 1620
agaguugugg gagggaggac ccggguggua ggacucccag cuuggggauu agucuggggg 1680 gggugu aaua agauuagggg uaacacuccg ucuuccagca cuucaacucu guagucuguu 1740
guaaggcuuu ggaagacccu ugggaauccg gccuuugaug ucuucugguu gcuucucagg 1800
ggcagcugca ggagucuugg guccauggau ugucagaggg cggcugucug gggucgccua 1860
guauguaugu ucugugaaca cgaauaaacu ugauuugccu gucauuauua ucugcaguuc 1920
ucgaagugua ucauucag 1938

<210> SEQ ID NO 103
<211> LENGTH: 3036
<212> TYPE: RNA
<213> ORGANISM: Homo sapiens

<400> SEQUENCE: 103
gacagcggag cgcgguggcg ucgacgucua gugucucagu gcucccgucu guggcuaacu 60
aagcagccag cagccaggca gcucgcgacc ugcggccagg cagccaacca ugcucaacuu 120
cggcgcuucu cuccagcaag cuucggaggg gaaaauggaa cuaauuucug aaaagcccag 180
agaggggaug caucccuggg acaaagcuga gcagagugac uuugaagcgg uggaagcgcu 240
cauguccaug agcugcgacu ggaagucuca uuucaagaaa uaccuugaaa acaggccugu 300
cacaccagug ucugauaccu ccgaggauga cagcuugcuu ccagggacgc cugaccuuca 360
gacaguccca gcauuuuguu uaacgccacc uuacagcccc ucugacuucg aacccuccca 420
agggucaaau cugacugcau cagcgccauc uacuggccac uucaaaucuu ucuccgaugc 480
ugccaagccu ccaggcgcca cuccuuucaa agaggaggaa aagaauccuu uagcugcccc 540
uccucuuccu aaggcucaag ccaccagugu cauccgucac acagcugaug cccaacugug 600
caaccaccag uccugccccg ugaaagcagc uagcauccuc aacuaucagg acaauucuuu 660
ccggagaaga acccacggaa auguugaggc uacucgaaag aacauacccu gugcugcagu 720
gucaccaaac agauccaagc cugagcccag cacaguuucc gauggugaug agaaggcggg 780
cgcugcacua uaugacuuug cugugccuuc cucagagaca guaauuugua ggucucagcc 840
agcuccuucg uccccagugc agaagucagu acuggugucu ucaccuacag uauccacugg 900
gggagugcca ccccugccug ucaucugcca gaugguuccc cuuccugcca acaacucucu 960
uguuagcaca guuguucccca gcacuccucc uagccagcca ccagcugucu gcucaccugu 1020
guuguucaug ggcacucagg ugccugaggg caccgucgug uuuguggu ac cccagcccgu 1080 ugugcagagc ccaaggccuc caguggugag ccccaguggc accagacugu cucccauugc 1140
cccugcuccu ggauucucuc cuucagcagc aagggucacu ccucagauug acucguccag 1200
aguaagaagu cacaucugua gccacccagg guguggcaag acuuacuuua aaaguuccca 1260
ucugaaggcc cacgugagga cacacacagg ggaaaaaccu uucagcugca gcuggaaagg 1320
cugugaaagg agguuugcuc gcuccgauga acuguccaga caccggcgga cacacacagg 1380
ugagaagaag uuugccuguc ccaugugug a ccgucgguuu augaggagcg accauuuaac 1440
caagcaugcc cgacgccacc uaucagccaa gaagcugcca aacuggcaaa uggaaguuag 1500
caaguuaaau gacauugcuc ugccuccgac cccugcuucc gcacagugac ggccagaaga 1560
uggagacgca gaauaaacuu uggucagagu caggagccag ugauggu guc aagugcuucu 1620 gcaaggcugu ggcccuccaa aagggccuaa aguagaagcc cuggccuggg ggaggccccg 1680
ccugggugaa augacaagaa gugcuucagc cacaggcagg ucacagagga cagggcucag 1740
uucuuaccac agagagagag gagaacccuu uuauuccucc cuuauuuuag ucuggaaagu 1800
uucggcugag gugagcgcag cacagguuuu gaaucacaua cacauugggg acuuuguuuu 1860
ugccauuuau acuugagacc agcuuugcag ugugauucuu ucaaaggauu gguuucaaga 1920
auauagaggc uggaaauuac gguacagaaa uggagcuaga aaaugaguuu guguuacaca 1980
gagaugucau cuucuccuag aguuaucuug uuucuuauuc cuagucuuuc cagucaaauc 2040
cguggaugua gcuaaguaua ucuaaaacuc auuuuuccac uauuguuggu auuugaaguu 2100
gaacagcugu acauugcugu gggggagcca aaggauugga acccucauua auuuaauugc 2160
uuggaaaugc agcuaaaauu cuucuuuggc auuuuguuuu gaaaguuuag gcauuuuacu 2220
cuacuuuaga uuuuaguuug cuugcaguuu uuuguguaga uuugaaaauu guauaccaau 2280
guguuuucug uaggcuuaaa auacacugca cuuuguuuag aaaaaaaucu ggagaugaaa 2340
auauguauua uaaagaagag augucaagaa uuugagauaa cuccuugaga aaguuggcuu 2400
uaugucauca gcaaaggaca cuuaacguca agcauacacu gugguuuuuu uguuuuuuug 2460
uuuuuuuuuu ucaaauuaga aaguuuaaug accguuacag auggacagug ucuuuuuauu 2520
uauaggaguu uuucaggaug ucagaguaga uagguaggaa aauuguuauu agaacauucg 2580
cuucuaccuu gaaaaggaug uuaauguggu cauguucuua gcaccacagu gucugggcau 2640
cugggaaacu ccgagacuuu uuuaaagugu caugauguga ucacaccugc aguuuggggc 2700
aucgaaucca gggccuugca ugucuucugu aagagcucuc aucgcugacc uguaucccccc 2760 gcaagagcaa ugacuuuugc uaacaguauu ucuuuucugu uguaaagugg acagaugaua 2820
cacuuggucg caaagguaaa uuauucaaaa uccacaguga aaaccucacc acacuuuccc 2880
auuuaaacua uuuccauauc ucagagguuu cugacaugca aacuugaacc cuugaaagaa 2940
gaguuuucuu aaaaauuaua aaaaaucacg aguuacaauu ugcacaauau uuuuuguuga 3000
acuuuauacc uuguuuacaa uaaagacuuu ucuuug 3036

<210> SEQ ID NO 104
<211> LENGTH: 279
<212> TYPE: RNA
<213> ORGANISM: Homo sapiens

<400> SEQUENCE: 104
uuuuuuuuuu uuuuuuuaaa uugccgaauu aaguucuuuu aauagauugc auauauagau 60
guuuagccau acucuagauc aacucuuuaa gaguagaauu uuauauccaa uuuacaugcu 120
ucagauauca ccucuguuug uuacauaagg ucuuguaucc aaauguccac uuguacacug 180
agagcuuuag gaacaaaaaa ggacacagag agaguugcca uuuuuagcag caaugaaaca 240
ucacuaaccc cuuuuuacau accgaauuca agucacuac 279

<210> SEQ ID NO 105
<211> LENGTH: 143
<212> TYPE: RNA
<213> ORGANISM: Homo sapiens

<400> SEQUENCE: 105
cggccgccgg uauuuuuuug caaguauuga gaguucugua uguuuugaaa agaguaauuu 60
uaacguuugg gugccaagaa gugggguuuc ucagagucca uugccggcaa ugggcaagcc 120
uggcgguacu ccucgugccg aau 143

<210> SEQ ID NO 106
<211> LENGTH: 989
<212> TYPE: RNA
<213> ORGANISM: Homo sapiens

<400> SEQUENCE: 106
auggcgcugg gaacgcugcu ccugcugcug gcggccgccc uggcccggac ccagaaccga 60
gccggugagu gcagggucgg gagggaaaca gaacuuucca aacagucugc ggggaggggc 120
gggugcggca ccggggaagc cgcgugcccg cgucgcccac cagacccucc gucucuuuac 180
ccgcgucccu agccccgcgc ccugcucccc uccugucccg cgcauccgcc cggggucccg 240
ggagaagguc ggggucucac cgcgcgccgc ccccaggcuc acacucgaug cgguauuucg 300
agaccgucgu gucccggccg ggccucgggg agccccggua cgucucuguc ggcuacgugg 360
acgacacgga guucgugcgc uucgacagcg acgcggagaa accgagguau gagccgcggg 420
cgcgguggau ggagcaggag gggccggagu auugggagcg gaucacgcag aucgccaagg 480
gccaugagca gugguuccga gugagccuga ggaaacugcu aggcuacuac aaccagagcg 540
cgggcgguga gugaccccgg gucggagguc aggccccucc acuucccgac acagggacgc 600
ugacguccug guucccaagu cugagguucg ggaacagaac ggacccggga ccgguuuccc 660
uuucaguuug gaggaguccg cgggugggcg gggcugaccg cggggucccg cagguucuca 720
cacacuccag gagauguaug gcugugaugu gggaucggac gggcgccucc uccgcgggua 780
ccggcagucc gccuaugaug gcugcgauua cauugcccug aacgaagacc ugaaaaccug 840
gacugcgaag gauguggcag cgcugaucac cagacgcaag ugggagcagg auggugcugc 900
agaguauuac aaggcuuaca uggagggcga gugcgugcag ucgcuccgca gauaccugga 960
gcucgggaag gagacgcugc ugcgcacag 989

<210> SEQ ID NO 107
<211> LENGTH: 4484
<212> TYPE: RNA
<213> ORGANISM: Homo sapiens

<400> SEQUENCE: 107
auggcgucaa caaugcugcu ucugcuggug gcagucgccc agacccugau cgagauccgc 60
gcgggugagu accggguccg gagggaaaug gccucugagg aaaggggagg gggcggcacg 120
ggggaagccg cgucccggcg ucgcccaccu gacccuccgc cccuucucca cccuagcccc 180
gcgcccugcu ccccucccgg cccgcucacc cgcgggggguc ccggaaggag uucggggucu 240
caccgcgccc ugccuccagg cccacacuug cugaguuauu ucuacaccuc cgugucccgg 300
ccgggccuug gggagccccg guucaucucu gucgguuacg uggacaacac ggaguucgug 360
cgcuucgaca gcgacgcgga gaauccgaga uaugagccgc gggcaccgug gauggagcag 420
gaggggccgg aguauuggga gcgggaaaca cagaaagcca agggcaauga gcagauuuuc 480
cgagugaacc ugaggacccu gcucagcuac uacaaccaga gcgcgggcgg ugagugaccc 540
cggaucggag gucacgaccc cuccacgucc caaaacaggg gcccgagacg ucccgggccc 600
caaguucgag guucugagca gaacggacgc gggacugguu ucccuuucag uuuggaggag 660
ccgcgggugg gcggggccgg ggcgugugggg cggggcugac cgcggggucc cgcaggcucu 720
cacacuauuc aggugaucuc uggcugugaa guggggguccg acgggcgccu ccuccgcggg 780
uaccagcagu ucgccuacga cggccgcgau uacaucgccc ugaacgaaga ccugaaaacg 840
uggacggcgg cggacauggc ggcacagauc acccgacgca agugggagca ggcuggugcu 900

-continued

```
acagagaaaa gcaaggccua ccuggagggc gcgugcgugc agucccuccg cagauaccug    960
gagcucggga aggagacgcu gcugcgcaca ggugcagggg ccgcgggcag cuccucccuc   1020
ugcccucggg cuggggcuca guccugggga agaagaaacc cucagcuggg gugaugcccc   1080
ugucucagag ggagagagug acccuggucu ccugaucccu caucacagug acugcacuga   1140
cucucccagg gcucagccuu cucccuggac agugcccagg cugucucagg agggaaggag   1200
agaauuuccc ugagguaaca acagcugcuc ccuucaguuc cccuguagcc ucugucagcc   1260
auggccucuc ccaggccggg uucucagccc acugucugua gacacugacu ccuguccugc   1320
ugagugugu c agcccuuaca ccucaggacc agaagucgcc uuuaacugau cggagacaug   1380
gacuacccua cacuaggcug auugccucag uuuccugaau uuucaaaaga auacauucuc   1440
ccagaucccu cccugucugu gggguuucca ccccuucgac aaccuaauuc ucucuauucc   1500
uauaguggug gucacaucag cccuuauggg guacccugga ggaauaucaa uaguggaauu   1560
ucuucuucuu cuucuucuuc uucuucuucu ucuucuucuu cuucuucuuc uucuucuucu   1620
ucuucuucuu cuucuucuuc uucuucuucu uccuucucuc ucucucucuc ucucucucuc   1680
ucucucucuc ucucucucuc ucucucucuc ucucucucuu cuucaguuuu ugagauaggg   1740
uuucucugua ugcccuggcu guccuggaac ucacuuguag accaggaugg ccucgaccuc   1800
agaaauccgc cugccucugc cucccagugc ugggauuaaa ggcguguggc caccuugccc   1860
agccuuucuu auuuucuuua cuuuuuuuuu uuuuuuugga gggguaauu uuguuucuag    1920
ucaucuuuug ucuuuugucu gcacuggagu gauccuguuu cucccugccc uuauauuauc   1980
auguguauca gucuccacag gugccaggga aguuaagaca aguuaaauca ggguucucuu   2040
uaaaggagag auuccuguga acuuagacug uuuccuguca gaacuaaaca uccagaagcc   2100
uccugcucuu ccucuguccc acaaguuaca gugcuccccc cccccccca gugaaucugg    2160
acuuggacuc ugagagacag ggucuucugc aauccagggc uggagugaga gggaagacca   2220
cacacccugu gagcccacug uguugcagug agugcugcac uggggucccac agcauacucc  2280
agggauccug ugugacacac cuguaccuug ucccccagag ucaggggcug gaagucauuu   2340
ucucuggcug agugucagag guugacacca uuucugcuac acacucugug auggcugcuc   2400
acuuggacug gcgguuaugc uaguuagcaa gaugaacaca gugguuuacg ucucaguugu   2460
cacacccuuc caguggcaua uggcucuaau uucuacuuuu gauacgaacu caaacacuua   2520
uuaaauuagu uaguuuccau uccaucuucc auucuagucc auucaugcua aagaacauca   2580
cauaaggacu gccaggauga cccacuggcu cauguggauu ccccucuuagc uucugagucc  2640
cccagaaaaa ugugcagcug aggaaaccag cucugccugc aggucaccag ugccaugaca   2700
guugaagugu caaacagaca cauuguucag ugucaucagu gauuuaacug ugccuugugu   2760
agauuucaga gggucuuguu aauuguggua cuuuuuuuug uuuuuuguuu uuuuuuuuuu   2820
uuguuuuguu uucaagacag gauuuuucug uauagcccug gcuguccugg aacucacauu   2880
guggaccagg cugaccacga acucagaaau cugccugccu cugccucccg agugcuggga   2940
uuaaaggcgu gugccaccac caaccagcua aucgugagau uucuuucuuu uuucuuuucu   3000
uuucuucuuu uuuuuuuuuu uuuuguuguu guuguuuugu uuuuugagac aggguucucu   3060
guguaucccu ggcuguccuu gaacucacuu uguagaccag gcuggccuug aacuuagaaa   3120
uuugccugcc ucugcuccgg agugcuggga uuaaaggcau gugccacuac caaccagcua   3180
auugugggau uucuuaaauc uuccacacag auccuccaaa ggcacaugug acaugucacc   3240
acagaucuga cggugauguc acccugaggu gcugggcccu gggcuucuac ccugcuaaca   3300
```

```
ucauccugac cuggcaguug aaugggggagg agcugaccca ggacauggag cuuguggaga   3360
ccaggccuuc aggggaugga accuuccaga agugggcauc uguggguggug ccucuuggga   3420
aggagcagaa uuacacaugc caugugcacc augaggggcu gccugagccc cucacccuga   3480
gaugggguaa ggagggugug ggugcagagc ugggggucagg gaaagcugga gccuuuugca   3540
gacccugagc ugcucagggc ugagagcugg ggucaugacc ucaccuucau uuccuguacc   3600
uguccuuccc agagccuccu ccauccacug ucuccaacau ggcgaacgua gcuguucugg   3660
uuguccuugg agcuuggcca ucauugcagc uguggguggcu uuugugauga agagaaggag   3720
acacacaggu aggaaagggc agagucugag uuuucucuca gccuccuuua gagugugcuc   3780
ugcucaucaa uggggaacac aggcacaccc cacauugcua cugucuguaa cugugucugc   3840
ucucaguucu gggaacuucc uagugucaag cucuuccuug aacucucaca gcuuuccuuc   3900
ucacaggugg acaaggaggg gacuaugcuc uggcuccagg uuagugugggg ggacagaguu   3960
guccugaggu cauuggagug aagcuggagu uguugggugc ucugggaacc cauaauagcu   4020
ucucuguugu aauccucugg uggccugugu cagaucuugc uauagauaua ucuuuguaua   4080
uauuuuuccc uaggcaggga cagcucccag agcucugaua uguuucucuc aagauuguaa   4140
aggugacauu cuauggccug auugcagagg ggcacugugg acaugguugu guuucaggga   4200
cucccacaau ccccugugag ugguggguug uugggauauu gucuucauug uggugguucc   4260
ugacccucau ucucuaucau gaagacagcu gccuggagug gacuuaguga cagccagugu   4320
gaccuugggu cuucauuuuu cuuuagagaa cagcgccuga uguucccugu gagccuaugg   4380
gcucaaugug aagaauugug gagcccagcc uucgccuaca caccaggacc ugucucuugc   4440
auugcccugu guucccuucc accgccaacc uuccgggucu gcag                     4484
```

<210> SEQ ID NO 108
<211> LENGTH: 385
<212> TYPE: RNA
<213> ORGANISM: Homo sapiens

<400> SEQUENCE: 108

```
uuuuuuuuuu uuuuuuucag aauaauugca gacaaauucc auuuauuuuu cuaaaaaccu     60
cauuaucuaa aauuuauaca gccucacauu ccuaaaccac cucuggcacu uuucuugaau    120
uaagucaagg cguacacagc uccgaaagaa aaauagagau ccgguuccag gaagauggcc    180
augaggacuc gcagauaugu cuccucggac cuggaagcgu gucagccaug ggauccacua    240
auccaccauc cgguacacag ggucacccac ucucaggcuc ccaagcuucu ccaccgagaa    300
auacauccca aaaagugggag augacuggua uauacucuuc acagaaggau cacacaggcg    360
auagcucuuc agggucucca guggc                                          385
```

<210> SEQ ID NO 109
<211> LENGTH: 2247
<212> TYPE: RNA
<213> ORGANISM: Homo sapiens

<400> SEQUENCE: 109

```
cucuagauga auacacucuc augagggcca ccuucucugg uaguucaggu cgccucugcc     60
cauccuuccc ugcguccucu cccaaagugg ccuacaaccc uuacccagag gacuauggag    120
acauugagau ugguucucac aagaguucca gcaguaaccu gggggcagau gauggcuaca    180
ugcccaugac cccuggggca gcccuuagga gugguggucc caauagcugc aagagcgaug    240
```

-continued acuacaugcc caugagcccc acaagcgugu cugcucccaa gcagauccug cagccacgcu 300
uggcagcggc cuugcccccu uccggagcag ccgugccagc acccccuuca ggggugggca 360
ggaccuuccc aguaaacgga gguggcuaca aagccagcuc cccagcggag agcuccccag 420
aagacagugg guacaugcga auguggugug gcuccaagcu gucuauggag aacccagacc 480
cuaagcuacu ccccaacggg gacuaccuca acaugucccc cagcgaggca ggcacugcag 540
ggaccccacc ugacuucuca gcagcuuugc guggaggcag ugaaggccuc aaaggcaucc 600
cgggccacug cuacagcucu uugccccgcu cuuauaaggc ucccuguucc ugcagcggag 660
acaaugacca guaugugcuc augagcuccc cugugggccg gaucuuggaa gaggagagac 720
uggagcccca ggccacccca ggggcuggca ccuuuggggc agcugguggu agucauaccc 780
agccucauca cucagcagug ccuuccucca ugaggccgag ugccaucggu ggccgcccug 840
agggcuuccu gggccagcga ugucgggcag ugcggccuac acgccuaucg cuagagggac 900
ugcagacccu ucccagcaug caagaguacc cucuacccac agagcccaag agcccuggcg 960
aguacaucaa cauugacuuu ggugaggcag guacccgucu gucuccgccu gcccccccac 1020
uacuggcauc cgcggccuca ucuucuucac ugcucucagc uaguaguccu gcuucauccc 1080
uggguucagg aaccccaggc accagcagcg acagccggca gcgcucucca cucucugacu 1140
auaugaaccu ggacuucagu ucucccaagu cccccaagcc uagcacccgc aguggggaca 1200
caguaggcuc cauggauggc cuucucucuc cagaggcuuc auccccauac ccaccacugc 1260
ccccacgucc uuccacuucc ccuuccuccu uacagcagcc ucugccaccu gccccgggag 1320
accuauaccg ccugccucca gcaucagcug ccacuuccca ggguccccacu gcuggcuccu 1380 caauguccuc cgagccuggg gauaauggug acuauaccga gauggccuuu ggugugggcug 1440 caaccccgcc acaaccuauc guggcaccuc caaagccaga aggugcccga guggccaguc 1500
ccacaucggg cuugaagcgg cuaagucuca uggaucaggu aucuggggug gaggcuuucc 1560
uucaagucag ccagcccccu gacccccacc ggggugcuaa ggucauccgu gcagacccac 1620 agggggggacg ucgucgccac aguucagaga ccuuuuccuc uaccaccacc gucaccccag 1680
uguccccauc cuuugcccac aauuccaagc gccacaauuc ggccucugug gaaaaugucu 1740
cacucaggaa aagcagugaa ggcagcagua cccugggagg aggugaugag ccgcccacau 1800
ccccaggaca ggcacagccc uugguggcug ugcccccagu gccacaggcu aggccgugga 1860
accccgguca gcccggagcu uugauuggcu guccuggagg cagcaguucu cccaugcgca 1920
gagagaccuc cgugggguuuc cagaacggcc ucaacuauau cgccaucgau gugagaggcg 1980 agcaggggguc cuuggcgcag ucucagccgc agccaggaga caagaacucc uggagccgga 2040
cccguagccu uggggggcuc cucggcaccg ucggaggcuc uggcgccagc ggagugugug 2100 ggggguccagg cacuggagcu uugcccucug ccagcaccua ugcaagcauc gacuuccugu 2160
cccaucacuu gaaggaagcc acagucguga aaggugaggc ccuuugaccu ugaggauggg 2220
ggagggagag uggaguauug gguggcu 2247

<210> SEQ ID NO 110
<211> LENGTH: 315
<212> TYPE: RNA
<213> ORGANISM: Homo sapiens

<400> SEQUENCE: 110
uuuuuuuuuu uuuuuuucag cugugaacua uuggauuuga gacaggaaca gaacaaaucg 60
acgggccaga ggagggugga gagagcacga gugguuuaaa uaggggagga ugggagcaug 120 gcggugggggg ugggggaaga guuauuuaca agaaggcuca gggggccaga ggcucaucuu 180
ggaauauuuu auaacaauau auauaagauu cugguuugcu uuuccuuuuc gucucguaaa 240
ggagagagaa uugcauaguu cgauucuguc caagggggca gcugcauaug gucggccggg 300
cgggucacug gucgu 315

<210> SEQ ID NO 111
<211> LENGTH: 481
<212> TYPE: RNA
<213> ORGANISM: Homo sapiens

<400> SEQUENCE: 111
uuuuuuuuuu uuuuuuuaag ugucaccacu ugugacaguc agcauguuac uaucagcucc 60
agccgcagcg uuuuuaaggc guuauagauu aggcaggcaa uacaaggaac acgauuaaga 120
aacugacacg uaccacacga gcaauuucca gaggcuccuc uucugcggug cacacguaac 180
agugcucuug uugacauuca gacaguucug agggccacuc ugagaggcgc cuuccuguuc 240
ucaccugaca aggauauugu uugguuuggu uugguuuggu uuugccuuac uauggcuuuu 300
cuuucaacua cauuuugugu caugcuuguu agcuaacuca aauuuugucu uuguauauuu 360
acuacuguaa aauuagaaua auuuacuguu caucucaucc ucugucacug auggaaccua 420
gagacgccac aagagccacu gccgugacau accucacaag cuacaucccu guccucaaaa 480
u 481

<210> SEQ ID NO 112
<211> LENGTH: 379
<212> TYPE: RNA
<213> ORGANISM: Homo sapiens

<400> SEQUENCE: 112
cggccgcggc caccggccug cgccaagcug cugcugcggc agccaguacc ucggugaagc 60
ccauuuucag ucgcgaccug aacgaggcca agcggagggu gcgcgagcuc uaccgcgcuu 120
gguaucggga gcgugccgaa caccgugcac uuaaugcagc uggauaucac ggugaaacaa 180
ggacgggaua aaguccgaga aauguucaug aagaaugccc augucacaga ccccagagug 240
guugaucugc uggucauuaa gggaaagaug gagcuccagg aaaccaucaa aguauggaag 300
cagcggacac acguuaugcg guuuuuccau gaaacagaaa caccaaggcc aaaggauuuc 360
uuauccaagu ucuauaugg 379

<210> SEQ ID NO 113
<211> LENGTH: 3733
<212> TYPE: RNA
<213> ORGANISM: Homo sapiens

<400> SEQUENCE: 113
gcaccugagc gcgggugccu ggcgcgcccg augggaucgu ugagaggccc ucgacggaaa 60
gucccaaacu cggaucgcau ucagccaaag ugaggcggcg ccauggagcu ccgagcgcug 120
cugugcuggg cuucccucgc cacugcuuua gaagagaccc uguugaacac aaaacuggaa 180
acggcggauc ugaaaugggu gacuuacccu caggcagagg gccaguggga ggagcuaagc 240
ggccuggaug aggaacagca cagcguccgc accuaugagg ugugcgacau gaagcgucca 300
gggggccagg cucacuggcu gcgcacuggc uggguccaa ggcgaggugc uguccacgug 360
uaugccacga uacgcuucac caugauggaa ugccuguccc ugccgagggc cagucgcucc 420

```
ugcaaggaga cauucacugu cuucuauuac gagagcgaac gugauacggc cacggcccau    480
acgcccgccu ggauggagaa ccccuacauc aagguggaca caguggccgc agaacaucug    540
acucggaagc gcccuggagc ugaagccaca gggaaaguua auaucaagac gcugcgccug    600
gguccucuca gcaaagcugg cuucuaccug gcuuuccagg accaaggagc cugcauggcu    660
cugcucuccc ugcaucucuu uuacaagaag ugcuccuggc ugaucacgaa cuugaccuac    720
uuccccgaga cggugccucg ggagcucgug gugccggugg cagguagcug cguggccaac    780
gcgguccua ccgccaaccc cagccccagc cucuacugcc gggaagaugg ucaaugggcu    840
gagcagcagg ucacgggcug cagcugcgcg ccaggguacg aggcugcgga aagcaacaaa    900
guaugcagag ccuguggcca gggaaccuuc aagccccaaa uaggagacga guccugccug    960
ccgugcccag ccaacagcca cucgaauaac auugggucuc cugucugccu gugucgaauu   1020
ggguauuacc gggcccgcuc agacccccgg aguucaccuu gcacuacccc acccucugcu   1080
ccaagaagcg ugguucacca uuugaauggu uccacccugc gccuggagug gagugcuccc   1140
cuugaguccg gaaggccgag agaccucacu uaugcuguuc gcugccgaga gugccguccu   1200
gggggguucu gcuugcccug ugggggcgac augaccuucg accccggucc ucgagaccug   1260
guugagcgcu ggguggcaau ccgagggcug cguccugaug ucaccuauac cuuugagguu   1320
gcugcuuuga augguguguc uaccuuagcc acuggaccac cuccuuuuga gccugucaau   1380
gucaccacug accgugaggu gccuccugca gugucugaca uccgagugac ucggucguca   1440
cccagcagcu ugauccuguc augggcuauc cccagagcac ccagugggc cgugcuggac   1500
uacgagguca aguaucauga gaagggcgca gagggcccca gcaguguucg uuuccugaag   1560
acaucagaaa accgagcuga gcuccggggg cugaagcggg gagccagcua ucugguccag   1620
guacgcgcac gguccgaggc uggcuacggu cccuucggcc aggagcauca cagucagacu   1680
caacuggaug agagcgagag cuggcgggag cagcuggccc ugauugcagg cacugcgguu   1740
gugggugugg uccugguccu gguggucguc aucauugcag uucucugccu caggaagcag   1800
agcaauggga gggaaguuga guacucggau aagcaugggc aguaucucau cgggcacggu   1860
accaaggucu acauugaucc uuuuacuuac gaagacccua augaggcagu gagggaauuu   1920
gccaaagaga ucgaugucuc cuaugucaag auugaagagg uaauuggugc aggugaguuc   1980
ggcgaggugu gccggggucg gcugaaggca ccagggaaaa aggagagcug uguggccauc   2040
aagacucuga aggguggcua caccgagcgc cagagggcug aguuccugag cgaggccucc   2100
aucaugggcc aguucgagca ucccaacauc auccgccucg agggcguggu caccaacagu   2160
gugccgguua ugauccucac ggaauucaug gagaacggag cccuggacuc cuuccugcgg   2220
cugaacgacg ggcaguucac agucauccag cugguggggca ugcugagggg caucgccucg   2280
ggcaugcggu accuggcuga aaugagcuau guccaccgag accuggcugc ucggaacauc   2340
uuggucaaca guaaccuggu cugcaaggug uccgacuuug gccucuccag auucuuggag   2400
gagaacuccu cugaucccac cuacacaagu ucccugggag gcaagauucc cauccgaugg   2460
accgccccug aagccauugc cuucaggaag uucaccucug ccagugaugc cuggcgcuau   2520
gggaucguca ugugggaggu caugucuuuu ggggaacggc cauacuggga caugagcaac   2580
caggauguga ucaaugccau ugaacaggac uaccggcugc cuccuccucc agacugcccc   2640
accucccucc accagcucau gcuggacugu uggcagaagg accggaaugc ccggccccgc   2700
uuuccccagg uggucagcgc ucuggacaag augauccgga aucccgcuag ccucaaaauc   2760
guggccaggg agaauggcgg ggccucacau ccacucuugg accaacggca gccucacuac   2820
```

ucugcuuucg guucuguggu cgaguggcuu cgagccauca agaugggaag auacgaggaa 2880
aguuuugcag cggcuggauu cggcuccuuu gagaugguca gucagaucuc ugccgaggac 2940
cuucuccgaa uuggagucac ucuggcagga caccagaaga aaaucuuggc caguguggcag 3000 cauaugaagu gggaagcuaa gccaggagcc ccugguggga caggggggacc agcccagcag 3060 uucugaccuc caaggacuca ccaccguggc agauucuucu uuccgggagg cagaguuggg 3120
uggggacuca caagaugagc cccuccccccu cgucacagcc uucccauugg auugcacuuu 3180
gaacagaggg ggucggagac acagauuugg ggaaccgugc cauaugggau cauacaugug 3240
cccuccaggc ggggaacccc aaacucagag ugagucuuuc ccucaagacu gggcaaagaa 3300
acaucccuac gucucuaacc ucccaucuuc ccagaggcuc ucuccccaag cgccuuccac 3360
cucaacgggc augucccugc agaccaaaga gaaaggguga ccagccugcc aacuugggag 3420
uggaaaaugc cgucccagga ggcaggaagg ggcugucagg acccggugau guaaucauug 3480
gguuuugaug uccugacuug cugucaccac caaaggcaau cauuuuuccc uuguaaaugc 3540
cccuccccuc aucugccuuc auauugaagg uucugaaguu uuacuguuuu uuauuuuguu 3600
aauuuuuucc uccuuccccc cucccucccc uucuugucca gauuuugugu guuaaagggc 3660
accugguucc acuaucuccu guugggaaca aggacccauc gauauguucu agaacagugc 3720
cuuggaaaug cca 3733

<210> SEQ ID NO 114
<211> LENGTH: 560
<212> TYPE: RNA
<213> ORGANISM: Homo sapiens
<220> FEATURE:
<221> NAME/KEY: misc_feature
<222> LOCATION: (107)..(107)
<223> OTHER INFORMATION: n is a, c, g, or u

<400> SEQUENCE: 114
ggcagcgaga cgagcucacg gucgaggaua cgggugaagc gggacaggag caggagccgg 60
agccgggcca aagcagaagg ugcaggucgg cgccggcggu ugggcangac ccagucaagc 120
cggacaguga ggagcggaug cagacggcac gaccauggcc acgauggugc uuccucgaga 180
ggagaagcug agucaggacg agauagugcu gggcaccaag gcggugaucc aggguuuaga 240
gacccugaga ggggagcauc gugcccugcu agcuccccua gcuucucaug aagcaggcga 300
ggcugagcgg gcucacagga gcgcugccuc cuccugcgcc gcucccugga ggccaucgag 360
cuggggcuug gggaggcuca ggugauccug gcauuaucaa gccaucuggg ggcuguggag 420
ucagagaagc agaagcugcg ggcucaggug cggcccuggu acaagagaac agugguugcg 480
ugaggagcug gcagggacac agcagaagcu cagcgcagug aacaggcggu ggcucagcug 540
gagaagagag cagcacaucu 560

<210> SEQ ID NO 115
<211> LENGTH: 560
<212> TYPE: RNA
<213> ORGANISM: Homo sapiens
<220> FEATURE:
<221> NAME/KEY: misc_feature
<222> LOCATION: (107)..(107)
<223> OTHER INFORMATION: n is a, c, g, or u

<400> SEQUENCE: 115
ggcagcgaga cgagcucacg gucgaggaua cgggugaagc gggacaggag caggagccgg 60

-continued

```
agccgggcca aagcagaagg ugcaggucgg cgccggcggu ugggcangac ccagucaagc    120
cggacaguga ggagcggaug cagacggcac gaccauggcc acgauggugc uuccucgaga    180
ggagaagcug agucaggacg agauagugcu gggcaccaag gcggugaucc aggguuuaga    240
gacccugaga ggggagcauc gugcccugcu agcuccccua gcuucucaug aagcaggcga    300
ggcugagcgg gcucacagga gcgcugccuc cuccugcgcc gcucccugga ggccaucgag    360
cuggggcuug gggaggcuca ggugauccug gcauuaucaa gccaucuggg ggcuguggag    420
ucagagaagc agaagcugcg ggcucaggug cggcccuggu acaagagaac agugguugcg    480
ugaggagcug gcagggacac agcagaagcu cagcgcagug aacaggcggu ggcucagcug    540
gagaagagag cagcacaucu                                                560
```

<210> SEQ ID NO 116
<211> LENGTH: 1649
<212> TYPE: RNA
<213> ORGANISM: Homo sapiens

<400> SEQUENCE: 116

```
augaugugug gcgcgccauc ugccacaaug ccagccacgg ccgagacgca ggaggucgcc     60
gaccagguga ggcugggccc aggucaggcc agucugagcc aggccugcgg agacccggcg    120
gccucaggga ccggccugcc cagacugguc agguccugca gcggguuucc ggggcggcca    180
caagugugac ugggagcugg gggcucugga ucugguugga agauucaggg ccgggaacug    240
gggcgagucu ucugccgcuu gcauacaaga gggccacuca ccuauuaggg aacuagcccc    300
gggaucggug gagggauccg guggucccag agaauucagg aaggcagugu uagaaccuag    360
acggcaccuu uuugacuuac acccaggccu aaacaagaga aagccagacu gggcuacugu    420
gcuugucucc ucaaaagaaa gagcuaggac uguuuagcuc aguggcagga auucaacuga    480
uaccaccacc accaucacca acaccgcccc ucagggaaaa aaaaaaggau caaaaccaga    540
aguuguagaa cuugcuugug ccuagucuga aacgaggggg uggaccuugg gccugggcug    600
cccuuccugu gacuguuagc agagcagaga uucaguacaa gguaggggga gguucagggu    660
auuagcaaga gaagaaaagu uaaacaaauc cucucuucag cucuccugcc acgccccaag    720
cccaggaccc uguccacuaa gccuagcuga ucuugggagg uguuugcucu gaacugaagu    780
ggccaagaag gaagugaguc agcuccauga gacccuagaa augaggaaau guuacagaca    840
cacuggccag gcaagggaac cuuggccacg ugccacauca gcacucagga ggcagagaca    900
ggcgagucuc ucugaauuug aagccagccc aguuugcuua guuccaugcc agccauagcu    960
acauagugag acccuguccc cccccccccc aaaaaaaagg agcuguguug uucuuuauca   1020
guggggccaa caguuuacca ugucccccgg aaugaggagu auugaaggcu ggcagugugu   1080
gugugugggg gcaccugugc augaaucuaa guccuuccuu cucacccacc auccagguga   1140
agucccagcu ugaaucgaaa gaaaaucaga aguuugaugu cuuuaaagcc auauccuuca   1200
agagacagau aguggcuggc accaaccucu ucaucaaggu ggguacugau aguagcuugc   1260
caugaacugg ggacauaguc ucagaguaga gcagaguguc cugcaacuuc cugcagagaa   1320
ccccuuaagg ggacauguac auguucugag aggaugaauu uggggguuua ggguucccgg   1380
ccuuaaagga ggagacaagg guuaucacug gcuaaguuag uggcuggugg ccuguucugg   1440
cucaguuucu aaggcugggu uaagccugga acuggaaccu uaccuuucac ucacaugucu   1500
gucugucugu cuuccuccag guugauguug guggagauaa augcgugcac uugagggugu   1560
uucaaccccu cccccaugaa aacaagccuu ugacccuguc uuccuaucag accaacaaag   1620
```

aaaggcacga ugagcucucc uacuucuga 1649

<210> SEQ ID NO 117
<211> LENGTH: 334
<212> TYPE: RNA
<213> ORGANISM: Homo sapiens

<400> SEQUENCE: 117
gaaaauguua agagccauca aauuucugga uauuuugcua ggaaaaugaa auucuacacu 60
uauuuuuugu agacuuuuuu uaaaugcugu uuacaugaau uguauuuugg aaaaaauauu 120
auacugugca cccugugaug caugaaguga uuuuauguau ggucugcuau gugggcagag 180
gucaccuuau uccuaugauc uggaauuguu uacuuucuac aaaguaagcu uuguggggau 240
uuugcuuuca uuuucuuugu agcugauguu auuuuaccag gugugcagca ggaauuacac 300
cacugugugg aauuauaaau acaucccaug ugca 334

<210> SEQ ID NO 118
<211> LENGTH: 481
<212> TYPE: RNA
<213> ORGANISM: Homo sapiens

<400> SEQUENCE: 118
uuuuuuuuuu uuuuuuuccu ggugaauauu uuuauuagag gugacaguuu cccaggugac 60
aguuuuuccc aaggaagcaa aucucugcgu cuauaaggga agaccacaga accuucacuu 120
uguaauuuac cuguguaauu uauccaagaa cacagcacag caauugcuuu augugguacu 180
cugaccuuaa guaacaaguu guuaacagaa aacacaucaa acaaaaggau aauucucuaa 240
uuaucaaguc agccaucagc uuuucuuagg agagagagag agagugugug ugugugugug 300
ugugugugug ugugugugug ugucugucug ucugucuggg uaucccacuu agggccaugu 360
gcauguuagg uaaaugcucc accacugagc uguuucuuag ccgcacuuuu cucagauuuc 420
agguuuguuu guuuguuugu uuguuuuuua acuaggcaug aaaauaaacu ucacuucaaa 480
u 481

<210> SEQ ID NO 119
<211> LENGTH: 481
<212> TYPE: RNA
<213> ORGANISM: Homo sapiens

<400> SEQUENCE: 119
uuuuuuuuuu uuuuuuuccu ggugaauauu uuuauuagag gugacaguuu cccaggugac 60
aguuuuuccc aaggaagcaa aucucugcgu cuauaaggga agaccacaga accuucacuu 120
uguaauuuac cuguguaauu uauccaagaa cacagcacag caauugcuuu augugguacu 180
cugaccuuaa guaacaaguu guuaacagaa aacacaucaa acaaaaggau aauucucuaa 240
uuaucaaguc agccaucagc uuuucuuagg agagagagag agagugugug ugugugugug 300
ugugugugug ugugugugug ugucugucug ucugucuggg uaucccacuu agggccaugu 360
gcauguuagg uaaaugcucc accacugagc uguuucuuag ccgcacuuuu cucagauuuc 420
agguuuguuu guuuguuugu uuguuuuuua acuaggcaug aaaauaaacu ucacuucaaa 480
u 481

<210> SEQ ID NO 120
<211> LENGTH: 302
<212> TYPE: RNA

<213> ORGANISM: Homo sapiens

<400> SEQUENCE: 120
uuuuuuuuuu uuuuuuugug gaaauuacuc uuuauugaaa aauaccagua auacugacag 60
acuucaaaau caauuuacgg uuccagaaua caaaguacuu aauacauuuu uuuccaaacc 120
uguuuguauc ucaaaguuag cauuuuugua aaucaagaua caaauaugau aacuucacua 180
aaauauuuuc cagcuuuauu cuuuaaggag cuguauaacc uucaaaguca ggguccegag 240 gucagcaggg cauggggcag aaugcaccug gcacucccug ugcagcagac ugcaaccaca 300
uu 302

<210> SEQ ID NO 121
<211> LENGTH: 1266
<212> TYPE: RNA
<213> ORGANISM: Homo sapiens

<400> SEQUENCE: 121
auggccagcu uucccccgag gguuaacgag aaagagaucg ugagaucacg uacuauaggg 60
gaacucuugg cuccagcagc uccuuuugac aagaaaugug guggugagaa cuggacgguu 120
gcuuuugcuc cugaugguuc cuacuuugcg uggucacaag gauaucgcau agugaagcuu 180
gucccguggu cccagugccg uaagaacuuu cuuuugcaug guuccaaaaa uguuaccaau 240
ucaagcuguc uaaaaauuggc aagacaaaac aguaaauggug gucagaaaaa caagccuccu 300
gagcacguua uagacugugg agacauaguc uggagucuug cuuuugggguc uucaguucca 360 gaaaaacaga gucguugcgu uaauauagaa uggcaucggu uccgauuugg acaggaucag 420
cuacuccuug ccacaggauu aaacaauggu cgcaucaaaa ucugggaugu auauacagga 480
aaacuccucc uuaauuuggu agaccacauu gaaaugguua gagauuuaac uuuugcucca 540
gaugggagcu uacuccuugu aucagcuuca agagacaaaa cucuaagagu gugggaccug 600
aaagaugaug gaaacauggu gaaaguauug cgggcacauc agaauugggu guacaguugu 660
gcauucucuc ccgacuguuc uaugcugugu ucaguuggcg ccaguaaagc aguuuuccuu 720
uggaauaugg auaaaauacac caugauuagg aagcuggaag gucaucacca ugauguugua 780
gcuugugacu uuucuccuga uggagcauug cuagcuacug cauccuauga cacucgugug 840
uaugucuggg auccacacaa uggagaccuu cugauggagu uugggcaccu guuucccucg 900
cccacuccaa uauuugcugg aggagcaaau gaccgauggg ugagagcugu gucuuucagu 960
caugauggac ugcauguugc cagccuugcu gaugauaaaa uggugagguu cuggagaauc 1020
gaugaggauu guccgguaca aguugcaccu uugagcaaug gucuuugcug ugccuuuucu 1080
acugauggca guguuuuagc ugcugggaca caugauggaa guguguauuu uugggccacu 1140
ccaaggcaag ucccuagccu ucaacauaua ugucgcaugu caauccgaag agugaugucc 1200
acccaagaag uccaaaaacu gccuguuccu uccaaaauau uggcguuucu cuccuaccgc 1260
gguuag 1266

<210> SEQ ID NO 122
<211> LENGTH: 1266
<212> TYPE: RNA
<213> ORGANISM: Homo sapiens

<400> SEQUENCE: 122
auggccagcu uucccccgag gguuaacgag aaagagaucg ugagaucacg uacuauaggg 60
gaacucuugg cuccagcagc uccuuuugac aagaaaugug guggugagaa cuggacgguu 120
gcuuuugcuc cugaugguuc cuacuuugcg uggucacaag gauaucgcau agugaagcuu 180
gucccguggu cccagugccg uaagaacuuu cuuuugcaug guuccaaaaa uguuaccaau 240
ucaagcuguc uaaaauuggc aagacaaaac aguaaauggug gucagaaaaa caagccuccu 300
gagcacguua uagacugugg agacauaguc uggagucuug cuuuugggguc uucaguucca 360 gaaaaacaga gucguugcgu uaauauagaa uggcaucggu uccgauuugg acaggaucag 420
cuacuccuug ccacaggauu aaacaauggu cgcaucaaaa ucugggaugu auauacagga 480
aaacuccucc uuaauuuggu agaccacauu gaaaugguua gagauuuaac uuuugcucca 540
gaugggagcu uacuccuugu aucagcuuca agagacaaaa cucuaagagu gugggaccug 600
aaagaugaug gaaacauggu gaaaguauug cgggcacauc agaauugggu guacaguugu 660
gcauucucuc ccgacuguuc uaugcugugu ucaguuggcg ccaguaaagc aguuuuccuu 720
uggaauaugg auaaaauacac caugauuagg aagcuggaag gucaucacca ugauguugua 780
gcuugugacu uuucuccuga uggagcauug cuagcuacug cauccuauga cacucgugug 840
uaugucuggg auccacacaa uggagaccuu cugauggagu uugggcaccu guuucccucg 900
cccacuccaa uauuugcugg aggagcaaau gaccgauggg ugagagcugu gucuuucagu 960
caugauggac ugcauguugc cagccuugcu gaugauaaaa uggugagguu cuggagaauc 1020
gaugaggauu guccgguaca aguugcaccu uugagcaaug gucuuugcug ugccuuuucu 1080
acugauggca guguuuuagc ugcugggaca caugauggaa guguguauuu uugggccacu 1140
ccaaggcaag ucccuagccu ucaacauaua ugucgcaugu caauccgaag agugaugucc 1200
acccaagaag uccaaaaacu gccuguuccu uccaaaauau uggcguuucu cuccuaccgc 1260
gguuag 1266

<210> SEQ ID NO 123
<211> LENGTH: 1287
<212> TYPE: RNA
<213> ORGANISM: Homo sapiens

<400> SEQUENCE: 123
gaauuccgug ugcaaggcga ggucuguaag cuggagcggg gcagaggcug gcgggcaccc 60
cuuccugacc gcuggugccg ccgccgccgc cuucgggagg aucagacaug gcccagaacu 120
ugaaggacuu agcuggacgc cugcccgccg ggccucgggg caugggcacg gcgcugaagc 180
ugcugcuggg ggccggggcg guggccuacg gcguccgcga auccguguuc accguggaag 240
gcggucauag agccaucuuu uuuaaucgua uugguggcgu gcagcaggac acgauccugg 300
ccgaauuuca cuucaggauc cccugguucc aguaccccau caucuaugac auucgggcca 360
gaccucggaa aaucuccucc cccacaggcu ccaaagaccu gcagauggug aacaucuccc 420
ugcgugugcu gucccgaccc aaugcccagg agcuccccag cauguaccag cgucuagggc 480
uggacuauga ggagcgagug cugccgucca uuguuaauga ggugcucaag agugugguggg 540 ccaaguucaa ugccucgcag cugaucaccc agcgggcuca ggugucccug uugauccgaa 600
gagagcugac agagcgcgcc aaggacuuca gccucauccu ggaugaugua gcuaucacag 660
agcugagcuu cagccgagag uacacagcug cuguagaagc caagcaagug gcccagcagg 720
aagcccagcg ggcccaguuu uugguggaga aagcgaagca ggaacagcga cagaagauug 780
ugcaggcuga gggggaggcg gaggcugcca agaugcuugg agaagcacug agcaagaauc 840
cuggcuauau caagcuccga aagauccggg ccgcccagaa caucucuaaa acgaucgcca 900

-continued

```
caucacagaa ccgaaucuau cucacagcug acaaccuugu gcugaaucua caggaugaaa    960

guuuuacucg gggaagugac agccucauua aggguaagaa augagugugg acaucaagaa   1020

ccccaccacc agagaaguug gcacacuugu ccagcuugga ggagccagcu cggggucaag   1080

cacagcccac ccugccccag gcaucaugug auggacuuuu cuguaucugc ccucuuggau   1140

uaaggaagac ugagaccagc ccuuucagag gcuuuccucc uuccuguguu ggcugggaag   1200

cggggugac aaugugauuu cuccgugauu uccuacagcc uugagccucu cccagagugg   1260

gggagauaac caccaugcca ggaauuc                                     1287
```

<210> SEQ ID NO 124
<211> LENGTH: 612
<212> TYPE: RNA
<213> ORGANISM: Homo sapiens

<400> SEQUENCE: 124

```
acccaccggc uuucggacca uggccaaccu cgagcguacc uucauugcca ucaagccaga     60

uggcgugcag cgcggccugg ugggcgagau caucaaacgg uucgagcaga aggggguuccg   120

ccugguggcc augaaguucc uucgggccuc ugaagaacac cugaagcagc auuacaucga   180

ccugaaagac cguccuuucu ucccggggcu ggugaaguac augaacucgg ggcccguggu   240

ggccaugguc ugggaggggc ucaauguggu gaaaacgggc cgagugaugc ugggggagac   300

caauccagcu gauucaaaac caggcaccau ccguggggau uucugcauuc aaguuggcag   360

gaacaucauu cauggcagug auucagugga gagugcugag aaagagaucc aucugugguu   420

uaagcccgaa gaacugaucg acuacaaguc uugugcccau gacugggugu acgaguagac   480

augaagaaac cagaauccuu uucagcacua cugaugggu ucuggacaga gcucuucauc   540

ccacugacag gauggaucau cuuuucuaaa acaauaaaga cuuuggaacu gaaaaaaaaa   600

aaaaaaaaaa aa                                                      612
```

<210> SEQ ID NO 125
<211> LENGTH: 529
<212> TYPE: RNA
<213> ORGANISM: Homo sapiens

<400> SEQUENCE: 125

```
uuuugcuuuc aacaugacag augccgcugu guccuucgcc aaggacuucu uggccggugg     60

aguggccgca gcaucuccaa gacagcgguc acaccaucga gagggucaag cugcugcugc   120

aggugcacau gccagcaagc aaaucacggc agauaaagcaa uacaagggca ucauagacug   180

cgugguucgu auccccaagg aacagggagu gcucuggucc uuugggcgug ggaaccgggc   240

caaugucauc agauacuucc ccaccaaggc ucucaacuug gccuucaaag uuaauuccaa   300

gcagaucuuu cuggguggug uugacaagag gacccaguuc uggcgcuacu uuugcaggga   360

accuggcauc agguguugc cgcuggggcu acauccuugg gcuuugugua cccucuugau   420

uuuugccggu accgucuagc agcugaugug ggcaagcugg agcuaaaggg aauucaaggg   480

ccuugggacu gccugguaag acuucaaucu gaugggauaa gggcuguac               529
```

<210> SEQ ID NO 126
<211> LENGTH: 291
<212> TYPE: RNA
<213> ORGANISM: Homo sapiens

<400> SEQUENCE: 126

```
auccgggacc cccacggccc cuuugcagcu ugccacaagg uucugagccc cuuggaauac     60
```

-continued

```
uuccgccaau guguguauga caugugugcc cauaagggug acaaagccua ucucugccgu    120

agccuggcug cuuauacugc agccugucag gcagcugggg cagcagugaa gcccuggagg    180

acagacagcg ucugcccucu ccagugucu  gcccacagcc acuacuccau cugcacccgc    240

uccugccagg gcuuccugug cugcucucuc uggccucacu ggcugcacca c             291
```

```
<210> SEQ ID NO 127
<211> LENGTH: 3454
<212> TYPE: RNA
<213> ORGANISM: Homo sapiens

<400> SEQUENCE: 127

ggcacgagcc gaguuggagg aagcagcggc agcggcagcg gcagcgguag cggugaggac     60

ggcugugcag ccaaggaacc gggacagcga agcgacggca ggucgcagcu ggaucgcagg    120

agccugggag cugggagcuu cagaggccgc ugaagcccag gcugggcaga ggaaggaagc    180

gagccgaccc ggaggugaag cugagagugg agcguggcag uaaaaucaga cgacagaugg    240

acagugugac aggaacguca gagaggauug ggccucgcug cgagagucag ccuggaguca    300

agguguugac aaguugcuga gaaggacacg ugggaggacg guggcgcgcg gagggagagc    360

ccugucuuca gucaccccgu ugauggagga cagauggaca gcagccggac ggccagucac    420

cucucuuaaa ccuuuggaua gugguccuuu gugcucugcu ggacaccugu uggggauuuu    480

agcccauucu cugaacucac uuucucuuaa aacguaaacu cggacggcag ugugcgagcc    540

agcuccucug uggcagggca cuagagcugc agacaugagu gcagagggcu accaguacag    600

agcacuguac gacuacaaga aggagcgaga ggaagacauu gaccuacacc ugggggacau    660

acugacugug aauaaaggcu ccuuaguggc acuuggauuc agugauggcc aggaagcccg    720

gccugaagau auuggcuggu uaaauggcua caaugaaacc acuggggaga ggggagacuu    780

uccaggaacu uacguugaau acauuggaag gaaaagaauu ucacccccua cucccaagcc    840

ucggccccc u cgaccgcuuc cuguugcucc ggguucuuca aaaacugaag cugacacgga    900

gcagcaagcg uugccccuuc cugaccuggc cgagcaguuu gccccuccug auguugcccc    960

gccucuccuu auaaagcucc uggaagccau ugagaagaaa ggacuggaau guucgacucu   1020

auacagaaca caaagcucca gcaacccugc agaauuacga cagcuucuug auugugaugc   1080

cgcgucagug gacuuggaga ugaucgacgu acacgucuua gcagaugcuu ucaaacgcua   1140

ucucgccgac uuaccaaauc cugucauucc uguagcuguu uacaaugaga ugaugucuuu   1200

agcccaagaa cuacagagcc cugaagacug cauccagcug uugaagaagc ucauuagauu   1260

gccuaauaua ccucaucagu guuggcuuac gcuucaguau uugcucaagc auuuuuucaa   1320

gcucucucaa gccuccagca aaaaccuuuu gaaugcaaga guccucucug agauuuucag   1380

ccccgugcuu uucagauuuc cagccgccag cucugauaau acugaacacc ucauaaaagc   1440

gauagagauu uuaaucucaa cggaauggaa ugagagacag ccagcaccag cacugccccc   1500

caaaccaccc aagcccacua cuguagccaa caacagcaug aacaacaaua uguccuugca   1560

ggaugcugaa ugguacuggg gagacaucuc aagggaagaa gugaaugaaa aacuccgaga   1620

cacugcugau gggaccuuuu ugguacgaga cgcaucuacu aaaaugcacg gcgauuacac   1680

ucuuacaccu aggaaaggag gaaauaacaa auuaaucaaa aucuuucacc gugauggaaa   1740

auauggcuuc ucugauccau uaaccuucaa cucugugguu gaguuaauaa accacuaccg   1800

gaaugagucu uuagcucagu acaaccccaa gcuggaugug aaguugcucu acccaguguc   1860
```

caaauaccag caggaucaag uugucaaaga agauaaauau gaagcuguag ggaaaaaauu 1920
acaugaauau aauacucaau uucaagaaaa aagucgggaa uaugauagau uauaugagga 1980
guacacccgu acuucccagg aaauccaaau gaaaagaacg gcuaucgaag cauuuaauga 2040
aaccauaaaa auauuugaag aacaaugcca aacccaggag cgguacagca aagaauacau 2100
agagaaguuu aaacgcgaag gcaacgagaa agaaauucaa aggauuaugc auaaccauga 2160
uaagcugaag ucgcguauca gugagaucau ugacaguagg aggagguugg aagaagacuu 2220
gaagaagcag gcagcugagu accgagagau cgacaaacgc augaacagua uuaagccgga 2280
ccucauccag uugagaaaga caagagacca auacuugaug uggcugacgc agaaaggugu 2340
gcggcagaag aagcugaacg aguggcuggg gaaugaaaau accgaagauc aauacucccu 2400
gguagaagau gaugaggauu ugccccacca ugacgagaag acguggaaug ucgggagcag 2460
caaccgaaac aaagcggaga accuauugcg agggaagcga gacggcacuu uccuuguccg 2520
ggagagcagu aagcagggcu gcuaugccug cuccguagug guagacggcg aagucaagca 2580
uugcgucauu aacaagacug ccaccggcua uggcuuugcc gagcccuaca accuguacag 2640
cucccugaag gagcuggugc uacauuauca acacaccucc cucgugcagc acaaugacuc 2700
ccucaauguc acacuagcau acccaguaua ugcacaacag aggcgaugaa gcgcugcccu 2760
cggauccagu uccucaccuu caagccaccc aaggccucug agaagcaaag ggcuccucuc 2820
cagcccgacc ugugaacuga gcugcagaaa ugaagccggc ugucugcaca ugggacuaga 2880
gcuuucuugg acaaaaagaa gucggggaag acacgcagcc ucggacuguu ggaugaccag 2940
acguuucuaa ccuuauccuc uuucuuucuu ucuuucuuuc uuucuuucuu ucuuucuuuc 3000
uuucuuucuu ucuuucuuuc uuucuaauuu aaagccacaa cacacaacca acacacagag 3060
agaaagaaau gcaaaaaucu cuccgugcag ggacaaagag gccuuuaacc auggugcuug 3120
uuaacgcuuu cugaagcuuu accagcuaca aguugggacu uuggagacca gaagguagac 3180
agggccgaag agccugcgcc uggggccgcu ugguccagcc ugguguagcc ugggugucgc 3240 ugggugugu gaacccagac acaucacacu guggauuauu uccuuuuuaa aagagcgaau 3300
gauauguauc agagagccgc gucugcucac gcaggacacu uugagagaac auugaugcag 3360
ucuguucgga ggaaaaauga aacaccagaa aacguuuuug uuuaaacuua ucaagucagc 3420
aaccaacaac ccaccaacag aaaaaaaaaa aaaa 3454

<210> SEQ ID NO 128
<211> LENGTH: 199
<212> TYPE: RNA
<213> ORGANISM: Homo sapiens
<220> FEATURE:
<221> NAME/KEY: misc_feature
<222> LOCATION: (136)..(136)
<223> OTHER INFORMATION: n is a, c, g, or u

<400> SEQUENCE: 128
uuuuuuuuuu uuguuuuaau uuggcuccaa ugaucgcauu cucaaacucc uuugggaggg 60
cauuagauga cccaguaucc gacgacuuag auucacacgu guuuuucucc ucugagcucu 120
uuucuccagg cucacngucu uuguuuuuca agcuuucuug ggccuuugaa caauuuucuu 180
ccuuugaaga uucuccugg 199

<210> SEQ ID NO 129
<211> LENGTH: 1706
<212> TYPE: RNA
<213> ORGANISM: Homo sapiens -continued

<400> SEQUENCE: 129
agccgaguag gaccgagcug cugcagacgc gccgggucac ucgagccagc accaccguuc 60
ucacgcccug agcugcagac agcuaggcgg uuuuaucuag uuugaaccag gcugcuggag 120
cuugcucccu cccgcccucu cucuuuuuuu uccacggggc uguuuuuuua auuuggcugc 180
aauugcauga aaucccaaug guguagacca guggcgaugg aucuaggagu uuaccaacug 240
agacauuuuu ccauuucuuu cuugucgucu uugcugggaa ccgaaaacgc uuccgugaga 300
cuugacaaua gcucuggugc aaguguggua gcuaucgaca acaaaauaga gcaagcuaug 360
gaucugguga aaagccauuu gauguaugcg gugagggagg aaguggaagu ucugaaggag 420
cagaucaaag aacuaauaga gaaaaacucc cagcuggagc aggagaacaa ucugcugaag 480
acgcuggcca guccggagca gcucgcccag uuucaggccc agcugcagac uggcuccccu 540
ccggccacca cgcagccaca ggggaccaca cagcccccug cacagccagc aucccagggc 600
ucaggaucaa ccgcauagcc ucccuaggccc caacagaacu ggcugcugcu gcugcugucu 660
gaacugaaca gaccgaagag augugcuaga gagaagccgc cuccacaguc acccauuuca 720
uugcugucua cgaaagagac gugagacuca cacgcuguuc ucgcuuucuc cccaguauua 780
agcacucaua agcuuuuggc uugaagaaau guacuaguug agugaauuaa agguuaauca 840
gagagugagc agggaugugc ccugugcaac guggcagaug ucugaggaau gguuuaauug 900
accccgagga gcucugugcc uuuucaaccc uccccagccg cccacccugc uucugagagc 960
ucgggcggcu cgccuucgug gggcucgccu gcgugggguu cgaaaguggg cugcuccugg 1020
auucugcgcu cucuucuccu ucccuucaaa gaacucggag aggccagaaa caagacugca 1080
augggggggcg gggggaggga ugaugcaguc cuuauacaaa accgacaacu gucaccaaag 1140
cuuauaaaac acgauaguac ugucccucuu uucugaacca ucagaagaca caaaacuguu 1200
agugacacaa cggugacagg uagcugggac cuaggcuauc uuauuaugaa gguuguuuug 1260
cuuguuguau auuuguguau guaguguaac gaauuuguac cauagaggac uguccguaac 1320
uacuguuuag cuucuacaca uugaaaugua gauguuucau uggcugucug aaaaggugug 1380
gcuuguccuu ccuagagaga ucuacuuaaa aacugcuuug uggcaaaaac cacaccugaa 1440
gaaauuuuaa gaauuuggcc caguuaguca cucuguguaa ucccggaauc uagcugcuga 1500
agucuugcga aguaaacucc ccgugaccga ugucaguuaa gcuggugaua ccuggagaag 1560
uggucaguug cuaaggaagu ggauuuccca guaggggguuu cugcaccuca ccuguauagu 1620
cguucugcgc augucccccca cacaguccccc accuguauuu accuguucua cuugucaccu 1680
uucaauaaag cauaucaaau guugau 1706

<210> SEQ ID NO 130
<211> LENGTH: 2175
<212> TYPE: RNA
<213> ORGANISM: Homo sapiens

<400> SEQUENCE: 130
auggcugcgc acgucuggcu ggcggccgcc cugcuccuuc ugguggacug gcugcugcug 60
cggcccaugc ucccgggaau cuucucccug uugguucccg aggugccgcu gcuccggguc 120
ugggugguggg gccugagucg cugggccauc cuaggacuag gggucgcgg gguccucggg 180
gucaccgcag gagcccaugg cuggcuggcu gcuuugcagc cgcugguggc cgcacugagu 240
uuggcccugc cuggacuugc cuuguuccga gagcuggccg ccuggggaac acuccgggag 300
ggugacagcg cuggauuacu guacuggaac agucguccag augccuucgc uaucaguuau 360
guggcagcau ugcccgcagc cgcccugugg cacaaguugg ggagccucug ggcgcccagc 420
ggcaacaggg acgcuggaga caugcugugu cggaugcugg gcuuccuggg cccuaagaag 480
agacgucucu accugguucu gguucucuug auucucucuu ggcuugggga aauggccauu 540
cccuucuuca cgggccgcau cacugacugg auucuucagg auaagacagu uccuagcuuc 600
acccgcaaca uauggcucau guccauucuc accauagcca gcacagcgcu ggaguuugca 660
agugauggaa ucuacaacau caccauggga cacaugcacg gccgugugca cagagaggug 720
uuucgggccg uccuucgcca ggagacaggg uuuuuccuga agaacccagc agguuccauc 780
acaucucggg ugacugagga cacagccaac gugugcgagu ccauuaguga cacgcugagc 840
cugcugcugu gguaccuggg gcgagcccug ugucucuugg uguucauguu uugggggguca 900 ccguaccuca cucuggucac ccugaucaau cugccccugc uuuuucuuuu gccuaagaag 960
cugggaaaag ugcaccaguc acuggcagug aaggugcagg agucucuagc aaaguccacg 1020
cagguggccc uugaggccuu aucggcgaug ccuaccgugc ggagcuuugc caacgaggag 1080
ggugaggccc agaaguucag gcagaaguug gaagaaauga agacgcuaaa caagaaggag 1140
gccuuggcuu acgucgcuga agucuggacc acgagugucu cgggaaugcu gcugaaggug 1200
ggaauucugu accugggcgg gcagcuggug aucagaggga cugucagcag cggcaaccuu 1260
gucucauucg uucucuacca gcuucaguuc acccaggcug uucaggugcu gcucucccuc 1320
uaccccucca ugcagaaggc ugugggcucc ucagagaaaa uauucgaaua cuuggaccgg 1380
acuccuugcu cuccacucag uggcucguug gcacccucaa acaugaaagg ccuuguggag 1440
uuccaagaug ucucuuuugc cuacccaaac cagcccaaag uccaggugcu ucaggggcug 1500
acguucaccc ugcauccugg aacggugaca gcguuggugg gacccaaugg aucagggaag 1560
agcaccgugg cugcccugcu gcagaaccug uaccagccca ccgggggcca gcugcugcug 1620
gauggccagc gccuggucca guaugaucac cauuaccugc acacucaggu ggccgcagug 1680
ggacaagagc cgcugcuauu uggaagaagu uuucgagaaa auauugcgua uggccugaac 1740
cggacuccaa ccauggagga aaucacagcu guggccgugg agucuggagc ccacgauuuc 1800
aucucugggu ucccucaggg cuaugacaca gagguaggug agacugggaa ccagcuguca 1860
ggaggucagc gacaggcagu ggccuuggcc cgagccuuga uccggaagcc acuccugcuu 1920
aucuuggaug augccaccag ugcccuggau gcuggcaacc agcuacgggu ccagcggcuc 1980
cuguaugaga gccccaagcg ggcuucucgg acgguucuuc uuaucaccca gcagcucagc 2040
cuggcagagc aggcccacca cauccucuuu cucagagaag gcucugucgg cgagcagggc 2100
acccaccugc agcucaugaa gagaggaggg ugcuaccggg ccaugguaga ggcucuugcg 2160
gcuccugcag acuga 2175

<210> SEQ ID NO 131
<211> LENGTH: 970
<212> TYPE: RNA
<213> ORGANISM: Homo sapiens

<400> SEQUENCE: 131
gaauuccggg gccgcucucu ccggcaggau cgccgcgaug gccgcccagg gagagccgca 60
gguccaguuc aaggucgucc uggugggcga cggcggcacc ggaaagacga cauucaugaa 120
gcgccacuug accggagagu uugagaagga guauguagcc acccugggcg uggaggugca 180
cacauuaguc uuccauacca acagaggacc uaucaaguuc aaugugugg acacagccgg 240 ucaggagaag uucgggggc ugcgcgaugg cuacuacauc caagcccagu gugccauuau 300
aauguuugac guaacaucaa gaguuacuua caagaaugug ccuagcuggc auaaagaucu 360
agugcgugug ugugaaaaca uccccauugu auugugugc aacaaagugg auguuaaaga 420
caugaaagug aaggcaaaac cuauucucuu ccaccgaaag aagaaucuuc aguacuauga 480
cauuucugcc agaaguaacu acaacuuuga aaagccuuuc uucuggcuug ccagaaagcu 540
cauuggagau ccuaacuugg aguucguugc caugccugcu cuugccccac cugagguagu 600
cauggaccca gcuuuggcag cacaguacga gcaugauuua gagguugcuc agacgacugc 660
ucucccagau gaggaagaug accugugaga aagugaagcu ggagcccugc gucagaaguc 720
uauuuuaggc aacuguccug ugaugccagc cagcggugca gugugugugc caccuuauuu 780
agcuaaagga gaucgugcaa uucauuggga ugcugaagga gaugaauggg cuucggagug 840
aauguggcag uuaaaauaca ccuucauuuu uuuggacuug cguauuuagc cccuggaac 900 agaguuguuc uggauuucaa agauaagacu gcuaccguag caucacaaua gucaguggug 960
accggaauuc 970

<210> SEQ ID NO 132
<211> LENGTH: 356
<212> TYPE: RNA
<213> ORGANISM: Homo sapiens

<400> SEQUENCE: 132
uuuuuuuuuu uuuuuuugau uuaugaaaag uuuuauuuau caguacugug aagaauucuc 60
aucauaauug cuacguuaau caaggaaaag gcacagagaa gcaugugucg uuugaguccu 120
cgauacugga ccucccagcc caugcucccu augaggaguc uagcugcugu gguggucuuc 180
acagcuuugg uuuucuggag acgaagcuca ugauugcguu caugcacucc ucugacagcc 240
accuugcuug cagaguagug cacucuucag cguugacugc guagagcuuu ucuuucucau 300
uuuuucugau uaacucuuug gaaauucuca uuggguuugg cgggagcuuc gcauau 356

<210> SEQ ID NO 133
<211> LENGTH: 626
<212> TYPE: RNA
<213> ORGANISM: Homo sapiens

<400> SEQUENCE: 133
ucgggaaucg auugagagac cgcgaaccug uaaacggaug auaccgaguc gggcaggcgu 60
uaugccagcc caacucggga ccucgcauca uguccgcggc uaccuuagag uguuucggga 120
augauuugcg guggaugaac gaaaccccgg uacguccugu gccaaggagc auaugucagg 180
acggacgcuc guuaaugccu caguggugg gcaacguucg cucucuaucu auacgacucu 240
cgacaaugga uaucucggcu cucgcaucga ugaagaacgu agcgaaaugc gauacuuggu 300
gugaauugca gaauccugug aaccaucgag ucuuugaacg caaguugcgc ccgaggccuu 360
ucgguugagg gcacgccugc cugggcguca cgccuuguuu ugcucugugc ccgugcucuu 420
ucgggggcgg ucauggaugc ggagauuggc ccuccgugcc ucgugugcgg cgggcuuaag 480
cgcggggugu cggcgucggg aagggcacga cgaguggugg acggagcacc agcaggaugu 540
uguggucccc cgucaccuua aggggcucaa gagacccgga cuaggcgagc cgcgcuucgu 600
aagaggaggg cgagcugucu cgcaau 626

<210> SEQ ID NO 134

<211> LENGTH: 495
<212> TYPE: RNA
<213> ORGANISM: Homo sapiens
<220> FEATURE:
<221> NAME/KEY: misc_feature
<222> LOCATION: (485)..(485)
<223> OTHER INFORMATION: n is a, c, g, or u

<400> SEQUENCE: 134
uuuuuuuuuu uuuuuuugaa guugcugccc cuuuauuggu gacccgggca aguuuaagga 60
gaacaacauu aaagcacaca aaguguaucc augucaccag cucaaccagg aggagugagg 120
gucacggcag gguucuccca ugguguaaga aaucaacgca auuucaucac accccguuac 180
uuuccaaguu aacgaaccga uaagaaaaga uucucccuua aacugacaag uacaauguac 240
auguacauga uuuuggaaua auuuaauacu uuaaccucaa gauacaacua uauucuaaga 300
ccauuauuuu aaaggaacgg auccuuacaa aaccaaaaua acccauauag cacgagguug 360
guuuagccuu ucuucuucuu ucaacaaacg ugcaccacau guuucaguag caaggccgau 420
gccauggaua ugagagcugu gauuugcagg gaccaaccac aucuagaacc ggggaggcca 480
aucanacggu ggguu 495

<210> SEQ ID NO 135
<211> LENGTH: 257
<212> TYPE: RNA
<213> ORGANISM: Homo sapiens
<220> FEATURE:
<221> NAME/KEY: misc_feature
<222> LOCATION: (254)..(254)
<223> OTHER INFORMATION: n is a, c, g, or u

<400> SEQUENCE: 135
cccuuggagg auaguuuuau ugacaagucg aguuagguuu uagaguaaac uuuuaucacc 60
ccagucaggc cccuucccag gggaggcucg cugguagcuc agauggccuu gguggugggc 120
agauuguugu aguugucuuc cuggcccucc agcaggcuuc gggagguggc uaucuccugc 180
uccagccugg acuugauguc caguagcugc uuauacuccg gguucuggcg cucuaugugc 240
ggcacgcagg ugcngcg 257

<210> SEQ ID NO 136
<211> LENGTH: 1186
<212> TYPE: RNA
<213> ORGANISM: Homo sapiens

<400> SEQUENCE: 136
ggacugacuc cuugggcaga uugccucucc uccuucucau gccagaggcu gcugaugagg 60
aaagguccag gggacugucc augcugucuu cauccucaga gucacugccu gaugcugcaa 120
caagacccuu cuuguuuagc aauagugguu ggaacacucu cuuguaaguu accggagcac 180
uaguauagga ggaggaucau cgacuacccu cccgccacuc cacggcugcu ggcuccuaga 240
aaccccagcu ucaccucuca cugggacucg aguuccagaa ugaaaagcaa gaagggucuu 300
guugcagcau caggcaguga cucugaggau gaagacagca uggacagucc ccuggaccuu 360
uccucaucag cagccucugg caugagaagg aggagaggca aucugcccaa ggagucaguc 420
cagauucugc gagacuggcu guaugaacac agauacaacg ccuaucccuc agagcaagag 480
aaagcacugc ugucccagca gacacaccug uccacacuac aggucuguaa cugguucauc 540
aacgcccgcc gcaggcuccu uccugacaug cugagaaagg auggcaaaga uccaaaucag 600
uucacgauuu cccgccgugg ggccaagauu ucagaagcua gcucuauuga agcugcaaug 660

```
gguaucaaaa acuucaugcc aacucuagaa gagagcccau uucauuccug cguaguugga    720
cccaacccaa cccuagggag accagugucu cccaaaccuc ccuccccagg auccauuuug    780
gcucgcccgu cagugaucug ccauaccacu gugacugcau ugaaggaugg gccuuucucu    840
cucugucagc cgauuggugu gggacagagu acagauguac cgcaaauagc acccagcaac    900
uuuacagaca ccucucucgu guacccagag gacacuugca aaucuggacc caguccaaac    960
ccucagagug gucuuuucaa cacuccuccc ccuacuccac cagaccucaa ccaggauuuu   1020
aguggauucc agcuucuagu ggauguugca cucaaacgag cggcagagau ggagcuucag   1080
gccaaacuca cagcuuaacc guuuuuucaa acaaaacagu ucuccaaaau acgguccuga   1140
uugccggggg ugauggcaag agaugcauua uuuuauauau uuuuc                   1186
```

<210> SEQ ID NO 137
<211> LENGTH: 455
<212> TYPE: RNA
<213> ORGANISM: Homo sapiens

<400> SEQUENCE: 137

```
uuuuuuuuuu uuuuuuuggu gguuaucaag ugcacuuuau ugaauccacu guggauagau     60
aaaugagugu uacaccugcg uguagggagg ggcaaggagg gacgcagcug cggagggguga   120
agcacuucag gaccggaagu cggaauccuc uauuaagugu gaagguuuug agcguuaaga    180
acaaugauga ugacacuaac aauggugaua acaaccauca ggaugcugag gaccaaggug    240
cugauguuca ggcacuuagc aguggaggcg uaggccuggg cuccagucac aucacccacc    300
aucuuccgau cccuagacuu cacggaguag gcauaggcua ugaagcccag gcagcagaag    360
uucaugaaga guguauugaa cagggaccag accacauggu caggcaccga caccucucug    420
ggcauguuga ucacaguagu ucugacagaa gccga                               455
```

<210> SEQ ID NO 138
<211> LENGTH: 1797
<212> TYPE: RNA
<213> ORGANISM: Homo sapiens

<400> SEQUENCE: 138

```
aagcuucagg auacagugca cacucguaaa uaaaaacuac aggcugcugc gaauuauauu     60
ucaacugacc ggagaggcaa agccugacug uccauuaacc cuuaacuucc aaacgcaaac    120
ugcuuacugc aucuuuuggc auuuuaccuu augccuuguu agguccaagg caagagaagc    180
gucaucaaua accacgcaug ugcaacagcu uuuccagagg aaaggugugg guggcucuua    240
aaagagccuu ugaguuagga gugugaguua aacgagcuca cuuggagcug guguacuugg    300
ugacugccuu ggugcccucc gacaccgcgu gcuuggccag cuccccgggc agcagcaggc    360
gcacggccgu cuggaucucc cgggacguga uggucgagcg cuuguuguaa ugcgccaggc    420
gggaagccuc gcucgcgaug cgcucgaaga ugucguucac gaacgaguuc augaugccca    480
uggccuugga ggagaugccg gugucggggu gcacuugcuu cagcaccuug uacacguaca    540
ccgaguagcu cuccuugcgg cugcgcuugc gcuucuugcc guccuucuuc ugggccuugg    600
ugacggccuu cuuggagccc uucuucgggg cgggagcgga cuuggcgggc ucaggcauac    660
ugagaggaug aagugaacua aguugaaaaa ggauaacuaa aaguuaauga cuguucuggc    720
ugcaauuuua aacaaacuua cggcuauggc aaccugaauc accauacguc auguacuaac    780
aguccaauca aaacaaggga uuuucaaacc agggcgccau ugguaaccaa uguguaacca    840
```

augaaaucuc uccguuuucg cguccagccu ugacuauaua uacuaugcgu auacguuuuu 900
gcuucuuacu gcggugguua ucuacagcug aguuaugucu ggacguggca agcaaggacg 960
uggcaagcaa ggaggcaagg cccgcgccaa ggccaagacg cgcuccuccc gggccggccu 1020
gcaguucccc gugggccgcg ugcaccggcu gcuccgcaag ggcaacuacu cggagcgcgu 1080
gggcgccggc gccccggugu accuggcggc cgugcuggag uaccugacgg ccgagauccu 1140
ggagcuggcg ggcaacgcgg cccgcgacaa caagaagacg cgcaucaucc cgcgccaccu 1200
gcagcuggcc auccgcaacg acgaggagcu caacaagcug cugggccgcg ugaccaucgc 1260
gcagggcggc guccugccca acauccaggc cgugcugcug cccaagaaga ccgagagcca 1320
ccacaaggcc aaggggaagu gaaaccaaac auuacgaauc accaaggcuc uuuucagagc 1380
cacucacuuu cucaaagaga ccuaacacua cugggauagu gcauuguggg aaauacgugu 1440
auuaaccuuc cuccuauuuu cccugcuugu gguuaguuca accccuaagc cuuaggcuaa 1500
gaguauauug guuuuuggaa ggcaggcacc caaccucgga ccuaguacau aaaacagaca 1560
caucuugaac uccaggccag ccuacucugc aggacgaguu ccaggacaga ccggacugca 1620
caaagaauug ucuugaaaug uuccuuuauc agcacauaug cugauaaaca acuaaucacu 1680
guacaaucaa uccucacuug aauccuguuu auguggcaug auugacaagu ccugccauuu 1740
ggcaaaguca aaaucagcaa aggauguuaa agcauuuggu gguaucacag cuaaaac 1797

<210> SEQ ID NO 139
<211> LENGTH: 376
<212> TYPE: RNA
<213> ORGANISM: Homo sapiens

<400> SEQUENCE: 139
uuuuuuuuuu uuuuuaugca aauaguuuuc aagauuuuau ugcaaaccaa aauugguuua 60
ucgcacacaa aaaaaguugu gugguaagga ggaggaauug uacaggauua uaacccaugu 120
uaauuacagu acauuaaaau gaugguuuac aaauaagccu guaaguuuaa auaucuagug 180
uuauaaccca auguacagac uuccuuuaca cgauacauac aauaaucagg aaugcaaaag 240
aauaugaaca aagggaaaaa aaacauaaau aaugcccguu uuauagguga cauuuuaaac 300
aauugaaaac accaaccggc uuugacugac aacuggggca uugguccaua aaaacccuuu 360
cuaaaaauag aaauau 376

<210> SEQ ID NO 140
<211> LENGTH: 1068
<212> TYPE: RNA
<213> ORGANISM: Homo sapiens

<400> SEQUENCE: 140
gaggcugcuc aagagcugcg guugggucac cgcuucaugu uucucugccg auucugggga 60
aagauggcaa cgaaugaugc uguucugaag aggcuggagc agaagggugc agaggcggau 120
cagaucaucg aauaucucaa gcagcagguu gcucuucuua aggagaaagc aauuuugcag 180
gcaacaauga gagaagaaaa gaaacuucga guugaaaaug cuaaacugaa aaaagaaaua 240
gaagagcuaa agcaagagcu gauucuggca gaaauucaua acggagugga gcaagugcgu 300
guucgauuga guacuccacu gcagacgaac uguacugcuu cugaaagugu ggugcagucu 360
ccaucaguag caaccaccgc cucuccugcu acaaaagagc agaucaaagc gggagaagaa 420 aagaaggug a aagagaagac ugaaaagaaa ggagagaaaa aggagaagca gcagucggca 480
gcagcaagua cugacuccaa gccuaucgac gcaucgcguc uggaucuucg aauugguugu 540
auuguuacug ccaagaagca cccugaugca gauucacugu auguggagga aguagaugug 600
ggagaagcag ccccgcgcac ggucgucagc gggcugguga aucauguucc ucuagaacag 660
augcaaaauc guaugguggu uuuacucugu aaucugaagc cugcaaagau gcggggaguu 720
cugucucaag ccauggugau gugugccagu ucaccagaga aaguggagau ucuggccccu 780
cccaacgggu ccguuccugg ggacagaauu acuuuugaug cuuuuccugg agagccugac 840
aaggagcuaa acccuaagaa gaagaucugg gagcagaucc agccugaccu gcacaccaau 900
gcugagugug uggccacaua caaaggagcu cccuuugagg ugaaggggaa gggaguuugc 960
agagcccaaa ccauggccaa uaguggaauu aaauaagugc ucuguaacug aaagacauug 1020
gcgaaaacuu aauaacaaua aagagaagug uguuuaucac uuacauau 1068

<210> SEQ ID NO 141
<211> LENGTH: 165
<212> TYPE: RNA
<213> ORGANISM: Homo sapiens

<400> SEQUENCE: 141
ggccuuguuu uugguuugca auaaagagua uuucuuuaaa aggcacauuu uguuaaauag 60
gcaguucccc uccugccucu uccuuuguag caguguacug cauccuagaa acauuuagca 120
aagcagcccu uagccucccc gacccccuuu cccucccucc cagca 165

<210> SEQ ID NO 142
<211> LENGTH: 324
<212> TYPE: RNA
<213> ORGANISM: Homo sapiens

<400> SEQUENCE: 142
uuuuuuuuuu uuuuuuuaaa caaugacgcc guuuauuuaa aauguuuacu cccagaaaua 60
uagauauaaa aaaaaaaaua agacaauuaa cagcacuaaa ccaggcaccu ucaaccgaau 120
cccaccaucc ucguuaacuc ccuuccuguu acccuuugua gaugaccaga agauuucagg 180
agccccugga cagccagagu gguuccugcc cagggcuucc cgccuuccuc cuguccuaga 240
gcuucccgug ggaaagcuug ggugagaauu uuagccuaaa gggagggggc uguggccggg 300
cacuuugcgc ucauccacug cagg 324

<210> SEQ ID NO 143
<211> LENGTH: 2473
<212> TYPE: RNA
<213> ORGANISM: Homo sapiens

<400> SEQUENCE: 143
acaggguaca guugugcguc agggcgugga ggucuggcgg gagacgcaua guuacagcgc 60
guccguucuc cgucucgcag ccggcacagc uagagcuucg agcgcagcgc ggccauggau 120
cccagcagca agaaggugac gggccgccuc auguuggcug ugggaggagc agugcucgga 180
ucacugcagu ucggcuauaa cacuggugcc aucaacgccc cccagaaggu uauugaggag 240
uucuacaauc aaacauggaa ccaccgcuac ggagagccca ucccauccac cacacucacc 300
acgcuuuggu cucucuccgu ggccaucuuc ucugucgggg gcaugauugg uuccuucucu 360
gucggccucu uuguuaaucg cuuuggcagg cggaacucca ugcugaugau gaaccuguug 420
gccuuugugg cugcugugcu uaugggcuuc uccaaacugg gcaaguccuu ugagaugcug 480
auccugggcc gcuucaucau cgguguguac ugcggccuga cuacuggcuu ugugcccaug 540

-continued

```
uaugugggag aggugucacc uacagcucua cguggagccc uaggcacacu gcaccagcug    600

ggaaucgucg uuggcauccu uauugcccag guguuuggcu uagacuccau caugggcaau    660

gcagacuugu ggccucugcu gcucagugug aucuucaucc cagcccugcu acaguguauc    720

cuguugcccu ucugccccga gagcccccgc uuccugcuca ucaaucguaa cgaggagaac    780

cgggccaaga gugugcugaa gaagcuucga gggacagccg augugacccg agaccugcag    840

gagaugaaag aagagggucg gcagaugaug cgggagaaga aggucaccau cuuggagcug    900

uuccgcucac ccgccuaccg ccagcccauc cucaucgcug uggugcugca gcugucccag    960

cagcugucgg guaucaaugc uguguucuac uacucaacga gcaucuucga gaaggcaggu   1020

gugcagcagc cuguguacgc caccaucggc uccgguaucg ucaacacggc cuucacugug   1080

gugucgcugu uuguuguaga gcgagcugga cgacggaccc ugcaccucau uggccuggcu   1140

ggcauggcag gcugugcugu gcucaugacc aucgcccugg ccuugcugga acggcugccu   1200

uggauguccu aucugagcau cguggccauc uuuggcuuug uggccuucuu ugaaguaggc   1260

ccugguccua uuccauggu cauuguggcc gagcuguuca gccaggggcc ccguccugcu   1320

gcuauugcug uggcuggcuu cuccaacugg accucaaacu ucauuguggg caugugcuuc   1380

caguaugugg agcaacugug cggccccuac gucuucauca ucuucacggu gcuccucgug   1440

cucuucuuca ucuucaccua cuucaaaguc ccugagacca aaggccgaac cuucgaugag   1500

aucgcuuccg gcuuccggca gggggugcc agccaaagug acaagacacc cgaggagcuc   1560

uuccacccuc ugggggcgga cucccaagug ugaggagccc cacacccagc ccggccugcu   1620

cccugcagcc caaggaucuc ucuggagcac aggcagcuag augagaccuc uuccgaaccg   1680

acagaucucg ggcaagccgg gccugggcgc cuuuccucag ccagcaguga aguccaggag   1740

gauauucagg acuuugaugg cuccagaauu uuuaaugaaa gcaagacugc ugcucagauc   1800

uauucagaua agcagcaggu uuuauaauuu uuuuauuacu gauuuuguua uuuuuuuuuu   1860

uuaucagcca cucuccuauc uccacacugu agucuucacc uugauuggcc cagugccuga   1920

gggugggac cacgcccugu ccagacacuu gccuucuuug ccaagcuaau cuguagggcu   1980

ggaccuaugg ccaaggacac acuaauaccg aacucugagc uaggaggcuu uacgcuggag   2040

gcgguagcug ccacccacuu ccgcaggccu ggaccucggc accauagggg uccggacucc   2100

auuuuaggau ucgcccauuc cugucucuuc cuacccaacc acucaauuaa ucuuuccuug   2160

ccugagacca guuggaagca cuggagugca gggaggagag ggaagggcca ggcugggcug   2220

ccagguucua gucuccugug cacugagggc cacacaaaca ccaugagaag gaccucggag   2280

gcugagaacu uaacugcuga agacacggac acuccugccc ugcuguguau agauggaaga   2340

uauuuauaua uuuuuugguu gucaauauua aauacagaca cuaaguuaua guauaucugg   2400

acaaacccac uuguaaauac accaacaaac uccuguaacu uuaccuaagc agauauaaau   2460

ggcugguuuu uag                                                     2473
```

<210> SEQ ID NO 144
<211> LENGTH: 2125
<212> TYPE: RNA
<213> ORGANISM: Homo sapiens

<400> SEQUENCE: 144

```
gcuuucuaaa cuagcaagca ucgugugggu ccuucaggag ugggagugca gacagaccug     60

acagcguccg cuaagcgaca cugacuguac uuccacuccu gaaggaccca cacgaugcuu    120

ucuaaacuag caagucugca gaccauugcu gcucugcgcc gaggagucca caccucaguc    180
```

gccucugcca cgucuguugc cacaaagaag acagagcaag gcccaccauc cucccgaguac 240 auuuuugaac gggaaucuaa auauggugca cacaauuacc auccuuugcc uguagcccug 300
gagagaggaa aaggcauuua uaugugggau guggaaggca ggcaguacuu cgauuuccug 360
agugcuuaug gugcugucag ccaaggacac ugccacccaa agaucauaga ugccaugaag 420
agucaggugg acaagcugac auuaacaucu cgggcuuucu auaacaaugu ccuuggugaa 480
uacgaggagu acaucaccaa gcuuuucaac uacaacaaag uucucccuau gaauacagga 540
guggaggcug gagagacugc auguaagcuc gcucgucguu ggggcuacac cgugaaaggc 600
auccagaaau acaaagcaaa gauuguuuuu gcugauggga acuuuugggg ucgaacacua 660
ucugcaaucu ccaguuccac agauccgacc aguuaugaug gcuuuggacc cuucaugcca 720
ggcuuugaaa ccaucccaua uaacgaucug cccgcacugg agcgugcucu ucaggaucca 780
aauguugcug ccuucauggu ggagcccauc cagggugaag caggcguuau cguuccggau 840
ccaggauacc ugacaggagu ucgggaacuc ugcaccaggc accagguccu guuuauugcu 900
gaugaaauac agacaggauu ggccagaacu gguagauggc uggcugugga ucaugagaau 960
gucagaccug auaugguucu ucuugggaag gcccuuucug gcgguuuaua cccugugucu 1020
gcagugcugu gugacgauga gauaaugcug accauuaaac caggcgagca cggcuccaca 1080
uacggcggaa acccacuagg cugccgaauu gccauugcgg cucuugaggu uuuagaagag 1140
gagaaucuug cugagaaugc agacaagaug ggcgcuaucc ugaggaagga gcucaugaag 1200
cugcccucug acguugugac cucagugaga gggaaagggu ugcuaaaugc cauugucauc 1260
agagaaacca aagacuguga ugcuuggaag gugugccugc gacuucgaga uaacgggcuu 1320
cuggccaagc caacccacgg ugauaucauc aggcuugccc cuccccuugu gaucaaggag 1380
gaugagaucc gggaguccgu ggagaucauc aacaagacua ucuuguccuu cugagaguag 1440
gaacucuggg gagccaucuu cagacagggc ucuugugaaa cucugcuugc aguggccaga 1500
gccugucucc ugaaaggcau auauuucagu ugaugcauaa uagagugaca ccuaggaacc 1560
ugcagguggc ugcgugacag aaaagugaga gcgagaggcg aggcgucucu uuguugaggu 1620
uugacugugu gggaacuuuc uaaggagaaa cggacccauc ugcguacagc cugcagaugg 1680
aggccugcag ucauuuacgu gcgucuuuac aguuuccuug cugaugugaa ugguuuguau 1740
uuagaaguua uuucugagau acuacagaac aguuaaauca uuauaaucaa ugaauguuaa 1800
guugauugaa gguuaagcau auguaaaaua cuaguuuaaa guaaacuuuu cauuggccaa 1860
caccagaaug uauuauauag auucugagaa uucauuacua aauuacacuu ugcuugauug 1920
caauuuguaa aacauuuauu uucaguauuu cuuugaauaa agcuuaaugu uucuuuuuac 1980
gccaacagag uauuuuguau uuccauuuug guaauaauca guguauuauu ucauccugau 2040
gacuggcauu ucaucaccua uugagaucac ugggugugu ucaggccuuu uauucuaaau 2100
aaagcuauga ccaguuucug ucugu 2125

<210> SEQ ID NO 145
<211> LENGTH: 199
<212> TYPE: RNA
<213> ORGANISM: Homo sapiens

<400> SEQUENCE: 145
uuuuuuuuuu uucuuuuccg acgcccacaa gaggaauaag agauuuaaug auggaaagua 60
uggggaaauc acaguuuuca gacaugagua aucaaaaacu ugacauuuuu cuugauaucc 120
aaaucuagau gucuguauca aaccagaggu gauggccuug gggauggcag ugaagacugu 180
uaggaccauu agaucagau 199

<210> SEQ ID NO 146
<211> LENGTH: 412
<212> TYPE: RNA
<213> ORGANISM: Homo sapiens

<400> SEQUENCE: 146
uuuuuuuuuu uuuuuuuaca guuuuaaaac aauacacagc uuucucgggc ugaagcaauu 60
gcaagaacgu auugguauug guauauuaca gcuacauaca agguuuauga auagcaaugg 120
agaaaaauaa guuauuuaaa uauugacuuc auaaagagaa agugcaaugu uguuaguugu 180
cauaucacuu gcuugacagu uuguggggu ucuucccuau caauuuuaac aaucaagaua 240
acauggacuc aagacagaau uuuucgggaa ccucacucag uccucacaca gcagugacuu 300
gggaaucuac guguguucca ccgcaguugu gaaacacacu acuccguguc caggacucau 360
uucucagaga agaaucaauu cgaguuccau ccacaccugg ggucgggaca ca 412

<210> SEQ ID NO 147
<211> LENGTH: 2373
<212> TYPE: RNA
<213> ORGANISM: Homo sapiens

<400> SEQUENCE: 147
ccgggcucga auucucuaga cucgaguuua gagaauucga gcucucccag uuuuaaagca 60
aaauuuugga cugugaagca aggcacuggg caaacacaac auggccuccc cggcugacag 120
cuguauccag uuuacccggc acgcuaguga uguucuucuc aaccuuaauc gccuccggag 180
ucgggacauc uugacggacg uugucaucgu ggugagccgu gagcaguuua gagcccauaa 240
gacagugcuc auggccugca gcggccuguu cuacaguauc uucacugacc aguugaaaug 300
caaccuuagu guaaucaauc uagauccuga aaucagcccu gaggggguuu gcauccuccu 360
ggacuucaug uacacaucua ggcucaaccu gagggaaggc aauaucaugg cggugaugac 420
cacagccaug uaccugcaga uggagcaugu ugucgacaca ugcaggaagu ucaucaaggc 480
cagugaagca gaaauggccc cugcacuuaa accuccccgu gaagaguucc ugaacagccg 540
gaugcugaug ccccaugaca ucauggccua ccgaggucgu gaggucgugg agaacaauau 600
gccacugaga aauacucccg ggugugagag cagagcuuuu gcuccuccuc uguacagugg 660
ccugucaaca ccaccagccu cuuaucccau guacagccau cucccgcuca gcaccuuccu 720
cuucucugau gaggagcucc gagaugcccc ccgaaugccu guggccaacc cuuuucccaa 780
ggagcgugcc cuccccugcg acagugccag gcaagucccu aaugaguaua gcaggccagc 840
cauggaggug ucccccaguu ugugucacag caacaucuac ucgcccaagg aggcaguccc 900
agaggaggcu cggagugaca uacacuacag ugugccugag ggccccaagc cugcuguccc 960
uucugcucgg aaugcuccau acuuccccug ugacaaagcc agcaaagaag aagagagacc 1020
uucuucggag gaugagauug cccugcauuu cgagcccccc aaugcacccu ugaaccggaa 1080
gggucugguu aguccccaga guccccagaa auccgacugc cagcccaacu cacccacaga 1140
guccugcagc agcaagaacg ccugcauccu ucaggccucu ggcucuccgc cagccaagag 1200
ccccacugac ccgaaagccu gcaacuggaa gaaguauaag uucaucguuc ucaacagccu 1260
caaucagaau gccaaacccg agggcucuga gcaggcagag cugggucgcc ucuccccucg 1320
agccuacccu gcaccgcccg cuugccagcc gccuauggag cccgcgaacc uugaucucca 1380

```
guccccgacc aagcucagug ccagugggga ggacucuacc aucccccaag ccagccggcu   1440

caauaaucuc gugaacaggu cccugggagg cuccccccga agcagcagug agagucacuc   1500

accacucuac augcaccccc caaagugcac auccugcggc ucucaguccc cacagcauac   1560

agagaugugc cuccauacug cugggcccac guucccggag gagauggggg aaacccaguc   1620

agaguauucg gauucuagcu gugagaaugg gaccuucuuc ugcaacgaau gugacugccg   1680

uuucucugag gaggccucgc ucaagaggca cacgcugcag acgcacagug acaaaccaua   1740

caaaugugau cgcugccagg ccuccuuccg cuacaagggc aaccucgcca gccacaagac   1800

uguccacacg ggugagaaac ccuaucgcug uaacauuugu ggagcgcagu ucaaucggcc   1860

agccaaccug aagacccaca cucgaauuca cucuggagaa aagcccuaca aaugugaaac   1920

cuguggggcc agguuuguuc agguggccca ccuccgugcc cacgugcuca uccacacugg   1980

agagaagccg uaccccugug aaaucugugg cacucgcuuc cggcaccuuc agacucugaa   2040

gagccaucug cgcauccaca caggagagaa accuuaccau ugugagaagu guaaccugca   2100

cuuucgucac aaaagccaac ugcgacuuca uuugcgccag aagcacggcg ccaucaccaa   2160

caccaaggug caauaccgcg ugucggccgc ugaccugccu ccggagcucc ccaaagccug   2220

cugaaugaag cauggagugu uccucgcccu uuccucucca gccccuucuc agaaucuacc   2280

caaaggaugc uguaacacuu uauacaaagg ucaucccaug auguagugcc ucucucaucc   2340

acuagugcaa aucauaguug gggugggggu ggg                                2373
```

<210> SEQ ID NO 148
<211> LENGTH: 989
<212> TYPE: RNA
<213> ORGANISM: Homo sapiens

<400> SEQUENCE: 148

```
ucgcgguccg acggaggagu gggcgcuggg aucucgcuga gcguccgccu ggccucgucu     60

cuuccucgcu cgucggagcu ucagcacggu ccgagauggc uggcgguaag gcuggaaagg    120

acuccggaaa ggccaagaca aaggcgguuu cccgcucgca gcgagccggc uugcaguucc    180

cugugggccg uauucaucga caccugaaau cuaggacaac cagccacgga cgugugggcg    240

cgaccgccgc uguguacagc gcagccaucc uggaguaccu caccgcagag guacuugagu    300

uggcaggaaa ugcgucaaaa gacuuaaagg uaaagcguau cacccccucgu cacuugcagc   360

uugcuauacg uggagaugaa gaauuggauu cucugaucaa agcuaccauu gcuggguggug   420

gugucauccc acacauccac aaaucgcuga ucgggaagaa aggacaacag aagacuguuu    480

aaggaugccu ggauuccuua uuaucucagg acucuaaaua uuccuaacag cuguccagug    540

uuggugauuc caguggacug uaucucugug aaaaacacaa uuuugccuuu uuguaauucu    600

auuugagcaa guuggaggcu uaauuagccu uccaaccaac caaauuucug cauucgaguc    660

uuaaccauau uuaaguguua cuguggcuuc aaagaagcua uugauucuga aguagugggu    720

uuugauugag uugacuguuu uuaaaaaacu guuuggauuu uaauugugau gcagaaguua    780

uaguaacaag cauuugguuu uguacagaca uuguuuccac ucuggugau aagcucaaua     840

aaggucauau cccaaacuag cuuuaaacuu gcuuaauaau cgggucuuac cuuagaucuc    900

acucagcaac aaguacauuc ucugcuuacu aauuaaacag ugcaucugua gucauaaaaa    960

aaaaaaaaaa aaaaaaaaaa aaaaaaaaa                                      989
```

<210> SEQ ID NO 149

<211> LENGTH: 6342
<212> TYPE: RNA
<213> ORGANISM: Homo sapiens
<220> FEATURE:
<221> NAME/KEY: misc_feature
<222> LOCATION: (439)..(538)
<223> OTHER INFORMATION: n is a, c, g, or u
<220> FEATURE:
<221> NAME/KEY: misc_feature
<222> LOCATION: (1133)..(1232)
<223> OTHER INFORMATION: n is a, c, g, or u
<220> FEATURE:
<221> NAME/KEY: misc_feature
<222> LOCATION: (1698)..(1797)
<223> OTHER INFORMATION: n is a, c, g, or u
<220> FEATURE:
<221> NAME/KEY: misc_feature
<222> LOCATION: (2105)..(2204)
<223> OTHER INFORMATION: n is a, c, g, or u
<220> FEATURE:
<221> NAME/KEY: misc_feature
<222> LOCATION: (2861)..(2960)
<223> OTHER INFORMATION: n is a, c, g, or u
<220> FEATURE:
<221> NAME/KEY: misc_feature
<222> LOCATION: (3546)..(3645)
<223> OTHER INFORMATION: n is a, c, g, or u
<220> FEATURE:
<221> NAME/KEY: misc_feature
<222> LOCATION: (4057)..(4156)
<223> OTHER INFORMATION: n is a, c, g, or u
<220> FEATURE:
<221> NAME/KEY: misc_feature
<222> LOCATION: (4736)..(4835)
<223> OTHER INFORMATION: n is a, c, g, or u
<220> FEATURE:
<221> NAME/KEY: misc_feature
<222> LOCATION: (5487)..(5586)
<223> OTHER INFORMATION: n is a, c, g, or u

<400> SEQUENCE: 149
caccaccgug cacgcagcuc cgggcccgug ggguguuggu ucuugcccuc guaacccccu 60
cuguccagcc accaugauaa gcgccagcag agccgcggcc gcgcgucucg ugggcaccgc 120
ugcgucccgg agccccgcag ccgcccgucc ccaggugaga agcugccaug ccuuccggug 180
ggggcuccag gcccggacuc gagugaggca ggccuugccu ucgggucaga cucuaggaaa 240
aauccggagc gaagggaugu aacggaccuu cugugggcau uguuggccuu cuugcagggc 300
uuuagcuucg aacugugcug agucacaauc cuuggcguuc cuaagucuuu accccgcuaa 360
uugagacguc uguccccccu cuaaccugug cgcuuugaau gugccuggac uuaggcagug 420
gacguaguuu acuggaaann nnnnnnnnnn nnnnnnnnnn nnnnnnnnnn nnnnnnnnnn 480
nnnnnnnnnn nnnnnnnnnn nnnnnnnnnn nnnnnnnnnn nnnnnnnnnn nnnnnnnnuu 540
uuacauacua aggacuaaag cuugcaugug uuccucagaa uaugaaaagc ccaaguucuu 600
guguaguuga uggcugaugc aacuuuuuuc cccccaggau ggcuggaaug gccuuagcca 660
ugaggcuuuu agauuuguuu caagaagaga uuaugcguaa guacaaccuc aguuucucug 720
agaaaaaaaa aaaacacuua uugaaccuca aagcuuggau ggguugggug cguuauacau 780
uuguacuugu aguuuauuca auaugccacu gguaacacca acauaaaaca caguucuucg 840
uauuggagac cacuguucag augaccaugg aauuucauuu cuuacagauc agaagcaauc 900
aagggugcag ugguugguau ugauuugggu acuacuaacu ccugugugge uguuauggag 960 ggcaaacaag caaaggugag caugauugga aaccugaggu cacuuagaua cccagucugg 1020
cauuaaguac auaggaaugc ugagucggag cccagguuag uggugggcac uuuaauccua 1080
guaaaggcag agggaucucu gaguucagga ccagccuaga guacaaagug agnnnnnnnn 1140

-continued

```
nnnnnnnnnn nnnnnnnnnn nnnnnnnnnn nnnnnnnnnn nnnnnnnnnn nnnnnnnnnn   1200
nnnnnnnnnn nnnnnnnnnn nnnnnnnnnn nnacuuuaau cagugucuuu gggaauuuua   1260
gguccuggag aaugcugaag gugccagaac uaccccuucu gugguugccu uuacagcaga   1320
uggagaacga cuuguuggua ugccagcaaa acggcaagcu gucaccaauc caaacaauac   1380
cuucuaugcu acuaagcguc uuauuggacg acgauaugau gacccugaag uacagaaaga   1440
cacgugagua auaggaaaau caguccagaa gacuggugcu uugaucaaag uucuguggau   1500
accuugaguu cuguggauca ccuuggauca cuuuuucauu auuucugcuu gggaagaaau   1560
cacaccacca ucagaggcau auagguuuuu uuuuuguuau uucuuuguug uuguuguuuu   1620
ccuauuuauu uguuuguuug uuuggggggg gguuucuuug uguauuuucc uggaacucau   1680
ucuguagacc aggcuggnnn nnnnnnnnnn nnnnnnnnnn nnnnnnnnnn nnnnnnnnnn   1740
nnnnnnnnnn nnnnnnnnnn nnnnnnnnnn nnnnnnnnnn nnnnnnnnnn nnnnnnnuca   1800
ugugauauau gaugaacuua gagugguuaa guuucacagg gauaguuuac uuacauaauc   1860
uuucugucuu uaaguaagaa uguuccuuuu aaaauugucc gugccuccaa uggugaugcu   1920
uggguugagg cucauggaaa acucuauucu ccaagucaga uuggagcauu uguguugaug   1980
aagaugaaag agacugcagg uaaguggauu uauuucacau uuaggaaaau uggaaugugc   2040
uguuuauuuc ucugcauuaa uacugauuaa cuucauauuc uguagauaau ggagucugaa   2100
gcuunnnnnn nnnnnnnnnn nnnnnnnnnn nnnnnnnnnn nnnnnnnnnn nnnnnnnnnn   2160
nnnnnnnnnn nnnnnnnnnn nnnnnnnnnn nnnnnnnnnn nnnngaauuc augcuccucc   2220
ugcugccucc ugggugcuaa guugcaaggu gauagcucag guacucacuc uagugucuuu   2280
cuuggggugc ucuuuuccaa ggccucucua cauauuaagc cacaaaggag ucuguugccc   2340
cucaagagga ugagaugugg aauauuaggc uacaguuuug uugccuuuuu uuuauuuucc   2400
uaacauggua ccacaauuga auuuuauucu uuguuuccca gaaaauuacu ugggccacac   2460
agcaaaaaau gcugugauca caguccugc uuauuucaau gauucacagc gacagguaaa   2520
auuagaucuc uuguuugcug ggaguggagg uggggguaccu gaguuaaagg auggaaagau   2580
agauuuauuu cuacuuucuc uaggccacua aggaugcugg ccagauaucu gggcuaaaug   2640
ugcuucgagu gaucaaugag ccuacagcug cugcucuagc uuacggucug gacaaaucug   2700
aagauaaagu guaaguuggu cagaugacgu agcauuaccu gcauuuacag ggguugugug   2760
ugugugugug uguguguaau uuuacuacaa uuugugugg uccguguguu gugguacauu   2820
uguacauuug uacauggcau ggauauggau gucaaagauu nnnnnnnnnn nnnnnnnnnn   2880
nnnnnnnnnn nnnnnnnnnn nnnnnnnnnn nnnnnnnnnn nnnnnnnnnn nnnnnnnnnn   2940
nnnnnnnnnn nnnnnnnnnn aaaccaguag uuggugugguu acuaauuuua cuuguuucug   3000
uaugacaugc uuauaugaua cguuaacagg caugccacuu agguugauaa cuacauucag   3060
uuauuaagua uuucaggaaa uaucauaguu aauaauuaaa cuuuuggucu uuuaauucgu   3120
uccuuuguuu uguuccuugg aacuuaacuu acuuauuuau uuuuuagcau ugcuguguau   3180
gauuuaggug guggaaccuu ugacauuucu auccuggaaa uucagaaagg aguguuugag   3240
gugaaaucua ccaaugggga cacuuucuua ggaggggaag acuuugacca agcuuuguug   3300
cggcacauug ucaaggaguu caagagagag guuaguuacc acugcuuagu caccacuggu   3360
uaaggugauag gcguuggguu guugagaauu uuuguuuguu ugcauugcuu uuagcuuugu   3420
uaauagcuuu uuuauacuaa gguaacuaac uauacuucag auucaugggu aaacuaaacc   3480
```

-continued

```
aguuuaguua uauaaucuua gauugggaac aaaagaccaa gugacagugu uauaguaggg   3540
agaagnnnnn nnnnnnnnnn nnnnnnnnnn nnnnnnnnnn nnnnnnnnnn nnnnnnnnnn   3600
nnnnnnnnnn nnnnnnnnnn nnnnnnnnnn nnnnnnnnnn nnnnnacuac ucucucgcag   3660
ucuauauaug ucuccuaauc cuauuuauag acagggguug auuugaccaa agacaacaug   3720
gcgcuucaga ggguucggga agcugcugag aaggcuaaau gugaacuuuc cucaucugug   3780
caggugaggg auggaaaaau cccaguacug agcauauuug aauaguguau ucuaauuuac   3840
cuaaugucag uguagcucuu uacaguuuuc uguuggcuga aaacuugggg caugagcaaa   3900
ggaacaacuu gaugaucagu ucuuuucauu ugaaugaaug aaguagauuu auggaugugu   3960
guaucuuuug ccugcaugug ugucuguacu acauuugugc uugguuucug uggcggccag   4020
aagaggguau cagaacugac augucagugu uggggannnn nnnnnnnnnn nnnnnnnnnn   4080
nnnnnnnnnn nnnnnnnnnn nnnnnnnnnn nnnnnnnnnn nnnnnnnnnn nnnnnnnnnn   4140
nnnnnnnnnn nnnnnncaca cugagucuaa auucugauca ugucuuucag ucguguuaug   4200
uuacuuugag ugaguaucaa agaucacguc ucccaucuga cguguggucc ugugcagacu   4260
gacaucaacu ugccauaccu uaccauggau gcuucuggac caaagcauuu gaauaugaag   4320
cugacucgag cucaguuuga aggcauuguc acagaucuaa ucaagagaac uauugcuccg   4380
ugucagaaag cuaugcagga ugcagaaguc agcaagagug acauaggaga agugauucug   4440
guugguggca ugacaaggau gcccaaggua uggacucaug guauuucucc uagaggaaaa   4500
aaauaacaau gcauucuuga ggcaaauggc uuguguugug uguggaaaca aaugugaucc   4560
auucuucuag uguucuuuaa agagugguga gaccagacuc accaaaaagu gcuuuuaguc   4620
gccugugaug gcucauguag gaggauggcc uugaguucug gguaagaugc agcuacagaa   4680
uucuaccuug cacacacacu uaaacccagu cugguaaaga gaaguuguua agcuunnnnn   4740
nnnnnnnnnn nnnnnnnnnn nnnnnnnnnn nnnnnnnnnn nnnnnnnnnn nnnnnnnnnn   4800
nnnnnnnnnn nnnnnnnnnn nnnnnnnnnn nnnnncagau guaaaauuga uaauacuucu   4860
uccuaagauu gggcgauugu guagaauaug agaacuguau uuuauaaccc cuugucaugu   4920
gccuucuauu ucaaaugaua ucccucuggga agcuagauaa uuaaauucuu cucucauuua   4980
aguggacagu ggaugagaug cucugaaguu gucaaauaca aacaagucug cagucuugga   5040
uaugaaucuc ucugacuugc ugucuggcag gcguauucug uuuggcucca ucagucgccc   5100
uggguguugg cuaacagguu cuuucucccu gaugcuuagg uucagcagac uguacaagau   5160
cuuuuuggca gagccccgag uaaagcuguu aauccugaug aggcuguagc caucggagcu   5220
gccauccagg gaggugugu u ggcuggugac guuacagacg ugcugcuccu ggaugucacu   5280
ccccucucuc uggguauuga gacucuggga ggcgucuuua ccaaacuuau uaauaggaac   5340
accacuauuc caaccaaaaa gagccaggua agagccauuc uuuuuuccug ccuauuaaca   5400
gucccaaguu guacaagugc uguuuacaau cacuuuauga acucuuuaaa acuuuguuuc   5460
uaagacuaua cuaacuggac ugggugnnnn nnnnnnnnnn nnnnnnnnnn nnnnnnnnnn   5520
nnnnnnnnnn nnnnnnnnnn nnnnnnnnnn nnnnnnnnnn nnnnnnnnnn nnnnnnnnnn   5580
nnnnnnccua gguguuuucu acugcugcug auggacaaac ucaaguagag auuaaagugu   5640
gucaggggga acgagagaug gcuggagaca acaaacuucu aggacaguuc acuuugguaa   5700
guguuuuuga gucugaguau caugcuuuug gggucuauag cuugcaaagc uccaaacugc   5760
ugacauuaca ggcauauugu guuauuuuuu aaaaagaacg uuauguacau gaguuaugaa   5820
acccaugauu uuaguuuuuu accuaaagug cuuuguguuu ucagaauuug aaauuuucaa   5880
```

agccugggaa auguucagac ucagaagcaa ugcuaacuca gaaguuaguu uuauccugau 5940
uacucauuuu aaaaaacuua auagcuacug guucugguca gcauugcuac aguagagaag 6000
uuuauuugcu guaaauucug ggcacauaua accaucaugg uuauuaacuu cuugaagccc 6060
agugauuuca gaaagcacua aaacuaccac caucacuuaa aaucucaagg uuuugaacau 6120
ucagugaaga uacuuguuuu aggaaacaag ugguuaguug gccugauuug gaaaugagaa 6180
uacaugggcc uuucaaagga gcucacucug gauauuuauu uuagauugga auucccccag 6240
ccccucgugg agugccccag auugaaguua cauuugacau ugaugccaau gggauugugc 6300
acguuucugc caaagauaaa ggcacugguc gugagcaaca ga 6342

<210> SEQ ID NO 150
<211> LENGTH: 4145
<212> TYPE: RNA
<213> ORGANISM: Homo sapiens
<220> FEATURE:
<221> NAME/KEY: misc_feature
<222> LOCATION: (4045)..(4045)
<223> OTHER INFORMATION: n is a, c, g, or u

<400> SEQUENCE: 150
auaaauucuu auuuugacac ucaccaaaau agucaccugg aaaacccgcu uuuugugaca 60
aaguacagaa ggcuugguca cauuuaaauc acugagaacu agagagaaau acuaucgcaa 120
acuguaauag acauuacauc cauaaaaguu uccccagucc uuauuguaau auugcacagu 180
gcaauugcua cauggcaaac uaguguagca uagaagucaa agcaaaaaca aaccaaagaa 240
aggagccaca agaguaaaac uguucaacag uuaauaguuc aaacuaagcc auugaaucua 300
ucauugggau cguuaaaaug aaucuuccua caccuugcag uguaugauuu aacuuuuaca 360
gaacacaagc caaguuuaaa aucagcagua gagauauuaa aaugaaaagg uuugcuaaua 420
gaguaacauu aaauacccug aaggaaaaaa aaccuaaaua ucaaaauaac ugauuaaaau 480
ucacuugcaa auuagcacac gaauaugcaa cuuggaaauc augcaguguu uuauuuaaga 540
aaacauaaaa caaaacuauu aaaauaguuu uagagggggu aaaauccagg uccucugcca 600
ggaugcuaaa auuagacuuc aggggaauuu ugaagucuuc aauuuugaaa ccuauuaaaa 660
agcccaugau uacaguuaau uaagagcagu gcacgcaaca gugacacgcc uuuagagagc 720
auuacugugu augaacaugu uggcugcuac cagccacagu caauuuaaca aggcugcuca 780
gucaugaacu uaauacagag agagcacgcc uaggcagcaa gcacagcuug cugggccacu 840
uuccucccug ucgugacaca aucaauccgu guacuuggug uaucugaagc gcacgcugca 900
ccgcggcacu gcccggcggg uuucugggcg gggagcgauc cccgcgucgc cccccgugaa 960
accgacagag ccuggacuuu caggagguac agcggcgguc ugaaggggau cugggaucuu 1020
gcagagggaa cuugcaucga aacuugggca guucuccgaa ccggagacua agcuuccccg 1080
agcagcgcac uuuggagacg uguccggucu acuccggacu cgcaucucau uccacucggc 1140
cauagccuug gcuucccggc gaccucagcg uggucacagg ggccccccug ugcccaggga 1200
aauguuucaa gcuuuucccg gagacuacga cuccggcucc cgguguagcu caucacccuc 1260
cgccgagucu caguaccugu cuucggugga cuccuucggc aguccaccca ccgccgccgc 1320
cucccaggag ugcgccgguc ucggggaaau gcccggcucc uucgugccaa cggucaccgc 1380
aaucacaacc agccaggauc uucaguggcu cgugcaaccc acccucaucu cuuccauggc 1440
ccagucccag gggcagccac uggccuccca gccuccagcu guugacccuu augacaugcc 1500

-continued

```
aggaaccagc uacucaaccc caggccugag ugccuacagc acuggcgggg caagcggaag   1560
uggugggccu ucaaccagca caaccaccag uggaccugug ucugcccguc cagccagagc   1620
caggccuaga agaccccgag aagagacacu uaccccagaa gaagaagaaa agcgaagggu   1680
ucgcagagag cggaacaagc uggcugcagc uaagugcagg aaccgucgga gggagcugac   1740
agaucgacuu caggcggaaa cugaucagcu ugaagaggaa aaggcagagc uggagucgga   1800
gaucgccgag cugcaaaaag agaaggaacg ccuggaguuu guccuggugg cccacaaacc   1860
gggcugcaag auccccuacg aagaggggcc ggggccaggc ccgcuggccg aggugagaga   1920
uuugccaggg ucaacauccg cuaaggaaga cggcuucggc uggcugcugc cgccccccucc   1980
accaccccccc cugcccuucc agagcagccg agacgcaccc cccaaccuga cggcuucucu   2040
cuuuacacac agugaaguuc aaguccucgg cgaccccuuc cccguuguua gcccuucgua   2100
cacuuccucg uuuguccuca ccugcccgga ggucuccgcg uucgccggcg cccaacgcac   2160
cagcggcagc gagcagccgu ccgacccgcu gaacucgccc ucccuucuug cucuguaaac   2220
ucuuuagaca aacaaaacaa acaaacccgc aaggaacaag gaggaggaag augaggagga   2280
gaggggagga agcaguccgg gggugugugu guggacccuu ugacucuucu gucugaccac   2340
cugccgccuc ugccaucgga caugacggaa ggaccuccuu uguguuuugu gcuccgucuc   2400
ugguuuucug ugccccggcg agaccggaga gcuggugacu uuggggacag gggguggggc   2460
ggggauggac accccuccug cauaucuuug uccuguuacu ucaacccaac uucuggggau   2520
agauggcugg cugggugggu agggugggu gcaacgccca ccuuuggcgu cuugcgugag   2580
gcuggagggg aaagggugcu gagugugggg ugcagggugg guugaggucg agcuggcaug   2640
caccuccaga gagacccaac gaggaaauga cagcaccguc cuguccuucu uuucccccac   2700
ccacccaucc acccucaagg gugcagggug accaagauag cucuguuuug cucccucggg   2760
ccuuagcuga uuaacuuaac auuuccaaga gguuacaacc ucucuccugga cgaauugagc   2820
ccccgacuga gggaagucga ugcccccuuu gggagucugc uaaccccacu ucccgcugau   2880
uccaaaaugu gaaccccuau cugacugcuc agucuuuccc uccugggaaa acuggcucag   2940
guuggauuuu uuuccucguc ugcuacagag cccccuccca acucaggccc gcucccaccc   3000
cugugcagua uuaugcuaug ucccucucac ccucaccccc accccaggcg cccuuggccg   3060
uccucguugg gccuuacugg uuuugggcag cagggggcgc ugcgacgccc aucuugcugg   3120
agcgcuuuau acugugaaug aguggucgga uugcugggug cgccggaugg gauugacccc   3180
cagcccucca aaacuuuccc ugggccuccc cuucuuccac uugcuuccuc ccuccccuug   3240
acagggaguu agacucgaaa ggaugaccac gacgcauccc gguggccuuc uugcucaggc   3300
cccagacuuu uucucuuuaa guccuucgcc uuccccagcc uaggacgcca acuucucccc   3360
acccugggag ccccgcaucc ucucacagag gucgaggcaa uuuucagaga aguuucagg   3420
gcugaggcuu uggcuccccu auccucgaua uuugaauccc caaauauuuu uggacuagca   3480
uacuuaagag gggcugagu ucccacuauc ccacuccauc caauuccuuc aguccccaaag   3540
acgaguucug ucccuucccu ccagcuuuca ccucgugaga aucccacgag ucagauuucu   3600
auuuuuuaau auuggggaga ugggcccuac cgcccguccc ccgugcugca uggaacauuc   3660
cauacccugu ccugggcccu agguuccaaa ccuaauccca aaccccaccc ccagcuauuu   3720
aucccuuucc ugguucccaa aaagcacuua uaucuauuau guauaaauaa auauauuaua   3780
uaugagugug cgugugugug cgugugcgug cgugcgugcg ugcgugcgag cuuccuuguu   3840
uucaagugug cuguggaguu caaaaucgcu ucuggggauu ugagucagac uuucuggcug   3900
```

```
ucccuuuuug ucaccuuuuu guuguugucu cggcuccucu ggcuguugga gacagucccg   3960

gccucucccu uuauccuuuc ucaagucugu cucgcucaga ccacuuccaa caugucucca   4020

cucucaauga cucugaucuc cggunugucu guuaauucug gauuugucgg ggacaugcaa   4080

uuuuacuucu guaaguaagu gugacugggu gguagauuuu uuacaaucua uaucguugag   4140

aauuc                                                               4145
```

<210> SEQ ID NO 151
<211> LENGTH: 1756
<212> TYPE: RNA
<213> ORGANISM: Homo sapiens

<400> SEQUENCE: 151

```
caccugauuc ccggaggccc gagcccuuag ucugggcggg guggcgcggg ccggaaggac     60

gccaucccgg ccugggccau ggaggcuccc gcaccguccc ucacggagga ggauuugacu    120

gaagugaaga aggacgcuuu agagaauuua cguguuuacc ugugugagaa aaucauagcu    180

gagagacauu uugaucaucu acgugcaaaa aaaauacuaa guagagaaga cacugaagaa    240

auuucuugcc gaacuucaag uagaaaacgg gcugggaagu uguuagacua cuuacaggag    300

aaccccaggg gccuggacac ccugguggaa uccauccgca gggagaaaac acagagcuuc    360

cugauucaga agauaacgga ugaggugcua aagcuucgga auauaaaacu ggagcacccuc    420

aaaggccuga agugcagcag cugugagccc uuugcagccg gagccaccaa caaccucucu    480

aggugcaauu ccgaugagag caaucucucu gagaaacaga gagcauccac ugucauguac    540

cacccggagg gagaguccag cacggcuccc uucuucucua uggcgucguc ccugaacuug    600

ccaguccugg aaguuggcag gacugaaaac agcagcuucu cuucagccac ucuuccucga    660

ccuggggacc cuggggcucc cccuuugccc ccagaccuuc gguuggaaga gggggggaagu    720

uguggaaacu caagugagau guuucucccc uuacggucac gggcucuuuc acgccaauga    780

uacaucaccg ccuaguuguu uuacuaguga ugcaaaaugc ugugaaggag gccaucuuuc    840

uauacaaacc acggugacag gucacucaca uucgaugcgu gccuuuaaaa ucaguguaca    900

cauucucugu aaauaggauu uguuagggua aagaagcgcu cuggggcggc gugguguaau    960

caugguggguc gugacuuuuc cauaaugucc uuucuuuuuu auuauuuuua ggugguuugcg   1020

uauuuugaac uuuucauaag auuaauuuua ucggaauauu ucucaauuug agaaaacaac   1080

uuguggauug ggaauaaugu uuuuagcaca uuuaugcuac aaauuuucag ucugauuguu   1140

uuucccacug aucuggcagu auauuuuagc aguaagcugu ugugugucag gaaagcugga   1200

cacgggaaag cugccgacac acucagcagu gucccacucc uuaguucuga gaagccgucg   1260

gguucugagg agacaccugg uggcacugag ccuggugacc ucagugggcc aaaauuuguu   1320

uuauacucac ccugccagcg ugagugucuu acuuucacag gccuuguguc cucagucuua   1380

ucuuaaagga uguuaucuug gcagggcauc acuuguaauu aauggaugau acuuguaauu   1440

gacuaaaguc cucgcucuga gccguuuguu cuggcuccga gagcgcugac augugaagca   1500

uggugagcag cgagggaacu gacaggaugu ggccguggcc aguguggcuu uaguguuugc   1560

aucaggcagc caccagcucc auccguguuc uuacugcuuu acaaaguuug acuaacuuua   1620

cacauuuuaa aaaugcugau ugucuucguu uaaauuauaa uuuuaccuau uucuugacau   1680

cuaacuccua uuuauuucua uuauuuaaaa auuaagaaau gaaaauuugc uauuaacaau   1740

aaaguuuuuu uaaugu                                                   1756
```

<210> SEQ ID NO 152
<211> LENGTH: 1113
<212> TYPE: RNA
<213> ORGANISM: Homo sapiens

<400> SEQUENCE: 152
gggggggggg ggucagcgcc gacguccccu gccgccacca ugcccaaaag aaaggcugaa 60
ggggaugcua aaggagacaa aaccaaggug aaggacgagc cacagagaag aucugcaagg 120
uugucugcua aaccugcucc uccaaagcca gagcccaaac cuaaaaaggc cccugcgaag 180
aagggagaga agguacccaa ggggaagaag gggaaagcug acgccgggaa ggaugcgaau 240
aauccugcag aaaauggaga ugccaaaaca gaccaggcac agaaagcuga aggugcugga 300
gaugccaagu gaugugugug cauuuuugau aacuguguac uucuggugac uguacaguuu 360
gaaauacuau uuuuuaucaa guuuuauaaa aaugcagaau uucguuuuac uuuuuuuuuu 420
uuuuuaagcu auauuguuag cacacagaac acuucauuac ugggugggg aaggaucaug 480 ugucaguaac aaaaucucuc ccaagcugga uugaggacag aaaaccucuu ucccugauaa 540
uuuuggaagg cuccuguugg cucccaggag agagauccug gucuugaccu agguggccac 600
caaggcacaa caaugccuug uggucuggga aaacuauaaa uucacuuuua uauccucuuc 660
ccccuguacu aucaacauag acuuaauucc cuuaaaaacc agagaccugu uggaaccugg 720
cccccaaaau ugguuuccca guccauugag ugauggggac uuugcaguga cuucauugag 780
uguucucaaa agagcacugg uuccuuuuau aaaagauugu ggaucuucag auugauaauu 840
cugccuaaaa gucagggucg gcuugugaaa aguuguuaaa acaacauccu uaaugugaaa 900
ugucaacccu cacucuaagc uacuuccccc uuuucaaagc auugaaugaa gacuucauug 960
gguuuuauag uggcuuucug auuuugguag ucauaucaga agggaauuug gaaguucuug 1020
uauauuguug cauugucugc ccauguccug ccugaauacc augauuguuu augaaagaau 1080
cuuaauaaag cugguuacag uuaggcugga aaa 1113

<210> SEQ ID NO 153
<211> LENGTH: 321
<212> TYPE: RNA
<213> ORGANISM: Homo sapiens

<400> SEQUENCE: 153
uuuuuuuuuu uuuuuuugga aguccauaag uaguuuauug ucuucaagac uacagugugg 60
auuccucucc cagagaaggg ucuuucagag gcaggggacu gucacccagg ugcaggccgu 120
cuacuuguca uuuucauaca uggcuggauu cuuccuuuuc gacugcucaa acuccugguu 180
gccccaugug uagaucaggu agaccacuac aaacggcggc gccacgcgca ggaugcgcuc 240
gcgagugcgg cgcaacacgu uggggaugcc uuugcugaaa uagcuuggga aggcgcgcug 300
cucaaagggc gacaagcugu a 321

<210> SEQ ID NO 154
<211> LENGTH: 1720
<212> TYPE: RNA
<213> ORGANISM: Homo sapiens
<220> FEATURE:
<221> NAME/KEY: misc_feature
<222> LOCATION: (952)..(952)
<223> OTHER INFORMATION: n is a, c, g, or u

<400> SEQUENCE: 154
caugaagcca gagaugugga agaugugucu agacugcauc aaugaacuga uggauacguu 60
ggaugcacau uccaacaucu cugucggaga gaacauuuug gcagagagug agaacuuaca 120
caacuuugau caguucacuc cguguacgac gcugcauccu aacuuuggug gagcgaaugg 180
augaagaauu uaccaaaaua augcaaaaua cugauccuca cucccaagag uauguggagc 240
accugaagga ugaggcacaa gugugugcau cauugagcga gugcagcgcu accuggagga 300
gaaagguacc acugaggaga ucugccagau cuacuuaagg cgcauccugc acacguacua 360
caaguuugac uacaaggccc aucagcggca cguuacuccu ccugaaggau ccucaaaguc 420
ugagcaagac caggcagaaa augaggguga ggacucagcu gugcuaaugg aaagacugug 480
caaguacauc uaugccaagg accguacaga ccggauccgu accugugcca uccucugcca 540
uaucuaccau caugcgcucc acucccgcug guaucaggcc cgugaccuca ugcucaugag 600
ccaccuacag gacaacauuc agcacgcaga cccgccggug cagauccugu auaaccguac 660
uauggugcaa cugggcaucu gugcuuuccg ccaaggccug acaaaggaug cacacaaugg 720
cacuucugga uauucaguca agugguggug ccaaggagcu ucuaggucag gguuugcugc 780
ugcgcgcuug caggagcgaa aucaggaaca ggaaaaggua gagcgacgcc ggcaggugcc 840
cuuucaccug cacaucaacc uggagcugcu ggagugug uc uaucuggugu cagcuaugcu 900
ccuggagauc cccuacaugg cugcccauga gagcgaugcc cgccgacgca unaucagcaa 960
gcaguuccac caccaacugc gggugggcga gcggcacgcc cugcuagguc cucccgaguc 1020
aaugagggag cauguggucg cugccuccaa ggccaugaag augggcgacu ggaagaccug 1080
ccacaguuuc aucauuaaug aaaagaugaa ugggaaagug ugggaccuuu ucccugaggc 1140
ugacaaaguu cgcaccaugc uaguucggaa gauccaggaa gagucucuga ggaccuaccu 1200
uuuuaccuac agcagugucu augacucaau caguauggag acacuaucag auauguuuga 1260
gcuggaucua cccacuguuc acuccaucau cagcaagaug aucauuaacg aagaauugau 1320
ggcuucccug gaccagccga cacagacugu ggugaugcac cguacugagc ccucugccca 1380
gcaagaaacu uggcucugca agcuggcuga gaaaacuugg cacccuagug gagaauaaug 1440
gacggguguu ugaccaaaaa cagggaaccu augguggcua uuuccgagac cccaagggug 1500
gcuaccggaa aaauggaggc uaaaugcccc gugguggcua cccccagcaa cagucucaga 1560
caaccuccug aguuccccac uucagucacc cuguggacag accaucuaac cuuuuucucc 1620
uaacucaccc caaucauuaa agaucuuuug aggaauuaaa aaaaaagaaa gaaaaaaaaa 1680
aaaaaaaaaa aaaaaaaaaa aaaaaaaaaa aaaaaaaaaa 1720

<210> SEQ ID NO 155
<211> LENGTH: 453
<212> TYPE: RNA
<213> ORGANISM: Homo sapiens

<400> SEQUENCE: 155
uuauuaauua aaaaacaauu uauugaaaaa gaguagugcu uuguacaaau ucccauugca 60
gcccccagau aucaacugau cucuuuccag cuuugguagu aggguauaaa aauaucaaaa 120
cuagguaagu ucugauguaa gauuucuaug ggauuauuuu agaauauaua gauuugugua 180
guuuggcaag uaucauuucu augcauuuac auuacauauu aagcacagau ucuguggcaa 240
aacaucuuug caugauuacu uuacacacac aaauauagua aaacuuacau aguacaaauu 300
cacauaagac uccauucugu cuauaacuuc auccaugugg uuuuaccaug aauuauaauu 360
cuuaaccucu ccuauaacug ucagcuucca uuuaauuuug aaaguaucac uucacaaaga 420
gcacuucauu ugcuuuuaga guauacauag acu 453

<210> SEQ ID NO 156
<211> LENGTH: 361
<212> TYPE: RNA
<213> ORGANISM: Homo sapiens
<220> FEATURE:
<221> NAME/KEY: misc_feature
<222> LOCATION: (230)..(230)
<223> OTHER INFORMATION: n is a, c, g, or u

<400> SEQUENCE: 156
cggccgccaa gaaguauaac augcgagugg aagacuacga gccauacccc gaugauggca 60 uggggguaugg cgacuacccg augcucccca accgaucaca gcaugagagg gauccguggu 120
aucaguggga ccacucagaa cucaggauga acugggguga accgauacac ugggaccuag 180
acauguacau caggaaucgu guggacacgu caccuacccc uguguccugn gaugucaugu 240
guaaacaucu cuucggcuuu guggcuuuca ugguuuucau guucugggua gggcacgugu 300
ucccuuccua ccagccugug gguccgaagc aguacccuua caaaaaucug uaccuggagc 360
g 361

<210> SEQ ID NO 157
<211> LENGTH: 452
<212> TYPE: RNA
<213> ORGANISM: Homo sapiens

<400> SEQUENCE: 157
uuuuuuuuuu uuuuuuugau gcaaaugucu uuauuuucca cuuaaacaag uuucccuuuu 60
gcacuggccu guggcacaaa acagauggcu ggguggugac auuaacuguc aaguuaguga 120
gaugcagaga uggugagaca cugcauuuga gugcauaaua cuuuuauucc agaggaacgc 180
caugcagccc aguuacaccu uuaggucaga aaggcugaug cgugaccagc cucuauugcc 240
ucccuuggua agaaggaccc acaagugcag aguccaacag augcuggcuc ugagcugaac 300
ucagggcauu ccaauuacca cuuucuucuu caccuacaca gggccugcuc agauguccuu 360
uuuacaacuc cauaagcccu uuggccaaag ucccugcagu guuuggggag gaccuuccca 420
cccuucacca gucagugucu gaucuggugg ag 452

<210> SEQ ID NO 158
<211> LENGTH: 392
<212> TYPE: RNA
<213> ORGANISM: Homo sapiens

<400> SEQUENCE: 158
uuuuuuuuuu uuuuuuuaau aucuguaaua guuuauuuca aagauuugac auuuacaagu 60
agaggcacca caugcuaucu gacaguaaaa uacugcaggg acugaaggcc aaggagagag 120
auccacagaa gacaggccug uagugcaggc auugcaucga ccuugcccac agugcuuugu 180
ucccaacuca ggacaguacu uuagugcuug cuucauuuac uggaaaaguu cacuggacau 240
aguuuccacu ucuuccccca cagcuuccag cucagcaaac uuaagcuacu acuccucgau 300
gcucucauag aggcucuuga uuugugucug gaagaacuug gcaagcucua cucguuuggc 360
uuucaguguc ggugucagaa guccguuuuc aa 392

<210> SEQ ID NO 159
<211> LENGTH: 217
<212> TYPE: RNA
<213> ORGANISM: Homo sapiens

<400> SEQUENCE: 159
uuuuuuuuuu uuuuuuucug agguauuaaa auaucuagac ugaauuuugc caaauguaag 60
agggagaaag uuccugaaga cucugacuac uugcuuauuu uugauugacc uucuaugcuu 120
augucauuac ugccucacaa cguguuugau guccuuuaau gauacaaagu gagccugugc 180
cuucauuuuc uugcccauuu ugguaccccu cgugccg 217

<210> SEQ ID NO 160
<211> LENGTH: 1515
<212> TYPE: RNA
<213> ORGANISM: Homo sapiens

<400> SEQUENCE: 160
gcgcccgaac gucuagcaga guaccugcug cuguaagcuu gucgucuggg cugcaccgcc 60
cgucuuaacc cauucucgac uuaacuacuc ucgucgaaca agcauggaag uacagaaaga 120
agcgcagcgc aucaugacuc ugucgguaug gaagauguac cacucucgca ugcagcgagg 180
uggcuugcga cuccaccgga gucugcagcu aucccucguu augcgcagcg cucgagagcu 240
cuaccucuca gccaagguag aagcccacca gcccgaguuc ccgccauccc gcagggcucu 300
ugacccucgc cugcacccgc cgcgggaagc cgaaguugca guggaaguag cguccccega 360 agccgugcag ccuccggagc ccauggauac gcaagaggaa gugcugcgag uccaggagac 420
cccugcgcuc ugugacccgc cccccgcuag agucagccgc aagcgccgga gcagcagcga 480
uuugagcgac aguagugaug ccggacuggu accaagcaag aaggcccguc uagaagaggu 540
ggagggggag gcgacgucgg agguucccga ucgccugcag cuucccuccgg cacaaagcga 600 aggugccuuc ccuaaccucg cccgcguccu ccaaaggcgc uucuccaguc uccugaacug 660
uggacccgcc gugcccccgc cgacgccccc cacgugcgag gccaagccag ccugccgccc 720
ggccgacaau augcucaacg ugcuggugcg agcuguggug gccuucugag agcucuggug 780
gcuucuuucg agcggcgcca ccggagcgga gaacgcacac ccgaggcgaa ggccggcggg 840
ggccgugaag aagagccgcg gcccgagcug ccgagaggcc agggcaagga cugaggagcg 900
aggggcgcgg gcgccuucuc ccagacgugc guccauaggu gcuauuaaag gacuguccu 960 uccuuggcuu ggagaaggga caccuagauc uugaaucuca gggucgaacu cucuaggggc 1020
caggcugccc uuucaaggcc guuucacuac cauucgcguu ucggccccua caagugggca 1080
cgcuugugca agcggucaga guugcgucau gggacagacg cgggugcuuc cuguugccuu 1140
gcgugggugu ggggccuggg aggaggccag gguguggacc cgcccuaggg acugggaagu 1200
gacuugaguc accucgcccc cacaggcugc ugugggugag ccugaacuga accaaucaaa 1260
ucugcgcaga guugaagugg cuggagaccc cgggacuggu caaccuagau gaucgccugg 1320
cguggaccac cgcgggacgg gugggccgcu ggucguaguu gcugccguag acacagcuuc 1380
uucgggcagg aaagaaaauu uuuuuuuuac cagcguguuu aagaaagucu guuuacuuuu 1440
cccacggugg guuguuuaau uagcaacuac cuggaguuuu acaaugucag cuaggaaaau 1500
aaagaccauc ggugu 1515

<210> SEQ ID NO 161
<211> LENGTH: 801
<212> TYPE: RNA
<213> ORGANISM: Homo sapiens

<400> SEQUENCE: 161

-continued

```
cugagaggcc aggugggcgg cgaaaucaac guggagaugg augccgcucc cgguguggac     60

cugagccgca uccugucaga gaugcgugau caguacgaga agauggcgga gaagaaccgc    120

aaggaugccg aagacugguu cuucagcaag accgaggagc ugaaccgcga gguggccacc    180

aacagcgagc uggugcagag cggcaagagc gagaucuccg agcucaggcg caccaugcag    240

gcccuggaga uugagcugca gucccagcuc agcaugaaag caucucugga gggcagccug    300

gcagagacag agaaccgcua cugcgugcag cugucucaga uccaggggcu gaucggcagu    360

guggaggagc agcuggcuca gcugcgcugc gagauggagc agcagaacca ggaguacaag    420

auccugcugg augugaagac aaggcuggag caggagaucg ccaccuaccg ccgucugcug    480

gagggagagg augcccaccu gacucaguac aagccaaaag aaccugugac cacccgccag    540

gugcgcacca uuguggaaga aguucaggau ggcaagguca ucucaucccg ggaacaggug    600

caccagacca cccguuaagg acucagcucc uuccgcccag uuccccgagg cugcagagag    660

gcagcuuccc ucuccgcucc ggcaucaccc uccugcuaca gccucucccc agcauuccua    720

ugcuugagac cauuaaagcu ugcugaccug aagugaacug uggccuuugu ucugaacacu    780

gaaauaaaug accaugguga c                                              801
```

<210> SEQ ID NO 162
<211> LENGTH: 447
<212> TYPE: RNA
<213> ORGANISM: Homo sapiens

<400> SEQUENCE: 162

```
uuuuuuuuuu uuuuuuuggu uccacuuaag uugcauguuu uauuucuccc aaucccagca     60

auagcacaga agcccaucau guccauccca gacugguuuc uaguaggcug agaugacagg    120

gagccucagu aacgcuaaug gcacagaggg cucccaaaug ccaggcacaa cugugccucc    180

acacugguga cugcccagag ugcccuggcc ccagugugu ggcacucagu cugacuuuac    240

aacgcaaccu gcaccuuuga aagggacagu cugggagugg ggagugugag ggagugaagc    300

ucaaacugcc uccugucagc ucacccuuuc aacauuaaac agagaccaag agagaaacag    360

uuccaauauu ucacauauau uucuucuugu gcagucuaag ccgagaaugc cauguaaaug    420

ggucacugcg aaaugcagca auuuagu                                        447
```

<210> SEQ ID NO 163
<211> LENGTH: 475
<212> TYPE: RNA
<213> ORGANISM: Homo sapiens

<400> SEQUENCE: 163

```
gucucgggcg agauggcuuc aagguuacuu cgcggagugg gcgcuuuggc ggcgcaggcc     60

cugaggcgca cggcccgugg cgcggccgug acccgcucca uggcuucugg agguggucuc    120

cccacugaug aggagcaggc uacugggcug gagagggaga ucaugauagc agcacagaag    180

ggacuggacc cauacaauau gcuaccucca aaggcagcuu caggcaccaa ggaagacccu    240

aaucuagucc cguccaucag caacaagaga auagugggcu gcaucugu ga agaggacaac    300

uguacuguca ucugguuuug gcugcacaaa ggcgagaguc agcgaugccc caacugugga    360

acccauuaca agcuggugcc ccaccaaaug gcccacugag ccccuguguu aucuuuucag    420

aauguaaaga aaaacuucuc ucuaauaaag acuagccauu gcaccugcuc cuccc         475
```

<210> SEQ ID NO 164
<211> LENGTH: 1897

<212> TYPE: RNA
<213> ORGANISM: Homo sapiens

<400> SEQUENCE: 164
gaauucggca cgagcagcga gacgccgcgc acggugcuuc cccaguggag ccaaucggcu 60
aacccgcgcu ccggcagagu ccuuggcgcu cgcccgccgg cgggacagac cacccgccuc 120
uggccgcucu cuggacccug gccgccccga gcgaagacug gagcaaaaug augcuucaac 180
auccaggcca ggucucugcc ucagaaguca gugcgaccgc cauugucccc ugccucucac 240 cuccugggucc acugguauuu gaggauuuug cuaaccugac acccuuuguc aaggaagagc 300
ugagauucgc cauccagaau aaacaccucu gccaucggau guccucugcg cuggagucag 360
uuaccgucaa caacagaccc cuggagaugu cagucaccaa gucugaggcg gccccugaag 420
aagaugagag gaaaaggagg cggcgagaaa gaaauaaaau ugcugcugcc aagugucgaa 480
acaagaaaaa ggagaagaca gagugccugc agaaagaguc agagaaacug gagaguguga 540
augcugagcu gaaggcccag auugaggagc ugaagaauga gaaacagcau uugauauaca 600
ugcucaaccu gcaccggccc accuguaucg uccgggcuca gaauggacgg acaccggaag 660
acgagaggaa ccucuuuauc caacagauaa aagaaggaac auugcagagc uaagcagagg 720
uggcacggag gcaauugggg aguucuuacu gaauccuccu uuuccacccc acacccugaa 780
gccauuggaa aacuggcuuc cugugcacuu cuagaauccc agcagccaag agccguuggg 840
gcaggagggc cuguggugac cuacugcauu gacccacucu gcccccgagu gaaccgugga 900
gcaggcagga gcauccuuug ucucaccaau uccaggauuu aggccuuauc aucccggcca 960
gucucagaug accuagcugg ccccaggcug ggguccuaug caaagcagga ucccacuaau 1020
gggauucagg cagaaguguc uaccuugaua ggugggggugg gaccacaucc uccacugugg 1080
cugacaacgc ccuuccaagg gaauauggaa ugagaacauu cauuauugag guuguccaau 1140
ggccagggua ugcuuucuag aaaauaugcu guucugcccc agaaugacug ugcauagggu 1200
auccguuuca gagccuggug uugugcuauu uagauguuug ucuugcacaa cauuggcaug 1260
auuuuuccgg gaguuucauc agaucugauu ucugagaguc uggggaucug ccauggugga 1320
aagugccccu caaaagcauu uguguggcca caugaacugg cuggcaccag gggagugaaa 1380
cuggcugaug accagcugag ccacuuugug ccaacagagg auggacgaca ccuuucccug 1440
uacccacugc agaggaagaa cccugggcac agcagcuuug uccuuggcua caaacuguua 1500
caacgucaca caaugaaggc acaaagucca acuuucaaag gguguaggac uccauacuca 1560
gugacagggc aggaagagcc aaagauaacc acagccacag ccuguggaga ccaggguugg 1620
aagccaggug cagggccagg caucugcauu gugggauguu aauggcacuu uugucuugua 1680
gcuauuuuga gauguggucc agagcauuuc agcugggaga ucucccucug gccaccagga 1740
cucuggcuac uguuaaaauc cugauguuuc uguggaaucc ucaguguuua aucccacuca 1800
auaguaucau uacaguuuuc uguaagagaa aauauuacuu auuuauccca guauuccuag 1860
ccugucaaca uaauaaauau cggaacaaaa ccuggua 1897

<210> SEQ ID NO 165
<211> LENGTH: 2167
<212> TYPE: RNA
<213> ORGANISM: Homo sapiens

<400> SEQUENCE: 165
gcgcaccgcc ygyguygcgc gscagcgucg ucuaggugca ucgcgggccc ccgcagrwag 60

-continued

```
aaaaauaugg cucaggagac uaaccagacc ccagggccca ugcuguguag uacaggaugu    120
ggcuuuuaug ggaauccuag gacaaaugga auguguucug uuugcuacaa agaacaucuu    180
cagagacagc agaauagugg cagaaugagc ccaaugggga cagcuagugg uuccaacagu    240
ccuaccucag auucugcauc uguacagaga gcagaugcug guuuaaacaa cugugaaggu    300
gcugcuggca gcacaucuga aaaaucaaga aaugugccug uggcugccuu gccuguaacu    360
caacaaauga cagaaaugag cauuucaaga gaggacaaaa uaacuacccc gaaaacagag    420
gugucagagc caguugucac ucagcccagu ccaucaguuu cucagcccag uucuucucaa    480
agugaagaaa aagcuccuga guugcccaaa ccaaagaaga acagauguuu uauguguaga    540
aagaaaguug gccuuacagg guuugacugc cgaugugggaa auuuguuuug uggacuucac    600
cguuacucug acaagcacaa cuguccauau gauuacaaag cagaagcugc agcaaaaauc    660
agaaaagaaa auccaguugu uguggcugaa aaaauccaga gaauauaaaa uuacuacaug    720
ugaagagacu gaaacuuugu uuuuauuuua auauaucgua ggaaaacauu aaagagcaga    780
ugcauggcca uuuuccuuug auguucucca gaguuuugcu uuauacuugu cugucauaua    840
auugaucuuu uaggauguuu gggguguuugu uacaggcaga auuggauaga uacagcccua    900
caaauguaua ugcccucccc ucaguaaaau uggacaaaaa uaugcacaac aaauugaaau    960
acacauauac uaggaacaaa auuuaguucc acgugccaaa cuaaaggaau gaaaucucug   1020
cauguuugca gcauaucugc cuuuugggaa uguaaucaag guauaaucuu uggcuagugu   1080
uaugugccug uacuuaaaaa aaaaaaaaug guacaccaga aaaggacugg cagucuacua   1140
ccauagucaa acuucaccuu aauuucgaca ugacuuuugg aagcaggaag aaagcuacaa   1200
aacugguauu ugguaccaug ugugagccug guuaaauugg ucuucuaaaa gcugucaauu   1260
aggacauucu gcgaaaggua acaucacaac ugguucuaag ucaaaccauc aagucaacag   1320
cagggugccu gagauaaucu uggaagcuua uugugcuggc cugcaccaga agauaucugc   1380
auucucauua cuaaaauugu agcacagaac ugcacuagga uuuguuuaca aggagaaauu   1440
aaacucuguu ugguuuucac auauagcagc ucuguuaaau aacaugcauc ugaauuuuaa   1500
guugcaaagg uaucugaaca guuaauuuuu caugugcauc uuuuguugaa uguuuugguu   1560
caagaaagaa uguuuaaagc uuuuuaaaga cuucaguucu uaauguaacu guacccuucu   1620
gcauggaaaa ucauaaccaa cauggcugca guagacuucu uuagugguau ccagcaccac   1680
uugcagaggg cugcuuuauc auauuguacu ugggguguagg acucuagugu ucuugggugu   1740
auugcauggg cugcauuauc uacagcauug uacaauaaca acuagaaaag gcgguauacu   1800
ucacugaugc uugucuggua auaucacuuc uguguuaaaa uggaagguuu uuugugaugu   1860
augaaacuug uguuuuuuau auauaaauga guauaguuag auuaguguug ugguaaugcc   1920
uguuuucauc uguaaauagu uaaguaugua cacaacaagg cacuacuucu gauuuuugca   1980
guguucaguc cuaguuuuuc uuuauuaaaa cauugaguuu ugcuucaauu uuauguaccu   2040
uaguucuaag uuagauuugc agauguguac agauaguuca uauuuaugua uugcacauaa   2100
ucaugcuauu cagcauugau gcuauauugu auuauguaaa uaauaaaagc aguguacaga   2160
gggaaaa                                                             2167
```

<210> SEQ ID NO 166
<211> LENGTH: 897
<212> TYPE: RNA
<213> ORGANISM: Homo sapiens

<400> SEQUENCE: 166
augacagaug ccgcugugue cuucgccaag gacuucuugg ccgguggagu ggccgcagcc 60
aucuccaaga cagcgguagc acccaucgag agggucaagc ugcugcugca ggugcagcau 120
gccagcaagc aaaucacggc agauaagcaa uacaagggca ucauagacug cgugguucgu 180
auccccaagg aacagggagu ccuguccuuc uggcguggga accuggccaa ugucaucaga 240
uacuucccca cccaggcucu caacuuugcc uucaaagaua aauacaagca gaucuuucug 300
gguggugugg acaagaggac ccaguucugg cgcuacuuug cagggaaccu ggcaucaggu 360
ggugccgcug gggcuacauc cuugugcuuu guguacccuc uugauuuugc ccguacccgu 420
cuagcagcug augugggcaa agcuggagcu gaaagggaau ucaaaggccu uggugacugc 480
cugguuaaga ucuacaaauc ugaugggauu aagggccugu accaaggcuu uaauguguca 540
guacagggca uuaucaucua ccgagcugcc uacuuuggua ucuaugacac ugcaaaggga 600
augcucccag aucccaagaa uacucacauc uucaucagcu ggaugauugc acagucuguc 660
acugcugucg cuggccugac uuccuauccu uuugacacgg uucgccgucg uaugaugaug 720
cagucuggac gcaaaggaac ugauaucaug uacacaggca cgcuugacug cuggcggaag 780
aucgcgcgcg augaagggag caaggcuuuu uucaagggcg cauggucca cguucucaga 840
ggcaugggug gcgccuuugu gcuugucuug uaugaugaga ucaagaaaua cacauaa 897

<210> SEQ ID NO 167
<211> LENGTH: 3873
<212> TYPE: RNA
<213> ORGANISM: Homo sapiens

<400> SEQUENCE: 167
cguagaaguu gucucugucg gcgggcgggc gggcaggauu ggggcaccga gaccggcgug 60
cggacagcag ggaucgcggg gagcgagggg ugcggcaugg agcuccgggc agucgguuuc 120
ugccuggcgc ugcuguggg uugcgcgcug gcggccgcgg cggcacaggg aaaggaaguu 180
guuuuguugg acuucgcagc aaugaaggga gagcucggcu ggcucacgca ccccuauggc 240
aaagggguggg accugaugca gaacaucaug gacgacaugc cuaucuacau guacucggug 300
ugcaacgugg uauccggcga ccaggacaac uggcuccgca ccaacugggu guaccgggag 360
gaggccgagc gcaucuuuau ugagcucaag uucacggugc gagacuguaa cagcuucccg 420
gguggcgccc augccugcaa agagaccuuc aaccucuacu augcagaguc agauguggac 480
uauggcacca acuuccagaa gcgccaguuc accaagauug acaccaucgc cccugacgag 540
aucacgguca gcagugacuu cgaggcucgc aacgucaagc ugaacguaga ggagcgcaug 600
guggggcccc uuacccggaa gggcuucuac cuggccuucc aggacaucgg cgccugcgug 660
cggcugcucu ccguucgcgu cuacuacaag aaguguccg agaugcugca gagcuuggcc 720
ugcuuccccg agaccauugc ugucgcuguu uccgauacac aaccccuggc cacgguggcc 780
gguaccugcg uggaccaugc cgugguggccu uauggggggcg agggggcucu caugcacugc 840
acgguggaug gcgaguggcu ggugccaucc gagugccugu gccaggaagg cuacgagaag 900
gucgaggaug ccugccgagc cuguucucca ggauucuuca agucugaggc aucugagagc 960
ccuucccugg aguguccaga gcauacccug ccauccacag agggugccac cuccugccag 1020
ugugaagaag gcuauuucag ggcaccugag gacccacugu ccaugucuug cacacgucca 1080
cccucugccc cuaacuaccu cacggcaugc augggugcca aaguagaacu gcguuggaca 1140
gcucccaagg acacuggugg ccgccaggac auugucuaca gugucacuug ugaacagugc 1200

-continued

```
ugcgcagagu cuggcgagug ugggcccugu gaggccacgg ugcgcuauuc agaaccuccu   1260

cacgcccuga cccgcacgag ugugacaguc agugaccugg agccccacau gaacuauacc   1320

uucgcugucg aagcacgcaa uggcgucuca ggccugguga cuagccgaag cuuccggacu   1380

gccagcguca guauuaacca aacagagccc cccaaaguga ggcuggagga ccgaagcacc   1440

accucccuga gugucaccag gagcaucccg gugucacagc agagccgugu guggaaguac   1500

gaagucaccu accgcaagaa gggggaugcc aacagcuaua auggccgccg cacggaaggc   1560

uucuccguga cccuggauga ccuugcuccg gauaccacgu accuggugca ggugcaggca   1620

uggacgcagg agggccaagg agccggcagc aaagugcacg aguuccagac gcuguccacg   1680

gaaggaucuc gcaacauggc ggugaucggc gguguggcug uagguguugu uuugcuucug   1740

guacuggcag gaguuggccu cuucauccau cgaaggagga ggaaccugcg ggcucgccag   1800

uccucugagg auguccguuu uuccaaguca gaacaacuaa agccccugaa gaccuaugug   1860

gauccucaca cuuacgaaga ccccaaccag gcuguacuca aguuuaccac cgagauccac   1920

ccauccugug uggcaaggca gaaggucauu ggagcaggag aguuuggaga ggucuauaaa   1980

gggacgcuga aggcauccuc ggggaagaag gagauaccgg uggccaucaa gacacugaaa   2040

gcgggcuaca cugagaagca gcgggугgac uuccugagcg aggccagcau caugggccag   2100

uuuagccacc acaauaucau ccgccuggag gcgguggucu cuaaauacaa acccaugaug   2160

auuaucacag aguacaugga gaauggagcg cuagacaagu uccuuaggga gaaggauggu   2220

gaguucagcg uacuucaguu ggugggcaug cugaggggua ucgcauccgg caugaaguac   2280

cuggccaaca ugaacuacgu gcacagagac cuggcugccc gcaacauccu cgucaacagc   2340

aaccuggugu gcaaggugцc cgauuuuggc cugucgcgug ugcuggagga ugaccccgag   2400

gccaccuaca ccacaagugg cggcaagauc ccuauucgau ggacagcccc agaggccauu   2460

uccuaccgca aguucaccuc agccagcgau guguggagcu acggcauugu caugugggaa   2520

gugaugacuu auggcgaacg gcccuuacug gaacugucaa accacgaggu caugaaagcc   2580

aucaacgacg gcuuccggcu ccccacgccc auggacugcc cuucagccau uuaccagcuc   2640

augaugcagu gcuggcagca agagcgcucc cgccggccca aguuugccga caucguuagc   2700

auccuggaca agcucauccg acgccccgac ucccucaaga cgcuggcuga cuucgauccc   2760

cgagugucca uccggcugcc cagcaccagc ggcucggagg gaguccccuu ccguacggug   2820

uccgaguggc uggagagcau caagaucgaa caguacacgg aacacuucau gguggcuggc   2880

uacacggcca ucgagaaggu gguacagaug uccaacgaag acaucaaaag gaucggagug   2940

cgucuuccug gccaccagaa gcgcauugcc uacagccugc ugggacucaa ggaccagguc   3000

aacacagugg ggauuccuau cugaguccau uggggcuguc acacaauacu ugaagagcca   3060

caguggucuc ccugccgauc uggugcuggc ccacuggaac uuuauuuauu ucuguuuccu   3120

cgucuaugcc ucccuaggac ucugcagggg cuuuuugaau gacaccugcc ugagccuggg   3180

aaacuuggau ugcuggucag ggcucucuuu ccccugaaaa ggacccagcu aagaacuuag   3240

caguuugcca uggccuuccc agcaucccccu gaggcuaaag uuccaccaag agucgauauc   3300

gacgagggac auuuccaaac ggaccucccc aucuucauuu ggccuccuga gaagccacuc   3360

uggagcugag gcuaagcacu aagcccagga ccauaugacu agcacuguac cgcccgcccc   3420

uaguuagagg guagguuuug gacuuggcug gguuguggцc acaagcaauc ucccagugcc   3480

uuuuacagac cccagucugc ccucccgucg agggccagcu ucuugcuuuc cuagggcccu   3540

cucaggaugc uuggcugugc ugagguuuuu auuaaauaua uauuuuauac uugcggaaag   3600
```

aaugagugug uggcagggac uugccagggc uggagacaga ggaucccccug caacaagaca 3660 uucccgggcu gggggcuggc ggaccugcag gagacuuucc gccaccaccc cgucuccagc 3720
cccuuuggac aaaugucgcu gucagugua cagauuucuu uuauugguu guuuuuuugu 3780 uguauuuuuu ugaaccuuaa cuuauuauuu uuuuuauauu uauuguuaga aaaugacuua 3840
uuucugcucu ggaauaaagu ugcagauggu uca 3873

<210> SEQ ID NO 168
<211> LENGTH: 1591
<212> TYPE: RNA
<213> ORGANISM: Homo sapiens

<400> SEQUENCE: 168
ccaaaaaccu uaauuuucuu ucuuguucgg uaccuacauu ggaaccacca aaaacaauua 60
uuucaguaaa ccguagccau gagggaaauc gugcacaucc aggccggaca guguggcaac 120
cagaucggug cuaaguucug ggaggucaua agcgaugaac auggcaucga ccccaccggu 180
accuaccacg gugacagcga ccugcagcug gaccgaaucu cuguguacua uaaugaagcc 240
acagguggca aguaugucccc ucgagcuauc uugguggauc uagaaccugg gacuauggac 300
uccguucgcu cagguccuuu uggccagauc uucagaccag acaacuucgu uuucggucag 360
ucuggggcag gcaacaacug ggcuaaaggc cacuacacag agggagcuga guugguugac 420
ucugucuugg auguggugcg gaaggaggcg gagagcugug auugccugca aggcuuucag 480
cugacccacu cacugggugg aggcacuggc ucuggcaugg gcacccugcu caucagcaag 540
auccgggaag aauauccuga ccguaucaug aauaccuuca guguggugcc cucgcccaaa 600
gucucugaua ccguggucga gcccuacaau gccacccugu cuguccauca guugguugag 660
aacacggaug agaccuacug caucgacaac gaggcccucu acgacaucug cuuccguacc 720
cucaagcuca ccacgccaac cuacggagac cugaaccauc ucgucucggc caccaugagc 780
ggcgucacca ccugccuccg uuucccgggc cagcuuaaug cugaccuucg aaagcuggcu 840
gucaacaugg ugccauuccc acgucuccac uucuucaugc cuggcuuugc cccucucacc 900
agccguggaa gccagcagua ccgggcccuc acugugccug aacuuaccca gcaggucuuc 960
gaugccaaga acaugauggc cgccugcgac ccgcgccacg gccgguaccu cacaguugcc 1020
gccgucuucc guggacggau guccaugaag gagguggaug agcagaugcu caacgugcag 1080
aacaagaaua gcagcuacuu cguggaaugg auccccaaca augucaagac agcugucugu 1140
gacaucccac cgcguggccu caagauggca gucaccuuca uuggaaacag cacagccauc 1200
caggagcugu ucaagcgcau cucugagcag uuuacggcua uguuccgccg gaaggcuuuc 1260
cuccacuggu acacggguga gggcauggac gagauggagu ucaccgaggc ugagagcaac 1320
augaacgacc uggugucuga guaccagcag uaccaggaug ccaccgcgga agaggaagag 1380
gauuucggag aggaggcaga agaggaggcc uaacggcaga gagcccugca ucagcucagg 1440
cugcuuagau cccucagccu uucuccaacu gcccuuuguc cuccaguuuc uuucugcugc 1500
cucugucuug uauuuguuuu gcuucuguuu ucucauuggg gguaaauggu gccuggcaca 1560
uggcaggcac ucaauaaaua uuuguuugug g 1591

<210> SEQ ID NO 169
<211> LENGTH: 1992
<212> TYPE: RNA
<213> ORGANISM: Homo sapiens

<400> SEQUENCE: 169

```
ggcagacaaa agaggccggc agugcagcuc gcgggacgca uggccgggcg cggaggacgg     60
gugcugcugg cgcugugugc cgcgcuggug gccggcgggu ggcugcugac gcgugaagcc    120
caggagcccg gggcgccagc ggcuggcaug aggcgccgcc ggcggcucca gcaagaggac    180
ggcaucuccu ucgaguacca ccgcuaucca gagcugcgcg aggcgcuggu gucgguaugg    240
cugcagugca ccgccaucag cagaaucuac acagugggcg ccagcuucga gggccgggag    300
cuccugguca ucgagcuguc ugacaacccc ggggucca ug agccgggu ga accugaauuu    360
aaauacaucg ggaacaugca uggcaaugag gcgguuggac gggaauugcu cauuuucuug    420
gcccaguacc uguguaacga guaccagaaa ggcaaugaga caauugucaa ccugauccac    480
agcacccgaa uucauaucau gcccuccuug aaccccgacg gcuuugagaa agccgcaugg    540
cagcccgggc agcugaagga cugguuugug ggccgcagca acgcccaggg aauagaucug    600
aaccguaacu ucccagaccu ggacaggauc guauauguua augagaaaga aggcgguccc    660
aacaaccacc ugcugaagaa ucugaagaaa auuguggacc aaaauucaaa gcuugccccc    720
gagaccaagg cugucauuca cuggaucaug gacauuccau uugugcuuuc ugccaaucug    780
cacggaggag accuuguggc uaauuaccca uaugaugaga cacggagcgg uacugcucac    840
gaauacaguu ccugcccuga ugacgcaauu uuccaaagcu uggcucgcgc guacucuucu    900
uucaacccag ucaugucuga ccccaaucga ccucccugcu gcaagaauga cgaugacagc    960
agcuuugaug auggaacgac caaugguggu gcaugguaca gcguccccgg uggaaugcaa   1020
gacuucaauu accugagcag cagcaacugc uuugagauca cuguggagcu uacgugugag   1080
aaguucccac cugaagagac ucucaaaagc uacugggaag auaacaaaaa cucccucauc   1140
aacuaccugg agcagauaca ccgaggugu u aaaggguuug uccgugaccu ucaggguaac   1200
ccgaaugcca acgcaaccau cucuguggau gggauagacc augaugucac cucggcuaag   1260
gauggggauu acuggcgauu gcuugcuccu ggaaacuaua aacuuacagc cuccgauccu   1320
ggcuaccugg caaucacaaa gaaaguggca guuccuuuua gcccugcugu uggggguggac   1380
uuugagcuug agucuuucuc ugaaaggaag gaggaggaga aggaagaauu gauggagugg   1440
uggaaaauga ugucagaaac uuugaauuuu uaagaaaggc uucuaacuaa uugcuuucau   1500
cuaucuauag acuguaguaa gaugcaaugu ggcucuuuuc uuuuagguug ugugcaguug   1560
auauuuaaca uugauuuauu uuugaucauu aaguaaauagu uacuaaucac guaaauacac   1620
ccggacagaa auauaaugcu ggacaucuuc auucuacauc aacauucgcu uaaaucauuc   1680
gaagccucuu uuaacguaau gggugacaau gucacuugac agaugcauga gagucacgau   1740
auagcugacu gugacccugc acugcaauca cauaguucca uauaaguugu ccuuagucuc   1800
uugugcugau ucacuguaua agcaugaucc ugguaaugca cuuuggaugg gaagaaaaug   1860
uacgugcuuu ucagaggggc ucugaacaga augaaaaccu aguucuugcg uguacuuuga   1920
agaauggaau uguauuaguc agcuguuaau gccacuucag aaguuugggg uuuugucuug   1980
auuguagauu gg                                                       1992
```

<210> SEQ ID NO 170
<211> LENGTH: 1828
<212> TYPE: RNA
<213> ORGANISM: Homo sapiens

<400> SEQUENCE: 170

```
gccacggacg ccucucugaa cggggaucca ggcaggauua gagcugccuc acugacuaca     60
```

```
ggccgugucg ugucaccguu ucugcaggca ccaugagcca ggacaccgaa guggacauga    120

aagaugugga gcugaacgag cuagaaccgg agaagcagcc caugaaugca gcggacgggg    180

cggcggccgg ggagaagaac ggucugguga agaucaaggu ggcggaggac gagacggagg    240

ccggggucaa guucaccggc uuauccaagg aggagcuacu gaagguagcg ggcagcccug    300

gcugggugcg cacccgcugg gcgcugcugc ugcucuucug gcucgguugg cugggcaugc    360

uggcgggcgc cgugguuauc aucguucggg cgccgcgcug ccgugagcug ccuguacaga    420

ggugguggca caagggcgcc cucuaccgca ucggcgaccu ucaggccuuu guaggccggg    480

augcgggagg cauagcuggu cugaagagcc aucuggagua cuugagcacc cugaagguga    540

agggccuggu guuaggccca auucacaaga accagaagga ugaaaucaau gaaaccgacc    600

ugaaacagau uaaucccacu uugggcuccc aggaagauuu uaaagaccuu cuacaaagug    660

ccaagaaaaa gagcauucac aucauuuugg accucacucc caacuaccag ggccagaaug    720

cgugguuccu cccugcucag gcugacauug uagccaccaa aaugaaggaa gcucugaguu    780

cuuggcugca ggacggugug gaugguuucc aauuccggga ugugggaaag cugaugaaug    840

cacccuugua cuuggcugag uggcagaaua ucaccaagaa cuuaagugag gacaggcuuu    900

ugauugcagg gacugagucc ucugaccugc agcaaauugu caacauacuu gaauccacca    960

gcgaccugcu guugaccagc uccuaccugu caaauuccac uuucacuggg gagcguacug   1020

aaucccuagu cacuagguuu uugaaugcca cuggcagcca auggugcagc uggagugugu   1080

cgcaagcagg acuccucgca gacuuuauac cggaccaucu ucuccgacuc uaccagcugc   1140

ugcucuucac ucugccaggg acuccuguuu uuagcuacgg ggaugagcuu ggccuucagg   1200

gugcccuucc uggacagccu gcgaaggccc cacucaugcc guggaaugag uccagcaucu   1260

uucacauccc aagaccugua agccucaaca ugacagugaa gggccagaau gaagacccug   1320

gcucccuccu uacccaguuc cggcggcuga gugaccuucg ggguaaggag cgcucucugu   1380

ugcacgguga cuuccaugca cugucuuccu caccugaccu cuucuccuac auacgacacu   1440

gggaccagaa ugagcguuac cugguggugc ucaacuuccg agauucgggc cggucagcca   1500

ggcuaggggc cuccaaccuc ccugcuggca uaagccugcc agccagcgcu aaacuuuugc   1560

uuaguaccga cagugcccgg caaagccgug aggaggacac cucccugaag cuggaaaacc   1620

ugagccugaa uccuuaugag ggcuugcugu uacaguuccc cuuuguggcc ugauccuucc   1680

uaugcagaac cuaccacccu ccuuuguucu ccccaggccu uuuggauucu agucuuccuc   1740

uccuuguuuu uaaacuuuug cagauuacau acgaauucuu auacugggug uuuuugucuu   1800

caaauaaaaa caucaccccu gccucaug                                       1828
```

```
<210> SEQ ID NO 171
<211> LENGTH: 2610
<212> TYPE: RNA
<213> ORGANISM: Homo sapiens
<220> FEATURE:
<221> NAME/KEY: misc_feature
<222> LOCATION: (2)..(2)
<223> OTHER INFORMATION: n is a, c, g, or u
<220> FEATURE:
<221> NAME/KEY: misc_feature
<222> LOCATION: (11)..(11)
<223> OTHER INFORMATION: n is a, c, g, or u
<220> FEATURE:
<221> NAME/KEY: misc_feature
<222> LOCATION: (26)..(26)
<223> OTHER INFORMATION: n is a, c, g, or u
<220> FEATURE:
```

<221> NAME/KEY: misc_feature
<222> LOCATION: (41)..(41)
<223> OTHER INFORMATION: n is a, c, g, or u
<220> FEATURE:
<221> NAME/KEY: misc_feature
<222> LOCATION: (45)..(45)
<223> OTHER INFORMATION: n is a, c, g, or u
<220> FEATURE:
<221> NAME/KEY: misc_feature
<222> LOCATION: (56)..(56)
<223> OTHER INFORMATION: n is a, c, g, or u
<220> FEATURE:
<221> NAME/KEY: misc_feature
<222> LOCATION: (70)..(70)
<223> OTHER INFORMATION: n is a, c, g, or u
<220> FEATURE:
<221> NAME/KEY: misc_feature
<222> LOCATION: (2262)..(2262)
<223> OTHER INFORMATION: n is a, c, g, or u
<220> FEATURE:
<221> NAME/KEY: misc_feature
<222> LOCATION: (2276)..(2276)
<223> OTHER INFORMATION: n is a, c, g, or u
<220> FEATURE:
<221> NAME/KEY: misc_feature
<222> LOCATION: (2288)..(2288)
<223> OTHER INFORMATION: n is a, c, g, or u
<220> FEATURE:
<221> NAME/KEY: misc_feature
<222> LOCATION: (2290)..(2290)
<223> OTHER INFORMATION: n is a, c, g, or u
<220> FEATURE:
<221> NAME/KEY: misc_feature
<222> LOCATION: (2298)..(2298)
<223> OTHER INFORMATION: n is a, c, g, or u
<220> FEATURE:
<221> NAME/KEY: misc_feature
<222> LOCATION: (2309)..(2309)
<223> OTHER INFORMATION: n is a, c, g, or u
<220> FEATURE:
<221> NAME/KEY: misc_feature
<222> LOCATION: (2311)..(2311)
<223> OTHER INFORMATION: n is a, c, g, or u
<220> FEATURE:
<221> NAME/KEY: misc_feature
<222> LOCATION: (2324)..(2324)
<223> OTHER INFORMATION: n is a, c, g, or u
<220> FEATURE:
<221> NAME/KEY: misc_feature
<222> LOCATION: (2333)..(2333)
<223> OTHER INFORMATION: n is a, c, g, or u
<220> FEATURE:
<221> NAME/KEY: misc_feature
<222> LOCATION: (2335)..(2335)
<223> OTHER INFORMATION: n is a, c, g, or u
<220> FEATURE:
<221> NAME/KEY: misc_feature
<222> LOCATION: (2412)..(2412)
<223> OTHER INFORMATION: n is a, c, g, or u
<220> FEATURE:
<221> NAME/KEY: misc_feature
<222> LOCATION: (2418)..(2418)
<223> OTHER INFORMATION: n is a, c, g, or u
<220> FEATURE:
<221> NAME/KEY: misc_feature
<222> LOCATION: (2435)..(2435)
<223> OTHER INFORMATION: n is a, c, g, or u
<220> FEATURE:
<221> NAME/KEY: misc_feature
<222> LOCATION: (2447)..(2447)
<223> OTHER INFORMATION: n is a, c, g, or u
<220> FEATURE:
<221> NAME/KEY: misc_feature
<222> LOCATION: (2462)..(2462)
<223> OTHER INFORMATION: n is a, c, g, or u
<220> FEATURE:
<221> NAME/KEY: misc_feature
<222> LOCATION: (2475)..(2475)
<223> OTHER INFORMATION: n is a, c, g, or u
<220> FEATURE:
<221> NAME/KEY: misc_feature
<222> LOCATION: (2483)..(2483)
<223> OTHER INFORMATION: n is a, c, g, or u
<220> FEATURE:
<221> NAME/KEY: misc_feature
<222> LOCATION: (2493)..(2493)
<223> OTHER INFORMATION: n is a, c, g, or u
<220> FEATURE:
<221> NAME/KEY: misc_feature
<222> LOCATION: (2513)..(2513)
<223> OTHER INFORMATION: n is a, c, g, or u
<220> FEATURE:
<221> NAME/KEY: misc_feature
<222> LOCATION: (2523)..(2523)
<223> OTHER INFORMATION: n is a, c, g, or u
<220> FEATURE:
<221> NAME/KEY: misc_feature
<222> LOCATION: (2535)..(2535)
<223> OTHER INFORMATION: n is a, c, g, or u
<220> FEATURE:
<221> NAME/KEY: misc_feature
<222> LOCATION: (2552)..(2552)
<223> OTHER INFORMATION: n is a, c, g, or u
<220> FEATURE:
<221> NAME/KEY: misc_feature
<222> LOCATION: (2555)..(2555)
<223> OTHER INFORMATION: n is a, c, g, or u
<220> FEATURE:
<221> NAME/KEY: misc_feature
<222> LOCATION: (2566)..(2566)
<223> OTHER INFORMATION: n is a, c, g, or u
<220> FEATURE:
<221> NAME/KEY: misc_feature
<222> LOCATION: (2590)..(2590)
<223> OTHER INFORMATION: n is a, c, g, or u

<400> SEQUENCE: 171
gncuuaagcc ncguuuauuu ugaugnccug uuggcucagu naugnccaag augccnauug 60
uuuuugcccn aaauaaauuu acugaacuug ggcuaaaacc aaaccuuggc acacaggugu 120
gauacaacuu aacaggaauc aucgauucau ccauaaaauaa uauaaggaaa aacucaagug 180
guagccuguc uuaaggcuuu ugauacuugc agauugggga aaaacaaaca acaaacgucu 240
ugaagcauau uaauggaauu aguuucuaau guggcaaacu guauuaaguu aaaaguucug 300
auuugcucac ucuauccugg auagguauuu agaaccugau aauagucuuu aaacaagcca 360
uuccagucau gaugaggug a uguauggaua caugcauaca uucaaagcac uguucucaaa 420
guuaaugcaa guaaauacag caauuccucu uucaauguuu aggcagaucg uuaacuauga 480
gcuagccaaa ugugggcaug uuauuacagg gaaaguuuaa aggucugaua acuugaaaua 540
gguuuaggag aauucaucua cuuagacuuu uuaaaugccu gccauaaaaa auugaaaugg 600
uagaauggcu gaccacagca augaccagcc cucaccuagg gcucuggaug auuuuugguc 660
uaauaacgca ugcuaguguu gauguuuuuu ggucaagaug ggaaugaaca ggaagaauua 720
ugcagcaggc uuuauuuuaa augccgauuc acauuacucu guucaagcug cguugagaug 780
uuaaacuggc uuacuauaga cuuuguaaaa aaaaaaaaaa ccaaacaaau ggcuccagaa 840
gaguaacaaa cugaaaucug agaucacaca gguuggaaau auguacauaa cugaacaagg 900
ugucaauucu gcucuacagu gcaguuuagu caguuuuagu ugcauagguu uccauuguuu 960
uuauagucug uuuaugcuaa aucuggccaa agaugagcau uguccaccac uaaaaugccu 1020
augccacugg gaauucuggg uuaauuuugu gaccagaaug cagugaucaa aauguucaau 1080
cuuuuuacag uggcauagga agauggcaaa aauuuccuaa agugcaauag auuuucaagu 1140
guauugugcc uuguucuaaa acuuuuauua aguaggugca cuugacagua uugaggucau 1200

-continued

```
uuguuauggu gcuauuucaa uuagucuagg uuuaggcccu uguacauuug gcccauaacu   1260

uuuuacaaag uacuucuuuu auugcacauu cagagaauuu uauauauaug ucuugugugc   1320

guguccuuaa acuuccaauc uuauuuuguc ucuuggagau uguugaacgc agcuugucua   1380

ggaaagggau gggacuagau ucuaaaauuu auuugggacc augggaauga uaguugggaa   1440

gaaacuuugc acacgacaga uuucuagaua cuuuuugcug cuaguuuuau guaauauuua   1500

uugaacauuu ugacaaauau uuauuuuugu aagccuaaaa gugauucuuu gaaaguuuaa   1560

agaaacuuga ccaaaagaca guacaaaaac acuggcacuu gaauguugaa ugucaccgua   1620

ugcgugaaau uauauauuuc gggguagugu gagcuuuuaa uguuaaguca uaauaaacuc   1680

uuaagucaaa uuaagcagac ccggcauugg cguguagcca uaacuuucug auguuaguaa   1740

aaacaaaauu ggcgacuuga aacuaaauca ugccaagguu ugauacacuu gucuugagau   1800

auuaacgaaa cacuuccaaa cacugauaca aaguguccag auucucagau guuuguugug   1860

ugaguuuugu uuaguuguau uuuuuuuuca gugaaugucu ggcacauugc aauccucaaa   1920

cauguggua ucuuuguugu auuggcauau ucagugacuu guacauucag caauagcauu   1980

ugagcaaguu uuaucagcaa gcaauauuuu caguuauguu uccaaauuaa gaauggguuu   2040

aaacuugcug aauguaaaga uugacccuca agucacugua gcuuuaguag uugcuuauug   2100

uauuaguuua gaugcuagca cugcaugugc ugugcauauu cugguuuuau uaaaauaaaa   2160

aguugaacug cacagucucc uuuguuguug ucaauugugg uuuacuuuua gaggugaaaa   2220

uaaaguugug cucuugccuc gugccaauau guacauaacu gnacaaggug ucaauncugc   2280

ucuacagngn aguuuagnca guuuuagung nauagguucc caunguuuuu aungncuguu   2340

uaugcuaaau cuggccaaag augagcauug cccaccacua aaaugccuau gccacuggga   2400

auccuggguu anuuuggnga ccagaaugaa gugancaaaa uguccanucu uuuuacagug   2460

gnauaggaag auggnaaaaa uunccuaaag ugnaauagau uuccaagugu uungugccug   2520

guncuaaaac uuuunuuaag uagggugcac unganaguau ugaggncauu gguuauggug   2580

cuauuuccan uuagucuagg uuuaggcccu                                     2610
```

<210> SEQ ID NO 172
<211> LENGTH: 3657
<212> TYPE: RNA
<213> ORGANISM: Homo sapiens

<400> SEQUENCE: 172

```
cucggucucc aagauggugg cuaacaaaac gugaggccua gagguugauc cuaggucacu     60

ggaagcaugu ccuugaagag gacuaugggc aucuggguuc uuccucuucu acuuggccac    120

gagguaaccg gcuucuugua ccacgugugc ucaccucuac aaucugugcg gauucagacu    180

ccaagcaacu aggcuaccca gugacaggcu aaaaacuaca gcucuaacgu cuuggaaggc    240

gauuccaugg accaggaugu ggaaagccca guggccauuc accagccaaa guugccuaag    300

caggccaggg acgaccugcc gagacacauc agccgagaca ggaccaaaag gaaaauccag    360

agguacguga ggaaggaugg gaagugcaac guucaccacg gcaaugugcg ggagacguac    420

cgauaccuga cggacaucuu caccacccug guggaccuga aguggagauu caaccuguug    480

aucuuuguca uggucuacac agugacgugg cuuuucuuug ggaugaucug guggcugauu    540

gcguacaucc ggggagauau ggaccacaua gaggaccccu cguggacucc uugugucacc    600

aaccucaacg gguuugucuc ugcuuuuuua uucuccauag agacagaaac caccaucggu    660

uauggcuacc gggucaucac ggacaagugc ccugagggga uuauucuccu cuuaauccag    720
```

-continued

```
uccguguugg gguccauugu caacgccuuc augguaggau guauguuugu gaaaauaucc    780
caacccaaga agagggcaga gacccugguc uuuuccaccc acgcggugau cuccaugcgg    840
gaugggaaac ugugcuugau guuccgggug ggggacuuga ggaauucuca cauuguggag    900
gcauccauca gagccaaguu gaucaagucc aaacagacuu cagaggggga guuuauuccc    960
cucaaccaga cugauaucaa cgugggguac uacacagggg acgaccggcu cuuucuggug   1020
ucaccauuga uuauuagcca ugaaauuaac caacagaguc ccuucuggga gaucuccaaa   1080
gcgcagcugc cuaaagagga acuggagauu guggucaucc uggagggaau gguggaagcc   1140
acagggcagu ucugaaaucg aaaucaagca gaggucuaua agaacacccu ggagaccccc   1200
augcugcugg aucuugggguc caugaacugc uuuuauuugc ugcaaucaaa aaugcuaguc   1260
gcugaucuga uaggagagga aacgagacuc agagccugaa ggauaaacacg cugagggcug   1320
auuucauaca cucuucccgg cuggaucauc ccagccccca cagcguccag gcuuaguuuc   1380
uuccuuuguu uuaacaaucu auacuuccuc cagccugggc gagcuaguau acccagaguu   1440
ugguuuuguu ucuuuucaga gcuguaagcc cagugcccag ugaccucauc ugggaggaga   1500
guuaagcaau aagaccugaa augcuaaacu cugggguaga aaaccucugc agagacagcg   1560
ucucugggaa gucucuacag agacagagua gggaagucuc acgaagguca gagucuuacu   1620
uccauaccug gagaaauccg cccguccguu cagugccggu uucaacuccu cugccaaaga   1680
cuucuuucca agacacuggu aucagcuauc ccagcaguaa cuuuggcagu auauaaauca   1740
auggcacugc cccauaaaac cccguugagu aaaaccuaug gucuucaaca gcuggggagc   1800
cuguagccca gcuccugugu gaggcuaagg cuguggagac caugccugcu caccuccucg   1860
uugaaaagca aaacacugua agaaaccuaa caugacuuuu uccaacauuu cucaggcugg   1920
ggagaagacu ugguccacaa agagcuugag gucuugaucu ggaucccuag cauccaugga   1980
agaaggugggg caugaucacc cacacuccuc aucccauagc ucugaaugag guaggcagau   2040
uccuggggcu caccagcuca uccuaacagc caggucccaa ugagggacug ucuacaaaag   2100
aacaagaggu ggauccugag aagcgacacc caagcuugac cucuagcccc uguacacacc   2160
uguuaagcac cugggcaucg ggacacacac ucgcaauuug caaacaaggc aaauucucac   2220
acuucagaag gcacugagag aaucccauaa gcucaaaaag uuaggagcca agauugacca   2280
uuaaugacuu ggguugaaaa gacuaaacca cuggauagaa uguuucauua cuaaaacacc   2340
uuaccugaaa aguauuacug cucuucuuuc ugcaacugga ccaugcagag auccacaaag   2400
agaugcccag agauuauuag ugauggucau augauauaca caauguggac ucuaagccaa   2460
ggccccauca acucagaucc agaggcugac agugugcuua ucuuagagau accacagugg   2520
cugccuaauc accacguccu uaagucaggg gaguuugauu auuuccuaug aacaccgagu   2580
ggggacagcg gauuaccaau gaagcaaucc aaccugacaa uccuaaccac ccagaagagg   2640
aucgcugggg gaaagcauga auuauuuacg ugucaacaug ugcacacucc ggccacgcag   2700
cucaacagcc aggagugcuu cuccacuuag cccugcccug gcauccauuu augaucucgu   2760
cuguuguguu aauuacccag cuagcuuuuu ucucaaaaau aauaucuccc agccauagac   2820
cuacucaucu guguccucuu uaauuucaac ccacaguuac aucauucacu ggcuugcuca   2880
guuucuucaa cucugaaaug ggaaugauga ugaugaugcc ucuuccccca agccaccauc   2940
cucccccgug accuuccuag guacagacuc aaaccaggga agauuauuuc cuucucauag   3000
gccacagggu gaaaugcaau aaagaacaaa gccuuguagg gaggcagagg gaaagaccag   3060
```

-continued

```
uccucacaag aggcuccauu guuuccaggg acuuugaagc uuggacagaa ugucagauga   3120

uccccuuuga aggugcucca aagagucaau gugaaaaaua uugacugaug ugugcccguc   3180

cacaagccaa ggugccucug cccuggucac cuaccaugaa uuauaaacug augauauuug   3240

aaauaauaag gaacacugga gccggccaga aaggauucug caguccccaua aauagcaaca   3300

uucaucacua caaugccugc caacgguggc cgugaaugua gauuaccccc ggcucuucug   3360

aggccacuga ggacagggca aacuaccucu gagaauggag gcucacuguu cugcauccca   3420

cuucuaaaug uuccaugaau uuuuugagac aucucccaua ucccuguuag aaagauucaa   3480

ccuugugcua uuaaccaaau cauuuugaau uccauaaacc ucuacucuaa aguauacacu   3540

uaauucuaca auacagacaa caaauaugac uuuuuccuau gaaagaguga uaaagauacu   3600

guaucagucu gcuuugacuc aaaaaaaaaa aaaaaaaaaa aaaaaaaaaa aaaaaaa      3657
```

<210> SEQ ID NO 173
<211> LENGTH: 2267
<212> TYPE: RNA
<213> ORGANISM: Homo sapiens

<400> SEQUENCE: 173

```
uggaaugggu gcuaggugaa ggcuuuguug aaucaggaug cugagcuggu guuuuuacag     60

guccagauau gaugagcugg aguuuuggua ggcccaggua ccuccuccaa aauugaccac    120

auaauugguc acaaaucagg ccuccacaga uacaaaaaua uugaaauuau cccaugcauc    180

cugucugauc accacagacu aaggcugauc uucaauaaca acauaaaaau agaaagccag    240

guucacugcu gcggcugcgc cuccuuguuc ucagcgucac cacugccgcc augcccggag    300

gguugcuucu cggggacgaa gcccccaacu uugaggccaa uaccaccauc ggccgcaucc    360

gcuuccacga uuuccuggga gauucauggg gcauucucuu uucccaccca cgggacuuua    420

ccccagugug caccacagaa cuuggcagag cugcaaagcu ggcgccagag uucgccaaga    480

ggaauguuaa guugauugcu cuuucaauag acaguguuga ggaucaucuu gccuggagca    540

aggacaucaa ugcuuacaau ggugaaacac ccacggaaaa guugccauuu cccaucauug    600

augauaaggg cagggaccuu gccauccuuu ugggcauguu ggauccaguc gagaaggacg    660

auaacaacau gccugugacg gcccgugugg uguucauuuu uggcccugac aagaaacuga    720

agcugucuau ccucuacccu gccaccacga gcaggaacuu ugaugagauu cucagagugg    780

uugacucucu ccagcugaca ggcacaaagc cgguugccac cccaguugac uggaagaagg    840

gagagagcgu gaugguaguc ccccacccucu ccgaagagga agccaaacaa uguuucccua    900

aaggagucuu caccaaagag cucccgucug gcaaaaaaua ccuccguuau acaccccagc    960

cuuaagucuu ugcggaaauu ggggcugcau cugcacgucc agcacugggg ccugaggacg   1020

ucagccggca gccgugggguc cuugcagcag guccguagaa agaucguggc augaucacag   1080

ccgguccugu agaucgcucg cuauacuacu gggucauuaa auggaaaugg caccaaaacc   1140

uucucgggau ucuuuacucu gugccuucgc cagcauucug ccccucugcc ugucacagug   1200

cccuacugac uggcucucuu ugaaacgaau uauguauuga agauuccuua ggucucugca   1260

gggucuuuga ucagcaagca agguaguguc aguguggggcu cugugcuaga augaugaaac   1320

accuuuugua gcuuuccgaa cggaaucuuc uguuacccau uuuggagagc acugacaugg   1380

ggagaagcuu ucaauucugu auuuuuagua aauaaagugg ggacagccgg gagaauucuu   1440

acagggaauc uauuguaagu uucuaucgaa gugggcucag aaagccuuuc gccucccaag   1500

agugcgcaug uaccuccuag aguuuccaca ucugcucucu ggugaugucu gccugugaac   1560
```

gcaccuuaua aaagacgggc ggugacagug uuuuaccacu caguguccua guagugggug 1620
gccauuucug aauucugcuu uuugagguuc aacaaauaaa auccugauca gaaaaaaaaa 1680
aaaauagaaa gccaacauuc auguggaaac ugaacaacac uacucaauga uuccuugguc 1740
agagaugaaa uaaagaaaga aauuaaagac uuuuuagagu uuaaugaaaa ugaagccaca 1800
acauacccaa acuuauggga cacaaugaag gcauuucuaa gaggaaaacu cauagcccug 1860
agugcaucca aaggaaaaaa aaaaaaaccu agagagagug uacacuagca gccugacugc 1920
acacuuagaa gcucugcaaa aaaaggaauc aaauucaccc aagaggaaua gacagcagga 1980
aauaaucaaa cuuagggcug aaaucaacca aauggaaaca aaaagaacua uucaaagagu 2040
gggccaaacc aggagcuagu ucuuugagaa aaucaacaag auagauaaac ccuuagccag 2100
acucacuaga gggcacaggg acagcauccu aauuaacaaa aucagaacug aaaagggaga 2160
cauaacaaca gauccugaag aaauccaaaa caccaccaga uccucuacaa aaggcuauac 2220
ucaacaaaac uggaaaaccu ggaugaaagg aaaagcuucu agacaga 2267

<210> SEQ ID NO 174
<211> LENGTH: 2834
<212> TYPE: RNA
<213> ORGANISM: Homo sapiens

<400> SEQUENCE: 174
augagcaccg cggaucugau gcgucgcugg gucaucgccc ugcuccuugc ugcugccgga 60
guugcaguag aagacucagg cagcaggaac gaguuccagu guagagacgg aaaaugcauc 120
gcuagcaagu gggugugcga uggcagcccc gagugcccgg auggcuccga ugagucccca 180
aagacaugca ugucugucac cugucagucc aaucaauuca gcuguggagg ccgugucagc 240
cgaugcauuc cugacuccug gagaugugau ggacagguag acugugaaaa ugacucagac 300
gaacaaggcu guccccccaa gacgugcucc caggaugacu uccgaugcca ggauggcaag 360
ugcaucuccc cgcaguuugu gugugaugga gaccgagauu gccuagaugg cucugaugag 420
gcccacugcc cagccaccac uuguggcccc gcccacuucc gcugcaaauc auccauaugc 480
auccccaguc uuugggccug cgacggggau gucgacugug uugacggcuc ccaugagugg 540
ccacagaacu gccaggccga agacacggcc uccaaaggcg uuagcagccc cugcuccucc 600
cuggaguucc acugugguag cagugagugu auccaucgca gcugggucug ugacggcgag 660
gcagacugca aggacaaguc agaugaggag cacugcgcgg uggccaccug ccgaccugau 720
gaauuccagu gugcagaugg cuccugcauu cacgguagcc gccaguguga ccgugaacau 780
gacugcaagg acaugagcga cgagcucggc ugcgucaaug ugacacagug ugauggcccc 840
aacaaguuca agugucacag uggggagugc aucagcuugg acaaggugug cgacuccgcc 900
cgcgacugcc aggacugguc ggaugagccc aucaaggagu gcaagaccaa cgaguguuug 960
gacaacaaug guggcuguuc ccacaucugc aaggaccuca agauuggcuc ugagugccug 1020
ugucccagcg gcuuccgguu gguggaccuc cacaggugug aagauauuga cgagugucag 1080
gagccagaca ccugcagcca gcucugugug aaccuggaag gcagcuacaa gugugagugc 1140
caggccggcu uccacaugga cccacacacc agggucugca aggcuguggg cuccauaggc 1200
uaucugcucu ucaccaaccg ccacgagguc cggaagauga cccuggaccg cagcgaguac 1260
accagucugc uccccaaccu gaagaaugug guggcucucg acacggaggu gaccaacaau 1320
agaaucuacu gguccgaccu gucccaaaaa aagaucuaca gcgcccugau ggaccaggcc 1380
ccuaacuugu ccuacgacac caucaucagu gaggaccugc augccccuga cgggcuggcg 1440
guagacugga uccaccgcaa caucuacugg acagauucag ucccaggcag cguaucugug 1500
gcugacacca agggcguaaa gaggaggaca cuguuccaag aggcaggguc cagacccaga 1560
gccaucguag uggacccugu gcauggcuuc auguacugga cagauugggg aacacccgcc 1620
aagaucaaga aagggggguuu gaauggugug gacauccacu cacuggugac cgaaaacauc 1680
caguggccaa auggcaucac acuagaucuu uccaguggcc gucucuauug gguugauucc 1740
aaacuccacu cuaucuccag caucgauguc aaugggggca aucggaaaac cauuuuggag 1800
gaugagaacc ggcuggccca ccccuucucc uuggccaucu augaggacaa aguguauugg 1860
acagauguca uaaacgaagc cauuuucagu gccaaucgac ucacggguuc agaugugaau 1920
uugguggcug aaaaccucuu guccccggag gacauugucc uguuccacaa ggucacacag 1980
ccuagagggg ugaacuggug ugagacaaca gcccuccucc ccaauggugg uugccaguac 2040
cugugccugc ccgccccaca gaucggaccc cacucgccca aauucaccug cgccugcccu 2100
gauggcaugc ugcuggccaa ggacaugcgg agcugccuca cagaagucga cacuguacug 2160
accacccagg ggacauccgc cguccggccu guggucaccg caucagcuac caggccaccg 2220
aagcacagug aggaucucuc agcucccagu acuccuaggc agccugugga caccccaggg 2280
cucagcacag uggcgucagu gacagugucc caccaagucc agggugacau ggcuggcaga 2340
gggaaugagg agcagccaca ugguaugagg uuccugucca ucuucuuccc uauugcacug 2400
guugcccucc uuguccuugg ggccguccug cuguggagga acuggcggcu gaagaacauc 2460
acaaucaaca gcauaaacuu ugacaaccca gucuaccaga agaccacaga ggacgagcuc 2520
cacauuugcc gaagccagga uggcuauacc uaccccucaa gacagauggu cagccuggag 2580
gacgaugugg caugagcagc cgggagagcc gucucuuucc gggauccauu gccaagcuua 2640
ggcagaaaag acacucucuc cagaccuccc cauccagcac ugguccugcc accucccugg 2700
gucuguguug cucaaagcaa gauagagcaa agcugggcug gggggccaag cucagcuucc 2760
ugucugcccc agguucuguu uuauauauuu auugucuggg acagaaaagg cuacuggcug 2820
ugcuugaaau ucga 2834

<210> SEQ ID NO 175
<211> LENGTH: 2940
<212> TYPE: RNA
<213> ORGANISM: Homo sapiens

<400> SEQUENCE: 175
accggucauc gggcucuucc uugggcucag ggcacggauc aaguccucgg cucgcucggc 60
cagcaccgcg gcaccauggc gcaggagcug cagcaccccg aguucgcgcg cgcaggccag 120
caggcugggc ugcaggugug gagggucgag aagcuggaac ugguaccggu gccccagggu 180
gccuauggug acuuuuacgu cggagagccc uaccuggugc ugcacaccac caaguccagc 240
aggggcuucu ccuaccgccu gcauuucugg cugggaaagg aguguucccca ggaugagagc 300 acagcggcug ccaucuuuac gguccagaug gacgacuauu uggguggcaa gccaguccag 360
agcagagagc uucaaggcua ugagucgacu gauuuugugg gcuauuucaa aggcggucug 420
aaguacaagg cuggaggugu ggcuucugga cuaaaccaug uccucaccaa ugaucugacu 480
gcgaaaagac uucugcacgu gaagggucgg agagugguca gagccacuga aguuccccuc 540
agcugggaga gcuucaacaa gggcgacugc uucaucauug accuuggcac cgaaauuuac 600
caguggugug guuccuccug caacaaauau gagcgucuga aagcaagcca gguggccauu 660

```
ggcauccggg acaaugagag gaaaggaaga ucucaacuca uuguggugga agaaggaagu    720
gaaccaucag agcucaugaa gguuuuaggg agaaagccug agcuuccaga uggggacaau    780
gaugacgaug ucguagcaga cauaaguaac aggaagaugg cgaagcucua caugguuuca    840
gaugcaagug gguccaugaa aguaacacug guggcugaag aaaacccguu cuccauggga    900
auguugcuuu cugaagaaug cuucauuuug gaccauggug cugcaaaaca aauuuuugua    960
uggaaaggua aaaaugcuaa cccacaggag aggaagacug ccaugaagac agcugaggag   1020
uuuuuacaga aaaugaagua uucuacuaau acucaaauuc agguucuucc ggaaggcggu   1080
gaaacaccaa uuuucaaaca guucuuuaag gacuggaagg auaaagacca gagugauggc   1140
uuugggaagg uguacaucac ggagaaagug gcucagauaa agcagauucc guuugaugcc   1200
ucaaaacugc acaguucucc gcagauggca gcccagcaca acauggugga cgauggcucu   1260
ggcggggugg agaucuggcg uguagagaac aguggguagag uccagauuga cccaagcucc   1320
uauggcgagu ucuauggcgg ugacugcuac auuauccucu acacuuaucc cagaggacag   1380
aucaucuaca cauggcaagg agcaaaugcu accagagaug aacugaccau guccgcguuu   1440
cugacugucc aguuggaccg gucccuugga gggcaggcug ugcagguccg ugucucucaa   1500
ggcaaagagc cugcucaccu gcugaguuug uucaaagaca aaccacucau uauuuauaag   1560
aaugggacau ccaagaaaga agggcaggca ccggcucccc cuacacgccu uuuucaaguc   1620
cggaggaacc uggcaucuau caccagaauu guggagguug acguugaugc aaauucauua   1680
aauucuaaug acacuuuugu ccuaaaacug ccacgaaaca auggcuucau cuggauagga   1740
aaaggugcua gccaggagga ggagaaagga gcagaguaug uggcugaugu ccucaagugc   1800
aaagcuucaa gaauucaaga aggcaaggaa ccagaggaau ucuggaacuc ucuuggaggg   1860
aggggagacu accagacuuc accauugcua gaaacucggg cugaagacca uccaccucgg   1920
cuuuaugguu gcuccaacaa aacuggaaga uucauuauug aagaaguucc gggagaguuc   1980
acccaggaug accuggcaga agaugauguc augcuacuug augcguggga acagaucuuu   2040
auuuggauug gcaaagaugc caaugaaguu gagaaaaagg aaucagugaa gucugccaaa   2100
auguaccugg agacagaccc uucuggaaga gacaagagga caccgauugu caucaucaag   2160
caagggcacg agccccccac auucacaggc ugguuucugg gcugggacuc cagcaggugg   2220
uaaaaccagc aacuauccug gcugcauugg ggcagcugcc acuuuguugu uggggaauug   2280
uuuacuuuuu guuauuggcu uuugaagaua aacuccugcc aaauggauau auaucuauau   2340
cuauaucuau aucuauaucu auaucuauau cuauaucuau aucuauaucu aucuauaucu   2400
aaucuauauc uaucuaucua ucuaucuauc uaucuaucua ucuaucuauc uaucuauaug   2460
cuccucuuuu ccuucucuuu caaagggaau ugcuguaugu uacuauacug aaauaaccua   2520
aagcaaccau uuguuuucga gcaauuuugc aaucuggggga ccucugagga aguaauuuug   2580
ucauucagcc acugcuagcc aaacuugucu uuucccauag agaggaagga gagccacagu   2640
gcuucuaagc auuuccccgu cugcuacucu guuugcagug agcuuuacuu uauguauggc   2700
uuuaacaaug ccuugcuguu ucccaucuca agucaaugcc acuuggaugc cauucacucc   2760
caaguguccu uacauaggau gaacuucuuu agcuuuuuua gaaaacuaaa aucaugucuu   2820
uuaugauaaa acacauuuua uuucuauaag uuuaacuuua uauauuugau agcacaugcu   2880
caauagcaua aagaauaugc auugaaugau guuuuucaua auuaaaauau auccuuuugg   2940
```

<210> SEQ ID NO 176

<211> LENGTH: 1714
<212> TYPE: RNA
<213> ORGANISM: Homo sapiens

<400> SEQUENCE: 176 cagggguugag agcaagaagg ugcaggaugu aggccagcag aauuaucaga cccaguggcg 60
gcuucugcca cuggaagaau uuccaacaua aaacagauga ucaguuuggg acaaucgauu 120
cugcgaccag agguagugc aucugguuac uuuuaaaauu cagauugucu gguguuuucc 180
aaucacucgc gacuguaauu ugaaguugga uucugagaua auacaaucgc ugucgcucua 240
guuuauaaag cuguccaaga ucugcccagu cccagauguc cugggucuc agggcggcug 300 uggucugcgc ccuucuccug cagcuggaug ccagaccauc cuggacucgg aucccuuugg 360
guucacacuc gcuuagguau uucuacaccg cuguguccg gccuggccuu ggggagcccu 420
gguucauaau cgucggcuau guggacgaca ugcagguccu gcgcuucagc agcaaggagg 480
agacuccgag gauggcaccc uggcuggagc aggaggaagc agaugacugg gaacagcaga 540
cucauauagu cacaauucaa ggacagcugu cugaaaggaa ucugaugacc cugguucauu 600
uuuacaacaa gagcauggac gacucucaca cacuacagug gcugcaggac ugcgaugugg 660
agccagaucg gcaccugugu cucugguaca accagcucgc cuaugauagc gaggaucucc 720
ccacccugag cgaaaaccca aguuccugua caguggggaaa cagcacugua ccucagaucu 780
cucagcaccu ggagggccac ugcucagaug ugcugcagaa auaccuggaa aaagggaagg 840
agaggcugcu gcguucagac ccccccaaagg cacaugugac ccgucacccc agaccugaag 900
gugaugucac ccugaggugc ugggcccugg guuucuaccc ugcugacauc acccugaccu 960
ggcagaagga uggggaggag cugacccaag auguggaguu uguggagacc aggccugcag 1020
gggauggaac cuuccagaag ugggcagcug uggugugcc ucuuggaaag gugcagaguu 1080
acacgugcca uguggaccau gaggggcugc cugagccccu cacccugaga ugggagccug 1140
caugguacca aaagccuugg auuuggauug uugccacggu uuuuuccauu uugcucauuu 1200
gucucugugu ggcucgcaga cccaugaaga agaaugcagg ugggagagga aggcgugaca 1260
cccaagaagc aggcagagac aguccccaag acucuagcaa gacuguugug gaugaugagg 1320 agauggggu uugcuuuugg aagauuaagu ccuguaaaac uugucuaggc cacuccccag 1380
gaacuucagg aucaucuggg agaugccccu uugaguggcu gggcugugag gacagcaggc 1440
caguucuugc cacccuggac agaaacacau cucaccuuuc uggcucgagg aucugaacac 1500
cugucucuug ccuacucggc uucuagucag gcauuuuguc accuugucaa gggucccagg 1560
gacacaaagc ucccuccucu cacccacagc acucuggguc cuaccccccaa ugcuucaggg 1620 acauuuaauc aggucaaauu gggaucaaug gcuuugaugc agaaaagaac uguggacuaa 1680
uagagauagg guuuaauaaa aaaaauaucu uuuu 1714

<210> SEQ ID NO 177
<211> LENGTH: 467
<212> TYPE: RNA
<213> ORGANISM: Homo sapiens

<400> SEQUENCE: 177
uuuuuuuuuu uuuuuuucaa cuuuaaagac uggauuugag guucagucug ggucucuggg 60
ggggaccucu gucaucacgc cuauaaucau cccgagagua gucaucccug gagcuccacg 120
accgaucauc ccgucuguca uagcggucuu cauagcgguc cccaccuccu cuguagucau 180
caucucuccg guacccacuu ccaaaugccc uucugccacu gccuauccug gagucauagc 240
cucggucaua gucucugcug ccucggucau cauagcgauc ccggccccca uagcggucca 300
ugucucugcg ugggccgucc cgauauccgu cccuauaccc aucccgauac cggucugaau 360
cguaacgauc ucgauacuug ucuccaaagc uaucaucgcc ucuucuaggu ggguagucau 420
cacaacuguc uguggugga cgggcccucc agucuguguc uguuuug 467

<210> SEQ ID NO 178
<211> LENGTH: 346
<212> TYPE: RNA
<213> ORGANISM: Homo sapiens

<400> SEQUENCE: 178
uuuuuuuuuu uuuuuuuggc ccccaggcuc ugucucaagg augggaauag aucaagccaa 60
acagugaaaa auaaggcaaa ucguggcuuc ggggguuugag acuggcacca auggcaaauc 120
agcagaggag augcaaaugg gguaacaauc acaguuagug ggguaacaug agcaggcagg 180
aaacccuuga gacaacaccc aagguccacg ucuucgcaug ugcagggcac aacuccagca 240
gcaguuucug ggcuuggagg cuuguuacuc uuccuaccuu ucccaccccc uaaaagacac 300
caagauggag cccacgaaga gauuacauca agcucuucug gcuggg 346

<210> SEQ ID NO 179
<211> LENGTH: 4902
<212> TYPE: RNA
<213> ORGANISM: Homo sapiens

<400> SEQUENCE: 179
ucuaggacag ccagggcuac acagagaaac ccugucucaa cuaaaacaaa gcaaaccccc 60
cgaauauugu uuuuuauuug cggaugucug uuuauugaga cgggguucau ggcagacaug 120
agugucucag ugcauuugcu auccucucuu cuaaaggggc gggggggggg gugcgcugga 180
gagguggcuc agcaguuaag agcacugacu ucucuuccag agguccugag uucaauuccc 240
agcaaccaca ugguggcuua uaaccaucua uagugagauc ugaugccuuc uucuugccug 300
uaggcagacc acuguauaca uaauaaauaa aucuuaaaag gggggggaag guguggagcu 360
aaaaguaugg caauaugcau aaguuuagcu auuucuguug uuuugcaguc aucagugagc 420
caaacuaauu cgaaugggua gcuagaucuu guugcuuuua gcgaauauau auugagugaa 480
uggaauugac agucuucugu auucucauuc aguuuguuug uguucuuccc caucagugau 540
aacauguagu gaacuaaccc guguggacca ucuuaaccau ggcuucuccu uccuuuucug 600
uuuuaaacau aggacaugga uuugauugac auccuuugga ggcaagacau agaucuugga 660
guaagucgag aaguguuuga cuuuagucag cgacagaagg acuaugagcu ggaaaaacag 720
aaaaaacucg aaaaggaaag acaagagcaa cuccagaagg aacaggagaa ggccuuuuuc 780
gcucaguuuc aacuggauga agaaacagga gaauuccucc caauucagcc ggcccagcau 840
auccagacag acaccagugg auccgccagc uacucccagg uacacucguc gugguggggag 900 cuaaggaaaa cucuagugag aaagcagacu cucuggaguu gaguucuugg ucugccauuu 960
acugugucuu uugugaggag gagaaguucu caaacuucgc uucuugauaa ucaggacaca 1020
gaucacaggg aggacuuugu gaguucagaa acauccucug uggugaugaa acagcggcag 1080
aaauacuguu gggaguaaaa gaaguaggca uugcucauug ugguaggcag ggcccugauu 1140 guaugggguaa cugacuuaac uguguuaagu augauuccca uuuuauauuc ccaugucuaa 1200
acaacuaaag cauuugccca gaacacucag aaagaaauga agggagguua uugccuagca 1260

-continued

```
cagagcccug guucaguccc ccacgcuguu cguuaaaggg gagggacuaa uaauuugaac   1320
acaaucuggu uugaaucuau gcaaaucgau uucugaaaug agaccauagg uuauuuuaug   1380
aacaagucuu auugcucguu gugacccugu gcuuagaaca uuucauaaau gaugcucucu   1440
gugccuuucc ccuuccucca gguugcccac auucccaaac aagaugccuu guacuuugaa   1500
gacuguaugc agcuuuuggc agagacauuc ccauuuguag augaccauga gguauaaaaa   1560
uguuuguuua acagcaaaac ucccuuaucu gauauuaguu ccuuucaugu gucuccaauu   1620
aagagaagaa aagaaaauuu uagaaggaaa aaauugauca aagaaauugu caaguaaacu   1680
guaugagagc uauauaaugc uuaaaaaauaa gaccuguaug ggcuggugag auggcucagu   1740
ugguaagagu acccgacugc ucuuccgaag guccagaguu caaaucccag caaccacaag   1800
guggcucaca acauccauaa caagaucuga cucccucuuc uggagugucu gaagacagcu   1860
acaguguacu uacauauaau aaauaaauaa aucuuuaaaa aaaaaaaaua aggccuguaa   1920
acuacaaguc cauuuuacug uauagcugga aacaggaauc agaauaauuu ucccuggaaa   1980
cuggauauag auauauaaaa uauuuugacu aguaaagaac aacuauuaau cagcauuugg   2040
auuaaaaaau cuuaaucugu uguuugaagc auucugcuag auauuauggg uacagauuaa   2100
guccuaauga auguuuuuau ccauuuugaa gucugccuuu aaauacaugg agugaaauaa   2160
ccuaggagug uauuaauaug gagucacugg gaggaggaaa uguuucauuu uauaaaagca   2220
gccugagagc uguaggcccu gcugcugucu guucuucaug ccuuggcucu cacucacaug   2280
aaucaauguc acgucaaucu uggcuuucuu cacuugcauu ucagucgcuu gcccuggaua   2340
uccccagcca cgcugaaagu ucagucuuca cugccccuca ucaggcccag ucccucaaua   2400
gcucucugga ggcagccaug acugauuuaa gcagcauaga gcaggacaug gagcaaguuu   2460
ggcaggagcu auuuuccauu cccgaauuac agguaagaga gcucuaggag ugugcuguuu   2520
ucugcgggcc cuuuuaaauu agucauccua guuauuuauu auuuacaugc uaccuccuca   2580
aaggaagaaa uugauggugu auuuaaauua cucaugagag cuucccagac ucacuuaaca   2640
cacauaguuu uuagguaauc agacugaaua uuucuggaua aauucauuca aagacugaaa   2700
gcuaauuuag aguucugaca aagauaaaau acuuaucuau ugaaaaaugg gaguugaagg   2760
aauuauugaa aagaacaccu uggauuuggg gguagggaau ugaucuaaaa ugcacuuagc   2820
cucugcucau acaaugugac cuucuuuccu agugucuuaa uaccgaaaac aagcagcugg   2880
cugauacuac cgcuguuccc agcccagaag ccacacugac agaaauggac agcaauuacc   2940
auuuuuacuc aucgaucucc ucgcuggaaa aagaagu ggg caacuguggu ccacauuucc   3000
uucaugguuu ugaggauucu uucagcagca uccucuccac ugaugaugcc agccagcuga   3060
ccuccuuaga cucaaauccc accuuaaaca cagauuuugg cgaugaauuu uauucugcuu   3120
ucauagcaga gcccagugac gguggcagca ugccuuccuc cgcugccauc agucagucac   3180
ucucugaacu ccuggacggg acuauugaag gcugugaccu gucacugugu aaagcuuuca   3240
acccgaagca cgcugaaggc acaauggaau ucaaugacuc ugacucuggc auuucacuga   3300
acacaagucc cagccgagcg uccccagagc acuccgugga gucuuccauu uacggagacc   3360
caccgccugg guucagugac ucggaaaugg aggagcuaga uagugccccu ggaaguguca   3420
aacagaacgg cccuaaagca cagccagcac auucuccugg agacacagua cagccucugu   3480
caccagcuca agggcacagu gcuccuaugc gugaauccca augugaaaau acaacaaaaa   3540
aagaaguucc cgugaguccu ggucaucaaa aagccccauu cacaaaagac aaacauucaa   3600
gccgcuuaga ggcucaucuc acacgagaug agcuuagggc aaaagcucuc cauauuccau   3660
```

ucccugucga aaaaaucauu aaccucccug uugaugacuu caaugaaaug auguccaagg 3720
agcaauucaa ugaagcucag cucgcauuga uccgagauau acgcaggaga gguaagaaua 3780
aagucgccgc ccagaacugu aggaaaagga agcuggagaa cauugucgag cuggagcaag 3840
acuugggcca cuuaaaagac gagagagaaa aacuacucag agaaaaggga gaaaacgaca 3900
gaaaccucca ucuacugaaa aggcggcuca gcaccuugua ucuugaaguc uucagcaugu 3960
uacgugauga ggauggaaag ccuuacucuc ccagugaaua cucucugcag caaaccagag 4020
auggcaaugu guuccuuguu cccaaaagca agaagccaga uacaaagaaa aacuagguuc 4080
gggaggaugg agccuuuucu gagcuagugu uuguuuugua cugcuaaaac uuccuacugu 4140
gaugugaaau gcagaaacac uuuauaagua acuaugcaga auuauagcca aagcuaguau 4200
agcaauaaua ugaaacuuua caaagcauua aagucucaau guugaaucag uuucauuuua 4260
acucucaagu uaauuucuua ggcaccauuu gggagaguuu cuguuuaagu guaaauacua 4320
cagaacuuau uuauacuauu cucacuuguu acagucauag acuuauauga caucuggcua 4380
aaagcaaacu auugaaaacu aaccagacca cuauacuuuu uuauauacug uaugaacagg 4440
aaaugacauu uuuauauuaa auuguuuagc ucauaaaaau uaaaaggagc uagcacuaau 4500
aaaagaauau caugacuuaa acuacuuugg acuuuuugaa uuuauucaca cuauuuucca 4560
uaggacaauc acucauuuac cacauuuggu uauuuuacau uuucaaaaug gguuugaaaa 4620
uacagaggca uuuuauagcc auguguggca guccaugauu uuuuauuccc gacauucagg 4680
aggcagaagc aggcagaucc cugggcucca ggacggccaa ggcuacauga gagccugucu 4740
caagaaagac aaacccuuuc uauacuaaac guuagcuagg auugucaagg agaugguaua 4800
uauccacaau gguaugccug cuguacagua cuguggcaca gagaacaaaa ccuguaaccu 4860
ccuguguucu uagaaguggc auucuaagaa gggcuaggaa ga 4902

<210> SEQ ID NO 180
<211> LENGTH: 462
<212> TYPE: RNA
<213> ORGANISM: Homo sapiens

<400> SEQUENCE: 180
ggccagcagg acucuccuug cagcagcggc ccgaguucag aguccggagc ugcgguggug 60
gcggcgaagg cgagagucau ggcuggacaa gcuuuuagga aguuucuucc gcucuuugac 120
agaguauugg uugaaaggag ugccgccgaa acuguaacca aaggugGcau uaugcuucca 180
gaaaagucuc aaggaaaagu guugcaagca acggucgugg cuguggggguc aggagggaaa 240 ggaaagagug gagagauuga accugucagu gugaaaguug gagauaaagu ucuucuccca 300
gaauauggag gcaccaaagu aguucuagau gacaaggauu auuucuuauu uagagauagu 360
gacauucuug gaaaguaugu cgacugaaau cacuguugaa auggugucac gugaagcugc 420
cauuccacug augucugaac uauuucauca uguaaauaau uu 462

<210> SEQ ID NO 181
<211> LENGTH: 417
<212> TYPE: RNA
<213> ORGANISM: Homo sapiens

<400> SEQUENCE: 181
uuuuuuuuuu uuuuuuucag gucucauuuu cguuuauuug aaauucggug cucguguaag 60
uuuuuucucu uccccucaaa uuuuauuuca guaaaaggag acuugggcga gguggauacc 120
ccacagccgg auucuucccc cccugccccc cagggguggcu aaugcuaucu ggggaagucg 180
ucauagggaa gagaacuaug ggugggcucc ugccugaggc cuccaaucuc agcccagugg 240
acauaucaca ggcagcuuaa aaaaaaaacc cuaaaaaaaa caccccaaaa cacacauuua 300
aauagguauu caagacagcu uuaaaaaaug cacccacuca caccccccuc ccuuuucuuu 360
uuggaaaaaa aaauaggaaa aaaaaaaaaa ccaaaccgaa uucucgcuug gccucua 417

<210> SEQ ID NO 182
<211> LENGTH: 1160
<212> TYPE: RNA
<213> ORGANISM: Homo sapiens

<400> SEQUENCE: 182
auuuggcucc gaggccaaga auucggaucc aaggcgggcg cggggaaaau ggcggcggca 60
gcugcggcgg gggcgaaugg gagcggaggc agcagcggca uggaagugga ugcagcaguc 120
cccagcguga uggccuccgg agugacuggg aguguuuccg ucgcucuuca uccccuuguc 180
auccuuaaca ucucagacca uuggauccgc augcgcuccc aggaggggcg gccuaugcag 240
gugauugggg cucugaucgg gaagcaggag gggcgaaaua ucgaagugau gaacuccuuu 300
gagcugcugu cccacaccgu ggaagagaag auuaucauug acaaagaaua uuauuacacc 360
aaggaggagc aguuuaaaca gguuuucaag gagcuggagu uucuggguug guauaccaca 420
ggggggccac cugaccccuc agacauccac guccauaagc agguguguga gauaauugag 480
aguccgcucu uucugaaguu gaacccuaug accaagcaca cagaucuucc ugucagcguu 540
uuugagucug ucaucgauau aaucaaugga gaggccacaa ugcuguuugc ugagcucacu 600
uacacucugg ccacugagga agcugaacgg aucgguguag accacguggc ccggaugaca 660
gcaacaggca guggggagaa cuccacugug gcugaacacc ugauagcuca gcauagugcc 720
aucaagaugc ugcacagccg ugugaagcuc auuuuagaau augucaaggc cucugaagca 780
ggagagguuc ccuucaacca ugagauccug cgggaggccu augcccuaug ucacugucuc 840
ccaguucuca gcacugacaa guucaagaca gacuuuuaug aucaaugcaa ugacgugggg 900
cucauggccu accucggcac caucaccaaa acgugcaaca caaugaacca guuugugaac 960
aaguucaacg uccucuacga ccgacaaggc auuggccggc gaaugcgggg acuguuuuuc 1020
ugaugauggu ucuggaaggg auggugugug gggcucagac agcuguucca uggaccugag 1080
uaccacauuc ccuuuagaga aacucauuaa uaaaagagca gccccuuaaa aaaaaaaaaa 1140
aaaaaaaaaa aaaaaaaaaa 1160

<210> SEQ ID NO 183
<211> LENGTH: 8322
<212> TYPE: RNA
<213> ORGANISM: Homo sapiens
<220> FEATURE:
<221> NAME/KEY: misc_feature
<222> LOCATION: (1298)..(1397)
<223> OTHER INFORMATION: n is a, c, g, or u
<220> FEATURE:
<221> NAME/KEY: misc_feature
<222> LOCATION: (2040)..(2139)
<223> OTHER INFORMATION: n is a, c, g, or u
<220> FEATURE:
<221> NAME/KEY: misc_feature
<222> LOCATION: (2495)..(2594)
<223> OTHER INFORMATION: n is a, c, g, or u
<220> FEATURE:
<221> NAME/KEY: misc_feature
<222> LOCATION: (3800)..(3899)
<223> OTHER INFORMATION: n is a, c, g, or u
<220> FEATURE:
<221> NAME/KEY: misc_feature
<222> LOCATION: (4897)..(4897)
<223> OTHER INFORMATION: n is a, c, g, or u
<220> FEATURE:
<221> NAME/KEY: misc_feature
<222> LOCATION: (4909)..(4909)
<223> OTHER INFORMATION: n is a, c, g, or u

<400> SEQUENCE: 183
aaaacccaau guuugguuuu aaagccaaaa auauaaggga agugcauagg uuuggguuuu 60
guuuuuuguu uuuucccgag guccuugauc uuugcccccca aauuugaggg cauaaaguaa 120
ucccucaguu accuaaaaac acagccauuc cuuugccauu ccacucuccu ggauuggccg 180
cuucugugcg cgggggagag gugacucacu auuacuacug aggaaagggg agccaguggu 240
ggaagugggg ugagucacug augggcagca gcuucagccc uccccccaac uuccuuggcu 300
cucuggggau gccugauccu cucccucacu uugcaccuac uuccccuggu cccucaccac 360
uacccuuugc ccacccacuc aaauucuuug gcucugcucu uuacuccaga aggccaaagg 420
caagcuuaga guugaguagg caggaaccaa cauugugaag ccccaggcca gaaaggggug 480
uucugcagag ugaggguugg caugcuggcu ccuccucacc auaccugccc ccgccccuuu 540
ggguacagga uggcuccuuu aagagcagug gauccacccc cuguagagga gggccuauua 600
gagccucugc cuggcuguca gugacucagu guucgcggga acgcugccuc agccucaaca 660
ccagccaacc cagaucccga ggugcgccag cgcccagccc agaucuccac gccugccagg 720
agcgagcuuc gccggcucgc ugucccccug agcagccucu guccuucugu ccaagucccg 780
cgcccuucuc gggaccccug cccagcgggc agcacuguca cccugccggc cauggagacc 840
ccgucacagc ggcgcgccac ccgcaguggg gcgcaggcca gcucuacccc acugucgccc 900
acucggauca cccggcugca ggagaaggag gaccugcagg agcucaauga ccgccuggcc 960
guguacaucg aucgcgugcg uucccuggag accgagaacg cggggcugcg ccuucgcauc 1020
acugagucug aagagguggu cagccgagag guguccggca ucaaggcggc cuacgaggcc 1080
gagcuggggg augcccgcaa gacccuugau ucuguggcca aggagcgcgc ccgccuccag 1140
cuagagcuga gcaaagugcg ugaggaguuc aaggagcuga aggcucggug agugaggccc 1200
ggccggccgg caccagggag gcagcagucg ccuguaacug gccaucuagu ccccucccuc 1260
cccggaacug ccucccgcgg gugacuggca gugccaannn nnnnnnnnnn nnnnnnnnnn 1320
nnnnnnnnnn nnnnnnnnnn nnnnnnnnnn nnnnnnnnnn nnnnnnnnnn nnnnnnnnnn 1380
nnnnnnnnnn nnnnnnngcu aggccagaua uagaaagcuu ucuguauuua auacacagua 1440
caugcaucau ucaugucuac auaauuaaga uaaaggaagc ugcauuguua augggaaaaa 1500
aaauaggguc ugggaaugua gugugccuag cauuuacgaa cuucgggguu uggguuugau 1560
cccagcaucu cacaaaccac guguaauccc agcacuugga agguagaggc cggaggaucc 1620
gaaguuuaag gucauucuug acuacuuagc aaauucgggg cacccuagga uaccugagac 1680
ccugucauga auaaaaauaa auaauaaaua aaccaauaug ggucuagguu gagcagcagc 1740
uugggcaggg uagggccgga aguuagccag guagaggguu gcagucccag gaggacccug 1800
gcugggagca gcaccucagu ccccugccca accacagggg gccaccgggu cuuuccggaa 1860
cuccugaggg cgcaaggccu ugcucucucu ggcccagcca uggggaacgc ggagggccgg 1920
ugaggcaggc ggcaggcggg cgggcggggc gcgggccguc auccccuccu gcuccuuauu 1980
uuuagcccag uguagagucu gggccgccug ucccucccccc aggacagggg gaggaaauun 2040

-continued

```
nnnnnnnnnn nnnnnnnnnn nnnnnnnnnn nnnnnnnnnn nnnnnnnnnn nnnnnnnnnn   2100
nnnnnnnnnn nnnnnnnnnn nnnnnnnnnn nnnnnnnnng augccaacaa uccuaaugua   2160
augaugcccu cuucugacag cugcggggac cgcagagagg ucccauccca gaugcacucc   2220
ugaaaccugc uuuucuuuuu cuagcaacac caagaaggag ggggacuugu uggcugcgca   2280
ggcccggcuc aaggaccucg aggcucuucu caacuccaag gaagcugccc ugagcacugc   2340
ucucagugag aagcgcacau uggagggcga gcuccaugac cugcgggggc agguagccaa   2400
gguaggccgc uguccuguga ccccagugac cccaccuggu ccgacauauc auucggucce   2460
auuugccugc ucaccuucac uucuccaguc uagannnnnn nnnnnnnnnn nnnnnnnnnn   2520
nnnnnnnnnn nnnnnnnnnn nnnnnnnnnn nnnnnnnnnn nnnnnnnnnn nnnnnnnnnn   2580
nnnnnnnnnn nnnnucuaga uggggacagc caucaccucu ccuuuggcau uuccugaacc   2640
cccucccacc ucuccaugaa cuuggcuuuc ucccucucag cuugaggcgg cccugggaga   2700
ggcuaagaag cagcuucagg augagaugcu gaggcgagug gaugcugaga acaggcuaca   2760
gacgcugaag gaggagcuug acuuccagaa gaacauuuac agcgagguaa gcgucccgcu   2820
guacaggucu uucuuacugu ggacagcugg gaggggucac cuaauaaugc caggcuaagc   2880
gagggcugcc cgugccuggc cgguggaguu acgacuucug gucucagcuu cuaaggaacc   2940
auugcgaugu ucuaaucuaa gugucucccc uuaaccuuuc aggaacugcg ugagaccaag   3000
cgccggcaug agacgcggcu uguggagauc gauaacggga agcagcgaga guuugagagc   3060
cggcuggcag augcccugca ggagcugcgg gcucagcaug aggaccaggu ggaacaguau   3120
aagaaggagc uagaaaagac auacuccgcc aaggugcugg ccucauccug uccucucccu   3180
ggugcugccc uggggacggg uggguggugg caggggggca gggaugccuu ccucaggccc   3240
ccagcuccag guuccugcuc ucauaacugu gugcucccug cagcuggaua augccaggca   3300
gucugcugag aggaacagca accucguggg ggcugcccau gaggaacugc agcagucucg   3360
aauccgcauu gacagccucu cggcccagcu cagccagcuc caaaagcagg ugacccucag   3420
uuuaccccuc ccaccuuggc ucuggucuaa gcagauacug cagaagccca cugagaaggg   3480
gguggggggag ggacuccagg accacaugcu augguucuga aucugaugcc ugucuggcuu   3540
uccagggcuc uccuuuagcu agcccugauc cucagagccu cuauuuuacu gugcaugaag   3600
gguuuuucau guuucuucug ugccugccgg agacugaacc agaggccucu ugcuugguag   3660
auaggugcuu ucucacugag uuacaaaccc agccgcauuc ccuacuugga gauagagcuu   3720
cccuuggacu ggacauguag cucaguuggu acagugcuug cuuauuauac acgauggccu   3780
ggcuucuauc cccaggaccn nnnnnnnnnn nnnnnnnnnn nnnnnnnnnn nnnnnnnnnn   3840
nnnnnnnnnn nnnnnnnnnn nnnnnnnnnn nnnnnnnnnn nnnnnnnnnn nnnnnnnnnu   3900
cuagagagag ccuacagauc cugagugucc cucugccugc cccugugccc cucccucuuc   3960
aucgacauca gcccuuggga gcucaucaga cccuuugucu uccccgcccc aguuggcagc   4020
caaggaggca aagcugcgug accuggagga cucgcuggcc cgugagcgcg auaccagccg   4080
gcgccugcug gcugagaaag agcgagagau ggcggagaug cgggcgagga ugcagcagca   4140
gcuggacgag uaccaggagc ugcuggacau caagcuggcc cuggacaugg agauccaugc   4200
cuaucgaaag cugcuggagg gcgaggagga gaggugaacu aggaggggguc uacagaacuu   4260
gucaggggcc ucuggccgca acuaccauga cuaaccccgc accgugucuc caccuucccc   4320
aggcugcgcc uguccccag cccuaccucg cagcgcagcc guggccgcgc cuccucccac   4380
ucaucccagu cucagggugg aggcagcguc accaaaaagc gcaagcugga gucuuccgag   4440
```

agccggagca gcuucucgca gcaugcucgc acuagcgggc guguggcggu agaggaaguc 4500
gaugaagagg gaaaguucgu gcggcugcgc aacaagucca acgaggugggg ccugugaacc 4560
agggugggucu uuucaguggc ugggaguucu ugguucucgu ggagcaucug ucucccuauc 4620
ugagaauuug gagugugugg uaguccuguc aucuuuaaau uguugggaag augcaugaua 4680
uagggauggg ugacccuuga gccaauaguc uagguuugau gccagaggua gugguggaag 4740
ccugucuuuc uuuucuuuuu cuuuuucuuu uucuuuuucu uuuucucuuu cuucucucuu 4800
uuuuuuuuuu ccgaugggggu cuugcccagg uuggcuuuga ucucccuagu uaagcuguuc 4860
cccugccuca gccuccauag uagcuggaac ugcaggngca cacuggcgnc cagccuaccu 4920
aagcuccuga gugagauaau ccaagagucg guugaacucc cuguccuccu uccuccuucc 4980
uccuuccucc acccuacuuc aggaccaguc caugggcaac uggcagauca ggcgucagaa 5040
uggugacgau ccuuugauga ccuaucgcuu cccaccgaag uucacccuaa aggcugggca 5100
gguggugacg gugaguggaa gggcacuugg gacucuggcu ggaguggaga aguuggccuc 5160
aggacaggag cauuaaaaau aagcacaucu cuuaaaccau cuuuucccag aucugggcuu 5220
caggagcugg ggccacccau agcccccccua cugacuuggu guggaaggcg cagaacaccu 5280
ggggcugugg gagcagccuu cgcaccgcuc ucaucaacuc cacuggagaa gugaguaugu 5340
ugcagccggu agcuugcugg acaaggcucc cccgggugac cauaauggga acuagcuacc 5400
uccaacccaa gggaaccugc cuuggguuua ggaucgcuuu ccugagccca agucccaccc 5460
aguaagcaag ccagaagucu ccccaguaga auaaugggug gaagucagcc agugagugu u 5520
aauagcagac uccagcuuac agagcaccga gcucucaguu guguccuuuu ugcgcgugcg 5580
ugcgcgcgug ugcacaugug cauguguuua uccuuagucc ccagcaucag agguuggaca 5640
agguuguaua aaggcccggg acaguucuaa gugguuacua uggguagaca ggcugcacag 5700
cccucacccc cugacucuug ggccugggcu uauguccccca caggaagugg ccaugcgcaa 5760
gcuggugcgc ucacugacca ugguugagga caaugaggau gacgacgagg auggagaaga 5820
gcuccuccau caccaccgug ugaguggcag ccgccgcuga ggcccagccc acaaggguag 5880
cccugccagc cuagggcagc ucucccaccu ccaugccaaa gucuuuucau uaaagaaugu 5940
uuuggaaugc cacuugcugc ccuggccuuu cuucucucuc cucccucuac cuugaacagg 6000
gaacccaggu gucugguaag gaagggagug gggacuugcu gaugccaugg auacuccacg 6060
guggcagugg acaggguucu ggauuugugu ccugggaagg ggcugggagg acagaggugg 6120
ccccagcccu gccucucuuc cucacuccca uugcaugcac acuucucucc ucucuccuuc 6180
cacccuauug caugcuucuc cucagauuuc ccugcaacaa uguucucuuu ccuuccuguc 6240
cccucacaaa uuaagucucu ccaucuuugc ucuuccucuu gauugcccca uaagugucua 6300
agauucagga gagaguuaaa gccacagcuc uuuauuucga aggcuuccug gcuauuuccc 6360
ccaucaugcc cuuccuccca gccacagguc ucccaagucc ccaucacuug guugucuggg 6420
uacagacaga ggucaccuuc cugcccaaug gccaggaagc uccaagagcc cacagccuag 6480
gugccggucc uaagaaguca gucccaaacu cgcuguccccu ccugagccuu gucucccuuc 6540
ccaggguucc cacugcagcg gcucggggga ccccgcugag uacaaccugc gcucacgcac 6600
cgugcugugc gggacgugug ggcagccugc ugacaaggcu gccgguggag cgggagccca 6660
ggugggcgga uccaucuccu cuggcucuuc ugccuccagu gucacaguca cucgaagcuu 6720
ccgcagugug gggggcagug gggguggcag cuucggggac aaccuaguca cccgcuccua 6780
ccuccugggc aacuccaguc cccggagcca ggugagucau cucugcccua cagcaggaca 6840
cugcucacug agcagcaggg cagggcagcc caagggagug gggucccccu ccuugcaguc 6900
ccucuugcau ccugccccuc cugucugaac cccagacucg aggucagggc aaggcccaga 6960
gugugagggu uggggagaca accccuuugg ggucagggag ggagaggaag ggccagccac 7020
ugcugcucac accucugccu ucucuucucu cuuagagcuc ccagaacugc agcaucaugu 7080
aaucugggac cugccaggca gggcuggggg cagaggccac cugcuccccc cucaccacau 7140
gccaccuccu gucugcuccu uaggagagca ggccugaagc caaagaaaaa uuuauccccu 7200
gccuuugguu uuuuuuuuuc uucuauuuuu uuuucuuuuu cuaagagaag uuauuuucua 7260
cagugguuuu auacugaagg aaaaacucaa gcaaaaaaaa aaaucuuuau cucaauccua 7320
aguccuuccc cuuucuuucc uuguaucugc cuuaaaacca aagggcuucu cuaggagccc 7380
agggaaagga cugcuuuuua uagagucuag auuuuugucc ugcugccuug gcuuuacccu 7440
caucccagga cccugugaca auggugccug agaggcaggc auggaguucu cuucaccagc 7500
cuccuccaac agcuggccca cugccacgcc agcugcagag aaauggggcg cagagaggau 7560
gacugagaag gucaagcccc uccccggcac uacacgaggc cgaggcuccu cugccugccu 7620
uaccuucuuc cugcccuucc cuagccuggg gcgaguggau ucccagaggc aaaucugccg 7680
ugcuugcuuu uucuauauuu uauuuagaca agagauggga augacgggga aggagaaggg 7740
aagaucaguu ugagccuacc uuuucccagc uucugagccu ggugggcucu gucucaauga 7800
uggagggcaa ugucaagugg gauacaggga agaguggggg acgaaggcuc ccagagaugg 7860
ggagaaccug cuggggcugg ugagaagucu agaggugcgg cgauuggugg cuacagcaaa 7920
cacuaaggaa cccuucaccc cauuucccau cugcaccucu gcucuccccu ccaaaucaau 7980
acacuaguug uuuccauccc agaugcugug gugucucuuu guugggugug augugugguuu 8040 ucaggggcag acacaugcac acagaggugc cacacauuca cuauauauuc acuacccagc 8100
uauaaaggug uguaugaggg agacuucuag aaaggucagc auauguggggg ugagcgaggg 8160 guguccuucc uaucccucau ccauccagca ccuuuuaaaa ggggccagca auccacaugu 8220
gcaucagaca caggagcaca gagagacgga ggguagagua gggcagagua gcagagcuuc 8280
cuugcugccc uguagucgca ggcucuugau cgugugaucg cu 8322

<210> SEQ ID NO 184
<211> LENGTH: 1054
<212> TYPE: RNA
<213> ORGANISM: Homo sapiens

<400> SEQUENCE: 184
gcggugcgaa gcgggccucc gccaacaugu acuacaaguu uagcaguuuc acgcagaagu 60
uggcuggagc uugggcuucg gaagccuaca ccccgcaggg guuaaagcca guuuccacag 120
aagcaccacc uaucauauuu gccacaccaa ccaaacugac cuccagugug acagcauaug 180
auuauucugg gaagaacaaa guuccagagc ugcagaaguu uuuccagaag gcugaugguu 240
uccaccugaa acgaggccuu ccagaccaaa ugcuuuaccg gaccaccaug gcucugacac 300
ugggagggac caucuacugc cugaucgccc ucuacauggc cucgcagccc agaaacaaau 360
gagcuugccu guggaggacu gguucacuuu guggcacaaa cccuuugaau ccucacguuu 420
cauguuuucc acuuggauag ucuacuuaac auuuugcaaa caaaggaaaa gauaagaaua 480
cauuguuuug auuuguuuau ggugugcaga uggccuguca gaugucagag cugguuugac 540
aguuaaaacu auuguuuaag gaaaugucac ugagccauca cugagcugug cuucugcucc 600

```
ugauuucccu ggaguucugc aggaaaguug cucuccagcu cauucguggc cagccgugcu    660
cagggccucg ggacucaggc ggugucugag cgggaagcga acgcggaagc cuuuuggagu    720
guagguguga uugaggaagg aaaacaaaag ccagcggaca gguggugaag ugagggcuga    780
guuagccacc cuagggauuc guccgccuug cagaaaacau ugagaggaau gauagcaacc    840
ugccucuauu ugugggcagu ugguuucaaa ggguugugug ucucgcccag aaccuaggga    900
aaugggguuu uguuccaucg ugggaggagc accugucagu gcugcacauu agacagcugu    960
gucaggacuu cuccuuuaau aaugcugugg cuuuacguua ugauugaccg gacugcggaa   1020
uaaacacugg aaucaaaaaa aaaaaaaaaa aaaa                               1054
```

<210> SEQ ID NO 185
<211> LENGTH: 4208
<212> TYPE: RNA
<213> ORGANISM: Homo sapiens

<400> SEQUENCE: 185

```
cugagacaga acgaaacguc cgcagauaac uacccguucu ggcucuuguu aguucuaugu     60
guauggauaa ugucuuggga gguuuugaaa ugccacaagc cuugcuggcc cagggugcag    120
cugccucugc cguucagacc ucagauuaua aggacagaac acagcacgga agugggggga    180
ucagaaccau gggagaucca ggacgaaggg uccugugcgc aggugcggca ccgaauccua    240
uauuugacau ugaagcuguc gucagcccaa cuagugugu auuaacaugg aagcacaaug    300
acucaggcgc uucagaaugu agaauagaga auaagaugga gagcaaucug acguuuccug    360
uuaaaaacca gacaucaugu aacauuacag gcuuaagccc agguacuucg uauacauucu    420
ccaucaucuc uguaacaacc aaugagaccu ugaacaaaac uaucacaaca gagcccuggc    480
cagugucuga ucuccauguc accucugugg gugugacaca ggcucgucuc accuggagca    540
augcaaaugg cacugccucc uaccggaugc ugauugaaga guugaccaca cauuccucag    600
ucaauauuuc aggucugaag ccggggacca auaauacguu cgcuuuccca gaaucaaaug    660
agacacaggc ugacuuugca guugcagagg aggucccgga ugccaauggu accaagagaa    720
ucccagugac caaccuaucc caaccacaca agaauucucu ugccucugug gacccacccu    780
cuggccagga ucccucccuc acagagaucu ugcuuacuga ccuaaagccu gauacucagu    840
acaaugccac caucuauucu caagcagcaa auggcacuga aggacagccc aggaacaaag    900
uguuuaaaac aaauuccacc cagguuucug acguccgagc uaugaacauc agugccucaa    960
gcaugacccu gaccuggaaa agcaauuacg augggucccg uacuucaauu gucuacaaaa   1020
uacacguggc ugggggggac cacuccguca accaaacugu caauaagacu gaggccauca   1080
uccucggacu cagcuccagc accuuguaca acaucacagu ucauccuuuc cugggucaga   1140
cggagggcac accaggcuuc cuccaagugu acacuucccc cgaucagguc ucugacuucc   1200
gagugacaaa ugucagcaca agggcaauug guuuggcuug gaggagcaau gacuccaagu   1260
ccuucgagau uuucaucaag caggacggag gugagaagca ucgaaaugcu ucgacgggaa   1320
accagagcua uaugguugaa gauuuaaagc cuggaaccag uuaccauuuu gagauaauuc   1380
cacgaggacc agacggggaca gaagggcugu ccaguacagu gaaugggagc acugacccca   1440
gugccgugac ugacauccgg guggucaaca uuagcaccac ugaaaugcag uuggaguggc   1500
agaauacgga cgaugccucu ggauacacuu accauuuagu ucuagagucu aaaaguggcu   1560
ccaucaucag gaccaacagu ucucagaagu ggaucacagu agggagccuc accccaggca   1620
```

-continued

```
ccuuauacaa ugucacaauc uuuccagaag uggaccagau ccagggaauc uccaacucca   1680
uuacccagua cacacggccc agcagugugu cccacauuga aguaaacacc accaccacca   1740
cggcagccau ccgauggaag aacgaggaca cagccucugc uuccuaugcc uacuccgucc   1800
uuaucuugaa gacuggagau ggcagcaaug uaaccagcaa cuucacaaaa gacccuucua   1860
uucuaauccc ugaguuaauc ccuggcgucu cuuacacagu gaagauccuu acacaaguug   1920
gggaugguac aacaucacug guaccugguu ggaagcuguu cuguacggaa ccugaaucag   1980
ugaccuccuu ccacugugaa guggucccua aggagccagc auugguucuc aagugggccu   2040
gccccuuugg cauguacaca ggcuucgagc ugggggucag gagugauucc ugggacaaua   2100
ugacacgccu agagaacugc acaucggaug augacacaga gugcaggacg gaagucgccu   2160
auuugaauuu uucuaccucg uacaacauca gcaucgccac cuugucaugu gggaagaugg   2220
cgcuucccgc ccagaacauc ugcaccacug gcaucacaga cccaccuacu ccggauggau   2280
ccccuaauau uacaucgguc agucacaauu caguaaaggu uaaguucagc ggguuugaag   2340
ccagccacgg accuaucaaa gccuaugcug ucauccucac caccggggaa gcugcccaac   2400
cuucugcaga uguuuugaag uacacguaug aggauuucaa aaggggagcc ucggauacuu   2460
augucacaua ccucauaaga auagaagaga agggacaguc ucagggcuug ucugaagucu   2520
ugaacuauga aauugaugug gggaaccaau ccacuacccu cggcuacuac aacgggaggc   2580
uggagccucu gggcuccuac cgggauugug uugcuggcuu uaccaauauu accuacaacc   2640
uucagaauga cggccucauc aauggggaug agagcuaugu gucuuucagu ccauauucag   2700
aggccguguu cuugccccag gauccaggug ucaucugcgg agcaguguuu ggauguaucu   2760
uuggugcccu ggccaucaca gcugugggag gcuucaucuu cuggagaaag aaaaggacag   2820
augccaagaa uaaugaagug uccuuuucuc aaauuaaacc uaaaaaaucc aaguuaaucc   2880
gaguggagaa uuuugaggcc uacuuuaaga aacagcaagc ugacucuaac uguggguuug   2940
cagaggaaua ugaggaccug aagcugauug ggauaaguuu accuaaauac acagcugaga   3000
uagccgagaa cagagggaag aaccgcuaca acaauguucu gcccuaugau auuucucgag   3060
ucaaacuuuc aguccagacc cauucgacag augacuacau caaugccaac uauaugccug   3120
gcuaccauuc caagaaagau uucauugcca cacaaggacc uuuacccaac acuuugaaag   3180
auuucuggcg uaugguuugg gagaaaaacg uauaugccau uguuauguug accaaaugcg   3240
uggagcaggg aaggaccaaa ugugaggagu acuggccuuc caagcaggcu caggacuacg   3300
gggacauaac uguggcgaug acaucagaag ucguucuucc agaauggacc aucagagauu   3360
uuguggugaa aaauaugcag aauagcgaga gccauccucu gcggcaguuc cauuucaccu   3420
ccuggccuga ccacggugu u ccugacacca cugaccugcu caucaacuuu cgguaccugg   3480
uccgggauua caugaagcag auacccccg agucaccaau ucuggugcau ugcagugcug   3540
ggguuggaag gacgggcacu uucaucgcca ucgaucgccu gaucuaucag auagagaaug   3600
agaacaccgu ggacguguau gggauugucu augaccuucg gaugcacagg ccucugaugg   3660
ugcagacaga ggaccaguau guuuuccuca aucagugugu uuuggauauu aucagagccc   3720
agaaagacuc aaaaguugau cucaucuauc agaacacaac ggcaaugaca aucuaugaaa   3780
accucgagcc aaguuccuug aaugugacua uguugcuuca uccacagcug aacgauuuug   3840
gauguugggu ucuaggyccu ggcuguugcu ggucugcuag gauccagggc cuuguugaca   3900
ucugggaaga uguaaauugu cccgcugaag gccgcaguuu uagauguggc cacuagaugg   3960
agccagagca cugguaugaa ggagcaccag ggccguguaa ggcaaaagag gacccagaaa   4020
```

aagaaacuua acuuguucac uccugagaaa ccugcaaguc aacaagccaa ggaagugccu 4080
uugcaugcau uugguagccu uuccaauccc gcuuauuaca uaauauguuc auguucaugg 4140
caaaaaaaaa aaaaauaaaa uaaaauaaau aaaaaaggaa aacaaaauaa aaaaaaucuu 4200
agaacauu 4208

<210> SEQ ID NO 186
<211> LENGTH: 249
<212> TYPE: RNA
<213> ORGANISM: Homo sapiens

<400> SEQUENCE: 186
gcccccucaa gggcauccug ggcuacacug agcaccaggu ggucuccucu gacuucaaca 60
gcgacaccca cuccuccacc ugacgcuggg gcuggcauug cccucaacga ccacuuuguc 120
aagcucauuu ccugguauga caacgaauuu gcuacagcaa cagggugugg accucauggc 180
ccacauggcc uccaagguaa gccccuggac caccagcccc agcaaggcac aagaggaagg 240
agagacccu 249

<210> SEQ ID NO 187
<211> LENGTH: 410
<212> TYPE: RNA
<213> ORGANISM: Homo sapiens

<400> SEQUENCE: 187
uuuuuuuuuu uuuuuuucau auuaaacuug uaguuuuauu cagguuugau uuuuaacaaa 60
ugugucaggg agagagccca caggaaaggg uaaagcccgu gggggcaagg ccuucccaga 120
ugccugagga gggaucgugu ccccuccccc ccuccucuuc ucaccacccc uacaggggguu 180 ugggaagaga cacaggcagg gaaggggcug guccccaguc uguacagugg ugcuuggggg 240
ugaaggacua uggagaacag gggaccagau cggggaugag uaggauaaag ggcacaagac 300
cauuuaccag aauccagcuu ucugauucca aauugaauua aaaagaaaaa aaggagaggg 360
gaaccuaaac cacaagcagu acccaacucc cuuuccccca ucagggcugc 410

<210> SEQ ID NO 188
<211> LENGTH: 382
<212> TYPE: RNA
<213> ORGANISM: Homo sapiens

<400> SEQUENCE: 188
uuuuuuuuuu uuuuuuuagg gaagaggcug augccagaua aguuuuuauu auauuaaaaa 60
aaaaaaaaaa accagugcaa cuggaaauca gggugagucg cuggagguga gugagagucg 120
gaaggcccuc cacaccucag ugguggcagg aucuggaccc guagccuaag ccuggucuga 180
uccagccgag augcuggaaa gcagagcaca cgguggugcc caucagggca aagagggcaa 240
gagagcccac ggcuccucca uaccgcuugc uagggucucc uguguaguag ccauaugcgu 300
aaaggacucg cccaauaauc caggccaggc ccaggccaga agcuaugcgc gggugguaaa 360
caccucccac cguuaggaaa aa 382

<210> SEQ ID NO 189
<211> LENGTH: 253
<212> TYPE: RNA
<213> ORGANISM: Homo sapiens
<220> FEATURE:
<221> NAME/KEY: misc_feature
<222> LOCATION: (32)..(32)

<223> OTHER INFORMATION: n is a, c, g, or u
<220> FEATURE:
<221> NAME/KEY: misc_feature
<222> LOCATION: (41)..(41)
<223> OTHER INFORMATION: n is a, c, g, or u

<400> SEQUENCE: 189
cggccgcgug aguuuugacu gagcuucugc angaaguuca naugcaacuc cauacaucag 60
uucauuuucu agcauuacca cuggguuauu aucacgaaug gccgauuuaa uaaguccuuu 120
ugcauccucg gaauuccagg ggcugaccac uuuuaaaccu gggcagugcc cauaccaugc 180
agcaaagcau ugcgagugcu gagcagcuac accugcugag gcgccauugg gcccccugaa 240
uacuaugggc aca 253

<210> SEQ ID NO 190
<211> LENGTH: 371
<212> TYPE: RNA
<213> ORGANISM: Homo sapiens

<400> SEQUENCE: 190
uuuuuuuuuu uuuuuuugaa gggccauugg aguuuauuua cagacaaccu uaggugaggc 60
cuuuuccucu aggaucuaca ugcuuuugaa guuacuuggu uucaggcuuc uugucuccag 120
cuucgagcuu gagacucuca ggaggcuggc gauaggcagg gaaagccucc caggggcugu 180
ucaggucaaa cuugcggaau ucuugugcca gcuccacugg uucagccacu acccgcuuua 240
ccucaucguc guaacgaagc ucaacauagc cagugagggg aaagucuuuc cggaaaggau 300
gucccucgaa gccauaaucu gucaggaucc uucuuaaauc agggugguua aaaaaaaaaa 360
aaaaaaaaaa a 371

<210> SEQ ID NO 191
<211> LENGTH: 324
<212> TYPE: RNA
<213> ORGANISM: Homo sapiens

<400> SEQUENCE: 191
uuuuuuuuuu uuuuuuuggg gggcagcgaa cuuuauugau gguauucaaa aaaauaggga 60
gggcucccua ggcccccccu guuauuaugg gggucuggga uggaaauuuu gagggaaaug 120
cucaauuuug ggggcccauu ugggaaaagg ccccccuugc ccaauguccu ugcuggggug 180
ggugguccaa gguuucuuac uccuuggagg ccauuuuggc caagaggucc accacccugu 240
ugcuguagcc guauucauug ucaaaccaag aaaugagcuu gacaaauuug ucauugaaaa 300
aaaugccaac cccggaauca aagg 324

<210> SEQ ID NO 192
<211> LENGTH: 2110
<212> TYPE: RNA
<213> ORGANISM: Homo sapiens

<400> SEQUENCE: 192
gcuccucauc ucacucgggc cuaugccaaa gauguaaaau uuggugcgga ugcucgagcc 60 uuaaaugcuuc aagguguaga ccuuuuagcc gaugcuguag cuguuacaau ggggccaaag 120
ggaagaacag ugauuauuga acagaguugg ggaagucccca aaguaacaaa agauggggguc 180 acuguugcaa agucaauuga uuuaaaggau aaauacaaaa auaucggagc uaagcuuguu 240
caggauguug ccaauaacac aaaugaagag gcuggggaug gcaccaccac ugccacuguu 300
cuggcacggu cuauugccaa ggagggcuuu gagaagauca gcaaaggggc uaauccagug 360
gaaauccgga gaggugugau guuggcugug gaugcuguaa uugcugaacu uaagaaacag 420
ucuaaaccug ugacaacccc ugaagaaauu gcucagguug cuacaauuuc ugcaaacgga 480
gacaaagaca uugggaacau cauuucugau gcaaugaaga agguuggaag aaagggugu c 540 aucacaguga aggauggaaa aacccugaau gaugagcuag aaauuauuga aggcaugaag 600
uuugauagag gauauauuuc cccauauuuu auuaacacau caaaagguca aaaaugugaa 660
uuccaagaug ccuauguuuu guugagugaa aagaaauuuu ccaguguuca guccauuguc 720
ccugcucuug aaauugcuaa ugcucaucgg aagccauugg ucauaaaucgc cgaagauguu 780 gacggagaag cucuaagcac gcugguuuug aacaggcuaa aaguuggcu ucagguugua 840 gcagucaaag cuccaggguu uggggacaac aggaagaacc agcuuaaaga uauggcuauc 900
gcuacuggug gugcggugu u uggagaagag gguuugaauc uaaaucuuga agauguucaa 960
gcucaugauu uagggaaagu uggagagguc aucgucacca aagaugaugc caugcuuuug 1020
aaaggaaaag gugacaaagc ucacauugaa aaacguauuc aagaaaucac ugagcagcua 1080
gacaucacaa cuagugaaua ugaaaaagaa aagcugaacg agcgacuugc uaaacuuuca 1140
gauggaguag cuguguugaa gguuggagga acaagugaug uugaagugaa ugagaagaaa 1200
gacagaguua cugaugcucu caaugcuaca agagcagcug uugaagaagg cauuguucua 1260
ggagggggcu gcgcucugcu ucggugcauc ccagccuugg auucauuaaa gccugcuaau 1320
gaagaccaga aaauagguau agaaauuauu aaaagagcac uuaaaauucc ugcaaugacg 1380
auugcuaaga augcaggugu ugaaggaucu uugauaguug agaaaauucu gcagaguucc 1440
ucagaaguug guuaugacgc caugcuugga gauuuuguga acauggugga aaaagggauc 1500
auugauccaa caaagguugu gagaacugcc uuacuggaug cugcuggggu ggccuccuug 1560
cuaacuacag ccgaagcugu agugacagaa auuccuaaag aagagaagga cccuggaaug 1620
ggugcaaugg guggcauggg aggggguaug ggaggcggca uguucuaacu ccuagaguag 1680
ugcuuugccc uuaucaauga acugugacag gaagcucaag gcagguuccu caccaauaac 1740
uucagagaag ucaccuggag aaaaugacug aagagaaggc uggcugacca cuguaaucau 1800
caguuacugg uuuccuuuga cgauauauaa ugguuuacug cugucauugu ccaugccuac 1860
agauaauuua uuuuguauuu uugaauaaag aacauuugua cauuccugau gcugguugca 1920
agagccauau accagugucc ugcuuucaac uuaaaucacu gaggcaucuc uacucuucug 1980
ugagucauca ggacuguagc gcugugucaa caaaacauag agaguucaga agacagccuu 2040
ucuguggaag ggugggaaug auuguguaca aaguagagaa guauccaauu augugacaac 2100
cuuuguguaa 2110

<210> SEQ ID NO 193
<211> LENGTH: 1228
<212> TYPE: RNA
<213> ORGANISM: Homo sapiens

<400> SEQUENCE: 193
acagccgcau cuucuugugc agugccagcc ucgucccgua gacaaaaugg ugaaggucgg 60
ugugaacgga uuuggccgua uugggcgccu ggucaccagg gcugccauuu gcaguggcaa 120
aguggagauu guugccauca acgaccccuu cauugaccuc aacuacaugg ucuacauguu 180
ccaguaugac uccacucacg gcaaauucaa cggcacaguc aaggccgaga augggaagcu 240
ugucaucaac gggaagccca ucaccaucuu ccaggagcga gaccccacua acaucaaaug 300

-continued gggugaggcc ggugcugagu augucgugga gucuacuggu gucuucacca ccauggagaa 360
ggccggggcc cacuugaagg guggagccaa acgggucauc aucuccgccc cuucugccga 420 ugccccccaug uuugugaugg gugugaacca cgagaaauau gacaacucac ucaagauugu 480
cagcaaugca uccugcacca ccaacugcuu agcccccccug gccaagguca uccaugacaa 540
cuuuggcauu guggaagggc ucaugaccac aguccaugcc aucacugcca cccagaagac 600
uguggauggc cccucuggaa agcuguggcg ugauggccgu ggggcugccc agaacaucau 660
cccugcaucc acuggugcug ccaaggcugu gggcaagguc aucccagagc ugaacgggaa 720
gcucacuggc auggccuucc guguuccuac ccccaaugug uccgucgugg aucugacgug 780
ccgccuggag aaaccugcca aguaugauga caucaagaag guggugaagc aggcaucuga 840
gggcccacug aagggcaucu ugggcuacac ugaggaccag guugucuccu gcgacuucaa 900
cagcaacucc cacucuucca ccuucgaugc cggggcuggc auugcucuca augacaacuu 960
ugucaagcuc auuuccuggu augacaauga auacggcuac agcaacaggg ugguggaccu 1020
cauggccuac auggccucca aggaguaaga aacccuggac cacccacccc agcaaggaca 1080
cugagcaaga gaggcccuau cccaacucgg cccccaacac ugagcaucuc ccucacaauu 1140
uccaucccag acccccauaa uaacaggagg ggccuaggga gcccucccua cucucuugaa 1200
uaccaucaau aaaguucgcu gcacccac 1228

<210> SEQ ID NO 194
<211> LENGTH: 723
<212> TYPE: RNA
<213> ORGANISM: Homo sapiens

<400> SEQUENCE: 194
agaagcuucc uaaggaacaa gcaaguugaa uagagaaaau agugaucaau aauaggcauu 60
uuaguggucu uuuuaauguu uucugcugcg gaacauuuca agauuuauug auuuccuccu 120
ccccccauuu uuuucccacc acacucacac acgcacgcuc acacuuuuua uuugccauaa 180
ugaaccgucc agccccugug gagaucucuu augagaacau gcguuuucug auaacucaca 240
accccaccaa ugcgacucuc aacaaguuca cagaggaacu uaagaaguac ggagugacaa 300
cuuugguucg aguuugugau gcuacauaug auaaagcucc aguugaaaaa gaaggaaucc 360
acguucuaga uuggccguuu gaugauggag cuccaccccc uaaucagaua guagaugauu 420
ggcuaaaccu guuaaaaacc aaauuucgug aagagccagg cuguuguguu gcagugcauu 480
guguugcagg auugggaagg gcuccugugc uaguugcgcu ugcauugauu gaaugcggaa 540
ugaaguauga agaugcuguu caauuuauaa gacaaaaaag aagaggagca uucaauucca 600
aacagcugcu uuacuuggag aaguaccgac cuaagaugcg guuacgcuuc agagauacca 660
augggcacug cuguguucag uagaaguaga agcaggcugg cuggaucgug gcauuagagg 720
gaa 723

<210> SEQ ID NO 195
<211> LENGTH: 2690
<212> TYPE: RNA
<213> ORGANISM: Homo sapiens

<400> SEQUENCE: 195
auucagguuc cucacagacc caggggguga ggauguugcu uuuugcccac uugcuucagc 60
ugcuggucag cgccacaguc ccgacccaga guaguaagug aggggagggg ugaggggagg 120
gguugggagc gaaaaagacu cugugaggaa aagcgggagg guggugguggg cggaggugca 180

-continued

```
gcaccccaag uuccgccgcc cuguccuagu cccuccccg ccuuuaccug ggaccuugag    240
ccugggggag gucggggucu caccgcgcgc cgcccccagg cccacacucg cugcgguauu    300
ucaccaccgc cguguccegg cccggccucg gggagccccg guucaucauu gucggcuacg    360
uggacgacac gcaguucgug cgcuucgaca gcgacgcgga aaauccgagg auggagccuc    420
gggcgcggug gauugagcag gaggggccgg aguauuggga gcgggagacu uggaaagcca    480
gggacauggg gaggaacuuc agaguaaacc ugaggacccu gcucggcuac uacaaucaga    540
guaacgacgg ugagugcggc ugggaucaca gcuaugauca cuccaugucc ccugagacgg    600
gccuggguca ucuugacccg cugagacaaa guuucaucca aacgccuacc cagaaccuca    660
gacaaaaaag cccccgcaga guucugcuua gguuuggggu uguacuuuug uuucucuuuu    720
guuuugagau aucuacuaac auugggcaaa guggccacag guggcgcuca ucagcguauc    780
ccuuccagaa ucucacacgc ugcaguggau guacggcugc gacguggggc ccgaugggcg    840
ccugcuccgc ggguauuguc aggaggccua cgauggccag gauuacaucu cccugaacga    900
ggaccugcgu uccuggaccg cgaaugacau agccucacag aucucuaagc acaagucaga    960
ggcagucgau gaggcccacc aacagagggc auaccugcaa gguccuugcg uggaguggcu   1020
ccauagauac cuacggcugg gaaaugagac acugcagcgc ucaggugccc uggagagcuc   1080
uccucacuuu uccucugcgg uuugggggaa auccuugagg uauaaccuca ggggcagaac   1140
gcuguucagc gggcacagcg cggaggagga gggagaggga cucccaaaac ugcuuuuccc   1200
cuguagggau ucuaauccuu aacaaaagca gaucaggcuc gacaauggcc cuggacccau   1260
gggggaggg ggcucuuucu caggccuccc uccuugcccu acucaguguc ucuauaguca   1320
gacuccagcu uuucucaauc ucuuggcccu cauccagcuc aggaccagaa gcccuuccca   1380
ugagucugca gagaccugga gccuccuguc cauguugucc ugcucacauc cuaaggcauc   1440
ccuaagagca gauccuccca ggugcaggug cucuagcugg ugucuagaug auggacacca   1500
uaaucccacc gcaguccucc uguccacccc aggacgguca caugaacacu gcugaguccc   1560
cagaagaaag caagaugccu cauccuuuca acucucuccc ucagacccuc caaaggcaca   1620
ugugacccau cacccuagau cugaagauga agucacccug aggugcuggg cccugggcuu   1680
cuacccugcu gacaucaccc ugaccuggca guugaauggg gaggagcuga cccaggacau   1740
ggagcuugug gagaccaggc cugcagggga uggaaccuuc cagaaguggg cagcugucgu   1800
ggugccucuu gggaaggagc aguauuacac augccaugug uaccaugagg ggcugccuga   1860
gccccucacc cugagauggg guaaggaggg ugugggugcu gaacuggggu cagggaaagc   1920
uggagccuuc ugcagacccu gaguugguca uggcucagag cugggaucau aacccucacc   1980
uucauuuccu guaccugucc uucccagagc cuccuccauc cacugucucc aacaugguaa   2040
ucauagcugu ucugguuguc cuuggagcug ugaucauccu uggagcugug guggcuuuug   2100
ugaugaagag gaggagacac auagguagga aagggcaggg ucugaguuuu cucucagccu   2160
ccuuuugcag ugugcucugc uccuuaaugg gaaacauagc cacacccaca uugcugcagu   2220
cuccaacugg gucagcuguc aguuccggga acucccuagg gcugguguuu cucuggucuc   2280
ucauggcuuu ucuucucaca gguguaaaag gaugcuaugc ucauguucua gguaagugcg   2340
agagaggggc aggggacacc cuugucccug aggcucucag gauggagcug ggauuuguuc   2400
cagcccauaa ucuccucuug ccacauccuc ucugucuccu cugugugccu uguuaucucu   2460
ucuacugcag gcagcaagag cuuccagacc ucugacuggc cucagaaggc augaaaaucc   2520
```

cugggggggc uggugagaug gcucaguggg uaagagcacu gacugcucuu cugaaggucc 2580
agaguucaaa ucccagcaac cacauggugg cucacaacca uccguaacga gaucugacuc 2640
ccucuucugg agugucugaa gacagcuaca auguacuuac auauaauaaa 2690

<210> SEQ ID NO 196
<211> LENGTH: 269
<212> TYPE: RNA
<213> ORGANISM: Homo sapiens

<400> SEQUENCE: 196
uuuuuuuuuu uguucccuug aaagccagau guuccaaaaa guagccugcu ccauuguucu 60
ucucagucuc auagcgacug ccagcgucaa uccacacucc caccgugcag guagcaugcg 120
aggacugcuc cgaggccaca cgcagcccgu uguccaagau gcugaccugg gucuccggca 180
cgcucuggag ggccugggcg aagguugcgg uaccccgcaa ggcagguaac cucagcaggg 240
ccggcgagcg gcgggugcgc cucgugccg 269

<210> SEQ ID NO 197
<211> LENGTH: 1335
<212> TYPE: RNA
<213> ORGANISM: Homo sapiens

<400> SEQUENCE: 197
ggugcuuaau guuuugaccu guagaggucc ucacuuuucg ucauggcgcu gaagguggcg 60
auagcugcug gcggugcugc aaaggcaaug cucaagccaa cucuccucug ccguccuugg 120
gagguucugg cugcccaugu ggccccccga aggagcauuu ccucacaaca aacaauuccu 180
ccaucugcua aguauggugg gcggcauaca gugacuauga ucccagggga uggcaucggc 240
ccagagcuca uguugcaugu uaagucugua uucaggcaug caugugugcc gguggacuuu 300
gaagaggugc auguaagcuc caacgcugau gaggaggaca uccgcaaugc caucauggcc 360
auccgccgga accguguggc ccugaagggc aacauugaaa caaaucauaa ccugccacca 420
ucccacaaau cucgaaacaa cauccuucgc accagccuag accucuaugc caacgucauc 480
cacuguaaga gccugccagg aguggugacc cggcacaagg acauagacau ccucauugua 540
cgggaaaaca cagaaggcga guacagcagc cuggagcaug agagcguagc aggaguggug 600
gagagcuuga agauuaucac caaagccaag ucccugcgca uugcugaaua ugcuuucaag 660
cuggcccagg agagugggcg uaagaaagug acggcugugc acaaggccaa caucaugaaa 720
cugggugaug gacucuuccu ccagugcugc agggaaguag cagcccacua cccucagauc 780
accuuugaca gcaugauugu agacaacaca acaaugcagc ugguaucccg gccucagcag 840
uuugauguca uggugaugcc uaaucucuau gguaacauug ucaacaacgu cugugcaggg 900
cuaguuggag gcccaggccu uguggcuggg gccaacuaug gccauguqua ugcaguauuc 960 gagacagcua caaggaacac aggcaaaagu auugccaaua agaacauugc uaacccgacu 1020
gccacacugc uagcaagcug caugaugcua gaccaccuca agcuccacuc cuaugccacu 1080
uccauccgca aagcugucuu agcauccaug gacaaugaaa auaugcauac cccagauauu 1140
ggaggccagg gcaccacauc ccaagccauc caggacauca uucgucauau ccgcaucauu 1200
aauggacggg cuguggaggc uuagcuaucc cuacaguuuu gcucagcuug ucuguaggac 1260
ucucuucuca cuuuagcacu ccagcuagcu ugggggacag gacccagaau aaagccacuu 1320
cuguuccaga aaaaa 1335

<210> SEQ ID NO 198
<211> LENGTH: 382
<212> TYPE: RNA
<213> ORGANISM: Homo sapiens

<400> SEQUENCE: 198
uuuuuuuuuu uuuuuuuguu cuuaauagaa aacuuuauuu ucacugauaa ugucacugua 60
acauaauuuc auagcagacc ugugcaaaag aucccacauc accaaugucu ccaagagauu 120
ucacacacuu cugggcagga cgcacagcuc ugccccccacc cccguguuga cagucaacau 180 uuuaccccccg cuaugaguac agaaaggcga ggcaucauaa cgaagccgcc ugaaggcagc 240
gugagcugaa gucggacgcu ugccaccucu gaaugaaugg ucaccacagc aacagcacau 300
gguugccuca gugugcucag ggugggucuu ugaaaaaacg ucccacuaug uaaauaugcu 360
gcacuuaucc cuucaacauu gu 382

<210> SEQ ID NO 199
<211> LENGTH: 1992
<212> TYPE: RNA
<213> ORGANISM: Homo sapiens

<400> SEQUENCE: 199
ggcagacaaa agaggccggc agugcagcuc gcgggacgca uggccgggcg cggaggacgg 60
gugcugcugg cgcugugugc cgcgcuggug gccggcgggu ggcugcugac gcgugaagcc 120
caggagcccg gggcgccagc ggcuggcaug aggcgccgcc ggcggcucca gcaagaggac 180
ggcaucuccu ucgaguacca ccgcuaucca gagcugcgcg aggcgcuggu gucgguaugg 240
cugcagugca ccgccaucag cagaaucuac acagugggcg ccagcuucga gggccgggag 300
cuccugguca ucgagcuguc ugacaacccc ggggguccaug agccgggugga accugaauuu 360 aaauacaucg ggaacaugca uggcaaugag gcgguuggac gggaauugcu cauuuucuug 420
gcccaguacc uguguaacga guaccagaaa ggcaaugaga caauugucaa ccugauccac 480
agcacccgaa uucauaucau gcccuccuug aaccccgacg gcuuugagaa agccgcaugg 540
cagcccgggc agcugaagga cugguuugug ggccgcagca acgcccaggg aauagaucug 600
aaccguaacu ucccagaccu ggacaggauc guauauguua augagaaaga aggcgguccc 660
aacaaccacc ugcugaagaa ucugaagaaa auuguggacc aaaauucaaa gcuugccccc 720
gagaccaagg cugucauuca cuggaucaug gacauuccau uugugcuuuc ugccaaucug 780
cacggaggag accuugugc uaauuaccca uaugaugaga cacggagcgg uacugcucac 840
gaauacaguu ccugcccuga ugacgcaauu uuccaaagcu uggcucgcgc guacucuucu 900
uucaacccag ucaugucuga ccccaaucga ccucccugcu gcaagaauga cgaugacagc 960
agcuuugaug auggaacgac caaugguggu gcaugguaca gcguccccgg uggaaugcaa 1020
gacuucaauu accugagcag cagcaacugc uuugagauca cuguggagcu uacgugugag 1080
aaguucccac cugaagagac ucucaaaagc uacugggaag auaacaaaaa cucccucauc 1140
aacuaccugg agcagauaca ccgagguguu aaagguuug uccgugaccu ucaggguaac 1200
ccgaaugcca acgcaaccau cucuguggau gggauagacc augaugucac cucggcuaag 1260
gauggggauu acuggcgauu gcuugcuccu ggaaacuaua aacuuacagc cuccgauccu 1320
ggcuaccugg caaucacaaa gaaaguggca guuccuuuua gcccugcugu uggggguggac 1380 uuugagcuug agucuuucuc ugaaaggaag gaggaggaga aggaagaauu gauggagugg 1440
uggaaaauga ugucagaaac uuugaauuuu uaagaaaggc uucuaacuaa uugcuuucau 1500
cuaucuauag acuguaguaa gaugcaaugu ggcucuuuuc uuuuagguug ugugcaguug 1560
auauuuaaca uugauuuauu uuugaucauu aaguaauagu uacuaaucac guaaauacac 1620
ccggacagaa auauaaugcu ggacaucuuc auucuacauc aacauucgcu uaaaucauuc 1680
gaagccucuu uuaacguaau gggugacaau gucacuugac agaugcauga gagucacgau 1740
auagcugacu gugacccugc acugcaauca cauaguucca uauaaguugu ccuuagucuc 1800
uugugcugau ucacuguaua agcaugaucc ugguaaugca cuuuggaugg gaagaaaaug 1860
uacgugcuuu ucagaggggc ucugaacaga augaaaaccu aguucuugcg uguacuuuga 1920
agaauggaau uguauuaguc agcuguuaau gccacuucag aaguuugggg uuuugucuug 1980
auuguagauu gg 1992

<210> SEQ ID NO 200
<211> LENGTH: 210
<212> TYPE: RNA
<213> ORGANISM: Homo sapiens
<220> FEATURE:
<221> NAME/KEY: misc_feature
<222> LOCATION: (118)..(121)
<223> OTHER INFORMATION: n is a, c, g, or u

<400> SEQUENCE: 200
gauccuguau augugcguuu ugggggagcu augauaaguu uuauggcaaa cgguugguau 60
uguuaacuuu uuauugucau caaaaguuca uaaaaguccu auuaaucccc auauucunnn 120
ncugcccuua acucugguau acaccaaaaa gaaaucuuua cuuuccuugu uuuaucauua 180
uaaaaauaaa guauuuugcu aguauggaaa 210

<210> SEQ ID NO 201
<211> LENGTH: 677
<212> TYPE: RNA
<213> ORGANISM: Homo sapiens

<400> SEQUENCE: 201
aguccgcguc ccggcgucgg cccgucccgc accauggaga cgcucgccga gcugcuggcg 60
cugcuggccg cgcugcuggc cacggccucg ggcuacuuug ucagcaucga cgcgcacgcc 120
gaggagugcu ucuucgagcg ggucaccucc ggcaccaaga ugggccucau cuucgaggug 180
gcggagggcg gcuuccugga caucgacgug gagaucacag gaccagauaa uaaaggaauc 240
uauaaaggag accgggaguc cagcgggaag uacacauuug cagcccacau ggaugggaca 300
uacaaguucu gcuuuagcaa uaggaugucc acuaugacuc caaagauagu aauguucacc 360
auugacauug gggaggcucc caaaggacaa gacauggaga cagaagcuca ucagaacaag 420
cuagaagaaa ugauuaauga gcuggcagug gcaaugacag ccguaaagca cgaacaggag 480
uacauggaag uccgggagag aauacacaga gccaucaaug acaacacaaa cagcagagug 540
guccuuuggu ccuucuucga agcucuuguu cuaguugcca ugacauuggg acagaucuac 600
uaccugaaga gauuuuuuga aguccggagg guuguuuaaa aggccuuuuc cuguugaucc 660
caaauucaug auuuacu 677

<210> SEQ ID NO 202
<211> LENGTH: 2849
<212> TYPE: RNA
<213> ORGANISM: Homo sapiens
<220> FEATURE:
<221> NAME/KEY: misc_feature
<222> LOCATION: (2158)..(2158)
<223> OTHER INFORMATION: n is a, c, g, or u

<400> SEQUENCE: 202
gcauuggcuc ugggcugcgg ccggcucggc gacgcuccuc gggcagcuca cugcaugguc 60
gucuggugcc cccgccgccu gcaucccgc cgccgccccg cgacgcccac cgccgccugc 120
ccugccgccg ccgccugcgc cgccucggga ccggcuguau gauuaggcca caaucuucaa 180
ugaguagaca uauuccucag uucuguggug uucucgguca cacauuuaug gaguuucuga 240
agggcagugg agauuacugc caggcacagc acgaccucua ugcagacaag ugaacuguag 300
aaauucauua cuacuccacc aagaaacccc cauaagagug gauaaccugg acacaggcgu 360
guugaauuga aaucugcaca gcauuugaga agagcucaga ccuggauggg guaaaccuca 420
gugccacuuc cuuuguauug ccucuaguau uacugggauu gaagagucac ugcuucuugu 480
uuaggagguu cauuucauug gcccguuucu cccaauuuca uacucaagca cugagaauuu 540
caaguggagu auaucgaaua ucgaaguaga cuucagguug uuuuuugguu uuguuuuguu 600
uuuuuuuugu uuugguuuuu uuuuuuuuuu ucuguuuugg uuuaaaucau uucuguauuc 660
aauuuuuuaa uucuuucaua acccuauugg guguuuuuuu aaacuaaauu aacauggcuc 720
gaaugaaccg cccugcuccu guggaaguca cauacaagaa caugcgauuu cuuauuacac 780
acaauccaac caaugcgacc uuaaacaaau uuauagagga acuuaagaag uauggaguua 840
ccacaauagu aagaguaugu gaagcaacuu acgacacuac ucuuguggag aaagaaggca 900
uucauguucu ugacuggccu uuugaugaug gugcaccacc auccaaccag auugucgaug 960
acuggcuaag ucuugugaag auuaaguuuc gugaagaacc ugguugcugu auugcugucc 1020
auugugucgc aggccuuggc agagcuccgg ugcuuguugc ccuagcauua auugaaggug 1080
gaaugaaaua ugaagaugca guacaauuca uaagacaaaa gcggcgugga gcuuuuaaca 1140
gcaagcaacu uuuguaucug gagaaguacc guccgaaaau gcggcuccgc uucaaggauu 1200
ccaaugguca uagaaacaac uguuguauuc aauaaaacug gggugccuga ugccauugcc 1260
uuggaagugg aacuucagau gggaccugau uugucaugca uauuacccaa ugugucggcu 1320
uacugaauaa gucuacugca gcuccacagg aauacugaaa aaccagucuu accaggccac 1380
aaguuugaca gaauugcaac cucuauauuu gggcuaugau caacauguuu ggacacuuag 1440
caaaagauuu uugcuguuca gcauuuaaaa ugugcuuauu auuuguacca auugaccuuu 1500
ccuaaaauaa gguauugagu uaugucauua aauguacucc ugugccagaa uauuauuagu 1560
cuauaaggaa uuuagaagga uuaggugcca aaauacccag cacaauacuu guauauuuuu 1620
agcaucauac agaaccaaaa uugcaggaac ugagaacucu cagaccaucc augguguauu 1680
ccuucaguca uuucaaacac ugcagggcuc cucucguuau cugccugcuc acucuguuua 1740
caucucccac acuuaugcca gaauacguca gguuugcuua gccauccuuu auuuuuuuua 1800
uuuuuuuuuu uaacuaaguc uugcgcugau uauuuaauau gucugucuca uuuuguuuug 1860
uuuugggaaa ccucugucug aaaaaucaac uuuguuacag aagcacauau cuucaacaau 1920
gucuccagac aaaaagccuu auaguuaauu uaauguuugc acucagaagu gcaaccuaac 1980
agggagggcc ugaaaaagaa acgagaggag gcuauuaaau auuuuuagua auauguugcc 2040
uuugucaugu gcagaacaug uagaguaugc ucuuaauuua guaaauauuu uuaagacaua 2100
gagauacaug uguagcuaac ccauucuuau ucaaaauucu ggaauuuugu guuuuccnau 2160
accuaucagg aaguuuccag cuuguuugaa uuauggcuuu ccucuuccca aucucuugca 2220
aaaaagacaa agugggauga aucugcuagu gaacugagca gaaauguuuu auaacgccuu 2280

-continued

```
uugagcuaug uaacuuaaua auuggauacu ugaucauuug uuuuauuaug uaaucggaua   2340

aaauggugau guguauuaaa guuaguucaa ccauauauuu auacugucug ggaaugugug   2400

guuauaguuc ugugggagaa auaguuuguc aguguucacc agcuuguaaa aacuuaguau   2460

gagagcuuca acauuuaaau aaaugaugaa ccgcauucgu cacugaggac acuuuugccu   2520

aaaauuaacu uaauuuguag aaaacaaugg auucaguuaa uaucauuuca auuuauggaa   2580

aaaauuguua ggguugccaa gugcuuuuua uuaaaaguuu cucuuuaaag gucuagauaa   2640

uugugaauca guugaauguu gggcaccgag gggaaacagu uuguaauaga ugaucuagau   2700

uuuucaguuc aguuccauca gucacuugua gcucugcaau uuccagacca guuuucucau   2760

uuuuaaguuc auuacaugcc uguauauauu uugaaauuaa cuugaaccug aguauuuggc   2820

acaugauggc uuaauaaauu uuaacuuuc                                     2849
```

```
<210> SEQ ID NO 203
<211> LENGTH: 3023
<212> TYPE: RNA
<213> ORGANISM: Homo sapiens

<400> SEQUENCE: 203

acgcucccca accuccaccu ccccucgcuc ggccucuaua ugcucccggg cucccuagug     60

uuggcuggaa gugggugacu uagaggcuua aaggaggggc gccuaaccac ggaccacgug    120

ugugcggggg cgacagcgcc gccgggguggg ggcugagcgc ugcaagccgg guucgccuug    180

cagcgcagga gucagugggc guugcgccac gaucucucuc cacuagcacu augcucccgc    240

cccacucacc gccuuggaaa gucacaggag aaggcgggcu cuaagaccca gcaggcacca    300

uccuacuggc gccuucgauc cgagacccgu uuggacacca gggggcgaug ccgacccucu    360

auaaaagcgg uccccgcgcg ggccuggcca uucgcgaccc gaagcugcgc gggcgcgagc    420

caguuggggc acuggguggg cggcggcgac agcggcgcca cgcgcaggcu ggaggccgcc    480

gaggcucgcc augccgggag aacucuaacu cccccaugga gucggccgac uucuacgagg    540

uggagccgcg gcccccgaug agcagucacc uccagagccc cccgcacgcg cccagcaacg    600

cccgccuuug gcuuuccccg gggcgcgggc cccgcgccgc ccccagcccc accugccgcc    660

ccggagccgc ugggcggauc ugcgagcacg agacgucuau agacaucagc gccuacaucg    720

acccggccgc cuucaacgac gaguuccugg ccgaccucuu ccagcacagc cgacagcagg    780

agaaggccaa ggcggcggcg ggccccgcgg guggcggcgg ugacuuugac uacccgggag    840

ccccggcggg ccccggcggc gcggucaugu ccgcgggggc gcacgggccc ccucccggcu    900

acggcugugc ggcggccggc uaccuggacg gcaggcugga gccccuguac gagcgcgucg    960

gggcgcccgc gcuacggccg cuggugauca aacaagagcc ccgcgaggag gacgaggcga   1020

agcagcuggc gcuggccggc cucuuccccu accagccacc gccgccaccg ccaccgccgc   1080

acccgcacgc gucucccgcg caccuggccg ccccccacuu gcaguuccag aucgcgcacu   1140

gcggccagac caccaugcac cuacagccug gccaccccac accgccgccc acgcccgugc   1200

ccagcccgca cgcugcgccc gccuugggug cugcgggccu gccuggcccc gggagcgcgc   1260

ucaagggcuu ggccggugcg caccccgacc uccgcacggg aggcggcggc gguggcagcg   1320

gugccggugc gggcaaagcc aagaagucgg uggacaagaa cagcaacgag uaccggguac   1380

ggcgggaacg caacaacauc gcggugcgca agagccgaga uaaagccaaa caacgcaacg   1440

uggagacgca acagaaggug cuggaguuga ccagugacaa ugaccgccug cgcaagcggg   1500

uggaacagcu gagccgugaa cuggacacgc ugcggggcau cuuccgccag cugccugaga   1560
```

gcuccuuggu caaggccaug gcaacugcgc gugaggcgcg cggcugcggg accgccuugg 1620
gccggccccc uggcuggaga cccagaggau gguuucgggu cgcuggaucu cuaggcugcc 1680
cgggccgcgc aagccaggac uaggagauuc cggugug gcc ugaaagccug gccugcuccg 1740
cguguccccu cccuuccucu gagccggacu cggugcgucu aagaugaggg agucaggccg 1800 ugguggguuuc uccuugagac cgagagacuu uuccgcggag cugagcuggg ggcccggcag 1860
uacuaguauu aaggaaguaa ccuugugccu uggauacuca aaacucgcuc cuuuuccuac 1920
cgaguagggg gagcaaaaau gugccuugau auuuuauuug gaggauuccu gcuuccucuc 1980
gggccucagc uggcccccgu gagaaaaaug aagggugcag gcccagggca ggaggaagau 2040
acaggaagcu gagaucccgg cagugcccug agcugccccu caguccc ugu cuuuagaggg 2100 gagggacuua ggugu ugggg auuugagucu guguccucac ccccagcuac agggaggugg 2160
agggcuccua aucccuugcu uuuugcaccu ccaccuacau cccccccccc ccacucagcu 2220
uacaacaggc cagguuuccu gggugaguuc auggagaaug ggggcaccac ccccagucag 2280
acagaaagcu gaguugugag uuagccaugu gguaggagac agagaccuag guuucugggc 2340
uuuguggggu gggggauagg aggacacggg gaccauuagc cuugugugua cuguaugucg 2400
ccagccgcug uugcugaagg aacuugaagc acaaucgauc caucccagag ggacuggagu 2460
uaugacaagc uucccaaaua uuuugcuuua ucauccgaua ucaacacuug uaucuggucu 2520 cugugucca gcggugccuu gugcaauggc agugugcacg ucuaugcuaa accaccauuu 2580
uauuuggucu uuuguuuugu uuugguuuug cucugauucu ugccaaacug agacucuuca 2640
cuaacggcug ggggaaggag cugagugagg cucucauucu uuuugguuua gggauguuug 2700
gguuuuuucg ucugccuccc agaggaccaa ugaaaugaag ugggcuuccc ccucuccccu 2760
aguuguccaa ggguguaugu aguagugggu cuuagcuucc uccggcuaag acuuaggcuu 2820
ccccacccac ccaaccccau ccccaacggc ccuggcucug ggucuggaaa gaaggccacc 2880
uccagccagu ucauacacac accccugugg cugggagcag ggcuggaccg cuuccuucuc 2940
uucuuuuuuu gggggggggg acacaaaguu ucaugcuaga ugucguaugu auuauaucua 3000
uaauauaaac auaucaaacu caa 3023

<210> SEQ ID NO 204
<211> LENGTH: 380
<212> TYPE: RNA
<213> ORGANISM: Homo sapiens
<220> FEATURE:
<221> NAME/KEY: misc_feature
<222> LOCATION: (76)..(76)
<223> OTHER INFORMATION: n is a, c, g, or u

<400> SEQUENCE: 204
gaagcucagu gucgugaaau ggaaaccaaa ccuuggagcc aucgcugagu auaaaaaaaa 60
ggaagauuua uauucngcaa agaguagccg aacuggacaa aauuacuucu gaaagagaua 120
auuuuagaca agcauaugaa gaucuucgaa aacaaaggcu gaaugaauuu auggcugguu 180
uuuacguaau aacaaauaaa cuaaaagaaa acuaccagau gcucacauug ggaggagaug 240
cugaacugga gcuuguggac aguuuagauc cuuuuucuga aggaaucaug uucaguguuc 300
ggccaccuaa gaaaaguugg aagaagaucu uuaaccucuc aggaggcgag aaaacccuua 360
guuccuggcc uuaguguuug 380

<210> SEQ ID NO 205

<211> LENGTH: 1391
<212> TYPE: RNA
<213> ORGANISM: Homo sapiens

<400> SEQUENCE: 205
gccgguuuga guugugcgcu cgggugucce uuuccucuuc cccucccgca gggcuugcgg 60
ccaccauggc guauuagagg cagcagugcc ugcggcagcg uuggccuuug cagcggcggc 120
agcagcacca ggcucugcag cggcaacccc caccggccua agccauggcg cucuucacga 180
aauccagcag caguguugcu guaacggaca aagauaccuu cgaguuaagc acauuccugg 240
aauccagcaa agccccacaa caugaccgag augagcuucc ugaacagcga aguguuggcg 300
ggggacuuga uguccccuu cgaccagucg gguuuggggg cugaagaaag ccuaggucuc 360
uuagaugacu aucuggaggu ggccaagcac uugaaaccuc augguucuc cagcgacaag 420 gcgggcuccu cggaauggcc ggcuauggau gauggcuugg ccagugccuc agacaccggc 480
aaggaggaug ccuuuuccgg gacagauugg auguuggaga aaauggaucu gaaagaguuu 540
gacuucgaug cucuguuucg aauggaugac cuggaaacca ugccagauga gcucuugacc 600
acguuggaug acacauguga ucuuuuugcc ccucuagucc aagagacuaa uaaggagccc 660
ccucagacag ugaacccaau uggccaucuc ccagaaaguu uaauaaaagu cgaccagguu 720
gcccccuuua cauucuugca gccuuucccc uguuccccag ggguucuguc uuccacucca 780
gagcauuccu uuaguuuaga gcuaggcagu gaaguugaua ucucugaagg agacaggaag 840
ccugacucug cugcuuacau uacucuaauc ccuccaugug uaaaggagga agacacuccc 900
ucugacaaug acaguggcau cuguaugagc ccggaguccu accugggcuc uccccagcau 960
agccccucca ccuccagggc cccaccagac aaucugccuu cuccaggugg uucccguggg 1020
ucuccucggc ccaaaccuua ugacccaccu ggaguuaguu ugacagcuaa agugaagacu 1080
gagaaauugg auaagaagcu gaaaaagaug gagcaaaaca agacagcagc cacuagguac 1140
cgccagaaga agcgggcuga gcaggaggcc cucacuggcg aguguaagga gcuagaaaaa 1200
aagaaugagg cucugaaaga gaaggcagau ucucuggcca aggagaucca guaucugaaa 1260
gaccugauag aagagguccg uaaggcaagg gggaagaaga gaguuccgua auaggguagu 1320
caggugcuuu gugcuuguac auagucuugu guugcugugu uugcuguaau aaauuauuuu 1380
guagugaaag u 1391

<210> SEQ ID NO 206
<211> LENGTH: 356
<212> TYPE: RNA
<213> ORGANISM: Homo sapiens

<400> SEQUENCE: 206
uuuuuuuuuu uuuuuaugua gggaaguuca uauuuuauuu guccagugac auuuuuuaca 60
guugaauaca aguuaaaggc cugcuugcac accaaagcca gguccuuugg gugguucagu 120
caaagaagua aggccuccag cuggcucaca acagaagcgg ccacuccuug gcccugguuu 180
gggaacuuuu ccagcuuuga guucaucaau aaucucuuca auauccuugg gugucagauc 240
cucauaguag uugucauuua uuugaaccau cggugcauuu acacaggccc cuaaacauuc 300
cacuucuaua agagugaaaa guuugucagg uguagucucu ccaaccuuua uuccaa 356

<210> SEQ ID NO 207
<211> LENGTH: 413
<212> TYPE: RNA
<213> ORGANISM: Homo sapiens

<400> SEQUENCE: 207
uuuuuuuuuu uuuuuuuggg gugaauauag ccaaguauuc cauuuauuaa caaaauaguc 60
uuagcaaggg agagcucugu ucaccccaca agaggccccg cagccgaggc cggccccgaag 120 ccccagcgcu gcugcguaag accgggaggg agggaaggug uuggggagaa gacuuguauu 180
aagucuuuaa uccuagccac cgcaggaacc cacggaaacc uaaugccagc uuuggcgauu 240
gcuggcucag gucugggaca uggcgaaggg agugcucuga uccuagggcu cccugagucc 300
ccagccugcc cccaacagag cuccuaaagu ugucuggucu gcugacuuga ggacugguaa 360
gcuuuggagg gauccaucaa ggauuccccg accccacccc uaucgccagg gga 413

<210> SEQ ID NO 208
<211> LENGTH: 1707
<212> TYPE: RNA
<213> ORGANISM: Homo sapiens

<400> SEQUENCE: 208
ccucugcggc gcgguccucg gagcggcgcg guucucggag ccacgcgucu gucuuccucc 60
guggucaugg cggacuaccu gauuagcgga ggcaccucuu acgugccgga cgacgggcuc 120
acagcgcagc agcucuucaa cugcggggac ggccucaccu acaaugauuu ucucauucuu 180
ccuggguaua ucgacuucac ugcagaucag guggacuuga cgucugcucu aacuaagaag 240
auuacacuaa agaccccauu gguuuccuca cccauggaca cugucacaga ggcuggaaug 300
gccaucgcga uggcgcuuac aggagguauu gguuucaucc accacaacug cacaccugaa 360
uuccaggcca augaaguucg gaaagugaag aaauacgaac agggauucau cacugacccc 420
gugguccuua gccccaagga ucguguacgc gauguuuuug aggccaaagc caggcauggc 480
uucuguggua uccccaucac agauacaggc cggaugggga gucgauuggu gggcaucauc 540
uccucaaggg acauugauuu ccucaaggag gaagagcaug accgguucuu ggaagagauc 600
augacuaaga gggaagauuu gguggucgcc ccugccggcg ucacucugaa agaggcaaau 660
gagauucugc agcgaaguaa aaagggaaag uugcccauug ugaaugaaaa ugaugagcug 720
guagccauca uugcccggac agaccuaaag aagaaucgug auuacccccu ggccuccaaa 780
gaugccaaga agcaacugcu guguggggca gccauuggca cucaugagga ugacaaguau 840
aggcuggacu uacuggcccu ugcuggugug gauguagugg uuuuggacuc uucccaggga 900
aacuccaucu uccaaaucaa uaugaucaaa uacaucaagg agaaguaucc cagucuacag 960
gucauuggag gcaauguagu cacugcugcg caagccaaga accucauaga ugcaggugua 1020
gaugcuuugc gagucggcau gggaagugguu uccaucugca ucacccagga aguguuggcc 1080
ugugggcggc cccaagccac agcaguguac aaggucucug aguaugcccg ucgcuuuggu 1140
guuccuguua uugcugaugg aggaauccaa aaugugggguc auauugccaa agcuuuggcu 1200
cuuggggcuu ccacagucau gaugggcucc cuccuggcug ccaccacuga ggccccuggc 1260
gaguacuucu ucucagaugg gauccggcug aagaaauacc gagguauggg uucucuugau 1320
gccauggaca aacaucucag cagccagaac cgauacuuca gugaagcuga caaaaucaaa 1380
guggcccaag gaguuucagg ggcagugcag gacaaggggu cuauccacaa guucguuccu 1440
uaccugauug cuggcaucca gcauuccugu caagacauug gugccaagag uuuaacccaa 1500
gucagagcca ugacguacuc gggggagcuu aaauuugaga agaggacauc cucugcucag 1560
guggaaggug gcguccacag ccuccauucg uacgagaaac ggcuuuucug aaaacagauc 1620
caguauaugc cuugaauuuu ucaauaaaag uuugggaaaa aaaaagugaa aaaaaaaaaa 1680
aaaaaaaaaa aaaaaaaaaa aaaaaaa 1707

<210> SEQ ID NO 209
<211> LENGTH: 261
<212> TYPE: RNA
<213> ORGANISM: Homo sapiens

<400> SEQUENCE: 209
gugugggugc agagcugggg ucagggaaag cuggagccuu uugcagaccc ugagcugcuc 60
acggcugaga gcugggguca uuacccucac cuucauuucc uguaccuguc cuuccccagag 120 ccuccuccau ccacugucuc caacauggcg aacguagcug uucugguugu ccuuggagcu 180
uggccaucau ugcagcugug guggcuuuug ugaugaagag aaggagacac acagguagga 240
aagggcagag ucugaguuuu u 261

<210> SEQ ID NO 210
<211> LENGTH: 173
<212> TYPE: RNA
<213> ORGANISM: Homo sapiens

<400> SEQUENCE: 210
acaggagggg aaggccaaag caagaaugaa aguccccccgc cccguaucac cacgggcacu 60
cggggucacc cucaggaaca ugcagucucu gcacgugagg aaagaaacac gcagagaugg 120
acgagcacuu uuacacccua auaaaauuag augcacuaac cacagacccc ccu 173

<210> SEQ ID NO 211
<211> LENGTH: 494
<212> TYPE: RNA
<213> ORGANISM: Homo sapiens

<400> SEQUENCE: 211
uuuuuuuuuu uuuuuuuaaa aaaaaaaaug gcaucuuuua uucaucaauc ccuguuacac 60
acugaaauac augcaucuuu cuuauguuac uuagcaacgu ccuuucuauc cuuucaccca 120
uaaaucaguc ugaugaauuc aucuuuaaau ucaagaaguu uuucuuuuug aaacgcuacu 180
uacauuuuau ugucucaaua ucaaagccaa ucuagagauu uauucuuccu acaggugaaa 240
uagauguuaa uacgggaaca gucaguacau guucaagaug acaucaaagu uaugcccuaa 300
gcagauauuu caaggcaaua ucaugccacu agcucugaga cucuaaguau cacugauagu 360
acuaaaaggu agaagucagc uucaaaaaca cacucuugca auggacacug cucaugaugu 420
cuaagauugu ucacucccac agucaugauu ucagaugcac aguuuuuuuu gcuuuccuga 480
gcauucgguu ugac 494

<210> SEQ ID NO 212
<211> LENGTH: 384
<212> TYPE: RNA
<213> ORGANISM: Homo sapiens

<400> SEQUENCE: 212
uuuuuuuuuu uuuuuuuaag agugucacca aagcuuuauu uacaugcguc aucaucucuu 60
uuacaaacua gauuaugguu uuaaauggaa uacacaggca auaucuacaa acgccacggg 120
aaguacgcac cuccauucca ccgggaaggg gcagauuccc aaaucaaacu gguuuugauc 180
cuugagaaga aaggcggcag agcuaacuca cggcagcgua ugguuagaca agguccucag 240
uacccagaau gcagcaggau ugcgucugcc ucaaaccaga cgaccaacug cugcaggugu 300
uuaaacaugg ccacgcgcca cacgaaauuc uaguuugugu gggguagaag caagaaaaaa 360
aaaaaaccau ggcgccucgu gccg 384

<210> SEQ ID NO 213
<211> LENGTH: 982
<212> TYPE: RNA
<213> ORGANISM: Homo sapiens

<400> SEQUENCE: 213
gguccggaua guaaacugcu cccuuacauc uccuuaaaua uaaaguaagg aaaaagaaaa 60
aacucaguuc ggguaaccaa guucaacaag uaauccuugg ggccgcugug guaucgccaa 120
aaucuacaua guaucucuua uuaaaauguu uugacgaaaa uguaacaauu acgguacuua 180
augguaacaa uguggcugag gaagcaauag uuaacaaaga ggagcuaagc uaugcaacaa 240
accagauuuc uauuggucac aaauuugaag uugagaccug uuauccaauu accaaguacu 300
uccgcauaca ucaucauagg cauuugaaga uuucaaccaa ucaggagcau guuccuucua 360
uaaaggaacc cagaaccuaa ccucugcauu uccuauuucu uuguagaaau ggcucguacg 420
aagcagaccg cucgcaaguc cacuggcggc aaggccccgc gcaagcagcu ggccaccaag 480
gccgcccgca agagcgcccc ggccaccggc ggcgugaaga aaccucaccg cuaccguccc 540
ggcaccgugg cgcugcgcga gauccggcgc uaccagaagu cgaccgagcu gcugauccgc 600
aagcugccgu uccagcgccu ggugcgcgag aucgcgcagg acuucaagac cgaccugcgc 660
uuccagagcu cggccgucau ggcucugcag gaggcgagcg aggccuaccu ugugggucug 720
uuugaggaca ccaaccugug cgccauccac gccaagcgug ucaccaucau gcccaaggac 780
auccagcugg cccgccguau ccgcggcgag cgggcuuaau aggcacgcuu ucuacacugg 840
cacguaaacc aaaacggcuc uuuuaagagc caccuccauu auccaccaaa gaugcuugaa 900
guacaaguug ugagaguuuu cuaggguuuc cuauuauagc cuuucuugac aaugugagca 960
ccacccgacg aagcagucug ag 982

<210> SEQ ID NO 214
<211> LENGTH: 424
<212> TYPE: RNA
<213> ORGANISM: Homo sapiens

<400> SEQUENCE: 214
uuuuuuuuuu uuuuuuugga cuucugcggc uuuuauuuuu gcauguaaac cacugggggg 60
agggggaucu ugaugguggg cacccuagag auuacacugg aguuccgagg gcuccagaca 120
cuagcuggga agucagguga cagaaacaau gauucagacc aaucacauga uugcaaaacu 180
gggucuccag cagggauucu ggugguuagg uguggaugcc uaaggaagca gugacauggg 240
aggggcacgc acugggcugg ccuugagcug cugggaugac aucagggaua gaggaccuag 300
cagcuggugg cuccagggau cuccggucca ugcuuuauuu ggccaggggg uuccugaagg 360
accugccagc aaacuuggcu uugcugccca gcucuuccuc aauucugagg aucugauugu 420
acuu 424

<210> SEQ ID NO 215
<211> LENGTH: 1407
<212> TYPE: RNA
<213> ORGANISM: Homo sapiens

<400> SEQUENCE: 215

```
auucuaagga ucaugucugc gagucaggau ucucgaucca gagacaaugg ccccgacggg     60

auggagccgg aaggcgucau cgagaguaac uggaacgaga uuguggauag cuuugaugac    120

augaaucucu cagagucccu ccuccguggu auuuaugccu augguuuuga gaagcccucu    180

gccauccagc agcgagcuau ucuuccuugu aucaaggguu augaugugau ugcucaagcc    240

cagucuggga cugggaaaac agcuacauuu gccauaucaa uucugcagca gauugaauua    300

gaucuaaagg ccacucaggc uuugguucug gcacccacac gugaauuggc ucagcagaua    360

caaaaggugg uuauggcauu aggagacuac augggugccu cuugucaugc cugcauuggg    420

ggcaccaaug ugcgugcuga ggugcagaag cugcagaugg aagcucccca uaucaucgug    480

gguaccccug gccggguguu ugacaugcuu aaccggagau accugucccc caaauacauc    540

aagauguucg uacuggauga agcagaugaa auguuaagcc gaggguucaa ggaucagauc    600

uaugacauau uccagaagcu caacagcaac acacagguag uuuuguuguc ugcuacaaug    660

ccuucugaug uccuugaggu gaccaagaaa uuuaugagag acccuauucg gauucuuguc    720

aagaaggaag aauugacccu ggaggguauc cgccaauucu acaucaaugu ggaacgagag    780

gaguggaagc uugacacauu gugugacuug uaugagacgc ugaccaucac ccaggcaguc    840

aucuuuauca acaccagaag gaagguggac uggcucaccg agaagaugca ugcccgagau    900

uucacuguuu cugccaugca cggagauaug gaccaaaagg aacgagaugu gaucaugagg    960

gaguuccggu cuggcucuag cagaguauua auuaccacug accuguuggc cagaggcauu   1020

gaugugcagc aggucuccuu agucaucaac uaugaccuuc ccaccaacag ggaaaacuac   1080

auccacagaa ucggucgagg uggucgguuu ggucguaagg guguggcuau uaacauggug   1140

accgaagaag acaagaggac ucuucgagac auugagacuu ucuacaacac cuccauugaa   1200

gagaugcccc ucaacguugc ugaccucauu ugaggggcug uccugcgacc uggcccuagc   1260

ccaggguuca guccuggggu ggggcuaagg aagagcugga gggggggaggg gagggagcca   1320

agggauggac aucuuguuuu uguuuuggcu uuuuuuuuuu uuuguuucag uuuuuuuucu   1380

cuaugaauaa augucacuuu uugaggc                                       1407
```

<210> SEQ ID NO 216
<211> LENGTH: 562
<212> TYPE: RNA
<213> ORGANISM: Homo sapiens

<400> SEQUENCE: 216

```
uuuuuuuuuu uuuuuuugcc aggauauauu uauuacugaa aguacaagca acugagguuu     60

acccugggaa cacccacaau gaaacgugua ucuucccugu uucucagaug cugccuccuu    120

ccacagagug aguuuucguu uaaaacucau aaugaggaga aggcaggggg cuccaccccu    180

uuccuguuca aucugaagac ugaauugggc uacacuggga uggagauuuc aggugcugca    240

ggucaguguc aaccaagggu ucguguguca ggaacucugg cugguaagau gacacaaagg    300

cuucaugcug aagcucaggg agguccaggg agccuggcag aauggaauca ucauggucau    360

caucaaacgu cugugucugg aaggcuucaa ggcucauaau ugcaucauuc ucuggcaguu    420

ccugagagag cugccccuuc cuggguuugc acgcaucaaa uuucacccac ugguaauuga    480

cacaguuuug agcuucggga caacucuuaa ucagguugug gaugguugga ugagaaaacc    540

caaagaaguc ggcaccgcau ga                                             562
```

<210> SEQ ID NO 217
<211> LENGTH: 1238

<212> TYPE: RNA
<213> ORGANISM: Homo sapiens

<400> SEQUENCE: 217
auuguaacag aagaaggaaa ggaaaagaaa guuaacauug acuuugaacc uuucaaacca 60
auuaauacau cauuguauuu gugcgacaau aaguuucaua cagaggcucu uacagcguua 120
cuuucagaug acagcaaguu ugguuuuauu guaauagacg gaaguggugc ucuuuuuggc 180
acgcuccaag gaaacaccag agaaguccug cacaaauuca cuguggaucu cccaaagaaa 240
cacggcagag gaggucaauc agccuugcgu uuugcccguu uaagaaugga aaagagacau 300
aacuauguuc ggaaaguagc cgagacugcu gugcagcugu uuauuucugg agaccaagug 360
aauguggcug guuugguuuu agcuggauca gcugacuuua aaacugaacu aagucaaucu 420
gacauguuug accagagguu gcaaucuaaa guuuuaaaau uaguugauau auccuauggu 480
ggugaaaaug gauucaacca agcuauugaa uuaucuacug aaguucucuc caacgugaag 540
uucauucaag agaagaaauu aauaggacga uauuuugaug aaauuagcca ggacacaggc 600
aaguacuguu uuggaguuga agauacacua aaggcuuugg aaaugggagc uguacaaauu 660
cuaauagucu augaaaaucu ggauauaaug agauacguuc uucauugcca aggcacagaa 720
gaggagaaaa uucucuauuu aacuccagaa caagagaagg auaaaaucuca cuucacagac 780 aaagagacug gacaggaaca cgaacugaua gaaagcaugc cucucuugga augguuugcu 840
aacaacuaua aaaaauuugg agcuacacua gaaauuguca cagauaaguc acaagaagga 900
ucacaguuug ugaaaggauu ugguggaauu ggagguaucu ugcgguaccg aguagauuuc 960
cagggaaugg aguaccaagg aggagaugau gaauuuuuug accuugauga cuacuaggua 1020
gucgacaugg guccggcaac cgugccucac ccuccagcau ucaacccaag gagcauaccc 1080
gugguggagu ccaacagauc ccugccuuac aauuggagca uuuccagaac uuaauccgug 1140
agcauuggau acugaaaaga aaagugaaac aaaaccagac ccaacccuac acuuugguuu 1200 gucgugugu cagcgcagca gccgacaacu aagucucu 1238

<210> SEQ ID NO 218
<211> LENGTH: 464
<212> TYPE: RNA
<213> ORGANISM: Homo sapiens

<400> SEQUENCE: 218
cagaggaguc auuguugcug ugguggcuuu ugugaugaag aggaggagaa acacagcgua 60
agccagcugc cuggagugga cuaagugaca gacaaugucu ucacacaucu ccugugacau 120
ccagagcccu caguuuucuu uagucaagua ucugauguuc ccugugagcc uaugggucaa 180
agugaagaac ugugcagccc agccugcccu gcacacagaa cccugucccu gcacugcccu 240
ggguucccuu ccacagccaa ccuugcugcu ccagccaaac acugggcgac aucugcaucc 300
ugccagcucc augcugcccu gagcugcagc uccucacuuc cacacugaga guaagaaucu 360
gaaugggacc uugauucuua acauccugac cgaggguuga uuucuuguua auuucaugga 420
uugagaauac uuagaguuuu gguuugucuu gauuuuuuuu caag 464

<210> SEQ ID NO 219
<211> LENGTH: 841
<212> TYPE: RNA
<213> ORGANISM: Homo sapiens

<400> SEQUENCE: 219

-continued

```
ugaauaaaaa cgaggagccg aagauucuag ggggcuacag cugcgcuuuu gcagcacuga     60
acaugguucc ggguacucaa gauauugcgu uuguguuugg agagguguag auuguagauu    120
ccagccgaga agaccaggaa aagauaagga uaaagaaugu cauauaucuc aggagcuaga    180
ucacuucccg augaacaagu aagaauugcc ucaacaaaaa uggauggaau uggaccgaaa    240
aaagccauuc agcuucguua ucgauuaggu aucaguggga acaucaagau gaaugaguua    300
acuaaguauc agaucgacca aauugaacaa augauagcuc aagaucaugu uguucauugg    360
gaauugaaga ggggagaacg agcagacauc gaacgauuaa uuucuauuuc ucguuaucgu    420
ggaauucguc aucaagaugg aucgcccuua cgcggucaac gaacucauac uaaugcaagg    480
acugcucgca agcaaauucg gaaaugaaag aaggcuaccg aaagaacaag caacggauuu    540
cgcgcucauc ccuugcuaaa gcgcauacgu uuucuugcuc cuugguacuu gucugaucaa    600
ucacacuguu cauuaguuca cuugauuuuu cguucgaugu cuugaaccgc uuacuaauca    660
cguauacgua uaguaggccc ccuucgccac uccacgucug gcccgucuug gucucgcuca    720
cuucgcccgc cuaucguauc ggcucggcuu cguccgucaa gcgacagcuu cugccucuga    780
cggcuucacu aucgcucaug acugguagua cucuauguag uagucggccu uuguuaagcu    840
u                                                                    841
```

```
<210> SEQ ID NO 220
<211> LENGTH: 136
<212> TYPE: RNA
<213> ORGANISM: Homo sapiens

<400> SEQUENCE: 220

uauaaccaug uuagaagcgg aaguuggccu gaaaaccuga ggcuuaggcu ucauagcugg     60
gcuguagauu ggauuuaaac ccaguuggag ugcaaaguca uggugugcuc aaggugauga    120
cagugaacag aguaug                                                    136
```

```
<210> SEQ ID NO 221
<211> LENGTH: 752
<212> TYPE: RNA
<213> ORGANISM: Homo sapiens

<400> SEQUENCE: 221

caugggccuc cugagagauc cuuagaucca gguuagugca uaggaaagug ucccccccacu     60
accuacagcu aagggauugg gguggugggga ucauggugga gggccguggu gaauacuagc    120
gauguccccc gcuacccgug cgucugccuc cagggugccc cuccaaccag gaugaggcuc    180
uucaucgcuc uuccuguccu gauuguggug guagccauga ccuuggaagg uaagaaagag    240
ccuuggaagg uaagaaagau gcuuggaagu gugaaguugg ccuugugccu gcggcccagg    300
cuuagaagac ccucgaggag ggcucugagg ucccuuucug ugucaucauu ccacuaccgc    360
ccucccaucg ucccccaucc caccugccag gugccuuauu uuugugucaa agugggugcu    420
gaaggaggca acucugucca gaaaagacgc aguaaccaau gaccuaggau accacccuuu    480
ggaauuggcu aaucuuccua gaaggggcgg acgguaaaaa caaggaggug agaggugcag    540
uaaaaucaag uguccaauac ccuccccccau gcuaaugagu uugcucgcaa cccucucgcg    600
gcaggcccag cccccgccca ggcggccccg gauuuguccg gaacauugga gagcauaccg    660
gauaaacuga aggaguuugg gaacacuuug gaagacaagg cccgggcagc cauugaacau    720
aucaaacaga aggaaauuuu gaccaagacc cg                                  752
```

<210> SEQ ID NO 222
<211> LENGTH: 2858
<212> TYPE: RNA
<213> ORGANISM: Homo sapiens

<400> SEQUENCE: 222
cagcgccugg ggcgcggcgg gcgucggccc aggagacgcg uggcggcgcu cggccucgcg 60
gcaucggcgg cugccuggcc guuggcggcg agcgcacuug cgccugcgca gcggggucg 120 ugccccuccu ccccugggcg gcccccccac ccccccggcg gcgugugaau ggcggccucg 180
gcggcagcga cugcagcggc cucggccgcg acggccgccu cggcggccuc ugguagccca 240
gggucgggcg agggcucggc gggcggugag aagcguccgg cugcuucccuc agccgcggcg 300 gccucugcag ccgcgucguc cccugcgggg ggcgguggcg aggcgcagga gcuucuggag 360
cacugcggcg ugugucgcga gcgccugcgg cccgagcggg auccucggcu gcugcccugu 420
cuacauucgg ccugcagugc cugccugggc cccgcuacac ccgccgcagc gaauaauucg 480
ggggauggcg gcucggcggg cgacggcgcu augguggauu guccagugug caaacagcag 540
ugcuacucca aagacaucgu ggagaauuau uuuaugcgug auaguggcag uaaggccucu 600
ucugauuccc aggaugcuaa ccagugcugc acuagcugug aagauaaugc cccagccacu 660
agcuauugug uggagugcuc ugaaccacuu ugugagaccu guguggaggc ucaccagcgg 720
gugaaauaca ccaaggacca cacugugcgc uccacaggac cugcuaagac ucgagaugga 780
gagcgaacag ucuacuguaa ugugcacaag caugagcccc ucgugcuguu cugugagagc 840
ugugacacac ucaccugccg cgacugccag cucaacgcuc acaaggacca ucaguaccag 900
uuuuuggaag augcagugag gaaccaacgu aaacucuugg cuucacuggu gaaacgucuu 960
ggggacaaac augccacacu ucagaaaaac accaaggagg uucgaagcuc gauccgccag 1020
gugucugaug ugcagaagcg agugcagguu gaugucaaga uggccauucu gcagaucaug 1080
aaggagcuga auaagcgggg ucgaguucug gucaaugaug cccagaaggu gaccgagggu 1140
cagcaggaac gucuggagcg ccagcacugg accaugacca aaauucagaa gcaccaggaa 1200
cacauuuugc guuuugccuc uugggcucug gagagugaua acaauacagc ucucuugcuc 1260
ucuaagaagc ugaucuauuu ccagcugcau cgggcccuca aaaugauugu ggauccugug 1320
gagccucaug gugagaugaa guuucagugg gaucucaaug ccuggaccaa gagugcugaa 1380
gccuuuggca agauuguggc ugagcguccu gguacgaacu ccacaggucc ugggcccaug 1440
gcuccuccaa gagccccagg ccccucuaagc aagcaagguu cuggcaguag ccagcccaug 1500
gaaguacaag agggauaugg cuuuggguca gaugaucccu auucaagugc agagccgcau 1560
guaucaggca ugaagcgguc ccgcucuggu gagggagagg uaaguggccu cuuaaggaag 1620
gugccacgug ugagccuuga acgccuggau cuggaccuca ccucugacag ccagccacca 1680
gucuucaagg ucuuuccugg aagcacuacu gaggacuaca aucugauugu uauugagcgu 1740
ggugcugcug cagcagcugc uggucaggcu gggacugugc caccaggagc cccuggugcc 1800
ccaccccuuc cuggcauggc cauugucaag gaagaagaga cagaagcugc uauuggagcu 1860
cccccggcug cccccgaggg uccugaaacc aagccugugu ugaugccucu gacugaaggu 1920
ccuggugccg agggaccucg ucuagcuuca ccuaguggca guaccagcuc aggcuuggag 1980
gugguggcuc cugagguuac uucagcccca guaagugggc cagguauccu ggaugacagu 2040
gccacuaucu gccgagucug ccagaaacca ggugaccugg ucaugugUaa ccagugcgaa 2100
uuuugcuucc accuggauug ccaccucccu gcccugcagg auguuccagg ggaggaaugg 2160

```
aguugcucac ucugccacgu gcucccugac cuaaaggagg aagauggaag ccucagccug   2220

gauggagcag auagcacugg ugugguagcu aaacucucac cagccaacca gcggaaaugu   2280

gagcguguuc uccuggcccu guucugccau gaaccaugcc gucccuugca ucagcuggcu   2340

accgacucua cauucuccau ggagcagccu ggugguaccc uagaccugac cuugauucgu   2400

gcucgccucc aagagaagcu gucaccuccu uauagcuccc cccaggaguu ugcucaagau   2460

gugggccgca uguucaaaca guucaacaag cugacugagg acaaggcaga uguucagucc   2520

aucaucggcu ugcagcgcuu cuuugagaca cgcaugaaug augccuuugg ugacaccaag   2580

uuuucugcug ugcugguaga accaccacca uugaaccuuc ccagugcugg ccuaaguucu   2640

caggagcucu cuggcccugg ugauggcccc ugaagcuggg gcucuugugg ucagcccagu   2700

ccagcucugg ucucuguauu uucaccccau acccuguccu uugguggccu gacuccuguu   2760

cuugcuggcc ccaucguccc cucagucccu cuucacaaaa ugguuuuuac uucuguggau   2820

uuaauaaaaa cuucacugag ucaguuaaaa aaaaaaaa                           2858
```

<210> SEQ ID NO 223
<211> LENGTH: 420
<212> TYPE: RNA
<213> ORGANISM: Homo sapiens

<400> SEQUENCE: 223

```
uuuuuuuuuu uuuuuuuaaa aauaauuuca uuuuuuaaua uucuguacaa aauuucucaa     60

ccuaugaaaa uaaaguuugc aaaagucaaa guaguacaug ggccugcccu ggagccaggc    120

ccagccggau cuacacuaug uacaggucuc ccagggugag ccucagcuag ggaaaagcca    180

cuaaggugcc uacagagcaa gagggugcca ucgggccagu gcagcccucug caauuuccag   240

aucugccacu agaggucggc augguccuga uugcuuguca ggcucacccu cuggaagacc    300

acagccaaug acaaagguccc ucaagggaaa gcuuuggggu cuagcuggaa gugacggugg   360

guccgccgcc caggcgcagg agcaucugcu ggcaguccag caguaaccgg ugaucgccaa    420
```

<210> SEQ ID NO 224
<211> LENGTH: 963
<212> TYPE: RNA
<213> ORGANISM: Homo sapiens

<400> SEQUENCE: 224

```
uccgucguaa ccuguugagu aacuauggaa gacuauauca aaauagagaa aauuggagaa     60

gguacuuacg guguggugua uaaggguaga cacagaguca cuggccagau aguggccaug    120

aagaagauca gacuugaaag cgaggaagaa ggagugccca guacugcaau ucgggaaauc    180

ucucuauuaa aagaacuucg acauccaaau auagucagcc ugcaggaugu gcucaugcag    240

gacuccaggc uguaucucau cuuugaguuc cuguccaugg accucaagaa guaccuggac    300

uccaucccuc cugggcaguu cauggauucu ucacucguua agaguuacuu acaccaaauc    360

cuccagggaa uuguguuuug ccacucccgg cgaguucuuc acagagacuu gaaaccucaa    420

aaucuauuga uugaugacaa aggaacaauc aaacuggcug auuucggccu ugccagagcg    480

uuuggaauac cgauacgagu guacacacac gagguaguga cgcuguggua ccgaucucca    540

gaaguguugc ugggcucggc ucguuacucc acuccgguug acaucuggag uauagggacc    600

auauuugcag aacuggccac caagaagccg cuuuuccacg gcgacucaga gauugaccag    660

cucuucagga ucuucagagc ucugggcacu ccuaacaacg aaguguggcc agaagucgag    720

ucccugcagg acuacaagaa caccuuuccc aaguggaagc cggggagccu cgcaucccac    780
```

gucaagaacc uggacgagaa cggcuuggau uugcucucaa aaaugcuagu cuaugauccu 840
gccaaacgaa ucucuggcaa aauggcccug aagcacccgu acuuugauga cuuggacaau 900
cagauuaaga agauguagcc cucuggaugg augucccugu cugcuggucg uaggggaaga 960
ucg 963

<210> SEQ ID NO 225
<211> LENGTH: 479
<212> TYPE: RNA
<213> ORGANISM: Homo sapiens

<400> SEQUENCE: 225
uuuuuuuuuu uuuuuuuacu aggcaaagaa uuuuauuaac ccuuuccaaa cuuuauuccc 60
aggcuucuuc agcuuuauuu gccgcaaaga augaauuagg uauagcgaaa acugaaaaga 120
gcugcagugu ccgggggcuu gggcuuaaaa auauuagaga ucuagauuuu aucagaucca 180
uaauaaacaa aaaaauuuua aaaagcaguc augauauaaa auagcagcuc cuguaauuuc 240
ugcaaguauc accuucuuca gaaguugcuu caauucaguu ugccucauuc uuagaagccu 300
caucaaaauu cuccaccaga ucuggaacuu caucaucauc auccucucca guagcaaggg 360
gugcuuuucc auccacagau uguuugggca gagcuucagc cagucuccuu aaacuaguca 420
ggcugucugc accaagcugg uugaggaugc ugggaagcau uucugucagc ugcuuuguc 479

<210> SEQ ID NO 226
<211> LENGTH: 520
<212> TYPE: RNA
<213> ORGANISM: Homo sapiens

<400> SEQUENCE: 226
uuuuuuuuuu uuuuuuuauu caugcuugcc uagggauggg gaauagauca uucaauaaaa 60
acauacagua aaaacagggg guggggaggg ggaaggcuua ucauguacaa uguuuaaacu 120
acaauaguga uguaccuuaa uuacuuccau gcacacaagu cuaacauuac aaguuuuuaa 180
aaaauaaaca ccauuaagac uucuaggagc auuuuauaau aaauuccuaa uuuuuucuuu 240
guagauagau caagcaccuc caaaauacag auuccuauac acagugagca cuuuacuuaa 300
cguacaugga cagccucagg acgagcugac gucucggauc agcucggcag gcaacaaacc 360
auagugccaa auggaaagaa gggcaguugc aaauaaacuu aaaacuaagu uaacuuuuau 420
aauuaaauac agaaaauaua cugauuugcu aaaaauaaau aagaugugau guauuuaaca 480
cuucacuaua aagaaugaac accaugacau ccucgugccg 520

<210> SEQ ID NO 227
<211> LENGTH: 468
<212> TYPE: RNA
<213> ORGANISM: Homo sapiens

<400> SEQUENCE: 227
agaagaagga ggaguggac cgcaagcaug aggaugcuag uagggaguau gagaaaggca 60
ugaaagagua ugaaggagga agaggggacu caucuaaaag ggacaagucu aagaagaaaa 120
agaaaguaaa agcaaagaug gaaaaaaagu ccacuccuuc ccggggcucg ucauccaagu 180
cuucauccag gcaguugagu gacagcuuca agagcaaaga guuuguguccc agugaugaga 240 gcucuucagg cgagaacaag agcaaaaaga agaggaggcg gacgaggacu cugaagagga 300
gcuagccagu accccuccaa gcucagagga cucugccucg ggaucugaug aauaaaggag 360

-continued

```
ggaauuccca ccccgucaca gcuccagucu cucacauagu ccuuggauuc ugugccaucu    420

gaguaacugc ucuuggugge uuccacugcc cugaggcuuu gagggaag                 468


<210> SEQ ID NO 228
<211> LENGTH: 1740
<212> TYPE: RNA
<213> ORGANISM: Homo sapiens

<400> SEQUENCE: 228

aucgucguaa ucguuugcag acuucucgcc gucgccuugu aagcuuuguc uucgccuugc     60

aagcuuuguc uucaggguug gaaagaugag acauucaaag agaacuuacu guccugacug    120

ggaugaaaga gacugggauu auggaacaug gagaagcagc agcagucaca aaagaaagaa    180

gagaucacau agcagcgccc gugagcaaaa gcgcugcagg uacgaucacu ccaaaacgac    240

agacagcuau uaucuggaaa gcagauccau aaaugagaaa gcuuaucaua gucgacgcua    300

uguugaugaa uacaggaaug acuacauggg cuacgagcca gggcaucccu auggagaacc    360

uggaagcaga uaccagaugc auaguagcaa guccucuggu aggaguggaa gaagcaguua    420

caaaaguaaa cacaggaguc gccaccacac aucgcagcac cauucacacg ggaagaguca    480

ccgaaggaaa agaucgagga guguagagga ugaugaggag ggucaccuga ucugucagag    540

uggagacgua cuaagugcaa gauaugaaau uguugauacu uuaggugaag gugcuuucgg    600

aaaaguggug gaaugcaucg aucauaaagu gggagguaga cguguagcag uaaaaauagu    660

uaaaaaugug gauagauacu gugaagcugc ucaaucggaa auacaaguuu uggaacacuu    720

gaauacaaca gacccccaua guacuuuccg uuguguccag auguuggagu gguuugagca    780

ucgaggucac auuugcauug uguuugaacu ucuggggcuu aguacuuaug auuucauuaa    840

ggaaaacagu uuucugccgu uucgaaugga ucauaucagg aagauggcau aucaaauaug    900

caaaucugua aacuuuuugc auaguaauaa auugacucau acagacuuga agccugaaaa    960

caucuuauuu gugaagucug acuacacaga ggcuuauaau cccaaaauga aacgugauga   1020

acguacuaua guaaauccag auauuaaagu gguggacuuu ggaagugcaa cauaugauga   1080

ugaacaccac agcacauugg uaucuacaag acauuauaga gcaccggaag uuauuuuagc   1140

ccucgggugg ucacagccau gugaugucug gagcauagga uguauucuua ucgaguauua   1200

ucuuggauuu acaguuuuuu cgacucauga uagcagggaa cauuuagcaa ugauggaaag   1260

gauucuugga ccacuaccaa agcacaugau acagaaaacc aggaaacgca gauauuucca   1320

ucaugaucga uuagauuggg augaacacag uucugcuggc agauauguuu cucggcgcug   1380

uaaaccucug aaggaguuua ugcuaucuca ggaugccgaa caugagcuuc ucuuugaccu   1440

cauugggaaa auguuggagu augaucccgc caaaagaauu acucucaaag aagcccuaaa   1500

gcauccuuuc uuuuacccac uuaaaaagca uacgugauuu auaaacacag ugcucugaaa   1560

ggaaucuuac agacuguauc agucuagcuu uuaauuaagu uauuuuguau agcuuaauuu   1620

guaaaacauu uuauguuuuu uagaugcuuu auuaaauaca uggccaaacc aaauaacauc   1680

uuucaguaau uauagaauga uuuauuugga auaaaauuug ugcuuaugaa uguaaaaaaa   1740


<210> SEQ ID NO 229
<211> LENGTH: 815
<212> TYPE: RNA
<213> ORGANISM: Homo sapiens

<400> SEQUENCE: 229

ggacucgcga caagcguccu cagcgcgaag aggcggacuc ggaguccucg ccuugagccu     60
```

```
ugcaucugag aaguuccagg uacuuuguac aacugcaucc cagaaccugu guguuuucag    120

caccuuuaua agugauggcu gccaucagga agaaacuggu gauuguuggu gauggagcuu    180

gugguaagac augcuugcuc auagucuuca gcaaggacca guucccagag gucuaugugc    240

ccacggugu ugaaaacuau guggcggaua ucgaggugga ugggaagcag guagaguugg    300

cuuuauggga cacagcugga caggaagauu augacugccu gaggccucuc ucuuauccag    360

acaccgaugu uauauugaug uguuuuucca uugacagccc ugauaguuua gaaaacaucc    420

cagaaaaaug gacuccagaa gucaagcauu ucuguccaaa ugugcccauc auccugguug    480

ggaacaagaa ggaccuucgg aaugacgagc acacgagacg ggaguuggcc aaaaugaagc    540

aggagccggu aaaaccugaa gaaggcagag auauggcaaa caggauuggc gcuuuugggu    600

acauggagug uucagcaaag accaaagaug gagugagaga gguuuuugag auggccacga    660

gagcugcucu gcaagcuaga cgugggaaga aaaagucugg gugccucauc uugugaagcc    720

uugugaacgc agccucaugc gguuaauuug aagugcuguu uauuaaucuu aguguaugau    780

uacuggccuu ucauuuaucu auaauuuacc uaaga                              815
```

<210> SEQ ID NO 230
<211> LENGTH: 287
<212> TYPE: RNA
<213> ORGANISM: Homo sapiens

<400> SEQUENCE: 230

```
uucaagaccg accugcgcuu ccagagcucg gccgucaugg cucugcagga ggcgagcgag     60

gccuaccucg ugggucuguu ugaggacacc aaccugugcg ccauccacgc caagcguguc    120

accaucaugc ccaaggacau ccagcuggcc cgucgcauuc guggggagag ggcguaaauu    180

aggguaguga gugaauuugg accccaaagg cucuuuucag agccacccac auuuucuaua    240

aaaggcugua uaucgauaag cuuuuauaaa ccccacucag caacucc                  287
```

<210> SEQ ID NO 231
<211> LENGTH: 945
<212> TYPE: RNA
<213> ORGANISM: Homo sapiens

<400> SEQUENCE: 231

```
uuaugugaua aaaaaauuca acuugguauu aacuuaacua agggccuugg ugcuggugcu     60

uugccugaug uugguaaagg ugcagcagaa gaaucaauug augaaauuau ggagcauaua    120

aaagauagcc auaugcucuu uaucacagca gggaugggug gugguacugg aacaggugcu    180

gcaccgguaa uugcaaaagc agccagagaa gcaagagcgg uaguuaaaga uaaaggagca    240

aaagaaaaaa agauacugac uguuggaguu guaacuaagc cguucgguuu ugaaggugug    300

cgacguaugc gcauugcaga gcuuggacuu gaagaguugc aaaaauacgu agauacacuu    360

auugucauuc ccaaucaaaa uuuauuuaga auugcuaacg agaaaacuac auuugcugac    420

gcauuucaac ucgccgauaa uguucugcau auuggcauaa gaggaguaac ugauuugaug    480

aucaugccag gacugauuaa ucuugauuuu gcugauauag aaacaguaau gagugagaug    540

gguaaggcaa ugauugguac uggagaagca gaaggagaag auagggcaau uagugcugca    600

gaggcugcga uaucuaaucc auugcuugac aauguaucaa ugaaaggugc gcaaggaaua    660

uugauuaaua uuacuggugg uggagacaug acucuauuug aaguugauuc ugcagccaau    720

agagugcgug aagaagugga ugaaaaugca aauauaauau uuggugccac uuuugaucag    780
```

gcgauggagg gaagaguuag aguuucuguu cuugcaacug gcauugauag cuguaacgac 840
aauucaucug uuaaucaaaa caagauccca gcagaggaaa aaaauuuuaa auggccuuau 900
aaucaaauuc caacauuaga aacaaaagaa uaugcuucaa cugag 945

<210> SEQ ID NO 232
<211> LENGTH: 238
<212> TYPE: RNA
<213> ORGANISM: Homo sapiens

<400> SEQUENCE: 232
ugaucagguc acauuccggu gccuuccacc cccuauggca cgggcgcccc gccuugccau 60
accacagcuc ccuccaggcu uagaccuggc uucaccgcau uucaggugcu auaccccccc 120
cugcuuuucc ccccauugcc cuuaaaugcc ccucggcccc uccaucccccc cggaacaggg 180 uggcacuugc cacucucagg accaccuugc caaggagaau aaaccgaauc cuguugcu 238

<210> SEQ ID NO 233
<211> LENGTH: 341
<212> TYPE: RNA
<213> ORGANISM: Homo sapiens

<400> SEQUENCE: 233
uuuuuuuuuu uuuuuuucac ucaucacguu uauucagaag agaauacacc caauccucuc 60
aucucuggaa aguuuuguuc cuagccauca uuaagaucag gaccccuguu cuccccuuaa 120
ccccaggaga ggaagcuuau agucuuugua gauauucuga accucugauc acaaaggguu 180 auaaaaauagu gaaggggguuu ggacuaggaa aggcacagac ugaaaggaau cugccagggg 240
acugaggcca cagcuccccc aggagucaga ggaagggggga agucacguau uuuauagaag 300
gccaagggcc ucagagcaag aguauuccuu ugaagagcuc a 341

<210> SEQ ID NO 234
<211> LENGTH: 495
<212> TYPE: RNA
<213> ORGANISM: Homo sapiens

<400> SEQUENCE: 234
ugguggagca ggucucagga aucucuucgc uucagcuuca aucauggccu guggucuggu 60
cgccagcaac cugaaucuca aaccugggga augucucaaa guucggggag agguggccuc 120
ggacgccaag agcuuugugc ugaaccuggg aaaagacagc aacaaccugu gccuacacuu 180
caauccucgc uucaaugccc auggagacgc caacaccauu guguguaaca ccaaggaaga 240
ugggaccugg ggaaccgaac accgggaacc ugccuucccc uuccagcccg ggagcaucac 300
agaggugugc aucaccuuug accaggcuga ccugaccauc aagcugccag acggacauga 360
auucaaguuc cccaaccgcc ucaacaugga ggccaucaac uacauggcgg cggauggaga 420
cuucaagauu aagugcgugg ccuuugagug aagccagcca gccuguagcc cucaauaaag 480
gcagcugccu cugcu 495

<210> SEQ ID NO 235
<211> LENGTH: 861
<212> TYPE: RNA
<213> ORGANISM: Homo sapiens

<400> SEQUENCE: 235
gugguucuuc ggcgccaggu ucgcccgcuu cugcccuuag guaacauucu cuaaacugcg 60
uuucucuccc aaucuuuugc aggcauuugg ggacuuuuuc uuuucuuuuu acuuucucuu 120
uuucuuuugc acaagaagaa gucuacaaga ucuuuuaaga cuuuuguuau cagccauuuc 180
accaggagaa cacguugaau ggaccuuuuu aaaaagaaag cggaaggaaa acuaaggaug 240
aucgucuugc ccaggugucu uguucuccgg ccuggacugu gauaccguua uuuaugagag 300
acuuucagug cccuuucuac aguuggaagg uuuucuuuau auacuauucc caccaugggg 360
agcgaaaagg uuaaaaaaaa gaaaaaaauc acaaggaauu gcccaaugua agcagacuuu 420
gccuuuucac aaagguggag cgugaauucc aggaggaccc aguauucggu uacuuaaaug 480
aagucuucgg ucagaaaugg ccuuuuugac acgagccuac ugaaugcugu guauauauuu 540
auauauaaau auauauauau ugagugaacc uuguggacuc uuuaauuaga guuuucuugu 600
auaguggcag aaauaaccua uuucugcauu aaaauguaau gacguacuua ugcuaaacuu 660
uuuauaaaag uuuaguugua aacuuaaccc uuuuauacaa aauaaaucaa guguguuuau 720
ugaauguuga uugcuugcuu uauuucagac aaccagugcu uugauuuuuu uuuaugcuau 780
guuauaacug aacccaaaua aauaccaguu caaauuuaug uagacuguau uaagauuaua 840
auaaaaugug ucugacauca a 861

<210> SEQ ID NO 236
<211> LENGTH: 830
<212> TYPE: RNA
<213> ORGANISM: Homo sapiens

<400> SEQUENCE: 236
cgaugaaggc ggugagcccg gugcgccccu cgggccgcaa ggcgccgucg ggcugcggcg 60
gcggggagcu ggcgcuacgc ugccuggcgg agcacggcca cagccugggu ggcucggcag 120
ccgccgccgc cgcugcggcg gccgcgcgcu gcaaggcggc cgaggcggcg gccgaugagc 180
cggcgcugug ccugcagugc gauaugaacg acugcuacag ucgccugcgg aggcucgugc 240
cuaccauccc gcccaacaag aaagucagca aaguggagau ccugcagcac guuaucgacu 300
acauccugga ccugcagcug gcgcuggaga cucacccugc uuugcugaga cagccgccac 360
cgcccgcgcc accucuccac ccggccgggg cuuguccggu cgcgccgccg cggaccccac 420
ucaccgcgcu caacacugac ccggugagaa gccuuggcgg gcacccuggg caucgcggga 480
aagguggcgg ggcggcgaga uacgggugg u cuugcuccuc ucagggaaug acagccgcuu 540
cucccgucuc caccgagagc cgccugcugg gcuuggugau ccacugguccc cugagccgag 600 ggcgguuggg cuuggagccc ugcgucuccg gaguguccu ugcaucacag gaggcuuccc 660
cagcuucggg cucggguggg gacucugcuc accugccuag uuuuccagga cgucuccugg 720
gugguggcga cacugugaua ugcgcacucu aaccgcuuuu ccccuuggug uuggguugcu 780
guuccaggcc ggcgccguga acaagcaggg ugacagcauu cucugccgcu 830

<210> SEQ ID NO 237
<211> LENGTH: 5560
<212> TYPE: RNA
<213> ORGANISM: Homo sapiens

<400> SEQUENCE: 237
acuagucucg accauguacc aucacggaga cgacaccaac agugacauga acagugacga 60
cgacaugagc cgaaguggga gagaaacccc acccccucga ccaucucaug cuuuuggcag 120
ugagcgagac cuggagcgca ggggcagaag cagagaugug gagccucgag accgcuggcc 180
auacaccagg aaucccagaa gcaggcugcc ucaacgggau cuuucucuuc cugugauguc 240

-continued

```
aagaccacau uuuggacugg acagagauga ugacagacgu uccauggauu augagucucg    300
aucccaggau gccgagucau accagaaugu uguggaacuc aaagaggaca agaagccuca    360
gaauccaauu caggacaacc uggagaacua cagaaagcug cucucgcugg gaguccagcu    420
ugccgaagau gaccgacacu cucacaugac acaaggccac ucaucgaggu ccaagagagc    480
ugccuaccca agcaccagcc gaggucucaa acccaugccu gaggccaaaa agccauccca    540
caggcguggg aucugugagg acgagucuuc ucauggagug auaauggaaa aauucaucaa    600
ggauguggcu cgcaacccca aauccggaag agcaagggag cugaacgagc guccuccucc    660
aagguucccc aggccuaaug auaacuggaa ggacaguucc uccagcagaa gagagucagu    720
gauccaggag agggguuaug aagggagcgc auuuaggggc ggcuuccggu ucaacgcaga    780
ccuggcuucc agaagcagag cucuagaaag gaagaggcgu uaccacuuug auucugauga    840
gcgggguucg ggccaugagc auaaaagcug ugugaggaag aagccuuuug agugugggugc    900
ugagaugaga caggcuauga gcaugggcaa ccugaacagc ccuuccuucu cugagucgca    960
gucaaucgau uuggggccca acccauacgu gugugaugag ugcgggaggc aguucagugu   1020
caucucugag uuuguugagc accagaucau gcacacuagg gagaaccucu augaauaugg   1080
agaguccuuu auucauagcg uggcugucaa ugaggugcaa agaagucagg guggggggaa   1140
acgcuuugag uguaaggaau guggagaaac cuucaguagg agugcugccc uggcagagca   1200
ccgccaaauc caugcuagag aauaucuugc agaauguaga gaucaggagg augaggagac   1260
caucaugccu agcccgaccu uuagugagcu gcagaagaug uauggcaaag auaaguucua   1320
ugagugcaag gugugcaagg agaccuuucu gcacaguucc gcccugauug agcaccagaa   1380
aauccauggu agaggcaacu cagaugacag agauaaugag cgugaacgcg aacgugaucg   1440
ucuacgugca cgugcacgag agcagcguga gcgcgaacgu gaacgggagc gugagcguga   1500
gcuuggggaa cccuuucuga ccuguccaaa cuucaaugag uuucggaaga uguacaggaa   1560
agacaaaauc uaugagugca aagugugugg ggagagcuuu cuucaucucu caucccugag   1620
ggagcaucag aaaauccaua cuagaggaaa cccauuugaa aauaagagca ggaugugcga   1680
ggagaccuuu gucccuaguc agucucuccg acggcgccag aaaacuuaca gagagaagcu   1740
guucgacuuu aacaaugcca gggaugcacu gaugggaaac ucagacucca gcgagcauca   1800
gaaaaaccgu ucccgaagga acuucuuuga gggcagagga uuugagaaac ccuucguuga   1860
aucucagaag agucauacua uaacaagacc accugaaaac aaagacgaug acaagccguu   1920
cacaaucagu gucaacccua augacaagcu gaaacucccc aucauggaaa auggcuccca   1980
gggcaaaucc ugugagaggu cuguuauuca uagcuugggc uccgcagaag cucagaagag   2040
ucauggugga cuggggguuca guaaaccaag accaguggca gagucuagca cccagagcuc   2100
aagcagcauu uacuacccca gagcacacuc uggaggcaac accuaugaag gaaaagaaua   2160
caaggacucu aucauccaua gcuugccagc uccucgaccu cugaaacguc auagagcaaa   2220
ugaccauauu caaugugaug agggggggaga auccuccauu uauaucccag auauuauuaa   2280
uaagggaagg aagauuccug ccagagaaga ugcuuaugaa ggaaguagca gcagcaacua   2340
ccacacacca aauguauccc gugcugagcc uccaagucuu ucuggagagu cccaugacuc   2400
uaagcaggau gucacguuuu caguucccag cucaagugu u cgugaacacc agaaagcucg   2460
ugccaaaaag aaguacauug agcccaggaa caacgagacc ucuguuaucc acucccuacc   2520
uuuuggugag uugcuugcag gucaccguag ggcaaaguuc uuugaguguc aggaaugcgg   2580
ggaggccuuu gcucguaggu cugagcucau ugagcaccag aagauucaug auagagaaag   2640
```

```
accuucugga agccgacauu augagcgcuc ugucauccgc agccuugcgc ccagugaccc   2700
ucagaccagu uaugcccaag aacguuucau ccaagaacaa gugcguaaau ucagagcguu   2760
uggacaacgc ucaacuacca gcaacaaccu caguguacag aaaaucuaug cccaagagac   2820
auuuaaugcc gaggagcccc augauaaaga aacucauggu caaaaaauuc augacaaaga   2880
gccauauggu aaggagccca guggcaagga gccccauggu gaugagcccc aggacaaaga   2940
accccuuguu caggagaugc gcagugaaga gccccaugau gauaagcccc auggccagga   3000
gccccaugau gauaagcccc auggccagga gccccaugau gauaagcccc auggccagga   3060
gccccacggu gaugagcccc auggccagga gccccacggu gaugagcccc augacaagga   3120
acccauugau caggagaugc gcagugaaga gccccacagu gaagagucuc auggugauga   3180
gccccauggu gaagaguccc auggccagga gaaaguugaa gaugcuacca uucaggccuc   3240
aguuucugaa gagcaucaga aagaugacgc uggugaugca aucuaugaau gccaggacug   3300
ugggcugggc uuuacugauc ucaaugaccu cacaagccac caggacaccc auagcagaaa   3360
ggcucugguu gacagucgug aauaugcaca uucugaaguu caugcccacu ccgucagcga   3420
auuugagaaa aaaugcucug gagagaaacu auaugaaugu ccaaaaugug gggagucuuu   3480
cauucacagc ucguuacuuu ucgagcacca gagaguucac gaacaagacc agcuguauuc   3540
cguaaaggcc uguuaugacg cuuucaucgc ucuguugccc guuagaccaa ggagaaauug   3600
cacuguugaa aggaauccug ccguuucugg gucagccauu cgaugccguc agugugggaca   3660
aggcuucauu cacaguucug cccuaaauga gcacaugaga cagcacagag auaaugaaau   3720
aauggaacag agugagcuuu cagaugagau uuucauucaa ggccuagccc ucacugagua   3780
ucaggggagu gaaacagaag agaagcuuuu cgagugcaca aucuguggggg aaugcuucuu   3840
cacugccaaa cagcucgggg accaccacac caaaguucac aaggaugagc ccuaugagua   3900
ugggcccucc uacacccaug ccuccuuucu caccgagccc cucaggaagc acaucccacu   3960
guacgaaugc aaagauugcg gccaguccuu ccuagacgac acugucaucg cugagcgcau   4020
gguguuucau ccugagcgag aaggugggguc agaaauagua gcugccacug cccaagaggu   4080
cgaagccaau guccucaucc cacaagaagu acugcgaauc cagggggucaa augcagaagc   4140
ugcugagccc gaaguggagg cugcagagcc cgagguggag gcugcagagc cugaggugga   4200
ggcugcagag ccuauuggag aggcugaagg gccagaugga gaagcugcug agccugaugg   4260
cgaggcugag cagcccaaug gagaggcuga acagccaaac ggugaugcug acgagccaga   4320
cggagccggg aucgaagacc cagaagagag agcugacgag ccugaggaag acgucgaaga   4380
gccagaggga gaugcagaug agcccgaugg ugcagacauu gaagacccag aagaggaagg   4440
agaagaucaa gagauugagg uugaagaacc auacuacaac ugucaugaau gcgcagaaac   4500
guucgcuucc agcucagccu uuggcgagca ucugaaaagu cacgccagug ugaucaucuu   4560
cgagccggcc aaugcuccug gagagugcuc uggcuacauu gaacgggcca gcaccagugc   4620
agguggugcg gagcaggcag acgacaagua cuucaaaugu gaugugugcg ggcaacucuu   4680
caacgaccgc cucucccuug ccagacacca gaauucucac acugguugag uaaccaggcu   4740
gaagaaaaga agagcaaagc caaaccuucu ucccagaacc agacccuuaa uaaaucacaa   4800
agagagccua aaccaaccca uaaugucuau aagaaauuca ccuuccugua uacauaccgg   4860
acuucacauc aaagacuuuc acucucauca cagacugaaa aaagaaaaga cauugaacgc   4920
agggacucuu ucaguuuuag cuguucccua uggaacauca guguauauuu gggaaagcua   4980
```

gagugaacau cuacaucuuc cauuucaucu aaguaacuag auugagggaa accuagugac 5040
aauuccagac cacagagguu gccccagucg acuguaaaug auaccccuuu cauacccuau 5100
acauaaugau uccugccaug uauauaaaug agcaaaucag ugauacauau auuuggauuu 5160
agugugcuau agaauuuaca guuuacucua cagagcuacc uagccuggua cucugauuuu 5220
uucccugagg aggaagagag caacaauuua gcauauauuu guaaguauug uccaugcaga 5280
agcuuuucug ugcaucauuu gaaccccauu aguauccuuu ccaguaaugg aguguucugu 5340
ccccuaccuc uuagauaguc cugugaaggu gugggaguga aagaucgugu gucuuugaau 5400
ccuggcugug uggaaacagg cauuuuagcu ucuacagcca uuuggugugc acccagaccc 5460
cuugagacug auuguguaac ccuuuacaau auauggauuu gucucuguga cccaaaucaa 5520
cccaucccua cauuuauaua ccuuacagug guuuucuugc 5560

<210> SEQ ID NO 238
<211> LENGTH: 416
<212> TYPE: RNA
<213> ORGANISM: Homo sapiens

<400> SEQUENCE: 238
uuuuuuuuuu uuuuuuuacc guucuuuauu uaaaaaaaua aaauaggagu ccguagggug 60
cacccucccc ccuccugagu gaaggagggc acggugcagu ccggaccugg gagaggggaa 120
agcccggcag gcaggcgaga ccgcuucaca caguggucuc gccaugccgg cuguugguga 180
gacgagugua gaacuuccuc cacgagugca gugucuugcc ggaccagauc cagaagcccg 240
acgugaugcc cacgaugagc gucaugaggu auuugaucau guagacugug aagucgggcg 300
acaugcgggg cguguagugg gccgggcagg ggauggcuag gcucuugcag ugcuggcuua 360
cccaggagcg cucccagugc ucgcggaagg ccugcucaua gaaguagcag gcgaug 416

<210> SEQ ID NO 239
<211> LENGTH: 2380
<212> TYPE: RNA
<213> ORGANISM: Homo sapiens

<400> SEQUENCE: 239
ggccgcgucg acgccucucc agcugcucug uggcagccca gcuaccgguc gugaccagau 60
ccagcuugca gcucagcuuu guucauucga auugggcggc ggccagcgcg gaacaaacau 120
gcagcggcuc gggggtauuu ugcuguguac acugcuggcg gcggcggucc ccacugcucc 180
ugcuccuucc ccgacgguca cuuggacucc ggcggagccg ggcccagcuc ucaacuaccc 240
ucaggaggaa gcuacgcuca augagauguu ucgagaggug gaggagcuga uggaagacac 300
ucagcacaaa cugcgcagug ccguggagga gauggaggcg gaagaagcag cugcuaaaac 360
guccucugag gugaaccugg caagcuuacc ucccaacuau cacaaugaga ccagcacgga 420
gaccagggug ggaaauaaca caguccaugu gcaccaggaa guucacaaga uaaccaacaa 480
ccagagugga cagguggucu uuucugagac agucauuaca ucuguagggg augaagaagg 540
caagaggagc caugaaugua ucauugauga agacuguggg cccaccaggu acugccaguu 600
cuccagcuuc aaguacaccu gccagccaug ccgggaccag cagaugcuau gcacccgaga 660
cagugagugc uguggagacc agcugugugc cuggggucac ugcacccaaa aggccaccaa 720
agguggcaau gggaccaucu gugacaacca gagggauugc cagccuggcc uguguugugc 780
cuuccaaaga ggccugcugu uccccgugug cacaccccug cccguggagg gagagcucug 840
ccaugacccc accagccagc ugcuggaucu caucaccugg gaacuggagc cugaaggagc 900

```
uuuggaccga ugccccugcg ccaguggccu ccuaugccag ccacacagcc acagucuggu    960

guacaugugc aagccagccu ucguggcag ccaugaccac agugaggaga gccagcugcc   1020

cagggaggcc ccggaugagu acgaagaugu uggcuucaua ggggaagugc gccaggagcu   1080

ggaagaccug gagcggagcc uagcccagga gauggcauuu gaggggccug ccccugugga   1140

gucacuaggc ggagaggagg agauuuaggc ccagacccag cugagucacu gguagaugug   1200

caauagaaau ggcuaauuua uuuucccagg agugucccca aguguggaau ggccgcagcu   1260

ccuucccagu agcuuuuccu cuggcuugac aagguacagu gcaguacauu ucuuccagcc   1320

gcccugcuuc ucuggcuugg gaaagacagg cauggcgggu aagggcagcg gugagucguc   1380

ccucgcuguu gcuagaaacg cugucuuguu cuucauggau ggaagauuug uuugaaggga   1440

gaggauggga aggggugaag ucugcucaug auggauuugg gggauacagg gaggaggaug   1500

ccugccuugc agacguggac uuggcaaaau guaaccuuug cuuuugucuu gcgccgcucc   1560

caugggcuga ggcaguggcu acacaagagc uaugcugcuc uguggccucc cacauauuca   1620

ucccuguguu ucagcuccua ccucacuguc agcacagccc uucauagcca cgcccccucu   1680

ugcucaccac agccuaggag gggaccagag gggacuucuc ucagagcccc augcucucuc   1740

ucucaacccc auaccagccu cugugccagc gacagcccuu ccaaauggag ggagugaaau   1800

ccuuugguuu uauuauuuuc uccuucaagg cacgccugcc acuaagguca ggcugacuug   1860

caugucccuc uaacguucgu agcagugugg uggacacugu cuuccaccga cugcuucaau   1920

accucugaaa gccagugcuc ggagugcagu ucguguaaau uaauuugcag gaaguauacu   1980

uggcuaauug uagggcuagg auugugaaug aaauuugcaa agucgcuuag caacaaugga   2040

aagccuuucu cagucacacc gagaagucac aaccaagcca gguuguguag aguacagcug   2100

ugacauacag acagaagaag gcugggcugg augucaggcc ucagaugacg guuucaggug   2160

ccaggaacua uuaccauucu guaucuaucc agaguuauua aaauugaaag uugcacacau   2220

uuguauaagc augccuuucu ccugaguuuu aaauuauaug uauacacaaa caugugggccc   2280

ucaaagauca ugcacaaacc acuacucuuu gcuaauucuu ggacuuuucu cuuugauuuu   2340

caauaaauac aaaucccuu caugcaaaaa aaaaaaaaaa                         2380
```

<210> SEQ ID NO 240
<211> LENGTH: 2659
<212> TYPE: RNA
<213> ORGANISM: Homo sapiens
<220> FEATURE:
<221> NAME/KEY: misc_feature
<222> LOCATION: (1274)..(1274)
<223> OTHER INFORMATION: n is a, c, g, or u
<220> FEATURE:
<221> NAME/KEY: misc_feature
<222> LOCATION: (1358)..(1358)
<223> OTHER INFORMATION: n is a, c, g, or u
<220> FEATURE:
<221> NAME/KEY: misc_feature
<222> LOCATION: (1507)..(1508)
<223> OTHER INFORMATION: n is a, c, g, or u

<400> SEQUENCE: 240

```
gcacgagcag cccgcagccc gccgcgccug ugcgagccgg gacagcacuc ggccccgcgc     60

gcuccccgcc ccgcgccagc cccgccgcgg cgaccugcug cagcggagga ccccaucgau    120

cggagacccg gggagcagcg cgcagcccgc gagccgacgg gccccgacug cgucuuuguc    180

cccggaggcu ccgggaaguu ugcagcggga cgcgcgcgug aaggcagcgu gggcagcccc    240
```

-continued

```
gacgucgccg agcaacaugg gcgucgggcg cagcgcgcgg ggucgcggcg gggccgccuc    300
gggagugcug cuggcguugg ccgccgcucu gcuggccgcg gguucggcca gcgaguacga    360
cuacgugagc uuccaguccg acaucggcuc guaucagagc gggcgcuucu acaccaagcc    420
cccgcagugc guggacaucc cgguggaccu gaggcugugc cacaacgugg gcuacaagaa    480
gauggugcug cccaaccugc uggagcacga gaccauggca gaggugaagc agcaggccag    540
cagcugggug ccgcugcuca acaagaacug ccacaugggc acccaggucu uccucuguuc    600
gcucuucgcg cccgucuguc uggaccggcc caucuacccg ugucgcuggc ucugcgaggc    660
cgugcgcgac ucgugcgagc cggucaugca guucuucggc uucuacuggc ccgagaugcu    720
caaaugugac aaguuccccg agggcgacgu cugcaucgcc augaccccgc ccaauaccac    780
ggaagccucu aagccccaag guacaaccgu guguccucca ugcgacaacg aguugaaguc    840
agaggccauc auugaacauc ucugugcaag cgaguuugca cugaggauga aaaucaaaga    900
agugaagaag gaaaacggug acaagaagau uguccccaag aagaagaaac ccuugaagcu    960
ggggcccauc aagaagaagg agcugaaggc gcuugugcug uuccugaaga acggugccga   1020
cugucccugc caccagcugg acaaccucag ccacaacuuu cucaucaugg gccgcaaggu   1080
gaagagccag uaccugcuga cagccauuca caagugggac aagaaaaaca aggaguucaa   1140
aaacuucaug aagagaauga aaaccacgga gugucccacc uuccagucug uuuuuaagug   1200
auacuggggc ggacuggggga aggggagugu ggcuuggggu gagggugggg gcgcguggau   1260
gacccuggcu cuunggggcu cacauauugc ucucacccau acaguugugg cuuuugcauu   1320
gcaccuggcu cuguuccuac agcgaacccu cucccuuncc uccauagcca cauccagcua   1380
aggccacggc cuuuagauua ggaaggcuuu uuuuuuuuua agggcugcag cagggccagc   1440
agcgacgugc aaaaggagag gcagaauccu uucacugagc cuggggcaca aaaaacagaa   1500
aauguunncc gguuuggaaa aacaaaacaa aacggauugu aaagaacugc agacggacag   1560
cugcucagcu caacguuguu cgggacauca uuaccaauug cuuguggagu cuaagccucu   1620
acagguagaa gagucugauc auugccaagc caggcugcuu ucaguuuauu auuaaucccc   1680
cucuuucugc cuuagauaga ccaucgccac cuucaaaaca cacacacaca cacacacaca   1740
cacacacaca cacacacaca cacacacaca cacuucugaa aguagccagg guaucccagu   1800
auagaacggg auagcuaagg guuugggugg gaggccacug cuacucuacc uucagcuuuu   1860
gaacuggcca ccuuugauag gaaacugagg ucucagaugg acacuucuac caguccaucg   1920
ggauacaagg augccaggca agggucugcu uuugucugaa ggagguacgu gggcaugaag   1980
agacaugagg cauuucaggc ugagaagcaa cagcuacuag uuuucaacaa uagaguggaa   2040
gaaaugagca aagguagaaa ugucaagcag gucacaaguc agggugauug ggggaauccu   2100
gugccaacag ccucacuuug uaauuccauc ugucacuuuc aaaagaacag cagcauaaga   2160
cagggauaaa agcccacaua cccuccaagg cuugaguaaa aguccacacu cagcauuuca   2220
aagacuaacg ucguugacug cccaaggcug cccucuuaau acaccgccua ugcaugugcu   2280
guggaaggca acucugugca ugugcugugg aggagauggg ccucauggcu gugcuggcug   2340
cccggaauca guauagcgug gaaggagaca guauccauag acucugcuuu ucugcaagga   2400
aagcccuuuu ccuuauacau gauugccuau aauucagaca aauuuaaaau cgcugccugc   2460
cugagcccuc caccuuuacu uuugcauucu ccggucauau ucuuuugagg cuaaagugcc   2520
cuauccgagg agaugguuuc aaaggcuaac uaaucugcag cuuucccaag ugcccagagg   2580
uauuucucaa aguugguaug cuuaauaagu gauguaaaua uuccaguucu cuuaggcagc   2640
```

cuuacuccug uuguccug 2659

<210> SEQ ID NO 241
<211> LENGTH: 3347
<212> TYPE: RNA
<213> ORGANISM: Homo sapiens

<400> SEQUENCE: 241
aauuccgagu ggccgcgcgg cuauuuaagu ggcguuacuc cgcguccucg gcgcugcagc 60
cuugaggcuu cgggcgcggg ggaagucaug cuggcuccac agaagcacua gcuaguccgu 120
guacuuugug gguucugucc uuuugagacc ugcccgccgg ggauuggcug guaucaguga 180
cugucuacug cuggauuuuc ugcuugccuu cccgucaugu cuaacgaagu agaaacaagc 240
acaaccaaug gccagccuga ccaacaggcu gccccgaaag cgccaucaaa gaaggagaag 300
aagaaagguu cugaaaagac agacgaguac uuguuggcca gguucaaagg ugauggucuu 360
aaauacaagg ccaagcuaau cgguauugau gaugugccug augcucgagg agacaaaaug 420
agucaggauu cuaugaugaa acucaaggga auggcagcag cuggucgcuc ucagggacaa 480
cacaagcaaa gaaucugggu caacauuucc uugucuggca uaaaaaucau ugaugagaaa 540
acugggguaa uugaacauga acauccagua aauaagauuu ccuucauugc ucgugaugug 600
acagacaaca gagcauuugg uuaugugugu ggaggugaag gccagcauca auuuuuugcu 660
auaaaaacag ggcaacaggc ugagccauua gucgucgauc uuaaagaccu uuuucaaguu 720
aucuauaaug uaaagaaaaa ggaagaagau aagaaaaagg uugaagaagc caacaaagca 780
gaagagaaug gaagugaggc ccuaaugacc cuugaugauc aagcuaacaa auugaagcug 840 ggguguugacc agauggauuu guuuggggac augucuacac cuccugaccu aaauagucca 900
acagaaagca aagauauccu guuaguggau cuaaacucug aaaucgacac caaucagaac 960
ucuuuaagag aaaauccauu cuuaacaaau ggagucaccu ccuguucucu cccucgacca 1020
aagccucagg cauccuucuu gccugagaac gccuuuucug ccaaucucaa cuucuuuccc 1080
accccuaacc cugauccuuu ccgugaugau cccuuugcac agccagacca aucggcaccc 1140
ucuucguucg auucucucac aucuccagau cagaagaaag cgagucugag uagcucgucu 1200
acuccacaga guaaagggcc ccugaacguc gauacugauu acuuugguca gcaauuugac 1260
cagcucucua accggacugg caaaccggaa gcucagggag gcccguggcc cuacccaagu 1320
ucgcagaccc agcaagcagu gagaacucaa aaugggguau cugaaagaga acagaacggc 1380
uuccauauca aaucuucccc gaacccuuuu gugggaagcc cucccaaagg acuaucggua 1440
ccgaauggcg uaaagcagga cuuggaaagu ucuguccagu ccucagcaca ugacuccaua 1500
gccauuaucc caccuccaca aaguaccaaa ccaggaagag gcagaaggac ugcuaagucu 1560
ucagcaaacg acuugccugc uucagacauc uuugccucag aaccuccagg ccagaugucc 1620
cccacaggac aaccugcagu cccgcagucg aacuuccugg aucucuucaa aggcaaugcu 1680 ccuccccccag uggggccccu uguaggucua gguacggucc caguaacacc cccccaagca 1740
ggacccugga cgccuguugu cuacaguccu ucgacaacug uggucccagg agccauaaua 1800
aguggccagc cucccaguuu ucgccagcca cucguuuuug guacaacccc agcaguacaa 1860
gucuggaauc agucuccauc auuugcaacc ccagcuuccc cuccaccccc cacaguuugg 1920
uguccuacca caucuguggc gcccaacgcu uggucaucca caagcccucu ggggaauccu 1980
uuucagagua auaauaucuu uccaccuccc accaugucca cucaguccuc uccucagccu 2040
augauguccu cuguucuggc cacaccgccu caaccaccuc cccgaaaugg cccacuaaag 2100
gacauuccca gugacgcuuu cacuggcuua gacccccuug gggauaaaga ggucaaggaa 2160
gugaaagaaa uguuuaagga cuuccagcug cggcagccac cucuuguucc cucaaggaag 2220
ggggagacgc cucccucugg gacuucaagc gccuucucca guuacuucaa caauaaaguu 2280
ggcauuccuc aggagcaugu agaccaugau gauuuugaug ccaaucaacu guugaacaag 2340
auuaaugaac caccaaagcc agccccgaga caaggugucc ucuuggguac caagucugcu 2400
gacaauucac ucgagaaccc uuucuccaaa ggguucagcu caucaaaccc cucugugguu 2460
ucucagccug caucuucuga uccccacagg agcccuuucg gaaauccuuu ugccuagcuu 2520
cugaaguugu aaugaugacu auccagauga gcaaaagacu ggcuuugguc aagaaugaag 2580
cagacagcca gaaacauguu gaccucuguc cucgcuccag cuuugacgua uuaucuguua 2640
cccuauuugu uuuggccucu uguacuugua aaaugccuuu cauuuuccug ucuaggcuaa 2700
agcuaaacuu aaacuauggc uuuacguaaa uuaagcuccu aaacucucua gcuccaauau 2760
aaaugaagua gcuucccuau caaaucccug ucuguugugc ccccuugaaa cuuccagaau 2820
auucuccauu cuacccucca uuugggagga gcggcuaccu uuacccuuaa uaucacacug 2880
ccuugaguca auguccaaau acucauagcu cucaaaguca uuuggggguuc cugguguggcg 2940 gccuaaaccu aaagcauccu auuaauaggg aaguaagaca ccuugcuucc uauguccacu 3000
cagggagaau uuuauuuaau aaaaugaaag caagacuaac uucucaaauc cacccaagga 3060
ccauuuugag auggucguuu cucagcuaac ugcaccauuu accaauccug ccccaagugg 3120
ugcuuacauu ugacuugaag aagagaaaga gcuaacucaa aacacaaggc auuauucaaa 3180
gcuaauaaaa caauuucucc cuggggcccc acauuguuuu cauuccagau acguugcagc 3240
uguuugaccc ugaugacauu augcccuaca uuuuccuuga agauccugau uuuauuucau 3300
gugauuuuug uuucucaaua aagaugauua uugugugcac ggaauuc 3347

<210> SEQ ID NO 242
<211> LENGTH: 555
<212> TYPE: RNA
<213> ORGANISM: Homo sapiens

<400> SEQUENCE: 242
augaaucgca ccgcauacac ugugggagcg uugcuucucc uccuggggac ccuacugcca 60
acagcugagg ggaaaaagaa agguucccaa ggagccauuc cgccuccuga caaggcucag 120
cacaaugacu cugagcagac ccagucccca ccacaaccug gcuccaggac ccgggggcgg 180
ggccaggggc ggggcaccgc caugccugga gaggaggugc uugaguccag ccaagaggcc 240
cugcacguga cagagcgcaa guaucugaag cgagauuggu gcaaaacuca gccccugaag 300
cagaccaucc acgaggaggg cugcaacagc cgcacuauca ucaaccgcuu cuguuauggc 360
cagugcaacu ccuucuacau ccccaggcac auccgaaagg aggaagggc cuuucagucu 420 ugcuccuucu gcaagcccaa gaaguucacc accaugaugg ucacacucaa cuguccugag 480
cuacagccac ccaccaagaa gaaaagggguc acacgcguga agcagugccg uugcauaucc 540
aucgacuugg auuaa 555

<210> SEQ ID NO 243
<211> LENGTH: 2526
<212> TYPE: RNA
<213> ORGANISM: Homo sapiens

<400> SEQUENCE: 243
guggaauauc cauggaggua cggagccuug uuaccaaccu uuaaccgcag aacugggaug 60
uggggcugga agugccuccu cuucugggcu gugcugguca cagccacucu cugcacugcc 120
aggccagccc caaccuugcc cgaacaagcu cagcccuggg gagucccugu ggaaguggag 180
ucucuccugg uccacccugg cgaccugcua cagcuucgcu gucggcuucg cgaugaugug 240
cagagcauca acuggcugcg ggaugggggug cagcuggugg agagcaaccg uacccgcauc 300
acaggggagg agguggaggu gcgggacucc auccccgcug acucuggccu cuacgcuugc 360
gugaccagca gccccucugg cagcgauacc accuacuucu ccgucaaugu cucagaugca 420
cucccauccu cggaagauga ugacgacgac gaugacuccu ccucggagga gaaagagacg 480
gacaacacca aaccaaaccg uaggccugua gcucccuacu ggacaucccc agagaaaaug 540
gagaagaaac ugcaugcggu gcccgcugcc aagacgguga aguucaagug cccgucgagu 600
gggacaccca accccacucu gcgcugguug aaaaauggca aagaguuuaa gccugaccac 660
cgaauuggag gcuacaaggu ucgcuaugcc accuggagca ucauaaugga uucuguggug 720
ccuucugaca agggcaacua caccugcauc guggagaaug aguaugggag caucaaccac 780
accuaccagc uugacgucgu ggaacgaucu ccgcaccgac ccauccuuca ggcagggcug 840
ccugccaacg agacaguggc ccugggcagc aauguggagu ucauguguaa gguguacagc 900
gauccgcagc cucacauuca guggcugaag cacaucgagg ugaacgggag uaagaucggg 960
ccagacaacu ugccguaugu ccagauccug aagacugcug gaguuaauac caccgacaag 1020
gaaauggagg ugcuucaucu acggaauguc uccuuugagg augcgggga guauacgugc 1080
uuggcgggua acucuaucgg acucucccau cacucugcau gguugaccgu ucuggaagcc 1140
cuggaagaga gaccagcugu gaugaccuca ccgcucuacc uggagaucau uaucuacugc 1200
accggggccu uccugaucuc cugcauguug ggcucuguca ucaucuauaa gaugaagagc 1260
ggcaccaaga agagcgacuu ccauagccag auggcugugc acaagcuggc caagagcauc 1320
ccucugcgca gacagguaac agugucagcu gacuccagug cauccaugaa cucuggggguu 1380
cuccugguuc ggcccucacg gcucuccucc agcgggaccc ccaugccggc uggagucucc 1440
gaauaugagc ucccugagga uccccgcugg gagcugccac gagacagacu ggucuuaggc 1500
aaaccacuug gcgagggcug cuucgggcag gugguguugg cugaggccau cgggcuggau 1560
aaggacaaac ccaaccgugu gaccaaagug gccgugaaga uguugaaguc cgacgcaacg 1620
gagaaggacc ugucggaucu gaucucggag auggagauga ugaaaaugau ugggaagcac 1680
aagaauauca ucaaccuucu gggagcgugc acacaggaug guccucuuua ugucauugug 1740
gaguacgccu ccaaaggcaa ccuccgggag uaucuacagg cccggaggcc uccugggcug 1800
gaguacugcu auaaccccag ccacaacccc gaggaacagc ugucuuccaa agaucuggua 1860
uccugugccu aucagguggc ucggggcaug gaguaucuug ccucuaagaa guguauacac 1920
cgagaccugg cugcuaggaa cguccuggug accgaggaua acguaaugaa gaucgcagac 1980
uuuggcuuag cucgagacau ucaucauauc gacuacuaca agaaaaccac caacggccgg 2040
cugccuguga aguggauggc cccugaggcg uuguuugacc ggaucuacac acaccagagc 2100
gaugugggu cuuuuggagu gcucuugugg gagaucuuca cucugggugg cuccccauac 2160
cccggugugc cuguggagga acuuuucaag cugcugaagg agggucaucg aauggacaag 2220
cccaguaacu guaccaauga gcuguacaug augaugcggg acugcuggca ugcagugccc 2280
ucucagagac cuacguucaa gcaguuggug gaagaccugg accgcauugu ggccuugacc 2340
uccagccagg aguaucugga ccuguccaua ccgcuggacc aguacucacc cagcuuuccc 2400
gacacacgga gcuccaccug cuccucaggg gaggacucug ucuucucuca ugagccguua 2460
ccugaggagc ccugucugcc ucgacacccc acccagcuug ccaacagugg acucaaacgg 2520
cgcuga 2526

<210> SEQ ID NO 244
<211> LENGTH: 468
<212> TYPE: RNA
<213> ORGANISM: Homo sapiens

<400> SEQUENCE: 244
auggcugaag gggagaucac aaccuucgca gcccugaccg agagguucaa ccugccucua 60
ggaaacuaca aaaagcccaa acugcucuac ugcagcaacg ggggccacuu cuugaggauc 120
cuuccugaug gcaccgugga ugggacaagg gacaggagcg accagcacau ucagcugcag 180
cucagugcgg aaagugcggg cgaaguguau auaaagggua cggagaccgg ccaguacuug 240
gccauggaca ccgaagggcu uuuauacggc ucgcagacac caaaugagga augucuguuc 300
cuggaaaggc uggaagaaaa ccauuauaac acuuacaccu ccaagaagca ugcggagaag 360
aacugguuug ugggccucaa gaagaacggg agcuguaagc gcgguccucg gacucacuau 420
ggccagaaag ccaucuuguu ucugccccuc ccggugucuu cugacuag 468

<210> SEQ ID NO 245
<211> LENGTH: 3115
<212> TYPE: RNA
<213> ORGANISM: Homo sapiens

<400> SEQUENCE: 245
auggacaccu ccugcgucca caugcuccug uccuugcugg cgcugcugca guugguggcc 60
gccggcagcu caccgggacc agaugcgaua ccgcggggcu gcccaucaca cugucacugu 120
gagcuggaug gcaggaugcu gcucagggug gacugcucgg accuggggcu cucggagcug 180
cccuccaacc ucagcgucuu caccuccuac cuggaccuca guaugaacaa caucagucag 240
cuacccgcca gucuccuaca ucgccucugc uuccuagaag aguuacgucu ugcuggaaau 300
gcuuugacac acauucccaa gggagcguuc acgggccuuc acagccucaa agugcuuaug 360
cugcagaaca accagcugag aaagguuccg gaggaagcgc uacagaauuu gagaagccuu 420
caaucccugc gccuagaugc caaccacauc agcuacgugc cacccagcug uuucagcggc 480
cugcacuccc ugaggcaccu guggcuagau gacaaugcuc ucacagacgu cccuguccag 540
gcuuucagaa guuuaucagc ccugcaagcc augaccuugg cccugaacaa aauacaccac 600
auagcagacu acgccuuugg aaaccucucc agccucgugg uucugcaucu ccauaauaau 660
agaauccacu cccugggaaa gaaaugcuuu gauggacucc acagccugga gacuuuagau 720
uuaaauuaua auaaccuuga ugaauucccc acugcaauca agacacucuc caaccuuaag 780
gaacuaggau uccacagcaa caacaucagg ucaauaccgg agcgagcguu cguaggcaac 840
ccuucucuua ucacaauaca cuucuaugac aaccccaucc aauuuguugg aguaucugcu 900
uuucagcauu ugccugaacu aagaacacug acuuugaaug gugccucgca cauuacugaa 960
uuuccucacu ugacaggaac ugccacccug gagagucuga cuuuaacugg agcaaagauc 1020
ucaucucuuc cccaggccgu cugugaucag uuaccuaauc uccaagugcu agauuugucu 1080
uacaaccuac ucgaagacuu acccaguuug ucaggcugcc aaaaacuuca gaaaauugac 1140
cugaggcaua acgagaucua ugaaauuaag ggcagcacuu uucagcaguu guuuaaccuc 1200

-continued

```
cgaucucuga acuuagcaug gaauaaaauu gcuaucauuc accccaaugc guuuucuacg   1260

uugccgucuc uaauaaaguu ggaccuauca uccaaucucc ugucguccuu cccugugacu   1320

ggguuacaug guuuaacuca cuuaaaauua acagggaacc gagccuuaca gagccugaua   1380

ccaucugcaa acuucccaga gcucaagauu auagaaaugc caucugcuua ccaguguugu   1440

gcauuugggg ggugugagaa ugucuauaaa auuucuaacc aauggaauaa agacgacggc   1500

aacagugugg acgaccuuca uaagaaagac gcuggguuau uucaaguuca agaugagcgg   1560

gaccuugaag auuuccuacu ugacuuugag gaagaccuga augcccuuca cucggugcag   1620

ugcucgccuu ccccaggucc cuucaagccc ugugagcacc uauuugguag cuggcugauc   1680

cgaaucgggg uguggaccac ggcaguacug acgcuuuccu gcaaugccuu ggugcuuug   1740

accguguuca gaacucccu guacaucucu uccauaaagc ugcuaauugg gguaaucgcg   1800

guaguggaca uucucauggg ggucuccagu gcugugcugg cugccgugga ugcauucacu   1860

uuuggccguu uugcucagca cggugcgugg ugggaagacg gaaucggcug ccaaaucguu   1920

ggcuuccugu ccauuuuugc uuccgaaucg ucgaucuucc ugcucacucu ggcagcgcug   1980

gaacgagguu uuucugucaa gugcucuucg aaguuugaag ugaaagcucc ccuuuuuagc   2040

cugagagcga ucguuuugcu auguguccug uuggcccuga ccauugccac aaucccccuug   2100

cuaggaggca guaaguacaa ugccucuccc cucugccugc ccuugcccuu uggggagccc   2160

agcaccacgg gcuacauggu ggcucucgug uugcucaacu cucucuguuu ccucauaaug   2220

accauugccu acacaaagcu cuacugcagu uuggagaaag gagagcugga gaaucuuugg   2280

gauuguucga uggugaagca cauugcucug uugcucuucg ccaacugcau ccuuuacugc   2340

cccguggcuu ucuuauccuu cuccucuuug cuaaaccuca ccuuuaucag uccugacguc   2400

auuaaauuua uacuucucgu gaucguccca cuuccuuccu gucucaaccc acuucucuac   2460

auugucuuca aucccauuu uaaggaggau augggcagcc ugggaaagca uacccguuuc   2520

uggaugagau caaaacacgc gagucugcug uccauuaacu cggacgaugu ugagaaacgg   2580

uccugugagu caacccaagc cuuaguaucc uuuacccacg ccagcauagc cuaugacuug   2640

ccuuccacuu ccggggcauc accagcuuac cccaugacug aaagcuguca ucucucuuca   2700

guugcauuug ucccaugucu cuagugacua ugagagagga acguuuuuaa gaguuggaaa   2760

ccugaaaagu gauuucuauc agagcaguag cuaagaaaag cugagcuaaa aaccuaccuu   2820

aaaacccaag caaacaucuc uaaauuggug uggaaacagu ggugccuuag agcaggagag   2880

caucauuaaa caccgcuugu aucauuuguu cagcuaagaa ggaaagccau caagucacuu   2940

aggugaaccc agaugagaaa agcagccuga aaugcucuuc gcauuguagu cucuucugac   3000

ucaccagcau agucucccau agugagaaga cucguuggau gacucaaugg guguauuuaa   3060

auccacaaau uccuuguuua aaagguuaga guuuuaagaa aaaaaaaaaa aaaaa        3115
```

<210> SEQ ID NO 246
<211> LENGTH: 5561
<212> TYPE: RNA
<213> ORGANISM: Homo sapiens
<220> FEATURE:
<221> NAME/KEY: misc_feature
<222> LOCATION: (4879)..(4879)
<223> OTHER INFORMATION: n is a, c, g, or u
<220> FEATURE:
<221> NAME/KEY: misc_feature
<222> LOCATION: (5116)..(5116)
<223> OTHER INFORMATION: n is a, c, g, or u

<400> SEQUENCE: 246
uuuuuuuucu ucaccuccuc ccuuuucaag gccuccaagc uaauuauuuc uguugcuuug 60
gagugagcaa uucugugguu cucuccacca ccacccccaa uucugacccg aucccgccug 120
gggguuucua cggucuccgc ucacucugcg ugcaccuggc gcgccucuuu uuuucacccc 180
caaccuguug caagucuuua auccucgcaa uugggacuug cgugcaggca ccugaauccu 240
ccuugccuca uauuuugcaa guguuugggg gagagcaccu gcucuaccug caagagauuu 300
aaaaggaaaa aaaucuccag gcucccucuu ucuccacaca cucucgcucu ccugccccgc 360
cccgagguaa agccagacuc cgagaaaaug gugaucagcg ugguccuccu gcugcuggcc 420
gccuaugccg uaccggcuca aggccugggu ucuuucgugc auugugaacc cugcgacgag 480
aaagcucugu ccauguguccc ccccagcccu cugggcugug agcuggucaa agagcccggc 540
uguggcugcu gcaugacuug cgcccuggcg gagggacagu cguguggugu cuacacagag 600
cgcugcgccc aggguuugcg cugccucccc cggcaggaug aggagaagcc gcugcacgcc 660
cugcugcacg gccgcggggu uugccucaac gaaaagagcu acggcgagca aaccaagaua 720
gagagagacu cucgggaaca cgaggaaccc accaccuccg agauggcuga agagaccuac 780
ucccccaagg ucuuccggcc caagcacacu cgcauuuccg agcugaaggc ugaggcugug 840
aagaaggacc gcagaaagaa gcugacccag uccaaguuug ugggggggugc agagaacacu 900
gcccacccca gagucauccc ugcaccugag augagacagg aauccgaaca aggccccugc 960
cgcagacaca uggaagcuuc ccuccaggag uucaaagcca gcccacgcau ggugccccgu 1020
gcuguguacc ugcccaacug ugaccgcaaa ggauucuaca agagaaagca guguaagccc 1080
ucccguggcc gcaaacgugg caucugcugg ugugugggaca aguacggaau gaagcugccg 1140
ggcauggagu acguggaugg ggacuuucag ugccacgccu ucgacagcag uaacguugag 1200
ugacgcgucc ccucccuucc ucccccuauc cuacccccccc agccccaacu ccagccagcg 1260
ccucccucca ccccaggacg ucacucauuu caucucauuu aggggaaaua uauauacaua 1320
uauauuugag gaaacugagg accucggaau cucuagcaag ggcuaaggag acacuccccca 1380
ccaugacccc ggaaauguau uccuuuuuga agcaaguuga acggacagag aagggaagga 1440
gagaagaagc aagagggagc gagagaugga aagaaagcaa agcguuggaa uagaggaaaa 1500
gagggaagga cagauaggau uagagagaga agagagaaac agcaaggcag aaaggacucc 1560
acaaccaagg cugaaucugc ccuuuugcuu ucagcucuag ccugggguca gaaaaagugu 1620
ggcauucagu gacacccagu uuagauuggu caaggggaga aaagaaacaa ggugugucag 1680
ugccucucgg gucuguccccc uccugcagcc agcagugugg auggcuagac cccucacccu 1740
ccucuccucu uacccaagug cagggugauu ucauccccaa auuuacaaag acuaaaaugc 1800
auuccauccc ucugaaaaua aacaaaagug agugauugaa gauagguuuu cccccagcag 1860
acaagugaac ucagaaugug ugcaaauuuu acucuuguua aagauuuuuu uaagaaguca 1920
guacgcaccc ccaacacugg aaagacuuga uucuccaggg ugacaagcaa uucagaagcg 1980
cguggcuucg gcccuugauu ucacuagacu caaagcuggc ccggcagccu cuguggagga 2040
ggaugagagg uggagaaaac caaggggcuu guacucaccc acaagacucc auguagacuu 2100
uauaggcaua uaaaucuauu uucuuuaccu uuuuuucccu uucccuuucu uucgaaguuu 2160
ugcauuaccu cuuuaaagua guuuuuuuua ggacacugaa gaucuuccuc auucugggaa 2220
aaauccauau uucacaaaua caacccagaa cgccagcuug gccugcgucc aggcagccuu 2280
ucucgugagc uacaagugug gcucuuuugu ggggcaccga uuuggaucuu cucaugauuc 2340

-continued

```
caaacgugug uugaagugaa uccaccaagc cagguaacug ccagcaccca agggugcauc   2400
aagugcauag cccaggucac cccauuucag ccuuccaacc cgcagaaagu aacugucuca   2460
caccacacca cauaaaccug ccagauccau cuguaaccca cuggccugcc cagaccuuuu   2520
uuucccaucu gcauuuuuuu uuuugaacug cauuuugaaa gccucccuca gaugccaggc   2580
ugacagauca gagagaaacu aacaugagag augacagagg aggaggaagu ggagggu ggg   2640
ggcagagacu uccacagaga gacauagaag auggagcaga ggucuggggg uggggaggac   2700
aagaaagaga cagagagagg aaaauaccaa uagaauuuuc cuuggugucu cccaucuaau   2760
caacucucug agauuugaga ggaaaaagaa ggcaggggaa gaacuugagg uagaaaugag   2820
gucaguucaa gucacagggc ccagauggug gguaacugag gcaggaucca gacuugagac   2880
acacgguugg aaacaaggcu gguuagccug acuggguauu gaagggugaa gaggaugccu   2940
uggaaagaca gcacaacuuc aguucaacuu caggccccca aggaggaacu gaggccaaag   3000
aauccuucaa gugcuucaug agucuccucu gcccgacuca aacauccuuc ccugugaugg   3060
aggaugguag aaagcccagg acaacucagg cccggaucuu cacgacuguu gucauuugcc   3120
agccugauuu ugauccaaga gaagcaucuc auugcccacu ggcuucuuca acaaagaggu   3180
gcuuaacaaa aggcucagga cuaucuuuga agacugaaga uaaccuucca ggagaggaga   3240
cucggacauu gguacaggag gccccuuuug gcgggggaca cagcucuuug cgcucucuug   3300
auggcauggc auaguagagg cccccuccaa cccggaacau ggagcaacac aaagggagag   3360
caaagaaacu gacgugcguc gacucauagg acaugggugg cugcgggcac agaaagggau   3420
gccuccuguu gccuggacag gacaguuggc ugggaaggaa agagaaaauu gaucuucaua   3480
agacaaaggg ccugauggga uggcaauaga aggacuuacc agaccugcag ggucaguaua   3540
cccaucaccc cgcacaacau ccccagcccc caacucaaac uucaauauau cuuaggccag   3600
uauccuagac cuaagucucu ccuuucugcc auuauuucuc cgcaucuuga gcagucaucu   3660
gacugagauu ugccaagugg auacuggggu accacugccc cccaagaaaa gacugagcca   3720
ggaacugccu acucgcuccc ccucccgagc cuggagcuaa cuccugugag gggugcucuc   3780
uucaccccac aacuuacuag accuugagug agccucuguc ccuuaugugg gcucuucgcu   3840
gugagccaca gauggagguc auuguauaga caguuagccu uccccagguc agccuaccuc   3900
ccccaaacuu gugagucucc ccgcugcuca uauggagagg caugucuaag acagcaaguc   3960
uucuagagga agcuugccuu uaacagacag auggaacuaa accuuccaaa ugggagaucu   4020
ggcugaaccc aggauacaga gaccauggac auggaugggg ucaucaagag aagagggaug   4080
uccuucucca gguuagggag agagaaggca aguuugcaac gaucccauca ugcccugagc   4140
aagaagcuuu uggcccaggc uagccuuuaa cuccauuaga ggccucucug uuggguuuau   4200
ccacagcagu aggcccaagu auggccuguc cccaccucua cuaucccgug gaagguuucu   4260
ucccaccccu uuuugacaaa ugccucacuc gagcagugga aagauagcuc ucuuccccu   4320
cuucugccag guaacaaaga gaccuaacca ggaccuauuc uccaccccag ccagucuuga   4380
ccagccagaa caaagcaggg aaccuggaga auaaaagacu cuacguuccu cugacaaaga   4440
cucuacguuu cucugacggc caggccuaaa cagacaaggc uugggaacau cugccccaca   4500
ggauacggag gaggucagcu gugcucacuc cucuucuccu uccaagaccc ucuuccgacc   4560
augacuuauc uccaugguaa cauccucacc aucauucucc cacuaccaag gguugccaug   4620
gcaaccuccc aaccaccugc ccaucccagg caggcagcug uccuucugcu cagaacccua   4680
```

gaggacucua ggugaaauuu uacagcuuaa gagaggagug agccaaggag aagagacccu 4740
guaguccucu ggcuuucaag agaaagaagg cuaugauuua aaacacagua gaagggaaag 4800
aggucucguc gaggucgacc ucuccgggg agcuuagggg uuguacuguc uuuauuuuuu 4860
aaaccacuaa agugcaaunu uuccugcacu cuuguuaccc cgccucucuu cccuguuagg 4920
uuuucauuuc cuugagcaga cuuucuuggu uuuuuaaugg aguauagacu uucaccacuu 4980
cacagacucu ggccuccucu ccaagucucu cuggaugggg aaaaggaagg uagaggguca 5040
gaggggaagg ggucccucgu caccccgcau ccauucaccc ccacuucucu ggucccuagu 5100
caccggcuuc accccnaucu ccgacaccau cacugucaca caguagccug ucacacggau 5160
aguacaguuc agacaagacu ccuucagauu ccgagacgcc uaccgguugu uuuugguuuu 5220
uguuuuguuu ucuuuuguuu guuuguuugu uuguuuuuua caacagcaau aaccacauca 5280
cauauuacug uagcucucua uaguguuacg uucagacacc guagcucugu ccucucuuau 5340
uuuguugguu uugacuuaaa aaaaaauacu uaugcuuuuu acuggugaaa cagauugaaa 5400
aaaaaauuga acaacaaacc aguuugugaa aaaaaaaaaa aaugugaaaa aaaaucaccc 5460
cgauguggaa gagcucggcu ccucuuuagc auuuuguacu uaaggaaaua aaaaagaaaa 5520
accuggaaga ucucacauuu uauuacaaag ugaaaaaaaa a 5561

<210> SEQ ID NO 247
<211> LENGTH: 1113
<212> TYPE: RNA
<213> ORGANISM: Homo sapiens

<400> SEQUENCE: 247
guccagucug cagucuguau ucggaagaca uagauacuaa auacauggca acucuuuuuu 60
uuguuuguuu uaauucauca ggauguggag cgcuagucug gguaggagag ccagucaccc 120
ugaggacagc ugaaacaauc gcuggcaagu auggagugug gaugagagac cccaagccca 180
cccaccccua cacccaggaa agcacaugga ggauugacac gguuggcaca gagauccgcc 240
agguguuuga guacagucag auaagccagu ucgagcaggg cuauccuucc aagguccaug 300
ugcucccucg ggcacuggag agcacgggug cuguggugua ugcggggagc cucuauuucc 360
agggggcuga guccagaacu guggucaggu augagcuaga cacggagacc gugaaggcag 420
agaaggaaau uccuggagcu ggcuaccacg gacacuuccc guacgcgugg gguggcuaca 480
cagacauuga cuuagcugug gaugagagcg gccucugggu caucuacagc acggaggaag 540
ccaagggggc cauaguccuc uccaaauuga acccagcgaa ccuggaacuu gagcguaccu 600
gggagacuaa cauccguaag cagucugugg ccaaugccuu uguuaucugu ggcaucuugu 660
acacggugag cagcuacucu ucagcccaug caaccgucaa cuucgccuac gacacuaaaa 720
cggggaccag uaagacccug accaucccau ucacgaaucg cuacaaguac agcaguauga 780
uugacuacaa cccccuggag aggaagcugu uugccuggga caacuucaac augguccaccu 840 augauaucaa gcucuuggag augugaggag ccucuaugcc uaccagcaaa ggccagaaaa 900
ggugaaguuc cgggcucccg ggugaagcag cugucagcag aggcagccag augcauggag 960
uuucuccucc ugcuaaagau uuuguuuauc cgggucaaug uacagcuagc uccccucuga 1020
cugacacguc cuccaggcuu guauagucgc auagacucug uucucuucug ucagcuuuca 1080
aagggcuguu ccucuuuuaa aaaucacaua gug 1113

<210> SEQ ID NO 248
<211> LENGTH: 1635

<212> TYPE: RNA
<213> ORGANISM: Homo sapiens

<400> SEQUENCE: 248
gggagaccug agcucgcugc ugccugugga agacugggag aggagacacu aagugcugcu 60
caagcaagcg cgauccucuc cucuuucaac cugcagccca agauacugau ucgagccgcg 120
ccuuaccgcg cagcccgaag auucaccaug gugaagaucg ccuucaacac cccuacggcg 180
gugcaaaagg aggaggcgcg gcaagauaua gaggcgcucg ucagucgcac uguccgagcu 240
caaauccuga cuggcaagga gcucagaguu gucccgcagg agaaagaugg cucaucuggg 300
agaugcaugc uuacucuccu aggccucuca uucaucuugg caggacugau uguuggugga 360
gccugcauuu acaaguacuu caugcccaag agcaccauuu accaugguga gaugugcuuc 420
uuugauucug aggauccugu caauuccauu ccuggaggag agccauacuu ucugccugug 480
acugaggagg cugauauccg ugaggaugac aacauugcca ucauugaugu gccugugccc 540
aguuucucug auagcgaucc ggcggcaauu auucacgacu uugagaaggg aaugacugcu 600
uaccuggacu ugcuuuuggg aaacuguuau cugaugcccc ucaauacuuc cauuguuaug 660
acuccaaaga aucuggugga acuuuuugga aaacuggcaa guggcaagua uuugccucau 720
acuuaugugg uucgugaaga ccugguugcu guggaagaaa uucgugaugu uaguaaccuu 780
gguauuuuua uuuaccaacu uugcaacaac cgaaaauccu uccgccuuag acgcagagac 840
cuucugcugg guuucaacaa gcgugccauu gacaaaugcu ggaagauuag acacuucccc 900
aaugaauuua ucguugaaac caagaucugu caggagugaa augugacaga uaaagaguau 960
ccuugauaau aagaagucag gaacuuaccg ucugacuugg aaaauugaaa uugaugggau 1020
acucaugcua uuuacucaua cauuuacucu auugcuuaua cuggaaaagg aaagggaaag 1080
gggggagaaa acuacuaacc acugcaagcg auuguccaau ucuacuuuaa uugacauugc 1140
uugcuguuuu caacaaguca aaugauuauc uuuucucuug aauuuauagg guuuagauuu 1200
cugaaagcag caugaaugug ucaucuuacc auccugacaa uaaagcccau ccucugguuu 1260
uauuuaaagc aagcucuuuc caacaucacu uggcuagagc augcuuuaaa uuuaaaauau 1320
uugaaauuug uuuuugacau uuuuuugugu gaaacauguc aaaucucuua ccauucuuug 1380
guuuucuucu uuauuauguu caacucuccu gauuucagaa guuacauuuu ugcauuucua 1440
ucaggugcug uguaacgaau cugacugaua ugugaacaau cuucaugagg aagcaauuuu 1500
uuacucaugu aaugauucuu ucucacugau aucuguauug ugaaauccac agaacuguac 1560
aggugcugaa ugcuguaagg aguucugguu guaugaauuc uacaacccua uaauaaaguu 1620
uaccguauuc aauca 1635

<210> SEQ ID NO 249
<211> LENGTH: 3550
<212> TYPE: RNA
<213> ORGANISM: Homo sapiens

<400> SEQUENCE: 249
ggccauuacc aaucgcgacc cgcgcacaca cggcccgggc ggcgggcgaa gcgggcuccc 60
ggggcgcugg gcgcagggcg cggggcaagc cccagcagcg ugucugcaac ggggcgcggc 120
gggcgcucca gcuccgggau cuuucucccu cggucaccuc ccucgcgucu agggaggucg 180
uggcacuccc ugaggagcgc ggcugcucgg agggcggauc cuagaacaga ggcgugagag 240
ccggcaugaa uggucauaug ucuaaccgcu ccagugggua uggagucuac ccuucucaac 300

-continued

```
ugaaugguua cggaucuuca ccacccuauu cccagaugga cagagaacac agcucaagaa    360
caagugcaaa ggcccuuuau gaacaaagga agaacuaugc ccgagacagu gucagcagug    420
ugucggacgu gucccaguac cgcguggaac acuugaccac cuucgugcug gaucggaaag    480
augcaaugau cacugucgag gacggaauaa gaaagcugaa guugcuggau gccaagggca    540
aaguguggac ucaagauaug auucuccaag uggaugaccg agcugugagc cugauugacu    600
uagagucaaa gaaugaauug gagaauuuuc cucuaaacac aaucucgcau ugucaagcag    660
uggugcaugc augcagcuau gacuccauuc ucgccuuggu augcaaagag ccaacgcaga    720
gcaagccaga ccuucaccuu uuccagugug augagguuaa ggcaaaccua auuagugaag    780
auaucgaaag ugcaaucagu gacaguaaag gugggaaaca gaagaggcgg ccggaggccc    840
ugaggaugau ugccaaagca gauccuggca ucccuccucc ucccagagcu ccugccccug    900
ugccaccggg gacugucaca cagguggacg uuaggagucg cguagcagcc uggucugccu    960
gggcagcuga ccagggugac uucgagaagc cccggcagua ccacgagcaa gaagagacgc   1020
ccgagaugau ggcagcccgg aucgacaggg augugcaaau cuuaaaccau auuuuggaug   1080
acauugaauu uuuuaucacc aaacuccaaa aagccgccga agcguuuucu gagcuuucua   1140
aaaggaagaa aaguaagaaa aguaaaagga aaggaccugg agagggcguu uuaacacuga   1200
gggcaaaacc gccaccuccu gacgaguuug uugacuguuu ccagaaguuu aaacauggau   1260
ucaaccuucu ggccaaguug aagucccaua uccagaaccc gagugcuuca gaucugguuc   1320
auuuuuuguu uacuccacua aauauggugg uccaggcaac agguggcccu gaacuggcca   1380
guucgguacu cagcccacug uugacaaaag acacaguuga uuucuuaaac uacacagcca   1440
cugcggagga acggaagcug uggaugucac ugggagauag uugggugaaa gugagagcag   1500
aguggccgaa agaacaguuc aucccaccuu acgucccgag guuccgcaac ggcugggagc   1560
ccccgaugcu gaacuucaug ggcgcgccca cagagcaaga cauguaucaa cuggccgagu   1620
ccguggccaa cgcagaacac cagcgcaaac aggacagcaa gaggcugucc acagagcauu   1680
ccaaugugucc cgacuauccu ccagccgacg gauaugcgua caguagcagc auguaccaca   1740
gaggaccaca ugcagaccac ggggaggcug ccaugccuuu caagucaacu ccuaaucacc   1800
aaguagauag gaauuaugac gcagucaaaa cacaacccaa gaaauacgcc aaauccaagu   1860
acgacuuugu ggcgaggaac agcagcgagc ucucgguuau gaaagaugau gucuuagaga   1920
uacucgacga ucgaaggcag ugguggaaag uccggaaugc caguggagac ucuggguuug   1980
ugccaaauaa cauucuggau aucaugagaa cuccagaauc uggagugggg cgcgcugacc   2040
ccccauacac acauaccaua cagaaacaaa ggacggaaua cggccugaga ucagcugaca   2100
cuccuucugc cccaucaccc ccuccaacgc cagcacccgu uccggucccc cuuccaccuu   2160
cuguaccagc acccguuucu gugcccaagg uuccagcaga ugucacccgc cagaacagca   2220
gcuccaguga caguggggggc agcauugugc gggacagcca gagauacaaa caacucccag   2280
uggaccgaag gaagucccag auggaagagg uucaggauga gcucuuccag aggcugacca   2340
ucgggcgcag ugcugcgcag aggaaguucc acgugccacg gcagaacguu ccagugauca   2400
auaucacuua ugacuccuca ccggaagaag uaaagacuug gcugcaguca aagggauuca   2460
aucccgugac ugucaauagc cucgggggugu ugaacggagc acaacucuuu ucucucaaca   2520
aagacgaacu gaggucuguc ugcccggaag gugccagagu cuuuaaccaa aucacuguuc   2580
agaaagcugc uuuggaggac aguaauggaa gcuccgaguu acaagagauc augcggagac   2640
ggcaggagaa gaucagcgcc gcugcgagcg acucgggagu ggagucuuuu gaugaaggga   2700
```

-continued gcagccacug aguccaugaa cuuccuuauu cuuggugugg ucguugaaca gugauggaca 2760
ugcuuuguuu uaagaagccu ugaagggaau gucaaagcug ucgucuuggu auauguaauu 2820
uaucgccaua uaaggaaaca guauaugccu gaguaagcag aggacccgcu gcuucugugc 2880
acauuaguuu gauuaaaacu gagaagcggg uaggugagau ggcucagcaa guaaaggugc 2940
uugcugccaa gcccaaugac ccaaguucga gucccugggu cuacauggua ggagagagcu 3000
ggcuucugca aguuguccuc ugaccaccac acauaaauaa auaacaaaug uaauuuacaa 3060
acuuuuaaaa gaaaauguaa uuuaaaaaac cagacguucu agacuguucu gggcuuggga 3120
aauauuuuuu ucacuuuccu aagguguacu uuccuuugcu acauuaauua uugcagccuu 3180
guucgaugau cuaagugggg auauuugaca auggcagauu uauucauugc aacaaggaaa 3240
gacacagcca uugaugaaaa aaaaaagaaa gucucagcuu ucagugacug ggauaccugc 3300
uguccaggga ggaggcucag uuagacuacc cucugcuuac uugaggucug acaugcccaa 3360
ugagagugua uuuagcuuua uuuaaaguuc uuaaugccaa caguuuuaaa aaucacauuu 3420
aaaugaacug uacaagguag ccagaccuug aauguaugaa uagacuauau aauauguccc 3480
gagaaacuuu guuacucuca gcucuguuga uugcgaaauc uugcauagau uaugcuuuga 3540
uuuaguuucu 3550

<210> SEQ ID NO 250
<211> LENGTH: 2299
<212> TYPE: RNA
<213> ORGANISM: Homo sapiens

<400> SEQUENCE: 250
ccugggcccc gccgcggacg cgcggagccg ccugggccgc gccggaggag ggcggggaga 60
ggaccaugug aaugugcucc ggagcugagc gccaagccaa gcaguguuug aaaggaacag 120
gaugcugauc uaaucguggc aaaaagucag uccgaccgcu gguuucgaag acauguggug 180
uauauaaagu uugugauagu ugguggaaau uugggagcuu ggauaauggg cugugugcaa 240
uguaaggaua aagaagcagc gaaacugaca gaggagaggg acggcagccu gaaccagagc 300
ucuggguacc gcuauggcac agaccccacc ccucagcacu accccagcuu cggcgugacc 360
uccaucccga acuacaacaa cuuccacgca gcugggggcc agggacucac cgucuuuggg 420
ggugugaacu ccuccucuca cacugggacc cuacgcacga gaggagggac aggagugaca 480
cuguuugugg cgcuuuauga cuaugaagca cggacggaag augaccugag uuucacaaa 540 ggagaaaaau uucaaauauu gaacagcucg gaaggagauu gguggggaagc ccgcuccuug 600 acaaccgggg aaacugguua cauucccagc aauuacgugg cuccaguuga cuccauccag 660
gcagaagagu gguacuuugg aaaacuuggc cgcaaagaug cugagagaca gcuccugucc 720
uuuggaaacc caagagguac cuuucuuauc cgcgagagcc aaaccaccaa aggugccuac 780
ucacuuucca uccgugauug ggaugauaug aaaggggacc acgucaaaca uuauaaaauc 840
cgcaagcuug acaauggugg auacuauauc acaacgcggg cccaguuuga aacacuucag 900
caacugguac agcauuacuc agagaaagcu gaugguuugu guuuuaacuu aacuguggu 960 ucaucaaguu guaccccaca aacuucugga uuggcuaaag augcuuggga aguugcacgu 1020
gacucguugu uucuggagaa gaagcugggg caggggguguu ucgcugaagu guggcuuggu 1080
accuggaaug gaaauacaaa aguagccaua aagacccuua agccaggcac caugucuccg 1140
gaguccuucc uggaggaggc gcagaucaug aagaagcuga agcaugacaa gcuggugcag 1200
cucuacgcgg ucgugucuga ggagcccauu uacaucguca cggaguacau gagcaaagga 1260
aguuugcuug acuucuuaaa agauggugaa ggaagagcuc ugaaguugcc aaaccuugug 1320
gacauggcgg cacagguugc ugcaggaaug gcuuacaucg agcgcaugaa uuauauccac 1380
agagaucugc gaucagcaaa cauucuagug gggaauggac uaauuugcaa gauugcugac 1440
uuuggauugg cucgguugau ugaagacaau gaauacacag caagacaagg ugcgaaguuu 1500
cccauuaagu ggacagcccc cgaagcggcc cuguauggaa gguucacaau caagucugac 1560
guauggucuu uuggaaucuu acucacagag cuggucacca aaggaagagu gccauaccca 1620
ggcaugaaca accgggaggu gcuggagcag guggagagag gcuauaggau gcccugccca 1680
caggacugcc cgaucucccu gcacgagcuc augauccacu gcuggaaaaa ggauccggaa 1740
gagcgcccga ccuucgagua cuugcagggc uuccuggagg acuacuuuac ggccacagag 1800
ccccaguauc agcccgguga aaaccuguga gagccugcgc uucagacgcc ucuucccgag 1860 gccuccccuac cccuccccau uagcuuccaa uucuguagcc agcugcccca gagcaggaga 1920
accguccagg aucagauugc augugacucu ugaagcugaa cuuccacggc ccucauuaau 1980
gacacuuguc ccccaguccg aaccuccucu gugaaccauc ugagacagaa gcguguuauu 2040
ucucagacuu ggaaaugcau uguaucgaug uuaugucaaa ggccaaaccu cuguucagug 2100
uaaauagcug cuccugugcc aacaauccca gugcuuuccu uuuuuaaaaa agaaaaagca 2160
aauccuaugu gauuuuaacu cugauuucac cugauucaac uaaaaaaaaa aaaguauuau 2220
uuuccaaaag uggccucuuu gucuaaaaca auaaaaauuu uuuucauguu uuaacaaaaa 2280
aaaaaaaaaa aaaaaaaaa 2299

<210> SEQ ID NO 251
<211> LENGTH: 3991
<212> TYPE: RNA
<213> ORGANISM: Homo sapiens

<400> SEQUENCE: 251
cccucccugg cucucuccuc agcucugggc ucugacugca gcaagcagag acaaccucuc 60
acucugccuu ucccagcgcc cacccugacc cuggcccaca uuugacggug acucgcaggc 120
cagccagaaa caugaggcug gcccacgcuc ugcugccccu gcugcuacaa gccugcuggg 180
uggccacaca ggacauccag ggcuccaaag cgauugccuu ccaagacugc ccuguggauc 240
uauucuucgu gcucgacacc ucggagagug uggccuugag gcugaaaccu uauggggccu 300
ugguggacaa ggugaagucc uucacuaagc gcuucauuga caaccugaga gacagguacu 360
accgguguga ccgcaaccug guuuggaaug cgggugcgcu gcacuacagu gacgaggugg 420
agaucauccg agggcucacg cgcaugccca guggccgcga ugagcucaag gccagcgugg 480
augcggucaa guacuucggg aaaggcaccu acaccgacug cgccauuaag aaggggcugg 540
aggagcugcu cauagggggc ucccaccuga aggagaacaa guacuugauc guggugaccg 600
acgggcaucc ucuagagggc uacaaggaac caugcggggg ucuggaagau gcaguaaaug 660
aggccaaaca ccugggcauc aaggucuuuu cuguggccau cacaccugac caccuggagc 720
cacgucuaag uaucauugcc acagaccaca cauaccggcg caauuucacg gcagcugacu 780
gggggcauag ccgcgaugca gaagagguca ucagccagac cauugacacc auuguggaca 840
ugauuaaaaa uaacguggaa caagugugu guucuuuuga gugccaggcu gccagaggac 900
cuccagggcc ccgaggcgac ccugggguaug agggggagcg aggaaagcca ggucuuccgg 960
gagagaaggg agaagcugga gacccuggac gaccuggga ucuuggacca gucggguacc 1020

-continued

```
aggguaugaa gggagaaaag gggagccgug gagagaaggg uuccagagga ccgaaagguu   1080
acaagggcga gaaaggcaag cgcggaaucg acggggucga cggcaugaag ggagagacgg   1140
gguacccagg acuaccgggc ugcaagggcu ccccaggauu ugauggcauu caaggacccc   1200
cggguuccaa gggugaugcu ggugccuuug ggaugaaggg agaaaagggu gaagcuggag   1260
cagacgguga ggcugggaga ccagggaacu cagggucacc uggagaugag ggugauccug   1320
gagagccugg ucccccccgga gaaaaaggag aggccgguga ugaaggaaau gcuggcccag   1380
acggugcccc uggagagagg gguggcccug gugaaagagg accucgggg accccuggug   1440
ugagaggacc aaggggagac ccgggugaag cuggaccaca gggugaccaa ggaagagagg   1500
ggcccgucgg caucccugga gacucgggug aggcuggccc cauuggaccu aaaggauacc   1560
gaggugauga ggguccucca gguccugagg gccucagagg agccccagga ccuguuggug   1620
cuccuggaga ccccggacug augggugaga gaggugagga uggaccacca ggaaacggca   1680
cggaagguuu ccccggcuuc ccugggguauc caggcaacag aggcccuccu gggcuaaaug   1740
gcacaaaagg cuacccuggc cucaaggggg augagggguga agugggagac ccaggagagg   1800
auaacaacga cauuucaccc cguggggguca aaggggcaaa gggauaccga ggcccagaag   1860
gaccccaggg accuccagga caugugggac caccugggcc agaugagugu gagauccugg   1920
auaucaucau gaaaaugugc uccugcugug agugcacaug uggacccauu gacauccucu   1980
ucgugcugga cagcucggag agcauuggcc uacagaacuu ugagauugcc aaggacuuca   2040
ucaucaaggu cauugaccgg uugagcaagg augagcuggu caaauuugag ccagggcagu   2100
cucacgcggg cgugguacag uacagccaca accagaugca agagcacgug gacaugcgga   2160
gccccaacgu ccgcaacgcc caggacuuca aagaagcugu caagaagcua caauggaugg   2220
cugguggcac auucaccgga gaagcgcugc aguacacccg ggaccggcua cucccaccca   2280
cacagaacaa ccgaauugcc cugguccauua cggauggacg uucugacacu caacgggaca   2340
cgacaccucu cagugugcuc uguggugcag acauucaggu aguuucugug ggaaucaagg   2400
augugguuugg cuuugguggcg ggcuccgacc agcucaaugu cauuuccugc caaggcuuau   2460
cgcaaggucg uccagguauc ucccugguga aggagaacua ugcagagcuu cucgaugacg   2520
gcuuucugaa gaacauaaca gcccagaucu guauagauaa gaaguguccg gauuauaccu   2580
guccaaucac auucuccucc ccggcugaca ucaccauccu gcuagacagc ucagccagug   2640
ucggcagcca caacuucgaa accaccaagg ucuucgccaa gcgccuagcu gagcgauucc   2700
ugucagcagg cagggcggau ccuucccagg augugcgggu ggccguggua caguauagug   2760
gccaggggca gcaacagcca ggucgggcgg cucuucaguu cuuacagaau uacacagugc   2820
uggccagcuc uguggacagc auggauuuca ucaacgacgc cacagacguc aacgaugcuc   2880
ugagcuacgu gacucguuuc uaccgggaag ccucgucagg ugccaccaag aagagagugc   2940
uguuguuuuc agacggcaac ucucaggggg ccacagcaga ggccauugag aaggcugugc   3000
aggaggccca gcgugcaggc auugagaucu uugugguggu ggugggaccc caggugaacg   3060
agccccacau ccgugugcuu gucacuggca agacugcaga guacgacgug gccuuuggcg   3120
agcgccaccu auuccgugua ccaaacuacc aggcccugcu acguggcgua cucuaccaga   3180
cagucuccag gaagguggca cugggcuaga gggccacaca cguggcugga cacacauggc   3240
auggagacac auuucaacag gccuucccgc ccuucccacu gacaaaacag gaauaggaaa   3300
ugugacccaa cuggucaacu caacugucuu aaagggaacg cugagaugca cacucuuugc   3360
```

uuuguguaau guccccugug gcucaccuga gcuccuaucu agaucccgcc cuugguuugu 3420
acaucauggu ggccaucuug cugaccccuc ccccaucugg gacuggaucc agccaucucg 3480
ucuuccuccu cacugccccu aaccuauccg uggugucuuc acaccaucac ugcaguuucc 3540
gucuguguuc ugucuuccau gcucaacaug aagcagaccu ucucaugagu ucagcuugcu 3600
ggauuauggc uuuuaggaaa uugaacacag gaggaguucc aaacacaaac uuggaggaga 3660
ccccuccucu ucaucaggug cuugucagug accuacaugc aucuuggucu gguccuuagu 3720
ggcuaguccu uccacucuga aagcaaaggu gcuaucuauc uguaagggcu cucucuacac 3780
acccagaggc uuagcuugga caguucacac ucaagugucc ugucagaauc aauccagagc 3840
uuucucccuc aaaauaguga cuugucuccc ccugguccccc aaaggcuccc cuuuaguuag 3900
uuucuucaug gcuccccccac auuccccgua aucugaucca agccagcuau cucugcuaau 3960
aaagguuucc auuuuucaaa aaaaaaaaaa a 3991

<210> SEQ ID NO 252
<211> LENGTH: 235
<212> TYPE: RNA
<213> ORGANISM: Homo sapiens

<400> SEQUENCE: 252
accccaugcc ccaccccccac cuucgauguu uugaacauuu cuaacaacug aagccaguaa 60
agucauauuc uuuaaauuuc caggacauuc auauuauuca cauaaucaug gucaugguga 120
ugauggaaac ugaggacuuu aaaagagauu uucccuuccc aaacguuucu ggacaguacc 180
ugauuguauu uuuuuuguuu uguuuuguuu uuuaauaaaa gcacaguacu uuucc 235

<210> SEQ ID NO 253
<211> LENGTH: 2005
<212> TYPE: RNA
<213> ORGANISM: Homo sapiens

<400> SEQUENCE: 253
gucugcccug ccguuucucu acuucccagc cuucucaucu ccaggaacca ugucuaccaa 60
aaccaccauc aaaagucaaa ccagccaccg uggcuacagu gccagcucag ccagagugcu 120
uggacucaac cgcucgggcu ucagcagugu guccgugugc cgcucccggg gcagcggugg 180
cuccagugca augugguggag gagcuggcuu uggcagcagg agccucuaug gugugggggag 240 cuccaagagg aucuccaucg gagggggcag cuguggcauu ggaggaggcu auggcagccg 300
auucggagga agcuucggca uugguggugg agcugguagu ggcuuuggcu ucgguggugg 360
agcuggcuuu gguggugggcu auggggggagc uggcuucccg gugugcccac uuggaggcau 420
ccaagagguc accaucaacc agagccuccu cacaccccug aaccugcaaa uugaccccac 480
cauccagcgg gucaggacug aggagaggga gcagaucaag acccucaaua acaaguuugc 540
cuccuucauc gacaaggugc gguucaugga gcagcagaac aaggucaugg acaccaagug 600
ggcccugcug caagagcagg acaccaagac cgugaggcag aacauggagc ccauguuuga 660
gcaguacauc agcaaccucc gcagacagcu ggacagcauc auuggagaga ggggucgcau 720
gaacucagag cugaggaaca ugcaggaacu cguagaagaa cuacggaaca aauaugaaga 780
ugaaaucaac aagcgcacag acgcagagaa ugaauucgug acccugaaga aggauguaga 840
ugcugccuac augaacaaag uugaacugca agccaaggca gacagucuaa cagaugauau 900
caacuucuug agagcucucu augaagcaga acugucucag augcaaacuc acaucucaga 960
cacaucugug guccucucca uggucaacaa ccguagccuc guccuagaca gcaucaucgc 1020

```
ugaggucaag gcccaguuug aggucauagc ucagagaagu cgggcugaag cugagucauu   1080

guaccagacu aaauaugagg agcugcaggu cacagcuggc agacaugggg acgaccugcg   1140

caacaccaag caggagauug cugagaucaa ccgcaugauc cagaggcuga gaucugagau   1200

cgaccacguu aagaagcagu gugccaaccu gcaagcugcu auugcugaug cugagcaacg   1260

uggggagaug gcccugaagg augcaagggg caagcuggaa gggcuggagg augcccugca   1320

gaaggccaaa caggacaugg ccaugcugcu gaaggaguac caugaacuca ugaaugucaa   1380

gcuggcccuu gauguggaaa uugccaccua caggaagcug cuggaaggag aggagugcag   1440

guugaauggu gaagguguug gaccagucaa caucucugug gugcagucca ccguguccag   1500

cggcuauggc agugccgggg gugccagcag cagcuuaggc augggguggag gcagcagcua   1560

cuccuauagc agcagccaug gccuuggagg uggcuucagu gcuggcagug gcagagccau   1620

cggaggugggc cucagcucuu cuggugggccu cagcucuucu accaucaaau acaccaccac   1680

cuccuccagc aagaagagcu acaggcagug aauucuguca ccaagagcuu gucucugguc   1740

ccagauguca uggcugcagc ugaaccacau gcuuugguuc ccggaaggga acgaauccca   1800

accucuggcc ucccccauggc ucaguucuac auuuguguug cacgucagca ccuauacaug   1860

uucuuuggug acccagaccc caaaaauguug cagaauguag accuccaaga cgaaacccca   1920

aacccuaccc agaauaccca ccuaaaauucu gucaugguuc ugacuuccuc cagagucugu   1980

aaaauaaaau gcccccacaa caaac                                    2005
```

<210> SEQ ID NO 254
<211> LENGTH: 357
<212> TYPE: RNA
<213> ORGANISM: Homo sapiens

<400> SEQUENCE: 254

```
uuuuuuuuuu uuuuuuugau uuuaauuaca aacuuuauuu guccuccagu ucacaguuua     60

uacgugguac aucccaccau gucagcuucc agaacggcua uucaggagau gggugggagcu    120

uucuuuguaa aggaacccga cauuuuaaaa uuuugguuag aaucuucaua gguuuauaaa    180

aguacucucu gcaagcgaac uggauauauu uacauuuaua gcuuaaaauuc aaauuuugga    240

aaauaggaau cuuuuugugu uuuuaaacau ccugggguuua ugucuuaaga cuuuacucug    300

aaugccacau gaucacguaa gcccaagccu cccccagaag ggaaaaauca guuuugc       357
```

<210> SEQ ID NO 255
<211> LENGTH: 271
<212> TYPE: RNA
<213> ORGANISM: Homo sapiens

<400> SEQUENCE: 255

```
uuuuuuuuuu uuuuuuuggg ugccaugcca cagcaagggg ccuuuauuag auguucaggg     60

cacagacagg uggaugcuag auggguguagc acaccuucuc aggguggagu ggugccugga    120

uguccaguuu gcgggucuug cuguccuuau caaugaucuc cagucgcaau guagguggac    180

gcuucucagc cuggggugag ggcagcucac ggcucuugag gaggugcuug uccgaauccu    240

ccacagugau acccagggug caaccccug g                              271
```

<210> SEQ ID NO 256
<211> LENGTH: 255
<212> TYPE: RNA
<213> ORGANISM: Homo sapiens -continued

<400> SEQUENCE: 256
uuuuuuuuuu uuuuucugac acaguaguaa uccuuccaga cuccuuacac aauauuacaa 60 cuccccccagu acauaaaugu uccuauacca ugcacacagc aacauggggu ccacugaugu 120
cgcaggcgac uuuucuaaug guggaacaua gcaccucaag uucugccauc uacacaguga 180
agggacguga uggucggggc uccagaguga cagcaaacug ccucuugggu gacacgcuug 240
uggcgaagug ccucc 255

<210> SEQ ID NO 257
<211> LENGTH: 4031
<212> TYPE: RNA
<213> ORGANISM: Homo sapiens

<400> SEQUENCE: 257
gagaauguug cugaggaggu ggggcugcug cagcuccuug gagaccccccu accugagaag 60 aucucacaaa ucgaugaccc ucacgucggg ccggccuaca ucuuuggacc agacuccaac 120
aguggccagg uggcccagua ucauuuccca aaacucuucu uccgggacuu uucgcugcug 180
uuucaugucc ggccagccac agaggcagca ggggugcuau uugccaucac agaugcugcc 240 cagguggua g ucucacuggg cgugaagcuc ucagaggucc gagauggaca gcaaaacauc 300
ucauugcucu acacggagcc ugggggccagc cagacccaga cgggagccag cuuccgccua 360
ccugcauuug uugggcagug gacacacuuc gcgcucagcg ucgacggagg cucuguggcu 420
cucuacguag acugugaaga auuccagagg gugccauuug cucgggccuc gcagggacug 480
gagcuagagc guggcgcugg ccucuuugug ggucaggcug gaacagcaga cccugacaag 540
uuccagggga ugaucucaga gcugaaggua cgcaaaaccc cccgggugag cccugugcac 600
ugucuggaug aagaagauga ugaugaagac cgggcaucug gagauuuugg aaguggcuuu 660
gaagaaagca gcaagucaca caaggaggau acaucucuac uaccugggcu cccucagcca 720
ccuccuguca cuuccccacc ccuggcugga ggcagcacca cagaagaucc uagaacagaa 780
gaaacggagg aagacgccgc gguagauucu auaggagcug agacccuucc uggcacaggu 840
ucaagcggug caugggauga ggcuauccag aaccccggaa ggggcuugau aaagggaggu 900
augaaaggac aaaagggaga accaggugcc cagggcccac cuggcccagc uggcccccag 960
gguccugccg guccaguggu ccagagcccc aacucacaac cugucccugg agcacaagga 1020
cccccgggac cucaggggcc accagggaag gauggcacuc caggaaggga uggugaaccg 1080
ggugacccug gugaagaugg gagaccgggu gacacuggac cucaaggcuu uccagggacc 1140
ccaggagaug ugggcccuaa gggcgagaag ggagauccug guauugggcc ccgaggaccu 1200
ccagggccuc cagggccacc aggacccucc uucagacaag acaagcugac cuucauugac 1260
auggagggau ccgguuucag cggagacaua gagagccuua gaggcccacg aggcuucccu 1320 ggcccccccgg ggcccccugg ugucccagga cuuccuggug agccaggacg cuuugggauc 1380
aaugguuccu augcaccagg accugcaggc cuuccuggug uaccugggaa ggaaggaccc 1440
cccgguuuuc caggucccccc gggaccucca gguccuccag gcaaagaggg cccaccagga 1500
guggccggcc agaaaggcag uguuggugau gugggcaucc caggacccaa ggggagcaaa 1560
ggagaccuug ggcccaucgg uaugccuggc aagucuggcu uggcuggauc cccugggcca 1620
guuggacccc caggaccucc agggccucca gggccaccag gaccaggauu ugcugcugga 1680
uucgaugaua uggaaggcuc uggaauaccc cucuggacaa cagcccgaag cucugauggg 1740
cugcagggac cucccgggcuc gccgggacuc aagggggauc cuggaguggc aggccuaccu 1800

```
ggagccaagg gagaaguugg agcagaugga gcccagggca ucccuggucc cccaggaaga   1860

gaaggugcag cuggaucucc ggggccaaaa ggagagaagg ggaugccggg agaaaaggga   1920

aacccaggaa aagauggagu gggccggccg ggccucccug ggccuccagg accuccaggg   1980

cuggugaucu augugucaag ugaggauaaa gcaauaguga gcacgccagg accugagggc   2040

aagccagggu acgcaggcuu uccuggaccu gcuggaccga agggugaccu ggguuccaaa   2100

ggcgagcagg gucuuccggg guuuaagggu gagaagggag agccaggcac uaucuuuagu   2160

ccugauggca gacgucuggg ccauccccag aagggagcca agggagagcc aggcuuucga   2220

ggacccccgg guccuuaugg acgaccuggg cacaagggug aaauuggcuu cccuggacgg   2280

ccgggucgac cuggaacgaa uggcuuaaag ggagagaagg gagagccugg agaugccagc   2340

cuuggguuca gcaugagggg auugccuggc cccccugggc cuccaggacc cccagguccu   2400

ccugggaugc ccaucuauga cagcaaugca uuuguggagu cuggccgacc uggacuacca   2460

ggacagcagg gugugcaggg gccuucagga ccaaagggug acaaaggaga gguggggcca   2520

ccugggccac cagggcaauu ccccauugac cucuuccacc uggaagcgga aaugaagggg   2580

gacaagggag accgagggga ugcuggacag aaaggagaga ggggagaacc uggggcuccu   2640

gguggugga u ucuucagcuc aaguguaccu ggcccacccg gcccaccugg auacccugga   2700

auuccggguc caaagggaga gagcauccgg gggccaccug gcccuccugg cccgcaggga   2760

ccuccuggca uuggcuauga gggucgccag gguccccag gaccuccagg accuccagga   2820

ccucccuccu ucccuggccc ucacagacag acugucagug uuccuggucc uccgggccca   2880

ccugguccuc cagguccccc aggagccaug ggugccucug cugggcaggu gaggaucugg   2940

gccacauacc agaccaugcu ggacaagauc cgggaggugc cggagggcug gcucaucuuu   3000

guggccgaga gggaagagcu cuauguacgc guuagaaaug gcuuccggaa ggugcugcug   3060

gaggcccgga cagcccuccu gagaggcacg ggcaaugagg uggcugcuuu ccagcccccca   3120

uugguccagc uucaugaggg caguccauac acccggaggg aguacuccua uuccacggca   3180

cgacccuggc gagcagauga cauccuggcc aacccaccgc gccugccaga ccgccagccu   3240

uacccuggag uuccacauca ccacaguucc uaugugcacc ugccgccagc ccgcccacc   3300

cucucacuug cucauacuca ucaggacuuu cagccagugc uccaccuggu ggcacugaac   3360

acccccugu cuggaggcau gcgugguauc cguggagcag auuuccagug cuuccagcaa   3420

gcccgagccg uggggcuguc gggcaccuuc cgggcuuucc uguccucuag gcugcaggau   3480

cucuauagca ucgugcgccg ugcugaccgg gggucugugc ccaucgucaa ccugaaggac   3540

gaggugcuau cucccagcug ggacucccug uuuucuggcu cccaggguca agugcaaccc   3600

ggggcccgca ucuuuucuuu ugacggcaga gauguccuga gacacccagc cuggccgcag   3660

aagagcguau ggcacggcuc ggaccccagu gggcggaggc ugauggagag uuacugugag   3720

acauggcgaa cugaaacuac uggggcuaca ggucaggccu ccucccugcu gucaggcagg   3780

cuccuggaac agaaagcugc gagcugccac aacagcuaca ucguccugug cauugagaau   3840

agcuucauga ccucuuucuc caaauaggcc ucugccagcu aggguggcag acagaggcca   3900

ugcagaacuu ugacacagcg cagggagcau ucagucagca cccagggcuc uggcugggau   3960

acaacuccug uauaguuccc auuuuuaugu aauccucaag aaauaaaagg aagccaaaga   4020

guaaaaaaaa a                                                        4031
```

<210> SEQ ID NO 258

<211> LENGTH: 1503
<212> TYPE: RNA
<213> ORGANISM: Homo sapiens

<400> SEQUENCE: 258
aacugccuuc gagaagcguu agccuagaga uccgagccuc uucuccauac cauaguuggu 60
ucaggugguu uccucuucaa accuugcguc ugcggauaau ccgcgcggcc gggcguuaag 120
cuccaggucc cugucgcucc gucgaggugg caagccaugg ccggcugcug cuguuugucu 180
gcggaggaga aagagucuca gcgcaucagc gcggagaucg agcggcacgu ucgccgcgac 240
aagaaggacg cgcgccggga gcucaagcug cuguugcugg gaaccgguga gagugggaaa 300
agcaccuuua ucaagcagau gaggauaauc caugggucug gcuacaguga ugaagauaga 360
aagggcuuca cgaagcuggu uuaccaaaac auauucacgg ccaugcaagc caugaucaga 420
gcaauggaua cccugaggau acaauacaug ugugagcaga auaaggaaaa ugcccagauc 480
aucagggaag uggaaguaga caaggucacu gcacucucua gagaccaggu ggcagccauc 540
aagcagcugu ggcuggaucc cggaauccag gaguguuacg acaggaggag ggaguaccag 600
cugucagacu cugccaaaua uuaccugacg gacauugagc guaucgccau gcccucuuuc 660
gugccaacac aacaggaugu gcuucguguu agagugccca ccacuggcau cauagaauau 720
ccauucgacc uggaaaacau caucuuccga augguggaug uugguggcca gcgaucugaa 780
cgacggaaau ggauucacug cuuugagagu gucaccucca ucauuuucuu gguugcucug 840
agugaauaug accagguucu ggcugagugu gacaaugaga accgcaugga ggagagcaaa 900
gcccuguuua gaaccaucau caccuacccc ugguuucuga acuccuccgu gauucuguuc 960
uuaaacaaga aggaucuucu agaggagaaa aucauguacu cucaucuaau uagcuacuuc 1020
ccagaguaca caggaccaaa gcaagauguc aaagcggcca gggacuuuau ccugaagcug 1080
uaucaagacc agaauccuga caaagagaag guuaucuauu cucacuucac uugugcuaca 1140
gacaccgaga auauccgcuu uguguuugcu gcugucaaag acacaauccu acagcuaaac 1200
cuacgggagu ucaacuuggu guaaauggag ggccuacucc uccgagacag agggugaucu 1260
gagcccuucc ugccugaucu acaagugcuu cuggaccagg accuaaggac auuauguagc 1320
ccacaggaca gagaugggua gugcaaugug aaaaauacuu caccaacccu uuuaaguguc 1380
uuuaauucuu cacugucuaa cucuuuucuc gccuuuuggu ugaacgauua gguaucauuu 1440
uugaguggUU cccccucucc uauuuuuuua aacuaguguu caacaguuau uaaaaaauca 1500
ugc 1503

<210> SEQ ID NO 259
<211> LENGTH: 876
<212> TYPE: RNA
<213> ORGANISM: Homo sapiens

<400> SEQUENCE: 259
gaauucccug caaccuuguc ugagaggaag caaggacugg ugugaggagg gagcugugag 60
guuuuaucug ugcagcccuu cucugaggau ggacacuucu cacacuacaa aguccuguuu 120
gcugauucuu cuuguggccc uacugugugc agaaagagcu cagggacugg aguguuacca 180
gugcuaugga gucccauuug agacuucuug cccaucaauu accugccccu acccugaugg 240
agucuguguu acucaggagg cagcaguuau ugugggguucu caaacaagga aaguaaagaa 300
caaucuuugc uuacccaucu gcccuccuaa uauugaaagu auggagaucc uggguacuaa 360
ggucaaugug aagacuuccu guugccagga agaccucugc aaugcagcag uucccaaugg 420
aggcagcacc uggaccaugg caggggugcu ucuguucagc cugagcucag uccuccugca 480
gaccuugcuc ugauggucu cccaaugacc uccacccuug uccuuuuauc cucaugugca 540
acaauucuuc cuggagcccu cuagugauga auuaugaguu auagaagcuc caagguggga 600
guagugugug aaauaccaug uuuugccuuu auagcccugc uggguaggua ggugcucuaa 660
uccucucuag ggcuuucaag ucuguacuuc cuagaauguc auuuuguugu ggauugcugc 720
ucaugacccu ggaggcacac agccagcaca gugaagaggc agaauuccaa gguauuaugc 780
uaucaccauc cacacauaag uaucuggggu ccugcaaugu ucccacaugu auccugaaug 840
ucccccuguu gaguccaaua aacccuuugu ucuccc 876

<210> SEQ ID NO 260
<211> LENGTH: 6929
<212> TYPE: RNA
<213> ORGANISM: Homo sapiens
<220> FEATURE:
<221> NAME/KEY: misc_feature
<222> LOCATION: (2080)..(2080)
<223> OTHER INFORMATION: n is a, c, g, or u
<220> FEATURE:
<221> NAME/KEY: misc_feature
<222> LOCATION: (2082)..(2082)
<223> OTHER INFORMATION: n is a, c, g, or u
<220> FEATURE:
<221> NAME/KEY: misc_feature
<222> LOCATION: (4019)..(4019)
<223> OTHER INFORMATION: n is a, c, g, or u
<220> FEATURE:
<221> NAME/KEY: misc_feature
<222> LOCATION: (4119)..(4119)
<223> OTHER INFORMATION: n is a, c, g, or u
<220> FEATURE:
<221> NAME/KEY: misc_feature
<222> LOCATION: (5039)..(5039)
<223> OTHER INFORMATION: n is a, c, g, or u
<220> FEATURE:
<221> NAME/KEY: misc_feature
<222> LOCATION: (5048)..(5048)
<223> OTHER INFORMATION: n is a, c, g, or u
<220> FEATURE:
<221> NAME/KEY: misc_feature
<222> LOCATION: (5054)..(5054)
<223> OTHER INFORMATION: n is a, c, g, or u
<220> FEATURE:
<221> NAME/KEY: misc_feature
<222> LOCATION: (5079)..(5079)
<223> OTHER INFORMATION: n is a, c, g, or u
<220> FEATURE:
<221> NAME/KEY: misc_feature
<222> LOCATION: (5131)..(5131)
<223> OTHER INFORMATION: n is a, c, g, or u

<400> SEQUENCE: 260
ggaagaaaga gagggaggga aaagagaagg aaggaguaga ugugagaggg uggugcugag 60
ggugggaagg caagagcgcg aggccuggcc cggaagcuag gugaguucgg cauccgagcu 120
gagagacccc agccuaagac gccugcgcug caacccagcc ugaguaucug gucuccgucc 180
cugaugggau ucucgucuaa accgucuugg agccugcagc gauccagucu cuggcccucg 240
accagguuca uugcagcuuu cuagaggucc ccagaagcag cugcuggcga gcccgcuucu 300
gcaggaacca auggugagca gggcaaccug gagaggggcg cuauucugag gauucgaggu 360
gcacccguag uagaagcugg ggauggggcu caggcuguaa ccgaggcaaa aguuggccua 420
uuccuccuuc cuucuccaac aguguuggag gugggaugau ggaggcuaaa aggcaccucc 480
auauauguua cugcgucuau caaccuacuu uagggaggug cgggccagga gaggcgggaa 540

-continued

```
ggagagaagg ccuuggaaga gaggucauug ggaagaacug ugggguuugg ugggguuugcu    600
uccacuuaga cuauaagagu gggagaggag ggagucaacu cuaaguuuca acaccagugg    660
gggacugagg acugcuucau uaggagagag aaccuagcca gagcuagcuu ugcaaaagag    720
gcuguagucc ugcuuugcuc uaaagcgcga cccgggauag agaggcuucc uugagcgggg    780
ugucaccuaa ucuugucccc aacgcacccc cucccagccc cugagagcua gcgaacugua    840
gguacacaac ucgcucccau cuccaggagc uauuuucuua gacaugggca cccaugauuc    900
ugccuucugg uacucucccc ucccugggaa aggggugvaa gguuccgacg gaaccguggc    960
caggaugccg aaaggcuacc ugugcggguc uucugccaug cugugucugu gcggacaugc   1020
cagcagggcu aaugaggagc uugcgauacu ccaaaggguu cgggaauugc ggggguccuua  1080
cacgcagugg aguugggccc cuuuuacuca gaagguuucc gccacggcuu ugguugauag   1140
uuuuuuuagu auccugguuu augaacugaa gguuuuguga gauguugaau cacuagcagg   1200
gucauauuug gcaaaccgag gcuacuauua aauuuugguu uuagaagaag auucugggga   1260
gaaagugaag gguaacugcc uccaggagcu guaucaaccc cauuaagaaa aaaaaaaaua   1320
ccaggagaug aaaauuuacu uugaucugua uuuuuuaauu aaaaaaaauc agggaagaaa   1380
ggagugauua gaaagggauc cugagcgucg gcgguuccac ggugcccucg cuccgcgugc   1440
gccagucgcu agcauaucgc caucucuuuc ccccuuaaaa gcaaauaaac aaaucaacaa   1500
uaagcccuuu gcccuuucca gcgcuuuccc aguuauuccc agcggcgacg cgugucgggg   1560
aauagagaaa ucgucucaga aagcugcgcu gauggguggug agagcggacu gucgcucagg  1620
ggcgcccgcg gucucugcac ccagggcagc agugugggau ggcgcugggc agccaccgcc   1680
gccaggaagg acgugacucu ccauccuuua cacuucuuuc ucaaagguuu cccgaaagug   1740
ccccccgccu cgaaaacugg ggccggugcg gggggggga gagguuaggu ugaaaaccag    1800
cuggacacgu cgaguuccua agugaggcaa agaggcgggg uggagcgggc ucuggagcgg   1860
gggaguccug ggacucgguc cucggaugga ccccgugcaa agaccuguug gaacaagagu   1920
ugcgcuuccg agguuagaac aggccaggca ucuuaggaua gucaggucac cccccccccc   1980
aaccccaccc gaguuguguu ggugaauuuc uuggaggaau cuuagccgcg auucuguagc   2040
uggugcaaaa ggaggaaagg ggugggggaa ggaaguggcn gngcgggggu ggcggugggg   2100
guggaggugg uuuaaaaagu aagccaagcc agagggagag gucgagugca ggccgaaagc   2160
uguucucggg uuuguagacg cuugggaucg cgcuuggggu cuccuuucgu gccggguagg   2220
aguuguaaag ccuuugcaac ucugagaucg uaaaaaaaau gugaugcgcu cuuucuuugg   2280
cgacgccugu uuuggaaucu guccggaguu agaagcucag acguccaccc cccaccccc    2340
gcccaccccc ucugccuuga auggcaccgc cgaccgguuu cugaaggauc ugcuuggcug   2400
gagcggacgc ugagguuggc agacacggug uggggacucu ggcggggcua cuagacagua   2460
cuucagaagc cgcuccuucu aacuuuccca caccgcucaa accccgacac ccccgcggcg   2520
gacugaguug gcgacggggu cagagucuuc uggcugaaag uuagauccgc uaggggucgg   2580
cugccugucg cuagaagcau uauuuggccu cucggagacc cguguggagg aagugcugga   2640
gugugcgagu guguuugcgu gugugugugu gugugugugu gugugugugu gugugugugu   2700
gugcgcgcgc ccuuggaggg ucccuaugcg cuuuccuuuu cauggaacgc ugucgugagg   2760
cuuugguaaa cugucuuuuc gguuccucuc ucggcugcac uuaagcuuug ucggcgcugu   2820
aaagagacgc gucuucaagu gcacccugau ccucaggcuu cagauaaccc gucccccgaac  2880
cuggccagau gcauugcacu gcgcgccgca gguagagacg ugccccacgu ccccugcgug   2940
```

-continued

```
cagcgacuac gaccgagagc cgcgccagug uggugucccg ccgagaguuc cucagagcag   3000
gcggggacaa cucccagacg gcuggggcuc cagcugcggg cgcggagguu ggccucgcuc   3060
gcaggggcug gacccagccg gggugggagg auggaggagg ggcgggcggg cucuucggug   3120
aguggggcgg ggccucuggg uccacgugac uccuaggggc uggaagaaaa acagagccug   3180
ucugcuccag agucucauua uaucaaauau cauuuuagga gccauuccgu agugccauuc   3240
ggagcgacgc acugccgcag cuucucugag ccuuuccagc aaguuuguuc aagauuggcu   3300
cccaagaauc auggacuguu auuaugccuu guuuucuguc agugaguaga caccucuucu   3360
uucccuucuu gggauuucac ucuguccucc caucccugac cacugucugu cccucccguc   3420
ggacuuccau uucagugccc cgcgcccuac ucucaggcag cgcuagguu cucuuucugg   3480
ucccugcaag gccagacacu cgaaauguac gggcuccuuu uaaagcgcuc ccacuguuuu   3540
cucugauccg cugcguugca agaaagaggg agcgcgaggg accaaauaga ugaaaggucc   3600
ucagguuggg gcugucccuu gaagggcuaa ccacucccuu accagucccg auauauccac   3660
uagccuggga aggccaguuc cuugccucau aaaaaaaaaa aaaaaaacaa aaaacaaaca   3720
gucguuuggg aacaagacuc uuuagugagc auuuucaacg cagcgaccac aaugaaauaa   3780
aucacaaagu cacuggggca gccccuugac uccuuuuccc agucacugga ccuugcugcc   3840
cgguccaagc ccugccggca cagcucuguu cuccccuccu ccuguucuua accagcugga   3900
aguuguggaa auugggcugg agggcggagg aagggcgggg guggggggu ggagaaggug   3960
gggggggggg aggcugaagg uccgaaguga agagcgaugg cauuuuaauu cucccuccnc   4020
cuccccccuu uaccuccuca auguuaacug uuuauccuug aagaagccac gcugagauca   4080
uggcucagau agccguuggg acaggaugga ggcuaucuna uuuggggua uuugagugua   4140
aacaaguuag accaaguaau uacagggcga uucuuacuuu cgggccgugc auggcugcag   4200
cuggugugug uguguguagg gugugaggga gaaaacacaa acuugaucuu ucggaccugu   4260
uuuacaucuu gaccgucggu ugcuaccccu auaugcauau gcagagacau cucuauuucu   4320
cgcuauugau cgguguuuau uuauucuuua accuuccacc ccaaccccu ccccagagac   4380
accaugauuc cugguaaccg aaugcugaug gucguuuuau uaugccaagu ccugcuagga   4440
ggcgcgagcc augcuaguuu gauaccugag accgggaaga aaaaagucgc cgagauucag   4500
ggccacgcgg gaggacgccg cucagggcag agccaugagc uccugcggga cuucgaggcg   4560
acacuucuac agauguuugg gcugcgccgc cguccgcagc cuagcaagag cgccgucauu   4620
ccggauuaca ugagggaucu uuaccggcuc cagucugggg aggaggagga ggaagagcag   4680
agccagggaa ccgggcuuga guacccggag cgucccgcca gccgagccaa cacugugagg   4740
aguuuccauc acgaagguca guuucugcuc uuaguccugg cgguguaggg ugggguagag   4800
crccggggca gaggguggg ggugggcagc uggcagggca agcugaaggg guuguggaag   4860
cccccgggga agaagaguuc auguuacauc aaagcuccga guccuggaga cuguggaaca   4920
gggccucuua ccuucaacuu uccagagcug ccucugaggg uacuuucugg agaccaagua   4980
gugguggua ugggggaggg gguuacuuug ggagaagcgg acugacacca cucagacunc   5040
ugcuaccncc cagngggugu ucuuuagcua uaccaaagnc agggauucug cccguuuugu   5100
uccaaagcac cuacugaauu uaauauuaca ncugugugu ugucagguuu aucaauaggg   5160
gccuuguaau acgaucugaa uguuuccuag cggauguuuc uuuuccaaag uaaaucugag   5220
uuauuaaucc uccagcauca uuacuguguu ggaauuuauu uucccuucug uaacaugauc   5280
```

-continued

```
aacaaggcgu gcucuguguu ucuaggaucg cuggggaaau guuugguaac auacucaaaa   5340
guggagaggg agagagggug gccccucuuu uucuuuacaa ccacuuguaa agaaaacugu   5400
acacaaagcc aagagggggc uuuaaaaggg gaguccaagg gugguggagu aaaagaguug   5460
acacauggaa auuauuaggc auauaaagga gguugggaga uacuuucugu cuuuggugu u  5520
ugacaaaugu gagcuaaguu uugcugguuu gcuagcugcu ccacaacucu gcuccuucaa   5580
auuaaaaggc acaguaauuu ccucccccuua gguuucuacu auauaagcag aauucaacca  5640
auucugcuau uuuuuguuuu uguuucuugu uuuuguuuug uuugguuuuu uuuuuuuuuu   5700
uuuuuuuuuu gucucagaaa agcucauggg ccuuuucuuu uccccuuuca acugugccua   5760
gaacaucugg agaacauccc agggaccagu gagagcucug cuuuucguuu ccucuucaac   5820
cucagcagca ucccagaaaa ugaggugauc uccucggcag agcuccggcu cuuucgggag   5880
cagguggacc agggcccuga cugggaacag ggcuuccacc guauaaacau uuaugagguu   5940
augaagcccc cagcagaaau gguuccugga caccucauca cacgacuacu ggacaccaga   6000
cuaguccauc acaaugugac acggugggaa acuuucgaug ugagcccugc aguccuucgc   6060
uggacccggg aaaagcaacc caauuauggg cuggccauug aggugacuca ccuccaccag   6120
acacggaccc accagggcca gcaugucaga aucagccgau cguuaccuca agggagugga   6180
gauugggccc aacuccgccc ccuccugguc acuuuuggcc augauggccg gggccauacc   6240
uugacccgca ggagggccaa acguaguccc aagcaucacc cacagcgguc caggaagaag   6300
aauaagaacu gccgucgcca uucacuauac guggacuuca gugacguggg cuggaaugau   6360
uggauugugg ccccacccgg cuaccaggcc uucuacugcc augggggacug ucccuuucca  6420
cuggcugauc accucaacuc aaccaaccau gccauugugc agacccuagu caacucuguu   6480
aauucuagua ucccuaaggc cuguugugue cccacugaac ugagugccau uuccauguug   6540
uaccuggaug aguaugacaa gguggugug aaaaaauuauc aggagauggu gguagagggg   6600
uguggaugcc gcugagauca gacaguccgg agggcggaca cacacacaca cacacacaca   6660
cacacacaca cacacacaca cacguuccca uucaaccacc uacacauacc acacaaacug   6720
cuucccuaua gcuggacuuu uaucuuaaaa aaaaaaaaaa gaaagaaaga aagaaagaaa   6780
gaaaaaaaau gaaagacaga aaagaaaaaa aaaacccuaa acaacucacc uugaccuuau   6840
uuaugacuuu acgugcaaau guuuugacca uauugaucau auuuugacaa auauauuuau   6900
aacuacauau uaaaagaaaa uaaaaugag                                     6929
```

<210> SEQ ID NO 261
<211> LENGTH: 277
<212> TYPE: RNA
<213> ORGANISM: Homo sapiens

<400> SEQUENCE: 261

```
gaaucccacu uacaugcgag caucucuaua uacauccuca aucuaucccc ucgaauccac     60
ggacuuauca gucaaucaau acuacaguca aagaauuuuu uucuacguua uccuggagca    120
uugcgcuggc accucuuuuu cuaaucaucu ugguuguggg gccaauaugg augcgcagac    180
gguguaaacg cagggcugga aagacauaug gacugaccaa gcuacggacu gacaaccagg    240
acuucccuuc cagcccaaac uaaauaaagg aaaugaa                              277
```

<210> SEQ ID NO 262
<211> LENGTH: 2810
<212> TYPE: RNA
<213> ORGANISM: Homo sapiens

<400> SEQUENCE: 262
gaauucaugu cuuacgguca aggcagaggg cccagcgcca cugcagccgc gccaccuccc 60
agggccgggc cagcccaggc guccgcgcuc ucggggugga cuccccccgc ugcgcgcuca 120
agccggcgau ggcuccucuc ggauaccucu uagugcucug cagccugaag caggcucugg 180
gcagcuaccc gaucuggugg uccuuggcug ugggacccca guacuccucu cugagcacuc 240
agcccauucu cugugccagc aucccaggcc ugguaccgaa gcagcugcgc uucugcagga 300
acuacgugga gaucaugccc agcguggcug agggugucaa agcgggcauc caggagugcc 360
agcaccaguu ccgaggccgg cguuggaacu gcaccaccgu cagcaacagc cuggccaucu 420
uuggcccugu ucuggacaaa gccacccggg agucagccuu uguccaugcc aucgccuccg 480
cuggaguagc uuucgcagug acacgcuccu gugcagaggg aucagcugcu aucugugggu 540
gcagcagccg ccuccagggc uccccaggcg agggcuggaa gugggggcggc uguagugagg 600
acauugaauu uggaggaaug gucucucggg aguuugccga ugccagggag aaccggccgg 660
augcccgcuc ugccaugaac cgucacaaca augaggcugg gcgccaggcc aucgccaguc 720
acaugcaccu caagugcaaa ugccacgggc uaucuggcag cugugaagug aagaccugcu 780
gguggucgca gccggacuuc cgcaccaucg gggauuuccu caaggacaag uaugacagug 840
ccucggagau ggugguagag aaacaccgag agucucgugg cuggguggag acccugaggc 900
cacguuacac guacuucaag gugccgacag aacgcgaccu ggucuacuac gaggccucac 960
ccaacuucug cgaaccuaac cccgaaaccg gcuccuucgg gacgcgugac cgcaccugca 1020
augugagcuc gcauggcaua gaugggugcg accuguugug cugcgggcgc gggcauaacg 1080
cgcgcacuga gcgacggagg gagaaaugcc acuguguuuu ccauuggugc ugcuacguca 1140
gcugccagga gugcacacgu gucuaugacg ugcacaccug caaguaggag agcuccuaac 1200
acgggagcag gguucauucc gaggggcaag guuccuaccu gggggcgggg uuccuacuug 1260
gaggggucuc uuacuugggg acucgguucu uacuugaggg cggagauccu accugugagg 1320
gucucauacc uaaggacccg guuucugccu ucagccuggg cuccuauuug ggaucugggu 1380
uccuuuuuag gggagaagcu ccugucuggg auacggguuu cugcccgagg gugggggcucc 1440
acuuggggau ggaauuccaa uuugggccgg aaguccuacc ucaauggcuu ggacuccucu 1500
cuugacccga cagggcucaa auggagacag guaagcuacu cccucaacua ggugggguuc 1560
gugcggaugg gugggagggg agagauuagg gucccuccuc ccagaggcac ugcucuaucu 1620
agauacauga gagggugcuu cagggugggc ccuauuuggg cuugaggauc ccguggggggc 1680
ggggcuucac cccgacuggg uggaacuuuu ggagaccccc uuccacuggg gcaaggcuuc 1740
acugaagacu caugggaugg agcuccacgg aaggaggagu uccugagcga gccugggcuc 1800
ugagcaggcc auccagcucc caucuggccc cuuuccaguc cuggguguaag guucaaccug 1860
caagccucau cugcgcagag caggaucucc uggcagaaug aggcauggag aagaacucag 1920
gggugauacc aagaccuaac aaaccccgug ccugggguacc ucuuuuaaag cucugcaccc 1980
cuucuucaag ggcuuuccua gucuccuugg cagagcuuuc cugaggaaga uuugcagucc 2040
cccagaguuc aagugaacac ccauagaaca gaacagacuc uauccugagu agagaggguu 2100
cucuaggaau cucuaugggg acugcuagga aggauccugg gcaugacagc cucguaugau 2160
agccugcauc cgcucugaca cuuaauacuc agaucucccg ggaaacccag cucauccggu 2220
ccgugauguc caugccccaa augccucaga gauguugccu cacuuugagu uguaugaacu 2280

-continued

```
ucggagacau ggggacacag ucaagccgca gagccagggu uguuucagga cccaucugau   2340

uccccagagc cugcuguuga ggcaaugguc accagauccg uuggccacca cccugucccg   2400

agcuucucua gugucugucu ggccuggaag ugaggugcua cauacagccc aucugccaca   2460

agagcuuccu gauugguacc acugugaacc gucccucccc cuccagacag gggaggggau   2520

guggccauac aggagugugc ccggagagcg cggaaagagg aagagaggcu gcacacgcgu   2580

ggugacugac ugucuucugc cuggaacuuu gcguucgcgc uuguaacuuu auuuucaaug   2640

cugcuauauc cacccaccac uggauuuaga caaaagugau uuucuuuuuu uuuuuuucuu   2700

uucuuucuau gaaagaaauu auuuuaguuu auaguauguu uguuucaaau aauggggaaa   2760

guaaaaagag agaaaaaaaa aaaaaaaaaa aaaaaaaaaa aaaaaaaaaa              2810
```

<210> SEQ ID NO 263
<211> LENGTH: 2948
<212> TYPE: RNA
<213> ORGANISM: Homo sapiens

<400> SEQUENCE: 263

```
cgcaccggag guccacacug ccgcguggac uccagcgaug gcgcugcgcu aggcuagcgg     60

gugccaggau cccucucugc guccugugcg cgggaagagc ucuggagaac cagaguugca    120

uucuggaguu gaagacucau ggcacagacu guuagagaau gcucauuggc acuucuuuuu    180

uuguucaugu ggcugcugau uaaagcaaau auagaugugu gcaagcuugg cacugugacc    240

guccagccug ccccugugau ucccucuugg ucagcugcca auauuuccug cuccuugaau    300

cccaagcaag gcuguucaca uuaucccagu ucuaacgaau uaauccucuu aaaguuuguc    360

aaugaugucc uuguugaaaa ucuccauggc aagaaagucc augaccacac uggucacucc    420

uccacuuuuc aagucaccaa ccugucccuu gguaugaccu uguuugucug caagcuaaac    480

uguagcaacu cucaaaagaa gccaccaguc ccaguaugug ggguggagau cucaguuggu    540

guugcuccag agccaccuca aaacauauca ugugucccagg aaggagaaaa uggaacugug    600

gccuguuccu ggaacucugg aaaaguuacu uaucugaaaa ccaauuacac uuuacaguua    660

aguggaccaa acaaucugac cugucagaaa caauguuuuu cugacaaucg ucagaauugc    720

aaucgccugg aucuugggau caaucuaagc ccugauuuag cugaauccag guucauaguc    780

cguguuacug ccaucaacga ucuuggaaau ucuucuucac uuccgcauac guucacguuc    840

uuggacauag ugauccucu uccuccgugg gacaucagaa ucaacuuucu aaaugcuucu    900

gggagcagag guacacugca gugggaagau gaggggcaag ugguacucaa ucaacucaga    960

uaucagccuc uuaacagcac guccuggaac augguucaaug cuacaaaugc caaaggaaaa   1020

uaugaccugc gagaucugag accguuuaca gaauaugaau uucaaaucuc cucuaagcua   1080

caucucucug gaggaaguug gaguaauugg agugagucac ugagaacacg aacaccagag   1140

gaagagccug uugggauauu agacaucugg uacaugaaac aagacaucga cuaugacaga   1200

cagcagaucu cucuuuucug gaagagucug aauccaucag aggcaagggg gaagauccuc   1260

cacuaucagg ugacguuaca agaggugaca aagaaaacaa cacugcagaa uacuacaaga   1320

cacaccuccu ggaccagggu cauccccga acuggggcuu ggacggcauc agugucugca   1380

gccaacucaa aaggcgcuuc ugcacccacu cacauuaaca uaguggaccu auguggcacu   1440

ggguugcugg cuccucacca ggucucugca aagucggaga acauggacaa cauucuagug   1500

accuggcagc cuccuaagaa agcugauucu gcuguucggg aguacauagu ggaauggaga   1560

gcucuccaac cagggagcau cacgaaguuu cccccacacu ggcugcggau ccccccggac   1620
```

aacaugucug cucugauuuc agagaacaua aagcccuaua ucuguuauga aaucagggug 1680
caugcacugu cagagagcca aggagggugc agcucccaucc ggggugacuc caagcacaaa 1740
gcaccaguga guggcccuca cauuacugcc aucacagaga aaaaggaacg ccuuuucauu 1800
uccuggaccc acauuccauu cccggagcaa aggggcugca ucccuccauua cagaauauac 1860 uggaaagaac gagacucgac agcacaaccu gagcucugcg aaauucagua ccgacgcucu 1920
caaaacucac auccaauaag cagccuacag cccaggguga cauauguccu auggaugaca 1980
gcugugacag cugcugguga aaguccccaa ggaaaugaaa gggaauuuug uccacagggc 2040
aaagccaacu ggaaagcauu cgugauauca agcauuugca ucgcuaucau cacggugggc 2100
acguucucaa uucguuacuu ccggcaaaag gcauuuacuc uccugucuac ucucaaaccu 2160
caaugguaua gcagaaccau uccagaucca gcaaacagca cuuggguaaa gaaguauccc 2220
auucuggagg agaagaucca gcuaccuacg gauaaucucc ugauggcaug gcccacuccu 2280
gaagagccug agccccugau cauccaugaa guccucuacc acaugauccc aguugucaga 2340
caaccauauu acuucaaaag aggccaagga uuccaaggcu acucuaccuc caagcaagau 2400
gcaauguaua uugccaaucc acaagcuaca ggaacucuca cagcugagac cagacaacua 2460
gugaaccuau acaaggugcu agaaagcaga gacccugacu caaaacuggc caaccugacc 2520
agccccuuga cagucacccc agugaacuac cuuccuagcc augaaggcua uuuacccucc 2580
aacauagaag aucugucacc acaugaggcu gacccaacug auucuuuuga ccuggagcau 2640
caacauauuu cucuuuccau uuuugcauca aguucucucc gcccacucau cuucggugguu 2700 gagcggcuga cucuagaucg guuaaagaug ggcuaugacu cccucaugag uaaugaggcu 2760
ugauacuaga aagccaacgu accucauuuu aucugcccag uuccuacucc aaaggucugu 2820
gacagugaag acaagccagc ugucucugga uaaaguuagc uucaccauag guacuuaagu 2880
cuuauggaua agguggcaau acaccaacac ugauaucaua uagaaaggac cccaagauag 2940
ucaugcuc 2948

<210> SEQ ID NO 264
<211> LENGTH: 2487
<212> TYPE: RNA
<213> ORGANISM: Homo sapiens

<400> SEQUENCE: 264
ggcacgaguu cacccucugc augcguuccc cuccccccuc uccagcaaac acggcgcgcc 60
aguccaaagc ggacucagug gccucgggga cgggagcaug ccaccuccug uggugacguc 120
acuuggggua gaacccuuag acacuacaug gggggggggg guacagaacu cccgagccag 180
gacagucacu cacucuucag gcgguggggc ugggccagac aguaccgccc ccaccgcgcc 240
cgccucgcac acccucggaa gcgcaggcuc gcagcgcggc gcuggggugg ggggiuugcgc 300 cccagaacuu cggccuccag uccccagccc gcugcaccuc cuuacccucu agaggccccc 360
ucccccuuac ccucuagagg caccaggagu ugucgcaagg ggcccuuggg aaauucccug 420
gaccccugug ccaggaggug cccgguucgc ccgcucccca ucccaccccc cgagggcggu 480
gcccgggggc gcugccccau ggagcgggga ggcgggcgcc gucugcugcg ggagcuguga 540
ccugaguagg agcugugugu cgcagccgcc ccaccccugc cgaucaugcg ccggcgaccc 600
ugguucgcca gucccacugg gcugugagcc ccccacuccu ggccugucac ggcccgcgcg 660
ccaugggcag cgcccacccu cgccccuggc ugcggcuccc acaagggccc cagccgcggc 720
cugaguucug ggcgcuccug uucuuccuac ugcugcuggc ugccgcugug cccaggucag 780
cacccaacga cauccugggc cuccgccuac ccccagagcc cgugcucaac gccaacacag 840
ugugccugac auugcccggc cugagccggc ggcagaugga ggugugugug cgucacccug 900
acguggccgc cucugcuauc cagggcaucc agaucgccau ccaugagugc cagcaucagu 960
uccgggacca gcgcuggaac ugcuccagcc uggagacucg gaacaaaguc cccuacgaga 1020
gccccaucuu cagccgaggu uuucgagaga gugcuuucgc cuacgccaua gcagcugccg 1080 gggugggugca cgcagugucc aacgcgugcg cucuggguaa acugaaggcu ugcgguugcg 1140
acgccuccag acguggggac gaagaagcuu uccgucggaa gcugcaccgc uugcagcugg 1200
acgcgcugca gcgcggaaag ggcuugagcc acggggaccc ugaacacccg gccauacuuc 1260
cugccagccc aggucugcag gacuccuggg aguggggugg cugcaguccg gaugugggcu 1320
ucggagaacg cuucucuaag gacuuucugg acucccgaga gccucacaga gacauccaug 1380
cucgaaugag acuccacaac aaccgugugg gccggcaggc ggugauggag aacaugcggc 1440
guaagugcaa augccacggc accucaggca gcugccagcu caagaccugc uggcagguga 1500
cgccugaguu ccgcacagua ggggcgcugc ugcgcaaccg cuuccaccgc gccacgcuca 1560
uccggccgca caaccgcaac gguggccagc uggagcccgg ccccgcggga gcacccucgc 1620
cagcaccggg cacuccaggg cugcgccgca gggccagcca cuccgaccug gucuacuuug 1680
agaaaucucc cgacuucugu gagcgcgagc cgcgccugga cucggcaggc acugugggcc 1740
gccugugcaa uaagagcagc acgggucccg auggcugcgg cagcaugugc uguggccgcg 1800
gccacaacau ucugcgccag acgcgcagcg agcgcugcca cugccgguuc cacugguguc 1860
gcuucguggu cugcgaagaa ugccgcauca ccgaguggu cagcgucugc aagugagcag 1920
acccaagcuc cucugggucu caagaauggu uguccucuug gugccuggcu ucugccgcua 1980
gcggaucuga gccaggcagc aagcagcagc cuuggcuccu gagagaggug guuggcucuu 2040
acagccccga gggucuacaa ucaccagaca guccagaucu gauugacauu ccuccgcuca 2100
ccucuguagg uuccccucuu ucuguuccua gcucagacag cugggggguga uaguggagac 2160 uguuccacac ccuaggacag gucaccaaag cagcccagcc uggcaugccu accuccuguc 2220
aucucuucuu cccuucccca ggagugauag gcaaugcacu gaagcugaug ggcaccgggg 2280
aagaaaacua aaaggcagaa auggccguca ucgggcugaa gugacucuaa gggcuccaga 2340
ccucugcucc ugucuuucac uuaacagaua uuuauuuuug cgcucucuuu gagacacucu 2400
cuggggaaaa agaagcuccg gagucuacag gcugauuaag ggacauggac aauaaaccag 2460
uaaacacaca aaaaaaaaaa aaaaaaa 2487

<210> SEQ ID NO 265
<211> LENGTH: 2093
<212> TYPE: RNA
<213> ORGANISM: Homo sapiens

<400> SEQUENCE: 265
gaauuccggg ccgcuugcac uuggcgacua gucugcggcg gacgugacgc caaggccacg 60
ggcagcgcgg guccccuguc agaggugucc cucgcgcagg aaugggcccg caggcggcag 120
cuggcaggau gauucugcug guggguccuga ugcugucugc gaaggucggg aguggagcuu 180
ugacgagcac cgaggauccu gagccucccu cggugccugu accgacgaau guucuaauua 240
agucuuauaa cuugaacccu gucguaugcu gggaauacca gaacauguca cagacuccua 300
uuuuuacugu acagguaaag guguauucgg guuccuggac ugauuccugc accaacauuu 360
cugaucauug uuguaauauc uaugaacaaa uuauguaucc ugauguaucu gccugggcca 420
gaguuaaagc uaagguugga caaaaagaau cugacuaugc acggucaaaa gaguuccuua 480
ugugccuaaa gggaaagguc gggcccccug gccuggagau caggaggaag aaggaagaac 540
agcucuccgu ccucguauuu cacccugaag ucguugugaa uggagagagc cagggaacca 600
uguuugguga cgggagcacc uguuacacau ucgacuauac uguguaugug gagcauaacc 660
ggagugggga gauccuacau acgaaacaua cggucgaaaa agaagagugu aaugagacuc 720
ugugugaguu aaacaucuca guauccacac uggauuccag auauuguauu ucaguagacg 780
gaaucucauc uuucuggcaa guuagaacag aaaaaucgaa agacgucugu aucccuccuu 840
uccaugauga cagaaaggau ucaauuugga uucuggugu ugcuccucuu accgucuuua 900
caguaguuau ccugguauuu gcguauuggu auacuaagaa gaauucauuc aagagaaaaa 960 gcauaaauguu accuaagucc uugcucucug ugguaaaaag ugccacguua gagacaaaac 1020
cugaaucgaa guauucacuu gucacaccgc accagccagc uguccuagag agugagacgg 1080
ugaucuguga agagccccug uccacaguga cagcuccaga cagccccgaa gcagcagaac 1140
aggaagaacu uucaaaagaa acaaaggcuc uggaggcugg aggaagcacg ucugccauga 1200
ccccagacag cccuccaacu ccgacacaaa gacgcagcuu uucccuguua aguaguaacc 1260
agucaggccc uuguagccuc accgccuauc acucccgaaa cggcucugac aguggccucg 1320
ugggaucggg cagcuccaua ucggacuugg aaucucuccc aaacaacaac ucagaaacaa 1380
agauggcaga gcacgacccu ccacccguga gaaaggcccc cauggccucc gguuaugaca 1440
aaccgcacau guuggugggac gugcuugugg auguuggggg gaaggagucu cucaugggggu 1500 auagacucac aggagaggcc caggagcugu ccuaaggucu cccgaggccu gcugguggua 1560
aagaaacuga ccuuuuaggc aguuuuucug cauugauuuc augaaagaag cuauacauua 1620
gcuaauacua accacauaga auaucagacu uagauacgug aauaaggauc cugugggcac 1680
ugcugggucc acucugcaaa ugccaagacu aucaaaggaa cguauugucg cuucuggcuc 1740
cuucccaggu gggcuagcau cugugaguuu gccucggcua gccuugcuuc cuacagccgc 1800
cacugcuccu ccacccugau caucucacag gacagggugg accggguuuu uuuuuuuuuu 1860
ucacacaccu uuguauaugu aaguucaugu auauaauaug uuuacauguu ucacuuugaa 1920
cugaaagcua cucaaagcca gccguaaguc uaugguagaa ugugauggaa cauguuggug 1980
gaagcuugua caauagaaca cauuggugggg agcuuguaca uacuuuuuua uggagcauua 2040
cuuacgauuu uuuaaguaaa auguuuugaa accaaaaaaa aaaaaaggaa uuc 2093

<210> SEQ ID NO 266
<211> LENGTH: 756
<212> TYPE: RNA
<213> ORGANISM: Homo sapiens

<400> SEQUENCE: 266
augagacucc acagccucau ccugcucucc uuccuucucc uggcuacuca ggcguucuca 60
gaaaagguca gaaagagagc caagaacgca ccacacagca cagcggagga gggggguagag 120 gguucagcuc ccucguuagg gaaggcccag aauaagcaga gaagcaggac aucuaaaucu 180
cugacgcaug gcaaguuugu caccaaagac caagccacau gcagaugggc ugugacugag 240
gaggagcagg gcaucagccu gaagguccag ugcacacaag ccgaucagga guuuucuugu 300
guuuuugcug gugacccaac ugacugccuu aaacacgaca aagaccagau cuacuggaaa 360

```
cagguugccc gcacgcugcg caaacagaaa aauaucugca ggaacgccaa gagugucuug    420

aagaccagag ugugcagaaa gagauuucca gagucuaacc ucaagcuggu gaaccccaac    480

gcacguggaa acacgaagcc caggaaggag aaagcagagg ucuccgcaag ggagcacaac    540

aagguccaag aagcugucuc cacggagcca aacaggguca aagaagacau cacacucaau    600

ccagcugcga cccagaccau ggccauuaga gauccagagu gucuagagga uccagaugug    660

cucaaccaga ggaagaccgc ccuggaguuc uguggggaau cuuggagcuc cauuugcaca    720

uucuuccuca acauguuaca ggcgacauca ugcuaa                              756
```

<210> SEQ ID NO 267
<211> LENGTH: 181
<212> TYPE: RNA
<213> ORGANISM: Homo sapiens

<400> SEQUENCE: 267

```
aauucgucga caugcgccgu uccagugcau ggugugccaa cgcagcuucu cccgcuccga     60

ccaccucgcg cugcacauga agcgccacca gaacugagcg agcgagcgcu gccccacccg    120

ccugacgccu ugcaguccgc ucugccaucc uuuaaaccgc agaccuaacu ucauaaaaag    180

a                                                                    181
```

<210> SEQ ID NO 268
<211> LENGTH: 2056
<212> TYPE: RNA
<213> ORGANISM: Homo sapiens
<220> FEATURE:
<221> NAME/KEY: misc_feature
<222> LOCATION: (1942)..(1943)
<223> OTHER INFORMATION: n is a, c, g, or u

<400> SEQUENCE: 268

```
gcuaaacuau cccgcaaaga uuuuucuuuc cucccuaaac ccuccuuuuu gcucuccuuu     60

ucuauacccu uaacugcaaa caaaccauua aacgaccccu cuccugggcc uccgacggca    120

ggaguccgcg gaccucccag gccgacagcc cucccucuac ccgcgagguu ccgggccggg    180

cgagagggcg cgagcacagc cgaggacaug gaggugacug cggaccagcc gcgcugggug    240

agccaccauc accccgcggu ccucaacggu cagcacccag acacgcacca cccgggccuc    300

ggccauucgu acauggaagc ucaguauccg cugacggaag agguggacgu acuuuuuaac    360

aucgaugguc aaggcaacca cgucccgucc uacuacggaa acuccgucag ggcuacggug    420

cagagguauc cuccgaccca ccacgggagc cagguaugcc gcccgccucu gcugcacgga    480

ucucugcccu ggcuggaugg cggcaaagcc cugagcagcc accacaccgc cucgcccugg    540

aaccucagcc ccuucuccaa gacguccauc caccacggcu cuccggggcc ucuguccguu    600

uacccuccgg cuucauccuc uucucuggcg gccggccacu ccaguccuca ucucuucacc    660

uucccgccca ccccgccgaa agacgucucc ccagacccgu cgcuguccac cccgggaucc    720

gccgggucgg ccaggcaaga ugagaaagag ugccucaagu aucaggugca gcugccagau    780

agcaugaagc uggagacguc ucacucucga ggcagcauga ccacccuggg uggggccuca    840

uccucagccc accaccccau uaccaccuau ccgcccuaug ugcccgagua cagcucugga    900

cucuucccac ccagcagccu gcugggagga uccccuaccg gguucggaug uaagucgagg    960

cccaaggcac gauccagcac agaaggcagg gaguguguga acugcggggc aaccucuacc   1020

ccacuguggc ggcgagaugg uaccgggcac uaccuuugca augccugcgg acucuaccau   1080

aaaaugaaug ggcagaaccg gccccuuauc aagcccaagc gaaggcuguc ggcagcaagg   1140
```

agagcaggga cauccugcgc gaacugucag accaccacca ccacccucug gaggaggaac 1200
gcuaaugggg acccggucug caaugccugu gggcuguacu acaagcuuca uaauauuaac 1260
agaccccuga cuaugaagaa agaaggcauc cagacccgaa accggaagau gucuagcaaa 1320
ucgaaaaagu gcaaaaaggu gcaugacgcg cuggaggacu uccccaagag cagcuccuuc 1380
aacccggccg cucucuccag acacauguca ucccugagcc acaucucucc cuucagccac 1440
uccagccaca ugcugaccac accgacgccc augcauccgc ccuccggccu cuccuucgga 1500
ccucaccacc cuuccagcau ggucaccgcc augggguuaga gaggcagagc ccugcuccac 1560
augcgugagg agucuccaag ugugcgaaga guuccuccga ccccuucuac uugcguuuuu 1620
cgcaggagca guaucaugaa gcccgaaagc gacagaucug uguuuuugaa ggcagaaagc 1680
aaaauguuug cuucuuuuuu caaaggagcu cgagguggug ucugcauucc aaccacugaa 1740
uccggauccc auuugugaau aagccauuca gacucauauu cccuauuuaa cagggucucu 1800
agugcuguga aaaaaauauu gcugaacauu gcauauaacu uauauuguaa gaaauacugu 1860
acauuugagg aagacuuuau uguaccugga uagcuguaag aaaggcauga aggacgccaa 1920
gaguuuuaag gaauauaggg gnnuuaaagu auggagauac agaagaaacc acuaagucug 1980
auguccaaau gggcacacug ucaguuuugu uucccuucag uuguuugaug cauuuaaaaa 2040
aaaaaaaaag aaagaa 2056

<210> SEQ ID NO 269
<211> LENGTH: 1508
<212> TYPE: RNA
<213> ORGANISM: Homo sapiens

<400> SEQUENCE: 269
caaccaccuc cuaccugccu gcccaaagcu ccagggcugg agcacggaga ccugucaggg 60
auggauuuug cccacaugua ccaaguguac aaguccaggc ggggaauaaa acggagcgaa 120
gacagcaagg aaacuuacaa acugccgcac cggcugauug agaaaaagag acgugaccgg 180
auuaacgagu gcauugccca gcugaaggau cuccuacccg aacaucucaa acuuacuacu 240
uugggucacu uggaaaaagc agugguucug gagcuuacgu ugaagcacgu gaaagcauug 300
acaaaucuaa uugaucagca gcagcagaaa aucauugccc ugcagagcgg uuuacaagcu 360
ggugauuugu cgggaagaaa ucucgaggca gggcaagaaa uguucugcuc agguuuccag 420
acuugugccc gugagguacu ucaguaccug gcgaagcaug agaacacucg ggaccugaaa 480
ucuucccagc ucgucacuca ucuccaucgu gugguucucgg agcugcugca ggguggugcu 540
uccaggaaac cauuggacuc ggcucccaaa gccgucgacu ugaaagagaa gcccagcuuc 600
cuagccaagg gaucagaagg cccagggaaa aacugugugc cagucaucca gcggacuuuu 660
gcucccucgg gugggggagca gagcggcagu gacacggaca cagacagugg cuauggaggu 720
gaauuggaga aaggggacuu gcgcagugaa cagccguacu ucaaaagcga ccauggacgc 780
agguucgccg ugggagaacg ugucagcaca auuaagcaag aauccgaaga gcccccccacc 840 acaaagagcc gaaugcagcu cucagaagag gaaggccacu ucgcgggcag ugaucugaug 900
gguuccccau uucuugggcc acacccacau cagccuccuu uuugccuucc cuucuaucuc 960
aucccaccau cggccacugc cuaccugccu augcuggaga aaugcuggua ccccaccucu 1020
gugccagugu uauacccagg ccucaacacc ucagcugcag cccucuccag cuucaugaac 1080
ccagacaaga uaccgacucc cuugcuucug ccccagagac ucccuucucc uuuggcacau 1140

```
ucgucccuug acucuucggc cuugcuccag gcuuugaagc agaucccucc uuuaaacuua   1200

gaaaccaaag acuaaacucu ggagggaucu ccugcugccu ugcuuucuuu ccucccuaau   1260

uccaaaaacc acgaagguuu cccugagugc agagagauca gcccacccug cagacccaca   1320

gagaagauuc agagugugug ugagagugag ugagugugcg ugcgugcgug cuuguaugua   1380

uguuuguaua uguaggacaa uaaguuccuu cugacacaag ggagacacga gaaggauagc   1440

cugacaucag augacagacu ggaggacugu agcacaucuc ugggcguuuc ccuacccaga   1500

gaagagcc                                                            1508
```

<210> SEQ ID NO 270
<211> LENGTH: 9471
<212> TYPE: RNA
<213> ORGANISM: Homo sapiens
<220> FEATURE:
<221> NAME/KEY: misc_feature
<222> LOCATION: (121)..(121)
<223> OTHER INFORMATION: n is a, c, g, or u

<400> SEQUENCE: 270

```
agucaccgac guuguauaac gacggccagu gaauuguaau acgacucacu auagggcgaa     60

uuggguaccg gccccccccu cgaggucgac gguaucgaua agcuugauau cgaauucucg    120

nccgcgugcg ggucuggucg gggcggagcg aaggccgcgg guggccgugg ucgguccucc    180

gcggcuaagg agccgagggc uccgacgcgg gcugcgcccg gugagcggcg gccagagcua    240

acuugcgcug acuggaccag cugaggagcg gcccggcggg gcgacugcga gcuucaccga    300

gaggcuucuc cgcccugguc cgcagucccg acggccgggc ggaccauggc guccucggcu    360

caccugguca ccaucaagcg gagcggcgau gacggcgcac acuucccgcu gagccucagc    420

uccugccugu uuggaaggag uauugaaugu gacauucgua uccagcugcc uguagugucu    480

caaagacauu gcccaauugu aguccaagag caagaggcga uauuauauaa uuucaguucu    540

accaauccaa cucaaguaaa cgggguuacu auagaugagc cugugaggcu gagacaugga    600

gacauaauaa ccaucauuga ccgcuccuuu agguaugaag auggaaauca ugaggaugga    660

agcaaaccaa cagaauuucc aggaaagucc cuuggaaagg aaccaucaag gcgagccuca    720

agagauagcu ucugugcuga cccugauggg gaaggucaag auaccaaagc uucaaaaaug    780

acugcuucaa gaagaucuuu uguguaugcc aagggccuuu cugcagauag cccugccuca    840

gauggcucaa agaacagugu uagccaagac ucaucagggc auguagaaca gcacacuggc    900

agaaacauag uagagcccac uucuggggga ucucuuuuaa gaaguccagg ucuacaggga    960

gcaguuacag ggaaccgaag ucuucuuccu acacagagcc uuagcaauag caacgaaaag   1020

gaaucucccu uugagaaacu uuaucaauca augaaggaag aguuggaugu aaaaucccag   1080

aaaucuugua ggaaaucaga accccaaccu gaccgugcag cagaggaauc gcgggagaca   1140

cagcuauugg ugucaggcag ggcaagagca aagucuagug gaagcacccc uguuacugca   1200

gccucuucac ccaaaguagg aaagaucugg acugagagau ggcgcggugg aaauggugccu  1260

guccagacuu ccacagagac agcuaaaaug aagaccccug ugcggcauuc acagcaacuu   1320

aaggaugaag acucucgugu uacuggcaga cgacauucug ugaaucugga ugaaggugga   1380

agugcccagg caguccauaa aacagucacu ccugggaaac uggcgacuag aaaccaaacu   1440

ccgguggagg cuggggaugu uggcagcccc gcugauacac cagaacauuc cucuuccccc   1500

cagagaagua uuccugcaaa gguagaggcu ccaucugcag agacacaaaa ucggcucucu   1560

uuaacucagc gccuuguucc aggugaaaag aaaacuccca aggguuccuu cagcaagccu   1620
```

-continued gagaaacugg ccacagccgc cgaacagacu ugcucuggcc uaccuggucu uaguuccguu 1680
gauaucagca acuuugguga uuccauuaac aagagugagg gaaugccuau gaagagaaga 1740
cguguauccu uugguggaca ucuaagaccu gaauuauuug augaaaacuu gccuccuaau 1800
acaccacuga aaagaggaga aacgccaacc aagaggaagu cucuuggcac ucacagccca 1860
gcuguccuca agacaaucau caaggaacgg ccccagucuc cagggaaaca agagucuccu 1920
gggauaacgc caccgaggac aaaugaucaa agacgcagau caggcaggac uuccagugga 1980
agcaauuucu uaugugagac agacauuccc aagaaagcag gcaggaagag cgguaaccug 2040
ccugcgaaga gagcauccau cagccggagu cagcauggca uucuacagau gauuugcucc 2100
aaaaggcgaa guggagcuuc ugaagccaac uugauuguug caaaaucaug ggcugauguu 2160
guaaaacuug gcgugaaaca aacacaaacg aaaguugcga aacaugaccc uccaaagcag 2220
acgagcaaga gacaaagaag acccagcacu ccaaagaaac ccacaagcaa ucuucacaau 2280
caauuuacua caggccaugc aaacucuccc uguaccauug uaguagguag agcgcagauu 2340
gaaaaaguaa gugugccugc ccgacccuac aaaaugcuga auaacuugau gcuaaaccga 2400
aaaguggacu ucagugaaga ucugucagga cuaacugaaa uguucaagac uccagugaag 2460
gagaagcagc agcagaugag ugauacaggc uccguacuuu ccaauucagc gaauuugucu 2520
gaaagacaau ugcaaguaac uaauucagga gacauaccug agcccaucac cacagagauu 2580
uugggagaaa aagugcuauc caguacucgg aaugcagcaa agcagcaguc ugauagauau 2640
ucugcaaguc cuaccuuaag acggcggagc aucaaacaug aaaacacagu gcaaacuccu 2700
aagaaugucc auaacauuac ugaccuugag aagaagacuc cggucucuga gacagagccc 2760
cugaagacug caucgagugu gagcaaguua agaagaucua gagagcucag acauacccuu 2820
guggaaacua ugaaugaaaa aacagaagca guccuugcug agaacaccac agcaagacau 2880
uuaaggggga cauuucgaga acaaaaagua gaucaacagg ugcaggacaa ugaaaacgcu 2940
ccucaaagau gcaaggaaag uggugaauua agugaagguu cagaaaagac aucagcuagg 3000
agaucaagug ccaggaagca gaagccgaca aaagacuuac uaggaaguca gauggucacc 3060
caaacagcag acuaugcuga ggaacuacuu agucaaggac aaggaaccau acaaaaccua 3120
gaggaaucca ugcacaugca aaacacauca auaagugagg aucaaggaau uacagaaaag 3180
aaagugaaca uaauaguaua ugcaaccaaa gagaagcacu cgccaaagac cccuggcaaa 3240
aaggcacaac cucuagaagg gccagcuggu cucaaggaac acuuugaaac accaaacccc 3300
aaagauaaac cuauaacgga agacagaacu agaguccuuu gcaaaucacc acaagucaca 3360
acagagaaua ucacaacaaa cacaaagcca cagacuagca caucugggaa gaaaguagac 3420
augaaggaag aaagcucugc cuugacaaaa cguauacaua ugccagggga auccaggcau 3480
aaucccaaaa uuuuaaaacu ugagugugag gauaucaaag cuuugaagca aucugaaaau 3540
gaaaugcuga ccucaacagu aaauggaagc aagaggacuu uaggaaaauc uaaaaaaaag 3600
gcucagcccc uggaagaccu gacuuguuuc caggaacucu uuauaucacc aguuccuacu 3660
aacauaauca aaaaaauucc cagcaaaucu ccacacacac aaccagucag aaccccagcg 3720
agcacaaaga gacucuccaa gacaggucuc aguaaaagugg augugagaca agaaccuuca 3780
acacuuggga aaagaacgaa gucaccaggc agagccccag gcacaccagc accagugcag 3840
gaagaaaaug acugcacagc cuacauggaa acuccaaagc agaaacugga gucuauagaa 3900
aauuuaacag ggcuuaggaa acaguccaga acaccuaaag acaucacugg uuuccaggau 3960

-continued agu uuccaaa uaccagauca ugcuaauggc ccauuagugg uugucaaaac caaaaaaaug 4020
uucuuuaauu cuccacaacc agaaagugcc auaacccgaa agagcagaga gagacagucu 4080
agggcaagua uaaguaaaau agauguuaaa gaagaacuuu uagaaucaga ggaacaccua 4140
caauuaggag aagguguaga cacauuucag guauccacca acaaagucau uagaucaucu 4200
aggaaaccug caaagcguaa acuggauuca acagcuggua ugccuaacag caagaggaug 4260
cgcuguucuu caaaggauaa cacaccaugc cuagaagacc ugaauggcuu ccaagagcuc 4320
uuccaaaugc caggcuaugc uaaugacucu uugaccacug gaaucucaac aaugcuugcu 4380
agaucaccac aauuaggacc aguuagaacc caaaucaaca aaaagagucu gcccaagauc 4440
aucuugagaa aaauggaugu gacagaagaa auuucagguc ucuggaagca gucacugggc 4500
agaguccaca ccacacaaga gcaggaggau aaugcaauca aagcaauuau ggagauucca 4560
aaggaaacac ugcagacugc agcagaugga acuaggcuua ccagacagcc acaaacaccu 4620
aaggaaaaag uucaaccgcu ggaagaucac agugucuucc aagaacucuu ccaaacauca 4680
cgcuacuguu cugauccauu aauugguaac aaacaaacaa gaauguccuu gagaucucca 4740
caaccaggau uuguuagaac uccacgaacc ucaaagagac uggcuaagac aaguguuggg 4800
aauauugcug ugagagaaaa gaucucucca gugagucugc cacagugugc uacaggggag 4860
guuguacaca uacccauagg gccagaagau gacacagaga acaaaggugu gaaggaaucc 4920
acaccucaga cacuggacuc aucagcaagu cgaacuguca gcaagaggca gcaaggggca 4980
caugaggaaa ggccucaguu cucaggagac uuauuucauc cccaagagcu cuuucaaaca 5040
ccagccagug gcaaagaccc aguaacuguu gaugaaacua caaaaauagc ucugcagucu 5100
ccacaaccag gacauaucau aaacccagca agcaugaaga gacaguccaa caugagucuc 5160
aggaaagaca ugagagaauu uuccauacuu gaaaaacaaa cacagucacg aggcagagac 5220
gcaggcacac cagcaccaau gcaggaagaa aauggcacca cagccauuau ggaaacacca 5280
aagcagaaac uggauuucau aggaaauuca acaggacaua agaggaggcc ucggacaccc 5340
aaaaacaggg cucagccccu agaagaccug gauggcuucc aagaacucuu ucaaacacca 5400
gcuggugcca gugacccugu gaguguugaa gaaagugcaa agauaucuuu ggcaucuuca 5460
caagcagaac cagucagaac ccccagcaagu acaaagagac gcuccaagac aggucucagu 5520
aaaguggaug ugagacaaga accuucaaca cuugggaaaa gaaugaaguc acuaggcaga 5580
gccccaggca caccagcacc agugcaggaa gaaaaugaca gcacagccuu cauggaaacu 5640
ccaaagcaga aacuggauuu cacaggaaau ucaucaggac auaagaggag gccacagaca 5700
ccuaagauca gggcucagcc ccuagaagac cuggauggcu uccaagaacu cuuccaaaca 5760
ccagcuggug ccaaugacuc agugacuguu gaggaaagug uaaagauguc uuuggaaucu 5820
ucacaagcag aaccagucaa aaccccggca agcacaaaga gacucuccaa gacaggucuc 5880
aguaaggugg augugagaga agacccuuca auacuugaga aaaaaacaaa gucaccaggc 5940
acaccagcac cagugcagga agaaaaugac ugcacagccu ucauggaaac uccaaagcag 6000
aaacuggauu ucacaggaaa uucaucagga cauaagagga ggccacggac accuaagauc 6060
agagcucagc cccuagaaga ccuggauggc uuccaagaac ucuuccaaac accagcuggu 6120
gcuagugacu cagugacugu ugaggaaagu gcaaagaugu cuuuggaauc uucacaagca 6180
aaaccaguca aaaccccggc aagcacaaag agacucucca agacaggucu caguaaggug 6240
gaugugagag aagacccuuc aacacuuggg aaaaaaacaa agucaccagg cagagcccca 6300
ggcacaccag caccagugca ggaagaaaau gacagcacag ccuucaugga aacuccaaag 6360

```
cagaaacugg auuuugcaga gaauucauca gggaguaaga gaaggucacg aacaucuaag   6420
aacaggucuc agccccuaga agaccuggau ggcuuccaag aacucuucca aacaccagcu   6480
ggugccagua acccugugag uguugaagaa agugcaaaga uaucuuugga aucuucacaa   6540
gcagaaccag ucagaacccg ggcaagcaca aagagacuuu ccaagacagg ucucaauaag   6600
auggauguga gagaagggca cucuccgcuc aguaagucaa gcugugcauc acagaaaguc   6660
augcaaaccc ucacacuugg agaagaucau ggcagagaga ccaaagaugg gaagguauug   6720
uuagcucaga aauuggaacc agcaauauau guuacucgug gcaagaggca gcaaagguca   6780
uguaagaaaa ggucccaguc cccagaagac cucucuggug uucaggaggu cuuccaaaca   6840
ucaggccaua acaaggauuc agugacagug gacaaucuug caaaacugcc cagcucgucu   6900
ccaccacuag agccaacaga cacuucagua accucacgga gacaggccag aacuggucug   6960
aggaaaguuc acgugaaaaa ugaacuuuca ggaggcauaa ugcauccaca aauaucaggg   7020
gaaauugugg acuuaccuag agaaccagaa ggugaaggca aagucauuaa aacaaggaag   7080
caaucuguaa aacggaaauu ggacacagaa gucaaugugc cucgcaguaa gaggcaaaga   7140
auuacaagag cagaaaagac ccuagaggau cugccuggcu uccaagagcu cugccaagcu   7200
ccaagcuugg uaauggacuc aguuauuguu gagaaaaccc caaagaugcc cgacaaaucu   7260
ccagaaccug uggauacaac uucagagaca caggcaagaa gaagacucag gagacugguu   7320
guuacugaag agcccauacc acaaagaaag acuacaagag uuguaaggca aaccagaaac   7380
acacagaaag agcccauaag ugacaaucaa gguauggaag aguuuaagga aucuucagua   7440
cagaaacaag acccaagugu aaguuuaacu ggcaggagga accaaccaag gacaguuaag   7500
gagaaaaccc aacccuuaga agaacucacc aguuuccaag aggaaacugc caaaagaaua   7560
ucuuccaaau cuccacaacc ggaagagaag gaaaccuuag cagguuuaaa gaggcagcuc   7620
agaauacaac uaaucaacga ugguguaaaa gaagagccca cagcacagag aaagcaacca   7680
uccagggaaa ccaggaacac acucaaagag ccuguaggug acaguauaaa uguugaagag   7740
guuaagaagu cuacaaagca gaaaauugau ccaguagcaa gugugccugu cagcaagagg   7800
ccacggaggg uacccaagga aaaggcacag gcccuagaau uggcuggucu caaaggacca   7860
auccaaaccc uaggccacac ugaugaauca gcaagugaua aaggacccac acagaugccc   7920
uguaauucuc uacaaccaga gcaaguugac agcuuccaaa gcucaccaag gcgacccagg   7980
acaagacgug ggaaaguaga ggcagaugaa gagccuucag caguaagaaa gacaguauca   8040
acaucaaggc aaacuaugcg aucccgcaag gucccugaaa uugguaacaa ugguacccaa   8100
guuucaaagg ccuccauaaa gcagacauua gauacaguag ccaaaguaac uggcagcagg   8160
aggcagcuaa ggacacauaa aggauggggu ucaacccucu ugaaguuguu aggugacucc   8220
aaagaaauaa cccaaauauc agaucacucu gagaaacuag cacaugacac caguauccuu   8280
aagagcacuc aacagcaaaa gccagacuca guaaaaccuc ugagaacaug cagaagagug   8340
cugagggccu cuaaagaggu ccccaaggaa guguuggugg acaccagaga ccaugcaaca   8400
uuacaaagca aaagcaaccc uuugcugucc ccgaagagga agucugcaag agauggaagc   8460
auugugagaa ccagggcuuu gcgcucuuua gcaccaaagc aggaagcaac agaugagaag   8520
ccuguaccug agaaaaaaag ggcugcuucc agcaagaggu auguaucacc ugagccugug   8580
aagaugaaac accugaaaau cgugucaaac aaacuugaau cuguggaaga gcagguuagc   8640
acuguuauga aaacagaaga aauggaagcc aaaagagaaa auccugucac uccagaucag   8700
```

aacucuaggu accgaaagaa aaccaaugua aaacagccaa ggcccaaguu ugaugcaucu 8760
gcagagaaug ucgggauaaa gaaaaacgag aagacuauga agacugccuc ccaggagaca 8820
gagcugcaga auccagauga uggagccaag aaaucuacau cucggggcca agucaguggg 8880
aaaagaacau gcuugagguc uagaggaacg acugagaugc cccagccuug ugaagcagaa 8940
gagaaaacaa gcaaaccagc ugcagaaauc uugauaaagc cucaggaaga gaaaggaguc 9000
ucuggagagu cugauguuag guguuugagg uccagaaaaa cuagagucgc uuuggacagu 9060
gaaccuaagc caaggguaac ucguggaacc aagaaagaug caaaaacucu gaaggaggau 9120
gaagacauug uaugcaccaa gaaguuaaga acaagaaguu aagaacaaga aguuaccaga 9180
aaagugaaac uauguagcaa agacauuuaa gaaggaaaag uaaauuugac uuagugauaa 9240
guuccagugu gguuuucacc uccaguguaa agaugaacug uaaauacuac ugcuacugcc 9300
ugaguuuaag gaaggaagcu uugagcuuuc cuggucauac ucucuucaga cgccaaugga 9360
ggucaugagg aagaucacca gggaucucag cgcaauuaca guuuaggggu gagcaggcag 9420
aaauguggcc cucuguccua uccaauaaag cucugaaauu cgcugccaaa a 9471

<210> SEQ ID NO 271
<211> LENGTH: 463
<212> TYPE: RNA
<213> ORGANISM: Homo sapiens

<400> SEQUENCE: 271
gacguagagc cccuugcgcc cgguuuccug aucccgcuua cuccucugcg cgccggcagg 60
auggcccaca agcagaucua cuacucagac aaguacuucg augagcacua cgaguaccgg 120
caugucaugu uacccagaga acucucuaaa caaguaccca aaacucaucu gauguccgaa 180
gaggagugga ggagacuugg uguccaacag agucuaggau ggguucauua caugauucau 240
gagccagaac cgcauauucu ucucuuuaga cgaccucuuc caaaagaaca acaaaaauga 300
agugcagcug ggaucaucua aucuuuuuca aauuuaaugu auauguguau auaagguagu 360
auucagugaa uacuugaaaa guguacaaac cuuucaucca uaccugugca ugcgcuguau 420
ucuucacagc aacagagcuc agucaaaugc aacugcaagu agg 463

<210> SEQ ID NO 272
<211> LENGTH: 1280
<212> TYPE: RNA
<213> ORGANISM: Homo sapiens

<400> SEQUENCE: 272
cuacccuaga caaucacggc uuagccggcg cgcggagucg aucgucucgg ucgcuagagc 60
uguccugagc ucgaacgguc cgacgccccc gccgcgccgg uccgugacgc cggggccgac 120
acgaugaagg auuuggggc caagcacuug gcagguggcg aaggggguuca gcuuuucgga 180 uuguugaacu ucuaccugga acaagaacag agauaccaac cucgggaaaa agggcugauc 240
uugauggagg cuaccccgga gaaugauaac acuuugguu caagacugag aaaugccaaa 300
guggaagauu uaagaaguuu aacuaacuuc uuuggaucug gcacugaaac uuucguucug 360
gcugucaaua uuuuggauag auucuuggcc cuuaugaagg ugaaaccgaa acaccugucc 420
ugcauuggcg ucugcugcuu uuugcuggcc gccaggcugg cggaagaaga aggugacguu 480
ccccccacgc acgacgugau ccgcaucagu caguguaaau gcacagcguc ugacauuaaa 540
cgcauggaga aaaucaucuc agagaaacug cacuaugagc uggaagcuac cacugccuua 600
aacuuuuugc acuuguacca cgcgauugua uuuugucaca cuucagaaag gaaggagauu 660

-continued

```
cucagccucg auaaacucga agcgcagcug aaagcuugca acugccgagu ugucuucucc     720

aaagcaagac caucuguauu agcucugugc cuucucaauu uggaaauaga aacgauaaaa     780

uccguggaac ugcuggaaau ucucuugcuu guuaaaaaac auuugaagcu cagcgacacu     840

gaauucuuuu acuggaggga acugguuucu aaaugucuag cagaguauuc uucgccucgc     900

ugcugcaagc cugaucugaa gaagcuggua uggauuguuu cgcgacgcac ugcgcagaac     960

cuccacagca gcuacuacag uguuccugag cugcccacua ucccagaggg ggguugcuuu    1020

gacggaagug aaagugagga cucuggugaa gacaugaguu guggagagga gagucucagc    1080

agcuccccac ccagcgauca ggagugcacc uucuucuuug acuuccaagu ggcucagaca    1140

cugugcuuuc caccauagag gaaucugaca uuguucugug ucagggaauu uauaagugug    1200

uguaccuagg uuucaaagca auaaacuugg ggguugaaua ggguaguuuu ccuagguuuc    1260

cagcccccg ucuagucagg                                                 1280


<210> SEQ ID NO 273
<211> LENGTH: 291
<212> TYPE: RNA
<213> ORGANISM: Homo sapiens

<400> SEQUENCE: 273

aacuaccuug ggcagguucu auuaacugca ccuaacucag acgugaguag gacagaagga      60

agcugucccg ggcgaacuga ggucacaaag acuugcuuuu gauucaagag agaccuuaaa     120

ggcuaguuau gauaguuaag uacaaguuuu aacaucuggu agcuaacuuu uuuucucuac     180

cccguaauuc uacuaugacu gcucuucuag agguccugag uucaaauccc agcaaccaca     240

ugguggcuca caaccaucua uaaugggauc ugaugcccuc uucuggugug c             291
```